US010370401B2

(12) United States Patent
Beigelman et al.

(10) Patent No.: US 10,370,401 B2
(45) Date of Patent: Aug. 6, 2019

(54) SUBSTITUTED NUCLEOSIDES, NUCLEOTIDES AND ANALOGS THEREOF

(71) Applicant: Alios BioPharma, Inc., South San Francisco, CA (US)

(72) Inventors: Leonid Beigelman, San Mateo, CA (US); Guangyi Wang, Carlsbad, CA (US); David Bernard Smith, San Mateo, CA (US); Marija Prhavc, Encinitas, CA (US); Christian Andreas Jekle, San Francisco, CA (US); Jerome Deval, Pacifica, CA (US)

(73) Assignee: Janssen BioPharma, Inc., South San Francisco, CA (US)

( * ) Notice: Subject to any disclaimer, the term of this patent is extended or adjusted under 35 U.S.C. 154(b) by 0 days.

(21) Appl. No.: 15/790,764

(22) Filed: Oct. 23, 2017

(65) Prior Publication Data

US 2018/0044369 A1 Feb. 15, 2018

Related U.S. Application Data

(63) Continuation of application No. 14/510,451, filed on Oct. 9, 2014, now Pat. No. 9,862,743.

(60) Provisional application No. 62/016,288, filed on Jun. 24, 2014, provisional application No. 61/890,136, filed on Oct. 11, 2013.

(51) Int. Cl.
| | |
|---|---|
| *A61K 31/7076* | (2006.01) |
| *A61K 31/708* | (2006.01) |
| *C07H 19/20* | (2006.01) |
| *C07H 19/06* | (2006.01) |
| *C07H 19/16* | (2006.01) |
| *C07H 19/10* | (2006.01) |
| *A61K 31/7064* | (2006.01) |
| *A61K 31/7052* | (2006.01) |
| *A61K 31/7072* | (2006.01) |
| *C07H 19/11* | (2006.01) |
| *C07H 19/207* | (2006.01) |
| *C07H 19/213* | (2006.01) |

(52) U.S. Cl.
CPC .......... *C07H 19/20* (2013.01); *A61K 31/708* (2013.01); *A61K 31/7052* (2013.01); *A61K 31/7064* (2013.01); *A61K 31/7072* (2013.01); *A61K 31/7076* (2013.01); *C07H 19/06* (2013.01); *C07H 19/10* (2013.01); *C07H 19/11* (2013.01); *C07H 19/16* (2013.01); *C07H 19/207* (2013.01); *C07H 19/213* (2013.01); *Y02A 50/463* (2018.01)

(58) Field of Classification Search
None
See application file for complete search history.

(56) References Cited

U.S. PATENT DOCUMENTS

| | | | |
|---|---|---|---|
| 4,542,021 A | 9/1985 | Kodama et al. | |
| 5,432,272 A | 7/1995 | Benner et al. | |
| 6,110,901 A | 8/2000 | Gluzman et al. | |
| 6,787,525 B1 | 9/2004 | Schott et al. | |
| 7,125,855 B2 | 10/2006 | Bhat et al. | |
| 7,125,982 B1 | 10/2006 | Frayne | |
| 9,603,864 B2* | 3/2017 | Blatt | A61K 31/708 |
| 9,815,864 B2* | 11/2017 | Beigelman | C07H 19/20 |
| 2003/0064945 A1 | 4/2003 | Akhtar et al. | |
| 2003/0124513 A1 | 7/2003 | McSwiggen | |
| 2003/0236216 A1 | 12/2003 | Devos et al. | |
| 2004/0002596 A1 | 1/2004 | Hong et al. | |
| 2004/0110717 A1 | 6/2004 | Carroll et al. | |
| 2004/0181052 A1 | 9/2004 | Sourena et al. | |
| 2004/0229839 A1 | 11/2004 | Babu et al. | |
| 2004/0229840 A1 | 11/2004 | Bhat et al. | |
| 2004/0259934 A1 | 12/2004 | Olsen et al. | |
| 2005/0009737 A1 | 1/2005 | Clark et al. | |
| 2008/0255038 A1 | 10/2008 | Hopkins et al. | |
| 2009/0176732 A1 | 7/2009 | Beigelman et al. | |
| 2010/0099079 A1 | 4/2010 | Uprichard et al. | |
| 2010/0151001 A1 | 6/2010 | Schott et al. | |
| 2010/0240604 A1 | 9/2010 | Beigelman et al. | |
| 2010/0331397 A1 | 12/2010 | Beigelman et al. | |
| 2011/0171192 A1 | 7/2011 | Tomiyama et al. | |
| 2012/0040968 A1 | 2/2012 | Shimada et al. | |
| 2012/0070411 A1 | 3/2012 | Beigelman et al. | |
| 2012/0070415 A1 | 3/2012 | Beigelman et al. | |
| 2012/0071434 A1 | 3/2012 | Smith et al. | |
| 2012/0165286 A1 | 6/2012 | Beigelman et al. | |
| 2012/0263678 A1 | 10/2012 | Cho et al. | |
| 2013/0164261 A1 | 6/2013 | Wang et al. | |
| 2013/0165400 A1 | 6/2013 | Beigelman et al. | |

(Continued)

FOREIGN PATENT DOCUMENTS

| | | |
|---|---|---|
| CA | 2600359 | 9/2006 |
| CL | 2392-14 | 3/2015 |

(Continued)

OTHER PUBLICATIONS

Office Action dated Jun. 25, 2018 for Colombian Application No. 16-098.063, filed Oct. 9, 2014.

(Continued)

*Primary Examiner* — Traviss C McIntosh, III

(74) *Attorney, Agent, or Firm* — Knobbe Martens Olson & Bear LLP

(57) ABSTRACT

Disclosed herein are nucleosides, nucleotides and nucleotide analogs, methods of synthesizing the same and methods of treating diseases and/or conditions such as a Picornavirus and/or Flaviviridae infection with one or more nucleosides, nucleotides and nucleotide analogs.

41 Claims, 99 Drawing Sheets

(56) References Cited

U.S. PATENT DOCUMENTS

| | | |
|---|---|---|
| 2013/0252920 A1 | 9/2013 | Blatt et al. |
| 2013/0253181 A1 | 9/2013 | Serebryany et al. |
| 2013/0281687 A1 | 10/2013 | Serebryany et al. |
| 2014/0179627 A1 | 6/2014 | Beigelman et al. |
| 2014/0179910 A1 | 6/2014 | Beigelman et al. |
| 2014/0221425 A1 | 8/2014 | Yun et al. |
| 2014/0303108 A1 | 10/2014 | Beigelman et al. |
| 2014/0303113 A1 | 10/2014 | Krop et al. |
| 2015/0005251 A1 | 1/2015 | Dyatkina et al. |
| 2015/0011497 A1 | 1/2015 | Beigelman et al. |
| 2015/0038451 A1 | 2/2015 | Smith et al. |
| 2015/0051167 A1 | 2/2015 | Wang et al. |
| 2015/0105341 A1 | 4/2015 | Beigelman et al. |
| 2015/0141363 A1 | 5/2015 | Wang et al. |
| 2015/0175647 A1 | 6/2015 | Kuldipkumar et al. |
| 2015/0183819 A1 | 7/2015 | Beigelman et al. |
| 2015/0315228 A1 | 11/2015 | Beigelman et al. |
| 2015/0366887 A1 | 12/2015 | Blatt et al. |
| 2015/0366888 A1 | 12/2015 | Blatt et al. |
| 2015/0368286 A1 | 12/2015 | Serebryany et al. |
| 2016/0016987 A1 | 1/2016 | Beigelman et al. |
| 2016/0022724 A1 | 1/2016 | Chanda et al. |
| 2016/0024136 A1 | 1/2016 | Beigelman et al. |
| 2016/0039858 A1 | 2/2016 | Beigelman et al. |
| 2016/0039861 A1 | 2/2016 | Smith et al. |
| 2016/0115190 A1 | 4/2016 | Serebryany et al. |
| 2016/0176910 A1 | 6/2016 | Wang et al. |
| 2016/0176911 A1 | 6/2016 | Beigelman et al. |
| 2016/0264610 A1 | 9/2016 | Beigelman et al. |
| 2016/0318967 A1 | 11/2016 | Dyatkina et al. |
| 2016/0318969 A1 | 11/2016 | Kuldipkumar et al. |
| 2016/0331770 A1 | 11/2016 | Beigelman et al. |
| 2017/0002037 A1 | 1/2017 | Beigelman et al. |
| 2017/0037075 A1 | 2/2017 | Beigelman et al. |
| 2017/0037077 A1 | 2/2017 | Beigelman et al. |
| 2017/0143749 A1 | 5/2017 | Blatt et al. |
| 2017/0143751 A1 | 5/2017 | Blatt et al. |
| 2018/0079774 A1 | 3/2018 | Beigelman et al. |
| 2018/0117042 A1 | 5/2018 | Chanda et al. |
| 2018/0155384 A1 | 6/2018 | Wang et al. |
| 2018/0186825 A1 | 7/2018 | Serebryany et al. |
| 2018/0194793 A1 | 7/2018 | Dyatkina et al. |

FOREIGN PATENT DOCUMENTS

| | | |
|---|---|---|
| CL | 1699-15 | 10/2015 |
| CN | 102516339 | 6/2012 |
| CN | 102816197 | 12/2012 |
| CN | 103209987 A | 7/2013 |
| CO | 15141920 | 10/2015 |
| DE | 19855963 | 6/2000 |
| DE | 20121305 | 10/2002 |
| EA | 201590943 | 1/2016 |
| EA | 201592184 | 4/2016 |
| EP | 2264169 | 12/2010 |
| EP | 2332953 | 6/2011 |
| ES | 2013-12572 | 1/2015 |
| IE | PI-2014-10277 | 9/2015 |
| IE | PI-2015-31144 | 11/2015 |
| JP | 07-242544 | 9/1995 |
| JP | 2008-214305 | 9/2008 |
| JP | 2011-515397 | 5/2011 |
| JP | 2013-537907 | 10/2013 |
| SE | 7905375 | 12/1979 |
| WO | WO 1996/040705 | 12/1996 |
| WO | WO 1997/026883 | 7/1997 |
| WO | WO 1998/016184 | 4/1998 |
| WO | WO 1998/016186 | 4/1998 |
| WO | WO 1999/061583 | 12/1999 |
| WO | WO 2000/034298 | 6/2000 |
| WO | WO 2000/069876 | 11/2000 |
| WO | WO 2001/068663 | 9/2001 |
| WO | WO 2002/003997 | 1/2002 |
| WO | WO 2002/057287 | 7/2002 |
| WO | WO 2002/057425 | 7/2002 |
| WO | WO 2002/100415 | 12/2002 |
| WO | WO 2003/022859 | 3/2003 |
| WO | WO 2003/026589 | 4/2003 |
| WO | WO 2003/026675 | 4/2003 |
| WO | WO 2003/039523 | 5/2003 |
| WO | WO 2003/062255 | 7/2003 |
| WO | WO 2003/062256 | 7/2003 |
| WO | WO 2003/068244 | 8/2003 |
| WO | WO 2003/070193 | 8/2003 |
| WO | WO 2003/070912 | 8/2003 |
| WO | WO 2003/073989 | 9/2003 |
| WO | WO 2003/099840 | 12/2003 |
| WO | WO 2003/100017 | 12/2003 |
| WO | WO 2004/000858 | 12/2003 |
| WO | WO 2004/002999 | 1/2004 |
| WO | WO 2004/003000 | 1/2004 |
| WO | WO 2004/003138 | 1/2004 |
| WO | WO 2004/007512 | 1/2004 |
| WO | WO 2004/014312 | 2/2004 |
| WO | WO 2004/037159 | 5/2004 |
| WO | WO 2004/80466 | 9/2004 |
| WO | WO 2004/091499 | 10/2004 |
| WO | WO 2004/106356 | 12/2004 |
| WO | WO 2005/003147 | 1/2005 |
| WO | WO 2005/007810 | 1/2005 |
| WO | WO 2005/009418 | 2/2005 |
| WO | WO 2005/020884 | 3/2005 |
| WO | WO 2005/020885 | 3/2005 |
| WO | WO 2005/021568 | 3/2005 |
| WO | WO 2006/000922 | 1/2006 |
| WO | WO 2006/033709 | 3/2006 |
| WO | WO 2006/063717 | 6/2006 |
| WO | WO 2006/094347 | 9/2006 |
| WO | WO 2006/105440 | 10/2006 |
| WO | WO 2006/116512 | 11/2006 |
| WO | WO 2007/020018 | 2/2007 |
| WO | WO 2007/020193 | 2/2007 |
| WO | WO 2007/038507 | 4/2007 |
| WO | WO 2007/113538 | 10/2007 |
| WO | WO 2008/012555 | 1/2008 |
| WO | WO 2008/082601 | 7/2008 |
| WO | WO 2008/085508 | 7/2008 |
| WO | WO 2008/089105 | 7/2008 |
| WO | WO 2008/089439 | 7/2008 |
| WO | WO 2008/095040 | 8/2008 |
| WO | WO 2008/115499 | 9/2008 |
| WO | WO 2008/117047 | 10/2008 |
| WO | WO 2008/121634 | 10/2008 |
| WO | WO 2008/125583 | 10/2008 |
| WO | WO 2009/001097 | 12/2008 |
| WO | WO 2009/003042 | 12/2008 |
| WO | WO 2009/040269 | 4/2009 |
| WO | WO 2009/067409 | 5/2009 |
| WO | WO 2009/071488 | 6/2009 |
| WO | WO 2009/086192 | 7/2009 |
| WO | WO 2009/086201 | 7/2009 |
| WO | WO 2009/105712 | 8/2009 |
| WO | WO 2009/117097 | 9/2009 |
| WO | WO 2009/129120 | 10/2009 |
| WO | WO 2009/152095 | 12/2009 |
| WO | WO 2010/015643 | 2/2010 |
| WO | WO 2010/026153 | 3/2010 |
| WO | WO 2010/027005 | 3/2010 |
| WO | WO 2010/030858 | 3/2010 |
| WO | WO 2010/036407 | 4/2010 |
| WO | WO 2010/075554 | 7/2010 |
| WO | WO 2010/088924 | 8/2010 |
| WO | WO 2010/089128 | 8/2010 |
| WO | WO 2010-091386 | 8/2010 |
| WO | WO 2010/108135 | 9/2010 |
| WO | WO 2010/108140 | 9/2010 |
| WO | WO 2010/128659 | 11/2010 |
| WO | WO 2010-145778 | 12/2010 |
| WO | WO 2011/005860 | 1/2011 |
| WO | WO 2011/057204 | 5/2011 |
| WO | WO 2011/133871 | 11/2011 |
| WO | WO 2012/012465 | 1/2012 |
| WO | WO 2012/040127 | 3/2012 |
| WO | WO 2012/041965 | 4/2012 |

(56) References Cited

FOREIGN PATENT DOCUMENTS

| WO | WO 2012/074547 | 6/2012 |
|---|---|---|
| WO | WO 2012/088155 | 6/2012 |
| WO | WO 2012/094248 | 7/2012 |
| WO | WO 2012/142085 | 10/2012 |
| WO | WO 2013/019874 | 2/2013 |
| WO | WO 2013/040801 | 3/2013 |
| WO | WO 2013/044030 | 3/2013 |
| WO | WO 2013/092481 | 6/2013 |
| WO | WO 2013/096679 | 6/2013 |
| WO | WO 2013/096680 | 6/2013 |
| WO | WO 2013/142124 | 9/2013 |
| WO | WO 2013/142125 | 9/2013 |
| WO | WO 2013/142157 | 9/2013 |
| WO | WO 2013/142159 | 9/2013 |
| WO | WO 2013/142525 | 9/2013 |
| WO | WO 2014/070771 | 5/2014 |
| WO | WO 2014/099941 | 6/2014 |
| WO | WO 2014/100498 | 6/2014 |
| WO | WO 2014/100505 | 6/2014 |
| WO | WO 2014/134251 | 9/2014 |
| WO | WO 2014/164533 | 10/2014 |
| WO | WO 2014/165704 | 10/2014 |
| WO | WO 2014/186637 | 11/2014 |
| WO | WO 2014/209979 | 12/2014 |
| WO | WO 2014/209983 | 12/2014 |
| WO | WO 2016/022464 | 2/2016 |
| WO | WO 2018/031818 | 2/2018 |

OTHER PUBLICATIONS

Substantive Examination Report dated Jun. 28, 2018 for CL Application No. 805-2016, filed Oct. 9, 2014.
Office Action dated Oct. 26, 2018 for CN Application No. 201480064612.5, filed Oct. 9, 2014.
Bondada, L. et al., "Adenosine Dioxolane Nucleoside Phosphoramidates as Antiviral Agents for Human Immunodeficiency and Hepatitis B Viruses" *ACS Medicinal Chemistry Letters*,(2013) 4(8):747-751.
CAS No. 636581-91-4, Entry Date Jan. 12, 2004, Retrieved Jan. 20, 2015.
CAS No. 636581-84-5, Entry Date Jan. 12, 2004, Retrieved Jan. 23, 2015.
CAS No. 1037071-04-7, Entry Date Jul. 31, 2008, Retrieved Jan. 23, 2015.
CAS No. 125911-76-4, Entry Date Mar. 16, 1990, Retrieved Jan. 23, 2015.
CAS No. 374750-27-3, Entry Date Dec. 12, 2001, Retrieved Jan. 23, 2015.
CAS No. 636582-01-9, Entry Date Jan. 12, 2004, Retrieved Jan. 23, 2015.
CAS No. 636581-94-7, Entry Date Jan. 12, 2004, Retrieved Jan. 23, 2015.
CAS Registry No. 1053631-52-9, STN Entry Date Sep. 28, 2008, retrieved on Sep. 16, 2015.
CAS Registry No. 232932-50-2, STN Entry Date Aug. 15, 1999, retrieved on Nov. 16, 2015.
Ethève, et al., "Synthesis of 2'-~-C-allenyl-2'-deoxyuridine : An Analogue of 2'-azido-2'-deoxyuridine, Known Inhibitor of Ribonucleotide Diphosphate Reductase (RDPR)", Tetrahedron Letters 40 (1999) pp. 4807-4810.
Greene, et al., Protective Groups in Organic Synthesis, 3. Ed., John Wiley & Sons, (1999) Cover & Contents pages.
Griffon et al., "Synthesis and Antiviral Evaluation of 4'-C-Azidomethyl-b-D-Ribofuranosyl Purine and Pyrimidine Nucleosides" *Nucleosides, Nucleotides and Nucleic Acids* (2009) 28:435-449.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.
Kodama, E.-I. et al., "4'-Ethynyl Nucleoside Analogs: Potent Inhibitors of Multidrug-Resistant Human Immunodeficiency Virus Variants in Vitro", Antimicrobial Agents and Chemotherapy (2001) 45(5):1539-1546.

Lefebre et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate" *J. Med. Chem.* (1995) 38:3941-3950.
McOmie, J. F. W., Protective Groups in Organic Chemistry, Plenum Press, 1973. Cover & Contents pages only.
McGuigan et al., "Phosphate Prodrugs Derived from N-Acetylglucosamine Have Enhanced Chondroprotective Activity in Explant Cultures and Represent a New Lead in Antiosteoarthritis Drug Discover" *J. Med. Chem.* (2008) 51:5807-5812.
Reddy et al., "Stereoselective Synthesis of PSI-352938: A β-D-2'-Deoxy-2'-α-fluoro-2'-β-C-methyl-3',5'-cyclic Phosphate Nucleotide Prodrug for the Treatment of HCV" *J. Org. Chem.* (2011) 76 (10):3782-3790.
Smith et al., "Design, synthesis, and antiviral properties of 4'-substituted ribonucleosides as inhibitors of hepatitis C virus replication: The discovery of R1479" Bioorganic & Medicinal Chemistry Letters (2007) 17(9):2570-2576.
Villard et al., "Phenyl phosphotriester derivaties of AZT: Variations upon the SATE moiety" *Bioorg. Med. Chem.* (2008) 16:7321-7329.
Zhang, et al., "Click-Connected Ligand:Scaffolds: Macrocyclic Chelates for Asymmetric Hydrogenation" *Org. Lett.* (2008) 10(4):545-548.
International Search Report and Written Opinion dated Jan. 20, 2015 for PCT Application No. PCT/US2014/059849 filed Oct. 9, 2014.
International Preliminary Report on Patentability dated Feb. 12, 2016 for PCT Application No. PCT/US2014/059849, filed Oct. 9, 2014.
Second Written Opinion dated Sep. 15, 2015 for PCT Application No. PCT/US2014/059849, filed Oct. 9, 2014.
Third Written Opinion dated Dec. 16, 2015 for PCT Application No. PCT/US2014/059849, filed Oct. 9, 2014.
Partial Supplementary European Search Report dated Jun. 28, 2017 for EP Patent Application No. 14851776.6, filed Oct. 9, 2014.
Notification-Demand dated Mar. 6, 2017 for Georgian Application No. 14137/01-16, filed Oct. 9, 2014.
Office Action dated May 31, 2016 for Colombian Application No. 16-098.063, filed Oct. 9, 2014.
Office Action dated Oct. 24, 2017 for Colombian Application No. 16-098.063, filed Oct. 9, 2014.
Office Action dated Aug. 9, 2017 for Eurasian Application No. 201690526, filed Oct. 9, 2014.
Substantive Examination Report dated Apr. 26, 2017 for CL Application No. 805-2016, filed Oct. 9, 2014.
Office Action dated Nov. 15, 2016 for U.S. Appl. No. 14/510,451, filed Oct. 9, 2014.
Search Report and Written Opinion dated Apr. 18, 2017 for Singapore Patent Application No. 11201602595T; filed Oct. 9, 2014.
Examination Report dated Jan. 10, 2018 for Australian Application No. 2014331863, filed Oct. 9, 2014.
Cheng et al., Encyclopedia for Science and Technology (1984) McGraw-Hill Book Co., $4^{th}$ ed., vol. 9, pp. 378-379.
Office Action dated Dec. 21, 2017 for CN Application No. 201480064612.5, filed Oct. 9, 2014.
Extended European Search Report dated Dec. 13, 2017 for EP Patent Application No. 14851776.6, filed Oct. 9, 2014.
Notification-Demand dated Apr. 11, 2018 for Georgian Application No. 14137/01-16, filed Oct. 9, 2014.
Documentary Conclusion and Search Report dated Jan. 17, 2019 for Georgian Application No. 14137/01-16, filed Oct. 9, 2014.
Byers et al., "An Epithelial—Mesenchymal Transition Gene Signature Predicts Resistance to EGFR and P13K Inhibitors and Identifies Axl as a Therapeutic Target for Overcoming EGFR Inhibitors and Identifies Axl as a Therapeutic Target for Overcoming EGFR Inhibitor Resistance"Clin. Cancer Res. (2013) 19(1):279-290.
Mollard et al., "Design, Synthesis, and Biological Evaluation of a Series of Novel AXL Kinase Inhibitors" ACS Med. Chem. Lett. (2011) 2(12):907-912.
Yakes et al., "Cabozantinib (XL184), a Novel MET and VEGFR2 Inhibitor, Simultaneously Suppresses Metastasis, Angiogenesis, and Tumor Growth"Mol. Cancer. Ther. (2011) 10(12):2298-2308.

(56) References Cited

OTHER PUBLICATIONS

Office Action dated Aug. 28, 2018 for Japanese Application No. 2016-521765, filed Oct. 9, 2018.
Office Action and Search Report dated Oct. 31, 2018 for TW Application No. 103135252, filed Oct. 9, 2014.
Office Action dated Oct. 31, 2018 for Uzbek Application No. IAP20160166, filed Oct. 9, 2014.
Opposition dated Dec. 8, 2018 for EC Application No. IEPI-2016-19202, filed Oct. 9, 2014.

* cited by examiner

Figure 1: HCV Protease Inhibitors

| # | Name | Structure |
|---|---|---|
| 1001 | Telaprevir VX-950 | 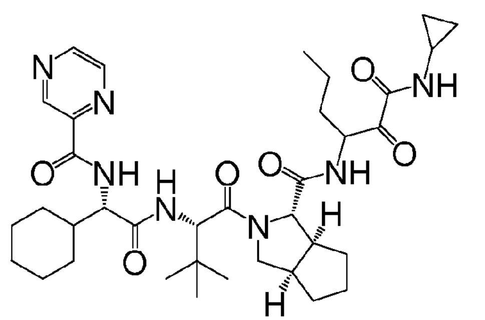 |
| 1002 | MK-5172 | 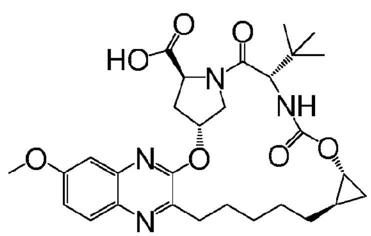 |
| 1003 | ABT-450 | |
| 1004 | BILN-2061 | |
| 1005 | BI-201335 BI335 | |

Figure 1 (cont.): HCV Protease Inhibitors

| # | Name | Structure |
|---|---|---|
| 1013 | TMC-435<br>TMC-435350 | 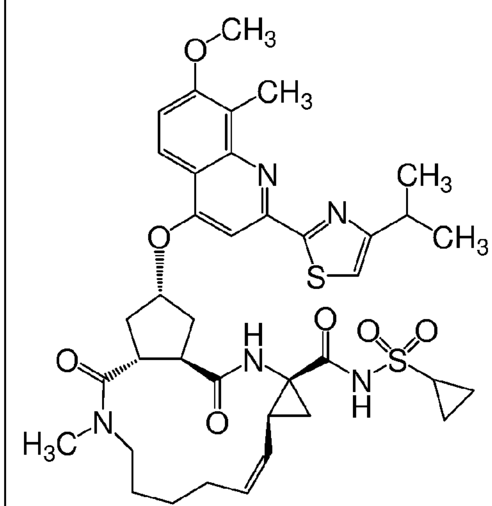 |
| 1014 | Danoprevir<br>ITMN-191<br>RG7227<br>RO5190591 | 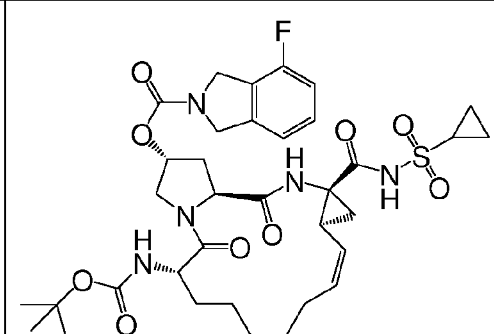 |

| # | Name | Structure |
|---|---|---|
| 1006 | BMS-650032<br>BM032<br>Asunaprevir | 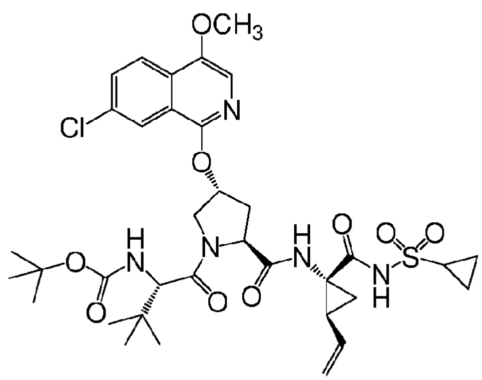 |
| 1007 | Boceprevir<br>SCH 503034 | 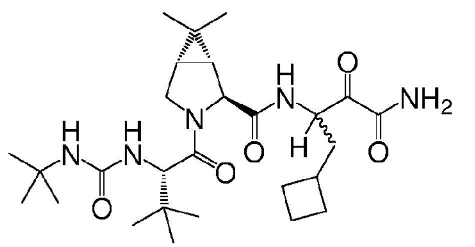 |
| 1008 | GS-9256 | |
| 1009 | GS-9451 | |
| 1010 | IDX-320 | |
| 1011 | ACH-1625 | |
| 1012 | ACH-2684 | |

Figure 1 (cont.): HCV Protease Inhibitors

| # | Name | Structure |
|---|---|---|
| 1015 | MK-7009 Vaniprevir | 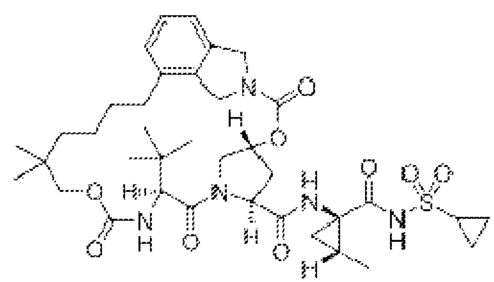 |
| 1016 | PHX1766 | |

Figure 2: HCV Polymerase Inhibitors – Nucleosides, Nucleotides and Analogs Thereof

| # | Name | Structure |
|---|------|-----------|
| 2001 | RG7128 Mericitabine | |
| 2002 | PSI-7851 | |
| 2003 | PSI-7977 GS-7977, Sofosbuvir | |
| 2004 | PSI-352938 GS-938 | 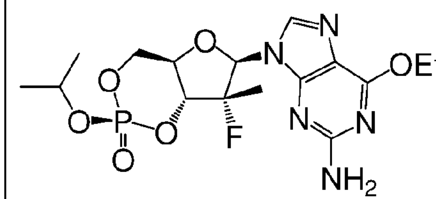 |
| 2005 | 4'-azidouridine and its prodrugs | 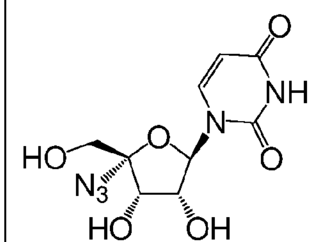 |
| 2006 | PSI-661 | 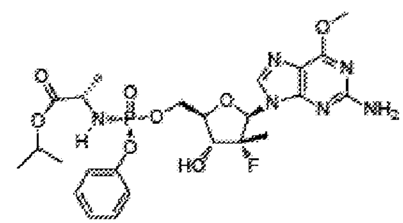 |
| 2007 | GS-6620 | |
| 2008 | TMC649128 | |

Figure 2 (cont.): HCV Polymerase Inhibitors – Nucleosides, Nucleotides and Analogs Thereof

| # | Name | Structure |
|---|---|---|
| 2009 | NM283 | ![structure with NH2, N, O, Me, OH, ValO, HO] |
| 2010 | BCX5191 | |
| 2011 | IDX19368 | |
| 2012 | IDX19370 | |

Figure 3: HCV Polymerase Inhibitors – Non-Nucleosides

| # | Name | Structure |
|---|---|---|
| 3001 | ABT-333 | |
| 3002 | ANA-598 Setrobuvir | |
| 3003 | VX-222 S1480 VCH-222 | |
| 3004 | HCV-796 | 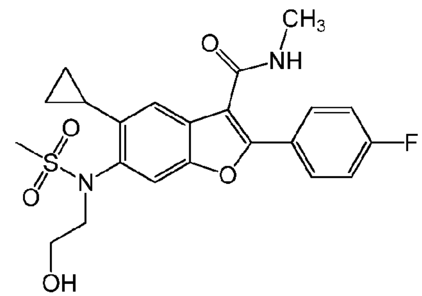 |
| 3005 | BI-207127 | |
| 3006 | GS-9190 | 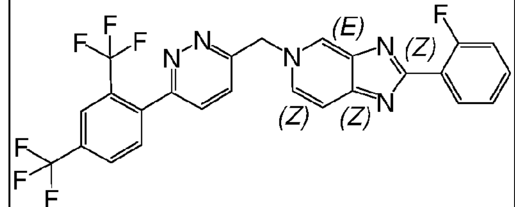 |
| 3007 | Filibuvir PF-00868554 | 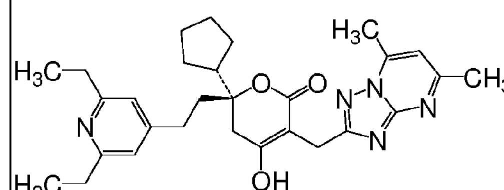 |

Figure 3 (cont.): HCV Polymerase Inhibitors – Non-Nucleosides
| # | Name | Structure |
|---|---|---|
| 3008 | VX-497 | 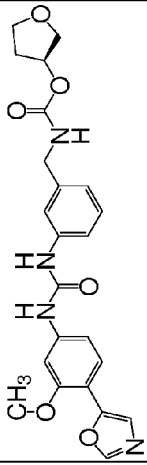 |
| 3009 | ABT-072 | |
| 3010 | MK-3281 | |
| # | Name | Structure |
|---|---|---|
| 3011 | TMC647055 | |
| 3012 | BMS-791325 | |
| 3013 | PPI-383 | |
| 3014 | GS9669 | |

Figure 4: NS5A Inhibitors

| # | Name | Structure |
|---|---|---|
| 4001 | BMS-790052 BMS052 S1482 Daclatasvir | (structure shown) |
| 4002 | PPI-461 | |
| 4003 | ACH-2928 | |
| 4004 | GS-5885 | |
| 4005 | BMS-824393 | |
| 4006 | ABT 267 | |
| 4007 | ACH-3102 | |
| 4008 | AZD-7295 | |
| 4009 | IDX719 | |
| 4010 | PPI-668 | |
| 4011 | MK8742 | |
| 4012 | GSK805 | |

Figure 5: Other Antivirals
| # | Name | Structure |
|---|---|---|
| 5001 | Debio-025 Alisporivir | |
| 5002 | MIR-122 inhibitor | |
| 5003 | clemizole | |
| 5004 | ITX 5061 | |
| 5005 | BIT225 | |
| 5006 | NIM811 | |
| 5007 | SCY-635 | |
| 5008 | Nitazoxanide | 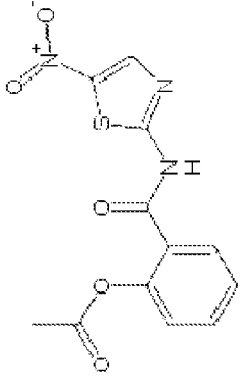 |
| 5009 | Miravirsen | |
| 5010 | Celgosivir | 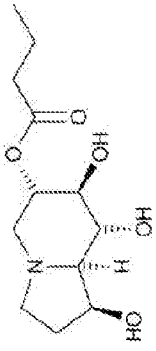 |
| 5011 | GS9620 | |

Figure 6: Compounds of Formula (CC) and alpha-thiotriphosphates thereof

| # | Structure |
|---|---|
| 6000 | |
| 6001 | |
| 6002 | 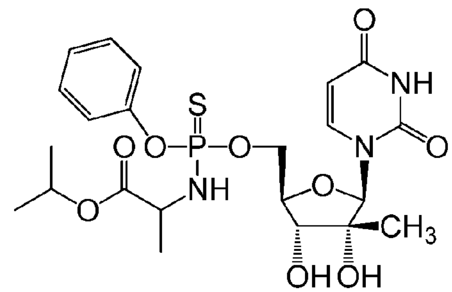 |
| 6003 | 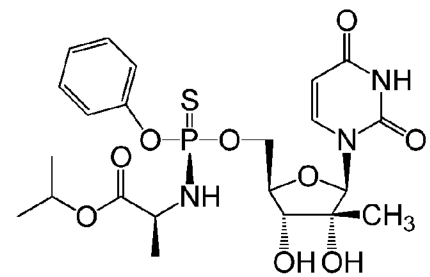 |
| 6004 | 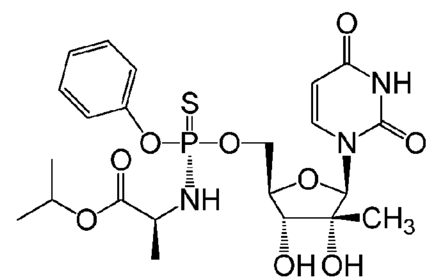 |

Figure 6 (cont.): Compounds of Formula (CC) and alpha-thiotriphosphates thereof

| # | Structure |
|---|-----------|
| 6005 | (structure) |
| 6006 | (structure) |//

| # | Structure |
|---|-----------|
| 6007 | (structure) |
| 6008 | (structure) |

Figure 6 (cont.): Compounds of Formula (CC) and alpha-thiotriphosphates thereof

| # | Structure |
|---|---|
| 6011 | 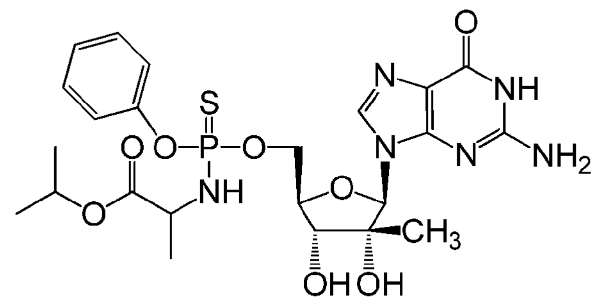 |
| 6012 | 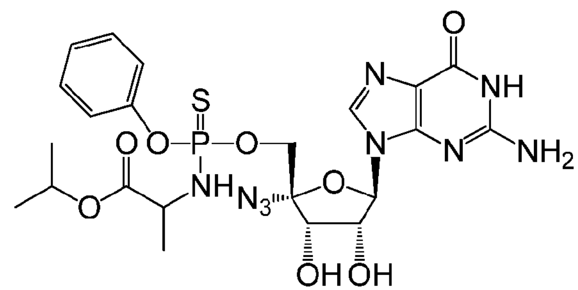 |
| 6013 | 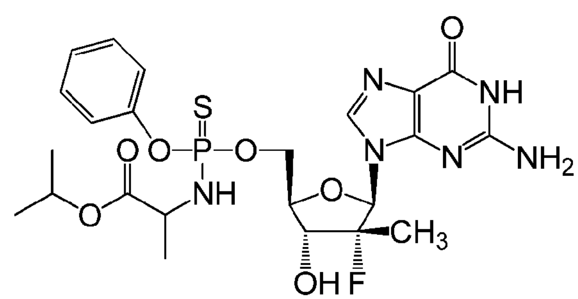 |

| # | Structure |
|---|---|
| 6009 | 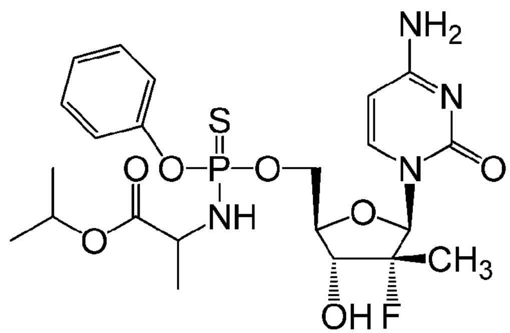 |
| 6010 | 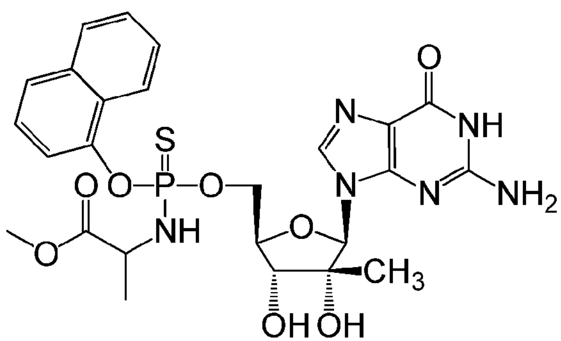 |

Figure 6 (cont.): Compounds of Formula (CC) and alpha-thiotriphosphates thereof

Figure 6 (cont.): Compounds of Formula (CC) and alpha-thiotriphosphates thereof

| # | Structure |
|---|---|
| 6021 | (uridine 2'-C-methyl-2'-OH α-thiotriphosphate) |
| 6022 | (uridine 2'-C-methyl-2'-F α-thiotriphosphate) |
| 6023 | (uridine 2'-C-methyl-2'-F α-thiotriphosphate, alternate stereochemistry) |

| # | Structure |
|---|---|
| 6018 | (6-methoxy-2-aminopurine 2'-C-methyl-2'-F nucleoside phenyl isopropyl alaninyl thiophosphoramidate) |
| 6019 | (uridine 2'-C-methyl-2'-OH α-thiotriphosphate) |
| 6020 | (uridine 2'-C-methyl-2'-OH α-thiotriphosphate, alternate stereochemistry) |

Figure 6 (cont.): Compounds of Formula (CC) and alpha-thiotriphosphates thereof

| # | Structure |
|---|---|
| 6027 | 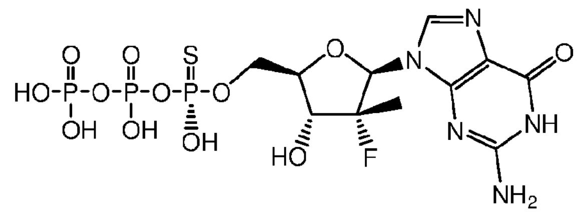 |
| 6028 | 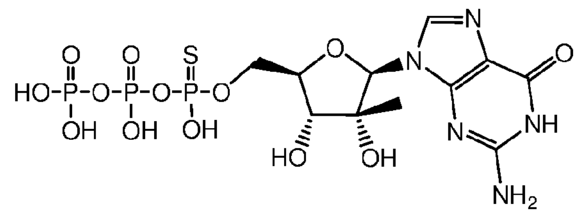 |
| 6029 | 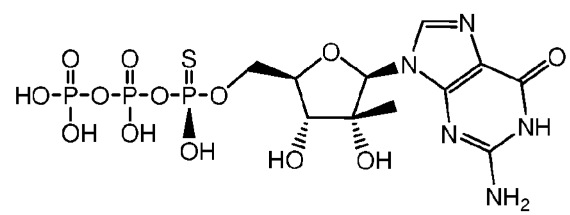 |
| 6030 | 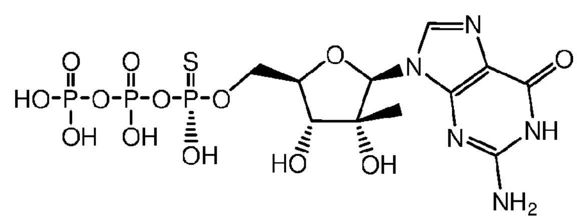 |

| # | Structure |
|---|---|
| 6024 | 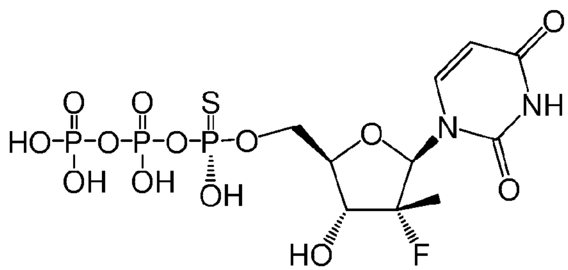 |
| 6025 | 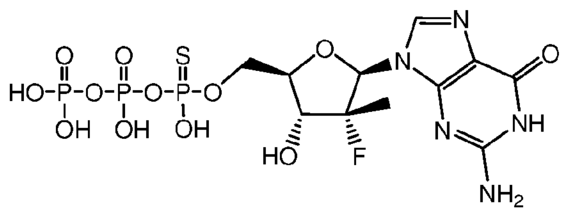 |
| 6026 | 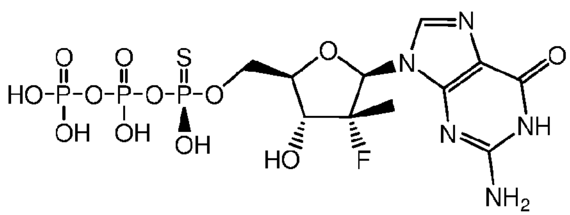 |

Figure 6 (cont.): Compounds of Formula (CC) and alpha-thiotriphosphates thereof

| # | Structure |
|---|---|
| 6034 | (structure) |
| 6035 | (structure) |
| 6036 | (structure) |

| # | Structure |
|---|---|
| 6031 | (structure) |
| 6032 | (structure) |
| 6033 | (structure) |

Figure 6 (cont.): Compounds of Formula (CC) and alpha-thiotriphosphates thereof

Figure 6 (cont.): Compounds of Formula (CC) and alpha-thiotriphosphates thereof

| # | Structure |
|---|---|
| 6046 | (structure) |
| 6047 | (structure) |
| 6048 | (structure) |

| # | Structure |
|---|---|
| 6043 | (structure) |
| 6044 | (structure) |
| 6045 | (structure) |

Figure 6 (cont.): Compounds of Formula (CC) and alpha-thiotriphosphates thereof

| # | Structure |
|---|---|
| 6049 | (structure) |
| 6050 | (structure) |

| # | Structure |
|---|---|
| 6051 | (structure) |
| 6052 | (structure) |

Figure 6 (cont.): Compounds of Formula (CC) and alpha-thiotriphosphates thereof

| # | Structure |
|---|---|
| 6055 | (structure) |
| 6056 | (structure) |
| 6057 | (structure) |

| # | Structure |
|---|---|
| 6053 | (structure) |
| 6054 | (structure) |

Figure 6 (cont.): Compounds of Formula (CC) and alpha-thiotriphosphates thereof

| # | Structure |
|---|---|
| 6060 | 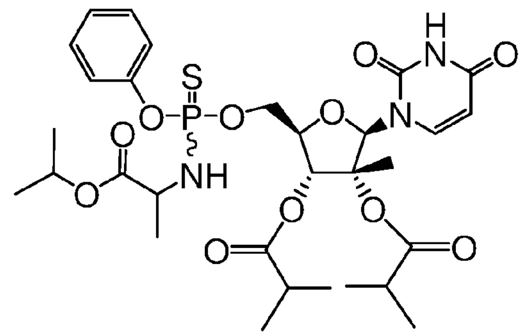 |
| 6061 | 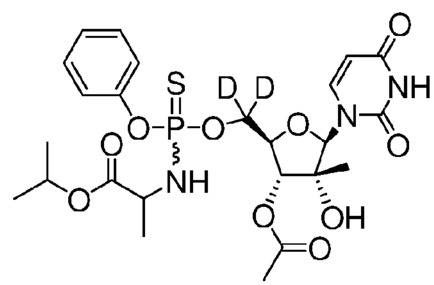 |
| 6062 | 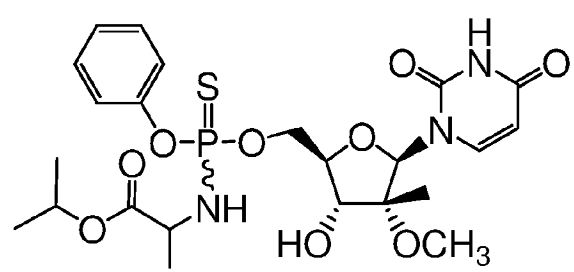 |

| # | Structure |
|---|---|
| 6058 | 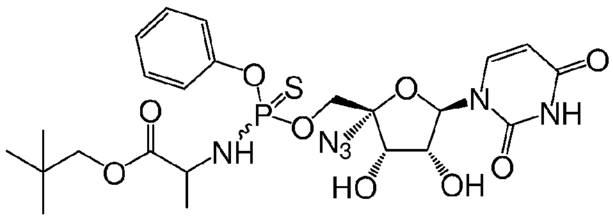 |
| 6059 | 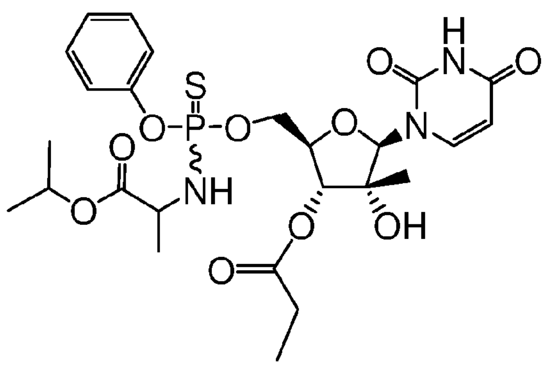 |

Figure 6 (cont.): Compounds of Formula (CC) and alpha-thiotriphosphates thereof

Figure 6 (cont.): Compounds of Formula (CC) and alpha-thiotriphosphates thereof

| # | Structure |
|---|---|
| 6072 | (structure) |
| 6073 | (structure) |
| 6074 | (structure) |

| # | Structure |
|---|---|
| 6069 | (structure) |
| 6070 | (structure) |
| 6071 | (structure) |

Figure 6 (cont.): Compounds of Formula (CC) and alpha-thiotriphosphates thereof

| # | Structure |
|---|---|
| 6077 | (structure) |
| 6078 | (structure) |
| 6075 | (structure) |
| 6076 | (structure) |

Figure 7: Compounds of Formula (AA)
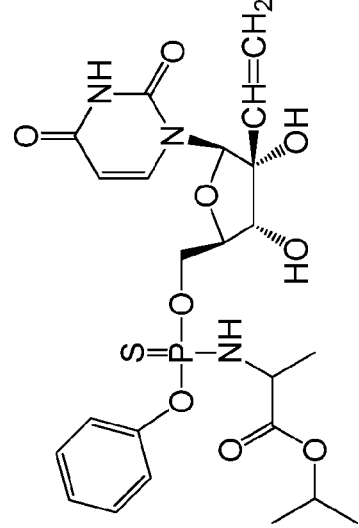

Figure 7 (cont.): Compounds of Formula (AA)

Figure 7 (cont.): Compounds of Formula (AA)

| # | Structure |
|---|---|
| 7010 | (4-fluorophenyl phosphorothioate prodrug structure) |
| 7011 | (4-chlorophenyl phosphorothioate prodrug structure) |
| 7008 | (phenyl phosphorothioate valine isopropyl ester prodrug structure) |
| 7009 | (phenyl phosphorothioate leucine isopropyl ester prodrug structure) |

Figure 7 (cont.): Compounds of Formula (AA)
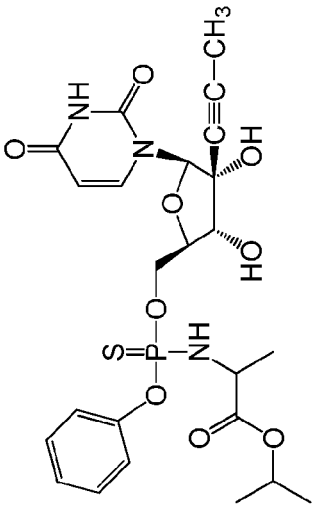

Figure 7 (cont.): Compounds of Formula (AA)

| # | Structure |
|---|---|
| 7016 | 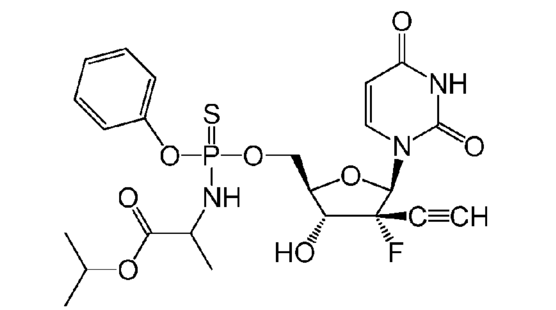 |
| 7017 | 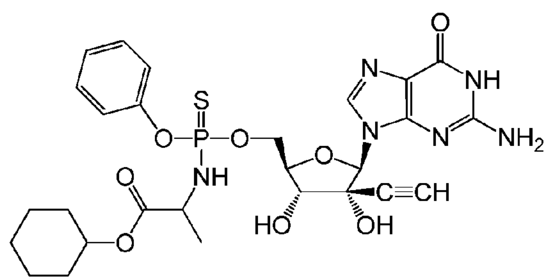 |
| 7018 | |
| 7019 | |

Figure 7 (cont.): Compounds of Formula (AA)
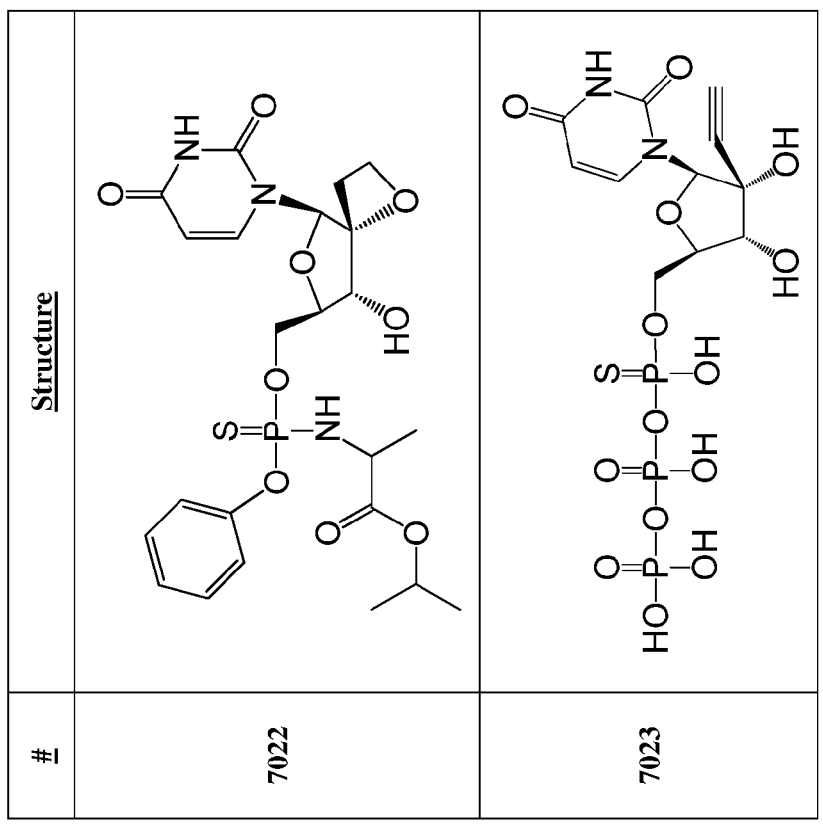
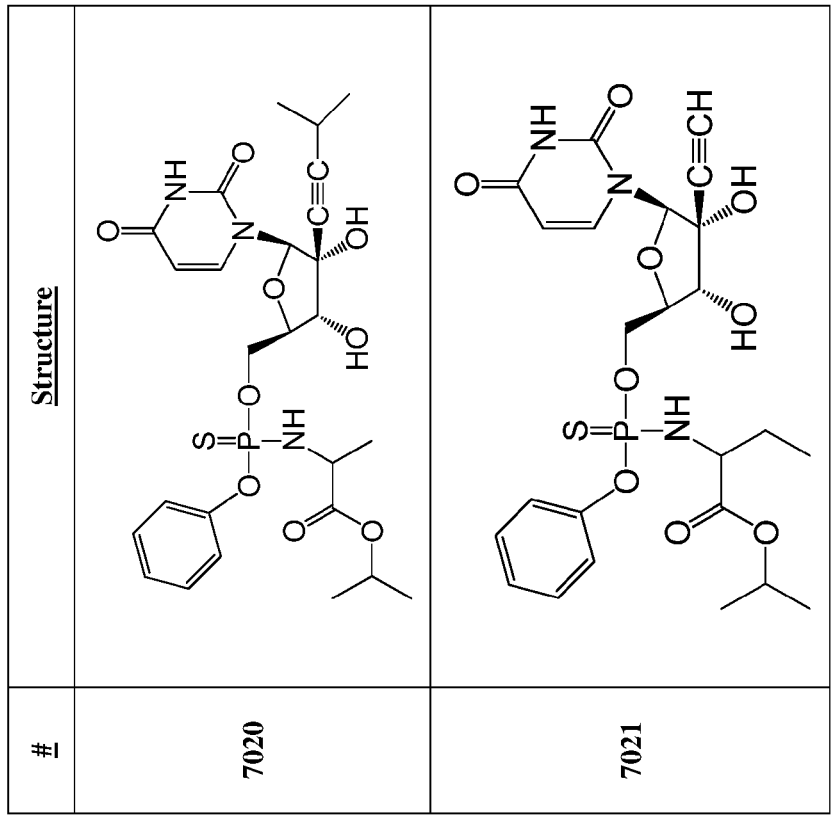

Figure 7 (cont.): Compounds of Formula (AA)
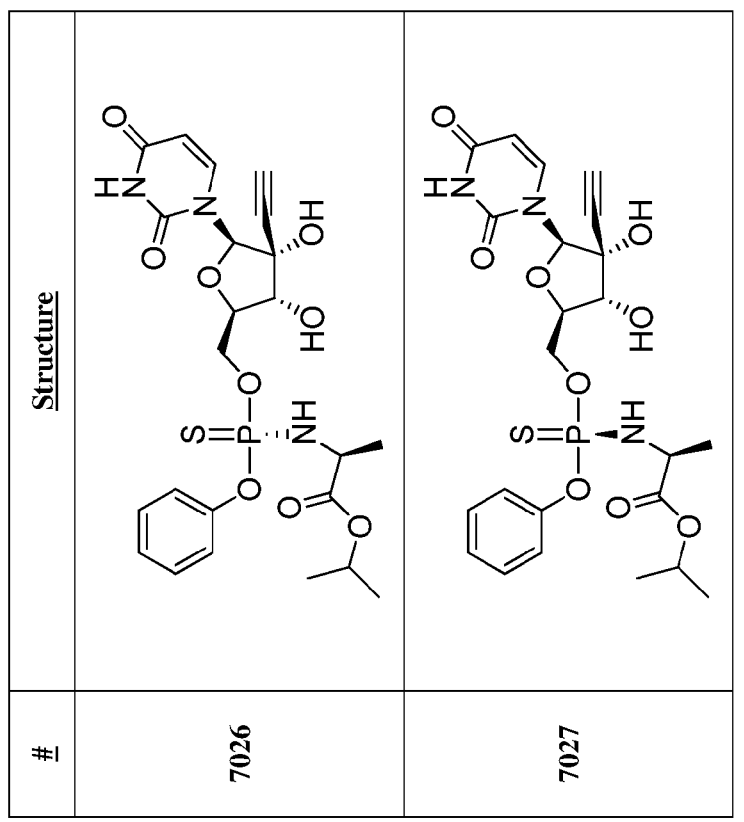
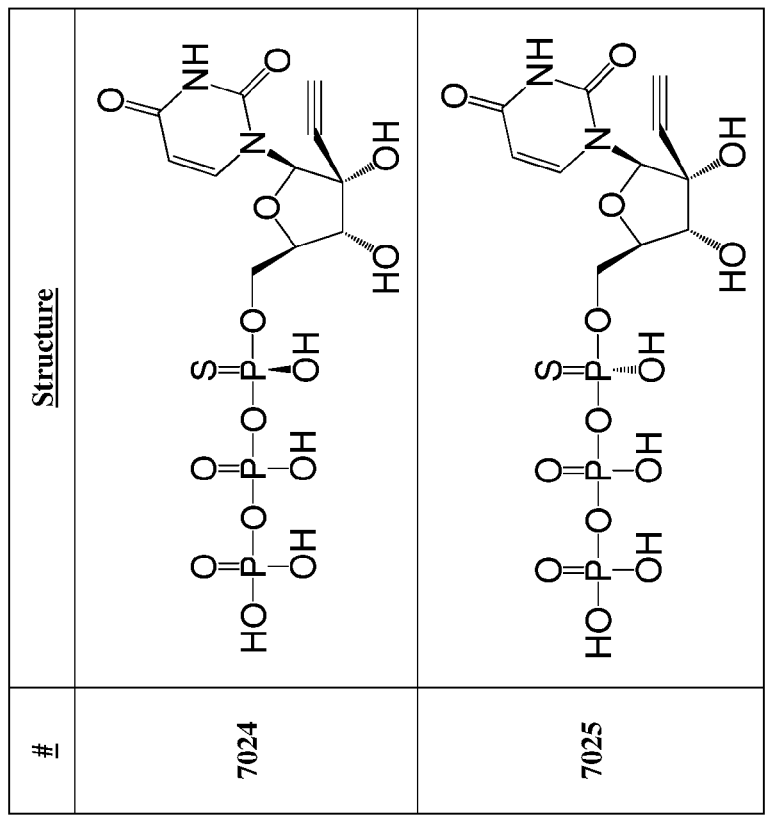

Figure 8: Compounds of Formula (BB)

Figure 8 (cont.): Compounds of Formula (BB)

| # | Structure |
|---|---|
| 8006 | 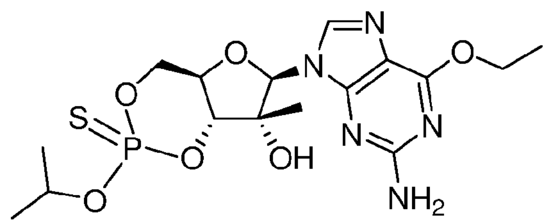 |
| 8007 | 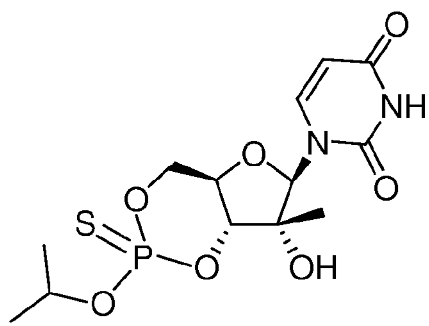 |
| 8008 | 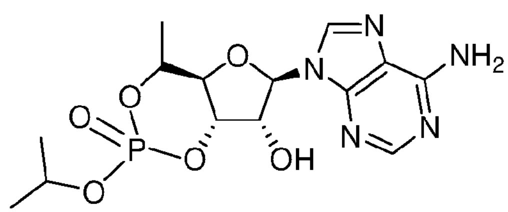 |
| 8009 | |
| 80010 | |
| 8011 | |

Figure 8 (cont.): Compounds of Formula (BB)

| # | Structure |
|---|---|
| 8012 | (structure) |
| 8013 | (structure) |
| 8014 | (structure) |
| 8015 | (structure) |
| 8016 | (structure) |

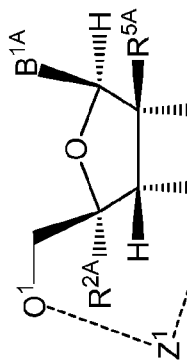
Figure 9: Compounds of Formula (I)

Figure 9 (cont.): Compounds of Formula (I)

| # | Structure |
|---|---|
| 9006 | (structure) |
| 9007 | (structure) |
| 9008 | (structure) |
| 9009 | (structure) |

Figure 9 (cont.): Compounds of Formula (I)

Figure 9 (cont.): Compounds of Formula (I)

Figure 9 (cont.): Compounds of Formula (I)

| # | Structure |
|---|---|
| 9019 | 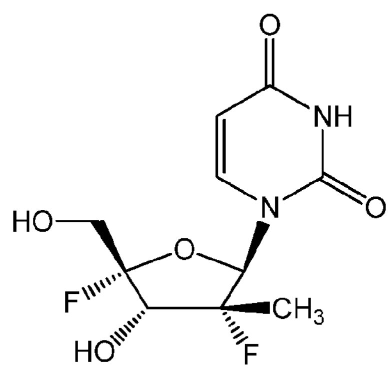 |
| 9020 | 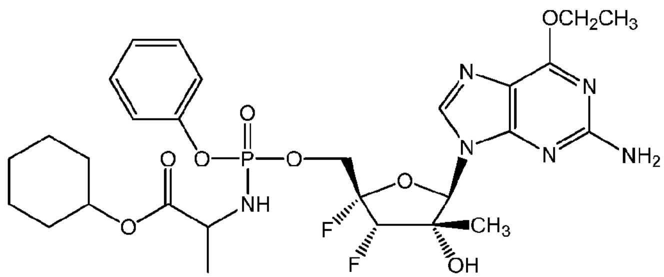 |
| 9021 | 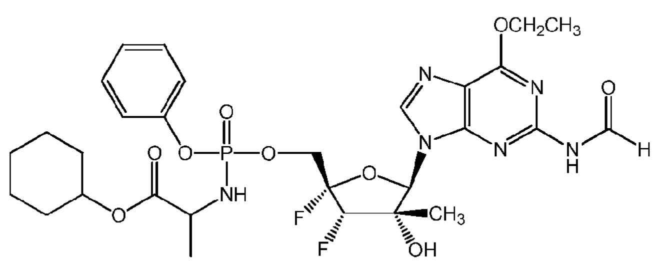 |
| 9022 | |
| 9023 | |
| 9024 | |

Figure 9 (cont.): Compounds of Formula (I)

| # | Structure |
|---|---|
| 9028 | 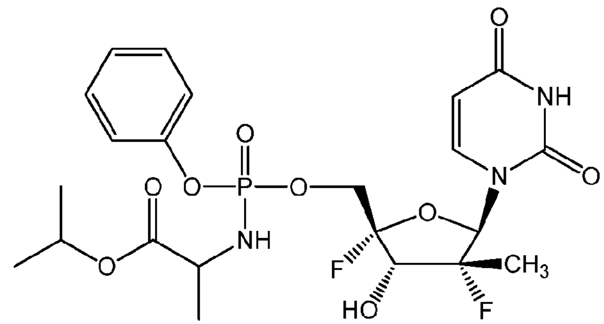 |
| 9029 | 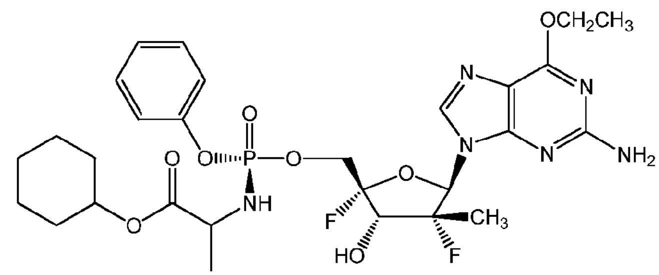 |
| 9030 | 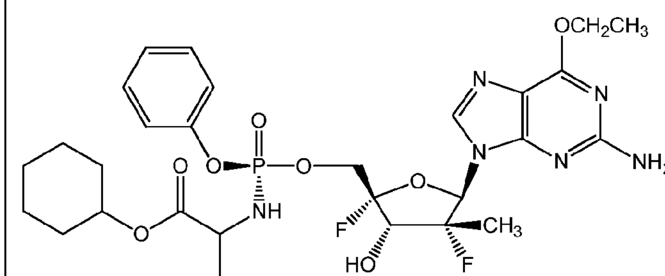 |

| # | Structure |
|---|---|
| 9025 | 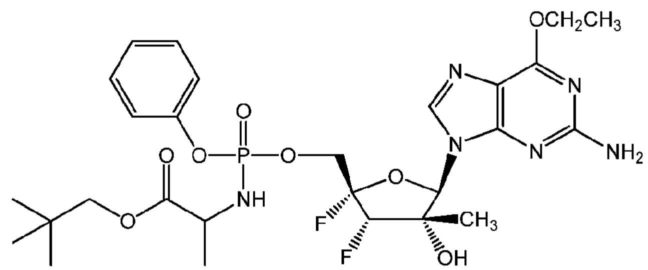 |
| 9026 | 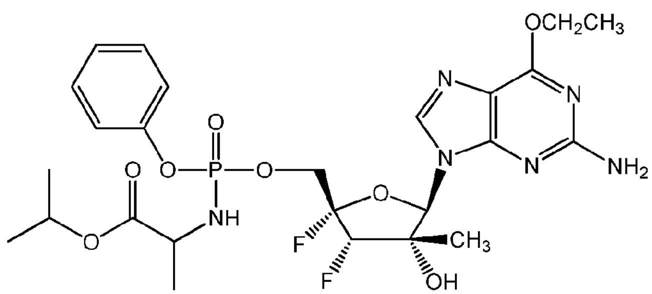 |
| 9027 | 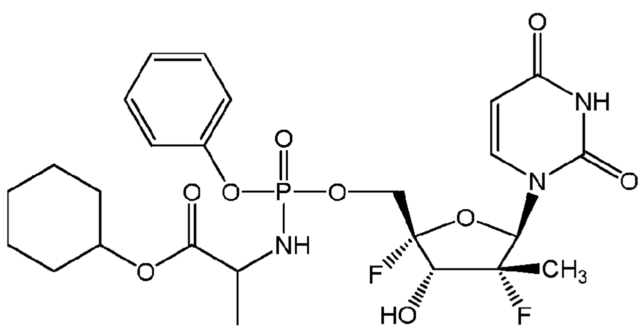 |

Figure 9 (cont.): Compounds of Formula (I)

| # | Structure |
|---|---|
| 9034 | 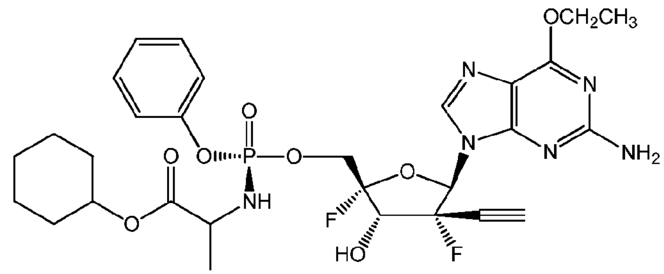 |
| 9035 | 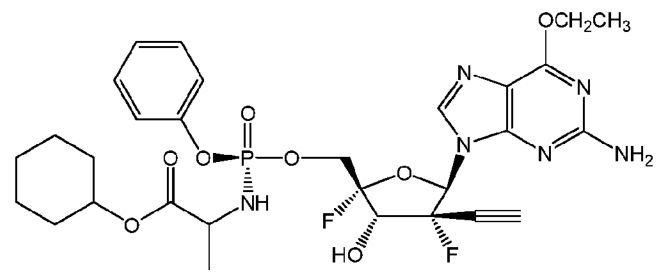 |
| 9036 | 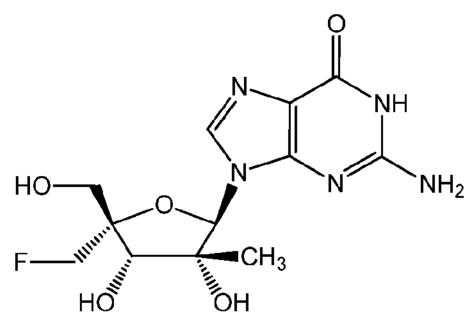 |

| # | Structure |
|---|---|
| 9031 | 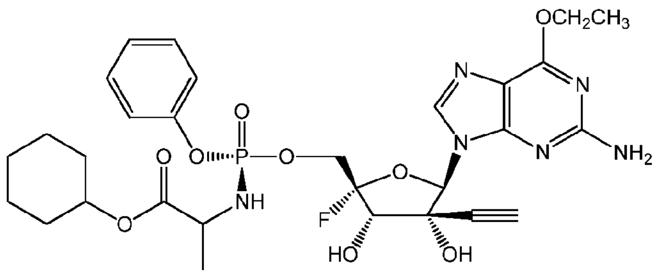 |
| 9032 | 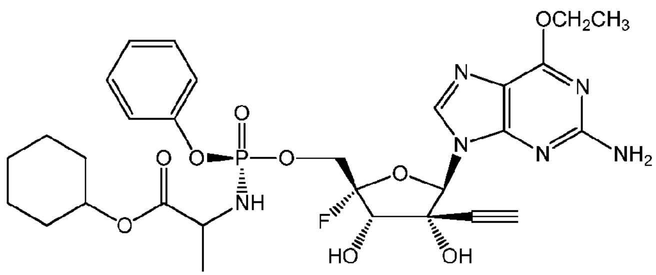 |
| 9033 | 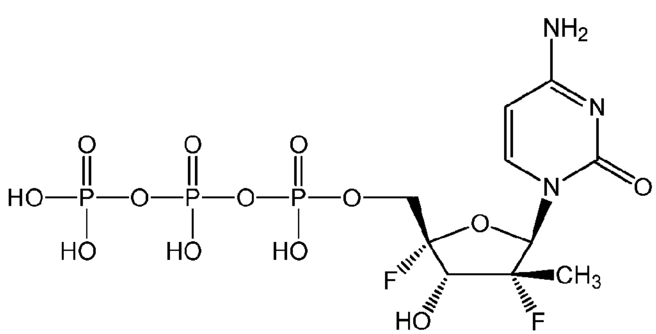 |

Figure 9 (cont.): Compounds of Formula (I)

| # | Structure |
|---|---|
| 9040 | (structure) |
| 9041 | (structure) |
| 9042 | (structure) |

| # | Structure |
|---|---|
| 9037 | (structure) |
| 9038 | (structure) |
| 9039 | (structure) |

Figure 9 (cont.): Compounds of Formula (I)

| # | Structure |
|---|---|
| 9043 | (cytosine N-glycoside with 2'-CH₃, 2'-OH, 3'-OH, 4'-CH₂Cl, 5'-CH₂OH ribose) |
| 9044 | (cytosine N-glycoside with 2'-CH₃, 2'-OH, 3'-OH, 4'-CH₂F, 5'-CH₂OH ribose) |
| 9045 | (cytosine N-glycoside with 2'-CH₃, 2'-OH, 3'-OH, 3'-CH₃, 5'-CH₂OH ribose) |
| 9046 | (cytosine N-glycoside with 2'-CH₃, 2'-OH, 3'-F, 3'-OH, 5'-CH₂OH ribose) |

Figure 9 (cont.): Compounds of Formula (I)
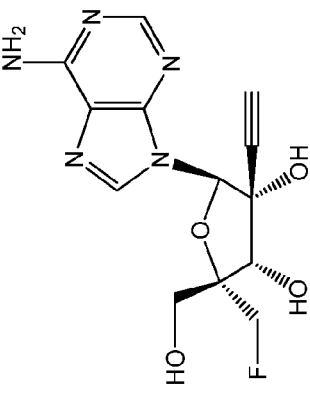
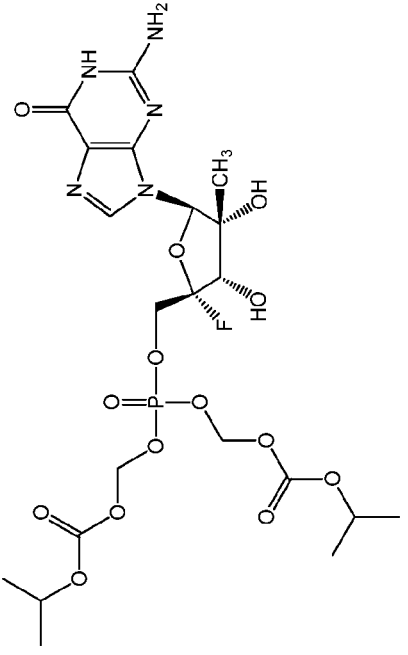
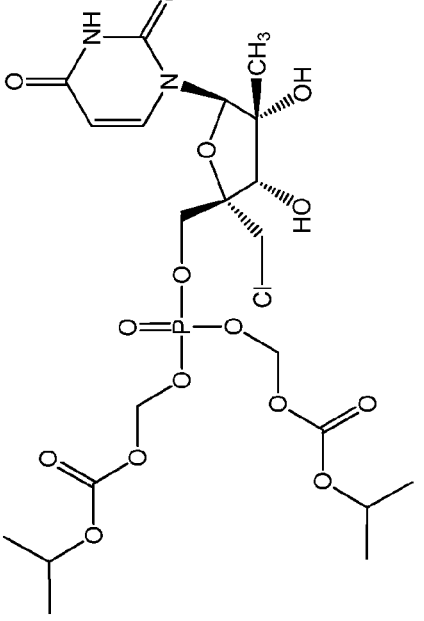
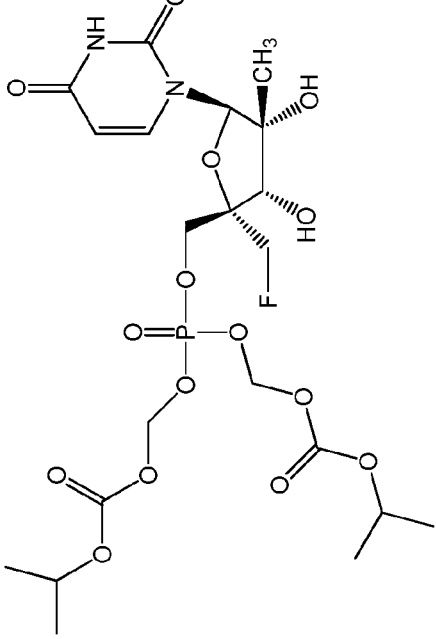

Figure 9 (cont.): Compounds of Formula (I)

| # | Structure |
|---|---|
| 9051 | (structure of nucleoside analog with uracil base, 2'-methyl, 2'-OH, 4'-fluoromethyl ribose) |
| 9052 | (structure of nucleoside analog with cytosine base, 2'-methyl, 2'-OH, 4'-fluoromethyl ribose) |
| 9053 | (structure of nucleoside analog with guanine base, 2'-fluoro, 3'-OH, 4'-chloromethyl ribose) |
| 9054 | (structure of nucleoside analog with adenine base, 2'-ethynyl, 2'-OH, 3'-OH, 4'-chloromethyl ribose) |

Figure 9 (cont.): Compounds of Formula (I)
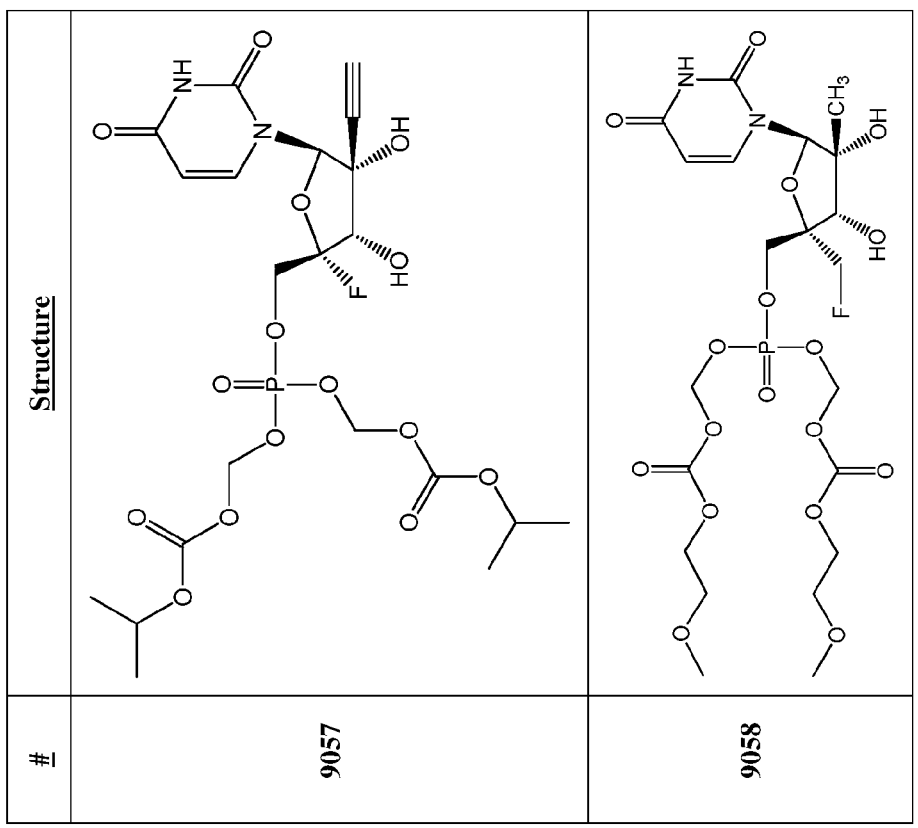
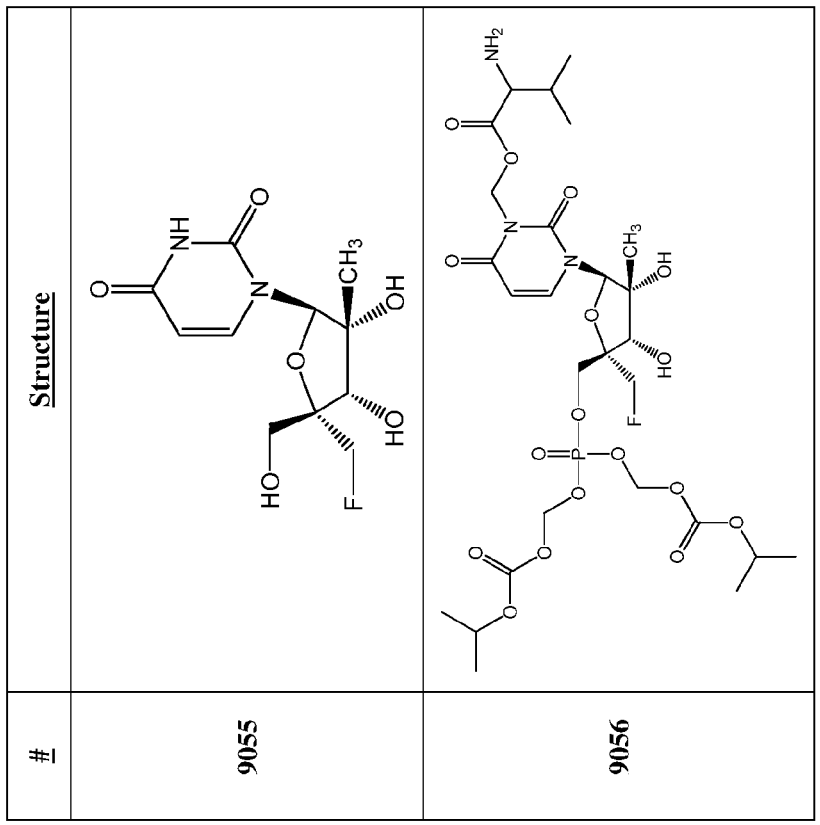

Figure 9 (cont.): Compounds of Formula (I)
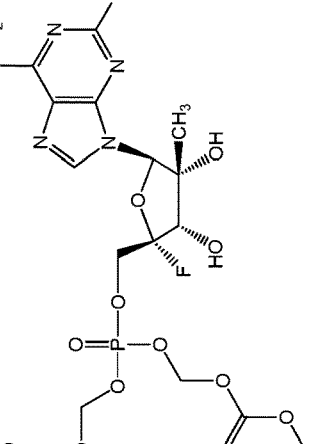
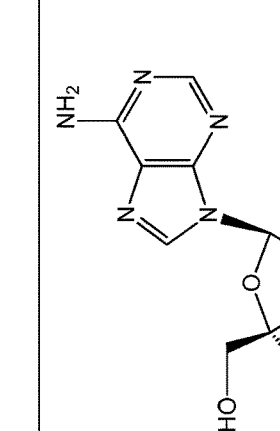

Figure 9 (cont.): Compounds of Formula (I)

| # | Structure |
|---|---|
| 9063 | (adenine nucleoside triphosphate with 2'-methyl, 2'-OH, and 1'-ethynyl substituents) |
| 9064 | (uridine nucleoside with 1'-ethynyl, 2'-OH, 3'-OH, 4'-fluoromethyl, and 5'-hydroxymethyl substituents) |
| 9065 | (uridine nucleoside triphosphate with 1'-ethynyl, 2'-OH, and 4'-fluoromethyl substituents) |
| 9066 | (uridine nucleoside triphosphate with 1'-ethynyl, 2'-OH, and 4'-chloromethyl substituents) |

Figure 9 (cont.): Compounds of Formula (I)
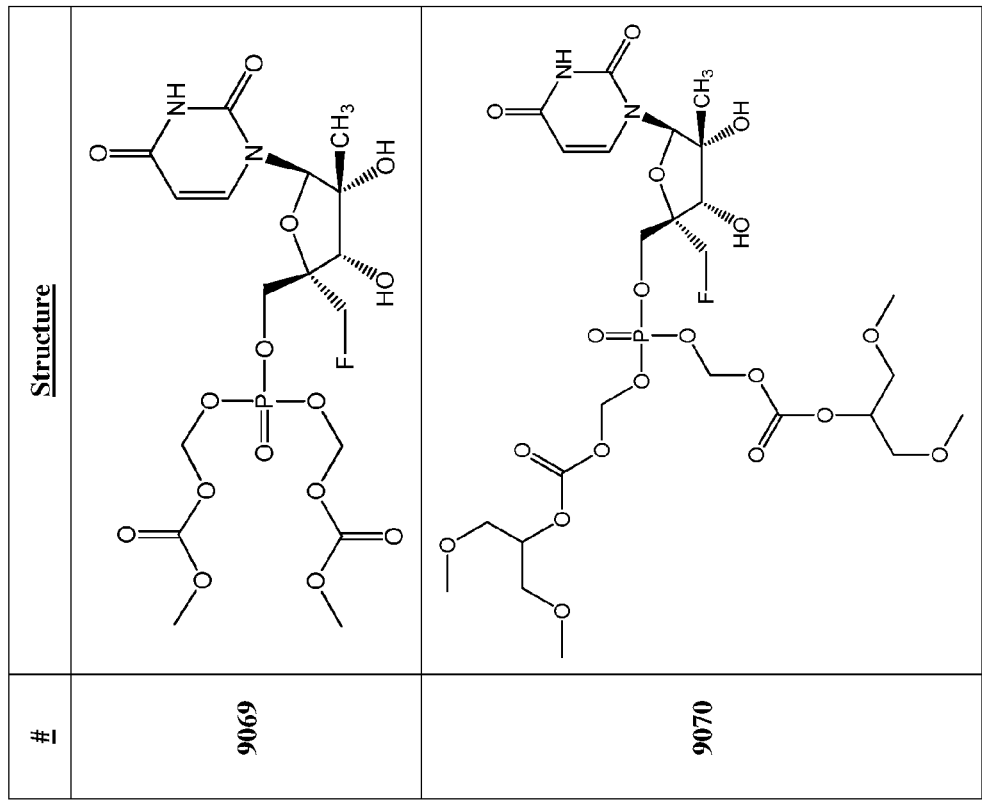
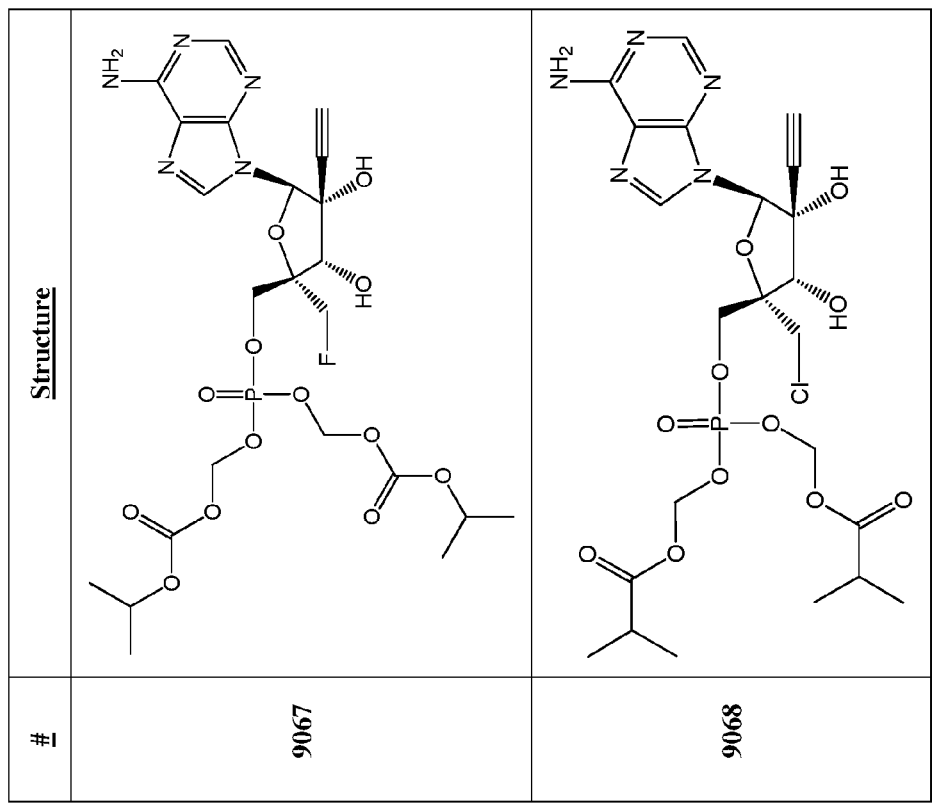

Figure 9 (cont.): Compounds of Formula (I)

| # | Structure |
|---|---|
| 9071 | 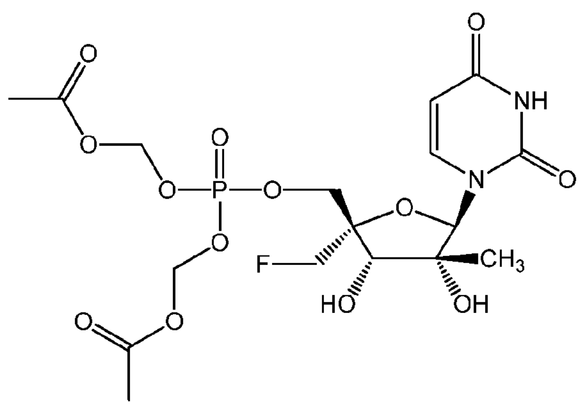 |
| 9072 | 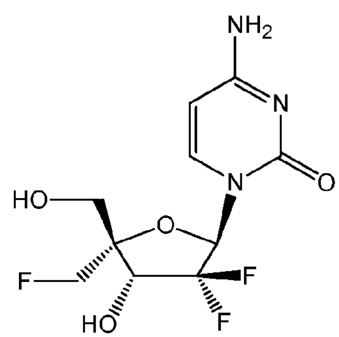 |
| 9073 | 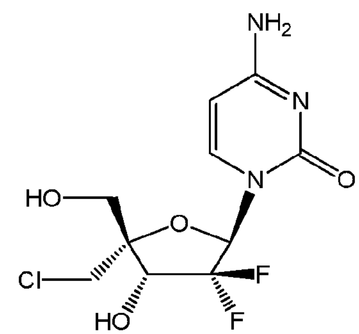 |
| 9074 | 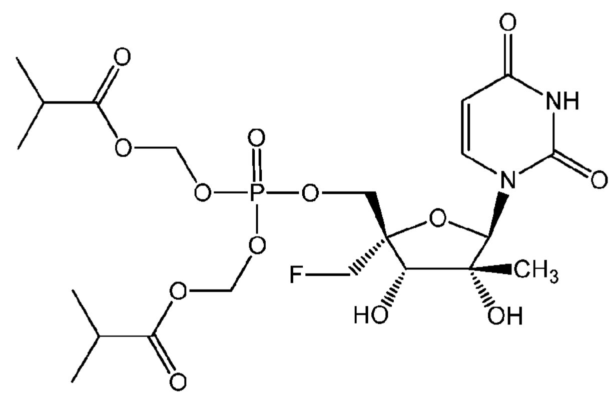 |

Figure 9 (cont.): Compounds of Formula (I)

| # | Structure |
|---|---|
| 9075 | (structure) |
| 9076 | (structure) |
| 9077 | (structure) |
| 9078 | (structure) |

Figure 9 (cont.): Compounds of Formula (I)
| # | Structure |
|---|---|
| 9081 | 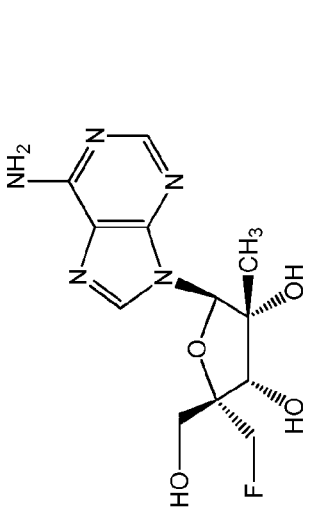 |
| 9082 | 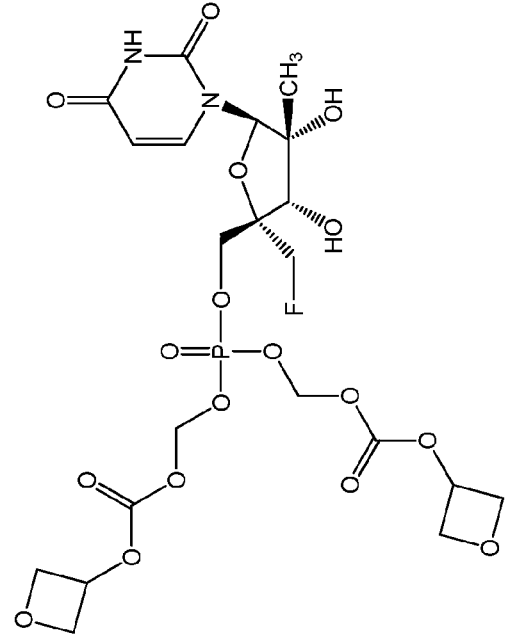 |
| # | Structure |
|---|---|
| 9079 | 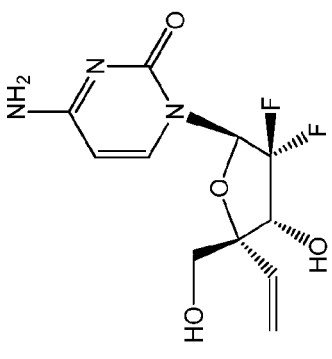 |
| 9080 | 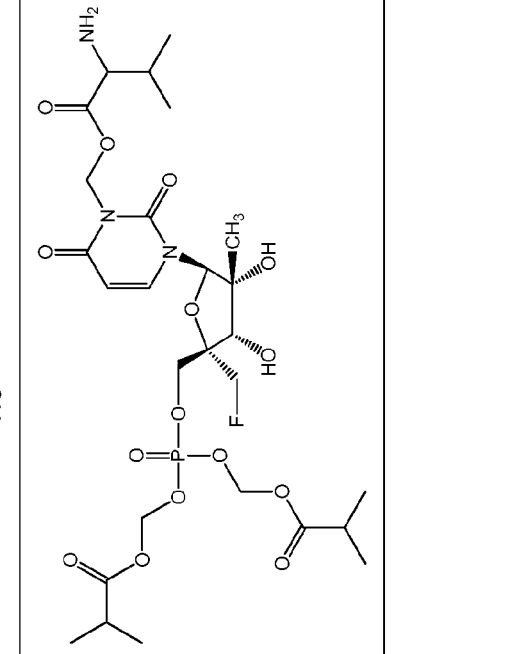 |

Figure 9 (cont.): Compounds of Formula (I)

| # | Structure |
|---|---|
| 9085 | (adenine nucleotide triphosphate with 2'-CH₃, 2'-OH, 3'-OH, 4'-CH₂F) |
| 9086 | (cytidine nucleotide triphosphate with 2',2'-diF, 3'-OH, 4'-CH₂F) |

| # | Structure |
|---|---|
| 9083 | (cytidine nucleotide triphosphate with 2',2'-diF, 3'-OH, 4'-vinyl) |
| 9084 | (cytidine nucleotide triphosphate with 2',2'-diF, 3'-OH, 4'-CH₂Cl) |

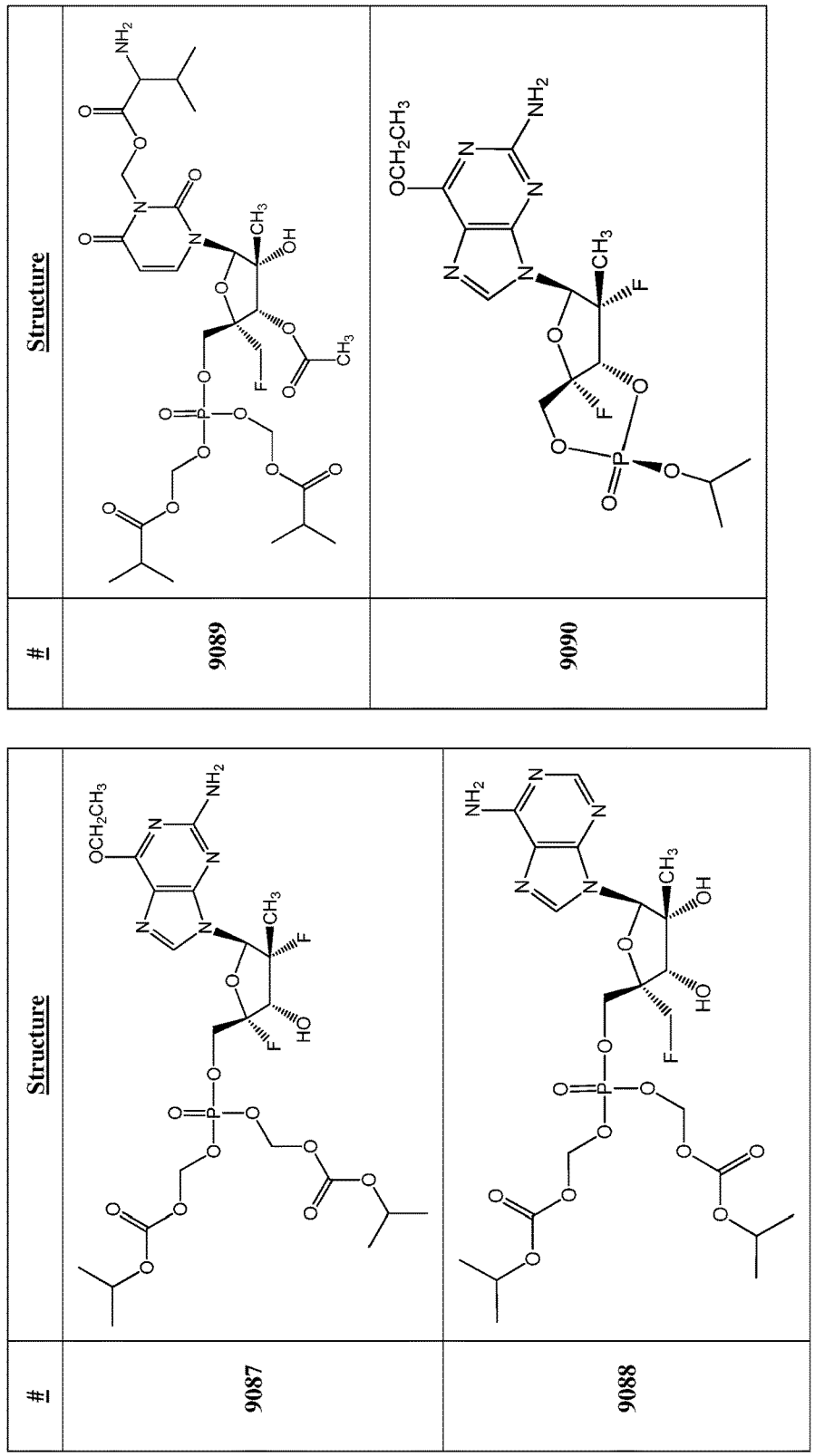
Figure 9 (cont.): Compounds of Formula (I)

Figure 9 (cont.): Compounds of Formula (I)
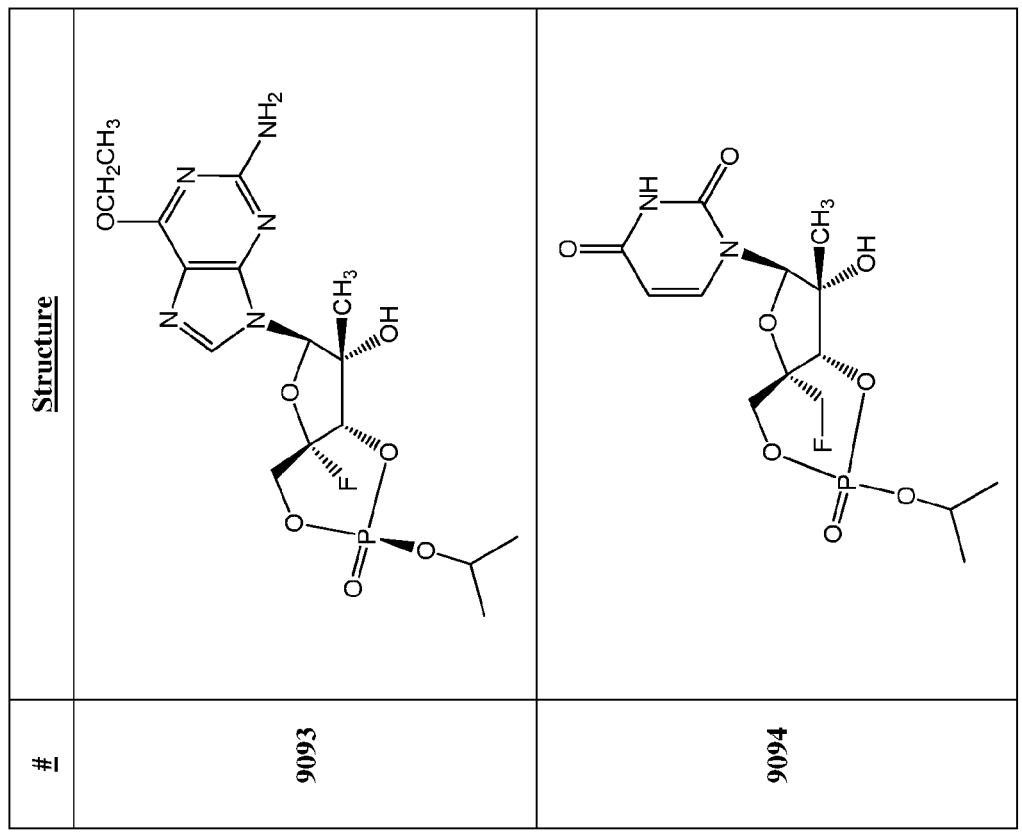
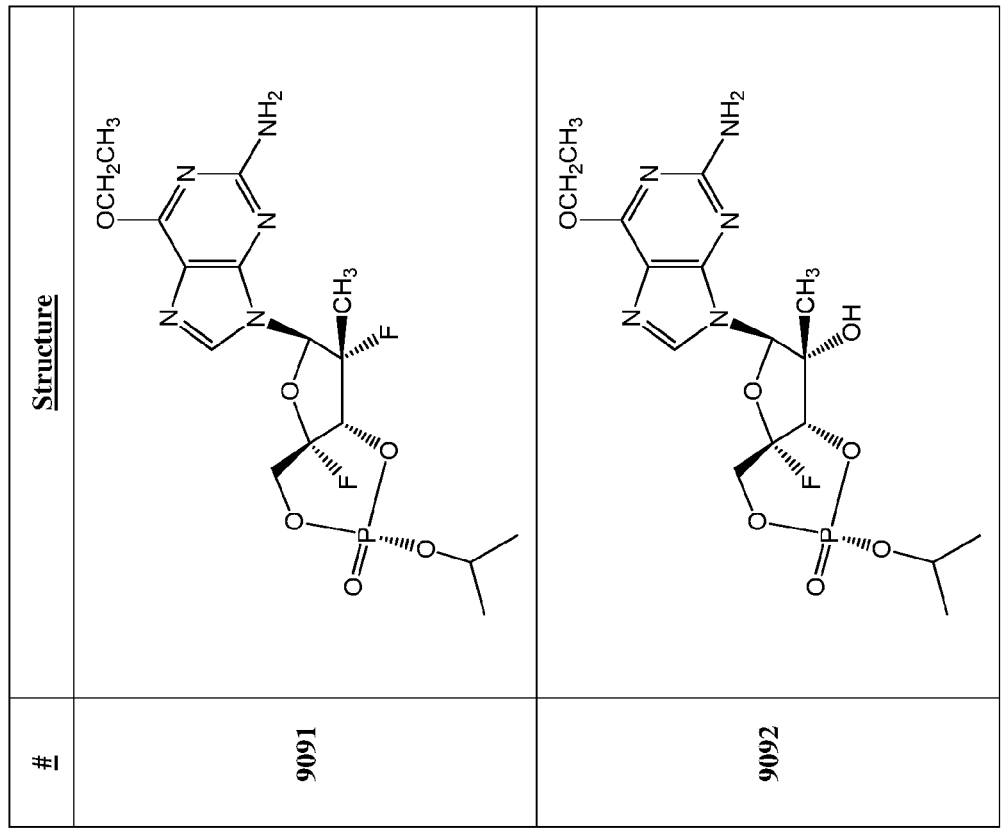

Figure 9 (cont.): Compounds of Formula (I)

| # | Structure |
|---|---|
| 9095 | (cytosine base, ribose with CH₃ and OH at 2'-position, 3'-OH, CH₂F at 4', triphosphate) |
| 9096 | (uracil base, ribose with CH₃ and OH at 2'-position, 3'-OH, CH₂F at 4', triphosphate) |
| 9097 | (7-deaza-7-ethynyl adenine base, ribose with OH at 2'-position, 3'-OH, CH₂F at 4', triphosphate) |
| 9098 | (cytosine base, ribose with CH₃ and OH at 2'-position, 3'-OH, CH₂F at 4', triphosphate) |

Figure 9 (cont.): Compounds of Formula (I)

| # | Structure |
|---|---|
| 9099 | 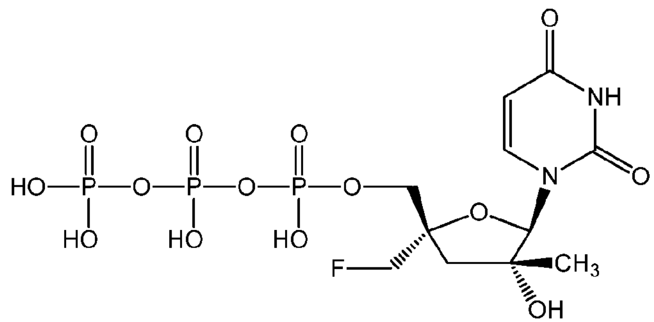 |
| 9100 | 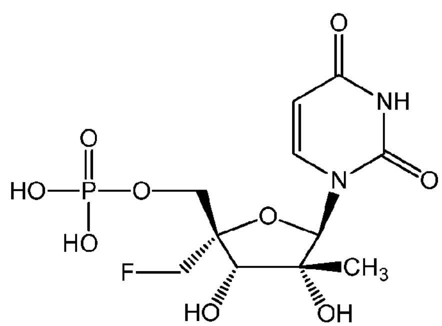 |
| 9101 | |
| 9102 | |

Figure 9 (cont.): Compounds of Formula (I)

| # | Structure |
|---|---|
| 9105 | (structure of guanine nucleoside triphosphate with 2'-CH₃, 2'-F, 3'-F, 3'-OH modifications) |
| 9106 | (structure of guanine nucleoside with 2'-ethynyl, 2'-OH, 3'-F, 4'-F modifications) |
| 9107 | (structure of guanine nucleoside triphosphate with 2'-ethynyl, 2'-OH, 3'-F, 3'-F modifications) |

| # | Structure |
|---|---|
| 9103 | (structure of uracil nucleoside with 2'-CH₃, 2'-OH, 3'-OH, 4'-CH₂F, and bis(ethoxycarbonyloxymethyl) phosphate prodrug) |
| 9104 | (structure of uracil nucleoside with 2'-CH₃, 2'-OH, 3'-OH, 4'-CH₂F, and bis(methoxy-PEG-carbonate) phosphate prodrug) |

Figure 9 (cont.): Compounds of Formula (I)

| # | Structure |
|---|---|
| 9108 | (structure) |
| 9109 | (structure) |
| 9110 | (structure) |
| 9111 | (structure) |
| 9112 | (structure) |

Figure 9 (cont.): Compounds of Formula (I)

| # | Structure |
|---|---|
| 9116 | (structure) |
| 9117 | (structure) |

| # | Structure |
|---|---|
| 9113 | (structure) |
| 9114 | (structure) |
| 9115 | (structure) |

Figure 9 (cont.): Compounds of Formula (I)

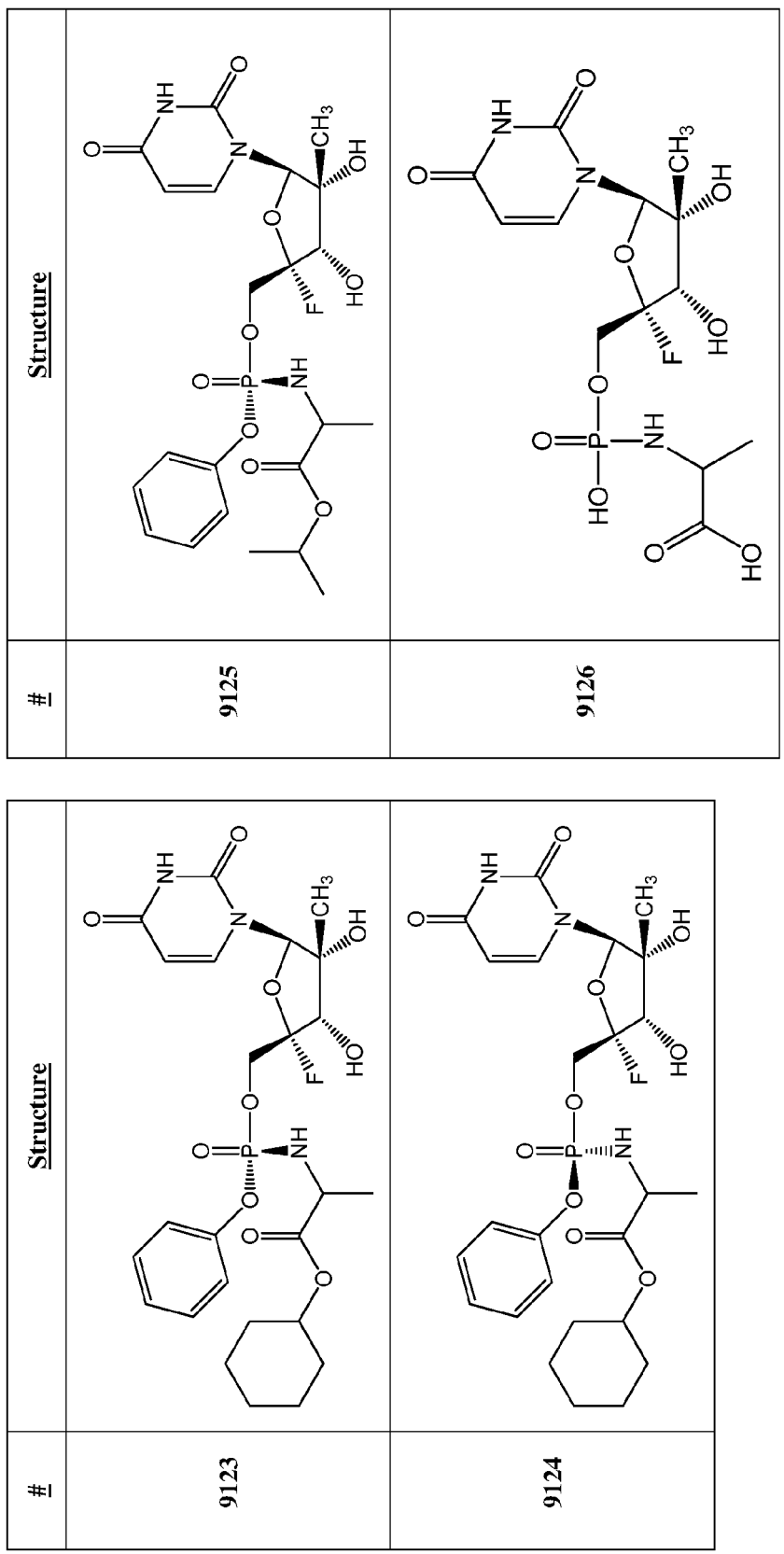
Figure 9 (cont.): Compounds of Formula (I)

Figure 9 (cont.): Compounds of Formula (I)
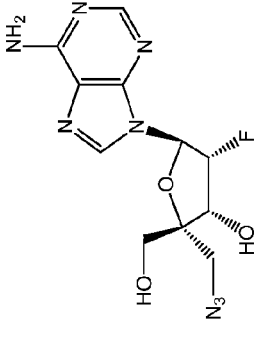

Figure 9 (cont.): Compounds of Formula (I)

| # | Structure |
|---|---|
| 9136 | 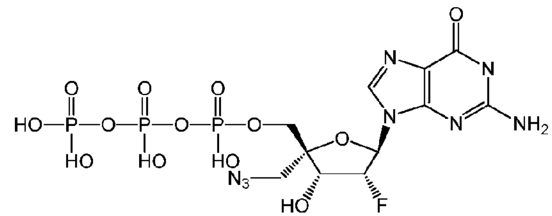 |
| 9137 | 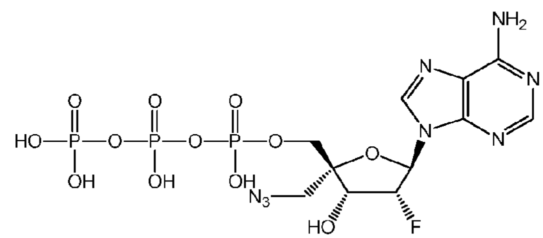 |
| 9138 | 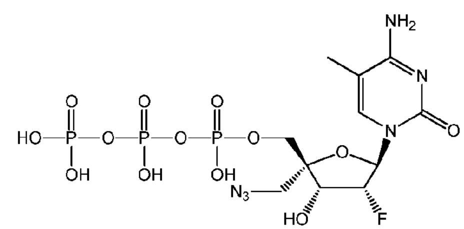 |

| # | Structure |
|---|---|
| 9133 | |
| 9134 | |
| 9135 | |

Figure 9 (cont.): Compounds of Formula (I)
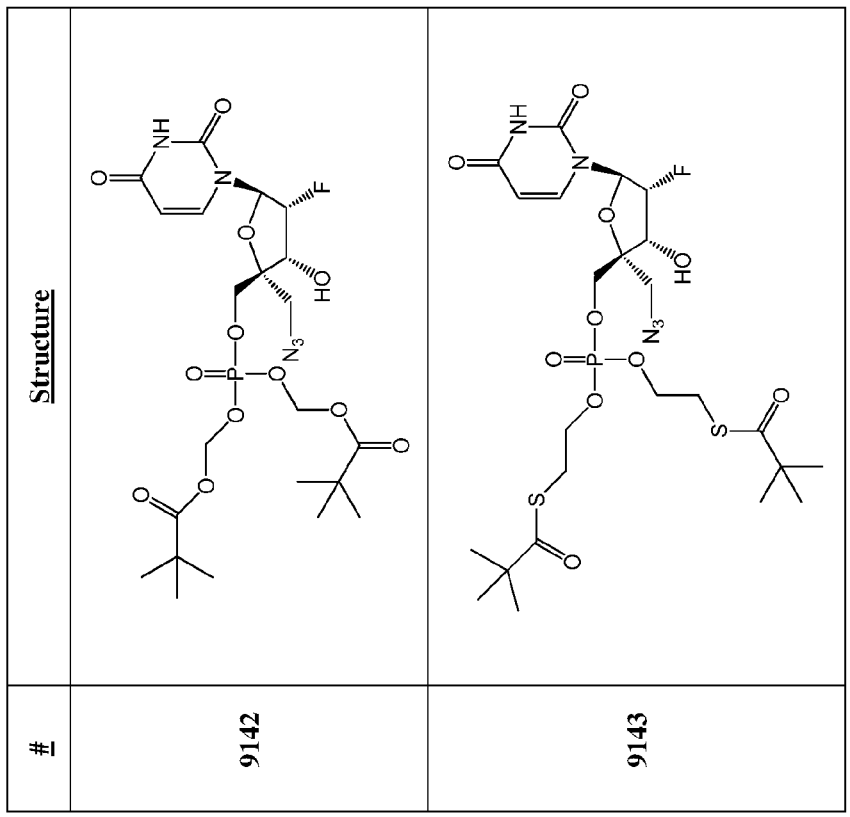
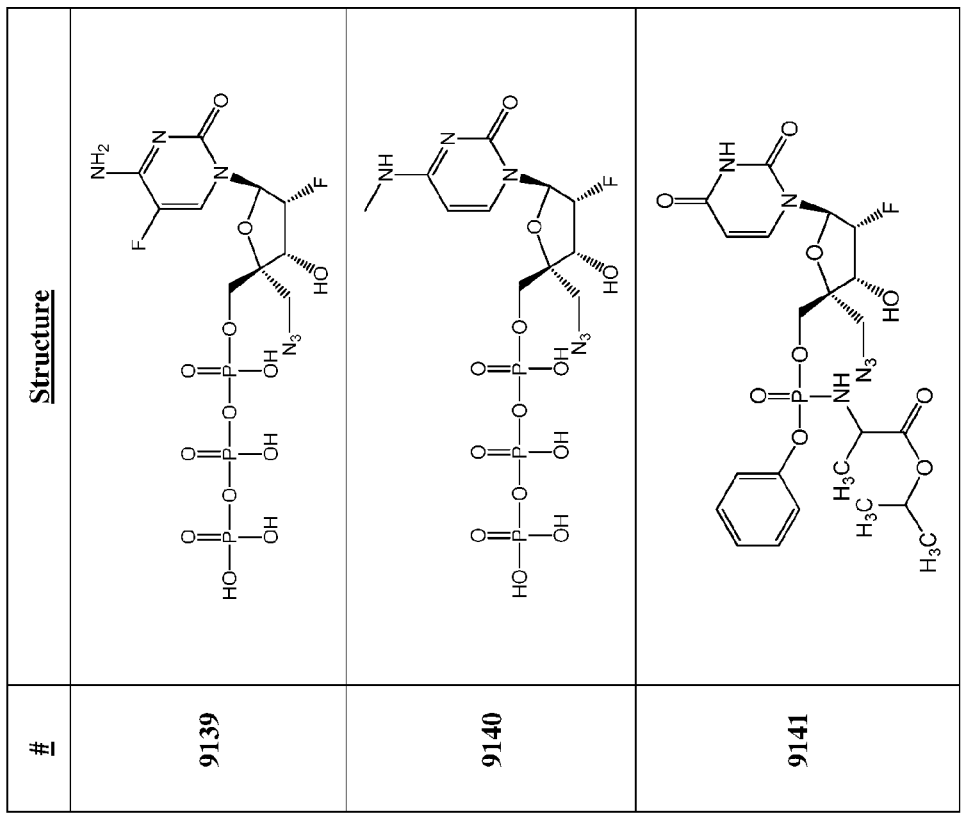

Figure 9 (cont.): Compounds of Formula (I)

| # | Structure |
|---|---|
| 9147 | 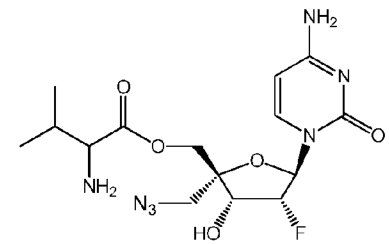 |
| 9148 | 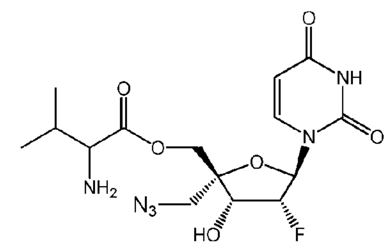 |
| 9149 | 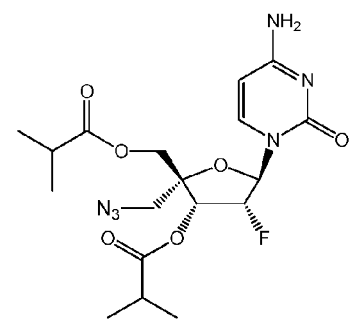 |

| # | Structure |
|---|---|
| 9144 | 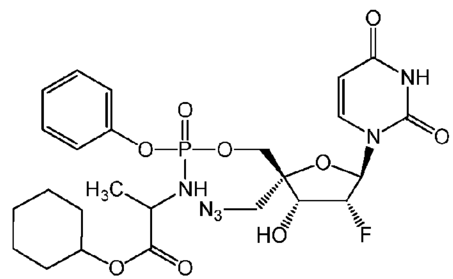 |
| 9145 | 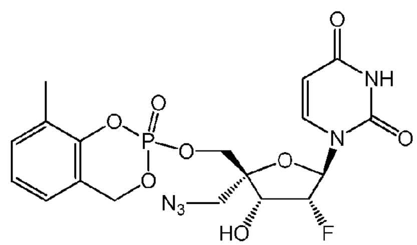 |
| 9146 | 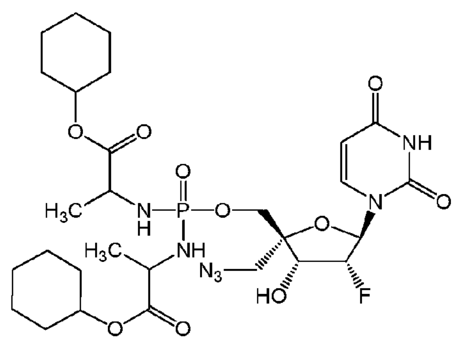 |

Figure 9 (cont.): Compounds of Formula (I)

| # | Structure |
|---|---|
| 9150 | (structure) |
| 9151 | (structure) |
| 9152 | (structure) |
| 9153 | (structure) |

Figure 9 (cont.): Compounds of Formula (I)

| # | Structure |
|---|---|
| 9154 | 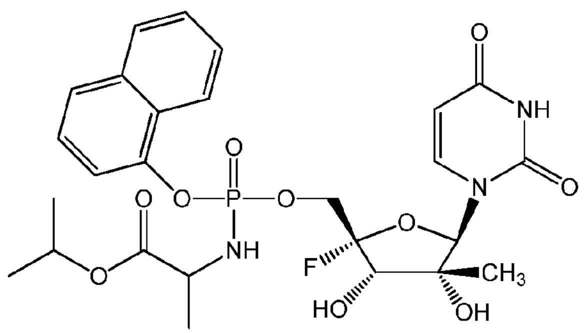 |
| 9155 | 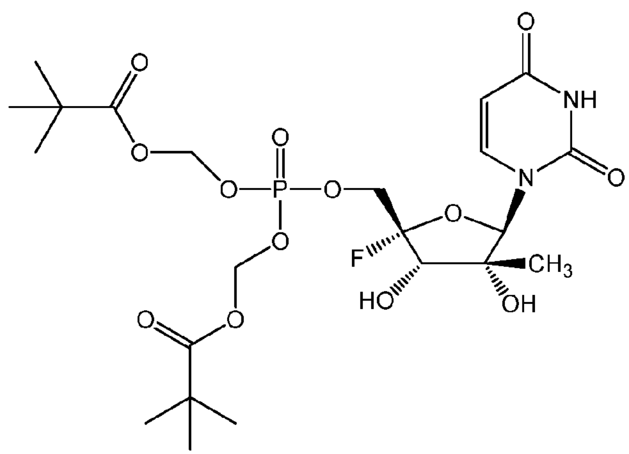 |
| 9156 | |
| 9157 | |

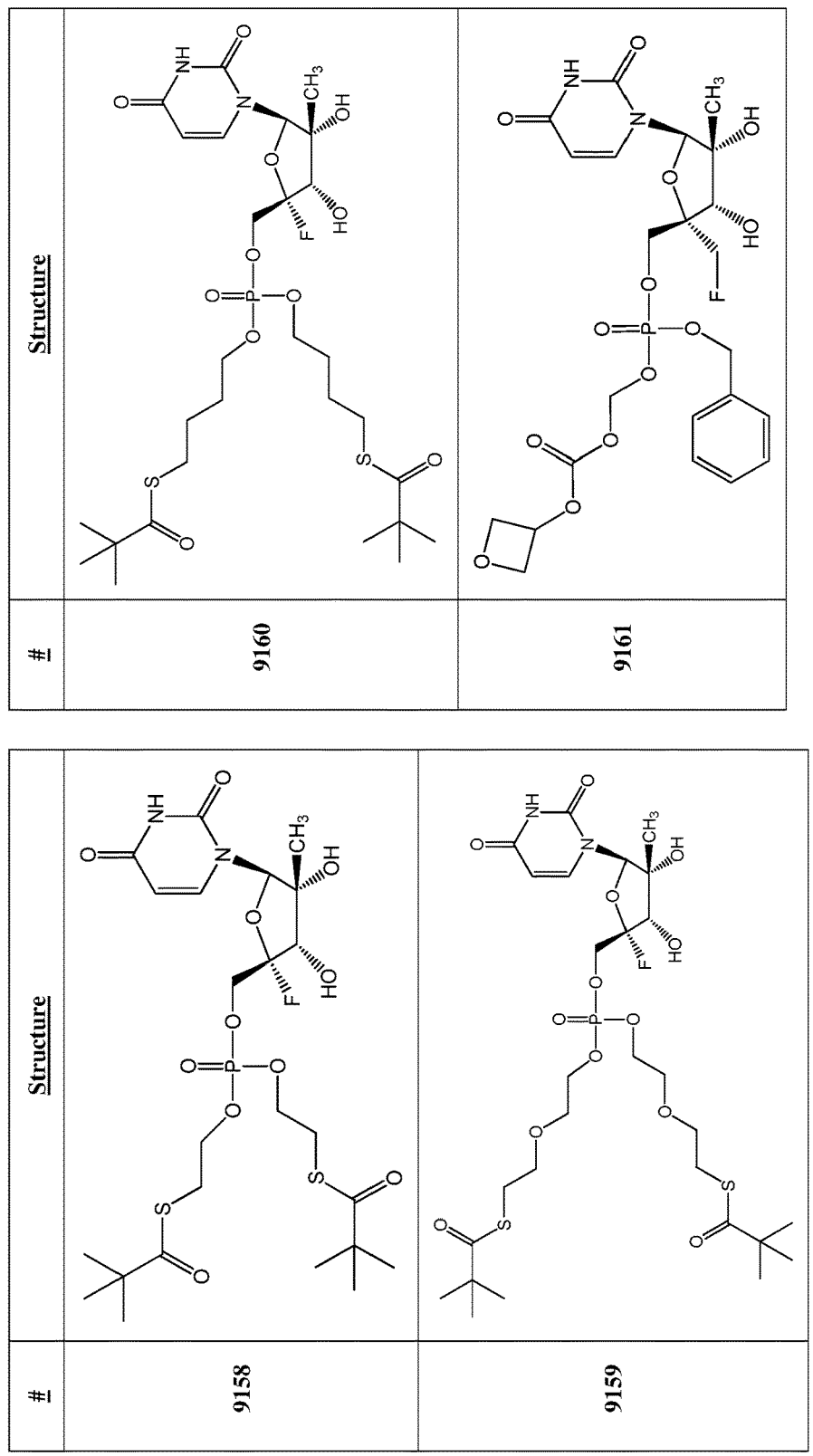
Figure 9 (cont.): Compounds of Formula (I)

Figure 9 (cont.): Compounds of Formula (I)
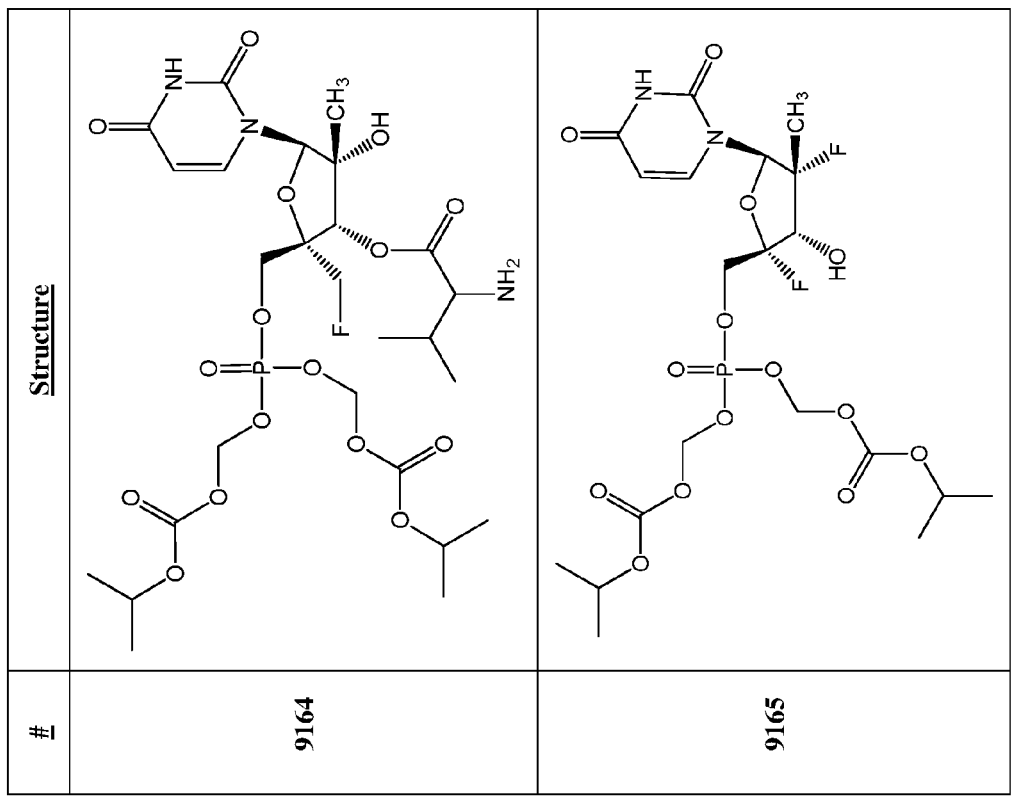
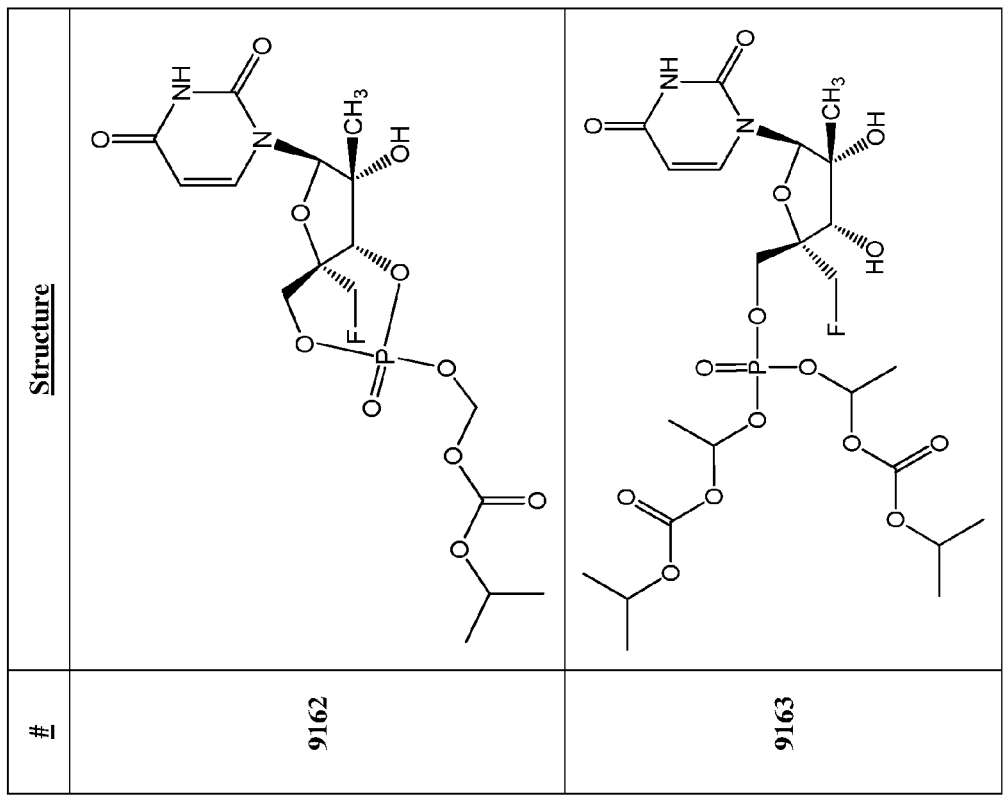

Figure 9 (cont.): Compounds of Formula (I)

| # | Structure |
|---|---|
| 9169 | 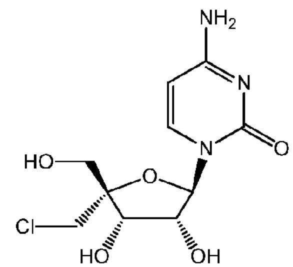 |
| 9170 | 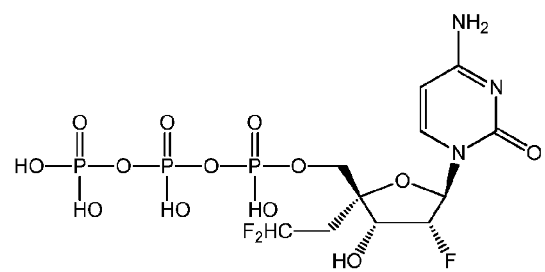 |
| 9171 | 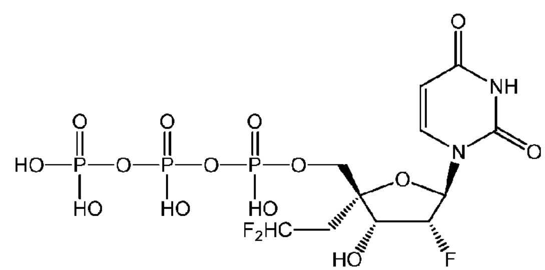 |

| # | Structure |
|---|---|
| 9166 | 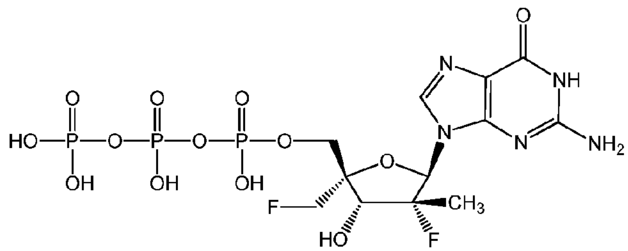 |
| 9167 | 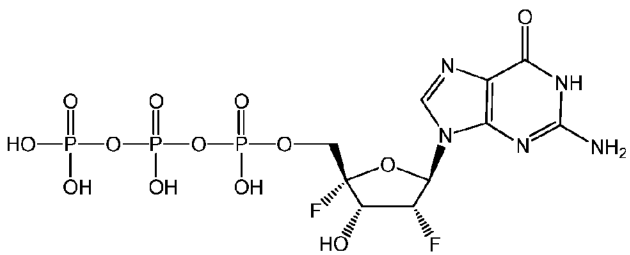 |
| 9168 | 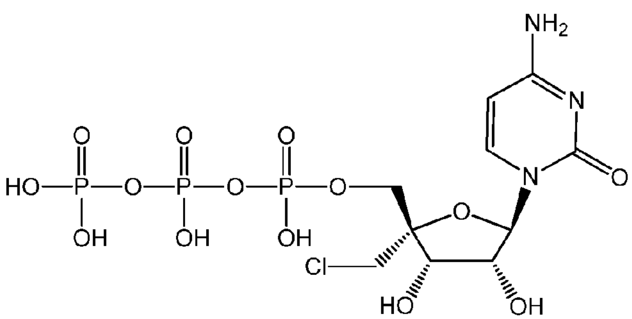 |

Figure 9 (cont.): Compounds of Formula (I)

| # | Structure |
|---|---|
| 9174 | |
| 9175 | |
| 9172 | 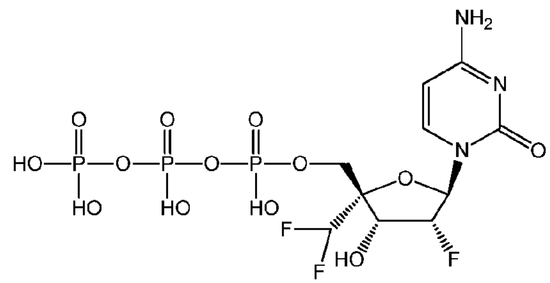 |
| 9173 | 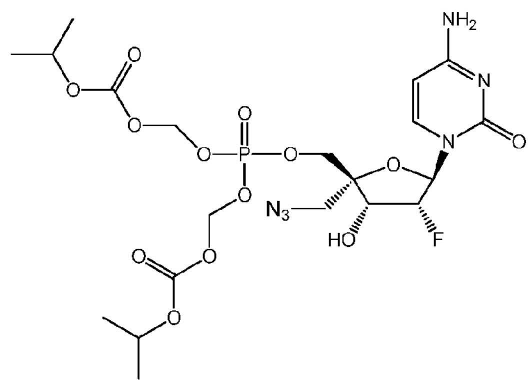 |

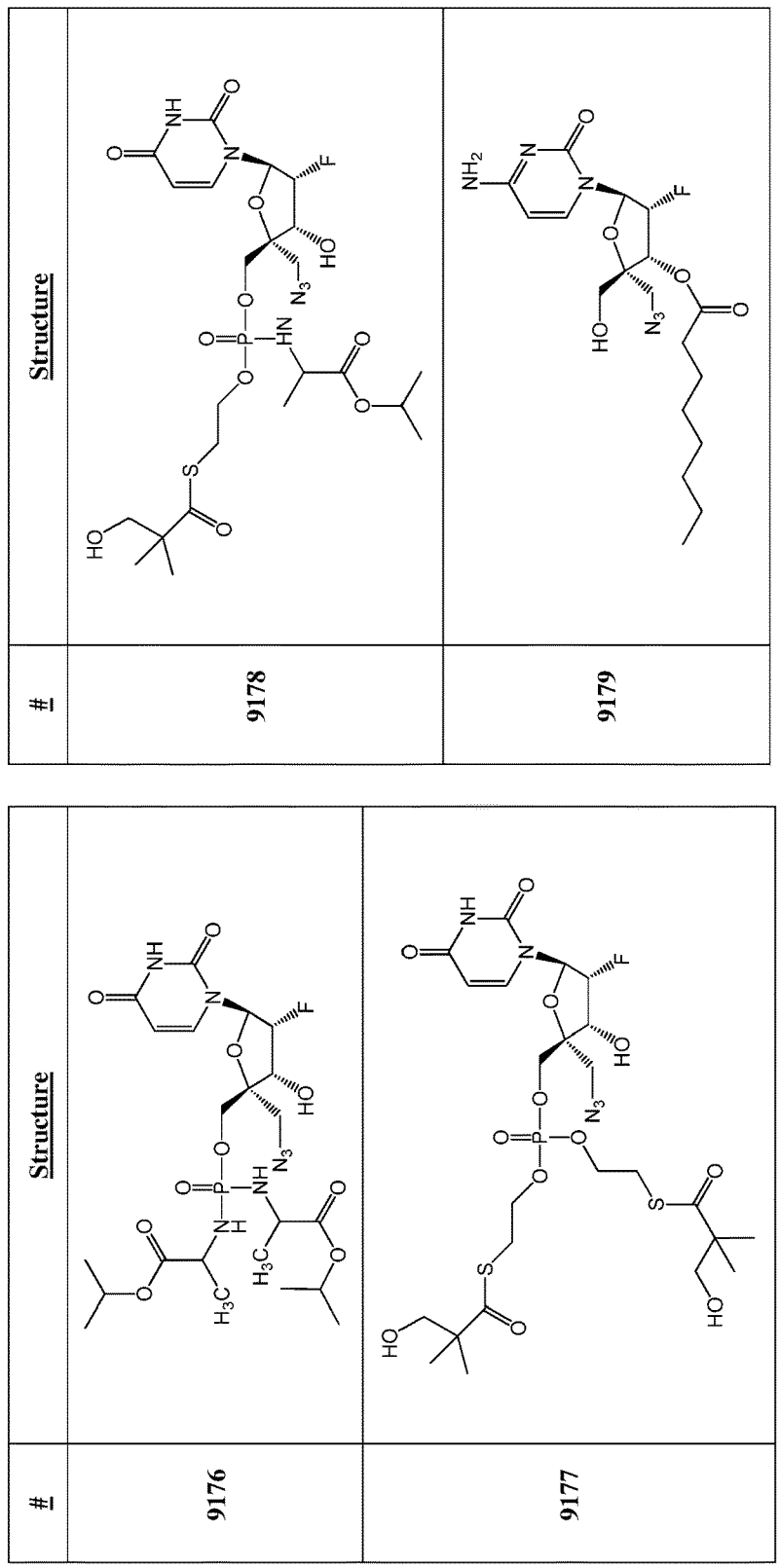
Figure 9 (cont.): Compounds of Formula (I)

Figure 9 (cont.): Compounds of Formula (I)
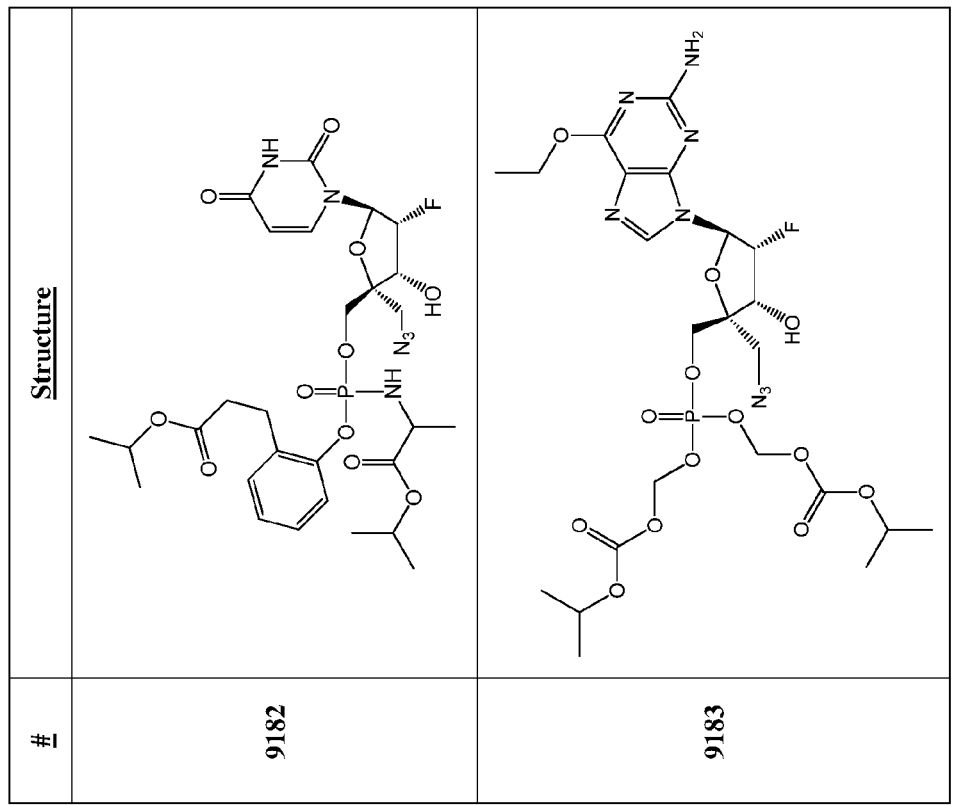
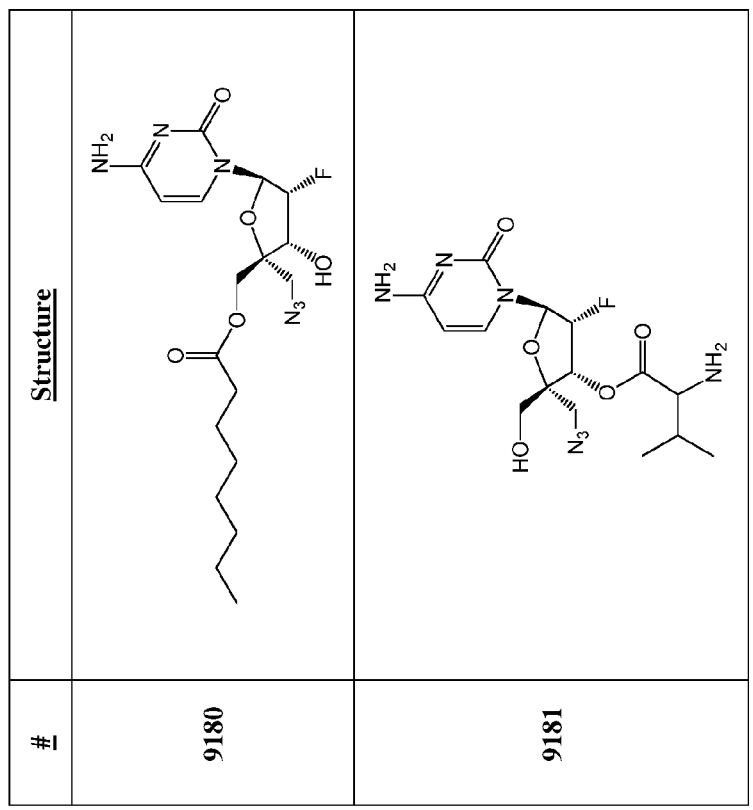

Figure 9 (cont.): Compounds of Formula (I)

| # | Structure |
|---|---|
| 9186 | (structure) |
| 9187 | (structure) |
| 9188 | (structure) |

| # | Structure |
|---|---|
| 9184 | (structure) |
| 9185 | (structure) |

Figure 9 (cont.): Compounds of Formula (I)

Figure 9 (cont.): Compounds of Formula (I)

| # | Structure |
|---|---|
| 9197 | 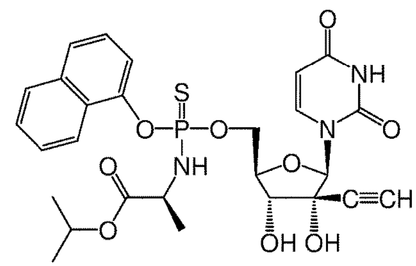 |
| 9198 | 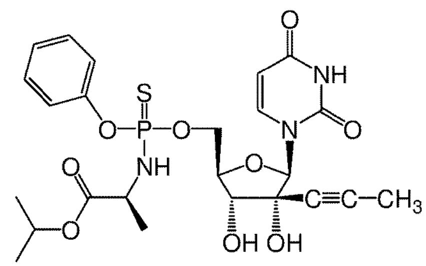 |
| 9199 | 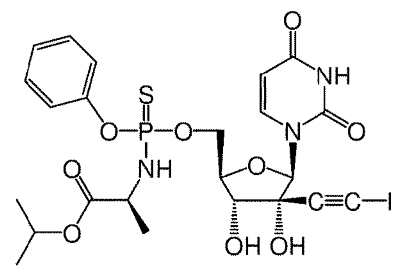 |

| # | Structure |
|---|---|
| 9194 | 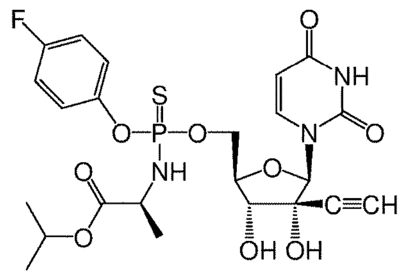 |
| 9195 | 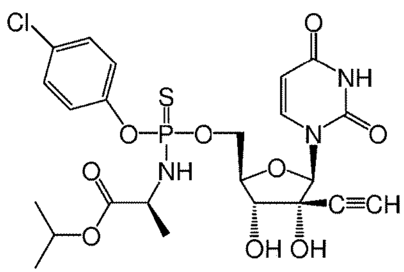 |
| 9196 | 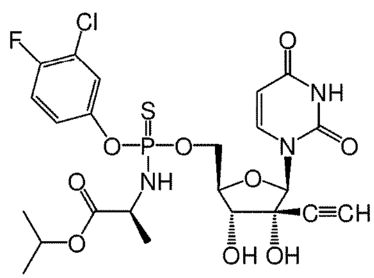 |

Figure 9 (cont.): Compounds of Formula (I)

| # | Structure |
|---|---|
| 9203 | 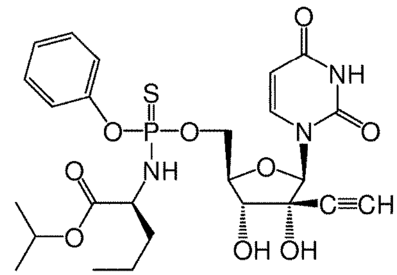 |
| 9204 | 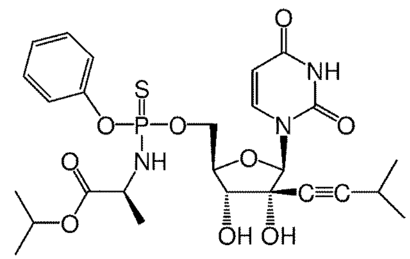 |
| 9205 | 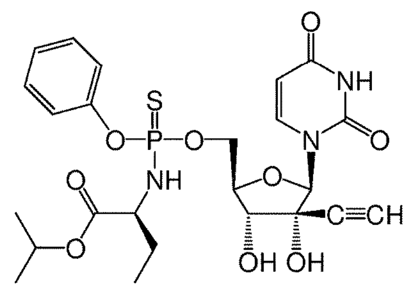 |

| # | Structure |
|---|---|
| 9200 | 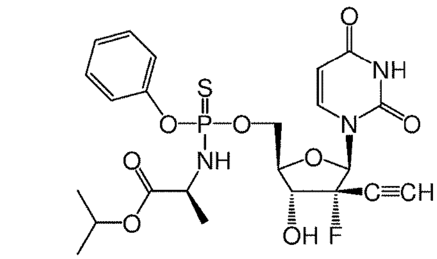 |
| 9201 | 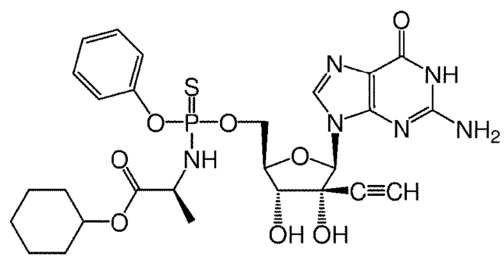 |
| 9202 | 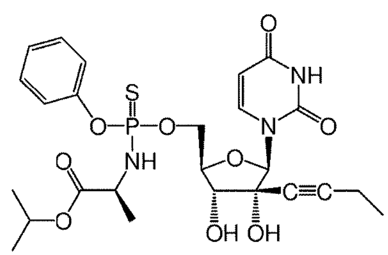 |

Figure 9 (cont.): Compounds of Formula (I)

| # | Structure |
|---|---|
| 9209 | (structure) |
| 9210 | (structure) |
| 9206 | (structure) |
| 9207 | (structure) |
| 9208 | (structure) |

Figure 9 (cont.): Compounds of Formula (I)

| # | Structure |
|---|---|
| 9214 | 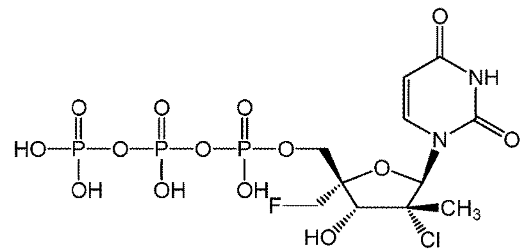 |
| 9215 | 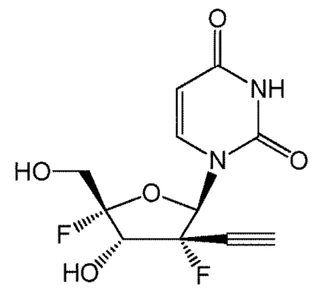 |
| 9216 | 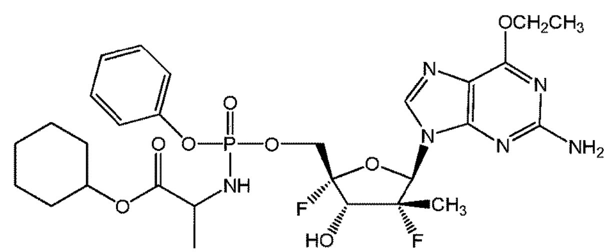 |

| # | Structure |
|---|---|
| 9211 | 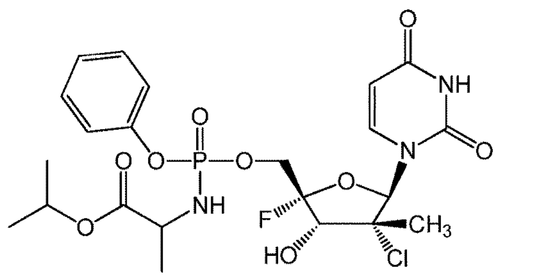 |
| 9212 | 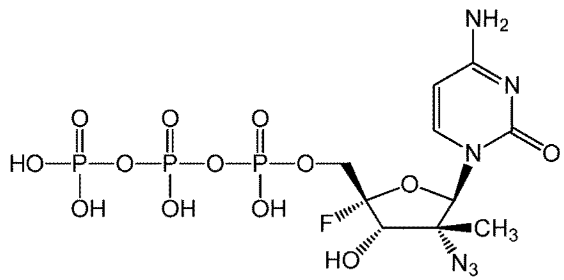 |
| 9213 | 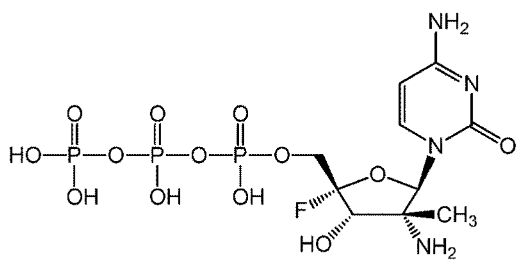 |

Figure 9 (cont.): Compounds of Formula (I)

| # | Structure |
|---|---|
| 9217 | 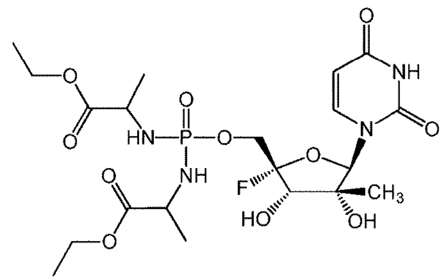 |
| 9218 | 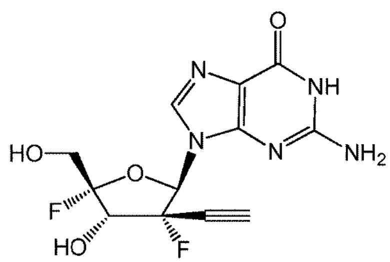 |
| 9219 | 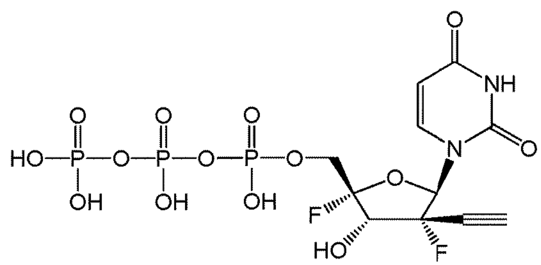 |

| # | Structure |
|---|---|
| 9220 | 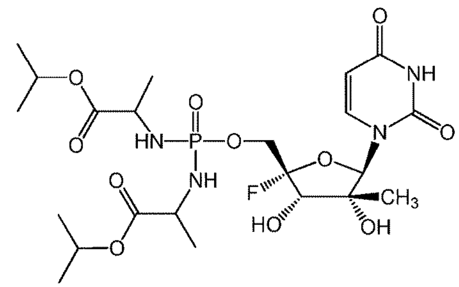 |
| 9221 | 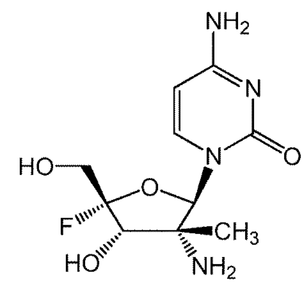 |
| 9222 | 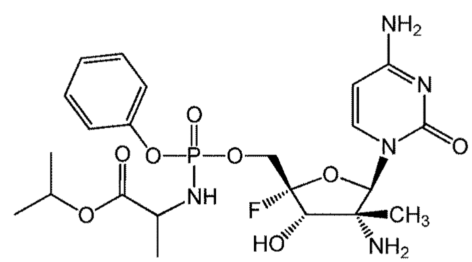 |

Figure 9 (cont.): Compounds of Formula (I)

| # | Structure |
|---|---|
| 9226 | (structure) |
| 9227 | (structure) |

| # | Structure |
|---|---|
| 9223 | (structure) |
| 9224 | (structure) |
| 9225 | (structure) |

Figure 9 (cont.): Compounds of Formula (I)

| # | Structure |
|---|---|
| 9230 | 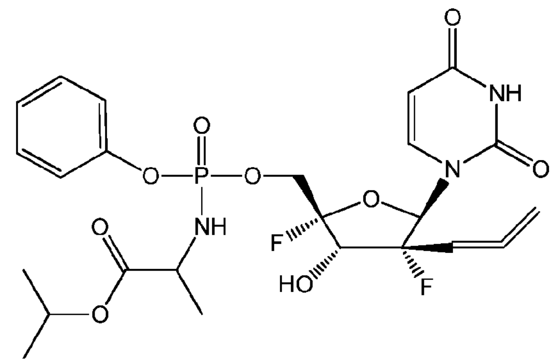 |
| 9231 | 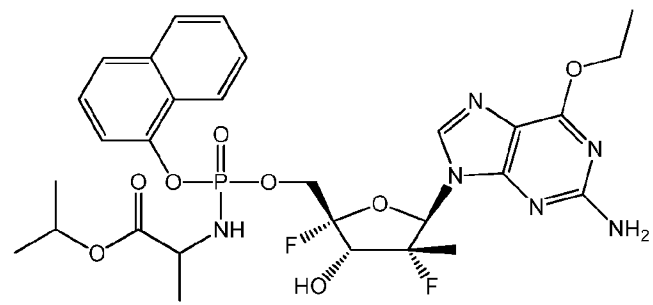 |

| # | Structure |
|---|---|
| 9228 | 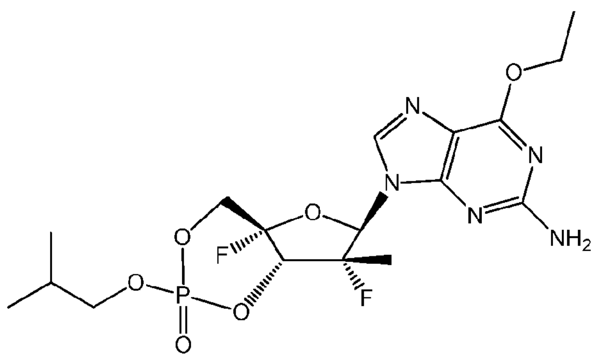 |
| 9229 | 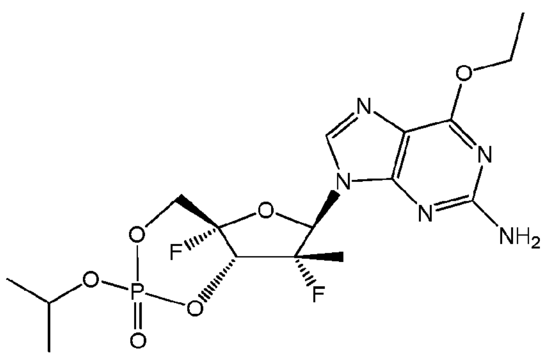 |

Figure 9 (cont.): Compounds of Formula (I)
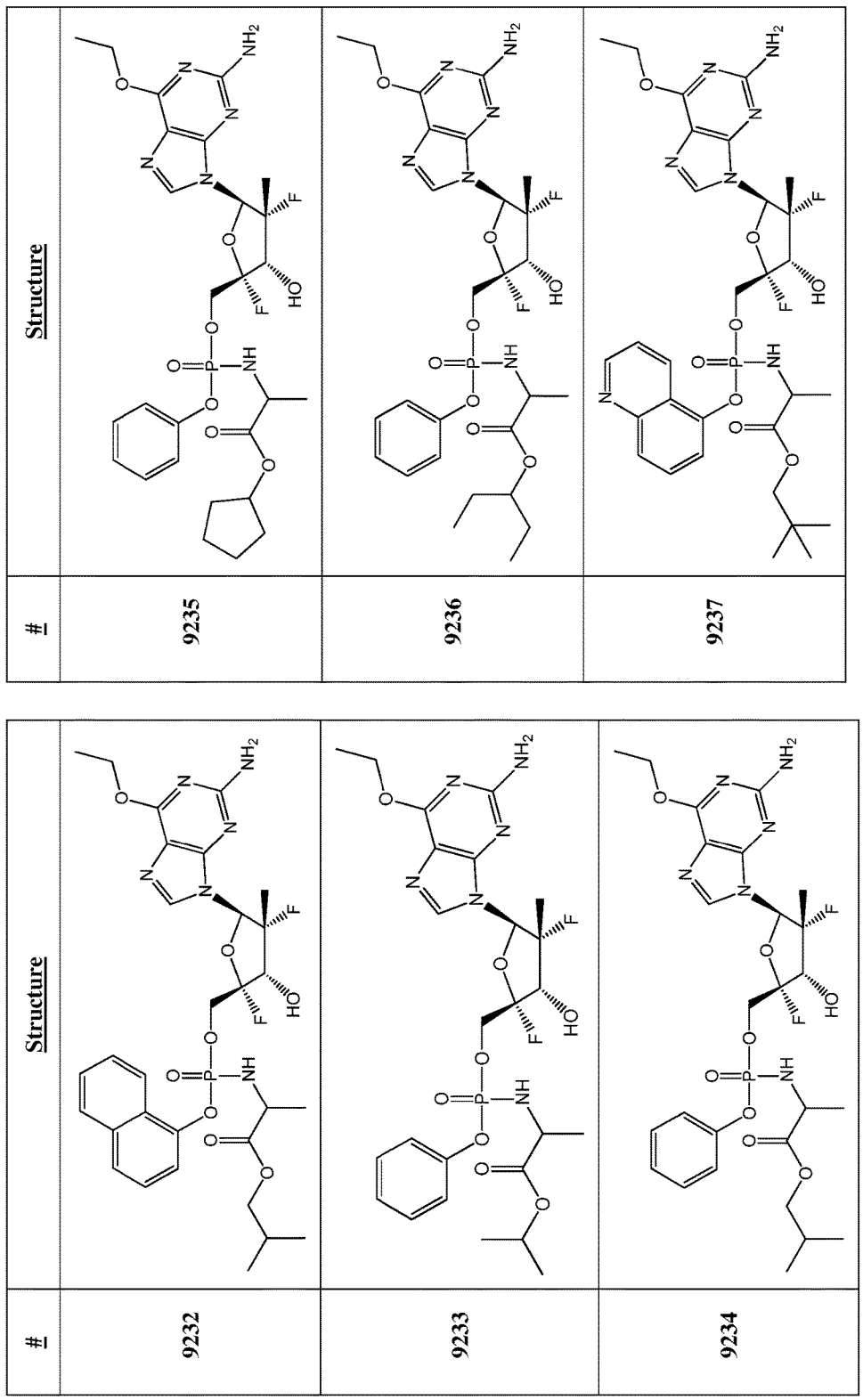

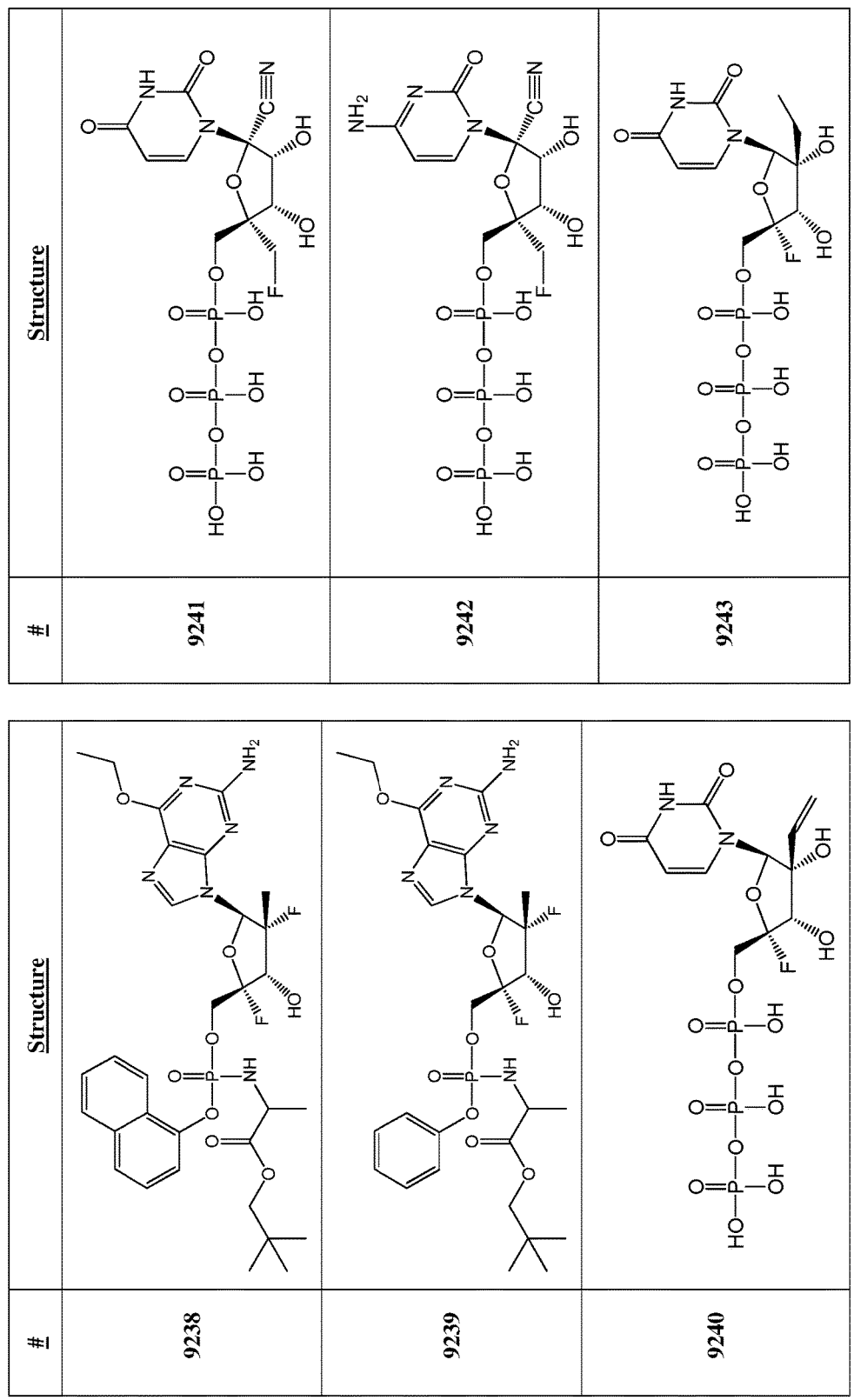
Figure 9 (cont.): Compounds of Formula (I)

Figure 9 (cont.): Compounds of Formula (I)

Figure 9 (cont.): Compounds of Formula (I)

| # | Structure |
|---|---|
| 9252 | (uracil nucleoside with 2',2'-difluoro and 4'-fluoromethyl substituents) |
| 9253 | (uracil nucleoside with 2'-methyl, 2'-OH, and 5'-azidomethyl triphosphate) |

| # | Structure |
|---|---|
| 9249 | (adenosine with 2'-ethynyl, 2'-OH, and 5'-chloromethyl triphosphate) |
| 9250 | (guanosine with 2'-methyl, 2'-chloro triphosphate) |
| 9251 | (uracil nucleoside with 2'-ethynyl, 2'-OH, and 4'-chloromethyl) |

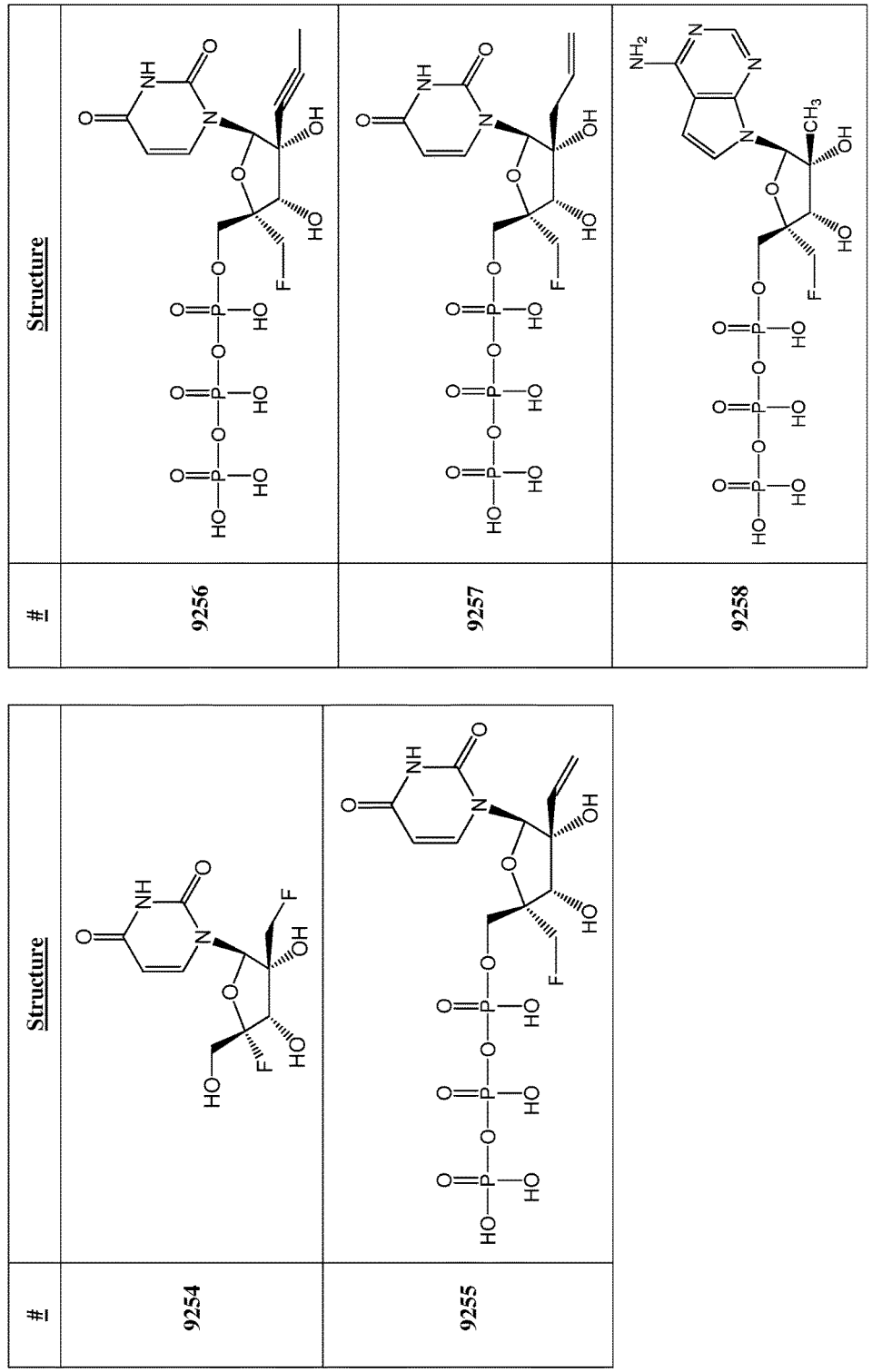
Figure 9 (cont.): Compounds of Formula (I)

Figure 9 (cont.): Compounds of Formula (I)

| # | Structure |
|---|---|
| 9261 | (structure) |
| 9262 | (structure) |
| 9263 | (structure) |

| # | Structure |
|---|---|
| 9259 | (structure) |
| 9260 | (structure) |

Figure 9 (cont.): Compounds of Formula (I)

Figure 9 (cont.): Compounds of Formula (I)

Figure 9 (cont.): Compounds of Formula (I)

| # | Structure |
|---|---|
| 9277 | 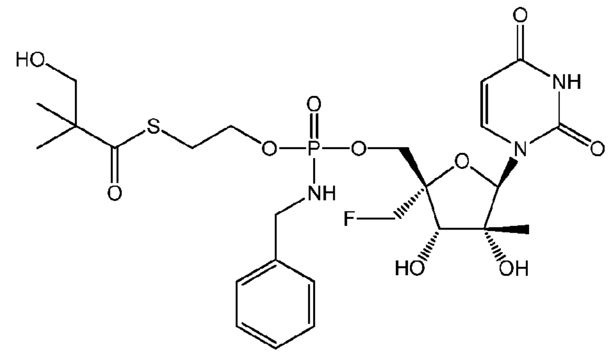 |
| 9278 | 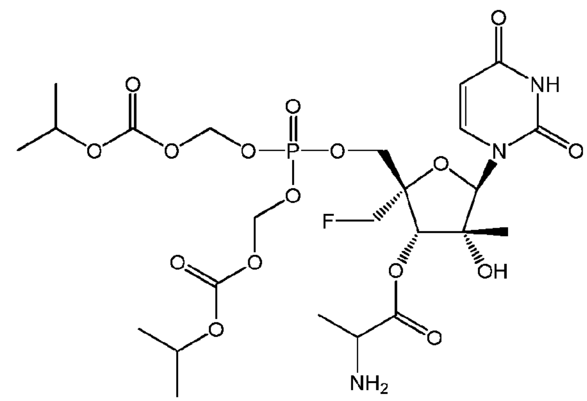 |

| # | Structure |
|---|---|
| 9274 | 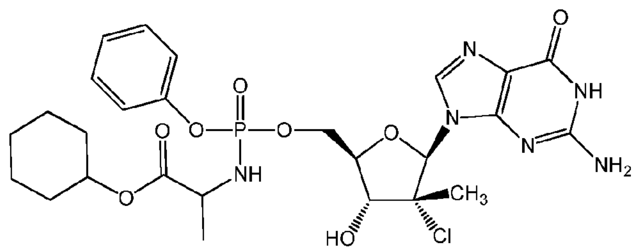 |
| 9275 | 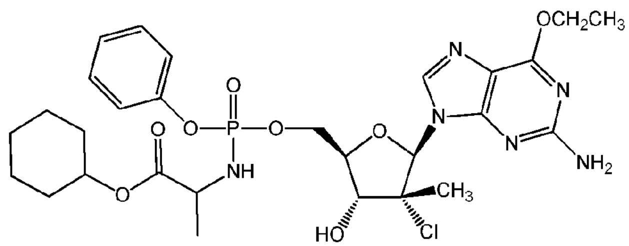 |
| 9276 | 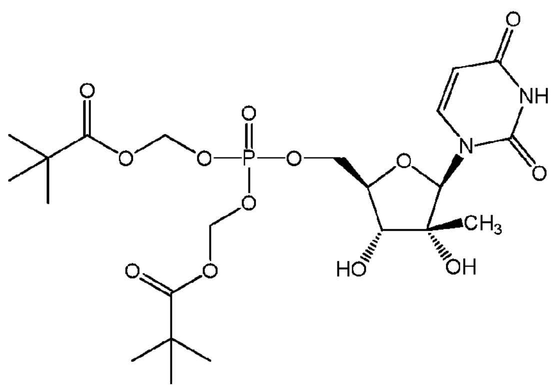 |

Figure 9 (cont.): Compounds of Formula (I)
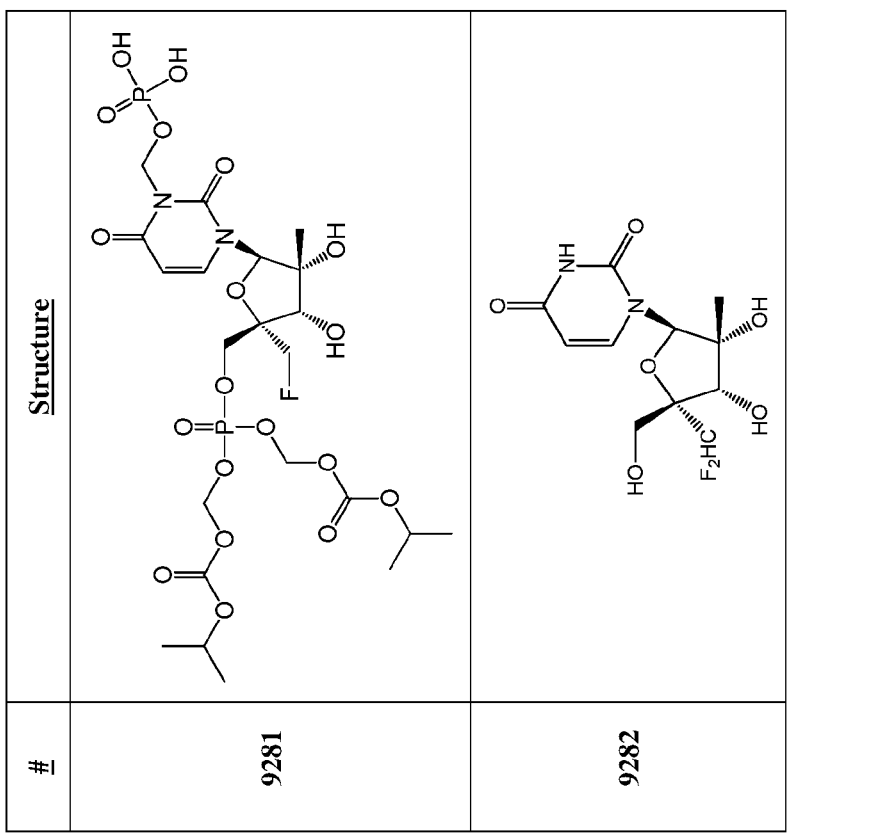
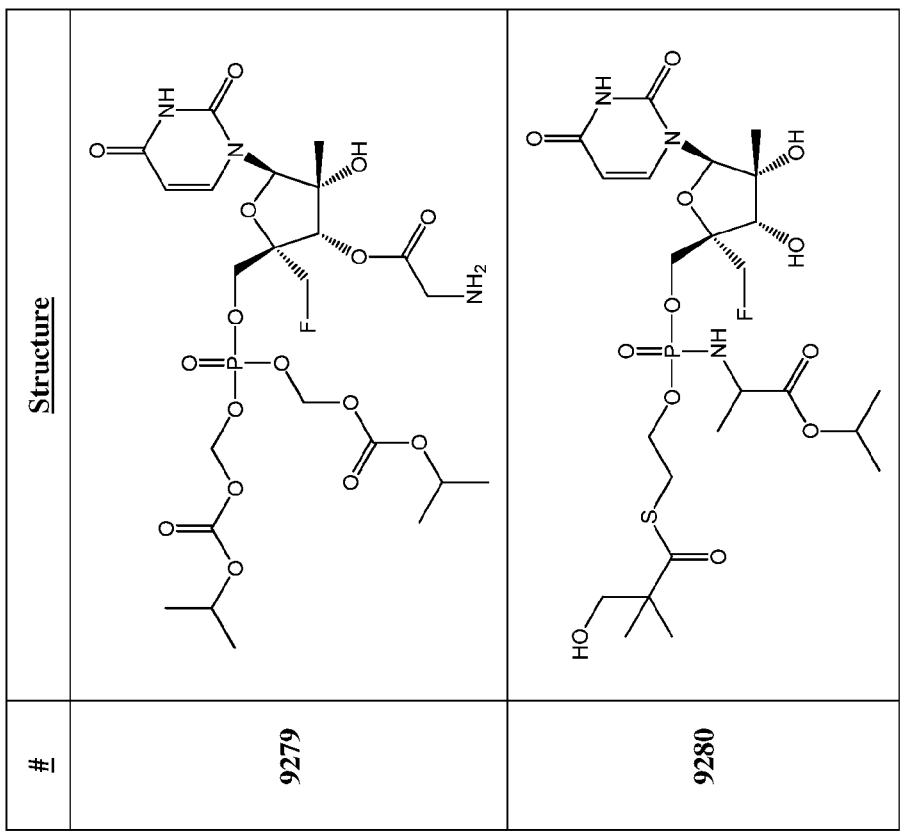

Figure 9 (cont.): Compounds of Formula (I)
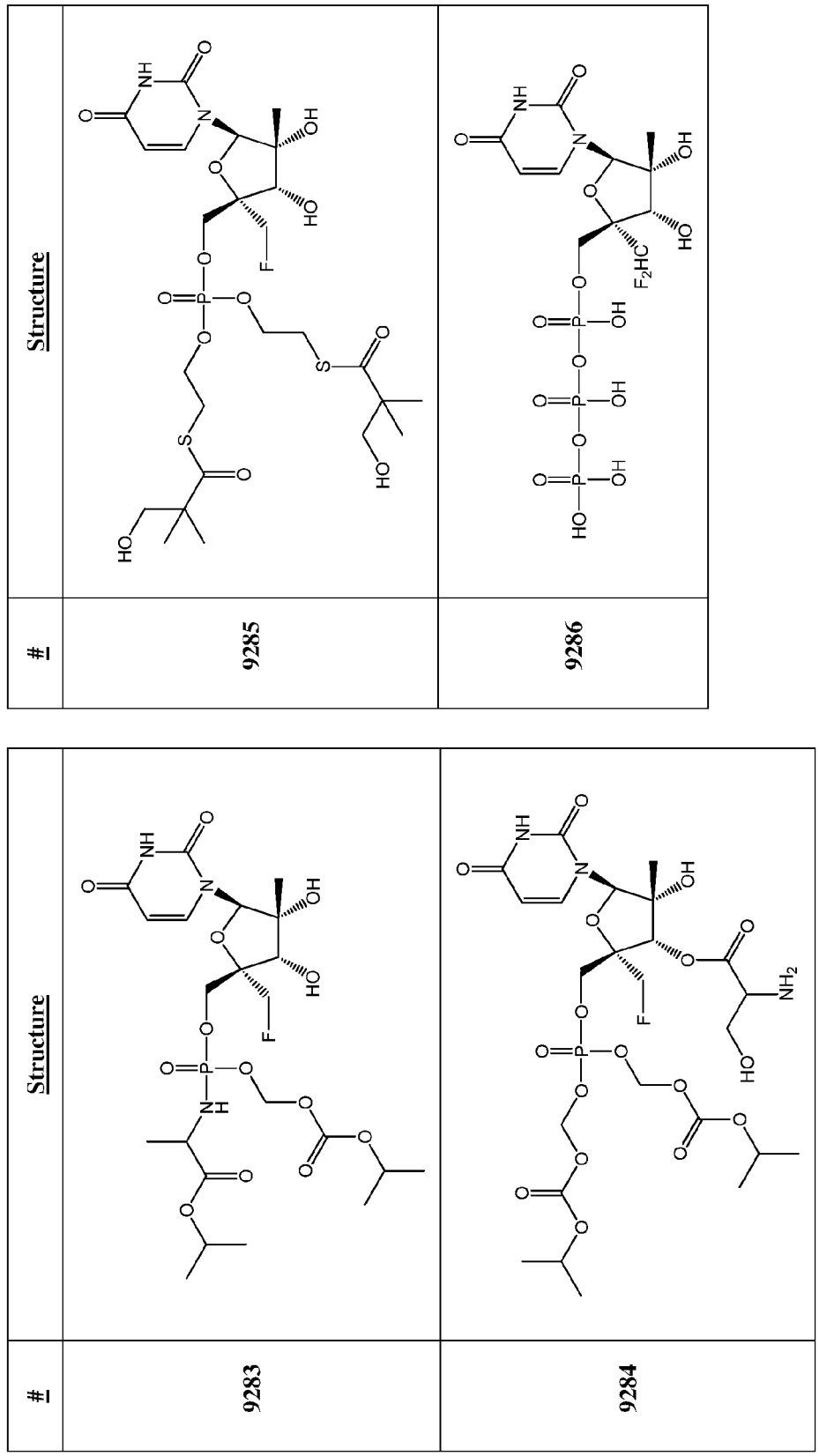

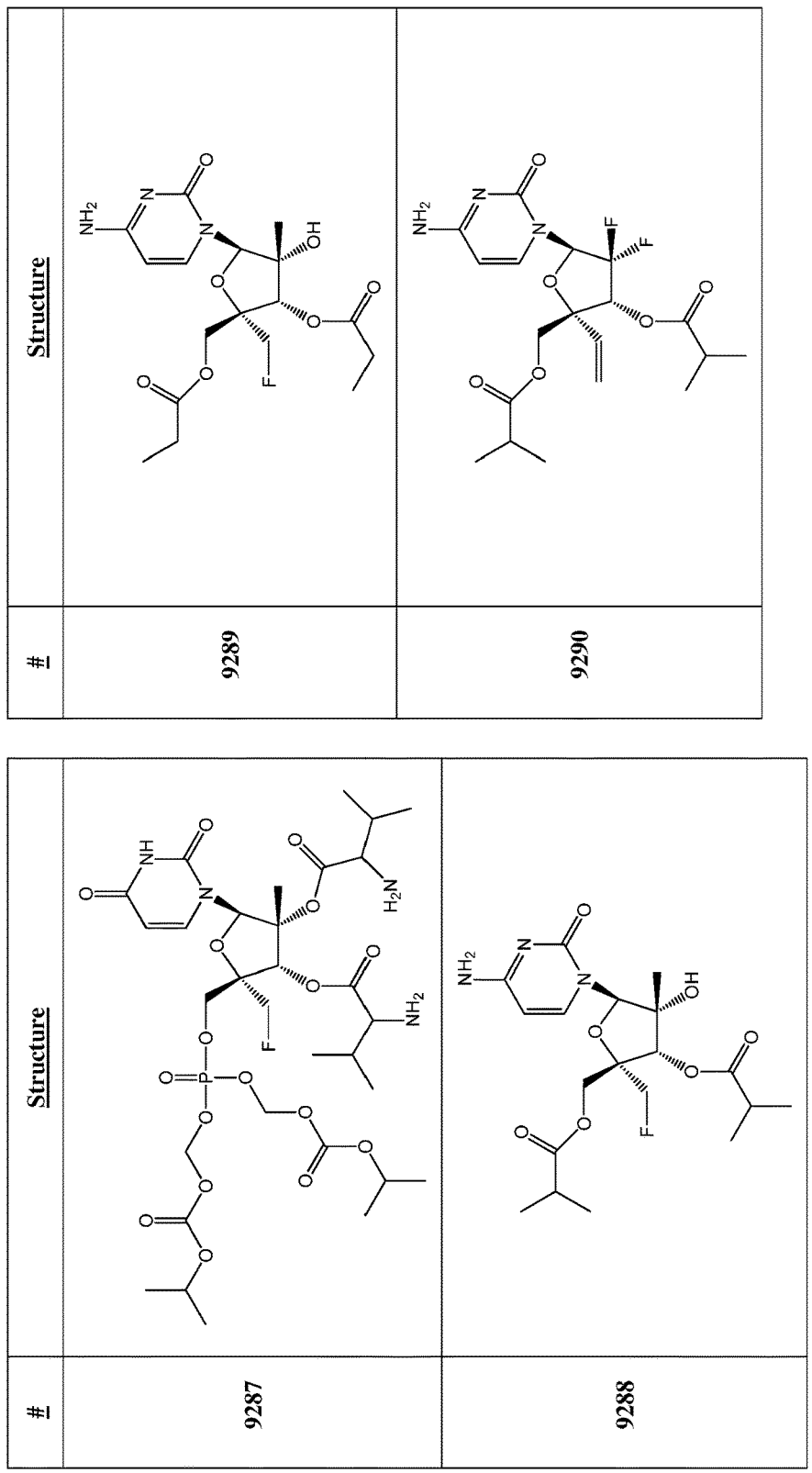
Figure 9 (cont.): Compounds of Formula (I)

Figure 9 (cont.): Compounds of Formula (I)

| # | Structure |
|---|---|
| 9293 | (cytidine analog with 4'-CH2F, 3'-OH, 2'-OH) |
| 9294 | (cytidine analog with 2',2'-difluoro, 4'-CH2N3, 3'-OH) |
| 9295 | (cytidine analog with 4'-CH2N3, 3'-OH, 2'-OH) |

| # | Structure |
|---|---|
| 9291 | (cytidine analog with 2',2'-difluoro, 4'-vinyl, 3'-O-propionyl, 5'-O-propionyl) |
| 9292 | (uridine analog with 2'-Me, 3'-OH, 4'-CH2F, 5'-phosphoramidate prodrug with 4-(aminomethyl)phenol and L-alanine isopropyl ester) |

Figure 9 (cont.): Compounds of Formula (I)
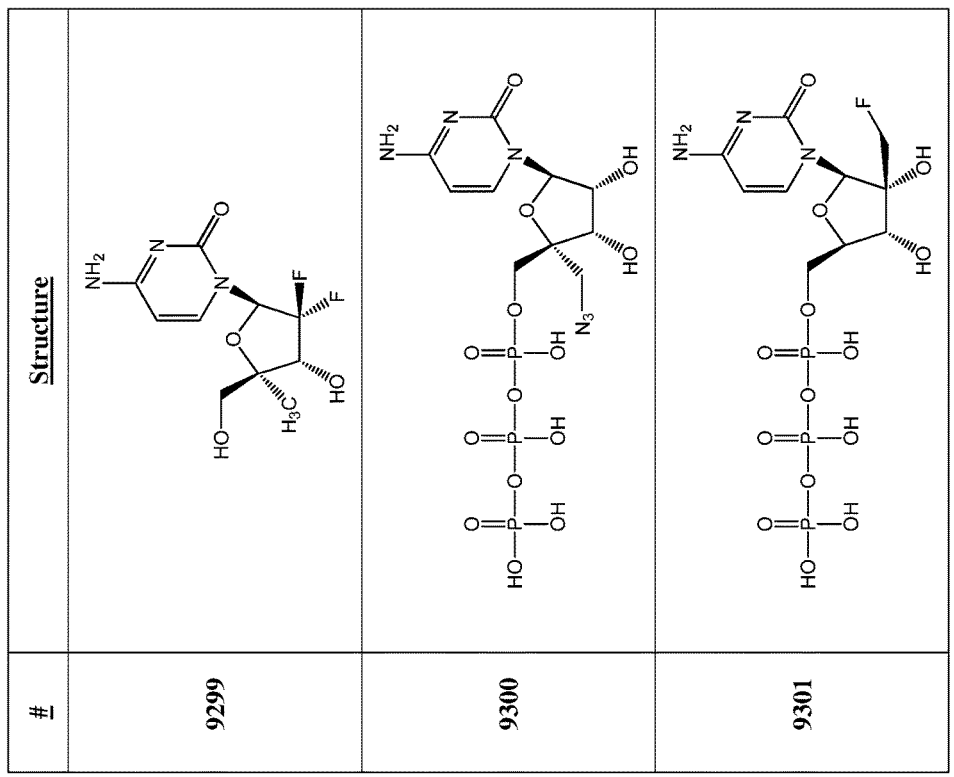
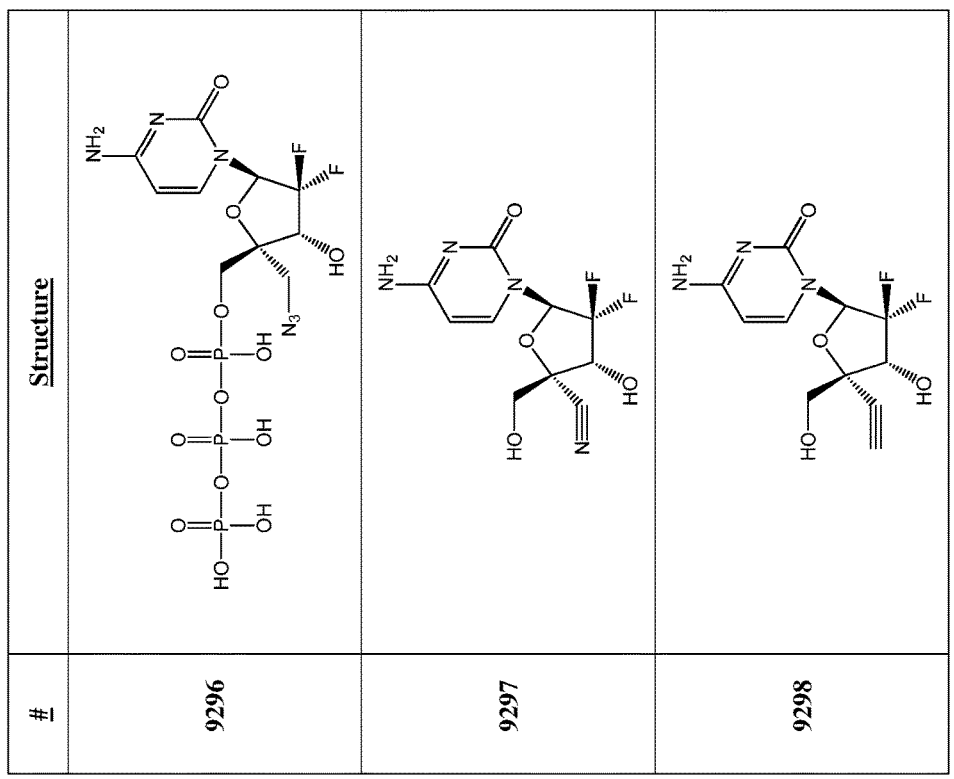

Figure 9 (cont.): Compounds of Formula (I)

| # | Structure |
|---|---|
| 9302 | 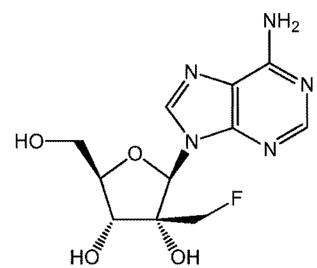 |
| 9303 | 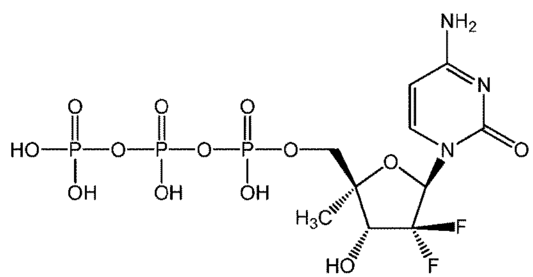 |
| 9304 | 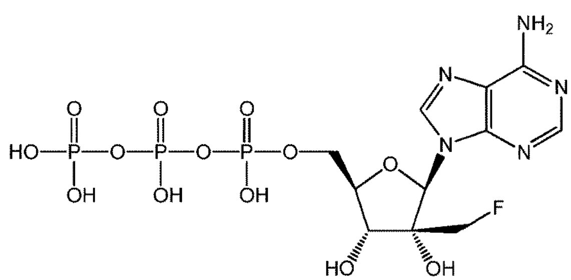 |
| 9305 | |
| 9306 | |
| 9307 | |

Figure 9 (cont.): Compounds of Formula (I)

| # | Structure |
|---|---|
| 9310 | (chemical structure) |
| 9308 | (chemical structure) |
| 9309 | (chemical structure) |

SUBSTITUTED NUCLEOSIDES, NUCLEOTIDES AND ANALOGS THEREOF

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6 including U.S. application Ser. No. 14/510,451, filed Oct. 9, 2014, now U.S. Pat. No. 9,862,743, and U.S. Provisional Application Nos. 61/890,136, filed Oct. 11, 2013 and 62/016,288, filed Jun. 24, 2014. The present application is a continuation of Ser. No. 14/510,451, filed Oct. 9, 2014, now U.S. Pat. No. 9,862,743, which claims priority to U.S. Provisional Application Nos. 61/890,136, filed Oct. 11, 2013 and 62/016,288, filed Jun. 24, 2014.

BACKGROUND

Field

The present application relates to the fields of chemistry, biochemistry and medicine. More particularly, disclosed herein are nucleosides, nucleotides and nucleotide analogs, pharmaceutical compositions that include one or more nucleosides, nucleotides and/or nucleotide analogs and methods of synthesizing the same. Also disclosed herein are methods of treating diseases and/or conditions with a nucleoside, a nucleotide and/or a nucleotide analog, alone or in combination therapy with one or more other agents.

Description

Nucleoside analogs are a class of compounds that have been shown to exert antiviral and anticancer activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I), or a pharmaceutically acceptable salt thereof. Other embodiments disclosed herein relate to a compound of Formula (II), or a pharmaceutically acceptable salt thereof.

Some embodiments disclosed herein relate to a method of ameliorating and/or treating a picornavirus infection that can include administering to a subject identified as suffering from the picornavirus infection an effective amount of one or more compounds of Formulae (I) and/or (II), or a pharmaceutically acceptable salt of the foregoing, or a pharmaceutical composition that includes one or more compounds of Formulae (I) and/or (II), or a pharmaceutically acceptable salt of the foregoing. Other embodiments described herein relate to using one or more compounds of Formulae (I) and/or (II), or a pharmaceutically acceptable salt of the foregoing, in the manufacture of a medicament for ameliorating and/or treating a picornavirus infection. Still other embodiments described herein relate to one or more compounds of Formulae (I) and/or (II), or a pharmaceutically acceptable salt of the foregoing, or a pharmaceutical composition that includes one or more compounds of Formulae (I) and/or (II), or a pharmaceutically acceptable salt of the foregoing, that can be used for ameliorating and/or treating a picornavirus infection.

Some embodiments disclosed herein relate to a method of ameliorating and/or treating a picornavirus infection that can include contacting a cell infected with the picornavirus with an effective amount of one or more compounds described herein (for example, a compound of Formulae (I) and/or (II), or a pharmaceutically acceptable salt of the foregoing), or a pharmaceutical composition that includes one or more compounds described herein, or a pharmaceutically acceptable salt thereof. Other embodiments described herein relate to using one or more compounds described herein (for example, a compound of Formulae (I) and/or (II), or a pharmaceutically acceptable salt thereof) in the manufacture of a medicament for ameliorating and/or treating a picornavirus infection that can include contacting a cell infected with the picornavirus with an effective amount of said compound(s). Still other embodiments described herein relate to one or more compounds described herein (for example, a compound of Formulae (I) and/or (II), or a pharmaceutically acceptable salt of the foregoing), or a pharmaceutical composition that includes one or more compounds described herein, or a pharmaceutically acceptable salt thereof, that can be used for ameliorating and/or treating a picornavirus infection by contacting a cell infected with the picornavirus with an effective amount of said compound(s).

Some embodiments disclosed herein relate to a method of inhibiting replication of a picornavirus that can include contacting a cell infected with the picornavirus with an effective amount of one or more compounds described herein (for example, a compound of Formulae (I) and/or (II), or a pharmaceutically acceptable salt of the foregoing), or a pharmaceutical composition that includes one or more compounds described herein, or a pharmaceutically acceptable salt thereof. Other embodiments described herein relate to using one or more compounds described herein (for example, a compound of Formulae (I) and/or (II), or a pharmaceutically acceptable salt thereof) in the manufacture of a medicament for inhibiting replication of a picornavirus that can include contacting a cell infected with the picornavirus with an effective amount of said compound(s). Still other embodiments described herein relate to one or more compounds described herein (for example, a compound of Formulae (I) and/or (II), or a pharmaceutically acceptable salt of the foregoing), or a pharmaceutical composition that includes one or more compounds described herein, or a pharmaceutically acceptable salt thereof, that can be used for inhibiting replication of a picornavirus by contacting a cell infected with the picornavirus with an effective amount of said compound(s). In some embodiments, the picornavirus can be selected from a rhinovirus, hepatitis A virus, a coxasackie virus and an enterovirus.

Some embodiments disclosed herein relate to a method of ameliorating and/or treating a Flaviviridae viral infection that can include administering to a subject identified as suffering from the Flaviviridae viral infection an effective amount of one or more compounds of Formulae (I) and/or (II), or a pharmaceutically acceptable salt of the foregoing, or a pharmaceutical composition that includes one or more compounds of Formulae (I) and/or (II), or a pharmaceutically acceptable salt of the foregoing. Other embodiments described herein relate to using one or more compounds of Formulae (I) and/or (II), or a pharmaceutically acceptable salt of the foregoing, in the manufacture of a medicament for ameliorating and/or treating a Flaviviridae viral infection. Still other embodiments described herein relate to one or more compounds of Formulae (I) and/or (II), or a pharmaceutically acceptable salt of the foregoing, or a pharmaceutical composition that includes one or more compounds of Formulae (I) and/or (II), or a pharmaceutically acceptable salt of the foregoing, that can be used for ameliorating and/or treating a Flaviviridae viral infection.

Some embodiments disclosed herein relate to a method of ameliorating and/or treating a Flaviviridae viral infection that can include contacting a cell infected with the Flaviviridae virus with an effective amount of one or more compounds described herein (for example, a compound of Formulae (I) and/or (II), or a pharmaceutically acceptable salt of the foregoing), or a pharmaceutical composition that includes one or more compounds described herein, or a pharmaceutically acceptable salt thereof. Other embodiments described herein relate to using one or more compounds described herein, or a pharmaceutically acceptable salt thereof, in the manufacture of a medicament for ameliorating and/or treating a Flaviviridae viral infection that can include contacting a cell infected with the Flaviviridae virus with an effective amount of said compound(s). Still other embodiments described herein relate to one or more compounds described herein (for example, a compound of Formulae (I) and/or (II), or a pharmaceutically acceptable salt of the foregoing), or a pharmaceutical composition that includes one or more compounds described herein, or a pharmaceutically acceptable salt thereof, that can be used for ameliorating and/or treating a Flaviviridae viral infection by contacting a cell infected with the Flaviviridae virus with an effective amount of said compound(s).

Some embodiments disclosed herein relate to a method of inhibiting replication of a Flaviviridae virus that can include contacting a cell infected with the Flaviviridae virus with an effective amount of one or more compounds described herein (for example, a compound of Formulae (I) and/or (II), or a pharmaceutically acceptable salt of the foregoing), or a pharmaceutical composition that includes one or more compounds described herein, or a pharmaceutically acceptable salt thereof. Other embodiments described herein relate to using one or more compounds described herein (for example, a compound of Formulae (I) and/or (II), or a pharmaceutically acceptable salt thereof) in the manufacture of a medicament for inhibiting replication of a Flaviviridae virus that can include contacting a cell infected with the Flaviviridae virus with an effective amount of said compound(s). Still other embodiments described herein relate to one or more compounds described herein (for example, a compound of Formulae (I) and/or (II), or a pharmaceutically acceptable salt of the foregoing), or a pharmaceutical composition that includes one or more compounds described herein, or a pharmaceutically acceptable salt thereof, that can be used for inhibiting replication of a Flaviviridae virus by contacting a cell infected with the Flaviviridae virus with an effective amount of said compound(s). In some embodiments, the Flaviviridae virus can be selected from hepatitis C virus, West Nile virus, yellow fever virus, dengue virus and an encephalitis virus from within the Flaviviridae virus family.

BRIEF DESCRIPTION OF THE DRAWINGS

FIG. 1 shows example HCV protease inhibitors.

FIG. 2 shows example nucleoside HCV polymerase inhibitors.

FIG. 3 shows example non-nucleoside HCV polymerase inhibitors.

FIG. 4 shows example NS5A inhibitors.

FIG. 5 shows example other antivirals.

FIG. 6 shows example compounds of Formula (CC) and alpha-thiotriphosphates thereof, wherein $R^{CC1}$, $R^{CC2}$, $R^{CC3a}$, $R^{CC3b}$, $R^{CC4}$, $R^{CC5}$, $R^{CC6}$, $R^{CC7}$, $R^{CC8}$, $R^{CC9}$ and $B^{CC1}$ are defined herein.

Figure 7:
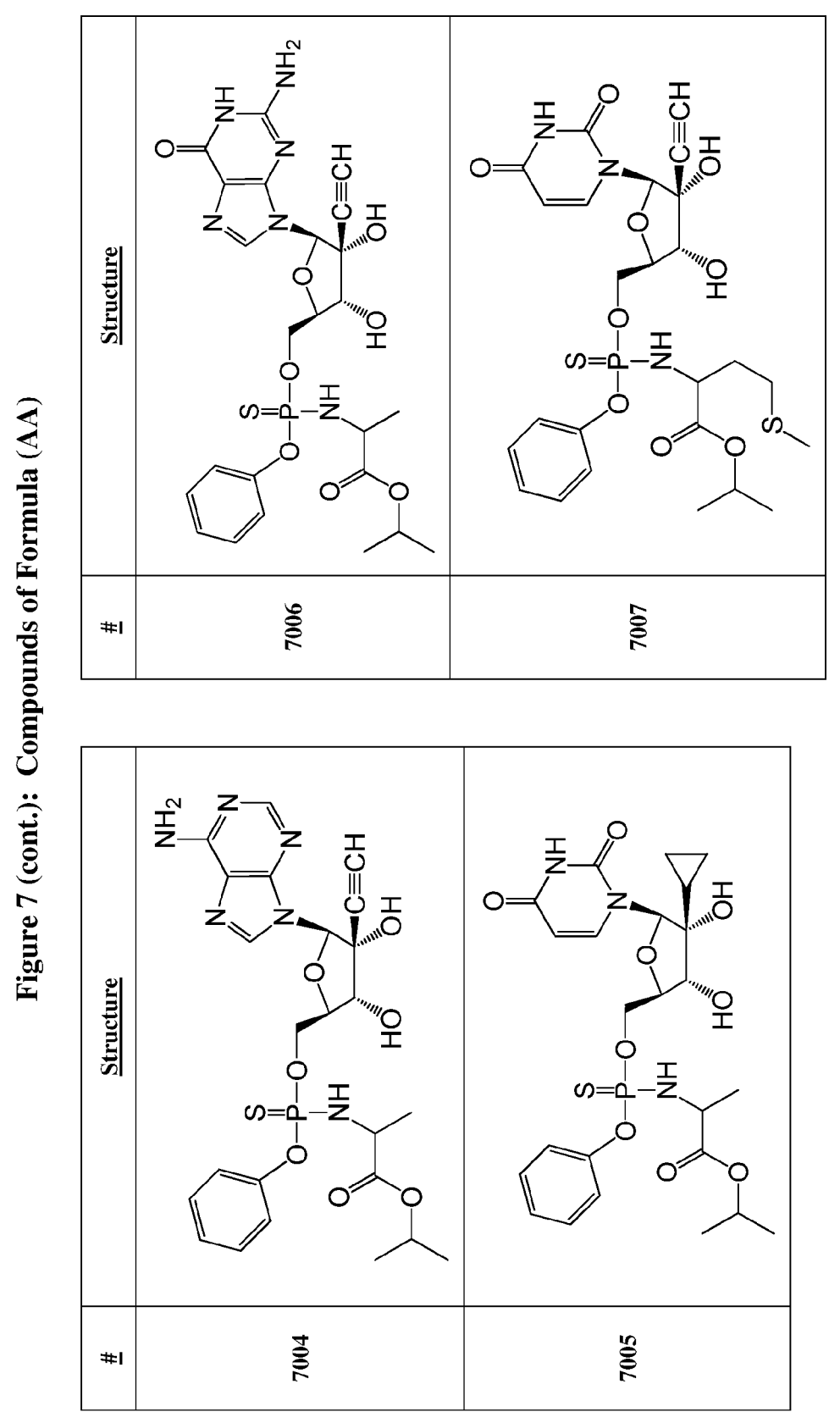

FIG. 7 shows example compounds of Formula (AA), wherein $R^{1AA}R^{2AA}$, $R^{3AA}$, $R^{4AA}$, $R^{5AA}$ and $B^{1AA}$ are defined herein.

Figure 8:
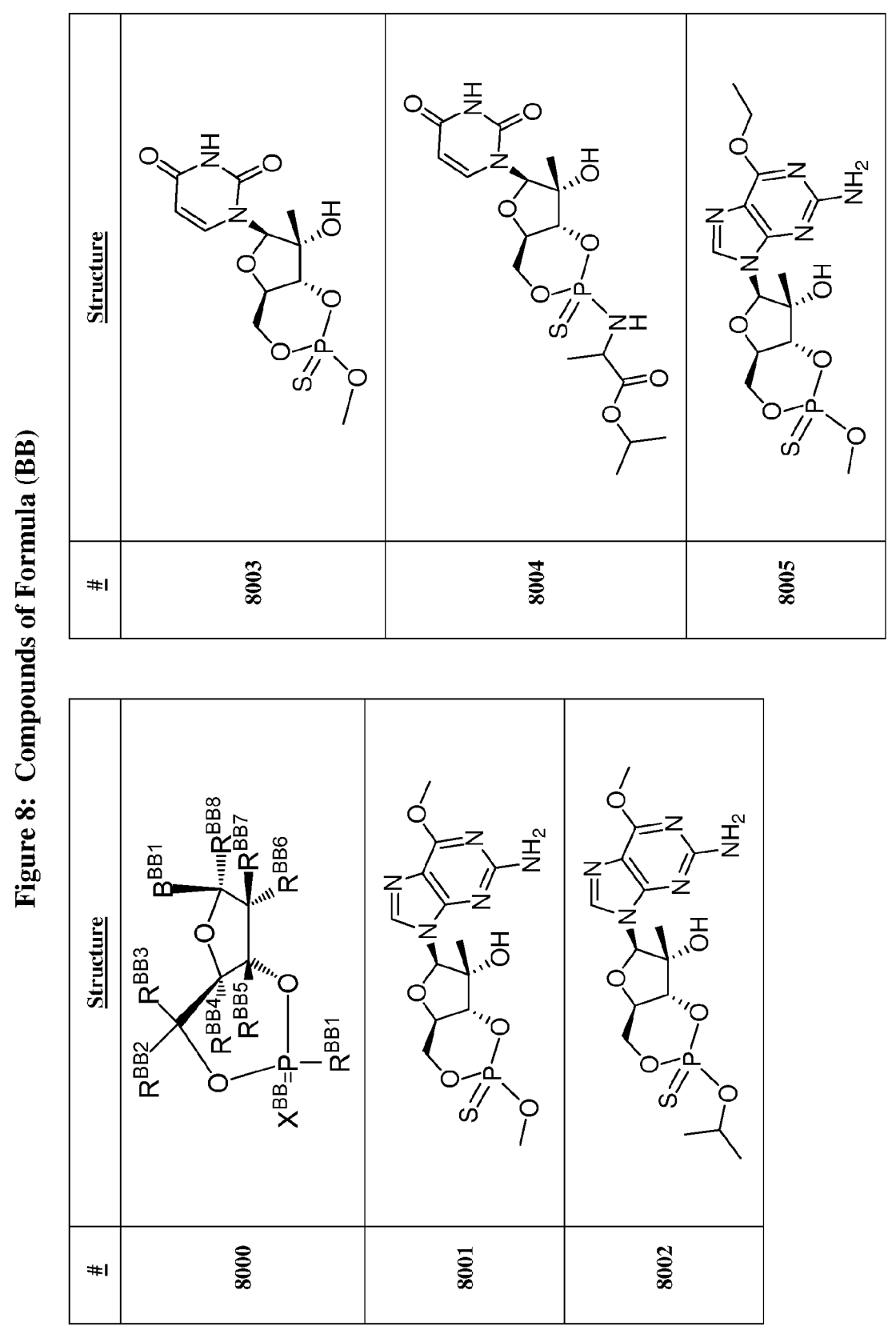

FIG. 8 shows example compounds of Formula (BB), wherein $R^{BB1}$, $R^{BB2}$, $R^{BB3}$, $R^{BB4}$, $R^{BB5}$, $R^{BB6}$, $R^{BB7}$, $R^{BB8}$, $X^{BB}$ and $B^{BB1}$ are defined herein.

FIG. 9 shows example compounds of Formula (I), wherein $Z^1$, $O^1$, $R^{1A}R^{2A}$, $R^{3A}$, $R^{4A}$, $R^{5A}$, $B^{1A}$, $Z^{1B}$, $R^{1B}$, $Z^2$, $O^2$, $R^{1C}$, $R^{2C}$, $R^{3C}$, $R^{4C}$, $R^{5C}$, $B^{1C}$, $Z^{1D}$ and $R^{1D}$ are defined herein.

DETAILED DESCRIPTION

The viruses within the Picornaviridae family are non-enveloped, positive sense, single-stranded, spherical RNA viruses with an icosahedral capsid. Picornavirus genomes are approximately 7-8 kilobases long and have an IRES (Internal Ribosomal Entry Site). These viruses are polyadenylated at the 3' end, and has a VPg protein at the 5' end in place of a cap. Genera within the Picornaviridae family include Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Rhinovirus, Salivirus, Sapelovirus, Senecavirus, Teschovirus and Tremovirus.

Enteroviruses are transmitted through the fecal-oral route and/or via aerosols of respiratory droplets, and are highly communicable. The genus of Enterovirus includes several species, including: enterovirus A, enterovirus B, enterovirus C, enterovirus D, enterovirus E, enterovirus F, enterovirus G, enterovirus Henterovirus J, rhinovirus A, rhinovirus B and rhinovirus C. Within a species of the aforementioned enteroviruses are the following serotypes: polioviruses, rhinoviruses, coxsackieviruses, echoviruses and enterovirus.

Rhinoviruses are the cause of the common cold. Rhinoviruses are named because of their transmission through the respiratory route and replication in the nose. A person can be infected with numerous rhinoviruses over their lifetime because immunity develops for each serotype. Thus, each serotype can cause a new infection.

A hepatitis A infection is the result of an infection with a Hepatitis A virus. Hepatovirus is transmitted through the fecal-oral route. Transmission can occur via person-to-person by ingestion of contaminated food or water, or through direct contact with an infectious person.

Parechovirus include human parechovirus 1 (echovirus 22), human parechovirus 2 (echovirus 23), human parechovirus 3, human parechovirus 4, human parechovirus 5 and human parechovirus 6.

The viruses with the Flaviviridae family are enveloped, positive sense, single-stranded, spherical RNA viruses with an icosahedral shaped capsid. These viruses are polyadenylated at the 5' end but lack a 3'polyadenylate tail. Genera within the Flaviviridae family include: Flavivirus, Pestivirus and Hepacivirus. Flaviviridae viruses are predominantly arthropod-borne, and are often transmitted via mosquitoes and ticks.

Flaviviruses include several encephalitis viruses (for example, Japanese Encephalitis virus (JEV), St. Louis encephalitis virus (SLEV) and tick-borne encephalitis virus (TBEV)), dengue virus 1-4 (DENV), West Nile virus (WNV) and yellow fever virus (YFV). Viruses within the Pestivirus genus include bovine viral diarrhea 1, bovine viral diarrhea 2, and classic swine fever virus.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^3$, $R^4$, $R^{5A}$, $R^{5B}$, $R^{6A}$, $R^{6B}$, $R^{6C}$, $R^{6D}$, $R^{6E}$, $R^{6F}$, $R^{6G}$, $R^{6H}$, $R^{7A}$, $R^{7B}$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{A1}$, $R^{A2}$, $R^{A3}$ and $R^{A4}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

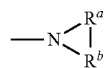

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl or a heteroalicyclyl may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaralkyl" and "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heteroalicyclyl)alkyl" and "(heterocyclyl)alkyl" refer to a heterocyclic or a heteroalicyclylic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aralkyl, heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heteroalicyclyl, aralkyl, heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N (R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N (R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N (R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N (R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine.

Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)— and naphthyl-O—C(=O)—. N-linked amino acid ester derivatives can be substituted or unsubstituted.

The term "—O-linked amino acid" refers to an amino acid that is attached to the indicated moiety via the hydroxy from its main-chain carboxylic acid group. When the amino acid is attached in an —O-linked amino acid, the hydrogen that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The terms "phosphorothioate" and "phosphothioate" refer to a compound of the general formula

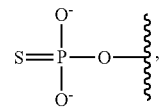

its protonated forms (for example,

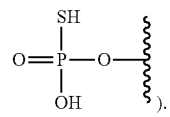

and its tautomers (such as

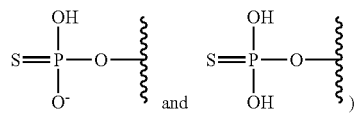 [SMILES: *OP([O-])(O)=S ; *OP(O)(O)=S]

As used herein, the term "phosphate" is used in its ordinary sense as understood by those skilled in the art, and includes its protonated forms (for example,

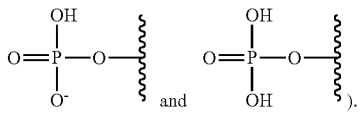

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

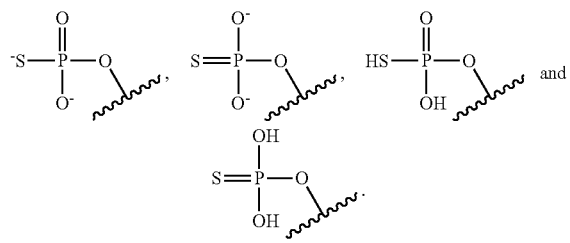

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Methods of Use

Some embodiments disclosed herein relate to a method of treating and/or ameliorating a Picornavirus infection that can include administering to a subject infected with the Picornavirus an effective amount of one or more compounds described herein (such as a compound of Formulae (I) and/or (II), or a pharmaceutically acceptable salt of the foregoing), or a pharmaceutical composition that includes a compound described herein (such as a compound of Formulae (I) and/or (II), or a pharmaceutically acceptable salt of the foregoing). Other embodiments disclosed herein relate to a method of treating and/or ameliorating a Picornavirus infection that can include administering to a subject identified as suffering from the viral infection an effective amount of one or more compounds described herein (such as a compound of Formulae (I) and/or (II), or a pharmaceutically acceptable salt of the foregoing), or a pharmaceutical composition that includes a compound described herein (such as a compound of Formulae (I) and/or (II), or a pharmaceutically acceptable salt of the foregoing).

Some embodiments described herein relate to using one or more compounds described herein (such as a compound of Formulae (I) and/or (II), or a pharmaceutically acceptable salt of the foregoing), in the manufacture of a medicament for ameliorating and/or treating a Picornavirus infection that can include administering to a subject infected with the Picornavirus an effective amount of one or more compounds described herein (such as a compound of Formulae (I) and/or (II), or a pharmaceutically acceptable salt of the foregoing). Still other embodiments described herein relate to one or more compounds described herein (such as a compound of Formulae (I) and/or (II), or a pharmaceutically acceptable salt of the foregoing) that can be used for ameliorating and/or treating a Picornavirus infection by administering to a subject infected with the Picornavirus an effective amount of one or more compounds described herein.

Some embodiments disclosed herein relate to methods of ameliorating and/or treating a Picornavirus infection that can include contacting a cell infected with the virus with an effective amount of one or more compounds described herein (such as a compound of Formulae (I) and/or (II), or a pharmaceutically acceptable salt of the foregoing), or a pharmaceutical composition that includes one or more compounds described herein (such as a compound of Formulae (I) and/or (II), or a pharmaceutically acceptable salt of the foregoing). Other embodiments described herein relate to using one or more compounds described herein (such as a compound of Formulae (I) and/or (II), or a pharmaceutically acceptable salt of the foregoing), in the manufacture of a medicament for ameliorating and/or treating a Picornavirus infection that can include contacting a cell infected with the virus with an effective amount of said compound(s). Still other embodiments described herein relate to one or more compounds described herein (such as a compound of Formulae (I) and/or (II), or a pharmaceutically acceptable salt of the foregoing), that can be used for ameliorating and/or treating a Picornavirus infection by contacting a cell infected with the virus with an effective amount of said compound(s).

Some embodiments disclosed herein relate to methods of inhibiting replication of a Picornavirus that can include contacting a cell infected with the virus with an effective amount of one or more compounds described herein (such as a compound of Formulae (I) and/or (II), or a pharmaceutically acceptable salt of the foregoing), or a pharmaceutical composition that includes one or more compounds described herein (such as a compound of Formulae (I) and/or (II), or a pharmaceutically acceptable salt of the foregoing). Other embodiments described herein relate to using one or more compounds described herein (such as a compound of Formulae (I) and/or (II), or a pharmaceutically acceptable salt of the foregoing), in the manufacture of a medicament for inhibiting replication of a Picornavirus that can include contacting a cell infected with the virus with an effective amount of said compound(s). Still other embodiments described herein relate to a compound described herein (such as a compound of Formulae (I) and/or (II), or a pharmaceutically acceptable salt of the foregoing), that can be used for inhibiting replication of a Picornavirus by contacting a cell infected with the virus with an effective amount of said compound(s). In some embodiments, a compound of Formulae (I) and/or (II), or a pharmaceutically acceptable salt of the foregoing, can inhibit a RNA dependent RNA polymerase of a picornavirus, and thus, inhibit the replication of RNA. In some embodiments, a polymerase of a picornavirus can be inhibited by contacting a cell infected with the picornavirus with a compound described herein (such as a compound of Formulae (I) and/or (II), or a pharmaceutically acceptable salt of the foregoing).

In some embodiments, the picornavirus can be selected from an Aphthovirus, an Enterovirus, a Rhinovirus, a Hepatovirus and a Parechovirus. Within the Enterovirus genus, there are several species of Enteroviruses including enterovirus A, enterovirus B, enterovirus C, enterovirus D, enterovirus E, enterovirus F, enterovirus G, enterovirus Henterovirus J. Each Enterovirus species includes several serotypes. Examples of Enterovirus serotypes include the following: poliovirus 1, poliovirus 2, poliovirus 3, echovirus 1, echovirus 2, echovirus 3, echovirus 4, echovirus 5, echovirus 6, echovirus 7, echovirus 9, echovirus 11, echovirus 12, echovirus 13, echovirus 14, echovirus 15, echovirus 16, echovirus 17, echovirus 18, echovirus 19, echovirus 20, echovirus 21, echovirus 24, echovirus 25, echovirus 26, echovirus 27, echovirus 29, echovirus 30, echovirus 31, echovirus 32, echovirus 33, enterovirus 68, enterovirus 69, enterovirus 70, enterovirus 71 and viluisk human encephalomyelitis virus. In some embodiments, a compound described herein (for example, a compound of Formulae (I) and/or (II), or a pharmaceutical acceptable salt of the foregoing) can ameliorate and/or treat an Enterovirus infection. For example, by administering an effective amount of a compound of Formulae (I) and/or (II), or a pharmaceutical acceptable salt of the foregoing, to a subject infected with the Enterovirus and/or by contacting a cell infected with the Enterovirus. In some embodiments, a compound described herein (for example, a compound of Formulae (I) and/or (II), or a pharmaceutical acceptable salt of the foregoing) can inhibit replication of an Enterovirus. In some embodiments, a compound of Formulae (I) and/or (II), or a pharmaceutical acceptable salt of the foregoing, can be effective against an Enterovirus, and thereby ameliorate one or more symptoms of an Enterovirus infection. In some embodiments, the Enterovirus can be Enterovirus A. In other embodiments, the Enterovirus can be Enterovirus B. In still other embodiments, the Enterovirus can be Enterovirus C. In yet still other embodiments, the Enterovirus can be Enterovirus D. In other embodiments, the Enterovirus can be Enterovirus E. In still other embodiments, the Enterovirus can be Enterovirus F. In yet still other embodiments, the Enterovirus can be Enterovirus G. In some embodiments, the Enterovirus can be Enterovirus H. In other embodiments, the Enterovirus can be Enterovirus J.

Coxsackieviruses are divided into group A and group B. Group A coxsackieviruses were noted to cause flaccid paralysis, while group B coxsackieviruses were noted to cause spastic paralysis. Over 20 serotypes of group A (CV-A1, CV-A2, CV-A3, CV-A4, CV-A5, CV-A6, CV-A7, CV-A8, CV-A9, CV-A10, CV-A11, CV-A12, CV-A13, CV-A14, CV-A15, CV-A16, CV-A17, CV-A18, CV-A19, CV-A20, CV-A21, CV-A22 and CV-A23) and 6 serotypes of group B (CV-B1, CV-B2, CV-B3, CV-B4, CV-B5 and CV-B6) are recognized. No specific treatment for coxsackievirus infections is currently approved. In some embodiments, a compound described herein (for example, a compound of Formulae (I) and/or (II), or a pharmaceutical acceptable salt of the foregoing) can ameliorate and/or treat a coxsackievirus infection. In some embodiments, a compound described herein (for example, a compound of Formulae (I) and/or (II), or a pharmaceutical acceptable salt of the foregoing) can inhibit replication of a coxsackievirus. In some embodiments, a compound of Formulae (I) and/or (II), or a pharmaceutical acceptable salt of the foregoing, can be effective against a coxsackievirus as demonstrated by the amelioration of one or more symptoms of a coxsackievirus infection. In some embodiments, a coxsackievirus infection can be ameliorated, treated and/or inhibited by administering an effective amount of a compound of Formulae (I) and/or (II), or a pharmaceutical acceptable salt of the foregoing, to a subject infected with the coxsackievirus and/or by contacting a cell infected with the coxsackievirus. In some embodiments, the coxsackievirus can be a coxsackievirus A. In other embodiments, the coxsackievirus can be a coxsackievirus B. In some embodiments, a compound described herein (one or more a compound of Formulae (I) and/or (II), or a pharmaceutical acceptable salt of the foregoing) can ameliorate and/or treat hand, food and mouth disease caused by a coxsackie A virus.

Additional species within the Enterovirus genus includes rhinovirus A, rhinovirus B and rhinovirus C. In some embodiments, a compound described herein (for example, a compound of Formulae (I) and/or (II), or a pharmaceutical acceptable salt of the foregoing) can ameliorate and/or treat a rhinovirus infection. In some embodiments, a compound described herein (for example, a compound of Formulae (I) and/or (II), or a pharmaceutical acceptable salt of the foregoing) can inhibit replication of a rhinovirus. In some embodiments, a compound described herein (for example, a compound of Formulae (I) and/or (II), or a pharmaceutical acceptable salt of the foregoing) can be effective against multiple serotypes of a rhinovirus. For example, a compound of Formulae (I) and/or (II), or a pharmaceutical acceptable salt of the foregoing, can be used to ameliorate and/or treat 2, 5, 10, 20, 40, 60, 80 or more serotypes of a rhinovirus. In some embodiments, a compound of Formulae (I) and/or (II), or a pharmaceutical acceptable salt of the foregoing, can be effective against rhinovirus, and thereby ameliorating one or more symptoms of a rhinovirus infection. In some embodiments, a rhinovirus infection can be ameliorated, treated and/or inhibited by administering an effective amount of a compound of Formulae (I) and/or (II), or a pharmaceutical acceptable salt of the foregoing, to a subject infected with the rhinovirus and/or by contacting a cell infected with the rhinovirus. In some embodiments, the coxsackievirus can be a coxsackievirus A. In some embodiments, the rhinovirus can be rhinovirus A. In other embodiments, the rhinovirus can be rhinovirus B. In still other embodiments, the rhinovirus can be rhinovirus C.

Another species of Enterovirus is Hepatovirus. Hepatitis A is a serotype of Hepatovirus. Several human genotypes of Hepatitis A are known, IA, IB, IIA, IIB, IIIA and IIIB. Genotype I is the most common. To date, there is no specific therapy for treating a hepatitis A infection. Rather, treatment is supportive in nature. In some embodiments, a compound described herein (for example, a compound of Formulae (I) and/or (II), or a pharmaceutical acceptable salt of the foregoing) can ameliorate and/or treat a Hepatovirus infection, such as a hepatitis A virus infection. In some embodiments, a compound described herein (for example, a compound of Formulae (I) and/or (II), or a pharmaceutical acceptable salt of the foregoing) can inhibit replication of a Hepatovirus (for example, a hepatitis A virus). In some embodiment, a compound of Formulae (I) and/or (II), or a pharmaceutical acceptable salt of the foregoing, can treat and/or ameliorate a genotype I of hepatitis A. In some embodiments, a compound of Formulae (I) and/or (II), or a pharmaceutical acceptable salt of the foregoing, is effective against more than one genotype of hepatitis A, for example, 2, 3, 4, 5 or 6 genotypes of hepatitis A. In some embodiments, a Hepatovirus infection can be ameliorated, treated and/or inhibited by administering an effective amount of a compound of Formulae (I) and/or (II), or a pharmaceutical acceptable salt of the foregoing, to a subject infected with the Hepatovirus and/or by contacting a cell infected with the Hepatovirus.

Parechovirus is another species of Enterovirus. Serotypes of Parechovirus includes human parechovirus 1 (echovirus 22), human parechovirus 2 (echovirus 23), human parechovirus 3, human parechovirus 4, human parechovirus 5 and human parechovirus 6. In some embodiments, a compound described herein (for example, a compound of Formulae (I) and/or (II), or a pharmaceutical acceptable salt of the foregoing) can ameliorate and/or treat a parechovirus infection. In some embodiments, a compound described herein (for example, a compound of Formulae (I) and/or (II), or a pharmaceutical acceptable salt of the foregoing) can inhibit replication of a parechovirus. In some embodiments, a compound of Formulae (I) and/or (II), or a pharmaceutical acceptable salt of the foregoing, is effective against more than one serotype of a parechovirus. In some embodiments, a parechovirus infection can be ameliorated, treated and/or inhibited by administering an effective amount of a compound of Formulae (I) and/or (II), or a pharmaceutical acceptable salt of the foregoing, to a subject infected with the parechovirus and/or by contacting a cell infected with the parechovirus.

Other genera of Picornavirus include the following: Aquamavirus, Avihepatovirus, Cardiovirus, Cosavirus, Dicipivirus, Erbovirus, Kobuvirus, Megrivirus, Salivirus, Sapelovirus, Senecavirus, Teschovirus and Tremovirus. In some embodiments, a compound described herein (for example, a compound of Formulae (I) and/or (II), or a pharmaceutical acceptable salt of the foregoing) can ameliorate and/or treat a picornavirus infection caused by a virus selected from Aquamavirus, Avihepatovirus, Cardiovirus, Cosavirus, Dicipivirus, Erbovirus, Kobuvirus, Megrivirus, Salivirus, Sapelovirus, Senecavirus, Teschovirus and Tremovirus. In some embodiments, a compound described herein (for example, a compound of Formulae (I) and/or (II), or a pharmaceutical acceptable salt of the foregoing) can inhibit replication of a picornavirus selected from Aquamavirus, Avihepatovirus, Cardiovirus, Cosavirus, Dicipivirus, Erbovirus, Kobuvirus, Megrivirus, Salivirus, Sapelovirus, Senecavirus, Teschovirus and Tremovirus. A compound described herein (for example, a compound of Formulae (I) and/or (II), or a pharmaceutical acceptable salt of the foregoing) can ameliorate, treat and/or inhibit a virus selected from Aquamavirus, Avihepatovirus, Cardiovirus, Cosavirus, Dicipivirus, Erbovirus, Kobuvirus, Megrivirus, Salivirus, Sapelovirus, Senecavirus, Teschovirus and Tremovirus by administering an effective amount of a compound described herein to a subject infected by the virus and/or by contacting a cell infected with the virus with an effective amount of a compound described herein.

In some embodiments, an effective amount of a compound of Formulae (I) and/(II), or a pharmaceutical acceptable salt of the foregoing, or a pharmaceutical composition that includes an effective amount of one or more compounds of Formulae (I) and/or (II), or a pharmaceutical acceptable salt of the foregoing, can be effective to treat more than one genera of Picornavirus. In some embodiments, a compound described herein (for example, a compound of Formulae (I) and/or (II), or a pharmaceutical acceptable salt of the foregoing) can be used to ameliorate and/or treat more than one species of a Picornavirus. As an example, a compound of Formulae (I) and/or (II), or a pharmaceutical acceptable salt of the foregoing, can be used to ameliorate and/or treat 2, 3, 4, 5, or more species of an Enterovirus. In some embodiments, a compound described herein (for example, a compound of Formulae (I) and/or (II), or a pharmaceutical acceptable salt of the foregoing) can be effective to treat multiple serotypes of a Picornavirus described herein. For example, a compound described herein (one or more a compound of Formulae (I) and/or (II), or a pharmaceutical acceptable salt of the foregoing) can be effective to treat 2, 5, 10, 15 or more serotypes of a coxsackie virus.

Some embodiments disclosed herein relate to a method of treating and/or ameliorating a Flaviviridae virus infection that can include administering to a subject infected with the Flaviviridae an effective amount of one or more compounds described herein (such as a compound of Formulae (I) and/or (II), or a pharmaceutically acceptable salt of the foregoing), or a pharmaceutical composition that includes a compound described herein (such as a compound of Formulae (I) and/or (II), or a pharmaceutically acceptable salt of the foregoing). Other embodiments disclosed herein relate to a method of treating and/or ameliorating a Flaviviridae virus infection that can include administering to a subject an effective amount of one or more compounds described herein (such as a compound of Formulae (I) and/or (II), or a pharmaceutically acceptable salt of the foregoing), or a pharmaceutical composition that includes a compound described herein (such as a compound of Formulae (I) and/or (II), or a pharmaceutically acceptable salt of the foregoing). Some embodiments described herein relate to using one or more compounds described herein (such as a compound of Formulae (I) and/or (II), or a pharmaceutically acceptable salt of the foregoing), in the manufacture of a medicament for ameliorating and/or treating a Flaviviridae virus infection that can include administering an effective amount of one or more compounds described herein (such as a compound of Formulae (I) and/or (II), or a pharmaceutically acceptable salt of the foregoing). Still other embodiments described herein relate to one or more compounds described herein (such as a compound of Formulae (I) and/or (II), or a pharmaceutically acceptable salt of the foregoing) that can be used for ameliorating and/or treating a Flaviviridae virus infection by administering to a subject an effective amount of one or more compounds described herein.

Some embodiments disclosed herein relate to methods of ameliorating and/or treating a Flaviviridae virus infection that can include contacting a cell infected with the virus with an effective amount of one or more compounds described herein (such as a compound of Formulae (I) and/or (II), or a pharmaceutically acceptable salt of the foregoing), or a pharmaceutical composition that includes one or more compounds described herein (such as a compound of Formulae (I) and/or (II), or a pharmaceutically acceptable salt of the foregoing). Other embodiments described herein relate to using one or more compounds described herein (such as a compound of Formulae (I) and/or (II), or a pharmaceutically acceptable salt of the foregoing), in the manufacture of a medicament for ameliorating and/or treating a Flaviviridae virus infection that can include contacting a cell infected with the virus with an effective amount of said compound(s). Still other embodiments described herein relate to one or more compounds described herein (such as a compound of Formulae (I) and/or (II), or a pharmaceutically acceptable salt of the foregoing), that can be used for ameliorating and/or treating a Flaviviridae virus infection by contacting a cell infected with the virus with an effective amount of said compound(s).

Some embodiments disclosed herein relate to methods of inhibiting replication of a Flaviviridae virus that can include contacting a cell infected with the virus with an effective amount of one or more compounds described herein (such as a compound of Formulae (I) and/or (II), or a pharmaceutically acceptable salt of the foregoing), or a pharmaceutical composition that includes one or more compounds described herein (such as a compound of Formulae (I) and/or (II), or a pharmaceutically acceptable salt of the foregoing). Other embodiments described herein relate to using one or more compounds described herein (such as a compound of Formulae (I) and/or (II), or a pharmaceutically acceptable salt of the foregoing), in the manufacture of a medicament for inhibiting replication of a Flaviviridae virus that can include contacting a cell infected with the virus with an effective amount of said compound(s). Still other embodiments described herein relate to a compound described herein (such as a compound of Formulae (I) and/or (II), or a pharmaceutically acceptable salt of the foregoing), that can be used for inhibiting replication of a Flaviviridae virus by contacting a cell infected with the virus with an effective amount of said compound(s). In some embodiments, a polymerase of a Flaviviridae virus can be inhibited by contacting a cell infected with the Flaviviridae virus with a compound described herein (such as a compound of Formulae (I) and/or (II), or a pharmaceutically acceptable salt of the foregoing), and thereby, inhibit the replication of RNA.

HCV is an enveloped positive strand RNA virus in the Flaviviridae family. There are various nonstructural proteins of HCV, such as NS2, NS3, NS4, NS4A, NS4B, NS5A and NS5B. NS5B is believed to be an RNA-dependent RNA polymerase involved in the replication of HCV RNA.

Some embodiments disclosed herein relate to methods of ameliorating and/or treating a HCV infection that can include contacting a cell infected with HCV with an effective amount of one or more compounds described herein (such as a compound of Formulae (I) and/or (II), or a pharmaceutically acceptable salt of the foregoing), or a pharmaceutical composition that includes one or more compounds described herein (such as a compound of Formulae (I) and/or (II), or a pharmaceutically acceptable salt of the foregoing). Other embodiments described herein relate to using one or more compounds described herein (such as a compound of Formulae (I) and/or (II), or a pharmaceutically acceptable salt of the foregoing), in the manufacture of a medicament for ameliorating and/or treating a HCV infection that can include contacting a cell infected with HCV with an effective amount of said compound(s). Still other embodiments described herein relate to one or more compounds described herein (such as a compound of Formulae (I) and/or (II), or a pharmaceutically acceptable salt of the foregoing), that can be used for ameliorating and/or treating a HCV infection by contacting a cell infected with HCV with an effective amount of said compound(s).

Some embodiments described herein relate to a method of inhibiting NS5B polymerase activity that can include contacting a cell infected with hepatitis C virus with an effective amount of a compound of Formulae (I) and/or (II), or a pharmaceutically acceptable salt of the foregoing. Some embodiments described herein relate to a method of inhibiting NS5B polymerase activity that can include administering to a subject infected with hepatitis C virus an effective amount of a compound of Formulae (I) and/or (II), or a pharmaceutically acceptable salt of the foregoing. In some embodiments, a compound of Formulae (I) and/or (II), or a pharmaceutically acceptable salt of the foregoing, can inhibit a RNA dependent RNA polymerase, and thus, inhibit the replication of HCV RNA. In some embodiments, a compound of Formulae (I) and/or (II), or a pharmaceutically acceptable salt of the foregoing, can inhibit a HCV polymerase (for example, NS5B polymerase).

Some embodiments described herein relate to a method of treating a condition selected from liver fibrosis, liver cirrhosis and liver cancer in a subject suffering from one or more of the aforementioned liver conditions that can include administering to the subject an effective amount of a compound or a pharmaceutical composition described herein (for example, a compound of Formulae (I) and/or (II), or a pharmaceutically acceptable salt of the foregoing), wherein the liver condition is caused by a HCV infection. Some embodiments described herein relate to a method of increasing liver function in a subject having a HCV infection that can include administering to the subject an effective amount of a compound or a pharmaceutical composition described herein (for example, a compound of Formulae (I) and/or (II), or a pharmaceutically acceptable salt of the foregoing). Also contemplated is a method for reducing or eliminating further virus-caused liver damage in a subject having an HCV infection by administering to the subject an effective amount of a compound or a pharmaceutical composition described herein (for example, a compound of Formulae (I) and/or (II), or a pharmaceutically acceptable salt of the foregoing). In some embodiments, this method can include slowing or halting the progression of liver disease. In other embodiments, the course of the disease can be reversed, and stasis or improvement in liver function is contemplated. In some embodiments, liver fibrosis, liver cirrhosis and/or liver cancer can be treated; liver function can be increased; virus-caused liver damage can be reduced or eliminated; progression of liver disease can be slowed or halted; the course of the liver disease can be reversed and/or liver function can be improved or maintained by contacting a cell infected with hepatitis C virus with an effective amount of a compound described herein (for example, a compound of Formulae (I) and/or (II), or a pharmaceutically acceptable salt of the foregoing.)

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4e; 5a; 6a; 7a-7b; 8a-8b; 9a; 10a; and 11a). In some embodiments, an effective amount of a compound of Formulae (I) and/or (II), or a pharmaceutical salt of the foregoing, or a pharmaceutical composition that includes an effective amount of a compound of Formulae (I) and/or (II), or a pharmaceutical acceptable salt of the foregoing, can be effective to treat at least one genotype of HCV. In some embodiments, a compound described herein (for example, a compound of Formulae (I) and/or (II), or a pharmaceutically acceptable salt of the foregoing) can be effective to treat all 11 genotypes of HCV. In some embodiments, a compound described herein (for example, a compound of Formulae (I) and/or (II), or a pharmaceutically acceptable salt of the foregoing) can be effective to treat 3 or more, 5 or more, 7 or more, or 9 or more genotypes of HCV. In some embodiments, a compound of Formulae (I) and/or (II), or a pharmaceutical acceptable salt of the foregoing, can be more effective against a larger number of HCV genotypes than the standard of care. In some embodiments, a compound of Formulae (I) and/or (II), or a pharmaceutically acceptable salt of the foregoing, can be more effective against a particular HCV genotype than the standard of care (such as genotype 1, 2, 3, 4, 5 and/or 6).

Various indicators for determining the effectiveness of a method for treating a HCV infection are known to those skilled in the art. Examples of suitable indicators include, but are not limited to, a reduction in viral load, a reduction in viral replication, a reduction in time to seroconversion (virus undetectable in patient serum), an increase in the rate of sustained viral response to therapy, a reduction of morbidity or mortality in clinical outcomes, a reduction in the rate of liver function decrease; stasis in liver function; improvement in liver function; reduction in one or more markers of liver dysfunction, including alanine transaminase, aspartate transaminase, total bilirubin, conjugated bilirubin, gamma glutamyl transpeptidase and/or other indicator of disease response. Similarly, successful therapy with an effective amount of a compound or a pharmaceutical composition described herein (for example, a compound of Formulae (I) and/or (II), or a pharmaceutically acceptable salt of the foregoing) can reduce the incidence of liver cancer in HCV infected subjects.

In some embodiments, an effective amount of a compound of Formulae (I) and/or (II), or a pharmaceutically acceptable salt of the foregoing, is an amount that is effective to reduce HCV viral titers to undetectable levels, for example, to about 100 to about 500, to about 50 to about 100, to about 10 to about 50, or to about 15 to about 25 international units/mL serum. In some embodiments, an effective amount of a compound of Formulae (I) and/or (II), or a pharmaceutically acceptable salt of the foregoing, is an amount that is effective to reduce HCV viral load compared to the HCV viral load before administration of the compound of Formulae (I) and/or (II), or a pharmaceutically acceptable salt of the foregoing. For example, wherein the HCV viral load is measured before administration of the compound of Formulae (I) and/or (II), or a pharmaceutically acceptable salt of the foregoing, and again after completion of the treatment regime with the compound of Formulae (I) and/or (II), or a pharmaceutically acceptable salt of the foregoing (for example, 1 month after completion). In some embodiments, an effective amount of a compound of Formulae (I) and/or (II), or a pharmaceutically acceptable salt of the foregoing, can be an amount that is effective to reduce HCV viral load to lower than about 25 international units/mL serum. In some embodiments, an effective amount of a compound of Formulae (I) and/or (II), or a pharmaceutically acceptable salt of the foregoing, is an amount that is effective to achieve a reduction in HCV viral titer in the serum of the subject in the range of about 1.5-log to about a 2.5-log reduction, about a 3-log to about a 4-log reduction, or a greater than about 5-log reduction compared to the viral load before administration of the compound of Formulae (I) and/or (II), or a pharmaceutically acceptable salt of the foregoing. For example, the HCV viral load can be measured before administration of the compound of Formulae (I) and/or (II), or a pharmaceutically acceptable salt of the foregoing, and again after completion of the treatment regime with the compound of Formulae (I) and/or (II), or a pharmaceutically acceptable salt of the foregoing (for example, 1 month after completion).

In some embodiments, a compound of Formulae (I) and/or (II), or a pharmaceutically acceptable salt of the foregoing, can result in at least a 1, 2, 3, 4, 5, 10, 15, 20, 25, 50, 75, 100-fold or more reduction in the replication of the hepatitis C virus relative to pre-treatment levels in a subject, as determined after completion of the treatment regime (for example 1 month after completion). In some embodiments, a compound of Formulae (I) and/or (II), or a pharmaceutically acceptable salt of the foregoing, can result in a reduction of the replication of the hepatitis C virus relative to pre-treatment levels in the range of about 2 to about 5 fold, about 10 to about 20 fold, about 15 to about 40 fold, or about 50 to about 100 fold. In some embodiments, a compound of Formulae (I) and/or (II), or a pharmaceutically acceptable salt of the foregoing, can result in a reduction of the hepatitis C virus replication in the range of 1 to 1.5 log, 1.5 log to 2 log, 2 log to 2.5 log, 2.5 to 3 log, 3 log to 3.5 log or 3.5 to 4 log more reduction of the hepatitis C virus replication compared to the reduction of the hepatitis C virus reduction achieved by pegylated interferon in combination with ribavirin, administered according to the standard of care, or may achieve the same reduction as that standard of care therapy in a shorter period of time, for example, in one month, two months, or three months, as compared to the reduction achieved after six months of standard of care therapy with ribavirin and pegylated interferon.

In some embodiments, an effective amount of a compound of Formulae (I) and/or (II), or a pharmaceutically acceptable salt of the foregoing, is an amount that is effective to achieve a sustained viral response, for example, non-detectable or substantially non-detectable HCV RNA (e.g., less than about 500, less than about 200, less than about 100, less than about 25, or less than about 15 international units per milliliter serum) is found in the subject's serum for a period of at least about one month, at least about two months, at least about three months, at least about four months, at least about five months, or at least about six months following cessation of therapy.

In some embodiments, an effective amount of a compound of Formulae (I) and/or (II), or a pharmaceutically acceptable salt of the foregoing, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of examples of markers includes measuring the levels of serum alanine aminotransferase (ALT), aspartate aminotransferase (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51 IU/L, TBIL in the range of 0.3-1.9 mg/dL is considered normal. In some embodiments, an effective amount of a compound of Formulae (I) and/or (II), or a pharmaceutically acceptable salt of the foregoing, can be an amount effective to reduce ALT, AST, ALP, GGT and/or TBIL levels to with what is considered a normal level.

Subjects who are clinically diagnosed with HCV infection include "naïve" subjects (e.g., subjects not previously treated for HCV, particularly those who have not previously received IFN-alpha-based and/or ribavirin-based therapy) and individuals who have failed prior treatment for HCV ("treatment failure" subjects). Treatment failure subjects include "non-responders" (i.e., subjects in whom the HCV titer was not significantly or sufficiently reduced by a previous treatment for HCV (≤0.5 log IU/mL), for example, a previous IFN-alpha monotherapy, a previous IFN-alpha and ribavirin combination therapy, or a previous pegylated IFN-alpha and ribavirin combination therapy); and "relapsers" (i.e., subjects who were previously treated for HCV, for example, who received a previous IFN-alpha monotherapy, a previous IFN-alpha and ribavirin combination therapy, or a previous pegylated IFN-alpha and ribavirin combination therapy, whose HCV titer decreased, and subsequently increased).

In some embodiments, a compound of Formulae (I) and/or (II), or a pharmaceutically acceptable salt of the foregoing, can be administered to a treatment failure subject suffering from HCV. In some embodiments, a compound of Formulae (I) and/or (II), or a pharmaceutically acceptable salt of the foregoing, can be administered to a non-responder subject suffering from HCV. In some embodiments, a compound of Formulae (I) and/or (II), or a pharmaceutically acceptable salt of the foregoing, can be administered to a relapsed subject suffering from HCV.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formulae (I) and/or (II), or a pharmaceutically acceptable salt of the foregoing, can be administered to a subject infected with an HCV strain that is resistant to one or more different anti-HCV agents (for example, an agent used in a conventional standard of care). In some embodiments, development of resistant HCV strains is delayed when a subject is treated with a compound of Formulae (I) and/or (II), or a pharmaceutically acceptable salt of the foregoing, compared to the development of HCV strains resistant to other HCV drugs (such as an agent used in a conventional standard of care).

In some embodiments, an effective amount of a compound of Formulae (I) and/or (II), or a pharmaceutically acceptable salt of the foregoing, can be administered to a subject for whom other anti-HCV medications are contraindicated. For example, administration of pegylated interferon alpha in combination with ribavirin is contraindicated in subjects with hemoglobinopathies (e.g., thalassemia major, sickle-cell anemia) and other subjects at risk from the hematologic side effects of current therapy. In some embodiments, a compound of Formulae (I) and/or (II), or a pharmaceutically acceptable salt of the foregoing, can be provided to a subject that is hypersensitive to interferon and/or ribavirin.

Some subjects being treated for HCV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, a compound of Formulae (I) and/or (II), or a pharmaceutically acceptable salt of the foregoing, can be administered to a subject experiencing viral load rebound, or can prevent such viral load rebound when used to treat the subject.

The standard of care for treating HCV has been associated with several side effects (adverse events). In some embodiments, a compound of Formulae (I) and/or (II), or a pharmaceutically acceptable salt of the foregoing, can decrease the number and/or severity of side effects that can be observed in HCV patients being treated with ribavirin and pegylated interferon according to the standard of care. Examples of side effects include, but are not limited to fever, malaise, tachycardia, chills, headache, arthralgias, myalgias, fatigue, apathy, loss of appetite, nausea, vomiting, cognitive changes, asthenia, drowsiness, lack of initiative, irritability, confusion, depression, severe depression, suicidal ideation, anemia, low white blood cell counts, and thinning of hair. In some embodiments, a compound of Formulae (I) and/or (II), or a pharmaceutically acceptable salt of the foregoing, can be provided to a subject that discontinued a HCV therapy because of one or more adverse effects or side effects associated with one or more other HCV agents (for example, an agent used in a conventional standard of care).

In some embodiments, a compound described herein (for example, a compound of Formulae (I) and/or (II), or a pharmaceutical acceptable salt of the foregoing) can be ameliorate and/or treat a Flavivirus infection. In some embodiments, a compound described herein (for example, a compound of Formulae (I) and/or (II), or a pharmaceutical acceptable salt of the foregoing) can inhibit replication of a Flavivirus.

In some embodiments, the Flavivirus can be a West Nile virus. A West Nile infection can lead to West Nile fever or severe West Nile disease (also called West Nile encephalitis or meningitis or West Nile poliomyelitis). Symptoms of West Nile fever include fever, headache, tiredness, body aches, nausea, vomiting, a skin rash (on the trunk of the body) and swollen lymph glands. Symptoms of West Nile disease include headache, high fever, neck stiffness, stupor, disorientation, coma, tremors, convulsions, muscle weakness and paralysis. Current treatment for a West Nile virus infection is supportive, and no vaccination is currently available for humans.

In some embodiments, a compound described herein (for example, a compound of Formulae (I) and/or (II), or a pharmaceutical acceptable salt of the foregoing) can treat and/or ameliorate a dengue virus, such as DENV-1, DENV-2, DENV-3 and DENV-4. A dengue virus infection can cause dengue hemorrhagic fever and/or dengue shock syndrome. In some embodiments, a compound described herein (for example, a compound of Formulae (I) and/or (II), or a pharmaceutical acceptable salt of the foregoing) can treat and/or ameliorate dengue hemorrhagic fever and/or dengue shock syndrome. According to the World Health Organization (WHO), global incidence of dengue has grown dramatically in recent decades. To date, there is no treatment for a dengue virus infection. Further, recovery from an infection of one serotype of dengue virus provides only partial and temporary immunity against the other serotypes. Subsequent infection(s) with another serotypes increases the likelihood of developing severe dengue (previously known as dengue hemorrhagic fever). A dengue infection is suspected with a high fever (approx. 104° F.) accompanied by one or more of the following symptoms: severe headache, pain behind the eyes, muscle and joint pain, nausea, vomiting, swollen glands and rash.

Yellow fever is an acute viral hemorrhagic disease. As provided by the WHO, up to 50% of severely affected persons without treatment die from yellow fever. An estimated 200,000 cases of yellow fever, causing 30,000 deaths, worldwide occur each year. As with other Flaviviruses, there is no cure or specific treatment for yellow fever, and treatment with ribavirin and interferons are insufficient. In some embodiments, the Flavivirus can be yellow fever virus. Symptoms of a yellow fever infection include fever, muscle pain with prominent backache, headache, shivers, loss of appetite, nausea, vomiting, jaundice and bleeding (for example from the mouth, nose, eyes and/or stomach).

In yet still other embodiments, the Flavivirus can be an encephalitis virus from within the Flavivirus genus. Examples of encephalitis viruses include, but are not limited to, Japanese encephalitis virus, St. Louis encephalitis virus and tick borne encephalitis. Viral encephalitis causes inflammation of the brain and/or meninges. Symptoms include high fever, headache, sensitivity to light, stiff neck and back, vomiting, confusion, seizures, paralysis and coma. There is no specific treatment for an encephalitis infection, such as Japanese encephalitis, St. Louis encephalitis and tick borne encephalitis.

Various indicators for determining the effectiveness of a method for treating an Picornavirus and/or Flaviviridae viral infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator(s) of disease response. Further indicators include one or more overall quality of life health indicators, such as reduced illness duration, reduced illness severity, reduced time to return to normal health and normal activity, and reduced time to alleviation of one or more symptoms. In some embodiments, a compound of Formulae (I) and/or (II), or a pharmaceutically acceptable salt of the foregoing, can result in the reduction, alleviation or positive indication of one or more of the aforementioned indicators compared to a subject who is receiving the standard of care (for HCV) or an untreated subject (picornavirus, and other Flaviviridae infections besides HCV). Effects/symptoms of a Picornavirus infection are described herein, and include, but are not limited to, fever, blisters, rash, meningitis, conjunctivitis, acute hemorrhagic conjunctivitis (AHC), sore throat, nasal congestion, runny nose, sneezing, coughing, loss of appetite, muscle aches, headache, fatigue, nausea, jaundice, encephalitis, herpangina, myocarditis, pericarditis, meningitis, Bornholm disease, myalgia, nasal congestion, muscle weakness, loss of appetite, fever, vomiting, abdominal pain, abdominal discomfort, dark urine and muscle pain. Effects/symptoms of a Flaviviridae virus infection are also described herein.

In some embodiments, a compound of Formulae (I) and/or (II), or a pharmaceutically acceptable salt of the foregoing, can result in a reduction in the length and/or severity of one or more symptoms associated with a Picornavirus or a Flaviviridae virus infection compared to a subject who is receiving the standard of care (for HCV) or an untreated subject (picornavirus, and other Flaviviridae infection besides HCV). Table 1 provides some embodiments of the percentage improvements obtained using a compound of Formulae (I) and/or (II), or a pharmaceutically acceptable salt of the foregoing, as compared to the standard of care (for HCV) or an untreated subject (picornavirus, and other Flaviviridae infection besides HCV). Examples include the following: in some embodiments, a compound of Formulae (I) and/or (II), or a pharmaceutically acceptable salt of the foregoing, results in a percentage of non-responders that is 10% less than the percentage of non-responders receiving the standard of care for HCV; in some embodiments, a compound of Formulae (I) and/or (II), or a pharmaceutically acceptable salt of the foregoing, results in a duration of illness that is in the range of about 10% to about 30% less than compared to the duration of illness experienced by a subject who is untreated for a yellow fever viral infection; and in some embodiments, a compound of Formulae (I) and/or (II), or a pharmaceutically acceptable salt of the foregoing, results in a severity of a symptom (such as one of those described herein) that is 25% less than compared to the severity of the same symptom experienced by a subject who is untreated for a dengue virus infection. Methods of quantifying the severity of a side effect and/or symptom are known to those skilled in the art.

TABLE 1

| Percentage of non-responders | Percentage of relapsers | Percentage of resistance | Percentage of viral load rebound | Number of side effects | Severity of side effect(s) |
|---|---|---|---|---|---|
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |
| Duration of illness | Duration of illness | Duration of illness | Severity of symptom(s) | Severity of symptom(s) | Severity of symptom(s) |
| 10% less | 60% less | about 10% to about 30% less | 10% less | 60% less | about 10% to about 30% less |
| 25% less | 70% less | about 20% to about 50% less | 25% less | 70% less | about 20% to about 50% less |
| 40% less | 80% less | about 30% to about 70% less | 40% less | 80% less | about 30% to about 70% less |
| 50% less | 90% less | about 20% to about 80% less | 50% less | 90% less | about 20% to about 80% less |

In some embodiments, the compound can be a compound of Formulae (I) and/or (II), or a pharmaceutical acceptable salt of the foregoing, wherein $R^{1A}$ is hydrogen. In other embodiments, the compound can be a compound of Formulae (I) and/or (II), wherein compound of Formulae (I) and/or (II) is a mono, di, or triphosphate, or a pharmaceutically acceptable salt of the foregoing. In still other embodiments, the compound can be a compound of Formulae (I) and/or (II), wherein compound of Formulae (I) and/or (II) is a thiomonophosphate, alpha-thiodiphosphate, or alpha-thiotriphosphate, or a pharmaceutically acceptable salt of the foregoing. In some embodiments, the compound of Formulae (I) and/or (II), or a pharmaceutical acceptable salt of the foregoing, that can be used to ameliorate and/or treat a Picornavirus infection and/or inhibit replication of a Picornavirus can be any of the embodiments provided in any of the embodiments described in the paragraphs that begins with the first paragraph under the heading "Compounds" and ends with the paragraph that follows and recites in its last lines

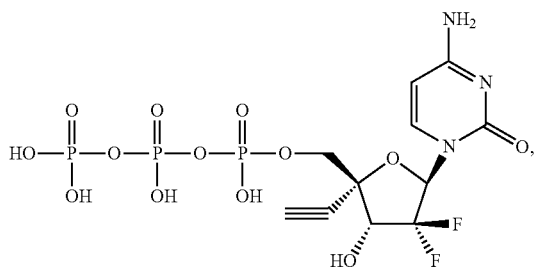

or a pharmaceutically acceptable salt of the foregoing."

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The terms "therapeutically effective amount" and "effective amount" are used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formulae (I) and/or (II), or a pharmaceutically acceptable salt of the foregoing, can be administered less frequently compared to the frequency of administration of an agent within the standard of care. In some embodiments, a compound of Formulae (I) and/or (II), or a pharmaceutically acceptable salt of the foregoing, can be administered one time per day. For example, a compound of Formulae (I) and/or (II), or a pharmaceutically acceptable salt of the foregoing, can be administered one time per day to a subject suffering from a HCV infection. In some embodiments, the total time of the treatment regime with a compound of Formulae (I) and/or (II), or a pharmaceutically acceptable salt of the foregoing, can less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, a compound of Formulae (I) and/or (II), or a pharmaceutically acceptable salt of the foregoing, can have a moiety(ies) that neutralize the charge of the phosphate or thiophosphate. By neutralizing the charge on the phosphate or thiophosphate, penetration of the cell membrane may be facilitated as a result of the increased lipophilicity of the compound. Once absorbed and taken inside the cell, the groups attached to the phosphorus can be easily removed by esterases, proteases and/or other enzymes. In some embodiments, the groups attached to the phosphorus can be removed by simple hydrolysis. Inside the cell, the phosphate thus released may then be metabolized by cellular enzymes to the diphosphate or the active triphosphate. Likewise, the thio-phosphate may be metabolized to the alpha-thiodiphosphate or the alpha-thiotriphosphate. Furthermore, in some embodiments, varying the substituents on a compound described herein, such as a compound of Formulae (I) and/or (II), or a pharmaceutically acceptable salt of the foregoing, can help maintain the efficacy of such the compound by reducing undesirable effects, such as isomerization.

In some embodiments, the phosphorylation of a thio-monophosphate of a compound of Formulae (I) and/or (II), or a pharmaceutically acceptable salt of the foregoing, can be stereoselective. For example, a thio-monophosphate of a compound of Formulae (I) and/or (II) can be phosphorylated to give an alpha-thiodiphosphate and/or an alpha-thiotriphosphate compound that can be enriched in the (R) or (S) diastereomer with respect to the 5'-O-phosphorous atom. For example, one of the (R) and (S) configuration with respect to the 5'-O-phosphorous atom of the alpha-thiodiphosphate and/or the alpha-thiotriphosphate compound can be present in an amount >50%, ≥75%, ≥90%, ≥95% or ≥99% compared to the amount of the other of the (R) or (S) configuration with respect to the 5'-O-phosphorous atom. In some embodiments, phosphorylation of a compound of Formulae (I) and/or (II), or a pharmaceutically acceptable salt of the foregoing, can result in the formation of a compound that has the (R)-configuration at the 5'-O-phosphorous atom. In some embodiments, phosphorylation of a compound of Formulae (I) and/or (II), or a pharmaceutically acceptable salt of the foregoing, can result in formation of a compound that has the (S)-configuration at the 5'-O-phosphorous atom.

In some embodiments, a compound of Formulae (I) and/or (II), or a pharmaceutically acceptable salt of the foregoing, can act as a chain terminator of RNA synthesis. For example, compounds of Formulae (I) and/or (II) can contain a moiety at the 2'-carbon position such that once the compound is incorporated into an RNA chain, no further elongation is observed to occur. For example, a compound of Formulae (I) and/or (II), or a pharmaceutically acceptable salt of the foregoing, can contain a non-hydrogen 2'-carbon modification such as an optionally substituted $C_{1-6}$ alkyl, an optionally substituted $C_{2-6}$ alkenyl or an optionally substituted $C_{2-6}$ alkynyl.

In some embodiments, a compound of Formulae (I) and/or (II), or a pharmaceutically acceptable salt of the foregoing, can have increased metabolic and/or plasma stability. In some embodiments, a compound of Formulae (I) and/or (II), or a pharmaceutically acceptable salt of the foregoing, can be more resistant to hydrolysis and/or more resistant to enzymatic transformations. For example, a compound of Formulae (I) and/or (II), or a pharmaceutically acceptable salt of the foregoing, can have increased metabolic stability, increased plasma stability, can be more resistant to hydrolysis and/or can be more resistant to enzymatic transformations compared to a compound that is identical in structure but for having $O^1$ as OH, $R^A$, $R^{2A}$, $R^{5A}$, $R^{a1}$ and $R^{a2}$ are each hydrogen and $R^{3A}$ and $R^{4A}$ are each OH. In some embodiments, a compound of Formulae (I) and/or (II), or a pharmaceutically acceptable salt of the foregoing, can have improved properties. A non-limiting list of example properties include, but are not limited to, increased biological half-life, increased bioavailability, increase potency, a sustained in vivo response, increased dosing intervals, decreased dosing amounts, decreased cytotoxicity, reduction in required amounts for treating disease conditions, reduction in viral load, reduction in time to seroconversion (i.e., the virus becomes undetectable in patient serum), increased sustained viral response, a reduction of morbidity or mortality in clinical outcomes, increased subject compliance, decreased liver conditions (such as liver fibrosis, liver cirrhosis and/or liver cancer), and compatibility with other medications. In some embodiments, a compound of Formulae (I) and/or (II), or a pharmaceutically acceptable salt of the foregoing, can have a biological half-life of greater than 24 hours. In some embodiments, a compound of Formulae (I) and/or (II), or a pharmaceutically acceptable salt of the foregoing, can have a biological half-life greater than a compound that is identical in structure but for having $O^1$ as OH, $R^A$, $R^{2A}$, $R^{5A}$, $R^{a1}$ and $R^{a2}$ are each hydrogen and $R^{3A}$ and $R^{4A}$ are each OH. In some embodiments, a compound of Formulae (I) and/or (II), or a pharmaceutically acceptable salt of the foregoing, can have more potent antiviral activity compared to a compound that is identical in structure but for having $O^1$ as OH, $R^A$, $R^{2A}$, $R^{5A}$, $R^{a1}$ and $R^{a2}$ are each hydrogen and $R^{3A}$ and $R^{4A}$ are each OH.

Additionally, in some embodiments, the presence of a moiety(ies) that neutralizes the charge of the phosphate or thiophosphate can increase the stability of the compound by inhibiting its degradation. Also, in some embodiments, the presence of a moiety(ies) that neutralizes the charge of the phosphate or thiophosphate can make the compound more resistant to cleavage in vivo and provide sustained, extended efficacy. In some embodiments, a moiety(ies) that neutralizes the charge of the phosphate or thiophosphate can facilitate the penetration of the cell membrane by a compound of Formulae (I) and/or (II) by making the compound more lipophilic. In some embodiments, a moiety(ies) that neutralizes the charge of the phosphate or thiophosphate can have improved oral bioavailability, improved aqueous stability and/or reduced risk of byproduct-related toxicity. In some embodiments, for comparison purposes, a compound of Formulae (I) and/or (II) can be compared to a compound that is identical in structure but for having $O^1$ as OH, $R^A$, $R^{2A}$, $R^{5A}$, $R^{a1}$ and $R^{a2}$ are each hydrogen and $R^{3A}$ and $R^{4A}$ are each OH.

Combination Therapies

In some embodiments, the compounds disclosed herein, such as a compound of Formulae (I) and/or (II), or a pharmaceutically acceptable salt of the foregoing, or a pharmaceutical composition that includes a compound described herein, or a pharmaceutically acceptable salt thereof, can be used in combination with one or more additional agent(s) for treating, ameliorating and/or inhibiting a Picornavirus and/or Flaviviridae viral infection.

In some embodiments, a compound of Formulae (I) and/or (II), or a pharmaceutically acceptable salt of the foregoing, can be administered with one or more additional agent(s) together in a single pharmaceutical composition. In some embodiments, a compound of Formulae (I) and/or (II), or a pharmaceutically acceptable salt of the foregoing, can be administered with one or more additional agent(s) as two or more separate pharmaceutical compositions. For example, a compound of Formulae (I) and/or (II), or a pharmaceutically acceptable salt of the foregoing, can be administered in one pharmaceutical composition, and at least one of the additional agents can be administered in a second pharmaceutical composition. If there are at least two additional agents, one or more of the additional agents can be in a first pharmaceutical composition that includes a compound of Formulae (I) and/or (II), or a pharmaceutically acceptable salt of the foregoing, and at least one of the other additional agent(s) can be in a second pharmaceutical composition.

The dosing amount(s) and dosing schedule(s) when using a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, and one or more additional agents are within the knowledge of those skilled in the art. For example, when performing a conventional standard of care therapy using art-recognized dosing amounts and dosing schedules, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be administered in addition to that therapy, or in place of one of the agents of a combination therapy, using effective amounts and dosing protocols as described herein.

The order of administration of a compound of Formulae (I) and/or (II), or a pharmaceutically acceptable salt of the foregoing, with one or more additional agent(s) can vary. In some embodiments, a compound of Formulae (I) and/or (II), or a pharmaceutically acceptable salt of the foregoing, can be administered prior to all additional agents. In other embodiments, a compound of Formulae (I) and/or (II), or a pharmaceutically acceptable salt of the foregoing, can be administered prior to at least one additional agent. In still other embodiments, a compound of Formulae (I) and/or (II), or a pharmaceutically acceptable salt of the foregoing, can be administered concomitantly with one or more additional agent(s). In yet still other embodiments, a compound of Formulae (I) and/or (II), or a pharmaceutically acceptable salt of the foregoing, can be administered subsequent to the administration of at least one additional agent. In some embodiments, a compound of Formulae (I) and/or (II), or a pharmaceutically acceptable salt of the foregoing, can be administered subsequent to the administration of all additional agents.

In some embodiments, the combination of a compound of Formulae (I) and/or (II), or a pharmaceutically acceptable salt of the foregoing, in combination with one or more additional agent(s) can result in an additive effect. In some embodiments, the combination of a compound of Formulae (I) and/or (II), or a pharmaceutically acceptable salt of the foregoing, used in combination with one or more additional agent(s) can result in a synergistic effect. In some embodiments, the combination of a compound of Formulae (I) and/or (II), or a pharmaceutically acceptable salt of the foregoing, used in combination with one or more additional agent(s) can result in a strongly synergistic effect. In some embodiments, the combination of a compound of Formulae (I) and/or (II), or a pharmaceutically acceptable salt of the foregoing, in combination with one or more additional agent(s) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formulae (I) and/or (II), or a pharmaceutically acceptable salt of the foregoing, in combination with one or more additional agent(s) may be a reduction in the required amount(s) of one or more additional agent(s) that is effective in treating a disease condition disclosed herein (for example, picornavirus and/or Flaviviridae virus infection), as compared to the amount required to achieve same therapeutic result when one or more additional agent(s) are administered without a compound of Formulae (I) and/or (II), or a pharmaceutically acceptable salt of the foregoing. For example, for treating HCV, the amount of a compound in FIGS. 1-9 (including a pharmaceutically acceptable salt thereof), can be less compared to the amount of the compound in FIGS. 1-9 (including a pharmaceutically acceptable salt thereof), needed to achieve the same viral load reduction when administered as a monotherapy. Another potential advantage of utilizing a compound of Formulae (I) and/or (II), or a pharmaceutically acceptable salt of the foregoing, in combination with one or more additional agent(s) is that the use of two or more compounds having different mechanism of actions can create a higher barrier to the development of resistant viral strains compared to the barrier when a compound is administered as monotherapy.

Additional advantages of utilizing a compound of Formulae (I) and/or (II), or a pharmaceutically acceptable salt of the foregoing, in combination with one or more additional agent(s) may include little to no cross resistance between a compound of Formulae (I) and/or (II), or a pharmaceutically acceptable salt of the foregoing, and one or more additional agent(s) thereof; different routes for elimination of a compound of Formulae (I) and/or (II), or a pharmaceutically acceptable salt of the foregoing, and one or more additional agent(s); little to no overlapping toxicities between a compound of Formulae (I) and/or (II), or a pharmaceutically acceptable salt of the foregoing, and one or more additional agent(s); little to no significant effects on cytochrome P450; little to no pharmacokinetic interactions between a compound of Formulae (I) and/or (II), or a pharmaceutically acceptable salt of the foregoing, and one or more additional agent(s); greater percentage of subjects achieving a sustained viral response compared to when a compound is administered as monotherapy and/or a decrease in treatment time to achieve a sustained viral response compared to when a compound is administered as monotherapy.

For treating of a picornavirus and/or a Flaviviridae virus infection other than HCV, examples of additional agents that can be used in combination with a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, include, but are not limited to, ribavirin and an interferon (including those described herein).

For the treatment of HCV, examples of additional agents that can be used in combination with a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, include, but are not limited to, agents currently used in a conventional standard of care for treating HCV, HCV protease inhibitors, HCV polymerase inhibitors, NS5A inhibitors, other antiviral compounds, compounds of Formula (AA), (including pharmaceutically acceptable salts and pharmaceutical compositions that can include a compound of Formula (AA), or a pharmaceutically acceptable salt thereof), compounds of Formula (BB) (including pharmaceutically acceptable salts and pharmaceutical compositions that can include a compound of Formula (BB), or a pharmaceutically acceptable salt thereof), compounds of Formula (CC) (including pharmaceutically acceptable salts and pharmaceutical compositions that can include a compound of Formula (CC), or a pharmaceutically acceptable salt thereof), and/or combinations thereof. In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used with one, two, three or more additional agents described herein. A non-limiting list of examples of combinations of a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, is provided in Tables A, B, C, D and E.

In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used in combination with an agent(s) currently used in a conventional standard of care therapy. For example, for the treatment of HCV, a compound disclosed herein can be used in combination with Pegylated interferon-alpha-2a (brand name PEGASYS®) and ribavirin, Pegylated interferon-alpha-2b (brand name PEG-INTRON®) and ribavirin, Pegylated interferon-alpha-2a, Pegylated interferon-alpha-2a, or ribavirin.

In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be substituted for an agent currently used in a conventional standard of care therapy. For example, for the treatment of HCV, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used in place of ribavirin.

In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used in combination with an interferon, such as a pegylated interferon. Examples of suitable interferons include, but are not limited to, Pegylated interferon-alpha-2a (brand name PEGASYS®), Pegylated interferon-alpha-2b (brand name PEG-INTRON®), interferon alfacon-1 (brand name INFERGEN®), pegylated interferon lambda and/or a combination thereof.

In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used in combination with a HCV protease inhibitor. A non-limiting list of example HCV protease inhibitors include the following: VX-950 (TELAPREVIR®), MK-5172, ABT-450, BILN-2061, BI-201335, BMS-650032, SCH 503034 (BOCEPREVIR®), GS-9256, GS-9451, IDX-320, ACH-1625, ACH-2684, TMC-435, ITMN-191 (DANOPREVIR®) and/or a combination thereof. Additional HCV protease inhibitors suitable for use in combination with a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, include VP-19744, PSI-879, VCH-759/VX-759, HCV-371, IDX-375, GL-60667, JTK-109, PSI-6130, R1479, R-1626, R-7182, MK-0608, INX-8014, INX-8018, A-848837, A-837093, BILB-1941, VCH-916, VCH-716, GSK-71185, GSK-625433, XTL-2125 and those disclosed in PCT Publication No. WO 2012/142085, which is hereby incorporated by reference for the limited purpose of its disclosure of HCV protease inhibitors, HCV polymerase inhibitors and NS5A inhibitors. A non-limiting list of example HCV protease inhibitors includes the compounds numbered 1001-1016 in FIG. 1.

In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used in combination with a HCV polymerase inhibitor. In some embodiments, the HCV polymerase inhibitor can be a nucleoside inhibitor. In other embodiments, the HCV polymerase inhibitor can be a non-nucleoside inhibitor. Examples of suitable nucleoside inhibitors include, but are not limited to, RG7128, PSI-7851, PSI-7977, INX-189, PSI-352938, PSI-661, 4'-azidouridine (including known prodrugs of 4'-azidouridine), GS-6620, IDX-184, and TMC649128 and/or combinations thereof. A non-limiting list of example nucleoside inhibitors includes compounds numbered 2001-2012 in FIG. 2. Examples of suitable non-nucleoside inhibitors include, but are not limited to, ABT-333, ANA-598, VX-222, HCV-796, BI-207127, GS-9190, PF-00868554 (FILIBUVIR®), VX-497 and/or combinations thereof. A non-limiting list of example non-nucleoside inhibitors includes the compounds numbered 3001-3014 in FIG. 3. Further HCV polymerase inhibitors suitable for use in combination with a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, include VX-500, VX-813, VBY-376, TMC-435350, EZ-058, EZ-063, GS-9132, ACH-1095, IDX-136, IDX-316, ITMN-8356, ITMN-8347, ITMN-8096, ITMN-7587, VX-985, and those disclosed in PCT Publication No. WO 2012/142085.

In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used in combination with a NS5A inhibitor. Examples of NS5A inhibitors include BMS-790052, PPI-461, ACH-2928, GS-5885, BMS-824393 and/or combinations thereof. A non-limiting list of example NS5A inhibitors includes the compounds numbered 4001-4012 in FIG. 4. Additional NS5A inhibitors suitable for use in combination with a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, include A-832, PPI-1301 and those disclosed in PCT Publication No. WO 2012/142085.

In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used in combination with other antiviral compounds. Examples of other antiviral compounds include, but are not limited to, Debio-025, a MIR-122 inhibitor (for example, Miravirsen (SPC3649)), cyclosporin A and/or combinations thereof. A non-limiting list of example other antiviral compounds includes the compounds numbered 5001-5011 in FIG. 5.

In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used in combination with a compound of Formula (AA), or a pharmaceutically acceptable salt thereof, or a pharmaceutical composition that includes a compound of Formula (AA), or a pharmaceutically acceptable salt thereof (see, U.S. Publication No. 2013/0164261 A1, filed Dec. 20, 2012, the contents of which are incorporated by reference in its entirety):

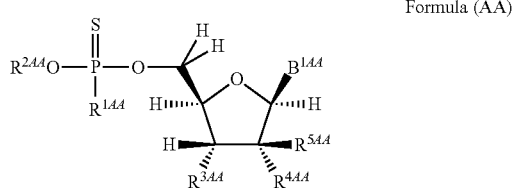

Formula (AA)

wherein: $B^{A A 1}$ can be an optionally substituted heterocyclic base or an optionally substituted heterocyclic base with a protected amino group; $R^{AA1}$ can be selected from O⁻, OH, an optionally substituted N-linked amino acid and an optionally substituted N-linked amino acid ester derivative; $R^{AA2}$ can be absent or selected from hydrogen, an optionally substituted aryl, an optionally substituted heteroaryl, an optionally substituted heterocyclyl and

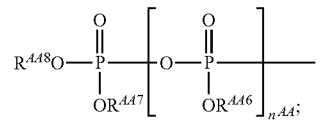

wherein $R^{AA6}$, $R^{AA7}$ and $R^{AA8}$ can be independently absent or hydrogen, and $n^{AA}$ can be 0 or 1; provided that when $R^{AA1}$ is O⁻ or OH, then $R^{AA2}$ is absent, hydrogen or

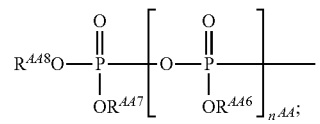

$R^{AA3}$ can be selected from hydrogen, halogen, —OR$^{AA9}$ and —OC(=O)R$^{AA10}$; $R^{AA4}$ can be selected from halogen, —OR$^{AA11}$ and —OC(=O)R$^{AA12}$; or $R^{AA3}$ and $R^{AA4}$ can be both an oxygen atom which are linked together by a carbonyl group; $R^{AA5}$ can be selected from an optionally substituted $C_{2-6}$ alkyl, an optionally substituted $C_{2-6}$ alkenyl, an optionally substituted $C_{2-6}$ alkynyl and an optionally substituted $C_{3-6}$ cycloalkyl; or $R^{AA4}$ and $R^{AA5}$ together can form —($C_{1-6}$ alkyl)-O— or —O—($C_{1-6}$ alkyl)-; $R^{AA9}$ and $R^{AA11}$ can be independently hydrogen or an optionally substituted $C_{1-6}$ alkyl; and $R^{AA10}$ and $R^{AA12}$ can be independently an optionally substituted $C_{1-6}$ alkyl or an optionally substituted $C_{3-6}$ cycloalkyl. A non-limiting list of examples of compounds of Formula (AA) includes the compounds numbered 7000-7027 in FIG. 7.

In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used in combination with a compound of Formula (BB), or a pharmaceutically acceptable salt thereof, or a pharmaceutical composition that includes a compound of Formula (BB), or a pharmaceutically acceptable salt thereof (see, U.S. Publication No. 2012/0165286, published Jun. 28, 2012, the contents of which are incorporated by reference in their entireties):

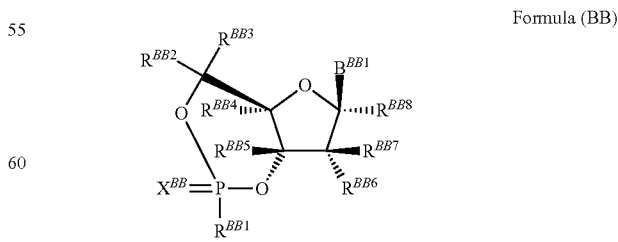

Formula (BB)

wherein $B^{BB1}$ can be an optionally substituted heterocyclic base or an optionally substituted heterocyclic base with a protected amino group; $X^{BB}$ can be O (oxygen) or S (sulfur);

$R^{BB1}$ can be selected from $-Z^{BB}-R^{BB9}$, an optionally substituted N-linked amino acid and an optionally substituted N-linked amino acid ester derivative; $Z^{BB}$ can be selected from O (oxygen), S (sulfur) and $N(R^{BB10})$; $R^{BB2}$ and $R^{BB3}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl); or $R^{BB2}$ and $R^{BB3}$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl; $R^{BB4}$ can be selected from hydrogen, halogen, azido, cyano, an optionally substituted $C_{1-6}$ alkyl, an optionally substituted $C_{2-6}$ alkenyl, an optionally substituted $C_{2-6}$ alkynyl and an optionally substituted allenyl; $R^{BB5}$ can be hydrogen or an optionally substituted $C_{1-6}$ alkyl; $R^{BB6}$ can be selected from hydrogen, halogen, azido, amino, cyano, an optionally substituted $C_{1-6}$ alkyl, $-OR^{BB11}$ and $-OC(=O)R^{BB12}$; $R^{BB7}$ can be selected from hydrogen, halogen, azido, cyano, an optionally substituted $C_{1-6}$ alkyl, $-OR^{BB13}$ and $-OC(=O)R^{BB14}$; $R^{BB8}$ can be selected from hydrogen, halogen, azido, cyano, an optionally substituted $C_{1-6}$ alkyl, $-OR^{BB15}$ and $-OC(=O)R^{BB16}$; $R^{BB9}$ can be selected from an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl($C_{1-6}$alkyl); $R^{BB10}$ can be selected from hydrogen, an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl ($C_{1-6}$alkyl); $R^{BB11}$, $R^{BB13}$ and $R^{BB15}$ can be independently hydrogen or an optionally substituted $C_{1-6}$ alkyl; and $R^{BB12}$, $R^{BB14}$ and $R^{BB16}$ can be independently an optionally substituted $C_{1-6}$ alkyl or an optionally substituted $C_{3-6}$ cycloalkyl. In some embodiments, at least one of $R^{BB2}$ and $R^{BB3}$ is not hydrogen. A non-limiting list of example compounds of Formula (BB) includes the compound numbered 8000-8016 in FIG. 8.

In some embodiments, a compound of Formulae (I) and/or (II), or a pharmaceutically acceptable salt of the foregoing, or a pharmaceutical composition that includes a compound of Formulae (I) and/or (II), or a pharmaceutically acceptable salt of the foregoing, can be used in combination with a compound of Formula (CC), or a pharmaceutically acceptable salt thereof, or a pharmaceutical composition that includes a compound of Formula (CC), or a pharmaceutically acceptable salt thereof (see, U.S. Publication No. 2012/0071434, published Mar. 22, 2012, the contents of which are incorporated by reference in its entirety):

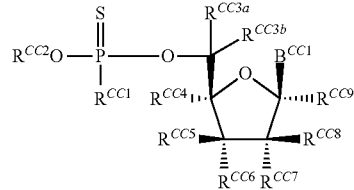

Formula (CC)

wherein $B^{CC1}$ can be an optionally substituted heterocyclic base or an optionally substituted heterocyclic base with a protected amino group; $R^{CC1}$ can be selected from $O^-$, OH, an optionally substituted N-linked amino acid and an optionally substituted N-linked amino acid ester derivative; $R^{CC2}$ can be selected from an optionally substituted aryl, an optionally substituted heteroaryl, an optionally substituted heterocyclyl and

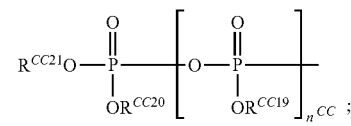

wherein $R^{CC19}$, $R^{CC20}$ and $R^{CC21}$ can be independently absent or hydrogen, and $n^{CC}$ can be 0 or 1; provided that when $R^{CC1}$ is $O^-$ or OH, then $R^{CC2}$ is

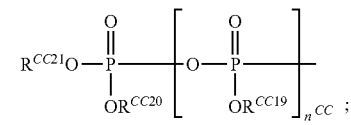

$R^{CC3a}$ and $R^{CC3b}$ can be independently selected from hydrogen, deuterium, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{CC3a}$ and $R^{CC3b}$ can be taken together to form an optionally substituted $C_{3-6}$ cycloalkyl; $R^{CC4}$ can be selected from hydrogen, azido, an optionally substituted $C_{1-6}$ alkyl, an optionally substituted $C_{2-6}$ alkenyl and an optionally substituted $C_{2-6}$ alkynyl; $R^{CC5}$ can be selected from hydrogen, halogen, azido, cyano, an optionally substituted $C_{1-6}$ alkyl, $-OR^{CC10}$ and $-OC(=O)R^{CC11}$; $R^{CC6}$ can be selected from hydrogen, halogen, azido, cyano, an optionally substituted $C_{1-6}$ alkyl, $-OR^{CC12}$ and $-OC(=O)R^{CC13}$; $R^{CC7}$ can be selected from hydrogen, halogen, azido, cyano, an optionally substituted $C_{1-6}$ alkyl, $-OR^{CC14}$ and $-OC(=O)R^{CC15}$; or $R^{CC6}$ and $R^{CC7}$ can be both oxygen atoms and linked together by a carbonyl group; $R^{CC8}$ can be selected from hydrogen, halogen, azido, cyano, an optionally substituted $C_{1-6}$ alkyl, $-OR^{CC16}$ and $-OC(=O)R^{CC17}$; $R^{CC9}$ can be selected from hydrogen, azido, cyano, an optionally substituted $C_{1-6}$ alkyl and $-OR^{CC18}$; $R^{CC10}$, $R^{CC12}$, $R^{CC14}$, $R^{CC16}$ and $R^{CC18}$ can be independently selected from hydrogen and an optionally substituted $C_{1-6}$ alkyl; and $R^{CC11}$, $R^{CC13}$, $R^{CC15}$ and $R^{CC17}$ can be independently selected from an optionally substituted $C_{1-6}$ alkyl and an optionally substituted $C_{3-6}$ cycloalkyl. In some embodiments, when $R^{CC3a}$, $R^{CC3b}$, $R^{CC4}$, $R^{CC5}$, $R^{CC7}$, $R^{CC8}$ and $R^{CC9}$ are all hydrogen, then $R^{CC6}$ is not azido. In some embodiments, $R^{CC2}$ cannot be

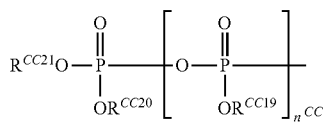

when $R^{CC3a}$ is hydrogen, $R^{CC3b}$ is hydrogen, $R^{CC4}$ is H, $R^{CC5}$ is OH or H, $R^{CC6}$ is hydrogen, OH, or —OC(=O)CH$_3$, $R^{CC7}$ is hydrogen, OH, OCH$_3$ or —OC(=O)CH$_3$, $R^{CC8}$ is hydrogen, OH or OCH$_3$, $R^{CC9}$ is H and $B^{CC1}$ is an optionally substituted adenine, an optionally substituted guanine, an optionally substituted uracil or an optionally substituted hypoxanthine. In some embodiments, $R^{CC2}$ cannot be

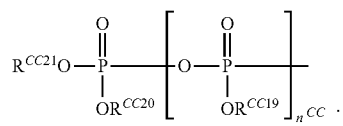

A non-limiting list of examples of compounds of Formula (CC) includes the compounds numbered 6000-6078 in FIG. 6.

Some embodiments described herein relate to a method of ameliorating or treating a Picornavirus and/or a Flaviviridae viral infection that can include contacting a cell infected with the virus with an effective amount of a compound of Formulae (I) and/or (II), or a pharmaceutically acceptable salt of the foregoing, in combination with one or more agents selected from an interferon, ribavirin, a compound of Formula (AA), a compound of Formula (BB) and a compound of Formula (CC), or a pharmaceutically acceptable salt of any of the aforementioned compounds. Some embodiments described herein relate to a method of ameliorating or treating a HCV infection that can include contacting a cell infected with the HCV infection with an effective amount of a compound of Formulae (I) and/or (II), or a pharmaceutically acceptable salt of the foregoing, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

Some embodiments described herein relate to a method of ameliorating or treating a Picornavirus and/or a Flaviviridae viral infection that can include administering to a subject suffering from the viral infection an effective amount of a compound of Formulae (I) and/or (II), or a pharmaceutically acceptable salt of the foregoing, in combination with one or more agents selected from an interferon, ribavirin, a compound of Formula (AA), a compound of Formula (BB) and a compound of Formula (CC), or a pharmaceutically acceptable salt of any of the aforementioned compounds. Some embodiments described herein relate to a method of ameliorating or treating a HCV infection that can include administering to a subject suffering from the HCV infection an effective amount of a compound of Formulae (I) and/or (II), or a pharmaceutically acceptable salt of the foregoing, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

Some embodiments described herein relate to a method of inhibiting the replication of a Picornavirus and/or a Flaviviridae virus that can include contacting a cell infected with the virus with an effective amount of a compound of Formulae (I) and/or (II), or a pharmaceutically acceptable salt of the foregoing, in combination with one or more agents selected from an interferon, ribavirin, a compound of Formula (AA), a compound of Formula (BB) and a compound of Formula (CC), or a pharmaceutically acceptable salt of any of the aforementioned compounds. Some embodiments described herein relate to a method of inhibiting the replication of a hepatitis C virus that can include contacting a cell infected with the hepatitis C virus with an effective amount of a compound of Formulae (I) and/or (II), or a pharmaceutically acceptable salt of the foregoing, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

Some embodiments described herein relate to a method of inhibiting the replication of a Picornavirus and/or a Flaviviridae virus that can include administering to a subject infected with the virus an effective amount of a compound of Formulae (I) and/or (II), or a pharmaceutically acceptable salt of the foregoing, in combination with one or more agents selected from an interferon, ribavirin, a compound of Formula (AA), a compound of Formula (BB) and a compound of Formula (CC), or a pharmaceutically acceptable salt of any of the aforementioned compounds. Some embodiments described herein relate to a method of inhibiting the replication of a hepatitis C virus that can include administering to a subject infected with the hepatitis C virus an effective amount of a compound of Formulae (I) and/or (II), or a pharmaceutically acceptable salt of the foregoing, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB), a compound of Formula (CC), or a pharmaceutically acceptable salt of any of the aforementioned compounds.

A non-limiting list of example combination of compounds of Formulae (I) and/or (II), or a pharmaceutically acceptable salt of the foregoing, or a pharmaceutical composition that includes a compound described herein, with one or more additional agent(s) are provided in Tables A, B, C, D and E. Each numbered X and Y compound in Tables A, B, C, D and E has a corresponding name and/or structure provided in FIGS. 1-9. The numbered compounds in Tables A, B, C, D and E includes pharmaceutically acceptable salts of the compounds and pharmaceutical compositions containing the compounds or a pharmaceutically acceptable salt thereof. For example, 1001 includes the compound corresponding to 1001, pharmaceutically acceptable salts thereof, and pharmaceutical compositions that include compound 1001 and/or a pharmaceutically acceptable salt thereof. The combinations exemplified in Tables A, B, C, D and E are designated by the formula X:Y, which represents a combination of a compound X with a compound Y. For example, the combination designated as 1001:9044 in Table A represents a combination of compound 1001 with compound 9044, including pharmaceutically acceptable salts of compound 1001 and/or 9044, and pharmaceutical compositions including compound 1001 and 9044 (including pharmaceutical compositions that include pharmaceutically acceptable salts of compound 1001 and/or compound 9044). Thus, the combination designated as 1001:9044 in Table A represents the combination of Telaprevir (compound 1001, as shown in FIG. 1) and

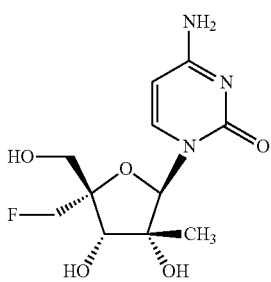 [SMILES: C[C@@]1(O)[C@H](O)[C@](CO)(CF)O[C@H]1n1ccc(N)nc1=O]

(compound 9044, as shown in FIG. 9), including pharmaceutically acceptable salts of compound 1001 and/or 9044, and pharmaceutical compositions including compound 1001 and 9044 (including pharmaceutical compositions that include pharmaceutically acceptable salts of compound 1001 and/or compound 9044). Each of the combinations provided in Tables A, B, C, D and E can be used with one, two, three or more additional agents described herein. In some embodiments described herein, the combination of agents can be used to treat, ameliorate and/or inhibit a virus and/or a viral infection, wherein the virus can be Picornavirus and/or Flaviviridae virus and the viral infection can be a Picornavirus viral infection and/or Flaviviridae virus.

TABLE A

Example combinations of a compound X with a compound Y.

| X:Y | X:Y | X:Y | X:Y | X:Y | X:Y |
|---|---|---|---|---|---|
| 1001:9006 | 1001:9007 | 1001:9008 | 1001:9018 | 1001:9020 | 1001:9021 |
| 1002:9006 | 1002:9007 | 1002:9008 | 1002:9018 | 1002:9020 | 1002:9021 |
| 1003:9006 | 1003:9007 | 1003:9008 | 1003:9018 | 1003:9020 | 1003:9021 |
| 1004:9006 | 1004:9007 | 1004:9008 | 1004:9018 | 1004:9020 | 1004:9021 |
| 1005:9006 | 1005:9007 | 1005:9008 | 1005:9018 | 1005:9020 | 1005:9021 |
| 1006:9006 | 1006:9007 | 1006:9008 | 1006:9018 | 1006:9020 | 1006:9021 |
| 1007:9006 | 1007:9007 | 1007:9008 | 1007:9018 | 1007:9020 | 1007:9021 |
| 1008:9006 | 1008:9007 | 1008:9008 | 1008:9018 | 1008:9020 | 1008:9021 |
| 1009:9006 | 1009:9007 | 1009:9008 | 1009:9018 | 1009:9020 | 1009:9021 |
| 1010:9006 | 1010:9007 | 1010:9008 | 1010:9018 | 1010:9020 | 1010:9021 |
| 1011:9006 | 1011:9007 | 1011:9008 | 1011:9018 | 1011:9020 | 1011:9021 |
| 1012:9006 | 1012:9007 | 1012:9008 | 1012:9018 | 1012:9020 | 1012:9021 |
| 1013:9006 | 1013:9007 | 1013:9008 | 1013:9018 | 1013:9020 | 1013:9021 |
| 1014:9006 | 1014:9007 | 1014:9008 | 1014:9018 | 1014:9020 | 1014:9021 |
| 1015:9006 | 1015:9007 | 1015:9008 | 1015:9018 | 1015:9020 | 1015:9021 |
| 1016:9006 | 1016:9007 | 1016:9008 | 1016:9018 | 1016:9020 | 1016:9021 |
| 2001:9006 | 2001:9007 | 2001:9008 | 2001:9018 | 2001:9020 | 2001:9021 |
| 2002:9006 | 2002:9007 | 2002:9008 | 2002:9018 | 2002:9020 | 2002:9021 |
| 2003:9006 | 2003:9007 | 2003:9008 | 2003:9018 | 2003:9020 | 2003:9021 |
| 2004:9006 | 2004:9007 | 2004:9008 | 2004:9018 | 2004:9020 | 2004:9021 |
| 2005:9006 | 2005:9007 | 2005:9008 | 2005:9018 | 2005:9020 | 2005:9021 |
| 2006:9006 | 2006:9007 | 2006:9008 | 2006:9018 | 2006:9020 | 2006:9021 |
| 2007:9006 | 2007:9007 | 2007:9008 | 2007:9018 | 2007:9020 | 2007:9021 |
| 2008:9006 | 2008:9007 | 2008:9008 | 2008:9018 | 2008:9020 | 2008:9021 |
| 2009:9006 | 2009:9007 | 2009:9008 | 2009:9018 | 2009:9020 | 2009:9021 |
| 2010:9006 | 2010:9007 | 2010:9008 | 2010:9018 | 2010:9020 | 2010:9021 |
| 2011:9006 | 2011:9007 | 2011:9008 | 2011:9018 | 2011:9020 | 2011:9021 |
| 2012:9006 | 2012:9007 | 2012:9008 | 2012:9018 | 2012:9020 | 2012:9021 |
| 1001:9025 | 1001:9026 | 1001:9036 | 1001:9038 | 1001:9039 | 1001:9040 |
| 1002:9025 | 1002:9026 | 1002:9036 | 1002:9038 | 1002:9039 | 1002:9040 |
| 1003:9025 | 1003:9026 | 1003:9036 | 1003:9038 | 1003:9039 | 1003:9040 |
| 1004:9025 | 1004:9026 | 1004:9036 | 1004:9038 | 1004:9039 | 1004:9040 |
| 1005:9025 | 1005:9026 | 1005:9036 | 1005:9038 | 1005:9039 | 1005:9040 |
| 1006:9025 | 1006:9026 | 1006:9036 | 1006:9038 | 1006:9039 | 1006:9040 |
| 1007:9025 | 1007:9026 | 1007:9036 | 1007:9038 | 1007:9039 | 1007:9040 |
| 1008:9025 | 1008:9026 | 1008:9036 | 1008:9038 | 1008:9039 | 1008:9040 |
| 1009:9025 | 1009:9026 | 1009:9036 | 1009:9038 | 1009:9039 | 1009:9040 |
| 1010:9025 | 1010:9026 | 1010:9036 | 1010:9038 | 1010:9039 | 1010:9040 |
| 1011:9025 | 1011:9026 | 1011:9036 | 1011:9038 | 1011:9039 | 1011:9040 |
| 1012:9025 | 1012:9026 | 1012:9036 | 1012:9038 | 1012:9039 | 1012:9040 |
| 1013:9025 | 1013:9026 | 1013:9036 | 1013:9038 | 1013:9039 | 1013:9040 |
| 1014:9025 | 1014:9026 | 1014:9036 | 1014:9038 | 1014:9039 | 1014:9040 |
| 1015:9025 | 1015:9026 | 1015:9036 | 1015:9038 | 1015:9039 | 1015:9040 |
| 1016:9025 | 1016:9026 | 1016:9036 | 1016:9038 | 1016:9039 | 1016:9040 |
| 2001:9025 | 2001:9026 | 2001:9036 | 2001:9038 | 2001:9039 | 2001:9040 |
| 2002:9025 | 2002:9026 | 2002:9036 | 2002:9038 | 2002:9039 | 2002:9040 |
| 2003:9025 | 2003:9026 | 2003:9036 | 2003:9038 | 2003:9039 | 2003:9040 |
| 2004:9025 | 2004:9026 | 2004:9036 | 2004:9038 | 2004:9039 | 2004:9040 |
| 2005:9025 | 2005:9026 | 2005:9036 | 2005:9038 | 2005:9039 | 2005:9040 |
| 2006:9025 | 2006:9026 | 2006:9036 | 2006:9038 | 2006:9039 | 2006:9040 |
| 2007:9025 | 2007:9026 | 2007:9036 | 2007:9038 | 2007:9039 | 2007:9040 |
| 2008:9025 | 2008:9026 | 2008:9036 | 2008:9038 | 2008:9039 | 2008:9040 |
| 2009:9025 | 2009:9026 | 2009:9036 | 2009:9038 | 2009:9039 | 2009:9040 |
| 2010:9025 | 2010:9026 | 2010:9036 | 2010:9038 | 2010:9039 | 2010:9040 |
| 2011:9025 | 2011:9026 | 2011:9036 | 2011:9038 | 2011:9039 | 2011:9040 |
| 2012:9025 | 2012:9026 | 2012:9036 | 2012:9038 | 2012:9039 | 2012:9040 |
| 1001:9041 | 1001:9042 | 1001:9043 | 1001:9044 | 1001:9045 | 1001:9047 |
| 1002:9041 | 1002:9042 | 1002:9043 | 1002:9044 | 1002:9045 | 1002:9047 |
| 1003:9041 | 1003:9042 | 1003:9043 | 1003:9044 | 1003:9045 | 1003:9047 |
| 1004:9041 | 1004:9042 | 1004:9043 | 1004:9044 | 1004:9045 | 1004:9047 |
| 1005:9041 | 1005:9042 | 1005:9043 | 1005:9044 | 1005:9045 | 1005:9047 |
| 1006:9041 | 1006:9042 | 1006:9043 | 1006:9044 | 1006:9045 | 1006:9047 |
| 1007:9041 | 1007:9042 | 1007:9043 | 1007:9044 | 1007:9045 | 1007:9047 |
| 1008:9041 | 1008:9042 | 1008:9043 | 1008:9044 | 1008:9045 | 1008:9047 |
| 1009:9041 | 1009:9042 | 1009:9043 | 1009:9044 | 1009:9045 | 1009:9047 |
| 1010:9041 | 1010:9042 | 1010:9043 | 1010:9044 | 1010:9045 | 1010:9047 |
| 1011:9041 | 1011:9042 | 1011:9043 | 1011:9044 | 1011:9045 | 1011:9047 |
| 1012:9041 | 1012:9042 | 1012:9043 | 1012:9044 | 1012:9045 | 1012:9047 |
| 1013:9041 | 1013:9042 | 1013:9043 | 1013:9044 | 1013:9045 | 1013:9047 |
| 1014:9041 | 1014:9042 | 1014:9043 | 1014:9044 | 1014:9045 | 1014:9047 |
| 1015:9041 | 1015:9042 | 1015:9043 | 1015:9044 | 1015:9045 | 1015:9047 |
| 1016:9041 | 1016:9042 | 1016:9043 | 1016:9044 | 1016:9045 | 1016:9047 |
| 2001:9041 | 2001:9042 | 2001:9043 | 2001:9044 | 2001:9045 | 2001:9047 |
| 2002:9041 | 2002:9042 | 2002:9043 | 2002:9044 | 2002:9045 | 2002:9047 |
| 2003:9041 | 2003:9042 | 2003:9043 | 2003:9044 | 2003:9045 | 2003:9047 |
| 2004:9041 | 2004:9042 | 2004:9043 | 2004:9044 | 2004:9045 | 2004:9047 |
| 2005:9041 | 2005:9042 | 2005:9043 | 2005:9044 | 2005:9045 | 2005:9047 |
| 2006:9041 | 2006:9042 | 2006:9043 | 2006:9044 | 2006:9045 | 2006:9047 |
| 2007:9041 | 2007:9042 | 2007:9043 | 2007:9044 | 2007:9045 | 2007:9047 |
| 2008:9041 | 2008:9042 | 2008:9043 | 2008:9044 | 2008:9045 | 2008:9047 |
| 2009:9041 | 2009:9042 | 2009:9043 | 2009:9044 | 2009:9045 | 2009:9047 |
| 2010:9041 | 2010:9042 | 2010:9043 | 2010:9044 | 2010:9045 | 2010:9047 |
| 2011:9041 | 2011:9042 | 2011:9043 | 2011:9044 | 2011:9045 | 2011:9047 |
| 2012:9041 | 2012:9042 | 2012:9043 | 2012:9044 | 2012:9045 | 2012:9047 |
| 1001:9048 | 1001:9049 | 1001:9051 | 1001:9052 | 1001:9053 | 1001:9054 |
| 1002:9048 | 1002:9049 | 1002:9051 | 1002:9052 | 1002:9053 | 1002:9054 |
| 1003:9048 | 1003:9049 | 1003:9051 | 1003:9052 | 1003:9053 | 1003:9054 |
| 1004:9048 | 1004:9049 | 1004:9051 | 1004:9052 | 1004:9053 | 1004:9054 |
| 1005:9048 | 1005:9049 | 1005:9051 | 1005:9052 | 1005:9053 | 1005:9054 |
| 1006:9048 | 1006:9049 | 1006:9051 | 1006:9052 | 1006:9053 | 1006:9054 |
| 1007:9048 | 1007:9049 | 1007:9051 | 1007:9052 | 1007:9053 | 1007:9054 |
| 1008:9048 | 1008:9049 | 1008:9051 | 1008:9052 | 1008:9053 | 1008:9054 |
| 1009:9048 | 1009:9049 | 1009:9051 | 1009:9052 | 1009:9053 | 1009:9054 |
| 1010:9048 | 1010:9049 | 1010:9051 | 1010:9052 | 1010:9053 | 1010:9054 |
| 1011:9048 | 1011:9049 | 1011:9051 | 1011:9052 | 1011:9053 | 1011:9054 |
| 1012:9048 | 1012:9049 | 1012:9051 | 1012:9052 | 1012:9053 | 1012:9054 |
| 1013:9048 | 1013:9049 | 1013:9051 | 1013:9052 | 1013:9053 | 1013:9054 |
| 1014:9048 | 1014:9049 | 1014:9051 | 1014:9052 | 1014:9053 | 1014:9054 |
| 1015:9048 | 1015:9049 | 1015:9051 | 1015:9052 | 1015:9053 | 1015:9054 |
| 1016:9048 | 1016:9049 | 1016:9051 | 1016:9052 | 1016:9053 | 1016:9054 |
| 2001:9048 | 2001:9049 | 2001:9051 | 2001:9052 | 2001:9053 | 2001:9054 |
| 2002:9048 | 2002:9049 | 2002:9051 | 2002:9052 | 2002:9053 | 2002:9054 |
| 2003:9048 | 2003:9049 | 2003:9051 | 2003:9052 | 2003:9053 | 2003:9054 |
| 2004:9048 | 2004:9049 | 2004:9051 | 2004:9052 | 2004:9053 | 2004:9054 |
| 2005:9048 | 2005:9049 | 2005:9051 | 2005:9052 | 2005:9053 | 2005:9054 |
| 2006:9048 | 2006:9049 | 2006:9051 | 2006:9052 | 2006:9053 | 2006:9054 |
| 2007:9048 | 2007:9049 | 2007:9051 | 2007:9052 | 2007:9053 | 2007:9054 |

TABLE A-continued

Example combinations of a compound X with a compound Y.

| X:Y | X:Y | X:Y | X:Y | X:Y | X:Y |
|---|---|---|---|---|---|
| 2008:9048 | 2008:9049 | 2008:9051 | 2008:9052 | 2008:9053 | 2008:9054 |
| 2009:9048 | 2009:9049 | 2009:9051 | 2009:9052 | 2009:9053 | 2009:9054 |
| 2010:9048 | 2010:9049 | 2010:9051 | 2010:9052 | 2010:9053 | 2010:9054 |
| 2011:9048 | 2011:9049 | 2011:9051 | 2011:9052 | 2011:9053 | 2011:9054 |
| 2012:9048 | 2012:9049 | 2012:9051 | 2012:9052 | 2012:9053 | 2012:9054 |
| 1001:9055 | 1001:9056 | 1001:9058 | 1001:9060 | 1001:9061 | 1001:9062 |
| 1002:9055 | 1002:9056 | 1002:9058 | 1002:9060 | 1002:9061 | 1002:9062 |
| 1003:9055 | 1003:9056 | 1003:9058 | 1003:9060 | 1003:9061 | 1003:9062 |
| 1004:9055 | 1004:9056 | 1004:9058 | 1004:9060 | 1004:9061 | 1004:9062 |
| 1005:9055 | 1005:9056 | 1005:9058 | 1005:9060 | 1005:9061 | 1005:9062 |
| 1006:9055 | 1006:9056 | 1006:9058 | 1006:9060 | 1006:9061 | 1006:9062 |
| 1007:9055 | 1007:9056 | 1007:9058 | 1007:9060 | 1007:9061 | 1007:9062 |
| 1008:9055 | 1008:9056 | 1008:9058 | 1008:9060 | 1008:9061 | 1008:9062 |
| 1009:9055 | 1009:9056 | 1009:9058 | 1009:9060 | 1009:9061 | 1009:9062 |
| 1010:9055 | 1010:9056 | 1010:9058 | 1010:9060 | 1010:9061 | 1010:9062 |
| 1011:9055 | 1011:9056 | 1011:9058 | 1011:9060 | 1011:9061 | 1011:9062 |
| 1012:9055 | 1012:9056 | 1012:9058 | 1012:9060 | 1012:9061 | 1012:9062 |
| 1013:9055 | 1013:9056 | 1013:9058 | 1013:9060 | 1013:9061 | 1013:9062 |
| 1014:9055 | 1014:9056 | 1014:9058 | 1014:9060 | 1014:9061 | 1014:9062 |
| 1015:9055 | 1015:9056 | 1015:9058 | 1015:9060 | 1015:9061 | 1015:9062 |
| 1016:9055 | 1016:9056 | 1016:9058 | 1016:9060 | 1016:9061 | 1016:9062 |
| 2001:9055 | 2001:9056 | 2001:9058 | 2001:9060 | 2001:9061 | 2001:9062 |
| 2002:9055 | 2002:9056 | 2002:9058 | 2002:9060 | 2002:9061 | 2002:9062 |
| 2003:9055 | 2003:9056 | 2003:9058 | 2003:9060 | 2003:9061 | 2003:9062 |
| 2004:9055 | 2004:9056 | 2004:9058 | 2004:9060 | 2004:9061 | 2004:9062 |
| 2005:9055 | 2005:9056 | 2005:9058 | 2005:9060 | 2005:9061 | 2005:9062 |
| 2006:9055 | 2006:9056 | 2006:9058 | 2006:9060 | 2006:9061 | 2006:9062 |
| 2007:9055 | 2007:9056 | 2007:9058 | 2007:9060 | 2007:9061 | 2007:9062 |
| 2008:9055 | 2008:9056 | 2008:9058 | 2008:9060 | 2008:9061 | 2008:9062 |
| 2009:9055 | 2009:9056 | 2009:9058 | 2009:9060 | 2009:9061 | 2009:9062 |
| 2010:9055 | 2010:9056 | 2010:9058 | 2010:9060 | 2010:9061 | 2010:9062 |
| 2011:9055 | 2011:9056 | 2011:9058 | 2011:9060 | 2011:9061 | 2011:9062 |
| 2012:9055 | 2012:9056 | 2012:9058 | 2012:9060 | 2012:9061 | 2012:9062 |
| 1001:9063 | 1001:9064 | 1001:9065 | 1001:9066 | 1001:9067 | 1001:9068 |
| 1002:9063 | 1002:9064 | 1002:9065 | 1002:9066 | 1002:9067 | 1002:9068 |
| 1003:9063 | 1003:9064 | 1003:9065 | 1003:9066 | 1003:9067 | 1003:9068 |
| 1004:9063 | 1004:9064 | 1004:9065 | 1004:9066 | 1004:9067 | 1004:9068 |
| 1005:9063 | 1005:9064 | 1005:9065 | 1005:9066 | 1005:9067 | 1005:9068 |
| 1006:9063 | 1006:9064 | 1006:9065 | 1006:9066 | 1006:9067 | 1006:9068 |
| 1007:9063 | 1007:9064 | 1007:9065 | 1007:9066 | 1007:9067 | 1007:9068 |
| 1008:9063 | 1008:9064 | 1008:9065 | 1008:9066 | 1008:9067 | 1008:9068 |
| 1009:9063 | 1009:9064 | 1009:9065 | 1009:9066 | 1009:9067 | 1009:9068 |
| 1010:9063 | 1010:9064 | 1010:9065 | 1010:9066 | 1010:9067 | 1010:9068 |
| 1011:9063 | 1011:9064 | 1011:9065 | 1011:9066 | 1011:9067 | 1011:9068 |
| 1012:9063 | 1012:9064 | 1012:9065 | 1012:9066 | 1012:9067 | 1012:9068 |
| 1013:9063 | 1013:9064 | 1013:9065 | 1013:9066 | 1013:9067 | 1013:9068 |
| 1014:9063 | 1014:9064 | 1014:9065 | 1014:9066 | 1014:9067 | 1014:9068 |
| 1015:9063 | 1015:9064 | 1015:9065 | 1015:9066 | 1015:9067 | 1015:9068 |
| 1016:9063 | 1016:9064 | 1016:9065 | 1016:9066 | 1016:9067 | 1016:9068 |
| 2001:9063 | 2001:9064 | 2001:9065 | 2001:9066 | 2001:9067 | 2001:9068 |
| 2002:9063 | 2002:9064 | 2002:9065 | 2002:9066 | 2002:9067 | 2002:9068 |
| 2003:9063 | 2003:9064 | 2003:9065 | 2003:9066 | 2003:9067 | 2003:9068 |
| 2004:9063 | 2004:9064 | 2004:9065 | 2004:9066 | 2004:9067 | 2004:9068 |
| 2005:9063 | 2005:9064 | 2005:9065 | 2005:9066 | 2005:9067 | 2005:9068 |
| 2006:9063 | 2006:9064 | 2006:9065 | 2006:9066 | 2006:9067 | 2006:9068 |
| 2007:9063 | 2007:9064 | 2007:9065 | 2007:9066 | 2007:9067 | 2007:9068 |
| 2008:9063 | 2008:9064 | 2008:9065 | 2008:9066 | 2008:9067 | 2008:9068 |
| 2009:9063 | 2009:9064 | 2009:9065 | 2009:9066 | 2009:9067 | 2009:9068 |
| 2010:9063 | 2010:9064 | 2010:9065 | 2010:9066 | 2010:9067 | 2010:9068 |
| 2011:9063 | 2011:9064 | 2011:9065 | 2011:9066 | 2011:9067 | 2011:9068 |
| 2012:9063 | 2012:9064 | 2012:9065 | 2012:9066 | 2012:9067 | 2012:9068 |
| 1001:9069 | 1001:9070 | 1001:9071 | 1001:9072 | 1001:9073 | 1001:9074 |
| 1002:9069 | 1002:9070 | 1002:9071 | 1002:9072 | 1002:9073 | 1002:9074 |
| 1003:9069 | 1003:9070 | 1003:9071 | 1003:9072 | 1003:9073 | 1003:9074 |
| 1004:9069 | 1004:9070 | 1004:9071 | 1004:9072 | 1004:9073 | 1004:9074 |
| 1005:9069 | 1005:9070 | 1005:9071 | 1005:9072 | 1005:9073 | 1005:9074 |
| 1006:9069 | 1006:9070 | 1006:9071 | 1006:9072 | 1006:9073 | 1006:9074 |
| 1007:9069 | 1007:9070 | 1007:9071 | 1007:9072 | 1007:9073 | 1007:9074 |
| 1008:9069 | 1008:9070 | 1008:9071 | 1008:9072 | 1008:9073 | 1008:9074 |
| 1009:9069 | 1009:9070 | 1009:9071 | 1009:9072 | 1009:9073 | 1009:9074 |
| 1010:9069 | 1010:9070 | 1010:9071 | 1010:9072 | 1010:9073 | 1010:9074 |
| 1011:9069 | 1011:9070 | 1011:9071 | 1011:9072 | 1011:9073 | 1011:9074 |
| 1012:9069 | 1012:9070 | 1012:9071 | 1012:9072 | 1012:9073 | 1012:9074 |
| 1013:9069 | 1013:9070 | 1013:9071 | 1013:9072 | 1013:9073 | 1013:9074 |
| 1014:9069 | 1014:9070 | 1014:9071 | 1014:9072 | 1014:9073 | 1014:9074 |
| 1015:9069 | 1015:9070 | 1015:9071 | 1015:9072 | 1015:9073 | 1015:9074 |
| 1016:9069 | 1016:9070 | 1016:9071 | 1016:9072 | 1016:9073 | 1016:9074 |
| 2001:9069 | 2001:9070 | 2001:9071 | 2001:9072 | 2001:9073 | 2001:9074 |
| 2002:9069 | 2002:9070 | 2002:9071 | 2002:9072 | 2002:9073 | 2002:9074 |
| 2003:9069 | 2003:9070 | 2003:9071 | 2003:9072 | 2003:9073 | 2003:9074 |
| 2004:9069 | 2004:9070 | 2004:9071 | 2004:9072 | 2004:9073 | 2004:9074 |
| 2005:9069 | 2005:9070 | 2005:9071 | 2005:9072 | 2005:9073 | 2005:9074 |
| 2006:9069 | 2006:9070 | 2006:9071 | 2006:9072 | 2006:9073 | 2006:9074 |
| 2007:9069 | 2007:9070 | 2007:9071 | 2007:9072 | 2007:9073 | 2007:9074 |
| 2008:9069 | 2008:9070 | 2008:9071 | 2008:9072 | 2008:9073 | 2008:9074 |
| 2009:9069 | 2009:9070 | 2009:9071 | 2009:9072 | 2009:9073 | 2009:9074 |
| 2010:9069 | 2010:9070 | 2010:9071 | 2010:9072 | 2010:9073 | 2010:9074 |
| 2011:9069 | 2011:9070 | 2011:9071 | 2011:9072 | 2011:9073 | 2011:9074 |
| 2012:9069 | 2012:9070 | 2012:9071 | 2012:9072 | 2012:9073 | 2012:9074 |
| 1001:9075 | 1001:9076 | 1001:9077 | 1001:9078 | 1001:9079 | 1001:9080 |
| 1002:9075 | 1002:9076 | 1002:9077 | 1002:9078 | 1002:9079 | 1002:9080 |
| 1003:9075 | 1003:9076 | 1003:9077 | 1003:9078 | 1003:9079 | 1003:9080 |
| 1004:9075 | 1004:9076 | 1004:9077 | 1004:9078 | 1004:9079 | 1004:9080 |
| 1005:9075 | 1005:9076 | 1005:9077 | 1005:9078 | 1005:9079 | 1005:9080 |
| 1006:9075 | 1006:9076 | 1006:9077 | 1006:9078 | 1006:9079 | 1006:9080 |
| 1007:9075 | 1007:9076 | 1007:9077 | 1007:9078 | 1007:9079 | 1007:9080 |
| 1008:9075 | 1008:9076 | 1008:9077 | 1008:9078 | 1008:9079 | 1008:9080 |
| 1009:9075 | 1009:9076 | 1009:9077 | 1009:9078 | 1009:9079 | 1009:9080 |
| 1010:9075 | 1010:9076 | 1010:9077 | 1010:9078 | 1010:9079 | 1010:9080 |
| 1011:9075 | 1011:9076 | 1011:9077 | 1011:9078 | 1011:9079 | 1011:9080 |
| 1012:9075 | 1012:9076 | 1012:9077 | 1012:9078 | 1012:9079 | 1012:9080 |
| 1013:9075 | 1013:9076 | 1013:9077 | 1013:9078 | 1013:9079 | 1013:9080 |
| 1014:9075 | 1014:9076 | 1014:9077 | 1014:9078 | 1014:9079 | 1014:9080 |
| 1015:9075 | 1015:9076 | 1015:9077 | 1015:9078 | 1015:9079 | 1015:9080 |
| 1016:9075 | 1016:9076 | 1016:9077 | 1016:9078 | 1016:9079 | 1016:9080 |
| 2001:9075 | 2001:9076 | 2001:9077 | 2001:9078 | 2001:9079 | 2001:9080 |
| 2002:9075 | 2002:9076 | 2002:9077 | 2002:9078 | 2002:9079 | 2002:9080 |
| 2003:9075 | 2003:9076 | 2003:9077 | 2003:9078 | 2003:9079 | 2003:9080 |
| 2004:9075 | 2004:9076 | 2004:9077 | 2004:9078 | 2004:9079 | 2004:9080 |
| 2005:9075 | 2005:9076 | 2005:9077 | 2005:9078 | 2005:9079 | 2005:9080 |
| 2006:9075 | 2006:9076 | 2006:9077 | 2006:9078 | 2006:9079 | 2006:9080 |
| 2007:9075 | 2007:9076 | 2007:9077 | 2007:9078 | 2007:9079 | 2007:9080 |
| 2008:9075 | 2008:9076 | 2008:9077 | 2008:9078 | 2008:9079 | 2008:9080 |
| 2009:9075 | 2009:9076 | 2009:9077 | 2009:9078 | 2009:9079 | 2009:9080 |
| 2010:9075 | 2010:9076 | 2010:9077 | 2010:9078 | 2010:9079 | 2010:9080 |
| 2011:9075 | 2011:9076 | 2011:9077 | 2011:9078 | 2011:9079 | 2011:9080 |
| 2012:9075 | 2012:9076 | 2012:9077 | 2012:9078 | 2012:9079 | 2012:9080 |
| 1001:9081 | 1001:9082 | 1001:9083 | 1001:9084 | 1001:9085 | 1001:9086 |
| 1002:9081 | 1002:9082 | 1002:9083 | 1002:9084 | 1002:9085 | 1002:9086 |
| 1003:9081 | 1003:9082 | 1003:9083 | 1003:9084 | 1003:9085 | 1003:9086 |
| 1004:9081 | 1004:9082 | 1004:9083 | 1004:9084 | 1004:9085 | 1004:9086 |
| 1005:9081 | 1005:9082 | 1005:9083 | 1005:9084 | 1005:9085 | 1005:9086 |
| 1006:9081 | 1006:9082 | 1006:9083 | 1006:9084 | 1006:9085 | 1006:9086 |
| 1007:9081 | 1007:9082 | 1007:9083 | 1007:9084 | 1007:9085 | 1007:9086 |
| 1008:9081 | 1008:9082 | 1008:9083 | 1008:9084 | 1008:9085 | 1008:9086 |
| 1009:9081 | 1009:9082 | 1009:9083 | 1009:9084 | 1009:9085 | 1009:9086 |
| 1010:9081 | 1010:9082 | 1010:9083 | 1010:9084 | 1010:9085 | 1010:9086 |
| 1011:9081 | 1011:9082 | 1011:9083 | 1011:9084 | 1011:9085 | 1011:9086 |
| 1012:9081 | 1012:9082 | 1012:9083 | 1012:9084 | 1012:9085 | 1012:9086 |
| 1013:9081 | 1013:9082 | 1013:9083 | 1013:9084 | 1013:9085 | 1013:9086 |
| 1014:9081 | 1014:9082 | 1014:9083 | 1014:9084 | 1014:9085 | 1014:9086 |
| 1015:9081 | 1015:9082 | 1015:9083 | 1015:9084 | 1015:9085 | 1015:9086 |
| 1016:9081 | 1016:9082 | 1016:9083 | 1016:9084 | 1016:9085 | 1016:9086 |
| 2001:9081 | 2001:9082 | 2001:9083 | 2001:9084 | 2001:9085 | 2001:9086 |
| 2002:9081 | 2002:9082 | 2002:9083 | 2002:9084 | 2002:9085 | 2002:9086 |
| 2003:9081 | 2003:9082 | 2003:9083 | 2003:9084 | 2003:9085 | 2003:9086 |
| 2004:9081 | 2004:9082 | 2004:9083 | 2004:9084 | 2004:9085 | 2004:9086 |
| 2005:9081 | 2005:9082 | 2005:9083 | 2005:9084 | 2005:9085 | 2005:9086 |
| 2006:9081 | 2006:9082 | 2006:9083 | 2006:9084 | 2006:9085 | 2006:9086 |
| 2007:9081 | 2007:9082 | 2007:9083 | 2007:9084 | 2007:9085 | 2007:9086 |
| 2008:9081 | 2008:9082 | 2008:9083 | 2008:9084 | 2008:9085 | 2008:9086 |
| 2009:9081 | 2009:9082 | 2009:9083 | 2009:9084 | 2009:9085 | 2009:9086 |
| 2010:9081 | 2010:9082 | 2010:9083 | 2010:9084 | 2010:9085 | 2010:9086 |
| 2011:9081 | 2011:9082 | 2011:9083 | 2011:9084 | 2011:9085 | 2011:9086 |
| 2012:9081 | 2012:9082 | 2012:9083 | 2012:9084 | 2012:9085 | 2012:9086 |
| 1001:9088 | 1001:9089 | 1001:9094 | 1001:9095 | 1001:9096 | 1001:9097 |
| 1002:9088 | 1002:9089 | 1002:9094 | 1002:9095 | 1002:9096 | 1002:9097 |
| 1003:9088 | 1003:9089 | 1003:9094 | 1003:9095 | 1003:9096 | 1003:9097 |
| 1004:9088 | 1004:9089 | 1004:9094 | 1004:9095 | 1004:9096 | 1004:9097 |
| 1005:9088 | 1005:9089 | 1005:9094 | 1005:9095 | 1005:9096 | 1005:9097 |
| 1006:9088 | 1006:9089 | 1006:9094 | 1006:9095 | 1006:9096 | 1006:9097 |
| 1007:9088 | 1007:9089 | 1007:9094 | 1007:9095 | 1007:9096 | 1007:9097 |

TABLE A-continued

Example combinations of a compound X with a compound Y.

| X:Y | X:Y | X:Y | X:Y | X:Y | X:Y |
|---|---|---|---|---|---|
| 1008:9088 | 1008:9089 | 1008:9094 | 1008:9095 | 1008:9096 | 1008:9097 |
| 1009:9088 | 1009:9089 | 1009:9094 | 1009:9095 | 1009:9096 | 1009:9097 |
| 1010:9088 | 1010:9089 | 1010:9094 | 1010:9095 | 1010:9096 | 1010:9097 |
| 1011:9088 | 1011:9089 | 1011:9094 | 1011:9095 | 1011:9096 | 1011:9097 |
| 1012:9088 | 1012:9089 | 1012:9094 | 1012:9095 | 1012:9096 | 1012:9097 |
| 1013:9088 | 1013:9089 | 1013:9094 | 1013:9095 | 1013:9096 | 1013:9097 |
| 1014:9088 | 1014:9089 | 1014:9094 | 1014:9095 | 1014:9096 | 1014:9097 |
| 1015:9088 | 1015:9089 | 1015:9094 | 1015:9095 | 1015:9096 | 1015:9097 |
| 1016:9088 | 1016:9089 | 1016:9094 | 1016:9095 | 1016:9096 | 1016:9097 |
| 2001:9088 | 2001:9089 | 2001:9094 | 2001:9095 | 2001:9096 | 2001:9097 |
| 2002:9088 | 2002:9089 | 2002:9094 | 2002:9095 | 2002:9096 | 2002:9097 |
| 2003:9088 | 2003:9089 | 2003:9094 | 2003:9095 | 2003:9096 | 2003:9097 |
| 2004:9088 | 2004:9089 | 2004:9094 | 2004:9095 | 2004:9096 | 2004:9097 |
| 2005:9088 | 2005:9089 | 2005:9094 | 2005:9095 | 2005:9096 | 2005:9097 |
| 2006:9088 | 2006:9089 | 2006:9094 | 2006:9095 | 2006:9096 | 2006:9097 |
| 2007:9088 | 2007:9089 | 2007:9094 | 2007:9095 | 2007:9096 | 2007:9097 |
| 2008:9088 | 2008:9089 | 2008:9094 | 2008:9095 | 2008:9096 | 2008:9097 |
| 2009:9088 | 2009:9089 | 2009:9094 | 2009:9095 | 2009:9096 | 2009:9097 |
| 2010:9088 | 2010:9089 | 2010:9094 | 2010:9095 | 2010:9096 | 2010:9097 |
| 2011:9088 | 2011:9089 | 2011:9094 | 2011:9095 | 2011:9096 | 2011:9097 |
| 2012:9088 | 2012:9089 | 2012:9094 | 2012:9095 | 2012:9096 | 2012:9097 |
| 1001:9098 | 1001:9099 | 1001:9100 | 1001:9101 | 1001:9102 | 1001:9103 |
| 1002:9098 | 1002:9099 | 1002:9100 | 1002:9101 | 1002:9102 | 1002:9103 |
| 1003:9098 | 1003:9099 | 1003:9100 | 1003:9101 | 1003:9102 | 1003:9103 |
| 1004:9098 | 1004:9099 | 1004:9100 | 1004:9101 | 1004:9102 | 1004:9103 |
| 1005:9098 | 1005:9099 | 1005:9100 | 1005:9101 | 1005:9102 | 1005:9103 |
| 1006:9098 | 1006:9099 | 1006:9100 | 1006:9101 | 1006:9102 | 1006:9103 |
| 1007:9098 | 1007:9099 | 1007:9100 | 1007:9101 | 1007:9102 | 1007:9103 |
| 1008:9098 | 1008:9099 | 1008:9100 | 1008:9101 | 1008:9102 | 1008:9103 |
| 1009:9098 | 1009:9099 | 1009:9100 | 1009:9101 | 1009:9102 | 1009:9103 |
| 1010:9098 | 1010:9099 | 1010:9100 | 1010:9101 | 1010:9102 | 1010:9103 |
| 1011:9098 | 1011:9099 | 1011:9100 | 1011:9101 | 1011:9102 | 1011:9103 |
| 1012:9098 | 1012:9099 | 1012:9100 | 1012:9101 | 1012:9102 | 1012:9103 |
| 1013:9098 | 1013:9099 | 1013:9100 | 1013:9101 | 1013:9102 | 1013:9103 |
| 1014:9098 | 1014:9099 | 1014:9100 | 1014:9101 | 1014:9102 | 1014:9103 |
| 1015:9098 | 1015:9099 | 1015:9100 | 1015:9101 | 1015:9102 | 1015:9103 |
| 1016:9098 | 1016:9099 | 1016:9100 | 1016:9101 | 1016:9102 | 1016:9103 |
| 2001:9098 | 2001:9099 | 2001:9100 | 2001:9101 | 2001:9102 | 2001:9103 |
| 2002:9098 | 2002:9099 | 2002:9100 | 2002:9101 | 2002:9102 | 2002:9103 |
| 2003:9098 | 2003:9099 | 2003:9100 | 2003:9101 | 2003:9102 | 2003:9103 |
| 2004:9098 | 2004:9099 | 2004:9100 | 2004:9101 | 2004:9102 | 2004:9103 |
| 2005:9098 | 2005:9099 | 2005:9100 | 2005:9101 | 2005:9102 | 2005:9103 |
| 2006:9098 | 2006:9099 | 2006:9100 | 2006:9101 | 2006:9102 | 2006:9103 |
| 2007:9098 | 2007:9099 | 2007:9100 | 2007:9101 | 2007:9102 | 2007:9103 |
| 2008:9098 | 2008:9099 | 2008:9100 | 2008:9101 | 2008:9102 | 2008:9103 |
| 2009:9098 | 2009:9099 | 2009:9100 | 2009:9101 | 2009:9102 | 2009:9103 |
| 2010:9098 | 2010:9099 | 2010:9100 | 2010:9101 | 2010:9102 | 2010:9103 |
| 2011:9098 | 2011:9099 | 2011:9100 | 2011:9101 | 2011:9102 | 2011:9103 |
| 2012:9098 | 2012:9099 | 2012:9100 | 2012:9101 | 2012:9102 | 2012:9103 |
| 1001:9104 | 1001:9105 | 1001:9106 | 1001:9107 | 1001:9108 | 1001:9109 |
| 1002:9104 | 1002:9105 | 1002:9106 | 1002:9107 | 1002:9108 | 1002:9109 |
| 1003:9104 | 1003:9105 | 1003:9106 | 1003:9107 | 1003:9108 | 1003:9109 |
| 1004:9104 | 1004:9105 | 1004:9106 | 1004:9107 | 1004:9108 | 1004:9109 |
| 1005:9104 | 1005:9105 | 1005:9106 | 1005:9107 | 1005:9108 | 1005:9109 |
| 1006:9104 | 1006:9105 | 1006:9106 | 1006:9107 | 1006:9108 | 1006:9109 |
| 1007:9104 | 1007:9105 | 1007:9106 | 1007:9107 | 1007:9108 | 1007:9109 |
| 1008:9104 | 1008:9105 | 1008:9106 | 1008:9107 | 1008:9108 | 1008:9109 |
| 1009:9104 | 1009:9105 | 1009:9106 | 1009:9107 | 1009:9108 | 1009:9109 |
| 1010:9104 | 1010:9105 | 1010:9106 | 1010:9107 | 1010:9108 | 1010:9109 |
| 1011:9104 | 1011:9105 | 1011:9106 | 1011:9107 | 1011:9108 | 1011:9109 |
| 1012:9104 | 1012:9105 | 1012:9106 | 1012:9107 | 1012:9108 | 1012:9109 |
| 1013:9104 | 1013:9105 | 1013:9106 | 1013:9107 | 1013:9108 | 1013:9109 |
| 1014:9104 | 1014:9105 | 1014:9106 | 1014:9107 | 1014:9108 | 1014:9109 |
| 1015:9104 | 1015:9105 | 1015:9106 | 1015:9107 | 1015:9108 | 1015:9109 |
| 1016:9104 | 1016:9105 | 1016:9106 | 1016:9107 | 1016:9108 | 1016:9109 |
| 2001:9104 | 2001:9105 | 2001:9106 | 2001:9107 | 2001:9108 | 2001:9109 |
| 2002:9104 | 2002:9105 | 2002:9106 | 2002:9107 | 2002:9108 | 2002:9109 |
| 2003:9104 | 2003:9105 | 2003:9106 | 2003:9107 | 2003:9108 | 2003:9109 |
| 2004:9104 | 2004:9105 | 2004:9106 | 2004:9107 | 2004:9108 | 2004:9109 |
| 2005:9104 | 2005:9105 | 2005:9106 | 2005:9107 | 2005:9108 | 2005:9109 |
| 2006:9104 | 2006:9105 | 2006:9106 | 2006:9107 | 2006:9108 | 2006:9109 |
| 2007:9104 | 2007:9105 | 2007:9106 | 2007:9107 | 2007:9108 | 2007:9109 |
| 2008:9104 | 2008:9105 | 2008:9106 | 2008:9107 | 2008:9108 | 2008:9109 |
| 2009:9104 | 2009:9105 | 2009:9106 | 2009:9107 | 2009:9108 | 2009:9109 |
| 2010:9104 | 2010:9105 | 2010:9106 | 2010:9107 | 2010:9108 | 2010:9109 |
| 2011:9104 | 2011:9105 | 2011:9106 | 2011:9107 | 2011:9108 | 2011:9109 |
| 2012:9104 | 2012:9105 | 2012:9106 | 2012:9107 | 2012:9108 | 2012:9109 |
| 1001:9110 | 1001:9111 | 1001:9129 | 1001:9130 | 1001:9131 | 1001:9132 |
| 1002:9110 | 1002:9111 | 1002:9129 | 1002:9130 | 1002:9131 | 1002:9132 |
| 1003:9110 | 1003:9111 | 1003:9129 | 1003:9130 | 1003:9131 | 1003:9132 |
| 1004:9110 | 1004:9111 | 1004:9129 | 1004:9130 | 1004:9131 | 1004:9132 |
| 1005:9110 | 1005:9111 | 1005:9129 | 1005:9130 | 1005:9131 | 1005:9132 |
| 1006:9110 | 1006:9111 | 1006:9129 | 1006:9130 | 1006:9131 | 1006:9132 |
| 1007:9110 | 1007:9111 | 1007:9129 | 1007:9130 | 1007:9131 | 1007:9132 |
| 1008:9110 | 1008:9111 | 1008:9129 | 1008:9130 | 1008:9131 | 1008:9132 |
| 1009:9110 | 1009:9111 | 1009:9129 | 1009:9130 | 1009:9131 | 1009:9132 |
| 1010:9110 | 1010:9111 | 1010:9129 | 1010:9130 | 1010:9131 | 1010:9132 |
| 1011:9110 | 1011:9111 | 1011:9129 | 1011:9130 | 1011:9131 | 1011:9132 |
| 1012:9110 | 1012:9111 | 1012:9129 | 1012:9130 | 1012:9131 | 1012:9132 |
| 1013:9110 | 1013:9111 | 1013:9129 | 1013:9130 | 1013:9131 | 1013:9132 |
| 1014:9110 | 1014:9111 | 1014:9129 | 1014:9130 | 1014:9131 | 1014:9132 |
| 1015:9110 | 1015:9111 | 1015:9129 | 1015:9130 | 1015:9131 | 1015:9132 |
| 1016:9110 | 1016:9111 | 1016:9129 | 1016:9130 | 1016:9131 | 1016:9132 |
| 2001:9110 | 2001:9111 | 2001:9129 | 2001:9130 | 2001:9131 | 2001:9132 |
| 2002:9110 | 2002:9111 | 2002:9129 | 2002:9130 | 2002:9131 | 2002:9132 |
| 2003:9110 | 2003:9111 | 2003:9129 | 2003:9130 | 2003:9131 | 2003:9132 |
| 2004:9110 | 2004:9111 | 2004:9129 | 2004:9130 | 2004:9131 | 2004:9132 |
| 2005:9110 | 2005:9111 | 2005:9129 | 2005:9130 | 2005:9131 | 2005:9132 |
| 2006:9110 | 2006:9111 | 2006:9129 | 2006:9130 | 2006:9131 | 2006:9132 |
| 2007:9110 | 2007:9111 | 2007:9129 | 2007:9130 | 2007:9131 | 2007:9132 |
| 2008:9110 | 2008:9111 | 2008:9129 | 2008:9130 | 2008:9131 | 2008:9132 |
| 2009:9110 | 2009:9111 | 2009:9129 | 2009:9130 | 2009:9131 | 2009:9132 |
| 2010:9110 | 2010:9111 | 2010:9129 | 2010:9130 | 2010:9131 | 2010:9132 |
| 2011:9110 | 2011:9111 | 2011:9129 | 2011:9130 | 2011:9131 | 2011:9132 |
| 2012:9110 | 2012:9111 | 2012:9129 | 2012:9130 | 2012:9131 | 2012:9132 |
| 1001:9133 | 1001:9134 | 1001:9135 | 1001:9136 | 1001:9137 | 1001:9138 |
| 1002:9133 | 1002:9134 | 1002:9135 | 1002:9136 | 1002:9137 | 1002:9138 |
| 1003:9133 | 1003:9134 | 1003:9135 | 1003:9136 | 1003:9137 | 1003:9138 |
| 1004:9133 | 1004:9134 | 1004:9135 | 1004:9136 | 1004:9137 | 1004:9138 |
| 1005:9133 | 1005:9134 | 1005:9135 | 1005:9136 | 1005:9137 | 1005:9138 |
| 1006:9133 | 1006:9134 | 1006:9135 | 1006:9136 | 1006:9137 | 1006:9138 |
| 1007:9133 | 1007:9134 | 1007:9135 | 1007:9136 | 1007:9137 | 1007:9138 |
| 1008:9133 | 1008:9134 | 1008:9135 | 1008:9136 | 1008:9137 | 1008:9138 |
| 1009:9133 | 1009:9134 | 1009:9135 | 1009:9136 | 1009:9137 | 1009:9138 |
| 1010:9133 | 1010:9134 | 1010:9135 | 1010:9136 | 1010:9137 | 1010:9138 |
| 1011:9133 | 1011:9134 | 1011:9135 | 1011:9136 | 1011:9137 | 1011:9138 |
| 1012:9133 | 1012:9134 | 1012:9135 | 1012:9136 | 1012:9137 | 1012:9138 |
| 1013:9133 | 1013:9134 | 1013:9135 | 1013:9136 | 1013:9137 | 1013:9138 |
| 1014:9133 | 1014:9134 | 1014:9135 | 1014:9136 | 1014:9137 | 1014:9138 |
| 1015:9133 | 1015:9134 | 1015:9135 | 1015:9136 | 1015:9137 | 1015:9138 |
| 1016:9133 | 1016:9134 | 1016:9135 | 1016:9136 | 1016:9137 | 1016:9138 |
| 2001:9133 | 2001:9134 | 2001:9135 | 2001:9136 | 2001:9137 | 2001:9138 |
| 2002:9133 | 2002:9134 | 2002:9135 | 2002:9136 | 2002:9137 | 2002:9138 |
| 2003:9133 | 2003:9134 | 2003:9135 | 2003:9136 | 2003:9137 | 2003:9138 |
| 2004:9133 | 2004:9134 | 2004:9135 | 2004:9136 | 2004:9137 | 2004:9138 |
| 2005:9133 | 2005:9134 | 2005:9135 | 2005:9136 | 2005:9137 | 2005:9138 |
| 2006:9133 | 2006:9134 | 2006:9135 | 2006:9136 | 2006:9137 | 2006:9138 |
| 2007:9133 | 2007:9134 | 2007:9135 | 2007:9136 | 2007:9137 | 2007:9138 |
| 2008:9133 | 2008:9134 | 2008:9135 | 2008:9136 | 2008:9137 | 2008:9138 |
| 2009:9133 | 2009:9134 | 2009:9135 | 2009:9136 | 2009:9137 | 2009:9138 |
| 2010:9133 | 2010:9134 | 2010:9135 | 2010:9136 | 2010:9137 | 2010:9138 |
| 2011:9133 | 2011:9134 | 2011:9135 | 2011:9136 | 2011:9137 | 2011:9138 |
| 2012:9133 | 2012:9134 | 2012:9135 | 2012:9136 | 2012:9137 | 2012:9138 |
| 1001:9139 | 1001:9140 | 1001:9141 | 1001:9142 | 1001:9143 | 1001:9144 |
| 1002:9139 | 1002:9140 | 1002:9141 | 1002:9142 | 1002:9143 | 1002:9144 |
| 1003:9139 | 1003:9140 | 1003:9141 | 1003:9142 | 1003:9143 | 1003:9144 |
| 1004:9139 | 1004:9140 | 1004:9141 | 1004:9142 | 1004:9143 | 1004:9144 |
| 1005:9139 | 1005:9140 | 1005:9141 | 1005:9142 | 1005:9143 | 1005:9144 |
| 1006:9139 | 1006:9140 | 1006:9141 | 1006:9142 | 1006:9143 | 1006:9144 |
| 1007:9139 | 1007:9140 | 1007:9141 | 1007:9142 | 1007:9143 | 1007:9144 |
| 1008:9139 | 1008:9140 | 1008:9141 | 1008:9142 | 1008:9143 | 1008:9144 |
| 1009:9139 | 1009:9140 | 1009:9141 | 1009:9142 | 1009:9143 | 1009:9144 |
| 1010:9139 | 1010:9140 | 1010:9141 | 1010:9142 | 1010:9143 | 1010:9144 |
| 1011:9139 | 1011:9140 | 1011:9141 | 1011:9142 | 1011:9143 | 1011:9144 |
| 1012:9139 | 1012:9140 | 1012:9141 | 1012:9142 | 1012:9143 | 1012:9144 |
| 1013:9139 | 1013:9140 | 1013:9141 | 1013:9142 | 1013:9143 | 1013:9144 |
| 1014:9139 | 1014:9140 | 1014:9141 | 1014:9142 | 1014:9143 | 1014:9144 |
| 1015:9139 | 1015:9140 | 1015:9141 | 1015:9142 | 1015:9143 | 1015:9144 |
| 1016:9139 | 1016:9140 | 1016:9141 | 1016:9142 | 1016:9143 | 1016:9144 |
| 2001:9139 | 2001:9140 | 2001:9141 | 2001:9142 | 2001:9143 | 2001:9144 |
| 2002:9139 | 2002:9140 | 2002:9141 | 2002:9142 | 2002:9143 | 2002:9144 |
| 2003:9139 | 2003:9140 | 2003:9141 | 2003:9142 | 2003:9143 | 2003:9144 |

TABLE A-continued

Example combinations of a compound X with a compound Y.

| X:Y | X:Y | X:Y | X:Y | X:Y | X:Y |
|---|---|---|---|---|---|
| 2004:9139 | 2004:9140 | 2004:9141 | 2004:9142 | 2004:9143 | 2004:9144 |
| 2005:9139 | 2005:9140 | 2005:9141 | 2005:9142 | 2005:9143 | 2005:9144 |
| 2006:9139 | 2006:9140 | 2006:9141 | 2006:9142 | 2006:9143 | 2006:9144 |
| 2007:9139 | 2007:9140 | 2007:9141 | 2007:9142 | 2007:9143 | 2007:9144 |
| 2008:9139 | 2008:9140 | 2008:9141 | 2008:9142 | 2008:9143 | 2008:9144 |
| 2009:9139 | 2009:9140 | 2009:9141 | 2009:9142 | 2009:9143 | 2009:9144 |
| 2010:9139 | 2010:9140 | 2010:9141 | 2010:9142 | 2010:9143 | 2010:9144 |
| 2011:9139 | 2011:9140 | 2011:9141 | 2011:9142 | 2011:9143 | 2011:9144 |
| 2012:9139 | 2012:9140 | 2012:9141 | 2012:9142 | 2012:9143 | 2012:9144 |
| 1001:9145 | 1001:9146 | 1001:9147 | 1001:9148 | 1001:9149 | 1001:9150 |
| 1002:9145 | 1002:9146 | 1002:9147 | 1002:9148 | 1002:9149 | 1002:9150 |
| 1003:9145 | 1003:9146 | 1003:9147 | 1003:9148 | 1003:9149 | 1003:9150 |
| 1004:9145 | 1004:9146 | 1004:9147 | 1004:9148 | 1004:9149 | 1004:9150 |
| 1005:9145 | 1005:9146 | 1005:9147 | 1005:9148 | 1005:9149 | 1005:9150 |
| 1006:9145 | 1006:9146 | 1006:9147 | 1006:9148 | 1006:9149 | 1006:9150 |
| 1007:9145 | 1007:9146 | 1007:9147 | 1007:9148 | 1007:9149 | 1007:9150 |
| 1008:9145 | 1008:9146 | 1008:9147 | 1008:9148 | 1008:9149 | 1008:9150 |
| 1009:9145 | 1009:9146 | 1009:9147 | 1009:9148 | 1009:9149 | 1009:9150 |
| 1010:9145 | 1010:9146 | 1010:9147 | 1010:9148 | 1010:9149 | 1010:9150 |
| 1011:9145 | 1011:9146 | 1011:9147 | 1011:9148 | 1011:9149 | 1011:9150 |
| 1012:9145 | 1012:9146 | 1012:9147 | 1012:9148 | 1012:9149 | 1012:9150 |
| 1013:9145 | 1013:9146 | 1013:9147 | 1013:9148 | 1013:9149 | 1013:9150 |
| 1014:9145 | 1014:9146 | 1014:9147 | 1014:9148 | 1014:9149 | 1014:9150 |
| 1015:9145 | 1015:9146 | 1015:9147 | 1015:9148 | 1015:9149 | 1015:9150 |
| 1016:9145 | 1016:9146 | 1016:9147 | 1016:9148 | 1016:9149 | 1016:9150 |
| 2001:9145 | 2001:9146 | 2001:9147 | 2001:9148 | 2001:9149 | 2001:9150 |
| 2002:9145 | 2002:9146 | 2002:9147 | 2002:9148 | 2002:9149 | 2002:9150 |
| 2003:9145 | 2003:9146 | 2003:9147 | 2003:9148 | 2003:9149 | 2003:9150 |
| 2004:9145 | 2004:9146 | 2004:9147 | 2004:9148 | 2004:9149 | 2004:9150 |
| 2005:9145 | 2005:9146 | 2005:9147 | 2005:9148 | 2005:9149 | 2005:9150 |
| 2006:9145 | 2006:9146 | 2006:9147 | 2006:9148 | 2006:9149 | 2006:9150 |
| 2007:9145 | 2007:9146 | 2007:9147 | 2007:9148 | 2007:9149 | 2007:9150 |
| 2008:9145 | 2008:9146 | 2008:9147 | 2008:9148 | 2008:9149 | 2008:9150 |
| 2009:9145 | 2009:9146 | 2009:9147 | 2009:9148 | 2009:9149 | 2009:9150 |
| 2010:9145 | 2010:9146 | 2010:9147 | 2010:9148 | 2010:9149 | 2010:9150 |
| 2011:9145 | 2011:9146 | 2011:9147 | 2011:9148 | 2011:9149 | 2011:9150 |
| 2012:9145 | 2012:9146 | 2012:9147 | 2012:9148 | 2012:9149 | 2012:9150 |
| 1001:9161 | 1001:9162 | 1001:9163 | 1001:9164 | 1001:9167 | 1001:9168 |
| 1002:9161 | 1002:9162 | 1002:9163 | 1002:9164 | 1002:9167 | 1002:9168 |
| 1003:9161 | 1003:9162 | 1003:9163 | 1003:9164 | 1003:9167 | 1003:9168 |
| 1004:9161 | 1004:9162 | 1004:9163 | 1004:9164 | 1004:9167 | 1004:9168 |
| 1005:9161 | 1005:9162 | 1005:9163 | 1005:9164 | 1005:9167 | 1005:9168 |
| 1006:9161 | 1006:9162 | 1006:9163 | 1006:9164 | 1006:9167 | 1006:9168 |
| 1007:9161 | 1007:9162 | 1007:9163 | 1007:9164 | 1007:9167 | 1007:9168 |
| 1008:9161 | 1008:9162 | 1008:9163 | 1008:9164 | 1008:9167 | 1008:9168 |
| 1009:9161 | 1009:9162 | 1009:9163 | 1009:9164 | 1009:9167 | 1009:9168 |
| 1010:9161 | 1010:9162 | 1010:9163 | 1010:9164 | 1010:9167 | 1010:9168 |
| 1011:9161 | 1011:9162 | 1011:9163 | 1011:9164 | 1011:9167 | 1011:9168 |
| 1012:9161 | 1012:9162 | 1012:9163 | 1012:9164 | 1012:9167 | 1012:9168 |
| 1013:9161 | 1013:9162 | 1013:9163 | 1013:9164 | 1013:9167 | 1013:9168 |
| 1014:9161 | 1014:9162 | 1014:9163 | 1014:9164 | 1014:9167 | 1014:9168 |
| 1015:9161 | 1015:9162 | 1015:9163 | 1015:9164 | 1015:9167 | 1015:9168 |
| 1016:9161 | 1016:9162 | 1016:9163 | 1016:9164 | 1016:9167 | 1016:9168 |
| 2001:9161 | 2001:9162 | 2001:9163 | 2001:9164 | 2001:9167 | 2001:9168 |
| 2002:9161 | 2002:9162 | 2002:9163 | 2002:9164 | 2002:9167 | 2002:9168 |
| 2003:9161 | 2003:9162 | 2003:9163 | 2003:9164 | 2003:9167 | 2003:9168 |
| 2004:9161 | 2004:9162 | 2004:9163 | 2004:9164 | 2004:9167 | 2004:9168 |
| 2005:9161 | 2005:9162 | 2005:9163 | 2005:9164 | 2005:9167 | 2005:9168 |
| 2006:9161 | 2006:9162 | 2006:9163 | 2006:9164 | 2006:9167 | 2006:9168 |
| 2007:9161 | 2007:9162 | 2007:9163 | 2007:9164 | 2007:9167 | 2007:9168 |
| 2008:9161 | 2008:9162 | 2008:9163 | 2008:9164 | 2008:9167 | 2008:9168 |
| 2009:9161 | 2009:9162 | 2009:9163 | 2009:9164 | 2009:9167 | 2009:9168 |
| 2010:9161 | 2010:9162 | 2010:9163 | 2010:9164 | 2010:9167 | 2010:9168 |
| 2011:9161 | 2011:9162 | 2011:9163 | 2011:9164 | 2011:9167 | 2011:9168 |
| 2012:9161 | 2012:9162 | 2012:9163 | 2012:9164 | 2012:9167 | 2012:9168 |
| 1001:9169 | 1001:9170 | 1001:9171 | 1001:9172 | 1001:9173 | 1001:9174 |
| 1002:9169 | 1002:9170 | 1002:9171 | 1002:9172 | 1002:9173 | 1002:9174 |
| 1003:9169 | 1003:9170 | 1003:9171 | 1003:9172 | 1003:9173 | 1003:9174 |
| 1004:9169 | 1004:9170 | 1004:9171 | 1004:9172 | 1004:9173 | 1004:9174 |
| 1005:9169 | 1005:9170 | 1005:9171 | 1005:9172 | 1005:9173 | 1005:9174 |
| 1006:9169 | 1006:9170 | 1006:9171 | 1006:9172 | 1006:9173 | 1006:9174 |
| 1007:9169 | 1007:9170 | 1007:9171 | 1007:9172 | 1007:9173 | 1007:9174 |
| 1008:9169 | 1008:9170 | 1008:9171 | 1008:9172 | 1008:9173 | 1008:9174 |
| 1009:9169 | 1009:9170 | 1009:9171 | 1009:9172 | 1009:9173 | 1009:9174 |
| 1010:9169 | 1010:9170 | 1010:9171 | 1010:9172 | 1010:9173 | 1010:9174 |
| 1011:9169 | 1011:9170 | 1011:9171 | 1011:9172 | 1011:9173 | 1011:9174 |
| 1012:9169 | 1012:9170 | 1012:9171 | 1012:9172 | 1012:9173 | 1012:9174 |
| 1013:9169 | 1013:9170 | 1013:9171 | 1013:9172 | 1013:9173 | 1013:9174 |
| 1014:9169 | 1014:9170 | 1014:9171 | 1014:9172 | 1014:9173 | 1014:9174 |
| 1015:9169 | 1015:9170 | 1015:9171 | 1015:9172 | 1015:9173 | 1015:9174 |
| 1016:9169 | 1016:9170 | 1016:9171 | 1016:9172 | 1016:9173 | 1016:9174 |
| 2001:9169 | 2001:9170 | 2001:9171 | 2001:9172 | 2001:9173 | 2001:9174 |
| 2002:9169 | 2002:9170 | 2002:9171 | 2002:9172 | 2002:9173 | 2002:9174 |
| 2003:9169 | 2003:9170 | 2003:9171 | 2003:9172 | 2003:9173 | 2003:9174 |
| 2004:9169 | 2004:9170 | 2004:9171 | 2004:9172 | 2004:9173 | 2004:9174 |
| 2005:9169 | 2005:9170 | 2005:9171 | 2005:9172 | 2005:9173 | 2005:9174 |
| 2006:9169 | 2006:9170 | 2006:9171 | 2006:9172 | 2006:9173 | 2006:9174 |
| 2007:9169 | 2007:9170 | 2007:9171 | 2007:9172 | 2007:9173 | 2007:9174 |
| 2008:9169 | 2008:9170 | 2008:9171 | 2008:9172 | 2008:9173 | 2008:9174 |
| 2009:9169 | 2009:9170 | 2009:9171 | 2009:9172 | 2009:9173 | 2009:9174 |
| 2010:9169 | 2010:9170 | 2010:9171 | 2010:9172 | 2010:9173 | 2010:9174 |
| 2011:9169 | 2011:9170 | 2011:9171 | 2011:9172 | 2011:9173 | 2011:9174 |
| 2012:9169 | 2012:9170 | 2012:9171 | 2012:9172 | 2012:9173 | 2012:9174 |
| 1001:9175 | 1001:9176 | 1001:9177 | 1001:9178 | 1001:9179 | 1001:9180 |
| 1002:9175 | 1002:9176 | 1002:9177 | 1002:9178 | 1002:9179 | 1002:9180 |
| 1003:9175 | 1003:9176 | 1003:9177 | 1003:9178 | 1003:9179 | 1003:9180 |
| 1004:9175 | 1004:9176 | 1004:9177 | 1004:9178 | 1004:9179 | 1004:9180 |
| 1005:9175 | 1005:9176 | 1005:9177 | 1005:9178 | 1005:9179 | 1005:9180 |
| 1006:9175 | 1006:9176 | 1006:9177 | 1006:9178 | 1006:9179 | 1006:9180 |
| 1007:9175 | 1007:9176 | 1007:9177 | 1007:9178 | 1007:9179 | 1007:9180 |
| 1008:9175 | 1008:9176 | 1008:9177 | 1008:9178 | 1008:9179 | 1008:9180 |
| 1009:9175 | 1009:9176 | 1009:9177 | 1009:9178 | 1009:9179 | 1009:9180 |
| 1010:9175 | 1010:9176 | 1010:9177 | 1010:9178 | 1010:9179 | 1010:9180 |
| 1011:9175 | 1011:9176 | 1011:9177 | 1011:9178 | 1011:9179 | 1011:9180 |
| 1012:9175 | 1012:9176 | 1012:9177 | 1012:9178 | 1012:9179 | 1012:9180 |
| 1013:9175 | 1013:9176 | 1013:9177 | 1013:9178 | 1013:9179 | 1013:9180 |
| 1014:9175 | 1014:9176 | 1014:9177 | 1014:9178 | 1014:9179 | 1014:9180 |
| 1015:9175 | 1015:9176 | 1015:9177 | 1015:9178 | 1015:9179 | 1015:9180 |
| 1016:9175 | 1016:9176 | 1016:9177 | 1016:9178 | 1016:9179 | 1016:9180 |
| 2001:9175 | 2001:9176 | 2001:9177 | 2001:9178 | 2001:9179 | 2001:9180 |
| 2002:9175 | 2002:9176 | 2002:9177 | 2002:9178 | 2002:9179 | 2002:9180 |
| 2003:9175 | 2003:9176 | 2003:9177 | 2003:9178 | 2003:9179 | 2003:9180 |
| 2004:9175 | 2004:9176 | 2004:9177 | 2004:9178 | 2004:9179 | 2004:9180 |
| 2005:9175 | 2005:9176 | 2005:9177 | 2005:9178 | 2005:9179 | 2005:9180 |
| 2006:9175 | 2006:9176 | 2006:9177 | 2006:9178 | 2006:9179 | 2006:9180 |
| 2007:9175 | 2007:9176 | 2007:9177 | 2007:9178 | 2007:9179 | 2007:9180 |
| 2008:9175 | 2008:9176 | 2008:9177 | 2008:9178 | 2008:9179 | 2008:9180 |
| 2009:9175 | 2009:9176 | 2009:9177 | 2009:9178 | 2009:9179 | 2009:9180 |
| 2010:9175 | 2010:9176 | 2010:9177 | 2010:9178 | 2010:9179 | 2010:9180 |
| 2011:9175 | 2011:9176 | 2011:9177 | 2011:9178 | 2011:9179 | 2011:9180 |
| 2012:9175 | 2012:9176 | 2012:9177 | 2012:9178 | 2012:9179 | 2012:9180 |
| 1001:9181 | 1001:9182 | 1001:9183 | 1001:9184 | 1001:9185 | 1001:9206 |
| 1002:9181 | 1002:9182 | 1002:9183 | 1002:9184 | 1002:9185 | 1002:9206 |
| 1003:9181 | 1003:9182 | 1003:9183 | 1003:9184 | 1003:9185 | 1003:9206 |
| 1004:9181 | 1004:9182 | 1004:9183 | 1004:9184 | 1004:9185 | 1004:9206 |
| 1005:9181 | 1005:9182 | 1005:9183 | 1005:9184 | 1005:9185 | 1005:9206 |
| 1006:9181 | 1006:9182 | 1006:9183 | 1006:9184 | 1006:9185 | 1006:9206 |
| 1007:9181 | 1007:9182 | 1007:9183 | 1007:9184 | 1007:9185 | 1007:9206 |
| 1008:9181 | 1008:9182 | 1008:9183 | 1008:9184 | 1008:9185 | 1008:9206 |
| 1009:9181 | 1009:9182 | 1009:9183 | 1009:9184 | 1009:9185 | 1009:9206 |
| 1010:9181 | 1010:9182 | 1010:9183 | 1010:9184 | 1010:9185 | 1010:9206 |
| 1011:9181 | 1011:9182 | 1011:9183 | 1011:9184 | 1011:9185 | 1011:9206 |
| 1012:9181 | 1012:9182 | 1012:9183 | 1012:9184 | 1012:9185 | 1012:9206 |
| 1013:9181 | 1013:9182 | 1013:9183 | 1013:9184 | 1013:9185 | 1013:9206 |
| 1014:9181 | 1014:9182 | 1014:9183 | 1014:9184 | 1014:9185 | 1014:9206 |
| 1015:9181 | 1015:9182 | 1015:9183 | 1015:9184 | 1015:9185 | 1015:9206 |
| 1016:9181 | 1016:9182 | 1016:9183 | 1016:9184 | 1016:9185 | 1016:9206 |
| 2001:9181 | 2001:9182 | 2001:9183 | 2001:9184 | 2001:9185 | 2001:9206 |
| 2002:9181 | 2002:9182 | 2002:9183 | 2002:9184 | 2002:9185 | 2002:9206 |
| 2003:9181 | 2003:9182 | 2003:9183 | 2003:9184 | 2003:9185 | 2003:9206 |
| 2004:9181 | 2004:9182 | 2004:9183 | 2004:9184 | 2004:9185 | 2004:9206 |
| 2005:9181 | 2005:9182 | 2005:9183 | 2005:9184 | 2005:9185 | 2005:9206 |
| 2006:9181 | 2006:9182 | 2006:9183 | 2006:9184 | 2006:9185 | 2006:9206 |
| 2007:9181 | 2007:9182 | 2007:9183 | 2007:9184 | 2007:9185 | 2007:9206 |
| 2008:9181 | 2008:9182 | 2008:9183 | 2008:9184 | 2008:9185 | 2008:9206 |
| 2009:9181 | 2009:9182 | 2009:9183 | 2009:9184 | 2009:9185 | 2009:9206 |
| 2010:9181 | 2010:9182 | 2010:9183 | 2010:9184 | 2010:9185 | 2010:9206 |
| 2011:9181 | 2011:9182 | 2011:9183 | 2011:9184 | 2011:9185 | 2011:9206 |
| 2012:9181 | 2012:9182 | 2012:9183 | 2012:9184 | 2012:9185 | 2012:9206 |
| 1001:9207 | 1001:9208 | 1001:9209 | 1001:9214 | 1001:9241 | 1001:9242 |
| 1002:9207 | 1002:9208 | 1002:9209 | 1002:9214 | 1002:9241 | 1002:9242 |
| 1003:9207 | 1003:9208 | 1003:9209 | 1003:9214 | 1003:9241 | 1003:9242 |

TABLE A-continued

Example combinations of a compound X with a compound Y.

| X:Y | X:Y | X:Y | X:Y | X:Y | X:Y |
|---|---|---|---|---|---|
| 1004:9207 | 1004:9208 | 1004:9209 | 1004:9214 | 1004:9241 | 1004:9242 |
| 1005:9207 | 1005:9208 | 1005:9209 | 1005:9214 | 1005:9241 | 1005:9242 |
| 1006:9207 | 1006:9208 | 1006:9209 | 1006:9214 | 1006:9241 | 1006:9242 |
| 1007:9207 | 1007:9208 | 1007:9209 | 1007:9214 | 1007:9241 | 1007:9242 |
| 1008:9207 | 1008:9208 | 1008:9209 | 1008:9214 | 1008:9241 | 1008:9242 |
| 1009:9207 | 1009:9208 | 1009:9209 | 1009:9214 | 1009:9241 | 1009:9242 |
| 1010:9207 | 1010:9208 | 1010:9209 | 1010:9214 | 1010:9241 | 1010:9242 |
| 1011:9207 | 1011:9208 | 1011:9209 | 1011:9214 | 1011:9241 | 1011:9242 |
| 1012:9207 | 1012:9208 | 1012:9209 | 1012:9214 | 1012:9241 | 1012:9242 |
| 1013:9207 | 1013:9208 | 1013:9209 | 1013:9214 | 1013:9241 | 1013:9242 |
| 1014:9207 | 1014:9208 | 1014:9209 | 1014:9214 | 1014:9241 | 1014:9242 |
| 1015:9207 | 1015:9208 | 1015:9209 | 1015:9214 | 1015:9241 | 1015:9242 |
| 1016:9207 | 1016:9208 | 1016:9209 | 1016:9214 | 1016:9241 | 1016:9242 |
| 2001:9207 | 2001:9208 | 2001:9209 | 2001:9214 | 2001:9241 | 2001:9242 |
| 2002:9207 | 2002:9208 | 2002:9209 | 2002:9214 | 2002:9241 | 2002:9242 |
| 2003:9207 | 2003:9208 | 2003:9209 | 2003:9214 | 2003:9241 | 2003:9242 |
| 2004:9207 | 2004:9208 | 2004:9209 | 2004:9214 | 2004:9241 | 2004:9242 |
| 2005:9207 | 2005:9208 | 2005:9209 | 2005:9214 | 2005:9241 | 2005:9242 |
| 2006:9207 | 2006:9208 | 2006:9209 | 2006:9214 | 2006:9241 | 2006:9242 |
| 2007:9207 | 2007:9208 | 2007:9209 | 2007:9214 | 2007:9241 | 2007:9242 |
| 2008:9207 | 2008:9208 | 2008:9209 | 2008:9214 | 2008:9241 | 2008:9242 |
| 2009:9207 | 2009:9208 | 2009:9209 | 2009:9214 | 2009:9241 | 2009:9242 |
| 2010:9207 | 2010:9208 | 2010:9209 | 2010:9214 | 2010:9241 | 2010:9242 |
| 2011:9207 | 2011:9208 | 2011:9209 | 2011:9214 | 2011:9241 | 2011:9242 |
| 2012:9207 | 2012:9208 | 2012:9209 | 2012:9214 | 2012:9241 | 2012:9242 |
| 1001:9244 | 1001:9245 | 1001:9246 | 1001:9247 | 1001:9248 | 1001:9249 |
| 1002:9244 | 1002:9245 | 1002:9246 | 1002:9247 | 1002:9248 | 1002:9249 |
| 1003:9244 | 1003:9245 | 1003:9246 | 1003:9247 | 1003:9248 | 1003:9249 |
| 1004:9244 | 1004:9245 | 1004:9246 | 1004:9247 | 1004:9248 | 1004:9249 |
| 1005:9244 | 1005:9245 | 1005:9246 | 1005:9247 | 1005:9248 | 1005:9249 |
| 1006:9244 | 1006:9245 | 1006:9246 | 1006:9247 | 1006:9248 | 1006:9249 |
| 1007:9244 | 1007:9245 | 1007:9246 | 1007:9247 | 1007:9248 | 1007:9249 |
| 1008:9244 | 1008:9245 | 1008:9246 | 1008:9247 | 1008:9248 | 1008:9249 |
| 1009:9244 | 1009:9245 | 1009:9246 | 1009:9247 | 1009:9248 | 1009:9249 |
| 1010:9244 | 1010:9245 | 1010:9246 | 1010:9247 | 1010:9248 | 1010:9249 |
| 1011:9244 | 1011:9245 | 1011:9246 | 1011:9247 | 1011:9248 | 1011:9249 |
| 1012:9244 | 1012:9245 | 1012:9246 | 1012:9247 | 1012:9248 | 1012:9249 |
| 1013:9244 | 1013:9245 | 1013:9246 | 1013:9247 | 1013:9248 | 1013:9249 |
| 1014:9244 | 1014:9245 | 1014:9246 | 1014:9247 | 1014:9248 | 1014:9249 |
| 1015:9244 | 1015:9245 | 1015:9246 | 1015:9247 | 1015:9248 | 1015:9249 |
| 1016:9244 | 1016:9245 | 1016:9246 | 1016:9247 | 1016:9248 | 1016:9249 |
| 2001:9244 | 2001:9245 | 2001:9246 | 2001:9247 | 2001:9248 | 2001:9249 |
| 2002:9244 | 2002:9245 | 2002:9246 | 2002:9247 | 2002:9248 | 2002:9249 |
| 2003:9244 | 2003:9245 | 2003:9246 | 2003:9247 | 2003:9248 | 2003:9249 |
| 2004:9244 | 2004:9245 | 2004:9246 | 2004:9247 | 2004:9248 | 2004:9249 |
| 2005:9244 | 2005:9245 | 2005:9246 | 2005:9247 | 2005:9248 | 2005:9249 |
| 2006:9244 | 2006:9245 | 2006:9246 | 2006:9247 | 2006:9248 | 2006:9249 |
| 2007:9244 | 2007:9245 | 2007:9246 | 2007:9247 | 2007:9248 | 2007:9249 |
| 2008:9244 | 2008:9245 | 2008:9246 | 2008:9247 | 2008:9248 | 2008:9249 |
| 2009:9244 | 2009:9245 | 2009:9246 | 2009:9247 | 2009:9248 | 2009:9249 |
| 2010:9244 | 2010:9245 | 2010:9246 | 2010:9247 | 2010:9248 | 2010:9249 |
| 2011:9244 | 2011:9245 | 2011:9246 | 2011:9247 | 2011:9248 | 2011:9249 |
| 2012:9244 | 2012:9245 | 2012:9246 | 2012:9247 | 2012:9248 | 2012:9249 |
| 1001:9250 | 1001:9251 | 1001:9252 | 1001:9253 | 1001:9255 | 1001:9256 |
| 1002:9250 | 1002:9251 | 1002:9252 | 1002:9253 | 1002:9255 | 1002:9256 |
| 1003:9250 | 1003:9251 | 1003:9252 | 1003:9253 | 1003:9255 | 1003:9256 |
| 1004:9250 | 1004:9251 | 1004:9252 | 1004:9253 | 1004:9255 | 1004:9256 |
| 1005:9250 | 1005:9251 | 1005:9252 | 1005:9253 | 1005:9255 | 1005:9256 |
| 1006:9250 | 1006:9251 | 1006:9252 | 1006:9253 | 1006:9255 | 1006:9256 |
| 1007:9250 | 1007:9251 | 1007:9252 | 1007:9253 | 1007:9255 | 1007:9256 |
| 1008:9250 | 1008:9251 | 1008:9252 | 1008:9253 | 1008:9255 | 1008:9256 |
| 1009:9250 | 1009:9251 | 1009:9252 | 1009:9253 | 1009:9255 | 1009:9256 |
| 1010:9250 | 1010:9251 | 1010:9252 | 1010:9253 | 1010:9255 | 1010:9256 |
| 1011:9250 | 1011:9251 | 1011:9252 | 1011:9253 | 1011:9255 | 1011:9256 |
| 1012:9250 | 1012:9251 | 1012:9252 | 1012:9253 | 1012:9255 | 1012:9256 |
| 1013:9250 | 1013:9251 | 1013:9252 | 1013:9253 | 1013:9255 | 1013:9256 |
| 1014:9250 | 1014:9251 | 1014:9252 | 1014:9253 | 1014:9255 | 1014:9256 |
| 1015:9250 | 1015:9251 | 1015:9252 | 1015:9253 | 1015:9255 | 1015:9256 |
| 1016:9250 | 1016:9251 | 1016:9252 | 1016:9253 | 1016:9255 | 1016:9256 |
| 2001:9250 | 2001:9251 | 2001:9252 | 2001:9253 | 2001:9255 | 2001:9256 |
| 2002:9250 | 2002:9251 | 2002:9252 | 2002:9253 | 2002:9255 | 2002:9256 |
| 2003:9250 | 2003:9251 | 2003:9252 | 2003:9253 | 2003:9255 | 2003:9256 |
| 2004:9250 | 2004:9251 | 2004:9252 | 2004:9253 | 2004:9255 | 2004:9256 |
| 2005:9250 | 2005:9251 | 2005:9252 | 2005:9253 | 2005:9255 | 2005:9256 |
| 2006:9250 | 2006:9251 | 2006:9252 | 2006:9253 | 2006:9255 | 2006:9256 |
| 2007:9250 | 2007:9251 | 2007:9252 | 2007:9253 | 2007:9255 | 2007:9256 |
| 2008:9250 | 2008:9251 | 2008:9252 | 2008:9253 | 2008:9255 | 2008:9256 |
| 2009:9250 | 2009:9251 | 2009:9252 | 2009:9253 | 2009:9255 | 2009:9256 |
| 2010:9250 | 2010:9251 | 2010:9252 | 2010:9253 | 2010:9255 | 2010:9256 |
| 2011:9250 | 2011:9251 | 2011:9252 | 2011:9253 | 2011:9255 | 2011:9256 |
| 2012:9250 | 2012:9251 | 2012:9252 | 2012:9253 | 2012:9255 | 2012:9256 |
| 1001:9257 | 1001:9258 | 1001:9259 | 1001:9260 | 1001:9262 | 1001:9263 |
| 1002:9257 | 1002:9258 | 1002:9259 | 1002:9260 | 1002:9262 | 1002:9263 |
| 1003:9257 | 1003:9258 | 1003:9259 | 1003:9260 | 1003:9262 | 1003:9263 |
| 1004:9257 | 1004:9258 | 1004:9259 | 1004:9260 | 1004:9262 | 1004:9263 |
| 1005:9257 | 1005:9258 | 1005:9259 | 1005:9260 | 1005:9262 | 1005:9263 |
| 1006:9257 | 1006:9258 | 1006:9259 | 1006:9260 | 1006:9262 | 1006:9263 |
| 1007:9257 | 1007:9258 | 1007:9259 | 1007:9260 | 1007:9262 | 1007:9263 |
| 1008:9257 | 1008:9258 | 1008:9259 | 1008:9260 | 1008:9262 | 1008:9263 |
| 1009:9257 | 1009:9258 | 1009:9259 | 1009:9260 | 1009:9262 | 1009:9263 |
| 1010:9257 | 1010:9258 | 1010:9259 | 1010:9260 | 1010:9262 | 1010:9263 |
| 1011:9257 | 1011:9258 | 1011:9259 | 1011:9260 | 1011:9262 | 1011:9263 |
| 1012:9257 | 1012:9258 | 1012:9259 | 1012:9260 | 1012:9262 | 1012:9263 |
| 1013:9257 | 1013:9258 | 1013:9259 | 1013:9260 | 1013:9262 | 1013:9263 |
| 1014:9257 | 1014:9258 | 1014:9259 | 1014:9260 | 1014:9262 | 1014:9263 |
| 1015:9257 | 1015:9258 | 1015:9259 | 1015:9260 | 1015:9262 | 1015:9263 |
| 1016:9257 | 1016:9258 | 1016:9259 | 1016:9260 | 1016:9262 | 1016:9263 |
| 2001:9257 | 2001:9258 | 2001:9259 | 2001:9260 | 2001:9262 | 2001:9263 |
| 2002:9257 | 2002:9258 | 2002:9259 | 2002:9260 | 2002:9262 | 2002:9263 |
| 2003:9257 | 2003:9258 | 2003:9259 | 2003:9260 | 2003:9262 | 2003:9263 |
| 2004:9257 | 2004:9258 | 2004:9259 | 2004:9260 | 2004:9262 | 2004:9263 |
| 2005:9257 | 2005:9258 | 2005:9259 | 2005:9260 | 2005:9262 | 2005:9263 |
| 2006:9257 | 2006:9258 | 2006:9259 | 2006:9260 | 2006:9262 | 2006:9263 |
| 2007:9257 | 2007:9258 | 2007:9259 | 2007:9260 | 2007:9262 | 2007:9263 |
| 2008:9257 | 2008:9258 | 2008:9259 | 2008:9260 | 2008:9262 | 2008:9263 |
| 2009:9257 | 2009:9258 | 2009:9259 | 2009:9260 | 2009:9262 | 2009:9263 |
| 2010:9257 | 2010:9258 | 2010:9259 | 2010:9260 | 2010:9262 | 2010:9263 |
| 2011:9257 | 2011:9258 | 2011:9259 | 2011:9260 | 2011:9262 | 2011:9263 |
| 2012:9257 | 2012:9258 | 2012:9259 | 2012:9260 | 2012:9262 | 2012:9263 |
| 1001:9264 | 1001:9265 | 1001:9266 | 1001:9267 | 1001:9268 | 1001:9269 |
| 1002:9264 | 1002:9265 | 1002:9266 | 1002:9267 | 1002:9268 | 1002:9269 |
| 1003:9264 | 1003:9265 | 1003:9266 | 1003:9267 | 1003:9268 | 1003:9269 |
| 1004:9264 | 1004:9265 | 1004:9266 | 1004:9267 | 1004:9268 | 1004:9269 |
| 1005:9264 | 1005:9265 | 1005:9266 | 1005:9267 | 1005:9268 | 1005:9269 |
| 1006:9264 | 1006:9265 | 1006:9266 | 1006:9267 | 1006:9268 | 1006:9269 |
| 1007:9264 | 1007:9265 | 1007:9266 | 1007:9267 | 1007:9268 | 1007:9269 |
| 1008:9264 | 1008:9265 | 1008:9266 | 1008:9267 | 1008:9268 | 1008:9269 |
| 1009:9264 | 1009:9265 | 1009:9266 | 1009:9267 | 1009:9268 | 1009:9269 |
| 1010:9264 | 1010:9265 | 1010:9266 | 1010:9267 | 1010:9268 | 1010:9269 |
| 1011:9264 | 1011:9265 | 1011:9266 | 1011:9267 | 1011:9268 | 1011:9269 |
| 1012:9264 | 1012:9265 | 1012:9266 | 1012:9267 | 1012:9268 | 1012:9269 |
| 1013:9264 | 1013:9265 | 1013:9266 | 1013:9267 | 1013:9268 | 1013:9269 |
| 1014:9264 | 1014:9265 | 1014:9266 | 1014:9267 | 1014:9268 | 1014:9269 |
| 1015:9264 | 1015:9265 | 1015:9266 | 1015:9267 | 1015:9268 | 1015:9269 |
| 1016:9264 | 1016:9265 | 1016:9266 | 1016:9267 | 1016:9268 | 1016:9269 |
| 2001:9264 | 2001:9265 | 2001:9266 | 2001:9267 | 2001:9268 | 2001:9269 |
| 2002:9264 | 2002:9265 | 2002:9266 | 2002:9267 | 2002:9268 | 2002:9269 |
| 2003:9264 | 2003:9265 | 2003:9266 | 2003:9267 | 2003:9268 | 2003:9269 |
| 2004:9264 | 2004:9265 | 2004:9266 | 2004:9267 | 2004:9268 | 2004:9269 |
| 2005:9264 | 2005:9265 | 2005:9266 | 2005:9267 | 2005:9268 | 2005:9269 |
| 2006:9264 | 2006:9265 | 2006:9266 | 2006:9267 | 2006:9268 | 2006:9269 |
| 2007:9264 | 2007:9265 | 2007:9266 | 2007:9267 | 2007:9268 | 2007:9269 |
| 2008:9264 | 2008:9265 | 2008:9266 | 2008:9267 | 2008:9268 | 2008:9269 |
| 2009:9264 | 2009:9265 | 2009:9266 | 2009:9267 | 2009:9268 | 2009:9269 |
| 2010:9264 | 2010:9265 | 2010:9266 | 2010:9267 | 2010:9268 | 2010:9269 |
| 2011:9264 | 2011:9265 | 2011:9266 | 2011:9267 | 2011:9268 | 2011:9269 |
| 2012:9264 | 2012:9265 | 2012:9266 | 2012:9267 | 2012:9268 | 2012:9269 |
| 1001:9270 | 1001:9271 | 1001:9272 | 1001:9273 | 1001:9274 | 1001:9275 |
| 1002:9270 | 1002:9271 | 1002:9272 | 1002:9273 | 1002:9274 | 1002:9275 |
| 1003:9270 | 1003:9271 | 1003:9272 | 1003:9273 | 1003:9274 | 1003:9275 |
| 1004:9270 | 1004:9271 | 1004:9272 | 1004:9273 | 1004:9274 | 1004:9275 |
| 1005:9270 | 1005:9271 | 1005:9272 | 1005:9273 | 1005:9274 | 1005:9275 |
| 1006:9270 | 1006:9271 | 1006:9272 | 1006:9273 | 1006:9274 | 1006:9275 |
| 1007:9270 | 1007:9271 | 1007:9272 | 1007:9273 | 1007:9274 | 1007:9275 |
| 1008:9270 | 1008:9271 | 1008:9272 | 1008:9273 | 1008:9274 | 1008:9275 |
| 1009:9270 | 1009:9271 | 1009:9272 | 1009:9273 | 1009:9274 | 1009:9275 |
| 1010:9270 | 1010:9271 | 1010:9272 | 1010:9273 | 1010:9274 | 1010:9275 |
| 1011:9270 | 1011:9271 | 1011:9272 | 1011:9273 | 1011:9274 | 1011:9275 |
| 1012:9270 | 1012:9271 | 1012:9272 | 1012:9273 | 1012:9274 | 1012:9275 |
| 1013:9270 | 1013:9271 | 1013:9272 | 1013:9273 | 1013:9274 | 1013:9275 |
| 1014:9270 | 1014:9271 | 1014:9272 | 1014:9273 | 1014:9274 | 1014:9275 |
| 1015:9270 | 1015:9271 | 1015:9272 | 1015:9273 | 1015:9274 | 1015:9275 |

TABLE A-continued

Example combinations of a compound X with a compound Y.

| X:Y | X:Y | X:Y | X:Y | X:Y | X:Y |
|---|---|---|---|---|---|
| 1016:9270 | 1016:9271 | 1016:9272 | 1016:9273 | 1016:9274 | 1016:9275 |
| 2001:9270 | 2001:9271 | 2001:9272 | 2001:9273 | 2001:9274 | 2001:9275 |
| 2002:9270 | 2002:9271 | 2002:9272 | 2002:9273 | 2002:9274 | 2002:9275 |
| 2003:9270 | 2003:9271 | 2003:9272 | 2003:9273 | 2003:9274 | 2003:9275 |
| 2004:9270 | 2004:9271 | 2004:9272 | 2004:9273 | 2004:9274 | 2004:9275 |
| 2005:9270 | 2005:9271 | 2005:9272 | 2005:9273 | 2005:9274 | 2005:9275 |
| 2006:9270 | 2006:9271 | 2006:9272 | 2006:9273 | 2006:9274 | 2006:9275 |
| 2007:9270 | 2007:9271 | 2007:9272 | 2007:9273 | 2007:9274 | 2007:9275 |
| 2008:9270 | 2008:9271 | 2008:9272 | 2008:9273 | 2008:9274 | 2008:9275 |
| 2009:9270 | 2009:9271 | 2009:9272 | 2009:9273 | 2009:9274 | 2009:9275 |
| 2010:9270 | 2010:9271 | 2010:9272 | 2010:9273 | 2010:9274 | 2010:9275 |
| 2011:9270 | 2011:9271 | 2011:9272 | 2011:9273 | 2011:9274 | 2011:9275 |
| 2012:9270 | 2012:9271 | 2012:9272 | 2012:9273 | 2012:9274 | 2012:9275 |
| 1001:9276 | 1001:9277 | 1001:9278 | 1001:9279 | 1001:9280 | 1001:9281 |
| 1002:9276 | 1002:9277 | 1002:9278 | 1002:9279 | 1002:9280 | 1002:9281 |
| 1003:9276 | 1003:9277 | 1003:9278 | 1003:9279 | 1003:9280 | 1003:9281 |
| 1004:9276 | 1004:9277 | 1004:9278 | 1004:9279 | 1004:9280 | 1004:9281 |
| 1005:9276 | 1005:9277 | 1005:9278 | 1005:9279 | 1005:9280 | 1005:9281 |
| 1006:9276 | 1006:9277 | 1006:9278 | 1006:9279 | 1006:9280 | 1006:9281 |
| 1007:9276 | 1007:9277 | 1007:9278 | 1007:9279 | 1007:9280 | 1007:9281 |
| 1008:9276 | 1008:9277 | 1008:9278 | 1008:9279 | 1008:9280 | 1008:9281 |
| 1009:9276 | 1009:9277 | 1009:9278 | 1009:9279 | 1009:9280 | 1009:9281 |
| 1010:9276 | 1010:9277 | 1010:9278 | 1010:9279 | 1010:9280 | 1010:9281 |
| 1011:9276 | 1011:9277 | 1011:9278 | 1011:9279 | 1011:9280 | 1011:9281 |
| 1012:9276 | 1012:9277 | 1012:9278 | 1012:9279 | 1012:9280 | 1012:9281 |
| 1013:9276 | 1013:9277 | 1013:9278 | 1013:9279 | 1013:9280 | 1013:9281 |
| 1014:9276 | 1014:9277 | 1014:9278 | 1014:9279 | 1014:9280 | 1014:9281 |
| 1015:9276 | 1015:9277 | 1015:9278 | 1015:9279 | 1015:9280 | 1015:9281 |
| 1016:9276 | 1016:9277 | 1016:9278 | 1016:9279 | 1016:9280 | 1016:9281 |
| 2001:9276 | 2001:9277 | 2001:9278 | 2001:9279 | 2001:9280 | 2001:9281 |
| 2002:9276 | 2002:9277 | 2002:9278 | 2002:9279 | 2002:9280 | 2002:9281 |
| 2003:9276 | 2003:9277 | 2003:9278 | 2003:9279 | 2003:9280 | 2003:9281 |
| 2004:9276 | 2004:9277 | 2004:9278 | 2004:9279 | 2004:9280 | 2004:9281 |
| 2005:9276 | 2005:9277 | 2005:9278 | 2005:9279 | 2005:9280 | 2005:9281 |
| 2006:9276 | 2006:9277 | 2006:9278 | 2006:9279 | 2006:9280 | 2006:9281 |
| 2007:9276 | 2007:9277 | 2007:9278 | 2007:9279 | 2007:9280 | 2007:9281 |
| 2008:9276 | 2008:9277 | 2008:9278 | 2008:9279 | 2008:9280 | 2008:9281 |
| 2009:9276 | 2009:9277 | 2009:9278 | 2009:9279 | 2009:9280 | 2009:9281 |
| 2010:9276 | 2010:9277 | 2010:9278 | 2010:9279 | 2010:9280 | 2010:9281 |
| 2011:9276 | 2011:9277 | 2011:9278 | 2011:9279 | 2011:9280 | 2011:9281 |
| 2012:9276 | 2012:9277 | 2012:9278 | 2012:9279 | 2012:9280 | 2012:9281 |
| 1001:9282 | 1001:9283 | 1001:9284 | 1001:9285 | 1001:9286 | 1001:9287 |
| 1002:9282 | 1002:9283 | 1002:9284 | 1002:9285 | 1002:9286 | 1002:9287 |
| 1003:9282 | 1003:9283 | 1003:9284 | 1003:9285 | 1003:9286 | 1003:9287 |
| 1004:9282 | 1004:9283 | 1004:9284 | 1004:9285 | 1004:9286 | 1004:9287 |
| 1005:9282 | 1005:9283 | 1005:9284 | 1005:9285 | 1005:9286 | 1005:9287 |
| 1006:9282 | 1006:9283 | 1006:9284 | 1006:9285 | 1006:9286 | 1006:9287 |
| 1007:9282 | 1007:9283 | 1007:9284 | 1007:9285 | 1007:9286 | 1007:9287 |
| 1008:9282 | 1008:9283 | 1008:9284 | 1008:9285 | 1008:9286 | 1008:9287 |
| 1009:9282 | 1009:9283 | 1009:9284 | 1009:9285 | 1009:9286 | 1009:9287 |
| 1010:9282 | 1010:9283 | 1010:9284 | 1010:9285 | 1010:9286 | 1010:9287 |
| 1011:9282 | 1011:9283 | 1011:9284 | 1011:9285 | 1011:9286 | 1011:9287 |
| 1012:9282 | 1012:9283 | 1012:9284 | 1012:9285 | 1012:9286 | 1012:9287 |
| 1013:9282 | 1013:9283 | 1013:9284 | 1013:9285 | 1013:9286 | 1013:9287 |
| 1014:9282 | 1014:9283 | 1014:9284 | 1014:9285 | 1014:9286 | 1014:9287 |
| 1015:9282 | 1015:9283 | 1015:9284 | 1015:9285 | 1015:9286 | 1015:9287 |
| 1016:9282 | 1016:9283 | 1016:9284 | 1016:9285 | 1016:9286 | 1016:9287 |
| 2001:9282 | 2001:9283 | 2001:9284 | 2001:9285 | 2001:9286 | 2001:9287 |
| 2002:9282 | 2002:9283 | 2002:9284 | 2002:9285 | 2002:9286 | 2002:9287 |
| 2003:9282 | 2003:9283 | 2003:9284 | 2003:9285 | 2003:9286 | 2003:9287 |
| 2004:9282 | 2004:9283 | 2004:9284 | 2004:9285 | 2004:9286 | 2004:9287 |
| 2005:9282 | 2005:9283 | 2005:9284 | 2005:9285 | 2005:9286 | 2005:9287 |
| 2006:9282 | 2006:9283 | 2006:9284 | 2006:9285 | 2006:9286 | 2006:9287 |
| 2007:9282 | 2007:9283 | 2007:9284 | 2007:9285 | 2007:9286 | 2007:9287 |
| 2008:9282 | 2008:9283 | 2008:9284 | 2008:9285 | 2008:9286 | 2008:9287 |
| 2009:9282 | 2009:9283 | 2009:9284 | 2009:9285 | 2009:9286 | 2009:9287 |
| 2010:9282 | 2010:9283 | 2010:9284 | 2010:9285 | 2010:9286 | 2010:9287 |
| 2011:9282 | 2011:9283 | 2011:9284 | 2011:9285 | 2011:9286 | 2011:9287 |
| 2012:9282 | 2012:9283 | 2012:9284 | 2012:9285 | 2012:9286 | 2012:9287 |
| 1001:9288 | 1001:9289 | 1001:9290 | 1001:9291 | 1001:9292 | 1001:9293 |
| 1002:9288 | 1002:9289 | 1002:9290 | 1002:9291 | 1002:9292 | 1002:9293 |
| 1003:9288 | 1003:9289 | 1003:9290 | 1003:9291 | 1003:9292 | 1003:9293 |
| 1004:9288 | 1004:9289 | 1004:9290 | 1004:9291 | 1004:9292 | 1004:9293 |
| 1005:9288 | 1005:9289 | 1005:9290 | 1005:9291 | 1005:9292 | 1005:9293 |
| 1006:9288 | 1006:9289 | 1006:9290 | 1006:9291 | 1006:9292 | 1006:9293 |
| 1007:9288 | 1007:9289 | 1007:9290 | 1007:9291 | 1007:9292 | 1007:9293 |
| 1008:9288 | 1008:9289 | 1008:9290 | 1008:9291 | 1008:9292 | 1008:9293 |
| 1009:9288 | 1009:9289 | 1009:9290 | 1009:9291 | 1009:9292 | 1009:9293 |
| 1010:9288 | 1010:9289 | 1010:9290 | 1010:9291 | 1010:9292 | 1010:9293 |
| 1011:9288 | 1011:9289 | 1011:9290 | 1011:9291 | 1011:9292 | 1011:9293 |
| 1012:9288 | 1012:9289 | 1012:9290 | 1012:9291 | 1012:9292 | 1012:9293 |
| 1013:9288 | 1013:9289 | 1013:9290 | 1013:9291 | 1013:9292 | 1013:9293 |
| 1014:9288 | 1014:9289 | 1014:9290 | 1014:9291 | 1014:9292 | 1014:9293 |
| 1015:9288 | 1015:9289 | 1015:9290 | 1015:9291 | 1015:9292 | 1015:9293 |
| 1016:9288 | 1016:9289 | 1016:9290 | 1016:9291 | 1016:9292 | 1016:9293 |
| 2001:9288 | 2001:9289 | 2001:9290 | 2001:9291 | 2001:9292 | 2001:9293 |
| 2002:9288 | 2002:9289 | 2002:9290 | 2002:9291 | 2002:9292 | 2002:9293 |
| 2003:9288 | 2003:9289 | 2003:9290 | 2003:9291 | 2003:9292 | 2003:9293 |
| 2004:9288 | 2004:9289 | 2004:9290 | 2004:9291 | 2004:9292 | 2004:9293 |
| 2005:9288 | 2005:9289 | 2005:9290 | 2005:9291 | 2005:9292 | 2005:9293 |
| 2006:9288 | 2006:9289 | 2006:9290 | 2006:9291 | 2006:9292 | 2006:9293 |
| 2007:9288 | 2007:9289 | 2007:9290 | 2007:9291 | 2007:9292 | 2007:9293 |
| 2008:9288 | 2008:9289 | 2008:9290 | 2008:9291 | 2008:9292 | 2008:9293 |
| 2009:9288 | 2009:9289 | 2009:9290 | 2009:9291 | 2009:9292 | 2009:9293 |
| 2010:9288 | 2010:9289 | 2010:9290 | 2010:9291 | 2010:9292 | 2010:9293 |
| 2011:9288 | 2011:9289 | 2011:9290 | 2011:9291 | 2011:9292 | 2011:9293 |
| 2012:9288 | 2012:9289 | 2012:9290 | 2012:9291 | 2012:9292 | 2012:9293 |
| 1001:9294 | 1001:9295 | 1001:9296 | 1001:9297 | 1001:9298 | 1001:9299 |
| 1002:9294 | 1002:9295 | 1002:9296 | 1002:9297 | 1002:9298 | 1002:9299 |
| 1003:9294 | 1003:9295 | 1003:9296 | 1003:9297 | 1003:9298 | 1003:9299 |
| 1004:9294 | 1004:9295 | 1004:9296 | 1004:9297 | 1004:9298 | 1004:9299 |
| 1005:9294 | 1005:9295 | 1005:9296 | 1005:9297 | 1005:9298 | 1005:9299 |
| 1006:9294 | 1006:9295 | 1006:9296 | 1006:9297 | 1006:9298 | 1006:9299 |
| 1007:9294 | 1007:9295 | 1007:9296 | 1007:9297 | 1007:9298 | 1007:9299 |
| 1008:9294 | 1008:9295 | 1008:9296 | 1008:9297 | 1008:9298 | 1008:9299 |
| 1009:9294 | 1009:9295 | 1009:9296 | 1009:9297 | 1009:9298 | 1009:9299 |
| 1010:9294 | 1010:9295 | 1010:9296 | 1010:9297 | 1010:9298 | 1010:9299 |
| 1011:9294 | 1011:9295 | 1011:9296 | 1011:9297 | 1011:9298 | 1011:9299 |
| 1012:9294 | 1012:9295 | 1012:9296 | 1012:9297 | 1012:9298 | 1012:9299 |
| 1013:9294 | 1013:9295 | 1013:9296 | 1013:9297 | 1013:9298 | 1013:9299 |
| 1014:9294 | 1014:9295 | 1014:9296 | 1014:9297 | 1014:9298 | 1014:9299 |
| 1015:9294 | 1015:9295 | 1015:9296 | 1015:9297 | 1015:9298 | 1015:9299 |
| 1016:9294 | 1016:9295 | 1016:9296 | 1016:9297 | 1016:9298 | 1016:9299 |
| 2001:9294 | 2001:9295 | 2001:9296 | 2001:9297 | 2001:9298 | 2001:9299 |
| 2002:9294 | 2002:9295 | 2002:9296 | 2002:9297 | 2002:9298 | 2002:9299 |
| 2003:9294 | 2003:9295 | 2003:9296 | 2003:9297 | 2003:9298 | 2003:9299 |
| 2004:9294 | 2004:9295 | 2004:9296 | 2004:9297 | 2004:9298 | 2004:9299 |
| 2005:9294 | 2005:9295 | 2005:9296 | 2005:9297 | 2005:9298 | 2005:9299 |
| 2006:9294 | 2006:9295 | 2006:9296 | 2006:9297 | 2006:9298 | 2006:9299 |
| 2007:9294 | 2007:9295 | 2007:9296 | 2007:9297 | 2007:9298 | 2007:9299 |
| 2008:9294 | 2008:9295 | 2008:9296 | 2008:9297 | 2008:9298 | 2008:9299 |
| 2009:9294 | 2009:9295 | 2009:9296 | 2009:9297 | 2009:9298 | 2009:9299 |
| 2010:9294 | 2010:9295 | 2010:9296 | 2010:9297 | 2010:9298 | 2010:9299 |
| 2011:9294 | 2011:9295 | 2011:9296 | 2011:9297 | 2011:9298 | 2011:9299 |
| 2012:9294 | 2012:9295 | 2012:9296 | 2012:9297 | 2012:9298 | 2012:9299 |
| 1001:9300 | 1001:9301 | 1001:9302 | 1001:9303 | 1001:9304 | 1001:9305 |
| 1002:9300 | 1002:9301 | 1002:9302 | 1002:9303 | 1002:9304 | 1002:9305 |
| 1003:9300 | 1003:9301 | 1003:9302 | 1003:9303 | 1003:9304 | 1003:9305 |
| 1004:9300 | 1004:9301 | 1004:9302 | 1004:9303 | 1004:9304 | 1004:9305 |
| 1005:9300 | 1005:9301 | 1005:9302 | 1005:9303 | 1005:9304 | 1005:9305 |
| 1006:9300 | 1006:9301 | 1006:9302 | 1006:9303 | 1006:9304 | 1006:9305 |
| 1007:9300 | 1007:9301 | 1007:9302 | 1007:9303 | 1007:9304 | 1007:9305 |
| 1008:9300 | 1008:9301 | 1008:9302 | 1008:9303 | 1008:9304 | 1008:9305 |
| 1009:9300 | 1009:9301 | 1009:9302 | 1009:9303 | 1009:9304 | 1009:9305 |
| 1010:9300 | 1010:9301 | 1010:9302 | 1010:9303 | 1010:9304 | 1010:9305 |
| 1011:9300 | 1011:9301 | 1011:9302 | 1011:9303 | 1011:9304 | 1011:9305 |
| 1012:9300 | 1012:9301 | 1012:9302 | 1012:9303 | 1012:9304 | 1012:9305 |
| 1013:9300 | 1013:9301 | 1013:9302 | 1013:9303 | 1013:9304 | 1013:9305 |
| 1014:9300 | 1014:9301 | 1014:9302 | 1014:9303 | 1014:9304 | 1014:9305 |
| 1015:9300 | 1015:9301 | 1015:9302 | 1015:9303 | 1015:9304 | 1015:9305 |
| 1016:9300 | 1016:9301 | 1016:9302 | 1016:9303 | 1016:9304 | 1016:9305 |
| 2001:9300 | 2001:9301 | 2001:9302 | 2001:9303 | 2001:9304 | 2001:9305 |
| 2002:9300 | 2002:9301 | 2002:9302 | 2002:9303 | 2002:9304 | 2002:9305 |
| 2003:9300 | 2003:9301 | 2003:9302 | 2003:9303 | 2003:9304 | 2003:9305 |
| 2004:9300 | 2004:9301 | 2004:9302 | 2004:9303 | 2004:9304 | 2004:9305 |
| 2005:9300 | 2005:9301 | 2005:9302 | 2005:9303 | 2005:9304 | 2005:9305 |
| 2006:9300 | 2006:9301 | 2006:9302 | 2006:9303 | 2006:9304 | 2006:9305 |
| 2007:9300 | 2007:9301 | 2007:9302 | 2007:9303 | 2007:9304 | 2007:9305 |
| 2008:9300 | 2008:9301 | 2008:9302 | 2008:9303 | 2008:9304 | 2008:9305 |
| 2009:9300 | 2009:9301 | 2009:9302 | 2009:9303 | 2009:9304 | 2009:9305 |
| 2010:9300 | 2010:9301 | 2010:9302 | 2010:9303 | 2010:9304 | 2010:9305 |
| 2011:9300 | 2011:9301 | 2011:9302 | 2011:9303 | 2011:9304 | 2011:9305 |

TABLE A-continued

Example combinations of a compound X with a compound Y.

| X:Y | X:Y | X:Y | X:Y | X:Y | X:Y |
|---|---|---|---|---|---|
| 2012:9300 | 2012:9301 | 2012:9302 | 2012:9303 | 2012:9304 | 2012:9305 |
| 1001:9306 | 1001:9307 | 1001:9308 | 1001:9309 | 1001:9310 | — |
| 1002:9306 | 1002:9307 | 1002:9308 | 1002:9309 | 1002:9310 | |
| 1003:9306 | 1003:9307 | 1003:9308 | 1003:9309 | 1003:9310 | |
| 1004:9306 | 1004:9307 | 1004:9308 | 1004:9309 | 1004:9310 | |
| 1005:9306 | 1005:9307 | 1005:9308 | 1005:9309 | 1005:9310 | |
| 1006:9306 | 1006:9307 | 1006:9308 | 1006:9309 | 1006:9310 | |
| 1007:9306 | 1007:9307 | 1007:9308 | 1007:9309 | 1007:9310 | |
| 1008:9306 | 1008:9307 | 1008:9308 | 1008:9309 | 1008:9310 | |
| 1009:9306 | 1009:9307 | 1009:9308 | 1009:9309 | 1009:9310 | |
| 1010:9306 | 1010:9307 | 1010:9308 | 1010:9309 | 1010:9310 | |
| 1011:9306 | 1011:9307 | 1011:9308 | 1011:9309 | 1011:9310 | |
| 1012:9306 | 1012:9307 | 1012:9308 | 1012:9309 | 1012:9310 | |
| 1013:9306 | 1013:9307 | 1013:9308 | 1013:9309 | 1013:9310 | |
| 1014:9306 | 1014:9307 | 1014:9308 | 1014:9309 | 1014:9310 | |
| 1015:9306 | 1015:9307 | 1015:9308 | 1015:9309 | 1015:9310 | |
| 1016:9306 | 1016:9307 | 1016:9308 | 1016:9309 | 1016:9310 | |
| 2001:9306 | 2001:9307 | 2001:9308 | 2001:9309 | 2001:9310 | |
| 2002:9306 | 2002:9307 | 2002:9308 | 2002:9309 | 2002:9310 | |
| 2003:9306 | 2003:9307 | 2003:9308 | 2003:9309 | 2003:9310 | |
| 2004:9306 | 2004:9307 | 2004:9308 | 2004:9309 | 2004:9310 | |
| 2005:9306 | 2005:9307 | 2005:9308 | 2005:9309 | 2005:9310 | |
| 2006:9306 | 2006:9307 | 2006:9308 | 2006:9309 | 2006:9310 | |
| 2007:9306 | 2007:9307 | 2007:9308 | 2007:9309 | 2007:9310 | |
| 2008:9306 | 2008:9307 | 2008:9308 | 2008:9309 | 2008:9310 | |
| 2009:9306 | 2009:9307 | 2009:9308 | 2009:9309 | 2009:9310 | |
| 2010:9306 | 2010:9307 | 2010:9308 | 2010:9309 | 2010:9310 | |
| 2011:9306 | 2011:9307 | 2011:9308 | 2011:9309 | 2011:9310 | |
| 2012:9306 | 2012:9307 | 2012:9308 | 2012:9309 | 2012:9310 | |

TABLE B

Example combinations of a compound X with a compound Y.

| X:Y | X:Y | X:Y | X:Y | X:Y | X:Y |
|---|---|---|---|---|---|
| 3002:9006 | 3002:9007 | 3002:9008 | 3002:9018 | 3002:9020 | 3002:9021 |
| 3003:9006 | 3003:9007 | 3003:9008 | 3003:9018 | 3003:9020 | 3003:9021 |
| 3004:9006 | 3004:9007 | 3004:9008 | 3004:9018 | 3004:9020 | 3004:9021 |
| 3005:9006 | 3005:9007 | 3005:9008 | 3005:9018 | 3005:9020 | 3005:9021 |
| 3006:9006 | 3006:9007 | 3006:9008 | 3006:9018 | 3006:9020 | 3006:9021 |
| 3007:9006 | 3007:9007 | 3007:9008 | 3007:9018 | 3007:9020 | 3007:9021 |
| 3008:9006 | 3008:9007 | 3008:9008 | 3008:9018 | 3008:9020 | 3008:9021 |
| 3009:9006 | 3009:9007 | 3009:9008 | 3009:9018 | 3009:9020 | 3009:9021 |
| 3010:9006 | 3010:9007 | 3010:9008 | 3010:9018 | 3010:9020 | 3010:9021 |
| 3011:9006 | 3011:9007 | 3011:9008 | 3011:9018 | 3011:9020 | 3011:9021 |
| 3012:9006 | 3012:9007 | 3012:9008 | 3012:9018 | 3012:9020 | 3012:9021 |
| 3013:9006 | 3013:9007 | 3013:9008 | 3013:9018 | 3013:9020 | 3013:9021 |
| 3014:9006 | 3014:9007 | 3014:9008 | 3014:9018 | 3014:9020 | 3014:9021 |
| 4001:9006 | 4001:9007 | 4001:9008 | 4001:9018 | 4001:9020 | 4001:9021 |
| 4002:9006 | 4002:9007 | 4002:9008 | 4002:9018 | 4002:9020 | 4002:9021 |
| 4003:9006 | 4003:9007 | 4003:9008 | 4003:9018 | 4003:9020 | 4003:9021 |
| 4004:9006 | 4004:9007 | 4004:9008 | 4004:9018 | 4004:9020 | 4004:9021 |
| 4005:9006 | 4005:9007 | 4005:9008 | 4005:9018 | 4005:9020 | 4005:9021 |
| 4006:9006 | 4006:9007 | 4006:9008 | 4006:9018 | 4006:9020 | 4006:9021 |
| 4007:9006 | 4007:9007 | 4007:9008 | 4007:9018 | 4007:9020 | 4007:9021 |
| 4008:9006 | 4008:9007 | 4008:9008 | 4008:9018 | 4008:9020 | 4008:9021 |
| 4009:9006 | 4009:9007 | 4009:9008 | 4009:9018 | 4009:9020 | 4009:9021 |
| 4010:9006 | 4010:9007 | 4010:9008 | 4010:9018 | 4010:9020 | 4010:9021 |
| 4011:9006 | 4011:9007 | 4011:9008 | 4011:9018 | 4011:9020 | 4011:9021 |
| 4012:9006 | 4012:9007 | 4012:9008 | 4012:9018 | 4012:9020 | 4012:9021 |
| 5001:9006 | 5001:9007 | 5001:9008 | 5001:9018 | 5001:9020 | 5001:9021 |
| 5002:9006 | 5002:9007 | 5002:9008 | 5002:9018 | 5002:9020 | 5002:9021 |
| 5003:9006 | 5003:9007 | 5003:9008 | 5003:9018 | 5003:9020 | 5003:9021 |
| 5004:9006 | 5004:9007 | 5004:9008 | 5004:9018 | 5004:9020 | 5004:9021 |
| 5005:9006 | 5005:9007 | 5005:9008 | 5005:9018 | 5005:9020 | 5005:9021 |
| 5006:9006 | 5006:9007 | 5006:9008 | 5006:9018 | 5006:9020 | 5006:9021 |
| 5007:9006 | 5007:9007 | 5007:9008 | 5007:9018 | 5007:9020 | 5007:9021 |
| 5008:9006 | 5008:9007 | 5008:9008 | 5008:9018 | 5008:9020 | 5008:9021 |
| 5009:9006 | 5009:9007 | 5009:9008 | 5009:9018 | 5009:9020 | 5009:9021 |
| 5010:9006 | 5010:9007 | 5010:9008 | 5010:9018 | 5010:9020 | 5010:9021 |
| 5011:9006 | 5011:9007 | 5011:9008 | 5011:9018 | 5011:9020 | 5011:9021 |
| 3002:9025 | 3002:9026 | 3002:9036 | 3002:9038 | 3002:9039 | 3002:9040 |

TABLE B-continued

Example combinations of a compound X with a compound Y.

| X:Y | X:Y | X:Y | X:Y | X:Y | X:Y |
|---|---|---|---|---|---|
| 3003:9025 | 3003:9026 | 3003:9036 | 3003:9038 | 3003:9039 | 3003:9040 |
| 3004:9025 | 3004:9026 | 3004:9036 | 3004:9038 | 3004:9039 | 3004:9040 |
| 3005:9025 | 3005:9026 | 3005:9036 | 3005:9038 | 3005:9039 | 3005:9040 |
| 3006:9025 | 3006:9026 | 3006:9036 | 3006:9038 | 3006:9039 | 3006:9040 |
| 3007:9025 | 3007:9026 | 3007:9036 | 3007:9038 | 3007:9039 | 3007:9040 |
| 3008:9025 | 3008:9026 | 3008:9036 | 3008:9038 | 3008:9039 | 3008:9040 |
| 3009:9025 | 3009:9026 | 3009:9036 | 3009:9038 | 3009:9039 | 3009:9040 |
| 3010:9025 | 3010:9026 | 3010:9036 | 3010:9038 | 3010:9039 | 3010:9040 |
| 3011:9025 | 3011:9026 | 3011:9036 | 3011:9038 | 3011:9039 | 3011:9040 |
| 3012:9025 | 3012:9026 | 3012:9036 | 3012:9038 | 3012:9039 | 3012:9040 |
| 3013:9025 | 3013:9026 | 3013:9036 | 3013:9038 | 3013:9039 | 3013:9040 |
| 3014:9025 | 3014:9026 | 3014:9036 | 3014:9038 | 3014:9039 | 3014:9040 |
| 4001:9025 | 4001:9026 | 4001:9036 | 4001:9038 | 4001:9039 | 4001:9040 |
| 4002:9025 | 4002:9026 | 4002:9036 | 4002:9038 | 4002:9039 | 4002:9040 |
| 4003:9025 | 4003:9026 | 4003:9036 | 4003:9038 | 4003:9039 | 4003:9040 |
| 4004:9025 | 4004:9026 | 4004:9036 | 4004:9038 | 4004:9039 | 4004:9040 |
| 4005:9025 | 4005:9026 | 4005:9036 | 4005:9038 | 4005:9039 | 4005:9040 |
| 4006:9025 | 4006:9026 | 4006:9036 | 4006:9038 | 4006:9039 | 4006:9040 |
| 4007:9025 | 4007:9026 | 4007:9036 | 4007:9038 | 4007:9039 | 4007:9040 |
| 4008:9025 | 4008:9026 | 4008:9036 | 4008:9038 | 4008:9039 | 4008:9040 |
| 4009:9025 | 4009:9026 | 4009:9036 | 4009:9038 | 4009:9039 | 4009:9040 |
| 4010:9025 | 4010:9026 | 4010:9036 | 4010:9038 | 4010:9039 | 4010:9040 |
| 4011:9025 | 4011:9026 | 4011:9036 | 4011:9038 | 4011:9039 | 4011:9040 |
| 4012:9025 | 4012:9026 | 4012:9036 | 4012:9038 | 4012:9039 | 4012:9040 |
| 5001:9025 | 5001:9026 | 5001:9036 | 5001:9038 | 5001:9039 | 5001:9040 |
| 5002:9025 | 5002:9026 | 5002:9036 | 5002:9038 | 5002:9039 | 5002:9040 |
| 5003:9025 | 5003:9026 | 5003:9036 | 5003:9038 | 5003:9039 | 5003:9040 |
| 5004:9025 | 5004:9026 | 5004:9036 | 5004:9038 | 5004:9039 | 5004:9040 |
| 5005:9025 | 5005:9026 | 5005:9036 | 5005:9038 | 5005:9039 | 5005:9040 |
| 5006:9025 | 5006:9026 | 5006:9036 | 5006:9038 | 5006:9039 | 5006:9040 |
| 5007:9025 | 5007:9026 | 5007:9036 | 5007:9038 | 5007:9039 | 5007:9040 |
| 5008:9025 | 5008:9026 | 5008:9036 | 5008:9038 | 5008:9039 | 5008:9040 |
| 5009:9025 | 5009:9026 | 5009:9036 | 5009:9038 | 5009:9039 | 5009:9040 |
| 5010:9025 | 5010:9026 | 5010:9036 | 5010:9038 | 5010:9039 | 5010:9040 |
| 5011:9025 | 5011:9026 | 5011:9036 | 5011:9038 | 5011:9039 | 5011:9040 |
| 3002:9041 | 3002:9042 | 3002:9043 | 3002:9044 | 3002:9045 | 3002:9047 |
| 3003:9041 | 3003:9042 | 3003:9043 | 3003:9044 | 3003:9045 | 3003:9047 |
| 3004:9041 | 3004:9042 | 3004:9043 | 3004:9044 | 3004:9045 | 3004:9047 |
| 3005:9041 | 3005:9042 | 3005:9043 | 3005:9044 | 3005:9045 | 3005:9047 |
| 3006:9041 | 3006:9042 | 3006:9043 | 3006:9044 | 3006:9045 | 3006:9047 |
| 3007:9041 | 3007:9042 | 3007:9043 | 3007:9044 | 3007:9045 | 3007:9047 |
| 3008:9041 | 3008:9042 | 3008:9043 | 3008:9044 | 3008:9045 | 3008:9047 |
| 3009:9041 | 3009:9042 | 3009:9043 | 3009:9044 | 3009:9045 | 3009:9047 |
| 3010:9041 | 3010:9042 | 3010:9043 | 3010:9044 | 3010:9045 | 3010:9047 |
| 3011:9041 | 3011:9042 | 3011:9043 | 3011:9044 | 3011:9045 | 3011:9047 |
| 3012:9041 | 3012:9042 | 3012:9043 | 3012:9044 | 3012:9045 | 3012:9047 |
| 3013:9041 | 3013:9042 | 3013:9043 | 3013:9044 | 3013:9045 | 3013:9047 |
| 3014:9041 | 3014:9042 | 3014:9043 | 3014:9044 | 3014:9045 | 3014:9047 |
| 4001:9041 | 4001:9042 | 4001:9043 | 4001:9044 | 4001:9045 | 4001:9047 |
| 4002:9041 | 4002:9042 | 4002:9043 | 4002:9044 | 4002:9045 | 4002:9047 |
| 4003:9041 | 4003:9042 | 4003:9043 | 4003:9044 | 4003:9045 | 4003:9047 |
| 4004:9041 | 4004:9042 | 4004:9043 | 4004:9044 | 4004:9045 | 4004:9047 |
| 4005:9041 | 4005:9042 | 4005:9043 | 4005:9044 | 4005:9045 | 4005:9047 |
| 4006:9041 | 4006:9042 | 4006:9043 | 4006:9044 | 4006:9045 | 4006:9047 |
| 4007:9041 | 4007:9042 | 4007:9043 | 4007:9044 | 4007:9045 | 4007:9047 |
| 4008:9041 | 4008:9042 | 4008:9043 | 4008:9044 | 4008:9045 | 4008:9047 |
| 4009:9041 | 4009:9042 | 4009:9043 | 4009:9044 | 4009:9045 | 4009:9047 |
| 4010:9041 | 4010:9042 | 4010:9043 | 4010:9044 | 4010:9045 | 4010:9047 |
| 4011:9041 | 4011:9042 | 4011:9043 | 4011:9044 | 4011:9045 | 4011:9047 |
| 4012:9041 | 4012:9042 | 4012:9043 | 4012:9044 | 4012:9045 | 4012:9047 |
| 5001:9041 | 5001:9042 | 5001:9043 | 5001:9044 | 5001:9045 | 5001:9047 |
| 5002:9041 | 5002:9042 | 5002:9043 | 5002:9044 | 5002:9045 | 5002:9047 |
| 5003:9041 | 5003:9042 | 5003:9043 | 5003:9044 | 5003:9045 | 5003:9047 |
| 5004:9041 | 5004:9042 | 5004:9043 | 5004:9044 | 5004:9045 | 5004:9047 |
| 5005:9041 | 5005:9042 | 5005:9043 | 5005:9044 | 5005:9045 | 5005:9047 |
| 5006:9041 | 5006:9042 | 5006:9043 | 5006:9044 | 5006:9045 | 5006:9047 |
| 5007:9041 | 5007:9042 | 5007:9043 | 5007:9044 | 5007:9045 | 5007:9047 |
| 5008:9041 | 5008:9042 | 5008:9043 | 5008:9044 | 5008:9045 | 5008:9047 |
| 5009:9041 | 5009:9042 | 5009:9043 | 5009:9044 | 5009:9045 | 5009:9047 |
| 5010:9041 | 5010:9042 | 5010:9043 | 5010:9044 | 5010:9045 | 5010:9047 |
| 5011:9041 | 5011:9042 | 5011:9043 | 5011:9044 | 5011:9045 | 5011:9047 |
| 3002:9048 | 3002:9049 | 3002:9051 | 3002:9052 | 3002:9053 | 3002:9054 |
| 3003:9048 | 3003:9049 | 3003:9051 | 3003:9052 | 3003:9053 | 3003:9054 |
| 3004:9048 | 3004:9049 | 3004:9051 | 3004:9052 | 3004:9053 | 3004:9054 |
| 3005:9048 | 3005:9049 | 3005:9051 | 3005:9052 | 3005:9053 | 3005:9054 |
| 3006:9048 | 3006:9049 | 3006:9051 | 3006:9052 | 3006:9053 | 3006:9054 |

TABLE B-continued

Example combinations of a compound X with a compound Y.

| X:Y | X:Y | X:Y | X:Y | X:Y | X:Y |
|---|---|---|---|---|---|
| 3007:9048 | 3007:9049 | 3007:9051 | 3007:9052 | 3007:9053 | 3007:9054 |
| 3008:9048 | 3008:9049 | 3008:9051 | 3008:9052 | 3008:9053 | 3008:9054 |
| 3009:9048 | 3009:9049 | 3009:9051 | 3009:9052 | 3009:9053 | 3009:9054 |
| 3010:9048 | 3010:9049 | 3010:9051 | 3010:9052 | 3010:9053 | 3010:9054 |
| 3011:9048 | 3011:9049 | 3011:9051 | 3011:9052 | 3011:9053 | 3011:9054 |
| 3012:9048 | 3012:9049 | 3012:9051 | 3012:9052 | 3012:9053 | 3012:9054 |
| 3013:9048 | 3013:9049 | 3013:9051 | 3013:9052 | 3013:9053 | 3013:9054 |
| 3014:9048 | 3014:9049 | 3014:9051 | 3014:9052 | 3014:9053 | 3014:9054 |
| 4001:9048 | 4001:9049 | 4001:9051 | 4001:9052 | 4001:9053 | 4001:9054 |
| 4002:9048 | 4002:9049 | 4002:9051 | 4002:9052 | 4002:9053 | 4002:9054 |
| 4003:9048 | 4003:9049 | 4003:9051 | 4003:9052 | 4003:9053 | 4003:9054 |
| 4004:9048 | 4004:9049 | 4004:9051 | 4004:9052 | 4004:9053 | 4004:9054 |
| 4005:9048 | 4005:9049 | 4005:9051 | 4005:9052 | 4005:9053 | 4005:9054 |
| 4006:9048 | 4006:9049 | 4006:9051 | 4006:9052 | 4006:9053 | 4006:9054 |
| 4007:9048 | 4007:9049 | 4007:9051 | 4007:9052 | 4007:9053 | 4007:9054 |
| 4008:9048 | 4008:9049 | 4008:9051 | 4008:9052 | 4008:9053 | 4008:9054 |
| 4009:9048 | 4009:9049 | 4009:9051 | 4009:9052 | 4009:9053 | 4009:9054 |
| 4010:9048 | 4010:9049 | 4010:9051 | 4010:9052 | 4010:9053 | 4010:9054 |
| 4011:9048 | 4011:9049 | 4011:9051 | 4011:9052 | 4011:9053 | 4011:9054 |
| 4012:9048 | 4012:9049 | 4012:9051 | 4012:9052 | 4012:9053 | 4012:9054 |
| 5001:9048 | 5001:9049 | 5001:9051 | 5001:9052 | 5001:9053 | 5001:9054 |
| 5002:9048 | 5002:9049 | 5002:9051 | 5002:9052 | 5002:9053 | 5002:9054 |
| 5003:9048 | 5003:9049 | 5003:9051 | 5003:9052 | 5003:9053 | 5003:9054 |
| 5004:9048 | 5004:9049 | 5004:9051 | 5004:9052 | 5004:9053 | 5004:9054 |
| 5005:9048 | 5005:9049 | 5005:9051 | 5005:9052 | 5005:9053 | 5005:9054 |
| 5006:9048 | 5006:9049 | 5006:9051 | 5006:9052 | 5006:9053 | 5006:9054 |
| 5007:9048 | 5007:9049 | 5007:9051 | 5007:9052 | 5007:9053 | 5007:9054 |
| 5008:9048 | 5008:9049 | 5008:9051 | 5008:9052 | 5008:9053 | 5008:9054 |
| 5009:9048 | 5009:9049 | 5009:9051 | 5009:9052 | 5009:9053 | 5009:9054 |
| 5010:9048 | 5010:9049 | 5010:9051 | 5010:9052 | 5010:9053 | 5010:9054 |
| 5011:9048 | 5011:9049 | 5011:9051 | 5011:9052 | 5011:9053 | 5011:9054 |
| 3002:9055 | 3002:9056 | 3002:9058 | 3002:9060 | 3002:9061 | 3002:9062 |
| 3003:9055 | 3003:9056 | 3003:9058 | 3003:9060 | 3003:9061 | 3003:9062 |
| 3004:9055 | 3004:9056 | 3004:9058 | 3004:9060 | 3004:9061 | 3004:9062 |
| 3005:9055 | 3005:9056 | 3005:9058 | 3005:9060 | 3005:9061 | 3005:9062 |
| 3006:9055 | 3006:9056 | 3006:9058 | 3006:9060 | 3006:9061 | 3006:9062 |
| 3007:9055 | 3007:9056 | 3007:9058 | 3007:9060 | 3007:9061 | 3007:9062 |
| 3008:9055 | 3008:9056 | 3008:9058 | 3008:9060 | 3008:9061 | 3008:9062 |
| 3009:9055 | 3009:9056 | 3009:9058 | 3009:9060 | 3009:9061 | 3009:9062 |
| 3010:9055 | 3010:9056 | 3010:9058 | 3010:9060 | 3010:9061 | 3010:9062 |
| 3011:9055 | 3011:9056 | 3011:9058 | 3011:9060 | 3011:9061 | 3011:9062 |
| 3012:9055 | 3012:9056 | 3012:9058 | 3012:9060 | 3012:9061 | 3012:9062 |
| 3013:9055 | 3013:9056 | 3013:9058 | 3013:9060 | 3013:9061 | 3013:9062 |
| 3014:9055 | 3014:9056 | 3014:9058 | 3014:9060 | 3014:9061 | 3014:9062 |
| 4001:9055 | 4001:9056 | 4001:9058 | 4001:9060 | 4001:9061 | 4001:9062 |
| 4002:9055 | 4002:9056 | 4002:9058 | 4002:9060 | 4002:9061 | 4002:9062 |
| 4003:9055 | 4003:9056 | 4003:9058 | 4003:9060 | 4003:9061 | 4003:9062 |
| 4004:9055 | 4004:9056 | 4004:9058 | 4004:9060 | 4004:9061 | 4004:9062 |
| 4005:9055 | 4005:9056 | 4005:9058 | 4005:9060 | 4005:9061 | 4005:9062 |
| 4006:9055 | 4006:9056 | 4006:9058 | 4006:9060 | 4006:9061 | 4006:9062 |
| 4007:9055 | 4007:9056 | 4007:9058 | 4007:9060 | 4007:9061 | 4007:9062 |
| 4008:9055 | 4008:9056 | 4008:9058 | 4008:9060 | 4008:9061 | 4008:9062 |
| 4009:9055 | 4009:9056 | 4009:9058 | 4009:9060 | 4009:9061 | 4009:9062 |
| 4010:9055 | 4010:9056 | 4010:9058 | 4010:9060 | 4010:9061 | 4010:9062 |
| 4011:9055 | 4011:9056 | 4011:9058 | 4011:9060 | 4011:9061 | 4011:9062 |
| 4012:9055 | 4012:9056 | 4012:9058 | 4012:9060 | 4012:9061 | 4012:9062 |
| 5001:9055 | 5001:9056 | 5001:9058 | 5001:9060 | 5001:9061 | 5001:9062 |
| 5002:9055 | 5002:9056 | 5002:9058 | 5002:9060 | 5002:9061 | 5002:9062 |
| 5003:9055 | 5003:9056 | 5003:9058 | 5003:9060 | 5003:9061 | 5003:9062 |
| 5004:9055 | 5004:9056 | 5004:9058 | 5004:9060 | 5004:9061 | 5004:9062 |
| 5005:9055 | 5005:9056 | 5005:9058 | 5005:9060 | 5005:9061 | 5005:9062 |
| 5006:9055 | 5006:9056 | 5006:9058 | 5006:9060 | 5006:9061 | 5006:9062 |
| 5007:9055 | 5007:9056 | 5007:9058 | 5007:9060 | 5007:9061 | 5007:9062 |
| 5008:9055 | 5008:9056 | 5008:9058 | 5008:9060 | 5008:9061 | 5008:9062 |
| 5009:9055 | 5009:9056 | 5009:9058 | 5009:9060 | 5009:9061 | 5009:9062 |
| 5010:9055 | 5010:9056 | 5010:9058 | 5010:9060 | 5010:9061 | 5010:9062 |
| 5011:9055 | 5011:9056 | 5011:9058 | 5011:9060 | 5011:9061 | 5011:9062 |
| 3002:9063 | 3002:9064 | 3002:9065 | 3002:9066 | 3002:9067 | 3002:9068 |
| 3003:9063 | 3003:9064 | 3003:9065 | 3003:9066 | 3003:9067 | 3003:9068 |
| 3004:9063 | 3004:9064 | 3004:9065 | 3004:9066 | 3004:9067 | 3004:9068 |
| 3005:9063 | 3005:9064 | 3005:9065 | 3005:9066 | 3005:9067 | 3005:9068 |
| 3006:9063 | 3006:9064 | 3006:9065 | 3006:9066 | 3006:9067 | 3006:9068 |
| 3007:9063 | 3007:9064 | 3007:9065 | 3007:9066 | 3007:9067 | 3007:9068 |
| 3008:9063 | 3008:9064 | 3008:9065 | 3008:9066 | 3008:9067 | 3008:9068 |
| 3009:9063 | 3009:9064 | 3009:9065 | 3009:9066 | 3009:9067 | 3009:9068 |
| 3010:9063 | 3010:9064 | 3010:9065 | 3010:9066 | 3010:9067 | 3010:9068 |
| 3011:9063 | 3011:9064 | 3011:9065 | 3011:9066 | 3011:9067 | 3011:9068 |
| 3012:9063 | 3012:9064 | 3012:9065 | 3012:9066 | 3012:9067 | 3012:9068 |
| 3013:9063 | 3013:9064 | 3013:9065 | 3013:9066 | 3013:9067 | 3013:9068 |
| 3014:9063 | 3014:9064 | 3014:9065 | 3014:9066 | 3014:9067 | 3014:9068 |
| 4001:9063 | 4001:9064 | 4001:9065 | 4001:9066 | 4001:9067 | 4001:9068 |
| 4002:9063 | 4002:9064 | 4002:9065 | 4002:9066 | 4002:9067 | 4002:9068 |
| 4003:9063 | 4003:9064 | 4003:9065 | 4003:9066 | 4003:9067 | 4003:9068 |
| 4004:9063 | 4004:9064 | 4004:9065 | 4004:9066 | 4004:9067 | 4004:9068 |
| 4005:9063 | 4005:9064 | 4005:9065 | 4005:9066 | 4005:9067 | 4005:9068 |
| 4006:9063 | 4006:9064 | 4006:9065 | 4006:9066 | 4006:9067 | 4006:9068 |
| 4007:9063 | 4007:9064 | 4007:9065 | 4007:9066 | 4007:9067 | 4007:9068 |
| 4008:9063 | 4008:9064 | 4008:9065 | 4008:9066 | 4008:9067 | 4008:9068 |
| 4009:9063 | 4009:9064 | 4009:9065 | 4009:9066 | 4009:9067 | 4009:9068 |
| 4010:9063 | 4010:9064 | 4010:9065 | 4010:9066 | 4010:9067 | 4010:9068 |
| 4011:9063 | 4011:9064 | 4011:9065 | 4011:9066 | 4011:9067 | 4011:9068 |
| 4012:9063 | 4012:9064 | 4012:9065 | 4012:9066 | 4012:9067 | 4012:9068 |
| 5001:9063 | 5001:9064 | 5001:9065 | 5001:9066 | 5001:9067 | 5001:9068 |
| 5002:9063 | 5002:9064 | 5002:9065 | 5002:9066 | 5002:9067 | 5002:9068 |
| 5003:9063 | 5003:9064 | 5003:9065 | 5003:9066 | 5003:9067 | 5003:9068 |
| 5004:9063 | 5004:9064 | 5004:9065 | 5004:9066 | 5004:9067 | 5004:9068 |
| 5005:9063 | 5005:9064 | 5005:9065 | 5005:9066 | 5005:9067 | 5005:9068 |
| 5006:9063 | 5006:9064 | 5006:9065 | 5006:9066 | 5006:9067 | 5006:9068 |
| 5007:9063 | 5007:9064 | 5007:9065 | 5007:9066 | 5007:9067 | 5007:9068 |
| 5008:9063 | 5008:9064 | 5008:9065 | 5008:9066 | 5008:9067 | 5008:9068 |
| 5009:9063 | 5009:9064 | 5009:9065 | 5009:9066 | 5009:9067 | 5009:9068 |
| 5010:9063 | 5010:9064 | 5010:9065 | 5010:9066 | 5010:9067 | 5010:9068 |
| 5011:9063 | 5011:9064 | 5011:9065 | 5011:9066 | 5011:9067 | 5011:9068 |
| 3002:9069 | 3002:9070 | 3002:9071 | 3002:9072 | 3002:9073 | 3002:9074 |
| 3003:9069 | 3003:9070 | 3003:9071 | 3003:9072 | 3003:9073 | 3003:9074 |
| 3004:9069 | 3004:9070 | 3004:9071 | 3004:9072 | 3004:9073 | 3004:9074 |
| 3005:9069 | 3005:9070 | 3005:9071 | 3005:9072 | 3005:9073 | 3005:9074 |
| 3006:9069 | 3006:9070 | 3006:9071 | 3006:9072 | 3006:9073 | 3006:9074 |
| 3007:9069 | 3007:9070 | 3007:9071 | 3007:9072 | 3007:9073 | 3007:9074 |
| 3008:9069 | 3008:9070 | 3008:9071 | 3008:9072 | 3008:9073 | 3008:9074 |
| 3009:9069 | 3009:9070 | 3009:9071 | 3009:9072 | 3009:9073 | 3009:9074 |
| 3010:9069 | 3010:9070 | 3010:9071 | 3010:9072 | 3010:9073 | 3010:9074 |
| 3011:9069 | 3011:9070 | 3011:9071 | 3011:9072 | 3011:9073 | 3011:9074 |
| 3012:9069 | 3012:9070 | 3012:9071 | 3012:9072 | 3012:9073 | 3012:9074 |
| 3013:9069 | 3013:9070 | 3013:9071 | 3013:9072 | 3013:9073 | 3013:9074 |
| 3014:9069 | 3014:9070 | 3014:9071 | 3014:9072 | 3014:9073 | 3014:9074 |
| 4001:9069 | 4001:9070 | 4001:9071 | 4001:9072 | 4001:9073 | 4001:9074 |
| 4002:9069 | 4002:9070 | 4002:9071 | 4002:9072 | 4002:9073 | 4002:9074 |
| 4003:9069 | 4003:9070 | 4003:9071 | 4003:9072 | 4003:9073 | 4003:9074 |
| 4004:9069 | 4004:9070 | 4004:9071 | 4004:9072 | 4004:9073 | 4004:9074 |
| 4005:9069 | 4005:9070 | 4005:9071 | 4005:9072 | 4005:9073 | 4005:9074 |
| 4006:9069 | 4006:9070 | 4006:9071 | 4006:9072 | 4006:9073 | 4006:9074 |
| 4007:9069 | 4007:9070 | 4007:9071 | 4007:9072 | 4007:9073 | 4007:9074 |
| 4008:9069 | 4008:9070 | 4008:9071 | 4008:9072 | 4008:9073 | 4008:9074 |
| 4009:9069 | 4009:9070 | 4009:9071 | 4009:9072 | 4009:9073 | 4009:9074 |
| 4010:9069 | 4010:9070 | 4010:9071 | 4010:9072 | 4010:9073 | 4010:9074 |
| 4011:9069 | 4011:9070 | 4011:9071 | 4011:9072 | 4011:9073 | 4011:9074 |
| 4012:9069 | 4012:9070 | 4012:9071 | 4012:9072 | 4012:9073 | 4012:9074 |
| 5001:9069 | 5001:9070 | 5001:9071 | 5001:9072 | 5001:9073 | 5001:9074 |
| 5002:9069 | 5002:9070 | 5002:9071 | 5002:9072 | 5002:9073 | 5002:9074 |
| 5003:9069 | 5003:9070 | 5003:9071 | 5003:9072 | 5003:9073 | 5003:9074 |
| 5004:9069 | 5004:9070 | 5004:9071 | 5004:9072 | 5004:9073 | 5004:9074 |
| 5005:9069 | 5005:9070 | 5005:9071 | 5005:9072 | 5005:9073 | 5005:9074 |
| 5006:9069 | 5006:9070 | 5006:9071 | 5006:9072 | 5006:9073 | 5006:9074 |
| 5007:9069 | 5007:9070 | 5007:9071 | 5007:9072 | 5007:9073 | 5007:9074 |
| 5008:9069 | 5008:9070 | 5008:9071 | 5008:9072 | 5008:9073 | 5008:9074 |
| 5009:9069 | 5009:9070 | 5009:9071 | 5009:9072 | 5009:9073 | 5009:9074 |
| 5010:9069 | 5010:9070 | 5010:9071 | 5010:9072 | 5010:9073 | 5010:9074 |
| 5011:9069 | 5011:9070 | 5011:9071 | 5011:9072 | 5011:9073 | 5011:9074 |
| 3002:9075 | 3002:9076 | 3002:9077 | 3002:9078 | 3002:9079 | 3002:9080 |
| 3003:9075 | 3003:9076 | 3003:9077 | 3003:9078 | 3003:9079 | 3003:9080 |
| 3004:9075 | 3004:9076 | 3004:9077 | 3004:9078 | 3004:9079 | 3004:9080 |
| 3005:9075 | 3005:9076 | 3005:9077 | 3005:9078 | 3005:9079 | 3005:9080 |
| 3006:9075 | 3006:9076 | 3006:9077 | 3006:9078 | 3006:9079 | 3006:9080 |
| 3007:9075 | 3007:9076 | 3007:9077 | 3007:9078 | 3007:9079 | 3007:9080 |
| 3008:9075 | 3008:9076 | 3008:9077 | 3008:9078 | 3008:9079 | 3008:9080 |
| 3009:9075 | 3009:9076 | 3009:9077 | 3009:9078 | 3009:9079 | 3009:9080 |
| 3010:9075 | 3010:9076 | 3010:9077 | 3010:9078 | 3010:9079 | 3010:9080 |
| 3011:9075 | 3011:9076 | 3011:9077 | 3011:9078 | 3011:9079 | 3011:9080 |
| 3012:9075 | 3012:9076 | 3012:9077 | 3012:9078 | 3012:9079 | 3012:9080 |
| 3013:9075 | 3013:9076 | 3013:9077 | 3013:9078 | 3013:9079 | 3013:9080 |
| 3014:9075 | 3014:9076 | 3014:9077 | 3014:9078 | 3014:9079 | 3014:9080 |

TABLE B-continued

Example combinations of a compound X with a compound Y.

| X:Y | X:Y | X:Y | X:Y | X:Y | X:Y |
|---|---|---|---|---|---|
| 4001:9075 | 4001:9076 | 4001:9077 | 4001:9078 | 4001:9079 | 4001:9080 |
| 4002:9075 | 4002:9076 | 4002:9077 | 4002:9078 | 4002:9079 | 4002:9080 |
| 4003:9075 | 4003:9076 | 4003:9077 | 4003:9078 | 4003:9079 | 4003:9080 |
| 4004:9075 | 4004:9076 | 4004:9077 | 4004:9078 | 4004:9079 | 4004:9080 |
| 4005:9075 | 4005:9076 | 4005:9077 | 4005:9078 | 4005:9079 | 4005:9080 |
| 4006:9075 | 4006:9076 | 4006:9077 | 4006:9078 | 4006:9079 | 4006:9080 |
| 4007:9075 | 4007:9076 | 4007:9077 | 4007:9078 | 4007:9079 | 4007:9080 |
| 4008:9075 | 4008:9076 | 4008:9077 | 4008:9078 | 4008:9079 | 4008:9080 |
| 4009:9075 | 4009:9076 | 4009:9077 | 4009:9078 | 4009:9079 | 4009:9080 |
| 4010:9075 | 4010:9076 | 4010:9077 | 4010:9078 | 4010:9079 | 4010:9080 |
| 4011:9075 | 4011:9076 | 4011:9077 | 4011:9078 | 4011:9079 | 4011:9080 |
| 4012:9075 | 4012:9076 | 4012:9077 | 4012:9078 | 4012:9079 | 4012:9080 |
| 5001:9075 | 5001:9076 | 5001:9077 | 5001:9078 | 5001:9079 | 5001:9080 |
| 5002:9075 | 5002:9076 | 5002:9077 | 5002:9078 | 5002:9079 | 5002:9080 |
| 5003:9075 | 5003:9076 | 5003:9077 | 5003:9078 | 5003:9079 | 5003:9080 |
| 5004:9075 | 5004:9076 | 5004:9077 | 5004:9078 | 5004:9079 | 5004:9080 |
| 5005:9075 | 5005:9076 | 5005:9077 | 5005:9078 | 5005:9079 | 5005:9080 |
| 5006:9075 | 5006:9076 | 5006:9077 | 5006:9078 | 5006:9079 | 5006:9080 |
| 5007:9075 | 5007:9076 | 5007:9077 | 5007:9078 | 5007:9079 | 5007:9080 |
| 5008:9075 | 5008:9076 | 5008:9077 | 5008:9078 | 5008:9079 | 5008:9080 |
| 5009:9075 | 5009:9076 | 5009:9077 | 5009:9078 | 5009:9079 | 5009:9080 |
| 5010:9075 | 5010:9076 | 5010:9077 | 5010:9078 | 5010:9079 | 5010:9080 |
| 5011:9075 | 5011:9076 | 5011:9077 | 5011:9078 | 5011:9079 | 5011:9080 |
| 3002:9081 | 3002:9082 | 3002:9083 | 3002:9084 | 3002:9085 | 3002:9086 |
| 3003:9081 | 3003:9082 | 3003:9083 | 3003:9084 | 3003:9085 | 3003:9086 |
| 3004:9081 | 3004:9082 | 3004:9083 | 3004:9084 | 3004:9085 | 3004:9086 |
| 3005:9081 | 3005:9082 | 3005:9083 | 3005:9084 | 3005:9085 | 3005:9086 |
| 3006:9081 | 3006:9082 | 3006:9083 | 3006:9084 | 3006:9085 | 3006:9086 |
| 3007:9081 | 3007:9082 | 3007:9083 | 3007:9084 | 3007:9085 | 3007:9086 |
| 3008:9081 | 3008:9082 | 3008:9083 | 3008:9084 | 3008:9085 | 3008:9086 |
| 3009:9081 | 3009:9082 | 3009:9083 | 3009:9084 | 3009:9085 | 3009:9086 |
| 3010:9081 | 3010:9082 | 3010:9083 | 3010:9084 | 3010:9085 | 3010:9086 |
| 3011:9081 | 3011:9082 | 3011:9083 | 3011:9084 | 3011:9085 | 3011:9086 |
| 3012:9081 | 3012:9082 | 3012:9083 | 3012:9084 | 3012:9085 | 3012:9086 |
| 3013:9081 | 3013:9082 | 3013:9083 | 3013:9084 | 3013:9085 | 3013:9086 |
| 3014:9081 | 3014:9082 | 3014:9083 | 3014:9084 | 3014:9085 | 3014:9086 |
| 4001:9081 | 4001:9082 | 4001:9083 | 4001:9084 | 4001:9085 | 4001:9086 |
| 4002:9081 | 4002:9082 | 4002:9083 | 4002:9084 | 4002:9085 | 4002:9086 |
| 4003:9081 | 4003:9082 | 4003:9083 | 4003:9084 | 4003:9085 | 4003:9086 |
| 4004:9081 | 4004:9082 | 4004:9083 | 4004:9084 | 4004:9085 | 4004:9086 |
| 4005:9081 | 4005:9082 | 4005:9083 | 4005:9084 | 4005:9085 | 4005:9086 |
| 4006:9081 | 4006:9082 | 4006:9083 | 4006:9084 | 4006:9085 | 4006:9086 |
| 4007:9081 | 4007:9082 | 4007:9083 | 4007:9084 | 4007:9085 | 4007:9086 |
| 4008:9081 | 4008:9082 | 4008:9083 | 4008:9084 | 4008:9085 | 4008:9086 |
| 4009:9081 | 4009:9082 | 4009:9083 | 4009:9084 | 4009:9085 | 4009:9086 |
| 4010:9081 | 4010:9082 | 4010:9083 | 4010:9084 | 4010:9085 | 4010:9086 |
| 4011:9081 | 4011:9082 | 4011:9083 | 4011:9084 | 4011:9085 | 4011:9086 |
| 4012:9081 | 4012:9082 | 4012:9083 | 4012:9084 | 4012:9085 | 4012:9086 |
| 5001:9081 | 5001:9082 | 5001:9083 | 5001:9084 | 5001:9085 | 5001:9086 |
| 5002:9081 | 5002:9082 | 5002:9083 | 5002:9084 | 5002:9085 | 5002:9086 |
| 5003:9081 | 5003:9082 | 5003:9083 | 5003:9084 | 5003:9085 | 5003:9086 |
| 5004:9081 | 5004:9082 | 5004:9083 | 5004:9084 | 5004:9085 | 5004:9086 |
| 5005:9081 | 5005:9082 | 5005:9083 | 5005:9084 | 5005:9085 | 5005:9086 |
| 5006:9081 | 5006:9082 | 5006:9083 | 5006:9084 | 5006:9085 | 5006:9086 |
| 5007:9081 | 5007:9082 | 5007:9083 | 5007:9084 | 5007:9085 | 5007:9086 |
| 5008:9081 | 5008:9082 | 5008:9083 | 5008:9084 | 5008:9085 | 5008:9086 |
| 5009:9081 | 5009:9082 | 5009:9083 | 5009:9084 | 5009:9085 | 5009:9086 |
| 5010:9081 | 5010:9082 | 5010:9083 | 5010:9084 | 5010:9085 | 5010:9086 |
| 5011:9081 | 5011:9082 | 5011:9083 | 5011:9084 | 5011:9085 | 5011:9086 |
| 3002:9088 | 3002:9089 | 3002:9094 | 3002:9095 | 3002:9096 | 3002:9097 |
| 3003:9088 | 3003:9089 | 3003:9094 | 3003:9095 | 3003:9096 | 3003:9097 |
| 3004:9088 | 3004:9089 | 3004:9094 | 3004:9095 | 3004:9096 | 3004:9097 |
| 3005:9088 | 3005:9089 | 3005:9094 | 3005:9095 | 3005:9096 | 3005:9097 |
| 3006:9088 | 3006:9089 | 3006:9094 | 3006:9095 | 3006:9096 | 3006:9097 |
| 3007:9088 | 3007:9089 | 3007:9094 | 3007:9095 | 3007:9096 | 3007:9097 |
| 3008:9088 | 3008:9089 | 3008:9094 | 3008:9095 | 3008:9096 | 3008:9097 |
| 3009:9088 | 3009:9089 | 3009:9094 | 3009:9095 | 3009:9096 | 3009:9097 |
| 3010:9088 | 3010:9089 | 3010:9094 | 3010:9095 | 3010:9096 | 3010:9097 |
| 3011:9088 | 3011:9089 | 3011:9094 | 3011:9095 | 3011:9096 | 3011:9097 |
| 3012:9088 | 3012:9089 | 3012:9094 | 3012:9095 | 3012:9096 | 3012:9097 |
| 3013:9088 | 3013:9089 | 3013:9094 | 3013:9095 | 3013:9096 | 3013:9097 |
| 3014:9088 | 3014:9089 | 3014:9094 | 3014:9095 | 3014:9096 | 3014:9097 |
| 4001:9088 | 4001:9089 | 4001:9094 | 4001:9095 | 4001:9096 | 4001:9097 |
| 4002:9088 | 4002:9089 | 4002:9094 | 4002:9095 | 4002:9096 | 4002:9097 |
| 4003:9088 | 4003:9089 | 4003:9094 | 4003:9095 | 4003:9096 | 4003:9097 |
| 4004:9088 | 4004:9089 | 4004:9094 | 4004:9095 | 4004:9096 | 4004:9097 |
| 4005:9088 | 4005:9089 | 4005:9094 | 4005:9095 | 4005:9096 | 4005:9097 |
| 4006:9088 | 4006:9089 | 4006:9094 | 4006:9095 | 4006:9096 | 4006:9097 |
| 4007:9088 | 4007:9089 | 4007:9094 | 4007:9095 | 4007:9096 | 4007:9097 |
| 4008:9088 | 4008:9089 | 4008:9094 | 4008:9095 | 4008:9096 | 4008:9097 |
| 4009:9088 | 4009:9089 | 4009:9094 | 4009:9095 | 4009:9096 | 4009:9097 |
| 4010:9088 | 4010:9089 | 4010:9094 | 4010:9095 | 4010:9096 | 4010:9097 |
| 4011:9088 | 4011:9089 | 4011:9094 | 4011:9095 | 4011:9096 | 4011:9097 |
| 4012:9088 | 4012:9089 | 4012:9094 | 4012:9095 | 4012:9096 | 4012:9097 |
| 5001:9088 | 5001:9089 | 5001:9094 | 5001:9095 | 5001:9096 | 5001:9097 |
| 5002:9088 | 5002:9089 | 5002:9094 | 5002:9095 | 5002:9096 | 5002:9097 |
| 5003:9088 | 5003:9089 | 5003:9094 | 5003:9095 | 5003:9096 | 5003:9097 |
| 5004:9088 | 5004:9089 | 5004:9094 | 5004:9095 | 5004:9096 | 5004:9097 |
| 5005:9088 | 5005:9089 | 5005:9094 | 5005:9095 | 5005:9096 | 5005:9097 |
| 5006:9088 | 5006:9089 | 5006:9094 | 5006:9095 | 5006:9096 | 5006:9097 |
| 5007:9088 | 5007:9089 | 5007:9094 | 5007:9095 | 5007:9096 | 5007:9097 |
| 5008:9088 | 5008:9089 | 5008:9094 | 5008:9095 | 5008:9096 | 5008:9097 |
| 5009:9088 | 5009:9089 | 5009:9094 | 5009:9095 | 5009:9096 | 5009:9097 |
| 5010:9088 | 5010:9089 | 5010:9094 | 5010:9095 | 5010:9096 | 5010:9097 |
| 5011:9088 | 5011:9089 | 5011:9094 | 5011:9095 | 5011:9096 | 5011:9097 |
| 3002:9098 | 3002:9099 | 3002:9100 | 3002:9101 | 3002:9102 | 3002:9103 |
| 3003:9098 | 3003:9099 | 3003:9100 | 3003:9101 | 3003:9102 | 3003:9103 |
| 3004:9098 | 3004:9099 | 3004:9100 | 3004:9101 | 3004:9102 | 3004:9103 |
| 3005:9098 | 3005:9099 | 3005:9100 | 3005:9101 | 3005:9102 | 3005:9103 |
| 3006:9098 | 3006:9099 | 3006:9100 | 3006:9101 | 3006:9102 | 3006:9103 |
| 3007:9098 | 3007:9099 | 3007:9100 | 3007:9101 | 3007:9102 | 3007:9103 |
| 3008:9098 | 3008:9099 | 3008:9100 | 3008:9101 | 3008:9102 | 3008:9103 |
| 3009:9098 | 3009:9099 | 3009:9100 | 3009:9101 | 3009:9102 | 3009:9103 |
| 3010:9098 | 3010:9099 | 3010:9100 | 3010:9101 | 3010:9102 | 3010:9103 |
| 3011:9098 | 3011:9099 | 3011:9100 | 3011:9101 | 3011:9102 | 3011:9103 |
| 3012:9098 | 3012:9099 | 3012:9100 | 3012:9101 | 3012:9102 | 3012:9103 |
| 3013:9098 | 3013:9099 | 3013:9100 | 3013:9101 | 3013:9102 | 3013:9103 |
| 3014:9098 | 3014:9099 | 3014:9100 | 3014:9101 | 3014:9102 | 3014:9103 |
| 4001:9098 | 4001:9099 | 4001:9100 | 4001:9101 | 4001:9102 | 4001:9103 |
| 4002:9098 | 4002:9099 | 4002:9100 | 4002:9101 | 4002:9102 | 4002:9103 |
| 4003:9098 | 4003:9099 | 4003:9100 | 4003:9101 | 4003:9102 | 4003:9103 |
| 4004:9098 | 4004:9099 | 4004:9100 | 4004:9101 | 4004:9102 | 4004:9103 |
| 4005:9098 | 4005:9099 | 4005:9100 | 4005:9101 | 4005:9102 | 4005:9103 |
| 4006:9098 | 4006:9099 | 4006:9100 | 4006:9101 | 4006:9102 | 4006:9103 |
| 4007:9098 | 4007:9099 | 4007:9100 | 4007:9101 | 4007:9102 | 4007:9103 |
| 4008:9098 | 4008:9099 | 4008:9100 | 4008:9101 | 4008:9102 | 4008:9103 |
| 4009:9098 | 4009:9099 | 4009:9100 | 4009:9101 | 4009:9102 | 4009:9103 |
| 4010:9098 | 4010:9099 | 4010:9100 | 4010:9101 | 4010:9102 | 4010:9103 |
| 4011:9098 | 4011:9099 | 4011:9100 | 4011:9101 | 4011:9102 | 4011:9103 |
| 4012:9098 | 4012:9099 | 4012:9100 | 4012:9101 | 4012:9102 | 4012:9103 |
| 5001:9098 | 5001:9099 | 5001:9100 | 5001:9101 | 5001:9102 | 5001:9103 |
| 5002:9098 | 5002:9099 | 5002:9100 | 5002:9101 | 5002:9102 | 5002:9103 |
| 5003:9098 | 5003:9099 | 5003:9100 | 5003:9101 | 5003:9102 | 5003:9103 |
| 5004:9098 | 5004:9099 | 5004:9100 | 5004:9101 | 5004:9102 | 5004:9103 |
| 5005:9098 | 5005:9099 | 5005:9100 | 5005:9101 | 5005:9102 | 5005:9103 |
| 5006:9098 | 5006:9099 | 5006:9100 | 5006:9101 | 5006:9102 | 5006:9103 |
| 5007:9098 | 5007:9099 | 5007:9100 | 5007:9101 | 5007:9102 | 5007:9103 |
| 5008:9098 | 5008:9099 | 5008:9100 | 5008:9101 | 5008:9102 | 5008:9103 |
| 5009:9098 | 5009:9099 | 5009:9100 | 5009:9101 | 5009:9102 | 5009:9103 |
| 5010:9098 | 5010:9099 | 5010:9100 | 5010:9101 | 5010:9102 | 5010:9103 |
| 5011:9098 | 5011:9099 | 5011:9100 | 5011:9101 | 5011:9102 | 5011:9103 |
| 3002:9104 | 3002:9105 | 3002:9106 | 3002:9107 | 3002:9108 | 3002:9109 |
| 3003:9104 | 3003:9105 | 3003:9106 | 3003:9107 | 3003:9108 | 3003:9109 |
| 3004:9104 | 3004:9105 | 3004:9106 | 3004:9107 | 3004:9108 | 3004:9109 |
| 3005:9104 | 3005:9105 | 3005:9106 | 3005:9107 | 3005:9108 | 3005:9109 |
| 3006:9104 | 3006:9105 | 3006:9106 | 3006:9107 | 3006:9108 | 3006:9109 |
| 3007:9104 | 3007:9105 | 3007:9106 | 3007:9107 | 3007:9108 | 3007:9109 |
| 3008:9104 | 3008:9105 | 3008:9106 | 3008:9107 | 3008:9108 | 3008:9109 |
| 3009:9104 | 3009:9105 | 3009:9106 | 3009:9107 | 3009:9108 | 3009:9109 |
| 3010:9104 | 3010:9105 | 3010:9106 | 3010:9107 | 3010:9108 | 3010:9109 |
| 3011:9104 | 3011:9105 | 3011:9106 | 3011:9107 | 3011:9108 | 3011:9109 |
| 3012:9104 | 3012:9105 | 3012:9106 | 3012:9107 | 3012:9108 | 3012:9109 |
| 3013:9104 | 3013:9105 | 3013:9106 | 3013:9107 | 3013:9108 | 3013:9109 |
| 3014:9104 | 3014:9105 | 3014:9106 | 3014:9107 | 3014:9108 | 3014:9109 |
| 4001:9104 | 4001:9105 | 4001:9106 | 4001:9107 | 4001:9108 | 4001:9109 |
| 4002:9104 | 4002:9105 | 4002:9106 | 4002:9107 | 4002:9108 | 4002:9109 |
| 4003:9104 | 4003:9105 | 4003:9106 | 4003:9107 | 4003:9108 | 4003:9109 |
| 4004:9104 | 4004:9105 | 4004:9106 | 4004:9107 | 4004:9108 | 4004:9109 |
| 4005:9104 | 4005:9105 | 4005:9106 | 4005:9107 | 4005:9108 | 4005:9109 |
| 4006:9104 | 4006:9105 | 4006:9106 | 4006:9107 | 4006:9108 | 4006:9109 |
| 4007:9104 | 4007:9105 | 4007:9106 | 4007:9107 | 4007:9108 | 4007:9109 |
| 4008:9104 | 4008:9105 | 4008:9106 | 4008:9107 | 4008:9108 | 4008:9109 |

TABLE B-continued

Example combinations of a compound X with a compound Y.

| X:Y | X:Y | X:Y | X:Y | X:Y | X:Y |
|---|---|---|---|---|---|
| 4009:9104 | 4009:9105 | 4009:9106 | 4009:9107 | 4009:9108 | 4009:9109 |
| 4010:9104 | 4010:9105 | 4010:9106 | 4010:9107 | 4010:9108 | 4010:9109 |
| 4011:9104 | 4011:9105 | 4011:9106 | 4011:9107 | 4011:9108 | 4011:9109 |
| 4012:9104 | 4012:9105 | 4012:9106 | 4012:9107 | 4012:9108 | 4012:9109 |
| 5001:9104 | 5001:9105 | 5001:9106 | 5001:9107 | 5001:9108 | 5001:9109 |
| 5002:9104 | 5002:9105 | 5002:9106 | 5002:9107 | 5002:9108 | 5002:9109 |
| 5003:9104 | 5003:9105 | 5003:9106 | 5003:9107 | 5003:9108 | 5003:9109 |
| 5004:9104 | 5004:9105 | 5004:9106 | 5004:9107 | 5004:9108 | 5004:9109 |
| 5005:9104 | 5005:9105 | 5005:9106 | 5005:9107 | 5005:9108 | 5005:9109 |
| 5006:9104 | 5006:9105 | 5006:9106 | 5006:9107 | 5006:9108 | 5006:9109 |
| 5007:9104 | 5007:9105 | 5007:9106 | 5007:9107 | 5007:9108 | 5007:9109 |
| 5008:9104 | 5008:9105 | 5008:9106 | 5008:9107 | 5008:9108 | 5008:9109 |
| 5009:9104 | 5009:9105 | 5009:9106 | 5009:9107 | 5009:9108 | 5009:9109 |
| 5010:9104 | 5010:9105 | 5010:9106 | 5010:9107 | 5010:9108 | 5010:9109 |
| 5011:9104 | 5011:9105 | 5011:9106 | 5011:9107 | 5011:9108 | 5011:9109 |
| 3002:9110 | 3002:9111 | 3002:9129 | 3002:9130 | 3002:9131 | 3002:9132 |
| 3003:9110 | 3003:9111 | 3003:9129 | 3003:9130 | 3003:9131 | 3003:9132 |
| 3004:9110 | 3004:9111 | 3004:9129 | 3004:9130 | 3004:9131 | 3004:9132 |
| 3005:9110 | 3005:9111 | 3005:9129 | 3005:9130 | 3005:9131 | 3005:9132 |
| 3006:9110 | 3006:9111 | 3006:9129 | 3006:9130 | 3006:9131 | 3006:9132 |
| 3007:9110 | 3007:9111 | 3007:9129 | 3007:9130 | 3007:9131 | 3007:9132 |
| 3008:9110 | 3008:9111 | 3008:9129 | 3008:9130 | 3008:9131 | 3008:9132 |
| 3009:9110 | 3009:9111 | 3009:9129 | 3009:9130 | 3009:9131 | 3009:9132 |
| 3010:9110 | 3010:9111 | 3010:9129 | 3010:9130 | 3010:9131 | 3010:9132 |
| 3011:9110 | 3011:9111 | 3011:9129 | 3011:9130 | 3011:9131 | 3011:9132 |
| 3012:9110 | 3012:9111 | 3012:9129 | 3012:9130 | 3012:9131 | 3012:9132 |
| 3013:9110 | 3013:9111 | 3013:9129 | 3013:9130 | 3013:9131 | 3013:9132 |
| 3014:9110 | 3014:9111 | 3014:9129 | 3014:9130 | 3014:9131 | 3014:9132 |
| 4001:9110 | 4001:9111 | 4001:9129 | 4001:9130 | 4001:9131 | 4001:9132 |
| 4002:9110 | 4002:9111 | 4002:9129 | 4002:9130 | 4002:9131 | 4002:9132 |
| 4003:9110 | 4003:9111 | 4003:9129 | 4003:9130 | 4003:9131 | 4003:9132 |
| 4004:9110 | 4004:9111 | 4004:9129 | 4004:9130 | 4004:9131 | 4004:9132 |
| 4005:9110 | 4005:9111 | 4005:9129 | 4005:9130 | 4005:9131 | 4005:9132 |
| 4006:9110 | 4006:9111 | 4006:9129 | 4006:9130 | 4006:9131 | 4006:9132 |
| 4007:9110 | 4007:9111 | 4007:9129 | 4007:9130 | 4007:9131 | 4007:9132 |
| 4008:9110 | 4008:9111 | 4008:9129 | 4008:9130 | 4008:9131 | 4008:9132 |
| 4009:9110 | 4009:9111 | 4009:9129 | 4009:9130 | 4009:9131 | 4009:9132 |
| 4010:9110 | 4010:9111 | 4010:9129 | 4010:9130 | 4010:9131 | 4010:9132 |
| 4011:9110 | 4011:9111 | 4011:9129 | 4011:9130 | 4011:9131 | 4011:9132 |
| 4012:9110 | 4012:9111 | 4012:9129 | 4012:9130 | 4012:9131 | 4012:9132 |
| 5001:9110 | 5001:9111 | 5001:9129 | 5001:9130 | 5001:9131 | 5001:9132 |
| 5002:9110 | 5002:9111 | 5002:9129 | 5002:9130 | 5002:9131 | 5002:9132 |
| 5003:9110 | 5003:9111 | 5003:9129 | 5003:9130 | 5003:9131 | 5003:9132 |
| 5004:9110 | 5004:9111 | 5004:9129 | 5004:9130 | 5004:9131 | 5004:9132 |
| 5005:9110 | 5005:9111 | 5005:9129 | 5005:9130 | 5005:9131 | 5005:9132 |
| 5006:9110 | 5006:9111 | 5006:9129 | 5006:9130 | 5006:9131 | 5006:9132 |
| 5007:9110 | 5007:9111 | 5007:9129 | 5007:9130 | 5007:9131 | 5007:9132 |
| 5008:9110 | 5008:9111 | 5008:9129 | 5008:9130 | 5008:9131 | 5008:9132 |
| 5009:9110 | 5009:9111 | 5009:9129 | 5009:9130 | 5009:9131 | 5009:9132 |
| 5010:9110 | 5010:9111 | 5010:9129 | 5010:9130 | 5010:9131 | 5010:9132 |
| 5011:9110 | 5011:9111 | 5011:9129 | 5011:9130 | 5011:9131 | 5011:9132 |
| 3002:9133 | 3002:9134 | 3002:9135 | 3002:9136 | 3002:9137 | 3002:9138 |
| 3003:9133 | 3003:9134 | 3003:9135 | 3003:9136 | 3003:9137 | 3003:9138 |
| 3004:9133 | 3004:9134 | 3004:9135 | 3004:9136 | 3004:9137 | 3004:9138 |
| 3005:9133 | 3005:9134 | 3005:9135 | 3005:9136 | 3005:9137 | 3005:9138 |
| 3006:9133 | 3006:9134 | 3006:9135 | 3006:9136 | 3006:9137 | 3006:9138 |
| 3007:9133 | 3007:9134 | 3007:9135 | 3007:9136 | 3007:9137 | 3007:9138 |
| 3008:9133 | 3008:9134 | 3008:9135 | 3008:9136 | 3008:9137 | 3008:9138 |
| 3009:9133 | 3009:9134 | 3009:9135 | 3009:9136 | 3009:9137 | 3009:9138 |
| 3010:9133 | 3010:9134 | 3010:9135 | 3010:9136 | 3010:9137 | 3010:9138 |
| 3011:9133 | 3011:9134 | 3011:9135 | 3011:9136 | 3011:9137 | 3011:9138 |
| 3012:9133 | 3012:9134 | 3012:9135 | 3012:9136 | 3012:9137 | 3012:9138 |
| 3013:9133 | 3013:9134 | 3013:9135 | 3013:9136 | 3013:9137 | 3013:9138 |
| 3014:9133 | 3014:9134 | 3014:9135 | 3014:9136 | 3014:9137 | 3014:9138 |
| 4001:9133 | 4001:9134 | 4001:9135 | 4001:9136 | 4001:9137 | 4001:9138 |
| 4002:9133 | 4002:9134 | 4002:9135 | 4002:9136 | 4002:9137 | 4002:9138 |
| 4003:9133 | 4003:9134 | 4003:9135 | 4003:9136 | 4003:9137 | 4003:9138 |
| 4004:9133 | 4004:9134 | 4004:9135 | 4004:9136 | 4004:9137 | 4004:9138 |
| 4005:9133 | 4005:9134 | 4005:9135 | 4005:9136 | 4005:9137 | 4005:9138 |
| 4006:9133 | 4006:9134 | 4006:9135 | 4006:9136 | 4006:9137 | 4006:9138 |
| 4007:9133 | 4007:9134 | 4007:9135 | 4007:9136 | 4007:9137 | 4007:9138 |
| 4008:9133 | 4008:9134 | 4008:9135 | 4008:9136 | 4008:9137 | 4008:9138 |
| 4009:9133 | 4009:9134 | 4009:9135 | 4009:9136 | 4009:9137 | 4009:9138 |
| 4010:9133 | 4010:9134 | 4010:9135 | 4010:9136 | 4010:9137 | 4010:9138 |
| 4011:9133 | 4011:9134 | 4011:9135 | 4011:9136 | 4011:9137 | 4011:9138 |
| 4012:9133 | 4012:9134 | 4012:9135 | 4012:9136 | 4012:9137 | 4012:9138 |
| 5001:9133 | 5001:9134 | 5001:9135 | 5001:9136 | 5001:9137 | 5001:9138 |
| 5002:9133 | 5002:9134 | 5002:9135 | 5002:9136 | 5002:9137 | 5002:9138 |
| 5003:9133 | 5003:9134 | 5003:9135 | 5003:9136 | 5003:9137 | 5003:9138 |
| 5004:9133 | 5004:9134 | 5004:9135 | 5004:9136 | 5004:9137 | 5004:9138 |
| 5005:9133 | 5005:9134 | 5005:9135 | 5005:9136 | 5005:9137 | 5005:9138 |
| 5006:9133 | 5006:9134 | 5006:9135 | 5006:9136 | 5006:9137 | 5006:9138 |
| 5007:9133 | 5007:9134 | 5007:9135 | 5007:9136 | 5007:9137 | 5007:9138 |
| 5008:9133 | 5008:9134 | 5008:9135 | 5008:9136 | 5008:9137 | 5008:9138 |
| 5009:9133 | 5009:9134 | 5009:9135 | 5009:9136 | 5009:9137 | 5009:9138 |
| 5010:9133 | 5010:9134 | 5010:9135 | 5010:9136 | 5010:9137 | 5010:9138 |
| 5011:9133 | 5011:9134 | 5011:9135 | 5011:9136 | 5011:9137 | 5011:9138 |
| 3002:9139 | 3002:9140 | 3002:9141 | 3002:9142 | 3002:9143 | 3002:9144 |
| 3003:9139 | 3003:9140 | 3003:9141 | 3003:9142 | 3003:9143 | 3003:9144 |
| 3004:9139 | 3004:9140 | 3004:9141 | 3004:9142 | 3004:9143 | 3004:9144 |
| 3005:9139 | 3005:9140 | 3005:9141 | 3005:9142 | 3005:9143 | 3005:9144 |
| 3006:9139 | 3006:9140 | 3006:9141 | 3006:9142 | 3006:9143 | 3006:9144 |
| 3007:9139 | 3007:9140 | 3007:9141 | 3007:9142 | 3007:9143 | 3007:9144 |
| 3008:9139 | 3008:9140 | 3008:9141 | 3008:9142 | 3008:9143 | 3008:9144 |
| 3009:9139 | 3009:9140 | 3009:9141 | 3009:9142 | 3009:9143 | 3009:9144 |
| 3010:9139 | 3010:9140 | 3010:9141 | 3010:9142 | 3010:9143 | 3010:9144 |
| 3011:9139 | 3011:9140 | 3011:9141 | 3011:9142 | 3011:9143 | 3011:9144 |
| 3012:9139 | 3012:9140 | 3012:9141 | 3012:9142 | 3012:9143 | 3012:9144 |
| 3013:9139 | 3013:9140 | 3013:9141 | 3013:9142 | 3013:9143 | 3013:9144 |
| 3014:9139 | 3014:9140 | 3014:9141 | 3014:9142 | 3014:9143 | 3014:9144 |
| 4001:9139 | 4001:9140 | 4001:9141 | 4001:9142 | 4001:9143 | 4001:9144 |
| 4002:9139 | 4002:9140 | 4002:9141 | 4002:9142 | 4002:9143 | 4002:9144 |
| 4003:9139 | 4003:9140 | 4003:9141 | 4003:9142 | 4003:9143 | 4003:9144 |
| 4004:9139 | 4004:9140 | 4004:9141 | 4004:9142 | 4004:9143 | 4004:9144 |
| 4005:9139 | 4005:9140 | 4005:9141 | 4005:9142 | 4005:9143 | 4005:9144 |
| 4006:9139 | 4006:9140 | 4006:9141 | 4006:9142 | 4006:9143 | 4006:9144 |
| 4007:9139 | 4007:9140 | 4007:9141 | 4007:9142 | 4007:9143 | 4007:9144 |
| 4008:9139 | 4008:9140 | 4008:9141 | 4008:9142 | 4008:9143 | 4008:9144 |
| 4009:9139 | 4009:9140 | 4009:9141 | 4009:9142 | 4009:9143 | 4009:9144 |
| 4010:9139 | 4010:9140 | 4010:9141 | 4010:9142 | 4010:9143 | 4010:9144 |
| 4011:9139 | 4011:9140 | 4011:9141 | 4011:9142 | 4011:9143 | 4011:9144 |
| 4012:9139 | 4012:9140 | 4012:9141 | 4012:9142 | 4012:9143 | 4012:9144 |
| 5001:9139 | 5001:9140 | 5001:9141 | 5001:9142 | 5001:9143 | 5001:9144 |
| 5002:9139 | 5002:9140 | 5002:9141 | 5002:9142 | 5002:9143 | 5002:9144 |
| 5003:9139 | 5003:9140 | 5003:9141 | 5003:9142 | 5003:9143 | 5003:9144 |
| 5004:9139 | 5004:9140 | 5004:9141 | 5004:9142 | 5004:9143 | 5004:9144 |
| 5005:9139 | 5005:9140 | 5005:9141 | 5005:9142 | 5005:9143 | 5005:9144 |
| 5006:9139 | 5006:9140 | 5006:9141 | 5006:9142 | 5006:9143 | 5006:9144 |
| 5007:9139 | 5007:9140 | 5007:9141 | 5007:9142 | 5007:9143 | 5007:9144 |
| 5008:9139 | 5008:9140 | 5008:9141 | 5008:9142 | 5008:9143 | 5008:9144 |
| 5009:9139 | 5009:9140 | 5009:9141 | 5009:9142 | 5009:9143 | 5009:9144 |
| 5010:9139 | 5010:9140 | 5010:9141 | 5010:9142 | 5010:9143 | 5010:9144 |
| 5011:9139 | 5011:9140 | 5011:9141 | 5011:9142 | 5011:9143 | 5011:9144 |
| 3002:9145 | 3002:9146 | 3002:9147 | 3002:9148 | 3002:9149 | 3002:9150 |
| 3003:9145 | 3003:9146 | 3003:9147 | 3003:9148 | 3003:9149 | 3003:9150 |
| 3004:9145 | 3004:9146 | 3004:9147 | 3004:9148 | 3004:9149 | 3004:9150 |
| 3005:9145 | 3005:9146 | 3005:9147 | 3005:9148 | 3005:9149 | 3005:9150 |
| 3006:9145 | 3006:9146 | 3006:9147 | 3006:9148 | 3006:9149 | 3006:9150 |
| 3007:9145 | 3007:9146 | 3007:9147 | 3007:9148 | 3007:9149 | 3007:9150 |
| 3008:9145 | 3008:9146 | 3008:9147 | 3008:9148 | 3008:9149 | 3008:9150 |
| 3009:9145 | 3009:9146 | 3009:9147 | 3009:9148 | 3009:9149 | 3009:9150 |
| 3010:9145 | 3010:9146 | 3010:9147 | 3010:9148 | 3010:9149 | 3010:9150 |
| 3011:9145 | 3011:9146 | 3011:9147 | 3011:9148 | 3011:9149 | 3011:9150 |
| 3012:9145 | 3012:9146 | 3012:9147 | 3012:9148 | 3012:9149 | 3012:9150 |
| 3013:9145 | 3013:9146 | 3013:9147 | 3013:9148 | 3013:9149 | 3013:9150 |
| 3014:9145 | 3014:9146 | 3014:9147 | 3014:9148 | 3014:9149 | 3014:9150 |
| 4001:9145 | 4001:9146 | 4001:9147 | 4001:9148 | 4001:9149 | 4001:9150 |
| 4002:9145 | 4002:9146 | 4002:9147 | 4002:9148 | 4002:9149 | 4002:9150 |
| 4003:9145 | 4003:9146 | 4003:9147 | 4003:9148 | 4003:9149 | 4003:9150 |
| 4004:9145 | 4004:9146 | 4004:9147 | 4004:9148 | 4004:9149 | 4004:9150 |
| 4005:9145 | 4005:9146 | 4005:9147 | 4005:9148 | 4005:9149 | 4005:9150 |
| 4006:9145 | 4006:9146 | 4006:9147 | 4006:9148 | 4006:9149 | 4006:9150 |
| 4007:9145 | 4007:9146 | 4007:9147 | 4007:9148 | 4007:9149 | 4007:9150 |
| 4008:9145 | 4008:9146 | 4008:9147 | 4008:9148 | 4008:9149 | 4008:9150 |
| 4009:9145 | 4009:9146 | 4009:9147 | 4009:9148 | 4009:9149 | 4009:9150 |
| 4010:9145 | 4010:9146 | 4010:9147 | 4010:9148 | 4010:9149 | 4010:9150 |
| 4011:9145 | 4011:9146 | 4011:9147 | 4011:9148 | 4011:9149 | 4011:9150 |
| 4012:9145 | 4012:9146 | 4012:9147 | 4012:9148 | 4012:9149 | 4012:9150 |
| 5001:9145 | 5001:9146 | 5001:9147 | 5001:9148 | 5001:9149 | 5001:9150 |
| 5002:9145 | 5002:9146 | 5002:9147 | 5002:9148 | 5002:9149 | 5002:9150 |
| 5003:9145 | 5003:9146 | 5003:9147 | 5003:9148 | 5003:9149 | 5003:9150 |
| 5004:9145 | 5004:9146 | 5004:9147 | 5004:9148 | 5004:9149 | 5004:9150 |

TABLE B-continued

Example combinations of a compound X with a compound Y.

| X:Y | X:Y | X:Y | X:Y | X:Y | X:Y |
|---|---|---|---|---|---|
| 5005:9145 | 5005:9146 | 5005:9147 | 5005:9148 | 5005:9149 | 5005:9150 |
| 5006:9145 | 5006:9146 | 5006:9147 | 5006:9148 | 5006:9149 | 5006:9150 |
| 5007:9145 | 5007:9146 | 5007:9147 | 5007:9148 | 5007:9149 | 5007:9150 |
| 5008:9145 | 5008:9146 | 5008:9147 | 5008:9148 | 5008:9149 | 5008:9150 |
| 5009:9145 | 5009:9146 | 5009:9147 | 5009:9148 | 5009:9149 | 5009:9150 |
| 5010:9145 | 5010:9146 | 5010:9147 | 5010:9148 | 5010:9149 | 5010:9150 |
| 5011:9145 | 5011:9146 | 5011:9147 | 5011:9148 | 5011:9149 | 5011:9150 |
| 3002:9161 | 3002:9162 | 3002:9163 | 3002:9164 | 3002:9167 | 3002:9168 |
| 3003:9161 | 3003:9162 | 3003:9163 | 3003:9164 | 3003:9167 | 3003:9168 |
| 3004:9161 | 3004:9162 | 3004:9163 | 3004:9164 | 3004:9167 | 3004:9168 |
| 3005:9161 | 3005:9162 | 3005:9163 | 3005:9164 | 3005:9167 | 3005:9168 |
| 3006:9161 | 3006:9162 | 3006:9163 | 3006:9164 | 3006:9167 | 3006:9168 |
| 3007:9161 | 3007:9162 | 3007:9163 | 3007:9164 | 3007:9167 | 3007:9168 |
| 3008:9161 | 3008:9162 | 3008:9163 | 3008:9164 | 3008:9167 | 3008:9168 |
| 3009:9161 | 3009:9162 | 3009:9163 | 3009:9164 | 3009:9167 | 3009:9168 |
| 3010:9161 | 3010:9162 | 3010:9163 | 3010:9164 | 3010:9167 | 3010:9168 |
| 3011:9161 | 3011:9162 | 3011:9163 | 3011:9164 | 3011:9167 | 3011:9168 |
| 3012:9161 | 3012:9162 | 3012:9163 | 3012:9164 | 3012:9167 | 3012:9168 |
| 3013:9161 | 3013:9162 | 3013:9163 | 3013:9164 | 3013:9167 | 3013:9168 |
| 3014:9161 | 3014:9162 | 3014:9163 | 3014:9164 | 3014:9167 | 3014:9168 |
| 4001:9161 | 4001:9162 | 4001:9163 | 4001:9164 | 4001:9167 | 4001:9168 |
| 4002:9161 | 4002:9162 | 4002:9163 | 4002:9164 | 4002:9167 | 4002:9168 |
| 4003:9161 | 4003:9162 | 4003:9163 | 4003:9164 | 4003:9167 | 4003:9168 |
| 4004:9161 | 4004:9162 | 4004:9163 | 4004:9164 | 4004:9167 | 4004:9168 |
| 4005:9161 | 4005:9162 | 4005:9163 | 4005:9164 | 4005:9167 | 4005:9168 |
| 4006:9161 | 4006:9162 | 4006:9163 | 4006:9164 | 4006:9167 | 4006:9168 |
| 4007:9161 | 4007:9162 | 4007:9163 | 4007:9164 | 4007:9167 | 4007:9168 |
| 4008:9161 | 4008:9162 | 4008:9163 | 4008:9164 | 4008:9167 | 4008:9168 |
| 4009:9161 | 4009:9162 | 4009:9163 | 4009:9164 | 4009:9167 | 4009:9168 |
| 4010:9161 | 4010:9162 | 4010:9163 | 4010:9164 | 4010:9167 | 4010:9168 |
| 4011:9161 | 4011:9162 | 4011:9163 | 4011:9164 | 4011:9167 | 4011:9168 |
| 4012:9161 | 4012:9162 | 4012:9163 | 4012:9164 | 4012:9167 | 4012:9168 |
| 5001:9161 | 5001:9162 | 5001:9163 | 5001:9164 | 5001:9167 | 5001:9168 |
| 5002:9161 | 5002:9162 | 5002:9163 | 5002:9164 | 5002:9167 | 5002:9168 |
| 5003:9161 | 5003:9162 | 5003:9163 | 5003:9164 | 5003:9167 | 5003:9168 |
| 5004:9161 | 5004:9162 | 5004:9163 | 5004:9164 | 5004:9167 | 5004:9168 |
| 5005:9161 | 5005:9162 | 5005:9163 | 5005:9164 | 5005:9167 | 5005:9168 |
| 5006:9161 | 5006:9162 | 5006:9163 | 5006:9164 | 5006:9167 | 5006:9168 |
| 5007:9161 | 5007:9162 | 5007:9163 | 5007:9164 | 5007:9167 | 5007:9168 |
| 5008:9161 | 5008:9162 | 5008:9163 | 5008:9164 | 5008:9167 | 5008:9168 |
| 5009:9161 | 5009:9162 | 5009:9163 | 5009:9164 | 5009:9167 | 5009:9168 |
| 5010:9161 | 5010:9162 | 5010:9163 | 5010:9164 | 5010:9167 | 5010:9168 |
| 5011:9161 | 5011:9162 | 5011:9163 | 5011:9164 | 5011:9167 | 5011:9168 |
| 3002:9169 | 3002:9170 | 3002:9171 | 3002:9172 | 3002:9173 | 3002:9174 |
| 3003:9169 | 3003:9170 | 3003:9171 | 3003:9172 | 3003:9173 | 3003:9174 |
| 3004:9169 | 3004:9170 | 3004:9171 | 3004:9172 | 3004:9173 | 3004:9174 |
| 3005:9169 | 3005:9170 | 3005:9171 | 3005:9172 | 3005:9173 | 3005:9174 |
| 3006:9169 | 3006:9170 | 3006:9171 | 3006:9172 | 3006:9173 | 3006:9174 |
| 3007:9169 | 3007:9170 | 3007:9171 | 3007:9172 | 3007:9173 | 3007:9174 |
| 3008:9169 | 3008:9170 | 3008:9171 | 3008:9172 | 3008:9173 | 3008:9174 |
| 3009:9169 | 3009:9170 | 3009:9171 | 3009:9172 | 3009:9173 | 3009:9174 |
| 3010:9169 | 3010:9170 | 3010:9171 | 3010:9172 | 3010:9173 | 3010:9174 |
| 3011:9169 | 3011:9170 | 3011:9171 | 3011:9172 | 3011:9173 | 3011:9174 |
| 3012:9169 | 3012:9170 | 3012:9171 | 3012:9172 | 3012:9173 | 3012:9174 |
| 3013:9169 | 3013:9170 | 3013:9171 | 3013:9172 | 3013:9173 | 3013:9174 |
| 3014:9169 | 3014:9170 | 3014:9171 | 3014:9172 | 3014:9173 | 3014:9174 |
| 4001:9169 | 4001:9170 | 4001:9171 | 4001:9172 | 4001:9173 | 4001:9174 |
| 4002:9169 | 4002:9170 | 4002:9171 | 4002:9172 | 4002:9173 | 4002:9174 |
| 4003:9169 | 4003:9170 | 4003:9171 | 4003:9172 | 4003:9173 | 4003:9174 |
| 4004:9169 | 4004:9170 | 4004:9171 | 4004:9172 | 4004:9173 | 4004:9174 |
| 4005:9169 | 4005:9170 | 4005:9171 | 4005:9172 | 4005:9173 | 4005:9174 |
| 4006:9169 | 4006:9170 | 4006:9171 | 4006:9172 | 4006:9173 | 4006:9174 |
| 4007:9169 | 4007:9170 | 4007:9171 | 4007:9172 | 4007:9173 | 4007:9174 |
| 4008:9169 | 4008:9170 | 4008:9171 | 4008:9172 | 4008:9173 | 4008:9174 |
| 4009:9169 | 4009:9170 | 4009:9171 | 4009:9172 | 4009:9173 | 4009:9174 |
| 4010:9169 | 4010:9170 | 4010:9171 | 4010:9172 | 4010:9173 | 4010:9174 |
| 4011:9169 | 4011:9170 | 4011:9171 | 4011:9172 | 4011:9173 | 4011:9174 |
| 4012:9169 | 4012:9170 | 4012:9171 | 4012:9172 | 4012:9173 | 4012:9174 |
| 5001:9169 | 5001:9170 | 5001:9171 | 5001:9172 | 5001:9173 | 5001:9174 |
| 5002:9169 | 5002:9170 | 5002:9171 | 5002:9172 | 5002:9173 | 5002:9174 |
| 5003:9169 | 5003:9170 | 5003:9171 | 5003:9172 | 5003:9173 | 5003:9174 |
| 5004:9169 | 5004:9170 | 5004:9171 | 5004:9172 | 5004:9173 | 5004:9174 |
| 5005:9169 | 5005:9170 | 5005:9171 | 5005:9172 | 5005:9173 | 5005:9174 |
| 5006:9169 | 5006:9170 | 5006:9171 | 5006:9172 | 5006:9173 | 5006:9174 |
| 5007:9169 | 5007:9170 | 5007:9171 | 5007:9172 | 5007:9173 | 5007:9174 |
| 5008:9169 | 5008:9170 | 5008:9171 | 5008:9172 | 5008:9173 | 5008:9174 |
| 5009:9169 | 5009:9170 | 5009:9171 | 5009:9172 | 5009:9173 | 5009:9174 |
| 5010:9169 | 5010:9170 | 5010:9171 | 5010:9172 | 5010:9173 | 5010:9174 |
| 5011:9169 | 5011:9170 | 5011:9171 | 5011:9172 | 5011:9173 | 5011:9174 |
| 3002:9175 | 3002:9176 | 3002:9177 | 3002:9178 | 3002:9179 | 3002:9180 |
| 3003:9175 | 3003:9176 | 3003:9177 | 3003:9178 | 3003:9179 | 3003:9180 |
| 3004:9175 | 3004:9176 | 3004:9177 | 3004:9178 | 3004:9179 | 3004:9180 |
| 3005:9175 | 3005:9176 | 3005:9177 | 3005:9178 | 3005:9179 | 3005:9180 |
| 3006:9175 | 3006:9176 | 3006:9177 | 3006:9178 | 3006:9179 | 3006:9180 |
| 3007:9175 | 3007:9176 | 3007:9177 | 3007:9178 | 3007:9179 | 3007:9180 |
| 3008:9175 | 3008:9176 | 3008:9177 | 3008:9178 | 3008:9179 | 3008:9180 |
| 3009:9175 | 3009:9176 | 3009:9177 | 3009:9178 | 3009:9179 | 3009:9180 |
| 3010:9175 | 3010:9176 | 3010:9177 | 3010:9178 | 3010:9179 | 3010:9180 |
| 3011:9175 | 3011:9176 | 3011:9177 | 3011:9178 | 3011:9179 | 3011:9180 |
| 3012:9175 | 3012:9176 | 3012:9177 | 3012:9178 | 3012:9179 | 3012:9180 |
| 3013:9175 | 3013:9176 | 3013:9177 | 3013:9178 | 3013:9179 | 3013:9180 |
| 3014:9175 | 3014:9176 | 3014:9177 | 3014:9178 | 3014:9179 | 3014:9180 |
| 4001:9175 | 4001:9176 | 4001:9177 | 4001:9178 | 4001:9179 | 4001:9180 |
| 4002:9175 | 4002:9176 | 4002:9177 | 4002:9178 | 4002:9179 | 4002:9180 |
| 4003:9175 | 4003:9176 | 4003:9177 | 4003:9178 | 4003:9179 | 4003:9180 |
| 4004:9175 | 4004:9176 | 4004:9177 | 4004:9178 | 4004:9179 | 4004:9180 |
| 4005:9175 | 4005:9176 | 4005:9177 | 4005:9178 | 4005:9179 | 4005:9180 |
| 4006:9175 | 4006:9176 | 4006:9177 | 4006:9178 | 4006:9179 | 4006:9180 |
| 4007:9175 | 4007:9176 | 4007:9177 | 4007:9178 | 4007:9179 | 4007:9180 |
| 4008:9175 | 4008:9176 | 4008:9177 | 4008:9178 | 4008:9179 | 4008:9180 |
| 4009:9175 | 4009:9176 | 4009:9177 | 4009:9178 | 4009:9179 | 4009:9180 |
| 4010:9175 | 4010:9176 | 4010:9177 | 4010:9178 | 4010:9179 | 4010:9180 |
| 4011:9175 | 4011:9176 | 4011:9177 | 4011:9178 | 4011:9179 | 4011:9180 |
| 4012:9175 | 4012:9176 | 4012:9177 | 4012:9178 | 4012:9179 | 4012:9180 |
| 5001:9175 | 5001:9176 | 5001:9177 | 5001:9178 | 5001:9179 | 5001:9180 |
| 5002:9175 | 5002:9176 | 5002:9177 | 5002:9178 | 5002:9179 | 5002:9180 |
| 5003:9175 | 5003:9176 | 5003:9177 | 5003:9178 | 5003:9179 | 5003:9180 |
| 5004:9175 | 5004:9176 | 5004:9177 | 5004:9178 | 5004:9179 | 5004:9180 |
| 5005:9175 | 5005:9176 | 5005:9177 | 5005:9178 | 5005:9179 | 5005:9180 |
| 5006:9175 | 5006:9176 | 5006:9177 | 5006:9178 | 5006:9179 | 5006:9180 |
| 5007:9175 | 5007:9176 | 5007:9177 | 5007:9178 | 5007:9179 | 5007:9180 |
| 5008:9175 | 5008:9176 | 5008:9177 | 5008:9178 | 5008:9179 | 5008:9180 |
| 5009:9175 | 5009:9176 | 5009:9177 | 5009:9178 | 5009:9179 | 5009:9180 |
| 5010:9175 | 5010:9176 | 5010:9177 | 5010:9178 | 5010:9179 | 5010:9180 |
| 5011:9175 | 5011:9176 | 5011:9177 | 5011:9178 | 5011:9179 | 5011:9180 |
| 3002:9181 | 3002:9182 | 3002:9183 | 3002:9184 | 3002:9185 | 3002:9206 |
| 3003:9181 | 3003:9182 | 3003:9183 | 3003:9184 | 3003:9185 | 3003:9206 |
| 3004:9181 | 3004:9182 | 3004:9183 | 3004:9184 | 3004:9185 | 3004:9206 |
| 3005:9181 | 3005:9182 | 3005:9183 | 3005:9184 | 3005:9185 | 3005:9206 |
| 3006:9181 | 3006:9182 | 3006:9183 | 3006:9184 | 3006:9185 | 3006:9206 |
| 3007:9181 | 3007:9182 | 3007:9183 | 3007:9184 | 3007:9185 | 3007:9206 |
| 3008:9181 | 3008:9182 | 3008:9183 | 3008:9184 | 3008:9185 | 3008:9206 |
| 3009:9181 | 3009:9182 | 3009:9183 | 3009:9184 | 3009:9185 | 3009:9206 |
| 3010:9181 | 3010:9182 | 3010:9183 | 3010:9184 | 3010:9185 | 3010:9206 |
| 3011:9181 | 3011:9182 | 3011:9183 | 3011:9184 | 3011:9185 | 3011:9206 |
| 3012:9181 | 3012:9182 | 3012:9183 | 3012:9184 | 3012:9185 | 3012:9206 |
| 3013:9181 | 3013:9182 | 3013:9183 | 3013:9184 | 3013:9185 | 3013:9206 |
| 3014:9181 | 3014:9182 | 3014:9183 | 3014:9184 | 3014:9185 | 3014:9206 |
| 4001:9181 | 4001:9182 | 4001:9183 | 4001:9184 | 4001:9185 | 4001:9206 |
| 4002:9181 | 4002:9182 | 4002:9183 | 4002:9184 | 4002:9185 | 4002:9206 |
| 4003:9181 | 4003:9182 | 4003:9183 | 4003:9184 | 4003:9185 | 4003:9206 |
| 4004:9181 | 4004:9182 | 4004:9183 | 4004:9184 | 4004:9185 | 4004:9206 |
| 4005:9181 | 4005:9182 | 4005:9183 | 4005:9184 | 4005:9185 | 4005:9206 |
| 4006:9181 | 4006:9182 | 4006:9183 | 4006:9184 | 4006:9185 | 4006:9206 |
| 4007:9181 | 4007:9182 | 4007:9183 | 4007:9184 | 4007:9185 | 4007:9206 |
| 4008:9181 | 4008:9182 | 4008:9183 | 4008:9184 | 4008:9185 | 4008:9206 |
| 4009:9181 | 4009:9182 | 4009:9183 | 4009:9184 | 4009:9185 | 4009:9206 |
| 4010:9181 | 4010:9182 | 4010:9183 | 4010:9184 | 4010:9185 | 4010:9206 |
| 4011:9181 | 4011:9182 | 4011:9183 | 4011:9184 | 4011:9185 | 4011:9206 |
| 4012:9181 | 4012:9182 | 4012:9183 | 4012:9184 | 4012:9185 | 4012:9206 |
| 5001:9181 | 5001:9182 | 5001:9183 | 5001:9184 | 5001:9185 | 5001:9206 |
| 5002:9181 | 5002:9182 | 5002:9183 | 5002:9184 | 5002:9185 | 5002:9206 |
| 5003:9181 | 5003:9182 | 5003:9183 | 5003:9184 | 5003:9185 | 5003:9206 |
| 5004:9181 | 5004:9182 | 5004:9183 | 5004:9184 | 5004:9185 | 5004:9206 |
| 5005:9181 | 5005:9182 | 5005:9183 | 5005:9184 | 5005:9185 | 5005:9206 |
| 5006:9181 | 5006:9182 | 5006:9183 | 5006:9184 | 5006:9185 | 5006:9206 |
| 5007:9181 | 5007:9182 | 5007:9183 | 5007:9184 | 5007:9185 | 5007:9206 |
| 5008:9181 | 5008:9182 | 5008:9183 | 5008:9184 | 5008:9185 | 5008:9206 |
| 5009:9181 | 5009:9182 | 5009:9183 | 5009:9184 | 5009:9185 | 5009:9206 |
| 5010:9181 | 5010:9182 | 5010:9183 | 5010:9184 | 5010:9185 | 5010:9206 |
| 5011:9181 | 5011:9182 | 5011:9183 | 5011:9184 | 5011:9185 | 5011:9206 |
| 3002:9207 | 3002:9208 | 3002:9209 | 3002:9214 | 3002:9241 | 3002:9242 |

TABLE B-continued

Example combinations of a compound X with a compound Y.

| X:Y | X:Y | X:Y | X:Y | X:Y | X:Y |
|---|---|---|---|---|---|
| 3003:9207 | 3003:9208 | 3003:9209 | 3003:9214 | 3003:9241 | 3003:9242 |
| 3004:9207 | 3004:9208 | 3004:9209 | 3004:9214 | 3004:9241 | 3004:9242 |
| 3005:9207 | 3005:9208 | 3005:9209 | 3005:9214 | 3005:9241 | 3005:9242 |
| 3006:9207 | 3006:9208 | 3006:9209 | 3006:9214 | 3006:9241 | 3006:9242 |
| 3007:9207 | 3007:9208 | 3007:9209 | 3007:9214 | 3007:9241 | 3007:9242 |
| 3008:9207 | 3008:9208 | 3008:9209 | 3008:9214 | 3008:9241 | 3008:9242 |
| 3009:9207 | 3009:9208 | 3009:9209 | 3009:9214 | 3009:9241 | 3009:9242 |
| 3010:9207 | 3010:9208 | 3010:9209 | 3010:9214 | 3010:9241 | 3010:9242 |
| 3011:9207 | 3011:9208 | 3011:9209 | 3011:9214 | 3011:9241 | 3011:9242 |
| 3012:9207 | 3012:9208 | 3012:9209 | 3012:9214 | 3012:9241 | 3012:9242 |
| 3013:9207 | 3013:9208 | 3013:9209 | 3013:9214 | 3013:9241 | 3013:9242 |
| 3014:9207 | 3014:9208 | 3014:9209 | 3014:9214 | 3014:9241 | 3014:9242 |
| 4001:9207 | 4001:9208 | 4001:9209 | 4001:9214 | 4001:9241 | 4001:9242 |
| 4002:9207 | 4002:9208 | 4002:9209 | 4002:9214 | 4002:9241 | 4002:9242 |
| 4003:9207 | 4003:9208 | 4003:9209 | 4003:9214 | 4003:9241 | 4003:9242 |
| 4004:9207 | 4004:9208 | 4004:9209 | 4004:9214 | 4004:9241 | 4004:9242 |
| 4005:9207 | 4005:9208 | 4005:9209 | 4005:9214 | 4005:9241 | 4005:9242 |
| 4006:9207 | 4006:9208 | 4006:9209 | 4006:9214 | 4006:9241 | 4006:9242 |
| 4007:9207 | 4007:9208 | 4007:9209 | 4007:9214 | 4007:9241 | 4007:9242 |
| 4008:9207 | 4008:9208 | 4008:9209 | 4008:9214 | 4008:9241 | 4008:9242 |
| 4009:9207 | 4009:9208 | 4009:9209 | 4009:9214 | 4009:9241 | 4009:9242 |
| 4010:9207 | 4010:9208 | 4010:9209 | 4010:9214 | 4010:9241 | 4010:9242 |
| 4011:9207 | 4011:9208 | 4011:9209 | 4011:9214 | 4011:9241 | 4011:9242 |
| 4012:9207 | 4012:9208 | 4012:9209 | 4012:9214 | 4012:9241 | 4012:9242 |
| 5001:9207 | 5001:9208 | 5001:9209 | 5001:9214 | 5001:9241 | 5001:9242 |
| 5002:9207 | 5002:9208 | 5002:9209 | 5002:9214 | 5002:9241 | 5002:9242 |
| 5003:9207 | 5003:9208 | 5003:9209 | 5003:9214 | 5003:9241 | 5003:9242 |
| 5004:9207 | 5004:9208 | 5004:9209 | 5004:9214 | 5004:9241 | 5004:9242 |
| 5005:9207 | 5005:9208 | 5005:9209 | 5005:9214 | 5005:9241 | 5005:9242 |
| 5006:9207 | 5006:9208 | 5006:9209 | 5006:9214 | 5006:9241 | 5006:9242 |
| 5007:9207 | 5007:9208 | 5007:9209 | 5007:9214 | 5007:9241 | 5007:9242 |
| 5008:9207 | 5008:9208 | 5008:9209 | 5008:9214 | 5008:9241 | 5008:9242 |
| 5009:9207 | 5009:9208 | 5009:9209 | 5009:9214 | 5009:9241 | 5009:9242 |
| 5010:9207 | 5010:9208 | 5010:9209 | 5010:9214 | 5010:9241 | 5010:9242 |
| 5011:9207 | 5011:9208 | 5011:9209 | 5011:9214 | 5011:9241 | 5011:9242 |
| 3002:9244 | 3002:9245 | 3002:9246 | 3002:9247 | 3002:9248 | 3002:9249 |
| 3003:9244 | 3003:9245 | 3003:9246 | 3003:9247 | 3003:9248 | 3003:9249 |
| 3004:9244 | 3004:9245 | 3004:9246 | 3004:9247 | 3004:9248 | 3004:9249 |
| 3005:9244 | 3005:9245 | 3005:9246 | 3005:9247 | 3005:9248 | 3005:9249 |
| 3006:9244 | 3006:9245 | 3006:9246 | 3006:9247 | 3006:9248 | 3006:9249 |
| 3007:9244 | 3007:9245 | 3007:9246 | 3007:9247 | 3007:9248 | 3007:9249 |
| 3008:9244 | 3008:9245 | 3008:9246 | 3008:9247 | 3008:9248 | 3008:9249 |
| 3009:9244 | 3009:9245 | 3009:9246 | 3009:9247 | 3009:9248 | 3009:9249 |
| 3010:9244 | 3010:9245 | 3010:9246 | 3010:9247 | 3010:9248 | 3010:9249 |
| 3011:9244 | 3011:9245 | 3011:9246 | 3011:9247 | 3011:9248 | 3011:9249 |
| 3012:9244 | 3012:9245 | 3012:9246 | 3012:9247 | 3012:9248 | 3012:9249 |
| 3013:9244 | 3013:9245 | 3013:9246 | 3013:9247 | 3013:9248 | 3013:9249 |
| 3014:9244 | 3014:9245 | 3014:9246 | 3014:9247 | 3014:9248 | 3014:9249 |
| 4001:9244 | 4001:9245 | 4001:9246 | 4001:9247 | 4001:9248 | 4001:9249 |
| 4002:9244 | 4002:9245 | 4002:9246 | 4002:9247 | 4002:9248 | 4002:9249 |
| 4003:9244 | 4003:9245 | 4003:9246 | 4003:9247 | 4003:9248 | 4003:9249 |
| 4004:9244 | 4004:9245 | 4004:9246 | 4004:9247 | 4004:9248 | 4004:9249 |
| 4005:9244 | 4005:9245 | 4005:9246 | 4005:9247 | 4005:9248 | 4005:9249 |
| 4006:9244 | 4006:9245 | 4006:9246 | 4006:9247 | 4006:9248 | 4006:9249 |
| 4007:9244 | 4007:9245 | 4007:9246 | 4007:9247 | 4007:9248 | 4007:9249 |
| 4008:9244 | 4008:9245 | 4008:9246 | 4008:9247 | 4008:9248 | 4008:9249 |
| 4009:9244 | 4009:9245 | 4009:9246 | 4009:9247 | 4009:9248 | 4009:9249 |
| 4010:9244 | 4010:9245 | 4010:9246 | 4010:9247 | 4010:9248 | 4010:9249 |
| 4011:9244 | 4011:9245 | 4011:9246 | 4011:9247 | 4011:9248 | 4011:9249 |
| 4012:9244 | 4012:9245 | 4012:9246 | 4012:9247 | 4012:9248 | 4012:9249 |
| 5001:9244 | 5001:9245 | 5001:9246 | 5001:9247 | 5001:9248 | 5001:9249 |
| 5002:9244 | 5002:9245 | 5002:9246 | 5002:9247 | 5002:9248 | 5002:9249 |
| 5003:9244 | 5003:9245 | 5003:9246 | 5003:9247 | 5003:9248 | 5003:9249 |
| 5004:9244 | 5004:9245 | 5004:9246 | 5004:9247 | 5004:9248 | 5004:9249 |
| 5005:9244 | 5005:9245 | 5005:9246 | 5005:9247 | 5005:9248 | 5005:9249 |
| 5006:9244 | 5006:9245 | 5006:9246 | 5006:9247 | 5006:9248 | 5006:9249 |
| 5007:9244 | 5007:9245 | 5007:9246 | 5007:9247 | 5007:9248 | 5007:9249 |
| 5008:9244 | 5008:9245 | 5008:9246 | 5008:9247 | 5008:9248 | 5008:9249 |
| 5009:9244 | 5009:9245 | 5009:9246 | 5009:9247 | 5009:9248 | 5009:9249 |
| 5010:9244 | 5010:9245 | 5010:9246 | 5010:9247 | 5010:9248 | 5010:9249 |
| 5011:9244 | 5011:9245 | 5011:9246 | 5011:9247 | 5011:9248 | 5011:9249 |
| 3002:9250 | 3002:9251 | 3002:9252 | 3002:9253 | 3002:9255 | 3002:9256 |
| 3003:9250 | 3003:9251 | 3003:9252 | 3003:9253 | 3003:9255 | 3003:9256 |
| 3004:9250 | 3004:9251 | 3004:9252 | 3004:9253 | 3004:9255 | 3004:9256 |
| 3005:9250 | 3005:9251 | 3005:9252 | 3005:9253 | 3005:9255 | 3005:9256 |
| 3006:9250 | 3006:9251 | 3006:9252 | 3006:9253 | 3006:9255 | 3006:9256 |
| 3007:9250 | 3007:9251 | 3007:9252 | 3007:9253 | 3007:9255 | 3007:9256 |
| 3008:9250 | 3008:9251 | 3008:9252 | 3008:9253 | 3008:9255 | 3008:9256 |
| 3009:9250 | 3009:9251 | 3009:9252 | 3009:9253 | 3009:9255 | 3009:9256 |
| 3010:9250 | 3010:9251 | 3010:9252 | 3010:9253 | 3010:9255 | 3010:9256 |
| 3011:9250 | 3011:9251 | 3011:9252 | 3011:9253 | 3011:9255 | 3011:9256 |
| 3012:9250 | 3012:9251 | 3012:9252 | 3012:9253 | 3012:9255 | 3012:9256 |
| 3013:9250 | 3013:9251 | 3013:9252 | 3013:9253 | 3013:9255 | 3013:9256 |
| 3014:9250 | 3014:9251 | 3014:9252 | 3014:9253 | 3014:9255 | 3014:9256 |
| 4001:9250 | 4001:9251 | 4001:9252 | 4001:9253 | 4001:9255 | 4001:9256 |
| 4002:9250 | 4002:9251 | 4002:9252 | 4002:9253 | 4002:9255 | 4002:9256 |
| 4003:9250 | 4003:9251 | 4003:9252 | 4003:9253 | 4003:9255 | 4003:9256 |
| 4004:9250 | 4004:9251 | 4004:9252 | 4004:9253 | 4004:9255 | 4004:9256 |
| 4005:9250 | 4005:9251 | 4005:9252 | 4005:9253 | 4005:9255 | 4005:9256 |
| 4006:9250 | 4006:9251 | 4006:9252 | 4006:9253 | 4006:9255 | 4006:9256 |
| 4007:9250 | 4007:9251 | 4007:9252 | 4007:9253 | 4007:9255 | 4007:9256 |
| 4008:9250 | 4008:9251 | 4008:9252 | 4008:9253 | 4008:9255 | 4008:9256 |
| 4009:9250 | 4009:9251 | 4009:9252 | 4009:9253 | 4009:9255 | 4009:9256 |
| 4010:9250 | 4010:9251 | 4010:9252 | 4010:9253 | 4010:9255 | 4010:9256 |
| 4011:9250 | 4011:9251 | 4011:9252 | 4011:9253 | 4011:9255 | 4011:9256 |
| 4012:9250 | 4012:9251 | 4012:9252 | 4012:9253 | 4012:9255 | 4012:9256 |
| 5001:9250 | 5001:9251 | 5001:9252 | 5001:9253 | 5001:9255 | 5001:9256 |
| 5002:9250 | 5002:9251 | 5002:9252 | 5002:9253 | 5002:9255 | 5002:9256 |
| 5003:9250 | 5003:9251 | 5003:9252 | 5003:9253 | 5003:9255 | 5003:9256 |
| 5004:9250 | 5004:9251 | 5004:9252 | 5004:9253 | 5004:9255 | 5004:9256 |
| 5005:9250 | 5005:9251 | 5005:9252 | 5005:9253 | 5005:9255 | 5005:9256 |
| 5006:9250 | 5006:9251 | 5006:9252 | 5006:9253 | 5006:9255 | 5006:9256 |
| 5007:9250 | 5007:9251 | 5007:9252 | 5007:9253 | 5007:9255 | 5007:9256 |
| 5008:9250 | 5008:9251 | 5008:9252 | 5008:9253 | 5008:9255 | 5008:9256 |
| 5009:9250 | 5009:9251 | 5009:9252 | 5009:9253 | 5009:9255 | 5009:9256 |
| 5010:9250 | 5010:9251 | 5010:9252 | 5010:9253 | 5010:9255 | 5010:9256 |
| 5011:9250 | 5011:9251 | 5011:9252 | 5011:9253 | 5011:9255 | 5011:9256 |
| 3002:9257 | 3002:9258 | 3002:9259 | 3002:9260 | 3002:9262 | 3002:9263 |
| 3003:9257 | 3003:9258 | 3003:9259 | 3003:9260 | 3003:9262 | 3003:9263 |
| 3004:9257 | 3004:9258 | 3004:9259 | 3004:9260 | 3004:9262 | 3004:9263 |
| 3005:9257 | 3005:9258 | 3005:9259 | 3005:9260 | 3005:9262 | 3005:9263 |
| 3006:9257 | 3006:9258 | 3006:9259 | 3006:9260 | 3006:9262 | 3006:9263 |
| 3007:9257 | 3007:9258 | 3007:9259 | 3007:9260 | 3007:9262 | 3007:9263 |
| 3008:9257 | 3008:9258 | 3008:9259 | 3008:9260 | 3008:9262 | 3008:9263 |
| 3009:9257 | 3009:9258 | 3009:9259 | 3009:9260 | 3009:9262 | 3009:9263 |
| 3010:9257 | 3010:9258 | 3010:9259 | 3010:9260 | 3010:9262 | 3010:9263 |
| 3011:9257 | 3011:9258 | 3011:9259 | 3011:9260 | 3011:9262 | 3011:9263 |
| 3012:9257 | 3012:9258 | 3012:9259 | 3012:9260 | 3012:9262 | 3012:9263 |
| 3013:9257 | 3013:9258 | 3013:9259 | 3013:9260 | 3013:9262 | 3013:9263 |
| 3014:9257 | 3014:9258 | 3014:9259 | 3014:9260 | 3014:9262 | 3014:9263 |
| 4001:9257 | 4001:9258 | 4001:9259 | 4001:9260 | 4001:9262 | 4001:9263 |
| 4002:9257 | 4002:9258 | 4002:9259 | 4002:9260 | 4002:9262 | 4002:9263 |
| 4003:9257 | 4003:9258 | 4003:9259 | 4003:9260 | 4003:9262 | 4003:9263 |
| 4004:9257 | 4004:9258 | 4004:9259 | 4004:9260 | 4004:9262 | 4004:9263 |
| 4005:9257 | 4005:9258 | 4005:9259 | 4005:9260 | 4005:9262 | 4005:9263 |
| 4006:9257 | 4006:9258 | 4006:9259 | 4006:9260 | 4006:9262 | 4006:9263 |
| 4007:9257 | 4007:9258 | 4007:9259 | 4007:9260 | 4007:9262 | 4007:9263 |
| 4008:9257 | 4008:9258 | 4008:9259 | 4008:9260 | 4008:9262 | 4008:9263 |
| 4009:9257 | 4009:9258 | 4009:9259 | 4009:9260 | 4009:9262 | 4009:9263 |
| 4010:9257 | 4010:9258 | 4010:9259 | 4010:9260 | 4010:9262 | 4010:9263 |
| 4011:9257 | 4011:9258 | 4011:9259 | 4011:9260 | 4011:9262 | 4011:9263 |
| 4012:9257 | 4012:9258 | 4012:9259 | 4012:9260 | 4012:9262 | 4012:9263 |
| 5001:9257 | 5001:9258 | 5001:9259 | 5001:9260 | 5001:9262 | 5001:9263 |
| 5002:9257 | 5002:9258 | 5002:9259 | 5002:9260 | 5002:9262 | 5002:9263 |
| 5003:9257 | 5003:9258 | 5003:9259 | 5003:9260 | 5003:9262 | 5003:9263 |
| 5004:9257 | 5004:9258 | 5004:9259 | 5004:9260 | 5004:9262 | 5004:9263 |
| 5005:9257 | 5005:9258 | 5005:9259 | 5005:9260 | 5005:9262 | 5005:9263 |
| 5006:9257 | 5006:9258 | 5006:9259 | 5006:9260 | 5006:9262 | 5006:9263 |
| 5007:9257 | 5007:9258 | 5007:9259 | 5007:9260 | 5007:9262 | 5007:9263 |
| 5008:9257 | 5008:9258 | 5008:9259 | 5008:9260 | 5008:9262 | 5008:9263 |
| 5009:9257 | 5009:9258 | 5009:9259 | 5009:9260 | 5009:9262 | 5009:9263 |
| 5010:9257 | 5010:9258 | 5010:9259 | 5010:9260 | 5010:9262 | 5010:9263 |
| 5011:9257 | 5011:9258 | 5011:9259 | 5011:9260 | 5011:9262 | 5011:9263 |
| 3002:9264 | 3002:9265 | 3002:9266 | 3002:9267 | 3002:9268 | 3002:9269 |
| 3003:9264 | 3003:9265 | 3003:9266 | 3003:9267 | 3003:9268 | 3003:9269 |
| 3004:9264 | 3004:9265 | 3004:9266 | 3004:9267 | 3004:9268 | 3004:9269 |
| 3005:9264 | 3005:9265 | 3005:9266 | 3005:9267 | 3005:9268 | 3005:9269 |
| 3006:9264 | 3006:9265 | 3006:9266 | 3006:9267 | 3006:9268 | 3006:9269 |
| 3007:9264 | 3007:9265 | 3007:9266 | 3007:9267 | 3007:9268 | 3007:9269 |
| 3008:9264 | 3008:9265 | 3008:9266 | 3008:9267 | 3008:9268 | 3008:9269 |
| 3009:9264 | 3009:9265 | 3009:9266 | 3009:9267 | 3009:9268 | 3009:9269 |
| 3010:9264 | 3010:9265 | 3010:9266 | 3010:9267 | 3010:9268 | 3010:9269 |

TABLE B-continued

Example combinations of a compound X with a compound Y.

| X:Y | X:Y | X:Y | X:Y | X:Y | X:Y |
|---|---|---|---|---|---|
| 3011:9264 | 3011:9265 | 3011:9266 | 3011:9267 | 3011:9268 | 3011:9269 |
| 3012:9264 | 3012:9265 | 3012:9266 | 3012:9267 | 3012:9268 | 3012:9269 |
| 3013:9264 | 3013:9265 | 3013:9266 | 3013:9267 | 3013:9268 | 3013:9269 |
| 3014:9264 | 3014:9265 | 3014:9266 | 3014:9267 | 3014:9268 | 3014:9269 |
| 4001:9264 | 4001:9265 | 4001:9266 | 4001:9267 | 4001:9268 | 4001:9269 |
| 4002:9264 | 4002:9265 | 4002:9266 | 4002:9267 | 4002:9268 | 4002:9269 |
| 4003:9264 | 4003:9265 | 4003:9266 | 4003:9267 | 4003:9268 | 4003:9269 |
| 4004:9264 | 4004:9265 | 4004:9266 | 4004:9267 | 4004:9268 | 4004:9269 |
| 4005:9264 | 4005:9265 | 4005:9266 | 4005:9267 | 4005:9268 | 4005:9269 |
| 4006:9264 | 4006:9265 | 4006:9266 | 4006:9267 | 4006:9268 | 4006:9269 |
| 4007:9264 | 4007:9265 | 4007:9266 | 4007:9267 | 4007:9268 | 4007:9269 |
| 4008:9264 | 4008:9265 | 4008:9266 | 4008:9267 | 4008:9268 | 4008:9269 |
| 4009:9264 | 4009:9265 | 4009:9266 | 4009:9267 | 4009:9268 | 4009:9269 |
| 4010:9264 | 4010:9265 | 4010:9266 | 4010:9267 | 4010:9268 | 4010:9269 |
| 4011:9264 | 4011:9265 | 4011:9266 | 4011:9267 | 4011:9268 | 4011:9269 |
| 4012:9264 | 4012:9265 | 4012:9266 | 4012:9267 | 4012:9268 | 4012:9269 |
| 5001:9264 | 5001:9265 | 5001:9266 | 5001:9267 | 5001:9268 | 5001:9269 |
| 5002:9264 | 5002:9265 | 5002:9266 | 5002:9267 | 5002:9268 | 5002:9269 |
| 5003:9264 | 5003:9265 | 5003:9266 | 5003:9267 | 5003:9268 | 5003:9269 |
| 5004:9264 | 5004:9265 | 5004:9266 | 5004:9267 | 5004:9268 | 5004:9269 |
| 5005:9264 | 5005:9265 | 5005:9266 | 5005:9267 | 5005:9268 | 5005:9269 |
| 5006:9264 | 5006:9265 | 5006:9266 | 5006:9267 | 5006:9268 | 5006:9269 |
| 5007:9264 | 5007:9265 | 5007:9266 | 5007:9267 | 5007:9268 | 5007:9269 |
| 5008:9264 | 5008:9265 | 5008:9266 | 5008:9267 | 5008:9268 | 5008:9269 |
| 5009:9264 | 5009:9265 | 5009:9266 | 5009:9267 | 5009:9268 | 5009:9269 |
| 5010:9264 | 5010:9265 | 5010:9266 | 5010:9267 | 5010:9268 | 5010:9269 |
| 5011:9264 | 5011:9265 | 5011:9266 | 5011:9267 | 5011:9268 | 5011:9269 |
| 3002:9270 | 3002:9271 | 3002:9272 | 3002:9273 | 3002:9274 | 3002:9275 |
| 3003:9270 | 3003:9271 | 3003:9272 | 3003:9273 | 3003:9274 | 3003:9275 |
| 3004:9270 | 3004:9271 | 3004:9272 | 3004:9273 | 3004:9274 | 3004:9275 |
| 3005:9270 | 3005:9271 | 3005:9272 | 3005:9273 | 3005:9274 | 3005:9275 |
| 3006:9270 | 3006:9271 | 3006:9272 | 3006:9273 | 3006:9274 | 3006:9275 |
| 3007:9270 | 3007:9271 | 3007:9272 | 3007:9273 | 3007:9274 | 3007:9275 |
| 3008:9270 | 3008:9271 | 3008:9272 | 3008:9273 | 3008:9274 | 3008:9275 |
| 3009:9270 | 3009:9271 | 3009:9272 | 3009:9273 | 3009:9274 | 3009:9275 |
| 3010:9270 | 3010:9271 | 3010:9272 | 3010:9273 | 3010:9274 | 3010:9275 |
| 3011:9270 | 3011:9271 | 3011:9272 | 3011:9273 | 3011:9274 | 3011:9275 |
| 3012:9270 | 3012:9271 | 3012:9272 | 3012:9273 | 3012:9274 | 3012:9275 |
| 3013:9270 | 3013:9271 | 3013:9272 | 3013:9273 | 3013:9274 | 3013:9275 |
| 3014:9270 | 3014:9271 | 3014:9272 | 3014:9273 | 3014:9274 | 3014:9275 |
| 4001:9270 | 4001:9271 | 4001:9272 | 4001:9273 | 4001:9274 | 4001:9275 |
| 4002:9270 | 4002:9271 | 4002:9272 | 4002:9273 | 4002:9274 | 4002:9275 |
| 4003:9270 | 4003:9271 | 4003:9272 | 4003:9273 | 4003:9274 | 4003:9275 |
| 4004:9270 | 4004:9271 | 4004:9272 | 4004:9273 | 4004:9274 | 4004:9275 |
| 4005:9270 | 4005:9271 | 4005:9272 | 4005:9273 | 4005:9274 | 4005:9275 |
| 4006:9270 | 4006:9271 | 4006:9272 | 4006:9273 | 4006:9274 | 4006:9275 |
| 4007:9270 | 4007:9271 | 4007:9272 | 4007:9273 | 4007:9274 | 4007:9275 |
| 4008:9270 | 4008:9271 | 4008:9272 | 4008:9273 | 4008:9274 | 4008:9275 |
| 4009:9270 | 4009:9271 | 4009:9272 | 4009:9273 | 4009:9274 | 4009:9275 |
| 4010:9270 | 4010:9271 | 4010:9272 | 4010:9273 | 4010:9274 | 4010:9275 |
| 4011:9270 | 4011:9271 | 4011:9272 | 4011:9273 | 4011:9274 | 4011:9275 |
| 4012:9270 | 4012:9271 | 4012:9272 | 4012:9273 | 4012:9274 | 4012:9275 |
| 5001:9270 | 5001:9271 | 5001:9272 | 5001:9273 | 5001:9274 | 5001:9275 |
| 5002:9270 | 5002:9271 | 5002:9272 | 5002:9273 | 5002:9274 | 5002:9275 |
| 5003:9270 | 5003:9271 | 5003:9272 | 5003:9273 | 5003:9274 | 5003:9275 |
| 5004:9270 | 5004:9271 | 5004:9272 | 5004:9273 | 5004:9274 | 5004:9275 |
| 5005:9270 | 5005:9271 | 5005:9272 | 5005:9273 | 5005:9274 | 5005:9275 |
| 5006:9270 | 5006:9271 | 5006:9272 | 5006:9273 | 5006:9274 | 5006:9275 |
| 5007:9270 | 5007:9271 | 5007:9272 | 5007:9273 | 5007:9274 | 5007:9275 |
| 5008:9270 | 5008:9271 | 5008:9272 | 5008:9273 | 5008:9274 | 5008:9275 |
| 5009:9270 | 5009:9271 | 5009:9272 | 5009:9273 | 5009:9274 | 5009:9275 |
| 5010:9270 | 5010:9271 | 5010:9272 | 5010:9273 | 5010:9274 | 5010:9275 |
| 5011:9270 | 5011:9271 | 5011:9272 | 5011:9273 | 5011:9274 | 5011:9275 |
| 3002:9276 | 3002:9277 | 3002:9278 | 3002:9279 | 3002:9280 | 3002:9281 |
| 3003:9276 | 3003:9277 | 3003:9278 | 3003:9279 | 3003:9280 | 3003:9281 |
| 3004:9276 | 3004:9277 | 3004:9278 | 3004:9279 | 3004:9280 | 3004:9281 |
| 3005:9276 | 3005:9277 | 3005:9278 | 3005:9279 | 3005:9280 | 3005:9281 |
| 3006:9276 | 3006:9277 | 3006:9278 | 3006:9279 | 3006:9280 | 3006:9281 |
| 3007:9276 | 3007:9277 | 3007:9278 | 3007:9279 | 3007:9280 | 3007:9281 |
| 3008:9276 | 3008:9277 | 3008:9278 | 3008:9279 | 3008:9280 | 3008:9281 |
| 3009:9276 | 3009:9277 | 3009:9278 | 3009:9279 | 3009:9280 | 3009:9281 |
| 3010:9276 | 3010:9277 | 3010:9278 | 3010:9279 | 3010:9280 | 3010:9281 |
| 3011:9276 | 3011:9277 | 3011:9278 | 3011:9279 | 3011:9280 | 3011:9281 |
| 3012:9276 | 3012:9277 | 3012:9278 | 3012:9279 | 3012:9280 | 3012:9281 |
| 3013:9276 | 3013:9277 | 3013:9278 | 3013:9279 | 3013:9280 | 3013:9281 |
| 3014:9276 | 3014:9277 | 3014:9278 | 3014:9279 | 3014:9280 | 3014:9281 |
| 4001:9276 | 4001:9277 | 4001:9278 | 4001:9279 | 4001:9280 | 4001:9281 |
| 4002:9276 | 4002:9277 | 4002:9278 | 4002:9279 | 4002:9280 | 4002:9281 |
| 4003:9276 | 4003:9277 | 4003:9278 | 4003:9279 | 4003:9280 | 4003:9281 |
| 4004:9276 | 4004:9277 | 4004:9278 | 4004:9279 | 4004:9280 | 4004:9281 |
| 4005:9276 | 4005:9277 | 4005:9278 | 4005:9279 | 4005:9280 | 4005:9281 |
| 4006:9276 | 4006:9277 | 4006:9278 | 4006:9279 | 4006:9280 | 4006:9281 |
| 4007:9276 | 4007:9277 | 4007:9278 | 4007:9279 | 4007:9280 | 4007:9281 |
| 4008:9276 | 4008:9277 | 4008:9278 | 4008:9279 | 4008:9280 | 4008:9281 |
| 4009:9276 | 4009:9277 | 4009:9278 | 4009:9279 | 4009:9280 | 4009:9281 |
| 4010:9276 | 4010:9277 | 4010:9278 | 4010:9279 | 4010:9280 | 4010:9281 |
| 4011:9276 | 4011:9277 | 4011:9278 | 4011:9279 | 4011:9280 | 4011:9281 |
| 4012:9276 | 4012:9277 | 4012:9278 | 4012:9279 | 4012:9280 | 4012:9281 |
| 5001:9276 | 5001:9277 | 5001:9278 | 5001:9279 | 5001:9280 | 5001:9281 |
| 5002:9276 | 5002:9277 | 5002:9278 | 5002:9279 | 5002:9280 | 5002:9281 |
| 5003:9276 | 5003:9277 | 5003:9278 | 5003:9279 | 5003:9280 | 5003:9281 |
| 5004:9276 | 5004:9277 | 5004:9278 | 5004:9279 | 5004:9280 | 5004:9281 |
| 5005:9276 | 5005:9277 | 5005:9278 | 5005:9279 | 5005:9280 | 5005:9281 |
| 5006:9276 | 5006:9277 | 5006:9278 | 5006:9279 | 5006:9280 | 5006:9281 |
| 5007:9276 | 5007:9277 | 5007:9278 | 5007:9279 | 5007:9280 | 5007:9281 |
| 5008:9276 | 5008:9277 | 5008:9278 | 5008:9279 | 5008:9280 | 5008:9281 |
| 5009:9276 | 5009:9277 | 5009:9278 | 5009:9279 | 5009:9280 | 5009:9281 |
| 5010:9276 | 5010:9277 | 5010:9278 | 5010:9279 | 5010:9280 | 5010:9281 |
| 5011:9276 | 5011:9277 | 5011:9278 | 5011:9279 | 5011:9280 | 5011:9281 |
| 3002:9282 | 3002:9283 | 3002:9284 | 3002:9285 | 3002:9286 | 3002:9287 |
| 3003:9282 | 3003:9283 | 3003:9284 | 3003:9285 | 3003:9286 | 3003:9287 |
| 3004:9282 | 3004:9283 | 3004:9284 | 3004:9285 | 3004:9286 | 3004:9287 |
| 3005:9282 | 3005:9283 | 3005:9284 | 3005:9285 | 3005:9286 | 3005:9287 |
| 3006:9282 | 3006:9283 | 3006:9284 | 3006:9285 | 3006:9286 | 3006:9287 |
| 3007:9282 | 3007:9283 | 3007:9284 | 3007:9285 | 3007:9286 | 3007:9287 |
| 3008:9282 | 3008:9283 | 3008:9284 | 3008:9285 | 3008:9286 | 3008:9287 |
| 3009:9282 | 3009:9283 | 3009:9284 | 3009:9285 | 3009:9286 | 3009:9287 |
| 3010:9282 | 3010:9283 | 3010:9284 | 3010:9285 | 3010:9286 | 3010:9287 |
| 3011:9282 | 3011:9283 | 3011:9284 | 3011:9285 | 3011:9286 | 3011:9287 |
| 3012:9282 | 3012:9283 | 3012:9284 | 3012:9285 | 3012:9286 | 3012:9287 |
| 3013:9282 | 3013:9283 | 3013:9284 | 3013:9285 | 3013:9286 | 3013:9287 |
| 3014:9282 | 3014:9283 | 3014:9284 | 3014:9285 | 3014:9286 | 3014:9287 |
| 4001:9282 | 4001:9283 | 4001:9284 | 4001:9285 | 4001:9286 | 4001:9287 |
| 4002:9282 | 4002:9283 | 4002:9284 | 4002:9285 | 4002:9286 | 4002:9287 |
| 4003:9282 | 4003:9283 | 4003:9284 | 4003:9285 | 4003:9286 | 4003:9287 |
| 4004:9282 | 4004:9283 | 4004:9284 | 4004:9285 | 4004:9286 | 4004:9287 |
| 4005:9282 | 4005:9283 | 4005:9284 | 4005:9285 | 4005:9286 | 4005:9287 |
| 4006:9282 | 4006:9283 | 4006:9284 | 4006:9285 | 4006:9286 | 4006:9287 |
| 4007:9282 | 4007:9283 | 4007:9284 | 4007:9285 | 4007:9286 | 4007:9287 |
| 4008:9282 | 4008:9283 | 4008:9284 | 4008:9285 | 4008:9286 | 4008:9287 |
| 4009:9282 | 4009:9283 | 4009:9284 | 4009:9285 | 4009:9286 | 4009:9287 |
| 4010:9282 | 4010:9283 | 4010:9284 | 4010:9285 | 4010:9286 | 4010:9287 |
| 4011:9282 | 4011:9283 | 4011:9284 | 4011:9285 | 4011:9286 | 4011:9287 |
| 4012:9282 | 4012:9283 | 4012:9284 | 4012:9285 | 4012:9286 | 4012:9287 |
| 5001:9282 | 5001:9283 | 5001:9284 | 5001:9285 | 5001:9286 | 5001:9287 |
| 5002:9282 | 5002:9283 | 5002:9284 | 5002:9285 | 5002:9286 | 5002:9287 |
| 5003:9282 | 5003:9283 | 5003:9284 | 5003:9285 | 5003:9286 | 5003:9287 |
| 5004:9282 | 5004:9283 | 5004:9284 | 5004:9285 | 5004:9286 | 5004:9287 |
| 5005:9282 | 5005:9283 | 5005:9284 | 5005:9285 | 5005:9286 | 5005:9287 |
| 5006:9282 | 5006:9283 | 5006:9284 | 5006:9285 | 5006:9286 | 5006:9287 |
| 5007:9282 | 5007:9283 | 5007:9284 | 5007:9285 | 5007:9286 | 5007:9287 |
| 5008:9282 | 5008:9283 | 5008:9284 | 5008:9285 | 5008:9286 | 5008:9287 |
| 5009:9282 | 5009:9283 | 5009:9284 | 5009:9285 | 5009:9286 | 5009:9287 |
| 5010:9282 | 5010:9283 | 5010:9284 | 5010:9285 | 5010:9286 | 5010:9287 |
| 5011:9282 | 5011:9283 | 5011:9284 | 5011:9285 | 5011:9286 | 5011:9287 |
| 3002:9288 | 3002:9289 | 3002:9290 | 3002:9291 | 3002:9292 | 3002:9293 |
| 3003:9288 | 3003:9289 | 3003:9290 | 3003:9291 | 3003:9292 | 3003:9293 |
| 3004:9288 | 3004:9289 | 3004:9290 | 3004:9291 | 3004:9292 | 3004:9293 |
| 3005:9288 | 3005:9289 | 3005:9290 | 3005:9291 | 3005:9292 | 3005:9293 |
| 3006:9288 | 3006:9289 | 3006:9290 | 3006:9291 | 3006:9292 | 3006:9293 |
| 3007:9288 | 3007:9289 | 3007:9290 | 3007:9291 | 3007:9292 | 3007:9293 |
| 3008:9288 | 3008:9289 | 3008:9290 | 3008:9291 | 3008:9292 | 3008:9293 |
| 3009:9288 | 3009:9289 | 3009:9290 | 3009:9291 | 3009:9292 | 3009:9293 |
| 3010:9288 | 3010:9289 | 3010:9290 | 3010:9291 | 3010:9292 | 3010:9293 |
| 3011:9288 | 3011:9289 | 3011:9290 | 3011:9291 | 3011:9292 | 3011:9293 |
| 3012:9288 | 3012:9289 | 3012:9290 | 3012:9291 | 3012:9292 | 3012:9293 |
| 3013:9288 | 3013:9289 | 3013:9290 | 3013:9291 | 3013:9292 | 3013:9293 |
| 3014:9288 | 3014:9289 | 3014:9290 | 3014:9291 | 3014:9292 | 3014:9293 |
| 4001:9288 | 4001:9289 | 4001:9290 | 4001:9291 | 4001:9292 | 4001:9293 |
| 4002:9288 | 4002:9289 | 4002:9290 | 4002:9291 | 4002:9292 | 4002:9293 |
| 4003:9288 | 4003:9289 | 4003:9290 | 4003:9291 | 4003:9292 | 4003:9293 |
| 4004:9288 | 4004:9289 | 4004:9290 | 4004:9291 | 4004:9292 | 4004:9293 |

TABLE B-continued

Example combinations of a compound X with a compound Y.

| X:Y | X:Y | X:Y | X:Y | X:Y | X:Y |
|---|---|---|---|---|---|
| 4005:9288 | 4005:9289 | 4005:9290 | 4005:9291 | 4005:9292 | 4005:9293 |
| 4006:9288 | 4006:9289 | 4006:9290 | 4006:9291 | 4006:9292 | 4006:9293 |
| 4007:9288 | 4007:9289 | 4007:9290 | 4007:9291 | 4007:9292 | 4007:9293 |
| 4008:9288 | 4008:9289 | 4008:9290 | 4008:9291 | 4008:9292 | 4008:9293 |
| 4009:9288 | 4009:9289 | 4009:9290 | 4009:9291 | 4009:9292 | 4009:9293 |
| 4010:9288 | 4010:9289 | 4010:9290 | 4010:9291 | 4010:9292 | 4010:9293 |
| 4011:9288 | 4011:9289 | 4011:9290 | 4011:9291 | 4011:9292 | 4011:9293 |
| 4012:9288 | 4012:9289 | 4012:9290 | 4012:9291 | 4012:9292 | 4012:9293 |
| 5001:9288 | 5001:9289 | 5001:9290 | 5001:9291 | 5001:9292 | 5001:9293 |
| 5002:9288 | 5002:9289 | 5002:9290 | 5002:9291 | 5002:9292 | 5002:9293 |
| 5003:9288 | 5003:9289 | 5003:9290 | 5003:9291 | 5003:9292 | 5003:9293 |
| 5004:9288 | 5004:9289 | 5004:9290 | 5004:9291 | 5004:9292 | 5004:9293 |
| 5005:9288 | 5005:9289 | 5005:9290 | 5005:9291 | 5005:9292 | 5005:9293 |
| 5006:9288 | 5006:9289 | 5006:9290 | 5006:9291 | 5006:9292 | 5006:9293 |
| 5007:9288 | 5007:9289 | 5007:9290 | 5007:9291 | 5007:9292 | 5007:9293 |
| 5008:9288 | 5008:9289 | 5008:9290 | 5008:9291 | 5008:9292 | 5008:9293 |
| 5009:9288 | 5009:9289 | 5009:9290 | 5009:9291 | 5009:9292 | 5009:9293 |
| 5010:9288 | 5010:9289 | 5010:9290 | 5010:9291 | 5010:9292 | 5010:9293 |
| 5011:9288 | 5011:9289 | 5011:9290 | 5011:9291 | 5011:9292 | 5011:9293 |
| 3002:9294 | 3002:9295 | 3002:9296 | 3002:9297 | 3002:9298 | 3002:9299 |
| 3003:9294 | 3003:9295 | 3003:9296 | 3003:9297 | 3003:9298 | 3003:9299 |
| 3004:9294 | 3004:9295 | 3004:9296 | 3004:9297 | 3004:9298 | 3004:9299 |
| 3005:9294 | 3005:9295 | 3005:9296 | 3005:9297 | 3005:9298 | 3005:9299 |
| 3006:9294 | 3006:9295 | 3006:9296 | 3006:9297 | 3006:9298 | 3006:9299 |
| 3007:9294 | 3007:9295 | 3007:9296 | 3007:9297 | 3007:9298 | 3007:9299 |
| 3008:9294 | 3008:9295 | 3008:9296 | 3008:9297 | 3008:9298 | 3008:9299 |
| 3009:9294 | 3009:9295 | 3009:9296 | 3009:9297 | 3009:9298 | 3009:9299 |
| 3010:9294 | 3010:9295 | 3010:9296 | 3010:9297 | 3010:9298 | 3010:9299 |
| 3011:9294 | 3011:9295 | 3011:9296 | 3011:9297 | 3011:9298 | 3011:9299 |
| 3012:9294 | 3012:9295 | 3012:9296 | 3012:9297 | 3012:9298 | 3012:9299 |
| 3013:9294 | 3013:9295 | 3013:9296 | 3013:9297 | 3013:9298 | 3013:9299 |
| 3014:9294 | 3014:9295 | 3014:9296 | 3014:9297 | 3014:9298 | 3014:9299 |
| 4001:9294 | 4001:9295 | 4001:9296 | 4001:9297 | 4001:9298 | 4001:9299 |
| 4002:9294 | 4002:9295 | 4002:9296 | 4002:9297 | 4002:9298 | 4002:9299 |
| 4003:9294 | 4003:9295 | 4003:9296 | 4003:9297 | 4003:9298 | 4003:9299 |
| 4004:9294 | 4004:9295 | 4004:9296 | 4004:9297 | 4004:9298 | 4004:9299 |
| 4005:9294 | 4005:9295 | 4005:9296 | 4005:9297 | 4005:9298 | 4005:9299 |
| 4006:9294 | 4006:9295 | 4006:9296 | 4006:9297 | 4006:9298 | 4006:9299 |
| 4007:9294 | 4007:9295 | 4007:9296 | 4007:9297 | 4007:9298 | 4007:9299 |
| 4008:9294 | 4008:9295 | 4008:9296 | 4008:9297 | 4008:9298 | 4008:9299 |
| 4009:9294 | 4009:9295 | 4009:9296 | 4009:9297 | 4009:9298 | 4009:9299 |
| 4010:9294 | 4010:9295 | 4010:9296 | 4010:9297 | 4010:9298 | 4010:9299 |
| 4011:9294 | 4011:9295 | 4011:9296 | 4011:9297 | 4011:9298 | 4011:9299 |
| 4012:9294 | 4012:9295 | 4012:9296 | 4012:9297 | 4012:9298 | 4012:9299 |
| 5001:9294 | 5001:9295 | 5001:9296 | 5001:9297 | 5001:9298 | 5001:9299 |
| 5002:9294 | 5002:9295 | 5002:9296 | 5002:9297 | 5002:9298 | 5002:9299 |
| 5003:9294 | 5003:9295 | 5003:9296 | 5003:9297 | 5003:9298 | 5003:9299 |
| 5004:9294 | 5004:9295 | 5004:9296 | 5004:9297 | 5004:9298 | 5004:9299 |
| 5005:9294 | 5005:9295 | 5005:9296 | 5005:9297 | 5005:9298 | 5005:9299 |
| 5006:9294 | 5006:9295 | 5006:9296 | 5006:9297 | 5006:9298 | 5006:9299 |
| 5007:9294 | 5007:9295 | 5007:9296 | 5007:9297 | 5007:9298 | 5007:9299 |
| 5008:9294 | 5008:9295 | 5008:9296 | 5008:9297 | 5008:9298 | 5008:9299 |
| 5009:9294 | 5009:9295 | 5009:9296 | 5009:9297 | 5009:9298 | 5009:9299 |
| 5010:9294 | 5010:9295 | 5010:9296 | 5010:9297 | 5010:9298 | 5010:9299 |
| 5011:9294 | 5011:9295 | 5011:9296 | 5011:9297 | 5011:9298 | 5011:9299 |
| 3002:9300 | 3002:9301 | 3002:9302 | 3002:9303 | 3002:9304 | 3002:9305 |
| 3003:9300 | 3003:9301 | 3003:9302 | 3003:9303 | 3003:9304 | 3003:9305 |
| 3004:9300 | 3004:9301 | 3004:9302 | 3004:9303 | 3004:9304 | 3004:9305 |
| 3005:9300 | 3005:9301 | 3005:9302 | 3005:9303 | 3005:9304 | 3005:9305 |
| 3006:9300 | 3006:9301 | 3006:9302 | 3006:9303 | 3006:9304 | 3006:9305 |
| 3007:9300 | 3007:9301 | 3007:9302 | 3007:9303 | 3007:9304 | 3007:9305 |
| 3008:9300 | 3008:9301 | 3008:9302 | 3008:9303 | 3008:9304 | 3008:9305 |
| 3009:9300 | 3009:9301 | 3009:9302 | 3009:9303 | 3009:9304 | 3009:9305 |
| 3010:9300 | 3010:9301 | 3010:9302 | 3010:9303 | 3010:9304 | 3010:9305 |
| 3011:9300 | 3011:9301 | 3011:9302 | 3011:9303 | 3011:9304 | 3011:9305 |
| 3012:9300 | 3012:9301 | 3012:9302 | 3012:9303 | 3012:9304 | 3012:9305 |
| 3013:9300 | 3013:9301 | 3013:9302 | 3013:9303 | 3013:9304 | 3013:9305 |
| 3014:9300 | 3014:9301 | 3014:9302 | 3014:9303 | 3014:9304 | 3014:9305 |
| 4001:9300 | 4001:9301 | 4001:9302 | 4001:9303 | 4001:9304 | 4001:9305 |
| 4002:9300 | 4002:9301 | 4002:9302 | 4002:9303 | 4002:9304 | 4002:9305 |
| 4003:9300 | 4003:9301 | 4003:9302 | 4003:9303 | 4003:9304 | 4003:9305 |
| 4004:9300 | 4004:9301 | 4004:9302 | 4004:9303 | 4004:9304 | 4004:9305 |
| 4005:9300 | 4005:9301 | 4005:9302 | 4005:9303 | 4005:9304 | 4005:9305 |
| 4006:9300 | 4006:9301 | 4006:9302 | 4006:9303 | 4006:9304 | 4006:9305 |
| 4007:9300 | 4007:9301 | 4007:9302 | 4007:9303 | 4007:9304 | 4007:9305 |
| 4008:9300 | 4008:9301 | 4008:9302 | 4008:9303 | 4008:9304 | 4008:9305 |
| 4009:9300 | 4009:9301 | 4009:9302 | 4009:9303 | 4009:9304 | 4009:9305 |
| 4010:9300 | 4010:9301 | 4010:9302 | 4010:9303 | 4010:9304 | 4010:9305 |
| 4011:9300 | 4011:9301 | 4011:9302 | 4011:9303 | 4011:9304 | 4011:9305 |
| 4012:9300 | 4012:9301 | 4012:9302 | 4012:9303 | 4012:9304 | 4012:9305 |
| 5001:9300 | 5001:9301 | 5001:9302 | 5001:9303 | 5001:9304 | 5001:9305 |
| 5002:9300 | 5002:9301 | 5002:9302 | 5002:9303 | 5002:9304 | 5002:9305 |
| 5003:9300 | 5003:9301 | 5003:9302 | 5003:9303 | 5003:9304 | 5003:9305 |
| 5004:9300 | 5004:9301 | 5004:9302 | 5004:9303 | 5004:9304 | 5004:9305 |
| 5005:9300 | 5005:9301 | 5005:9302 | 5005:9303 | 5005:9304 | 5005:9305 |
| 5006:9300 | 5006:9301 | 5006:9302 | 5006:9303 | 5006:9304 | 5006:9305 |
| 5007:9300 | 5007:9301 | 5007:9302 | 5007:9303 | 5007:9304 | 5007:9305 |
| 5008:9300 | 5008:9301 | 5008:9302 | 5008:9303 | 5008:9304 | 5008:9305 |
| 5009:9300 | 5009:9301 | 5009:9302 | 5009:9303 | 5009:9304 | 5009:9305 |
| 5010:9300 | 5010:9301 | 5010:9302 | 5010:9303 | 5010:9304 | 5010:9305 |
| 5011:9300 | 5011:9301 | 5011:9302 | 5011:9303 | 5011:9304 | 5011:9305 |
| 3002:9306 | 3002:9307 | 3002:9308 | 3002:9309 | 3002:9310 | — |
| 3003:9306 | 3003:9307 | 3003:9308 | 3003:9309 | 3003:9310 | |
| 3004:9306 | 3004:9307 | 3004:9308 | 3004:9309 | 3004:9310 | |
| 3005:9306 | 3005:9307 | 3005:9308 | 3005:9309 | 3005:9310 | |
| 3006:9306 | 3006:9307 | 3006:9308 | 3006:9309 | 3006:9310 | |
| 3007:9306 | 3007:9307 | 3007:9308 | 3007:9309 | 3007:9310 | |
| 3008:9306 | 3008:9307 | 3008:9308 | 3008:9309 | 3008:9310 | |
| 3009:9306 | 3009:9307 | 3009:9308 | 3009:9309 | 3009:9310 | |
| 3010:9306 | 3010:9307 | 3010:9308 | 3010:9309 | 3010:9310 | |
| 3011:9306 | 3011:9307 | 3011:9308 | 3011:9309 | 3011:9310 | |
| 3012:9306 | 3012:9307 | 3012:9308 | 3012:9309 | 3012:9310 | |
| 3013:9306 | 3013:9307 | 3013:9308 | 3013:9309 | 3013:9310 | |
| 3014:9306 | 3014:9307 | 3014:9308 | 3014:9309 | 3014:9310 | |
| 4001:9306 | 4001:9307 | 4001:9308 | 4001:9309 | 4001:9310 | |
| 4002:9306 | 4002:9307 | 4002:9308 | 4002:9309 | 4002:9310 | |
| 4003:9306 | 4003:9307 | 4003:9308 | 4003:9309 | 4003:9310 | |
| 4004:9306 | 4004:9307 | 4004:9308 | 4004:9309 | 4004:9310 | |
| 4005:9306 | 4005:9307 | 4005:9308 | 4005:9309 | 4005:9310 | |
| 4006:9306 | 4006:9307 | 4006:9308 | 4006:9309 | 4006:9310 | |
| 4007:9306 | 4007:9307 | 4007:9308 | 4007:9309 | 4007:9310 | |
| 4008:9306 | 4008:9307 | 4008:9308 | 4008:9309 | 4008:9310 | |
| 4009:9306 | 4009:9307 | 4009:9308 | 4009:9309 | 4009:9310 | |
| 4010:9306 | 4010:9307 | 4010:9308 | 4010:9309 | 4010:9310 | |
| 4011:9306 | 4011:9307 | 4011:9308 | 4011:9309 | 4011:9310 | |
| 4012:9306 | 4012:9307 | 4012:9308 | 4012:9309 | 4012:9310 | |
| 5001:9306 | 5001:9307 | 5001:9308 | 5001:9309 | 5001:9310 | |
| 5002:9306 | 5002:9307 | 5002:9308 | 5002:9309 | 5002:9310 | |
| 5003:9306 | 5003:9307 | 5003:9308 | 5003:9309 | 5003:9310 | |
| 5004:9306 | 5004:9307 | 5004:9308 | 5004:9309 | 5004:9310 | |
| 5005:9306 | 5005:9307 | 5005:9308 | 5005:9309 | 5005:9310 | |
| 5006:9306 | 5006:9307 | 5006:9308 | 5006:9309 | 5006:9310 | |
| 5007:9306 | 5007:9307 | 5007:9308 | 5007:9309 | 5007:9310 | |
| 5008:9306 | 5008:9307 | 5008:9308 | 5008:9309 | 5008:9310 | |
| 5009:9306 | 5009:9307 | 5009:9308 | 5009:9309 | 5009:9310 | |
| 5010:9306 | 5010:9307 | 5010:9308 | 5010:9309 | 5010:9310 | |
| 5011:9306 | 5011:9307 | 5011:9308 | 5011:9309 | 5011:9310 | |

TABLE C

Example combinations of a compound X with a compound Y.

| X:Y | X:Y | X:Y | X:Y | X:Y | X:Y |
|---|---|---|---|---|---|
| 9006:7000 | 9007:7000 | 9008:7000 | 9018:7000 | 9020:7000 | 9021:7000 |
| 9006:7001 | 9007:7001 | 9008:7001 | 9018:7001 | 9020:7001 | 9021:7001 |
| 9006:7002 | 9007:7002 | 9008:7002 | 9018:7002 | 9020:7002 | 9021:7002 |
| 9006:7003 | 9007:7003 | 9008:7003 | 9018:7003 | 9020:7003 | 9021:7003 |
| 9006:7004 | 9007:7004 | 9008:7004 | 9018:7004 | 9020:7004 | 9021:7004 |
| 9006:7005 | 9007:7005 | 9008:7005 | 9018:7005 | 9020:7005 | 9021:7005 |
| 9006:7006 | 9007:7006 | 9008:7006 | 9018:7006 | 9020:7006 | 9021:7006 |
| 9006:7007 | 9007:7007 | 9008:7007 | 9018:7007 | 9020:7007 | 9021:7007 |
| 9006:7008 | 9007:7008 | 9008:7008 | 9018:7008 | 9020:7008 | 9021:7008 |
| 9006:7009 | 9007:7009 | 9008:7009 | 9018:7009 | 9020:7009 | 9021:7009 |
| 9006:7010 | 9007:7010 | 9008:7010 | 9018:7010 | 9020:7010 | 9021:7010 |
| 9006:7011 | 9007:7011 | 9008:7011 | 9018:7011 | 9020:7011 | 9021:7011 |
| 9006:7012 | 9007:7012 | 9008:7012 | 9018:7012 | 9020:7012 | 9021:7012 |
| 9006:7013 | 9007:7013 | 9008:7013 | 9018:7013 | 9020:7013 | 9021:7013 |
| 9006:7014 | 9007:7014 | 9008:7014 | 9018:7014 | 9020:7014 | 9021:7014 |

TABLE C-continued

Example combinations of a compound X with a compound Y.

| X:Y | X:Y | X:Y | X:Y | X:Y | X:Y |
|---|---|---|---|---|---|
| 9006:7015 | 9007:7015 | 9008:7015 | 9018:7015 | 9020:7015 | 9021:7015 |
| 9006:7016 | 9007:7016 | 9008:7016 | 9018:7016 | 9020:7016 | 9021:7016 |
| 9006:7017 | 9007:7017 | 9008:7017 | 9018:7017 | 9020:7017 | 9021:7017 |
| 9006:7018 | 9007:7018 | 9008:7018 | 9018:7018 | 9020:7018 | 9021:7018 |
| 9006:7019 | 9007:7019 | 9008:7019 | 9018:7019 | 9020:7019 | 9021:7019 |
| 9006:7020 | 9007:7020 | 9008:7020 | 9018:7020 | 9020:7020 | 9021:7020 |
| 9006:7021 | 9007:7021 | 9008:7021 | 9018:7021 | 9020:7021 | 9021:7021 |
| 9006:7022 | 9007:7022 | 9008:7022 | 9018:7022 | 9020:7022 | 9021:7022 |
| 9006:7023 | 9007:7023 | 9008:7023 | 9018:7023 | 9020:7023 | 9021:7023 |
| 9006:7024 | 9007:7024 | 9008:7024 | 9018:7024 | 9020:7024 | 9021:7024 |
| 9006:7025 | 9007:7025 | 9008:7025 | 9018:7025 | 9020:7025 | 9021:7025 |
| 9006:7026 | 9007:7026 | 9008:7026 | 9018:7026 | 9020:7026 | 9021:7026 |
| 9006:7027 | 9007:7027 | 9008:7027 | 9018:7027 | 9020:7027 | 9021:7027 |
| 9025:7000 | 9026:7000 | 9036:7000 | 9038:7000 | 9039:7000 | 9040:7000 |
| 9025:7001 | 9026:7001 | 9036:7001 | 9038:7001 | 9039:7001 | 9040:7001 |
| 9025:7002 | 9026:7002 | 9036:7002 | 9038:7002 | 9039:7002 | 9040:7002 |
| 9025:7003 | 9026:7003 | 9036:7003 | 9038:7003 | 9039:7003 | 9040:7003 |
| 9025:7004 | 9026:7004 | 9036:7004 | 9038:7004 | 9039:7004 | 9040:7004 |
| 9025:7005 | 9026:7005 | 9036:7005 | 9038:7005 | 9039:7005 | 9040:7005 |
| 9025:7006 | 9026:7006 | 9036:7006 | 9038:7006 | 9039:7006 | 9040:7006 |
| 9025:7007 | 9026:7007 | 9036:7007 | 9038:7007 | 9039:7007 | 9040:7007 |
| 9025:7008 | 9026:7008 | 9036:7008 | 9038:7008 | 9039:7008 | 9040:7008 |
| 9025:7009 | 9026:7009 | 9036:7009 | 9038:7009 | 9039:7009 | 9040:7009 |
| 9025:7010 | 9026:7010 | 9036:7010 | 9038:7010 | 9039:7010 | 9040:7010 |
| 9025:7011 | 9026:7011 | 9036:7011 | 9038:7011 | 9039:7011 | 9040:7011 |
| 9025:7012 | 9026:7012 | 9036:7012 | 9038:7012 | 9039:7012 | 9040:7012 |
| 9025:7013 | 9026:7013 | 9036:7013 | 9038:7013 | 9039:7013 | 9040:7013 |
| 9025:7014 | 9026:7014 | 9036:7014 | 9038:7014 | 9039:7014 | 9040:7014 |
| 9025:7015 | 9026:7015 | 9036:7015 | 9038:7015 | 9039:7015 | 9040:7015 |
| 9025:7016 | 9026:7016 | 9036:7016 | 9038:7016 | 9039:7016 | 9040:7016 |
| 9025:7017 | 9026:7017 | 9036:7017 | 9038:7017 | 9039:7017 | 9040:7017 |
| 9025:7018 | 9026:7018 | 9036:7018 | 9038:7018 | 9039:7018 | 9040:7018 |
| 9025:7019 | 9026:7019 | 9036:7019 | 9038:7019 | 9039:7019 | 9040:7019 |
| 9025:7020 | 9026:7020 | 9036:7020 | 9038:7020 | 9039:7020 | 9040:7020 |
| 9025:7021 | 9026:7021 | 9036:7021 | 9038:7021 | 9039:7021 | 9040:7021 |
| 9025:7022 | 9026:7022 | 9036:7022 | 9038:7022 | 9039:7022 | 9040:7022 |
| 9025:7023 | 9026:7023 | 9036:7023 | 9038:7023 | 9039:7023 | 9040:7023 |
| 9025:7024 | 9026:7024 | 9036:7024 | 9038:7024 | 9039:7024 | 9040:7024 |
| 9025:7025 | 9026:7025 | 9036:7025 | 9038:7025 | 9039:7025 | 9040:7025 |
| 9025:7026 | 9026:7026 | 9036:7026 | 9038:7026 | 9039:7026 | 9040:7026 |
| 9025:7027 | 9026:7027 | 9036:7027 | 9038:7027 | 9039:7027 | 9040:7027 |
| 9041:7000 | 9042:7000 | 9043:7000 | 9044:7000 | 9045:7000 | 9047:7000 |
| 9041:7001 | 9042:7001 | 9043:7001 | 9044:7001 | 9045:7001 | 9047:7001 |
| 9041:7002 | 9042:7002 | 9043:7002 | 9044:7002 | 9045:7002 | 9047:7002 |
| 9041:7003 | 9042:7003 | 9043:7003 | 9044:7003 | 9045:7003 | 9047:7003 |
| 9041:7004 | 9042:7004 | 9043:7004 | 9044:7004 | 9045:7004 | 9047:7004 |
| 9041:7005 | 9042:7005 | 9043:7005 | 9044:7005 | 9045:7005 | 9047:7005 |
| 9041:7006 | 9042:7006 | 9043:7006 | 9044:7006 | 9045:7006 | 9047:7006 |
| 9041:7007 | 9042:7007 | 9043:7007 | 9044:7007 | 9045:7007 | 9047:7007 |
| 9041:7008 | 9042:7008 | 9043:7008 | 9044:7008 | 9045:7008 | 9047:7008 |
| 9041:7009 | 9042:7009 | 9043:7009 | 9044:7009 | 9045:7009 | 9047:7009 |
| 9041:7010 | 9042:7010 | 9043:7010 | 9044:7010 | 9045:7010 | 9047:7010 |
| 9041:7011 | 9042:7011 | 9043:7011 | 9044:7011 | 9045:7011 | 9047:7011 |
| 9041:7012 | 9042:7012 | 9043:7012 | 9044:7012 | 9045:7012 | 9047:7012 |
| 9041:7013 | 9042:7013 | 9043:7013 | 9044:7013 | 9045:7013 | 9047:7013 |
| 9041:7014 | 9042:7014 | 9043:7014 | 9044:7014 | 9045:7014 | 9047:7014 |
| 9041:7015 | 9042:7015 | 9043:7015 | 9044:7015 | 9045:7015 | 9047:7015 |
| 9041:7016 | 9042:7016 | 9043:7016 | 9044:7016 | 9045:7016 | 9047:7016 |
| 9041:7017 | 9042:7017 | 9043:7017 | 9044:7017 | 9045:7017 | 9047:7017 |
| 9041:7018 | 9042:7018 | 9043:7018 | 9044:7018 | 9045:7018 | 9047:7018 |
| 9041:7019 | 9042:7019 | 9043:7019 | 9044:7019 | 9045:7019 | 9047:7019 |
| 9041:7020 | 9042:7020 | 9043:7020 | 9044:7020 | 9045:7020 | 9047:7020 |
| 9041:7021 | 9042:7021 | 9043:7021 | 9044:7021 | 9045:7021 | 9047:7021 |
| 9041:7022 | 9042:7022 | 9043:7022 | 9044:7022 | 9045:7022 | 9047:7022 |
| 9041:7023 | 9042:7023 | 9043:7023 | 9044:7023 | 9045:7023 | 9047:7023 |
| 9041:7024 | 9042:7024 | 9043:7024 | 9044:7024 | 9045:7024 | 9047:7024 |
| 9041:7025 | 9042:7025 | 9043:7025 | 9044:7025 | 9045:7025 | 9047:7025 |
| 9041:7026 | 9042:7026 | 9043:7026 | 9044:7026 | 9045:7026 | 9047:7026 |
| 9041:7027 | 9042:7027 | 9043:7027 | 9044:7027 | 9045:7027 | 9047:7027 |
| 9048:7000 | 9049:7000 | 9051:7000 | 9052:7000 | 9053:7000 | 9054:7000 |
| 9048:7001 | 9049:7001 | 9051:7001 | 9052:7001 | 9053:7001 | 9054:7001 |
| 9048:7002 | 9049:7002 | 9051:7002 | 9052:7002 | 9053:7002 | 9054:7002 |
| 9048:7003 | 9049:7003 | 9051:7003 | 9052:7003 | 9053:7003 | 9054:7003 |
| 9048:7004 | 9049:7004 | 9051:7004 | 9052:7004 | 9053:7004 | 9054:7004 |
| 9048:7005 | 9049:7005 | 9051:7005 | 9052:7005 | 9053:7005 | 9054:7005 |
| 9048:7006 | 9049:7006 | 9051:7006 | 9052:7006 | 9053:7006 | 9054:7006 |
| 9048:7007 | 9049:7007 | 9051:7007 | 9052:7007 | 9053:7007 | 9054:7007 |
| 9048:7008 | 9049:7008 | 9051:7008 | 9052:7008 | 9053:7008 | 9054:7008 |
| 9048:7009 | 9049:7009 | 9051:7009 | 9052:7009 | 9053:7009 | 9054:7009 |
| 9048:7010 | 9049:7010 | 9051:7010 | 9052:7010 | 9053:7010 | 9054:7010 |
| 9048:7011 | 9049:7011 | 9051:7011 | 9052:7011 | 9053:7011 | 9054:7011 |
| 9048:7012 | 9049:7012 | 9051:7012 | 9052:7012 | 9053:7012 | 9054:7012 |
| 9048:7013 | 9049:7013 | 9051:7013 | 9052:7013 | 9053:7013 | 9054:7013 |
| 9048:7014 | 9049:7014 | 9051:7014 | 9052:7014 | 9053:7014 | 9054:7014 |
| 9048:7015 | 9049:7015 | 9051:7015 | 9052:7015 | 9053:7015 | 9054:7015 |
| 9048:7016 | 9049:7016 | 9051:7016 | 9052:7016 | 9053:7016 | 9054:7016 |
| 9048:7017 | 9049:7017 | 9051:7017 | 9052:7017 | 9053:7017 | 9054:7017 |
| 9048:7018 | 9049:7018 | 9051:7018 | 9052:7018 | 9053:7018 | 9054:7018 |
| 9048:7019 | 9049:7019 | 9051:7019 | 9052:7019 | 9053:7019 | 9054:7019 |
| 9048:7020 | 9049:7020 | 9051:7020 | 9052:7020 | 9053:7020 | 9054:7020 |
| 9048:7021 | 9049:7021 | 9051:7021 | 9052:7021 | 9053:7021 | 9054:7021 |
| 9048:7022 | 9049:7022 | 9051:7022 | 9052:7022 | 9053:7022 | 9054:7022 |
| 9048:7023 | 9049:7023 | 9051:7023 | 9052:7023 | 9053:7023 | 9054:7023 |
| 9048:7024 | 9049:7024 | 9051:7024 | 9052:7024 | 9053:7024 | 9054:7024 |
| 9048:7025 | 9049:7025 | 9051:7025 | 9052:7025 | 9053:7025 | 9054:7025 |
| 9048:7026 | 9049:7026 | 9051:7026 | 9052:7026 | 9053:7026 | 9054:7026 |
| 9048:7027 | 9049:7027 | 9051:7027 | 9052:7027 | 9053:7027 | 9054:7027 |
| 9055:7000 | 9056:7000 | 9058:7000 | 9060:7000 | 9061:7000 | 9062:7000 |
| 9055:7001 | 9056:7001 | 9058:7001 | 9060:7001 | 9061:7001 | 9062:7001 |
| 9055:7002 | 9056:7002 | 9058:7002 | 9060:7002 | 9061:7002 | 9062:7002 |
| 9055:7003 | 9056:7003 | 9058:7003 | 9060:7003 | 9061:7003 | 9062:7003 |
| 9055:7004 | 9056:7004 | 9058:7004 | 9060:7004 | 9061:7004 | 9062:7004 |
| 9055:7005 | 9056:7005 | 9058:7005 | 9060:7005 | 9061:7005 | 9062:7005 |
| 9055:7006 | 9056:7006 | 9058:7006 | 9060:7006 | 9061:7006 | 9062:7006 |
| 9055:7007 | 9056:7007 | 9058:7007 | 9060:7007 | 9061:7007 | 9062:7007 |
| 9055:7008 | 9056:7008 | 9058:7008 | 9060:7008 | 9061:7008 | 9062:7008 |
| 9055:7009 | 9056:7009 | 9058:7009 | 9060:7009 | 9061:7009 | 9062:7009 |
| 9055:7010 | 9056:7010 | 9058:7010 | 9060:7010 | 9061:7010 | 9062:7010 |
| 9055:7011 | 9056:7011 | 9058:7011 | 9060:7011 | 9061:7011 | 9062:7011 |
| 9055:7012 | 9056:7012 | 9058:7012 | 9060:7012 | 9061:7012 | 9062:7012 |
| 9055:7013 | 9056:7013 | 9058:7013 | 9060:7013 | 9061:7013 | 9062:7013 |
| 9055:7014 | 9056:7014 | 9058:7014 | 9060:7014 | 9061:7014 | 9062:7014 |
| 9055:7015 | 9056:7015 | 9058:7015 | 9060:7015 | 9061:7015 | 9062:7015 |
| 9055:7016 | 9056:7016 | 9058:7016 | 9060:7016 | 9061:7016 | 9062:7016 |
| 9055:7017 | 9056:7017 | 9058:7017 | 9060:7017 | 9061:7017 | 9062:7017 |
| 9055:7018 | 9056:7018 | 9058:7018 | 9060:7018 | 9061:7018 | 9062:7018 |
| 9055:7019 | 9056:7019 | 9058:7019 | 9060:7019 | 9061:7019 | 9062:7019 |
| 9055:7020 | 9056:7020 | 9058:7020 | 9060:7020 | 9061:7020 | 9062:7020 |
| 9055:7021 | 9056:7021 | 9058:7021 | 9060:7021 | 9061:7021 | 9062:7021 |
| 9055:7022 | 9056:7022 | 9058:7022 | 9060:7022 | 9061:7022 | 9062:7022 |
| 9055:7023 | 9056:7023 | 9058:7023 | 9060:7023 | 9061:7023 | 9062:7023 |
| 9055:7024 | 9056:7024 | 9058:7024 | 9060:7024 | 9061:7024 | 9062:7024 |
| 9055:7025 | 9056:7025 | 9058:7025 | 9060:7025 | 9061:7025 | 9062:7025 |
| 9055:7026 | 9056:7026 | 9058:7026 | 9060:7026 | 9061:7026 | 9062:7026 |
| 9055:7027 | 9056:7027 | 9058:7027 | 9060:7027 | 9061:7027 | 9062:7027 |
| 9063:7000 | 9064:7000 | 9065:7000 | 9066:7000 | 9067:7000 | 9068:7000 |
| 9063:7001 | 9064:7001 | 9065:7001 | 9066:7001 | 9067:7001 | 9068:7001 |
| 9063:7002 | 9064:7002 | 9065:7002 | 9066:7002 | 9067:7002 | 9068:7002 |
| 9063:7003 | 9064:7003 | 9065:7003 | 9066:7003 | 9067:7003 | 9068:7003 |
| 9063:7004 | 9064:7004 | 9065:7004 | 9066:7004 | 9067:7004 | 9068:7004 |
| 9063:7005 | 9064:7005 | 9065:7005 | 9066:7005 | 9067:7005 | 9068:7005 |
| 9063:7006 | 9064:7006 | 9065:7006 | 9066:7006 | 9067:7006 | 9068:7006 |
| 9063:7007 | 9064:7007 | 9065:7007 | 9066:7007 | 9067:7007 | 9068:7007 |
| 9063:7008 | 9064:7008 | 9065:7008 | 9066:7008 | 9067:7008 | 9068:7008 |
| 9063:7009 | 9064:7009 | 9065:7009 | 9066:7009 | 9067:7009 | 9068:7009 |
| 9063:7010 | 9064:7010 | 9065:7010 | 9066:7010 | 9067:7010 | 9068:7010 |
| 9063:7011 | 9064:7011 | 9065:7011 | 9066:7011 | 9067:7011 | 9068:7011 |
| 9063:7012 | 9064:7012 | 9065:7012 | 9066:7012 | 9067:7012 | 9068:7012 |
| 9063:7013 | 9064:7013 | 9065:7013 | 9066:7013 | 9067:7013 | 9068:7013 |
| 9063:7014 | 9064:7014 | 9065:7014 | 9066:7014 | 9067:7014 | 9068:7014 |
| 9063:7015 | 9064:7015 | 9065:7015 | 9066:7015 | 9067:7015 | 9068:7015 |
| 9063:7016 | 9064:7016 | 9065:7016 | 9066:7016 | 9067:7016 | 9068:7016 |
| 9063:7017 | 9064:7017 | 9065:7017 | 9066:7017 | 9067:7017 | 9068:7017 |
| 9063:7018 | 9064:7018 | 9065:7018 | 9066:7018 | 9067:7018 | 9068:7018 |
| 9063:7019 | 9064:7019 | 9065:7019 | 9066:7019 | 9067:7019 | 9068:7019 |
| 9063:7020 | 9064:7020 | 9065:7020 | 9066:7020 | 9067:7020 | 9068:7020 |
| 9063:7021 | 9064:7021 | 9065:7021 | 9066:7021 | 9067:7021 | 9068:7021 |
| 9063:7022 | 9064:7022 | 9065:7022 | 9066:7022 | 9067:7022 | 9068:7022 |
| 9063:7023 | 9064:7023 | 9065:7023 | 9066:7023 | 9067:7023 | 9068:7023 |
| 9063:7024 | 9064:7024 | 9065:7024 | 9066:7024 | 9067:7024 | 9068:7024 |
| 9063:7025 | 9064:7025 | 9065:7025 | 9066:7025 | 9067:7025 | 9068:7025 |
| 9063:7026 | 9064:7026 | 9065:7026 | 9066:7026 | 9067:7026 | 9068:7026 |

TABLE C-continued

Example combinations of a compound X with a compound Y.

| X:Y | X:Y | X:Y | X:Y | X:Y | X:Y |
|---|---|---|---|---|---|
| 9063:7027 | 9064:7027 | 9065:7027 | 9066:7027 | 9067:7027 | 9068:7027 |
| 9069:7000 | 9070:7000 | 9071:7000 | 9072:7000 | 9073:7000 | 9074:7000 |
| 9069:7001 | 9070:7001 | 9071:7001 | 9072:7001 | 9073:7001 | 9074:7001 |
| 9069:7002 | 9070:7002 | 9071:7002 | 9072:7002 | 9073:7002 | 9074:7002 |
| 9069:7003 | 9070:7003 | 9071:7003 | 9072:7003 | 9073:7003 | 9074:7003 |
| 9069:7004 | 9070:7004 | 9071:7004 | 9072:7004 | 9073:7004 | 9074:7004 |
| 9069:7005 | 9070:7005 | 9071:7005 | 9072:7005 | 9073:7005 | 9074:7005 |
| 9069:7006 | 9070:7006 | 9071:7006 | 9072:7006 | 9073:7006 | 9074:7006 |
| 9069:7007 | 9070:7007 | 9071:7007 | 9072:7007 | 9073:7007 | 9074:7007 |
| 9069:7008 | 9070:7008 | 9071:7008 | 9072:7008 | 9073:7008 | 9074:7008 |
| 9069:7009 | 9070:7009 | 9071:7009 | 9072:7009 | 9073:7009 | 9074:7009 |
| 9069:7010 | 9070:7010 | 9071:7010 | 9072:7010 | 9073:7010 | 9074:7010 |
| 9069:7011 | 9070:7011 | 9071:7011 | 9072:7011 | 9073:7011 | 9074:7011 |
| 9069:7012 | 9070:7012 | 9071:7012 | 9072:7012 | 9073:7012 | 9074:7012 |
| 9069:7013 | 9070:7013 | 9071:7013 | 9072:7013 | 9073:7013 | 9074:7013 |
| 9069:7014 | 9070:7014 | 9071:7014 | 9072:7014 | 9073:7014 | 9074:7014 |
| 9069:7015 | 9070:7015 | 9071:7015 | 9072:7015 | 9073:7015 | 9074:7015 |
| 9069:7016 | 9070:7016 | 9071:7016 | 9072:7016 | 9073:7016 | 9074:7016 |
| 9069:7017 | 9070:7017 | 9071:7017 | 9072:7017 | 9073:7017 | 9074:7017 |
| 9069:7018 | 9070:7018 | 9071:7018 | 9072:7018 | 9073:7018 | 9074:7018 |
| 9069:7019 | 9070:7019 | 9071:7019 | 9072:7019 | 9073:7019 | 9074:7019 |
| 9069:7020 | 9070:7020 | 9071:7020 | 9072:7020 | 9073:7020 | 9074:7020 |
| 9069:7021 | 9070:7021 | 9071:7021 | 9072:7021 | 9073:7021 | 9074:7021 |
| 9069:7022 | 9070:7022 | 9071:7022 | 9072:7022 | 9073:7022 | 9074:7022 |
| 9069:7023 | 9070:7023 | 9071:7023 | 9072:7023 | 9073:7023 | 9074:7023 |
| 9069:7024 | 9070:7024 | 9071:7024 | 9072:7024 | 9073:7024 | 9074:7024 |
| 9069:7025 | 9070:7025 | 9071:7025 | 9072:7025 | 9073:7025 | 9074:7025 |
| 9069:7026 | 9070:7026 | 9071:7026 | 9072:7026 | 9073:7026 | 9074:7026 |
| 9069:7027 | 9070:7027 | 9071:7027 | 9072:7027 | 9073:7027 | 9074:7027 |
| 9075:7000 | 9076:7000 | 9077:7000 | 9078:7000 | 9079:7000 | 9080:7000 |
| 9075:7001 | 9076:7001 | 9077:7001 | 9078:7001 | 9079:7001 | 9080:7001 |
| 9075:7002 | 9076:7002 | 9077:7002 | 9078:7002 | 9079:7002 | 9080:7002 |
| 9075:7003 | 9076:7003 | 9077:7003 | 9078:7003 | 9079:7003 | 9080:7003 |
| 9075:7004 | 9076:7004 | 9077:7004 | 9078:7004 | 9079:7004 | 9080:7004 |
| 9075:7005 | 9076:7005 | 9077:7005 | 9078:7005 | 9079:7005 | 9080:7005 |
| 9075:7006 | 9076:7006 | 9077:7006 | 9078:7006 | 9079:7006 | 9080:7006 |
| 9075:7007 | 9076:7007 | 9077:7007 | 9078:7007 | 9079:7007 | 9080:7007 |
| 9075:7008 | 9076:7008 | 9077:7008 | 9078:7008 | 9079:7008 | 9080:7008 |
| 9075:7009 | 9076:7009 | 9077:7009 | 9078:7009 | 9079:7009 | 9080:7009 |
| 9075:7010 | 9076:7010 | 9077:7010 | 9078:7010 | 9079:7010 | 9080:7010 |
| 9075:7011 | 9076:7011 | 9077:7011 | 9078:7011 | 9079:7011 | 9080:7011 |
| 9075:7012 | 9076:7012 | 9077:7012 | 9078:7012 | 9079:7012 | 9080:7012 |
| 9075:7013 | 9076:7013 | 9077:7013 | 9078:7013 | 9079:7013 | 9080:7013 |
| 9075:7014 | 9076:7014 | 9077:7014 | 9078:7014 | 9079:7014 | 9080:7014 |
| 9075:7015 | 9076:7015 | 9077:7015 | 9078:7015 | 9079:7015 | 9080:7015 |
| 9075:7016 | 9076:7016 | 9077:7016 | 9078:7016 | 9079:7016 | 9080:7016 |
| 9075:7017 | 9076:7017 | 9077:7017 | 9078:7017 | 9079:7017 | 9080:7017 |
| 9075:7018 | 9076:7018 | 9077:7018 | 9078:7018 | 9079:7018 | 9080:7018 |
| 9075:7019 | 9076:7019 | 9077:7019 | 9078:7019 | 9079:7019 | 9080:7019 |
| 9075:7020 | 9076:7020 | 9077:7020 | 9078:7020 | 9079:7020 | 9080:7020 |
| 9075:7021 | 9076:7021 | 9077:7021 | 9078:7021 | 9079:7021 | 9080:7021 |
| 9075:7022 | 9076:7022 | 9077:7022 | 9078:7022 | 9079:7022 | 9080:7022 |
| 9075:7023 | 9076:7023 | 9077:7023 | 9078:7023 | 9079:7023 | 9080:7023 |
| 9075:7024 | 9076:7024 | 9077:7024 | 9078:7024 | 9079:7024 | 9080:7024 |
| 9075:7025 | 9076:7025 | 9077:7025 | 9078:7025 | 9079:7025 | 9080:7025 |
| 9075:7026 | 9076:7026 | 9077:7026 | 9078:7026 | 9079:7026 | 9080:7026 |
| 9075:7027 | 9076:7027 | 9077:7027 | 9078:7027 | 9079:7027 | 9080:7027 |
| 9081:7000 | 9082:7000 | 9083:7000 | 9084:7000 | 9085:7000 | 9086:7000 |
| 9081:7001 | 9082:7001 | 9083:7001 | 9084:7001 | 9085:7001 | 9086:7001 |
| 9081:7002 | 9082:7002 | 9083:7002 | 9084:7002 | 9085:7002 | 9086:7002 |
| 9081:7003 | 9082:7003 | 9083:7003 | 9084:7003 | 9085:7003 | 9086:7003 |
| 9081:7004 | 9082:7004 | 9083:7004 | 9084:7004 | 9085:7004 | 9086:7004 |
| 9081:7005 | 9082:7005 | 9083:7005 | 9084:7005 | 9085:7005 | 9086:7005 |
| 9081:7006 | 9082:7006 | 9083:7006 | 9084:7006 | 9085:7006 | 9086:7006 |
| 9081:7007 | 9082:7007 | 9083:7007 | 9084:7007 | 9085:7007 | 9086:7007 |
| 9081:7008 | 9082:7008 | 9083:7008 | 9084:7008 | 9085:7008 | 9086:7008 |
| 9081:7009 | 9082:7009 | 9083:7009 | 9084:7009 | 9085:7009 | 9086:7009 |
| 9081:7010 | 9082:7010 | 9083:7010 | 9084:7010 | 9085:7010 | 9086:7010 |
| 9081:7011 | 9082:7011 | 9083:7011 | 9084:7011 | 9085:7011 | 9086:7011 |
| 9081:7012 | 9082:7012 | 9083:7012 | 9084:7012 | 9085:7012 | 9086:7012 |
| 9081:7013 | 9082:7013 | 9083:7013 | 9084:7013 | 9085:7013 | 9086:7013 |
| 9081:7014 | 9082:7014 | 9083:7014 | 9084:7014 | 9085:7014 | 9086:7014 |
| 9081:7015 | 9082:7015 | 9083:7015 | 9084:7015 | 9085:7015 | 9086:7015 |
| 9081:7016 | 9082:7016 | 9083:7016 | 9084:7016 | 9085:7016 | 9086:7016 |
| 9081:7017 | 9082:7017 | 9083:7017 | 9084:7017 | 9085:7017 | 9086:7017 |
| 9081:7018 | 9082:7018 | 9083:7018 | 9084:7018 | 9085:7018 | 9086:7018 |
| 9081:7019 | 9082:7019 | 9083:7019 | 9084:7019 | 9085:7019 | 9086:7019 |
| 9081:7020 | 9082:7020 | 9083:7020 | 9084:7020 | 9085:7020 | 9086:7020 |
| 9081:7021 | 9082:7021 | 9083:7021 | 9084:7021 | 9085:7021 | 9086:7021 |
| 9081:7022 | 9082:7022 | 9083:7022 | 9084:7022 | 9085:7022 | 9086:7022 |
| 9081:7023 | 9082:7023 | 9083:7023 | 9084:7023 | 9085:7023 | 9086:7023 |
| 9081:7024 | 9082:7024 | 9083:7024 | 9084:7024 | 9085:7024 | 9086:7024 |
| 9081:7025 | 9082:7025 | 9083:7025 | 9084:7025 | 9085:7025 | 9086:7025 |
| 9081:7026 | 9082:7026 | 9083:7026 | 9084:7026 | 9085:7026 | 9086:7026 |
| 9081:7027 | 9082:7027 | 9083:7027 | 9084:7027 | 9085:7027 | 9086:7027 |
| 9088:7000 | 9089:7000 | 9094:7000 | 9095:7000 | 9096:7000 | 9097:7000 |
| 9088:7001 | 9089:7001 | 9094:7001 | 9095:7001 | 9096:7001 | 9097:7001 |
| 9088:7002 | 9089:7002 | 9094:7002 | 9095:7002 | 9096:7002 | 9097:7002 |
| 9088:7003 | 9089:7003 | 9094:7003 | 9095:7003 | 9096:7003 | 9097:7003 |
| 9088:7004 | 9089:7004 | 9094:7004 | 9095:7004 | 9096:7004 | 9097:7004 |
| 9088:7005 | 9089:7005 | 9094:7005 | 9095:7005 | 9096:7005 | 9097:7005 |
| 9088:7006 | 9089:7006 | 9094:7006 | 9095:7006 | 9096:7006 | 9097:7006 |
| 9088:7007 | 9089:7007 | 9094:7007 | 9095:7007 | 9096:7007 | 9097:7007 |
| 9088:7008 | 9089:7008 | 9094:7008 | 9095:7008 | 9096:7008 | 9097:7008 |
| 9088:7009 | 9089:7009 | 9094:7009 | 9095:7009 | 9096:7009 | 9097:7009 |
| 9088:7010 | 9089:7010 | 9094:7010 | 9095:7010 | 9096:7010 | 9097:7010 |
| 9088:7011 | 9089:7011 | 9094:7011 | 9095:7011 | 9096:7011 | 9097:7011 |
| 9088:7012 | 9089:7012 | 9094:7012 | 9095:7012 | 9096:7012 | 9097:7012 |
| 9088:7013 | 9089:7013 | 9094:7013 | 9095:7013 | 9096:7013 | 9097:7013 |
| 9088:7014 | 9089:7014 | 9094:7014 | 9095:7014 | 9096:7014 | 9097:7014 |
| 9088:7015 | 9089:7015 | 9094:7015 | 9095:7015 | 9096:7015 | 9097:7015 |
| 9088:7016 | 9089:7016 | 9094:7016 | 9095:7016 | 9096:7016 | 9097:7016 |
| 9088:7017 | 9089:7017 | 9094:7017 | 9095:7017 | 9096:7017 | 9097:7017 |
| 9088:7018 | 9089:7018 | 9094:7018 | 9095:7018 | 9096:7018 | 9097:7018 |
| 9088:7019 | 9089:7019 | 9094:7019 | 9095:7019 | 9096:7019 | 9097:7019 |
| 9088:7020 | 9089:7020 | 9094:7020 | 9095:7020 | 9096:7020 | 9097:7020 |
| 9088:7021 | 9089:7021 | 9094:7021 | 9095:7021 | 9096:7021 | 9097:7021 |
| 9088:7022 | 9089:7022 | 9094:7022 | 9095:7022 | 9096:7022 | 9097:7022 |
| 9088:7023 | 9089:7023 | 9094:7023 | 9095:7023 | 9096:7023 | 9097:7023 |
| 9088:7024 | 9089:7024 | 9094:7024 | 9095:7024 | 9096:7024 | 9097:7024 |
| 9088:7025 | 9089:7025 | 9094:7025 | 9095:7025 | 9096:7025 | 9097:7025 |
| 9088:7026 | 9089:7026 | 9094:7026 | 9095:7026 | 9096:7026 | 9097:7026 |
| 9088:7027 | 9089:7027 | 9094:7027 | 9095:7027 | 9096:7027 | 9097:7027 |
| 9098:7000 | 9099:7000 | 9100:7000 | 9101:7000 | 9102:7000 | 9103:7000 |
| 9098:7001 | 9099:7001 | 9100:7001 | 9101:7001 | 9102:7001 | 9103:7001 |
| 9098:7002 | 9099:7002 | 9100:7002 | 9101:7002 | 9102:7002 | 9103:7002 |
| 9098:7003 | 9099:7003 | 9100:7003 | 9101:7003 | 9102:7003 | 9103:7003 |
| 9098:7004 | 9099:7004 | 9100:7004 | 9101:7004 | 9102:7004 | 9103:7004 |
| 9098:7005 | 9099:7005 | 9100:7005 | 9101:7005 | 9102:7005 | 9103:7005 |
| 9098:7006 | 9099:7006 | 9100:7006 | 9101:7006 | 9102:7006 | 9103:7006 |
| 9098:7007 | 9099:7007 | 9100:7007 | 9101:7007 | 9102:7007 | 9103:7007 |
| 9098:7008 | 9099:7008 | 9100:7008 | 9101:7008 | 9102:7008 | 9103:7008 |
| 9098:7009 | 9099:7009 | 9100:7009 | 9101:7009 | 9102:7009 | 9103:7009 |
| 9098:7010 | 9099:7010 | 9100:7010 | 9101:7010 | 9102:7010 | 9103:7010 |
| 9098:7011 | 9099:7011 | 9100:7011 | 9101:7011 | 9102:7011 | 9103:7011 |
| 9098:7012 | 9099:7012 | 9100:7012 | 9101:7012 | 9102:7012 | 9103:7012 |
| 9098:7013 | 9099:7013 | 9100:7013 | 9101:7013 | 9102:7013 | 9103:7013 |
| 9098:7014 | 9099:7014 | 9100:7014 | 9101:7014 | 9102:7014 | 9103:7014 |
| 9098:7015 | 9099:7015 | 9100:7015 | 9101:7015 | 9102:7015 | 9103:7015 |
| 9098:7016 | 9099:7016 | 9100:7016 | 9101:7016 | 9102:7016 | 9103:7016 |
| 9098:7017 | 9099:7017 | 9100:7017 | 9101:7017 | 9102:7017 | 9103:7017 |
| 9098:7018 | 9099:7018 | 9100:7018 | 9101:7018 | 9102:7018 | 9103:7018 |
| 9098:7019 | 9099:7019 | 9100:7019 | 9101:7019 | 9102:7019 | 9103:7019 |
| 9098:7020 | 9099:7020 | 9100:7020 | 9101:7020 | 9102:7020 | 9103:7020 |
| 9098:7021 | 9099:7021 | 9100:7021 | 9101:7021 | 9102:7021 | 9103:7021 |
| 9098:7022 | 9099:7022 | 9100:7022 | 9101:7022 | 9102:7022 | 9103:7022 |
| 9098:7023 | 9099:7023 | 9100:7023 | 9101:7023 | 9102:7023 | 9103:7023 |
| 9098:7024 | 9099:7024 | 9100:7024 | 9101:7024 | 9102:7024 | 9103:7024 |
| 9098:7025 | 9099:7025 | 9100:7025 | 9101:7025 | 9102:7025 | 9103:7025 |
| 9098:7026 | 9099:7026 | 9100:7026 | 9101:7026 | 9102:7026 | 9103:7026 |
| 9098:7027 | 9099:7027 | 9100:7027 | 9101:7027 | 9102:7027 | 9103:7027 |
| 9104:7000 | 9105:7000 | 9106:7000 | 9107:7000 | 9108:7000 | 9109:7000 |
| 9104:7001 | 9105:7001 | 9106:7001 | 9107:7001 | 9108:7001 | 9109:7001 |
| 9104:7002 | 9105:7002 | 9106:7002 | 9107:7002 | 9108:7002 | 9109:7002 |
| 9104:7003 | 9105:7003 | 9106:7003 | 9107:7003 | 9108:7003 | 9109:7003 |
| 9104:7004 | 9105:7004 | 9106:7004 | 9107:7004 | 9108:7004 | 9109:7004 |
| 9104:7005 | 9105:7005 | 9106:7005 | 9107:7005 | 9108:7005 | 9109:7005 |
| 9104:7006 | 9105:7006 | 9106:7006 | 9107:7006 | 9108:7006 | 9109:7006 |
| 9104:7007 | 9105:7007 | 9106:7007 | 9107:7007 | 9108:7007 | 9109:7007 |
| 9104:7008 | 9105:7008 | 9106:7008 | 9107:7008 | 9108:7008 | 9109:7008 |
| 9104:7009 | 9105:7009 | 9106:7009 | 9107:7009 | 9108:7009 | 9109:7009 |
| 9104:7010 | 9105:7010 | 9106:7010 | 9107:7010 | 9108:7010 | 9109:7010 |

TABLE C-continued

Example combinations of a compound X with a compound Y.

| X:Y | X:Y | X:Y | X:Y | X:Y | X:Y |
|---|---|---|---|---|---|
| 9104:7011 | 9105:7011 | 9106:7011 | 9107:7011 | 9108:7011 | 9109:7011 |
| 9104:7012 | 9105:7012 | 9106:7012 | 9107:7012 | 9108:7012 | 9109:7012 |
| 9104:7013 | 9105:7013 | 9106:7013 | 9107:7013 | 9108:7013 | 9109:7013 |
| 9104:7014 | 9105:7014 | 9106:7014 | 9107:7014 | 9108:7014 | 9109:7014 |
| 9104:7015 | 9105:7015 | 9106:7015 | 9107:7015 | 9108:7015 | 9109:7015 |
| 9104:7016 | 9105:7016 | 9106:7016 | 9107:7016 | 9108:7016 | 9109:7016 |
| 9104:7017 | 9105:7017 | 9106:7017 | 9107:7017 | 9108:7017 | 9109:7017 |
| 9104:7018 | 9105:7018 | 9106:7018 | 9107:7018 | 9108:7018 | 9109:7018 |
| 9104:7019 | 9105:7019 | 9106:7019 | 9107:7019 | 9108:7019 | 9109:7019 |
| 9104:7020 | 9105:7020 | 9106:7020 | 9107:7020 | 9108:7020 | 9109:7020 |
| 9104:7021 | 9105:7021 | 9106:7021 | 9107:7021 | 9108:7021 | 9109:7021 |
| 9104:7022 | 9105:7022 | 9106:7022 | 9107:7022 | 9108:7022 | 9109:7022 |
| 9104:7023 | 9105:7023 | 9106:7023 | 9107:7023 | 9108:7023 | 9109:7023 |
| 9104:7024 | 9105:7024 | 9106:7024 | 9107:7024 | 9108:7024 | 9109:7024 |
| 9104:7025 | 9105:7025 | 9106:7025 | 9107:7025 | 9108:7025 | 9109:7025 |
| 9104:7026 | 9105:7026 | 9106:7026 | 9107:7026 | 9108:7026 | 9109:7026 |
| 9104:7027 | 9105:7027 | 9106:7027 | 9107:7027 | 9108:7027 | 9109:7027 |
| 9110:7000 | 9111:7000 | 9129:7000 | 9130:7000 | 9131:7000 | 9132:7000 |
| 9110:7001 | 9111:7001 | 9129:7001 | 9130:7001 | 9131:7001 | 9132:7001 |
| 9110:7002 | 9111:7002 | 9129:7002 | 9130:7002 | 9131:7002 | 9132:7002 |
| 9110:7003 | 9111:7003 | 9129:7003 | 9130:7003 | 9131:7003 | 9132:7003 |
| 9110:7004 | 9111:7004 | 9129:7004 | 9130:7004 | 9131:7004 | 9132:7004 |
| 9110:7005 | 9111:7005 | 9129:7005 | 9130:7005 | 9131:7005 | 9132:7005 |
| 9110:7006 | 9111:7006 | 9129:7006 | 9130:7006 | 9131:7006 | 9132:7006 |
| 9110:7007 | 9111:7007 | 9129:7007 | 9130:7007 | 9131:7007 | 9132:7007 |
| 9110:7008 | 9111:7008 | 9129:7008 | 9130:7008 | 9131:7008 | 9132:7008 |
| 9110:7009 | 9111:7009 | 9129:7009 | 9130:7009 | 9131:7009 | 9132:7009 |
| 9110:7010 | 9111:7010 | 9129:7010 | 9130:7010 | 9131:7010 | 9132:7010 |
| 9110:7011 | 9111:7011 | 9129:7011 | 9130:7011 | 9131:7011 | 9132:7011 |
| 9110:7012 | 9111:7012 | 9129:7012 | 9130:7012 | 9131:7012 | 9132:7012 |
| 9110:7013 | 9111:7013 | 9129:7013 | 9130:7013 | 9131:7013 | 9132:7013 |
| 9110:7014 | 9111:7014 | 9129:7014 | 9130:7014 | 9131:7014 | 9132:7014 |
| 9110:7015 | 9111:7015 | 9129:7015 | 9130:7015 | 9131:7015 | 9132:7015 |
| 9110:7016 | 9111:7016 | 9129:7016 | 9130:7016 | 9131:7016 | 9132:7016 |
| 9110:7017 | 9111:7017 | 9129:7017 | 9130:7017 | 9131:7017 | 9132:7017 |
| 9110:7018 | 9111:7018 | 9129:7018 | 9130:7018 | 9131:7018 | 9132:7018 |
| 9110:7019 | 9111:7019 | 9129:7019 | 9130:7019 | 9131:7019 | 9132:7019 |
| 9110:7020 | 9111:7020 | 9129:7020 | 9130:7020 | 9131:7020 | 9132:7020 |
| 9110:7021 | 9111:7021 | 9129:7021 | 9130:7021 | 9131:7021 | 9132:7021 |
| 9110:7022 | 9111:7022 | 9129:7022 | 9130:7022 | 9131:7022 | 9132:7022 |
| 9110:7023 | 9111:7023 | 9129:7023 | 9130:7023 | 9131:7023 | 9132:7023 |
| 9110:7024 | 9111:7024 | 9129:7024 | 9130:7024 | 9131:7024 | 9132:7024 |
| 9110:7025 | 9111:7025 | 9129:7025 | 9130:7025 | 9131:7025 | 9132:7025 |
| 9110:7026 | 9111:7026 | 9129:7026 | 9130:7026 | 9131:7026 | 9132:7026 |
| 9110:7027 | 9111:7027 | 9129:7027 | 9130:7027 | 9131:7027 | 9132:7027 |
| 9133:7000 | 9134:7000 | 9135:7000 | 9136:7000 | 9137:7000 | 9138:7000 |
| 9133:7001 | 9134:7001 | 9135:7001 | 9136:7001 | 9137:7001 | 9138:7001 |
| 9133:7002 | 9134:7002 | 9135:7002 | 9136:7002 | 9137:7002 | 9138:7002 |
| 9133:7003 | 9134:7003 | 9135:7003 | 9136:7003 | 9137:7003 | 9138:7003 |
| 9133:7004 | 9134:7004 | 9135:7004 | 9136:7004 | 9137:7004 | 9138:7004 |
| 9133:7005 | 9134:7005 | 9135:7005 | 9136:7005 | 9137:7005 | 9138:7005 |
| 9133:7006 | 9134:7006 | 9135:7006 | 9136:7006 | 9137:7006 | 9138:7006 |
| 9133:7007 | 9134:7007 | 9135:7007 | 9136:7007 | 9137:7007 | 9138:7007 |
| 9133:7008 | 9134:7008 | 9135:7008 | 9136:7008 | 9137:7008 | 9138:7008 |
| 9133:7009 | 9134:7009 | 9135:7009 | 9136:7009 | 9137:7009 | 9138:7009 |
| 9133:7010 | 9134:7010 | 9135:7010 | 9136:7010 | 9137:7010 | 9138:7010 |
| 9133:7011 | 9134:7011 | 9135:7011 | 9136:7011 | 9137:7011 | 9138:7011 |
| 9133:7012 | 9134:7012 | 9135:7012 | 9136:7012 | 9137:7012 | 9138:7012 |
| 9133:7013 | 9134:7013 | 9135:7013 | 9136:7013 | 9137:7013 | 9138:7013 |
| 9133:7014 | 9134:7014 | 9135:7014 | 9136:7014 | 9137:7014 | 9138:7014 |
| 9133:7015 | 9134:7015 | 9135:7015 | 9136:7015 | 9137:7015 | 9138:7015 |
| 9133:7016 | 9134:7016 | 9135:7016 | 9136:7016 | 9137:7016 | 9138:7016 |
| 9133:7017 | 9134:7017 | 9135:7017 | 9136:7017 | 9137:7017 | 9138:7017 |
| 9133:7018 | 9134:7018 | 9135:7018 | 9136:7018 | 9137:7018 | 9138:7018 |
| 9133:7019 | 9134:7019 | 9135:7019 | 9136:7019 | 9137:7019 | 9138:7019 |
| 9133:7020 | 9134:7020 | 9135:7020 | 9136:7020 | 9137:7020 | 9138:7020 |
| 9133:7021 | 9134:7021 | 9135:7021 | 9136:7021 | 9137:7021 | 9138:7021 |
| 9133:7022 | 9134:7022 | 9135:7022 | 9136:7022 | 9137:7022 | 9138:7022 |
| 9133:7023 | 9134:7023 | 9135:7023 | 9136:7023 | 9137:7023 | 9138:7023 |
| 9133:7024 | 9134:7024 | 9135:7024 | 9136:7024 | 9137:7024 | 9138:7024 |
| 9133:7025 | 9134:7025 | 9135:7025 | 9136:7025 | 9137:7025 | 9138:7025 |
| 9133:7026 | 9134:7026 | 9135:7026 | 9136:7026 | 9137:7026 | 9138:7026 |
| 9133:7027 | 9134:7027 | 9135:7027 | 9136:7027 | 9137:7027 | 9138:7027 |
| 9139:7000 | 9140:7000 | 9141:7000 | 9142:7000 | 9143:7000 | 9144:7000 |
| 9139:7001 | 9140:7001 | 9141:7001 | 9142:7001 | 9143:7001 | 9144:7001 |
| 9139:7002 | 9140:7002 | 9141:7002 | 9142:7002 | 9143:7002 | 9144:7002 |
| 9139:7003 | 9140:7003 | 9141:7003 | 9142:7003 | 9143:7003 | 9144:7003 |
| 9139:7004 | 9140:7004 | 9141:7004 | 9142:7004 | 9143:7004 | 9144:7004 |
| 9139:7005 | 9140:7005 | 9141:7005 | 9142:7005 | 9143:7005 | 9144:7005 |
| 9139:7006 | 9140:7006 | 9141:7006 | 9142:7006 | 9143:7006 | 9144:7006 |
| 9139:7007 | 9140:7007 | 9141:7007 | 9142:7007 | 9143:7007 | 9144:7007 |
| 9139:7008 | 9140:7008 | 9141:7008 | 9142:7008 | 9143:7008 | 9144:7008 |
| 9139:7009 | 9140:7009 | 9141:7009 | 9142:7009 | 9143:7009 | 9144:7009 |
| 9139:7010 | 9140:7010 | 9141:7010 | 9142:7010 | 9143:7010 | 9144:7010 |
| 9139:7011 | 9140:7011 | 9141:7011 | 9142:7011 | 9143:7011 | 9144:7011 |
| 9139:7012 | 9140:7012 | 9141:7012 | 9142:7012 | 9143:7012 | 9144:7012 |
| 9139:7013 | 9140:7013 | 9141:7013 | 9142:7013 | 9143:7013 | 9144:7013 |
| 9139:7014 | 9140:7014 | 9141:7014 | 9142:7014 | 9143:7014 | 9144:7014 |
| 9139:7015 | 9140:7015 | 9141:7015 | 9142:7015 | 9143:7015 | 9144:7015 |
| 9139:7016 | 9140:7016 | 9141:7016 | 9142:7016 | 9143:7016 | 9144:7016 |
| 9139:7017 | 9140:7017 | 9141:7017 | 9142:7017 | 9143:7017 | 9144:7017 |
| 9139:7018 | 9140:7018 | 9141:7018 | 9142:7018 | 9143:7018 | 9144:7018 |
| 9139:7019 | 9140:7019 | 9141:7019 | 9142:7019 | 9143:7019 | 9144:7019 |
| 9139:7020 | 9140:7020 | 9141:7020 | 9142:7020 | 9143:7020 | 9144:7020 |
| 9139:7021 | 9140:7021 | 9141:7021 | 9142:7021 | 9143:7021 | 9144:7021 |
| 9139:7022 | 9140:7022 | 9141:7022 | 9142:7022 | 9143:7022 | 9144:7022 |
| 9139:7023 | 9140:7023 | 9141:7023 | 9142:7023 | 9143:7023 | 9144:7023 |
| 9139:7024 | 9140:7024 | 9141:7024 | 9142:7024 | 9143:7024 | 9144:7024 |
| 9139:7025 | 9140:7025 | 9141:7025 | 9142:7025 | 9143:7025 | 9144:7025 |
| 9139:7026 | 9140:7026 | 9141:7026 | 9142:7026 | 9143:7026 | 9144:7026 |
| 9139:7027 | 9140:7027 | 9141:7027 | 9142:7027 | 9143:7027 | 9144:7027 |
| 9145:7000 | 9146:7000 | 9147:7000 | 9148:7000 | 9149:7000 | 9150:7000 |
| 9145:7001 | 9146:7001 | 9147:7001 | 9148:7001 | 9149:7001 | 9150:7001 |
| 9145:7002 | 9146:7002 | 9147:7002 | 9148:7002 | 9149:7002 | 9150:7002 |
| 9145:7003 | 9146:7003 | 9147:7003 | 9148:7003 | 9149:7003 | 9150:7003 |
| 9145:7004 | 9146:7004 | 9147:7004 | 9148:7004 | 9149:7004 | 9150:7004 |
| 9145:7005 | 9146:7005 | 9147:7005 | 9148:7005 | 9149:7005 | 9150:7005 |
| 9145:7006 | 9146:7006 | 9147:7006 | 9148:7006 | 9149:7006 | 9150:7006 |
| 9145:7007 | 9146:7007 | 9147:7007 | 9148:7007 | 9149:7007 | 9150:7007 |
| 9145:7008 | 9146:7008 | 9147:7008 | 9148:7008 | 9149:7008 | 9150:7008 |
| 9145:7009 | 9146:7009 | 9147:7009 | 9148:7009 | 9149:7009 | 9150:7009 |
| 9145:7010 | 9146:7010 | 9147:7010 | 9148:7010 | 9149:7010 | 9150:7010 |
| 9145:7011 | 9146:7011 | 9147:7011 | 9148:7011 | 9149:7011 | 9150:7011 |
| 9145:7012 | 9146:7012 | 9147:7012 | 9148:7012 | 9149:7012 | 9150:7012 |
| 9145:7013 | 9146:7013 | 9147:7013 | 9148:7013 | 9149:7013 | 9150:7013 |
| 9145:7014 | 9146:7014 | 9147:7014 | 9148:7014 | 9149:7014 | 9150:7014 |
| 9145:7015 | 9146:7015 | 9147:7015 | 9148:7015 | 9149:7015 | 9150:7015 |
| 9145:7016 | 9146:7016 | 9147:7016 | 9148:7016 | 9149:7016 | 9150:7016 |
| 9145:7017 | 9146:7017 | 9147:7017 | 9148:7017 | 9149:7017 | 9150:7017 |
| 9145:7018 | 9146:7018 | 9147:7018 | 9148:7018 | 9149:7018 | 9150:7018 |
| 9145:7019 | 9146:7019 | 9147:7019 | 9148:7019 | 9149:7019 | 9150:7019 |
| 9145:7020 | 9146:7020 | 9147:7020 | 9148:7020 | 9149:7020 | 9150:7020 |
| 9145:7021 | 9146:7021 | 9147:7021 | 9148:7021 | 9149:7021 | 9150:7021 |
| 9145:7022 | 9146:7022 | 9147:7022 | 9148:7022 | 9149:7022 | 9150:7022 |
| 9145:7023 | 9146:7023 | 9147:7023 | 9148:7023 | 9149:7023 | 9150:7023 |
| 9145:7024 | 9146:7024 | 9147:7024 | 9148:7024 | 9149:7024 | 9150:7024 |
| 9145:7025 | 9146:7025 | 9147:7025 | 9148:7025 | 9149:7025 | 9150:7025 |
| 9145:7026 | 9146:7026 | 9147:7026 | 9148:7026 | 9149:7026 | 9150:7026 |
| 9145:7027 | 9146:7027 | 9147:7027 | 9148:7027 | 9149:7027 | 9150:7027 |
| 9161:7000 | 9162:7000 | 9163:7000 | 9164:7000 | 9167:7000 | 9168:7000 |
| 9161:7001 | 9162:7001 | 9163:7001 | 9164:7001 | 9167:7001 | 9168:7001 |
| 9161:7002 | 9162:7002 | 9163:7002 | 9164:7002 | 9167:7002 | 9168:7002 |
| 9161:7003 | 9162:7003 | 9163:7003 | 9164:7003 | 9167:7003 | 9168:7003 |
| 9161:7004 | 9162:7004 | 9163:7004 | 9164:7004 | 9167:7004 | 9168:7004 |
| 9161:7005 | 9162:7005 | 9163:7005 | 9164:7005 | 9167:7005 | 9168:7005 |
| 9161:7006 | 9162:7006 | 9163:7006 | 9164:7006 | 9167:7006 | 9168:7006 |
| 9161:7007 | 9162:7007 | 9163:7007 | 9164:7007 | 9167:7007 | 9168:7007 |
| 9161:7008 | 9162:7008 | 9163:7008 | 9164:7008 | 9167:7008 | 9168:7008 |
| 9161:7009 | 9162:7009 | 9163:7009 | 9164:7009 | 9167:7009 | 9168:7009 |
| 9161:7010 | 9162:7010 | 9163:7010 | 9164:7010 | 9167:7010 | 9168:7010 |
| 9161:7011 | 9162:7011 | 9163:7011 | 9164:7011 | 9167:7011 | 9168:7011 |
| 9161:7012 | 9162:7012 | 9163:7012 | 9164:7012 | 9167:7012 | 9168:7012 |
| 9161:7013 | 9162:7013 | 9163:7013 | 9164:7013 | 9167:7013 | 9168:7013 |
| 9161:7014 | 9162:7014 | 9163:7014 | 9164:7014 | 9167:7014 | 9168:7014 |
| 9161:7015 | 9162:7015 | 9163:7015 | 9164:7015 | 9167:7015 | 9168:7015 |
| 9161:7016 | 9162:7016 | 9163:7016 | 9164:7016 | 9167:7016 | 9168:7016 |
| 9161:7017 | 9162:7017 | 9163:7017 | 9164:7017 | 9167:7017 | 9168:7017 |
| 9161:7018 | 9162:7018 | 9163:7018 | 9164:7018 | 9167:7018 | 9168:7018 |
| 9161:7019 | 9162:7019 | 9163:7019 | 9164:7019 | 9167:7019 | 9168:7019 |
| 9161:7020 | 9162:7020 | 9163:7020 | 9164:7020 | 9167:7020 | 9168:7020 |
| 9161:7021 | 9162:7021 | 9163:7021 | 9164:7021 | 9167:7021 | 9168:7021 |
| 9161:7022 | 9162:7022 | 9163:7022 | 9164:7022 | 9167:7022 | 9168:7022 |

TABLE C-continued

Example combinations of a compound X with a compound Y.

| X:Y | X:Y | X:Y | X:Y | X:Y | X:Y |
|---|---|---|---|---|---|
| 9161:7023 | 9162:7023 | 9163:7023 | 9164:7023 | 9167:7023 | 9168:7023 |
| 9161:7024 | 9162:7024 | 9163:7024 | 9164:7024 | 9167:7024 | 9168:7024 |
| 9161:7025 | 9162:7025 | 9163:7025 | 9164:7025 | 9167:7025 | 9168:7025 |
| 9161:7026 | 9162:7026 | 9163:7026 | 9164:7026 | 9167:7026 | 9168:7026 |
| 9161:7027 | 9162:7027 | 9163:7027 | 9164:7027 | 9167:7027 | 9168:7027 |
| 9169:7000 | 9170:7000 | 9171:7000 | 9172:7000 | 9173:7000 | 9174:7000 |
| 9169:7001 | 9170:7001 | 9171:7001 | 9172:7001 | 9173:7001 | 9174:7001 |
| 9169:7002 | 9170:7002 | 9171:7002 | 9172:7002 | 9173:7002 | 9174:7002 |
| 9169:7003 | 9170:7003 | 9171:7003 | 9172:7003 | 9173:7003 | 9174:7003 |
| 9169:7004 | 9170:7004 | 9171:7004 | 9172:7004 | 9173:7004 | 9174:7004 |
| 9169:7005 | 9170:7005 | 9171:7005 | 9172:7005 | 9173:7005 | 9174:7005 |
| 9169:7006 | 9170:7006 | 9171:7006 | 9172:7006 | 9173:7006 | 9174:7006 |
| 9169:7007 | 9170:7007 | 9171:7007 | 9172:7007 | 9173:7007 | 9174:7007 |
| 9169:7008 | 9170:7008 | 9171:7008 | 9172:7008 | 9173:7008 | 9174:7008 |
| 9169:7009 | 9170:7009 | 9171:7009 | 9172:7009 | 9173:7009 | 9174:7009 |
| 9169:7010 | 9170:7010 | 9171:7010 | 9172:7010 | 9173:7010 | 9174:7010 |
| 9169:7011 | 9170:7011 | 9171:7011 | 9172:7011 | 9173:7011 | 9174:7011 |
| 9169:7012 | 9170:7012 | 9171:7012 | 9172:7012 | 9173:7012 | 9174:7012 |
| 9169:7013 | 9170:7013 | 9171:7013 | 9172:7013 | 9173:7013 | 9174:7013 |
| 9169:7014 | 9170:7014 | 9171:7014 | 9172:7014 | 9173:7014 | 9174:7014 |
| 9169:7015 | 9170:7015 | 9171:7015 | 9172:7015 | 9173:7015 | 9174:7015 |
| 9169:7016 | 9170:7016 | 9171:7016 | 9172:7016 | 9173:7016 | 9174:7016 |
| 9169:7017 | 9170:7017 | 9171:7017 | 9172:7017 | 9173:7017 | 9174:7017 |
| 9169:7018 | 9170:7018 | 9171:7018 | 9172:7018 | 9173:7018 | 9174:7018 |
| 9169:7019 | 9170:7019 | 9171:7019 | 9172:7019 | 9173:7019 | 9174:7019 |
| 9169:7020 | 9170:7020 | 9171:7020 | 9172:7020 | 9173:7020 | 9174:7020 |
| 9169:7021 | 9170:7021 | 9171:7021 | 9172:7021 | 9173:7021 | 9174:7021 |
| 9169:7022 | 9170:7022 | 9171:7022 | 9172:7022 | 9173:7022 | 9174:7022 |
| 9169:7023 | 9170:7023 | 9171:7023 | 9172:7023 | 9173:7023 | 9174:7023 |
| 9169:7024 | 9170:7024 | 9171:7024 | 9172:7024 | 9173:7024 | 9174:7024 |
| 9169:7025 | 9170:7025 | 9171:7025 | 9172:7025 | 9173:7025 | 9174:7025 |
| 9169:7026 | 9170:7026 | 9171:7026 | 9172:7026 | 9173:7026 | 9174:7026 |
| 9169:7027 | 9170:7027 | 9171:7027 | 9172:7027 | 9173:7027 | 9174:7027 |
| 9175:7000 | 9176:7000 | 9177:7000 | 9178:7000 | 9179:7000 | 9180:7000 |
| 9175:7001 | 9176:7001 | 9177:7001 | 9178:7001 | 9179:7001 | 9180:7001 |
| 9175:7002 | 9176:7002 | 9177:7002 | 9178:7002 | 9179:7002 | 9180:7002 |
| 9175:7003 | 9176:7003 | 9177:7003 | 9178:7003 | 9179:7003 | 9180:7003 |
| 9175:7004 | 9176:7004 | 9177:7004 | 9178:7004 | 9179:7004 | 9180:7004 |
| 9175:7005 | 9176:7005 | 9177:7005 | 9178:7005 | 9179:7005 | 9180:7005 |
| 9175:7006 | 9176:7006 | 9177:7006 | 9178:7006 | 9179:7006 | 9180:7006 |
| 9175:7007 | 9176:7007 | 9177:7007 | 9178:7007 | 9179:7007 | 9180:7007 |
| 9175:7008 | 9176:7008 | 9177:7008 | 9178:7008 | 9179:7008 | 9180:7008 |
| 9175:7009 | 9176:7009 | 9177:7009 | 9178:7009 | 9179:7009 | 9180:7009 |
| 9175:7010 | 9176:7010 | 9177:7010 | 9178:7010 | 9179:7010 | 9180:7010 |
| 9175:7011 | 9176:7011 | 9177:7011 | 9178:7011 | 9179:7011 | 9180:7011 |
| 9175:7012 | 9176:7012 | 9177:7012 | 9178:7012 | 9179:7012 | 9180:7012 |
| 9175:7013 | 9176:7013 | 9177:7013 | 9178:7013 | 9179:7013 | 9180:7013 |
| 9175:7014 | 9176:7014 | 9177:7014 | 9178:7014 | 9179:7014 | 9180:7014 |
| 9175:7015 | 9176:7015 | 9177:7015 | 9178:7015 | 9179:7015 | 9180:7015 |
| 9175:7016 | 9176:7016 | 9177:7016 | 9178:7016 | 9179:7016 | 9180:7016 |
| 9175:7017 | 9176:7017 | 9177:7017 | 9178:7017 | 9179:7017 | 9180:7017 |
| 9175:7018 | 9176:7018 | 9177:7018 | 9178:7018 | 9179:7018 | 9180:7018 |
| 9175:7019 | 9176:7019 | 9177:7019 | 9178:7019 | 9179:7019 | 9180:7019 |
| 9175:7020 | 9176:7020 | 9177:7020 | 9178:7020 | 9179:7020 | 9180:7020 |
| 9175:7021 | 9176:7021 | 9177:7021 | 9178:7021 | 9179:7021 | 9180:7021 |
| 9175:7022 | 9176:7022 | 9177:7022 | 9178:7022 | 9179:7022 | 9180:7022 |
| 9175:7023 | 9176:7023 | 9177:7023 | 9178:7023 | 9179:7023 | 9180:7023 |
| 9175:7024 | 9176:7024 | 9177:7024 | 9178:7024 | 9179:7024 | 9180:7024 |
| 9175:7025 | 9176:7025 | 9177:7025 | 9178:7025 | 9179:7025 | 9180:7025 |
| 9175:7026 | 9176:7026 | 9177:7026 | 9178:7026 | 9179:7026 | 9180:7026 |
| 9175:7027 | 9176:7027 | 9177:7027 | 9178:7027 | 9179:7027 | 9180:7027 |
| 9181:7000 | 9182:7000 | 9183:7000 | 9184:7000 | 9185:7000 | 9206:7000 |
| 9181:7001 | 9182:7001 | 9183:7001 | 9184:7001 | 9185:7001 | 9206:7001 |
| 9181:7002 | 9182:7002 | 9183:7002 | 9184:7002 | 9185:7002 | 9206:7002 |
| 9181:7003 | 9182:7003 | 9183:7003 | 9184:7003 | 9185:7003 | 9206:7003 |
| 9181:7004 | 9182:7004 | 9183:7004 | 9184:7004 | 9185:7004 | 9206:7004 |
| 9181:7005 | 9182:7005 | 9183:7005 | 9184:7005 | 9185:7005 | 9206:7005 |
| 9181:7006 | 9182:7006 | 9183:7006 | 9184:7006 | 9185:7006 | 9206:7006 |
| 9181:7007 | 9182:7007 | 9183:7007 | 9184:7007 | 9185:7007 | 9206:7007 |
| 9181:7008 | 9182:7008 | 9183:7008 | 9184:7008 | 9185:7008 | 9206:7008 |
| 9181:7009 | 9182:7009 | 9183:7009 | 9184:7009 | 9185:7009 | 9206:7009 |
| 9181:7010 | 9182:7010 | 9183:7010 | 9184:7010 | 9185:7010 | 9206:7010 |
| 9181:7011 | 9182:7011 | 9183:7011 | 9184:7011 | 9185:7011 | 9206:7011 |
| 9181:7012 | 9182:7012 | 9183:7012 | 9184:7012 | 9185:7012 | 9206:7012 |
| 9181:7013 | 9182:7013 | 9183:7013 | 9184:7013 | 9185:7013 | 9206:7013 |
| 9181:7014 | 9182:7014 | 9183:7014 | 9184:7014 | 9185:7014 | 9206:7014 |
| 9181:7015 | 9182:7015 | 9183:7015 | 9184:7015 | 9185:7015 | 9206:7015 |
| 9181:7016 | 9182:7016 | 9183:7016 | 9184:7016 | 9185:7016 | 9206:7016 |
| 9181:7017 | 9182:7017 | 9183:7017 | 9184:7017 | 9185:7017 | 9206:7017 |
| 9181:7018 | 9182:7018 | 9183:7018 | 9184:7018 | 9185:7018 | 9206:7018 |
| 9181:7019 | 9182:7019 | 9183:7019 | 9184:7019 | 9185:7019 | 9206:7019 |
| 9181:7020 | 9182:7020 | 9183:7020 | 9184:7020 | 9185:7020 | 9206:7020 |
| 9181:7021 | 9182:7021 | 9183:7021 | 9184:7021 | 9185:7021 | 9206:7021 |
| 9181:7022 | 9182:7022 | 9183:7022 | 9184:7022 | 9185:7022 | 9206:7022 |
| 9181:7023 | 9182:7023 | 9183:7023 | 9184:7023 | 9185:7023 | 9206:7023 |
| 9181:7024 | 9182:7024 | 9183:7024 | 9184:7024 | 9185:7024 | 9206:7024 |
| 9181:7025 | 9182:7025 | 9183:7025 | 9184:7025 | 9185:7025 | 9206:7025 |
| 9181:7026 | 9182:7026 | 9183:7026 | 9184:7026 | 9185:7026 | 9206:7026 |
| 9181:7027 | 9182:7027 | 9183:7027 | 9184:7027 | 9185:7027 | 9206:7027 |
| 9207:7000 | 9208:7000 | 9209:7000 | 9214:7000 | 9241:7000 | 9242:7000 |
| 9207:7001 | 9208:7001 | 9209:7001 | 9214:7001 | 9241:7001 | 9242:7001 |
| 9207:7002 | 9208:7002 | 9209:7002 | 9214:7002 | 9241:7002 | 9242:7002 |
| 9207:7003 | 9208:7003 | 9209:7003 | 9214:7003 | 9241:7003 | 9242:7003 |
| 9207:7004 | 9208:7004 | 9209:7004 | 9214:7004 | 9241:7004 | 9242:7004 |
| 9207:7005 | 9208:7005 | 9209:7005 | 9214:7005 | 9241:7005 | 9242:7005 |
| 9207:7006 | 9208:7006 | 9209:7006 | 9214:7006 | 9241:7006 | 9242:7006 |
| 9207:7007 | 9208:7007 | 9209:7007 | 9214:7007 | 9241:7007 | 9242:7007 |
| 9207:7008 | 9208:7008 | 9209:7008 | 9214:7008 | 9241:7008 | 9242:7008 |
| 9207:7009 | 9208:7009 | 9209:7009 | 9214:7009 | 9241:7009 | 9242:7009 |
| 9207:7010 | 9208:7010 | 9209:7010 | 9214:7010 | 9241:7010 | 9242:7010 |
| 9207:7011 | 9208:7011 | 9209:7011 | 9214:7011 | 9241:7011 | 9242:7011 |
| 9207:7012 | 9208:7012 | 9209:7012 | 9214:7012 | 9241:7012 | 9242:7012 |
| 9207:7013 | 9208:7013 | 9209:7013 | 9214:7013 | 9241:7013 | 9242:7013 |
| 9207:7014 | 9208:7014 | 9209:7014 | 9214:7014 | 9241:7014 | 9242:7014 |
| 9207:7015 | 9208:7015 | 9209:7015 | 9214:7015 | 9241:7015 | 9242:7015 |
| 9207:7016 | 9208:7016 | 9209:7016 | 9214:7016 | 9241:7016 | 9242:7016 |
| 9207:7017 | 9208:7017 | 9209:7017 | 9214:7017 | 9241:7017 | 9242:7017 |
| 9207:7018 | 9208:7018 | 9209:7018 | 9214:7018 | 9241:7018 | 9242:7018 |
| 9207:7019 | 9208:7019 | 9209:7019 | 9214:7019 | 9241:7019 | 9242:7019 |
| 9207:7020 | 9208:7020 | 9209:7020 | 9214:7020 | 9241:7020 | 9242:7020 |
| 9207:7021 | 9208:7021 | 9209:7021 | 9214:7021 | 9241:7021 | 9242:7021 |
| 9207:7022 | 9208:7022 | 9209:7022 | 9214:7022 | 9241:7022 | 9242:7022 |
| 9207:7023 | 9208:7023 | 9209:7023 | 9214:7023 | 9241:7023 | 9242:7023 |
| 9207:7024 | 9208:7024 | 9209:7024 | 9214:7024 | 9241:7024 | 9242:7024 |
| 9207:7025 | 9208:7025 | 9209:7025 | 9214:7025 | 9241:7025 | 9242:7025 |
| 9207:7026 | 9208:7026 | 9209:7026 | 9214:7026 | 9241:7026 | 9242:7026 |
| 9207:7027 | 9208:7027 | 9209:7027 | 9214:7027 | 9241:7027 | 9242:7027 |
| 9244:7000 | 9245:7000 | 9246:7000 | 9247:7000 | 9248:7000 | 9249:7000 |
| 9244:7001 | 9245:7001 | 9246:7001 | 9247:7001 | 9248:7001 | 9249:7001 |
| 9244:7002 | 9245:7002 | 9246:7002 | 9247:7002 | 9248:7002 | 9249:7002 |
| 9244:7003 | 9245:7003 | 9246:7003 | 9247:7003 | 9248:7003 | 9249:7003 |
| 9244:7004 | 9245:7004 | 9246:7004 | 9247:7004 | 9248:7004 | 9249:7004 |
| 9244:7005 | 9245:7005 | 9246:7005 | 9247:7005 | 9248:7005 | 9249:7005 |
| 9244:7006 | 9245:7006 | 9246:7006 | 9247:7006 | 9248:7006 | 9249:7006 |
| 9244:7007 | 9245:7007 | 9246:7007 | 9247:7007 | 9248:7007 | 9249:7007 |
| 9244:7008 | 9245:7008 | 9246:7008 | 9247:7008 | 9248:7008 | 9249:7008 |
| 9244:7009 | 9245:7009 | 9246:7009 | 9247:7009 | 9248:7009 | 9249:7009 |
| 9244:7010 | 9245:7010 | 9246:7010 | 9247:7010 | 9248:7010 | 9249:7010 |
| 9244:7011 | 9245:7011 | 9246:7011 | 9247:7011 | 9248:7011 | 9249:7011 |
| 9244:7012 | 9245:7012 | 9246:7012 | 9247:7012 | 9248:7012 | 9249:7012 |
| 9244:7013 | 9245:7013 | 9246:7013 | 9247:7013 | 9248:7013 | 9249:7013 |
| 9244:7014 | 9245:7014 | 9246:7014 | 9247:7014 | 9248:7014 | 9249:7014 |
| 9244:7015 | 9245:7015 | 9246:7015 | 9247:7015 | 9248:7015 | 9249:7015 |
| 9244:7016 | 9245:7016 | 9246:7016 | 9247:7016 | 9248:7016 | 9249:7016 |
| 9244:7017 | 9245:7017 | 9246:7017 | 9247:7017 | 9248:7017 | 9249:7017 |
| 9244:7018 | 9245:7018 | 9246:7018 | 9247:7018 | 9248:7018 | 9249:7018 |
| 9244:7019 | 9245:7019 | 9246:7019 | 9247:7019 | 9248:7019 | 9249:7019 |
| 9244:7020 | 9245:7020 | 9246:7020 | 9247:7020 | 9248:7020 | 9249:7020 |
| 9244:7021 | 9245:7021 | 9246:7021 | 9247:7021 | 9248:7021 | 9249:7021 |
| 9244:7022 | 9245:7022 | 9246:7022 | 9247:7022 | 9248:7022 | 9249:7022 |
| 9244:7023 | 9245:7023 | 9246:7023 | 9247:7023 | 9248:7023 | 9249:7023 |
| 9244:7024 | 9245:7024 | 9246:7024 | 9247:7024 | 9248:7024 | 9249:7024 |
| 9244:7025 | 9245:7025 | 9246:7025 | 9247:7025 | 9248:7025 | 9249:7025 |
| 9244:7026 | 9245:7026 | 9246:7026 | 9247:7026 | 9248:7026 | 9249:7026 |
| 9244:7027 | 9245:7027 | 9246:7027 | 9247:7027 | 9248:7027 | 9249:7027 |
| 9250:7000 | 9251:7000 | 9252:7000 | 9253:7000 | 9255:7000 | 9256:7000 |
| 9250:7001 | 9251:7001 | 9252:7001 | 9253:7001 | 9255:7001 | 9256:7001 |
| 9250:7002 | 9251:7002 | 9252:7002 | 9253:7002 | 9255:7002 | 9256:7002 |
| 9250:7003 | 9251:7003 | 9252:7003 | 9253:7003 | 9255:7003 | 9256:7003 |
| 9250:7004 | 9251:7004 | 9252:7004 | 9253:7004 | 9255:7004 | 9256:7004 |
| 9250:7005 | 9251:7005 | 9252:7005 | 9253:7005 | 9255:7005 | 9256:7005 |
| 9250:7006 | 9251:7006 | 9252:7006 | 9253:7006 | 9255:7006 | 9256:7006 |

TABLE C-continued

Example combinations of a compound X with a compound Y.

| X:Y | X:Y | X:Y | X:Y | X:Y | X:Y |
|---|---|---|---|---|---|
| 9250:7007 | 9251:7007 | 9252:7007 | 9253:7007 | 9255:7007 | 9256:7007 |
| 9250:7008 | 9251:7008 | 9252:7008 | 9253:7008 | 9255:7008 | 9256:7008 |
| 9250:7009 | 9251:7009 | 9252:7009 | 9253:7009 | 9255:7009 | 9256:7009 |
| 9250:7010 | 9251:7010 | 9252:7010 | 9253:7010 | 9255:7010 | 9256:7010 |
| 9250:7011 | 9251:7011 | 9252:7011 | 9253:7011 | 9255:7011 | 9256:7011 |
| 9250:7012 | 9251:7012 | 9252:7012 | 9253:7012 | 9255:7012 | 9256:7012 |
| 9250:7013 | 9251:7013 | 9252:7013 | 9253:7013 | 9255:7013 | 9256:7013 |
| 9250:7014 | 9251:7014 | 9252:7014 | 9253:7014 | 9255:7014 | 9256:7014 |
| 9250:7015 | 9251:7015 | 9252:7015 | 9253:7015 | 9255:7015 | 9256:7015 |
| 9250:7016 | 9251:7016 | 9252:7016 | 9253:7016 | 9255:7016 | 9256:7016 |
| 9250:7017 | 9251:7017 | 9252:7017 | 9253:7017 | 9255:7017 | 9256:7017 |
| 9250:7018 | 9251:7018 | 9252:7018 | 9253:7018 | 9255:7018 | 9256:7018 |
| 9250:7019 | 9251:7019 | 9252:7019 | 9253:7019 | 9255:7019 | 9256:7019 |
| 9250:7020 | 9251:7020 | 9252:7020 | 9253:7020 | 9255:7020 | 9256:7020 |
| 9250:7021 | 9251:7021 | 9252:7021 | 9253:7021 | 9255:7021 | 9256:7021 |
| 9250:7022 | 9251:7022 | 9252:7022 | 9253:7022 | 9255:7022 | 9256:7022 |
| 9250:7023 | 9251:7023 | 9252:7023 | 9253:7023 | 9255:7023 | 9256:7023 |
| 9250:7024 | 9251:7024 | 9252:7024 | 9253:7024 | 9255:7024 | 9256:7024 |
| 9250:7025 | 9251:7025 | 9252:7025 | 9253:7025 | 9255:7025 | 9256:7025 |
| 9250:7026 | 9251:7026 | 9252:7026 | 9253:7026 | 9255:7026 | 9256:7026 |
| 9250:7027 | 9251:7027 | 9252:7027 | 9253:7027 | 9255:7027 | 9256:7027 |
| 9257:7000 | 9258:7000 | 9259:7000 | 9260:7000 | 9262:7000 | 9263:7000 |
| 9257:7001 | 9258:7001 | 9259:7001 | 9260:7001 | 9262:7001 | 9263:7001 |
| 9257:7002 | 9258:7002 | 9259:7002 | 9260:7002 | 9262:7002 | 9263:7002 |
| 9257:7003 | 9258:7003 | 9259:7003 | 9260:7003 | 9262:7003 | 9263:7003 |
| 9257:7004 | 9258:7004 | 9259:7004 | 9260:7004 | 9262:7004 | 9263:7004 |
| 9257:7005 | 9258:7005 | 9259:7005 | 9260:7005 | 9262:7005 | 9263:7005 |
| 9257:7006 | 9258:7006 | 9259:7006 | 9260:7006 | 9262:7006 | 9263:7006 |
| 9257:7007 | 9258:7007 | 9259:7007 | 9260:7007 | 9262:7007 | 9263:7007 |
| 9257:7008 | 9258:7008 | 9259:7008 | 9260:7008 | 9262:7008 | 9263:7008 |
| 9257:7009 | 9258:7009 | 9259:7009 | 9260:7009 | 9262:7009 | 9263:7009 |
| 9257:7010 | 9258:7010 | 9259:7010 | 9260:7010 | 9262:7010 | 9263:7010 |
| 9257:7011 | 9258:7011 | 9259:7011 | 9260:7011 | 9262:7011 | 9263:7011 |
| 9257:7012 | 9258:7012 | 9259:7012 | 9260:7012 | 9262:7012 | 9263:7012 |
| 9257:7013 | 9258:7013 | 9259:7013 | 9260:7013 | 9262:7013 | 9263:7013 |
| 9257:7014 | 9258:7014 | 9259:7014 | 9260:7014 | 9262:7014 | 9263:7014 |
| 9257:7015 | 9258:7015 | 9259:7015 | 9260:7015 | 9262:7015 | 9263:7015 |
| 9257:7016 | 9258:7016 | 9259:7016 | 9260:7016 | 9262:7016 | 9263:7016 |
| 9257:7017 | 9258:7017 | 9259:7017 | 9260:7017 | 9262:7017 | 9263:7017 |
| 9257:7018 | 9258:7018 | 9259:7018 | 9260:7018 | 9262:7018 | 9263:7018 |
| 9257:7019 | 9258:7019 | 9259:7019 | 9260:7019 | 9262:7019 | 9263:7019 |
| 9257:7020 | 9258:7020 | 9259:7020 | 9260:7020 | 9262:7020 | 9263:7020 |
| 9257:7021 | 9258:7021 | 9259:7021 | 9260:7021 | 9262:7021 | 9263:7021 |
| 9257:7022 | 9258:7022 | 9259:7022 | 9260:7022 | 9262:7022 | 9263:7022 |
| 9257:7023 | 9258:7023 | 9259:7023 | 9260:7023 | 9262:7023 | 9263:7023 |
| 9257:7024 | 9258:7024 | 9259:7024 | 9260:7024 | 9262:7024 | 9263:7024 |
| 9257:7025 | 9258:7025 | 9259:7025 | 9260:7025 | 9262:7025 | 9263:7025 |
| 9257:7026 | 9258:7026 | 9259:7026 | 9260:7026 | 9262:7026 | 9263:7026 |
| 9257:7027 | 9258:7027 | 9259:7027 | 9260:7027 | 9262:7027 | 9263:7027 |
| 9264:7000 | 9265:7000 | 9266:7000 | 9267:7000 | 9268:7000 | 9269:7000 |
| 9264:7001 | 9265:7001 | 9266:7001 | 9267:7001 | 9268:7001 | 9269:7001 |
| 9264:7002 | 9265:7002 | 9266:7002 | 9267:7002 | 9268:7002 | 9269:7002 |
| 9264:7003 | 9265:7003 | 9266:7003 | 9267:7003 | 9268:7003 | 9269:7003 |
| 9264:7004 | 9265:7004 | 9266:7004 | 9267:7004 | 9268:7004 | 9269:7004 |
| 9264:7005 | 9265:7005 | 9266:7005 | 9267:7005 | 9268:7005 | 9269:7005 |
| 9264:7006 | 9265:7006 | 9266:7006 | 9267:7006 | 9268:7006 | 9269:7006 |
| 9264:7007 | 9265:7007 | 9266:7007 | 9267:7007 | 9268:7007 | 9269:7007 |
| 9264:7008 | 9265:7008 | 9266:7008 | 9267:7008 | 9268:7008 | 9269:7008 |
| 9264:7009 | 9265:7009 | 9266:7009 | 9267:7009 | 9268:7009 | 9269:7009 |
| 9264:7010 | 9265:7010 | 9266:7010 | 9267:7010 | 9268:7010 | 9269:7010 |
| 9264:7011 | 9265:7011 | 9266:7011 | 9267:7011 | 9268:7011 | 9269:7011 |
| 9264:7012 | 9265:7012 | 9266:7012 | 9267:7012 | 9268:7012 | 9269:7012 |
| 9264:7013 | 9265:7013 | 9266:7013 | 9267:7013 | 9268:7013 | 9269:7013 |
| 9264:7014 | 9265:7014 | 9266:7014 | 9267:7014 | 9268:7014 | 9269:7014 |
| 9264:7015 | 9265:7015 | 9266:7015 | 9267:7015 | 9268:7015 | 9269:7015 |
| 9264:7016 | 9265:7016 | 9266:7016 | 9267:7016 | 9268:7016 | 9269:7016 |
| 9264:7017 | 9265:7017 | 9266:7017 | 9267:7017 | 9268:7017 | 9269:7017 |
| 9264:7018 | 9265:7018 | 9266:7018 | 9267:7018 | 9268:7018 | 9269:7018 |
| 9264:7019 | 9265:7019 | 9266:7019 | 9267:7019 | 9268:7019 | 9269:7019 |
| 9264:7020 | 9265:7020 | 9266:7020 | 9267:7020 | 9268:7020 | 9269:7020 |
| 9264:7021 | 9265:7021 | 9266:7021 | 9267:7021 | 9268:7021 | 9269:7021 |
| 9264:7022 | 9265:7022 | 9266:7022 | 9267:7022 | 9268:7022 | 9269:7022 |
| 9264:7023 | 9265:7023 | 9266:7023 | 9267:7023 | 9268:7023 | 9269:7023 |
| 9264:7024 | 9265:7024 | 9266:7024 | 9267:7024 | 9268:7024 | 9269:7024 |
| 9264:7025 | 9265:7025 | 9266:7025 | 9267:7025 | 9268:7025 | 9269:7025 |
| 9264:7026 | 9265:7026 | 9266:7026 | 9267:7026 | 9268:7026 | 9269:7026 |
| 9264:7027 | 9265:7027 | 9266:7027 | 9267:7027 | 9268:7027 | 9269:7027 |
| 9270:7000 | 9271:7000 | 9272:7000 | 9273:7000 | 9274:7000 | 9275:7000 |
| 9270:7001 | 9271:7001 | 9272:7001 | 9273:7001 | 9274:7001 | 9275:7001 |
| 9270:7002 | 9271:7002 | 9272:7002 | 9273:7002 | 9274:7002 | 9275:7002 |
| 9270:7003 | 9271:7003 | 9272:7003 | 9273:7003 | 9274:7003 | 9275:7003 |
| 9270:7004 | 9271:7004 | 9272:7004 | 9273:7004 | 9274:7004 | 9275:7004 |
| 9270:7005 | 9271:7005 | 9272:7005 | 9273:7005 | 9274:7005 | 9275:7005 |
| 9270:7006 | 9271:7006 | 9272:7006 | 9273:7006 | 9274:7006 | 9275:7006 |
| 9270:7007 | 9271:7007 | 9272:7007 | 9273:7007 | 9274:7007 | 9275:7007 |
| 9270:7008 | 9271:7008 | 9272:7008 | 9273:7008 | 9274:7008 | 9275:7008 |
| 9270:7009 | 9271:7009 | 9272:7009 | 9273:7009 | 9274:7009 | 9275:7009 |
| 9270:7010 | 9271:7010 | 9272:7010 | 9273:7010 | 9274:7010 | 9275:7010 |
| 9270:7011 | 9271:7011 | 9272:7011 | 9273:7011 | 9274:7011 | 9275:7011 |
| 9270:7012 | 9271:7012 | 9272:7012 | 9273:7012 | 9274:7012 | 9275:7012 |
| 9270:7013 | 9271:7013 | 9272:7013 | 9273:7013 | 9274:7013 | 9275:7013 |
| 9270:7014 | 9271:7014 | 9272:7014 | 9273:7014 | 9274:7014 | 9275:7014 |
| 9270:7015 | 9271:7015 | 9272:7015 | 9273:7015 | 9274:7015 | 9275:7015 |
| 9270:7016 | 9271:7016 | 9272:7016 | 9273:7016 | 9274:7016 | 9275:7016 |
| 9270:7017 | 9271:7017 | 9272:7017 | 9273:7017 | 9274:7017 | 9275:7017 |
| 9270:7018 | 9271:7018 | 9272:7018 | 9273:7018 | 9274:7018 | 9275:7018 |
| 9270:7019 | 9271:7019 | 9272:7019 | 9273:7019 | 9274:7019 | 9275:7019 |
| 9270:7020 | 9271:7020 | 9272:7020 | 9273:7020 | 9274:7020 | 9275:7020 |
| 9270:7021 | 9271:7021 | 9272:7021 | 9273:7021 | 9274:7021 | 9275:7021 |
| 9270:7022 | 9271:7022 | 9272:7022 | 9273:7022 | 9274:7022 | 9275:7022 |
| 9270:7023 | 9271:7023 | 9272:7023 | 9273:7023 | 9274:7023 | 9275:7023 |
| 9270:7024 | 9271:7024 | 9272:7024 | 9273:7024 | 9274:7024 | 9275:7024 |
| 9270:7025 | 9271:7025 | 9272:7025 | 9273:7025 | 9274:7025 | 9275:7025 |
| 9270:7026 | 9271:7026 | 9272:7026 | 9273:7026 | 9274:7026 | 9275:7026 |
| 9270:7027 | 9271:7027 | 9272:7027 | 9273:7027 | 9274:7027 | 9275:7027 |
| 9276:7000 | 9277:7000 | 9278:7000 | 9279:7000 | 9280:7000 | 9281:7000 |
| 9276:7001 | 9277:7001 | 9278:7001 | 9279:7001 | 9280:7001 | 9281:7001 |
| 9276:7002 | 9277:7002 | 9278:7002 | 9279:7002 | 9280:7002 | 9281:7002 |
| 9276:7003 | 9277:7003 | 9278:7003 | 9279:7003 | 9280:7003 | 9281:7003 |
| 9276:7004 | 9277:7004 | 9278:7004 | 9279:7004 | 9280:7004 | 9281:7004 |
| 9276:7005 | 9277:7005 | 9278:7005 | 9279:7005 | 9280:7005 | 9281:7005 |
| 9276:7006 | 9277:7006 | 9278:7006 | 9279:7006 | 9280:7006 | 9281:7006 |
| 9276:7007 | 9277:7007 | 9278:7007 | 9279:7007 | 9280:7007 | 9281:7007 |
| 9276:7008 | 9277:7008 | 9278:7008 | 9279:7008 | 9280:7008 | 9281:7008 |
| 9276:7009 | 9277:7009 | 9278:7009 | 9279:7009 | 9280:7009 | 9281:7009 |
| 9276:7010 | 9277:7010 | 9278:7010 | 9279:7010 | 9280:7010 | 9281:7010 |
| 9276:7011 | 9277:7011 | 9278:7011 | 9279:7011 | 9280:7011 | 9281:7011 |
| 9276:7012 | 9277:7012 | 9278:7012 | 9279:7012 | 9280:7012 | 9281:7012 |
| 9276:7013 | 9277:7013 | 9278:7013 | 9279:7013 | 9280:7013 | 9281:7013 |
| 9276:7014 | 9277:7014 | 9278:7014 | 9279:7014 | 9280:7014 | 9281:7014 |
| 9276:7015 | 9277:7015 | 9278:7015 | 9279:7015 | 9280:7015 | 9281:7015 |
| 9276:7016 | 9277:7016 | 9278:7016 | 9279:7016 | 9280:7016 | 9281:7016 |
| 9276:7017 | 9277:7017 | 9278:7017 | 9279:7017 | 9280:7017 | 9281:7017 |
| 9276:7018 | 9277:7018 | 9278:7018 | 9279:7018 | 9280:7018 | 9281:7018 |
| 9276:7019 | 9277:7019 | 9278:7019 | 9279:7019 | 9280:7019 | 9281:7019 |
| 9276:7020 | 9277:7020 | 9278:7020 | 9279:7020 | 9280:7020 | 9281:7020 |
| 9276:7021 | 9277:7021 | 9278:7021 | 9279:7021 | 9280:7021 | 9281:7021 |
| 9276:7022 | 9277:7022 | 9278:7022 | 9279:7022 | 9280:7022 | 9281:7022 |
| 9276:7023 | 9277:7023 | 9278:7023 | 9279:7023 | 9280:7023 | 9281:7023 |
| 9276:7024 | 9277:7024 | 9278:7024 | 9279:7024 | 9280:7024 | 9281:7024 |
| 9276:7025 | 9277:7025 | 9278:7025 | 9279:7025 | 9280:7025 | 9281:7025 |
| 9276:7026 | 9277:7026 | 9278:7026 | 9279:7026 | 9280:7026 | 9281:7026 |
| 9276:7027 | 9277:7027 | 9278:7027 | 9279:7027 | 9280:7027 | 9281:7027 |
| 9282:7000 | 9283:7000 | 9284:7000 | 9285:7000 | 9286:7000 | 9287:7000 |
| 9282:7001 | 9283:7001 | 9284:7001 | 9285:7001 | 9286:7001 | 9287:7001 |
| 9282:7002 | 9283:7002 | 9284:7002 | 9285:7002 | 9286:7002 | 9287:7002 |
| 9282:7003 | 9283:7003 | 9284:7003 | 9285:7003 | 9286:7003 | 9287:7003 |
| 9282:7004 | 9283:7004 | 9284:7004 | 9285:7004 | 9286:7004 | 9287:7004 |
| 9282:7005 | 9283:7005 | 9284:7005 | 9285:7005 | 9286:7005 | 9287:7005 |
| 9282:7006 | 9283:7006 | 9284:7006 | 9285:7006 | 9286:7006 | 9287:7006 |
| 9282:7007 | 9283:7007 | 9284:7007 | 9285:7007 | 9286:7007 | 9287:7007 |
| 9282:7008 | 9283:7008 | 9284:7008 | 9285:7008 | 9286:7008 | 9287:7008 |
| 9282:7009 | 9283:7009 | 9284:7009 | 9285:7009 | 9286:7009 | 9287:7009 |
| 9282:7010 | 9283:7010 | 9284:7010 | 9285:7010 | 9286:7010 | 9287:7010 |
| 9282:7011 | 9283:7011 | 9284:7011 | 9285:7011 | 9286:7011 | 9287:7011 |
| 9282:7012 | 9283:7012 | 9284:7012 | 9285:7012 | 9286:7012 | 9287:7012 |
| 9282:7013 | 9283:7013 | 9284:7013 | 9285:7013 | 9286:7013 | 9287:7013 |
| 9282:7014 | 9283:7014 | 9284:7014 | 9285:7014 | 9286:7014 | 9287:7014 |
| 9282:7015 | 9283:7015 | 9284:7015 | 9285:7015 | 9286:7015 | 9287:7015 |
| 9282:7016 | 9283:7016 | 9284:7016 | 9285:7016 | 9286:7016 | 9287:7016 |
| 9282:7017 | 9283:7017 | 9284:7017 | 9285:7017 | 9286:7017 | 9287:7017 |
| 9282:7018 | 9283:7018 | 9284:7018 | 9285:7018 | 9286:7018 | 9287:7018 |

TABLE C-continued

Example combinations of a compound X with a compound Y.

| X:Y | X:Y | X:Y | X:Y | X:Y | X:Y |
|---|---|---|---|---|---|
| 9282:7019 | 9283:7019 | 9284:7019 | 9285:7019 | 9286:7019 | 9287:7019 |
| 9282:7020 | 9283:7020 | 9284:7020 | 9285:7020 | 9286:7020 | 9287:7020 |
| 9282:7021 | 9283:7021 | 9284:7021 | 9285:7021 | 9286:7021 | 9287:7021 |
| 9282:7022 | 9283:7022 | 9284:7022 | 9285:7022 | 9286:7022 | 9287:7022 |
| 9282:7023 | 9283:7023 | 9284:7023 | 9285:7023 | 9286:7023 | 9287:7023 |
| 9282:7024 | 9283:7024 | 9284:7024 | 9285:7024 | 9286:7024 | 9287:7024 |
| 9282:7025 | 9283:7025 | 9284:7025 | 9285:7025 | 9286:7025 | 9287:7025 |
| 9282:7026 | 9283:7026 | 9284:7026 | 9285:7026 | 9286:7026 | 9287:7026 |
| 9282:7027 | 9283:7027 | 9284:7027 | 9285:7027 | 9286:7027 | 9287:7027 |
| 9288:7000 | 9289:7000 | 9290:7000 | 9291:7000 | 9292:7000 | 9293:7000 |
| 9288:7001 | 9289:7001 | 9290:7001 | 9291:7001 | 9292:7001 | 9293:7001 |
| 9288:7002 | 9289:7002 | 9290:7002 | 9291:7002 | 9292:7002 | 9293:7002 |
| 9288:7003 | 9289:7003 | 9290:7003 | 9291:7003 | 9292:7003 | 9293:7003 |
| 9288:7004 | 9289:7004 | 9290:7004 | 9291:7004 | 9292:7004 | 9293:7004 |
| 9288:7005 | 9289:7005 | 9290:7005 | 9291:7005 | 9292:7005 | 9293:7005 |
| 9288:7006 | 9289:7006 | 9290:7006 | 9291:7006 | 9292:7006 | 9293:7006 |
| 9288:7007 | 9289:7007 | 9290:7007 | 9291:7007 | 9292:7007 | 9293:7007 |
| 9288:7008 | 9289:7008 | 9290:7008 | 9291:7008 | 9292:7008 | 9293:7008 |
| 9288:7009 | 9289:7009 | 9290:7009 | 9291:7009 | 9292:7009 | 9293:7009 |
| 9288:7010 | 9289:7010 | 9290:7010 | 9291:7010 | 9292:7010 | 9293:7010 |
| 9288:7011 | 9289:7011 | 9290:7011 | 9291:7011 | 9292:7011 | 9293:7011 |
| 9288:7012 | 9289:7012 | 9290:7012 | 9291:7012 | 9292:7012 | 9293:7012 |
| 9288:7013 | 9289:7013 | 9290:7013 | 9291:7013 | 9292:7013 | 9293:7013 |
| 9288:7014 | 9289:7014 | 9290:7014 | 9291:7014 | 9292:7014 | 9293:7014 |
| 9288:7015 | 9289:7015 | 9290:7015 | 9291:7015 | 9292:7015 | 9293:7015 |
| 9288:7016 | 9289:7016 | 9290:7016 | 9291:7016 | 9292:7016 | 9293:7016 |
| 9288:7017 | 9289:7017 | 9290:7017 | 9291:7017 | 9292:7017 | 9293:7017 |
| 9288:7018 | 9289:7018 | 9290:7018 | 9291:7018 | 9292:7018 | 9293:7018 |
| 9288:7019 | 9289:7019 | 9290:7019 | 9291:7019 | 9292:7019 | 9293:7019 |
| 9288:7020 | 9289:7020 | 9290:7020 | 9291:7020 | 9292:7020 | 9293:7020 |
| 9288:7021 | 9289:7021 | 9290:7021 | 9291:7021 | 9292:7021 | 9293:7021 |
| 9288:7022 | 9289:7022 | 9290:7022 | 9291:7022 | 9292:7022 | 9293:7022 |
| 9288:7023 | 9289:7023 | 9290:7023 | 9291:7023 | 9292:7023 | 9293:7023 |
| 9288:7024 | 9289:7024 | 9290:7024 | 9291:7024 | 9292:7024 | 9293:7024 |
| 9288:7025 | 9289:7025 | 9290:7025 | 9291:7025 | 9292:7025 | 9293:7025 |
| 9288:7026 | 9289:7026 | 9290:7026 | 9291:7026 | 9292:7026 | 9293:7026 |
| 9288:7027 | 9289:7027 | 9290:7027 | 9291:7027 | 9292:7027 | 9293:7027 |
| 9294:7000 | 9295:7000 | 9296:7000 | 9297:7000 | 9298:7000 | 9299:7000 |
| 9294:7001 | 9295:7001 | 9296:7001 | 9297:7001 | 9298:7001 | 9299:7001 |
| 9294:7002 | 9295:7002 | 9296:7002 | 9297:7002 | 9298:7002 | 9299:7002 |
| 9294:7003 | 9295:7003 | 9296:7003 | 9297:7003 | 9298:7003 | 9299:7003 |
| 9294:7004 | 9295:7004 | 9296:7004 | 9297:7004 | 9298:7004 | 9299:7004 |
| 9294:7005 | 9295:7005 | 9296:7005 | 9297:7005 | 9298:7005 | 9299:7005 |
| 9294:7006 | 9295:7006 | 9296:7006 | 9297:7006 | 9298:7006 | 9299:7006 |
| 9294:7007 | 9295:7007 | 9296:7007 | 9297:7007 | 9298:7007 | 9299:7007 |
| 9294:7008 | 9295:7008 | 9296:7008 | 9297:7008 | 9298:7008 | 9299:7008 |
| 9294:7009 | 9295:7009 | 9296:7009 | 9297:7009 | 9298:7009 | 9299:7009 |
| 9294:7010 | 9295:7010 | 9296:7010 | 9297:7010 | 9298:7010 | 9299:7010 |
| 9294:7011 | 9295:7011 | 9296:7011 | 9297:7011 | 9298:7011 | 9299:7011 |
| 9294:7012 | 9295:7012 | 9296:7012 | 9297:7012 | 9298:7012 | 9299:7012 |
| 9294:7013 | 9295:7013 | 9296:7013 | 9297:7013 | 9298:7013 | 9299:7013 |
| 9294:7014 | 9295:7014 | 9296:7014 | 9297:7014 | 9298:7014 | 9299:7014 |
| 9294:7015 | 9295:7015 | 9296:7015 | 9297:7015 | 9298:7015 | 9299:7015 |
| 9294:7016 | 9295:7016 | 9296:7016 | 9297:7016 | 9298:7016 | 9299:7016 |
| 9294:7017 | 9295:7017 | 9296:7017 | 9297:7017 | 9298:7017 | 9299:7017 |
| 9294:7018 | 9295:7018 | 9296:7018 | 9297:7018 | 9298:7018 | 9299:7018 |
| 9294:7019 | 9295:7019 | 9296:7019 | 9297:7019 | 9298:7019 | 9299:7019 |
| 9294:7020 | 9295:7020 | 9296:7020 | 9297:7020 | 9298:7020 | 9299:7020 |
| 9294:7021 | 9295:7021 | 9296:7021 | 9297:7021 | 9298:7021 | 9299:7021 |
| 9294:7022 | 9295:7022 | 9296:7022 | 9297:7022 | 9298:7022 | 9299:7022 |
| 9294:7023 | 9295:7023 | 9296:7023 | 9297:7023 | 9298:7023 | 9299:7023 |
| 9294:7024 | 9295:7024 | 9296:7024 | 9297:7024 | 9298:7024 | 9299:7024 |
| 9294:7025 | 9295:7025 | 9296:7025 | 9297:7025 | 9298:7025 | 9299:7025 |
| 9294:7026 | 9295:7026 | 9296:7026 | 9297:7026 | 9298:7026 | 9299:7026 |
| 9294:7027 | 9295:7027 | 9296:7027 | 9297:7027 | 9298:7027 | 9299:7027 |
| 9300:7000 | 9301:7000 | 9302:7000 | 9303:7000 | 9304:7000 | 9305:7000 |
| 9300:7001 | 9301:7001 | 9302:7001 | 9303:7001 | 9304:7001 | 9305:7001 |
| 9300:7002 | 9301:7002 | 9302:7002 | 9303:7002 | 9304:7002 | 9305:7002 |
| 9300:7003 | 9301:7003 | 9302:7003 | 9303:7003 | 9304:7003 | 9305:7003 |
| 9300:7004 | 9301:7004 | 9302:7004 | 9303:7004 | 9304:7004 | 9305:7004 |
| 9300:7005 | 9301:7005 | 9302:7005 | 9303:7005 | 9304:7005 | 9305:7005 |
| 9300:7006 | 9301:7006 | 9302:7006 | 9303:7006 | 9304:7006 | 9305:7006 |
| 9300:7007 | 9301:7007 | 9302:7007 | 9303:7007 | 9304:7007 | 9305:7007 |
| 9300:7008 | 9301:7008 | 9302:7008 | 9303:7008 | 9304:7008 | 9305:7008 |
| 9300:7009 | 9301:7009 | 9302:7009 | 9303:7009 | 9304:7009 | 9305:7009 |
| 9300:7010 | 9301:7010 | 9302:7010 | 9303:7010 | 9304:7010 | 9305:7010 |
| 9300:7011 | 9301:7011 | 9302:7011 | 9303:7011 | 9304:7011 | 9305:7011 |
| 9300:7012 | 9301:7012 | 9302:7012 | 9303:7012 | 9304:7012 | 9305:7012 |
| 9300:7013 | 9301:7013 | 9302:7013 | 9303:7013 | 9304:7013 | 9305:7013 |
| 9300:7014 | 9301:7014 | 9302:7014 | 9303:7014 | 9304:7014 | 9305:7014 |
| 9300:7015 | 9301:7015 | 9302:7015 | 9303:7015 | 9304:7015 | 9305:7015 |
| 9300:7016 | 9301:7016 | 9302:7016 | 9303:7016 | 9304:7016 | 9305:7016 |
| 9300:7017 | 9301:7017 | 9302:7017 | 9303:7017 | 9304:7017 | 9305:7017 |
| 9300:7018 | 9301:7018 | 9302:7018 | 9303:7018 | 9304:7018 | 9305:7018 |
| 9300:7019 | 9301:7019 | 9302:7019 | 9303:7019 | 9304:7019 | 9305:7019 |
| 9300:7020 | 9301:7020 | 9302:7020 | 9303:7020 | 9304:7020 | 9305:7020 |
| 9300:7021 | 9301:7021 | 9302:7021 | 9303:7021 | 9304:7021 | 9305:7021 |
| 9300:7022 | 9301:7022 | 9302:7022 | 9303:7022 | 9304:7022 | 9305:7022 |
| 9300:7023 | 9301:7023 | 9302:7023 | 9303:7023 | 9304:7023 | 9305:7023 |
| 9300:7024 | 9301:7024 | 9302:7024 | 9303:7024 | 9304:7024 | 9305:7024 |
| 9300:7025 | 9301:7025 | 9302:7025 | 9303:7025 | 9304:7025 | 9305:7025 |
| 9300:7026 | 9301:7026 | 9302:7026 | 9303:7026 | 9304:7026 | 9305:7026 |
| 9300:7027 | 9301:7027 | 9302:7027 | 9303:7027 | 9304:7027 | 9305:7027 |
| 9306:7000 | 9307:7000 | 9308:7000 | 9309:7000 | 9310:7000 | — |
| 9306:7001 | 9307:7001 | 9308:7001 | 9309:7001 | 9310:7001 | |
| 9306:7002 | 9307:7002 | 9308:7002 | 9309:7002 | 9310:7002 | |
| 9306:7003 | 9307:7003 | 9308:7003 | 9309:7003 | 9310:7003 | |
| 9306:7004 | 9307:7004 | 9308:7004 | 9309:7004 | 9310:7004 | |
| 9306:7005 | 9307:7005 | 9308:7005 | 9309:7005 | 9310:7005 | |
| 9306:7006 | 9307:7006 | 9308:7006 | 9309:7006 | 9310:7006 | |
| 9306:7007 | 9307:7007 | 9308:7007 | 9309:7007 | 9310:7007 | |
| 9306:7008 | 9307:7008 | 9308:7008 | 9309:7008 | 9310:7008 | |
| 9306:7009 | 9307:7009 | 9308:7009 | 9309:7009 | 9310:7009 | |
| 9306:7010 | 9307:7010 | 9308:7010 | 9309:7010 | 9310:7010 | |
| 9306:7011 | 9307:7011 | 9308:7011 | 9309:7011 | 9310:7011 | |
| 9306:7012 | 9307:7012 | 9308:7012 | 9309:7012 | 9310:7012 | |
| 9306:7013 | 9307:7013 | 9308:7013 | 9309:7013 | 9310:7013 | |
| 9306:7014 | 9307:7014 | 9308:7014 | 9309:7014 | 9310:7014 | |
| 9306:7015 | 9307:7015 | 9308:7015 | 9309:7015 | 9310:7015 | |
| 9306:7016 | 9307:7016 | 9308:7016 | 9309:7016 | 9310:7016 | |
| 9306:7017 | 9307:7017 | 9308:7017 | 9309:7017 | 9310:7017 | |
| 9306:7018 | 9307:7018 | 9308:7018 | 9309:7018 | 9310:7018 | |
| 9306:7019 | 9307:7019 | 9308:7019 | 9309:7019 | 9310:7019 | |
| 9306:7020 | 9307:7020 | 9308:7020 | 9309:7020 | 9310:7020 | |
| 9306:7021 | 9307:7021 | 9308:7021 | 9309:7021 | 9310:7021 | |
| 9306:7022 | 9307:7022 | 9308:7022 | 9309:7022 | 9310:7022 | |
| 9306:7023 | 9307:7023 | 9308:7023 | 9309:7023 | 9310:7023 | |
| 9306:7024 | 9307:7024 | 9308:7024 | 9309:7024 | 9310:7024 | |
| 9306:7025 | 9307:7025 | 9308:7025 | 9309:7025 | 9310:7025 | |
| 9306:7026 | 9307:7026 | 9308:7026 | 9309:7026 | 9310:7026 | |
| 9306:7027 | 9307:7027 | 9308:7027 | 9309:7027 | 9310:7027 | |

TABLE D

Example combinations of a compound X with a compound Y.

| X:Y | X:Y | X:Y | X:Y | X:Y | X:Y |
|---|---|---|---|---|---|
| 6000:9006 | 6040:9006 | 6000:9007 | 6040:9007 | 6000:9008 | 6040:9008 |
| 6001:9006 | 6041:9006 | 6001:9007 | 6041:9007 | 6001:9008 | 6041:9008 |
| 6002:9006 | 6042:9006 | 6002:9007 | 6042:9007 | 6002:9008 | 6042:9008 |
| 6003:9006 | 6043:9006 | 6003:9007 | 6043:9007 | 6003:9008 | 6043:9008 |
| 6004:9006 | 6044:9006 | 6004:9007 | 6044:9007 | 6004:9008 | 6044:9008 |
| 6005:9006 | 6045:9006 | 6005:9007 | 6045:9007 | 6005:9008 | 6045:9008 |
| 6006:9006 | 6046:9006 | 6006:9007 | 6046:9007 | 6006:9008 | 6046:9008 |
| 6007:9006 | 6047:9006 | 6007:9007 | 6047:9007 | 6007:9008 | 6047:9008 |
| 6008:9006 | 6048:9006 | 6008:9007 | 6048:9007 | 6008:9008 | 6048:9008 |
| 6009:9006 | 6049:9006 | 6009:9007 | 6049:9007 | 6009:9008 | 6049:9008 |
| 6010:9006 | 6050:9006 | 6010:9007 | 6050:9007 | 6010:9008 | 6050:9008 |
| 6011:9006 | 6051:9006 | 6011:9007 | 6051:9007 | 6011:9008 | 6051:9008 |
| 6012:9006 | 6052:9006 | 6012:9007 | 6052:9007 | 6012:9008 | 6052:9008 |
| 6013:9006 | 6053:9006 | 6013:9007 | 6053:9007 | 6013:9008 | 6053:9008 |
| 6014:9006 | 6054:9006 | 6014:9007 | 6054:9007 | 6014:9008 | 6054:9008 |
| 6015:9006 | 6055:9006 | 6015:9007 | 6055:9007 | 6015:9008 | 6055:9008 |
| 6016:9006 | 6056:9006 | 6016:9007 | 6056:9007 | 6016:9008 | 6056:9008 |
| 6017:9006 | 6057:9006 | 6017:9007 | 6057:9007 | 6017:9008 | 6057:9008 |
| 6018:9006 | 6058:9006 | 6018:9007 | 6058:9007 | 6018:9008 | 6058:9008 |
| 6019:9006 | 6059:9006 | 6019:9007 | 6059:9007 | 6019:9008 | 6059:9008 |
| 6020:9006 | 6060:9006 | 6020:9007 | 6060:9007 | 6020:9008 | 6060:9008 |

TABLE D-continued

Example combinations of a compound X with a compound Y.

| X:Y | X:Y | X:Y | X:Y | X:Y | X:Y |
|---|---|---|---|---|---|
| 6021:9006 | 6061:9006 | 6021:9007 | 6061:9007 | 6021:9008 | 6061:9008 |
| 6022:9006 | 6062:9006 | 6022:9007 | 6062:9007 | 6022:9008 | 6062:9008 |
| 6023:9006 | 6063:9006 | 6023:9007 | 6063:9007 | 6023:9008 | 6063:9008 |
| 6024:9006 | 6064:9006 | 6024:9007 | 6064:9007 | 6024:9008 | 6064:9008 |
| 6025:9006 | 6065:9006 | 6025:9007 | 6065:9007 | 6025:9008 | 6065:9008 |
| 6026:9006 | 6066:9006 | 6026:9007 | 6066:9007 | 6026:9008 | 6066:9008 |
| 6027:9006 | 6067:9006 | 6027:9007 | 6067:9007 | 6027:9008 | 6067:9008 |
| 6028:9006 | 6068:9006 | 6028:9007 | 6068:9007 | 6028:9008 | 6068:9008 |
| 6029:9006 | 6069:9006 | 6029:9007 | 6069:9007 | 6029:9008 | 6069:9008 |
| 6030:9006 | 6070:9006 | 6030:9007 | 6070:9007 | 6030:9008 | 6070:9008 |
| 6031:9006 | 6071:9006 | 6031:9007 | 6071:9007 | 6031:9008 | 6071:9008 |
| 6032:9006 | 6072:9006 | 6032:9007 | 6072:9007 | 6032:9008 | 6072:9008 |
| 6033:9006 | 6073:9006 | 6033:9007 | 6073:9007 | 6033:9008 | 6073:9008 |
| 6034:9006 | 6074:9006 | 6034:9007 | 6074:9007 | 6034:9008 | 6074:9008 |
| 6035:9006 | 6075:9006 | 6035:9007 | 6075:9007 | 6035:9008 | 6075:9008 |
| 6036:9006 | 6076:9006 | 6036:9007 | 6076:9007 | 6036:9008 | 6076:9008 |
| 6037:9006 | 6077:9006 | 6037:9007 | 6077:9007 | 6037:9008 | 6077:9008 |
| 6038:9006 | 6078:9006 | 6038:9007 | 6078:9007 | 6038:9008 | 6078:9008 |
| 6039:9006 | | 6039:9007 | | 6039:9008 | |
| 6000:9018 | 6040:9018 | 6000:9020 | 6040:9020 | 6000:9021 | 6040:9021 |
| 6001:9018 | 6041:9018 | 6001:9020 | 6041:9020 | 6001:9021 | 6041:9021 |
| 6002:9018 | 6042:9018 | 6002:9020 | 6042:9020 | 6002:9021 | 6042:9021 |
| 6003:9018 | 6043:9018 | 6003:9020 | 6043:9020 | 6003:9021 | 6043:9021 |
| 6004:9018 | 6044:9018 | 6004:9020 | 6044:9020 | 6004:9021 | 6044:9021 |
| 6005:9018 | 6045:9018 | 6005:9020 | 6045:9020 | 6005:9021 | 6045:9021 |
| 6006:9018 | 6046:9018 | 6006:9020 | 6046:9020 | 6006:9021 | 6046:9021 |
| 6007:9018 | 6047:9018 | 6007:9020 | 6047:9020 | 6007:9021 | 6047:9021 |
| 6008:9018 | 6048:9018 | 6008:9020 | 6048:9020 | 6008:9021 | 6048:9021 |
| 6009:9018 | 6049:9018 | 6009:9020 | 6049:9020 | 6009:9021 | 6049:9021 |
| 6010:9018 | 6050:9018 | 6010:9020 | 6050:9020 | 6010:9021 | 6050:9021 |
| 6011:9018 | 6051:9018 | 6011:9020 | 6051:9020 | 6011:9021 | 6051:9021 |
| 6012:9018 | 6052:9018 | 6012:9020 | 6052:9020 | 6012:9021 | 6052:9021 |
| 6013:9018 | 6053:9018 | 6013:9020 | 6053:9020 | 6013:9021 | 6053:9021 |
| 6014:9018 | 6054:9018 | 6014:9020 | 6054:9020 | 6014:9021 | 6054:9021 |
| 6015:9018 | 6055:9018 | 6015:9020 | 6055:9020 | 6015:9021 | 6055:9021 |
| 6016:9018 | 6056:9018 | 6016:9020 | 6056:9020 | 6016:9021 | 6056:9021 |
| 6017:9018 | 6057:9018 | 6017:9020 | 6057:9020 | 6017:9021 | 6057:9021 |
| 6018:9018 | 6058:9018 | 6018:9020 | 6058:9020 | 6018:9021 | 6058:9021 |
| 6019:9018 | 6059:9018 | 6019:9020 | 6059:9020 | 6019:9021 | 6059:9021 |
| 6020:9018 | 6060:9018 | 6020:9020 | 6060:9020 | 6020:9021 | 6060:9021 |
| 6021:9018 | 6061:9018 | 6021:9020 | 6061:9020 | 6021:9021 | 6061:9021 |
| 6022:9018 | 6062:9018 | 6022:9020 | 6062:9020 | 6022:9021 | 6062:9021 |
| 6023:9018 | 6063:9018 | 6023:9020 | 6063:9020 | 6023:9021 | 6063:9021 |
| 6024:9018 | 6064:9018 | 6024:9020 | 6064:9020 | 6024:9021 | 6064:9021 |
| 6025:9018 | 6065:9018 | 6025:9020 | 6065:9020 | 6025:9021 | 6065:9021 |
| 6026:9018 | 6066:9018 | 6026:9020 | 6066:9020 | 6026:9021 | 6066:9021 |
| 6027:9018 | 6067:9018 | 6027:9020 | 6067:9020 | 6027:9021 | 6067:9021 |
| 6028:9018 | 6068:9018 | 6028:9020 | 6068:9020 | 6028:9021 | 6068:9021 |
| 6029:9018 | 6069:9018 | 6029:9020 | 6069:9020 | 6029:9021 | 6069:9021 |
| 6030:9018 | 6070:9018 | 6030:9020 | 6070:9020 | 6030:9021 | 6070:9021 |
| 6031:9018 | 6071:9018 | 6031:9020 | 6071:9020 | 6031:9021 | 6071:9021 |
| 6032:9018 | 6072:9018 | 6032:9020 | 6072:9020 | 6032:9021 | 6072:9021 |
| 6033:9018 | 6073:9018 | 6033:9020 | 6073:9020 | 6033:9021 | 6073:9021 |
| 6034:9018 | 6074:9018 | 6034:9020 | 6074:9020 | 6034:9021 | 6074:9021 |
| 6035:9018 | 6075:9018 | 6035:9020 | 6075:9020 | 6035:9021 | 6075:9021 |
| 6036:9018 | 6076:9018 | 6036:9020 | 6076:9020 | 6036:9021 | 6076:9021 |
| 6037:9018 | 6077:9018 | 6037:9020 | 6077:9020 | 6037:9021 | 6077:9021 |
| 6038:9018 | 6078:9018 | 6038:9020 | 6078:9020 | 6038:9021 | 6078:9021 |
| 6039:9018 | | 6039:9020 | | 6039:9021 | |
| 6000:9025 | 6040:9025 | 6000:9026 | 6040:9026 | 6000:9036 | 6040:9036 |
| 6001:9025 | 6041:9025 | 6001:9026 | 6041:9026 | 6001:9036 | 6041:9036 |
| 6002:9025 | 6042:9025 | 6002:9026 | 6042:9026 | 6002:9036 | 6042:9036 |
| 6003:9025 | 6043:9025 | 6003:9026 | 6043:9026 | 6003:9036 | 6043:9036 |
| 6004:9025 | 6044:9025 | 6004:9026 | 6044:9026 | 6004:9036 | 6044:9036 |
| 6005:9025 | 6045:9025 | 6005:9026 | 6045:9026 | 6005:9036 | 6045:9036 |
| 6006:9025 | 6046:9025 | 6006:9026 | 6046:9026 | 6006:9036 | 6046:9036 |
| 6007:9025 | 6047:9025 | 6007:9026 | 6047:9026 | 6007:9036 | 6047:9036 |
| 6008:9025 | 6048:9025 | 6008:9026 | 6048:9026 | 6008:9036 | 6048:9036 |
| 6009:9025 | 6049:9025 | 6009:9026 | 6049:9026 | 6009:9036 | 6049:9036 |
| 6010:9025 | 6050:9025 | 6010:9026 | 6050:9026 | 6010:9036 | 6050:9036 |
| 6011:9025 | 6051:9025 | 6011:9026 | 6051:9026 | 6011:9036 | 6051:9036 |
| 6012:9025 | 6052:9025 | 6012:9026 | 6052:9026 | 6012:9036 | 6052:9036 |
| 6013:9025 | 6053:9025 | 6013:9026 | 6053:9026 | 6013:9036 | 6053:9036 |
| 6014:9025 | 6054:9025 | 6014:9026 | 6054:9026 | 6014:9036 | 6054:9036 |
| 6015:9025 | 6055:9025 | 6015:9026 | 6055:9026 | 6015:9036 | 6055:9036 |
| 6016:9025 | 6056:9025 | 6016:9026 | 6056:9026 | 6016:9036 | 6056:9036 |
| 6017:9025 | 6057:9025 | 6017:9026 | 6057:9026 | 6017:9036 | 6057:9036 |
| 6018:9025 | 6058:9025 | 6018:9026 | 6058:9026 | 6018:9036 | 6058:9036 |
| 6019:9025 | 6059:9025 | 6019:9026 | 6059:9026 | 6019:9036 | 6059:9036 |
| 6020:9025 | 6060:9025 | 6020:9026 | 6060:9026 | 6020:9036 | 6060:9036 |
| 6021:9025 | 6061:9025 | 6021:9026 | 6061:9026 | 6021:9036 | 6061:9036 |
| 6022:9025 | 6062:9025 | 6022:9026 | 6062:9026 | 6022:9036 | 6062:9036 |
| 6023:9025 | 6063:9025 | 6023:9026 | 6063:9026 | 6023:9036 | 6063:9036 |
| 6024:9025 | 6064:9025 | 6024:9026 | 6064:9026 | 6024:9036 | 6064:9036 |
| 6025:9025 | 6065:9025 | 6025:9026 | 6065:9026 | 6025:9036 | 6065:9036 |
| 6026:9025 | 6066:9025 | 6026:9026 | 6066:9026 | 6026:9036 | 6066:9036 |
| 6027:9025 | 6067:9025 | 6027:9026 | 6067:9026 | 6027:9036 | 6067:9036 |
| 6028:9025 | 6068:9025 | 6028:9026 | 6068:9026 | 6028:9036 | 6068:9036 |
| 6029:9025 | 6069:9025 | 6029:9026 | 6069:9026 | 6029:9036 | 6069:9036 |
| 6030:9025 | 6070:9025 | 6030:9026 | 6070:9026 | 6030:9036 | 6070:9036 |
| 6031:9025 | 6071:9025 | 6031:9026 | 6071:9026 | 6031:9036 | 6071:9036 |
| 6032:9025 | 6072:9025 | 6032:9026 | 6072:9026 | 6032:9036 | 6072:9036 |
| 6033:9025 | 6073:9025 | 6033:9026 | 6073:9026 | 6033:9036 | 6073:9036 |
| 6034:9025 | 6074:9025 | 6034:9026 | 6074:9026 | 6034:9036 | 6074:9036 |
| 6035:9025 | 6075:9025 | 6035:9026 | 6075:9026 | 6035:9036 | 6075:9036 |
| 6036:9025 | 6076:9025 | 6036:9026 | 6076:9026 | 6036:9036 | 6076:9036 |
| 6037:9025 | 6077:9025 | 6037:9026 | 6077:9026 | 6037:9036 | 6077:9036 |
| 6038:9025 | 6078:9025 | 6038:9026 | 6078:9026 | 6038:9036 | 6078:9036 |
| 6039:9025 | | 6039:9026 | | 6039:9036 | |
| 6000:9038 | 6040:9038 | 6000:9039 | 6040:9039 | 6000:9040 | 6040:9040 |
| 6001:9038 | 6041:9038 | 6001:9039 | 6041:9039 | 6001:9040 | 6041:9040 |
| 6002:9038 | 6042:9038 | 6002:9039 | 6042:9039 | 6002:9040 | 6042:9040 |
| 6003:9038 | 6043:9038 | 6003:9039 | 6043:9039 | 6003:9040 | 6043:9040 |
| 6004:9038 | 6044:9038 | 6004:9039 | 6044:9039 | 6004:9040 | 6044:9040 |
| 6005:9038 | 6045:9038 | 6005:9039 | 6045:9039 | 6005:9040 | 6045:9040 |
| 6006:9038 | 6046:9038 | 6006:9039 | 6046:9039 | 6006:9040 | 6046:9040 |
| 6007:9038 | 6047:9038 | 6007:9039 | 6047:9039 | 6007:9040 | 6047:9040 |
| 6008:9038 | 6048:9038 | 6008:9039 | 6048:9039 | 6008:9040 | 6048:9040 |
| 6009:9038 | 6049:9038 | 6009:9039 | 6049:9039 | 6009:9040 | 6049:9040 |
| 6010:9038 | 6050:9038 | 6010:9039 | 6050:9039 | 6010:9040 | 6050:9040 |
| 6011:9038 | 6051:9038 | 6011:9039 | 6051:9039 | 6011:9040 | 6051:9040 |
| 6012:9038 | 6052:9038 | 6012:9039 | 6052:9039 | 6012:9040 | 6052:9040 |
| 6013:9038 | 6053:9038 | 6013:9039 | 6053:9039 | 6013:9040 | 6053:9040 |
| 6014:9038 | 6054:9038 | 6014:9039 | 6054:9039 | 6014:9040 | 6054:9040 |
| 6015:9038 | 6055:9038 | 6015:9039 | 6055:9039 | 6015:9040 | 6055:9040 |
| 6016:9038 | 6056:9038 | 6016:9039 | 6056:9039 | 6016:9040 | 6056:9040 |
| 6017:9038 | 6057:9038 | 6017:9039 | 6057:9039 | 6017:9040 | 6057:9040 |
| 6018:9038 | 6058:9038 | 6018:9039 | 6058:9039 | 6018:9040 | 6058:9040 |
| 6019:9038 | 6059:9038 | 6019:9039 | 6059:9039 | 6019:9040 | 6059:9040 |
| 6020:9038 | 6060:9038 | 6020:9039 | 6060:9039 | 6020:9040 | 6060:9040 |
| 6021:9038 | 6061:9038 | 6021:9039 | 6061:9039 | 6021:9040 | 6061:9040 |
| 6022:9038 | 6062:9038 | 6022:9039 | 6062:9039 | 6022:9040 | 6062:9040 |
| 6023:9038 | 6063:9038 | 6023:9039 | 6063:9039 | 6023:9040 | 6063:9040 |
| 6024:9038 | 6064:9038 | 6024:9039 | 6064:9039 | 6024:9040 | 6064:9040 |
| 6025:9038 | 6065:9038 | 6025:9039 | 6065:9039 | 6025:9040 | 6065:9040 |
| 6026:9038 | 6066:9038 | 6026:9039 | 6066:9039 | 6026:9040 | 6066:9040 |
| 6027:9038 | 6067:9038 | 6027:9039 | 6067:9039 | 6027:9040 | 6067:9040 |
| 6028:9038 | 6068:9038 | 6028:9039 | 6068:9039 | 6028:9040 | 6068:9040 |
| 6029:9038 | 6069:9038 | 6029:9039 | 6069:9039 | 6029:9040 | 6069:9040 |
| 6030:9038 | 6070:9038 | 6030:9039 | 6070:9039 | 6030:9040 | 6070:9040 |
| 6031:9038 | 6071:9038 | 6031:9039 | 6071:9039 | 6031:9040 | 6071:9040 |
| 6032:9038 | 6072:9038 | 6032:9039 | 6072:9039 | 6032:9040 | 6072:9040 |
| 6033:9038 | 6073:9038 | 6033:9039 | 6073:9039 | 6033:9040 | 6073:9040 |
| 6034:9038 | 6074:9038 | 6034:9039 | 6074:9039 | 6034:9040 | 6074:9040 |
| 6035:9038 | 6075:9038 | 6035:9039 | 6075:9039 | 6035:9040 | 6075:9040 |
| 6036:9038 | 6076:9038 | 6036:9039 | 6076:9039 | 6036:9040 | 6076:9040 |
| 6037:9038 | 6077:9038 | 6037:9039 | 6077:9039 | 6037:9040 | 6077:9040 |
| 6038:9038 | 6078:9038 | 6038:9039 | 6078:9039 | 6038:9040 | 6078:9040 |
| 6039:9038 | | 6039:9039 | | 6039:9040 | |
| 6000:9041 | 6040:9041 | 6000:9042 | 6040:9042 | 6000:9043 | 6040:9043 |
| 6001:9041 | 6041:9041 | 6001:9042 | 6041:9042 | 6001:9043 | 6041:9043 |
| 6002:9041 | 6042:9041 | 6002:9042 | 6042:9042 | 6002:9043 | 6042:9043 |
| 6003:9041 | 6043:9041 | 6003:9042 | 6043:9042 | 6003:9043 | 6043:9043 |
| 6004:9041 | 6044:9041 | 6004:9042 | 6044:9042 | 6004:9043 | 6044:9043 |
| 6005:9041 | 6045:9041 | 6005:9042 | 6045:9042 | 6005:9043 | 6045:9043 |
| 6006:9041 | 6046:9041 | 6006:9042 | 6046:9042 | 6006:9043 | 6046:9043 |
| 6007:9041 | 6047:9041 | 6007:9042 | 6047:9042 | 6007:9043 | 6047:9043 |
| 6008:9041 | 6048:9041 | 6008:9042 | 6048:9042 | 6008:9043 | 6048:9043 |
| 6009:9041 | 6049:9041 | 6009:9042 | 6049:9042 | 6009:9043 | 6049:9043 |
| 6010:9041 | 6050:9041 | 6010:9042 | 6050:9042 | 6010:9043 | 6050:9043 |
| 6011:9041 | 6051:9041 | 6011:9042 | 6051:9042 | 6011:9043 | 6051:9043 |
| 6012:9041 | 6052:9041 | 6012:9042 | 6052:9042 | 6012:9043 | 6052:9043 |

TABLE D-continued

Example combinations of a compound X with a compound Y.

| X:Y | X:Y | X:Y | X:Y | X:Y | X:Y |
|---|---|---|---|---|---|
| 6013:9041 | 6053:9041 | 6013:9042 | 6053:9042 | 6013:9043 | 6053:9043 |
| 6014:9041 | 6054:9041 | 6014:9042 | 6054:9042 | 6014:9043 | 6054:9043 |
| 6015:9041 | 6055:9041 | 6015:9042 | 6055:9042 | 6015:9043 | 6055:9043 |
| 6016:9041 | 6056:9041 | 6016:9042 | 6056:9042 | 6016:9043 | 6056:9043 |
| 6017:9041 | 6057:9041 | 6017:9042 | 6057:9042 | 6017:9043 | 6057:9043 |
| 6018:9041 | 6058:9041 | 6018:9042 | 6058:9042 | 6018:9043 | 6058:9043 |
| 6019:9041 | 6059:9041 | 6019:9042 | 6059:9042 | 6019:9043 | 6059:9043 |
| 6020:9041 | 6060:9041 | 6020:9042 | 6060:9042 | 6020:9043 | 6060:9043 |
| 6021:9041 | 6061:9041 | 6021:9042 | 6061:9042 | 6021:9043 | 6061:9043 |
| 6022:9041 | 6062:9041 | 6022:9042 | 6062:9042 | 6022:9043 | 6062:9043 |
| 6023:9041 | 6063:9041 | 6023:9042 | 6063:9042 | 6023:9043 | 6063:9043 |
| 6024:9041 | 6064:9041 | 6024:9042 | 6064:9042 | 6024:9043 | 6064:9043 |
| 6025:9041 | 6065:9041 | 6025:9042 | 6065:9042 | 6025:9043 | 6065:9043 |
| 6026:9041 | 6066:9041 | 6026:9042 | 6066:9042 | 6026:9043 | 6066:9043 |
| 6027:9041 | 6067:9041 | 6027:9042 | 6067:9042 | 6027:9043 | 6067:9043 |
| 6028:9041 | 6068:9041 | 6028:9042 | 6068:9042 | 6028:9043 | 6068:9043 |
| 6029:9041 | 6069:9041 | 6029:9042 | 6069:9042 | 6029:9043 | 6069:9043 |
| 6030:9041 | 6070:9041 | 6030:9042 | 6070:9042 | 6030:9043 | 6070:9043 |
| 6031:9041 | 6071:9041 | 6031:9042 | 6071:9042 | 6031:9043 | 6071:9043 |
| 6032:9041 | 6072:9041 | 6032:9042 | 6072:9042 | 6032:9043 | 6072:9043 |
| 6033:9041 | 6073:9041 | 6033:9042 | 6073:9042 | 6033:9043 | 6073:9043 |
| 6034:9041 | 6074:9041 | 6034:9042 | 6074:9042 | 6034:9043 | 6074:9043 |
| 6035:9041 | 6075:9041 | 6035:9042 | 6075:9042 | 6035:9043 | 6075:9043 |
| 6036:9041 | 6076:9041 | 6036:9042 | 6076:9042 | 6036:9043 | 6076:9043 |
| 6037:9041 | 6077:9041 | 6037:9042 | 6077:9042 | 6037:9043 | 6077:9043 |
| 6038:9041 | 6078:9041 | 6038:9042 | 6078:9042 | 6038:9043 | 6078:9043 |
| 6039:9041 | | 6039:9042 | | 6039:9043 | |
| 6000:9044 | 6040:9044 | 6000:9045 | 6040:9045 | 6000:9047 | 6040:9047 |
| 6001:9044 | 6041:9044 | 6001:9045 | 6041:9045 | 6001:9047 | 6041:9047 |
| 6002:9044 | 6042:9044 | 6002:9045 | 6042:9045 | 6002:9047 | 6042:9047 |
| 6003:9044 | 6043:9044 | 6003:9045 | 6043:9045 | 6003:9047 | 6043:9047 |
| 6004:9044 | 6044:9044 | 6004:9045 | 6044:9045 | 6004:9047 | 6044:9047 |
| 6005:9044 | 6045:9044 | 6005:9045 | 6045:9045 | 6005:9047 | 6045:9047 |
| 6006:9044 | 6046:9044 | 6006:9045 | 6046:9045 | 6006:9047 | 6046:9047 |
| 6007:9044 | 6047:9044 | 6007:9045 | 6047:9045 | 6007:9047 | 6047:9047 |
| 6008:9044 | 6048:9044 | 6008:9045 | 6048:9045 | 6008:9047 | 6048:9047 |
| 6009:9044 | 6049:9044 | 6009:9045 | 6049:9045 | 6009:9047 | 6049:9047 |
| 6010:9044 | 6050:9044 | 6010:9045 | 6050:9045 | 6010:9047 | 6050:9047 |
| 6011:9044 | 6051:9044 | 6011:9045 | 6051:9045 | 6011:9047 | 6051:9047 |
| 6012:9044 | 6052:9044 | 6012:9045 | 6052:9045 | 6012:9047 | 6052:9047 |
| 6013:9044 | 6053:9044 | 6013:9045 | 6053:9045 | 6013:9047 | 6053:9047 |
| 6014:9044 | 6054:9044 | 6014:9045 | 6054:9045 | 6014:9047 | 6054:9047 |
| 6015:9044 | 6055:9044 | 6015:9045 | 6055:9045 | 6015:9047 | 6055:9047 |
| 6016:9044 | 6056:9044 | 6016:9045 | 6056:9045 | 6016:9047 | 6056:9047 |
| 6017:9044 | 6057:9044 | 6017:9045 | 6057:9045 | 6017:9047 | 6057:9047 |
| 6018:9044 | 6058:9044 | 6018:9045 | 6058:9045 | 6018:9047 | 6058:9047 |
| 6019:9044 | 6059:9044 | 6019:9045 | 6059:9045 | 6019:9047 | 6059:9047 |
| 6020:9044 | 6060:9044 | 6020:9045 | 6060:9045 | 6020:9047 | 6060:9047 |
| 6021:9044 | 6061:9044 | 6021:9045 | 6061:9045 | 6021:9047 | 6061:9047 |
| 6022:9044 | 6062:9044 | 6022:9045 | 6062:9045 | 6022:9047 | 6062:9047 |
| 6023:9044 | 6063:9044 | 6023:9045 | 6063:9045 | 6023:9047 | 6063:9047 |
| 6024:9044 | 6064:9044 | 6024:9045 | 6064:9045 | 6024:9047 | 6064:9047 |
| 6025:9044 | 6065:9044 | 6025:9045 | 6065:9045 | 6025:9047 | 6065:9047 |
| 6026:9044 | 6066:9044 | 6026:9045 | 6066:9045 | 6026:9047 | 6066:9047 |
| 6027:9044 | 6067:9044 | 6027:9045 | 6067:9045 | 6027:9047 | 6067:9047 |
| 6028:9044 | 6068:9044 | 6028:9045 | 6068:9045 | 6028:9047 | 6068:9047 |
| 6029:9044 | 6069:9044 | 6029:9045 | 6069:9045 | 6029:9047 | 6069:9047 |
| 6030:9044 | 6070:9044 | 6030:9045 | 6070:9045 | 6030:9047 | 6070:9047 |
| 6031:9044 | 6071:9044 | 6031:9045 | 6071:9045 | 6031:9047 | 6071:9047 |
| 6032:9044 | 6072:9044 | 6032:9045 | 6072:9045 | 6032:9047 | 6072:9047 |
| 6033:9044 | 6073:9044 | 6033:9045 | 6073:9045 | 6033:9047 | 6073:9047 |
| 6034:9044 | 6074:9044 | 6034:9045 | 6074:9045 | 6034:9047 | 6074:9047 |
| 6035:9044 | 6075:9044 | 6035:9045 | 6075:9045 | 6035:9047 | 6075:9047 |
| 6036:9044 | 6076:9044 | 6036:9045 | 6076:9045 | 6036:9047 | 6076:9047 |
| 6037:9044 | 6077:9044 | 6037:9045 | 6077:9045 | 6037:9047 | 6077:9047 |
| 6038:9044 | 6078:9044 | 6038:9045 | 6078:9045 | 6038:9047 | 6078:9047 |
| 6039:9044 | | 6039:9045 | | 6039:9047 | |
| 6000:9048 | 6040:9048 | 6000:9049 | 6040:9049 | 6000:9051 | 6040:9051 |
| 6001:9048 | 6041:9048 | 6001:9049 | 6041:9049 | 6001:9051 | 6041:9051 |
| 6002:9048 | 6042:9048 | 6002:9049 | 6042:9049 | 6002:9051 | 6042:9051 |
| 6003:9048 | 6043:9048 | 6003:9049 | 6043:9049 | 6003:9051 | 6043:9051 |
| 6004:9048 | 6044:9048 | 6004:9049 | 6044:9049 | 6004:9051 | 6044:9051 |
| 6005:9048 | 6045:9048 | 6005:9049 | 6045:9049 | 6005:9051 | 6045:9051 |
| 6006:9048 | 6046:9048 | 6006:9049 | 6046:9049 | 6006:9051 | 6046:9051 |
| 6007:9048 | 6047:9048 | 6007:9049 | 6047:9049 | 6007:9051 | 6047:9051 |
| 6008:9048 | 6048:9048 | 6008:9049 | 6048:9049 | 6008:9051 | 6048:9051 |
| 6009:9048 | 6049:9048 | 6009:9049 | 6049:9049 | 6009:9051 | 6049:9051 |
| 6010:9048 | 6050:9048 | 6010:9049 | 6050:9049 | 6010:9051 | 6050:9051 |
| 6011:9048 | 6051:9048 | 6011:9049 | 6051:9049 | 6011:9051 | 6051:9051 |
| 6012:9048 | 6052:9048 | 6012:9049 | 6052:9049 | 6012:9051 | 6052:9051 |
| 6013:9048 | 6053:9048 | 6013:9049 | 6053:9049 | 6013:9051 | 6053:9051 |
| 6014:9048 | 6054:9048 | 6014:9049 | 6054:9049 | 6014:9051 | 6054:9051 |
| 6015:9048 | 6055:9048 | 6015:9049 | 6055:9049 | 6015:9051 | 6055:9051 |
| 6016:9048 | 6056:9048 | 6016:9049 | 6056:9049 | 6016:9051 | 6056:9051 |
| 6017:9048 | 6057:9048 | 6017:9049 | 6057:9049 | 6017:9051 | 6057:9051 |
| 6018:9048 | 6058:9048 | 6018:9049 | 6058:9049 | 6018:9051 | 6058:9051 |
| 6019:9048 | 6059:9048 | 6019:9049 | 6059:9049 | 6019:9051 | 6059:9051 |
| 6020:9048 | 6060:9048 | 6020:9049 | 6060:9049 | 6020:9051 | 6060:9051 |
| 6021:9048 | 6061:9048 | 6021:9049 | 6061:9049 | 6021:9051 | 6061:9051 |
| 6022:9048 | 6062:9048 | 6022:9049 | 6062:9049 | 6022:9051 | 6062:9051 |
| 6023:9048 | 6063:9048 | 6023:9049 | 6063:9049 | 6023:9051 | 6063:9051 |
| 6024:9048 | 6064:9048 | 6024:9049 | 6064:9049 | 6024:9051 | 6064:9051 |
| 6025:9048 | 6065:9048 | 6025:9049 | 6065:9049 | 6025:9051 | 6065:9051 |
| 6026:9048 | 6066:9048 | 6026:9049 | 6066:9049 | 6026:9051 | 6066:9051 |
| 6027:9048 | 6067:9048 | 6027:9049 | 6067:9049 | 6027:9051 | 6067:9051 |
| 6028:9048 | 6068:9048 | 6028:9049 | 6068:9049 | 6028:9051 | 6068:9051 |
| 6029:9048 | 6069:9048 | 6029:9049 | 6069:9049 | 6029:9051 | 6069:9051 |
| 6030:9048 | 6070:9048 | 6030:9049 | 6070:9049 | 6030:9051 | 6070:9051 |
| 6031:9048 | 6071:9048 | 6031:9049 | 6071:9049 | 6031:9051 | 6071:9051 |
| 6032:9048 | 6072:9048 | 6032:9049 | 6072:9049 | 6032:9051 | 6072:9051 |
| 6033:9048 | 6073:9048 | 6033:9049 | 6073:9049 | 6033:9051 | 6073:9051 |
| 6034:9048 | 6074:9048 | 6034:9049 | 6074:9049 | 6034:9051 | 6074:9051 |
| 6035:9048 | 6075:9048 | 6035:9049 | 6075:9049 | 6035:9051 | 6075:9051 |
| 6036:9048 | 6076:9048 | 6036:9049 | 6076:9049 | 6036:9051 | 6076:9051 |
| 6037:9048 | 6077:9048 | 6037:9049 | 6077:9049 | 6037:9051 | 6077:9051 |
| 6038:9048 | 6078:9048 | 6038:9049 | 6078:9049 | 6038:9051 | 6078:9051 |
| 6039:9048 | | 6039:9049 | | 6039:9051 | |
| 6000:9052 | 6040:9052 | 6000:9053 | 6040:9053 | 6000:9054 | 6040:9054 |
| 6001:9052 | 6041:9052 | 6001:9053 | 6041:9053 | 6001:9054 | 6041:9054 |
| 6002:9052 | 6042:9052 | 6002:9053 | 6042:9053 | 6002:9054 | 6042:9054 |
| 6003:9052 | 6043:9052 | 6003:9053 | 6043:9053 | 6003:9054 | 6043:9054 |
| 6004:9052 | 6044:9052 | 6004:9053 | 6044:9053 | 6004:9054 | 6044:9054 |
| 6005:9052 | 6045:9052 | 6005:9053 | 6045:9053 | 6005:9054 | 6045:9054 |
| 6006:9052 | 6046:9052 | 6006:9053 | 6046:9053 | 6006:9054 | 6046:9054 |
| 6007:9052 | 6047:9052 | 6007:9053 | 6047:9053 | 6007:9054 | 6047:9054 |
| 6008:9052 | 6048:9052 | 6008:9053 | 6048:9053 | 6008:9054 | 6048:9054 |
| 6009:9052 | 6049:9052 | 6009:9053 | 6049:9053 | 6009:9054 | 6049:9054 |
| 6010:9052 | 6050:9052 | 6010:9053 | 6050:9053 | 6010:9054 | 6050:9054 |
| 6011:9052 | 6051:9052 | 6011:9053 | 6051:9053 | 6011:9054 | 6051:9054 |
| 6012:9052 | 6052:9052 | 6012:9053 | 6052:9053 | 6012:9054 | 6052:9054 |
| 6013:9052 | 6053:9052 | 6013:9053 | 6053:9053 | 6013:9054 | 6053:9054 |
| 6014:9052 | 6054:9052 | 6014:9053 | 6054:9053 | 6014:9054 | 6054:9054 |
| 6015:9052 | 6055:9052 | 6015:9053 | 6055:9053 | 6015:9054 | 6055:9054 |
| 6016:9052 | 6056:9052 | 6016:9053 | 6056:9053 | 6016:9054 | 6056:9054 |
| 6017:9052 | 6057:9052 | 6017:9053 | 6057:9053 | 6017:9054 | 6057:9054 |
| 6018:9052 | 6058:9052 | 6018:9053 | 6058:9053 | 6018:9054 | 6058:9054 |
| 6019:9052 | 6059:9052 | 6019:9053 | 6059:9053 | 6019:9054 | 6059:9054 |
| 6020:9052 | 6060:9052 | 6020:9053 | 6060:9053 | 6020:9054 | 6060:9054 |
| 6021:9052 | 6061:9052 | 6021:9053 | 6061:9053 | 6021:9054 | 6061:9054 |
| 6022:9052 | 6062:9052 | 6022:9053 | 6062:9053 | 6022:9054 | 6062:9054 |
| 6023:9052 | 6063:9052 | 6023:9053 | 6063:9053 | 6023:9054 | 6063:9054 |
| 6024:9052 | 6064:9052 | 6024:9053 | 6064:9053 | 6024:9054 | 6064:9054 |
| 6025:9052 | 6065:9052 | 6025:9053 | 6065:9053 | 6025:9054 | 6065:9054 |
| 6026:9052 | 6066:9052 | 6026:9053 | 6066:9053 | 6026:9054 | 6066:9054 |
| 6027:9052 | 6067:9052 | 6027:9053 | 6067:9053 | 6027:9054 | 6067:9054 |
| 6028:9052 | 6068:9052 | 6028:9053 | 6068:9053 | 6028:9054 | 6068:9054 |
| 6029:9052 | 6069:9052 | 6029:9053 | 6069:9053 | 6029:9054 | 6069:9054 |
| 6030:9052 | 6070:9052 | 6030:9053 | 6070:9053 | 6030:9054 | 6070:9054 |
| 6031:9052 | 6071:9052 | 6031:9053 | 6071:9053 | 6031:9054 | 6071:9054 |
| 6032:9052 | 6072:9052 | 6032:9053 | 6072:9053 | 6032:9054 | 6072:9054 |
| 6033:9052 | 6073:9052 | 6033:9053 | 6073:9053 | 6033:9054 | 6073:9054 |
| 6034:9052 | 6074:9052 | 6034:9053 | 6074:9053 | 6034:9054 | 6074:9054 |
| 6035:9052 | 6075:9052 | 6035:9053 | 6075:9053 | 6035:9054 | 6075:9054 |
| 6036:9052 | 6076:9052 | 6036:9053 | 6076:9053 | 6036:9054 | 6076:9054 |
| 6037:9052 | 6077:9052 | 6037:9053 | 6077:9053 | 6037:9054 | 6077:9054 |
| 6038:9052 | 6078:9052 | 6038:9053 | 6078:9053 | 6038:9054 | 6078:9054 |
| 6039:9052 | | 6039:9053 | | 6039:9054 | |
| 6000:9055 | 6040:9055 | 6000:9056 | 6040:9056 | 6000:9057 | 6040:9057 |
| 6001:9055 | 6041:9055 | 6001:9056 | 6041:9056 | 6001:9057 | 6041:9057 |
| 6002:9055 | 6042:9055 | 6002:9056 | 6042:9056 | 6002:9057 | 6042:9057 |
| 6003:9055 | 6043:9055 | 6003:9056 | 6043:9056 | 6003:9057 | 6043:9057 |
| 6004:9055 | 6044:9055 | 6004:9056 | 6044:9056 | 6004:9057 | 6044:9057 |

TABLE D-continued

Example combinations of a compound X with a compound Y.

| X:Y | X:Y | X:Y | X:Y | X:Y | X:Y |
|---|---|---|---|---|---|
| 6005:9055 | 6045:9055 | 6005:9056 | 6045:9056 | 6005:9057 | 6045:9057 |
| 6006:9055 | 6046:9055 | 6006:9056 | 6046:9056 | 6006:9057 | 6046:9057 |
| 6007:9055 | 6047:9055 | 6007:9056 | 6047:9056 | 6007:9057 | 6047:9057 |
| 6008:9055 | 6048:9055 | 6008:9056 | 6048:9056 | 6008:9057 | 6048:9057 |
| 6009:9055 | 6049:9055 | 6009:9056 | 6049:9056 | 6009:9057 | 6049:9057 |
| 6010:9055 | 6050:9055 | 6010:9056 | 6050:9056 | 6010:9057 | 6050:9057 |
| 6011:9055 | 6051:9055 | 6011:9056 | 6051:9056 | 6011:9057 | 6051:9057 |
| 6012:9055 | 6052:9055 | 6012:9056 | 6052:9056 | 6012:9057 | 6052:9057 |
| 6013:9055 | 6053:9055 | 6013:9056 | 6053:9056 | 6013:9057 | 6053:9057 |
| 6014:9055 | 6054:9055 | 6014:9056 | 6054:9056 | 6014:9057 | 6054:9057 |
| 6015:9055 | 6055:9055 | 6015:9056 | 6055:9056 | 6015:9057 | 6055:9057 |
| 6016:9055 | 6056:9055 | 6016:9056 | 6056:9056 | 6016:9057 | 6056:9057 |
| 6017:9055 | 6057:9055 | 6017:9056 | 6057:9056 | 6017:9057 | 6057:9057 |
| 6018:9055 | 6058:9055 | 6018:9056 | 6058:9056 | 6018:9057 | 6058:9057 |
| 6019:9055 | 6059:9055 | 6019:9056 | 6059:9056 | 6019:9057 | 6059:9057 |
| 6020:9055 | 6060:9055 | 6020:9056 | 6060:9056 | 6020:9057 | 6060:9057 |
| 6021:9055 | 6061:9055 | 6021:9056 | 6061:9056 | 6021:9057 | 6061:9057 |
| 6022:9055 | 6062:9055 | 6022:9056 | 6062:9056 | 6022:9057 | 6062:9057 |
| 6023:9055 | 6063:9055 | 6023:9056 | 6063:9056 | 6023:9057 | 6063:9057 |
| 6024:9055 | 6064:9055 | 6024:9056 | 6064:9056 | 6024:9057 | 6064:9057 |
| 6025:9055 | 6065:9055 | 6025:9056 | 6065:9056 | 6025:9057 | 6065:9057 |
| 6026:9055 | 6066:9055 | 6026:9056 | 6066:9056 | 6026:9057 | 6066:9057 |
| 6027:9055 | 6067:9055 | 6027:9056 | 6067:9056 | 6027:9057 | 6067:9057 |
| 6028:9055 | 6068:9055 | 6028:9056 | 6068:9056 | 6028:9057 | 6068:9057 |
| 6029:9055 | 6069:9055 | 6029:9056 | 6069:9056 | 6029:9057 | 6069:9057 |
| 6030:9055 | 6070:9055 | 6030:9056 | 6070:9056 | 6030:9057 | 6070:9057 |
| 6031:9055 | 6071:9055 | 6031:9056 | 6071:9056 | 6031:9057 | 6071:9057 |
| 6032:9055 | 6072:9055 | 6032:9056 | 6072:9056 | 6032:9057 | 6072:9057 |
| 6033:9055 | 6073:9055 | 6033:9056 | 6073:9056 | 6033:9057 | 6073:9057 |
| 6034:9055 | 6074:9055 | 6034:9056 | 6074:9056 | 6034:9057 | 6074:9057 |
| 6035:9055 | 6075:9055 | 6035:9056 | 6075:9056 | 6035:9057 | 6075:9057 |
| 6036:9055 | 6076:9055 | 6036:9056 | 6076:9056 | 6036:9057 | 6076:9057 |
| 6037:9055 | 6077:9055 | 6037:9056 | 6077:9056 | 6037:9057 | 6077:9057 |
| 6038:9055 | 6078:9055 | 6038:9056 | 6078:9056 | 6038:9057 | 6078:9057 |
| 6039:9055 | | 6039:9056 | | 6039:9057 | |
| 6000:9058 | 6040:9058 | 6000:9060 | 6040:9060 | 6000:9061 | 6040:9061 |
| 6001:9058 | 6041:9058 | 6001:9060 | 6041:9060 | 6001:9061 | 6041:9061 |
| 6002:9058 | 6042:9058 | 6002:9060 | 6042:9060 | 6002:9061 | 6042:9061 |
| 6003:9058 | 6043:9058 | 6003:9060 | 6043:9060 | 6003:9061 | 6043:9061 |
| 6004:9058 | 6044:9058 | 6004:9060 | 6044:9060 | 6004:9061 | 6044:9061 |
| 6005:9058 | 6045:9058 | 6005:9060 | 6045:9060 | 6005:9061 | 6045:9061 |
| 6006:9058 | 6046:9058 | 6006:9060 | 6046:9060 | 6006:9061 | 6046:9061 |
| 6007:9058 | 6047:9058 | 6007:9060 | 6047:9060 | 6007:9061 | 6047:9061 |
| 6008:9058 | 6048:9058 | 6008:9060 | 6048:9060 | 6008:9061 | 6048:9061 |
| 6009:9058 | 6049:9058 | 6009:9060 | 6049:9060 | 6009:9061 | 6049:9061 |
| 6010:9058 | 6050:9058 | 6010:9060 | 6050:9060 | 6010:9061 | 6050:9061 |
| 6011:9058 | 6051:9058 | 6011:9060 | 6051:9060 | 6011:9061 | 6051:9061 |
| 6012:9058 | 6052:9058 | 6012:9060 | 6052:9060 | 6012:9061 | 6052:9061 |
| 6013:9058 | 6053:9058 | 6013:9060 | 6053:9060 | 6013:9061 | 6053:9061 |
| 6014:9058 | 6054:9058 | 6014:9060 | 6054:9060 | 6014:9061 | 6054:9061 |
| 6015:9058 | 6055:9058 | 6015:9060 | 6055:9060 | 6015:9061 | 6055:9061 |
| 6016:9058 | 6056:9058 | 6016:9060 | 6056:9060 | 6016:9061 | 6056:9061 |
| 6017:9058 | 6057:9058 | 6017:9060 | 6057:9060 | 6017:9061 | 6057:9061 |
| 6018:9058 | 6058:9058 | 6018:9060 | 6058:9060 | 6018:9061 | 6058:9061 |
| 6019:9058 | 6059:9058 | 6019:9060 | 6059:9060 | 6019:9061 | 6059:9061 |
| 6020:9058 | 6060:9058 | 6020:9060 | 6060:9060 | 6020:9061 | 6060:9061 |
| 6021:9058 | 6061:9058 | 6021:9060 | 6061:9060 | 6021:9061 | 6061:9061 |
| 6022:9058 | 6062:9058 | 6022:9060 | 6062:9060 | 6022:9061 | 6062:9061 |
| 6023:9058 | 6063:9058 | 6023:9060 | 6063:9060 | 6023:9061 | 6063:9061 |
| 6024:9058 | 6064:9058 | 6024:9060 | 6064:9060 | 6024:9061 | 6064:9061 |
| 6025:9058 | 6065:9058 | 6025:9060 | 6065:9060 | 6025:9061 | 6065:9061 |
| 6026:9058 | 6066:9058 | 6026:9060 | 6066:9060 | 6026:9061 | 6066:9061 |
| 6027:9058 | 6067:9058 | 6027:9060 | 6067:9060 | 6027:9061 | 6067:9061 |
| 6028:9058 | 6068:9058 | 6028:9060 | 6068:9060 | 6028:9061 | 6068:9061 |
| 6029:9058 | 6069:9058 | 6029:9060 | 6069:9060 | 6029:9061 | 6069:9061 |
| 6030:9058 | 6070:9058 | 6030:9060 | 6070:9060 | 6030:9061 | 6070:9061 |
| 6031:9058 | 6071:9058 | 6031:9060 | 6071:9060 | 6031:9061 | 6071:9061 |
| 6032:9058 | 6072:9058 | 6032:9060 | 6072:9060 | 6032:9061 | 6072:9061 |
| 6033:9058 | 6073:9058 | 6033:9060 | 6073:9060 | 6033:9061 | 6073:9061 |
| 6034:9058 | 6074:9058 | 6034:9060 | 6074:9060 | 6034:9061 | 6074:9061 |
| 6035:9058 | 6075:9058 | 6035:9060 | 6075:9060 | 6035:9061 | 6075:9061 |
| 6036:9058 | 6076:9058 | 6036:9060 | 6076:9060 | 6036:9061 | 6076:9061 |
| 6037:9058 | 6077:9058 | 6037:9060 | 6077:9060 | 6037:9061 | 6077:9061 |
| 6038:9058 | 6078:9058 | 6038:9060 | 6078:9060 | 6038:9061 | 6078:9061 |
| 6039:9058 | | 6039:9060 | | 6039:9061 | |
| 6000:9062 | 6040:9062 | 6000:9063 | 6040:9063 | 6000:9064 | 6040:9064 |
| 6001:9062 | 6041:9062 | 6001:9063 | 6041:9063 | 6001:9064 | 6041:9064 |
| 6002:9062 | 6042:9062 | 6002:9063 | 6042:9063 | 6002:9064 | 6042:9064 |
| 6003:9062 | 6043:9062 | 6003:9063 | 6043:9063 | 6003:9064 | 6043:9064 |
| 6004:9062 | 6044:9062 | 6004:9063 | 6044:9063 | 6004:9064 | 6044:9064 |
| 6005:9062 | 6045:9062 | 6005:9063 | 6045:9063 | 6005:9064 | 6045:9064 |
| 6006:9062 | 6046:9062 | 6006:9063 | 6046:9063 | 6006:9064 | 6046:9064 |
| 6007:9062 | 6047:9062 | 6007:9063 | 6047:9063 | 6007:9064 | 6047:9064 |
| 6008:9062 | 6048:9062 | 6008:9063 | 6048:9063 | 6008:9064 | 6048:9064 |
| 6009:9062 | 6049:9062 | 6009:9063 | 6049:9063 | 6009:9064 | 6049:9064 |
| 6010:9062 | 6050:9062 | 6010:9063 | 6050:9063 | 6010:9064 | 6050:9064 |
| 6011:9062 | 6051:9062 | 6011:9063 | 6051:9063 | 6011:9064 | 6051:9064 |
| 6012:9062 | 6052:9062 | 6012:9063 | 6052:9063 | 6012:9064 | 6052:9064 |
| 6013:9062 | 6053:9062 | 6013:9063 | 6053:9063 | 6013:9064 | 6053:9064 |
| 6014:9062 | 6054:9062 | 6014:9063 | 6054:9063 | 6014:9064 | 6054:9064 |
| 6015:9062 | 6055:9062 | 6015:9063 | 6055:9063 | 6015:9064 | 6055:9064 |
| 6016:9062 | 6056:9062 | 6016:9063 | 6056:9063 | 6016:9064 | 6056:9064 |
| 6017:9062 | 6057:9062 | 6017:9063 | 6057:9063 | 6017:9064 | 6057:9064 |
| 6018:9062 | 6058:9062 | 6018:9063 | 6058:9063 | 6018:9064 | 6058:9064 |
| 6019:9062 | 6059:9062 | 6019:9063 | 6059:9063 | 6019:9064 | 6059:9064 |
| 6020:9062 | 6060:9062 | 6020:9063 | 6060:9063 | 6020:9064 | 6060:9064 |
| 6021:9062 | 6061:9062 | 6021:9063 | 6061:9063 | 6021:9064 | 6061:9064 |
| 6022:9062 | 6062:9062 | 6022:9063 | 6062:9063 | 6022:9064 | 6062:9064 |
| 6023:9062 | 6063:9062 | 6023:9063 | 6063:9063 | 6023:9064 | 6063:9064 |
| 6024:9062 | 6064:9062 | 6024:9063 | 6064:9063 | 6024:9064 | 6064:9064 |
| 6025:9062 | 6065:9062 | 6025:9063 | 6065:9063 | 6025:9064 | 6065:9064 |
| 6026:9062 | 6066:9062 | 6026:9063 | 6066:9063 | 6026:9064 | 6066:9064 |
| 6027:9062 | 6067:9062 | 6027:9063 | 6067:9063 | 6027:9064 | 6067:9064 |
| 6028:9062 | 6068:9062 | 6028:9063 | 6068:9063 | 6028:9064 | 6068:9064 |
| 6029:9062 | 6069:9062 | 6029:9063 | 6069:9063 | 6029:9064 | 6069:9064 |
| 6030:9062 | 6070:9062 | 6030:9063 | 6070:9063 | 6030:9064 | 6070:9064 |
| 6031:9062 | 6071:9062 | 6031:9063 | 6071:9063 | 6031:9064 | 6071:9064 |
| 6032:9062 | 6072:9062 | 6032:9063 | 6072:9063 | 6032:9064 | 6072:9064 |
| 6033:9062 | 6073:9062 | 6033:9063 | 6073:9063 | 6033:9064 | 6073:9064 |
| 6034:9062 | 6074:9062 | 6034:9063 | 6074:9063 | 6034:9064 | 6074:9064 |
| 6035:9062 | 6075:9062 | 6035:9063 | 6075:9063 | 6035:9064 | 6075:9064 |
| 6036:9062 | 6076:9062 | 6036:9063 | 6076:9063 | 6036:9064 | 6076:9064 |
| 6037:9062 | 6077:9062 | 6037:9063 | 6077:9063 | 6037:9064 | 6077:9064 |
| 6038:9062 | 6078:9062 | 6038:9063 | 6078:9063 | 6038:9064 | 6078:9064 |
| 6039:9062 | | 6039:9063 | | 6039:9064 | |
| 6000:9065 | 6040:9065 | 6000:9066 | 6040:9066 | 6000:9067 | 6040:9067 |
| 6001:9065 | 6041:9065 | 6001:9066 | 6041:9066 | 6001:9067 | 6041:9067 |
| 6002:9065 | 6042:9065 | 6002:9066 | 6042:9066 | 6002:9067 | 6042:9067 |
| 6003:9065 | 6043:9065 | 6003:9066 | 6043:9066 | 6003:9067 | 6043:9067 |
| 6004:9065 | 6044:9065 | 6004:9066 | 6044:9066 | 6004:9067 | 6044:9067 |
| 6005:9065 | 6045:9065 | 6005:9066 | 6045:9066 | 6005:9067 | 6045:9067 |
| 6006:9065 | 6046:9065 | 6006:9066 | 6046:9066 | 6006:9067 | 6046:9067 |
| 6007:9065 | 6047:9065 | 6007:9066 | 6047:9066 | 6007:9067 | 6047:9067 |
| 6008:9065 | 6048:9065 | 6008:9066 | 6048:9066 | 6008:9067 | 6048:9067 |
| 6009:9065 | 6049:9065 | 6009:9066 | 6049:9066 | 6009:9067 | 6049:9067 |
| 6010:9065 | 6050:9065 | 6010:9066 | 6050:9066 | 6010:9067 | 6050:9067 |
| 6011:9065 | 6051:9065 | 6011:9066 | 6051:9066 | 6011:9067 | 6051:9067 |
| 6012:9065 | 6052:9065 | 6012:9066 | 6052:9066 | 6012:9067 | 6052:9067 |
| 6013:9065 | 6053:9065 | 6013:9066 | 6053:9066 | 6013:9067 | 6053:9067 |
| 6014:9065 | 6054:9065 | 6014:9066 | 6054:9066 | 6014:9067 | 6054:9067 |
| 6015:9065 | 6055:9065 | 6015:9066 | 6055:9066 | 6015:9067 | 6055:9067 |
| 6016:9065 | 6056:9065 | 6016:9066 | 6056:9066 | 6016:9067 | 6056:9067 |
| 6017:9065 | 6057:9065 | 6017:9066 | 6057:9066 | 6017:9067 | 6057:9067 |
| 6018:9065 | 6058:9065 | 6018:9066 | 6058:9066 | 6018:9067 | 6058:9067 |
| 6019:9065 | 6059:9065 | 6019:9066 | 6059:9066 | 6019:9067 | 6059:9067 |
| 6020:9065 | 6060:9065 | 6020:9066 | 6060:9066 | 6020:9067 | 6060:9067 |
| 6021:9065 | 6061:9065 | 6021:9066 | 6061:9066 | 6021:9067 | 6061:9067 |
| 6022:9065 | 6062:9065 | 6022:9066 | 6062:9066 | 6022:9067 | 6062:9067 |
| 6023:9065 | 6063:9065 | 6023:9066 | 6063:9066 | 6023:9067 | 6063:9067 |
| 6024:9065 | 6064:9065 | 6024:9066 | 6064:9066 | 6024:9067 | 6064:9067 |
| 6025:9065 | 6065:9065 | 6025:9066 | 6065:9066 | 6025:9067 | 6065:9067 |
| 6026:9065 | 6066:9065 | 6026:9066 | 6066:9066 | 6026:9067 | 6066:9067 |
| 6027:9065 | 6067:9065 | 6027:9066 | 6067:9066 | 6027:9067 | 6067:9067 |
| 6028:9065 | 6068:9065 | 6028:9066 | 6068:9066 | 6028:9067 | 6068:9067 |
| 6029:9065 | 6069:9065 | 6029:9066 | 6069:9066 | 6029:9067 | 6069:9067 |
| 6030:9065 | 6070:9065 | 6030:9066 | 6070:9066 | 6030:9067 | 6070:9067 |
| 6031:9065 | 6071:9065 | 6031:9066 | 6071:9066 | 6031:9067 | 6071:9067 |
| 6032:9065 | 6072:9065 | 6032:9066 | 6072:9066 | 6032:9067 | 6072:9067 |
| 6033:9065 | 6073:9065 | 6033:9066 | 6073:9066 | 6033:9067 | 6073:9067 |
| 6034:9065 | 6074:9065 | 6034:9066 | 6074:9066 | 6034:9067 | 6074:9067 |
| 6035:9065 | 6075:9065 | 6035:9066 | 6075:9066 | 6035:9067 | 6075:9067 |
| 6036:9065 | 6076:9065 | 6036:9066 | 6076:9066 | 6036:9067 | 6076:9067 |

TABLE D-continued

Example combinations of a compound X with a compound Y.

| X:Y | X:Y | X:Y | X:Y | X:Y | X:Y |
|---|---|---|---|---|---|
| 6037:9065 | 6077:9065 | 6037:9066 | 6077:9066 | 6037:9067 | 6077:9067 |
| 6038:9065 | 6078:9065 | 6038:9066 | 6078:9066 | 6038:9067 | 6078:9067 |
| 6039:9065 | | 6039:9066 | | 6039:9067 | |
| 6000:9068 | 6040:9068 | 6000:9069 | 6040:9069 | 6000:9070 | 6040:9070 |
| 6001:9068 | 6041:9068 | 6001:9069 | 6041:9069 | 6001:9070 | 6041:9070 |
| 6002:9068 | 6042:9068 | 6002:9069 | 6042:9069 | 6002:9070 | 6042:9070 |
| 6003:9068 | 6043:9068 | 6003:9069 | 6043:9069 | 6003:9070 | 6043:9070 |
| 6004:9068 | 6044:9068 | 6004:9069 | 6044:9069 | 6004:9070 | 6044:9070 |
| 6005:9068 | 6045:9068 | 6005:9069 | 6045:9069 | 6005:9070 | 6045:9070 |
| 6006:9068 | 6046:9068 | 6006:9069 | 6046:9069 | 6006:9070 | 6046:9070 |
| 6007:9068 | 6047:9068 | 6007:9069 | 6047:9069 | 6007:9070 | 6047:9070 |
| 6008:9068 | 6048:9068 | 6008:9069 | 6048:9069 | 6008:9070 | 6048:9070 |
| 6009:9068 | 6049:9068 | 6009:9069 | 6049:9069 | 6009:9070 | 6049:9070 |
| 6010:9068 | 6050:9068 | 6010:9069 | 6050:9069 | 6010:9070 | 6050:9070 |
| 6011:9068 | 6051:9068 | 6011:9069 | 6051:9069 | 6011:9070 | 6051:9070 |
| 6012:9068 | 6052:9068 | 6012:9069 | 6052:9069 | 6012:9070 | 6052:9070 |
| 6013:9068 | 6053:9068 | 6013:9069 | 6053:9069 | 6013:9070 | 6053:9070 |
| 6014:9068 | 6054:9068 | 6014:9069 | 6054:9069 | 6014:9070 | 6054:9070 |
| 6015:9068 | 6055:9068 | 6015:9069 | 6055:9069 | 6015:9070 | 6055:9070 |
| 6016:9068 | 6056:9068 | 6016:9069 | 6056:9069 | 6016:9070 | 6056:9070 |
| 6017:9068 | 6057:9068 | 6017:9069 | 6057:9069 | 6017:9070 | 6057:9070 |
| 6018:9068 | 6058:9068 | 6018:9069 | 6058:9069 | 6018:9070 | 6058:9070 |
| 6019:9068 | 6059:9068 | 6019:9069 | 6059:9069 | 6019:9070 | 6059:9070 |
| 6020:9068 | 6060:9068 | 6020:9069 | 6060:9069 | 6020:9070 | 6060:9070 |
| 6021:9068 | 6061:9068 | 6021:9069 | 6061:9069 | 6021:9070 | 6061:9070 |
| 6022:9068 | 6062:9068 | 6022:9069 | 6062:9069 | 6022:9070 | 6062:9070 |
| 6023:9068 | 6063:9068 | 6023:9069 | 6063:9069 | 6023:9070 | 6063:9070 |
| 6024:9068 | 6064:9068 | 6024:9069 | 6064:9069 | 6024:9070 | 6064:9070 |
| 6025:9068 | 6065:9068 | 6025:9069 | 6065:9069 | 6025:9070 | 6065:9070 |
| 6026:9068 | 6066:9068 | 6026:9069 | 6066:9069 | 6026:9070 | 6066:9070 |
| 6027:9068 | 6067:9068 | 6027:9069 | 6067:9069 | 6027:9070 | 6067:9070 |
| 6028:9068 | 6068:9068 | 6028:9069 | 6068:9069 | 6028:9070 | 6068:9070 |
| 6029:9068 | 6069:9068 | 6029:9069 | 6069:9069 | 6029:9070 | 6069:9070 |
| 6030:9068 | 6070:9068 | 6030:9069 | 6070:9069 | 6030:9070 | 6070:9070 |
| 6031:9068 | 6071:9068 | 6031:9069 | 6071:9069 | 6031:9070 | 6071:9070 |
| 6032:9068 | 6072:9068 | 6032:9069 | 6072:9069 | 6032:9070 | 6072:9070 |
| 6033:9068 | 6073:9068 | 6033:9069 | 6073:9069 | 6033:9070 | 6073:9070 |
| 6034:9068 | 6074:9068 | 6034:9069 | 6074:9069 | 6034:9070 | 6074:9070 |
| 6035:9068 | 6075:9068 | 6035:9069 | 6075:9069 | 6035:9070 | 6075:9070 |
| 6036:9068 | 6076:9068 | 6036:9069 | 6076:9069 | 6036:9070 | 6076:9070 |
| 6037:9068 | 6077:9068 | 6037:9069 | 6077:9069 | 6037:9070 | 6077:9070 |
| 6038:9068 | 6078:9068 | 6038:9069 | 6078:9069 | 6038:9070 | 6078:9070 |
| 6039:9068 | | 6039:9069 | | 6039:9070 | |
| 6000:9071 | 6040:9071 | 6000:9072 | 6040:9072 | 6000:9072 | 6040:9072 |
| 6001:9071 | 6041:9071 | 6001:9072 | 6041:9072 | 6001:9072 | 6041:9072 |
| 6002:9071 | 6042:9071 | 6002:9072 | 6042:9072 | 6002:9072 | 6042:9072 |
| 6003:9071 | 6043:9071 | 6003:9072 | 6043:9072 | 6003:9072 | 6043:9072 |
| 6004:9071 | 6044:9071 | 6004:9072 | 6044:9072 | 6004:9072 | 6044:9072 |
| 6005:9071 | 6045:9071 | 6005:9072 | 6045:9072 | 6005:9072 | 6045:9072 |
| 6006:9071 | 6046:9071 | 6006:9072 | 6046:9072 | 6006:9072 | 6046:9072 |
| 6007:9071 | 6047:9071 | 6007:9072 | 6047:9072 | 6007:9072 | 6047:9072 |
| 6008:9071 | 6048:9071 | 6008:9072 | 6048:9072 | 6008:9072 | 6048:9072 |
| 6009:9071 | 6049:9071 | 6009:9072 | 6049:9072 | 6009:9072 | 6049:9072 |
| 6010:9071 | 6050:9071 | 6010:9072 | 6050:9072 | 6010:9072 | 6050:9072 |
| 6011:9071 | 6051:9071 | 6011:9072 | 6051:9072 | 6011:9072 | 6051:9072 |
| 6012:9071 | 6052:9071 | 6012:9072 | 6052:9072 | 6012:9072 | 6052:9072 |
| 6013:9071 | 6053:9071 | 6013:9072 | 6053:9072 | 6013:9072 | 6053:9072 |
| 6014:9071 | 6054:9071 | 6014:9072 | 6054:9072 | 6014:9072 | 6054:9072 |
| 6015:9071 | 6055:9071 | 6015:9072 | 6055:9072 | 6015:9072 | 6055:9072 |
| 6016:9071 | 6056:9071 | 6016:9072 | 6056:9072 | 6016:9072 | 6056:9072 |
| 6017:9071 | 6057:9071 | 6017:9072 | 6057:9072 | 6017:9072 | 6057:9072 |
| 6018:9071 | 6058:9071 | 6018:9072 | 6058:9072 | 6018:9072 | 6058:9072 |
| 6019:9071 | 6059:9071 | 6019:9072 | 6059:9072 | 6019:9072 | 6059:9072 |
| 6020:9071 | 6060:9071 | 6020:9072 | 6060:9072 | 6020:9072 | 6060:9072 |
| 6021:9071 | 6061:9071 | 6021:9072 | 6061:9072 | 6021:9072 | 6061:9072 |
| 6022:9071 | 6062:9071 | 6022:9072 | 6062:9072 | 6022:9072 | 6062:9072 |
| 6023:9071 | 6063:9071 | 6023:9072 | 6063:9072 | 6023:9072 | 6063:9072 |
| 6024:9071 | 6064:9071 | 6024:9072 | 6064:9072 | 6024:9072 | 6064:9072 |
| 6025:9071 | 6065:9071 | 6025:9072 | 6065:9072 | 6025:9072 | 6065:9072 |
| 6026:9071 | 6066:9071 | 6026:9072 | 6066:9072 | 6026:9072 | 6066:9072 |
| 6027:9071 | 6067:9071 | 6027:9072 | 6067:9072 | 6027:9072 | 6067:9072 |
| 6028:9071 | 6068:9071 | 6028:9072 | 6068:9072 | 6028:9072 | 6068:9072 |
| 6029:9071 | 6069:9071 | 6029:9072 | 6069:9072 | 6029:9072 | 6069:9072 |
| 6030:9071 | 6070:9071 | 6030:9072 | 6070:9072 | 6030:9072 | 6070:9072 |
| 6031:9071 | 6071:9071 | 6031:9072 | 6071:9072 | 6031:9072 | 6071:9072 |
| 6032:9071 | 6072:9071 | 6032:9072 | 6072:9072 | 6032:9072 | 6072:9072 |
| 6033:9071 | 6073:9071 | 6033:9072 | 6073:9072 | 6033:9072 | 6073:9072 |
| 6034:9071 | 6074:9071 | 6034:9072 | 6074:9072 | 6034:9072 | 6074:9072 |
| 6035:9071 | 6075:9071 | 6035:9072 | 6075:9072 | 6035:9072 | 6075:9072 |
| 6036:9071 | 6076:9071 | 6036:9072 | 6076:9072 | 6036:9072 | 6076:9072 |
| 6037:9071 | 6077:9071 | 6037:9072 | 6077:9072 | 6037:9072 | 6077:9072 |
| 6038:9071 | 6078:9071 | 6038:9072 | 6078:9072 | 6038:9072 | 6078:9072 |
| 6039:9071 | | 6039:9072 | | 6039:9072 | |
| 6000:9073 | 6040:9073 | 6000:9074 | 6040:9074 | 6000:9075 | 6040:9075 |
| 6001:9073 | 6041:9073 | 6001:9074 | 6041:9074 | 6001:9075 | 6041:9075 |
| 6002:9073 | 6042:9073 | 6002:9074 | 6042:9074 | 6002:9075 | 6042:9075 |
| 6003:9073 | 6043:9073 | 6003:9074 | 6043:9074 | 6003:9075 | 6043:9075 |
| 6004:9073 | 6044:9073 | 6004:9074 | 6044:9074 | 6004:9075 | 6044:9075 |
| 6005:9073 | 6045:9073 | 6005:9074 | 6045:9074 | 6005:9075 | 6045:9075 |
| 6006:9073 | 6046:9073 | 6006:9074 | 6046:9074 | 6006:9075 | 6046:9075 |
| 6007:9073 | 6047:9073 | 6007:9074 | 6047:9074 | 6007:9075 | 6047:9075 |
| 6008:9073 | 6048:9073 | 6008:9074 | 6048:9074 | 6008:9075 | 6048:9075 |
| 6009:9073 | 6049:9073 | 6009:9074 | 6049:9074 | 6009:9075 | 6049:9075 |
| 6010:9073 | 6050:9073 | 6010:9074 | 6050:9074 | 6010:9075 | 6050:9075 |
| 6011:9073 | 6051:9073 | 6011:9074 | 6051:9074 | 6011:9075 | 6051:9075 |
| 6012:9073 | 6052:9073 | 6012:9074 | 6052:9074 | 6012:9075 | 6052:9075 |
| 6013:9073 | 6053:9073 | 6013:9074 | 6053:9074 | 6013:9075 | 6053:9075 |
| 6014:9073 | 6054:9073 | 6014:9074 | 6054:9074 | 6014:9075 | 6054:9075 |
| 6015:9073 | 6055:9073 | 6015:9074 | 6055:9074 | 6015:9075 | 6055:9075 |
| 6016:9073 | 6056:9073 | 6016:9074 | 6056:9074 | 6016:9075 | 6056:9075 |
| 6017:9073 | 6057:9073 | 6017:9074 | 6057:9074 | 6017:9075 | 6057:9075 |
| 6018:9073 | 6058:9073 | 6018:9074 | 6058:9074 | 6018:9075 | 6058:9075 |
| 6019:9073 | 6059:9073 | 6019:9074 | 6059:9074 | 6019:9075 | 6059:9075 |
| 6020:9073 | 6060:9073 | 6020:9074 | 6060:9074 | 6020:9075 | 6060:9075 |
| 6021:9073 | 6061:9073 | 6021:9074 | 6061:9074 | 6021:9075 | 6061:9075 |
| 6022:9073 | 6062:9073 | 6022:9074 | 6062:9074 | 6022:9075 | 6062:9075 |
| 6023:9073 | 6063:9073 | 6023:9074 | 6063:9074 | 6023:9075 | 6063:9075 |
| 6024:9073 | 6064:9073 | 6024:9074 | 6064:9074 | 6024:9075 | 6064:9075 |
| 6025:9073 | 6065:9073 | 6025:9074 | 6065:9074 | 6025:9075 | 6065:9075 |
| 6026:9073 | 6066:9073 | 6026:9074 | 6066:9074 | 6026:9075 | 6066:9075 |
| 6027:9073 | 6067:9073 | 6027:9074 | 6067:9074 | 6027:9075 | 6067:9075 |
| 6028:9073 | 6068:9073 | 6028:9074 | 6068:9074 | 6028:9075 | 6068:9075 |
| 6029:9073 | 6069:9073 | 6029:9074 | 6069:9074 | 6029:9075 | 6069:9075 |
| 6030:9073 | 6070:9073 | 6030:9074 | 6070:9074 | 6030:9075 | 6070:9075 |
| 6031:9073 | 6071:9073 | 6031:9074 | 6071:9074 | 6031:9075 | 6071:9075 |
| 6032:9073 | 6072:9073 | 6032:9074 | 6072:9074 | 6032:9075 | 6072:9075 |
| 6033:9073 | 6073:9073 | 6033:9074 | 6073:9074 | 6033:9075 | 6073:9075 |
| 6034:9073 | 6074:9073 | 6034:9074 | 6074:9074 | 6034:9075 | 6074:9075 |
| 6035:9073 | 6075:9073 | 6035:9074 | 6075:9074 | 6035:9075 | 6075:9075 |
| 6036:9073 | 6076:9073 | 6036:9074 | 6076:9074 | 6036:9075 | 6076:9075 |
| 6037:9073 | 6077:9073 | 6037:9074 | 6077:9074 | 6037:9075 | 6077:9075 |
| 6038:9073 | 6078:9073 | 6038:9074 | 6078:9074 | 6038:9075 | 6078:9075 |
| 6039:9073 | | 6039:9074 | | 6039:9075 | |
| 6000:9076 | 6040:9076 | 6000:9077 | 6040:9077 | 6000:9078 | 6040:9078 |
| 6001:9076 | 6041:9076 | 6001:9077 | 6041:9077 | 6001:9078 | 6041:9078 |
| 6002:9076 | 6042:9076 | 6002:9077 | 6042:9077 | 6002:9078 | 6042:9078 |
| 6003:9076 | 6043:9076 | 6003:9077 | 6043:9077 | 6003:9078 | 6043:9078 |
| 6004:9076 | 6044:9076 | 6004:9077 | 6044:9077 | 6004:9078 | 6044:9078 |
| 6005:9076 | 6045:9076 | 6005:9077 | 6045:9077 | 6005:9078 | 6045:9078 |
| 6006:9076 | 6046:9076 | 6006:9077 | 6046:9077 | 6006:9078 | 6046:9078 |
| 6007:9076 | 6047:9076 | 6007:9077 | 6047:9077 | 6007:9078 | 6047:9078 |
| 6008:9076 | 6048:9076 | 6008:9077 | 6048:9077 | 6008:9078 | 6048:9078 |
| 6009:9076 | 6049:9076 | 6009:9077 | 6049:9077 | 6009:9078 | 6049:9078 |
| 6010:9076 | 6050:9076 | 6010:9077 | 6050:9077 | 6010:9078 | 6050:9078 |
| 6011:9076 | 6051:9076 | 6011:9077 | 6051:9077 | 6011:9078 | 6051:9078 |
| 6012:9076 | 6052:9076 | 6012:9077 | 6052:9077 | 6012:9078 | 6052:9078 |
| 6013:9076 | 6053:9076 | 6013:9077 | 6053:9077 | 6013:9078 | 6053:9078 |
| 6014:9076 | 6054:9076 | 6014:9077 | 6054:9077 | 6014:9078 | 6054:9078 |
| 6015:9076 | 6055:9076 | 6015:9077 | 6055:9077 | 6015:9078 | 6055:9078 |
| 6016:9076 | 6056:9076 | 6016:9077 | 6056:9077 | 6016:9078 | 6056:9078 |
| 6017:9076 | 6057:9076 | 6017:9077 | 6057:9077 | 6017:9078 | 6057:9078 |
| 6018:9076 | 6058:9076 | 6018:9077 | 6058:9077 | 6018:9078 | 6058:9078 |
| 6019:9076 | 6059:9076 | 6019:9077 | 6059:9077 | 6019:9078 | 6059:9078 |
| 6020:9076 | 6060:9076 | 6020:9077 | 6060:9077 | 6020:9078 | 6060:9078 |
| 6021:9076 | 6061:9076 | 6021:9077 | 6061:9077 | 6021:9078 | 6061:9078 |
| 6022:9076 | 6062:9076 | 6022:9077 | 6062:9077 | 6022:9078 | 6062:9078 |
| 6023:9076 | 6063:9076 | 6023:9077 | 6063:9077 | 6023:9078 | 6063:9078 |
| 6024:9076 | 6064:9076 | 6024:9077 | 6064:9077 | 6024:9078 | 6064:9078 |
| 6025:9076 | 6065:9076 | 6025:9077 | 6065:9077 | 6025:9078 | 6065:9078 |
| 6026:9076 | 6066:9076 | 6026:9077 | 6066:9077 | 6026:9078 | 6066:9078 |
| 6027:9076 | 6067:9076 | 6027:9077 | 6067:9077 | 6027:9078 | 6067:9078 |
| 6028:9076 | 6068:9076 | 6028:9077 | 6068:9077 | 6028:9078 | 6068:9078 |

TABLE D-continued

Example combinations of a compound X with a compound Y.

| X:Y | X:Y | X:Y | X:Y | X:Y | X:Y |
|---|---|---|---|---|---|
| 6029:9076 | 6069:9076 | 6029:9077 | 6069:9077 | 6029:9078 | 6069:9078 |
| 6030:9076 | 6070:9076 | 6030:9077 | 6070:9077 | 6030:9078 | 6070:9078 |
| 6031:9076 | 6071:9076 | 6031:9077 | 6071:9077 | 6031:9078 | 6071:9078 |
| 6032:9076 | 6072:9076 | 6032:9077 | 6072:9077 | 6032:9078 | 6072:9078 |
| 6033:9076 | 6073:9076 | 6033:9077 | 6073:9077 | 6033:9078 | 6073:9078 |
| 6034:9076 | 6074:9076 | 6034:9077 | 6074:9077 | 6034:9078 | 6074:9078 |
| 6035:9076 | 6075:9076 | 6035:9077 | 6075:9077 | 6035:9078 | 6075:9078 |
| 6036:9076 | 6076:9076 | 6036:9077 | 6076:9077 | 6036:9078 | 6076:9078 |
| 6037:9076 | 6077:9076 | 6037:9077 | 6077:9077 | 6037:9078 | 6077:9078 |
| 6038:9076 | 6078:9076 | 6038:9077 | 6078:9077 | 6038:9078 | 6078:9078 |
| 6039:9076 | | 6039:9077 | | 6039:9078 | |
| 6000:9079 | 6040:9079 | 6000:9080 | 6040:9080 | 6000:9081 | 6040:9081 |
| 6001:9079 | 6041:9079 | 6001:9080 | 6041:9080 | 6001:9081 | 6041:9081 |
| 6002:9079 | 6042:9079 | 6002:9080 | 6042:9080 | 6002:9081 | 6042:9081 |
| 6003:9079 | 6043:9079 | 6003:9080 | 6043:9080 | 6003:9081 | 6043:9081 |
| 6004:9079 | 6044:9079 | 6004:9080 | 6044:9080 | 6004:9081 | 6044:9081 |
| 6005:9079 | 6045:9079 | 6005:9080 | 6045:9080 | 6005:9081 | 6045:9081 |
| 6006:9079 | 6046:9079 | 6006:9080 | 6046:9080 | 6006:9081 | 6046:9081 |
| 6007:9079 | 6047:9079 | 6007:9080 | 6047:9080 | 6007:9081 | 6047:9081 |
| 6008:9079 | 6048:9079 | 6008:9080 | 6048:9080 | 6008:9081 | 6048:9081 |
| 6009:9079 | 6049:9079 | 6009:9080 | 6049:9080 | 6009:9081 | 6049:9081 |
| 6010:9079 | 6050:9079 | 6010:9080 | 6050:9080 | 6010:9081 | 6050:9081 |
| 6011:9079 | 6051:9079 | 6011:9080 | 6051:9080 | 6011:9081 | 6051:9081 |
| 6012:9079 | 6052:9079 | 6012:9080 | 6052:9080 | 6012:9081 | 6052:9081 |
| 6013:9079 | 6053:9079 | 6013:9080 | 6053:9080 | 6013:9081 | 6053:9081 |
| 6014:9079 | 6054:9079 | 6014:9080 | 6054:9080 | 6014:9081 | 6054:9081 |
| 6015:9079 | 6055:9079 | 6015:9080 | 6055:9080 | 6015:9081 | 6055:9081 |
| 6016:9079 | 6056:9079 | 6016:9080 | 6056:9080 | 6016:9081 | 6056:9081 |
| 6017:9079 | 6057:9079 | 6017:9080 | 6057:9080 | 6017:9081 | 6057:9081 |
| 6018:9079 | 6058:9079 | 6018:9080 | 6058:9080 | 6018:9081 | 6058:9081 |
| 6019:9079 | 6059:9079 | 6019:9080 | 6059:9080 | 6019:9081 | 6059:9081 |
| 6020:9079 | 6060:9079 | 6020:9080 | 6060:9080 | 6020:9081 | 6060:9081 |
| 6021:9079 | 6061:9079 | 6021:9080 | 6061:9080 | 6021:9081 | 6061:9081 |
| 6022:9079 | 6062:9079 | 6022:9080 | 6062:9080 | 6022:9081 | 6062:9081 |
| 6023:9079 | 6063:9079 | 6023:9080 | 6063:9080 | 6023:9081 | 6063:9081 |
| 6024:9079 | 6064:9079 | 6024:9080 | 6064:9080 | 6024:9081 | 6064:9081 |
| 6025:9079 | 6065:9079 | 6025:9080 | 6065:9080 | 6025:9081 | 6065:9081 |
| 6026:9079 | 6066:9079 | 6026:9080 | 6066:9080 | 6026:9081 | 6066:9081 |
| 6027:9079 | 6067:9079 | 6027:9080 | 6067:9080 | 6027:9081 | 6067:9081 |
| 6028:9079 | 6068:9079 | 6028:9080 | 6068:9080 | 6028:9081 | 6068:9081 |
| 6029:9079 | 6069:9079 | 6029:9080 | 6069:9080 | 6029:9081 | 6069:9081 |
| 6030:9079 | 6070:9079 | 6030:9080 | 6070:9080 | 6030:9081 | 6070:9081 |
| 6031:9079 | 6071:9079 | 6031:9080 | 6071:9080 | 6031:9081 | 6071:9081 |
| 6032:9079 | 6072:9079 | 6032:9080 | 6072:9080 | 6032:9081 | 6072:9081 |
| 6033:9079 | 6073:9079 | 6033:9080 | 6073:9080 | 6033:9081 | 6073:9081 |
| 6034:9079 | 6074:9079 | 6034:9080 | 6074:9080 | 6034:9081 | 6074:9081 |
| 6035:9079 | 6075:9079 | 6035:9080 | 6075:9080 | 6035:9081 | 6075:9081 |
| 6036:9079 | 6076:9079 | 6036:9080 | 6076:9080 | 6036:9081 | 6076:9081 |
| 6037:9079 | 6077:9079 | 6037:9080 | 6077:9080 | 6037:9081 | 6077:9081 |
| 6038:9079 | 6078:9079 | 6038:9080 | 6078:9080 | 6038:9081 | 6078:9081 |
| 6039:9079 | | 6039:9080 | | 6039:9081 | |
| 6000:9082 | 6040:9082 | 6000:9083 | 6040:9083 | 6000:9084 | 6040:9084 |
| 6001:9082 | 6041:9082 | 6001:9083 | 6041:9083 | 6001:9084 | 6041:9084 |
| 6002:9082 | 6042:9082 | 6002:9083 | 6042:9083 | 6002:9084 | 6042:9084 |
| 6003:9082 | 6043:9082 | 6003:9083 | 6043:9083 | 6003:9084 | 6043:9084 |
| 6004:9082 | 6044:9082 | 6004:9083 | 6044:9083 | 6004:9084 | 6044:9084 |
| 6005:9082 | 6045:9082 | 6005:9083 | 6045:9083 | 6005:9084 | 6045:9084 |
| 6006:9082 | 6046:9082 | 6006:9083 | 6046:9083 | 6006:9084 | 6046:9084 |
| 6007:9082 | 6047:9082 | 6007:9083 | 6047:9083 | 6007:9084 | 6047:9084 |
| 6008:9082 | 6048:9082 | 6008:9083 | 6048:9083 | 6008:9084 | 6048:9084 |
| 6009:9082 | 6049:9082 | 6009:9083 | 6049:9083 | 6009:9084 | 6049:9084 |
| 6010:9082 | 6050:9082 | 6010:9083 | 6050:9083 | 6010:9084 | 6050:9084 |
| 6011:9082 | 6051:9082 | 6011:9083 | 6051:9083 | 6011:9084 | 6051:9084 |
| 6012:9082 | 6052:9082 | 6012:9083 | 6052:9083 | 6012:9084 | 6052:9084 |
| 6013:9082 | 6053:9082 | 6013:9083 | 6053:9083 | 6013:9084 | 6053:9084 |
| 6014:9082 | 6054:9082 | 6014:9083 | 6054:9083 | 6014:9084 | 6054:9084 |
| 6015:9082 | 6055:9082 | 6015:9083 | 6055:9083 | 6015:9084 | 6055:9084 |
| 6016:9082 | 6056:9082 | 6016:9083 | 6056:9083 | 6016:9084 | 6056:9084 |
| 6017:9082 | 6057:9082 | 6017:9083 | 6057:9083 | 6017:9084 | 6057:9084 |
| 6018:9082 | 6058:9082 | 6018:9083 | 6058:9083 | 6018:9084 | 6058:9084 |
| 6019:9082 | 6059:9082 | 6019:9083 | 6059:9083 | 6019:9084 | 6059:9084 |
| 6020:9082 | 6060:9082 | 6020:9083 | 6060:9083 | 6020:9084 | 6060:9084 |
| 6021:9082 | 6061:9082 | 6021:9083 | 6061:9083 | 6021:9084 | 6061:9084 |
| 6022:9082 | 6062:9082 | 6022:9083 | 6062:9083 | 6022:9084 | 6062:9084 |
| 6023:9082 | 6063:9082 | 6023:9083 | 6063:9083 | 6023:9084 | 6063:9084 |
| 6024:9082 | 6064:9082 | 6024:9083 | 6064:9083 | 6024:9084 | 6064:9084 |

TABLE D-continued

Example combinations of a compound X with a compound Y.

| X:Y | X:Y | X:Y | X:Y | X:Y | X:Y |
|---|---|---|---|---|---|
| 6025:9082 | 6065:9082 | 6025:9083 | 6065:9083 | 6025:9084 | 6065:9084 |
| 6026:9082 | 6066:9082 | 6026:9083 | 6066:9083 | 6026:9084 | 6066:9084 |
| 6027:9082 | 6067:9082 | 6027:9083 | 6067:9083 | 6027:9084 | 6067:9084 |
| 6028:9082 | 6068:9082 | 6028:9083 | 6068:9083 | 6028:9084 | 6068:9084 |
| 6029:9082 | 6069:9082 | 6029:9083 | 6069:9083 | 6029:9084 | 6069:9084 |
| 6030:9082 | 6070:9082 | 6030:9083 | 6070:9083 | 6030:9084 | 6070:9084 |
| 6031:9082 | 6071:9082 | 6031:9083 | 6071:9083 | 6031:9084 | 6071:9084 |
| 6032:9082 | 6072:9082 | 6032:9083 | 6072:9083 | 6032:9084 | 6072:9084 |
| 6033:9082 | 6073:9082 | 6033:9083 | 6073:9083 | 6033:9084 | 6073:9084 |
| 6034:9082 | 6074:9082 | 6034:9083 | 6074:9083 | 6034:9084 | 6074:9084 |
| 6035:9082 | 6075:9082 | 6035:9083 | 6075:9083 | 6035:9084 | 6075:9084 |
| 6036:9082 | 6076:9082 | 6036:9083 | 6076:9083 | 6036:9084 | 6076:9084 |
| 6037:9082 | 6077:9082 | 6037:9083 | 6077:9083 | 6037:9084 | 6077:9084 |
| 6038:9082 | 6078:9082 | 6038:9083 | 6078:9083 | 6038:9084 | 6078:9084 |
| 6039:9082 | | 6039:9083 | | 6039:9084 | |
| 6000:9085 | 6040:9085 | 6000:9086 | 6040:9086 | 6000:9088 | 6040:9088 |
| 6001:9085 | 6041:9085 | 6001:9086 | 6041:9086 | 6001:9088 | 6041:9088 |
| 6002:9085 | 6042:9085 | 6002:9086 | 6042:9086 | 6002:9088 | 6042:9088 |
| 6003:9085 | 6043:9085 | 6003:9086 | 6043:9086 | 6003:9088 | 6043:9088 |
| 6004:9085 | 6044:9085 | 6004:9086 | 6044:9086 | 6004:9088 | 6044:9088 |
| 6005:9085 | 6045:9085 | 6005:9086 | 6045:9086 | 6005:9088 | 6045:9088 |
| 6006:9085 | 6046:9085 | 6006:9086 | 6046:9086 | 6006:9088 | 6046:9088 |
| 6007:9085 | 6047:9085 | 6007:9086 | 6047:9086 | 6007:9088 | 6047:9088 |
| 6008:9085 | 6048:9085 | 6008:9086 | 6048:9086 | 6008:9088 | 6048:9088 |
| 6009:9085 | 6049:9085 | 6009:9086 | 6049:9086 | 6009:9088 | 6049:9088 |
| 6010:9085 | 6050:9085 | 6010:9086 | 6050:9086 | 6010:9088 | 6050:9088 |
| 6011:9085 | 6051:9085 | 6011:9086 | 6051:9086 | 6011:9088 | 6051:9088 |
| 6012:9085 | 6052:9085 | 6012:9086 | 6052:9086 | 6012:9088 | 6052:9088 |
| 6013:9085 | 6053:9085 | 6013:9086 | 6053:9086 | 6013:9088 | 6053:9088 |
| 6014:9085 | 6054:9085 | 6014:9086 | 6054:9086 | 6014:9088 | 6054:9088 |
| 6015:9085 | 6055:9085 | 6015:9086 | 6055:9086 | 6015:9088 | 6055:9088 |
| 6016:9085 | 6056:9085 | 6016:9086 | 6056:9086 | 6016:9088 | 6056:9088 |
| 6017:9085 | 6057:9085 | 6017:9086 | 6057:9086 | 6017:9088 | 6057:9088 |
| 6018:9085 | 6058:9085 | 6018:9086 | 6058:9086 | 6018:9088 | 6058:9088 |
| 6019:9085 | 6059:9085 | 6019:9086 | 6059:9086 | 6019:9088 | 6059:9088 |
| 6020:9085 | 6060:9085 | 6020:9086 | 6060:9086 | 6020:9088 | 6060:9088 |
| 6021:9085 | 6061:9085 | 6021:9086 | 6061:9086 | 6021:9088 | 6061:9088 |
| 6022:9085 | 6062:9085 | 6022:9086 | 6062:9086 | 6022:9088 | 6062:9088 |
| 6023:9085 | 6063:9085 | 6023:9086 | 6063:9086 | 6023:9088 | 6063:9088 |
| 6024:9085 | 6064:9085 | 6024:9086 | 6064:9086 | 6024:9088 | 6064:9088 |
| 6025:9085 | 6065:9085 | 6025:9086 | 6065:9086 | 6025:9088 | 6065:9088 |
| 6026:9085 | 6066:9085 | 6026:9086 | 6066:9086 | 6026:9088 | 6066:9088 |
| 6027:9085 | 6067:9085 | 6027:9086 | 6067:9086 | 6027:9088 | 6067:9088 |
| 6028:9085 | 6068:9085 | 6028:9086 | 6068:9086 | 6028:9088 | 6068:9088 |
| 6029:9085 | 6069:9085 | 6029:9086 | 6069:9086 | 6029:9088 | 6069:9088 |
| 6030:9085 | 6070:9085 | 6030:9086 | 6070:9086 | 6030:9088 | 6070:9088 |
| 6031:9085 | 6071:9085 | 6031:9086 | 6071:9086 | 6031:9088 | 6071:9088 |
| 6032:9085 | 6072:9085 | 6032:9086 | 6072:9086 | 6032:9088 | 6072:9088 |
| 6033:9085 | 6073:9085 | 6033:9086 | 6073:9086 | 6033:9088 | 6073:9088 |
| 6034:9085 | 6074:9085 | 6034:9086 | 6074:9086 | 6034:9088 | 6074:9088 |
| 6035:9085 | 6075:9085 | 6035:9086 | 6075:9086 | 6035:9088 | 6075:9088 |
| 6036:9085 | 6076:9085 | 6036:9086 | 6076:9086 | 6036:9088 | 6076:9088 |
| 6037:9085 | 6077:9085 | 6037:9086 | 6077:9086 | 6037:9088 | 6077:9088 |
| 6038:9085 | 6078:9085 | 6038:9086 | 6078:9086 | 6038:9088 | 6078:9088 |
| 6039:9085 | | 6039:9086 | | 6039:9088 | |
| 6000:9089 | 6040:9089 | 6000:9094 | 6040:9094 | 6000:9095 | 6040:9095 |
| 6001:9089 | 6041:9089 | 6001:9094 | 6041:9094 | 6001:9095 | 6041:9095 |
| 6002:9089 | 6042:9089 | 6002:9094 | 6042:9094 | 6002:9095 | 6042:9095 |
| 6003:9089 | 6043:9089 | 6003:9094 | 6043:9094 | 6003:9095 | 6043:9095 |
| 6004:9089 | 6044:9089 | 6004:9094 | 6044:9094 | 6004:9095 | 6044:9095 |
| 6005:9089 | 6045:9089 | 6005:9094 | 6045:9094 | 6005:9095 | 6045:9095 |
| 6006:9089 | 6046:9089 | 6006:9094 | 6046:9094 | 6006:9095 | 6046:9095 |
| 6007:9089 | 6047:9089 | 6007:9094 | 6047:9094 | 6007:9095 | 6047:9095 |
| 6008:9089 | 6048:9089 | 6008:9094 | 6048:9094 | 6008:9095 | 6048:9095 |
| 6009:9089 | 6049:9089 | 6009:9094 | 6049:9094 | 6009:9095 | 6049:9095 |
| 6010:9089 | 6050:9089 | 6010:9094 | 6050:9094 | 6010:9095 | 6050:9095 |
| 6011:9089 | 6051:9089 | 6011:9094 | 6051:9094 | 6011:9095 | 6051:9095 |
| 6012:9089 | 6052:9089 | 6012:9094 | 6052:9094 | 6012:9095 | 6052:9095 |
| 6013:9089 | 6053:9089 | 6013:9094 | 6053:9094 | 6013:9095 | 6053:9095 |
| 6014:9089 | 6054:9089 | 6014:9094 | 6054:9094 | 6014:9095 | 6054:9095 |
| 6015:9089 | 6055:9089 | 6015:9094 | 6055:9094 | 6015:9095 | 6055:9095 |
| 6016:9089 | 6056:9089 | 6016:9094 | 6056:9094 | 6016:9095 | 6056:9095 |
| 6017:9089 | 6057:9089 | 6017:9094 | 6057:9094 | 6017:9095 | 6057:9095 |
| 6018:9089 | 6058:9089 | 6018:9094 | 6058:9094 | 6018:9095 | 6058:9095 |
| 6019:9089 | 6059:9089 | 6019:9094 | 6059:9094 | 6019:9095 | 6059:9095 |
| 6020:9089 | 6060:9089 | 6020:9094 | 6060:9094 | 6020:9095 | 6060:9095 |

TABLE D-continued

Example combinations of a compound X with a compound Y.

| X:Y | X:Y | X:Y | X:Y | X:Y | X:Y |
|---|---|---|---|---|---|
| 6021:9089 | 6061:9089 | 6021:9094 | 6061:9094 | 6021:9095 | 6061:9095 |
| 6022:9089 | 6062:9089 | 6022:9094 | 6062:9094 | 6022:9095 | 6062:9095 |
| 6023:9089 | 6063:9089 | 6023:9094 | 6063:9094 | 6023:9095 | 6063:9095 |
| 6024:9089 | 6064:9089 | 6024:9094 | 6064:9094 | 6024:9095 | 6064:9095 |
| 6025:9089 | 6065:9089 | 6025:9094 | 6065:9094 | 6025:9095 | 6065:9095 |
| 6026:9089 | 6066:9089 | 6026:9094 | 6066:9094 | 6026:9095 | 6066:9095 |
| 6027:9089 | 6067:9089 | 6027:9094 | 6067:9094 | 6027:9095 | 6067:9095 |
| 6028:9089 | 6068:9089 | 6028:9094 | 6068:9094 | 6028:9095 | 6068:9095 |
| 6029:9089 | 6069:9089 | 6029:9094 | 6069:9094 | 6029:9095 | 6069:9095 |
| 6030:9089 | 6070:9089 | 6030:9094 | 6070:9094 | 6030:9095 | 6070:9095 |
| 6031:9089 | 6071:9089 | 6031:9094 | 6071:9094 | 6031:9095 | 6071:9095 |
| 6032:9089 | 6072:9089 | 6032:9094 | 6072:9094 | 6032:9095 | 6072:9095 |
| 6033:9089 | 6073:9089 | 6033:9094 | 6073:9094 | 6033:9095 | 6073:9095 |
| 6034:9089 | 6074:9089 | 6034:9094 | 6074:9094 | 6034:9095 | 6074:9095 |
| 6035:9089 | 6075:9089 | 6035:9094 | 6075:9094 | 6035:9095 | 6075:9095 |
| 6036:9089 | 6076:9089 | 6036:9094 | 6076:9094 | 6036:9095 | 6076:9095 |
| 6037:9089 | 6077:9089 | 6037:9094 | 6077:9094 | 6037:9095 | 6077:9095 |
| 6038:9089 | 6078:9089 | 6038:9094 | 6078:9094 | 6038:9095 | 6078:9095 |
| 6039:9089 |  | 6039:9094 |  | 6039:9095 |  |
| 6000:9096 | 6040:9096 | 6000:9097 | 6040:9097 | 6000:9098 | 6040:9098 |
| 6001:9096 | 6041:9096 | 6001:9097 | 6041:9097 | 6001:9098 | 6041:9098 |
| 6002:9096 | 6042:9096 | 6002:9097 | 6042:9097 | 6002:9098 | 6042:9098 |
| 6003:9096 | 6043:9096 | 6003:9097 | 6043:9097 | 6003:9098 | 6043:9098 |
| 6004:9096 | 6044:9096 | 6004:9097 | 6044:9097 | 6004:9098 | 6044:9098 |
| 6005:9096 | 6045:9096 | 6005:9097 | 6045:9097 | 6005:9098 | 6045:9098 |
| 6006:9096 | 6046:9096 | 6006:9097 | 6046:9097 | 6006:9098 | 6046:9098 |
| 6007:9096 | 6047:9096 | 6007:9097 | 6047:9097 | 6007:9098 | 6047:9098 |
| 6008:9096 | 6048:9096 | 6008:9097 | 6048:9097 | 6008:9098 | 6048:9098 |
| 6009:9096 | 6049:9096 | 6009:9097 | 6049:9097 | 6009:9098 | 6049:9098 |
| 6010:9096 | 6050:9096 | 6010:9097 | 6050:9097 | 6010:9098 | 6050:9098 |
| 6011:9096 | 6051:9096 | 6011:9097 | 6051:9097 | 6011:9098 | 6051:9098 |
| 6012:9096 | 6052:9096 | 6012:9097 | 6052:9097 | 6012:9098 | 6052:9098 |
| 6013:9096 | 6053:9096 | 6013:9097 | 6053:9097 | 6013:9098 | 6053:9098 |
| 6014:9096 | 6054:9096 | 6014:9097 | 6054:9097 | 6014:9098 | 6054:9098 |
| 6015:9096 | 6055:9096 | 6015:9097 | 6055:9097 | 6015:9098 | 6055:9098 |
| 6016:9096 | 6056:9096 | 6016:9097 | 6056:9097 | 6016:9098 | 6056:9098 |
| 6017:9096 | 6057:9096 | 6017:9097 | 6057:9097 | 6017:9098 | 6057:9098 |
| 6018:9096 | 6058:9096 | 6018:9097 | 6058:9097 | 6018:9098 | 6058:9098 |
| 6019:9096 | 6059:9096 | 6019:9097 | 6059:9097 | 6019:9098 | 6059:9098 |
| 6020:9096 | 6060:9096 | 6020:9097 | 6060:9097 | 6020:9098 | 6060:9098 |
| 6021:9096 | 6061:9096 | 6021:9097 | 6061:9097 | 6021:9098 | 6061:9098 |
| 6022:9096 | 6062:9096 | 6022:9097 | 6062:9097 | 6022:9098 | 6062:9098 |
| 6023:9096 | 6063:9096 | 6023:9097 | 6063:9097 | 6023:9098 | 6063:9098 |
| 6024:9096 | 6064:9096 | 6024:9097 | 6064:9097 | 6024:9098 | 6064:9098 |
| 6025:9096 | 6065:9096 | 6025:9097 | 6065:9097 | 6025:9098 | 6065:9098 |
| 6026:9096 | 6066:9096 | 6026:9097 | 6066:9097 | 6026:9098 | 6066:9098 |
| 6027:9096 | 6067:9096 | 6027:9097 | 6067:9097 | 6027:9098 | 6067:9098 |
| 6028:9096 | 6068:9096 | 6028:9097 | 6068:9097 | 6028:9098 | 6068:9098 |
| 6029:9096 | 6069:9096 | 6029:9097 | 6069:9097 | 6029:9098 | 6069:9098 |
| 6030:9096 | 6070:9096 | 6030:9097 | 6070:9097 | 6030:9098 | 6070:9098 |
| 6031:9096 | 6071:9096 | 6031:9097 | 6071:9097 | 6031:9098 | 6071:9098 |
| 6032:9096 | 6072:9096 | 6032:9097 | 6072:9097 | 6032:9098 | 6072:9098 |
| 6033:9096 | 6073:9096 | 6033:9097 | 6073:9097 | 6033:9098 | 6073:9098 |
| 6034:9096 | 6074:9096 | 6034:9097 | 6074:9097 | 6034:9098 | 6074:9098 |
| 6035:9096 | 6075:9096 | 6035:9097 | 6075:9097 | 6035:9098 | 6075:9098 |
| 6036:9096 | 6076:9096 | 6036:9097 | 6076:9097 | 6036:9098 | 6076:9098 |
| 6037:9096 | 6077:9096 | 6037:9097 | 6077:9097 | 6037:9098 | 6077:9098 |
| 6038:9096 | 6078:9096 | 6038:9097 | 6078:9097 | 6038:9098 | 6078:9098 |
| 6039:9096 |  | 6039:9097 |  | 6039:9098 |  |
| 6000:9099 | 6040:9099 | 6000:9100 | 6040:9100 | 6000:9101 | 6040:9101 |
| 6001:9099 | 6041:9099 | 6001:9100 | 6041:9100 | 6001:9101 | 6041:9101 |
| 6002:9099 | 6042:9099 | 6002:9100 | 6042:9100 | 6002:9101 | 6042:9101 |
| 6003:9099 | 6043:9099 | 6003:9100 | 6043:9100 | 6003:9101 | 6043:9101 |
| 6004:9099 | 6044:9099 | 6004:9100 | 6044:9100 | 6004:9101 | 6044:9101 |
| 6005:9099 | 6045:9099 | 6005:9100 | 6045:9100 | 6005:9101 | 6045:9101 |
| 6006:9099 | 6046:9099 | 6006:9100 | 6046:9100 | 6006:9101 | 6046:9101 |
| 6007:9099 | 6047:9099 | 6007:9100 | 6047:9100 | 6007:9101 | 6047:9101 |
| 6008:9099 | 6048:9099 | 6008:9100 | 6048:9100 | 6008:9101 | 6048:9101 |
| 6009:9099 | 6049:9099 | 6009:9100 | 6049:9100 | 6009:9101 | 6049:9101 |
| 6010:9099 | 6050:9099 | 6010:9100 | 6050:9100 | 6010:9101 | 6050:9101 |
| 6011:9099 | 6051:9099 | 6011:9100 | 6051:9100 | 6011:9101 | 6051:9101 |
| 6012:9099 | 6052:9099 | 6012:9100 | 6052:9100 | 6012:9101 | 6052:9101 |
| 6013:9099 | 6053:9099 | 6013:9100 | 6053:9100 | 6013:9101 | 6053:9101 |
| 6014:9099 | 6054:9099 | 6014:9100 | 6054:9100 | 6014:9101 | 6054:9101 |
| 6015:9099 | 6055:9099 | 6015:9100 | 6055:9100 | 6015:9101 | 6055:9101 |
| 6016:9099 | 6056:9099 | 6016:9100 | 6056:9100 | 6016:9101 | 6056:9101 |
| 6017:9099 | 6057:9099 | 6017:9100 | 6057:9100 | 6017:9101 | 6057:9101 |
| 6018:9099 | 6058:9099 | 6018:9100 | 6058:9100 | 6018:9101 | 6058:9101 |
| 6019:9099 | 6059:9099 | 6019:9100 | 6059:9100 | 6019:9101 | 6059:9101 |
| 6020:9099 | 6060:9099 | 6020:9100 | 6060:9100 | 6020:9101 | 6060:9101 |
| 6021:9099 | 6061:9099 | 6021:9100 | 6061:9100 | 6021:9101 | 6061:9101 |
| 6022:9099 | 6062:9099 | 6022:9100 | 6062:9100 | 6022:9101 | 6062:9101 |
| 6023:9099 | 6063:9099 | 6023:9100 | 6063:9100 | 6023:9101 | 6063:9101 |
| 6024:9099 | 6064:9099 | 6024:9100 | 6064:9100 | 6024:9101 | 6064:9101 |
| 6025:9099 | 6065:9099 | 6025:9100 | 6065:9100 | 6025:9101 | 6065:9101 |
| 6026:9099 | 6066:9099 | 6026:9100 | 6066:9100 | 6026:9101 | 6066:9101 |
| 6027:9099 | 6067:9099 | 6027:9100 | 6067:9100 | 6027:9101 | 6067:9101 |
| 6028:9099 | 6068:9099 | 6028:9100 | 6068:9100 | 6028:9101 | 6068:9101 |
| 6029:9099 | 6069:9099 | 6029:9100 | 6069:9100 | 6029:9101 | 6069:9101 |
| 6030:9099 | 6070:9099 | 6030:9100 | 6070:9100 | 6030:9101 | 6070:9101 |
| 6031:9099 | 6071:9099 | 6031:9100 | 6071:9100 | 6031:9101 | 6071:9101 |
| 6032:9099 | 6072:9099 | 6032:9100 | 6072:9100 | 6032:9101 | 6072:9101 |
| 6033:9099 | 6073:9099 | 6033:9100 | 6073:9100 | 6033:9101 | 6073:9101 |
| 6034:9099 | 6074:9099 | 6034:9100 | 6074:9100 | 6034:9101 | 6074:9101 |
| 6035:9099 | 6075:9099 | 6035:9100 | 6075:9100 | 6035:9101 | 6075:9101 |
| 6036:9099 | 6076:9099 | 6036:9100 | 6076:9100 | 6036:9101 | 6076:9101 |
| 6037:9099 | 6077:9099 | 6037:9100 | 6077:9100 | 6037:9101 | 6077:9101 |
| 6038:9099 | 6078:9099 | 6038:9100 | 6078:9100 | 6038:9101 | 6078:9101 |
| 6039:9099 |  | 6039:9100 |  | 6039:9101 |  |
| 6000:9102 | 6040:9102 | 6000:9103 | 6040:9103 | 6000:9104 | 6040:9104 |
| 6001:9102 | 6041:9102 | 6001:9103 | 6041:9103 | 6001:9104 | 6041:9104 |
| 6002:9102 | 6042:9102 | 6002:9103 | 6042:9103 | 6002:9104 | 6042:9104 |
| 6003:9102 | 6043:9102 | 6003:9103 | 6043:9103 | 6003:9104 | 6043:9104 |
| 6004:9102 | 6044:9102 | 6004:9103 | 6044:9103 | 6004:9104 | 6044:9104 |
| 6005:9102 | 6045:9102 | 6005:9103 | 6045:9103 | 6005:9104 | 6045:9104 |
| 6006:9102 | 6046:9102 | 6006:9103 | 6046:9103 | 6006:9104 | 6046:9104 |
| 6007:9102 | 6047:9102 | 6007:9103 | 6047:9103 | 6007:9104 | 6047:9104 |
| 6008:9102 | 6048:9102 | 6008:9103 | 6048:9103 | 6008:9104 | 6048:9104 |
| 6009:9102 | 6049:9102 | 6009:9103 | 6049:9103 | 6009:9104 | 6049:9104 |
| 6010:9102 | 6050:9102 | 6010:9103 | 6050:9103 | 6010:9104 | 6050:9104 |
| 6011:9102 | 6051:9102 | 6011:9103 | 6051:9103 | 6011:9104 | 6051:9104 |
| 6012:9102 | 6052:9102 | 6012:9103 | 6052:9103 | 6012:9104 | 6052:9104 |
| 6013:9102 | 6053:9102 | 6013:9103 | 6053:9103 | 6013:9104 | 6053:9104 |
| 6014:9102 | 6054:9102 | 6014:9103 | 6054:9103 | 6014:9104 | 6054:9104 |
| 6015:9102 | 6055:9102 | 6015:9103 | 6055:9103 | 6015:9104 | 6055:9104 |
| 6016:9102 | 6056:9102 | 6016:9103 | 6056:9103 | 6016:9104 | 6056:9104 |
| 6017:9102 | 6057:9102 | 6017:9103 | 6057:9103 | 6017:9104 | 6057:9104 |
| 6018:9102 | 6058:9102 | 6018:9103 | 6058:9103 | 6018:9104 | 6058:9104 |
| 6019:9102 | 6059:9102 | 6019:9103 | 6059:9103 | 6019:9104 | 6059:9104 |
| 6020:9102 | 6060:9102 | 6020:9103 | 6060:9103 | 6020:9104 | 6060:9104 |
| 6021:9102 | 6061:9102 | 6021:9103 | 6061:9103 | 6021:9104 | 6061:9104 |
| 6022:9102 | 6062:9102 | 6022:9103 | 6062:9103 | 6022:9104 | 6062:9104 |
| 6023:9102 | 6063:9102 | 6023:9103 | 6063:9103 | 6023:9104 | 6063:9104 |
| 6024:9102 | 6064:9102 | 6024:9103 | 6064:9103 | 6024:9104 | 6064:9104 |
| 6025:9102 | 6065:9102 | 6025:9103 | 6065:9103 | 6025:9104 | 6065:9104 |
| 6026:9102 | 6066:9102 | 6026:9103 | 6066:9103 | 6026:9104 | 6066:9104 |
| 6027:9102 | 6067:9102 | 6027:9103 | 6067:9103 | 6027:9104 | 6067:9104 |
| 6028:9102 | 6068:9102 | 6028:9103 | 6068:9103 | 6028:9104 | 6068:9104 |
| 6029:9102 | 6069:9102 | 6029:9103 | 6069:9103 | 6029:9104 | 6069:9104 |
| 6030:9102 | 6070:9102 | 6030:9103 | 6070:9103 | 6030:9104 | 6070:9104 |
| 6031:9102 | 6071:9102 | 6031:9103 | 6071:9103 | 6031:9104 | 6071:9104 |
| 6032:9102 | 6072:9102 | 6032:9103 | 6072:9103 | 6032:9104 | 6072:9104 |
| 6033:9102 | 6073:9102 | 6033:9103 | 6073:9103 | 6033:9104 | 6073:9104 |
| 6034:9102 | 6074:9102 | 6034:9103 | 6074:9103 | 6034:9104 | 6074:9104 |
| 6035:9102 | 6075:9102 | 6035:9103 | 6075:9103 | 6035:9104 | 6075:9104 |
| 6036:9102 | 6076:9102 | 6036:9103 | 6076:9103 | 6036:9104 | 6076:9104 |
| 6037:9102 | 6077:9102 | 6037:9103 | 6077:9103 | 6037:9104 | 6077:9104 |
| 6038:9102 | 6078:9102 | 6038:9103 | 6078:9103 | 6038:9104 | 6078:9104 |
| 6039:9102 |  | 6039:9103 |  | 6039:9104 |  |
| 6000:9105 | 6040:9105 | 6000:9106 | 6040:9106 | 6000:9107 | 6040:9107 |
| 6001:9105 | 6041:9105 | 6001:9106 | 6041:9106 | 6001:9107 | 6041:9107 |
| 6002:9105 | 6042:9105 | 6002:9106 | 6042:9106 | 6002:9107 | 6042:9107 |
| 6003:9105 | 6043:9105 | 6003:9106 | 6043:9106 | 6003:9107 | 6043:9107 |
| 6004:9105 | 6044:9105 | 6004:9106 | 6044:9106 | 6004:9107 | 6044:9107 |
| 6005:9105 | 6045:9105 | 6005:9106 | 6045:9106 | 6005:9107 | 6045:9107 |
| 6006:9105 | 6046:9105 | 6006:9106 | 6046:9106 | 6006:9107 | 6046:9107 |
| 6007:9105 | 6047:9105 | 6007:9106 | 6047:9106 | 6007:9107 | 6047:9107 |
| 6008:9105 | 6048:9105 | 6008:9106 | 6048:9106 | 6008:9107 | 6048:9107 |
| 6009:9105 | 6049:9105 | 6009:9106 | 6049:9106 | 6009:9107 | 6049:9107 |
| 6010:9105 | 6050:9105 | 6010:9106 | 6050:9106 | 6010:9107 | 6050:9107 |
| 6011:9105 | 6051:9105 | 6011:9106 | 6051:9106 | 6011:9107 | 6051:9107 |
| 6012:9105 | 6052:9105 | 6012:9106 | 6052:9106 | 6012:9107 | 6052:9107 |

TABLE D-continued

Example combinations of a compound X with a compound Y.

| X:Y | X:Y | X:Y | X:Y | X:Y | X:Y |
|---|---|---|---|---|---|
| 6013:9105 | 6053:9105 | 6013:9106 | 6053:9106 | 6013:9107 | 6053:9107 |
| 6014:9105 | 6054:9105 | 6014:9106 | 6054:9106 | 6014:9107 | 6054:9107 |
| 6015:9105 | 6055:9105 | 6015:9106 | 6055:9106 | 6015:9107 | 6055:9107 |
| 6016:9105 | 6056:9105 | 6016:9106 | 6056:9106 | 6016:9107 | 6056:9107 |
| 6017:9105 | 6057:9105 | 6017:9106 | 6057:9106 | 6017:9107 | 6057:9107 |
| 6018:9105 | 6058:9105 | 6018:9106 | 6058:9106 | 6018:9107 | 6058:9107 |
| 6019:9105 | 6059:9105 | 6019:9106 | 6059:9106 | 6019:9107 | 6059:9107 |
| 6020:9105 | 6060:9105 | 6020:9106 | 6060:9106 | 6020:9107 | 6060:9107 |
| 6021:9105 | 6061:9105 | 6021:9106 | 6061:9106 | 6021:9107 | 6061:9107 |
| 6022:9105 | 6062:9105 | 6022:9106 | 6062:9106 | 6022:9107 | 6062:9107 |
| 6023:9105 | 6063:9105 | 6023:9106 | 6063:9106 | 6023:9107 | 6063:9107 |
| 6024:9105 | 6064:9105 | 6024:9106 | 6064:9106 | 6024:9107 | 6064:9107 |
| 6025:9105 | 6065:9105 | 6025:9106 | 6065:9106 | 6025:9107 | 6065:9107 |
| 6026:9105 | 6066:9105 | 6026:9106 | 6066:9106 | 6026:9107 | 6066:9107 |
| 6027:9105 | 6067:9105 | 6027:9106 | 6067:9106 | 6027:9107 | 6067:9107 |
| 6028:9105 | 6068:9105 | 6028:9106 | 6068:9106 | 6028:9107 | 6068:9107 |
| 6029:9105 | 6069:9105 | 6029:9106 | 6069:9106 | 6029:9107 | 6069:9107 |
| 6030:9105 | 6070:9105 | 6030:9106 | 6070:9106 | 6030:9107 | 6070:9107 |
| 6031:9105 | 6071:9105 | 6031:9106 | 6071:9106 | 6031:9107 | 6071:9107 |
| 6032:9105 | 6072:9105 | 6032:9106 | 6072:9106 | 6032:9107 | 6072:9107 |
| 6033:9105 | 6073:9105 | 6033:9106 | 6073:9106 | 6033:9107 | 6073:9107 |
| 6034:9105 | 6074:9105 | 6034:9106 | 6074:9106 | 6034:9107 | 6074:9107 |
| 6035:9105 | 6075:9105 | 6035:9106 | 6075:9106 | 6035:9107 | 6075:9107 |
| 6036:9105 | 6076:9105 | 6036:9106 | 6076:9106 | 6036:9107 | 6076:9107 |
| 6037:9105 | 6077:9105 | 6037:9106 | 6077:9106 | 6037:9107 | 6077:9107 |
| 6038:9105 | 6078:9105 | 6038:9106 | 6078:9106 | 6038:9107 | 6078:9107 |
| 6039:9105 | | 6039:9106 | | 6039:9107 | |
| 6000:9108 | 6040:9108 | 6000:9109 | 6040:9109 | 6000:9110 | 6040:9110 |
| 6001:9108 | 6041:9108 | 6001:9109 | 6041:9109 | 6001:9110 | 6041:9110 |
| 6002:9108 | 6042:9108 | 6002:9109 | 6042:9109 | 6002:9110 | 6042:9110 |
| 6003:9108 | 6043:9108 | 6003:9109 | 6043:9109 | 6003:9110 | 6043:9110 |
| 6004:9108 | 6044:9108 | 6004:9109 | 6044:9109 | 6004:9110 | 6044:9110 |
| 6005:9108 | 6045:9108 | 6005:9109 | 6045:9109 | 6005:9110 | 6045:9110 |
| 6006:9108 | 6046:9108 | 6006:9109 | 6046:9109 | 6006:9110 | 6046:9110 |
| 6007:9108 | 6047:9108 | 6007:9109 | 6047:9109 | 6007:9110 | 6047:9110 |
| 6008:9108 | 6048:9108 | 6008:9109 | 6048:9109 | 6008:9110 | 6048:9110 |
| 6009:9108 | 6049:9108 | 6009:9109 | 6049:9109 | 6009:9110 | 6049:9110 |
| 6010:9108 | 6050:9108 | 6010:9109 | 6050:9109 | 6010:9110 | 6050:9110 |
| 6011:9108 | 6051:9108 | 6011:9109 | 6051:9109 | 6011:9110 | 6051:9110 |
| 6012:9108 | 6052:9108 | 6012:9109 | 6052:9109 | 6012:9110 | 6052:9110 |
| 6013:9108 | 6053:9108 | 6013:9109 | 6053:9109 | 6013:9110 | 6053:9110 |
| 6014:9108 | 6054:9108 | 6014:9109 | 6054:9109 | 6014:9110 | 6054:9110 |
| 6015:9108 | 6055:9108 | 6015:9109 | 6055:9109 | 6015:9110 | 6055:9110 |
| 6016:9108 | 6056:9108 | 6016:9109 | 6056:9109 | 6016:9110 | 6056:9110 |
| 6017:9108 | 6057:9108 | 6017:9109 | 6057:9109 | 6017:9110 | 6057:9110 |
| 6018:9108 | 6058:9108 | 6018:9109 | 6058:9109 | 6018:9110 | 6058:9110 |
| 6019:9108 | 6059:9108 | 6019:9109 | 6059:9109 | 6019:9110 | 6059:9110 |
| 6020:9108 | 6060:9108 | 6020:9109 | 6060:9109 | 6020:9110 | 6060:9110 |
| 6021:9108 | 6061:9108 | 6021:9109 | 6061:9109 | 6021:9110 | 6061:9110 |
| 6022:9108 | 6062:9108 | 6022:9109 | 6062:9109 | 6022:9110 | 6062:9110 |
| 6023:9108 | 6063:9108 | 6023:9109 | 6063:9109 | 6023:9110 | 6063:9110 |
| 6024:9108 | 6064:9108 | 6024:9109 | 6064:9109 | 6024:9110 | 6064:9110 |
| 6025:9108 | 6065:9108 | 6025:9109 | 6065:9109 | 6025:9110 | 6065:9110 |
| 6026:9108 | 6066:9108 | 6026:9109 | 6066:9109 | 6026:9110 | 6066:9110 |
| 6027:9108 | 6067:9108 | 6027:9109 | 6067:9109 | 6027:9110 | 6067:9110 |
| 6028:9108 | 6068:9108 | 6028:9109 | 6068:9109 | 6028:9110 | 6068:9110 |
| 6029:9108 | 6069:9108 | 6029:9109 | 6069:9109 | 6029:9110 | 6069:9110 |
| 6030:9108 | 6070:9108 | 6030:9109 | 6070:9109 | 6030:9110 | 6070:9110 |
| 6031:9108 | 6071:9108 | 6031:9109 | 6071:9109 | 6031:9110 | 6071:9110 |
| 6032:9108 | 6072:9108 | 6032:9109 | 6072:9109 | 6032:9110 | 6072:9110 |
| 6033:9108 | 6073:9108 | 6033:9109 | 6073:9109 | 6033:9110 | 6073:9110 |
| 6034:9108 | 6074:9108 | 6034:9109 | 6074:9109 | 6034:9110 | 6074:9110 |
| 6035:9108 | 6075:9108 | 6035:9109 | 6075:9109 | 6035:9110 | 6075:9110 |
| 6036:9108 | 6076:9108 | 6036:9109 | 6076:9109 | 6036:9110 | 6076:9110 |
| 6037:9108 | 6077:9108 | 6037:9109 | 6077:9109 | 6037:9110 | 6077:9110 |
| 6038:9108 | 6078:9108 | 6038:9109 | 6078:9109 | 6038:9110 | 6078:9110 |
| 6039:9108 | | 6039:9109 | | 6039:9110 | |
| 6000:9111 | 6040:9111 | 6000:9129 | 6040:9129 | 6000:9130 | 6040:9130 |
| 6001:9111 | 6041:9111 | 6001:9129 | 6041:9129 | 6001:9130 | 6041:9130 |
| 6002:9111 | 6042:9111 | 6002:9129 | 6042:9129 | 6002:9130 | 6042:9130 |
| 6003:9111 | 6043:9111 | 6003:9129 | 6043:9129 | 6003:9130 | 6043:9130 |
| 6004:9111 | 6044:9111 | 6004:9129 | 6044:9129 | 6004:9130 | 6044:9130 |
| 6005:9111 | 6045:9111 | 6005:9129 | 6045:9129 | 6005:9130 | 6045:9130 |
| 6006:9111 | 6046:9111 | 6006:9129 | 6046:9129 | 6006:9130 | 6046:9130 |
| 6007:9111 | 6047:9111 | 6007:9129 | 6047:9129 | 6007:9130 | 6047:9130 |
| 6008:9111 | 6048:9111 | 6008:9129 | 6048:9129 | 6008:9130 | 6048:9130 |
| 6009:9111 | 6049:9111 | 6009:9129 | 6049:9129 | 6009:9130 | 6049:9130 |
| 6010:9111 | 6050:9111 | 6010:9129 | 6050:9129 | 6010:9130 | 6050:9130 |
| 6011:9111 | 6051:9111 | 6011:9129 | 6051:9129 | 6011:9130 | 6051:9130 |
| 6012:9111 | 6052:9111 | 6012:9129 | 6052:9129 | 6012:9130 | 6052:9130 |
| 6013:9111 | 6053:9111 | 6013:9129 | 6053:9129 | 6013:9130 | 6053:9130 |
| 6014:9111 | 6054:9111 | 6014:9129 | 6054:9129 | 6014:9130 | 6054:9130 |
| 6015:9111 | 6055:9111 | 6015:9129 | 6055:9129 | 6015:9130 | 6055:9130 |
| 6016:9111 | 6056:9111 | 6016:9129 | 6056:9129 | 6016:9130 | 6056:9130 |
| 6017:9111 | 6057:9111 | 6017:9129 | 6057:9129 | 6017:9130 | 6057:9130 |
| 6018:9111 | 6058:9111 | 6018:9129 | 6058:9129 | 6018:9130 | 6058:9130 |
| 6019:9111 | 6059:9111 | 6019:9129 | 6059:9129 | 6019:9130 | 6059:9130 |
| 6020:9111 | 6060:9111 | 6020:9129 | 6060:9129 | 6020:9130 | 6060:9130 |
| 6021:9111 | 6061:9111 | 6021:9129 | 6061:9129 | 6021:9130 | 6061:9130 |
| 6022:9111 | 6062:9111 | 6022:9129 | 6062:9129 | 6022:9130 | 6062:9130 |
| 6023:9111 | 6063:9111 | 6023:9129 | 6063:9129 | 6023:9130 | 6063:9130 |
| 6024:9111 | 6064:9111 | 6024:9129 | 6064:9129 | 6024:9130 | 6064:9130 |
| 6025:9111 | 6065:9111 | 6025:9129 | 6065:9129 | 6025:9130 | 6065:9130 |
| 6026:9111 | 6066:9111 | 6026:9129 | 6066:9129 | 6026:9130 | 6066:9130 |
| 6027:9111 | 6067:9111 | 6027:9129 | 6067:9129 | 6027:9130 | 6067:9130 |
| 6028:9111 | 6068:9111 | 6028:9129 | 6068:9129 | 6028:9130 | 6068:9130 |
| 6029:9111 | 6069:9111 | 6029:9129 | 6069:9129 | 6029:9130 | 6069:9130 |
| 6030:9111 | 6070:9111 | 6030:9129 | 6070:9129 | 6030:9130 | 6070:9130 |
| 6031:9111 | 6071:9111 | 6031:9129 | 6071:9129 | 6031:9130 | 6071:9130 |
| 6032:9111 | 6072:9111 | 6032:9129 | 6072:9129 | 6032:9130 | 6072:9130 |
| 6033:9111 | 6073:9111 | 6033:9129 | 6073:9129 | 6033:9130 | 6073:9130 |
| 6034:9111 | 6074:9111 | 6034:9129 | 6074:9129 | 6034:9130 | 6074:9130 |
| 6035:9111 | 6075:9111 | 6035:9129 | 6075:9129 | 6035:9130 | 6075:9130 |
| 6036:9111 | 6076:9111 | 6036:9129 | 6076:9129 | 6036:9130 | 6076:9130 |
| 6037:9111 | 6077:9111 | 6037:9129 | 6077:9129 | 6037:9130 | 6077:9130 |
| 6038:9111 | 6078:9111 | 6038:9129 | 6078:9129 | 6038:9130 | 6078:9130 |
| 6039:9111 | | 6039:9129 | | 6039:9130 | |
| 6000:9131 | 6040:9131 | 6000:9132 | 6040:9132 | 6000:9133 | 6040:9133 |
| 6001:9131 | 6041:9131 | 6001:9132 | 6041:9132 | 6001:9133 | 6041:9133 |
| 6002:9131 | 6042:9131 | 6002:9132 | 6042:9132 | 6002:9133 | 6042:9133 |
| 6003:9131 | 6043:9131 | 6003:9132 | 6043:9132 | 6003:9133 | 6043:9133 |
| 6004:9131 | 6044:9131 | 6004:9132 | 6044:9132 | 6004:9133 | 6044:9133 |
| 6005:9131 | 6045:9131 | 6005:9132 | 6045:9132 | 6005:9133 | 6045:9133 |
| 6006:9131 | 6046:9131 | 6006:9132 | 6046:9132 | 6006:9133 | 6046:9133 |
| 6007:9131 | 6047:9131 | 6007:9132 | 6047:9132 | 6007:9133 | 6047:9133 |
| 6008:9131 | 6048:9131 | 6008:9132 | 6048:9132 | 6008:9133 | 6048:9133 |
| 6009:9131 | 6049:9131 | 6009:9132 | 6049:9132 | 6009:9133 | 6049:9133 |
| 6010:9131 | 6050:9131 | 6010:9132 | 6050:9132 | 6010:9133 | 6050:9133 |
| 6011:9131 | 6051:9131 | 6011:9132 | 6051:9132 | 6011:9133 | 6051:9133 |
| 6012:9131 | 6052:9131 | 6012:9132 | 6052:9132 | 6012:9133 | 6052:9133 |
| 6013:9131 | 6053:9131 | 6013:9132 | 6053:9132 | 6013:9133 | 6053:9133 |
| 6014:9131 | 6054:9131 | 6014:9132 | 6054:9132 | 6014:9133 | 6054:9133 |
| 6015:9131 | 6055:9131 | 6015:9132 | 6055:9132 | 6015:9133 | 6055:9133 |
| 6016:9131 | 6056:9131 | 6016:9132 | 6056:9132 | 6016:9133 | 6056:9133 |
| 6017:9131 | 6057:9131 | 6017:9132 | 6057:9132 | 6017:9133 | 6057:9133 |
| 6018:9131 | 6058:9131 | 6018:9132 | 6058:9132 | 6018:9133 | 6058:9133 |
| 6019:9131 | 6059:9131 | 6019:9132 | 6059:9132 | 6019:9133 | 6059:9133 |
| 6020:9131 | 6060:9131 | 6020:9132 | 6060:9132 | 6020:9133 | 6060:9133 |
| 6021:9131 | 6061:9131 | 6021:9132 | 6061:9132 | 6021:9133 | 6061:9133 |
| 6022:9131 | 6062:9131 | 6022:9132 | 6062:9132 | 6022:9133 | 6062:9133 |
| 6023:9131 | 6063:9131 | 6023:9132 | 6063:9132 | 6023:9133 | 6063:9133 |
| 6024:9131 | 6064:9131 | 6024:9132 | 6064:9132 | 6024:9133 | 6064:9133 |
| 6025:9131 | 6065:9131 | 6025:9132 | 6065:9132 | 6025:9133 | 6065:9133 |
| 6026:9131 | 6066:9131 | 6026:9132 | 6066:9132 | 6026:9133 | 6066:9133 |
| 6027:9131 | 6067:9131 | 6027:9132 | 6067:9132 | 6027:9133 | 6067:9133 |
| 6028:9131 | 6068:9131 | 6028:9132 | 6068:9132 | 6028:9133 | 6068:9133 |
| 6029:9131 | 6069:9131 | 6029:9132 | 6069:9132 | 6029:9133 | 6069:9133 |
| 6030:9131 | 6070:9131 | 6030:9132 | 6070:9132 | 6030:9133 | 6070:9133 |
| 6031:9131 | 6071:9131 | 6031:9132 | 6071:9132 | 6031:9133 | 6071:9133 |
| 6032:9131 | 6072:9131 | 6032:9132 | 6072:9132 | 6032:9133 | 6072:9133 |
| 6033:9131 | 6073:9131 | 6033:9132 | 6073:9132 | 6033:9133 | 6073:9133 |
| 6034:9131 | 6074:9131 | 6034:9132 | 6074:9132 | 6034:9133 | 6074:9133 |
| 6035:9131 | 6075:9131 | 6035:9132 | 6075:9132 | 6035:9133 | 6075:9133 |
| 6036:9131 | 6076:9131 | 6036:9132 | 6076:9132 | 6036:9133 | 6076:9133 |
| 6037:9131 | 6077:9131 | 6037:9132 | 6077:9132 | 6037:9133 | 6077:9133 |
| 6038:9131 | 6078:9131 | 6038:9132 | 6078:9132 | 6038:9133 | 6078:9133 |
| 6039:9131 | | 6039:9132 | | 6039:9133 | |
| 6000:9134 | 6040:9134 | 6000:9135 | 6040:9135 | 6000:9136 | 6040:9136 |
| 6001:9134 | 6041:9134 | 6001:9135 | 6041:9135 | 6001:9136 | 6041:9136 |
| 6002:9134 | 6042:9134 | 6002:9135 | 6042:9135 | 6002:9136 | 6042:9136 |
| 6003:9134 | 6043:9134 | 6003:9135 | 6043:9135 | 6003:9136 | 6043:9136 |
| 6004:9134 | 6044:9134 | 6004:9135 | 6044:9135 | 6004:9136 | 6044:9136 |

TABLE D-continued

Example combinations of a compound X with a compound Y.

| X:Y | X:Y | X:Y | X:Y | X:Y | X:Y |
|---|---|---|---|---|---|
| 6005:9134 | 6045:9134 | 6005:9135 | 6045:9135 | 6005:9136 | 6045:9136 |
| 6006:9134 | 6046:9134 | 6006:9135 | 6046:9135 | 6006:9136 | 6046:9136 |
| 6007:9134 | 6047:9134 | 6007:9135 | 6047:9135 | 6007:9136 | 6047:9136 |
| 6008:9134 | 6048:9134 | 6008:9135 | 6048:9135 | 6008:9136 | 6048:9136 |
| 6009:9134 | 6049:9134 | 6009:9135 | 6049:9135 | 6009:9136 | 6049:9136 |
| 6010:9134 | 6050:9134 | 6010:9135 | 6050:9135 | 6010:9136 | 6050:9136 |
| 6011:9134 | 6051:9134 | 6011:9135 | 6051:9135 | 6011:9136 | 6051:9136 |
| 6012:9134 | 6052:9134 | 6012:9135 | 6052:9135 | 6012:9136 | 6052:9136 |
| 6013:9134 | 6053:9134 | 6013:9135 | 6053:9135 | 6013:9136 | 6053:9136 |
| 6014:9134 | 6054:9134 | 6014:9135 | 6054:9135 | 6014:9136 | 6054:9136 |
| 6015:9134 | 6055:9134 | 6015:9135 | 6055:9135 | 6015:9136 | 6055:9136 |
| 6016:9134 | 6056:9134 | 6016:9135 | 6056:9135 | 6016:9136 | 6056:9136 |
| 6017:9134 | 6057:9134 | 6017:9135 | 6057:9135 | 6017:9136 | 6057:9136 |
| 6018:9134 | 6058:9134 | 6018:9135 | 6058:9135 | 6018:9136 | 6058:9136 |
| 6019:9134 | 6059:9134 | 6019:9135 | 6059:9135 | 6019:9136 | 6059:9136 |
| 6020:9134 | 6060:9134 | 6020:9135 | 6060:9135 | 6020:9136 | 6060:9136 |
| 6021:9134 | 6061:9134 | 6021:9135 | 6061:9135 | 6021:9136 | 6061:9136 |
| 6022:9134 | 6062:9134 | 6022:9135 | 6062:9135 | 6022:9136 | 6062:9136 |
| 6023:9134 | 6063:9134 | 6023:9135 | 6063:9135 | 6023:9136 | 6063:9136 |
| 6024:9134 | 6064:9134 | 6024:9135 | 6064:9135 | 6024:9136 | 6064:9136 |
| 6025:9134 | 6065:9134 | 6025:9135 | 6065:9135 | 6025:9136 | 6065:9136 |
| 6026:9134 | 6066:9134 | 6026:9135 | 6066:9135 | 6026:9136 | 6066:9136 |
| 6027:9134 | 6067:9134 | 6027:9135 | 6067:9135 | 6027:9136 | 6067:9136 |
| 6028:9134 | 6068:9134 | 6028:9135 | 6068:9135 | 6028:9136 | 6068:9136 |
| 6029:9134 | 6069:9134 | 6029:9135 | 6069:9135 | 6029:9136 | 6069:9136 |
| 6030:9134 | 6070:9134 | 6030:9135 | 6070:9135 | 6030:9136 | 6070:9136 |
| 6031:9134 | 6071:9134 | 6031:9135 | 6071:9135 | 6031:9136 | 6071:9136 |
| 6032:9134 | 6072:9134 | 6032:9135 | 6072:9135 | 6032:9136 | 6072:9136 |
| 6033:9134 | 6073:9134 | 6033:9135 | 6073:9135 | 6033:9136 | 6073:9136 |
| 6034:9134 | 6074:9134 | 6034:9135 | 6074:9135 | 6034:9136 | 6074:9136 |
| 6035:9134 | 6075:9134 | 6035:9135 | 6075:9135 | 6035:9136 | 6075:9136 |
| 6036:9134 | 6076:9134 | 6036:9135 | 6076:9135 | 6036:9136 | 6076:9136 |
| 6037:9134 | 6077:9134 | 6037:9135 | 6077:9135 | 6037:9136 | 6077:9136 |
| 6038:9134 | 6078:9134 | 6038:9135 | 6078:9135 | 6038:9136 | 6078:9136 |
| 6039:9134 | | 6039:9135 | | 6039:9136 | |
| 6000:9137 | 6040:9137 | 6000:9138 | 6040:9138 | 6000:9139 | 6040:9139 |
| 6001:9137 | 6041:9137 | 6001:9138 | 6041:9138 | 6001:9139 | 6041:9139 |
| 6002:9137 | 6042:9137 | 6002:9138 | 6042:9138 | 6002:9139 | 6042:9139 |
| 6003:9137 | 6043:9137 | 6003:9138 | 6043:9138 | 6003:9139 | 6043:9139 |
| 6004:9137 | 6044:9137 | 6004:9138 | 6044:9138 | 6004:9139 | 6044:9139 |
| 6005:9137 | 6045:9137 | 6005:9138 | 6045:9138 | 6005:9139 | 6045:9139 |
| 6006:9137 | 6046:9137 | 6006:9138 | 6046:9138 | 6006:9139 | 6046:9139 |
| 6007:9137 | 6047:9137 | 6007:9138 | 6047:9138 | 6007:9139 | 6047:9139 |
| 6008:9137 | 6048:9137 | 6008:9138 | 6048:9138 | 6008:9139 | 6048:9139 |
| 6009:9137 | 6049:9137 | 6009:9138 | 6049:9138 | 6009:9139 | 6049:9139 |
| 6010:9137 | 6050:9137 | 6010:9138 | 6050:9138 | 6010:9139 | 6050:9139 |
| 6011:9137 | 6051:9137 | 6011:9138 | 6051:9138 | 6011:9139 | 6051:9139 |
| 6012:9137 | 6052:9137 | 6012:9138 | 6052:9138 | 6012:9139 | 6052:9139 |
| 6013:9137 | 6053:9137 | 6013:9138 | 6053:9138 | 6013:9139 | 6053:9139 |
| 6014:9137 | 6054:9137 | 6014:9138 | 6054:9138 | 6014:9139 | 6054:9139 |
| 6015:9137 | 6055:9137 | 6015:9138 | 6055:9138 | 6015:9139 | 6055:9139 |
| 6016:9137 | 6056:9137 | 6016:9138 | 6056:9138 | 6016:9139 | 6056:9139 |
| 6017:9137 | 6057:9137 | 6017:9138 | 6057:9138 | 6017:9139 | 6057:9139 |
| 6018:9137 | 6058:9137 | 6018:9138 | 6058:9138 | 6018:9139 | 6058:9139 |
| 6019:9137 | 6059:9137 | 6019:9138 | 6059:9138 | 6019:9139 | 6059:9139 |
| 6020:9137 | 6060:9137 | 6020:9138 | 6060:9138 | 6020:9139 | 6060:9139 |
| 6021:9137 | 6061:9137 | 6021:9138 | 6061:9138 | 6021:9139 | 6061:9139 |
| 6022:9137 | 6062:9137 | 6022:9138 | 6062:9138 | 6022:9139 | 6062:9139 |
| 6023:9137 | 6063:9137 | 6023:9138 | 6063:9138 | 6023:9139 | 6063:9139 |
| 6024:9137 | 6064:9137 | 6024:9138 | 6064:9138 | 6024:9139 | 6064:9139 |
| 6025:9137 | 6065:9137 | 6025:9138 | 6065:9138 | 6025:9139 | 6065:9139 |
| 6026:9137 | 6066:9137 | 6026:9138 | 6066:9138 | 6026:9139 | 6066:9139 |
| 6027:9137 | 6067:9137 | 6027:9138 | 6067:9138 | 6027:9139 | 6067:9139 |
| 6028:9137 | 6068:9137 | 6028:9138 | 6068:9138 | 6028:9139 | 6068:9139 |
| 6029:9137 | 6069:9137 | 6029:9138 | 6069:9138 | 6029:9139 | 6069:9139 |
| 6030:9137 | 6070:9137 | 6030:9138 | 6070:9138 | 6030:9139 | 6070:9139 |
| 6031:9137 | 6071:9137 | 6031:9138 | 6071:9138 | 6031:9139 | 6071:9139 |
| 6032:9137 | 6072:9137 | 6032:9138 | 6072:9138 | 6032:9139 | 6072:9139 |
| 6033:9137 | 6073:9137 | 6033:9138 | 6073:9138 | 6033:9139 | 6073:9139 |
| 6034:9137 | 6074:9137 | 6034:9138 | 6074:9138 | 6034:9139 | 6074:9139 |
| 6035:9137 | 6075:9137 | 6035:9138 | 6075:9138 | 6035:9139 | 6075:9139 |
| 6036:9137 | 6076:9137 | 6036:9138 | 6076:9138 | 6036:9139 | 6076:9139 |
| 6037:9137 | 6077:9137 | 6037:9138 | 6077:9138 | 6037:9139 | 6077:9139 |
| 6038:9137 | 6078:9137 | 6038:9138 | 6078:9138 | 6038:9139 | 6078:9139 |
| 6039:9137 | | 6039:9138 | | 6039:9139 | |
| 6000:9140 | 6040:9140 | 6000:9141 | 6040:9141 | 6000:9142 | 6040:9142 |

TABLE D-continued

Example combinations of a compound X with a compound Y.

| X:Y | X:Y | X:Y | X:Y | X:Y | X:Y |
|---|---|---|---|---|---|
| 6001:9140 | 6041:9140 | 6001:9141 | 6041:9141 | 6001:9142 | 6041:9142 |
| 6002:9140 | 6042:9140 | 6002:9141 | 6042:9141 | 6002:9142 | 6042:9142 |
| 6003:9140 | 6043:9140 | 6003:9141 | 6043:9141 | 6003:9142 | 6043:9142 |
| 6004:9140 | 6044:9140 | 6004:9141 | 6044:9141 | 6004:9142 | 6044:9142 |
| 6005:9140 | 6045:9140 | 6005:9141 | 6045:9141 | 6005:9142 | 6045:9142 |
| 6006:9140 | 6046:9140 | 6006:9141 | 6046:9141 | 6006:9142 | 6046:9142 |
| 6007:9140 | 6047:9140 | 6007:9141 | 6047:9141 | 6007:9142 | 6047:9142 |
| 6008:9140 | 6048:9140 | 6008:9141 | 6048:9141 | 6008:9142 | 6048:9142 |
| 6009:9140 | 6049:9140 | 6009:9141 | 6049:9141 | 6009:9142 | 6049:9142 |
| 6010:9140 | 6050:9140 | 6010:9141 | 6050:9141 | 6010:9142 | 6050:9142 |
| 6011:9140 | 6051:9140 | 6011:9141 | 6051:9141 | 6011:9142 | 6051:9142 |
| 6012:9140 | 6052:9140 | 6012:9141 | 6052:9141 | 6012:9142 | 6052:9142 |
| 6013:9140 | 6053:9140 | 6013:9141 | 6053:9141 | 6013:9142 | 6053:9142 |
| 6014:9140 | 6054:9140 | 6014:9141 | 6054:9141 | 6014:9142 | 6054:9142 |
| 6015:9140 | 6055:9140 | 6015:9141 | 6055:9141 | 6015:9142 | 6055:9142 |
| 6016:9140 | 6056:9140 | 6016:9141 | 6056:9141 | 6016:9142 | 6056:9142 |
| 6017:9140 | 6057:9140 | 6017:9141 | 6057:9141 | 6017:9142 | 6057:9142 |
| 6018:9140 | 6058:9140 | 6018:9141 | 6058:9141 | 6018:9142 | 6058:9142 |
| 6019:9140 | 6059:9140 | 6019:9141 | 6059:9141 | 6019:9142 | 6059:9142 |
| 6020:9140 | 6060:9140 | 6020:9141 | 6060:9141 | 6020:9142 | 6060:9142 |
| 6021:9140 | 6061:9140 | 6021:9141 | 6061:9141 | 6021:9142 | 6061:9142 |
| 6022:9140 | 6062:9140 | 6022:9141 | 6062:9141 | 6022:9142 | 6062:9142 |
| 6023:9140 | 6063:9140 | 6023:9141 | 6063:9141 | 6023:9142 | 6063:9142 |
| 6024:9140 | 6064:9140 | 6024:9141 | 6064:9141 | 6024:9142 | 6064:9142 |
| 6025:9140 | 6065:9140 | 6025:9141 | 6065:9141 | 6025:9142 | 6065:9142 |
| 6026:9140 | 6066:9140 | 6026:9141 | 6066:9141 | 6026:9142 | 6066:9142 |
| 6027:9140 | 6067:9140 | 6027:9141 | 6067:9141 | 6027:9142 | 6067:9142 |
| 6028:9140 | 6068:9140 | 6028:9141 | 6068:9141 | 6028:9142 | 6068:9142 |
| 6029:9140 | 6069:9140 | 6029:9141 | 6069:9141 | 6029:9142 | 6069:9142 |
| 6030:9140 | 6070:9140 | 6030:9141 | 6070:9141 | 6030:9142 | 6070:9142 |
| 6031:9140 | 6071:9140 | 6031:9141 | 6071:9141 | 6031:9142 | 6071:9142 |
| 6032:9140 | 6072:9140 | 6032:9141 | 6072:9141 | 6032:9142 | 6072:9142 |
| 6033:9140 | 6073:9140 | 6033:9141 | 6073:9141 | 6033:9142 | 6073:9142 |
| 6034:9140 | 6074:9140 | 6034:9141 | 6074:9141 | 6034:9142 | 6074:9142 |
| 6035:9140 | 6075:9140 | 6035:9141 | 6075:9141 | 6035:9142 | 6075:9142 |
| 6036:9140 | 6076:9140 | 6036:9141 | 6076:9141 | 6036:9142 | 6076:9142 |
| 6037:9140 | 6077:9140 | 6037:9141 | 6077:9141 | 6037:9142 | 6077:9142 |
| 6038:9140 | 6078:9140 | 6038:9141 | 6078:9141 | 6038:9142 | 6078:9142 |
| 6039:9140 | | 6039:9141 | | 6039:9142 | |
| 6000:9143 | 6040:9143 | 6000:9144 | 6040:9144 | 6000:9145 | 6040:9145 |
| 6001:9143 | 6041:9143 | 6001:9144 | 6041:9144 | 6001:9145 | 6041:9145 |
| 6002:9143 | 6042:9143 | 6002:9144 | 6042:9144 | 6002:9145 | 6042:9145 |
| 6003:9143 | 6043:9143 | 6003:9144 | 6043:9144 | 6003:9145 | 6043:9145 |
| 6004:9143 | 6044:9143 | 6004:9144 | 6044:9144 | 6004:9145 | 6044:9145 |
| 6005:9143 | 6045:9143 | 6005:9144 | 6045:9144 | 6005:9145 | 6045:9145 |
| 6006:9143 | 6046:9143 | 6006:9144 | 6046:9144 | 6006:9145 | 6046:9145 |
| 6007:9143 | 6047:9143 | 6007:9144 | 6047:9144 | 6007:9145 | 6047:9145 |
| 6008:9143 | 6048:9143 | 6008:9144 | 6048:9144 | 6008:9145 | 6048:9145 |
| 6009:9143 | 6049:9143 | 6009:9144 | 6049:9144 | 6009:9145 | 6049:9145 |
| 6010:9143 | 6050:9143 | 6010:9144 | 6050:9144 | 6010:9145 | 6050:9145 |
| 6011:9143 | 6051:9143 | 6011:9144 | 6051:9144 | 6011:9145 | 6051:9145 |
| 6012:9143 | 6052:9143 | 6012:9144 | 6052:9144 | 6012:9145 | 6052:9145 |
| 6013:9143 | 6053:9143 | 6013:9144 | 6053:9144 | 6013:9145 | 6053:9145 |
| 6014:9143 | 6054:9143 | 6014:9144 | 6054:9144 | 6014:9145 | 6054:9145 |
| 6015:9143 | 6055:9143 | 6015:9144 | 6055:9144 | 6015:9145 | 6055:9145 |
| 6016:9143 | 6056:9143 | 6016:9144 | 6056:9144 | 6016:9145 | 6056:9145 |
| 6017:9143 | 6057:9143 | 6017:9144 | 6057:9144 | 6017:9145 | 6057:9145 |
| 6018:9143 | 6058:9143 | 6018:9144 | 6058:9144 | 6018:9145 | 6058:9145 |
| 6019:9143 | 6059:9143 | 6019:9144 | 6059:9144 | 6019:9145 | 6059:9145 |
| 6020:9143 | 6060:9143 | 6020:9144 | 6060:9144 | 6020:9145 | 6060:9145 |
| 6021:9143 | 6061:9143 | 6021:9144 | 6061:9144 | 6021:9145 | 6061:9145 |
| 6022:9143 | 6062:9143 | 6022:9144 | 6062:9144 | 6022:9145 | 6062:9145 |
| 6023:9143 | 6063:9143 | 6023:9144 | 6063:9144 | 6023:9145 | 6063:9145 |
| 6024:9143 | 6064:9143 | 6024:9144 | 6064:9144 | 6024:9145 | 6064:9145 |
| 6025:9143 | 6065:9143 | 6025:9144 | 6065:9144 | 6025:9145 | 6065:9145 |
| 6026:9143 | 6066:9143 | 6026:9144 | 6066:9144 | 6026:9145 | 6066:9145 |
| 6027:9143 | 6067:9143 | 6027:9144 | 6067:9144 | 6027:9145 | 6067:9145 |
| 6028:9143 | 6068:9143 | 6028:9144 | 6068:9144 | 6028:9145 | 6068:9145 |
| 6029:9143 | 6069:9143 | 6029:9144 | 6069:9144 | 6029:9145 | 6069:9145 |
| 6030:9143 | 6070:9143 | 6030:9144 | 6070:9144 | 6030:9145 | 6070:9145 |
| 6031:9143 | 6071:9143 | 6031:9144 | 6071:9144 | 6031:9145 | 6071:9145 |
| 6032:9143 | 6072:9143 | 6032:9144 | 6072:9144 | 6032:9145 | 6072:9145 |
| 6033:9143 | 6073:9143 | 6033:9144 | 6073:9144 | 6033:9145 | 6073:9145 |
| 6034:9143 | 6074:9143 | 6034:9144 | 6074:9144 | 6034:9145 | 6074:9145 |
| 6035:9143 | 6075:9143 | 6035:9144 | 6075:9144 | 6035:9145 | 6075:9145 |
| 6036:9143 | 6076:9143 | 6036:9144 | 6076:9144 | 6036:9145 | 6076:9145 |

TABLE D-continued

Example combinations of a compound X with a compound Y.

| X:Y | X:Y | X:Y | X:Y | X:Y | X:Y |
|---|---|---|---|---|---|
| 6037:9143 | 6077:9143 | 6037:9144 | 6077:9144 | 6037:9145 | 6077:9145 |
| 6038:9143 | 6078:9143 | 6038:9144 | 6078:9144 | 6038:9145 | 6078:9145 |
| 6039:9143 | | 6039:9144 | | 6039:9145 | |
| 6000:9146 | 6040:9146 | 6000:9147 | 6040:9147 | 6000:9148 | 6040:9148 |
| 6001:9146 | 6041:9146 | 6001:9147 | 6041:9147 | 6001:9148 | 6041:9148 |
| 6002:9146 | 6042:9146 | 6002:9147 | 6042:9147 | 6002:9148 | 6042:9148 |
| 6003:9146 | 6043:9146 | 6003:9147 | 6043:9147 | 6003:9148 | 6043:9148 |
| 6004:9146 | 6044:9146 | 6004:9147 | 6044:9147 | 6004:9148 | 6044:9148 |
| 6005:9146 | 6045:9146 | 6005:9147 | 6045:9147 | 6005:9148 | 6045:9148 |
| 6006:9146 | 6046:9146 | 6006:9147 | 6046:9147 | 6006:9148 | 6046:9148 |
| 6007:9146 | 6047:9146 | 6007:9147 | 6047:9147 | 6007:9148 | 6047:9148 |
| 6008:9146 | 6048:9146 | 6008:9147 | 6048:9147 | 6008:9148 | 6048:9148 |
| 6009:9146 | 6049:9146 | 6009:9147 | 6049:9147 | 6009:9148 | 6049:9148 |
| 6010:9146 | 6050:9146 | 6010:9147 | 6050:9147 | 6010:9148 | 6050:9148 |
| 6011:9146 | 6051:9146 | 6011:9147 | 6051:9147 | 6011:9148 | 6051:9148 |
| 6012:9146 | 6052:9146 | 6012:9147 | 6052:9147 | 6012:9148 | 6052:9148 |
| 6013:9146 | 6053:9146 | 6013:9147 | 6053:9147 | 6013:9148 | 6053:9148 |
| 6014:9146 | 6054:9146 | 6014:9147 | 6054:9147 | 6014:9148 | 6054:9148 |
| 6015:9146 | 6055:9146 | 6015:9147 | 6055:9147 | 6015:9148 | 6055:9148 |
| 6016:9146 | 6056:9146 | 6016:9147 | 6056:9147 | 6016:9148 | 6056:9148 |
| 6017:9146 | 6057:9146 | 6017:9147 | 6057:9147 | 6017:9148 | 6057:9148 |
| 6018:9146 | 6058:9146 | 6018:9147 | 6058:9147 | 6018:9148 | 6058:9148 |
| 6019:9146 | 6059:9146 | 6019:9147 | 6059:9147 | 6019:9148 | 6059:9148 |
| 6020:9146 | 6060:9146 | 6020:9147 | 6060:9147 | 6020:9148 | 6060:9148 |
| 6021:9146 | 6061:9146 | 6021:9147 | 6061:9147 | 6021:9148 | 6061:9148 |
| 6022:9146 | 6062:9146 | 6022:9147 | 6062:9147 | 6022:9148 | 6062:9148 |
| 6023:9146 | 6063:9146 | 6023:9147 | 6063:9147 | 6023:9148 | 6063:9148 |
| 6024:9146 | 6064:9146 | 6024:9147 | 6064:9147 | 6024:9148 | 6064:9148 |
| 6025:9146 | 6065:9146 | 6025:9147 | 6065:9147 | 6025:9148 | 6065:9148 |
| 6026:9146 | 6066:9146 | 6026:9147 | 6066:9147 | 6026:9148 | 6066:9148 |
| 6027:9146 | 6067:9146 | 6027:9147 | 6067:9147 | 6027:9148 | 6067:9148 |
| 6028:9146 | 6068:9146 | 6028:9147 | 6068:9147 | 6028:9148 | 6068:9148 |
| 6029:9146 | 6069:9146 | 6029:9147 | 6069:9147 | 6029:9148 | 6069:9148 |
| 6030:9146 | 6070:9146 | 6030:9147 | 6070:9147 | 6030:9148 | 6070:9148 |
| 6031:9146 | 6071:9146 | 6031:9147 | 6071:9147 | 6031:9148 | 6071:9148 |
| 6032:9146 | 6072:9146 | 6032:9147 | 6072:9147 | 6032:9148 | 6072:9148 |
| 6033:9146 | 6073:9146 | 6033:9147 | 6073:9147 | 6033:9148 | 6073:9148 |
| 6034:9146 | 6074:9146 | 6034:9147 | 6074:9147 | 6034:9148 | 6074:9148 |
| 6035:9146 | 6075:9146 | 6035:9147 | 6075:9147 | 6035:9148 | 6075:9148 |
| 6036:9146 | 6076:9146 | 6036:9147 | 6076:9147 | 6036:9148 | 6076:9148 |
| 6037:9146 | 6077:9146 | 6037:9147 | 6077:9147 | 6037:9148 | 6077:9148 |
| 6038:9146 | 6078:9146 | 6038:9147 | 6078:9147 | 6038:9148 | 6078:9148 |
| 6039:9146 | | 6039:9147 | | 6039:9148 | |
| 6000:9149 | 6040:9149 | 6000:9150 | 6040:9150 | 6000:9161 | 6040:9161 |
| 6001:9149 | 6041:9149 | 6001:9150 | 6041:9150 | 6001:9161 | 6041:9161 |
| 6002:9149 | 6042:9149 | 6002:9150 | 6042:9150 | 6002:9161 | 6042:9161 |
| 6003:9149 | 6043:9149 | 6003:9150 | 6043:9150 | 6003:9161 | 6043:9161 |
| 6004:9149 | 6044:9149 | 6004:9150 | 6044:9150 | 6004:9161 | 6044:9161 |
| 6005:9149 | 6045:9149 | 6005:9150 | 6045:9150 | 6005:9161 | 6045:9161 |
| 6006:9149 | 6046:9149 | 6006:9150 | 6046:9150 | 6006:9161 | 6046:9161 |
| 6007:9149 | 6047:9149 | 6007:9150 | 6047:9150 | 6007:9161 | 6047:9161 |
| 6008:9149 | 6048:9149 | 6008:9150 | 6048:9150 | 6008:9161 | 6048:9161 |
| 6009:9149 | 6049:9149 | 6009:9150 | 6049:9150 | 6009:9161 | 6049:9161 |
| 6010:9149 | 6050:9149 | 6010:9150 | 6050:9150 | 6010:9161 | 6050:9161 |
| 6011:9149 | 6051:9149 | 6011:9150 | 6051:9150 | 6011:9161 | 6051:9161 |
| 6012:9149 | 6052:9149 | 6012:9150 | 6052:9150 | 6012:9161 | 6052:9161 |
| 6013:9149 | 6053:9149 | 6013:9150 | 6053:9150 | 6013:9161 | 6053:9161 |
| 6014:9149 | 6054:9149 | 6014:9150 | 6054:9150 | 6014:9161 | 6054:9161 |
| 6015:9149 | 6055:9149 | 6015:9150 | 6055:9150 | 6015:9161 | 6055:9161 |
| 6016:9149 | 6056:9149 | 6016:9150 | 6056:9150 | 6016:9161 | 6056:9161 |
| 6017:9149 | 6057:9149 | 6017:9150 | 6057:9150 | 6017:9161 | 6057:9161 |
| 6018:9149 | 6058:9149 | 6018:9150 | 6058:9150 | 6018:9161 | 6058:9161 |
| 6019:9149 | 6059:9149 | 6019:9150 | 6059:9150 | 6019:9161 | 6059:9161 |
| 6020:9149 | 6060:9149 | 6020:9150 | 6060:9150 | 6020:9161 | 6060:9161 |
| 6021:9149 | 6061:9149 | 6021:9150 | 6061:9150 | 6021:9161 | 6061:9161 |
| 6022:9149 | 6062:9149 | 6022:9150 | 6062:9150 | 6022:9161 | 6062:9161 |
| 6023:9149 | 6063:9149 | 6023:9150 | 6063:9150 | 6023:9161 | 6063:9161 |
| 6024:9149 | 6064:9149 | 6024:9150 | 6064:9150 | 6024:9161 | 6064:9161 |
| 6025:9149 | 6065:9149 | 6025:9150 | 6065:9150 | 6025:9161 | 6065:9161 |
| 6026:9149 | 6066:9149 | 6026:9150 | 6066:9150 | 6026:9161 | 6066:9161 |
| 6027:9149 | 6067:9149 | 6027:9150 | 6067:9150 | 6027:9161 | 6067:9161 |
| 6028:9149 | 6068:9149 | 6028:9150 | 6068:9150 | 6028:9161 | 6068:9161 |
| 6029:9149 | 6069:9149 | 6029:9150 | 6069:9150 | 6029:9161 | 6069:9161 |
| 6030:9149 | 6070:9149 | 6030:9150 | 6070:9150 | 6030:9161 | 6070:9161 |
| 6031:9149 | 6071:9149 | 6031:9150 | 6071:9150 | 6031:9161 | 6071:9161 |
| 6032:9149 | 6072:9149 | 6032:9150 | 6072:9150 | 6032:9161 | 6072:9161 |
| 6033:9149 | 6073:9149 | 6033:9150 | 6073:9150 | 6033:9161 | 6073:9161 |
| 6034:9149 | 6074:9149 | 6034:9150 | 6074:9150 | 6034:9161 | 6074:9161 |
| 6035:9149 | 6075:9149 | 6035:9150 | 6075:9150 | 6035:9161 | 6075:9161 |
| 6036:9149 | 6076:9149 | 6036:9150 | 6076:9150 | 6036:9161 | 6076:9161 |
| 6037:9149 | 6077:9149 | 6037:9150 | 6077:9150 | 6037:9161 | 6077:9161 |
| 6038:9149 | 6078:9149 | 6038:9150 | 6078:9150 | 6038:9161 | 6078:9161 |
| 6039:9149 | | 6039:9150 | | 6039:9161 | |
| 6000:9162 | 6040:9162 | 6000:9163 | 6040:9163 | 6000:9164 | 6040:9164 |
| 6001:9162 | 6041:9162 | 6001:9163 | 6041:9163 | 6001:9164 | 6041:9164 |
| 6002:9162 | 6042:9162 | 6002:9163 | 6042:9163 | 6002:9164 | 6042:9164 |
| 6003:9162 | 6043:9162 | 6003:9163 | 6043:9163 | 6003:9164 | 6043:9164 |
| 6004:9162 | 6044:9162 | 6004:9163 | 6044:9163 | 6004:9164 | 6044:9164 |
| 6005:9162 | 6045:9162 | 6005:9163 | 6045:9163 | 6005:9164 | 6045:9164 |
| 6006:9162 | 6046:9162 | 6006:9163 | 6046:9163 | 6006:9164 | 6046:9164 |
| 6007:9162 | 6047:9162 | 6007:9163 | 6047:9163 | 6007:9164 | 6047:9164 |
| 6008:9162 | 6048:9162 | 6008:9163 | 6048:9163 | 6008:9164 | 6048:9164 |
| 6009:9162 | 6049:9162 | 6009:9163 | 6049:9163 | 6009:9164 | 6049:9164 |
| 6010:9162 | 6050:9162 | 6010:9163 | 6050:9163 | 6010:9164 | 6050:9164 |
| 6011:9162 | 6051:9162 | 6011:9163 | 6051:9163 | 6011:9164 | 6051:9164 |
| 6012:9162 | 6052:9162 | 6012:9163 | 6052:9163 | 6012:9164 | 6052:9164 |
| 6013:9162 | 6053:9162 | 6013:9163 | 6053:9163 | 6013:9164 | 6053:9164 |
| 6014:9162 | 6054:9162 | 6014:9163 | 6054:9163 | 6014:9164 | 6054:9164 |
| 6015:9162 | 6055:9162 | 6015:9163 | 6055:9163 | 6015:9164 | 6055:9164 |
| 6016:9162 | 6056:9162 | 6016:9163 | 6056:9163 | 6016:9164 | 6056:9164 |
| 6017:9162 | 6057:9162 | 6017:9163 | 6057:9163 | 6017:9164 | 6057:9164 |
| 6018:9162 | 6058:9162 | 6018:9163 | 6058:9163 | 6018:9164 | 6058:9164 |
| 6019:9162 | 6059:9162 | 6019:9163 | 6059:9163 | 6019:9164 | 6059:9164 |
| 6020:9162 | 6060:9162 | 6020:9163 | 6060:9163 | 6020:9164 | 6060:9164 |
| 6021:9162 | 6061:9162 | 6021:9163 | 6061:9163 | 6021:9164 | 6061:9164 |
| 6022:9162 | 6062:9162 | 6022:9163 | 6062:9163 | 6022:9164 | 6062:9164 |
| 6023:9162 | 6063:9162 | 6023:9163 | 6063:9163 | 6023:9164 | 6063:9164 |
| 6024:9162 | 6064:9162 | 6024:9163 | 6064:9163 | 6024:9164 | 6064:9164 |
| 6025:9162 | 6065:9162 | 6025:9163 | 6065:9163 | 6025:9164 | 6065:9164 |
| 6026:9162 | 6066:9162 | 6026:9163 | 6066:9163 | 6026:9164 | 6066:9164 |
| 6027:9162 | 6067:9162 | 6027:9163 | 6067:9163 | 6027:9164 | 6067:9164 |
| 6028:9162 | 6068:9162 | 6028:9163 | 6068:9163 | 6028:9164 | 6068:9164 |
| 6029:9162 | 6069:9162 | 6029:9163 | 6069:9163 | 6029:9164 | 6069:9164 |
| 6030:9162 | 6070:9162 | 6030:9163 | 6070:9163 | 6030:9164 | 6070:9164 |
| 6031:9162 | 6071:9162 | 6031:9163 | 6071:9163 | 6031:9164 | 6071:9164 |
| 6032:9162 | 6072:9162 | 6032:9163 | 6072:9163 | 6032:9164 | 6072:9164 |
| 6033:9162 | 6073:9162 | 6033:9163 | 6073:9163 | 6033:9164 | 6073:9164 |
| 6034:9162 | 6074:9162 | 6034:9163 | 6074:9163 | 6034:9164 | 6074:9164 |
| 6035:9162 | 6075:9162 | 6035:9163 | 6075:9163 | 6035:9164 | 6075:9164 |
| 6036:9162 | 6076:9162 | 6036:9163 | 6076:9163 | 6036:9164 | 6076:9164 |
| 6037:9162 | 6077:9162 | 6037:9163 | 6077:9163 | 6037:9164 | 6077:9164 |
| 6038:9162 | 6078:9162 | 6038:9163 | 6078:9163 | 6038:9164 | 6078:9164 |
| 6039:9162 | | 6039:9163 | | 6039:9164 | |
| 6000:9167 | 6040:9167 | 6000:9168 | 6040:9168 | 6000:9169 | 6040:9169 |
| 6001:9167 | 6041:9167 | 6001:9168 | 6041:9168 | 6001:9169 | 6041:9169 |
| 6002:9167 | 6042:9167 | 6002:9168 | 6042:9168 | 6002:9169 | 6042:9169 |
| 6003:9167 | 6043:9167 | 6003:9168 | 6043:9168 | 6003:9169 | 6043:9169 |
| 6004:9167 | 6044:9167 | 6004:9168 | 6044:9168 | 6004:9169 | 6044:9169 |
| 6005:9167 | 6045:9167 | 6005:9168 | 6045:9168 | 6005:9169 | 6045:9169 |
| 6006:9167 | 6046:9167 | 6006:9168 | 6046:9168 | 6006:9169 | 6046:9169 |
| 6007:9167 | 6047:9167 | 6007:9168 | 6047:9168 | 6007:9169 | 6047:9169 |
| 6008:9167 | 6048:9167 | 6008:9168 | 6048:9168 | 6008:9169 | 6048:9169 |
| 6009:9167 | 6049:9167 | 6009:9168 | 6049:9168 | 6009:9169 | 6049:9169 |
| 6010:9167 | 6050:9167 | 6010:9168 | 6050:9168 | 6010:9169 | 6050:9169 |
| 6011:9167 | 6051:9167 | 6011:9168 | 6051:9168 | 6011:9169 | 6051:9169 |
| 6012:9167 | 6052:9167 | 6012:9168 | 6052:9168 | 6012:9169 | 6052:9169 |
| 6013:9167 | 6053:9167 | 6013:9168 | 6053:9168 | 6013:9169 | 6053:9169 |
| 6014:9167 | 6054:9167 | 6014:9168 | 6054:9168 | 6014:9169 | 6054:9169 |
| 6015:9167 | 6055:9167 | 6015:9168 | 6055:9168 | 6015:9169 | 6055:9169 |
| 6016:9167 | 6056:9167 | 6016:9168 | 6056:9168 | 6016:9169 | 6056:9169 |
| 6017:9167 | 6057:9167 | 6017:9168 | 6057:9168 | 6017:9169 | 6057:9169 |
| 6018:9167 | 6058:9167 | 6018:9168 | 6058:9168 | 6018:9169 | 6058:9169 |
| 6019:9167 | 6059:9167 | 6019:9168 | 6059:9168 | 6019:9169 | 6059:9169 |
| 6020:9167 | 6060:9167 | 6020:9168 | 6060:9168 | 6020:9169 | 6060:9169 |
| 6021:9167 | 6061:9167 | 6021:9168 | 6061:9168 | 6021:9169 | 6061:9169 |
| 6022:9167 | 6062:9167 | 6022:9168 | 6062:9168 | 6022:9169 | 6062:9169 |
| 6023:9167 | 6063:9167 | 6023:9168 | 6063:9168 | 6023:9169 | 6063:9169 |
| 6024:9167 | 6064:9167 | 6024:9168 | 6064:9168 | 6024:9169 | 6064:9169 |
| 6025:9167 | 6065:9167 | 6025:9168 | 6065:9168 | 6025:9169 | 6065:9169 |
| 6026:9167 | 6066:9167 | 6026:9168 | 6066:9168 | 6026:9169 | 6066:9169 |
| 6027:9167 | 6067:9167 | 6027:9168 | 6067:9168 | 6027:9169 | 6067:9169 |
| 6028:9167 | 6068:9167 | 6028:9168 | 6068:9168 | 6028:9169 | 6068:9169 |

TABLE D-continued

Example combinations of a compound X with a compound Y.

| X:Y | X:Y | X:Y | X:Y | X:Y | X:Y |
|---|---|---|---|---|---|
| 6029:9167 | 6069:9167 | 6029:9168 | 6069:9168 | 6029:9169 | 6069:9169 |
| 6030:9167 | 6070:9167 | 6030:9168 | 6070:9168 | 6030:9169 | 6070:9169 |
| 6031:9167 | 6071:9167 | 6031:9168 | 6071:9168 | 6031:9169 | 6071:9169 |
| 6032:9167 | 6072:9167 | 6032:9168 | 6072:9168 | 6032:9169 | 6072:9169 |
| 6033:9167 | 6073:9167 | 6033:9168 | 6073:9168 | 6033:9169 | 6073:9169 |
| 6034:9167 | 6074:9167 | 6034:9168 | 6074:9168 | 6034:9169 | 6074:9169 |
| 6035:9167 | 6075:9167 | 6035:9168 | 6075:9168 | 6035:9169 | 6075:9169 |
| 6036:9167 | 6076:9167 | 6036:9168 | 6076:9168 | 6036:9169 | 6076:9169 |
| 6037:9167 | 6077:9167 | 6037:9168 | 6077:9168 | 6037:9169 | 6077:9169 |
| 6038:9167 | 6078:9167 | 6038:9168 | 6078:9168 | 6038:9169 | 6078:9169 |
| 6039:9167 |  | 6039:9168 |  | 6039:9169 |  |
| 6000:9170 | 6040:9170 | 6000:9171 | 6040:9171 | 6000:9172 | 6040:9172 |
| 6001:9170 | 6041:9170 | 6001:9171 | 6041:9171 | 6001:9172 | 6041:9172 |
| 6002:9170 | 6042:9170 | 6002:9171 | 6042:9171 | 6002:9172 | 6042:9172 |
| 6003:9170 | 6043:9170 | 6003:9171 | 6043:9171 | 6003:9172 | 6043:9172 |
| 6004:9170 | 6044:9170 | 6004:9171 | 6044:9171 | 6004:9172 | 6044:9172 |
| 6005:9170 | 6045:9170 | 6005:9171 | 6045:9171 | 6005:9172 | 6045:9172 |
| 6006:9170 | 6046:9170 | 6006:9171 | 6046:9171 | 6006:9172 | 6046:9172 |
| 6007:9170 | 6047:9170 | 6007:9171 | 6047:9171 | 6007:9172 | 6047:9172 |
| 6008:9170 | 6048:9170 | 6008:9171 | 6048:9171 | 6008:9172 | 6048:9172 |
| 6009:9170 | 6049:9170 | 6009:9171 | 6049:9171 | 6009:9172 | 6049:9172 |
| 6010:9170 | 6050:9170 | 6010:9171 | 6050:9171 | 6010:9172 | 6050:9172 |
| 6011:9170 | 6051:9170 | 6011:9171 | 6051:9171 | 6011:9172 | 6051:9172 |
| 6012:9170 | 6052:9170 | 6012:9171 | 6052:9171 | 6012:9172 | 6052:9172 |
| 6013:9170 | 6053:9170 | 6013:9171 | 6053:9171 | 6013:9172 | 6053:9172 |
| 6014:9170 | 6054:9170 | 6014:9171 | 6054:9171 | 6014:9172 | 6054:9172 |
| 6015:9170 | 6055:9170 | 6015:9171 | 6055:9171 | 6015:9172 | 6055:9172 |
| 6016:9170 | 6056:9170 | 6016:9171 | 6056:9171 | 6016:9172 | 6056:9172 |
| 6017:9170 | 6057:9170 | 6017:9171 | 6057:9171 | 6017:9172 | 6057:9172 |
| 6018:9170 | 6058:9170 | 6018:9171 | 6058:9171 | 6018:9172 | 6058:9172 |
| 6019:9170 | 6059:9170 | 6019:9171 | 6059:9171 | 6019:9172 | 6059:9172 |
| 6020:9170 | 6060:9170 | 6020:9171 | 6060:9171 | 6020:9172 | 6060:9172 |
| 6021:9170 | 6061:9170 | 6021:9171 | 6061:9171 | 6021:9172 | 6061:9172 |
| 6022:9170 | 6062:9170 | 6022:9171 | 6062:9171 | 6022:9172 | 6062:9172 |
| 6023:9170 | 6063:9170 | 6023:9171 | 6063:9171 | 6023:9172 | 6063:9172 |
| 6024:9170 | 6064:9170 | 6024:9171 | 6064:9171 | 6024:9172 | 6064:9172 |
| 6025:9170 | 6065:9170 | 6025:9171 | 6065:9171 | 6025:9172 | 6065:9172 |
| 6026:9170 | 6066:9170 | 6026:9171 | 6066:9171 | 6026:9172 | 6066:9172 |
| 6027:9170 | 6067:9170 | 6027:9171 | 6067:9171 | 6027:9172 | 6067:9172 |
| 6028:9170 | 6068:9170 | 6028:9171 | 6068:9171 | 6028:9172 | 6068:9172 |
| 6029:9170 | 6069:9170 | 6029:9171 | 6069:9171 | 6029:9172 | 6069:9172 |
| 6030:9170 | 6070:9170 | 6030:9171 | 6070:9171 | 6030:9172 | 6070:9172 |
| 6031:9170 | 6071:9170 | 6031:9171 | 6071:9171 | 6031:9172 | 6071:9172 |
| 6032:9170 | 6072:9170 | 6032:9171 | 6072:9171 | 6032:9172 | 6072:9172 |
| 6033:9170 | 6073:9170 | 6033:9171 | 6073:9171 | 6033:9172 | 6073:9172 |
| 6034:9170 | 6074:9170 | 6034:9171 | 6074:9171 | 6034:9172 | 6074:9172 |
| 6035:9170 | 6075:9170 | 6035:9171 | 6075:9171 | 6035:9172 | 6075:9172 |
| 6036:9170 | 6076:9170 | 6036:9171 | 6076:9171 | 6036:9172 | 6076:9172 |
| 6037:9170 | 6077:9170 | 6037:9171 | 6077:9171 | 6037:9172 | 6077:9172 |
| 6038:9170 | 6078:9170 | 6038:9171 | 6078:9171 | 6038:9172 | 6078:9172 |
| 6039:9170 |  | 6039:9171 |  | 6039:9172 |  |
| 6000:9173 | 6040:9173 | 6000:9174 | 6040:9174 | 6000:9175 | 6040:9175 |
| 6001:9173 | 6041:9173 | 6001:9174 | 6041:9174 | 6001:9175 | 6041:9175 |
| 6002:9173 | 6042:9173 | 6002:9174 | 6042:9174 | 6002:9175 | 6042:9175 |
| 6003:9173 | 6043:9173 | 6003:9174 | 6043:9174 | 6003:9175 | 6043:9175 |
| 6004:9173 | 6044:9173 | 6004:9174 | 6044:9174 | 6004:9175 | 6044:9175 |
| 6005:9173 | 6045:9173 | 6005:9174 | 6045:9174 | 6005:9175 | 6045:9175 |
| 6006:9173 | 6046:9173 | 6006:9174 | 6046:9174 | 6006:9175 | 6046:9175 |
| 6007:9173 | 6047:9173 | 6007:9174 | 6047:9174 | 6007:9175 | 6047:9175 |
| 6008:9173 | 6048:9173 | 6008:9174 | 6048:9174 | 6008:9175 | 6048:9175 |
| 6009:9173 | 6049:9173 | 6009:9174 | 6049:9174 | 6009:9175 | 6049:9175 |
| 6010:9173 | 6050:9173 | 6010:9174 | 6050:9174 | 6010:9175 | 6050:9175 |
| 6011:9173 | 6051:9173 | 6011:9174 | 6051:9174 | 6011:9175 | 6051:9175 |
| 6012:9173 | 6052:9173 | 6012:9174 | 6052:9174 | 6012:9175 | 6052:9175 |
| 6013:9173 | 6053:9173 | 6013:9174 | 6053:9174 | 6013:9175 | 6053:9175 |
| 6014:9173 | 6054:9173 | 6014:9174 | 6054:9174 | 6014:9175 | 6054:9175 |
| 6015:9173 | 6055:9173 | 6015:9174 | 6055:9174 | 6015:9175 | 6055:9175 |
| 6016:9173 | 6056:9173 | 6016:9174 | 6056:9174 | 6016:9175 | 6056:9175 |
| 6017:9173 | 6057:9173 | 6017:9174 | 6057:9174 | 6017:9175 | 6057:9175 |
| 6018:9173 | 6058:9173 | 6018:9174 | 6058:9174 | 6018:9175 | 6058:9175 |
| 6019:9173 | 6059:9173 | 6019:9174 | 6059:9174 | 6019:9175 | 6059:9175 |
| 6020:9173 | 6060:9173 | 6020:9174 | 6060:9174 | 6020:9175 | 6060:9175 |
| 6021:9173 | 6061:9173 | 6021:9174 | 6061:9174 | 6021:9175 | 6061:9175 |
| 6022:9173 | 6062:9173 | 6022:9174 | 6062:9174 | 6022:9175 | 6062:9175 |
| 6023:9173 | 6063:9173 | 6023:9174 | 6063:9174 | 6023:9175 | 6063:9175 |
| 6024:9173 | 6064:9173 | 6024:9174 | 6064:9174 | 6024:9175 | 6064:9175 |
| 6025:9173 | 6065:9173 | 6025:9174 | 6065:9174 | 6025:9175 | 6065:9175 |
| 6026:9173 | 6066:9173 | 6026:9174 | 6066:9174 | 6026:9175 | 6066:9175 |
| 6027:9173 | 6067:9173 | 6027:9174 | 6067:9174 | 6027:9175 | 6067:9175 |
| 6028:9173 | 6068:9173 | 6028:9174 | 6068:9174 | 6028:9175 | 6068:9175 |
| 6029:9173 | 6069:9173 | 6029:9174 | 6069:9174 | 6029:9175 | 6069:9175 |
| 6030:9173 | 6070:9173 | 6030:9174 | 6070:9174 | 6030:9175 | 6070:9175 |
| 6031:9173 | 6071:9173 | 6031:9174 | 6071:9174 | 6031:9175 | 6071:9175 |
| 6032:9173 | 6072:9173 | 6032:9174 | 6072:9174 | 6032:9175 | 6072:9175 |
| 6033:9173 | 6073:9173 | 6033:9174 | 6073:9174 | 6033:9175 | 6073:9175 |
| 6034:9173 | 6074:9173 | 6034:9174 | 6074:9174 | 6034:9175 | 6074:9175 |
| 6035:9173 | 6075:9173 | 6035:9174 | 6075:9174 | 6035:9175 | 6075:9175 |
| 6036:9173 | 6076:9173 | 6036:9174 | 6076:9174 | 6036:9175 | 6076:9175 |
| 6037:9173 | 6077:9173 | 6037:9174 | 6077:9174 | 6037:9175 | 6077:9175 |
| 6038:9173 | 6078:9173 | 6038:9174 | 6078:9174 | 6038:9175 | 6078:9175 |
| 6039:9173 |  | 6039:9174 |  | 6039:9175 |  |
| 6000:9176 | 6040:9176 | 6000:9177 | 6040:9177 | 6000:9178 | 6040:9178 |
| 6001:9176 | 6041:9176 | 6001:9177 | 6041:9177 | 6001:9178 | 6041:9178 |
| 6002:9176 | 6042:9176 | 6002:9177 | 6042:9177 | 6002:9178 | 6042:9178 |
| 6003:9176 | 6043:9176 | 6003:9177 | 6043:9177 | 6003:9178 | 6043:9178 |
| 6004:9176 | 6044:9176 | 6004:9177 | 6044:9177 | 6004:9178 | 6044:9178 |
| 6005:9176 | 6045:9176 | 6005:9177 | 6045:9177 | 6005:9178 | 6045:9178 |
| 6006:9176 | 6046:9176 | 6006:9177 | 6046:9177 | 6006:9178 | 6046:9178 |
| 6007:9176 | 6047:9176 | 6007:9177 | 6047:9177 | 6007:9178 | 6047:9178 |
| 6008:9176 | 6048:9176 | 6008:9177 | 6048:9177 | 6008:9178 | 6048:9178 |
| 6009:9176 | 6049:9176 | 6009:9177 | 6049:9177 | 6009:9178 | 6049:9178 |
| 6010:9176 | 6050:9176 | 6010:9177 | 6050:9177 | 6010:9178 | 6050:9178 |
| 6011:9176 | 6051:9176 | 6011:9177 | 6051:9177 | 6011:9178 | 6051:9178 |
| 6012:9176 | 6052:9176 | 6012:9177 | 6052:9177 | 6012:9178 | 6052:9178 |
| 6013:9176 | 6053:9176 | 6013:9177 | 6053:9177 | 6013:9178 | 6053:9178 |
| 6014:9176 | 6054:9176 | 6014:9177 | 6054:9177 | 6014:9178 | 6054:9178 |
| 6015:9176 | 6055:9176 | 6015:9177 | 6055:9177 | 6015:9178 | 6055:9178 |
| 6016:9176 | 6056:9176 | 6016:9177 | 6056:9177 | 6016:9178 | 6056:9178 |
| 6017:9176 | 6057:9176 | 6017:9177 | 6057:9177 | 6017:9178 | 6057:9178 |
| 6018:9176 | 6058:9176 | 6018:9177 | 6058:9177 | 6018:9178 | 6058:9178 |
| 6019:9176 | 6059:9176 | 6019:9177 | 6059:9177 | 6019:9178 | 6059:9178 |
| 6020:9176 | 6060:9176 | 6020:9177 | 6060:9177 | 6020:9178 | 6060:9178 |
| 6021:9176 | 6061:9176 | 6021:9177 | 6061:9177 | 6021:9178 | 6061:9178 |
| 6022:9176 | 6062:9176 | 6022:9177 | 6062:9177 | 6022:9178 | 6062:9178 |
| 6023:9176 | 6063:9176 | 6023:9177 | 6063:9177 | 6023:9178 | 6063:9178 |
| 6024:9176 | 6064:9176 | 6024:9177 | 6064:9177 | 6024:9178 | 6064:9178 |
| 6025:9176 | 6065:9176 | 6025:9177 | 6065:9177 | 6025:9178 | 6065:9178 |
| 6026:9176 | 6066:9176 | 6026:9177 | 6066:9177 | 6026:9178 | 6066:9178 |
| 6027:9176 | 6067:9176 | 6027:9177 | 6067:9177 | 6027:9178 | 6067:9178 |
| 6028:9176 | 6068:9176 | 6028:9177 | 6068:9177 | 6028:9178 | 6068:9178 |
| 6029:9176 | 6069:9176 | 6029:9177 | 6069:9177 | 6029:9178 | 6069:9178 |
| 6030:9176 | 6070:9176 | 6030:9177 | 6070:9177 | 6030:9178 | 6070:9178 |
| 6031:9176 | 6071:9176 | 6031:9177 | 6071:9177 | 6031:9178 | 6071:9178 |
| 6032:9176 | 6072:9176 | 6032:9177 | 6072:9177 | 6032:9178 | 6072:9178 |
| 6033:9176 | 6073:9176 | 6033:9177 | 6073:9177 | 6033:9178 | 6073:9178 |
| 6034:9176 | 6074:9176 | 6034:9177 | 6074:9177 | 6034:9178 | 6074:9178 |
| 6035:9176 | 6075:9176 | 6035:9177 | 6075:9177 | 6035:9178 | 6075:9178 |
| 6036:9176 | 6076:9176 | 6036:9177 | 6076:9177 | 6036:9178 | 6076:9178 |
| 6037:9176 | 6077:9176 | 6037:9177 | 6077:9177 | 6037:9178 | 6077:9178 |
| 6038:9176 | 6078:9176 | 6038:9177 | 6078:9177 | 6038:9178 | 6078:9178 |
| 6039:9176 |  | 6039:9177 |  | 6039:9178 |  |
| 6000:9179 | 6040:9179 | 6000:9180 | 6040:9180 | 6000:9181 | 6040:9181 |
| 6001:9179 | 6041:9179 | 6001:9180 | 6041:9180 | 6001:9181 | 6041:9181 |
| 6002:9179 | 6042:9179 | 6002:9180 | 6042:9180 | 6002:9181 | 6042:9181 |
| 6003:9179 | 6043:9179 | 6003:9180 | 6043:9180 | 6003:9181 | 6043:9181 |
| 6004:9179 | 6044:9179 | 6004:9180 | 6044:9180 | 6004:9181 | 6044:9181 |
| 6005:9179 | 6045:9179 | 6005:9180 | 6045:9180 | 6005:9181 | 6045:9181 |
| 6006:9179 | 6046:9179 | 6006:9180 | 6046:9180 | 6006:9181 | 6046:9181 |
| 6007:9179 | 6047:9179 | 6007:9180 | 6047:9180 | 6007:9181 | 6047:9181 |
| 6008:9179 | 6048:9179 | 6008:9180 | 6048:9180 | 6008:9181 | 6048:9181 |
| 6009:9179 | 6049:9179 | 6009:9180 | 6049:9180 | 6009:9181 | 6049:9181 |
| 6010:9179 | 6050:9179 | 6010:9180 | 6050:9180 | 6010:9181 | 6050:9181 |
| 6011:9179 | 6051:9179 | 6011:9180 | 6051:9180 | 6011:9181 | 6051:9181 |
| 6012:9179 | 6052:9179 | 6012:9180 | 6052:9180 | 6012:9181 | 6052:9181 |
| 6013:9179 | 6053:9179 | 6013:9180 | 6053:9180 | 6013:9181 | 6053:9181 |
| 6014:9179 | 6054:9179 | 6014:9180 | 6054:9180 | 6014:9181 | 6054:9181 |
| 6015:9179 | 6055:9179 | 6015:9180 | 6055:9180 | 6015:9181 | 6055:9181 |
| 6016:9179 | 6056:9179 | 6016:9180 | 6056:9180 | 6016:9181 | 6056:9181 |
| 6017:9179 | 6057:9179 | 6017:9180 | 6057:9180 | 6017:9181 | 6057:9181 |
| 6018:9179 | 6058:9179 | 6018:9180 | 6058:9180 | 6018:9181 | 6058:9181 |
| 6019:9179 | 6059:9179 | 6019:9180 | 6059:9180 | 6019:9181 | 6059:9181 |
| 6020:9179 | 6060:9179 | 6020:9180 | 6060:9180 | 6020:9181 | 6060:9181 |

TABLE D-continued

Example combinations of a compound X with a compound Y.

| X:Y | X:Y | X:Y | X:Y | X:Y | X:Y |
|---|---|---|---|---|---|
| 6021:9179 | 6061:9179 | 6021:9180 | 6061:9180 | 6021:9181 | 6061:9181 |
| 6022:9179 | 6062:9179 | 6022:9180 | 6062:9180 | 6022:9181 | 6062:9181 |
| 6023:9179 | 6063:9179 | 6023:9180 | 6063:9180 | 6023:9181 | 6063:9181 |
| 6024:9179 | 6064:9179 | 6024:9180 | 6064:9180 | 6024:9181 | 6064:9181 |
| 6025:9179 | 6065:9179 | 6025:9180 | 6065:9180 | 6025:9181 | 6065:9181 |
| 6026:9179 | 6066:9179 | 6026:9180 | 6066:9180 | 6026:9181 | 6066:9181 |
| 6027:9179 | 6067:9179 | 6027:9180 | 6067:9180 | 6027:9181 | 6067:9181 |
| 6028:9179 | 6068:9179 | 6028:9180 | 6068:9180 | 6028:9181 | 6068:9181 |
| 6029:9179 | 6069:9179 | 6029:9180 | 6069:9180 | 6029:9181 | 6069:9181 |
| 6030:9179 | 6070:9179 | 6030:9180 | 6070:9180 | 6030:9181 | 6070:9181 |
| 6031:9179 | 6071:9179 | 6031:9180 | 6071:9180 | 6031:9181 | 6071:9181 |
| 6032:9179 | 6072:9179 | 6032:9180 | 6072:9180 | 6032:9181 | 6072:9181 |
| 6033:9179 | 6073:9179 | 6033:9180 | 6073:9180 | 6033:9181 | 6073:9181 |
| 6034:9179 | 6074:9179 | 6034:9180 | 6074:9180 | 6034:9181 | 6074:9181 |
| 6035:9179 | 6075:9179 | 6035:9180 | 6075:9180 | 6035:9181 | 6075:9181 |
| 6036:9179 | 6076:9179 | 6036:9180 | 6076:9180 | 6036:9181 | 6076:9181 |
| 6037:9179 | 6077:9179 | 6037:9180 | 6077:9180 | 6037:9181 | 6077:9181 |
| 6038:9179 | 6078:9179 | 6038:9180 | 6078:9180 | 6038:9181 | 6078:9181 |
| 6039:9179 | | 6039:9180 | | 6039:9181 | |
| 6000:9182 | 6040:9182 | 6000:9183 | 6040:9183 | 6000:9184 | 6040:9184 |
| 6001:9182 | 6041:9182 | 6001:9183 | 6041:9183 | 6001:9184 | 6041:9184 |
| 6002:9182 | 6042:9182 | 6002:9183 | 6042:9183 | 6002:9184 | 6042:9184 |
| 6003:9182 | 6043:9182 | 6003:9183 | 6043:9183 | 6003:9184 | 6043:9184 |
| 6004:9182 | 6044:9182 | 6004:9183 | 6044:9183 | 6004:9184 | 6044:9184 |
| 6005:9182 | 6045:9182 | 6005:9183 | 6045:9183 | 6005:9184 | 6045:9184 |
| 6006:9182 | 6046:9182 | 6006:9183 | 6046:9183 | 6006:9184 | 6046:9184 |
| 6007:9182 | 6047:9182 | 6007:9183 | 6047:9183 | 6007:9184 | 6047:9184 |
| 6008:9182 | 6048:9182 | 6008:9183 | 6048:9183 | 6008:9184 | 6048:9184 |
| 6009:9182 | 6049:9182 | 6009:9183 | 6049:9183 | 6009:9184 | 6049:9184 |
| 6010:9182 | 6050:9182 | 6010:9183 | 6050:9183 | 6010:9184 | 6050:9184 |
| 6011:9182 | 6051:9182 | 6011:9183 | 6051:9183 | 6011:9184 | 6051:9184 |
| 6012:9182 | 6052:9182 | 6012:9183 | 6052:9183 | 6012:9184 | 6052:9184 |
| 6013:9182 | 6053:9182 | 6013:9183 | 6053:9183 | 6013:9184 | 6053:9184 |
| 6014:9182 | 6054:9182 | 6014:9183 | 6054:9183 | 6014:9184 | 6054:9184 |
| 6015:9182 | 6055:9182 | 6015:9183 | 6055:9183 | 6015:9184 | 6055:9184 |
| 6016:9182 | 6056:9182 | 6016:9183 | 6056:9183 | 6016:9184 | 6056:9184 |
| 6017:9182 | 6057:9182 | 6017:9183 | 6057:9183 | 6017:9184 | 6057:9184 |
| 6018:9182 | 6058:9182 | 6018:9183 | 6058:9183 | 6018:9184 | 6058:9184 |
| 6019:9182 | 6059:9182 | 6019:9183 | 6059:9183 | 6019:9184 | 6059:9184 |
| 6020:9182 | 6060:9182 | 6020:9183 | 6060:9183 | 6020:9184 | 6060:9184 |
| 6021:9182 | 6061:9182 | 6021:9183 | 6061:9183 | 6021:9184 | 6061:9184 |
| 6022:9182 | 6062:9182 | 6022:9183 | 6062:9183 | 6022:9184 | 6062:9184 |
| 6023:9182 | 6063:9182 | 6023:9183 | 6063:9183 | 6023:9184 | 6063:9184 |
| 6024:9182 | 6064:9182 | 6024:9183 | 6064:9183 | 6024:9184 | 6064:9184 |
| 6025:9182 | 6065:9182 | 6025:9183 | 6065:9183 | 6025:9184 | 6065:9184 |
| 6026:9182 | 6066:9182 | 6026:9183 | 6066:9183 | 6026:9184 | 6066:9184 |
| 6027:9182 | 6067:9182 | 6027:9183 | 6067:9183 | 6027:9184 | 6067:9184 |
| 6028:9182 | 6068:9182 | 6028:9183 | 6068:9183 | 6028:9184 | 6068:9184 |
| 6029:9182 | 6069:9182 | 6029:9183 | 6069:9183 | 6029:9184 | 6069:9184 |
| 6030:9182 | 6070:9182 | 6030:9183 | 6070:9183 | 6030:9184 | 6070:9184 |
| 6031:9182 | 6071:9182 | 6031:9183 | 6071:9183 | 6031:9184 | 6071:9184 |
| 6032:9182 | 6072:9182 | 6032:9183 | 6072:9183 | 6032:9184 | 6072:9184 |
| 6033:9182 | 6073:9182 | 6033:9183 | 6073:9183 | 6033:9184 | 6073:9184 |
| 6034:9182 | 6074:9182 | 6034:9183 | 6074:9183 | 6034:9184 | 6074:9184 |
| 6035:9182 | 6075:9182 | 6035:9183 | 6075:9183 | 6035:9184 | 6075:9184 |
| 6036:9182 | 6076:9182 | 6036:9183 | 6076:9183 | 6036:9184 | 6076:9184 |
| 6037:9182 | 6077:9182 | 6037:9183 | 6077:9183 | 6037:9184 | 6077:9184 |
| 6038:9182 | 6078:9182 | 6038:9183 | 6078:9183 | 6038:9184 | 6078:9184 |
| 6039:9182 | | 6039:9183 | | 6039:9184 | |
| 6000:9185 | 6040:9185 | 6000:9206 | 6040:9206 | 6000:9207 | 6040:9207 |
| 6001:9185 | 6041:9185 | 6001:9206 | 6041:9206 | 6001:9207 | 6041:9207 |
| 6002:9185 | 6042:9185 | 6002:9206 | 6042:9206 | 6002:9207 | 6042:9207 |
| 6003:9185 | 6043:9185 | 6003:9206 | 6043:9206 | 6003:9207 | 6043:9207 |
| 6004:9185 | 6044:9185 | 6004:9206 | 6044:9206 | 6004:9207 | 6044:9207 |
| 6005:9185 | 6045:9185 | 6005:9206 | 6045:9206 | 6005:9207 | 6045:9207 |
| 6006:9185 | 6046:9185 | 6006:9206 | 6046:9206 | 6006:9207 | 6046:9207 |
| 6007:9185 | 6047:9185 | 6007:9206 | 6047:9206 | 6007:9207 | 6047:9207 |
| 6008:9185 | 6048:9185 | 6008:9206 | 6048:9206 | 6008:9207 | 6048:9207 |
| 6009:9185 | 6049:9185 | 6009:9206 | 6049:9206 | 6009:9207 | 6049:9207 |
| 6010:9185 | 6050:9185 | 6010:9206 | 6050:9206 | 6010:9207 | 6050:9207 |
| 6011:9185 | 6051:9185 | 6011:9206 | 6051:9206 | 6011:9207 | 6051:9207 |
| 6012:9185 | 6052:9185 | 6012:9206 | 6052:9206 | 6012:9207 | 6052:9207 |
| 6013:9185 | 6053:9185 | 6013:9206 | 6053:9206 | 6013:9207 | 6053:9207 |
| 6014:9185 | 6054:9185 | 6014:9206 | 6054:9206 | 6014:9207 | 6054:9207 |
| 6015:9185 | 6055:9185 | 6015:9206 | 6055:9206 | 6015:9207 | 6055:9207 |
| 6016:9185 | 6056:9185 | 6016:9206 | 6056:9206 | 6016:9207 | 6056:9207 |
| 6017:9185 | 6057:9185 | 6017:9206 | 6057:9206 | 6017:9207 | 6057:9207 |
| 6018:9185 | 6058:9185 | 6018:9206 | 6058:9206 | 6018:9207 | 6058:9207 |
| 6019:9185 | 6059:9185 | 6019:9206 | 6059:9206 | 6019:9207 | 6059:9207 |
| 6020:9185 | 6060:9185 | 6020:9206 | 6060:9206 | 6020:9207 | 6060:9207 |
| 6021:9185 | 6061:9185 | 6021:9206 | 6061:9206 | 6021:9207 | 6061:9207 |
| 6022:9185 | 6062:9185 | 6022:9206 | 6062:9206 | 6022:9207 | 6062:9207 |
| 6023:9185 | 6063:9185 | 6023:9206 | 6063:9206 | 6023:9207 | 6063:9207 |
| 6024:9185 | 6064:9185 | 6024:9206 | 6064:9206 | 6024:9207 | 6064:9207 |
| 6025:9185 | 6065:9185 | 6025:9206 | 6065:9206 | 6025:9207 | 6065:9207 |
| 6026:9185 | 6066:9185 | 6026:9206 | 6066:9206 | 6026:9207 | 6066:9207 |
| 6027:9185 | 6067:9185 | 6027:9206 | 6067:9206 | 6027:9207 | 6067:9207 |
| 6028:9185 | 6068:9185 | 6028:9206 | 6068:9206 | 6028:9207 | 6068:9207 |
| 6029:9185 | 6069:9185 | 6029:9206 | 6069:9206 | 6029:9207 | 6069:9207 |
| 6030:9185 | 6070:9185 | 6030:9206 | 6070:9206 | 6030:9207 | 6070:9207 |
| 6031:9185 | 6071:9185 | 6031:9206 | 6071:9206 | 6031:9207 | 6071:9207 |
| 6032:9185 | 6072:9185 | 6032:9206 | 6072:9206 | 6032:9207 | 6072:9207 |
| 6033:9185 | 6073:9185 | 6033:9206 | 6073:9206 | 6033:9207 | 6073:9207 |
| 6034:9185 | 6074:9185 | 6034:9206 | 6074:9206 | 6034:9207 | 6074:9207 |
| 6035:9185 | 6075:9185 | 6035:9206 | 6075:9206 | 6035:9207 | 6075:9207 |
| 6036:9185 | 6076:9185 | 6036:9206 | 6076:9206 | 6036:9207 | 6076:9207 |
| 6037:9185 | 6077:9185 | 6037:9206 | 6077:9206 | 6037:9207 | 6077:9207 |
| 6038:9185 | 6078:9185 | 6038:9206 | 6078:9206 | 6038:9207 | 6078:9207 |
| 6039:9185 | | 6039:9206 | | 6039:9207 | |
| 6000:9208 | 6040:9208 | 6000:9209 | 6040:9209 | 6000:9214 | 6040:9214 |
| 6001:9208 | 6041:9208 | 6001:9209 | 6041:9209 | 6001:9214 | 6041:9214 |
| 6002:9208 | 6042:9208 | 6002:9209 | 6042:9209 | 6002:9214 | 6042:9214 |
| 6003:9208 | 6043:9208 | 6003:9209 | 6043:9209 | 6003:9214 | 6043:9214 |
| 6004:9208 | 6044:9208 | 6004:9209 | 6044:9209 | 6004:9214 | 6044:9214 |
| 6005:9208 | 6045:9208 | 6005:9209 | 6045:9209 | 6005:9214 | 6045:9214 |
| 6006:9208 | 6046:9208 | 6006:9209 | 6046:9209 | 6006:9214 | 6046:9214 |
| 6007:9208 | 6047:9208 | 6007:9209 | 6047:9209 | 6007:9214 | 6047:9214 |
| 6008:9208 | 6048:9208 | 6008:9209 | 6048:9209 | 6008:9214 | 6048:9214 |
| 6009:9208 | 6049:9208 | 6009:9209 | 6049:9209 | 6009:9214 | 6049:9214 |
| 6010:9208 | 6050:9208 | 6010:9209 | 6050:9209 | 6010:9214 | 6050:9214 |
| 6011:9208 | 6051:9208 | 6011:9209 | 6051:9209 | 6011:9214 | 6051:9214 |
| 6012:9208 | 6052:9208 | 6012:9209 | 6052:9209 | 6012:9214 | 6052:9214 |
| 6013:9208 | 6053:9208 | 6013:9209 | 6053:9209 | 6013:9214 | 6053:9214 |
| 6014:9208 | 6054:9208 | 6014:9209 | 6054:9209 | 6014:9214 | 6054:9214 |
| 6015:9208 | 6055:9208 | 6015:9209 | 6055:9209 | 6015:9214 | 6055:9214 |
| 6016:9208 | 6056:9208 | 6016:9209 | 6056:9209 | 6016:9214 | 6056:9214 |
| 6017:9208 | 6057:9208 | 6017:9209 | 6057:9209 | 6017:9214 | 6057:9214 |
| 6018:9208 | 6058:9208 | 6018:9209 | 6058:9209 | 6018:9214 | 6058:9214 |
| 6019:9208 | 6059:9208 | 6019:9209 | 6059:9209 | 6019:9214 | 6059:9214 |
| 6020:9208 | 6060:9208 | 6020:9209 | 6060:9209 | 6020:9214 | 6060:9214 |
| 6021:9208 | 6061:9208 | 6021:9209 | 6061:9209 | 6021:9214 | 6061:9214 |
| 6022:9208 | 6062:9208 | 6022:9209 | 6062:9209 | 6022:9214 | 6062:9214 |
| 6023:9208 | 6063:9208 | 6023:9209 | 6063:9209 | 6023:9214 | 6063:9214 |
| 6024:9208 | 6064:9208 | 6024:9209 | 6064:9209 | 6024:9214 | 6064:9214 |
| 6025:9208 | 6065:9208 | 6025:9209 | 6065:9209 | 6025:9214 | 6065:9214 |
| 6026:9208 | 6066:9208 | 6026:9209 | 6066:9209 | 6026:9214 | 6066:9214 |
| 6027:9208 | 6067:9208 | 6027:9209 | 6067:9209 | 6027:9214 | 6067:9214 |
| 6028:9208 | 6068:9208 | 6028:9209 | 6068:9209 | 6028:9214 | 6068:9214 |
| 6029:9208 | 6069:9208 | 6029:9209 | 6069:9209 | 6029:9214 | 6069:9214 |
| 6030:9208 | 6070:9208 | 6030:9209 | 6070:9209 | 6030:9214 | 6070:9214 |
| 6031:9208 | 6071:9208 | 6031:9209 | 6071:9209 | 6031:9214 | 6071:9214 |
| 6032:9208 | 6072:9208 | 6032:9209 | 6072:9209 | 6032:9214 | 6072:9214 |
| 6033:9208 | 6073:9208 | 6033:9209 | 6073:9209 | 6033:9214 | 6073:9214 |
| 6034:9208 | 6074:9208 | 6034:9209 | 6074:9209 | 6034:9214 | 6074:9214 |
| 6035:9208 | 6075:9208 | 6035:9209 | 6075:9209 | 6035:9214 | 6075:9214 |
| 6036:9208 | 6076:9208 | 6036:9209 | 6076:9209 | 6036:9214 | 6076:9214 |
| 6037:9208 | 6077:9208 | 6037:9209 | 6077:9209 | 6037:9214 | 6077:9214 |
| 6038:9208 | 6078:9208 | 6038:9209 | 6078:9209 | 6038:9214 | 6078:9214 |
| 6039:9208 | | 6039:9209 | | 6039:9214 | |
| 6000:9241 | 6040:9241 | 6000:9242 | 6040:9242 | 6000:9244 | 6040:9244 |
| 6001:9241 | 6041:9241 | 6001:9242 | 6041:9242 | 6001:9244 | 6041:9244 |
| 6002:9241 | 6042:9241 | 6002:9242 | 6042:9242 | 6002:9244 | 6042:9244 |
| 6003:9241 | 6043:9241 | 6003:9242 | 6043:9242 | 6003:9244 | 6043:9244 |
| 6004:9241 | 6044:9241 | 6004:9242 | 6044:9242 | 6004:9244 | 6044:9244 |
| 6005:9241 | 6045:9241 | 6005:9242 | 6045:9242 | 6005:9244 | 6045:9244 |
| 6006:9241 | 6046:9241 | 6006:9242 | 6046:9242 | 6006:9244 | 6046:9244 |
| 6007:9241 | 6047:9241 | 6007:9242 | 6047:9242 | 6007:9244 | 6047:9244 |
| 6008:9241 | 6048:9241 | 6008:9242 | 6048:9242 | 6008:9244 | 6048:9244 |
| 6009:9241 | 6049:9241 | 6009:9242 | 6049:9242 | 6009:9244 | 6049:9244 |
| 6010:9241 | 6050:9241 | 6010:9242 | 6050:9242 | 6010:9244 | 6050:9244 |
| 6011:9241 | 6051:9241 | 6011:9242 | 6051:9242 | 6011:9244 | 6051:9244 |
| 6012:9241 | 6052:9241 | 6012:9242 | 6052:9242 | 6012:9244 | 6052:9244 |

TABLE D-continued

Example combinations of a compound X with a compound Y.

| X:Y | X:Y | X:Y | X:Y | X:Y | X:Y |
|---|---|---|---|---|---|
| 6013:9241 | 6053:9241 | 6013:9242 | 6053:9242 | 6013:9244 | 6053:9244 |
| 6014:9241 | 6054:9241 | 6014:9242 | 6054:9242 | 6014:9244 | 6054:9244 |
| 6015:9241 | 6055:9241 | 6015:9242 | 6055:9242 | 6015:9244 | 6055:9244 |
| 6016:9241 | 6056:9241 | 6016:9242 | 6056:9242 | 6016:9244 | 6056:9244 |
| 6017:9241 | 6057:9241 | 6017:9242 | 6057:9242 | 6017:9244 | 6057:9244 |
| 6018:9241 | 6058:9241 | 6018:9242 | 6058:9242 | 6018:9244 | 6058:9244 |
| 6019:9241 | 6059:9241 | 6019:9242 | 6059:9242 | 6019:9244 | 6059:9244 |
| 6020:9241 | 6060:9241 | 6020:9242 | 6060:9242 | 6020:9244 | 6060:9244 |
| 6021:9241 | 6061:9241 | 6021:9242 | 6061:9242 | 6021:9244 | 6061:9244 |
| 6022:9241 | 6062:9241 | 6022:9242 | 6062:9242 | 6022:9244 | 6062:9244 |
| 6023:9241 | 6063:9241 | 6023:9242 | 6063:9242 | 6023:9244 | 6063:9244 |
| 6024:9241 | 6064:9241 | 6024:9242 | 6064:9242 | 6024:9244 | 6064:9244 |
| 6025:9241 | 6065:9241 | 6025:9242 | 6065:9242 | 6025:9244 | 6065:9244 |
| 6026:9241 | 6066:9241 | 6026:9242 | 6066:9242 | 6026:9244 | 6066:9244 |
| 6027:9241 | 6067:9241 | 6027:9242 | 6067:9242 | 6027:9244 | 6067:9244 |
| 6028:9241 | 6068:9241 | 6028:9242 | 6068:9242 | 6028:9244 | 6068:9244 |
| 6029:9241 | 6069:9241 | 6029:9242 | 6069:9242 | 6029:9244 | 6069:9244 |
| 6030:9241 | 6070:9241 | 6030:9242 | 6070:9242 | 6030:9244 | 6070:9244 |
| 6031:9241 | 6071:9241 | 6031:9242 | 6071:9242 | 6031:9244 | 6071:9244 |
| 6032:9241 | 6072:9241 | 6032:9242 | 6072:9242 | 6032:9244 | 6072:9244 |
| 6033:9241 | 6073:9241 | 6033:9242 | 6073:9242 | 6033:9244 | 6073:9244 |
| 6034:9241 | 6074:9241 | 6034:9242 | 6074:9242 | 6034:9244 | 6074:9244 |
| 6035:9241 | 6075:9241 | 6035:9242 | 6075:9242 | 6035:9244 | 6075:9244 |
| 6036:9241 | 6076:9241 | 6036:9242 | 6076:9242 | 6036:9244 | 6076:9244 |
| 6037:9241 | 6077:9241 | 6037:9242 | 6077:9242 | 6037:9244 | 6077:9244 |
| 6038:9241 | 6078:9241 | 6038:9242 | 6078:9242 | 6038:9244 | 6078:9244 |
| 6039:9241 |  | 6039:9242 |  | 6039:9244 |  |
| 6000:9245 | 6040:9245 | 6000:9246 | 6040:9246 | 6000:9247 | 6040:9247 |
| 6001:9245 | 6041:9245 | 6001:9246 | 6041:9246 | 6001:9247 | 6041:9247 |
| 6002:9245 | 6042:9245 | 6002:9246 | 6042:9246 | 6002:9247 | 6042:9247 |
| 6003:9245 | 6043:9245 | 6003:9246 | 6043:9246 | 6003:9247 | 6043:9247 |
| 6004:9245 | 6044:9245 | 6004:9246 | 6044:9246 | 6004:9247 | 6044:9247 |
| 6005:9245 | 6045:9245 | 6005:9246 | 6045:9246 | 6005:9247 | 6045:9247 |
| 6006:9245 | 6046:9245 | 6006:9246 | 6046:9246 | 6006:9247 | 6046:9247 |
| 6007:9245 | 6047:9245 | 6007:9246 | 6047:9246 | 6007:9247 | 6047:9247 |
| 6008:9245 | 6048:9245 | 6008:9246 | 6048:9246 | 6008:9247 | 6048:9247 |
| 6009:9245 | 6049:9245 | 6009:9246 | 6049:9246 | 6009:9247 | 6049:9247 |
| 6010:9245 | 6050:9245 | 6010:9246 | 6050:9246 | 6010:9247 | 6050:9247 |
| 6011:9245 | 6051:9245 | 6011:9246 | 6051:9246 | 6011:9247 | 6051:9247 |
| 6012:9245 | 6052:9245 | 6012:9246 | 6052:9246 | 6012:9247 | 6052:9247 |
| 6013:9245 | 6053:9245 | 6013:9246 | 6053:9246 | 6013:9247 | 6053:9247 |
| 6014:9245 | 6054:9245 | 6014:9246 | 6054:9246 | 6014:9247 | 6054:9247 |
| 6015:9245 | 6055:9245 | 6015:9246 | 6055:9246 | 6015:9247 | 6055:9247 |
| 6016:9245 | 6056:9245 | 6016:9246 | 6056:9246 | 6016:9247 | 6056:9247 |
| 6017:9245 | 6057:9245 | 6017:9246 | 6057:9246 | 6017:9247 | 6057:9247 |
| 6018:9245 | 6058:9245 | 6018:9246 | 6058:9246 | 6018:9247 | 6058:9247 |
| 6019:9245 | 6059:9245 | 6019:9246 | 6059:9246 | 6019:9247 | 6059:9247 |
| 6020:9245 | 6060:9245 | 6020:9246 | 6060:9246 | 6020:9247 | 6060:9247 |
| 6021:9245 | 6061:9245 | 6021:9246 | 6061:9246 | 6021:9247 | 6061:9247 |
| 6022:9245 | 6062:9245 | 6022:9246 | 6062:9246 | 6022:9247 | 6062:9247 |
| 6023:9245 | 6063:9245 | 6023:9246 | 6063:9246 | 6023:9247 | 6063:9247 |
| 6024:9245 | 6064:9245 | 6024:9246 | 6064:9246 | 6024:9247 | 6064:9247 |
| 6025:9245 | 6065:9245 | 6025:9246 | 6065:9246 | 6025:9247 | 6065:9247 |
| 6026:9245 | 6066:9245 | 6026:9246 | 6066:9246 | 6026:9247 | 6066:9247 |
| 6027:9245 | 6067:9245 | 6027:9246 | 6067:9246 | 6027:9247 | 6067:9247 |
| 6028:9245 | 6068:9245 | 6028:9246 | 6068:9246 | 6028:9247 | 6068:9247 |
| 6029:9245 | 6069:9245 | 6029:9246 | 6069:9246 | 6029:9247 | 6069:9247 |
| 6030:9245 | 6070:9245 | 6030:9246 | 6070:9246 | 6030:9247 | 6070:9247 |
| 6031:9245 | 6071:9245 | 6031:9246 | 6071:9246 | 6031:9247 | 6071:9247 |
| 6032:9245 | 6072:9245 | 6032:9246 | 6072:9246 | 6032:9247 | 6072:9247 |
| 6033:9245 | 6073:9245 | 6033:9246 | 6073:9246 | 6033:9247 | 6073:9247 |
| 6034:9245 | 6074:9245 | 6034:9246 | 6074:9246 | 6034:9247 | 6074:9247 |
| 6035:9245 | 6075:9245 | 6035:9246 | 6075:9246 | 6035:9247 | 6075:9247 |
| 6036:9245 | 6076:9245 | 6036:9246 | 6076:9246 | 6036:9247 | 6076:9247 |
| 6037:9245 | 6077:9245 | 6037:9246 | 6077:9246 | 6037:9247 | 6077:9247 |
| 6038:9245 | 6078:9245 | 6038:9246 | 6078:9246 | 6038:9247 | 6078:9247 |
| 6039:9245 |  | 6039:9246 |  | 6039:9247 |  |
| 6000:9248 | 6040:9248 | 6000:9249 | 6040:9249 | 6000:9250 | 6040:9250 |
| 6001:9248 | 6041:9248 | 6001:9249 | 6041:9249 | 6001:9250 | 6041:9250 |
| 6002:9248 | 6042:9248 | 6002:9249 | 6042:9249 | 6002:9250 | 6042:9250 |
| 6003:9248 | 6043:9248 | 6003:9249 | 6043:9249 | 6003:9250 | 6043:9250 |
| 6004:9248 | 6044:9248 | 6004:9249 | 6044:9249 | 6004:9250 | 6044:9250 |
| 6005:9248 | 6045:9248 | 6005:9249 | 6045:9249 | 6005:9250 | 6045:9250 |
| 6006:9248 | 6046:9248 | 6006:9249 | 6046:9249 | 6006:9250 | 6046:9250 |
| 6007:9248 | 6047:9248 | 6007:9249 | 6047:9249 | 6007:9250 | 6047:9250 |
| 6008:9248 | 6048:9248 | 6008:9249 | 6048:9249 | 6008:9250 | 6048:9250 |
| 6009:9248 | 6049:9248 | 6009:9249 | 6049:9249 | 6009:9250 | 6049:9250 |
| 6010:9248 | 6050:9248 | 6010:9249 | 6050:9249 | 6010:9250 | 6050:9250 |
| 6011:9248 | 6051:9248 | 6011:9249 | 6051:9249 | 6011:9250 | 6051:9250 |
| 6012:9248 | 6052:9248 | 6012:9249 | 6052:9249 | 6012:9250 | 6052:9250 |
| 6013:9248 | 6053:9248 | 6013:9249 | 6053:9249 | 6013:9250 | 6053:9250 |
| 6014:9248 | 6054:9248 | 6014:9249 | 6054:9249 | 6014:9250 | 6054:9250 |
| 6015:9248 | 6055:9248 | 6015:9249 | 6055:9249 | 6015:9250 | 6055:9250 |
| 6016:9248 | 6056:9248 | 6016:9249 | 6056:9249 | 6016:9250 | 6056:9250 |
| 6017:9248 | 6057:9248 | 6017:9249 | 6057:9249 | 6017:9250 | 6057:9250 |
| 6018:9248 | 6058:9248 | 6018:9249 | 6058:9249 | 6018:9250 | 6058:9250 |
| 6019:9248 | 6059:9248 | 6019:9249 | 6059:9249 | 6019:9250 | 6059:9250 |
| 6020:9248 | 6060:9248 | 6020:9249 | 6060:9249 | 6020:9250 | 6060:9250 |
| 6021:9248 | 6061:9248 | 6021:9249 | 6061:9249 | 6021:9250 | 6061:9250 |
| 6022:9248 | 6062:9248 | 6022:9249 | 6062:9249 | 6022:9250 | 6062:9250 |
| 6023:9248 | 6063:9248 | 6023:9249 | 6063:9249 | 6023:9250 | 6063:9250 |
| 6024:9248 | 6064:9248 | 6024:9249 | 6064:9249 | 6024:9250 | 6064:9250 |
| 6025:9248 | 6065:9248 | 6025:9249 | 6065:9249 | 6025:9250 | 6065:9250 |
| 6026:9248 | 6066:9248 | 6026:9249 | 6066:9249 | 6026:9250 | 6066:9250 |
| 6027:9248 | 6067:9248 | 6027:9249 | 6067:9249 | 6027:9250 | 6067:9250 |
| 6028:9248 | 6068:9248 | 6028:9249 | 6068:9249 | 6028:9250 | 6068:9250 |
| 6029:9248 | 6069:9248 | 6029:9249 | 6069:9249 | 6029:9250 | 6069:9250 |
| 6030:9248 | 6070:9248 | 6030:9249 | 6070:9249 | 6030:9250 | 6070:9250 |
| 6031:9248 | 6071:9248 | 6031:9249 | 6071:9249 | 6031:9250 | 6071:9250 |
| 6032:9248 | 6072:9248 | 6032:9249 | 6072:9249 | 6032:9250 | 6072:9250 |
| 6033:9248 | 6073:9248 | 6033:9249 | 6073:9249 | 6033:9250 | 6073:9250 |
| 6034:9248 | 6074:9248 | 6034:9249 | 6074:9249 | 6034:9250 | 6074:9250 |
| 6035:9248 | 6075:9248 | 6035:9249 | 6075:9249 | 6035:9250 | 6075:9250 |
| 6036:9248 | 6076:9248 | 6036:9249 | 6076:9249 | 6036:9250 | 6076:9250 |
| 6037:9248 | 6077:9248 | 6037:9249 | 6077:9249 | 6037:9250 | 6077:9250 |
| 6038:9248 | 6078:9248 | 6038:9249 | 6078:9249 | 6038:9250 | 6078:9250 |
| 6039:9248 |  | 6039:9249 |  | 6039:9250 |  |
| 6000:9251 | 6040:9251 | 6000:9252 | 6040:9252 | 6000:9253 | 6040:9253 |
| 6001:9251 | 6041:9251 | 6001:9252 | 6041:9252 | 6001:9253 | 6041:9253 |
| 6002:9251 | 6042:9251 | 6002:9252 | 6042:9252 | 6002:9253 | 6042:9253 |
| 6003:9251 | 6043:9251 | 6003:9252 | 6043:9252 | 6003:9253 | 6043:9253 |
| 6004:9251 | 6044:9251 | 6004:9252 | 6044:9252 | 6004:9253 | 6044:9253 |
| 6005:9251 | 6045:9251 | 6005:9252 | 6045:9252 | 6005:9253 | 6045:9253 |
| 6006:9251 | 6046:9251 | 6006:9252 | 6046:9252 | 6006:9253 | 6046:9253 |
| 6007:9251 | 6047:9251 | 6007:9252 | 6047:9252 | 6007:9253 | 6047:9253 |
| 6008:9251 | 6048:9251 | 6008:9252 | 6048:9252 | 6008:9253 | 6048:9253 |
| 6009:9251 | 6049:9251 | 6009:9252 | 6049:9252 | 6009:9253 | 6049:9253 |
| 6010:9251 | 6050:9251 | 6010:9252 | 6050:9252 | 6010:9253 | 6050:9253 |
| 6011:9251 | 6051:9251 | 6011:9252 | 6051:9252 | 6011:9253 | 6051:9253 |
| 6012:9251 | 6052:9251 | 6012:9252 | 6052:9252 | 6012:9253 | 6052:9253 |
| 6013:9251 | 6053:9251 | 6013:9252 | 6053:9252 | 6013:9253 | 6053:9253 |
| 6014:9251 | 6054:9251 | 6014:9252 | 6054:9252 | 6014:9253 | 6054:9253 |
| 6015:9251 | 6055:9251 | 6015:9252 | 6055:9252 | 6015:9253 | 6055:9253 |
| 6016:9251 | 6056:9251 | 6016:9252 | 6056:9252 | 6016:9253 | 6056:9253 |
| 6017:9251 | 6057:9251 | 6017:9252 | 6057:9252 | 6017:9253 | 6057:9253 |
| 6018:9251 | 6058:9251 | 6018:9252 | 6058:9252 | 6018:9253 | 6058:9253 |
| 6019:9251 | 6059:9251 | 6019:9252 | 6059:9252 | 6019:9253 | 6059:9253 |
| 6020:9251 | 6060:9251 | 6020:9252 | 6060:9252 | 6020:9253 | 6060:9253 |
| 6021:9251 | 6061:9251 | 6021:9252 | 6061:9252 | 6021:9253 | 6061:9253 |
| 6022:9251 | 6062:9251 | 6022:9252 | 6062:9252 | 6022:9253 | 6062:9253 |
| 6023:9251 | 6063:9251 | 6023:9252 | 6063:9252 | 6023:9253 | 6063:9253 |
| 6024:9251 | 6064:9251 | 6024:9252 | 6064:9252 | 6024:9253 | 6064:9253 |
| 6025:9251 | 6065:9251 | 6025:9252 | 6065:9252 | 6025:9253 | 6065:9253 |
| 6026:9251 | 6066:9251 | 6026:9252 | 6066:9252 | 6026:9253 | 6066:9253 |
| 6027:9251 | 6067:9251 | 6027:9252 | 6067:9252 | 6027:9253 | 6067:9253 |
| 6028:9251 | 6068:9251 | 6028:9252 | 6068:9252 | 6028:9253 | 6068:9253 |
| 6029:9251 | 6069:9251 | 6029:9252 | 6069:9252 | 6029:9253 | 6069:9253 |
| 6030:9251 | 6070:9251 | 6030:9252 | 6070:9252 | 6030:9253 | 6070:9253 |
| 6031:9251 | 6071:9251 | 6031:9252 | 6071:9252 | 6031:9253 | 6071:9253 |
| 6032:9251 | 6072:9251 | 6032:9252 | 6072:9252 | 6032:9253 | 6072:9253 |
| 6033:9251 | 6073:9251 | 6033:9252 | 6073:9252 | 6033:9253 | 6073:9253 |
| 6034:9251 | 6074:9251 | 6034:9252 | 6074:9252 | 6034:9253 | 6074:9253 |
| 6035:9251 | 6075:9251 | 6035:9252 | 6075:9252 | 6035:9253 | 6075:9253 |
| 6036:9251 | 6076:9251 | 6036:9252 | 6076:9252 | 6036:9253 | 6076:9253 |
| 6037:9251 | 6077:9251 | 6037:9252 | 6077:9252 | 6037:9253 | 6077:9253 |
| 6038:9251 | 6078:9251 | 6038:9252 | 6078:9252 | 6038:9253 | 6078:9253 |
| 6039:9251 |  | 6039:9252 |  | 6039:9253 |  |
| 6000:9255 | 6040:9255 | 6000:9256 | 6040:9256 | 6000:9257 | 6040:9257 |
| 6001:9255 | 6041:9255 | 6001:9256 | 6041:9256 | 6001:9257 | 6041:9257 |
| 6002:9255 | 6042:9255 | 6002:9256 | 6042:9256 | 6002:9257 | 6042:9257 |
| 6003:9255 | 6043:9255 | 6003:9256 | 6043:9256 | 6003:9257 | 6043:9257 |
| 6004:9255 | 6044:9255 | 6004:9256 | 6044:9256 | 6004:9257 | 6044:9257 |

TABLE D-continued

Example combinations of a compound X with a compound Y.

| X:Y | X:Y | X:Y | X:Y | X:Y | X:Y |
|---|---|---|---|---|---|
| 6005:9255 | 6045:9255 | 6005:9256 | 6045:9256 | 6005:9257 | 6045:9257 |
| 6006:9255 | 6046:9255 | 6006:9256 | 6046:9256 | 6006:9257 | 6046:9257 |
| 6007:9255 | 6047:9255 | 6007:9256 | 6047:9256 | 6007:9257 | 6047:9257 |
| 6008:9255 | 6048:9255 | 6008:9256 | 6048:9256 | 6008:9257 | 6048:9257 |
| 6009:9255 | 6049:9255 | 6009:9256 | 6049:9256 | 6009:9257 | 6049:9257 |
| 6010:9255 | 6050:9255 | 6010:9256 | 6050:9256 | 6010:9257 | 6050:9257 |
| 6011:9255 | 6051:9255 | 6011:9256 | 6051:9256 | 6011:9257 | 6051:9257 |
| 6012:9255 | 6052:9255 | 6012:9256 | 6052:9256 | 6012:9257 | 6052:9257 |
| 6013:9255 | 6053:9255 | 6013:9256 | 6053:9256 | 6013:9257 | 6053:9257 |
| 6014:9255 | 6054:9255 | 6014:9256 | 6054:9256 | 6014:9257 | 6054:9257 |
| 6015:9255 | 6055:9255 | 6015:9256 | 6055:9256 | 6015:9257 | 6055:9257 |
| 6016:9255 | 6056:9255 | 6016:9256 | 6056:9256 | 6016:9257 | 6056:9257 |
| 6017:9255 | 6057:9255 | 6017:9256 | 6057:9256 | 6017:9257 | 6057:9257 |
| 6018:9255 | 6058:9255 | 6018:9256 | 6058:9256 | 6018:9257 | 6058:9257 |
| 6019:9255 | 6059:9255 | 6019:9256 | 6059:9256 | 6019:9257 | 6059:9257 |
| 6020:9255 | 6060:9255 | 6020:9256 | 6060:9256 | 6020:9257 | 6060:9257 |
| 6021:9255 | 6061:9255 | 6021:9256 | 6061:9256 | 6021:9257 | 6061:9257 |
| 6022:9255 | 6062:9255 | 6022:9256 | 6062:9256 | 6022:9257 | 6062:9257 |
| 6023:9255 | 6063:9255 | 6023:9256 | 6063:9256 | 6023:9257 | 6063:9257 |
| 6024:9255 | 6064:9255 | 6024:9256 | 6064:9256 | 6024:9257 | 6064:9257 |
| 6025:9255 | 6065:9255 | 6025:9256 | 6065:9256 | 6025:9257 | 6065:9257 |
| 6026:9255 | 6066:9255 | 6026:9256 | 6066:9256 | 6026:9257 | 6066:9257 |
| 6027:9255 | 6067:9255 | 6027:9256 | 6067:9256 | 6027:9257 | 6067:9257 |
| 6028:9255 | 6068:9255 | 6028:9256 | 6068:9256 | 6028:9257 | 6068:9257 |
| 6029:9255 | 6069:9255 | 6029:9256 | 6069:9256 | 6029:9257 | 6069:9257 |
| 6030:9255 | 6070:9255 | 6030:9256 | 6070:9256 | 6030:9257 | 6070:9257 |
| 6031:9255 | 6071:9255 | 6031:9256 | 6071:9256 | 6031:9257 | 6071:9257 |
| 6032:9255 | 6072:9255 | 6032:9256 | 6072:9256 | 6032:9257 | 6072:9257 |
| 6033:9255 | 6073:9255 | 6033:9256 | 6073:9256 | 6033:9257 | 6073:9257 |
| 6034:9255 | 6074:9255 | 6034:9256 | 6074:9256 | 6034:9257 | 6074:9257 |
| 6035:9255 | 6075:9255 | 6035:9256 | 6075:9256 | 6035:9257 | 6075:9257 |
| 6036:9255 | 6076:9255 | 6036:9256 | 6076:9256 | 6036:9257 | 6076:9257 |
| 6037:9255 | 6077:9255 | 6037:9256 | 6077:9256 | 6037:9257 | 6077:9257 |
| 6038:9255 | 6078:9255 | 6038:9256 | 6078:9256 | 6038:9257 | 6078:9257 |
| 6039:9255 | | 6039:9256 | | 6039:9257 | |
| 6000:9258 | 6040:9258 | 6000:9259 | 6040:9259 | 6000:9260 | 6040:9260 |
| 6001:9258 | 6041:9258 | 6001:9259 | 6041:9259 | 6001:9260 | 6041:9260 |
| 6002:9258 | 6042:9258 | 6002:9259 | 6042:9259 | 6002:9260 | 6042:9260 |
| 6003:9258 | 6043:9258 | 6003:9259 | 6043:9259 | 6003:9260 | 6043:9260 |
| 6004:9258 | 6044:9258 | 6004:9259 | 6044:9259 | 6004:9260 | 6044:9260 |
| 6005:9258 | 6045:9258 | 6005:9259 | 6045:9259 | 6005:9260 | 6045:9260 |
| 6006:9258 | 6046:9258 | 6006:9259 | 6046:9259 | 6006:9260 | 6046:9260 |
| 6007:9258 | 6047:9258 | 6007:9259 | 6047:9259 | 6007:9260 | 6047:9260 |
| 6008:9258 | 6048:9258 | 6008:9259 | 6048:9259 | 6008:9260 | 6048:9260 |
| 6009:9258 | 6049:9258 | 6009:9259 | 6049:9259 | 6009:9260 | 6049:9260 |
| 6010:9258 | 6050:9258 | 6010:9259 | 6050:9259 | 6010:9260 | 6050:9260 |
| 6011:9258 | 6051:9258 | 6011:9259 | 6051:9259 | 6011:9260 | 6051:9260 |
| 6012:9258 | 6052:9258 | 6012:9259 | 6052:9259 | 6012:9260 | 6052:9260 |
| 6013:9258 | 6053:9258 | 6013:9259 | 6053:9259 | 6013:9260 | 6053:9260 |
| 6014:9258 | 6054:9258 | 6014:9259 | 6054:9259 | 6014:9260 | 6054:9260 |
| 6015:9258 | 6055:9258 | 6015:9259 | 6055:9259 | 6015:9260 | 6055:9260 |
| 6016:9258 | 6056:9258 | 6016:9259 | 6056:9259 | 6016:9260 | 6056:9260 |
| 6017:9258 | 6057:9258 | 6017:9259 | 6057:9259 | 6017:9260 | 6057:9260 |
| 6018:9258 | 6058:9258 | 6018:9259 | 6058:9259 | 6018:9260 | 6058:9260 |
| 6019:9258 | 6059:9258 | 6019:9259 | 6059:9259 | 6019:9260 | 6059:9260 |
| 6020:9258 | 6060:9258 | 6020:9259 | 6060:9259 | 6020:9260 | 6060:9260 |
| 6021:9258 | 6061:9258 | 6021:9259 | 6061:9259 | 6021:9260 | 6061:9260 |
| 6022:9258 | 6062:9258 | 6022:9259 | 6062:9259 | 6022:9260 | 6062:9260 |
| 6023:9258 | 6063:9258 | 6023:9259 | 6063:9259 | 6023:9260 | 6063:9260 |
| 6024:9258 | 6064:9258 | 6024:9259 | 6064:9259 | 6024:9260 | 6064:9260 |
| 6025:9258 | 6065:9258 | 6025:9259 | 6065:9259 | 6025:9260 | 6065:9260 |
| 6026:9258 | 6066:9258 | 6026:9259 | 6066:9259 | 6026:9260 | 6066:9260 |
| 6027:9258 | 6067:9258 | 6027:9259 | 6067:9259 | 6027:9260 | 6067:9260 |
| 6028:9258 | 6068:9258 | 6028:9259 | 6068:9259 | 6028:9260 | 6068:9260 |
| 6029:9258 | 6069:9258 | 6029:9259 | 6069:9259 | 6029:9260 | 6069:9260 |
| 6030:9258 | 6070:9258 | 6030:9259 | 6070:9259 | 6030:9260 | 6070:9260 |
| 6031:9258 | 6071:9258 | 6031:9259 | 6071:9259 | 6031:9260 | 6071:9260 |
| 6032:9258 | 6072:9258 | 6032:9259 | 6072:9259 | 6032:9260 | 6072:9260 |
| 6033:9258 | 6073:9258 | 6033:9259 | 6073:9259 | 6033:9260 | 6073:9260 |
| 6034:9258 | 6074:9258 | 6034:9259 | 6074:9259 | 6034:9260 | 6074:9260 |
| 6035:9258 | 6075:9258 | 6035:9259 | 6075:9259 | 6035:9260 | 6075:9260 |
| 6036:9258 | 6076:9258 | 6036:9259 | 6076:9259 | 6036:9260 | 6076:9260 |
| 6037:9258 | 6077:9258 | 6037:9259 | 6077:9259 | 6037:9260 | 6077:9260 |
| 6038:9258 | 6078:9258 | 6038:9259 | 6078:9259 | 6038:9260 | 6078:9260 |
| 6039:9258 | | 6039:9259 | | 6039:9260 | |
| 6000:9262 | 6040:9262 | 6000:9263 | 6040:9263 | 6000:9264 | 6040:9264 |
| 6001:9262 | 6041:9262 | 6001:9263 | 6041:9263 | 6001:9264 | 6041:9264 |
| 6002:9262 | 6042:9262 | 6002:9263 | 6042:9263 | 6002:9264 | 6042:9264 |
| 6003:9262 | 6043:9262 | 6003:9263 | 6043:9263 | 6003:9264 | 6043:9264 |
| 6004:9262 | 6044:9262 | 6004:9263 | 6044:9263 | 6004:9264 | 6044:9264 |
| 6005:9262 | 6045:9262 | 6005:9263 | 6045:9263 | 6005:9264 | 6045:9264 |
| 6006:9262 | 6046:9262 | 6006:9263 | 6046:9263 | 6006:9264 | 6046:9264 |
| 6007:9262 | 6047:9262 | 6007:9263 | 6047:9263 | 6007:9264 | 6047:9264 |
| 6008:9262 | 6048:9262 | 6008:9263 | 6048:9263 | 6008:9264 | 6048:9264 |
| 6009:9262 | 6049:9262 | 6009:9263 | 6049:9263 | 6009:9264 | 6049:9264 |
| 6010:9262 | 6050:9262 | 6010:9263 | 6050:9263 | 6010:9264 | 6050:9264 |
| 6011:9262 | 6051:9262 | 6011:9263 | 6051:9263 | 6011:9264 | 6051:9264 |
| 6012:9262 | 6052:9262 | 6012:9263 | 6052:9263 | 6012:9264 | 6052:9264 |
| 6013:9262 | 6053:9262 | 6013:9263 | 6053:9263 | 6013:9264 | 6053:9264 |
| 6014:9262 | 6054:9262 | 6014:9263 | 6054:9263 | 6014:9264 | 6054:9264 |
| 6015:9262 | 6055:9262 | 6015:9263 | 6055:9263 | 6015:9264 | 6055:9264 |
| 6016:9262 | 6056:9262 | 6016:9263 | 6056:9263 | 6016:9264 | 6056:9264 |
| 6017:9262 | 6057:9262 | 6017:9263 | 6057:9263 | 6017:9264 | 6057:9264 |
| 6018:9262 | 6058:9262 | 6018:9263 | 6058:9263 | 6018:9264 | 6058:9264 |
| 6019:9262 | 6059:9262 | 6019:9263 | 6059:9263 | 6019:9264 | 6059:9264 |
| 6020:9262 | 6060:9262 | 6020:9263 | 6060:9263 | 6020:9264 | 6060:9264 |
| 6021:9262 | 6061:9262 | 6021:9263 | 6061:9263 | 6021:9264 | 6061:9264 |
| 6022:9262 | 6062:9262 | 6022:9263 | 6062:9263 | 6022:9264 | 6062:9264 |
| 6023:9262 | 6063:9262 | 6023:9263 | 6063:9263 | 6023:9264 | 6063:9264 |
| 6024:9262 | 6064:9262 | 6024:9263 | 6064:9263 | 6024:9264 | 6064:9264 |
| 6025:9262 | 6065:9262 | 6025:9263 | 6065:9263 | 6025:9264 | 6065:9264 |
| 6026:9262 | 6066:9262 | 6026:9263 | 6066:9263 | 6026:9264 | 6066:9264 |
| 6027:9262 | 6067:9262 | 6027:9263 | 6067:9263 | 6027:9264 | 6067:9264 |
| 6028:9262 | 6068:9262 | 6028:9263 | 6068:9263 | 6028:9264 | 6068:9264 |
| 6029:9262 | 6069:9262 | 6029:9263 | 6069:9263 | 6029:9264 | 6069:9264 |
| 6030:9262 | 6070:9262 | 6030:9263 | 6070:9263 | 6030:9264 | 6070:9264 |
| 6031:9262 | 6071:9262 | 6031:9263 | 6071:9263 | 6031:9264 | 6071:9264 |
| 6032:9262 | 6072:9262 | 6032:9263 | 6072:9263 | 6032:9264 | 6072:9264 |
| 6033:9262 | 6073:9262 | 6033:9263 | 6073:9263 | 6033:9264 | 6073:9264 |
| 6034:9262 | 6074:9262 | 6034:9263 | 6074:9263 | 6034:9264 | 6074:9264 |
| 6035:9262 | 6075:9262 | 6035:9263 | 6075:9263 | 6035:9264 | 6075:9264 |
| 6036:9262 | 6076:9262 | 6036:9263 | 6076:9263 | 6036:9264 | 6076:9264 |
| 6037:9262 | 6077:9262 | 6037:9263 | 6077:9263 | 6037:9264 | 6077:9264 |
| 6038:9262 | 6078:9262 | 6038:9263 | 6078:9263 | 6038:9264 | 6078:9264 |
| 6039:9262 | | 6039:9263 | | 6039:9264 | |
| 6000:9265 | 6040:9265 | 6000:9266 | 6040:9266 | 6000:9267 | 6040:9267 |
| 6001:9265 | 6041:9265 | 6001:9266 | 6041:9266 | 6001:9267 | 6041:9267 |
| 6002:9265 | 6042:9265 | 6002:9266 | 6042:9266 | 6002:9267 | 6042:9267 |
| 6003:9265 | 6043:9265 | 6003:9266 | 6043:9266 | 6003:9267 | 6043:9267 |
| 6004:9265 | 6044:9265 | 6004:9266 | 6044:9266 | 6004:9267 | 6044:9267 |
| 6005:9265 | 6045:9265 | 6005:9266 | 6045:9266 | 6005:9267 | 6045:9267 |
| 6006:9265 | 6046:9265 | 6006:9266 | 6046:9266 | 6006:9267 | 6046:9267 |
| 6007:9265 | 6047:9265 | 6007:9266 | 6047:9266 | 6007:9267 | 6047:9267 |
| 6008:9265 | 6048:9265 | 6008:9266 | 6048:9266 | 6008:9267 | 6048:9267 |
| 6009:9265 | 6049:9265 | 6009:9266 | 6049:9266 | 6009:9267 | 6049:9267 |
| 6010:9265 | 6050:9265 | 6010:9266 | 6050:9266 | 6010:9267 | 6050:9267 |
| 6011:9265 | 6051:9265 | 6011:9266 | 6051:9266 | 6011:9267 | 6051:9267 |
| 6012:9265 | 6052:9265 | 6012:9266 | 6052:9266 | 6012:9267 | 6052:9267 |
| 6013:9265 | 6053:9265 | 6013:9266 | 6053:9266 | 6013:9267 | 6053:9267 |
| 6014:9265 | 6054:9265 | 6014:9266 | 6054:9266 | 6014:9267 | 6054:9267 |
| 6015:9265 | 6055:9265 | 6015:9266 | 6055:9266 | 6015:9267 | 6055:9267 |
| 6016:9265 | 6056:9265 | 6016:9266 | 6056:9266 | 6016:9267 | 6056:9267 |
| 6017:9265 | 6057:9265 | 6017:9266 | 6057:9266 | 6017:9267 | 6057:9267 |
| 6018:9265 | 6058:9265 | 6018:9266 | 6058:9266 | 6018:9267 | 6058:9267 |
| 6019:9265 | 6059:9265 | 6019:9266 | 6059:9266 | 6019:9267 | 6059:9267 |
| 6020:9265 | 6060:9265 | 6020:9266 | 6060:9266 | 6020:9267 | 6060:9267 |
| 6021:9265 | 6061:9265 | 6021:9266 | 6061:9266 | 6021:9267 | 6061:9267 |
| 6022:9265 | 6062:9265 | 6022:9266 | 6062:9266 | 6022:9267 | 6062:9267 |
| 6023:9265 | 6063:9265 | 6023:9266 | 6063:9266 | 6023:9267 | 6063:9267 |
| 6024:9265 | 6064:9265 | 6024:9266 | 6064:9266 | 6024:9267 | 6064:9267 |
| 6025:9265 | 6065:9265 | 6025:9266 | 6065:9266 | 6025:9267 | 6065:9267 |
| 6026:9265 | 6066:9265 | 6026:9266 | 6066:9266 | 6026:9267 | 6066:9267 |
| 6027:9265 | 6067:9265 | 6027:9266 | 6067:9266 | 6027:9267 | 6067:9267 |
| 6028:9265 | 6068:9265 | 6028:9266 | 6068:9266 | 6028:9267 | 6068:9267 |
| 6029:9265 | 6069:9265 | 6029:9266 | 6069:9266 | 6029:9267 | 6069:9267 |
| 6030:9265 | 6070:9265 | 6030:9266 | 6070:9266 | 6030:9267 | 6070:9267 |
| 6031:9265 | 6071:9265 | 6031:9266 | 6071:9266 | 6031:9267 | 6071:9267 |
| 6032:9265 | 6072:9265 | 6032:9266 | 6072:9266 | 6032:9267 | 6072:9267 |
| 6033:9265 | 6073:9265 | 6033:9266 | 6073:9266 | 6033:9267 | 6073:9267 |
| 6034:9265 | 6074:9265 | 6034:9266 | 6074:9266 | 6034:9267 | 6074:9267 |
| 6035:9265 | 6075:9265 | 6035:9266 | 6075:9266 | 6035:9267 | 6075:9267 |
| 6036:9265 | 6076:9265 | 6036:9266 | 6076:9266 | 6036:9267 | 6076:9267 |

TABLE D-continued

Example combinations of a compound X with a compound Y.

| X:Y | X:Y | X:Y | X:Y | X:Y | X:Y |
|---|---|---|---|---|---|
| 6037:9265 | 6077:9265 | 6037:9266 | 6077:9266 | 6037:9267 | 6077:9267 |
| 6038:9265 | 6078:9265 | 6038:9266 | 6078:9266 | 6038:9267 | 6078:9267 |
| 6039:9265 | | 6039:9266 | | 6039:9267 | |
| 6000:9268 | 6040:9268 | 6000:9269 | 6040:9269 | 6000:9270 | 6040:9270 |
| 6001:9268 | 6041:9268 | 6001:9269 | 6041:9269 | 6001:9270 | 6041:9270 |
| 6002:9268 | 6042:9268 | 6002:9269 | 6042:9269 | 6002:9270 | 6042:9270 |
| 6003:9268 | 6043:9268 | 6003:9269 | 6043:9269 | 6003:9270 | 6043:9270 |
| 6004:9268 | 6044:9268 | 6004:9269 | 6044:9269 | 6004:9270 | 6044:9270 |
| 6005:9268 | 6045:9268 | 6005:9269 | 6045:9269 | 6005:9270 | 6045:9270 |
| 6006:9268 | 6046:9268 | 6006:9269 | 6046:9269 | 6006:9270 | 6046:9270 |
| 6007:9268 | 6047:9268 | 6007:9269 | 6047:9269 | 6007:9270 | 6047:9270 |
| 6008:9268 | 6048:9268 | 6008:9269 | 6048:9269 | 6008:9270 | 6048:9270 |
| 6009:9268 | 6049:9268 | 6009:9269 | 6049:9269 | 6009:9270 | 6049:9270 |
| 6010:9268 | 6050:9268 | 6010:9269 | 6050:9269 | 6010:9270 | 6050:9270 |
| 6011:9268 | 6051:9268 | 6011:9269 | 6051:9269 | 6011:9270 | 6051:9270 |
| 6012:9268 | 6052:9268 | 6012:9269 | 6052:9269 | 6012:9270 | 6052:9270 |
| 6013:9268 | 6053:9268 | 6013:9269 | 6053:9269 | 6013:9270 | 6053:9270 |
| 6014:9268 | 6054:9268 | 6014:9269 | 6054:9269 | 6014:9270 | 6054:9270 |
| 6015:9268 | 6055:9268 | 6015:9269 | 6055:9269 | 6015:9270 | 6055:9270 |
| 6016:9268 | 6056:9268 | 6016:9269 | 6056:9269 | 6016:9270 | 6056:9270 |
| 6017:9268 | 6057:9268 | 6017:9269 | 6057:9269 | 6017:9270 | 6057:9270 |
| 6018:9268 | 6058:9268 | 6018:9269 | 6058:9269 | 6018:9270 | 6058:9270 |
| 6019:9268 | 6059:9268 | 6019:9269 | 6059:9269 | 6019:9270 | 6059:9270 |
| 6020:9268 | 6060:9268 | 6020:9269 | 6060:9269 | 6020:9270 | 6060:9270 |
| 6021:9268 | 6061:9268 | 6021:9269 | 6061:9269 | 6021:9270 | 6061:9270 |
| 6022:9268 | 6062:9268 | 6022:9269 | 6062:9269 | 6022:9270 | 6062:9270 |
| 6023:9268 | 6063:9268 | 6023:9269 | 6063:9269 | 6023:9270 | 6063:9270 |
| 6024:9268 | 6064:9268 | 6024:9269 | 6064:9269 | 6024:9270 | 6064:9270 |
| 6025:9268 | 6065:9268 | 6025:9269 | 6065:9269 | 6025:9270 | 6065:9270 |
| 6026:9268 | 6066:9268 | 6026:9269 | 6066:9269 | 6026:9270 | 6066:9270 |
| 6027:9268 | 6067:9268 | 6027:9269 | 6067:9269 | 6027:9270 | 6067:9270 |
| 6028:9268 | 6068:9268 | 6028:9269 | 6068:9269 | 6028:9270 | 6068:9270 |
| 6029:9268 | 6069:9268 | 6029:9269 | 6069:9269 | 6029:9270 | 6069:9270 |
| 6030:9268 | 6070:9268 | 6030:9269 | 6070:9269 | 6030:9270 | 6070:9270 |
| 6031:9268 | 6071:9268 | 6031:9269 | 6071:9269 | 6031:9270 | 6071:9270 |
| 6032:9268 | 6072:9268 | 6032:9269 | 6072:9269 | 6032:9270 | 6072:9270 |
| 6033:9268 | 6073:9268 | 6033:9269 | 6073:9269 | 6033:9270 | 6073:9270 |
| 6034:9268 | 6074:9268 | 6034:9269 | 6074:9269 | 6034:9270 | 6074:9270 |
| 6035:9268 | 6075:9268 | 6035:9269 | 6075:9269 | 6035:9270 | 6075:9270 |
| 6036:9268 | 6076:9268 | 6036:9269 | 6076:9269 | 6036:9270 | 6076:9270 |
| 6037:9268 | 6077:9268 | 6037:9269 | 6077:9269 | 6037:9270 | 6077:9270 |
| 6038:9268 | 6078:9268 | 6038:9269 | 6078:9269 | 6038:9270 | 6078:9270 |
| 6039:9268 | | 6039:9269 | | 6039:9270 | |
| 6000:9271 | 6040:9271 | 6000:9272 | 6040:9272 | 6000:9273 | 6040:9273 |
| 6001:9271 | 6041:9271 | 6001:9272 | 6041:9272 | 6001:9273 | 6041:9273 |
| 6002:9271 | 6042:9271 | 6002:9272 | 6042:9272 | 6002:9273 | 6042:9273 |
| 6003:9271 | 6043:9271 | 6003:9272 | 6043:9272 | 6003:9273 | 6043:9273 |
| 6004:9271 | 6044:9271 | 6004:9272 | 6044:9272 | 6004:9273 | 6044:9273 |
| 6005:9271 | 6045:9271 | 6005:9272 | 6045:9272 | 6005:9273 | 6045:9273 |
| 6006:9271 | 6046:9271 | 6006:9272 | 6046:9272 | 6006:9273 | 6046:9273 |
| 6007:9271 | 6047:9271 | 6007:9272 | 6047:9272 | 6007:9273 | 6047:9273 |
| 6008:9271 | 6048:9271 | 6008:9272 | 6048:9272 | 6008:9273 | 6048:9273 |
| 6009:9271 | 6049:9271 | 6009:9272 | 6049:9272 | 6009:9273 | 6049:9273 |
| 6010:9271 | 6050:9271 | 6010:9272 | 6050:9272 | 6010:9273 | 6050:9273 |
| 6011:9271 | 6051:9271 | 6011:9272 | 6051:9272 | 6011:9273 | 6051:9273 |
| 6012:9271 | 6052:9271 | 6012:9272 | 6052:9272 | 6012:9273 | 6052:9273 |
| 6013:9271 | 6053:9271 | 6013:9272 | 6053:9272 | 6013:9273 | 6053:9273 |
| 6014:9271 | 6054:9271 | 6014:9272 | 6054:9272 | 6014:9273 | 6054:9273 |
| 6015:9271 | 6055:9271 | 6015:9272 | 6055:9272 | 6015:9273 | 6055:9273 |
| 6016:9271 | 6056:9271 | 6016:9272 | 6056:9272 | 6016:9273 | 6056:9273 |
| 6017:9271 | 6057:9271 | 6017:9272 | 6057:9272 | 6017:9273 | 6057:9273 |
| 6018:9271 | 6058:9271 | 6018:9272 | 6058:9272 | 6018:9273 | 6058:9273 |
| 6019:9271 | 6059:9271 | 6019:9272 | 6059:9272 | 6019:9273 | 6059:9273 |
| 6020:9271 | 6060:9271 | 6020:9272 | 6060:9272 | 6020:9273 | 6060:9273 |
| 6021:9271 | 6061:9271 | 6021:9272 | 6061:9272 | 6021:9273 | 6061:9273 |
| 6022:9271 | 6062:9271 | 6022:9272 | 6062:9272 | 6022:9273 | 6062:9273 |
| 6023:9271 | 6063:9271 | 6023:9272 | 6063:9272 | 6023:9273 | 6063:9273 |
| 6024:9271 | 6064:9271 | 6024:9272 | 6064:9272 | 6024:9273 | 6064:9273 |
| 6025:9271 | 6065:9271 | 6025:9272 | 6065:9272 | 6025:9273 | 6065:9273 |
| 6026:9271 | 6066:9271 | 6026:9272 | 6066:9272 | 6026:9273 | 6066:9273 |
| 6027:9271 | 6067:9271 | 6027:9272 | 6067:9272 | 6027:9273 | 6067:9273 |
| 6028:9271 | 6068:9271 | 6028:9272 | 6068:9272 | 6028:9273 | 6068:9273 |
| 6029:9271 | 6069:9271 | 6029:9272 | 6069:9272 | 6029:9273 | 6069:9273 |
| 6030:9271 | 6070:9271 | 6030:9272 | 6070:9272 | 6030:9273 | 6070:9273 |
| 6031:9271 | 6071:9271 | 6031:9272 | 6071:9272 | 6031:9273 | 6071:9273 |
| 6032:9271 | 6072:9271 | 6032:9272 | 6072:9272 | 6032:9273 | 6072:9273 |
| 6033:9271 | 6073:9271 | 6033:9272 | 6073:9272 | 6033:9273 | 6073:9273 |
| 6034:9271 | 6074:9271 | 6034:9272 | 6074:9272 | 6034:9273 | 6074:9273 |
| 6035:9271 | 6075:9271 | 6035:9272 | 6075:9272 | 6035:9273 | 6075:9273 |
| 6036:9271 | 6076:9271 | 6036:9272 | 6076:9272 | 6036:9273 | 6076:9273 |
| 6037:9271 | 6077:9271 | 6037:9272 | 6077:9272 | 6037:9273 | 6077:9273 |
| 6038:9271 | 6078:9271 | 6038:9272 | 6078:9272 | 6038:9273 | 6078:9273 |
| 6039:9271 | | 6039:9272 | | 6039:9273 | |
| 6000:9274 | 6040:9274 | 6000:9275 | 6040:9275 | 6000:9276 | 6040:9276 |
| 6001:9274 | 6041:9274 | 6001:9275 | 6041:9275 | 6001:9276 | 6041:9276 |
| 6002:9274 | 6042:9274 | 6002:9275 | 6042:9275 | 6002:9276 | 6042:9276 |
| 6003:9274 | 6043:9274 | 6003:9275 | 6043:9275 | 6003:9276 | 6043:9276 |
| 6004:9274 | 6044:9274 | 6004:9275 | 6044:9275 | 6004:9276 | 6044:9276 |
| 6005:9274 | 6045:9274 | 6005:9275 | 6045:9275 | 6005:9276 | 6045:9276 |
| 6006:9274 | 6046:9274 | 6006:9275 | 6046:9275 | 6006:9276 | 6046:9276 |
| 6007:9274 | 6047:9274 | 6007:9275 | 6047:9275 | 6007:9276 | 6047:9276 |
| 6008:9274 | 6048:9274 | 6008:9275 | 6048:9275 | 6008:9276 | 6048:9276 |
| 6009:9274 | 6049:9274 | 6009:9275 | 6049:9275 | 6009:9276 | 6049:9276 |
| 6010:9274 | 6050:9274 | 6010:9275 | 6050:9275 | 6010:9276 | 6050:9276 |
| 6011:9274 | 6051:9274 | 6011:9275 | 6051:9275 | 6011:9276 | 6051:9276 |
| 6012:9274 | 6052:9274 | 6012:9275 | 6052:9275 | 6012:9276 | 6052:9276 |
| 6013:9274 | 6053:9274 | 6013:9275 | 6053:9275 | 6013:9276 | 6053:9276 |
| 6014:9274 | 6054:9274 | 6014:9275 | 6054:9275 | 6014:9276 | 6054:9276 |
| 6015:9274 | 6055:9274 | 6015:9275 | 6055:9275 | 6015:9276 | 6055:9276 |
| 6016:9274 | 6056:9274 | 6016:9275 | 6056:9275 | 6016:9276 | 6056:9276 |
| 6017:9274 | 6057:9274 | 6017:9275 | 6057:9275 | 6017:9276 | 6057:9276 |
| 6018:9274 | 6058:9274 | 6018:9275 | 6058:9275 | 6018:9276 | 6058:9276 |
| 6019:9274 | 6059:9274 | 6019:9275 | 6059:9275 | 6019:9276 | 6059:9276 |
| 6020:9274 | 6060:9274 | 6020:9275 | 6060:9275 | 6020:9276 | 6060:9276 |
| 6021:9274 | 6061:9274 | 6021:9275 | 6061:9275 | 6021:9276 | 6061:9276 |
| 6022:9274 | 6062:9274 | 6022:9275 | 6062:9275 | 6022:9276 | 6062:9276 |
| 6023:9274 | 6063:9274 | 6023:9275 | 6063:9275 | 6023:9276 | 6063:9276 |
| 6024:9274 | 6064:9274 | 6024:9275 | 6064:9275 | 6024:9276 | 6064:9276 |
| 6025:9274 | 6065:9274 | 6025:9275 | 6065:9275 | 6025:9276 | 6065:9276 |
| 6026:9274 | 6066:9274 | 6026:9275 | 6066:9275 | 6026:9276 | 6066:9276 |
| 6027:9274 | 6067:9274 | 6027:9275 | 6067:9275 | 6027:9276 | 6067:9276 |
| 6028:9274 | 6068:9274 | 6028:9275 | 6068:9275 | 6028:9276 | 6068:9276 |
| 6029:9274 | 6069:9274 | 6029:9275 | 6069:9275 | 6029:9276 | 6069:9276 |
| 6030:9274 | 6070:9274 | 6030:9275 | 6070:9275 | 6030:9276 | 6070:9276 |
| 6031:9274 | 6071:9274 | 6031:9275 | 6071:9275 | 6031:9276 | 6071:9276 |
| 6032:9274 | 6072:9274 | 6032:9275 | 6072:9275 | 6032:9276 | 6072:9276 |
| 6033:9274 | 6073:9274 | 6033:9275 | 6073:9275 | 6033:9276 | 6073:9276 |
| 6034:9274 | 6074:9274 | 6034:9275 | 6074:9275 | 6034:9276 | 6074:9276 |
| 6035:9274 | 6075:9274 | 6035:9275 | 6075:9275 | 6035:9276 | 6075:9276 |
| 6036:9274 | 6076:9274 | 6036:9275 | 6076:9275 | 6036:9276 | 6076:9276 |
| 6037:9274 | 6077:9274 | 6037:9275 | 6077:9275 | 6037:9276 | 6077:9276 |
| 6038:9274 | 6078:9274 | 6038:9275 | 6078:9275 | 6038:9276 | 6078:9276 |
| 6039:9274 | | 6039:9275 | | 6039:9276 | |
| 6000:9277 | 6040:9277 | 6000:9278 | 6040:9278 | 6000:9279 | 6040:9279 |
| 6001:9277 | 6041:9277 | 6001:9278 | 6041:9278 | 6001:9279 | 6041:9279 |
| 6002:9277 | 6042:9277 | 6002:9278 | 6042:9278 | 6002:9279 | 6042:9279 |
| 6003:9277 | 6043:9277 | 6003:9278 | 6043:9278 | 6003:9279 | 6043:9279 |
| 6004:9277 | 6044:9277 | 6004:9278 | 6044:9278 | 6004:9279 | 6044:9279 |
| 6005:9277 | 6045:9277 | 6005:9278 | 6045:9278 | 6005:9279 | 6045:9279 |
| 6006:9277 | 6046:9277 | 6006:9278 | 6046:9278 | 6006:9279 | 6046:9279 |
| 6007:9277 | 6047:9277 | 6007:9278 | 6047:9278 | 6007:9279 | 6047:9279 |
| 6008:9277 | 6048:9277 | 6008:9278 | 6048:9278 | 6008:9279 | 6048:9279 |
| 6009:9277 | 6049:9277 | 6009:9278 | 6049:9278 | 6009:9279 | 6049:9279 |
| 6010:9277 | 6050:9277 | 6010:9278 | 6050:9278 | 6010:9279 | 6050:9279 |
| 6011:9277 | 6051:9277 | 6011:9278 | 6051:9278 | 6011:9279 | 6051:9279 |
| 6012:9277 | 6052:9277 | 6012:9278 | 6052:9278 | 6012:9279 | 6052:9279 |
| 6013:9277 | 6053:9277 | 6013:9278 | 6053:9278 | 6013:9279 | 6053:9279 |
| 6014:9277 | 6054:9277 | 6014:9278 | 6054:9278 | 6014:9279 | 6054:9279 |
| 6015:9277 | 6055:9277 | 6015:9278 | 6055:9278 | 6015:9279 | 6055:9279 |
| 6016:9277 | 6056:9277 | 6016:9278 | 6056:9278 | 6016:9279 | 6056:9279 |
| 6017:9277 | 6057:9277 | 6017:9278 | 6057:9278 | 6017:9279 | 6057:9279 |
| 6018:9277 | 6058:9277 | 6018:9278 | 6058:9278 | 6018:9279 | 6058:9279 |
| 6019:9277 | 6059:9277 | 6019:9278 | 6059:9278 | 6019:9279 | 6059:9279 |
| 6020:9277 | 6060:9277 | 6020:9278 | 6060:9278 | 6020:9279 | 6060:9279 |
| 6021:9277 | 6061:9277 | 6021:9278 | 6061:9278 | 6021:9279 | 6061:9279 |
| 6022:9277 | 6062:9277 | 6022:9278 | 6062:9278 | 6022:9279 | 6062:9279 |
| 6023:9277 | 6063:9277 | 6023:9278 | 6063:9278 | 6023:9279 | 6063:9279 |
| 6024:9277 | 6064:9277 | 6024:9278 | 6064:9278 | 6024:9279 | 6064:9279 |
| 6025:9277 | 6065:9277 | 6025:9278 | 6065:9278 | 6025:9279 | 6065:9279 |
| 6026:9277 | 6066:9277 | 6026:9278 | 6066:9278 | 6026:9279 | 6066:9279 |
| 6027:9277 | 6067:9277 | 6027:9278 | 6067:9278 | 6027:9279 | 6067:9279 |
| 6028:9277 | 6068:9277 | 6028:9278 | 6068:9278 | 6028:9279 | 6068:9279 |

TABLE D-continued

Example combinations of a compound X with a compound Y.

| X:Y | X:Y | X:Y | X:Y | X:Y | X:Y |
|---|---|---|---|---|---|
| 6029:9277 | 6069:9277 | 6029:9278 | 6069:9278 | 6029:9279 | 6069:9279 |
| 6030:9277 | 6070:9277 | 6030:9278 | 6070:9278 | 6030:9279 | 6070:9279 |
| 6031:9277 | 6071:9277 | 6031:9278 | 6071:9278 | 6031:9279 | 6071:9279 |
| 6032:9277 | 6072:9277 | 6032:9278 | 6072:9278 | 6032:9279 | 6072:9279 |
| 6033:9277 | 6073:9277 | 6033:9278 | 6073:9278 | 6033:9279 | 6073:9279 |
| 6034:9277 | 6074:9277 | 6034:9278 | 6074:9278 | 6034:9279 | 6074:9279 |
| 6035:9277 | 6075:9277 | 6035:9278 | 6075:9278 | 6035:9279 | 6075:9279 |
| 6036:9277 | 6076:9277 | 6036:9278 | 6076:9278 | 6036:9279 | 6076:9279 |
| 6037:9277 | 6077:9277 | 6037:9278 | 6077:9278 | 6037:9279 | 6077:9279 |
| 6038:9277 | 6078:9277 | 6038:9278 | 6078:9278 | 6038:9279 | 6078:9279 |
| 6039:9277 |  | 6039:9278 |  | 6039:9279 |  |
| 6000:9280 | 6040:9280 | 6000:9281 | 6040:9281 | 6000:9282 | 6040:9282 |
| 6001:9280 | 6041:9280 | 6001:9281 | 6041:9281 | 6001:9282 | 6041:9282 |
| 6002:9280 | 6042:9280 | 6002:9281 | 6042:9281 | 6002:9282 | 6042:9282 |
| 6003:9280 | 6043:9280 | 6003:9281 | 6043:9281 | 6003:9282 | 6043:9282 |
| 6004:9280 | 6044:9280 | 6004:9281 | 6044:9281 | 6004:9282 | 6044:9282 |
| 6005:9280 | 6045:9280 | 6005:9281 | 6045:9281 | 6005:9282 | 6045:9282 |
| 6006:9280 | 6046:9280 | 6006:9281 | 6046:9281 | 6006:9282 | 6046:9282 |
| 6007:9280 | 6047:9280 | 6007:9281 | 6047:9281 | 6007:9282 | 6047:9282 |
| 6008:9280 | 6048:9280 | 6008:9281 | 6048:9281 | 6008:9282 | 6048:9282 |
| 6009:9280 | 6049:9280 | 6009:9281 | 6049:9281 | 6009:9282 | 6049:9282 |
| 6010:9280 | 6050:9280 | 6010:9281 | 6050:9281 | 6010:9282 | 6050:9282 |
| 6011:9280 | 6051:9280 | 6011:9281 | 6051:9281 | 6011:9282 | 6051:9282 |
| 6012:9280 | 6052:9280 | 6012:9281 | 6052:9281 | 6012:9282 | 6052:9282 |
| 6013:9280 | 6053:9280 | 6013:9281 | 6053:9281 | 6013:9282 | 6053:9282 |
| 6014:9280 | 6054:9280 | 6014:9281 | 6054:9281 | 6014:9282 | 6054:9282 |
| 6015:9280 | 6055:9280 | 6015:9281 | 6055:9281 | 6015:9282 | 6055:9282 |
| 6016:9280 | 6056:9280 | 6016:9281 | 6056:9281 | 6016:9282 | 6056:9282 |
| 6017:9280 | 6057:9280 | 6017:9281 | 6057:9281 | 6017:9282 | 6057:9282 |
| 6018:9280 | 6058:9280 | 6018:9281 | 6058:9281 | 6018:9282 | 6058:9282 |
| 6019:9280 | 6059:9280 | 6019:9281 | 6059:9281 | 6019:9282 | 6059:9282 |
| 6020:9280 | 6060:9280 | 6020:9281 | 6060:9281 | 6020:9282 | 6060:9282 |
| 6021:9280 | 6061:9280 | 6021:9281 | 6061:9281 | 6021:9282 | 6061:9282 |
| 6022:9280 | 6062:9280 | 6022:9281 | 6062:9281 | 6022:9282 | 6062:9282 |
| 6023:9280 | 6063:9280 | 6023:9281 | 6063:9281 | 6023:9282 | 6063:9282 |
| 6024:9280 | 6064:9280 | 6024:9281 | 6064:9281 | 6024:9282 | 6064:9282 |
| 6025:9280 | 6065:9280 | 6025:9281 | 6065:9281 | 6025:9282 | 6065:9282 |
| 6026:9280 | 6066:9280 | 6026:9281 | 6066:9281 | 6026:9282 | 6066:9282 |
| 6027:9280 | 6067:9280 | 6027:9281 | 6067:9281 | 6027:9282 | 6067:9282 |
| 6028:9280 | 6068:9280 | 6028:9281 | 6068:9281 | 6028:9282 | 6068:9282 |
| 6029:9280 | 6069:9280 | 6029:9281 | 6069:9281 | 6029:9282 | 6069:9282 |
| 6030:9280 | 6070:9280 | 6030:9281 | 6070:9281 | 6030:9282 | 6070:9282 |
| 6031:9280 | 6071:9280 | 6031:9281 | 6071:9281 | 6031:9282 | 6071:9282 |
| 6032:9280 | 6072:9280 | 6032:9281 | 6072:9281 | 6032:9282 | 6072:9282 |
| 6033:9280 | 6073:9280 | 6033:9281 | 6073:9281 | 6033:9282 | 6073:9282 |
| 6034:9280 | 6074:9280 | 6034:9281 | 6074:9281 | 6034:9282 | 6074:9282 |
| 6035:9280 | 6075:9280 | 6035:9281 | 6075:9281 | 6035:9282 | 6075:9282 |
| 6036:9280 | 6076:9280 | 6036:9281 | 6076:9281 | 6036:9282 | 6076:9282 |
| 6037:9280 | 6077:9280 | 6037:9281 | 6077:9281 | 6037:9282 | 6077:9282 |
| 6038:9280 | 6078:9280 | 6038:9281 | 6078:9281 | 6038:9282 | 6078:9282 |
| 6039:9280 |  | 6039:9281 |  | 6039:9282 |  |
| 6000:9283 | 6040:9283 | 6000:9284 | 6040:9284 | 6000:9285 | 6040:9285 |
| 6001:9283 | 6041:9283 | 6001:9284 | 6041:9284 | 6001:9285 | 6041:9285 |
| 6002:9283 | 6042:9283 | 6002:9284 | 6042:9284 | 6002:9285 | 6042:9285 |
| 6003:9283 | 6043:9283 | 6003:9284 | 6043:9284 | 6003:9285 | 6043:9285 |
| 6004:9283 | 6044:9283 | 6004:9284 | 6044:9284 | 6004:9285 | 6044:9285 |
| 6005:9283 | 6045:9283 | 6005:9284 | 6045:9284 | 6005:9285 | 6045:9285 |
| 6006:9283 | 6046:9283 | 6006:9284 | 6046:9284 | 6006:9285 | 6046:9285 |
| 6007:9283 | 6047:9283 | 6007:9284 | 6047:9284 | 6007:9285 | 6047:9285 |
| 6008:9283 | 6048:9283 | 6008:9284 | 6048:9284 | 6008:9285 | 6048:9285 |
| 6009:9283 | 6049:9283 | 6009:9284 | 6049:9284 | 6009:9285 | 6049:9285 |
| 6010:9283 | 6050:9283 | 6010:9284 | 6050:9284 | 6010:9285 | 6050:9285 |
| 6011:9283 | 6051:9283 | 6011:9284 | 6051:9284 | 6011:9285 | 6051:9285 |
| 6012:9283 | 6052:9283 | 6012:9284 | 6052:9284 | 6012:9285 | 6052:9285 |
| 6013:9283 | 6053:9283 | 6013:9284 | 6053:9284 | 6013:9285 | 6053:9285 |
| 6014:9283 | 6054:9283 | 6014:9284 | 6054:9284 | 6014:9285 | 6054:9285 |
| 6015:9283 | 6055:9283 | 6015:9284 | 6055:9284 | 6015:9285 | 6055:9285 |
| 6016:9283 | 6056:9283 | 6016:9284 | 6056:9284 | 6016:9285 | 6056:9285 |
| 6017:9283 | 6057:9283 | 6017:9284 | 6057:9284 | 6017:9285 | 6057:9285 |
| 6018:9283 | 6058:9283 | 6018:9284 | 6058:9284 | 6018:9285 | 6058:9285 |
| 6019:9283 | 6059:9283 | 6019:9284 | 6059:9284 | 6019:9285 | 6059:9285 |
| 6020:9283 | 6060:9283 | 6020:9284 | 6060:9284 | 6020:9285 | 6060:9285 |
| 6021:9283 | 6061:9283 | 6021:9284 | 6061:9284 | 6021:9285 | 6061:9285 |
| 6022:9283 | 6062:9283 | 6022:9284 | 6062:9284 | 6022:9285 | 6062:9285 |
| 6023:9283 | 6063:9283 | 6023:9284 | 6063:9284 | 6023:9285 | 6063:9285 |
| 6024:9283 | 6064:9283 | 6024:9284 | 6064:9284 | 6024:9285 | 6064:9285 |
| 6025:9283 | 6065:9283 | 6025:9284 | 6065:9284 | 6025:9285 | 6065:9285 |
| 6026:9283 | 6066:9283 | 6026:9284 | 6066:9284 | 6026:9285 | 6066:9285 |
| 6027:9283 | 6067:9283 | 6027:9284 | 6067:9284 | 6027:9285 | 6067:9285 |
| 6028:9283 | 6068:9283 | 6028:9284 | 6068:9284 | 6028:9285 | 6068:9285 |
| 6029:9283 | 6069:9283 | 6029:9284 | 6069:9284 | 6029:9285 | 6069:9285 |
| 6030:9283 | 6070:9283 | 6030:9284 | 6070:9284 | 6030:9285 | 6070:9285 |
| 6031:9283 | 6071:9283 | 6031:9284 | 6071:9284 | 6031:9285 | 6071:9285 |
| 6032:9283 | 6072:9283 | 6032:9284 | 6072:9284 | 6032:9285 | 6072:9285 |
| 6033:9283 | 6073:9283 | 6033:9284 | 6073:9284 | 6033:9285 | 6073:9285 |
| 6034:9283 | 6074:9283 | 6034:9284 | 6074:9284 | 6034:9285 | 6074:9285 |
| 6035:9283 | 6075:9283 | 6035:9284 | 6075:9284 | 6035:9285 | 6075:9285 |
| 6036:9283 | 6076:9283 | 6036:9284 | 6076:9284 | 6036:9285 | 6076:9285 |
| 6037:9283 | 6077:9283 | 6037:9284 | 6077:9284 | 6037:9285 | 6077:9285 |
| 6038:9283 | 6078:9283 | 6038:9284 | 6078:9284 | 6038:9285 | 6078:9285 |
| 6039:9283 |  | 6039:9284 |  | 6039:9285 |  |
| 6000:9286 | 6040:9286 | 6000:9287 | 6040:9287 | 6000:9288 | 6040:9288 |
| 6001:9286 | 6041:9286 | 6001:9287 | 6041:9287 | 6001:9288 | 6041:9288 |
| 6002:9286 | 6042:9286 | 6002:9287 | 6042:9287 | 6002:9288 | 6042:9288 |
| 6003:9286 | 6043:9286 | 6003:9287 | 6043:9287 | 6003:9288 | 6043:9288 |
| 6004:9286 | 6044:9286 | 6004:9287 | 6044:9287 | 6004:9288 | 6044:9288 |
| 6005:9286 | 6045:9286 | 6005:9287 | 6045:9287 | 6005:9288 | 6045:9288 |
| 6006:9286 | 6046:9286 | 6006:9287 | 6046:9287 | 6006:9288 | 6046:9288 |
| 6007:9286 | 6047:9286 | 6007:9287 | 6047:9287 | 6007:9288 | 6047:9288 |
| 6008:9286 | 6048:9286 | 6008:9287 | 6048:9287 | 6008:9288 | 6048:9288 |
| 6009:9286 | 6049:9286 | 6009:9287 | 6049:9287 | 6009:9288 | 6049:9288 |
| 6010:9286 | 6050:9286 | 6010:9287 | 6050:9287 | 6010:9288 | 6050:9288 |
| 6011:9286 | 6051:9286 | 6011:9287 | 6051:9287 | 6011:9288 | 6051:9288 |
| 6012:9286 | 6052:9286 | 6012:9287 | 6052:9287 | 6012:9288 | 6052:9288 |
| 6013:9286 | 6053:9286 | 6013:9287 | 6053:9287 | 6013:9288 | 6053:9288 |
| 6014:9286 | 6054:9286 | 6014:9287 | 6054:9287 | 6014:9288 | 6054:9288 |
| 6015:9286 | 6055:9286 | 6015:9287 | 6055:9287 | 6015:9288 | 6055:9288 |
| 6016:9286 | 6056:9286 | 6016:9287 | 6056:9287 | 6016:9288 | 6056:9288 |
| 6017:9286 | 6057:9286 | 6017:9287 | 6057:9287 | 6017:9288 | 6057:9288 |
| 6018:9286 | 6058:9286 | 6018:9287 | 6058:9287 | 6018:9288 | 6058:9288 |
| 6019:9286 | 6059:9286 | 6019:9287 | 6059:9287 | 6019:9288 | 6059:9288 |
| 6020:9286 | 6060:9286 | 6020:9287 | 6060:9287 | 6020:9288 | 6060:9288 |
| 6021:9286 | 6061:9286 | 6021:9287 | 6061:9287 | 6021:9288 | 6061:9288 |
| 6022:9286 | 6062:9286 | 6022:9287 | 6062:9287 | 6022:9288 | 6062:9288 |
| 6023:9286 | 6063:9286 | 6023:9287 | 6063:9287 | 6023:9288 | 6063:9288 |
| 6024:9286 | 6064:9286 | 6024:9287 | 6064:9287 | 6024:9288 | 6064:9288 |
| 6025:9286 | 6065:9286 | 6025:9287 | 6065:9287 | 6025:9288 | 6065:9288 |
| 6026:9286 | 6066:9286 | 6026:9287 | 6066:9287 | 6026:9288 | 6066:9288 |
| 6027:9286 | 6067:9286 | 6027:9287 | 6067:9287 | 6027:9288 | 6067:9288 |
| 6028:9286 | 6068:9286 | 6028:9287 | 6068:9287 | 6028:9288 | 6068:9288 |
| 6029:9286 | 6069:9286 | 6029:9287 | 6069:9287 | 6029:9288 | 6069:9288 |
| 6030:9286 | 6070:9286 | 6030:9287 | 6070:9287 | 6030:9288 | 6070:9288 |
| 6031:9286 | 6071:9286 | 6031:9287 | 6071:9287 | 6031:9288 | 6071:9288 |
| 6032:9286 | 6072:9286 | 6032:9287 | 6072:9287 | 6032:9288 | 6072:9288 |
| 6033:9286 | 6073:9286 | 6033:9287 | 6073:9287 | 6033:9288 | 6073:9288 |
| 6034:9286 | 6074:9286 | 6034:9287 | 6074:9287 | 6034:9288 | 6074:9288 |
| 6035:9286 | 6075:9286 | 6035:9287 | 6075:9287 | 6035:9288 | 6075:9288 |
| 6036:9286 | 6076:9286 | 6036:9287 | 6076:9287 | 6036:9288 | 6076:9288 |
| 6037:9286 | 6077:9286 | 6037:9287 | 6077:9287 | 6037:9288 | 6077:9288 |
| 6038:9286 | 6078:9286 | 6038:9287 | 6078:9287 | 6038:9288 | 6078:9288 |
| 6039:9286 |  | 6039:9287 |  | 6039:9288 |  |
| 6000:9289 | 6040:9289 | 6000:9290 | 6040:9290 | 6000:9291 | 6040:9291 |
| 6001:9289 | 6041:9289 | 6001:9290 | 6041:9290 | 6001:9291 | 6041:9291 |
| 6002:9289 | 6042:9289 | 6002:9290 | 6042:9290 | 6002:9291 | 6042:9291 |
| 6003:9289 | 6043:9289 | 6003:9290 | 6043:9290 | 6003:9291 | 6043:9291 |
| 6004:9289 | 6044:9289 | 6004:9290 | 6044:9290 | 6004:9291 | 6044:9291 |
| 6005:9289 | 6045:9289 | 6005:9290 | 6045:9290 | 6005:9291 | 6045:9291 |
| 6006:9289 | 6046:9289 | 6006:9290 | 6046:9290 | 6006:9291 | 6046:9291 |
| 6007:9289 | 6047:9289 | 6007:9290 | 6047:9290 | 6007:9291 | 6047:9291 |
| 6008:9289 | 6048:9289 | 6008:9290 | 6048:9290 | 6008:9291 | 6048:9291 |
| 6009:9289 | 6049:9289 | 6009:9290 | 6049:9290 | 6009:9291 | 6049:9291 |
| 6010:9289 | 6050:9289 | 6010:9290 | 6050:9290 | 6010:9291 | 6050:9291 |
| 6011:9289 | 6051:9289 | 6011:9290 | 6051:9290 | 6011:9291 | 6051:9291 |
| 6012:9289 | 6052:9289 | 6012:9290 | 6052:9290 | 6012:9291 | 6052:9291 |
| 6013:9289 | 6053:9289 | 6013:9290 | 6053:9290 | 6013:9291 | 6053:9291 |
| 6014:9289 | 6054:9289 | 6014:9290 | 6054:9290 | 6014:9291 | 6054:9291 |
| 6015:9289 | 6055:9289 | 6015:9290 | 6055:9290 | 6015:9291 | 6055:9291 |
| 6016:9289 | 6056:9289 | 6016:9290 | 6056:9290 | 6016:9291 | 6056:9291 |
| 6017:9289 | 6057:9289 | 6017:9290 | 6057:9290 | 6017:9291 | 6057:9291 |
| 6018:9289 | 6058:9289 | 6018:9290 | 6058:9290 | 6018:9291 | 6058:9291 |
| 6019:9289 | 6059:9289 | 6019:9290 | 6059:9290 | 6019:9291 | 6059:9291 |
| 6020:9289 | 6060:9289 | 6020:9290 | 6060:9290 | 6020:9291 | 6060:9291 |

TABLE D-continued

Example combinations of a compound X with a compound Y.

| X:Y | X:Y | X:Y | X:Y | X:Y | X:Y |
|---|---|---|---|---|---|
| 6021:9289 | 6061:9289 | 6021:9290 | 6061:9290 | 6021:9291 | 6061:9291 |
| 6022:9289 | 6062:9289 | 6022:9290 | 6062:9290 | 6022:9291 | 6062:9291 |
| 6023:9289 | 6063:9289 | 6023:9290 | 6063:9290 | 6023:9291 | 6063:9291 |
| 6024:9289 | 6064:9289 | 6024:9290 | 6064:9290 | 6024:9291 | 6064:9291 |
| 6025:9289 | 6065:9289 | 6025:9290 | 6065:9290 | 6025:9291 | 6065:9291 |
| 6026:9289 | 6066:9289 | 6026:9290 | 6066:9290 | 6026:9291 | 6066:9291 |
| 6027:9289 | 6067:9289 | 6027:9290 | 6067:9290 | 6027:9291 | 6067:9291 |
| 6028:9289 | 6068:9289 | 6028:9290 | 6068:9290 | 6028:9291 | 6068:9291 |
| 6029:9289 | 6069:9289 | 6029:9290 | 6069:9290 | 6029:9291 | 6069:9291 |
| 6030:9289 | 6070:9289 | 6030:9290 | 6070:9290 | 6030:9291 | 6070:9291 |
| 6031:9289 | 6071:9289 | 6031:9290 | 6071:9290 | 6031:9291 | 6071:9291 |
| 6032:9289 | 6072:9289 | 6032:9290 | 6072:9290 | 6032:9291 | 6072:9291 |
| 6033:9289 | 6073:9289 | 6033:9290 | 6073:9290 | 6033:9291 | 6073:9291 |
| 6034:9289 | 6074:9289 | 6034:9290 | 6074:9290 | 6034:9291 | 6074:9291 |
| 6035:9289 | 6075:9289 | 6035:9290 | 6075:9290 | 6035:9291 | 6075:9291 |
| 6036:9289 | 6076:9289 | 6036:9290 | 6076:9290 | 6036:9291 | 6076:9291 |
| 6037:9289 | 6077:9289 | 6037:9290 | 6077:9290 | 6037:9291 | 6077:9291 |
| 6038:9289 | 6078:9289 | 6038:9290 | 6078:9290 | 6038:9291 | 6078:9291 |
| 6039:9289 | | 6039:9290 | | 6039:9291 | |
| 6000:9292 | 6040:9292 | 6000:9293 | 6040:9293 | 6000:9294 | 6040:9294 |
| 6001:9292 | 6041:9292 | 6001:9293 | 6041:9293 | 6001:9294 | 6041:9294 |
| 6002:9292 | 6042:9292 | 6002:9293 | 6042:9293 | 6002:9294 | 6042:9294 |
| 6003:9292 | 6043:9292 | 6003:9293 | 6043:9293 | 6003:9294 | 6043:9294 |
| 6004:9292 | 6044:9292 | 6004:9293 | 6044:9293 | 6004:9294 | 6044:9294 |
| 6005:9292 | 6045:9292 | 6005:9293 | 6045:9293 | 6005:9294 | 6045:9294 |
| 6006:9292 | 6046:9292 | 6006:9293 | 6046:9293 | 6006:9294 | 6046:9294 |
| 6007:9292 | 6047:9292 | 6007:9293 | 6047:9293 | 6007:9294 | 6047:9294 |
| 6008:9292 | 6048:9292 | 6008:9293 | 6048:9293 | 6008:9294 | 6048:9294 |
| 6009:9292 | 6049:9292 | 6009:9293 | 6049:9293 | 6009:9294 | 6049:9294 |
| 6010:9292 | 6050:9292 | 6010:9293 | 6050:9293 | 6010:9294 | 6050:9294 |
| 6011:9292 | 6051:9292 | 6011:9293 | 6051:9293 | 6011:9294 | 6051:9294 |
| 6012:9292 | 6052:9292 | 6012:9293 | 6052:9293 | 6012:9294 | 6052:9294 |
| 6013:9292 | 6053:9292 | 6013:9293 | 6053:9293 | 6013:9294 | 6053:9294 |
| 6014:9292 | 6054:9292 | 6014:9293 | 6054:9293 | 6014:9294 | 6054:9294 |
| 6015:9292 | 6055:9292 | 6015:9293 | 6055:9293 | 6015:9294 | 6055:9294 |
| 6016:9292 | 6056:9292 | 6016:9293 | 6056:9293 | 6016:9294 | 6056:9294 |
| 6017:9292 | 6057:9292 | 6017:9293 | 6057:9293 | 6017:9294 | 6057:9294 |
| 6018:9292 | 6058:9292 | 6018:9293 | 6058:9293 | 6018:9294 | 6058:9294 |
| 6019:9292 | 6059:9292 | 6019:9293 | 6059:9293 | 6019:9294 | 6059:9294 |
| 6020:9292 | 6060:9292 | 6020:9293 | 6060:9293 | 6020:9294 | 6060:9294 |
| 6021:9292 | 6061:9292 | 6021:9293 | 6061:9293 | 6021:9294 | 6061:9294 |
| 6022:9292 | 6062:9292 | 6022:9293 | 6062:9293 | 6022:9294 | 6062:9294 |
| 6023:9292 | 6063:9292 | 6023:9293 | 6063:9293 | 6023:9294 | 6063:9294 |
| 6024:9292 | 6064:9292 | 6024:9293 | 6064:9293 | 6024:9294 | 6064:9294 |
| 6025:9292 | 6065:9292 | 6025:9293 | 6065:9293 | 6025:9294 | 6065:9294 |
| 6026:9292 | 6066:9292 | 6026:9293 | 6066:9293 | 6026:9294 | 6066:9294 |
| 6027:9292 | 6067:9292 | 6027:9293 | 6067:9293 | 6027:9294 | 6067:9294 |
| 6028:9292 | 6068:9292 | 6028:9293 | 6068:9293 | 6028:9294 | 6068:9294 |
| 6029:9292 | 6069:9292 | 6029:9293 | 6069:9293 | 6029:9294 | 6069:9294 |
| 6030:9292 | 6070:9292 | 6030:9293 | 6070:9293 | 6030:9294 | 6070:9294 |
| 6031:9292 | 6071:9292 | 6031:9293 | 6071:9293 | 6031:9294 | 6071:9294 |
| 6032:9292 | 6072:9292 | 6032:9293 | 6072:9293 | 6032:9294 | 6072:9294 |
| 6033:9292 | 6073:9292 | 6033:9293 | 6073:9293 | 6033:9294 | 6073:9294 |
| 6034:9292 | 6074:9292 | 6034:9293 | 6074:9293 | 6034:9294 | 6074:9294 |
| 6035:9292 | 6075:9292 | 6035:9293 | 6075:9293 | 6035:9294 | 6075:9294 |
| 6036:9292 | 6076:9292 | 6036:9293 | 6076:9293 | 6036:9294 | 6076:9294 |
| 6037:9292 | 6077:9292 | 6037:9293 | 6077:9293 | 6037:9294 | 6077:9294 |
| 6038:9292 | 6078:9292 | 6038:9293 | 6078:9293 | 6038:9294 | 6078:9294 |
| 6039:9292 | | 6039:9293 | | 6039:9294 | |
| 6000:9295 | 6040:9295 | 6000:9296 | 6040:9296 | 6000:9297 | 6040:9297 |
| 6001:9295 | 6041:9295 | 6001:9296 | 6041:9296 | 6001:9297 | 6041:9297 |
| 6002:9295 | 6042:9295 | 6002:9296 | 6042:9296 | 6002:9297 | 6042:9297 |
| 6003:9295 | 6043:9295 | 6003:9296 | 6043:9296 | 6003:9297 | 6043:9297 |
| 6004:9295 | 6044:9295 | 6004:9296 | 6044:9296 | 6004:9297 | 6044:9297 |
| 6005:9295 | 6045:9295 | 6005:9296 | 6045:9296 | 6005:9297 | 6045:9297 |
| 6006:9295 | 6046:9295 | 6006:9296 | 6046:9296 | 6006:9297 | 6046:9297 |
| 6007:9295 | 6047:9295 | 6007:9296 | 6047:9296 | 6007:9297 | 6047:9297 |
| 6008:9295 | 6048:9295 | 6008:9296 | 6048:9296 | 6008:9297 | 6048:9297 |
| 6009:9295 | 6049:9295 | 6009:9296 | 6049:9296 | 6009:9297 | 6049:9297 |
| 6010:9295 | 6050:9295 | 6010:9296 | 6050:9296 | 6010:9297 | 6050:9297 |
| 6011:9295 | 6051:9295 | 6011:9296 | 6051:9296 | 6011:9297 | 6051:9297 |
| 6012:9295 | 6052:9295 | 6012:9296 | 6052:9296 | 6012:9297 | 6052:9297 |
| 6013:9295 | 6053:9295 | 6013:9296 | 6053:9296 | 6013:9297 | 6053:9297 |
| 6014:9295 | 6054:9295 | 6014:9296 | 6054:9296 | 6014:9297 | 6054:9297 |
| 6015:9295 | 6055:9295 | 6015:9296 | 6055:9296 | 6015:9297 | 6055:9297 |
| 6016:9295 | 6056:9295 | 6016:9296 | 6056:9296 | 6016:9297 | 6056:9297 |
| 6017:9295 | 6057:9295 | 6017:9296 | 6057:9296 | 6017:9297 | 6057:9297 |
| 6018:9295 | 6058:9295 | 6018:9296 | 6058:9296 | 6018:9297 | 6058:9297 |
| 6019:9295 | 6059:9295 | 6019:9296 | 6059:9296 | 6019:9297 | 6059:9297 |
| 6020:9295 | 6060:9295 | 6020:9296 | 6060:9296 | 6020:9297 | 6060:9297 |
| 6021:9295 | 6061:9295 | 6021:9296 | 6061:9296 | 6021:9297 | 6061:9297 |
| 6022:9295 | 6062:9295 | 6022:9296 | 6062:9296 | 6022:9297 | 6062:9297 |
| 6023:9295 | 6063:9295 | 6023:9296 | 6063:9296 | 6023:9297 | 6063:9297 |
| 6024:9295 | 6064:9295 | 6024:9296 | 6064:9296 | 6024:9297 | 6064:9297 |
| 6025:9295 | 6065:9295 | 6025:9296 | 6065:9296 | 6025:9297 | 6065:9297 |
| 6026:9295 | 6066:9295 | 6026:9296 | 6066:9296 | 6026:9297 | 6066:9297 |
| 6027:9295 | 6067:9295 | 6027:9296 | 6067:9296 | 6027:9297 | 6067:9297 |
| 6028:9295 | 6068:9295 | 6028:9296 | 6068:9296 | 6028:9297 | 6068:9297 |
| 6029:9295 | 6069:9295 | 6029:9296 | 6069:9296 | 6029:9297 | 6069:9297 |
| 6030:9295 | 6070:9295 | 6030:9296 | 6070:9296 | 6030:9297 | 6070:9297 |
| 6031:9295 | 6071:9295 | 6031:9296 | 6071:9296 | 6031:9297 | 6071:9297 |
| 6032:9295 | 6072:9295 | 6032:9296 | 6072:9296 | 6032:9297 | 6072:9297 |
| 6033:9295 | 6073:9295 | 6033:9296 | 6073:9296 | 6033:9297 | 6073:9297 |
| 6034:9295 | 6074:9295 | 6034:9296 | 6074:9296 | 6034:9297 | 6074:9297 |
| 6035:9295 | 6075:9295 | 6035:9296 | 6075:9296 | 6035:9297 | 6075:9297 |
| 6036:9295 | 6076:9295 | 6036:9296 | 6076:9296 | 6036:9297 | 6076:9297 |
| 6037:9295 | 6077:9295 | 6037:9296 | 6077:9296 | 6037:9297 | 6077:9297 |
| 6038:9295 | 6078:9295 | 6038:9296 | 6078:9296 | 6038:9297 | 6078:9297 |
| 6039:9295 | | 6039:9296 | | 6039:9297 | |
| 6000:9298 | 6040:9298 | 6000:9299 | 6040:9299 | 6000:9300 | 6040:9300 |
| 6001:9298 | 6041:9298 | 6001:9299 | 6041:9299 | 6001:9300 | 6041:9300 |
| 6002:9298 | 6042:9298 | 6002:9299 | 6042:9299 | 6002:9300 | 6042:9300 |
| 6003:9298 | 6043:9298 | 6003:9299 | 6043:9299 | 6003:9300 | 6043:9300 |
| 6004:9298 | 6044:9298 | 6004:9299 | 6044:9299 | 6004:9300 | 6044:9300 |
| 6005:9298 | 6045:9298 | 6005:9299 | 6045:9299 | 6005:9300 | 6045:9300 |
| 6006:9298 | 6046:9298 | 6006:9299 | 6046:9299 | 6006:9300 | 6046:9300 |
| 6007:9298 | 6047:9298 | 6007:9299 | 6047:9299 | 6007:9300 | 6047:9300 |
| 6008:9298 | 6048:9298 | 6008:9299 | 6048:9299 | 6008:9300 | 6048:9300 |
| 6009:9298 | 6049:9298 | 6009:9299 | 6049:9299 | 6009:9300 | 6049:9300 |
| 6010:9298 | 6050:9298 | 6010:9299 | 6050:9299 | 6010:9300 | 6050:9300 |
| 6011:9298 | 6051:9298 | 6011:9299 | 6051:9299 | 6011:9300 | 6051:9300 |
| 6012:9298 | 6052:9298 | 6012:9299 | 6052:9299 | 6012:9300 | 6052:9300 |
| 6013:9298 | 6053:9298 | 6013:9299 | 6053:9299 | 6013:9300 | 6053:9300 |
| 6014:9298 | 6054:9298 | 6014:9299 | 6054:9299 | 6014:9300 | 6054:9300 |
| 6015:9298 | 6055:9298 | 6015:9299 | 6055:9299 | 6015:9300 | 6055:9300 |
| 6016:9298 | 6056:9298 | 6016:9299 | 6056:9299 | 6016:9300 | 6056:9300 |
| 6017:9298 | 6057:9298 | 6017:9299 | 6057:9299 | 6017:9300 | 6057:9300 |
| 6018:9298 | 6058:9298 | 6018:9299 | 6058:9299 | 6018:9300 | 6058:9300 |
| 6019:9298 | 6059:9298 | 6019:9299 | 6059:9299 | 6019:9300 | 6059:9300 |
| 6020:9298 | 6060:9298 | 6020:9299 | 6060:9299 | 6020:9300 | 6060:9300 |
| 6021:9298 | 6061:9298 | 6021:9299 | 6061:9299 | 6021:9300 | 6061:9300 |
| 6022:9298 | 6062:9298 | 6022:9299 | 6062:9299 | 6022:9300 | 6062:9300 |
| 6023:9298 | 6063:9298 | 6023:9299 | 6063:9299 | 6023:9300 | 6063:9300 |
| 6024:9298 | 6064:9298 | 6024:9299 | 6064:9299 | 6024:9300 | 6064:9300 |
| 6025:9298 | 6065:9298 | 6025:9299 | 6065:9299 | 6025:9300 | 6065:9300 |
| 6026:9298 | 6066:9298 | 6026:9299 | 6066:9299 | 6026:9300 | 6066:9300 |
| 6027:9298 | 6067:9298 | 6027:9299 | 6067:9299 | 6027:9300 | 6067:9300 |
| 6028:9298 | 6068:9298 | 6028:9299 | 6068:9299 | 6028:9300 | 6068:9300 |
| 6029:9298 | 6069:9298 | 6029:9299 | 6069:9299 | 6029:9300 | 6069:9300 |
| 6030:9298 | 6070:9298 | 6030:9299 | 6070:9299 | 6030:9300 | 6070:9300 |
| 6031:9298 | 6071:9298 | 6031:9299 | 6071:9299 | 6031:9300 | 6071:9300 |
| 6032:9298 | 6072:9298 | 6032:9299 | 6072:9299 | 6032:9300 | 6072:9300 |
| 6033:9298 | 6073:9298 | 6033:9299 | 6073:9299 | 6033:9300 | 6073:9300 |
| 6034:9298 | 6074:9298 | 6034:9299 | 6074:9299 | 6034:9300 | 6074:9300 |
| 6035:9298 | 6075:9298 | 6035:9299 | 6075:9299 | 6035:9300 | 6075:9300 |
| 6036:9298 | 6076:9298 | 6036:9299 | 6076:9299 | 6036:9300 | 6076:9300 |
| 6037:9298 | 6077:9298 | 6037:9299 | 6077:9299 | 6037:9300 | 6077:9300 |
| 6038:9298 | 6078:9298 | 6038:9299 | 6078:9299 | 6038:9300 | 6078:9300 |
| 6039:9298 | | 6039:9299 | | 6039:9300 | |
| 6000:9301 | 6040:9301 | 6000:9302 | 6040:9302 | 6000:9303 | 6040:9303 |
| 6001:9301 | 6041:9301 | 6001:9302 | 6041:9302 | 6001:9303 | 6041:9303 |
| 6002:9301 | 6042:9301 | 6002:9302 | 6042:9302 | 6002:9303 | 6042:9303 |
| 6003:9301 | 6043:9301 | 6003:9302 | 6043:9302 | 6003:9303 | 6043:9303 |
| 6004:9301 | 6044:9301 | 6004:9302 | 6044:9302 | 6004:9303 | 6044:9303 |
| 6005:9301 | 6045:9301 | 6005:9302 | 6045:9302 | 6005:9303 | 6045:9303 |
| 6006:9301 | 6046:9301 | 6006:9302 | 6046:9302 | 6006:9303 | 6046:9303 |
| 6007:9301 | 6047:9301 | 6007:9302 | 6047:9302 | 6007:9303 | 6047:9303 |
| 6008:9301 | 6048:9301 | 6008:9302 | 6048:9302 | 6008:9303 | 6048:9303 |
| 6009:9301 | 6049:9301 | 6009:9302 | 6049:9302 | 6009:9303 | 6049:9303 |
| 6010:9301 | 6050:9301 | 6010:9302 | 6050:9302 | 6010:9303 | 6050:9303 |
| 6011:9301 | 6051:9301 | 6011:9302 | 6051:9302 | 6011:9303 | 6051:9303 |
| 6012:9301 | 6052:9301 | 6012:9302 | 6052:9302 | 6012:9303 | 6052:9303 |

TABLE D-continued

Example combinations of a compound X with a compound Y.

| X:Y | X:Y | X:Y | X:Y | X:Y | X:Y |
|---|---|---|---|---|---|
| 6013:9301 | 6053:9301 | 6013:9302 | 6053:9302 | 6013:9303 | 6053:9303 |
| 6014:9301 | 6054:9301 | 6014:9302 | 6054:9302 | 6014:9303 | 6054:9303 |
| 6015:9301 | 6055:9301 | 6015:9302 | 6055:9302 | 6015:9303 | 6055:9303 |
| 6016:9301 | 6056:9301 | 6016:9302 | 6056:9302 | 6016:9303 | 6056:9303 |
| 6017:9301 | 6057:9301 | 6017:9302 | 6057:9302 | 6017:9303 | 6057:9303 |
| 6018:9301 | 6058:9301 | 6018:9302 | 6058:9302 | 6018:9303 | 6058:9303 |
| 6019:9301 | 6059:9301 | 6019:9302 | 6059:9302 | 6019:9303 | 6059:9303 |
| 6020:9301 | 6060:9301 | 6020:9302 | 6060:9302 | 6020:9303 | 6060:9303 |
| 6021:9301 | 6061:9301 | 6021:9302 | 6061:9302 | 6021:9303 | 6061:9303 |
| 6022:9301 | 6062:9301 | 6022:9302 | 6062:9302 | 6022:9303 | 6062:9303 |
| 6023:9301 | 6063:9301 | 6023:9302 | 6063:9302 | 6023:9303 | 6063:9303 |
| 6024:9301 | 6064:9301 | 6024:9302 | 6064:9302 | 6024:9303 | 6064:9303 |
| 6025:9301 | 6065:9301 | 6025:9302 | 6065:9302 | 6025:9303 | 6065:9303 |
| 6026:9301 | 6066:9301 | 6026:9302 | 6066:9302 | 6026:9303 | 6066:9303 |
| 6027:9301 | 6067:9301 | 6027:9302 | 6067:9302 | 6027:9303 | 6067:9303 |
| 6028:9301 | 6068:9301 | 6028:9302 | 6068:9302 | 6028:9303 | 6068:9303 |
| 6029:9301 | 6069:9301 | 6029:9302 | 6069:9302 | 6029:9303 | 6069:9303 |
| 6030:9301 | 6070:9301 | 6030:9302 | 6070:9302 | 6030:9303 | 6070:9303 |
| 6031:9301 | 6071:9301 | 6031:9302 | 6071:9302 | 6031:9303 | 6071:9303 |
| 6032:9301 | 6072:9301 | 6032:9302 | 6072:9302 | 6032:9303 | 6072:9303 |
| 6033:9301 | 6073:9301 | 6033:9302 | 6073:9302 | 6033:9303 | 6073:9303 |
| 6034:9301 | 6074:9301 | 6034:9302 | 6074:9302 | 6034:9303 | 6074:9303 |
| 6035:9301 | 6075:9301 | 6035:9302 | 6075:9302 | 6035:9303 | 6075:9303 |
| 6036:9301 | 6076:9301 | 6036:9302 | 6076:9302 | 6036:9303 | 6076:9303 |
| 6037:9301 | 6077:9301 | 6037:9302 | 6077:9302 | 6037:9303 | 6077:9303 |
| 6038:9301 | 6078:9301 | 6038:9302 | 6078:9302 | 6038:9303 | 6078:9303 |
| 6039:9301 | | 6039:9302 | | 6039:9303 | |
| 6000:9304 | 6040:9304 | 6000:9305 | 6040:9305 | 6000:9306 | 6040:9306 |
| 6001:9304 | 6041:9304 | 6001:9305 | 6041:9305 | 6001:9306 | 6041:9306 |
| 6002:9304 | 6042:9304 | 6002:9305 | 6042:9305 | 6002:9306 | 6042:9306 |
| 6003:9304 | 6043:9304 | 6003:9305 | 6043:9305 | 6003:9306 | 6043:9306 |
| 6004:9304 | 6044:9304 | 6004:9305 | 6044:9305 | 6004:9306 | 6044:9306 |
| 6005:9304 | 6045:9304 | 6005:9305 | 6045:9305 | 6005:9306 | 6045:9306 |
| 6006:9304 | 6046:9304 | 6006:9305 | 6046:9305 | 6006:9306 | 6046:9306 |
| 6007:9304 | 6047:9304 | 6007:9305 | 6047:9305 | 6007:9306 | 6047:9306 |
| 6008:9304 | 6048:9304 | 6008:9305 | 6048:9305 | 6008:9306 | 6048:9306 |
| 6009:9304 | 6049:9304 | 6009:9305 | 6049:9305 | 6009:9306 | 6049:9306 |
| 6010:9304 | 6050:9304 | 6010:9305 | 6050:9305 | 6010:9306 | 6050:9306 |
| 6011:9304 | 6051:9304 | 6011:9305 | 6051:9305 | 6011:9306 | 6051:9306 |
| 6012:9304 | 6052:9304 | 6012:9305 | 6052:9305 | 6012:9306 | 6052:9306 |
| 6013:9304 | 6053:9304 | 6013:9305 | 6053:9305 | 6013:9306 | 6053:9306 |
| 6014:9304 | 6054:9304 | 6014:9305 | 6054:9305 | 6014:9306 | 6054:9306 |
| 6015:9304 | 6055:9304 | 6015:9305 | 6055:9305 | 6015:9306 | 6055:9306 |
| 6016:9304 | 6056:9304 | 6016:9305 | 6056:9305 | 6016:9306 | 6056:9306 |
| 6017:9304 | 6057:9304 | 6017:9305 | 6057:9305 | 6017:9306 | 6057:9306 |
| 6018:9304 | 6058:9304 | 6018:9305 | 6058:9305 | 6018:9306 | 6058:9306 |
| 6019:9304 | 6059:9304 | 6019:9305 | 6059:9305 | 6019:9306 | 6059:9306 |
| 6020:9304 | 6060:9304 | 6020:9305 | 6060:9305 | 6020:9306 | 6060:9306 |
| 6021:9304 | 6061:9304 | 6021:9305 | 6061:9305 | 6021:9306 | 6061:9306 |
| 6022:9304 | 6062:9304 | 6022:9305 | 6062:9305 | 6022:9306 | 6062:9306 |
| 6023:9304 | 6063:9304 | 6023:9305 | 6063:9305 | 6023:9306 | 6063:9306 |
| 6024:9304 | 6064:9304 | 6024:9305 | 6064:9305 | 6024:9306 | 6064:9306 |
| 6025:9304 | 6065:9304 | 6025:9305 | 6065:9305 | 6025:9306 | 6065:9306 |
| 6026:9304 | 6066:9304 | 6026:9305 | 6066:9305 | 6026:9306 | 6066:9306 |
| 6027:9304 | 6067:9304 | 6027:9305 | 6067:9305 | 6027:9306 | 6067:9306 |
| 6028:9304 | 6068:9304 | 6028:9305 | 6068:9305 | 6028:9306 | 6068:9306 |
| 6029:9304 | 6069:9304 | 6029:9305 | 6069:9305 | 6029:9306 | 6069:9306 |
| 6030:9304 | 6070:9304 | 6030:9305 | 6070:9305 | 6030:9306 | 6070:9306 |
| 6031:9304 | 6071:9304 | 6031:9305 | 6071:9305 | 6031:9306 | 6071:9306 |
| 6032:9304 | 6072:9304 | 6032:9305 | 6072:9305 | 6032:9306 | 6072:9306 |
| 6033:9304 | 6073:9304 | 6033:9305 | 6073:9305 | 6033:9306 | 6073:9306 |
| 6034:9304 | 6074:9304 | 6034:9305 | 6074:9305 | 6034:9306 | 6074:9306 |
| 6035:9304 | 6075:9304 | 6035:9305 | 6075:9305 | 6035:9306 | 6075:9306 |
| 6036:9304 | 6076:9304 | 6036:9305 | 6076:9305 | 6036:9306 | 6076:9306 |
| 6037:9304 | 6077:9304 | 6037:9305 | 6077:9305 | 6037:9306 | 6077:9306 |
| 6038:9304 | 6078:9304 | 6038:9305 | 6078:9305 | 6038:9306 | 6078:9306 |
| 6039:9304 | | 6039:9305 | | 6039:9306 | |
| 6000:9307 | 6040:9307 | 6000:9308 | 6040:9308 | 6000:9309 | 6040:9309 |
| 6001:9307 | 6041:9307 | 6001:9308 | 6041:9308 | 6001:9309 | 6041:9309 |
| 6002:9307 | 6042:9307 | 6002:9308 | 6042:9308 | 6002:9309 | 6042:9309 |
| 6003:9307 | 6043:9307 | 6003:9308 | 6043:9308 | 6003:9309 | 6043:9309 |
| 6004:9307 | 6044:9307 | 6004:9308 | 6044:9308 | 6004:9309 | 6044:9309 |
| 6005:9307 | 6045:9307 | 6005:9308 | 6045:9308 | 6005:9309 | 6045:9309 |
| 6006:9307 | 6046:9307 | 6006:9308 | 6046:9308 | 6006:9309 | 6046:9309 |
| 6007:9307 | 6047:9307 | 6007:9308 | 6047:9308 | 6007:9309 | 6047:9309 |
| 6008:9307 | 6048:9307 | 6008:9308 | 6048:9308 | 6008:9309 | 6048:9309 |
| 6009:9307 | 6049:9307 | 6009:9308 | 6049:9308 | 6009:9309 | 6049:9309 |
| 6010:9307 | 6050:9307 | 6010:9308 | 6050:9308 | 6010:9309 | 6050:9309 |
| 6011:9307 | 6051:9307 | 6011:9308 | 6051:9308 | 6011:9309 | 6051:9309 |
| 6012:9307 | 6052:9307 | 6012:9308 | 6052:9308 | 6012:9309 | 6052:9309 |
| 6013:9307 | 6053:9307 | 6013:9308 | 6053:9308 | 6013:9309 | 6053:9309 |
| 6014:9307 | 6054:9307 | 6014:9308 | 6054:9308 | 6014:9309 | 6054:9309 |
| 6015:9307 | 6055:9307 | 6015:9308 | 6055:9308 | 6015:9309 | 6055:9309 |
| 6016:9307 | 6056:9307 | 6016:9308 | 6056:9308 | 6016:9309 | 6056:9309 |
| 6017:9307 | 6057:9307 | 6017:9308 | 6057:9308 | 6017:9309 | 6057:9309 |
| 6018:9307 | 6058:9307 | 6018:9308 | 6058:9308 | 6018:9309 | 6058:9309 |
| 6019:9307 | 6059:9307 | 6019:9308 | 6059:9308 | 6019:9309 | 6059:9309 |
| 6020:9307 | 6060:9307 | 6020:9308 | 6060:9308 | 6020:9309 | 6060:9309 |
| 6021:9307 | 6061:9307 | 6021:9308 | 6061:9308 | 6021:9309 | 6061:9309 |
| 6022:9307 | 6062:9307 | 6022:9308 | 6062:9308 | 6022:9309 | 6062:9309 |
| 6023:9307 | 6063:9307 | 6023:9308 | 6063:9308 | 6023:9309 | 6063:9309 |
| 6024:9307 | 6064:9307 | 6024:9308 | 6064:9308 | 6024:9309 | 6064:9309 |
| 6025:9307 | 6065:9307 | 6025:9308 | 6065:9308 | 6025:9309 | 6065:9309 |
| 6026:9307 | 6066:9307 | 6026:9308 | 6066:9308 | 6026:9309 | 6066:9309 |
| 6027:9307 | 6067:9307 | 6027:9308 | 6067:9308 | 6027:9309 | 6067:9309 |
| 6028:9307 | 6068:9307 | 6028:9308 | 6068:9308 | 6028:9309 | 6068:9309 |
| 6029:9307 | 6069:9307 | 6029:9308 | 6069:9308 | 6029:9309 | 6069:9309 |
| 6030:9307 | 6070:9307 | 6030:9308 | 6070:9308 | 6030:9309 | 6070:9309 |
| 6031:9307 | 6071:9307 | 6031:9308 | 6071:9308 | 6031:9309 | 6071:9309 |
| 6032:9307 | 6072:9307 | 6032:9308 | 6072:9308 | 6032:9309 | 6072:9309 |
| 6033:9307 | 6073:9307 | 6033:9308 | 6073:9308 | 6033:9309 | 6073:9309 |
| 6034:9307 | 6074:9307 | 6034:9308 | 6074:9308 | 6034:9309 | 6074:9309 |
| 6035:9307 | 6075:9307 | 6035:9308 | 6075:9308 | 6035:9309 | 6075:9309 |
| 6036:9307 | 6076:9307 | 6036:9308 | 6076:9308 | 6036:9309 | 6076:9309 |
| 6037:9307 | 6077:9307 | 6037:9308 | 6077:9308 | 6037:9309 | 6077:9309 |
| 6038:9307 | 6078:9307 | 6038:9308 | 6078:9308 | 6038:9309 | 6078:9309 |
| 6039:9307 | | 6039:9308 | | 6039:9309 | — |
| 6000:9310 | 6040:9310 | — | — | — | — |
| 6001:9310 | 6041:9310 | | | | |
| 6002:9310 | 6042:9310 | | | | |
| 6003:9310 | 6043:9310 | | | | |
| 6004:9310 | 6044:9310 | | | | |
| 6005:9310 | 6045:9310 | | | | |
| 6006:9310 | 6046:9310 | | | | |
| 6007:9310 | 6047:9310 | | | | |
| 6008:9310 | 6048:9310 | | | | |
| 6009:9310 | 6049:9310 | | | | |
| 6010:9310 | 6050:9310 | | | | |
| 6011:9310 | 6051:9310 | | | | |
| 6012:9310 | 6052:9310 | | | | |
| 6013:9310 | 6053:9310 | | | | |
| 6014:9310 | 6054:9310 | | | | |
| 6015:9310 | 6055:9310 | | | | |
| 6016:9310 | 6056:9310 | | | | |
| 6017:9310 | 6057:9310 | | | | |
| 6018:9310 | 6058:9310 | | | | |
| 6019:9310 | 6059:9310 | | | | |
| 6020:9310 | 6060:9310 | | | | |
| 6021:9310 | 6061:9310 | | | | |
| 6022:9310 | 6062:9310 | | | | |
| 6023:9310 | 6063:9310 | | | | |
| 6024:9310 | 6064:9310 | | | | |
| 6025:9310 | 6065:9310 | | | | |
| 6026:9310 | 6066:9310 | | | | |
| 6027:9310 | 6067:9310 | | | | |
| 6028:9310 | 6068:9310 | | | | |
| 6029:9310 | 6069:9310 | | | | |
| 6030:9310 | 6070:9310 | | | | |
| 6031:9310 | 6071:9310 | | | | |
| 6032:9310 | 6072:9310 | | | | |
| 6033:9310 | 6073:9310 | | | | |
| 6034:9310 | 6074:9310 | | | | |
| 6035:9310 | 6075:9310 | | | | |
| 6036:9310 | 6076:9310 | | | | |
| 6037:9310 | 6077:9310 | | | | |
| 6038:9310 | 6078:9310 | | | | |
| 6039:9310 | | | | | |

TABLE E

Example combinations of a compound X with a compound Y.

| X:Y | X:Y | X:Y | X:Y | X:Y | X:Y |
|---|---|---|---|---|---|
| 8000:9006 | 8000:9007 | 8000:9008 | 8000:9018 | 8000:9020 | 8000:9021 |
| 8001:9006 | 8001:9007 | 8001:9008 | 8001:9018 | 8001:9020 | 8001:9021 |
| 8002:9006 | 8002:9007 | 8002:9008 | 8002:9018 | 8002:9020 | 8002:9021 |
| 8003:9006 | 8003:9007 | 8003:9008 | 8003:9018 | 8003:9020 | 8003:9021 |
| 8004:9006 | 8004:9007 | 8004:9008 | 8004:9018 | 8004:9020 | 8004:9021 |
| 8005:9006 | 8005:9007 | 8005:9008 | 8005:9018 | 8005:9020 | 8005:9021 |
| 8006:9006 | 8006:9007 | 8006:9008 | 8006:9018 | 8006:9020 | 8006:9021 |
| 8007:9006 | 8007:9007 | 8007:9008 | 8007:9018 | 8007:9020 | 8007:9021 |
| 8008:9006 | 8008:9007 | 8008:9008 | 8008:9018 | 8008:9020 | 8008:9021 |
| 8009:9006 | 8009:9007 | 8009:9008 | 8009:9018 | 8009:9020 | 8009:9021 |
| 8010:9006 | 8010:9007 | 8010:9008 | 8010:9018 | 8010:9020 | 8010:9021 |
| 8011:9006 | 8011:9007 | 8011:9008 | 8011:9018 | 8011:9020 | 8011:9021 |
| 8012:9006 | 8012:9007 | 8012:9008 | 8012:9018 | 8012:9020 | 8012:9021 |
| 8013:9006 | 8013:9007 | 8013:9008 | 8013:9018 | 8013:9020 | 8013:9021 |
| 8014:9006 | 8014:9007 | 8014:9008 | 8014:9018 | 8014:9020 | 8014:9021 |
| 8015:9006 | 8015:9007 | 8015:9008 | 8015:9018 | 8015:9020 | 8015:9021 |
| 8016:9006 | 8016:9007 | 8016:9008 | 8016:9018 | 8016:9020 | 8016:9021 |
| 8000:9025 | 8000:9026 | 8000:9036 | 8000:9038 | 8000:9039 | 8000:9040 |
| 8001:9025 | 8001:9026 | 8001:9036 | 8001:9038 | 8001:9039 | 8001:9040 |
| 8002:9025 | 8002:9026 | 8002:9036 | 8002:9038 | 8002:9039 | 8002:9040 |
| 8003:9025 | 8003:9026 | 8003:9036 | 8003:9038 | 8003:9039 | 8003:9040 |
| 8004:9025 | 8004:9026 | 8004:9036 | 8004:9038 | 8004:9039 | 8004:9040 |
| 8005:9025 | 8005:9026 | 8005:9036 | 8005:9038 | 8005:9039 | 8005:9040 |
| 8006:9025 | 8006:9026 | 8006:9036 | 8006:9038 | 8006:9039 | 8006:9040 |
| 8007:9025 | 8007:9026 | 8007:9036 | 8007:9038 | 8007:9039 | 8007:9040 |
| 8008:9025 | 8008:9026 | 8008:9036 | 8008:9038 | 8008:9039 | 8008:9040 |
| 8009:9025 | 8009:9026 | 8009:9036 | 8009:9038 | 8009:9039 | 8009:9040 |
| 8010:9025 | 8010:9026 | 8010:9036 | 8010:9038 | 8010:9039 | 8010:9040 |
| 8011:9025 | 8011:9026 | 8011:9036 | 8011:9038 | 8011:9039 | 8011:9040 |
| 8012:9025 | 8012:9026 | 8012:9036 | 8012:9038 | 8012:9039 | 8012:9040 |
| 8013:9025 | 8013:9026 | 8013:9036 | 8013:9038 | 8013:9039 | 8013:9040 |
| 8014:9025 | 8014:9026 | 8014:9036 | 8014:9038 | 8014:9039 | 8014:9040 |
| 8015:9025 | 8015:9026 | 8015:9036 | 8015:9038 | 8015:9039 | 8015:9040 |
| 8016:9025 | 8016:9026 | 8016:9036 | 8016:9038 | 8016:9039 | 8016:9040 |
| 8000:9041 | 8000:9042 | 8000:9043 | 8000:9044 | 8000:9045 | 8000:9047 |
| 8001:9041 | 8001:9042 | 8001:9043 | 8001:9044 | 8001:9045 | 8001:9047 |
| 8002:9041 | 8002:9042 | 8002:9043 | 8002:9044 | 8002:9045 | 8002:9047 |
| 8003:9041 | 8003:9042 | 8003:9043 | 8003:9044 | 8003:9045 | 8003:9047 |
| 8004:9041 | 8004:9042 | 8004:9043 | 8004:9044 | 8004:9045 | 8004:9047 |
| 8005:9041 | 8005:9042 | 8005:9043 | 8005:9044 | 8005:9045 | 8005:9047 |
| 8006:9041 | 8006:9042 | 8006:9043 | 8006:9044 | 8006:9045 | 8006:9047 |
| 8007:9041 | 8007:9042 | 8007:9043 | 8007:9044 | 8007:9045 | 8007:9047 |
| 8008:9041 | 8008:9042 | 8008:9043 | 8008:9044 | 8008:9045 | 8008:9047 |
| 8009:9041 | 8009:9042 | 8009:9043 | 8009:9044 | 8009:9045 | 8009:9047 |
| 8010:9041 | 8010:9042 | 8010:9043 | 8010:9044 | 8010:9045 | 8010:9047 |
| 8011:9041 | 8011:9042 | 8011:9043 | 8011:9044 | 8011:9045 | 8011:9047 |
| 8012:9041 | 8012:9042 | 8012:9043 | 8012:9044 | 8012:9045 | 8012:9047 |
| 8013:9041 | 8013:9042 | 8013:9043 | 8013:9044 | 8013:9045 | 8013:9047 |
| 8014:9041 | 8014:9042 | 8014:9043 | 8014:9044 | 8014:9045 | 8014:9047 |
| 8015:9041 | 8015:9042 | 8015:9043 | 8015:9044 | 8015:9045 | 8015:9047 |
| 8016:9041 | 8016:9042 | 8016:9043 | 8016:9044 | 8016:9045 | 8016:9047 |
| 8000:9048 | 8000:9049 | 8000:9051 | 8000:9052 | 8000:9053 | 8000:9054 |
| 8001:9048 | 8001:9049 | 8001:9051 | 8001:9052 | 8001:9053 | 8001:9054 |
| 8002:9048 | 8002:9049 | 8002:9051 | 8002:9052 | 8002:9053 | 8002:9054 |
| 8003:9048 | 8003:9049 | 8003:9051 | 8003:9052 | 8003:9053 | 8003:9054 |
| 8004:9048 | 8004:9049 | 8004:9051 | 8004:9052 | 8004:9053 | 8004:9054 |
| 8005:9048 | 8005:9049 | 8005:9051 | 8005:9052 | 8005:9053 | 8005:9054 |
| 8006:9048 | 8006:9049 | 8006:9051 | 8006:9052 | 8006:9053 | 8006:9054 |
| 8007:9048 | 8007:9049 | 8007:9051 | 8007:9052 | 8007:9053 | 8007:9054 |
| 8008:9048 | 8008:9049 | 8008:9051 | 8008:9052 | 8008:9053 | 8008:9054 |
| 8009:9048 | 8009:9049 | 8009:9051 | 8009:9052 | 8009:9053 | 8009:9054 |
| 8010:9048 | 8010:9049 | 8010:9051 | 8010:9052 | 8010:9053 | 8010:9054 |
| 8011:9048 | 8011:9049 | 8011:9051 | 8011:9052 | 8011:9053 | 8011:9054 |
| 8012:9048 | 8012:9049 | 8012:9051 | 8012:9052 | 8012:9053 | 8012:9054 |
| 8013:9048 | 8013:9049 | 8013:9051 | 8013:9052 | 8013:9053 | 8013:9054 |
| 8014:9048 | 8014:9049 | 8014:9051 | 8014:9052 | 8014:9053 | 8014:9054 |
| 8015:9048 | 8015:9049 | 8015:9051 | 8015:9052 | 8015:9053 | 8015:9054 |
| 8016:9048 | 8016:9049 | 8016:9051 | 8016:9052 | 8016:9053 | 8016:9054 |
| 8000:9055 | 8000:9056 | 8000:9058 | 8000:9060 | 8000:9061 | 8000:9062 |
| 8001:9055 | 8001:9056 | 8001:9058 | 8001:9060 | 8001:9061 | 8001:9062 |
| 8002:9055 | 8002:9056 | 8002:9058 | 8002:9060 | 8002:9061 | 8002:9062 |
| 8003:9055 | 8003:9056 | 8003:9058 | 8003:9060 | 8003:9061 | 8003:9062 |
| 8004:9055 | 8004:9056 | 8004:9058 | 8004:9060 | 8004:9061 | 8004:9062 |
| 8005:9055 | 8005:9056 | 8005:9058 | 8005:9060 | 8005:9061 | 8005:9062 |
| 8006:9055 | 8006:9056 | 8006:9058 | 8006:9060 | 8006:9061 | 8006:9062 |
| 8007:9055 | 8007:9056 | 8007:9058 | 8007:9060 | 8007:9061 | 8007:9062 |
| 8008:9055 | 8008:9056 | 8008:9058 | 8008:9060 | 8008:9061 | 8008:9062 |
| 8009:9055 | 8009:9056 | 8009:9058 | 8009:9060 | 8009:9061 | 8009:9062 |
| 8010:9055 | 8010:9056 | 8010:9058 | 8010:9060 | 8010:9061 | 8010:9062 |
| 8011:9055 | 8011:9056 | 8011:9058 | 8011:9060 | 8011:9061 | 8011:9062 |
| 8012:9055 | 8012:9056 | 8012:9058 | 8012:9060 | 8012:9061 | 8012:9062 |
| 8013:9055 | 8013:9056 | 8013:9058 | 8013:9060 | 8013:9061 | 8013:9062 |
| 8014:9055 | 8014:9056 | 8014:9058 | 8014:9060 | 8014:9061 | 8014:9062 |
| 8015:9055 | 8015:9056 | 8015:9058 | 8015:9060 | 8015:9061 | 8015:9062 |
| 8016:9055 | 8016:9056 | 8016:9058 | 8016:9060 | 8016:9061 | 8016:9062 |
| 8000:9063 | 8000:9064 | 8000:9065 | 8000:9066 | 8000:9067 | 8000:9068 |
| 8001:9063 | 8001:9064 | 8001:9065 | 8001:9066 | 8001:9067 | 8001:9068 |
| 8002:9063 | 8002:9064 | 8002:9065 | 8002:9066 | 8002:9067 | 8002:9068 |
| 8003:9063 | 8003:9064 | 8003:9065 | 8003:9066 | 8003:9067 | 8003:9068 |
| 8004:9063 | 8004:9064 | 8004:9065 | 8004:9066 | 8004:9067 | 8004:9068 |
| 8005:9063 | 8005:9064 | 8005:9065 | 8005:9066 | 8005:9067 | 8005:9068 |
| 8006:9063 | 8006:9064 | 8006:9065 | 8006:9066 | 8006:9067 | 8006:9068 |
| 8007:9063 | 8007:9064 | 8007:9065 | 8007:9066 | 8007:9067 | 8007:9068 |
| 8008:9063 | 8008:9064 | 8008:9065 | 8008:9066 | 8008:9067 | 8008:9068 |
| 8009:9063 | 8009:9064 | 8009:9065 | 8009:9066 | 8009:9067 | 8009:9068 |
| 8010:9063 | 8010:9064 | 8010:9065 | 8010:9066 | 8010:9067 | 8010:9068 |
| 8011:9063 | 8011:9064 | 8011:9065 | 8011:9066 | 8011:9067 | 8011:9068 |
| 8012:9063 | 8012:9064 | 8012:9065 | 8012:9066 | 8012:9067 | 8012:9068 |
| 8013:9063 | 8013:9064 | 8013:9065 | 8013:9066 | 8013:9067 | 8013:9068 |
| 8014:9063 | 8014:9064 | 8014:9065 | 8014:9066 | 8014:9067 | 8014:9068 |
| 8015:9063 | 8015:9064 | 8015:9065 | 8015:9066 | 8015:9067 | 8015:9068 |
| 8016:9063 | 8016:9064 | 8016:9065 | 8016:9066 | 8016:9067 | 8016:9068 |
| 8000:9069 | 8000:9070 | 8000:9071 | 8000:9072 | 8000:9073 | 8000:9074 |
| 8001:9069 | 8001:9070 | 8001:9071 | 8001:9072 | 8001:9073 | 8001:9074 |
| 8002:9069 | 8002:9070 | 8002:9071 | 8002:9072 | 8002:9073 | 8002:9074 |
| 8003:9069 | 8003:9070 | 8003:9071 | 8003:9072 | 8003:9073 | 8003:9074 |
| 8004:9069 | 8004:9070 | 8004:9071 | 8004:9072 | 8004:9073 | 8004:9074 |
| 8005:9069 | 8005:9070 | 8005:9071 | 8005:9072 | 8005:9073 | 8005:9074 |
| 8006:9069 | 8006:9070 | 8006:9071 | 8006:9072 | 8006:9073 | 8006:9074 |
| 8007:9069 | 8007:9070 | 8007:9071 | 8007:9072 | 8007:9073 | 8007:9074 |
| 8008:9069 | 8008:9070 | 8008:9071 | 8008:9072 | 8008:9073 | 8008:9074 |
| 8009:9069 | 8009:9070 | 8009:9071 | 8009:9072 | 8009:9073 | 8009:9074 |
| 8010:9069 | 8010:9070 | 8010:9071 | 8010:9072 | 8010:9073 | 8010:9074 |
| 8011:9069 | 8011:9070 | 8011:9071 | 8011:9072 | 8011:9073 | 8011:9074 |
| 8012:9069 | 8012:9070 | 8012:9071 | 8012:9072 | 8012:9073 | 8012:9074 |
| 8013:9069 | 8013:9070 | 8013:9071 | 8013:9072 | 8013:9073 | 8013:9074 |
| 8014:9069 | 8014:9070 | 8014:9071 | 8014:9072 | 8014:9073 | 8014:9074 |
| 8015:9069 | 8015:9070 | 8015:9071 | 8015:9072 | 8015:9073 | 8015:9074 |
| 8016:9069 | 8016:9070 | 8016:9071 | 8016:9072 | 8016:9073 | 8016:9074 |
| 8000:9075 | 8000:9076 | 8000:9077 | 8000:9078 | 8000:9079 | 8000:9080 |
| 8001:9075 | 8001:9076 | 8001:9077 | 8001:9078 | 8001:9079 | 8001:9080 |
| 8002:9075 | 8002:9076 | 8002:9077 | 8002:9078 | 8002:9079 | 8002:9080 |
| 8003:9075 | 8003:9076 | 8003:9077 | 8003:9078 | 8003:9079 | 8003:9080 |
| 8004:9075 | 8004:9076 | 8004:9077 | 8004:9078 | 8004:9079 | 8004:9080 |
| 8005:9075 | 8005:9076 | 8005:9077 | 8005:9078 | 8005:9079 | 8005:9080 |
| 8006:9075 | 8006:9076 | 8006:9077 | 8006:9078 | 8006:9079 | 8006:9080 |
| 8007:9075 | 8007:9076 | 8007:9077 | 8007:9078 | 8007:9079 | 8007:9080 |
| 8008:9075 | 8008:9076 | 8008:9077 | 8008:9078 | 8008:9079 | 8008:9080 |
| 8009:9075 | 8009:9076 | 8009:9077 | 8009:9078 | 8009:9079 | 8009:9080 |
| 8010:9075 | 8010:9076 | 8010:9077 | 8010:9078 | 8010:9079 | 8010:9080 |
| 8011:9075 | 8011:9076 | 8011:9077 | 8011:9078 | 8011:9079 | 8011:9080 |
| 8012:9075 | 8012:9076 | 8012:9077 | 8012:9078 | 8012:9079 | 8012:9080 |
| 8013:9075 | 8013:9076 | 8013:9077 | 8013:9078 | 8013:9079 | 8013:9080 |
| 8014:9075 | 8014:9076 | 8014:9077 | 8014:9078 | 8014:9079 | 8014:9080 |
| 8015:9075 | 8015:9076 | 8015:9077 | 8015:9078 | 8015:9079 | 8015:9080 |
| 8016:9075 | 8016:9076 | 8016:9077 | 8016:9078 | 8016:9079 | 8016:9080 |
| 8000:9081 | 8000:9082 | 8000:9083 | 8000:9084 | 8000:9085 | 8000:9086 |
| 8001:9081 | 8001:9082 | 8001:9083 | 8001:9084 | 8001:9085 | 8001:9086 |
| 8002:9081 | 8002:9082 | 8002:9083 | 8002:9084 | 8002:9085 | 8002:9086 |
| 8003:9081 | 8003:9082 | 8003:9083 | 8003:9084 | 8003:9085 | 8003:9086 |
| 8004:9081 | 8004:9082 | 8004:9083 | 8004:9084 | 8004:9085 | 8004:9086 |
| 8005:9081 | 8005:9082 | 8005:9083 | 8005:9084 | 8005:9085 | 8005:9086 |
| 8006:9081 | 8006:9082 | 8006:9083 | 8006:9084 | 8006:9085 | 8006:9086 |
| 8007:9081 | 8007:9082 | 8007:9083 | 8007:9084 | 8007:9085 | 8007:9086 |
| 8008:9081 | 8008:9082 | 8008:9083 | 8008:9084 | 8008:9085 | 8008:9086 |
| 8009:9081 | 8009:9082 | 8009:9083 | 8009:9084 | 8009:9085 | 8009:9086 |
| 8010:9081 | 8010:9082 | 8010:9083 | 8010:9084 | 8010:9085 | 8010:9086 |
| 8011:9081 | 8011:9082 | 8011:9083 | 8011:9084 | 8011:9085 | 8011:9086 |
| 8012:9081 | 8012:9082 | 8012:9083 | 8012:9084 | 8012:9085 | 8012:9086 |
| 8013:9081 | 8013:9082 | 8013:9083 | 8013:9084 | 8013:9085 | 8013:9086 |
| 8014:9081 | 8014:9082 | 8014:9083 | 8014:9084 | 8014:9085 | 8014:9086 |
| 8015:9081 | 8015:9082 | 8015:9083 | 8015:9084 | 8015:9085 | 8015:9086 |

TABLE E-continued

Example combinations of a compound X with a compound Y.

| X:Y | X:Y | X:Y | X:Y | X:Y | X:Y |
|---|---|---|---|---|---|
| 8016:9081 | 8016:9082 | 8016:9083 | 8016:9084 | 8016:9085 | 8016:9086 |
| 8000:9088 | 8000:9089 | 8000:9094 | 8000:9095 | 8000:9096 | 8000:9097 |
| 8001:9088 | 8001:9089 | 8001:9094 | 8001:9095 | 8001:9096 | 8001:9097 |
| 8002:9088 | 8002:9089 | 8002:9094 | 8002:9095 | 8002:9096 | 8002:9097 |
| 8003:9088 | 8003:9089 | 8003:9094 | 8003:9095 | 8003:9096 | 8003:9097 |
| 8004:9088 | 8004:9089 | 8004:9094 | 8004:9095 | 8004:9096 | 8004:9097 |
| 8005:9088 | 8005:9089 | 8005:9094 | 8005:9095 | 8005:9096 | 8005:9097 |
| 8006:9088 | 8006:9089 | 8006:9094 | 8006:9095 | 8006:9096 | 8006:9097 |
| 8007:9088 | 8007:9089 | 8007:9094 | 8007:9095 | 8007:9096 | 8007:9097 |
| 8008:9088 | 8008:9089 | 8008:9094 | 8008:9095 | 8008:9096 | 8008:9097 |
| 8009:9088 | 8009:9089 | 8009:9094 | 8009:9095 | 8009:9096 | 8009:9097 |
| 8010:9088 | 8010:9089 | 8010:9094 | 8010:9095 | 8010:9096 | 8010:9097 |
| 8011:9088 | 8011:9089 | 8011:9094 | 8011:9095 | 8011:9096 | 8011:9097 |
| 8012:9088 | 8012:9089 | 8012:9094 | 8012:9095 | 8012:9096 | 8012:9097 |
| 8013:9088 | 8013:9089 | 8013:9094 | 8013:9095 | 8013:9096 | 8013:9097 |
| 8014:9088 | 8014:9089 | 8014:9094 | 8014:9095 | 8014:9096 | 8014:9097 |
| 8015:9088 | 8015:9089 | 8015:9094 | 8015:9095 | 8015:9096 | 8015:9097 |
| 8016:9088 | 8016:9089 | 8016:9094 | 8016:9095 | 8016:9096 | 8016:9097 |
| 8000:9098 | 8000:9099 | 8000:9100 | 8000:9101 | 8000:9102 | 8000:9103 |
| 8001:9098 | 8001:9099 | 8001:9100 | 8001:9101 | 8001:9102 | 8001:9103 |
| 8002:9098 | 8002:9099 | 8002:9100 | 8002:9101 | 8002:9102 | 8002:9103 |
| 8003:9098 | 8003:9099 | 8003:9100 | 8003:9101 | 8003:9102 | 8003:9103 |
| 8004:9098 | 8004:9099 | 8004:9100 | 8004:9101 | 8004:9102 | 8004:9103 |
| 8005:9098 | 8005:9099 | 8005:9100 | 8005:9101 | 8005:9102 | 8005:9103 |
| 8006:9098 | 8006:9099 | 8006:9100 | 8006:9101 | 8006:9102 | 8006:9103 |
| 8007:9098 | 8007:9099 | 8007:9100 | 8007:9101 | 8007:9102 | 8007:9103 |
| 8008:9098 | 8008:9099 | 8008:9100 | 8008:9101 | 8008:9102 | 8008:9103 |
| 8009:9098 | 8009:9099 | 8009:9100 | 8009:9101 | 8009:9102 | 8009:9103 |
| 8010:9098 | 8010:9099 | 8010:9100 | 8010:9101 | 8010:9102 | 8010:9103 |
| 8011:9098 | 8011:9099 | 8011:9100 | 8011:9101 | 8011:9102 | 8011:9103 |
| 8012:9098 | 8012:9099 | 8012:9100 | 8012:9101 | 8012:9102 | 8012:9103 |
| 8013:9098 | 8013:9099 | 8013:9100 | 8013:9101 | 8013:9102 | 8013:9103 |
| 8014:9098 | 8014:9099 | 8014:9100 | 8014:9101 | 8014:9102 | 8014:9103 |
| 8015:9098 | 8015:9099 | 8015:9100 | 8015:9101 | 8015:9102 | 8015:9103 |
| 8016:9098 | 8016:9099 | 8016:9100 | 8016:9101 | 8016:9102 | 8016:9103 |
| 8000:9104 | 8000:9105 | 8000:9106 | 8000:9107 | 8000:9108 | 8000:9109 |
| 8001:9104 | 8001:9105 | 8001:9106 | 8001:9107 | 8001:9108 | 8001:9109 |
| 8002:9104 | 8002:9105 | 8002:9106 | 8002:9107 | 8002:9108 | 8002:9109 |
| 8003:9104 | 8003:9105 | 8003:9106 | 8003:9107 | 8003:9108 | 8003:9109 |
| 8004:9104 | 8004:9105 | 8004:9106 | 8004:9107 | 8004:9108 | 8004:9109 |
| 8005:9104 | 8005:9105 | 8005:9106 | 8005:9107 | 8005:9108 | 8005:9109 |
| 8006:9104 | 8006:9105 | 8006:9106 | 8006:9107 | 8006:9108 | 8006:9109 |
| 8007:9104 | 8007:9105 | 8007:9106 | 8007:9107 | 8007:9108 | 8007:9109 |
| 8008:9104 | 8008:9105 | 8008:9106 | 8008:9107 | 8008:9108 | 8008:9109 |
| 8009:9104 | 8009:9105 | 8009:9106 | 8009:9107 | 8009:9108 | 8009:9109 |
| 8010:9104 | 8010:9105 | 8010:9106 | 8010:9107 | 8010:9108 | 8010:9109 |
| 8011:9104 | 8011:9105 | 8011:9106 | 8011:9107 | 8011:9108 | 8011:9109 |
| 8012:9104 | 8012:9105 | 8012:9106 | 8012:9107 | 8012:9108 | 8012:9109 |
| 8013:9104 | 8013:9105 | 8013:9106 | 8013:9107 | 8013:9108 | 8013:9109 |
| 8014:9104 | 8014:9105 | 8014:9106 | 8014:9107 | 8014:9108 | 8014:9109 |
| 8015:9104 | 8015:9105 | 8015:9106 | 8015:9107 | 8015:9108 | 8015:9109 |
| 8016:9104 | 8016:9105 | 8016:9106 | 8016:9107 | 8016:9108 | 8016:9109 |
| 8000:9110 | 8000:9111 | 8000:9129 | 8000:9130 | 8000:9131 | 8000:9132 |
| 8001:9110 | 8001:9111 | 8001:9129 | 8001:9130 | 8001:9131 | 8001:9132 |
| 8002:9110 | 8002:9111 | 8002:9129 | 8002:9130 | 8002:9131 | 8002:9132 |
| 8003:9110 | 8003:9111 | 8003:9129 | 8003:9130 | 8003:9131 | 8003:9132 |
| 8004:9110 | 8004:9111 | 8004:9129 | 8004:9130 | 8004:9131 | 8004:9132 |
| 8005:9110 | 8005:9111 | 8005:9129 | 8005:9130 | 8005:9131 | 8005:9132 |
| 8006:9110 | 8006:9111 | 8006:9129 | 8006:9130 | 8006:9131 | 8006:9132 |
| 8007:9110 | 8007:9111 | 8007:9129 | 8007:9130 | 8007:9131 | 8007:9132 |
| 8008:9110 | 8008:9111 | 8008:9129 | 8008:9130 | 8008:9131 | 8008:9132 |
| 8009:9110 | 8009:9111 | 8009:9129 | 8009:9130 | 8009:9131 | 8009:9132 |
| 8010:9110 | 8010:9111 | 8010:9129 | 8010:9130 | 8010:9131 | 8010:9132 |
| 8011:9110 | 8011:9111 | 8011:9129 | 8011:9130 | 8011:9131 | 8011:9132 |
| 8012:9110 | 8012:9111 | 8012:9129 | 8012:9130 | 8012:9131 | 8012:9132 |
| 8013:9110 | 8013:9111 | 8013:9129 | 8013:9130 | 8013:9131 | 8013:9132 |
| 8014:9110 | 8014:9111 | 8014:9129 | 8014:9130 | 8014:9131 | 8014:9132 |
| 8015:9110 | 8015:9111 | 8015:9129 | 8015:9130 | 8015:9131 | 8015:9132 |
| 8016:9110 | 8016:9111 | 8016:9129 | 8016:9130 | 8016:9131 | 8016:9132 |
| 8000:9133 | 8000:9134 | 8000:9135 | 8000:9136 | 8000:9137 | 8000:9138 |
| 8001:9133 | 8001:9134 | 8001:9135 | 8001:9136 | 8001:9137 | 8001:9138 |
| 8002:9133 | 8002:9134 | 8002:9135 | 8002:9136 | 8002:9137 | 8002:9138 |
| 8003:9133 | 8003:9134 | 8003:9135 | 8003:9136 | 8003:9137 | 8003:9138 |
| 8004:9133 | 8004:9134 | 8004:9135 | 8004:9136 | 8004:9137 | 8004:9138 |
| 8005:9133 | 8005:9134 | 8005:9135 | 8005:9136 | 8005:9137 | 8005:9138 |
| 8006:9133 | 8006:9134 | 8006:9135 | 8006:9136 | 8006:9137 | 8006:9138 |
| 8007:9133 | 8007:9134 | 8007:9135 | 8007:9136 | 8007:9137 | 8007:9138 |
| 8008:9133 | 8008:9134 | 8008:9135 | 8008:9136 | 8008:9137 | 8008:9138 |
| 8009:9133 | 8009:9134 | 8009:9135 | 8009:9136 | 8009:9137 | 8009:9138 |
| 8010:9133 | 8010:9134 | 8010:9135 | 8010:9136 | 8010:9137 | 8010:9138 |
| 8011:9133 | 8011:9134 | 8011:9135 | 8011:9136 | 8011:9137 | 8011:9138 |
| 8012:9133 | 8012:9134 | 8012:9135 | 8012:9136 | 8012:9137 | 8012:9138 |
| 8013:9133 | 8013:9134 | 8013:9135 | 8013:9136 | 8013:9137 | 8013:9138 |
| 8014:9133 | 8014:9134 | 8014:9135 | 8014:9136 | 8014:9137 | 8014:9138 |
| 8015:9133 | 8015:9134 | 8015:9135 | 8015:9136 | 8015:9137 | 8015:9138 |
| 8016:9133 | 8016:9134 | 8016:9135 | 8016:9136 | 8016:9137 | 8016:9138 |
| 8000:9139 | 8000:9140 | 8000:9141 | 8000:9142 | 8000:9143 | 8000:9144 |
| 8001:9139 | 8001:9140 | 8001:9141 | 8001:9142 | 8001:9143 | 8001:9144 |
| 8002:9139 | 8002:9140 | 8002:9141 | 8002:9142 | 8002:9143 | 8002:9144 |
| 8003:9139 | 8003:9140 | 8003:9141 | 8003:9142 | 8003:9143 | 8003:9144 |
| 8004:9139 | 8004:9140 | 8004:9141 | 8004:9142 | 8004:9143 | 8004:9144 |
| 8005:9139 | 8005:9140 | 8005:9141 | 8005:9142 | 8005:9143 | 8005:9144 |
| 8006:9139 | 8006:9140 | 8006:9141 | 8006:9142 | 8006:9143 | 8006:9144 |
| 8007:9139 | 8007:9140 | 8007:9141 | 8007:9142 | 8007:9143 | 8007:9144 |
| 8008:9139 | 8008:9140 | 8008:9141 | 8008:9142 | 8008:9143 | 8008:9144 |
| 8009:9139 | 8009:9140 | 8009:9141 | 8009:9142 | 8009:9143 | 8009:9144 |
| 8010:9139 | 8010:9140 | 8010:9141 | 8010:9142 | 8010:9143 | 8010:9144 |
| 8011:9139 | 8011:9140 | 8011:9141 | 8011:9142 | 8011:9143 | 8011:9144 |
| 8012:9139 | 8012:9140 | 8012:9141 | 8012:9142 | 8012:9143 | 8012:9144 |
| 8013:9139 | 8013:9140 | 8013:9141 | 8013:9142 | 8013:9143 | 8013:9144 |
| 8014:9139 | 8014:9140 | 8014:9141 | 8014:9142 | 8014:9143 | 8014:9144 |
| 8015:9139 | 8015:9140 | 8015:9141 | 8015:9142 | 8015:9143 | 8015:9144 |
| 8016:9139 | 8016:9140 | 8016:9141 | 8016:9142 | 8016:9143 | 8016:9144 |
| 8000:9145 | 8000:9146 | 8000:9147 | 8000:9148 | 8000:9149 | 8000:9150 |
| 8001:9145 | 8001:9146 | 8001:9147 | 8001:9148 | 8001:9149 | 8001:9150 |
| 8002:9145 | 8002:9146 | 8002:9147 | 8002:9148 | 8002:9149 | 8002:9150 |
| 8003:9145 | 8003:9146 | 8003:9147 | 8003:9148 | 8003:9149 | 8003:9150 |
| 8004:9145 | 8004:9146 | 8004:9147 | 8004:9148 | 8004:9149 | 8004:9150 |
| 8005:9145 | 8005:9146 | 8005:9147 | 8005:9148 | 8005:9149 | 8005:9150 |
| 8006:9145 | 8006:9146 | 8006:9147 | 8006:9148 | 8006:9149 | 8006:9150 |
| 8007:9145 | 8007:9146 | 8007:9147 | 8007:9148 | 8007:9149 | 8007:9150 |
| 8008:9145 | 8008:9146 | 8008:9147 | 8008:9148 | 8008:9149 | 8008:9150 |
| 8009:9145 | 8009:9146 | 8009:9147 | 8009:9148 | 8009:9149 | 8009:9150 |
| 8010:9145 | 8010:9146 | 8010:9147 | 8010:9148 | 8010:9149 | 8010:9150 |
| 8011:9145 | 8011:9146 | 8011:9147 | 8011:9148 | 8011:9149 | 8011:9150 |
| 8012:9145 | 8012:9146 | 8012:9147 | 8012:9148 | 8012:9149 | 8012:9150 |
| 8013:9145 | 8013:9146 | 8013:9147 | 8013:9148 | 8013:9149 | 8013:9150 |
| 8014:9145 | 8014:9146 | 8014:9147 | 8014:9148 | 8014:9149 | 8014:9150 |
| 8015:9145 | 8015:9146 | 8015:9147 | 8015:9148 | 8015:9149 | 8015:9150 |
| 8016:9145 | 8016:9146 | 8016:9147 | 8016:9148 | 8016:9149 | 8016:9150 |
| 8000:9161 | 8000:9162 | 8000:9163 | 8000:9164 | 8000:9167 | 8000:9168 |
| 8001:9161 | 8001:9162 | 8001:9163 | 8001:9164 | 8001:9167 | 8001:9168 |
| 8002:9161 | 8002:9162 | 8002:9163 | 8002:9164 | 8002:9167 | 8002:9168 |
| 8003:9161 | 8003:9162 | 8003:9163 | 8003:9164 | 8003:9167 | 8003:9168 |
| 8004:9161 | 8004:9162 | 8004:9163 | 8004:9164 | 8004:9167 | 8004:9168 |
| 8005:9161 | 8005:9162 | 8005:9163 | 8005:9164 | 8005:9167 | 8005:9168 |
| 8006:9161 | 8006:9162 | 8006:9163 | 8006:9164 | 8006:9167 | 8006:9168 |
| 8007:9161 | 8007:9162 | 8007:9163 | 8007:9164 | 8007:9167 | 8007:9168 |
| 8008:9161 | 8008:9162 | 8008:9163 | 8008:9164 | 8008:9167 | 8008:9168 |
| 8009:9161 | 8009:9162 | 8009:9163 | 8009:9164 | 8009:9167 | 8009:9168 |
| 8010:9161 | 8010:9162 | 8010:9163 | 8010:9164 | 8010:9167 | 8010:9168 |
| 8011:9161 | 8011:9162 | 8011:9163 | 8011:9164 | 8011:9167 | 8011:9168 |
| 8012:9161 | 8012:9162 | 8012:9163 | 8012:9164 | 8012:9167 | 8012:9168 |
| 8013:9161 | 8013:9162 | 8013:9163 | 8013:9164 | 8013:9167 | 8013:9168 |
| 8014:9161 | 8014:9162 | 8014:9163 | 8014:9164 | 8014:9167 | 8014:9168 |
| 8015:9161 | 8015:9162 | 8015:9163 | 8015:9164 | 8015:9167 | 8015:9168 |
| 8016:9161 | 8016:9162 | 8016:9163 | 8016:9164 | 8016:9167 | 8016:9168 |
| 8000:9169 | 8000:9170 | 8000:9171 | 8000:9172 | 8000:9173 | 8000:9174 |
| 8001:9169 | 8001:9170 | 8001:9171 | 8001:9172 | 8001:9173 | 8001:9174 |
| 8002:9169 | 8002:9170 | 8002:9171 | 8002:9172 | 8002:9173 | 8002:9174 |
| 8003:9169 | 8003:9170 | 8003:9171 | 8003:9172 | 8003:9173 | 8003:9174 |
| 8004:9169 | 8004:9170 | 8004:9171 | 8004:9172 | 8004:9173 | 8004:9174 |
| 8005:9169 | 8005:9170 | 8005:9171 | 8005:9172 | 8005:9173 | 8005:9174 |
| 8006:9169 | 8006:9170 | 8006:9171 | 8006:9172 | 8006:9173 | 8006:9174 |
| 8007:9169 | 8007:9170 | 8007:9171 | 8007:9172 | 8007:9173 | 8007:9174 |
| 8008:9169 | 8008:9170 | 8008:9171 | 8008:9172 | 8008:9173 | 8008:9174 |
| 8009:9169 | 8009:9170 | 8009:9171 | 8009:9172 | 8009:9173 | 8009:9174 |
| 8010:9169 | 8010:9170 | 8010:9171 | 8010:9172 | 8010:9173 | 8010:9174 |
| 8011:9169 | 8011:9170 | 8011:9171 | 8011:9172 | 8011:9173 | 8011:9174 |
| 8012:9169 | 8012:9170 | 8012:9171 | 8012:9172 | 8012:9173 | 8012:9174 |
| 8013:9169 | 8013:9170 | 8013:9171 | 8013:9172 | 8013:9173 | 8013:9174 |
| 8014:9169 | 8014:9170 | 8014:9171 | 8014:9172 | 8014:9173 | 8014:9174 |

TABLE E-continued

Example combinations of a compound X with a compound Y.

| X:Y | X:Y | X:Y | X:Y | X:Y | X:Y |
|---|---|---|---|---|---|
| 8015:9169 | 8015:9170 | 8015:9171 | 8015:9172 | 8015:9173 | 8015:9174 |
| 8016:9169 | 8016:9170 | 8016:9171 | 8016:9172 | 8016:9173 | 8016:9174 |
| 8000:9175 | 8000:9176 | 8000:9177 | 8000:9178 | 8000:9179 | 8000:9180 |
| 8001:9175 | 8001:9176 | 8001:9177 | 8001:9178 | 8001:9179 | 8001:9180 |
| 8002:9175 | 8002:9176 | 8002:9177 | 8002:9178 | 8002:9179 | 8002:9180 |
| 8003:9175 | 8003:9176 | 8003:9177 | 8003:9178 | 8003:9179 | 8003:9180 |
| 8004:9175 | 8004:9176 | 8004:9177 | 8004:9178 | 8004:9179 | 8004:9180 |
| 8005:9175 | 8005:9176 | 8005:9177 | 8005:9178 | 8005:9179 | 8005:9180 |
| 8006:9175 | 8006:9176 | 8006:9177 | 8006:9178 | 8006:9179 | 8006:9180 |
| 8007:9175 | 8007:9176 | 8007:9177 | 8007:9178 | 8007:9179 | 8007:9180 |
| 8008:9175 | 8008:9176 | 8008:9177 | 8008:9178 | 8008:9179 | 8008:9180 |
| 8009:9175 | 8009:9176 | 8009:9177 | 8009:9178 | 8009:9179 | 8009:9180 |
| 8010:9175 | 8010:9176 | 8010:9177 | 8010:9178 | 8010:9179 | 8010:9180 |
| 8011:9175 | 8011:9176 | 8011:9177 | 8011:9178 | 8011:9179 | 8011:9180 |
| 8012:9175 | 8012:9176 | 8012:9177 | 8012:9178 | 8012:9179 | 8012:9180 |
| 8013:9175 | 8013:9176 | 8013:9177 | 8013:9178 | 8013:9179 | 8013:9180 |
| 8014:9175 | 8014:9176 | 8014:9177 | 8014:9178 | 8014:9179 | 8014:9180 |
| 8015:9175 | 8015:9176 | 8015:9177 | 8015:9178 | 8015:9179 | 8015:9180 |
| 8016:9175 | 8016:9176 | 8016:9177 | 8016:9178 | 8016:9179 | 8016:9180 |
| 8000:9181 | 8000:9182 | 8000:9183 | 8000:9184 | 8000:9185 | 8000:9206 |
| 8001:9181 | 8001:9182 | 8001:9183 | 8001:9184 | 8001:9185 | 8001:9206 |
| 8002:9181 | 8002:9182 | 8002:9183 | 8002:9184 | 8002:9185 | 8002:9206 |
| 8003:9181 | 8003:9182 | 8003:9183 | 8003:9184 | 8003:9185 | 8003:9206 |
| 8004:9181 | 8004:9182 | 8004:9183 | 8004:9184 | 8004:9185 | 8004:9206 |
| 8005:9181 | 8005:9182 | 8005:9183 | 8005:9184 | 8005:9185 | 8005:9206 |
| 8006:9181 | 8006:9182 | 8006:9183 | 8006:9184 | 8006:9185 | 8006:9206 |
| 8007:9181 | 8007:9182 | 8007:9183 | 8007:9184 | 8007:9185 | 8007:9206 |
| 8008:9181 | 8008:9182 | 8008:9183 | 8008:9184 | 8008:9185 | 8008:9206 |
| 8009:9181 | 8009:9182 | 8009:9183 | 8009:9184 | 8009:9185 | 8009:9206 |
| 8010:9181 | 8010:9182 | 8010:9183 | 8010:9184 | 8010:9185 | 8010:9206 |
| 8011:9181 | 8011:9182 | 8011:9183 | 8011:9184 | 8011:9185 | 8011:9206 |
| 8012:9181 | 8012:9182 | 8012:9183 | 8012:9184 | 8012:9185 | 8012:9206 |
| 8013:9181 | 8013:9182 | 8013:9183 | 8013:9184 | 8013:9185 | 8013:9206 |
| 8014:9181 | 8014:9182 | 8014:9183 | 8014:9184 | 8014:9185 | 8014:9206 |
| 8015:9181 | 8015:9182 | 8015:9183 | 8015:9184 | 8015:9185 | 8015:9206 |
| 8016:9181 | 8016:9182 | 8016:9183 | 8016:9184 | 8016:9185 | 8016:9206 |
| 8000:9207 | 8000:9208 | 8000:9209 | 8000:9214 | 8000:9241 | 8000:9242 |
| 8001:9207 | 8001:9208 | 8001:9209 | 8001:9214 | 8001:9241 | 8001:9242 |
| 8002:9207 | 8002:9208 | 8002:9209 | 8002:9214 | 8002:9241 | 8002:9242 |
| 8003:9207 | 8003:9208 | 8003:9209 | 8003:9214 | 8003:9241 | 8003:9242 |
| 8004:9207 | 8004:9208 | 8004:9209 | 8004:9214 | 8004:9241 | 8004:9242 |
| 8005:9207 | 8005:9208 | 8005:9209 | 8005:9214 | 8005:9241 | 8005:9242 |
| 8006:9207 | 8006:9208 | 8006:9209 | 8006:9214 | 8006:9241 | 8006:9242 |
| 8007:9207 | 8007:9208 | 8007:9209 | 8007:9214 | 8007:9241 | 8007:9242 |
| 8008:9207 | 8008:9208 | 8008:9209 | 8008:9214 | 8008:9241 | 8008:9242 |
| 8009:9207 | 8009:9208 | 8009:9209 | 8009:9214 | 8009:9241 | 8009:9242 |
| 8010:9207 | 8010:9208 | 8010:9209 | 8010:9214 | 8010:9241 | 8010:9242 |
| 8011:9207 | 8011:9208 | 8011:9209 | 8011:9214 | 8011:9241 | 8011:9242 |
| 8012:9207 | 8012:9208 | 8012:9209 | 8012:9214 | 8012:9241 | 8012:9242 |
| 8013:9207 | 8013:9208 | 8013:9209 | 8013:9214 | 8013:9241 | 8013:9242 |
| 8014:9207 | 8014:9208 | 8014:9209 | 8014:9214 | 8014:9241 | 8014:9242 |
| 8015:9207 | 8015:9208 | 8015:9209 | 8015:9214 | 8015:9241 | 8015:9242 |
| 8016:9207 | 8016:9208 | 8016:9209 | 8016:9214 | 8016:9241 | 8016:9242 |
| 8000:9244 | 8000:9245 | 8000:9246 | 8000:9247 | 8000:9248 | 8000:9249 |
| 8001:9244 | 8001:9245 | 8001:9246 | 8001:9247 | 8001:9248 | 8001:9249 |
| 8002:9244 | 8002:9245 | 8002:9246 | 8002:9247 | 8002:9248 | 8002:9249 |
| 8003:9244 | 8003:9245 | 8003:9246 | 8003:9247 | 8003:9248 | 8003:9249 |
| 8004:9244 | 8004:9245 | 8004:9246 | 8004:9247 | 8004:9248 | 8004:9249 |
| 8005:9244 | 8005:9245 | 8005:9246 | 8005:9247 | 8005:9248 | 8005:9249 |
| 8006:9244 | 8006:9245 | 8006:9246 | 8006:9247 | 8006:9248 | 8006:9249 |
| 8007:9244 | 8007:9245 | 8007:9246 | 8007:9247 | 8007:9248 | 8007:9249 |
| 8008:9244 | 8008:9245 | 8008:9246 | 8008:9247 | 8008:9248 | 8008:9249 |
| 8009:9244 | 8009:9245 | 8009:9246 | 8009:9247 | 8009:9248 | 8009:9249 |
| 8010:9244 | 8010:9245 | 8010:9246 | 8010:9247 | 8010:9248 | 8010:9249 |
| 8011:9244 | 8011:9245 | 8011:9246 | 8011:9247 | 8011:9248 | 8011:9249 |
| 8012:9244 | 8012:9245 | 8012:9246 | 8012:9247 | 8012:9248 | 8012:9249 |
| 8013:9244 | 8013:9245 | 8013:9246 | 8013:9247 | 8013:9248 | 8013:9249 |
| 8014:9244 | 8014:9245 | 8014:9246 | 8014:9247 | 8014:9248 | 8014:9249 |
| 8015:9244 | 8015:9245 | 8015:9246 | 8015:9247 | 8015:9248 | 8015:9249 |
| 8016:9244 | 8016:9245 | 8016:9246 | 8016:9247 | 8016:9248 | 8016:9249 |
| 8000:9250 | 8000:9251 | 8000:9252 | 8000:9253 | 8000:9255 | 8000:9256 |
| 8001:9250 | 8001:9251 | 8001:9252 | 8001:9253 | 8001:9255 | 8001:9256 |
| 8002:9250 | 8002:9251 | 8002:9252 | 8002:9253 | 8002:9255 | 8002:9256 |
| 8003:9250 | 8003:9251 | 8003:9252 | 8003:9253 | 8003:9255 | 8003:9256 |
| 8004:9250 | 8004:9251 | 8004:9252 | 8004:9253 | 8004:9255 | 8004:9256 |
| 8005:9250 | 8005:9251 | 8005:9252 | 8005:9253 | 8005:9255 | 8005:9256 |
| 8006:9250 | 8006:9251 | 8006:9252 | 8006:9253 | 8006:9255 | 8006:9256 |
| 8007:9250 | 8007:9251 | 8007:9252 | 8007:9253 | 8007:9255 | 8007:9256 |
| 8008:9250 | 8008:9251 | 8008:9252 | 8008:9253 | 8008:9255 | 8008:9256 |
| 8009:9250 | 8009:9251 | 8009:9252 | 8009:9253 | 8009:9255 | 8009:9256 |
| 8010:9250 | 8010:9251 | 8010:9252 | 8010:9253 | 8010:9255 | 8010:9256 |
| 8011:9250 | 8011:9251 | 8011:9252 | 8011:9253 | 8011:9255 | 8011:9256 |
| 8012:9250 | 8012:9251 | 8012:9252 | 8012:9253 | 8012:9255 | 8012:9256 |
| 8013:9250 | 8013:9251 | 8013:9252 | 8013:9253 | 8013:9255 | 8013:9256 |
| 8014:9250 | 8014:9251 | 8014:9252 | 8014:9253 | 8014:9255 | 8014:9256 |
| 8015:9250 | 8015:9251 | 8015:9252 | 8015:9253 | 8015:9255 | 8015:9256 |
| 8016:9250 | 8016:9251 | 8016:9252 | 8016:9253 | 8016:9255 | 8016:9256 |
| 8000:9257 | 8000:9258 | 8000:9259 | 8000:9260 | 8000:9262 | 8000:9263 |
| 8001:9257 | 8001:9258 | 8001:9259 | 8001:9260 | 8001:9262 | 8001:9263 |
| 8002:9257 | 8002:9258 | 8002:9259 | 8002:9260 | 8002:9262 | 8002:9263 |
| 8003:9257 | 8003:9258 | 8003:9259 | 8003:9260 | 8003:9262 | 8003:9263 |
| 8004:9257 | 8004:9258 | 8004:9259 | 8004:9260 | 8004:9262 | 8004:9263 |
| 8005:9257 | 8005:9258 | 8005:9259 | 8005:9260 | 8005:9262 | 8005:9263 |
| 8006:9257 | 8006:9258 | 8006:9259 | 8006:9260 | 8006:9262 | 8006:9263 |
| 8007:9257 | 8007:9258 | 8007:9259 | 8007:9260 | 8007:9262 | 8007:9263 |
| 8008:9257 | 8008:9258 | 8008:9259 | 8008:9260 | 8008:9262 | 8008:9263 |
| 8009:9257 | 8009:9258 | 8009:9259 | 8009:9260 | 8009:9262 | 8009:9263 |
| 8010:9257 | 8010:9258 | 8010:9259 | 8010:9260 | 8010:9262 | 8010:9263 |
| 8011:9257 | 8011:9258 | 8011:9259 | 8011:9260 | 8011:9262 | 8011:9263 |
| 8012:9257 | 8012:9258 | 8012:9259 | 8012:9260 | 8012:9262 | 8012:9263 |
| 8013:9257 | 8013:9258 | 8013:9259 | 8013:9260 | 8013:9262 | 8013:9263 |
| 8014:9257 | 8014:9258 | 8014:9259 | 8014:9260 | 8014:9262 | 8014:9263 |
| 8015:9257 | 8015:9258 | 8015:9259 | 8015:9260 | 8015:9262 | 8015:9263 |
| 8016:9257 | 8016:9258 | 8016:9259 | 8016:9260 | 8016:9262 | 8016:9263 |
| 8000:9264 | 8000:9265 | 8000:9266 | 8000:9267 | 8000:9268 | 8000:9269 |
| 8001:9264 | 8001:9265 | 8001:9266 | 8001:9267 | 8001:9268 | 8001:9269 |
| 8002:9264 | 8002:9265 | 8002:9266 | 8002:9267 | 8002:9268 | 8002:9269 |
| 8003:9264 | 8003:9265 | 8003:9266 | 8003:9267 | 8003:9268 | 8003:9269 |
| 8004:9264 | 8004:9265 | 8004:9266 | 8004:9267 | 8004:9268 | 8004:9269 |
| 8005:9264 | 8005:9265 | 8005:9266 | 8005:9267 | 8005:9268 | 8005:9269 |
| 8006:9264 | 8006:9265 | 8006:9266 | 8006:9267 | 8006:9268 | 8006:9269 |
| 8007:9264 | 8007:9265 | 8007:9266 | 8007:9267 | 8007:9268 | 8007:9269 |
| 8008:9264 | 8008:9265 | 8008:9266 | 8008:9267 | 8008:9268 | 8008:9269 |
| 8009:9264 | 8009:9265 | 8009:9266 | 8009:9267 | 8009:9268 | 8009:9269 |
| 8010:9264 | 8010:9265 | 8010:9266 | 8010:9267 | 8010:9268 | 8010:9269 |
| 8011:9264 | 8011:9265 | 8011:9266 | 8011:9267 | 8011:9268 | 8011:9269 |
| 8012:9264 | 8012:9265 | 8012:9266 | 8012:9267 | 8012:9268 | 8012:9269 |
| 8013:9264 | 8013:9265 | 8013:9266 | 8013:9267 | 8013:9268 | 8013:9269 |
| 8014:9264 | 8014:9265 | 8014:9266 | 8014:9267 | 8014:9268 | 8014:9269 |
| 8015:9264 | 8015:9265 | 8015:9266 | 8015:9267 | 8015:9268 | 8015:9269 |
| 8016:9264 | 8016:9265 | 8016:9266 | 8016:9267 | 8016:9268 | 8016:9269 |
| 8000:9270 | 8000:9271 | 8000:9272 | 8000:9273 | 8000:9274 | 8000:9275 |
| 8001:9270 | 8001:9271 | 8001:9272 | 8001:9273 | 8001:9274 | 8001:9275 |
| 8002:9270 | 8002:9271 | 8002:9272 | 8002:9273 | 8002:9274 | 8002:9275 |
| 8003:9270 | 8003:9271 | 8003:9272 | 8003:9273 | 8003:9274 | 8003:9275 |
| 8004:9270 | 8004:9271 | 8004:9272 | 8004:9273 | 8004:9274 | 8004:9275 |
| 8005:9270 | 8005:9271 | 8005:9272 | 8005:9273 | 8005:9274 | 8005:9275 |
| 8006:9270 | 8006:9271 | 8006:9272 | 8006:9273 | 8006:9274 | 8006:9275 |
| 8007:9270 | 8007:9271 | 8007:9272 | 8007:9273 | 8007:9274 | 8007:9275 |
| 8008:9270 | 8008:9271 | 8008:9272 | 8008:9273 | 8008:9274 | 8008:9275 |
| 8009:9270 | 8009:9271 | 8009:9272 | 8009:9273 | 8009:9274 | 8009:9275 |
| 8010:9270 | 8010:9271 | 8010:9272 | 8010:9273 | 8010:9274 | 8010:9275 |
| 8011:9270 | 8011:9271 | 8011:9272 | 8011:9273 | 8011:9274 | 8011:9275 |
| 8012:9270 | 8012:9271 | 8012:9272 | 8012:9273 | 8012:9274 | 8012:9275 |
| 8013:9270 | 8013:9271 | 8013:9272 | 8013:9273 | 8013:9274 | 8013:9275 |
| 8014:9270 | 8014:9271 | 8014:9272 | 8014:9273 | 8014:9274 | 8014:9275 |
| 8015:9270 | 8015:9271 | 8015:9272 | 8015:9273 | 8015:9274 | 8015:9275 |
| 8016:9270 | 8016:9271 | 8016:9272 | 8016:9273 | 8016:9274 | 8016:9275 |
| 8000:9277 | 8000:9278 | 8000:9279 | 8000:9280 | 8000:9281 |  |
| 8001:9276 | 8001:9277 | 8001:9278 | 8001:9279 | 8001:9280 | 8001:9281 |
| 8002:9276 | 8002:9277 | 8002:9278 | 8002:9279 | 8002:9280 | 8002:9281 |
| 8003:9276 | 8003:9277 | 8003:9278 | 8003:9279 | 8003:9280 | 8003:9281 |
| 8004:9276 | 8004:9277 | 8004:9278 | 8004:9279 | 8004:9280 | 8004:9281 |
| 8005:9276 | 8005:9277 | 8005:9278 | 8005:9279 | 8005:9280 | 8005:9281 |
| 8006:9276 | 8006:9277 | 8006:9278 | 8006:9279 | 8006:9280 | 8006:9281 |
| 8007:9276 | 8007:9277 | 8007:9278 | 8007:9279 | 8007:9280 | 8007:9281 |
| 8008:9276 | 8008:9277 | 8008:9278 | 8008:9279 | 8008:9280 | 8008:9281 |
| 8009:9276 | 8009:9277 | 8009:9278 | 8009:9279 | 8009:9280 | 8009:9281 |
| 8010:9276 | 8010:9277 | 8010:9278 | 8010:9279 | 8010:9280 | 8010:9281 |
| 8011:9276 | 8011:9277 | 8011:9278 | 8011:9279 | 8011:9280 | 8011:9281 |
| 8012:9276 | 8012:9277 | 8012:9278 | 8012:9279 | 8012:9280 | 8012:9281 |
| 8013:9276 | 8013:9277 | 8013:9278 | 8013:9279 | 8013:9280 | 8013:9281 |

TABLE E-continued

Example combinations of a compound X with a compound Y.

| X:Y | X:Y | X:Y | X:Y | X:Y | X:Y |
|---|---|---|---|---|---|
| 8014:9276 | 8014:9277 | 8014:9278 | 8014:9279 | 8014:9280 | 8014:9281 |
| 8015:9276 | 8015:9277 | 8015:9278 | 8015:9279 | 8015:9280 | 8015:9281 |
| 8016:9276 | 8016:9277 | 8016:9278 | 8016:9279 | 8016:9280 | 8016:9281 |
| 8000:9282 | 8000:9283 | 8000:9284 | 8000:9285 | 8000:9286 | 8000:9287 |
| 8001:9282 | 8001:9283 | 8001:9284 | 8001:9285 | 8001:9286 | 8001:9287 |
| 8002:9282 | 8002:9283 | 8002:9284 | 8002:9285 | 8002:9286 | 8002:9287 |
| 8003:9282 | 8003:9283 | 8003:9284 | 8003:9285 | 8003:9286 | 8003:9287 |
| 8004:9282 | 8004:9283 | 8004:9284 | 8004:9285 | 8004:9286 | 8004:9287 |
| 8005:9282 | 8005:9283 | 8005:9284 | 8005:9285 | 8005:9286 | 8005:9287 |
| 8006:9282 | 8006:9283 | 8006:9284 | 8006:9285 | 8006:9286 | 8006:9287 |
| 8007:9282 | 8007:9283 | 8007:9284 | 8007:9285 | 8007:9286 | 8007:9287 |
| 8008:9282 | 8008:9283 | 8008:9284 | 8008:9285 | 8008:9286 | 8008:9287 |
| 8009:9282 | 8009:9283 | 8009:9284 | 8009:9285 | 8009:9286 | 8009:9287 |
| 8010:9282 | 8010:9283 | 8010:9284 | 8010:9285 | 8010:9286 | 8010:9287 |
| 8011:9282 | 8011:9283 | 8011:9284 | 8011:9285 | 8011:9286 | 8011:9287 |
| 8012:9282 | 8012:9283 | 8012:9284 | 8012:9285 | 8012:9286 | 8012:9287 |
| 8013:9282 | 8013:9283 | 8013:9284 | 8013:9285 | 8013:9286 | 8013:9287 |
| 8014:9282 | 8014:9283 | 8014:9284 | 8014:9285 | 8014:9286 | 8014:9287 |
| 8015:9282 | 8015:9283 | 8015:9284 | 8015:9285 | 8015:9286 | 8015:9287 |
| 8016:9282 | 8016:9283 | 8016:9284 | 8016:9285 | 8016:9286 | 8016:9287 |
| 8000:9288 | 8000:9289 | 8000:9290 | 8000:9291 | 8000:9292 | 8000:9293 |
| 8001:9288 | 8001:9289 | 8001:9290 | 8001:9291 | 8001:9292 | 8001:9293 |
| 8002:9288 | 8002:9289 | 8002:9290 | 8002:9291 | 8002:9292 | 8002:9293 |
| 8003:9288 | 8003:9289 | 8003:9290 | 8003:9291 | 8003:9292 | 8003:9293 |
| 8004:9288 | 8004:9289 | 8004:9290 | 8004:9291 | 8004:9292 | 8004:9293 |
| 8005:9288 | 8005:9289 | 8005:9290 | 8005:9291 | 8005:9292 | 8005:9293 |
| 8006:9288 | 8006:9289 | 8006:9290 | 8006:9291 | 8006:9292 | 8006:9293 |
| 8007:9288 | 8007:9289 | 8007:9290 | 8007:9291 | 8007:9292 | 8007:9293 |
| 8008:9288 | 8008:9289 | 8008:9290 | 8008:9291 | 8008:9292 | 8008:9293 |
| 8009:9288 | 8009:9289 | 8009:9290 | 8009:9291 | 8009:9292 | 8009:9293 |
| 8010:9288 | 8010:9289 | 8010:9290 | 8010:9291 | 8010:9292 | 8010:9293 |
| 8011:9288 | 8011:9289 | 8011:9290 | 8011:9291 | 8011:9292 | 8011:9293 |
| 8012:9288 | 8012:9289 | 8012:9290 | 8012:9291 | 8012:9292 | 8012:9293 |
| 8013:9288 | 8013:9289 | 8013:9290 | 8013:9291 | 8013:9292 | 8013:9293 |
| 8014:9288 | 8014:9289 | 8014:9290 | 8014:9291 | 8014:9292 | 8014:9293 |
| 8015:9288 | 8015:9289 | 8015:9290 | 8015:9291 | 8015:9292 | 8015:9293 |
| 8016:9288 | 8016:9289 | 8016:9290 | 8016:9291 | 8016:9292 | 8016:9293 |
| 8000:9294 | 8000:9295 | 8000:9296 | 8000:9297 | 8000:9298 | 8000:9299 |
| 8001:9294 | 8001:9295 | 8001:9296 | 8001:9297 | 8001:9298 | 8001:9299 |
| 8002:9294 | 8002:9295 | 8002:9296 | 8002:9297 | 8002:9298 | 8002:9299 |
| 8003:9294 | 8003:9295 | 8003:9296 | 8003:9297 | 8003:9298 | 8003:9299 |
| 8004:9294 | 8004:9295 | 8004:9296 | 8004:9297 | 8004:9298 | 8004:9299 |
| 8005:9294 | 8005:9295 | 8005:9296 | 8005:9297 | 8005:9298 | 8005:9299 |
| 8006:9294 | 8006:9295 | 8006:9296 | 8006:9297 | 8006:9298 | 8006:9299 |
| 8007:9294 | 8007:9295 | 8007:9296 | 8007:9297 | 8007:9298 | 8007:9299 |
| 8008:9294 | 8008:9295 | 8008:9296 | 8008:9297 | 8008:9298 | 8008:9299 |
| 8009:9294 | 8009:9295 | 8009:9296 | 8009:9297 | 8009:9298 | 8009:9299 |
| 8010:9294 | 8010:9295 | 8010:9296 | 8010:9297 | 8010:9298 | 8010:9299 |
| 8011:9294 | 8011:9295 | 8011:9296 | 8011:9297 | 8011:9298 | 8011:9299 |
| 8012:9294 | 8012:9295 | 8012:9296 | 8012:9297 | 8012:9298 | 8012:9299 |
| 8013:9294 | 8013:9295 | 8013:9296 | 8013:9297 | 8013:9298 | 8013:9299 |
| 8014:9294 | 8014:9295 | 8014:9296 | 8014:9297 | 8014:9298 | 8014:9299 |
| 8015:9294 | 8015:9295 | 8015:9296 | 8015:9297 | 8015:9298 | 8015:9299 |
| 8016:9294 | 8016:9295 | 8016:9296 | 8016:9297 | 8016:9298 | 8016:9299 |
| 8000:9300 | 8000:9301 | 8000:9302 | 8000:9303 | 8000:9304 | 8000:9305 |
| 8001:9300 | 8001:9301 | 8001:9302 | 8001:9303 | 8001:9304 | 8001:9305 |
| 8002:9300 | 8002:9301 | 8002:9302 | 8002:9303 | 8002:9304 | 8002:9305 |
| 8003:9300 | 8003:9301 | 8003:9302 | 8003:9303 | 8003:9304 | 8003:9305 |
| 8004:9300 | 8004:9301 | 8004:9302 | 8004:9303 | 8004:9304 | 8004:9305 |
| 8005:9300 | 8005:9301 | 8005:9302 | 8005:9303 | 8005:9304 | 8005:9305 |
| 8006:9300 | 8006:9301 | 8006:9302 | 8006:9303 | 8006:9304 | 8006:9305 |
| 8007:9300 | 8007:9301 | 8007:9302 | 8007:9303 | 8007:9304 | 8007:9305 |
| 8008:9300 | 8008:9301 | 8008:9302 | 8008:9303 | 8008:9304 | 8008:9305 |
| 8009:9300 | 8009:9301 | 8009:9302 | 8009:9303 | 8009:9304 | 8009:9305 |
| 8010:9300 | 8010:9301 | 8010:9302 | 8010:9303 | 8010:9304 | 8010:9305 |
| 8011:9300 | 8011:9301 | 8011:9302 | 8011:9303 | 8011:9304 | 8011:9305 |
| 8012:9300 | 8012:9301 | 8012:9302 | 8012:9303 | 8012:9304 | 8012:9305 |
| 8013:9300 | 8013:9301 | 8013:9302 | 8013:9303 | 8013:9304 | 8013:9305 |
| 8014:9300 | 8014:9301 | 8014:9302 | 8014:9303 | 8014:9304 | 8014:9305 |
| 8015:9300 | 8015:9301 | 8015:9302 | 8015:9303 | 8015:9304 | 8015:9305 |
| 8016:9300 | 8016:9301 | 8016:9302 | 8016:9303 | 8016:9304 | 8016:9305 |
| 8000:9306 | 8000:9307 | 8000:9308 | 8000:9309 | 8000:9310 | — |
| 8001:9306 | 8001:9307 | 8001:9308 | 8001:9309 | 8001:9310 | |
| 8002:9306 | 8002:9307 | 8002:9308 | 8002:9309 | 8002:9310 | |
| 8003:9306 | 8003:9307 | 8003:9308 | 8003:9309 | 8003:9310 | |
| 8004:9306 | 8004:9307 | 8004:9308 | 8004:9309 | 8004:9310 | |
| 8005:9306 | 8005:9307 | 8005:9308 | 8005:9309 | 8005:9310 | |
| 8006:9306 | 8006:9307 | 8006:9308 | 8006:9309 | 8006:9310 | |
| 8007:9306 | 8007:9307 | 8007:9308 | 8007:9309 | 8007:9310 | |
| 8008:9306 | 8008:9307 | 8008:9308 | 8008:9309 | 8008:9310 | |
| 8009:9306 | 8009:9307 | 8009:9308 | 8009:9309 | 8009:9310 | |
| 8010:9306 | 8010:9307 | 8010:9308 | 8010:9309 | 8010:9310 | |
| 8011:9306 | 8011:9307 | 8011:9308 | 8011:9309 | 8011:9310 | |
| 8012:9306 | 8012:9307 | 8012:9308 | 8012:9309 | 8012:9310 | |
| 8013:9306 | 8013:9307 | 8013:9308 | 8013:9309 | 8013:9310 | |
| 8014:9306 | 8014:9307 | 8014:9308 | 8014:9309 | 8014:9310 | |
| 8015:9306 | 8015:9307 | 8015:9308 | 8015:9309 | 8015:9310 | |
| 8016:9306 | 8016:9307 | 8016:9308 | 8016:9309 | 8016:9310 | |

Compounds

Some embodiments disclosed herein relate to a method and/or use of a compound of Formula (I), or a pharmaceutically acceptable salt thereof:

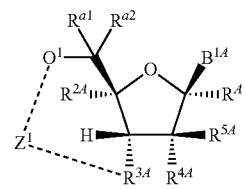

wherein: $B^{1A}$ can be an optionally substituted heterocyclic base or an optionally substituted heterocyclic base with a protected amino group; - - - - - - - - can be absent or a single bond, provided that both - - - - - - - - are absent or both - - - - - - - - are a single bond; when - - - - - - - - are both absent, then $Z^1$ can be absent, $O^1$ can be $OR^{1A}$, $R^{3A}$ can be selected from H, halo, OH, —OC(=O)R''$^A$ and an optionally substituted O-linked amino acid, $R^{4A}$ can be selected from H, OH, halo, $N_3$, —OC(=O)R''$^B$, an optionally substituted O-linked amino acid and NR''$^{B1}$R''$^{B2}$, or $R^{3A}$ and $R^{4A}$ can be both an oxygen atom connected via a carbonyl to form a 5-membered ring; when - - - - - - - - are each a single bond, then $Z^1$ can be

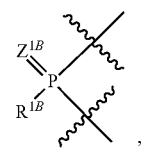

$O^1$ can be O, $R^{3A}$ can be O; $R^{4A}$ can be selected from H, OH, halo, $N_3$, —OC(=O)R''$^B$, an optionally substituted O-linked amino acid and NR''$^{B1}$R''$^{B2}$; and $R^{1B}$ can be selected from O$^-$, OH, an —O-optionally substituted $C_{1-6}$ alkyl.

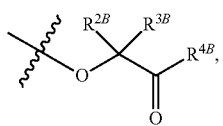

-continued

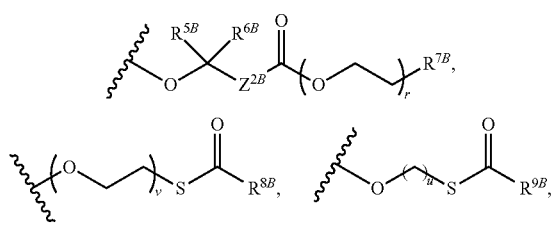

an optionally substituted N-linked amino acid and an optionally substituted N-linked amino acid ester derivative; $R^{a1}$ and $R^{a2}$ can be independently hydrogen or deuterium; $R^A$ can be hydrogen, deuterium, an unsubstituted $C_{1-3}$ alkyl, an unsubstituted $C_{2-4}$ alkenyl, an unsubstituted $C_{2-3}$ alkynyl or cyano; $R^{1A}$ can be selected from hydrogen, an optionally substituted acyl, an optionally substituted O-linked amino acid,

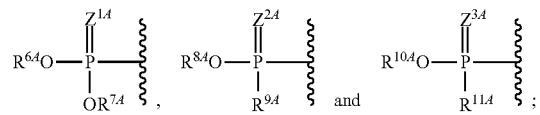

$R^{2A}$ can be hydrogen, halo, an unsubstituted $C_{1-4}$ alkyl, an unsubstituted $C_{2-4}$ alkenyl, an unsubstituted $C_{2-4}$ alkynyl, —$CHF_2$, —$(CH_2)_{1-6}$ halogen, —$(CH_2)_{1-6}N_3$, —$(CH_2)_{1-6}NH_2$ or —CN; $R^{5A}$ can be selected from H, halo, OH, an optionally substituted $C_{1-6}$ alkyl, an optionally substituted $C_{2-6}$ alkenyl and an optionally substituted $C_{2-6}$ alkynyl; $R^{6A}$, $R^{7A}$ and $R^{8A}$ can be independently selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—$(CR^{15A}R^{16A})_p$—O—$C_{1-24}$ alkyl, an optionally substituted *—$(CR^{17A}R^{18A})_q$—O—$C_{1-24}$ alkenyl,

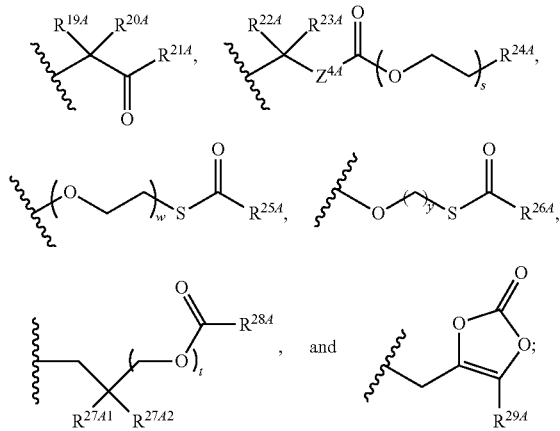

or $R^{6A}$ can be

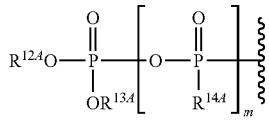

and $R^{7A}$ can be absent or hydrogen; or $R^{6A}$ and $R^{7A}$ can be taken together to form a moiety selected from an optionally substituted

and an optionally substituted

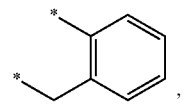 [SMILES: *Cc1ccccc1*]

wherein the oxygens connected to $R^{6A}$ and $R^{7A}$, the phosphorus and the moiety form a six-membered to ten-membered ring system; $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, $NR^{30A}R^{31A}$, an optionally substituted N-linked amino acid and an optionally substituted N-linked amino acid ester derivative; $R^{10A}$ and $R^{11A}$ can be independently an optionally substituted N-linked amino acid or an optionally substituted N-linked amino acid ester derivative; $R^{12A}$ and $R^{13A}$ can be independently absent or hydrogen; $R^{14A}$ can be O—, OH or methyl; each $R^{15A}$, each $R^{16A}$, each $R^{17A}$ and each $R^{18A}$ can be independently hydrogen, an optionally substituted $C_{1-24}$ alkyl or an alkoxy; $R^{19A}$, $R^{20A}R^{22A}$, $R^{23A}$, $R^{2B}$, $R^{3B}$, $R^{5B}$ and $R^{6B}$ can be independently selected from hydrogen, an optionally substituted $C_{1-24}$ alkyl and an optionally substituted aryl; $R^{21A}$ and $R^{4B}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; $R^{24A}$ and $R^{7B}$ can be independently selected from of hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

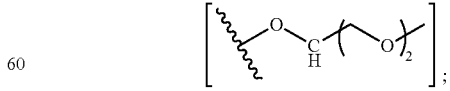

$R^{25A}$, $R^{26A}$, $R^{29A}$, $R^{8B}$ and $R^{9B}$ can be independently selected from hydrogen, an optionally substituted $C_{1-24}$ alkyl and an optionally substituted aryl; $R^{27A1}$ and $R^{27A2}$ can be independently selected from —C≡N, an optionally substituted $C_{2-8}$ organylcarbonyl, an optionally substituted $C_{2-8}$ alkoxycarbonyl and an optionally substituted $C_{2-8}$ organylaminocarbonyl; $R^{28A}$ can be selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R^{30A}$ and $R^{31A}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl and an optionally substituted aryl($C_{1-4}$ alkyl); $R'''^A$ and each $R'''^B$ can be independently an optionally substituted $C_{1-24}$ alkyl; each $R'''^{B1}$ and each $R'''^{B2}$ can be independently hydrogen or an optionally substituted $C_{1-6}$ alkyl; m, v and w can be independently 0 or 1; p and q can be independently 1, 2 or 3; r and s can be independently 0, 1, 2 or 3; t can be 1 or 2; u and y can be independently 3, 4 or 5; and $Z^{1A}$, $Z^{2A}$, $Z^{3A}$, $Z^{4A}$, $Z^{1B}$ and $Z^{2B}$ can be independently oxygen (O) or sulfur (S).

A compound of Formula (I) can be a nucleoside, a nucleotide (including a monophosphate, a diphosphate, a triphosphate, thiomonophosphate, alpha-thiodiphosphate and/or alpha-thiotriphosphate) or a nucleotide prodrug. In some embodiments, - - - - - - - - can be both absent, $Z^1$ can be absent, $O^1$ can be $OR^{1A}$, $R^{3A}$ can be selected from H, halo, OH, —OC(=O)$R'''^A$ and an optionally substituted O-linked amino acid, $R^{4A}$ can be selected from OH, halo, —OC(=O)$R'''^B$ and an optionally substituted O-linked amino acid, or $R^{3A}$ and $R^{4A}$ can be both an oxygen atom connected via a carbonyl to form a 5-membered ring.

Various substituents can be attached to the 5'-position of Formula (I) when both - - - - - - are absent. In some embodiments, $R^{1A}$ can be hydrogen. In some embodiments, $R^{1A}$ can be an optionally substituted acyl. For example, $R^{1A}$ can be —C(=O)$R^{39A}$, wherein $R^{39A}$ can be selected from an optionally substituted $C_{1-12}$ alkyl, an optionally substituted $C_{2-12}$ alkenyl, an optionally substituted $C_{2-12}$ alkynyl, an optionally substituted $C_{3-8}$ cycloalkyl, an optionally substituted $C_{5-8}$ cycloalkenyl, an optionally substituted $C_{6-10}$ aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, $R^{39A}$ can be a substituted $C_{1-12}$ alkyl. In other embodiments, $R^{39A}$ can be an unsubstituted $C_{1-12}$ alkyl. In some embodiments, $R^{1A}$ can be —C(=O)-unsubstituted $C_{1-4}$ alkyl. In some embodiments, both $R^{a1}$ and $R^{a2}$ can be hydrogen. In other embodiments, $R^{a1}$ can be hydrogen and $R^{a2}$ can be deuterium. In still other embodiments, both $R^{a1}$ and $R^{a2}$ can be deuterium.

In still other embodiments, $R^{1A}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. In some embodiments, the O-linked amino acid can have the structure

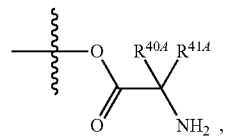

wherein $R^{40A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{41A}$ can be hydrogen or an optionally substituted $C_{1-4}$ alkyl; or $R^{40A}$ and $R^{41A}$ can be taken together to form an optionally substituted $C_{3-6}$ cycloalkyl. Those skilled in the art understand that when $R^{1A}$ is an optionally substituted O-linked amino acid, the oxygen of $R^{1A}O$— of Formula (I) is part of the optionally substituted O-linked amino acid. For example, when $R^{1A}$ is

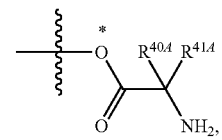

the oxygen indicated with "*" is the oxygen of $R^{1A}O$— of Formula (I).

When $R^{40A}$ is substituted, $R^{40A}$ can be substituted with one or more substituents selected from N-amido, mercapto, alkylthio, an optionally substituted aryl, hydroxy, an optionally substituted heteroaryl, O-carboxy and amino. In some embodiments, $R^{40A}$ can be an unsubstituted $C_{1-6}$ alkyl, such as those described herein. In some embodiments, $R^{40A}$ can be hydrogen. In other embodiments, $R^{40A}$ can be methyl. In some embodiments, $R^{41A}$ can be hydrogen. In other embodiments, $R^{41A}$ can be an optionally substituted $C_{1-4}$ alkyl, such as methyl, ethyl, n-propyl, isopropyl, n-butyl, isobutyl and tert-butyl. In some embodiments, $R^{41A}$ can be methyl. Depending on the groups that are selected for $R^{40A}$ and $R^{41A}$, the carbon to which $R^{40A}$ and $R^{41A}$ are attached may be a chiral center. In some embodiment, the carbon to which $R^{40A}$ and $R^{41A}$ are attached may be a (R)-chiral center. In other embodiments, the carbon to which $R^{40A}$ and $R^{41A}$ are attached may be a (S)-chiral center.

Examples of suitable

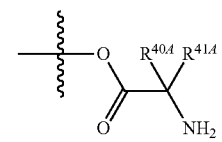

include the following:

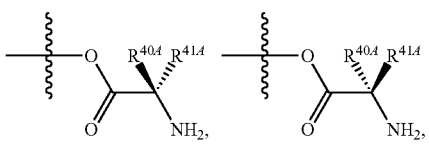

-continued

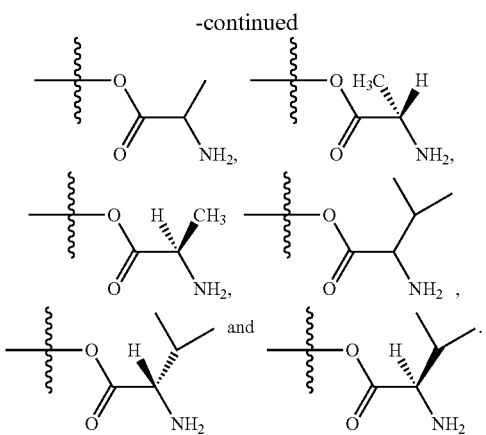

In some embodiments, $R^{1A}$ can be

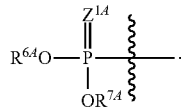

In some embodiments, $R^{6A}$ and $R^{7A}$ can be both hydrogen. In other embodiments, $R^{6A}$ and $R^{7A}$ can be both absent. In still other embodiments, at least one $R^{6A}$ and $R^{7A}$ can be absent. In yet still other embodiments, at least one $R^{6A}$ and $R^{7A}$ can be hydrogen. Those skilled in the art understand that when $R^{6A}$ and/or $R^{7A}$ are absent, the associated oxygen(s) will have a negative charge. For example, when $R^{6A}$ is absent, the oxygen associated with $R^{6A}$ will have a negative charge. In some embodiments, $Z^{1A}$ can be O (oxygen). In other embodiments, $Z^{1A}$ can be S (sulfur). In some embodiments, $R^{1A}$ can be a monophosphate. In other embodiments, $R^{1A}$ can be a monothiophosphate.

In some embodiments, $R^{1A}$ can be

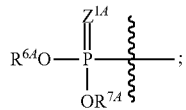

$R^{6A}$ can be

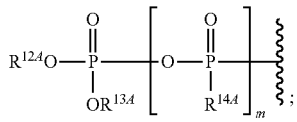

$R^{7A}$ can be absent or hydrogen; $R^{12A}$ and $R^{13A}$ can be independently absent or hydrogen; $R^{14A}$ can be O⁻, OH or methyl; and m can be 0 or 1. In some embodiments, m can be 0, and $R^{7A}$, $R^{12A}$ and $R^{13A}$ can be independently absent or hydrogen. In other embodiments, m can be 1, and $R^{7A}$, $R^{12A}$ and $R^{13A}$ can be independently absent or hydrogen; and $R^{14A}$ can be O⁻, OH or methyl. In some embodiments, m can be 1, and $R^{7A}$, $R^{12A}$ and $R^{13A}$ can be independently absent or hydrogen; and $R^{14A}$ can be O⁻ or OH. In other embodiments, m can be 1, and $R^{7A}$, $R^{12A}$ and $R^{13A}$ can be independently absent or hydrogen; and $R^{14A}$ can be methyl. Those skilled in the art understand that when m is 0, $R^{6A}$ can be a diphosphate, when $Z^{1A}$ is oxygen, or an alpha-thiodiphosphate, when $Z^{1A}$ is sulfur. Likewise, those skilled in the art understand that when m is 1, $R^{6A}$ can be a triphosphate, when $Z^{1A}$ is oxygen, or an alpha-thiotriphosphate, when $Z^{1A}$ is sulfur.

In some embodiments, when $R^{1A}$ is

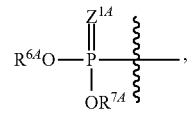

one of $R^{6A}$ and $R^{7A}$ can be hydrogen, and the other of $R^{6A}$ and $R^{7A}$ can be selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, one of $R^{6A}$ and $R^{7A}$ can be hydrogen, and the other of $R^{6A}$ and $R^{7A}$ can be an optionally substituted $C_{1-24}$ alkyl. In other embodiments, both $R^{6A}$ and $R^{7A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, both $R^{6A}$ and $R^{7A}$ can be an optionally substituted $C_{1-24}$ alkyl. In other embodiments, both $R^{6A}$ and $R^{7A}$ can be an optionally substituted $C_{2-24}$ alkenyl. In some embodiments, $R^{6A}$ and $R^{7A}$ can be independently an optionally substituted group selected from the following: myristoleyl, myristyl, palmitoleyl, palmityl, sapienyl, oleyl, elaidyl, vaccenyl, linoleyl, α-linolenyl, arachidonyl, eicosapentaenyl, erucyl, docosahexaenyl, caprylyl, capryl, lauryl, stearyl, arachidyl, behenyl, lignoceryl and cerotyl.

In some embodiments, at least one of $R^{6A}$ and $R^{7A}$ can be *—$(CR^{15A}R^{16A})_p$—O—$C_{1-24}$ alkyl. In other embodiments, $R^{6A}$ and $R^{7A}$ can be both *—$(CR^{15A}R^{16A})_p$—O—$C_{1-24}$ alkyl. In some embodiments, each $R^{15A}$ and each $R^{16A}$ can be hydrogen. In other embodiments, at least one of $R^{15A}$ and $R^{16A}$ can be an optionally substituted $C_{1-24}$ alkyl. In other embodiments, at least one of $R^{15A}$ and $R^{16A}$ can be an alkoxy (for example, benzoxy). In some embodiments, p can be 1. In other embodiments, p can be 2. In still other embodiments, p can be 3.

In some embodiments, at least one of $R^{6A}$ and $R^{7A}$ can be *—$(CR^{17A}R^{18A})_q$—O—$C_{2-24}$ alkenyl. In other embodiments, $R^{6A}$ and $R^{7A}$ can be both *—$(CR^{17A}R^{18A})_q$—O—$C_{2-24}$ alkenyl. In some embodiments, each $R^{17A}$ and each $R^{18A}$ can be hydrogen. In other embodiments, at least one of $R^{17A}$ and $R^{18A}$ can be an optionally substituted $C_{1-24}$ alkyl. In some embodiments, q can be 1. In other embodiments, q can be 2. In still other embodiments, q can be 3. When at least one of $R^{6A}$ and $R^{7A}$ is *—$(CR^{15A}R^{16A})_p$—O—$C_{1-24}$ alkyl or *—$(CR^{17A}R^{18A})_q$—O—$C_{2-24}$ alkenyl, the $C_{1-24}$ alkyl can be selected from caprylyl, capryl, lauryl, myristyl, palmityl, stearyl, arachidyl, behenyl, lignoceryl, and cerotyl, and the $C_{2-24}$ alkenyl can be selected from myristoleyl, palmitoleyl, sapienyl, oleyl, elaidyl, vaccenyl, linoleyl, α-linolenyl, arachidonyl, eicosapentaenyl, erucyl and docosahexaenyl.

In some embodiments, when $R^{1A}$ is

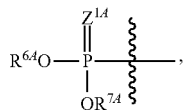

at least one of $R^{6A}$ and $R^{7A}$ can be selected from

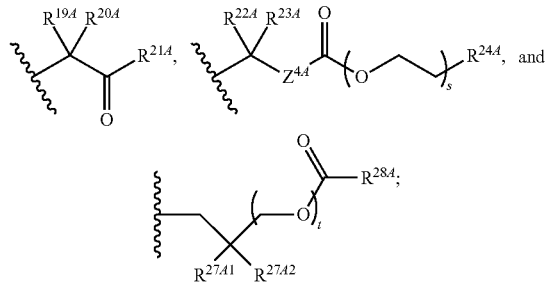

and the other of $R^{6A}$ and $R^{7A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl).

In some embodiments, at least one of $R^{6A}$ and $R^{7A}$ can be

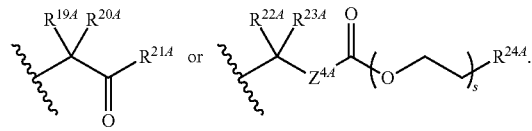

In some embodiments, both $R^{6A}$ and $R^{7A}$ can be

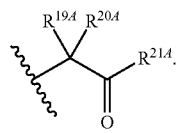

When one or both of $R^{6A}$ and $R^{7A}$ are

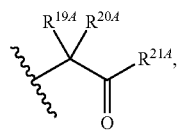

$R^{19A}$ and $R^{20A}$ can be independently selected from hydrogen, an optionally substituted $C_{1-24}$ alkyl and an optionally substituted aryl; and $R^{21A}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl. In some embodiments, $R^{19A}$ and $R^{20A}$ can be hydrogen. In other embodiments, at least one of $R^{19A}$ and $R^{20A}$ can be an optionally substituted $C_{1-24}$ alkyl or an optionally substituted aryl. In some embodiments, $R^{21A}$ can be an optionally substituted $C_{1-24}$ alkyl. In some embodiments, $R^{21A}$ can be an unsubstituted $C_{1-4}$ alkyl. In other embodiments, $R^{21A}$ can be an optionally substituted aryl. In still other embodiments, $R^{21A}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^{21A}$ can be an unsubstituted —O—$C_{1-4}$ alkyl.

In some embodiments, both $R^{6A}$ and $R^{7A}$ can be

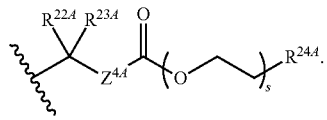

When one or both of $R^{6A}$ and $R^{7A}$ are

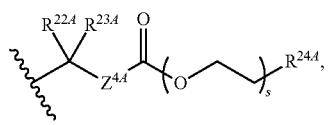

$R^{22A}$ and $R^{23A}$ can be independently selected from hydrogen, an optionally substituted $C_{1-24}$ alkyl and an optionally substituted aryl; $R^{24A}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; s can be 0, 1, 2 or 3; and $Z^{4A}$ can be independently O (oxygen) or S (sulfur). In some embodiments, $R^{22A}$ and $R^{23A}$ can be hydrogen. In other embodiments, at least one of $R^{22A}$ and $R^{23A}$ can be an optionally substituted $C_{1-24}$ alkyl or an optionally substituted aryl. In some embodiments, $R^{24A}$ can be an optionally substituted $C_{1-24}$ alkyl. In some embodiments, $R^{24A}$ can be an unsubstituted $C_{1-4}$ alkyl. In other embodiments, $R^{24A}$ can be an optionally substituted aryl. In still other embodiments, $R^{24A}$ can be an optionally substituted —O—$C_{1-24}$ alkyl, an optionally substituted —O-aryl, an optionally substituted —O-heteroaryl or an optionally substituted —O-monocyclic heterocyclyl. In yet still other embodiments, $R^{24A}$ can be

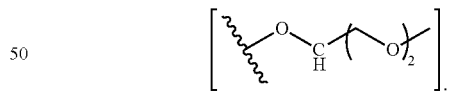

In some embodiments, $R^{24A}$ can be an unsubstituted —O—$C_{1-4}$ alkyl. In some embodiments, $Z^{4A}$ can be O (oxygen). In other embodiments, $Z^{4A}$ can be or S (sulfur). In some embodiments, s can be 0. In other embodiments, s can be 1. In still other embodiments, s can be 2. In yet still other embodiments, s can be 3. In some embodiments, s can be 0 and $R^{24A}$ can be

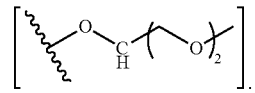

In some embodiments, one or both of $R^{6A}$ and $R^{7A}$ can be isopropyloxycarbonyloxymethyl (POC). In some embodiments, $R^{6A}$ and $R^{7A}$ can be both a isopropyloxycarbonyloxymethyl (POC) group, and form a bis(isopropyloxycarbonyloxymethyl) (bis(POC)) prodrug. In other embodiments, one or both of $R^{6A}$ and $R^{7A}$ can be pivaloyloxymethyl (POM). In some embodiments, $R^{6A}$ and $R^{7A}$ can be both a pivaloyloxymethyl (POM) group, and form a bis(pivaloyloxymethyl) (bis(POM)) prodrug.

In some embodiments, both $R^{6A}$ and $R^{7A}$ can be

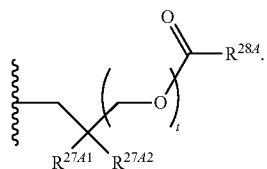

When one or both of $R^{6A}$ and $R^{7A}$ are

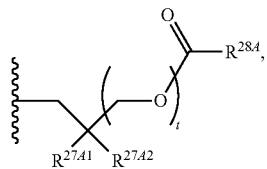

$R^{27A1}$ and $R^{27A2}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{28A}$ can be selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and t can be 1 or 2. In some embodiments, $R^{27A1}$ can be —C≡N and $R^{27A2}$ can be an optionally substituted $C_{2-8}$ alkoxycarbonyl, such as —C(=O)OCH$_3$. In other embodiments, $R^{27A1}$ can be —C≡N and $R^{27A2}$ can be an optionally substituted $C_{2-8}$ organylaminocarbonyl, for example, —C(=O)NHCH$_2$CH$_3$ and —C(=O)NHCH$_2$CH$_2$phenyl. In some embodiments, both $R^{27A1}$ and $R^{27A2}$ can be an optionally substituted $C_{2-8}$ organylcarbonyl, such as —C(=O)CH$_3$. In some embodiments, both $R^{27A1}$ and $R^{27A2}$ can be an optionally substituted $C_{1-8}$ alkoxycarbonyl, for example, —C(=O)OCH$_2$CH$_3$ and —C(=O)OCH$_3$. In some embodiments, including those described in this paragraph, $R^{28A}$ can be an optionally substituted $C_{1-4}$ alkyl. In some embodiment, $R^{28A}$ can be methyl or tert-butyl. In some embodiments, t can be 1. In other embodiments, t can be 2.

In some embodiments, $R^{6A}$ and $R^{7A}$ can be both an optionally substituted aryl. In some embodiments, at least one of $R^{6A}$ and $R^{7A}$ can be an optionally substituted aryl. For example, both $R^{6A}$ and $R^{7A}$ can be an optionally substituted phenyl or an optionally substituted naphthyl. When substituted, the substituted aryl can be substituted with 1, 2, 3 or more than 3 substituents. When more the two substituents are present, the substituents can be the same or different. In some embodiments, when at least one of $R^{6A}$ and $R^{7A}$ is a substituted phenyl, the substituted phenyl can be a para-, ortho- or meta-substituted phenyl.

In some embodiments, $R^{6A}$ and $R^{7A}$ can be both an optionally substituted aryl($C_{1-6}$ alkyl). In some embodiments, at least one of $R^{6A}$ and $R^{7A}$ can be an optionally substituted aryl($C_{1-6}$ alkyl). For example, both $R^{6A}$ and $R^{7A}$ can be an optionally substituted benzyl. When substituted, the substituted benzyl group can be substituted with 1, 2, 3 or more than 3 substituents. When more the two substituents are present, the substituents can be the same or different. In some embodiments, the aryl group of the aryl($C_{1-6}$ alkyl) can be a para-, ortho- or meta-substituted phenyl.

In some embodiments, $R^{6A}$ and $R^{7A}$ can be both

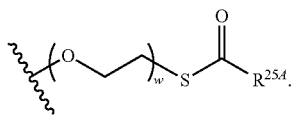

In some embodiments, at least one of $R^{6A}$ and $R^{7A}$ can be

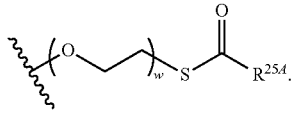

In some embodiments, $R^{25A}$ can be hydrogen. In other embodiments, $R^{25A}$ can be an optionally substituted $C_{1-24}$ alkyl. In still other embodiments, $R^{25A}$ can be an optionally substituted aryl (for example, an optionally substituted phenyl). In some embodiments, $R^{25A}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained). In some embodiments, w can be 0. In other embodiments, w can be 1. In some embodiments, $R^{6A}$ and $R^{7A}$ can be both a S-acylthioethyl (SATE) group and form a SATE ester prodrug.

In some embodiments, $R^{6A}$ and $R^{7A}$ can be both

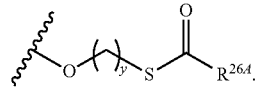

In some embodiments, at least one of $R^{6A}$ and $R^{7A}$ can be

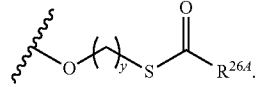

In some embodiments, $R^{26A}$ can be hydrogen. In other embodiments, $R^{26A}$ can be an optionally substituted $C_{1-24}$ alkyl. In still other embodiments, $R^{26A}$ can be an optionally substituted aryl, for example, an optionally substituted phenyl. In some embodiments, $R^{26A}$ can be an optionally substituted $C_{1-6}$ alkyl. In some embodiments, $R^{26A}$ can be an unsubstituted $C_{1-6}$ alkyl. In some embodiments, y can be 3. In other embodiments, y can be 4. In still other embodiments, y can be 5.

In some embodiments, $R^{6A}$ and $R^{7A}$ can be both

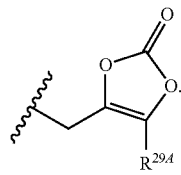

In some embodiments, at least one of $R^{6A}$ and $R^{7A}$ can be

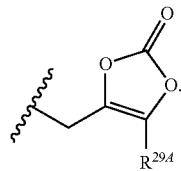

In some embodiments, $R^{29A}$ can be hydrogen. In other embodiments, $R^{29A}$ can be an optionally substituted $C_{1-24}$ alkyl. In some embodiments, $R^{29A}$ can be a $C_{1-4}$ alkyl, such as methyl, ethyl, n-propyl, iso-propyl, n-butyl, iso-butyl and t-butyl. In still other embodiments, $R^{29A}$ can be an optionally substituted aryl, such as an optionally substituted phenyl or an optionally substituted naphthyl. In some embodiments, $R^{6A}$ and $R^{7A}$ can be both a dioxolenone group and form a dioxolenone prodrug.

In some embodiments, $R^{6A}$ and $R^{7A}$ can be taken together to form an optionally substituted

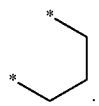

For example, $R^{1A}$ can be an optionally substituted

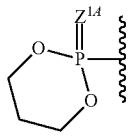

When substituted, the ring can be substituted 1, 2, 3 or 3 or more times. When substituted with multiple substituents, the substituents can be the same or different. In some embodiments, when $R^{1A}$ is

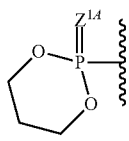

the ring can be substituted with an optionally substituted aryl group and/or an optionally substituted heteroaryl. An example of a suitable heteroaryl is pyridinyl. In some embodiments, $R^{6A}$ and $R^{7A}$ can be taken together to form an optionally substituted

such as

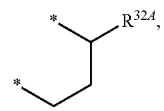

wherein $R^{32A}$ can be an optionally substituted aryl, an optionally substituted heteroaryl or an optionally substituted heterocyclyl. In some embodiments, $R^{6A}$ and $R^{7A}$ can form a cyclic 1-aryl-1,3-propanyl ester (HepDirect) prodrug moiety.

In some embodiments, $R^{6A}$ and $R^{7A}$ can be taken together to form an optionally substituted

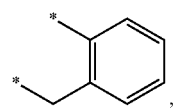

wherein the oxygens connected to $R^{6A}$ and $R^{7A}$, the phosphorus and the moiety form a six-membered to ten-membered ring system. Example of an optionally substituted

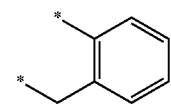

include

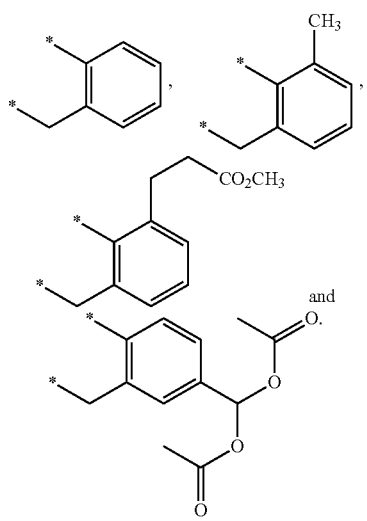

In some embodiments, $R^{6A}$ and $R^{7A}$ can form a cyclosaligenyl (cycloSal) prodrug.

In some embodiments, $R^{6A}$ and $R^{7A}$ can be the same. In some embodiments, $R^{6A}$ and $R^{7A}$ can be different.

In some embodiments, $Z^{1A}$ can be oxygen. In other embodiments, $Z^{1A}$ can be sulfur.

In some embodiments, $R^{1A}$ can be

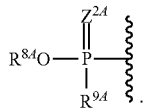

In some embodiments, $R^{8A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl.

In some embodiments, $R^{8A}$ can be hydrogen, and $R^{9A}$ can be an optionally substituted $C_{1-6}$ alkyl. Examples of suitable $C_{1-6}$ alkyls include methyl, ethyl, n-propyl, isopropyl, n-butyl, isobutyl, tert-butyl, pentyl (branched and straight-chained), and hexyl (branched and straight-chained). In other embodiments, $R^{8A}$ can be hydrogen, and $R^{9A}$ can be $NR^{30A}R^{31A}$, wherein $R^{30A}$ and $R^{31A}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl and an optionally substituted aryl($C_{1-4}$ alkyl). In some embodiments, one of $R^{30A}$ and $R^{31A}$ can be hydrogen and the other of $R^{30A}$ and $R^{31A}$ can be an optionally substituted $C_{1-6}$ alkyl, an optionally substituted $C_{2-6}$ alkenyl, an optionally substituted $C_{2-6}$ alkynyl, an optionally substituted $C_{3-6}$ cycloalkyl, an optionally substituted $C_{3-6}$ cycloalkenyl and an optionally substituted benzyl.

In some embodiments, $R^{8A}$ can be absent or hydrogen; and $R^{9A}$ can be an optionally substituted N-linked amino acid or an optionally substituted N-linked amino acid ester derivative. In other embodiments, $R^{8A}$ can be an optionally substituted aryl; and $R^{9A}$ can be an optionally substituted N-linked amino acid or an optionally substituted N-linked amino acid ester derivative. In still other embodiments, $R^{8A}$ can be an optionally substituted heteroaryl; and $R^{9A}$ can be an optionally substituted N-linked amino acid or an optionally substituted N-linked amino acid ester derivative. In some embodiments, $R^{9A}$ can be selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. Examples of an optionally substituted N-linked amino acid ester derivatives include optionally substituted versions of the following: N-alanine isopropyl ester, N-alanine cyclohexyl ester, N-alanine neopentyl ester, N-valine isopropyl ester and N-leucine isopropyl ester. In some embodiments, $R^{9A}$ can have the structure

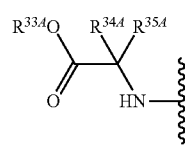

wherein $R^{33A}$ can be selected from hydrogen, an optionally substituted $C_{1-6}$ alkyl, an optionally substituted $C_{3-6}$ cycloalkyl, an optionally substituted aryl, an optionally substituted aryl($C_{1-6}$ alkyl) and an optionally substituted haloalkyl; $R^{34A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{35A}$ can be hydrogen or an optionally substituted $C_{1-4}$ alkyl; or $R^{34A}$ and $R^{35A}$ can be taken together to form an optionally substituted $C_{3-6}$ cycloalkyl.

When $R^{34A}$ is substituted, $R^{34A}$ can be substituted with one or more substituents selected from N-amido, mercapto, alkylthio, an optionally substituted aryl, hydroxy, an optionally substituted heteroaryl, O-carboxy and amino. In some embodiments, $R^{34A}$ can be an unsubstituted $C_{1-6}$ alkyl, such as those described herein. In some embodiments, $R^{34A}$ can be hydrogen. In other embodiments, $R^{34A}$ can be methyl. In some embodiments, $R^{33A}$ can be an optionally substituted $C_{1-6}$ alkyl. Examples of optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{33A}$ can be methyl or isopropyl. In some embodiments, $R^{33A}$ can be ethyl or neopentyl. In other embodiments, $R^{33A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{33A}$ can be an optionally substituted cyclohexyl. In still other embodiments, $R^{33A}$ can be an optionally substituted aryl, such as phenyl and naphthyl. In yet still other embodiments, $R^{33A}$ can be an optionally substituted aryl($C_{1-6}$ alkyl). In some embodiments, $R^{33A}$ can be an optionally substituted benzyl. In some embodiments, $R^{33A}$ can be an optionally substituted $C_{1-6}$ haloalkyl, for example, $CF_3$. In some embodiments, $R^{35A}$ can be hydrogen. In other embodiments, $R^{35A}$ can be an optionally substituted $C_{1-4}$ alkyl, such as methyl, ethyl, n-propyl, isopropyl, n-butyl, isobutyl and tert-butyl. In some embodiments, $R^{35A}$ can be methyl. In some embodiments, $R^{34A}$ and $R^{35A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{34A}$ and $R^{35A}$, the carbon to which $R^{34A}$ and $R^{35A}$ are attached may be a chiral center. In some embodiment, the carbon to which $R^{34A}$ and $R^{35A}$ are attached may be a (R)-chiral center. In other embodiments, the carbon to which $R^{34A}$ and $R^{35A}$ are attached may be a (S)-chiral center.

In some embodiments, when $R^{1A}$ is

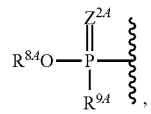

$Z^{2A}$ can be O (oxygen). In other embodiments, when $R^{1A}$ is

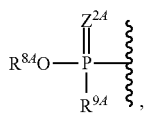

$Z^{2A}$ can be S (sulfur). In some embodiments, when $R^{1A}$ is

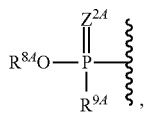

a compound of Formula (I) can be a phosphoramidate prodrug, such as an aryl phosphoramidate prodrug.

In some embodiments, $R^{1A}$ can be

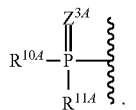

In some embodiments, $R^{10A}$ and $R^{11A}$ can be both an optionally substituted N-linked amino acid or an optionally substituted N-linked amino acid ester derivative. In some embodiments, $R^{10A}$ and $R^{11A}$ can be independently selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{10A}$ and $R^{11A}$ can be an optionally substituted version of the following: N-alanine isopropyl ester, N-alanine cyclohexyl ester, N-alanine neopentyl ester, N-valine isopropyl ester and N-leucine isopropyl ester. In some embodiments, $R^{10A}$ and $R^{11A}$ can independently have the structure

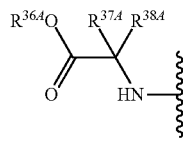

wherein $R^{36A}$ can be selected from hydrogen, an optionally substituted $C_{1-6}$ alkyl, an optionally substituted $C_{3-6}$ cycloalkyl, an optionally substituted aryl, an optionally substituted aryl($C_{1-6}$ alkyl) and an optionally substituted haloalkyl; $R^{37A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{38A}$ can be hydrogen or an optionally substituted $C_{1-4}$ alkyl; or $R^{37A}$ and $R^{38A}$ can be taken together to form an optionally substituted $C_{3-6}$ cycloalkyl.

When $R^{37A}$ is substituted, $R^{37A}$ can be substituted with one or more substituents selected from N-amido, mercapto, alkylthio, an optionally substituted aryl, hydroxy, an optionally substituted heteroaryl, O-carboxy and amino. In some embodiments, $R^{37A}$ can be an unsubstituted $C_{1-6}$ alkyl, such as those described herein. In some embodiments, $R^{37A}$ can be hydrogen. In other embodiments, $R^{37A}$ can be methyl. In some embodiments, $R^{36A}$ can be an optionally substituted $C_{1-6}$ alkyl. Examples of optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{36A}$ can be methyl or isopropyl. In some embodiments, $R^{36A}$ can be ethyl or neopentyl. In other embodiments, $R^{36A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{36A}$ can be an optionally substituted cyclohexyl. In still other embodiments, $R^{36A}$ can be an optionally substituted aryl, such as phenyl and naphthyl. In yet still other embodiments, $R^{36A}$ can be an optionally substituted aryl($C_{1-6}$ alkyl). In some embodiments, $R^{36A}$ can be an optionally substituted benzyl. In some embodiments, $R^{36A}$ can be an optionally substituted $C_{1-6}$ haloalkyl, for example, $CF_3$. In some embodiments, $R^{38A}$ can be hydrogen. In other embodiments, $R^{38A}$ can be an optionally substituted $C_{1-4}$ alkyl, such as methyl, ethyl, n-propyl, isopropyl, n-butyl, isobutyl and tert-butyl. In some embodiments, $R^{38A}$ can be methyl. In some embodiments, $R^{37A}$ and $R^{38A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{37A}$ and $R^{38A}$, the carbon to which $R^{37A}$ and $R^{38A}$ are attached may be a chiral center. In some embodiment, the carbon to which $R^{37A}$ and $R^{38A}$ are attached may be a (R)-chiral center. In other embodiments, the carbon to which $R^{37A}$ and $R^{38A}$ are attached may be a (S)-chiral center.

Examples of suitable

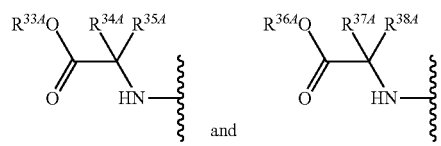

groups include the following:

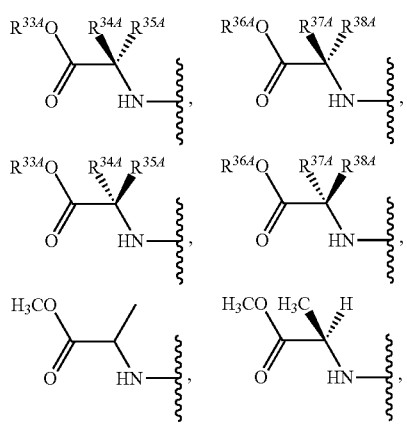

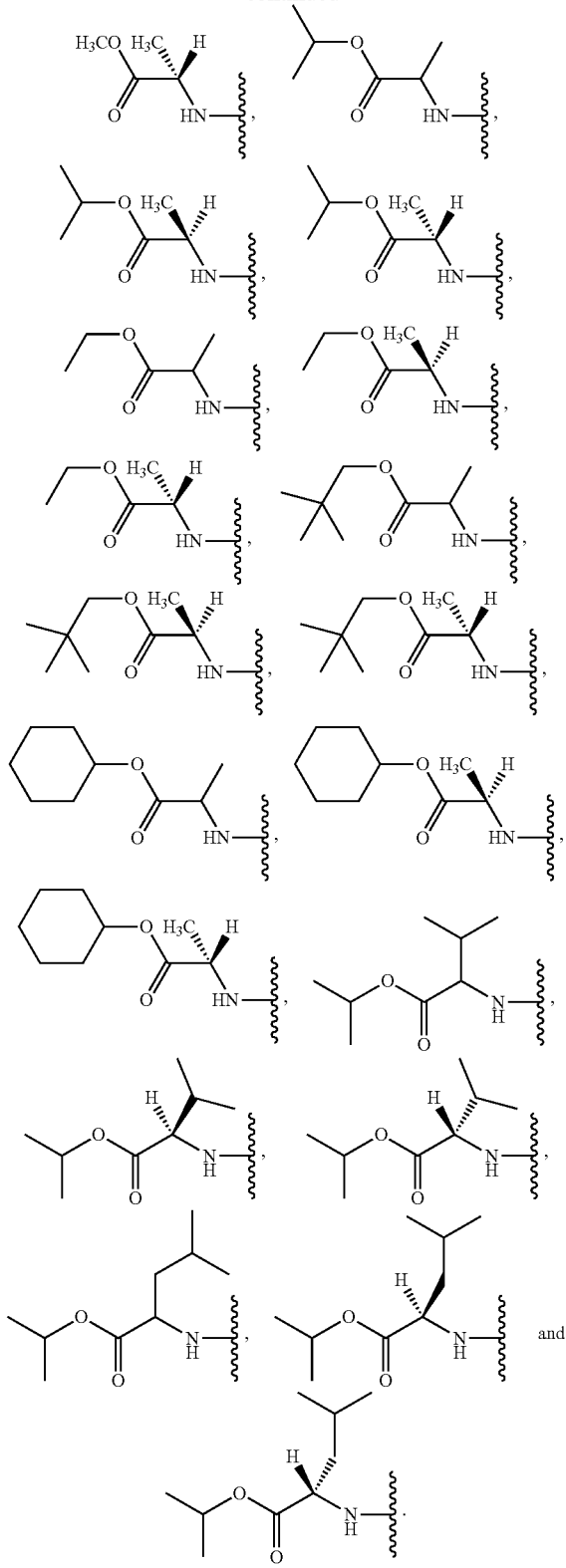

In some embodiments, $R^{10A}$ and $R^{11A}$ can be the same. In some embodiments, $R^{10A}$ and $R^{11A}$ can be different.

In some embodiments, $Z^{3A}$ can be O (oxygen). In other embodiments, $Z^{3A}$ can be S (sulfur). In some embodiments, when $R^{1A}$ is

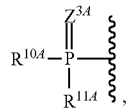

a compound of Formula (I) can be a phosphonic diamide prodrug.

Various substituents can be present at the 4'-position of the pentose ring. In some embodiments, $R^{2A}$ can be an unsubstituted $C_{1-4}$ alkyl. Unsubstituted $C_{1-4}$ alkyls include methyl, ethyl, n-propyl, iso-propyl, n-butyl, iso-butyl and tert-butyl. In other embodiments, $R^{2A}$ can be an unsubstituted $C_{2-4}$ alkenyl, such as ethenyl, propenyl and butenyl. In still other embodiments, $R^{2A}$ can be an unsubstituted $C_{2-4}$ alkynyl, for example, ethynyl, propynyl and butynyl. In yet still other embodiments, $R^{2A}$ can be a haloalkyl. Examples of a haloalkyls are —$(CH_2)_{1-6}$ halogen and —$CHF_2$. In some embodiments, the haloalkyl can be —$(CH_2)_{1-6}F$ or —$(CH_2)_{1-6}Cl$. In some embodiments, the haloalkyl can be fluoromethyl. In other embodiments, $R^{2A}$ can be —$CHF_2$. In yet still other embodiments, $R^{2A}$ can be a $C_{1-6}$ azidoalkyl. For example, $R^{2A}$ can be an azidomethyl, azidoethyl, azidopropyl, azidobutyl, azidopentyl or azidohexyl. In some embodiments, $R^{2A}$ can be a $C_{1-6}$ aminoalkyl. For example, $R^{2A}$ can be an aminomethyl, aminoethyl, aminopropyl, aminobutyl, aminopentyl or aminohexyl. In other embodiments, $R^{2A}$ can be halo. For example, $R^{2A}$ can be fluoro (F) or chloro (Cl). In still other embodiments, $R^{2A}$ can be hydrogen. In yet still other embodiments, $R^{2A}$ can be —CN. In some embodiments, $R^{2A}$ can be selected from halogen, an optionally substituted $C_{1-6}$ alkyl, an optionally substituted $C_{2-6}$ alkenyl, an optionally substituted $C_{2-6}$ alkynyl, an optionally substituted $C_{3-6}$ cycloalkyl, an optionally substituted —O—$C_{1-6}$ alkyl, an optionally substituted —O—$C_{3-6}$ alkenyl, an optionally substituted —O—$C_{3-6}$ alkynyl and cyano.

A variety of substituents can also be present at the 2'-position of the pentose ring. In some embodiments, $R^{4A}$ can be OH. In other embodiments, $R^{4A}$ can be —OC(=O)$R'''^B$, wherein $R'''^B$ can be an optionally substituted $C_{1-24}$ alkyl. In some embodiments, $R^{4A}$ can be —OC(=O)$R'''^B$, wherein $R'''^B$ can be an unsubstituted $C_{1-4}$ alkyl. In still other embodiments, $R^{4A}$ can be halo. In some embodiments, $R^{4A}$ can be F. In other embodiments, $R^{4A}$ can be $C_1$. In some embodiments, $R^{4A}$ can be $N_3$. In some embodiments, $R^{4A}$ can be $NR'''^{B1}R'''^{B2}$. For example, $R^{4A}$ can be $NH_2$. Other examples can be a mono-substituted $C_{1-6}$ alkyl-amine or a di-substituted $C_{1-6}$ alkyl-amine. In other embodiments, $R^{4A}$ can be hydrogen (H).

In still other embodiments, $R^{4A}$ can be an optionally substituted O-linked amino acid, such as a O-linked alpha-amino acid. In some embodiments, the O-linked amino acid can have the structure

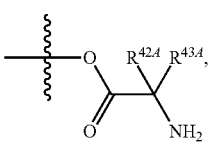

wherein $R^{42A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{43A}$ can be hydrogen or an optionally substituted $C_{1-4}$ alkyl; or $R^{42A}$ and $R^{43A}$ can be taken together to form an optionally substituted $C_{3-6}$ cycloalkyl.

When $R^{42A}$ is substituted, $R^{42A}$ can be substituted with one or more substituents selected from N-amido, mercapto, alkylthio, an optionally substituted aryl, hydroxy, an optionally substituted heteroaryl, O-carboxy and amino. In some embodiments, $R^{42A}$ can be an unsubstituted $C_{1-6}$ alkyl, such as those described herein. In some embodiments, $R^{42A}$ can be hydrogen. In other embodiments, $R^{42A}$ can be methyl. In some embodiments, $R^{43A}$ can be hydrogen. In other embodiments, $R^{43A}$ can be an optionally substituted $C_{1-4}$ alkyl, such as methyl, ethyl, n-propyl, isopropyl, n-butyl, isobutyl and tert-butyl. In some embodiments, $R^{43A}$ can be methyl. Depending on the groups that are selected for $R^{42A}$ and $R^{43A}$, the carbon to which $R^{42A}$ and $R^{43A}$ are attached may be a chiral center. In some embodiment, the carbon to which $R^{42A}$ and $R^{43A}$ are attached may be a (R)-chiral center. In other embodiments, the carbon to which $R^{42A}$ and $R^{43A}$ are attached may be a (S)-chiral center.

Examples of suitable

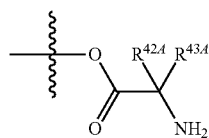

include the following:

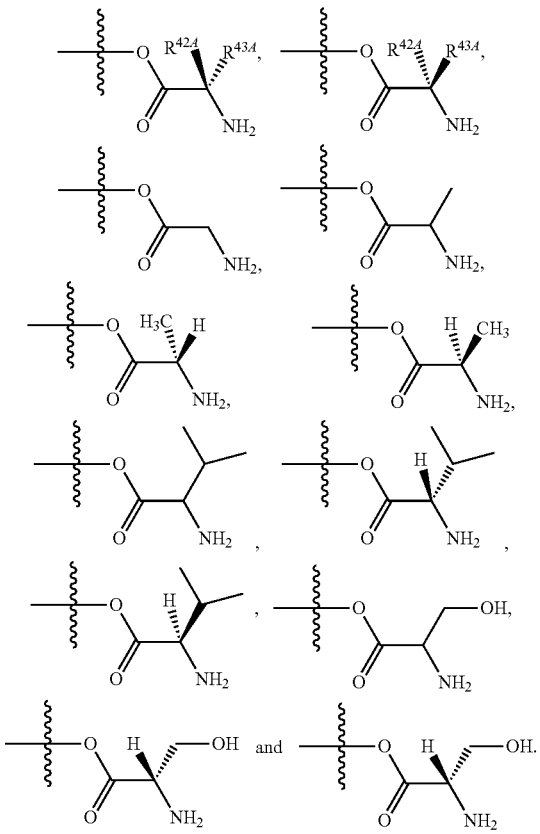

In some embodiments, $R^{5A}$ can be H. In other embodiments, $R^{5A}$ can be halo, including F and Cl. In still other embodiments, $R^{5A}$ can be an optionally substituted $C_{1-6}$ alkyl. For example, $R^{5A}$ can be a substituted or unsubstituted version of the following: methyl, ethyl, n-propyl, iso-propyl, n-butyl, iso-butyl, tert-butyl, pentyl (branched or straight) and hexyl (branched or straight). In some embodiments, $R^{5A}$ can be a halo-substituted $C_{1-6}$ alkyl, such as —$CH_2F$. In yet still other embodiments, $R^{5A}$ can be an optionally substituted $C_{2-6}$ alkenyl. In some embodiments, $R^{5A}$ can be an optionally substituted $C_{2-6}$ alkynyl. For example, $R^{5A}$ can be ethynyl. In some embodiments, $R^{5A}$ can be hydroxy (OH).

A variety of substituents can be present at the 1'-position of the pentose ring. In some embodiments, $R^A$ can be hydrogen. In some embodiments, $R^A$ can be deuterium. In still other embodiments, $R^A$ can be an unsubstituted $C_{1-3}$ alkyl (such as methyl, ethyl, n-propyl and iso-propyl). In yet still other embodiments, $R^A$ can be an unsubstituted $C_{2-4}$ alkenyl (for example, ethenyl, propenyl (branched or straight) and butenyl (branched or straight)). In some embodiments, $R^A$ can be an unsubstituted $C_{2-3}$ alkynyl (such as ethynyl and propynyl (branched or straight)). In other embodiments, $R^A$ can be an unsubstituted cyano.

In some embodiments, - - - - - - - - can be both absent such that a compound of Formula (I) has the structure:

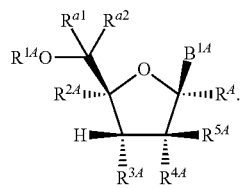

When - - - - - - - - are both absent, the 3'-position can have various groups present. In some embodiments, $R^{3A}$ can be H. In other embodiments, $R^{3A}$ can be halo. For example, $R^{3A}$ can be fluoro (F) or chloro (Cl). In still other embodiments, $R^{3A}$ can be OH. In some embodiments, $R^{3A}$ can be —OC(=O)$R'''^A$, wherein $R'''^A$ can be an optionally substituted $C_{1-24}$ alkyl. In some embodiments, $R^{3A}$ can be —OC(=O)$R'''^A$, wherein $R'''^A$ can be an unsubstituted $C_{1-4}$ alkyl. In other embodiments, $R^{3A}$ can be an optionally substituted O-linked amino acid, such as an optionally substituted O-linked alpha-amino acid. The optionally substituted O-linked amino acid can have the structure:

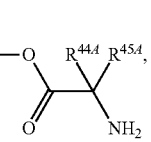

wherein $R^{44A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{45A}$ can be hydrogen or an optionally substituted $C_{1-4}$ alkyl; or $R^{44A}$ and $R^{45A}$ can be taken together to form an optionally substituted $C_{3-6}$ cycloalkyl.

When $R^{44A}$ is substituted, $R^{44A}$ can be substituted with one or more substituents selected from N-amido, mercapto, alkylthio, an optionally substituted aryl, hydroxy, an optionally substituted heteroaryl, O-carboxy and amino. In some embodiments, $R^{44A}$ can be an unsubstituted $C_{1-6}$ alkyl, such as those described herein. In some embodiments, $R^{44A}$ can be hydrogen. In other embodiments, $R^{44A}$ can be methyl. In some embodiments, $R^{45A}$ can be hydrogen. In other embodiments, $R^{45A}$ can be an optionally substituted $C_{1-4}$ alkyl, such as methyl, ethyl, n-propyl, isopropyl, n-butyl, isobutyl and tert-butyl. In some embodiments, $R^{45A}$ can be methyl. Depending on the groups that are selected for $R^{44A}$ and $R^{45A}$, the carbon to which $R^{44A}$ and $R^{45A}$ are attached may be a chiral center. In some embodiment, the carbon to which $R^{44A}$ and $R^{45A}$ are attached may be a (R)-chiral center. In other embodiments, the carbon to which $R^{44A}$ and $R^{45A}$ are attached may be a (S)-chiral center.

Examples of suitable

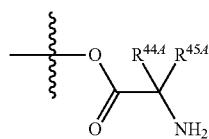

include the following:

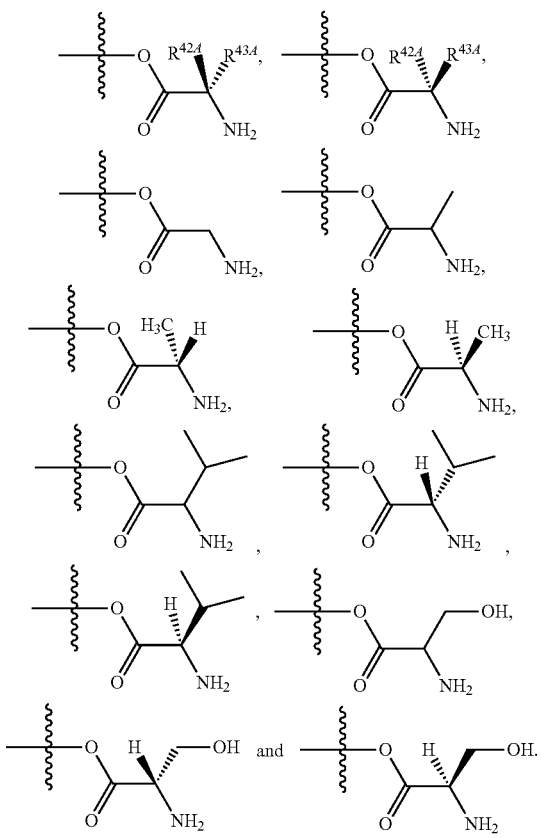

In some embodiments, $R^{3A}$ and $R^{4A}$ can be each an oxygen atom connected via a carbonyl to form a 5-membered ring.

In some embodiments, $R^{2A}$ can be fluoro and $R^{3A}$ can be fluoro. In some embodiments, $R^{2A}$ can be fluoro and $R^{4A}$ can be fluoro. In some embodiments, $R^{2A}$ can be fluoro, $R^{3A}$ can be fluoro and $R^{5A}$ can be an optionally substituted $C_{1-6}$ alkyl, an optionally substituted $C_{2-6}$ alkenyl and an optionally substituted $C_{2-6}$ alkynyl. In some embodiments, $R^{2A}$ can be fluoro, $R^{4A}$ can be fluoro and $R^{5A}$ can be an optionally substituted $C_{1-6}$ alkyl, an optionally substituted $C_{2-6}$ alkenyl and an optionally substituted $C_{2-6}$ alkynyl. In some embodiments, $R^{2A}$ can be fluoro, $R^{3A}$ can be fluoro and $R^{4A}$ can be OH or $-OC(=O)R'''^B$. In some embodiments, $R^{2A}$ can be fluoro, $R^{3A}$ can be OH or $-OC(=O)R'''^A$ and $R^{4A}$ can be fluoro. In some embodiments, $R^{4A}$ and $R^{5A}$ can be each F. In some embodiments, $R^{2A}$ can be *$-(CH_2)_{1-6}$halogen (for example, $-CH_2F$), $R^{3A}$ can be OH, $-OC(=O)R'''^A$ or an optionally substituted O-linked amino acid and $R^{4A}$ can be OH. In some embodiments, $R^{2A}$ can be $-(CH_2)_{1-6}$halogen (for example, $-CH_2F$), $R^{3A}$ can be OH, $-OC(=O)R'''^A$ or an optionally substituted O-linked amino acid, $R^{4A}$ can be OH, and $R^{5A}$ can be an unsubstituted $C_{1-6}$ alkyl. In some embodiments, $R^{2A}$ can be $-(CH_2)_{1-6}N_3$ (such as, $-CH_2N_3$), $R^{3A}$ can be OH and $R^{4A}$ can be fluoro.

In some embodiments, - - - - - - - - can be each a single bond such that a compound of Formula (I) has the structure:

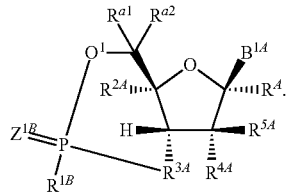

When - - - - - - - - are each a single bond, $R^{3A}$ can be oxygen (O). In some embodiments, when - - - - - - - - are each a single bond, $R^{1B}$ can be O⁻ or OH. In other embodiments, when - - - - - - - - are each a single bond, $R^{1B}$ can be an —O-optionally substituted $C_{1-6}$ alkyl. For example, $R^{1B}$ can be an —O-unsubstituted $C_{1-6}$ alkyl.

In some embodiments, when - - - - - - - - are each a single bond, $R^{1B}$ can be

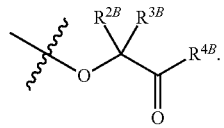

In other embodiments, $R^{1B}$ can be

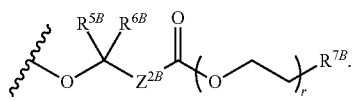

For example, $R^{1B}$ can be a isopropyloxycarbonyloxymethyloxy or pivaloyloxymethyloxy group. In still some embodiments, $R^{1B}$ can be

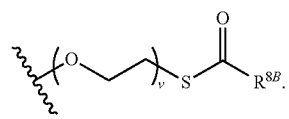

A S-acylthioethyl (SATE) group is an example of a

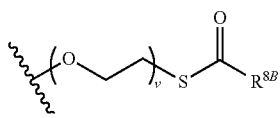

group. In yet still other embodiments, $R^{1B}$ can be an optionally substituted N-linked amino acid or an optionally substituted N-linked amino acid ester derivative, such as an optionally substituted N-linked alpha-amino acid or an optionally substituted N-linked alpha-amino acid ester derivative.

Examples of an optionally substituted N-linked amino acids and an optionally substituted N-linked amino acid ester derivatives are described herein. In some embodiments, $R^{1B}$ can be selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{1B}$ can be an optionally substituted version of the following: N-alanine isopropyl ester, N-alanine cyclohexyl ester, N-alanine neopentyl ester, N-valine isopropyl ester and N-leucine isopropyl ester. In some embodiments, $R^{1B}$ can have the structure

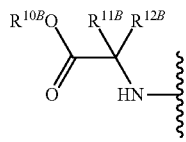

wherein $R^{10B}$ can be selected from hydrogen, an optionally substituted $C_{1-6}$ alkyl, an optionally substituted $C_{3-6}$ cycloalkyl, an optionally substituted aryl, an optionally substituted aryl($C_{1-6}$ alkyl) and an optionally substituted haloalkyl; $R^{11B}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{12B}$ can be hydrogen or an optionally substituted $C_{1-4}$ alkyl; or $R^{11B}$ and $R^{12B}$ can be taken together to form an optionally substituted $C_{3-6}$ cycloalkyl.

As described herein, $R^{11B}$ can be substituted. Examples of substituents include one or more substituents selected from N-amido, mercapto, alkylthio, an optionally substituted aryl, hydroxy, an optionally substituted heteroaryl, O-carboxy and amino. In some embodiments, $R^{11B}$ can be an unsubstituted $C_{1-6}$ alkyl, such as those described herein. In some embodiments, $R^{11B}$ can be hydrogen. In other embodiments, $R^{11B}$ can be methyl. In some embodiments, $R^{10B}$ can be an optionally substituted $C_{1-6}$ alkyl. In some embodiments, $R^{10B}$ can be methyl, ethyl, isopropyl or neopentyl. In other embodiments, $R^{10B}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{10B}$ can be an optionally substituted cyclohexyl. In still other embodiments, $R^{10B}$ can be an optionally substituted aryl, such as phenyl and naphthyl. In yet still other embodiments, $R^{10B}$ can be an optionally substituted aryl($C_{1-6}$ alkyl), for example, an optionally substituted benzyl. In some embodiments, $R^{10B}$ can be an optionally substituted $C_{1-6}$ haloalkyl, for example, $CF_3$. In some embodiments, $R^{12B}$ can be hydrogen. In other embodiments, $R^{12B}$ can be an optionally substituted $C_{1-4}$ alkyl, such as methyl, ethyl, n-propyl, isopropyl, n-butyl, isobutyl and tert-butyl. In some embodiments, $R^{12B}$ can be methyl. In some embodiments, $R^{11B}$ and $R^{12B}$ can be taken together to form an optionally substituted $C_{3-6}$ cycloalkyl. Depending on the groups that are selected for $R^{11B}$ and $R^{12B}$, the carbon to which $R^{11B}$ and $R^{12B}$ are attached may be a chiral center. In some embodiment, the carbon to which $R^{11B}$ and $R^{12B}$ are attached may be a (R)-chiral center. In other embodiments, the carbon to which $R^{11B}$ and $R^{12B}$ are attached may be a (S)-chiral center.

Examples of suitable

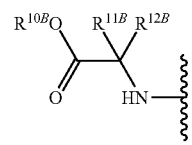

groups include the following:

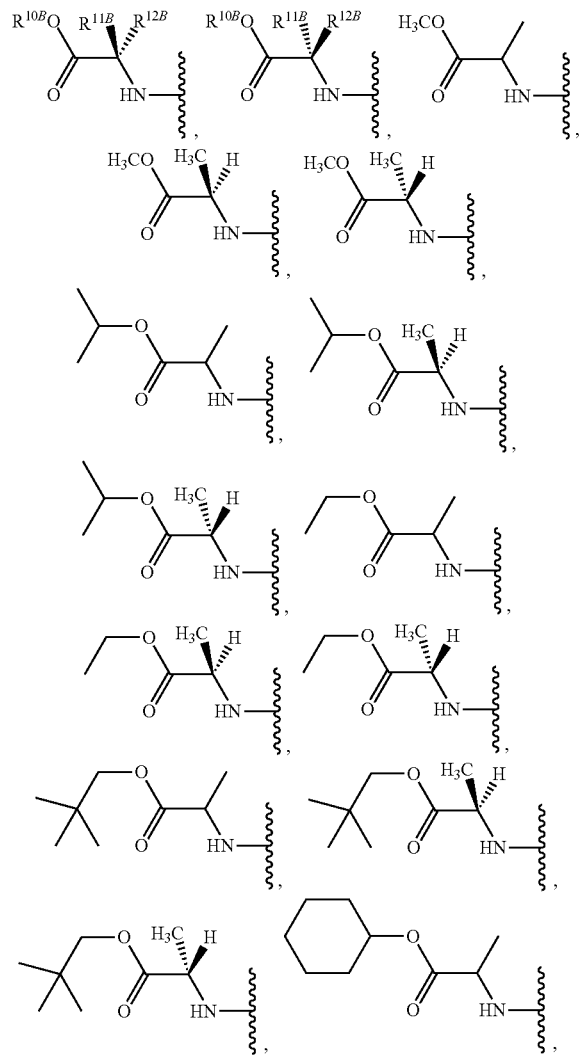

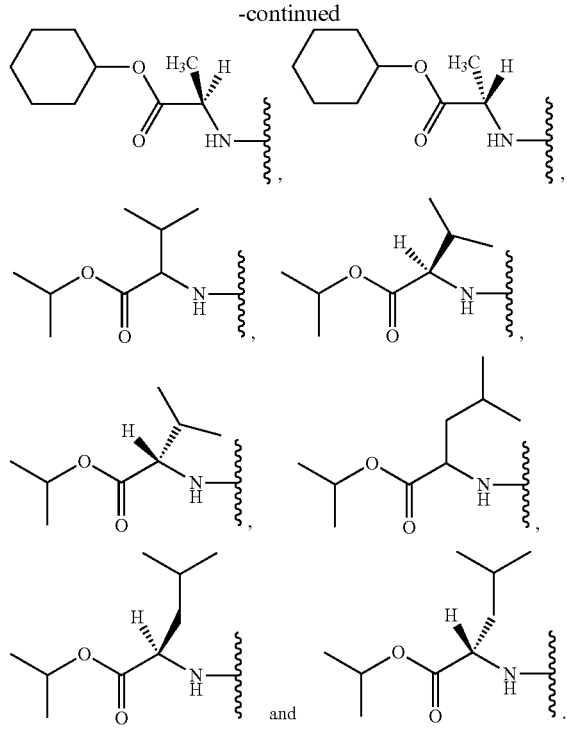

In some embodiments, $R^{1B}$ can be

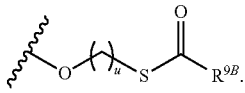

In some embodiments, $R^{9B}$ can be hydrogen. In other embodiments, $R^{9B}$ can be an optionally substituted $C_{1-24}$ alkyl. In still other embodiments, $R^{9B}$ can be an optionally substituted aryl, for example, an optionally substituted phenyl. In some embodiments, $R^{9B}$ can be an optionally substituted $C_{1-6}$ alkyl. In some embodiments, $R^{9B}$ can be an unsubstituted $C_{1-6}$ alkyl. In some embodiments, u can be 3. In other embodiments, u can be 4. In still other embodiments, u can be 5.

In some embodiments, $Z^{1B}$ can be oxygen (O). In other embodiments, $Z^{1B}$ can be S (sulfur).

Various optionally substituted heterocyclic bases can be attached to the pentose ring. In some embodiments, one or more of the amine and/or amino groups of the optionally substituted heterocyclic base may be protected with a suitable protecting group. For example, an amino group may be protected by transforming the amine and/or amino group to an amide or a carbamate. In some embodiments, an optionally substituted heterocyclic base or an optionally substituted heterocyclic base can include a group that improves the solubility of the compound (for example, —(CH$_2$)$_{1-2}$—O—P(=O)(OW$^{1A}$)$_2$). In some embodiments, an optionally substituted heterocyclic base or an optionally substituted heterocyclic base with one or more protected amino groups can have one of the following structures:

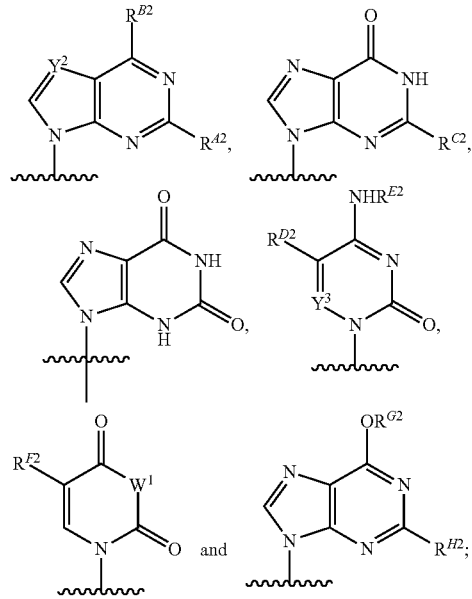

wherein: $R^{A2}$ can be selected from hydrogen, halogen and NHR$^{J2}$, wherein $R^{J2}$ can be selected from hydrogen, —C(=O)R$^{K2}$ and —C(=O)OR$^{L2}$; $R^{B2}$ can be halogen or NHR$^{W2}$, wherein $R^{W2}$ can be selected from hydrogen, an optionally substituted $C_{1-6}$ alkyl, an optionally substituted $C_{2-6}$ alkenyl, an optionally substituted $C_{3-8}$ cycloalkyl, —C(=O)R$^{M2}$ and —C(=O)OR$^{N2}$; $R^{C2}$ can be hydrogen or NHR$^{O2}$, wherein $R^{O2}$ can be selected from hydrogen, —C(=O)R$^{P2}$ and —C(=O)OR$^{Q2}$; $R^{D2}$ can be selected from hydrogen, deuterium, halogen, an optionally substituted $C_{1-6}$ alkyl, an optionally substituted $C_{2-6}$ alkenyl and an optionally substituted $C_{2-6}$ alkynyl; $R^{E2}$ can be selected from hydrogen, hydroxy, an optionally substituted $C_{1-6}$ alkyl, an optionally substituted $C_{3-8}$ cycloalkyl, —C(=O)R$^{R2}$ and —C(=O)OR$^{S2}$; $R^{F2}$ can be selected from hydrogen, halogen, an optionally substituted $C_{1-6}$ alkyl, an optionally substituted $C_{2-6}$ alkenyl and an optionally substituted $C_{2-6}$ alkynyl; $Y^2$ and $Y^3$ can be independently N (nitrogen) or CR$^{I2}$, wherein $R^{I2}$ can be selected from hydrogen, halogen, an optionally substituted $C_{1-6}$ alkyl, an optionally substituted $C_{2-6}$ alkenyl and an optionally substituted $C_{2-6}$ alkynyl; $W^1$ can be NH, —NCH$_2$—OC(=O)CH(NH$_2$)—CH(CH$_3$)$_2$ or —(CH$_2$)$_{1-2}$—O—P(=O)(OW$^{1A}$)$_2$, wherein $W^{1A}$ can be selected from absent hydrogen and an optionally substituted $C_{1-6}$ alkyl; $R^{G2}$ can be an optionally substituted $C_{1-6}$ alkyl; $R^{H2}$ can be hydrogen or NHR$^{T2}$, wherein $R^{T2}$ can be independently selected from hydrogen, —C(=O)R$^{U2}$ and —C(=O)OR$^{V2}$; and $R^{K2}$, $R^{L2}$, $R^{M2}$, $R^{N2}$, $R^{P2}$, $R^{Q2}$, $R^{R2}$, $R^{S2}$, $R^{U2}$ and $R^{V2}$ can be independently selected from hydrogen, $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heterocyclyl, aryl($C_{1-6}$ alkyl), heteroaryl($C_{1-6}$ alkyl) and heterocyclyl($C_{1-6}$ alkyl). In some embodiments, the structures shown above can be modified by replacing one or more hydrogens with substituents selected from the list of substituents provided for the definition of "substituted." Those skilled in the art understand that when $W^{1A}$ is absent, the oxygen atom will have an associated negative charge. In some embodiments, the substituent on the base can result in the formation of a salt of a compound of Formula (I).

In some embodiments, $B^{1A}$ can be an optionally substituted purine base. In other embodiments, $B^{1A}$ can be an optionally substituted pyrimidine base. In some embodiments, $B^{1A}$ can be

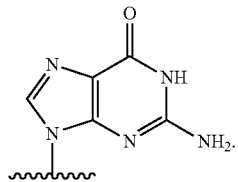 [SMILES: *n1cnc2c(=O)[nH]c(N)nc21]

In other embodiments, $B^{1A}$ can be

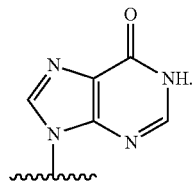 [SMILES: *n1cnc2c(=O)[nH]cnc21]

In still other embodiments, $B^{1A}$ can be

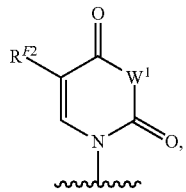

such as

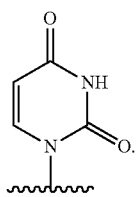 [SMILES: *n1ccc(=O)[nH]c1=O]

In yet still other embodiments, $B^{1A}$ can be

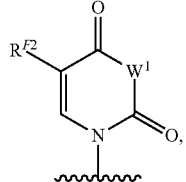

wherein $W^1$ can be —NCH$_2$—OC(=O)CH(NH$_2$)—CH(CH$_3$)$_2$ or —(CH$_2$)$_{1-2}$—O—P(=O)(OW$^{1A}$)$_2$. In some embodiments, $B^{1A}$ can be

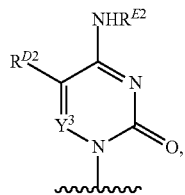

for example,

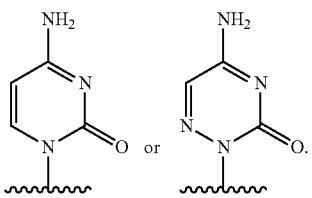 [SMILES: *n1ccc(N)nc1=O ; *n1ncc(N)nc1=O]

In other embodiments, $R^{D2}$ can be hydrogen. In still other embodiments, $B^{1A}$ can be

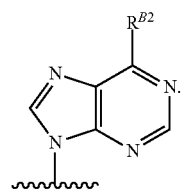

In some embodiments, $R^{B2}$ can be NH$_2$. In other embodiments, $R^{B2}$ can be NHR$^{W2}$, wherein $R^{W2}$ can be —C(=O)R$^{M2}$ or —C(=O)OR$^{N2}$. In still other embodiments, $B^{1A}$ can be

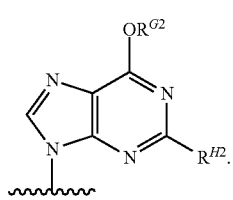

In some embodiments, $B^{1A}$ can be

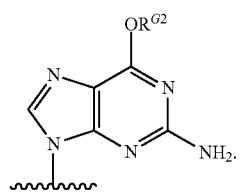

In some embodiments, a compound of Formula (I), or a pharmaceutically acceptable salt thereof, can be used to ameliorate or treat a viral infection, wherein: $B^{1A}$ can be an optionally substituted heterocyclic base or an optionally substituted heterocyclic base with a protected amino group; - - - - - - - - can be absent or a single bond, provided that both - - - - - - - - are absent or both - - - - - - - - are a single bond; when - - - - - - - - are both absent, then $Z^1$ can be absent, $O^1$ can be $OR^{1A}$, $R^{3A}$ can be selected from H, halo, OH, —OC(=O)$R''^A$ and an optionally substituted O-linked amino acid, $R^{4A}$ can be selected from OH, halo, —OC(=O)$R'''^B$ and an optionally substituted O-linked amino acid, or $R^{3A}$ and $R^{4A}$ can be both an oxygen atom connected via a carbonyl to form a 5-membered ring; when - - - - - - - - are each a single bond, then $Z^1$ can be

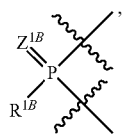

$O^1$ can be O, $R^{3A}$ can be O; $R^{4A}$ can be selected from OH, halo, —OC(=O)$R'''^B$ and an optionally substituted O-linked amino acid; and $R^{1B}$ can be selected from $O^-$, OH, an —O-optionally substituted $C_{1-6}$ alkyl.

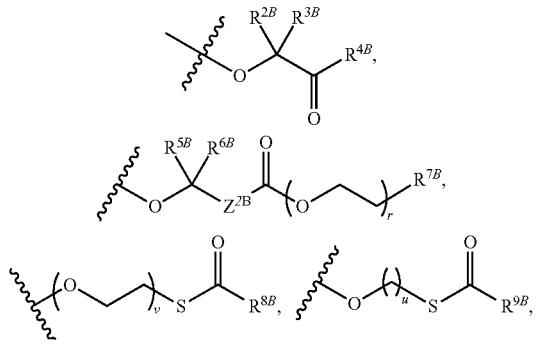

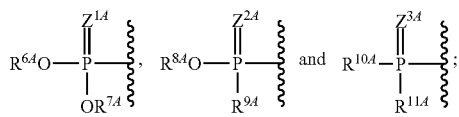

optionally substituted N-linked amino acid and an optionally substituted N-linked amino acid ester derivative; $R^{1A}$ can be selected from hydrogen, an optionally substituted acyl, an optionally substituted O-linked amino acid,

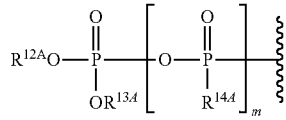

$R^{2A}$ can be halo, an unsubstituted $C_{1-4}$ alkyl, an unsubstituted $C_{2-4}$ alkenyl, —(CH$_2$)$_{1-6}$ halogen or —(CH$_2$)$_{1-6}$N$_3$; $R^{5A}$ can be selected from H, halo, an optionally substituted $C_{1-6}$ alkyl, an optionally substituted $C_{2-6}$ alkenyl and an optionally substituted $C_{2-6}$ alkynyl; $R^{6A}$, $R^{7A}$ and $R^{8A}$ can be independently selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—(CR$^{15A}$R$^{16A}$)$_p$—O—$C_{1-24}$ alkyl, an optionally substituted *—(CR$^{17A}$R$^{18A}$)$_q$—O—$C_{1-24}$ alkenyl,

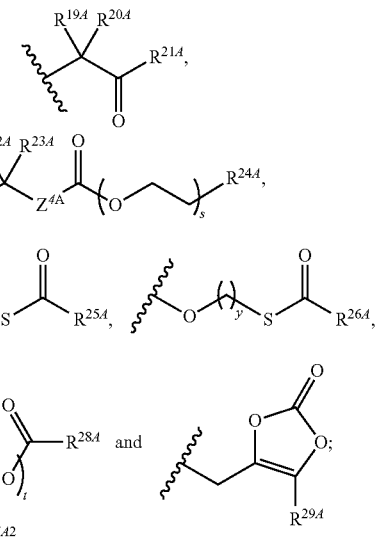

or $R^{6A}$ can be

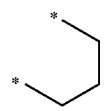

and $R^{7A}$ can be absent or hydrogen; or $R^{6A}$ and $R^{7A}$ can be taken together to form a moiety selected from an optionally substituted

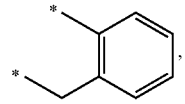

and an optionally substituted

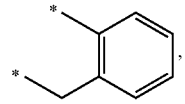

wherein the oxygens connected to $R^{6A}$ and $R^{7A}$, the phosphorus and the moiety form a six-membered to ten-membered ring system; $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, NR$^{30A}$R$^{31A}$, an optionally substituted N-linked amino acid and an optionally substituted N-linked amino acid ester derivative; $R^{10A}$ and $R^{11A}$ can be independently an optionally substituted N-linked amino acid or an optionally substituted N-linked amino acid ester derivative; $R^{12A}$ and $R^{13A}$ can be independently absent or hydrogen; $R^{14A}$ can be absent, hydrogen or methyl; each $R^{15A}$, each $R^{16A}$, each $R^{17A}$ and each $R^{18A}$ can be independently hydrogen, an optionally substituted $C_{1-24}$ alkyl or an alkoxy; $R^{19A}$, $R^{20A}$R$^{22A}$, $R^{23A}$, $R^{2B}$, $R^{3B}$, $R^{5B}$ and $R^{6B}$ can be independently selected from hydrogen, an optionally substituted $C_{1-24}$ alkyl and an optionally substituted aryl; $R^{21A}$ and $R^{4B}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; $R^{24A}$ and $R^{7B}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

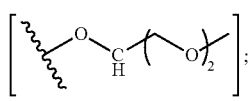

$R^{25A}$, $R^{26A}$, $R^{29A}$, $R^{8B}$ and $R^{9B}$ can be independently selected from hydrogen, an optionally substituted $C_{1-24}$ alkyl and an optionally substituted aryl; $R^{27A1}$ and $R^{27A2}$ can be independently selected from —C≡N, an optionally substituted $C_{2-8}$ organylcarbonyl, an optionally substituted $C_{2-8}$ alkoxycarbonyl and an optionally substituted $C_{2-8}$ organylaminocarbonyl; $R^{28A}$ is selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R^{30A}$ and $R^{31A}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R'''^{A}$ and $R'''^{B}$ can be independently an optionally substituted $C_{1-24}$ alkyl; m, v and w can be 0 or 1; p and q can be independently 1, 2 or 3; r and s can be independently 0, 1, 2 or 3; t is 1 or 2; u and y can be independently 3, 4 or 5; and $Z^{1A}$, $Z^{2A}$, $Z^{3A}$, $Z^{4A}$, $Z^{1B}$ and $Z^{2B}$ can be independently O or S; wherein the viral infection can be caused by a virus selected from a Picornaviridae virus and a Flaviviridae virus; and provided that when the Flaviviridae virus is hepatitis C virus, then the compound of Formula (I), or a pharmaceutically acceptable salt thereof, cannot be selected from:

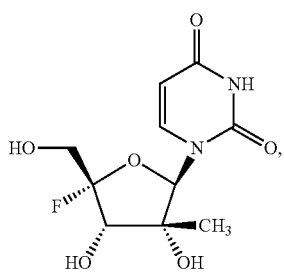

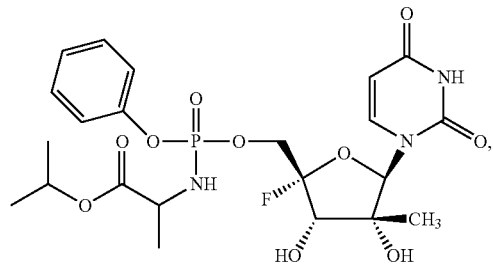

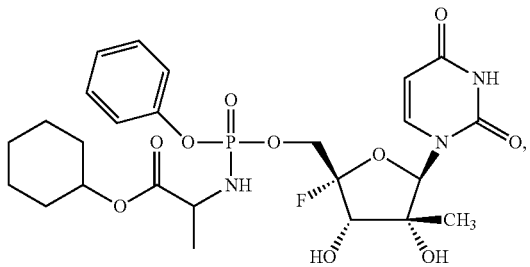

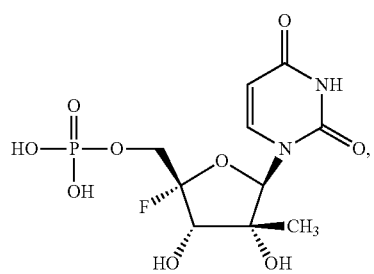

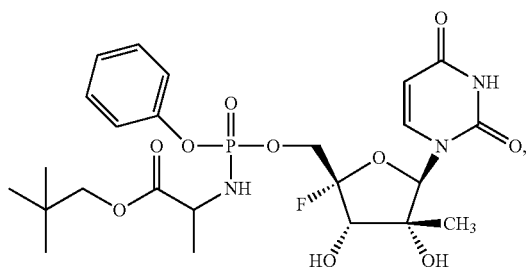

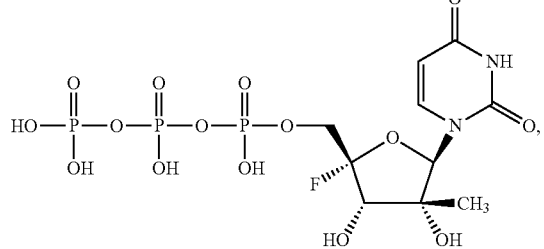

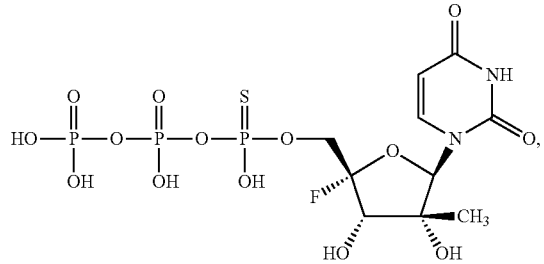

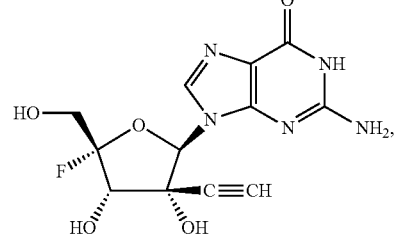

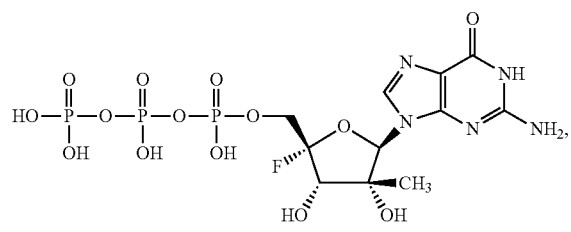
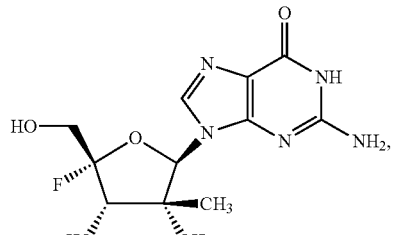
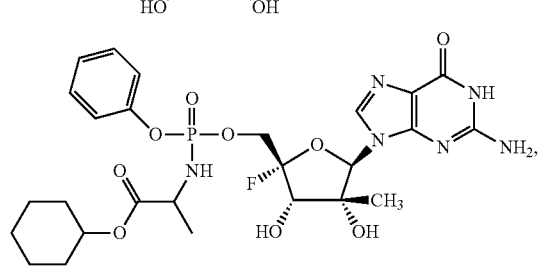
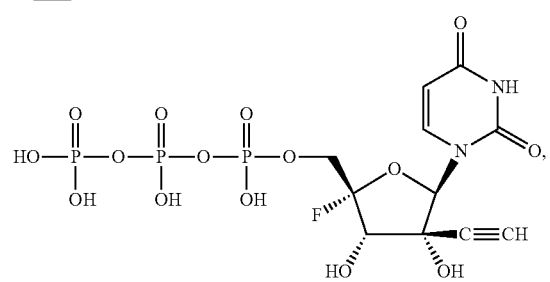
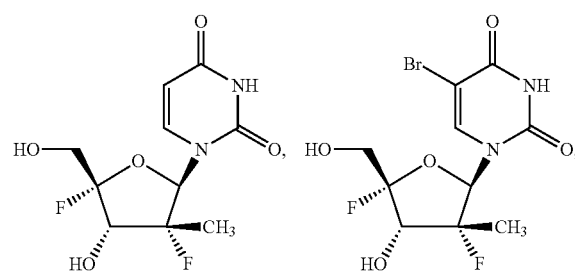
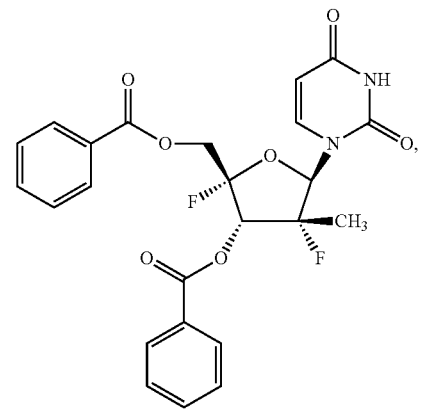
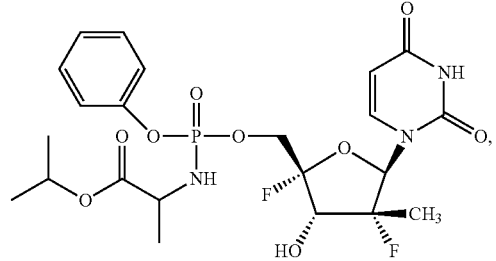
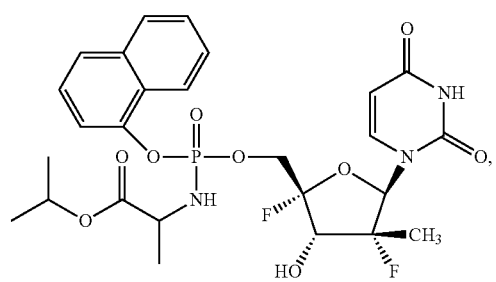
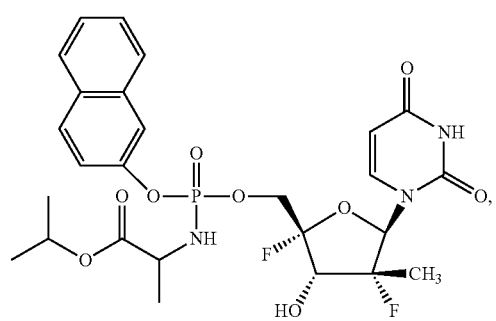
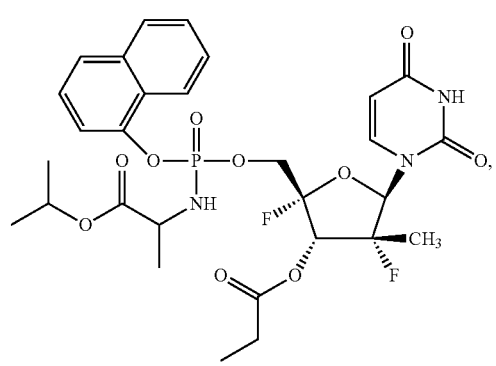
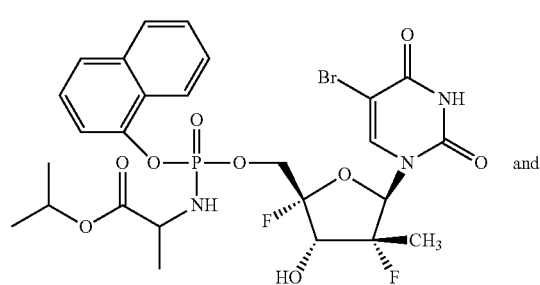

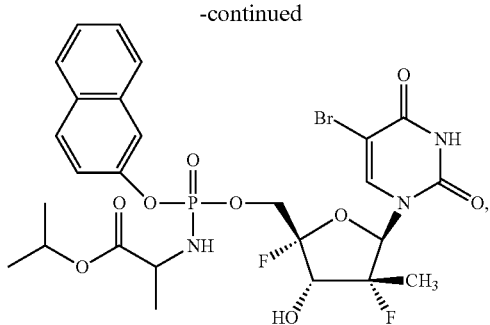

or a pharmaceutically acceptable salt of the foregoing.

In some embodiments, a compound of Formula (I), or a pharmaceutically acceptable salt thereof, can be used to ameliorate or treat a viral infection, wherein: $B^{1A}$ can be an optionally substituted heterocyclic base or an optionally substituted heterocyclic base with a protected amino group; -------- can be absent or a single bond, provided that both -------- are absent or both -------- are a single bond; when -------- are both absent, then $Z^1$ can be absent, $O^1$ can be $OR^{1A}$, $R^{3A}$ can be selected from H, halo, OH, —OC(=O)R''$^A$ and an optionally substituted O-linked amino acid, $R^{4A}$ can be selected from OH, halo, $N_3$, —OC(=O)R''$^B$, an optionally substituted O-linked amino acid and NR''$^{B1}$R''$^{B2}$, or $R^{3A}$ and $R^{4A}$ can be both an oxygen atom connected via a carbonyl to form a 5-membered ring; when -------- are each a single bond, then $Z^1$ can be

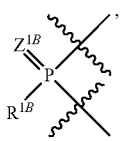

$O^1$ can be O, $R^{3A}$ can be O; $R^{4A}$ can be selected from OH, halo, $N_3$, —OC(=O)R''$^B$, an optionally substituted O-linked amino acid and NR''$^{B1}$R''$^{B2}$; and $R^{1B}$ can be selected from O$^-$, OH, an —O-optionally substituted $C_{1-6}$ alkyl.

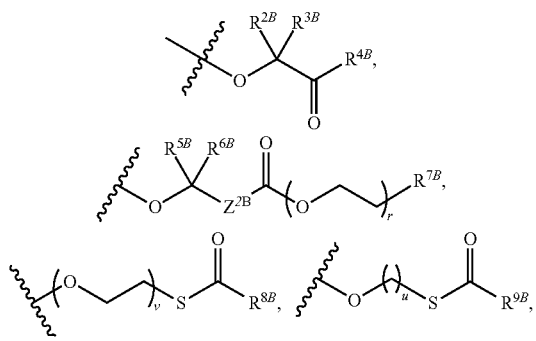

an optionally substituted N-linked amino acid and an optionally substituted N-linked amino acid ester derivative; R''$^a$ and R$^{a2}$ can be independently hydrogen or deuterium; $R^A$ can be hydrogen, deuterium, an unsubstituted $C_{1-3}$ alkyl, an unsubstituted $C_{2-4}$ alkenyl, an unsubstituted $C_{2-3}$ alkynyl or cyano; $R^{1A}$ can be selected from hydrogen, an optionally substituted acyl, an optionally substituted O-linked amino acid,

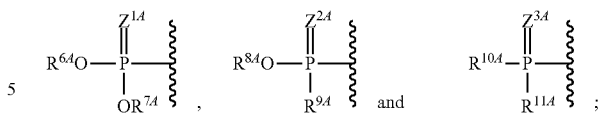

$R^{2A}$ can be hydrogen, halo, an unsubstituted $C_{1-4}$ alkyl, an unsubstituted $C_{2-4}$ alkenyl, —(CH$_2$)$_{1-6}$ halogen, —(CH$_2$)$_{1-6}$N$_3$ or —(CH$_2$)$_{1-6}$NH$_2$; $R^{5A}$ can be selected from the group consisting of H, halo, an optionally substituted $C_{1-6}$ alkyl, an optionally substituted $C_{2-6}$ alkenyl and an optionally substituted $C_{2-6}$ alkynyl; $R^{6A}$, $R^{7A}$ and $R^{8A}$ can be independently selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—(CR$^{15A}$R$^{16A}$)$_p$—O—$C_{1-24}$ alkyl, an optionally substituted *—(CR$^{17A}$R$^{18A}$)$_q$—O—$C_{1-24}$ alkenyl,

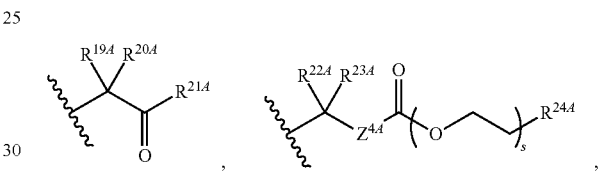

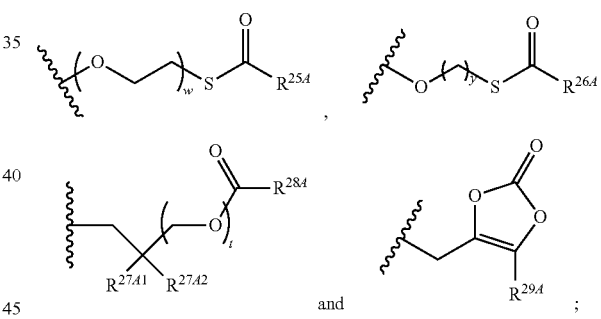

or $R^{6A}$ can be

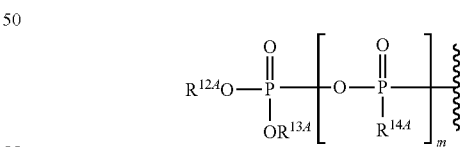

and $R^{7A}$ can be absent or hydrogen; or $R^{6A}$ and $R^{7A}$ can be taken together to form a moiety selected from an optionally substituted

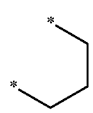

and an optionally substituted

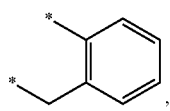, wherein the oxygens connected to $R^{6A}$ and $R^{7A}$, the phosphorus and the moiety form a six-membered to ten-membered ring system; $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, $NR^{30A}R^{31A}$, an optionally substituted N-linked amino acid and an optionally substituted N-linked amino acid ester derivative; $R^{10A}$ and $R^{11A}$ can be independently an optionally substituted N-linked amino acid or an optionally substituted N-linked amino acid ester derivative; $R^{12A}$ and $R^{13A}$ can be independently absent or hydrogen; $R^{14A}$ can be O−, OH or methyl; each $R^{15A}$, each $R^{16A}$, each $R^{17A}$ and each $R^{18A}$ can be independently hydrogen, an optionally substituted $C_{1-24}$ alkyl or an alkoxy; $R^{19A}$, $R^{20A}$, $R^{22A}R^{23A}$, $R^{2B}$, $R^{3B}$, $R^{5B}$ and $R^{6B}$ can be independently selected from hydrogen, an optionally substituted $C_{1-24}$ alkyl and an optionally substituted aryl; $R^{21A}$ and $R^{4B}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; $R^{24A}$ and $R^{7B}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

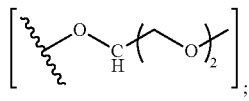;

$R^{25A}$, $R^{26A}$, $R^{29A}$, $R^{8B}$ and $R^{9B}$ can be independently selected from hydrogen, an optionally substituted $C_{1-24}$ alkyl and an optionally substituted aryl; $R^{27A1}$ and $R^{27A2}$ can be independently selected from —C≡N, an optionally substituted $C_{2-8}$ organylcarbonyl, an optionally substituted $C_{2-8}$ alkoxycarbonyl and an optionally substituted $C_{2-8}$ organylaminocarbonyl; $R^{28A}$ can be selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R^{30A}$ and $R^{31A}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R'''^A$ and $R'''^B$ can be independently an optionally substituted $C_{1-24}$ alkyl; $R'''^{B1}$ and $R'''^{B2}$ can be independently hydrogen and an optionally substituted $C_{1-6}$ alkyl; m, v and w can be 0 or 1; p and q can be independently 1, 2 or 3; r and s can be independently 0, 1, 2 or 3; t can be 1 or 2; u and y can be independently 3, 4 or 5; and $Z^{1A}$, $Z^{2A}$, $Z^{3A}$, $Z^{4A}$, $Z^{1B}$ and $Z^{2B}$ can be independently O or S; wherein the viral infection is caused by a virus selected from a Picornaviridae virus and a Flaviviridae virus; and provided that when the Flaviviridae virus is hepatitis C virus, then the compound of Formula (I), or a pharmaceutically acceptable salt thereof, cannot be selected from a compound that is shown in the paragraphs that begins with the paragraph that starts with the lines "In some embodiments, a compound of Formulae (I) and/or (II), or a pharmaceutically acceptable salt of the foregoing, may not be selected from:

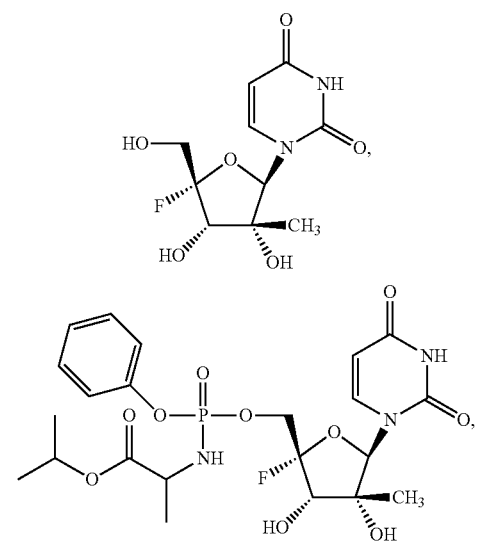

and ends with the paragraph that follows and recites in its last lines

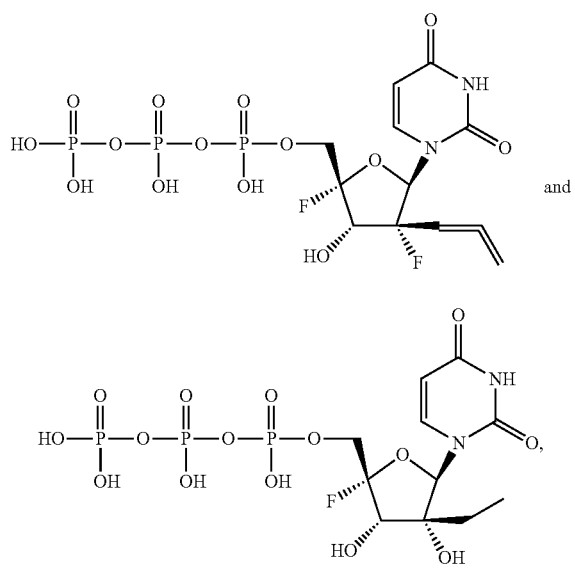 [SMILES: C=C=C[C@]1(F)[C@H](n2ccc(=O)[nH]c2=O)O[C@](F)(COP(=O)(O)OP(=O)(O)OP(=O)(O)O)[C@H]1O ; CC[C@]1(O)[C@H](n2ccc(=O)[nH]c2=O)O[C@](F)(COP(=O)(O)OP(=O)(O)OP(=O)(O)O)[C@H]1O]

or a pharmaceutically acceptable salt of the foregoing,

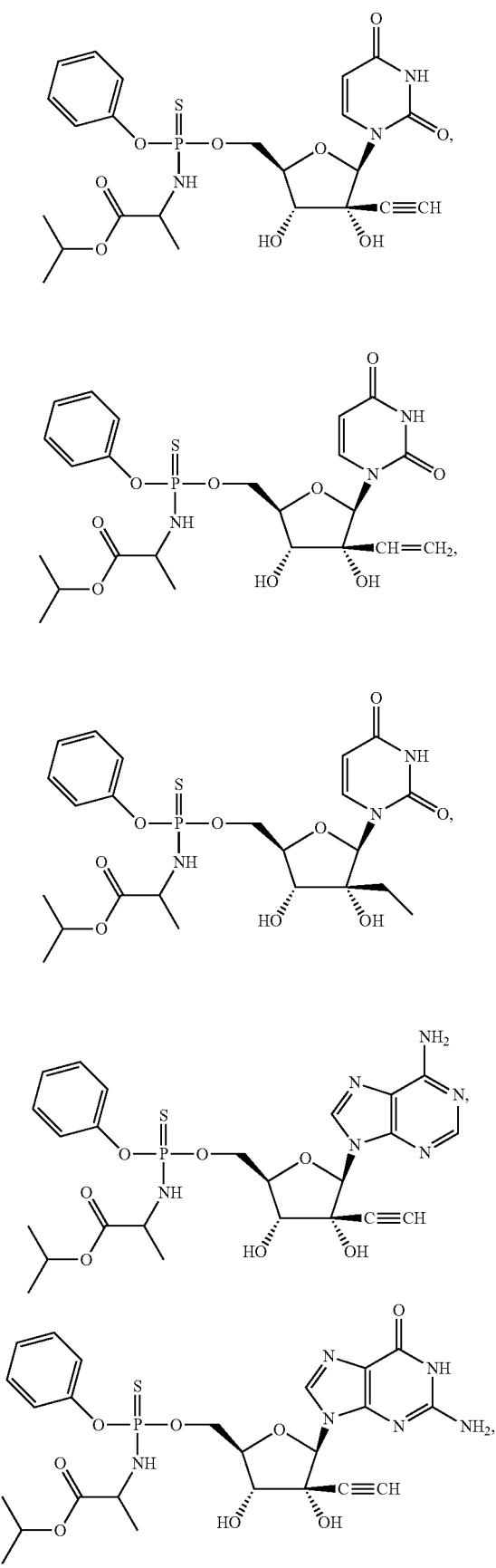
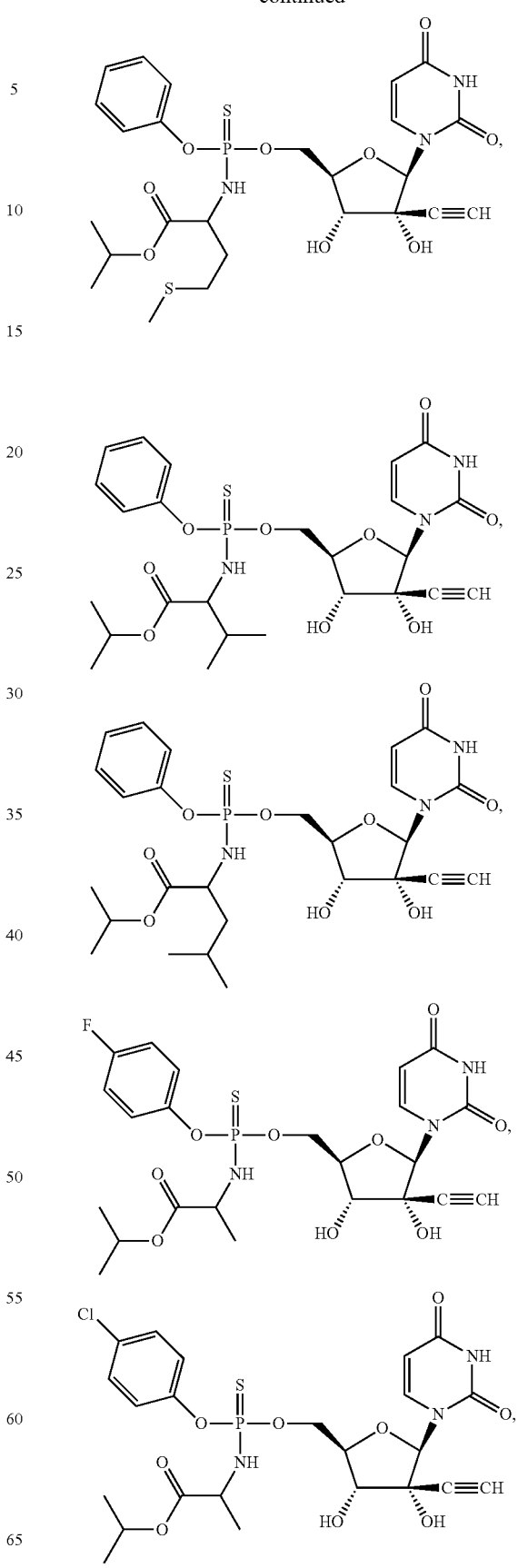

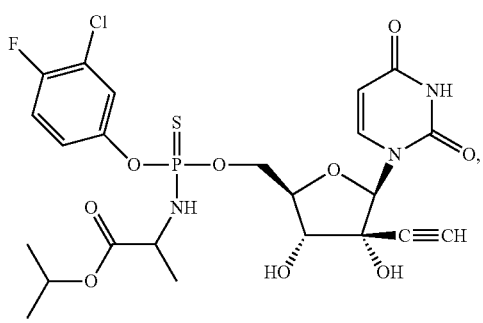
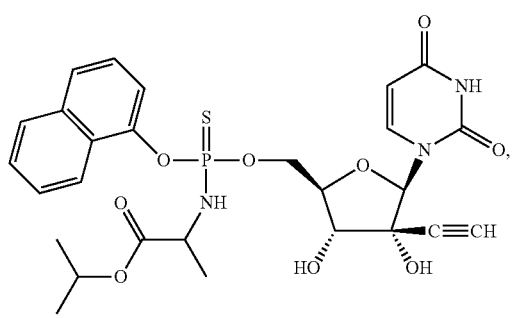
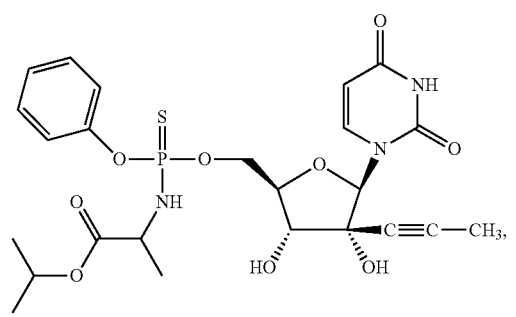
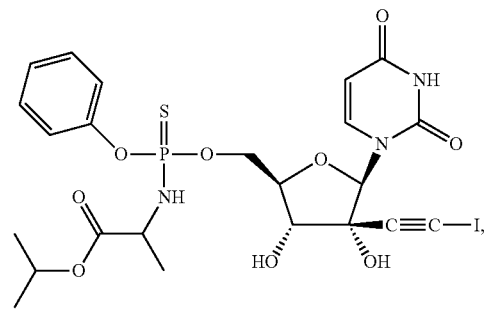
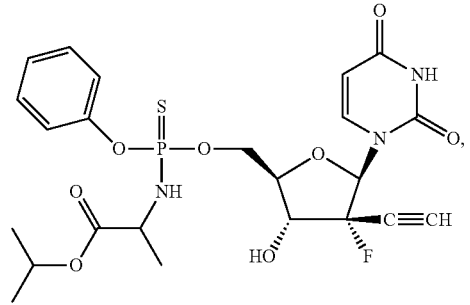
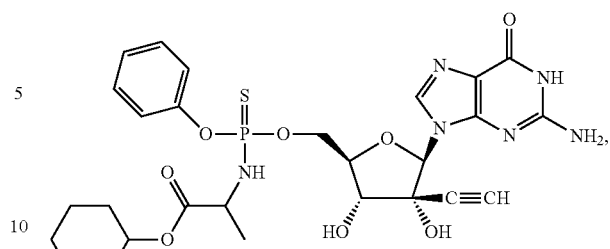
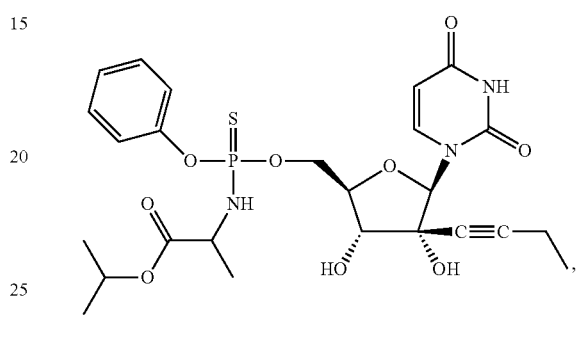
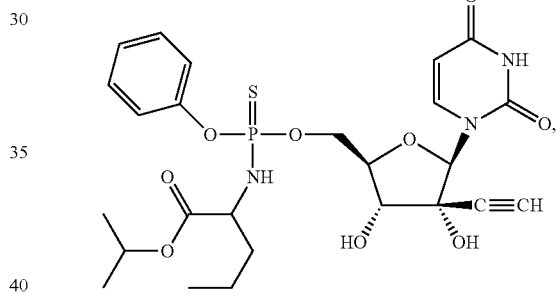
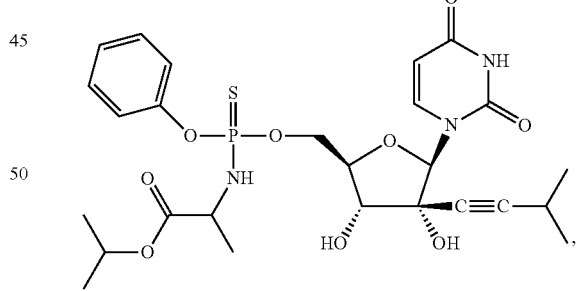
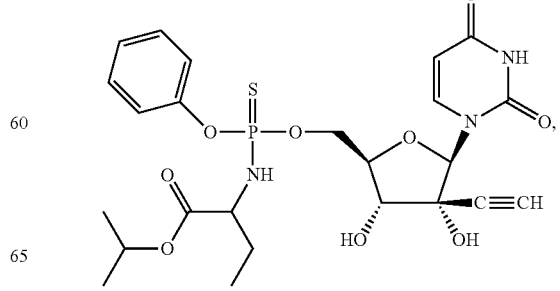

-continued

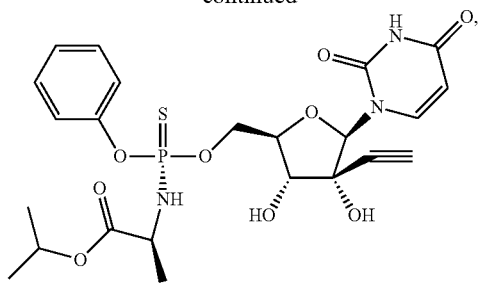

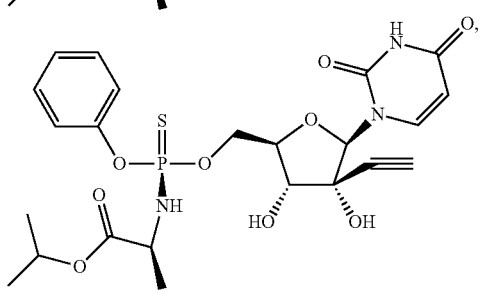

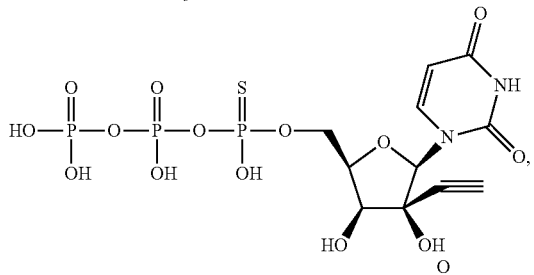

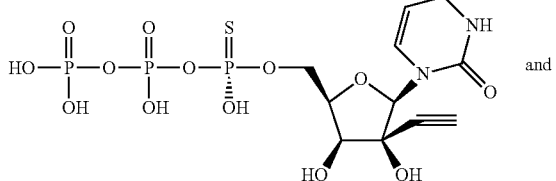

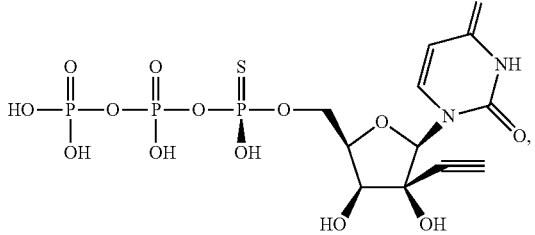

or a pharmaceutically acceptable salt of the foregoing.

In some embodiments, when $R^{2A}$ is halo (such as fluoro); - - - - - - - are both absent; $Z^1$ is absent; $O^1$ is $OR^{1A}$; $B^{1A}$ is selected from an optionally substituted

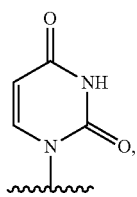 [SMILES: *n1ccc(=O)[nH]c1=O]

an optionally substituted

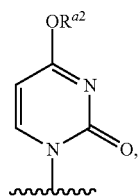

an optionally substituted

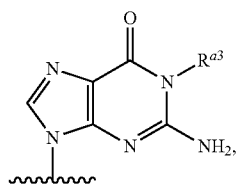

an optionally substituted

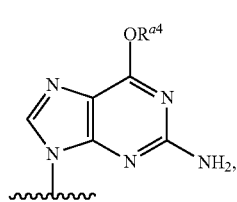

an optionally substituted

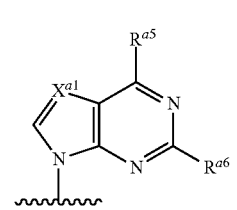

and an optionally substituted

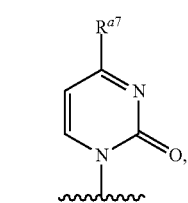

wherein $R^{a2}$ is an optionally substituted $C_{1-6}$ alkyl or an optionally substituted $C_{3-6}$ cycloalkyl, $R^{a3}$ and $R^{a4}$ are independently selected from hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl, $R^{a5}$ is $NHR^{a8}$, and $R^{a6}$ is hydrogen, halogen or $NHR^{a9}$; $R^{a7}$ is $NHR^{a10}$; $R^{a8}$ is selected from hydrogen, an optionally substituted $C_{1-6}$ alkyl, an optionally substituted $C_{3-6}$ alkenyl, an optionally substituted $C_{3-6}$ cycloalkyl, —C(=O)$R^{a11}$ and —C(=O) $OR^{a12}$; $R^{a9}$ is selected from hydrogen, an optionally substituted $C_{1-6}$ alkyl, an optionally substituted $C_{3-6}$ alkenyl, an optionally substituted $C_{3-6}$ cycloalkyl, —C(=O)$R^{a13}$ and —C(=O)O$R^{a14}$; $R^{a10}$ is selected from hydrogen, an optionally substituted $C_{1-6}$ alkyl, an optionally substituted $C_{3-6}$ alkenyl, an optionally substituted $C_{3-6}$ cycloalkyl, —C(=O)$R^{a15}$ and —C(=O)O$R^{a16}$; $X^{a1}$ is N or —C$R^{a17}$; $R^{a17}$ is selected from hydrogen, halogen, an optionally substituted $C_{1-6}$ alkyl, an optionally substituted $C_{2-6}$ alkenyl and an optionally substituted $C_{2-6}$ alkynyl; $R^{a11}$, $R^{a12}$, $R^{a13}$, $R^{a14}$, $R^{a15}$ and $R^{a16}$ are independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heterocyclyl, aryl($C_{1-6}$ alkyl), heteroaryl($C_{1-6}$ alkyl) and heterocyclyl($C_{1-6}$ alkyl); then $R^{3A}$ is selected from H, halo, and an optionally substituted O-linked amino acid; and $R^{4A}$ is selected from OH, halo, —OC(=O)$R^{nA}$ and an optionally substituted O-linked amino acid; or then $R^{4A}$ is an optionally substituted O-linked amino acid; and $R^{3A}$ is selected from H, halo, OH, —OC(=O)$R^{nA}$ and an optionally substituted O-linked amino acid; or then $R^{3A}$ and $R^{4A}$ are both an oxygen atom connected via a carbonyl to form a 5-membered ring; or then $R^{1A}$ is

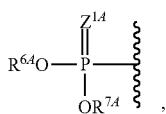

wherein $R^{6A}$ and $R^{7A}$ are independently

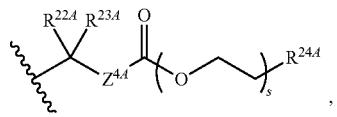

wherein s is 1, 2 or 3,

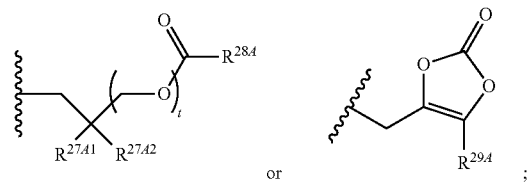

or then $R^{1A}$ is

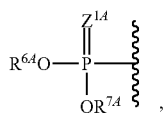

wherein $R^{6A}$ and $R^{7A}$ are taken together to form a moiety selected from an optionally substituted

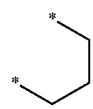 [SMILES: *CCC*]

and an optionally substituted

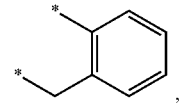

wherein the oxygens connected to $R^{6A}$ and $R^{7A}$, the phosphorus and the moiety form a six-membered to ten-membered ring system. In some embodiments, when $R^{2A}$ is halo (such as fluoro); -------- are each a single bond; then $R^{4A}$ is —OC(=O)$R^{nB}$ or an optionally substituted O-linked amino acid. In some embodiments, when $R^{2A}$ is an unsubstituted $C_{1-4}$ alkyl, an unsubstituted $C_{2-4}$ alkenyl, an unsubstituted $C_{2-4}$ alkynyl, —(CH$_2$)$_{1-6}$ halogen or —(CH$_2$)$_{1-6}$ N$_3$; -------- are both absent; $Z^1$ is absent; $O^1$ is O$R^{1A}$; $R^{3A}$ is OH, —OC(=O)$R^{nA}$ or an optionally substituted O-linked amino acid; and $R^{4A}$ is halo; then $R^{5A}$ is selected from an optionally substituted $C_{1-6}$ alkyl, an optionally substituted $C_{2-6}$ alkenyl and an optionally substituted $C_{2-6}$ alkynyl. In some embodiments, when $R^{2A}$ is an unsubstituted $C_{1-4}$ alkyl, an unsubstituted $C_{2-4}$ alkenyl, an unsubstituted $C_{2-4}$ alkynyl, —(CH$_2$)$_{1-6}$ halogen or —(CH$_2$)$_{1-6}$ N$_3$; -------- are both absent; $Z^1$ is absent; $O^1$ is O$R^{1A}$; $R^{4A}$ is halo; and $R^{5A}$ is H or halo; then $R^{3A}$ is H or halo. In some embodiments, when $R^{2A}$ is an unsubstituted $C_{1-4}$ alkyl, an unsubstituted $C_{2-4}$ alkenyl, an unsubstituted $C_{2-4}$ alkynyl, —(CH$_2$)$_{1-6}$ halogen or —(CH$_2$)$_{1-6}$N$_3$; -------- are both absent; $Z^1$ is absent; $O^1$ is O$R^{1A}$; $R^{3A}$ is OH, —OC(=O)$R^{nA}$ or an optionally substituted O-linked amino acid; $R^{4A}$ is halo; $R^{5A}$ is H or halo; and $R^{1A}$ is

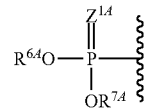

then at least one of $R^{6A}$ and $R^{7A}$ is

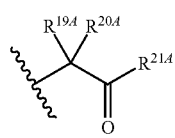

wherein $R^{21A}$ is independently selected from an optionally substituted —O-heteroaryl and an optionally substituted —O-monocyclic heterocyclyl; or then at least one of $R^{6A}$ and $R^{7A}$ is

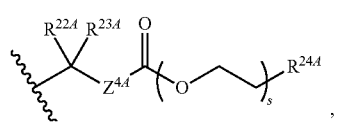

wherein s is 1, 2 or 3; or then at least one of $R^{6A}$ and $R^{7A}$ is

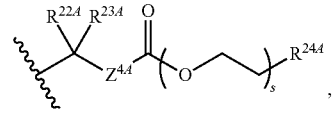

wherein s is 0 and $R^{24A}$ is an optionally substituted —O-heteroaryl or an optionally substituted —O-monocyclic heterocyclyl. In some embodiments, when $R^{2A}$ is an unsubstituted $C_{1-4}$ alkyl, an unsubstituted $C_{2-4}$ alkenyl, an unsubstituted $C_{2-4}$ alkynyl, —$(CH_2)_{1-6}$ halogen or —$(CH_2)_{1-6}N_3$; - - - - - - - - are both absent; $Z^1$ is absent; $O^1$ is $OR^{1A}$; $R^{3A}$ is OH, —OC(=O)R''$^A$ or an optionally substituted O-linked amino acid; $R^{4A}$ is halo; $R^{5A}$ is H or halo; and $R^{1A}$ is

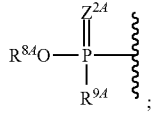

then $R^{8A}$ is

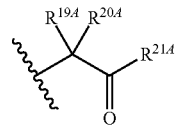

wherein $R^{21A}$ is independently selected from an optionally substituted —O-heteroaryl and an optionally substituted —O-monocyclic heterocyclyl; or then $R^{8A}$ is

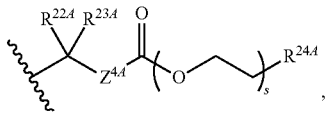

wherein s is 1, 2 or 3; or then $R^{8A}$ is

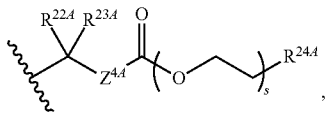

wherein s is 0 and $R^{24A}$ is an optionally substituted —O-heteroaryl, an optionally substituted —O-monocyclic heterocyclyl or

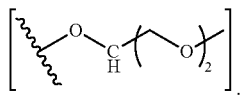

In some embodiments, when - - - - - - - - are both absent; $Z^1$ is absent; $O^1$ is OH; $R^{2A}$ is methyl; $R^{3A}$ is OH; then $R^{4A}$ is halo, —OC(=O)R'''$^B$ or an optionally substituted O-linked amino acid. In some embodiments, when - - - - - - - - are both absent; $Z^1$ is absent; $O^1$ is $OR^{1A}$; $R^{2A}$ is halo (for example, F); $R^{3A}$ is OH or —OC(=O)R''$^A$; $R^{4A}$ is halo (for example, F); and $R^{5A}$ is methyl, ethyl or ethenyl; then $R^{1A}$ cannot be selected from H,

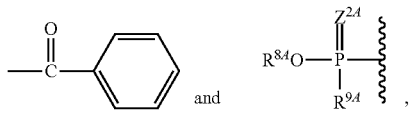

wherein $R^{8A}$ is an unsubstituted aryl; $R^{9A}$ is

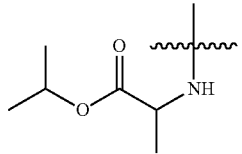 [SMILES: *NC(C)C(=O)OC(C)C]

and $Z^{2A}$ is oxygen. In some embodiments, $R^{1A}$ is not hydrogen (H), for example, when $R^{3A}$ is halo (such as fluoro) and $R^{4A}$ is OH. In some embodiments, $R^{1A}$ is not

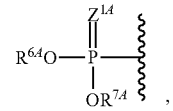

wherein $Z^{1A}$ is O and $R^{6A}$ is

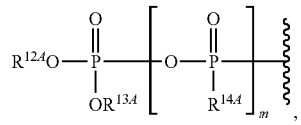

for example, when $R^{4A}$ is halo (such as fluoro) and $R^{3A}$ is OH. In some embodiments, $R^{2A}$ is not hydrogen (H). In some embodiments, $R^{2A}$ is not halogen. In some embodiments, $R^{2A}$ is not fluoro (F). In some embodiments, $R^{2A}$ is not —CN. In some embodiments, $R^{2A}$ is not —$CHF_2$. In some embodiments, $R^{5A}$ is not hydrogen or halo. In some embodiments, $R^{5A}$ is not —OH. In some embodiments, $R^{4A}$ is not hydrogen (H). In some embodiments, $R^{4A}$ is not halo. In some embodiments, $R^{4A}$ is not fluoro (F). In some embodiments, $R^{4A}$ is not chloro (Cl). In some embodiments, $R^{2A}$ is not an unsubstituted $C_{1-4}$ alkyl. In some embodiments, $R^{2A}$ is not an unsubstituted $C_{2-4}$ alkenyl. In some embodiments, $R^{2A}$ is not an unsubstituted $C_{2-4}$ alkynyl. In some embodiments, $R^{2A}$ is not —$(CH_2)_{1-6}$ halogen. In some embodiments, $R^{2A}$ is not —$(CH_2)_{1-6}N_3$. In some embodiments, $R^{4A}$ is not hydrogen, when $R^{5A}$ is fluoro. In some embodiments, $R^{6A}$ is not an optionally substituted aryl. In some embodiments, $R^{6A}$ is not an unsubstituted aryl. In some embodiments, $R^{9A}$ is not N-alanine isopropyl ester. In some embodiments, $R^{5A}$ is not an optionally substituted $C_{1-6}$ alkyl. For example, $R^{5A}$ is not an unsubstituted $C_{1-6}$ alkyl, such as methyl. In some embodiments, $B^{1A}$ is not an optionally substituted uracil, for example, a halo-substituted uracil. In some embodiments, when $R^{1A}$ is hydrogen, an optionally substituted acyl,

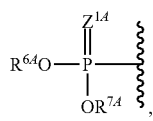

wherein $R^{6A}$ can be

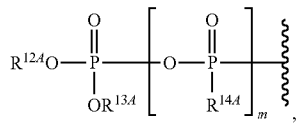

or

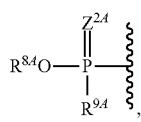

wherein $R^{8A}$ is an unsubstituted or substituted phenyl or an unsubstituted or substituted naphthyl and $R^{9A}$ is an optionally substituted N-linked amino acid or an optionally substituted N-linked amino acid ester; $R^{2A}$ is fluoro, $R^{3A}$ is OH or —C(=O)-unsubstituted or substituted phenyl; $R^{4A}$ is fluoro; and $R^{5A}$ is a $C_{1-4}$ alkyl (such as methyl); then $B^{1A}$ cannot be an optionally substituted pyrimidine base, such as

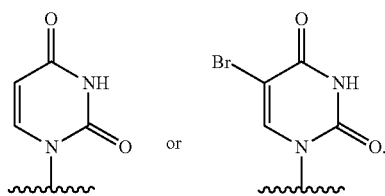 [SMILES: *n1ccc(=O)[nH]c1=O ; *n1cc(Br)c(=O)[nH]c1=O]

In some embodiments, when $R^{1A}$ is

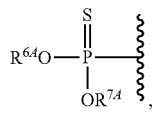

$R^{2A}$ is H, $R^{3A}$ is OH and $R^{4A}$ is OH or halogen (such as F), then $R^{5A}$ is not an optionally substituted $C_{1-6}$ alkyl, an optionally substituted $C_{2-6}$ alkenyl or an optionally substituted $C_{2-6}$ alkynyl.

Some embodiments disclosed herein relate to a compound of Formula (II), or a pharmaceutically acceptable salt thereof, and a use of a compound of Formula (II), or a pharmaceutically acceptable salt thereof:

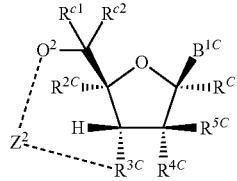

wherein: $B^{1C}$ can be an optionally substituted heterocyclic base or an optionally substituted heterocyclic base with a protected amino group; - - - - - - - - can be absent or a single bond, provided that both - - - - - - - - are absent or both - - - - - - - - are a single bond; when - - - - - - - - are both absent, then $Z^2$ can be absent, $O^2$ can be $OR^{1C}$, $R^{3C}$ can be selected from H, halo, OH, $N_3$, —OC(=O)$R''^C$, an optionally substituted O-linked amino acid and $NR''^{D1}R''^{D2}$, $R^{4C}$ can be selected from H, OH, halo, —OC(=O)$R''^D$, an optionally substituted O-linked amino acid and $NR''^{D}R''^{D2}$, or $R^{3C}$ and $R^{4C}$ can be both an oxygen atom connected via a carbonyl to form a 5-membered ring; when - - - - - - - - are each a single bond, then $Z^2$ can be

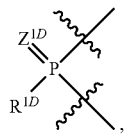

$O^2$ can be O, $R^{3C}$ can be O; $R^{4C}$ can be selected from OH, halo, $N_3$, —OC(=O)$R''^D$ and an optionally substituted O-linked amino acid; and $R^{1D}$ can be selected from O$^-$, OH, an —O-optionally substituted $C_{1-6}$ alkyl.

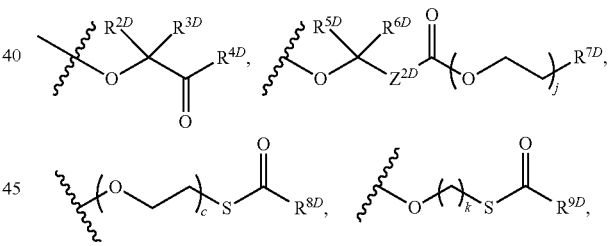

an optionally substituted N-linked amino acid and an optionally substituted N-linked amino acid ester derivative; $R^{c1}$ and $R^{c2}$ can be independently hydrogen or deuterium; $R^C$ can be hydrogen, deuterium, an unsubstituted $C_{1-3}$ alkyl, an unsubstituted $C_{2-4}$ alkenyl, an unsubstituted $C_{2-3}$ alkynyl or cyano; $R^{1C}$ can be selected from hydrogen, an optionally substituted acyl, an optionally substituted O-linked amino acid,

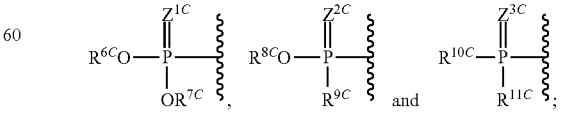

$R^{2C}$ can be halo, an unsubstituted $C_{1-4}$ alkyl, an unsubstituted $C_{2-4}$ alkenyl, an unsubstituted $C_{2-4}$ alkynyl, —CHF$_2$, —(CH$_2$)$_{1-6}$ halogen, —(CH$_2$)$_{1-6}$N$_3$, —(CH$_2$)$_{1-6}$NH$_2$ or —CN; $R^{5C}$ can be selected from H, halo, OH, an optionally substituted $C_{1-6}$ alkyl, an optionally substituted $C_{2-6}$ alkenyl and an optionally substituted $C_{2-6}$ alkynyl; $R^{6C}$, $R^{7C}$ and $R^{8C}$ can be independently selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—$(CR^{15C}R^{16C})_f$—O—$C_{1-24}$ alkyl, an optionally substituted *—$(CR^{17C}R^{18C})_g$—O—$C_{1-24}$ alkenyl,

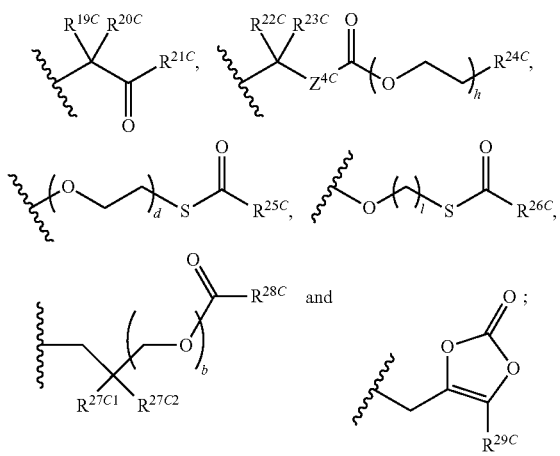

or $R^{6C}$ can be

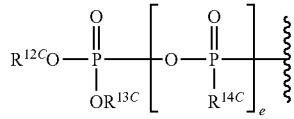

and $R^{7C}$ can be absent or hydrogen; or $R^{6C}$ and $R^{7C}$ can be taken together to form a moiety selected from an optionally substituted

and an optionally substituted

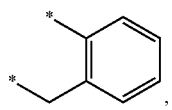

wherein the oxygens connected to $R^{6C}$ and $R^{7C}$, the phosphorus and the moiety form a six-membered to ten-membered ring system; $R^{9C}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, $NR^{30C}R^{31C}$, an optionally substituted N-linked amino acid and an optionally substituted N-linked amino acid ester derivative; $R^{10C}$ and $R^{11C}$ can be independently an optionally substituted N-linked amino acid or an optionally substituted N-linked amino acid ester derivative; $R^{12C}$ and $R^{13C}$ can be independently absent or hydrogen; $R^{14C}$ can be $O^-$, OH or methyl; each $R^{15C}$, each $R^{16C}$, each $R^{17C}$ and each $R^{18C}$ can be independently hydrogen, an optionally substituted $C_{1-24}$ alkyl or an alkoxy; $R^{19C}$, $R^{20C}$, $R^{22C}$, $R^{23C}$, $R^{2D}$, $R^{3D}$, $R^{5D}$ and $R^{6D}$ can be independently selected from hydrogen, an optionally substituted $C_{1-24}$ alkyl and an optionally substituted aryl; $R^{21C}$ and $R^{4D}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; $R^{24C}$ and $R^{7D}$ can be independently selected of hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

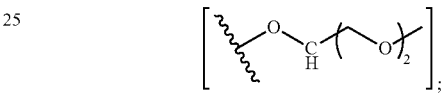

$R^{25C}$, $R^{26C}$, $R^{29C}$, $R^{8D}$ and $R^{9D}$ can be independently selected from hydrogen, an optionally substituted $C_{1-24}$ alkyl and an optionally substituted aryl; $R^{27C1}$ and $R^{27C2}$ can be independently selected from —C≡N, an optionally substituted $C_{2-8}$ organylcarbonyl, an optionally substituted $C_{2-8}$ alkoxycarbonyl and an optionally substituted $C_{2-8}$ organylaminocarbonyl; $R^{28C}$ can be selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R^{30C}$ and $R^{31C}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl and an optionally substituted aryl($C_{1-4}$ alkyl); $R'''^C$ and each $R'''^D$ can be independently an optionally substituted $C_{1-24}$ alkyl; each $R'''^{D1}$ and each $R'''^{D2}$ can be independently hydrogen or an optionally substituted $C_{1-6}$ alkyl; c, d and e can be independently 0 or 1; f and g can be independently 1, 2 or 3; h and j can be independently 0, 1, 2 or 3; b can be 1 or 2; k and l can be independently 3, 4 or 5; and $Z^{1C}$, $Z^{2C}$, $Z^{3C}$, $Z^{4C}$, $Z^{1D}$ and $Z^{2D}$ can be independently oxygen (O) or sulfur (S).

A compound of Formula (II) can be a nucleoside, a nucleotide (including a monophosphate, a diphosphate, a triphosphate, thiomonophosphate, alpha-thiodiphosphate and/or alpha-thiotriphosphate) or a nucleotide prodrug. In some embodiments, - - - - - - - - can be both absent, $Z^2$ can be absent, $O^2$ can be $OR^{1C}$, $R^{3C}$ can be selected from H, halo, OH, —OC(=O)R'''$^C$ and an optionally substituted O-linked amino acid, $R^{4C}$ can be selected from OH, halo, —OC(=O)R'''$^D$ and an optionally substituted O-linked amino acid, or $R^{3C}$ and $R^{4C}$ can be both an oxygen atom connected via a carbonyl to form a 5-membered ring.

A variety of substituents can be attached to the 5'-position of Formula (II) when both - - - - - - are absent. In some embodiments, $R^{1C}$ can be hydrogen. In some embodiments, $R^{1C}$ can be an optionally substituted acyl. For example, $R^{1C}$ can be —C(=O)$R^{39C}$, wherein $R^{39C}$ can be selected from an optionally substituted $C_{1-12}$ alkyl, an optionally substituted $C_{2-12}$ alkenyl, an optionally substituted $C_{2-12}$ alkynyl, an optionally substituted $C_{3-8}$ cycloalkyl, an optionally substituted $C_{5-8}$ cycloalkenyl, an optionally substituted $C_{6-10}$ aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, $R^{39C}$ can be a substituted $C_{1-12}$ alkyl. In other embodiments, $R^{39C}$ can be an unsubstituted $C_{1-12}$ alkyl. In some embodiments, $R^{1C}$ can be —C(=O)-unsubstituted $C_{1-4}$ alkyl. In some embodiments, both $R^{c1}$ and $R^{c2}$ can be hydrogen. In other embodiments, $R^{c1}$ can be hydrogen and $R^{c2}$ can be deuterium. In still other embodiments, both $R^{c1}$ and $R^{c2}$ can be deuterium.

In still other embodiments, $R^{1C}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. In some embodiments, the O-linked amino acid can have the structure

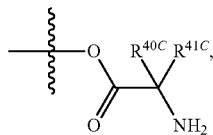

wherein $R^{40C}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{41C}$ can be hydrogen or an optionally substituted $C_{1-4}$ alkyl; or $R^{40C}$ and $R^{41C}$ can be taken together to form an optionally substituted $C_{3-6}$ cycloalkyl. Those skilled in the art understand that when $R^{1C}$ is an optionally substituted O-linked amino acid, the oxygen of $R^{1C}$O— of Formula (II) is part of the optionally substituted O-linked amino acid. For example, when $R^{1C}$ is

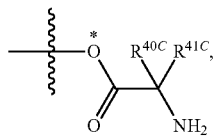

the oxygen indicated with "*" is the oxygen of $R^{1C}$O— of Formula (I).

When $R^{40C}$ is substituted, $R^{40C}$ can be substituted with one or more substituents selected from N-amido, mercapto, alkylthio, an optionally substituted aryl, hydroxy, an optionally substituted heteroaryl, O-carboxy and amino. In some embodiments, $R^{40C}$ can be an unsubstituted $C_{1-6}$ alkyl, such as those described herein. In some embodiments, $R^{40C}$ can be hydrogen. In other embodiments, $R^{40C}$ can be methyl. In some embodiments, $R^{41C}$ can be hydrogen. In other embodiments, $R^{41C}$ can be an optionally substituted $C_{1-4}$ alkyl, such as methyl, ethyl, n-propyl, isopropyl, n-butyl, isobutyl and tert-butyl. In some embodiments, $R^{41C}$ can be methyl. Depending on the groups that are selected for $R^{40C}$ and $R^{41C}$, the carbon to which $R^{40C}$ and $R^{41C}$ are attached may be a chiral center. In some embodiment, the carbon to which $R^{40C}$ and $R^{41C}$ are attached may be a (R)-chiral center. In other embodiments, the carbon to which $R^{40C}$ and $R^{41C}$ are attached may be a (S)-chiral center.

Examples of suitable

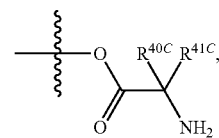

include the following:

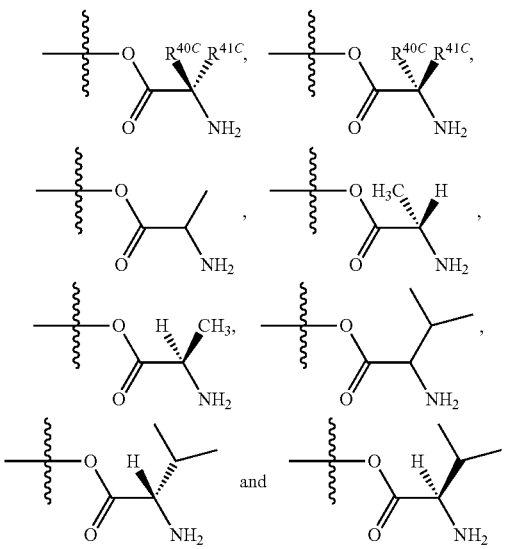

In some embodiments, $R^{1C}$ can be

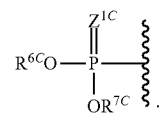

In some embodiments, $R^{6C}$ and $R^{7C}$ can be both hydrogen. In other embodiments, $R^{6C}$ and $R^{7C}$ can be both absent. In still other embodiments, at least one $R^{6C}$ and $R^{7C}$ can be absent. In yet still other embodiments, at least one $R^{6C}$ and $R^{7C}$ can be hydrogen. Those skilled in the art understand that when $R^{6C}$ and/or $R^{7C}$ are absent, the associated oxygen(s) will have a negative charge. For example, when $R^{6C}$ is absent, the oxygen associated with $R^{6C}$ will have a negative charge. In some embodiments, $Z^{1C}$ can be O (oxygen). In other embodiments, $Z^{1C}$ can be S (sulfur). In some embodiments, $R^{1C}$ can be a monophosphate. In other embodiments, $R^{1C}$ can be a monothiophosphate.

In some embodiments, $R^{1C}$ can be

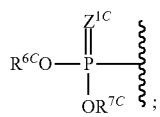

$R^{6C}$ can be

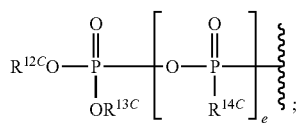

$R^{7C}$ can be absent or hydrogen; $R^{12C}$ and $R^{13C}$ can be independently absent or hydrogen; $R^{14C}$ can be O⁻, OH or methyl; and e can be 0 or 1. In some embodiments, e can be 0, and $R^{7C}$, $R^{12C}$ and $R^{13C}$ can be independently absent or hydrogen. In other embodiments, e can be 1, and $R^{7C}$, $R^{12C}$ and $R^{13C}$ can be independently absent or hydrogen; and $R^{14C}$ can be O⁻, OH or methyl. In some embodiments, e can be 1, and $R^{7C}$, $R^{12C}$ and $R^{13C}$ can be independently absent or hydrogen; and $R^{14C}$ can be O⁻ or OH. In other embodiments, e can be 1, and $R^{7C}$, $R^{12C}$ and $R^{13C}$ can be independently absent or hydrogen; and $R^{14C}$ can be methyl. Those skilled in the art understand that when e is 0, $R^{6C}$ can be a diphosphate, when $Z^{1C}$ is oxygen, or an alpha-thiodiphosphate, when $Z^{1C}$ is sulfur. Likewise, those skilled in the art understand that when e is 1, $R^{6C}$ can be a triphosphate, when $Z^{1C}$ is oxygen, or an alpha-thiotriphosphate, when $Z^{1C}$ is sulfur.

In some embodiments, when $R^{1C}$ is

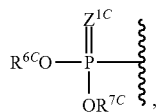

one of $R^{6C}$ and $R^{7C}$ can be hydrogen, and the other of $R^{6C}$ and $R^{7C}$ can be selected from an optionally substituted $C_1$ 24 alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, one of $R^{6C}$ and $R^{7C}$ can be hydrogen, and the other of $R^{6C}$ and $R^{7C}$ can be an optionally substituted $C_{1-24}$ alkyl. In other embodiments, both $R^{6C}$ and $R^{7C}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, both $R^{6C}$ and $R^{7C}$ can be an optionally substituted $C_{1-24}$ alkyl. In other embodiments, both $R^{6C}$ and $R^{7C}$ can be an optionally substituted $C_{2-24}$ alkenyl. In some embodiments, $R^{6C}$ and $R^{7C}$ can be independently an optionally substituted group selected from the following: myristoleyl, myristyl, palmitoleyl, palmityl, sapienyl, oleyl, elaidyl, vaccenyl, linoleyl, α-linolenyl, arachidonyl, eicosa-pentaenyl, erucyl, docosahexaenyl, caprylyl, capryl, lauryl, stearyl, arachidyl, behenyl, lignoceryl and cerotyl.

In some embodiments, at least one of $R^{6C}$ and $R^{7C}$ can be *—$(CR^{15C}R^{16C})_f$—O—$C_{1-24}$ alkyl. In other embodiments, $R^{6C}$ and $R^{7C}$ can be both *—$(CR^{15C}R^{16C})_f$—O—$C_{1-24}$ alkyl. In some embodiments, each $R^{15C}$ and each $R^{16C}$ can be hydrogen. In other embodiments, at least one of $R^{15C}$ and $R^{16C}$ can be an optionally substituted $C_{1-24}$ alkyl. In other embodiments, at least one of $R^{15C}$ and $R^{16C}$ can be an alkoxy (for example, benzoxy). In some embodiments, f can be 1. In other embodiments, f can be 2. In still other embodiments, f can be 3.

In some embodiments, at least one of $R^{6C}$ and $R^{7C}$ can be *—$(CR^{17C}R^{18C})_g$—O—$C_{2-24}$ alkenyl. In other embodiments, $R^{6C}$ and $R^{7C}$ can be both *—$(CR^{17C}R^{18C})_g$—O—$C_{2-24}$ alkenyl. In some embodiments, each $R^{17C}$ and each $R^{18C}$ can be hydrogen. In other embodiments, at least one of $R^{17C}$ and $R^{18C}$ can be an optionally substituted $C_{1-24}$ alkyl. In some embodiments, g can be 1. In other embodiments, g can be 2. In still other embodiments, g can be 3. When at least one of $R^{6C}$ and $R^{7C}$ is *—$(CR^{15C}R^{16C})_f$—O—$C_{1-24}$ alkyl or *—$(CR^{17C}R^{18C})_g$—O—$C_{2-24}$ alkenyl, the $C_{1-24}$ alkyl can be selected from caprylyl, capryl, lauryl, myristyl, palmityl, stearyl, arachidyl, behenyl, lignoceryl, and cerotyl, and the $C_{2-24}$ alkenyl can be selected from myristoleyl, palmitoleyl, sapienyl, oleyl, elaidyl, vaccenyl, linoleyl, α-linolenyl, arachidonyl, eicosapentaenyl, erucyl and docosahexaenyl.

In some embodiments, when $R^{1C}$ is

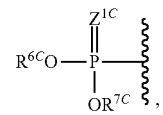

at least one of $R^{6C}$ and $R^{7C}$ can be selected from

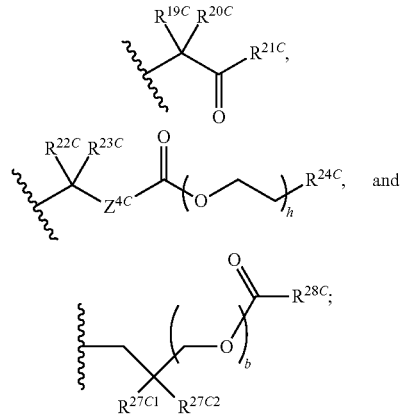

and the other of $R^{6C}$ and $R^{7C}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl).

In some embodiments, at least one of $R^{6C}$ and $R^{7C}$ can be

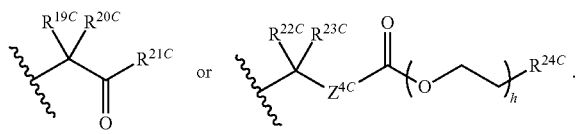

In some embodiments, both $R^{6C}$ and $R^{7C}$ can be

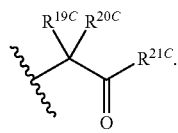

When one or both of $R^{6C}$ and $R^{7C}$ are

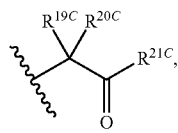

$R^{19C}$ and $R^{20C}$ can be independently selected from hydrogen, an optionally substituted $C_{1-24}$ alkyl and an optionally substituted aryl; and $R^{21C}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl. In some embodiments, $R^{19C}$ and $R^{20C}$ can be hydrogen. In other embodiments, at least one of $R^{19C}$ and $R^{20C}$ can be an optionally substituted $C_{1-24}$ alkyl or an optionally substituted aryl. In some embodiments, $R^{21C}$ can be an optionally substituted $C_{1-24}$ alkyl. In some embodiments, $R^{21C}$ can be an unsubstituted $C_{1-4}$ alkyl. In other embodiments, $R^{21C}$ can be an optionally substituted aryl. In still other embodiments, $R^{21C}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^{21C}$ can be an unsubstituted —O—$C_{1-4}$ alkyl.

In some embodiments, both $R^{6C}$ and $R^{7C}$ can be

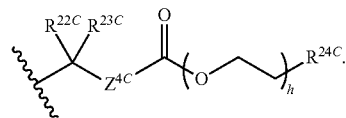

When one or both of $R^{6C}$ and $R^{7C}$ are

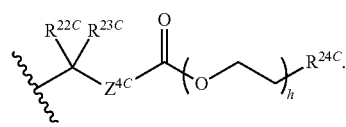

$R^{22C}$ and $R^{23C}$ can be independently selected from hydrogen, an optionally substituted $C_{1-24}$ alkyl and an optionally substituted aryl; $R^{24C}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; h can be 0, 1, 2 or 3; and $Z^{4C}$ can be independently O (oxygen) or S (sulfur). In some embodiments, $R^{22C}$ and $R^{23C}$ can be hydrogen. In other embodiments, at least one of $R^{22C}$ and $R^{23C}$ can be an optionally substituted $C_{1-24}$ alkyl or an optionally substituted aryl. In some embodiments, $R^{24C}$ can be an optionally substituted $C_{1-24}$ alkyl. In some embodiments, $R^{24C}$ can be an unsubstituted $C_{1-4}$ alkyl. In other embodiments, $R^{24C}$ can be an optionally substituted aryl. In still other embodiments, $R^{24C}$ can be an optionally substituted —O—$C_{1-24}$ alkyl, an optionally substituted —O-aryl, an optionally substituted —O-heteroaryl or an optionally substituted —O-monocyclic heterocyclyl. In yet still other embodiments, $R^{24C}$ can be

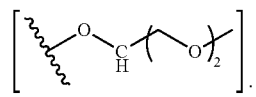

In some embodiments, $R^{24C}$ can be an unsubstituted —O—$C_{1-4}$ alkyl. In some embodiments, $Z^{4C}$ can be O (oxygen). In other embodiments, $Z^{4C}$ can be or S (sulfur). In some embodiments, h can be 0. In other embodiments, h can be 1. In still other embodiments, h can be 2. In yet still other embodiments, h can be 3. In some embodiments, h can be 0 and $R^{24C}$ can be

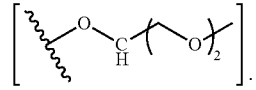

In some embodiments, one or both of $R^{6C}$ and $R^{7C}$ can be isopropyloxycarbonyloxymethyl (POC). In some embodiments, $R^{6C}$ and $R^{7C}$ can be both a isopropyloxycarbonyloxymethyl (POC) group, and form a bis(isopropyloxycarbonyloxymethyl) (bis(POC)) prodrug. In other embodiments, one or both of $R^{6C}$ and $R^{7C}$ can be pivaloyloxymethyl (POM). In some embodiments, $R^{6C}$ and $R^{7C}$ can be both a pivaloyloxymethyl (POM) group, and form a bis(pivaloyloxymethyl) (bis(POM)) prodrug.

In some embodiments, both $R^{6C}$ and $R^{7C}$ can be

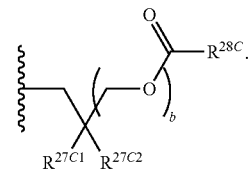

When one or both of $R^{6C}$ and $R^{7C}$ are

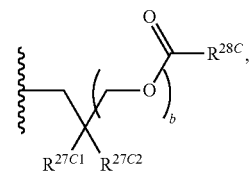

$R^{27C1}$ and $R^{27C2}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{28C}$ can be selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and b can be 1 or 2. In some embodiments, $R^{27C1}$ can be —C≡N and $R^{27C2}$ can be an optionally substituted $C_{2-8}$ alkoxycarbonyl, such as —C(=O)OCH$_3$. In other embodiments, $R^{27C1}$ can be —C≡N and $R^{27C2}$ can be an optionally substituted $C_{2-8}$ organylaminocarbonyl, for example, —C(=O)NHCH$_2$CH$_3$ and —C(=O)NHCH$_2$CH$_2$phenyl. In some embodiments, both $R^{27C1}$ and $R^{27C2}$ can be an optionally substituted $C_{2-8}$ organylcarbonyl, such as —C(=O)CH$_3$. In some embodiments, both $R^{27C1}$ and $R^{27C2}$ can be an optionally substituted $C_{1-8}$ alkoxycarbonyl, for example, —C(=O)OCH$_2$CH$_3$ and —C(=O)OCH$_3$. In some embodiments, including those described in this paragraph, $R^{28C}$ can be an optionally substituted $C_{1-4}$ alkyl. In some embodiment, $R^{28C}$ can be methyl or tert-butyl. In some embodiments, b can be 1. In other embodiments, b can be 2.

In some embodiments, $R^{6C}$ and $R^{7C}$ can be both an optionally substituted aryl. In some embodiments, at least one of $R^{6C}$ and $R^{7C}$ can be an optionally substituted aryl. For example, both $R^{6C}$ and $R^{7C}$ can be an optionally substituted phenyl or an optionally substituted naphthyl. When substituted, the substituted aryl can be substituted with 1, 2, 3 or more than 3 substituents. When more the two substituents are present, the substituents can be the same or different. In some embodiments, when at least one of $R^{6C}$ and $R^{7C}$ is a substituted phenyl, the substituted phenyl can be a para-, ortho- or meta-substituted phenyl.

In some embodiments, $R^{6C}$ and $R^{7C}$ can be both an optionally substituted aryl($C_{1-6}$ alkyl). In some embodiments, at least one of $R^{6C}$ and $R^{7C}$ can be an optionally substituted aryl($C_{1-6}$ alkyl). For example, both $R^{6C}$ and $R^{7C}$ can be an optionally substituted benzyl. When substituted, the substituted benzyl group can be substituted with 1, 2, 3 or more than 3 substituents. When more the two substituents are present, the substituents can be the same or different. In some embodiments, the aryl group of the aryl($C_{1-6}$ alkyl) can be a para-, ortho- or meta-substituted phenyl.

In some embodiments, $R^{6C}$ and $R^{7C}$ can be both

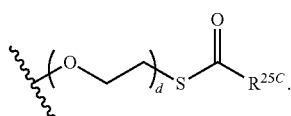

In some embodiments, at least one of $R^{6C}$ and $R^{7C}$ can be

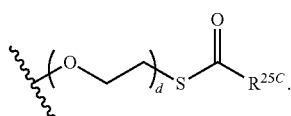

In some embodiments, $R^{25C}$ can be hydrogen. In other embodiments, $R^{25C}$ can be an optionally substituted $C_{1-24}$ alkyl. In still other embodiments, $R^{25C}$ can be an optionally substituted aryl (for example, an optionally substituted phenyl). In some embodiments, $R^{25C}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained). In some embodiments, d can be 0. In other embodiments, d can be 1. In some embodiments, $R^{6C}$ and $R^{7C}$ can be both a S-acylthioethyl (SATE) group and form a SATE ester prodrug.

In some embodiments, $R^{6C}$ and $R^{7C}$ can be both

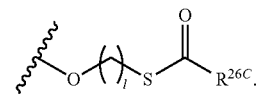

In some embodiments, at least one of $R^{6C}$ and $R^{7C}$ can be

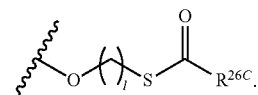

In some embodiments, $R^{26C}$ can be hydrogen. In other embodiments, $R^{26C}$ can be an optionally substituted $C_{1-24}$ alkyl. In still other embodiments, $R^{26C}$ can be an optionally substituted aryl, for example, an optionally substituted phenyl. In some embodiments, $R^{26C}$ can be an optionally substituted $C_{1-6}$ alkyl. In some embodiments, $R^{26C}$ can be an unsubstituted $C_{1-6}$ alkyl. In some embodiments, 1 can be 3. In other embodiments, 1 can be 4. In still other embodiments, 1 can be 5.

In some embodiments, $R^{6C}$ and $R^{7C}$ can be both

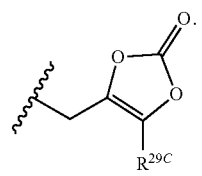

In some embodiments, at least one of $R^{6C}$ and $R^{7C}$ can be

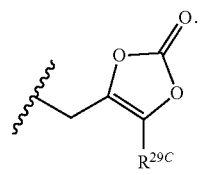

In some embodiments, $R^{29C}$ can be hydrogen. In other embodiments, $R^{29C}$ can be an optionally substituted $C_{1-24}$ alkyl. In some embodiments, $R^{29C}$ can be a $C_{1-4}$ alkyl, such as methyl, ethyl, n-propyl, iso-propyl, n-butyl, iso-butyl and t-butyl. In still other embodiments, $R^{29C}$ can be an optionally substituted aryl, such as an optionally substituted phenyl or an optionally substituted naphthyl. In some embodiments, $R^{6C}$ and $R^{7C}$ can be both a dioxolenone group and form a dioxolenone prodrug.

In some embodiments, $R^{6C}$ and $R^{7C}$ can be taken together to form an optionally substituted

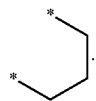

For example, $R^{1C}$ can be an optionally substituted

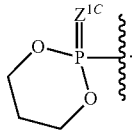

When substituted, the ring can be substituted 1, 2, 3 or more times. When substituted with multiple substituents, the substituents can be the same or different. In some embodiments, when $R^{1C}$ is

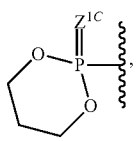

the ring can be substituted with an optionally substituted aryl group and/or an optionally substituted heteroaryl. An example of a suitable heteroaryl is pyridinyl. In some embodiments, $R^{6C}$ and $R^{7C}$ can be taken together to form an optionally substituted

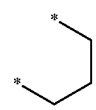

such as

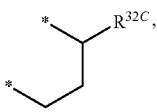

wherein $R^{32C}$ can be an optionally substituted aryl, an optionally substituted heteroaryl or an optionally substituted heterocyclyl. In some embodiments, $R^{6C}$ and $R^{7C}$ can form a cyclic 1-aryl-1,3-propanyl ester (HepDirect) prodrug moiety.

In some embodiments, $R^{6C}$ and $R^{7C}$ can be taken together to form an optionally substituted

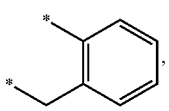

wherein the oxygens connected to $R^{6C}$ and $R^{7C}$, the phosphorus and the moiety form a six-membered to ten-membered ring system. Example of an optionally substituted

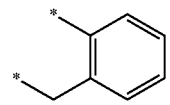

include

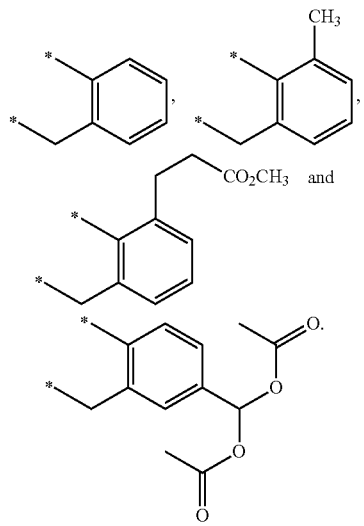

In some embodiments, $R^{6C}$ and $R^{7C}$ can form a cyclosaligenyl (cycloSal) prodrug.

In some embodiments, $R^{6C}$ and $R^{7C}$ can be the same. In some embodiments, $R^{6C}$ and $R^{7C}$ can be different.

In some embodiments, $Z^{1C}$ can be oxygen. In other embodiments, $Z^{1C}$ can be sulfur.

In some embodiments, $R^{1C}$ can be

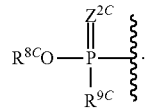

In some embodiments, $R^{8C}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and $R^{9C}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl.

In some embodiments, $R^{8C}$ can be hydrogen, and $R^{9C}$ can be an optionally substituted $C_{1-6}$ alkyl. Examples of suitable $C_{1-6}$ alkyls include methyl, ethyl, n-propyl, isopropyl, n-butyl, isobutyl, tert-butyl, pentyl (branched and straight-chained), and hexyl (branched and straight-chained). In other embodiments, $R^{8C}$ can be hydrogen, and $R^{9C}$ can be $NR^{30C}R^{31C}$, wherein $R^{30C}$ and $R^{31C}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl and an optionally substituted aryl($C_{1-4}$ alkyl). In some embodiments, one of $R^{30C}$ and $R^{31C}$ can be hydrogen and the other of $R^{30C}$ and $R^{31C}$ can be an optionally substituted $C_{1-6}$ alkyl, an optionally substituted $C_{2-6}$ alkenyl, an optionally substituted $C_{2-6}$ alkynyl, an optionally substituted $C_{3-6}$ cycloalkyl, an optionally substituted $C_{3-6}$ cycloalkenyl and an optionally substituted benzyl.

In some embodiments, $R^{8C}$ can be absent or hydrogen; and $R^{9C}$ can be an optionally substituted N-linked amino acid or an optionally substituted N-linked amino acid ester derivative. In other embodiments, $R^{8C}$ can be an optionally substituted aryl; and $R^{9C}$ can be an optionally substituted N-linked amino acid or an optionally substituted N-linked amino acid ester derivative. In still other embodiments, $R^{8C}$ can be an optionally substituted heteroaryl; and $R^{9C}$ can be an optionally substituted N-linked amino acid or an optionally substituted N-linked amino acid ester derivative. In some embodiments, $R^{9C}$ can be selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. Examples of an optionally substituted N-linked amino acid ester derivatives include optionally substituted versions of the following: N-alanine isopropyl ester, N-alanine cyclohexyl ester, N-alanine neopentyl ester, N-valine isopropyl ester and N-leucine isopropyl ester. In some embodiments, $R^{9C}$ can have the structure

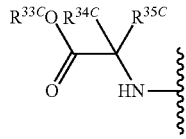

wherein $R^{33C}$ can be selected from hydrogen, an optionally substituted $C_{1-6}$ alkyl, an optionally substituted $C_{3-6}$ cycloalkyl, an optionally substituted aryl, an optionally substituted aryl($C_{1-6}$ alkyl) and an optionally substituted haloalkyl; $R^{34C}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{35C}$ can be hydrogen or an optionally substituted $C_{1-4}$ alkyl; or $R^{34C}$ and $R^{35C}$ can be taken together to form an optionally substituted $C_{3-6}$ cycloalkyl.

When $R^{34C}$ is substituted, $R^{34C}$ can be substituted with one or more substituents selected from N-amido, mercapto, alkylthio, an optionally substituted aryl, hydroxy, an optionally substituted heteroaryl, O-carboxy and amino. In some embodiments, $R^{34C}$ can be an unsubstituted $C_{1-6}$ alkyl, such as those described herein. In some embodiments, $R^{34C}$ can be hydrogen. In other embodiments, $R^{34C}$ can be methyl. In some embodiments, $R^{33C}$ can be an optionally substituted $C_{1-6}$ alkyl. Examples of optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{33C}$ can be methyl or isopropyl. In some embodiments, $R^{33C}$ can be ethyl or neopentyl. In other embodiments, $R^{33C}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{33C}$ can be an optionally substituted cyclohexyl. In still other embodiments, $R^{33C}$ can be an optionally substituted aryl, such as phenyl and naphthyl. In yet still other embodiments, $R^{33C}$ can be an optionally substituted aryl($C_{1-6}$ alkyl). In some embodiments, $R^{33C}$ can be an optionally substituted benzyl. In some embodiments, $R^{33C}$ can be an optionally substituted $C_{1-6}$ haloalkyl, for example, $CF_3$. In some embodiments, $R^{35C}$ can be hydrogen. In other embodiments, $R^{35C}$ can be an optionally substituted $C_{1-4}$ alkyl, such as methyl, ethyl, n-propyl, isopropyl, n-butyl, isobutyl and tert-butyl. In some embodiments, $R^{35C}$ can be methyl. In some embodiments, $R^{34C}$ and $R^{35C}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{34C}$ and $R^{35C}$, the carbon to which $R^{34C}$ and $R^{35C}$ are attached may be a chiral center. In some embodiment, the carbon to which $R^{34C}$ and $R^{35C}$ are attached may be a (R)-chiral center. In other embodiments, the carbon to which $R^{34C}$ and $R^{35C}$ are attached may be a (S)-chiral center.

In some embodiments, when $R^{1C}$ is

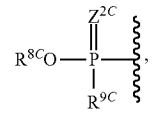

$Z^{2C}$ can be O (oxygen). In other embodiments, when $R^{1C}$ is

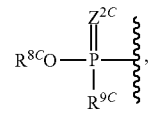

$Z^{2C}$ can be S (sulfur). In some embodiments, when $R^{1C}$ is

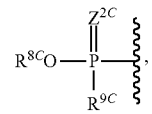

a compound of Formula (I) can be a phosphoramidate prodrug, such as an aryl phosphoramidate prodrug.

In some embodiments, $R^{1C}$ can be

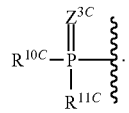

In some embodiments, $R^{10C}$ and $R^{11C}$ can be both an optionally substituted N-linked amino acid or an optionally substituted N-linked amino acid ester derivative. In some embodiments, $R^{10C}$ and $R^{11C}$ can be independently selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{10C}$ and $R^{11C}$ can be an optionally substituted version of the following: N-alanine isopropyl ester, N-alanine cyclohexyl ester, N-alanine neopentyl ester, N-valine isopropyl ester and N-leucine isopropyl ester. In some embodiments, $R^{10C}$ and $R^{11C}$ can independently have the structure

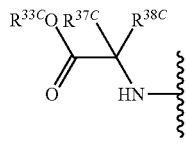

wherein $R^{36C}$ can be selected from hydrogen, an optionally substituted $C_{1-6}$ alkyl, an optionally substituted $C_{3-6}$ cycloalkyl, an optionally substituted aryl, an optionally substituted aryl($C_{1-6}$ alkyl) and an optionally substituted haloalkyl; $R^{37C}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{38C}$ can be hydrogen or an optionally substituted $C_{1-4}$ alkyl; or $R^{37C}$ and $R^{38C}$ can be taken together to form an optionally substituted $C_{3-6}$ cycloalkyl.

When $R^{37C}$ is substituted, $R^{37C}$ can be substituted with one or more substituents selected from N-amido, mercapto, alkylthio, an optionally substituted aryl, hydroxy, an optionally substituted heteroaryl, O-carboxy and amino. In some embodiments, $R^{37C}$ can be an unsubstituted $C_{1-6}$ alkyl, such as those described herein. In some embodiments, $R^{37C}$ can be hydrogen. In other embodiments, $R^{37C}$ can be methyl. In some embodiments, $R^{36C}$ can be an optionally substituted $C_{1-6}$ alkyl. Examples of optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{36C}$ can be methyl or isopropyl. In some embodiments, $R^{36C}$ can be ethyl or neopentyl. In other embodiments, $R^{36C}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{36C}$ can be an optionally substituted cyclohexyl. In still other embodiments, $R^{36C}$ can be an optionally substituted aryl, such as phenyl and naphthyl. In yet still other embodiments, $R^{36C}$ can be an optionally substituted aryl($C_{1-6}$ alkyl). In some embodiments, $R^{36C}$ can be an optionally substituted benzyl. In some embodiments, $R^{36C}$ can be an optionally substituted $C_{1-6}$ haloalkyl, for example, $CF_3$. In some embodiments, $R^{38C}$ can be hydrogen. In other embodiments, $R^{38C}$ can be an optionally substituted $C_{1-4}$ alkyl, such as methyl, ethyl, n-propyl, isopropyl, n-butyl, isobutyl and tert-butyl. In some embodiments, $R^{38C}$ can be methyl. In some embodiments, $R^{37C}$ and $R^{38C}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{37C}$ and $R^{38C}$, the carbon to which $R^{37C}$ and $R^{38C}$ are attached may be a chiral center. In some embodiment, the carbon to which $R^{37C}$ and $R^{38C}$ are attached may be a (R)-chiral center. In other embodiments, the carbon to which $R^{37C}$ and $R^{38C}$ are attached may be a (S)-chiral center.

Examples of suitable

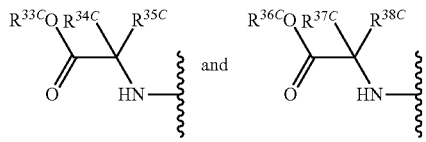

groups include the following:

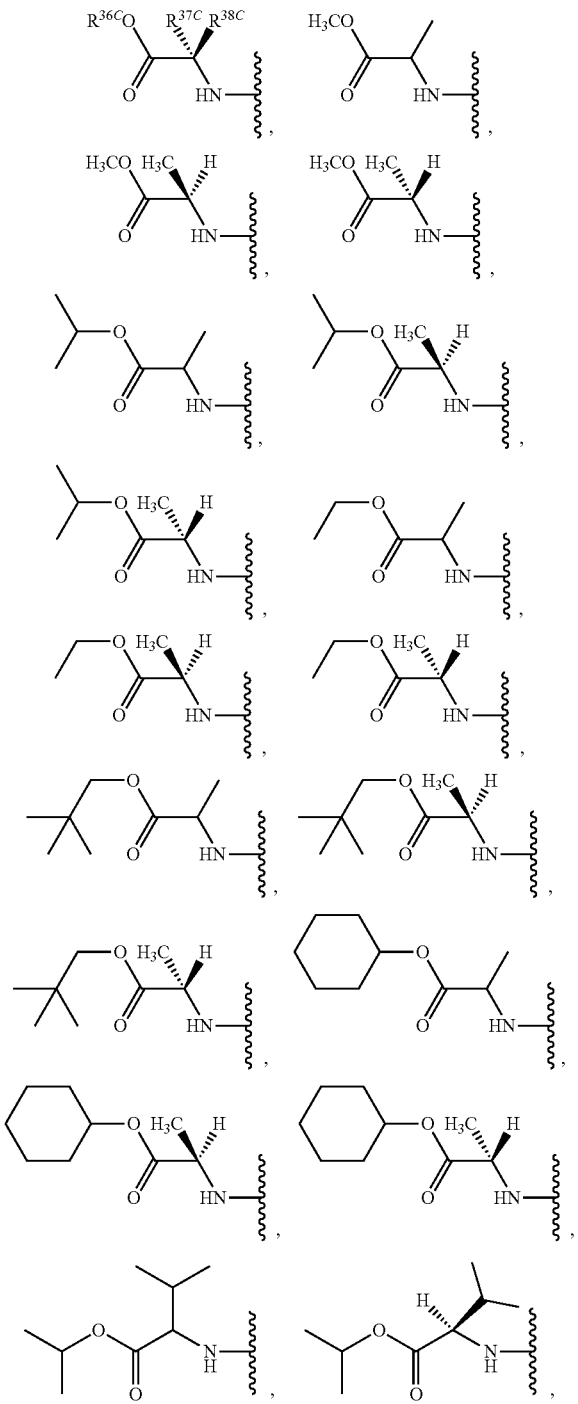

-continued

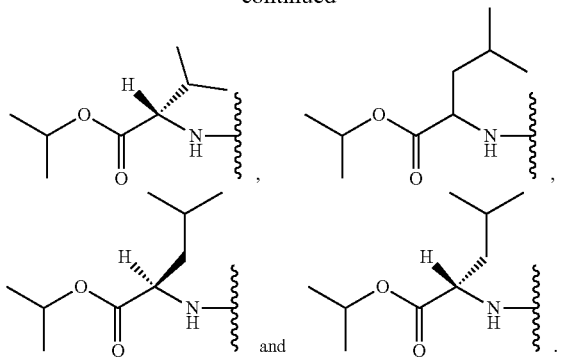
and

In some embodiments, $R^{10C}$ and $R^{11C}$ can be the same. In some embodiments, $R^{10C}$ and $R^{11C}$ can be different.

In some embodiments, $Z^{3C}$ can be O (oxygen). In other embodiments, $Z^{3C}$ can be S (sulfur). In some embodiments, when $R^{1C}$ is

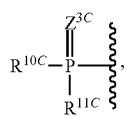

a compound of Formula (I) can be a phosphonic diamide prodrug.

Various substituents can be present at the 4'-position of the pentose ring. In some embodiments, $R^{2C}$ can be an unsubstituted $C_{1-4}$ alkyl. Unsubstituted $C_{1-4}$ alkyls include methyl, ethyl, n-propyl, iso-propyl, n-butyl, iso-butyl and tert-butyl. In other embodiments, $R^{2C}$ can be an unsubstituted $C_{2-4}$ alkenyl, such as ethenyl, propenyl and butenyl. In other embodiments, $R^{2C}$ can be an unsubstituted $C_{2-4}$ alkynyl, for example, ethynyl, propynyl and butynyl. In still other embodiments, $R^{2C}$ can be a haloalkyl. Examples of a haloalkyls are —$(CH_2)_{1-6}$ halogen and —$CHF_2$. In some embodiments, the haloalkyl can be —$(CH_2)_{1-6}F$ or —$(CH_2)_{1-6}C_1$. In some embodiments, the haloalkyl can be fluoromethyl. In other embodiments, $R^{2C}$ can be —$CHF_2$. In yet still other embodiments, $R^{2C}$ can be a $C_{1-6}$ azidoalkyl. For example, $R^{2C}$ can be an azidomethyl, azidoethyl, azidopropyl, azidobutyl, azidopentyl or azidohexyl. In some embodiments, $R^{2C}$ can be halo. In some embodiments, $R^{2C}$ can be fluoro. In some embodiments, $R^{2C}$ can be chloro. In still other embodiments, $R^{2C}$ can be —CN.

A variety of substituents can also be present at the 2'-position of the pentose ring. In some embodiments, $R^{4C}$ can be OH. In other embodiments, $R^{4C}$ can be —OC(=O)$R'''^{D}$, wherein $R'''^{D}$ can be an optionally substituted $C_{1-24}$ alkyl. In some embodiments, $R^{4C}$ can be —OC(=O)$R'''^{D}$, wherein $R'''^{D}$ can be an unsubstituted $C_{1-4}$ alkyl. In still other embodiments, $R^{4C}$ can be halo. In some embodiment, $R^{4C}$ can be F. In other embodiments, $R^{4C}$ can be Cl. In some embodiments, $R^{4C}$ can be $N_3$. In some embodiments, $R^{4C}$ can be $NR'''^{D1}R'''^{D2}$. For example, $R^{4C}$ can be $NH_2$. Other examples can be a mono-substituted $C_{1-6}$ alkyl-amine or a di-substituted $C_{1-6}$ alkyl-amine.

In still other embodiments, $R^{4C}$ can be an optionally substituted O-linked amino acid, such as a O-linked alpha-amino acid. In some embodiments, the O-linked amino acid can have the structure

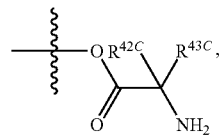

$NH_2$, wherein $R^{42C}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{43C}$ can be hydrogen or an optionally substituted $C_{1-4}$ alkyl; or $R^{42C}$ and $R^{43C}$ can be taken together to form an optionally substituted $C_{3-6}$ cycloalkyl.

When $R^{42C}$ is substituted, $R^{42C}$ can be substituted with one or more substituents selected from N-amido, mercapto, alkylthio, an optionally substituted aryl, hydroxy, an optionally substituted heteroaryl, O-carboxy and amino. In some embodiments, $R^{42C}$ can be an unsubstituted $C_{1-6}$ alkyl, such as those described herein. In some embodiments, $R^{42C}$ can be hydrogen. In other embodiments, $R^{42C}$ can be methyl. In some embodiments, $R^{43C}$ can be hydrogen. In other embodiments, $R^{43C}$ can be an optionally substituted $C_{1-4}$ alkyl, such as methyl, ethyl, n-propyl, isopropyl, n-butyl, isobutyl and tert-butyl. In some embodiments, $R^{43C}$ can be methyl. Depending on the groups that are selected for $R^{42C}$ and $R^{43C}$, the carbon to which $R^{42C}$ and $R^{43C}$ are attached may be a chiral center. In some embodiment, the carbon to which $R^{42C}$ and $R^{43C}$ are attached may be a (R)-chiral center. In other embodiments, the carbon to which $R^{42C}$ and $R^{43C}$ are attached may be a (S)-chiral center.

Examples of suitable

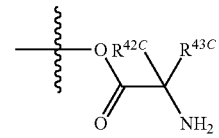

include the following:

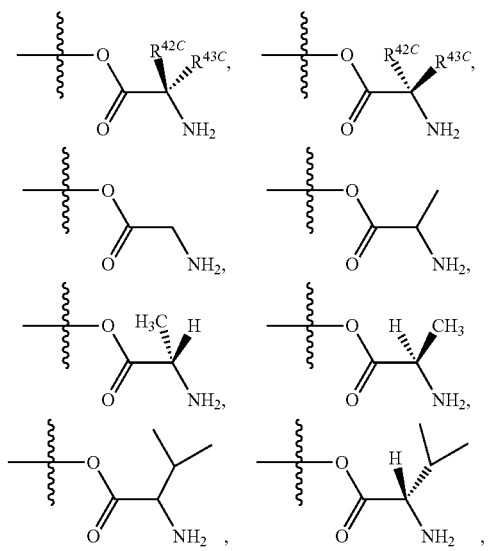

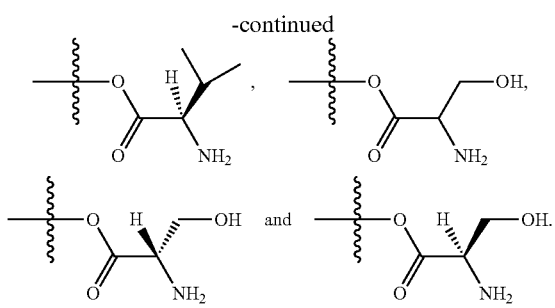

In some embodiments, $R^{5C}$ can be H. In other embodiments, $R^{5C}$ can be halo, including F and $C_1$. In still other embodiments, $R^{5C}$ can be an optionally substituted $C_{1-6}$ alkyl. For example, $R^{5C}$ can be an substituted or unsubstituted version of the following: methyl, ethyl, n-propyl, iso-propyl, n-butyl, iso-butyl, tert-butyl, pentyl (branched or straight) and hexyl (branched or straight). In some embodiments, $R^{5C}$ can be a halo-substituted $C_{1-6}$ alkyl, such as —CH$_2$F. In yet still other embodiments, $R^{5C}$ can be an optionally substituted $C_{2-6}$ alkenyl. In some embodiments, $R^{5C}$ can be an optionally substituted $C_{2-6}$ alkynyl. For example, $R^{5C}$ can be ethynyl. In some embodiments, $R^{5C}$ can be hydroxy (OH).

In some embodiments, - - - - - - - - can be both absent such that a compound of Formula (I) has the structure:

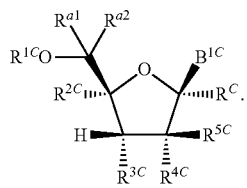

When - - - - - - - - are both absent, the 3'-position can have various groups present. In some embodiments, $R^{3C}$ can be H. In other embodiments, $R^{3C}$ can be halo, such as fluoro (F) or chloro (Cl). In still other embodiments, $R^{3C}$ can be OH. In some embodiments, $R^{3C}$ can be —OC(=O)R'''$^C$, wherein R'''$^C$ can be an optionally substituted $C_{1-24}$ alkyl. In some embodiments, $R^{3C}$ can be —OC(=O)R'''$^C$, wherein R'''$^C$ can be an unsubstituted $C_{1-4}$ alkyl. In other embodiments, $R^{3C}$ can be an optionally substituted O-linked amino acid, such as a O-linked alpha-amino acid. The optionally substituted O-linked amino acid can have the structure:

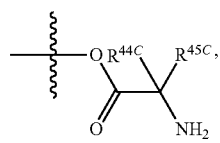

wherein $R^{44C}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{45C}$ can be hydrogen or an optionally substituted $C_{1-4}$ alkyl; or $R^{44C}$ and $R^{45C}$ can be taken together to form an optionally substituted $C_{3-6}$ cycloalkyl.

When $R^{44C}$ is substituted, $R^{44C}$ can be substituted with one or more substituents selected from N-amido, mercapto, alkylthio, an optionally substituted aryl, hydroxy, an optionally substituted heteroaryl, O-carboxy and amino. In some embodiments, $R^{44C}$ can be an unsubstituted $C_{1-6}$ alkyl, such as those described herein. In some embodiments, $R^{44C}$ can be hydrogen. In other embodiments, $R^{44C}$ can be methyl. In some embodiments, $R^{45C}$ can be hydrogen. In other embodiments, $R^{45C}$ can be an optionally substituted $C_{1-4}$ alkyl, such as methyl, ethyl, n-propyl, isopropyl, n-butyl, isobutyl and tert-butyl. In some embodiments, $R^{45A}$ can be methyl. Depending on the groups that are selected for $R^{44C}$ and $R^{45C}$, the carbon to which $R^{44C}$ and $R^{45C}$ are attached may be a chiral center. In some embodiment, the carbon to which $R^{44C}$ and $R^{45C}$ are attached may be a (R)-chiral center. In other embodiments, the carbon to which $R^{44C}$ and $R^{45C}$ are attached may be a (S)-chiral center.

Examples of suitable

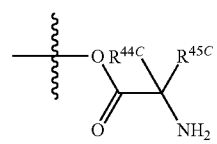

include the following:

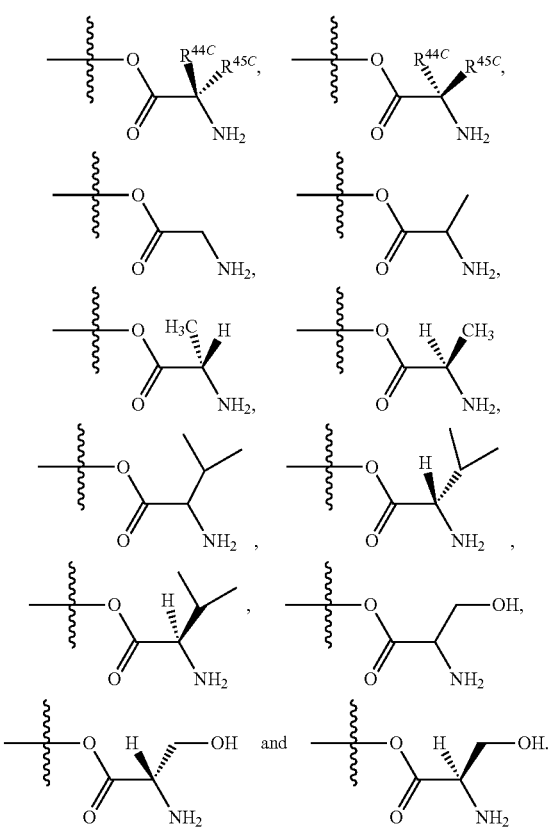

In some embodiments, $R^{3C}$ and $R^{4C}$ can be each an oxygen atom connected via a carbonyl to form a 5-membered ring.

In some embodiments, $R^{2C}$ can be fluoro and $R^{3C}$ can be fluoro. In some embodiments, $R^{2C}$ can be fluoro and $R^{4C}$ can be fluoro. In some embodiments, $R^{2C}$ can be fluoro, $R^{3C}$ can be fluoro and $R^{5C}$ can be an optionally substituted $C_{1-6}$ alkyl, an optionally substituted $C_{2-6}$ alkenyl and an optionally substituted $C_{2-6}$ alkynyl. In some embodiments, $R^{2C}$ can be fluoro, $R^{4C}$ can be fluoro and $R^{5C}$ can be an optionally substituted $C_{1-6}$ alkyl, an optionally substituted $C_{2-6}$ alkenyl and an optionally substituted $C_{2-6}$ alkynyl. In some embodiments, $R^{2C}$ can be fluoro, $R^{3C}$ can be fluoro and $R^{4C}$ can be OH or —OC(=O)R‴$^D$. In some embodiments, $R^{2C}$ can be fluoro, $R^{3C}$ can be OH or —OC(=O)R‴$^C$ and $R^{4C}$ can be fluoro. In some embodiments, $R^{4C}$ and $R^{5C}$ can be each F. In some embodiments, $R^{2C}$ can be *—$(CH_2)_{1-6}$halogen (for example, —$CH_2F$), $R^{3C}$ can be OH, —OC(=O)R‴$^C$ or an optionally substituted O-linked amino acid and $R^{4C}$ can be OH. In some embodiments, $R^{2C}$ can be —$(CH_2)_{1-6}$halogen (for example, —$CH_2F$), $R^{3C}$ can be OH, —OC(=O)R‴$^C$ or an optionally substituted O-linked amino acid, $R^{4C}$ can be OH, and $R^{5C}$ can be an unsubstituted $C_{1-6}$ alkyl. In some embodiments, $R^{2C}$ can be —$(CH_2)_{1-6}N_3$ (such as, —$CH_2N_3$), $R^{3C}$ can be OH and $R^{4C}$ can be F.

In some embodiments, - - - - - - - - can be each a single bond such that a compound of Formula (I) has the structure:

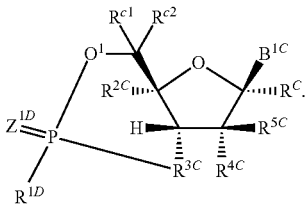

When - - - - - - - - are each a single bond, $R^{3C}$ can be oxygen (O). In some embodiments, when - - - - - - - - are each a single bond, $R^{1D}$ can be O⁻ or OH. In other embodiments, when - - - - - - - - are each a single bond, $R^{1D}$ can be an —O-optionally substituted $C_{1-6}$ alkyl. For example, $R^{1D}$ can be an —O-unsubstituted $C_{1-6}$ alkyl.

In some embodiments, when - - - - - - - - are each a single bond, $R^{1D}$ can be

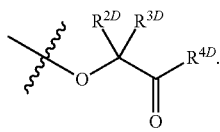

In other embodiments, $R^{1D}$ can be

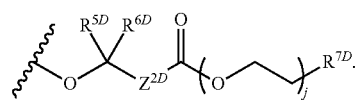

For example, $R^{1D}$ can be a isopropyloxycarbonyloxymethyloxy or pivaloyloxymethyloxy group. In still some embodiments, $R^{1B}$ can be

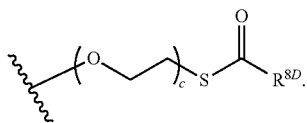

A S-acylthioethyl (SATE) group is an example of a

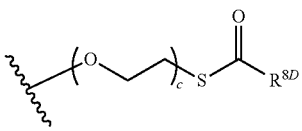

group. In yet still other embodiments, $R^{1D}$ can be an optionally substituted N-linked amino acid or an optionally substituted N-linked amino acid ester derivative.

Examples of an optionally substituted N-linked amino acids and an optionally substituted N-linked amino acid ester derivatives are described herein. In some embodiments, $R^{1D}$ can be selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{1D}$ can be an optionally substituted version of the following: N-alanine isopropyl ester, N-alanine cyclohexyl ester, N-alanine neopentyl ester, N-valine isopropyl ester and N-leucine isopropyl ester. In some embodiments, $R^{1D}$ can have the structure

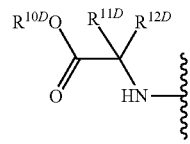

wherein $R^{10D}$ can be selected from hydrogen, an optionally substituted $C_{1-6}$ alkyl, an optionally substituted $C_{3-6}$ cycloalkyl, an optionally substituted aryl, an optionally substituted aryl($C_{1-6}$ alkyl) and an optionally substituted haloalkyl; $R^{11D}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{12D}$ can be hydrogen or an optionally substituted $C_{1-4}$ alkyl; or $R^{11D}$ and $R^{12D}$ can be taken together to form an optionally substituted $C_{3-6}$ cycloalkyl.

As described herein, $R^{11D}$ can be substituted. Examples of substituents include one or more substituents selected from N-amido, mercapto, alkylthio, an optionally substituted aryl, hydroxy, an optionally substituted heteroaryl, O-carboxy and amino. In some embodiments, $R^{11D}$ can be an unsubstituted $C_{1-6}$ alkyl, such as those described herein. In some embodiments, $R^{11D}$ can be hydrogen. In other embodiments, $R^{11D}$ can be methyl. In some embodiments, $R^{10D}$ can be an optionally substituted $C_{1-6}$ alkyl. In some embodiments, $R^{10D}$ can be methyl, ethyl, isopropyl or neopentyl. In other embodiments, $R^{10D}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{10D}$ can be an optionally substituted cyclohexyl. In still other embodiments, $R^{10D}$ can be an optionally substituted aryl, such as phenyl and naphthyl. In yet still other embodiments, $R^{10D}$ can be an optionally substituted aryl($C_{1-6}$ alkyl), for example, an optionally substituted benzyl. In some embodiments, $R^{10D}$ can be an optionally substituted $C_{1-6}$ haloalkyl, for example, $CF_3$. In some embodiments, $R^{12D}$ can be hydrogen. In other embodiments, $R^{12D}$ can be an optionally substituted $C_{1-4}$ alkyl, such as methyl, ethyl, n-propyl, isopropyl, n-butyl, isobutyl and tert-butyl. In some embodiments, $R^{12D}$ can be methyl. In some embodiments, $R^{11D}$ and $R^{12D}$ can be taken together to form an optionally substituted $C_{3-6}$ cycloalkyl. Depending on the groups that are selected for $R^{11D}$ and $R^{12D}$, the carbon to which $R^{11D}$ and $R^{12D}$ are attached may be a chiral center. In some embodiment, the carbon to which $R^{11D}$ and $R^{12D}$ are attached may be a (R)-chiral center. In other embodiments, the carbon to which $R^{11D}$ and $R^{12D}$ are attached may be a (S)-chiral center.

Examples of suitable

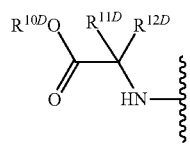

groups include the following:

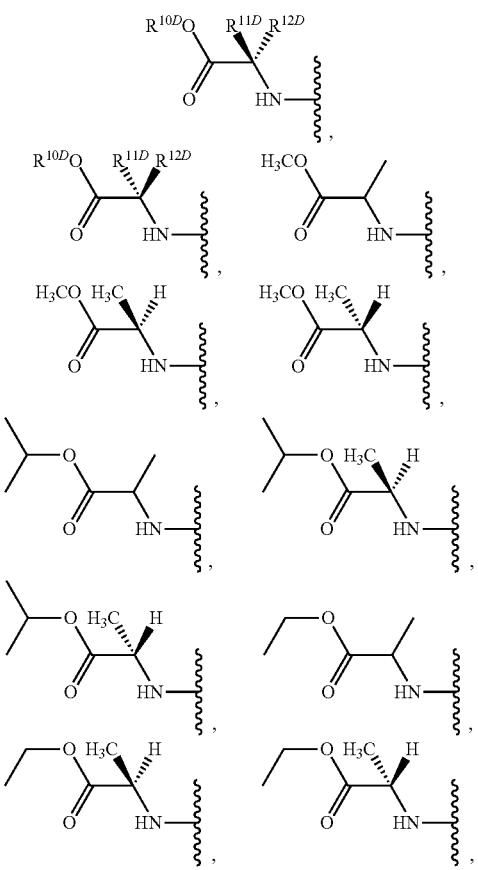

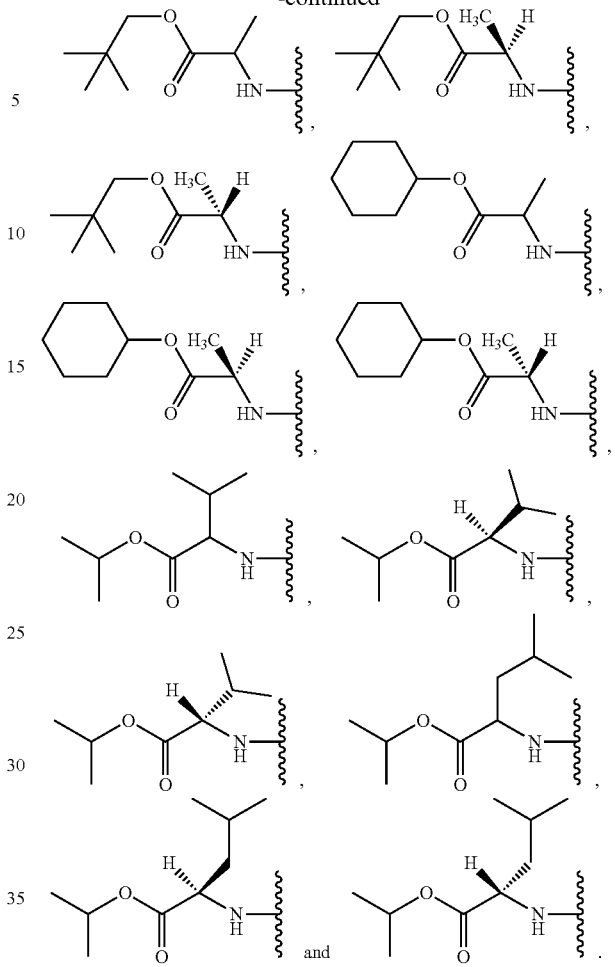

In some embodiments, $R^{1D}$ can be

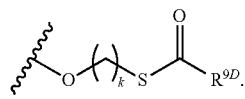

In some embodiments, $R^{9D}$ can be hydrogen. In other embodiments, $R^{9D}$ can be an optionally substituted $C_{1-24}$ alkyl. In still other embodiments, $R^{9D}$ can be an optionally substituted aryl, for example, an optionally substituted phenyl. In some embodiments, $R^{9D}$ can be an optionally substituted $C_{1-6}$ alkyl. In some embodiments, $R^{9D}$ can be an unsubstituted $C_{1-6}$ alkyl. In some embodiments, k can be 3. In other embodiments, k can be 4. In still other embodiments, k can be 5.

A variety of substituents can be present at the 1'-position of the pentose ring. In some embodiments, $R^C$ can be hydrogen. In some embodiments, $R^C$ can be deuterium. In still other embodiments, $R^C$ can be an unsubstituted $C_{1-3}$ alkyl (such as methyl, ethyl, n-propyl and iso-propyl). In yet still other embodiments, $R^C$ can be an unsubstituted $C_{2-4}$ alkenyl (for example, ethenyl, propenyl (branched or straight) and butenyl (branched or straight)). In some embodiments, $R^C$ can be an unsubstituted $C_{2-3}$ alkynyl (such as ethynyl and propynyl (branched or straight)). In other embodiments, $R^C$ can be an unsubstituted cyano.

In some embodiments, $Z^{1D}$ can be oxygen (O). In other embodiments, $Z^{1D}$ can be S (sulfur).

Various optionally substituted heterocyclic bases can be attached to the pentose ring. In some embodiments, one or more of the amine and/or amino groups of the optionally substituted heterocyclic base may be protected with a suitable protecting group. For example, an amino group may be protected by transforming the amine and/or amino group to an amide or a carbamate. In some embodiments, an optionally substituted heterocyclic base or an optionally substituted heterocyclic base can include a group that improves the solubility of the compound (for example, —(CH$_2$)$_{1-2}$—O—P(=O)(OW$^{2C}$)$_2$). In some embodiments, an optionally substituted heterocyclic base or an optionally substituted heterocyclic base with one or more protected amino groups can have one of the following structures:

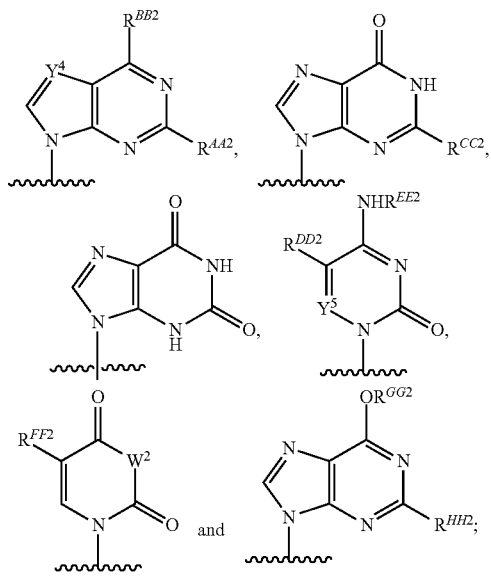

wherein: $R^{AA2}$ can be selected from hydrogen, halogen and NHR$^{JJ2}$, wherein R$^{JJ2}$ can be selected from hydrogen, —C(=O)R$^{KK2}$ and —C(=O)OR$^{LL2}$; R$^{BB2}$ can be halogen or NHR$^{WW2}$, wherein R$^{WW2}$ can be selected from hydrogen, an optionally substituted C$_{1-6}$ alkyl, an optionally substituted C$_{2-6}$ alkenyl, an optionally substituted C$_{3-8}$ cycloalkyl, —C(=O)R$^{MM2}$ and —C(=O)OR$^{NN2}$; R$^{CC2}$ can be hydrogen or NHR$^{OO2}$, wherein R$^{OO2}$ can be selected from hydrogen, —C(=O)R$^{PP2}$ and —C(=O)OR$^{QQ2}$; R$^{DD2}$ can be selected from hydrogen, deuterium, halogen, an optionally substituted C$_{1-6}$ alkyl, an optionally substituted C$_{2-6}$ alkenyl and an optionally substituted C$_{2-6}$ alkynyl; R$^{EE2}$ can be selected from hydrogen, hydroxy, an optionally substituted C$_{1-6}$ alkyl, an optionally substituted C$_{3-8}$ cycloalkyl, —C(=O)R$^{RR2}$ and —C(=O)OR$^{AA2}$; R$^{FF2}$ can be selected from hydrogen, halogen, an optionally substituted C$_{1-6}$ alkyl, an optionally substituted C$_{2-6}$ alkenyl and an optionally substituted C$_{2-6}$ alkynyl; Y$^4$ and Y$^5$ can be independently N (nitrogen) or CR$^{II2}$, wherein R$^{II2}$ can be selected from hydrogen, halogen, an optionally substituted C$_{1-6}$ alkyl, an optionally substituted C$_{2-6}$ alkenyl and an optionally substituted C$_{2-6}$ alkynyl; W$^2$ can be NH, —NCH$_2$—OC(=O)CH(NH$_2$)—CH(CH$_3$)$_2$ or —(CH$_2$)$_{1-2}$—O—P(=O)(OW$^{2C}$)$_2$, wherein W$^{2C}$ can be selected from absent, hydrogen and an optionally substituted C$_{1-6}$ alkyl; R$^{GG2}$ can be an optionally substituted C$_{1-6}$ alkyl; R$^{HH2}$ can be hydrogen or NHR$^{TT2}$, wherein R$^{TT2}$ can be independently selected from hydrogen, —C(=O)R$^{UU2}$ and —C(=O)OR$^{VV2}$; and R$^{KK2}$, R$^{LL2}$, R$^{MM2}$, R$^{NN2}$, R$^{PP2}$, R$^{QQ2}$, R$^{RR2}$, R$^{SS2}$, R$^{UU2}$ and R$^{VV2}$ can be independently selected from hydrogen, C$_{1-6}$ alkyl, C$_{2-6}$ alkenyl, C$_{2-6}$ alkynyl, C$_{3-6}$ cycloalkyl, C$_{3-6}$ cycloalkenyl, C$_{6-10}$ aryl, heteroaryl, heterocyclyl, aryl(C$_{1-6}$ alkyl), heteroaryl(C$_{1-6}$ alkyl) and heterocyclyl(C$_{1-6}$ alkyl). In some embodiments, the structures shown above can be modified by replacing one or more hydrogens with substituents selected from the list of substituents provided for the definition of "substituted." Those skilled in the art understand that when W$^{2C}$ is absent, the oxygen atom will have an associated negative charge. In some embodiments, the substituent on the base can result in the formation of a salt of a compound of Formula (II).

In some embodiments, B$^{1C}$ can be an optionally substituted purine base. In other embodiments, B$^{1C}$ can be an optionally substituted pyrimidine base. In some embodiments, B$^{1C}$ can be

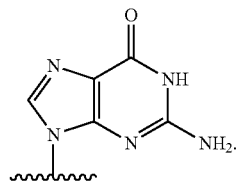 [SMILES: *n1cnc2c(=O)[nH]c(N)nc21]

In other embodiments, B$^{1C}$ can be

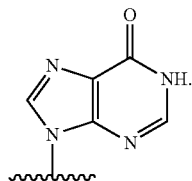 [SMILES: *n1cnc2c(=O)[nH]cnc21]

In still other embodiments, B$^{1C}$ can be

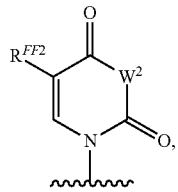

such as

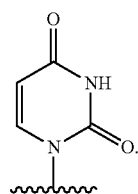

In yet still other embodiments, $B^{1C}$ can be

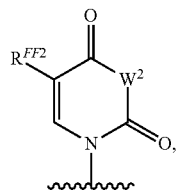

wherein $W^2$ can be —NCH$_2$—OC(=O)CH(NH$_2$)—CH(CH$_3$)$_2$ or —(CH$_2$)$_{1-2}$—O—P(=O)(OW$^{2C}$)$_2$, In some embodiments, $B^{1C}$ can be

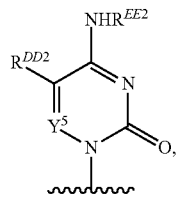

for example

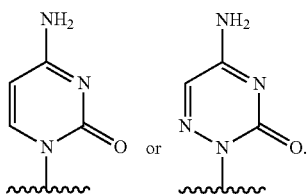 [SMILES: *n1ccc(N)nc1=O ; *n1ncc(N)nc1=O]

In other embodiments, $R^{DD2}$ can be hydrogen. In still other embodiments, $B^{1C}$ can be

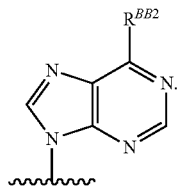

In some embodiments, $R^{BB2}$ can be NH$_2$. In other embodiments, $R^{BB2}$ can be NHR$^{WW2}$, wherein $R^{WW2}$ can be —C(=O)R$^{MM2}$ or —C(=O)OR$^{NN2}$. In still other embodiments, $B^{1C}$ can be

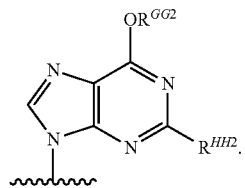

In some embodiments, $B^{1C}$ can be

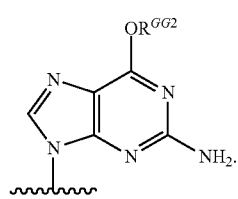

In some embodiments, when $R^{2C}$ is halo (such as fluoro); - - - - - - - are both absent; $Z^2$ is absent; $O^2$ is $OR^{1C}$; $B^{1C}$ is selected from an optionally substituted

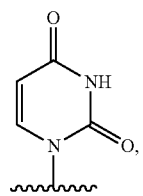 [SMILES: *n1ccc(=O)[nH]c1=O]

an optionally substituted

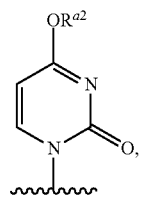

an optionally substituted

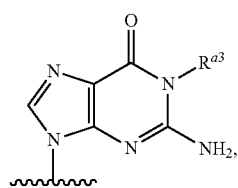

an optionally substituted

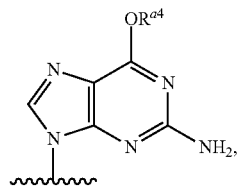

an optionally substituted

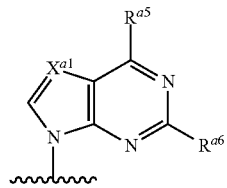

and an optionally substituted

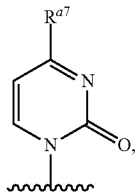

wherein $R^{a2}$ is an optionally substituted $C_{1-6}$ alkyl or an optionally substituted $C_{3-6}$ cycloalkyl, $R^{a3}$ and $R^{a4}$ are independently selected from hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl, $R^{a5}$ is $NHR^{a8}$, and $R^{a6}$ is hydrogen, halogen or $NHR^{a9}$; $R^{a7}$ is $NHR^{a10}$; $R^{a8}$ is selected from hydrogen, an optionally substituted $C_{1-6}$ alkyl, an optionally substituted $C_{3-6}$ alkenyl, an optionally substituted $C_{3-6}$ cycloalkyl, —C(=O)$R^{a11}$ and —C(=O)OR$^{a12}$; $R^{a9}$ is selected from hydrogen, an optionally substituted $C_{1-6}$ alkyl, an optionally substituted $C_{3-6}$ alkenyl, an optionally substituted $C_{3-6}$ cycloalkyl, —C(=O)$R^{a13}$ and —C(=O)OR$^{a14}$; $R^{a10}$ is selected from hydrogen, an optionally substituted $C_{1-6}$ alkyl, an optionally substituted $C_{3-6}$ alkenyl, an optionally substituted $C_{3-6}$ cycloalkyl, —C(=O)$R^{a15}$ and —C(=O)OR$^{a16}$; $X^{a1}$ is N or —CR$^{a17}$; $R^{a17}$ is selected from hydrogen, halogen, an optionally substituted $C_{1-6}$ alkyl, an optionally substituted $C_{2-6}$ alkenyl and an optionally substituted $C_{2-6}$ alkynyl; $R^{a11}$, $R^{a12}$, $R^{a13}$, $R^{a14}$, $R^{a15}$ and $R^{a16}$ are independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heterocyclyl, aryl($C_{1-6}$ alkyl), heteroaryl($C_{1-6}$ alkyl) and heterocyclyl($C_{1-6}$ alkyl); then $R^{3C}$ is selected from H, halo and an optionally substituted O-linked amino acid; and $R^{4C}$ is selected from OH, halo, $N_3$, —OC(=O)R"$^D$, an optionally substituted O-linked amino acid and NR"$^{D1}$R"$^{D2}$; or then $R^{4C}$ is an optionally substituted O-linked amino acid; and $R^{3C}$ is selected from H, halo, OH, —OC(=O)R"$^C$ and an optionally substituted O-linked amino acid; or then $R^{1C}$ is

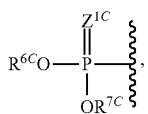

wherein $R^{6C}$ and $R^{7C}$ are independently

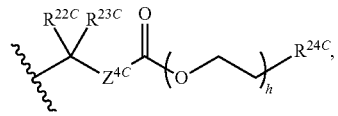

wherein h is 1, 2 or 3,

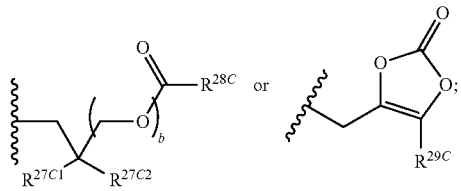

or then $R^{1C}$ is

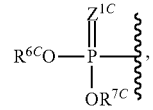

wherein $R^{6C}$ and $R^{7C}$ are taken together to form a moiety selected from an optionally substituted

and an optionally substituted

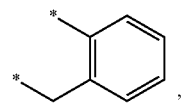

wherein the oxygens connected to $R^{6C}$ and $R^{7C}$, the phosphorus and the moiety form a six-membered to ten-membered ring system. In some embodiments, when $R^{2C}$ is halo (such as fluoro); - - - - - - - are each a single bond; then $R^{4C}$ is —OC(=O)R"$^D$ or an optionally substituted O-linked amino acid. In some embodiments, when $R^{2C}$ is an unsubstituted $C_{1-4}$ alkyl, an unsubstituted $C_{2-4}$ alkenyl, an unsubstituted $C_{2-4}$ alkynyl, —(CH$_2$)$_{1-6}$ halogen or —(CH$_2$)$_{1-6}$ N$_3$; - - - - - - - are both absent; $Z^2$ is absent; $O^2$ is OR$^{1C}$; $R^{3C}$ is OH, —OC(=O)R"$^C$ or an optionally substituted O-linked amino acid; and $R^{4C}$ is halo; then $R^{5C}$ is selected from an optionally substituted $C_{1-6}$ alkyl, an optionally substituted $C_{2-6}$ alkenyl and an optionally substituted $C_{2-6}$ alkynyl. In some embodiments, when $R^{2C}$ is an unsubstituted $C_{1-4}$ alkyl, an unsubstituted $C_{2-4}$ alkenyl, an unsubstituted $C_{2-4}$ alkynyl, —(CH$_2$)$_{1-6}$ halogen or —(CH$_2$)$_{1-6}$ N$_3$; - - - - - - - are both absent; $Z^2$ is absent; $O^2$ is OR$^{1C}$; $R^{4C}$ is halo; and $R^{5C}$ is H or halo; then $R^{3C}$ is H or halo. In some embodiments, when $R^{2C}$ is an unsubstituted $C_{1-4}$ alkyl, an unsubstituted $C_{2-4}$ alkenyl, an unsubstituted $C_{2-4}$ alkynyl, —(CH$_2$)$_{1-6}$ halogen or —(CH$_2$)$_{1-6}$N$_3$; - - - - - - - are both absent; $Z^2$ is absent; $O^2$ is OR$^{1C}$; $R^{3C}$ is OH, —OC(=O)R"$^C$ or an optionally substituted O-linked amino acid; $R^{4C}$ is halo; $R^{5C}$ is H or halo; and $R^{1C}$ is

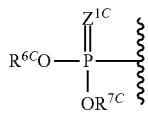

then at least one of $R^{6C}$ and $R^{7C}$ is

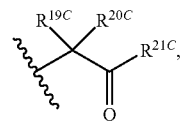

wherein $R^{21C}$ is independently selected from an optionally substituted —O— heteroaryl and an optionally substituted —O-monocyclic heterocyclyl; or then at least one of $R^{6C}$ and $R^{7C}$ is

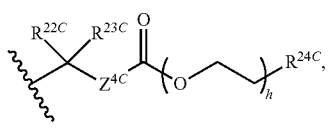

wherein h is 1, 2 or 3; or then at least one of $R^{6C}$ and $R^{7C}$ is

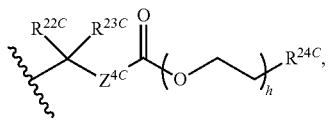

wherein h is 0 and $R^{24C}$ is an optionally substituted —O-heteroaryl or an optionally substituted —O-monocyclic heterocyclyl. In some embodiments, when $R^{2C}$ is an unsubstituted $C_{1-4}$ alkyl, an unsubstituted $C_{2-4}$ alkenyl, an unsubstituted $C_{2-4}$ alkynyl, —$(CH_2)_{1-6}$ halogen or —$(CH_2)_{1-6}N_3$; - - - - - - - - are both absent; $Z^2$ is absent; $O^2$ is $OR^{1C}$; $R^{3C}$ is OH, —OC(=O)$R'''^C$ or an optionally substituted O-linked amino optionally substituted —O-monocyclic heterocycyl; or then $R^{8C}$ is

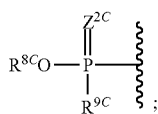

then $R^{8C}$ is

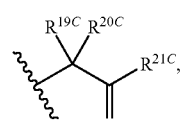

wherein $R^{21C}$ is independently selected from an optionally substituted —O-heteroaryl and an optionally substituted —O-monocyclic heterocyclyl; or then $R^{8C}$ is

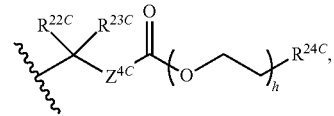

wherein h is 1, 2 or 3; or then $R^{8C}$ is

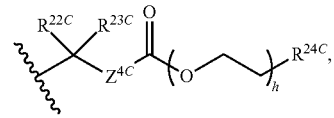

wherein h is 0 and $R^{24C}$ is an optionally substituted —O-heteroaryl, an optionally substituted —O-monocyclic heterocyclyl or

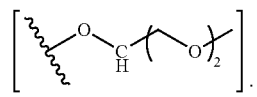

In some embodiments, when - - - - - - - - are both absent; $Z^2$ is absent; $O^2$ is OH; $R^{2C}$ is methyl; $R^{3C}$ is OH; then $R^{4C}$ is halo, —OC(=O)$R'''^D$ or an optionally substituted O-linked amino acid. In some embodiments, when - - - - - - - - are both absent; $Z^2$ is absent; $O^2$ is $OR^{1C}$; $R^{2C}$ is halo (for example, F); $R^{3C}$ is OH or —OC(=O)$R'''^C$; $R^{4C}$ is halo (for example, F); and $R^{5C}$ is methyl, ethyl or ethenyl; then $R^{1C}$ cannot be selected from H,

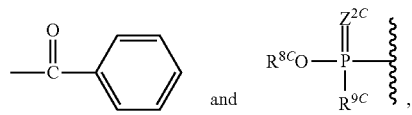

wherein $R^{8C}$ is an unsubstituted aryl; $R^{9C}$ is

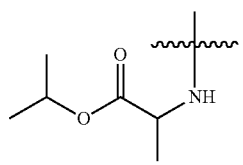 [SMILES: *NC(C)C(=O)OC(C)C]

and $Z^{2C}$ is oxygen. In some embodiments, when $R^{2C}$ is halo (such as F), $R^{3C}$ is OH, $R^{4C}$ is $NH_2$, $R^{4C}$ is an unsubstituted $C_{1-6}$ alkyl (such as $CH_3$) and - - - - - - - - are both absent, then $R^{1C}$ cannot be H. In some embodiments, when $R^{1C}$ is

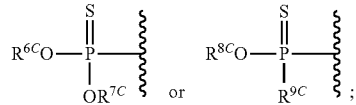

$R^{6C}$ is

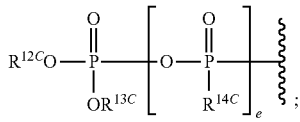

$R^{8C}$ is an optionally substituted aryl, $R^{9C}$ is an optionally substituted N-linked amino acid or an optionally substituted N-linked amino acid ester; then $R^{5C}$ is H, halo, an optionally substituted $C_{1-6}$ alkyl or an optionally substituted $C_{2-6}$ alkenyl. In some embodiments, $R^{1C}$ is not hydrogen (H), for example, when $R^{3C}$ is halo (such as fluoro) and $R^{4C}$ is OH. In some embodiments, $R^{1C}$ is not

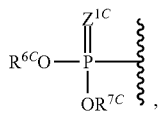

wherein $Z^{1C}$ is O and $R^{6C}$ is

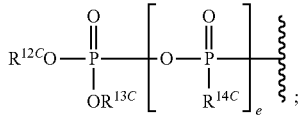

for example, when $R^{4C}$ is halo (such as fluoro) and $R^{3C}$ is OH. In some embodiments, $R^{2C}$ is not hydrogen (H). In some embodiments, $R^{2C}$ is not fluoro (F). In some embodiments, $R^{2C}$ is not —CN. In some embodiments, $R^{2C}$ is not —CHF$_2$. In some embodiments, $R^{5C}$ is not hydrogen or halo. In some embodiments, $R^{4C}$ is not halo. In some embodiments, $R^{4C}$ is not fluoro (F). In other embodiments, $R^{4C}$ is not chloro (Cl). In some embodiments, $R^{2C}$ is not an unsubstituted $C_{1-4}$ alkyl. In some embodiments, $R^{2C}$ is not an unsubstituted $C_{2-4}$ alkenyl. In some embodiments, $R^{2C}$ is not an unsubstituted $C_{2-4}$ alkynyl. In some embodiments, $R^{2C}$ is not —(CH$_2$)$_{1-6}$halogen. In some embodiments, $R^{2C}$ is not —(CH$_2$)$_{1-6}$N$_3$. In some embodiments, $R^{2C}$ is not —(CH$_2$)$_{1-6}$NH$_2$. In some embodiments, $R^{2C}$ is not halogen (for example, fluoro). In some embodiments, $R^{4C}$ is not hydrogen, when $R^{5C}$ is fluoro. In some embodiments, $R^{5C}$ is not an optionally substituted $C_{2-6}$ alkynyl. In some embodiments, $R^{5C}$ is not selected from an optionally substituted $C_{2-6}$ alkyl, an optionally substituted $C_{2-6}$ alkenyl and an optionally substituted $C_{2-6}$ alkynyl. In some embodiments, $R^{2C}$ is not hydrogen (H) when $R^{5C}$ is an optionally substituted $C_{2-6}$ alkynyl. In some embodiments, $R^{5C}$ is not —OH. In some embodiments, $R^{4C}$ is not hydrogen (H). In some embodiments, $R^{4A}$ is not N$_3$. In some embodiments, $R^{4A}$ is not NH$_2$. In some embodiments, $R^{6C}$ is not an optionally substituted aryl. In some embodiments, $R^{6C}$ is not an unsubstituted aryl. In some embodiments, $R^{9C}$ is not N-alanine isopropyl ester. In some embodiments, $R^{5C}$ is not an optionally substituted $C_{1-6}$ alkyl. For example, $R^{5C}$ is not an unsubstituted $C_{1-6}$ alkyl, such as methyl. In some embodiments, $B^{1C}$ is not an optionally substituted uracil, for example, a halo-substituted uracil. In some embodiments, when $R^{1C}$ is hydrogen, an optionally substituted acyl,

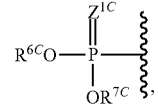

wherein $R^{6C}$ can be

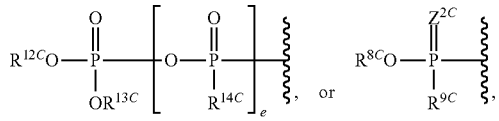

wherein $R^{8C}$ is an unsubstituted or substituted phenyl or an unsubstituted or substituted naphthyl and $R^{9C}$ is an optionally substituted N-linked amino acid or an optionally substituted N-linked amino acid ester; $R^{2C}$ is fluoro, $R^{3C}$ is OH or —C(=O)-unsubstituted or substituted phenyl; $R^{4C}$ is fluoro; and $R^{5C}$ is a $C_{1-4}$ alkyl (such as methyl); then B cannot be an optionally substituted pyrimidine base, such as

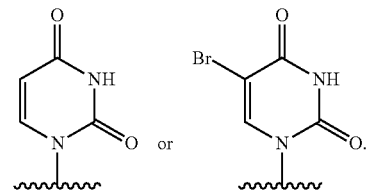 [SMILES: *n1ccc(=O)[nH]c1=O ; *n1cc(Br)c(=O)[nH]c1=O]

In some embodiments, when $R^{1C}$ is

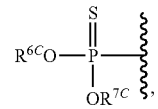

$R^{2C}$ is H, $R^{3C}$ is OH and $R^{4C}$ is OH or halogen (such as F), then $R^{5C}$ is not an optionally substituted $C_{1-6}$ alkyl, an optionally substituted $C_{2-6}$ alkenyl or an optionally substituted $C_{2-6}$ alkynyl.

Examples of compounds of Formulae (I) and/or (II), or a pharmaceutically acceptable salt of the foregoing, include, but are not limited to:

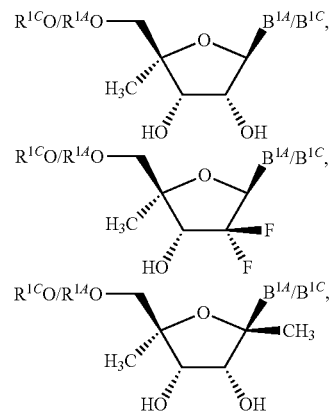

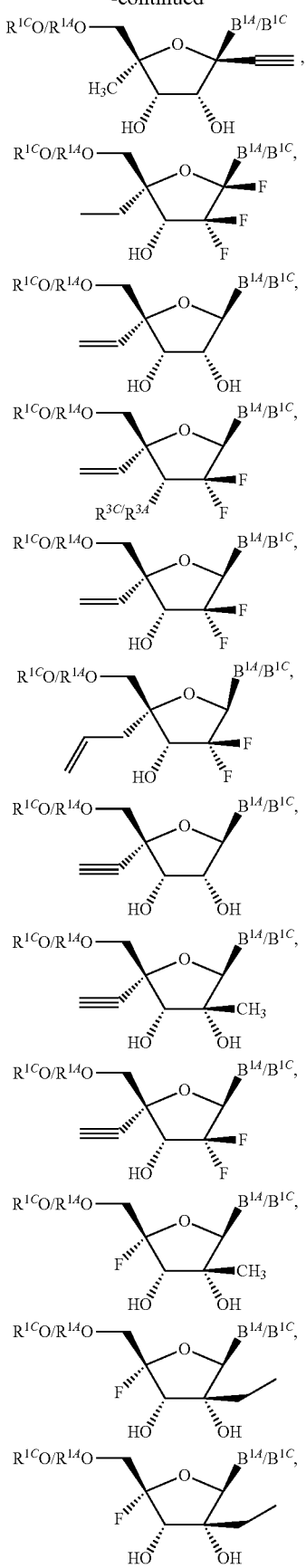
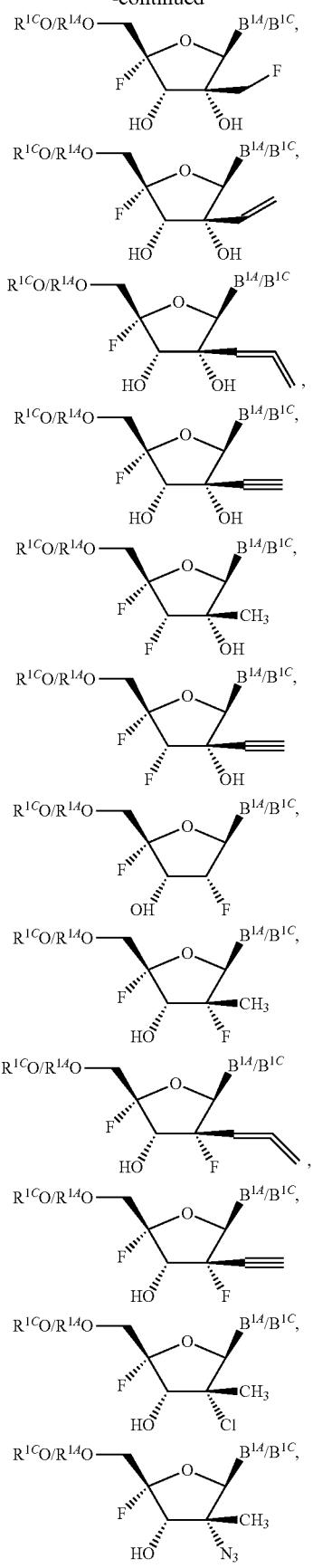

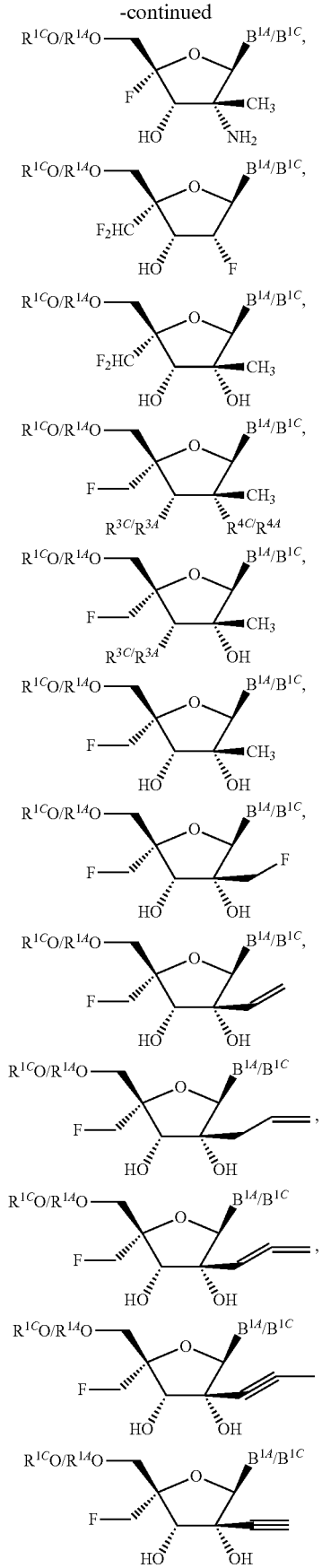
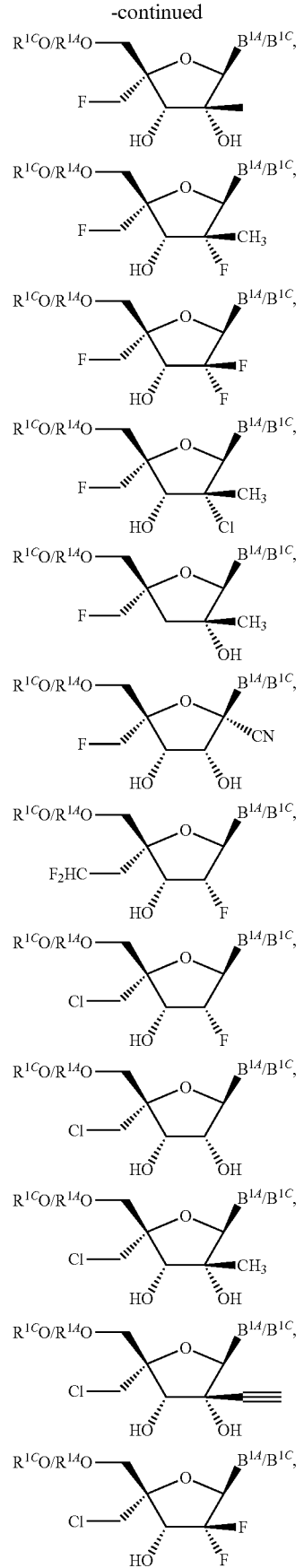

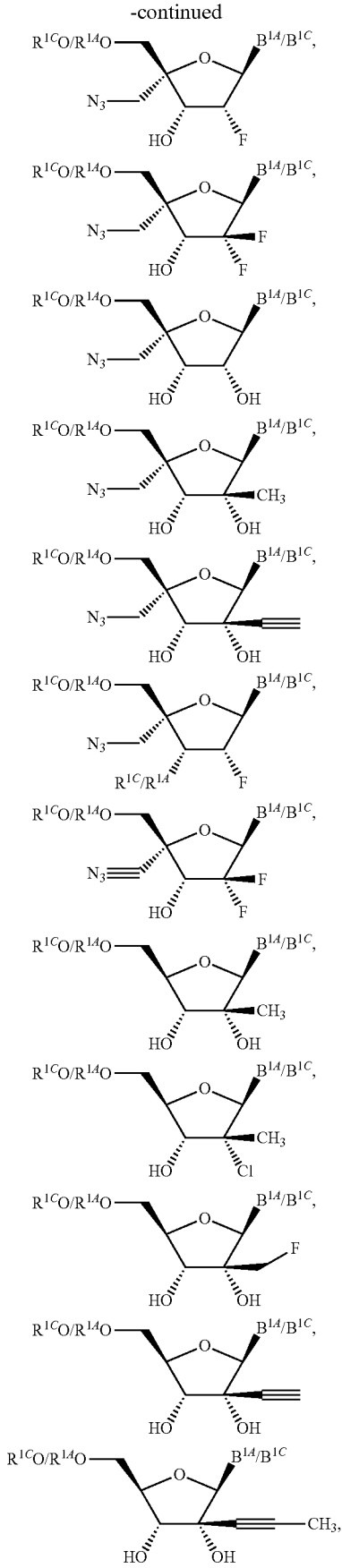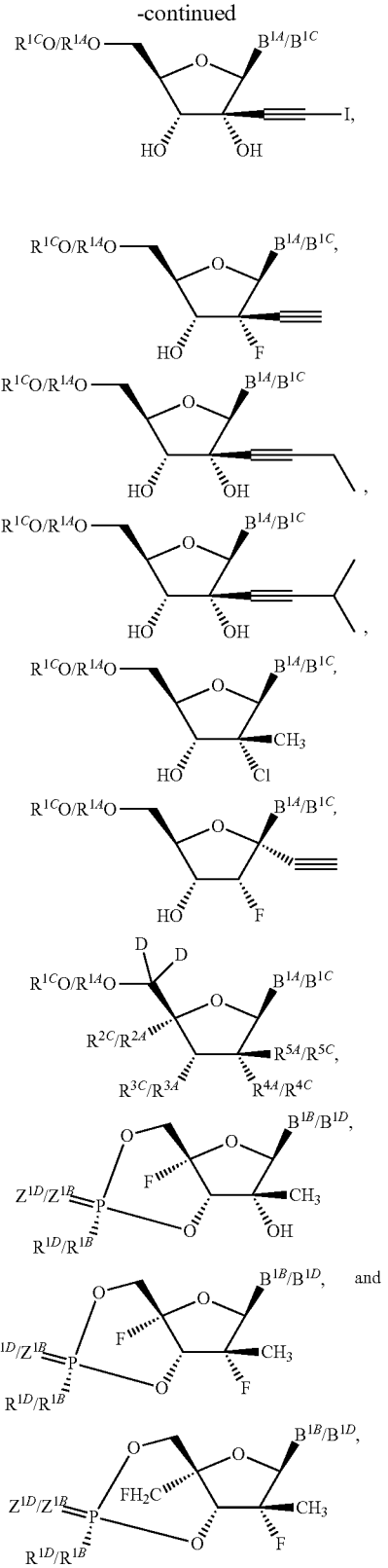
or a pharmaceutically acceptable salt of the foregoing.
Additional examples of compounds of Formulae (I) and/or (II), or a pharmaceutically acceptable salt of the foregoing, include, but are not limited to:

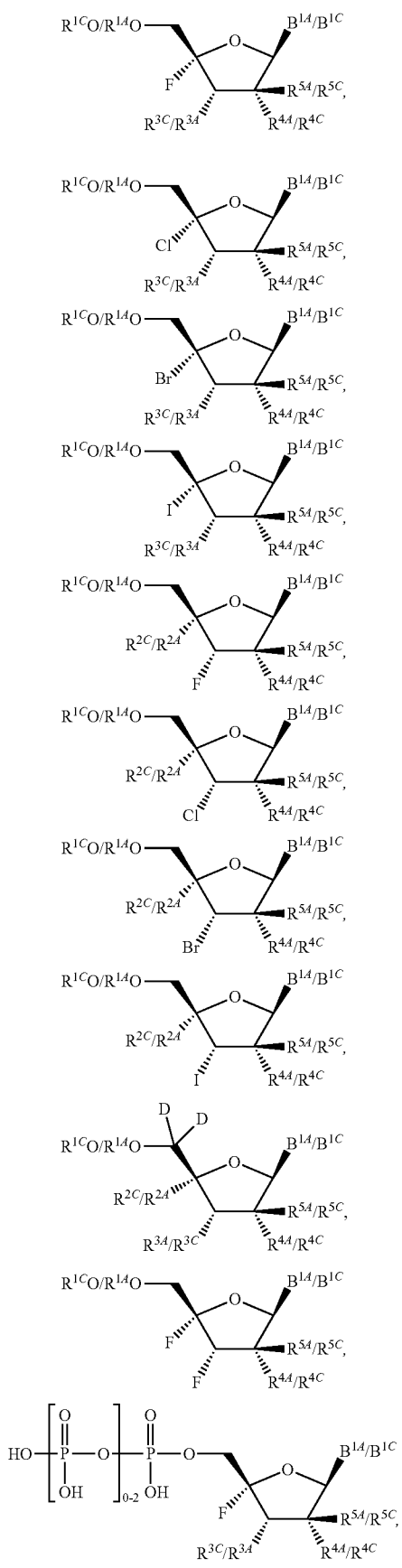
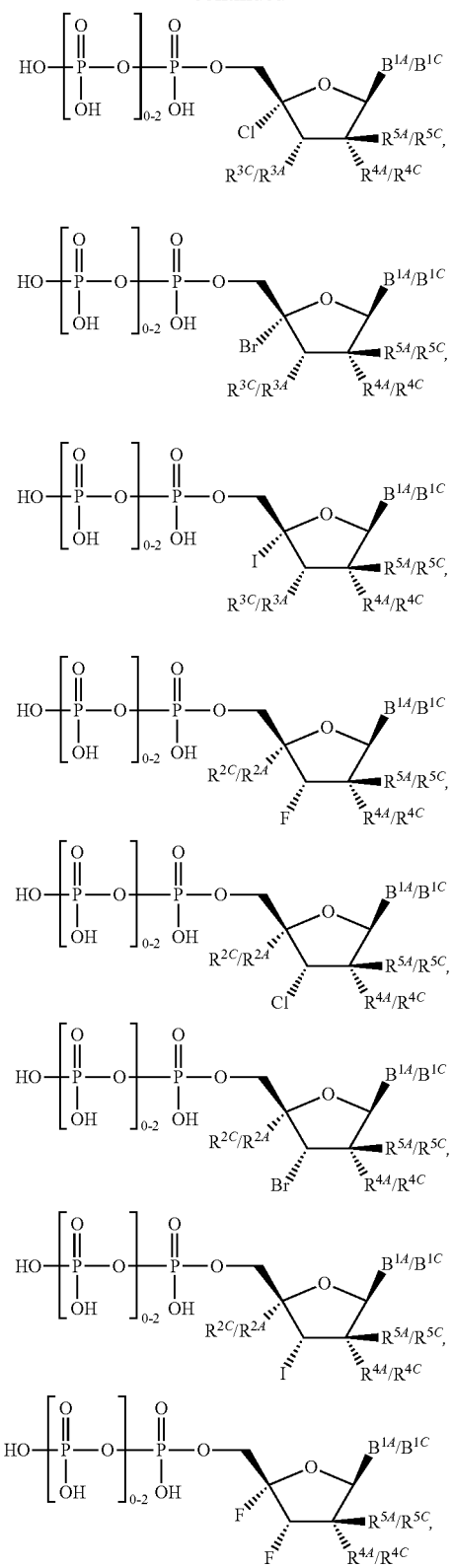
or a pharmaceutically acceptable salt of the foregoing.
In some embodiments, a compound of Formulae (I) and/or (II), or a pharmaceutically acceptable salt of the foregoing, may be selected from:

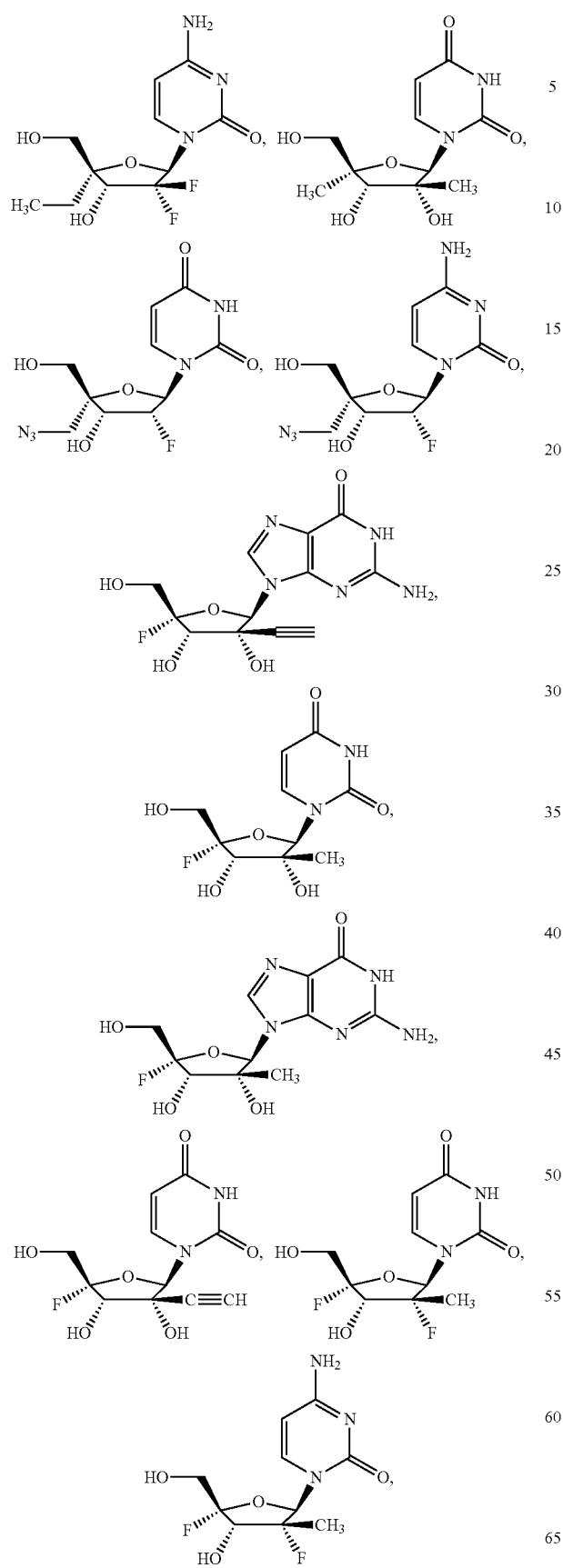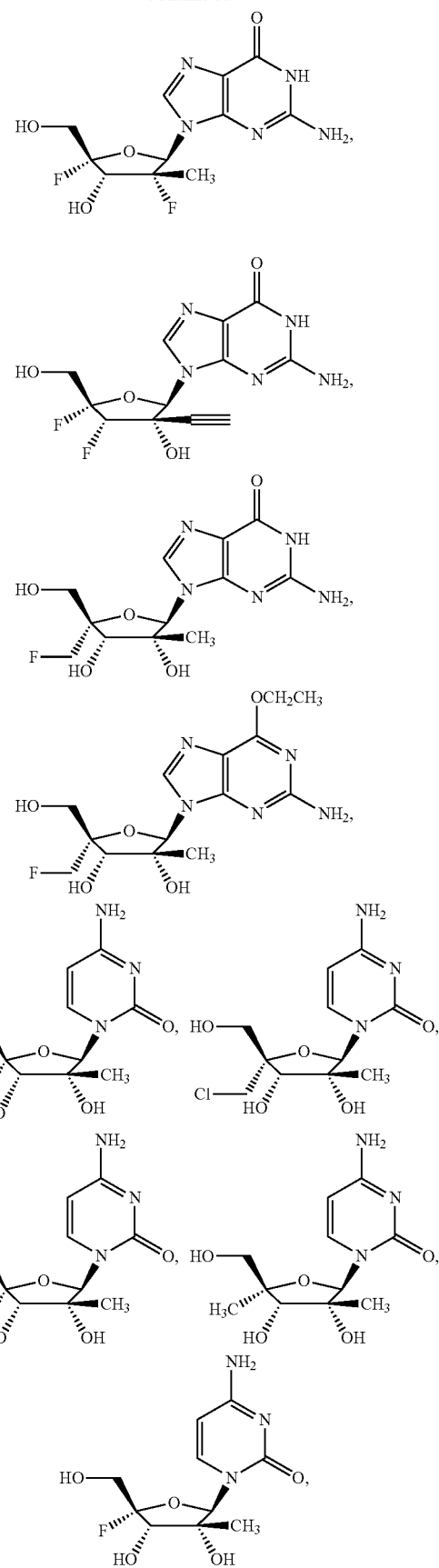

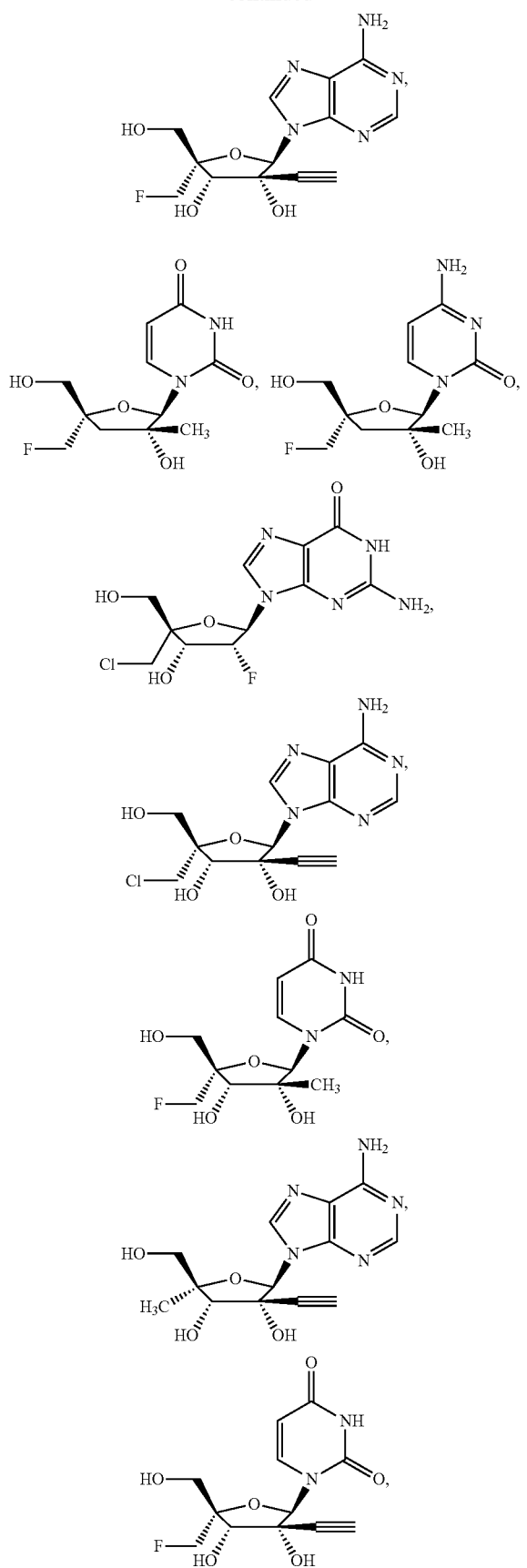
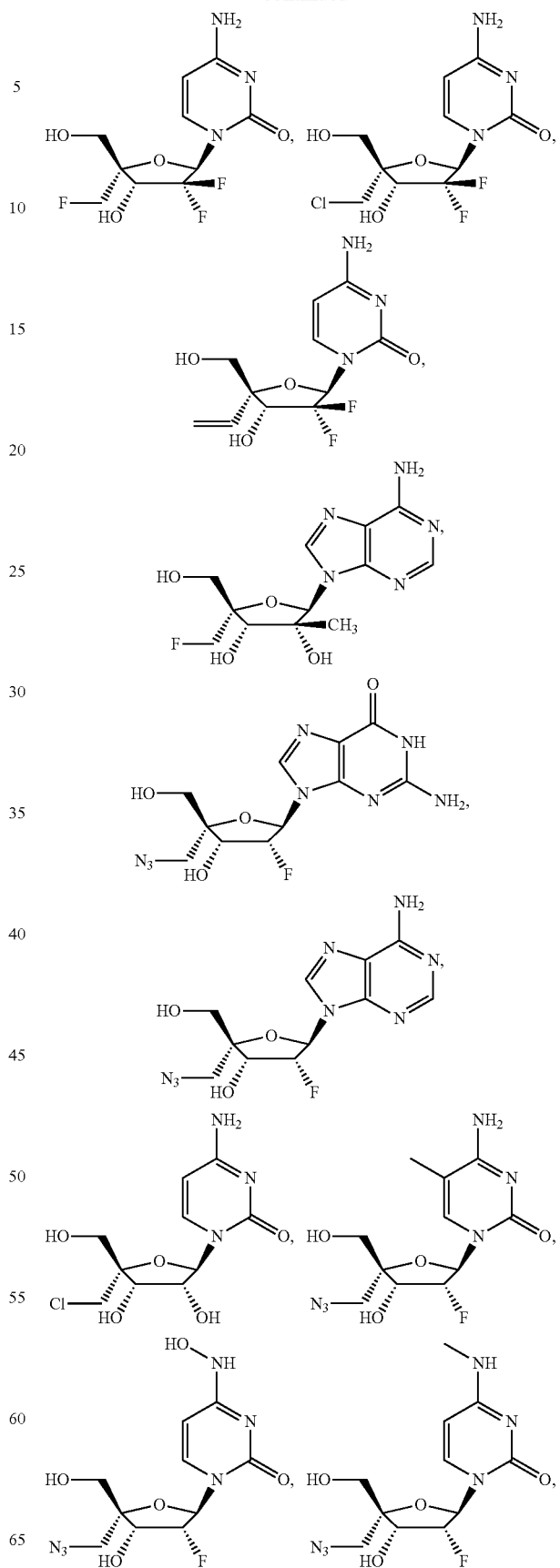

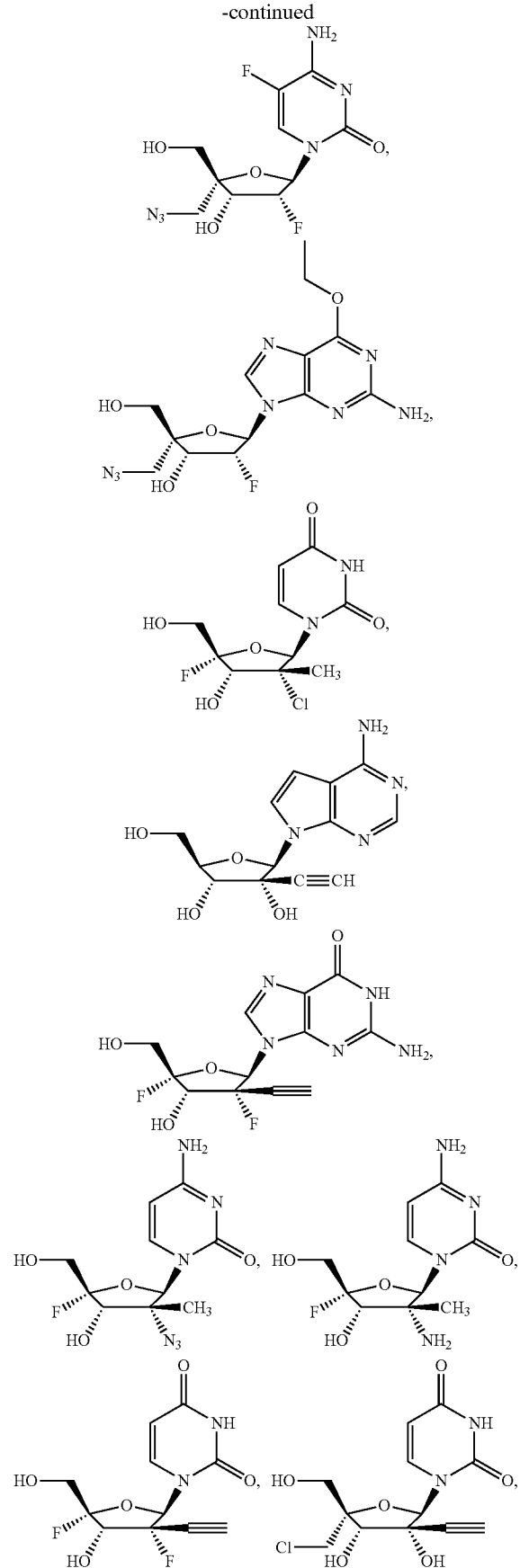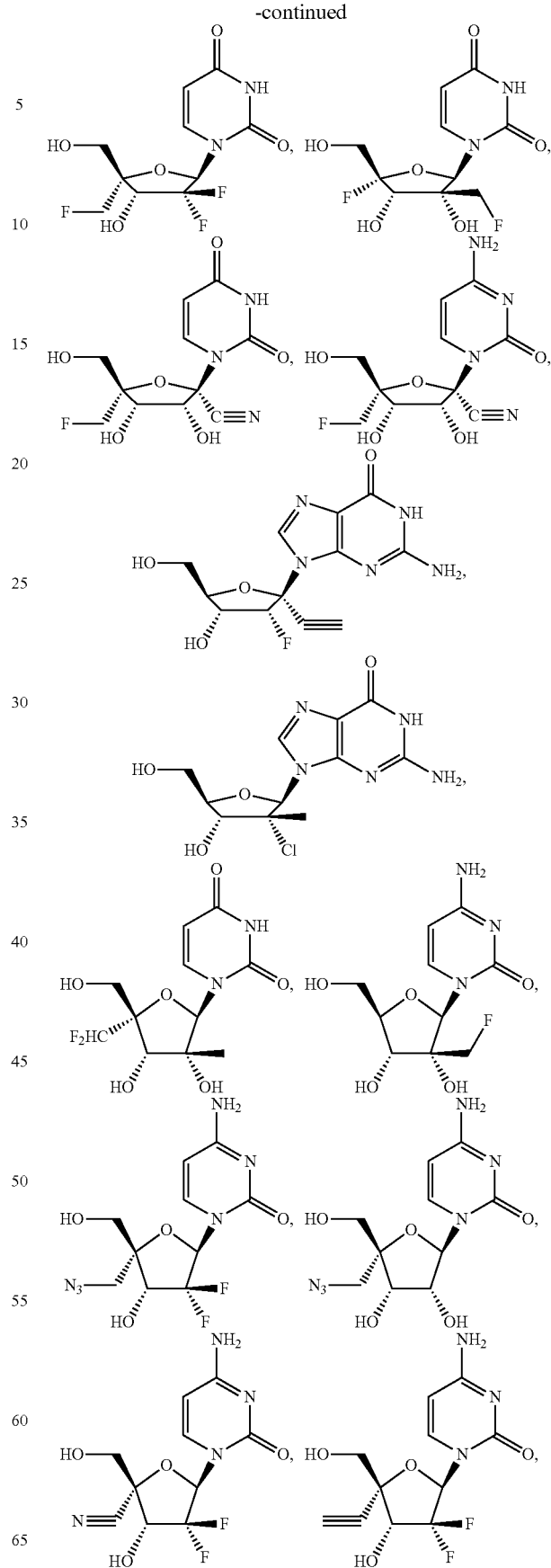

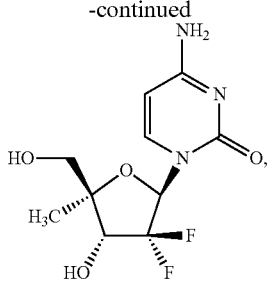
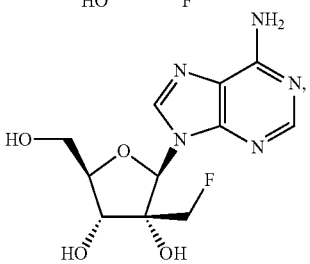
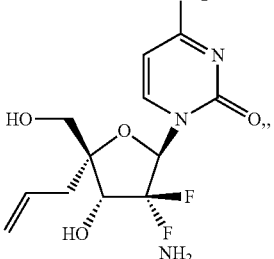
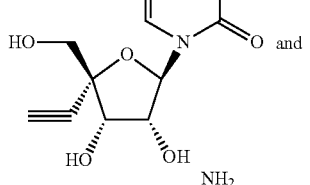
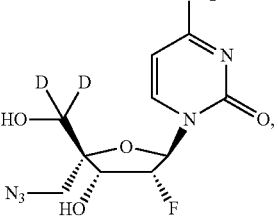
or a pharmaceutically acceptable salt of the foregoing.
In some embodiments, a compound of Formulae (I) and/or (II), or a pharmaceutically acceptable salt of the foregoing, may be selected from:
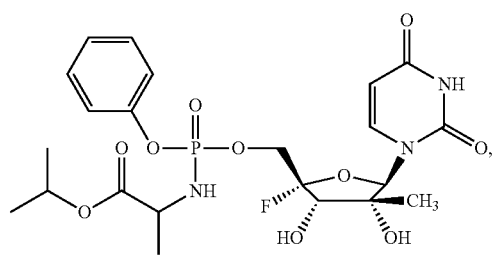
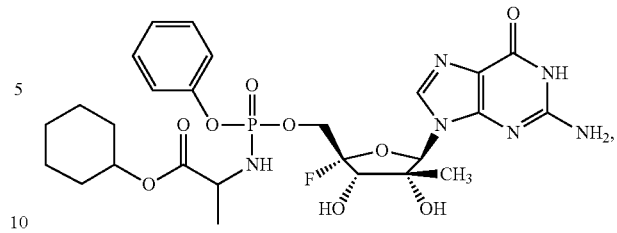
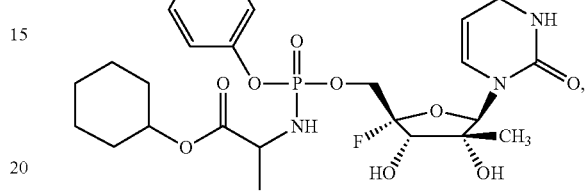
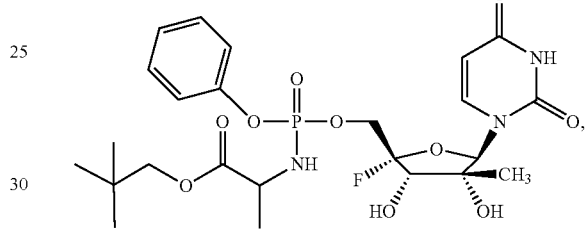
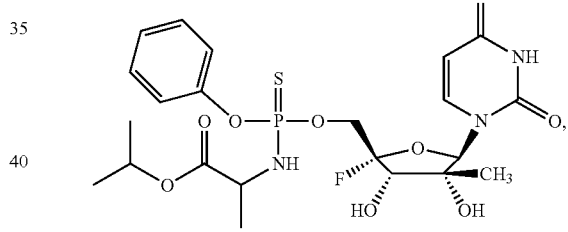
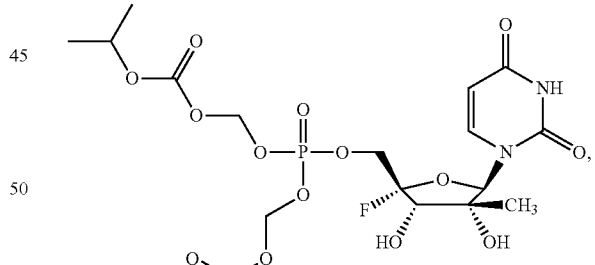
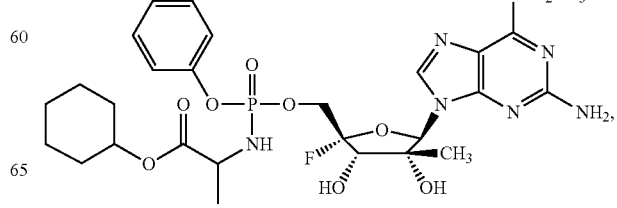

225
-continued
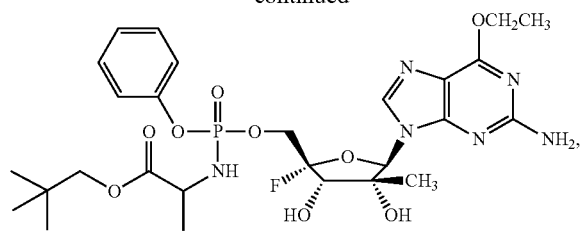
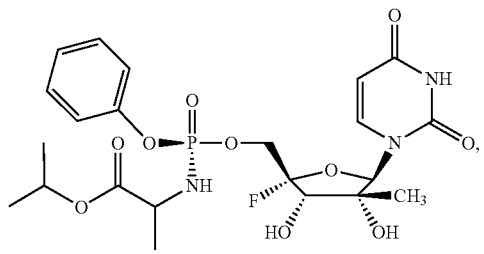
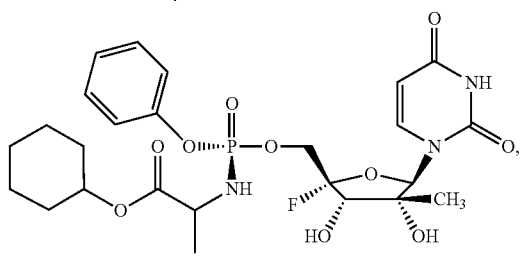
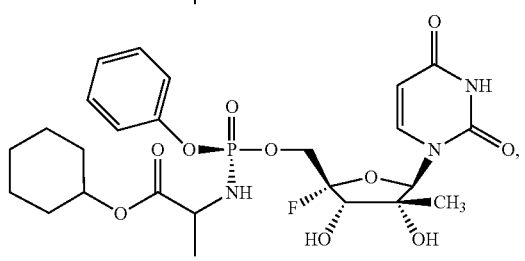
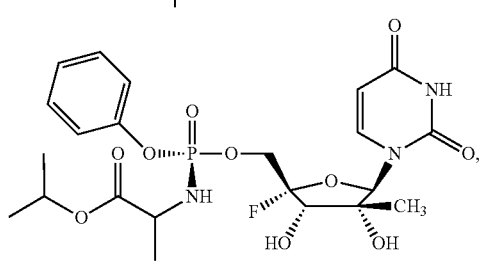
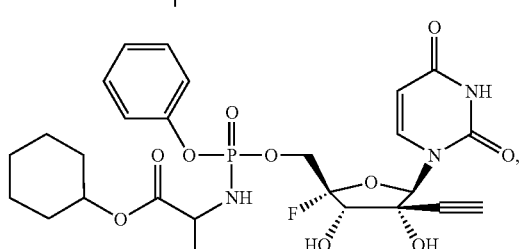
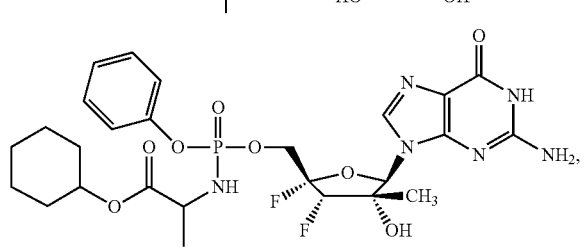
226
-continued
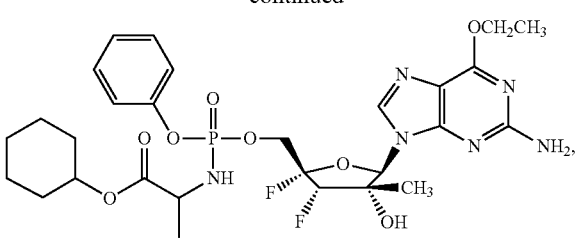
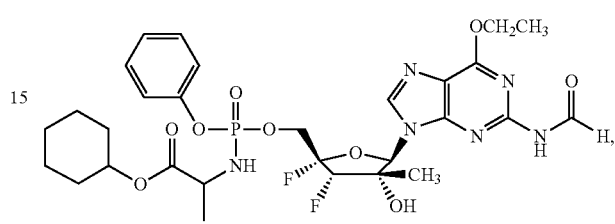
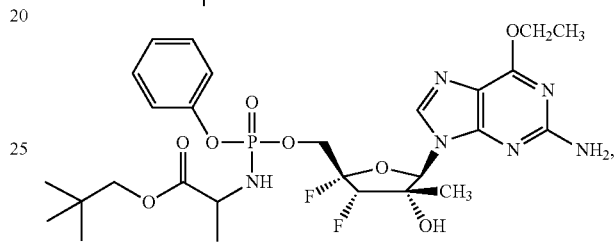
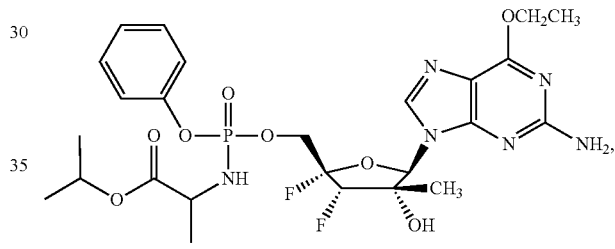
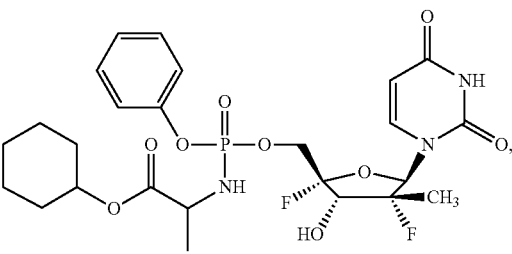
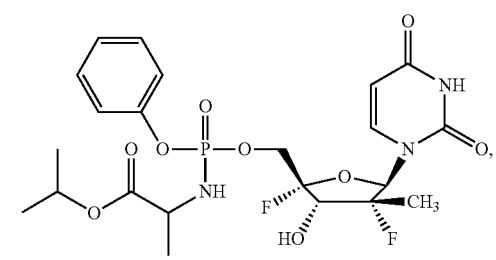
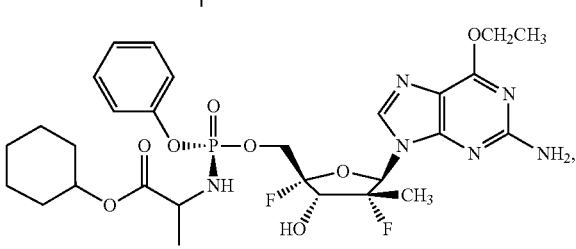

227
-continued
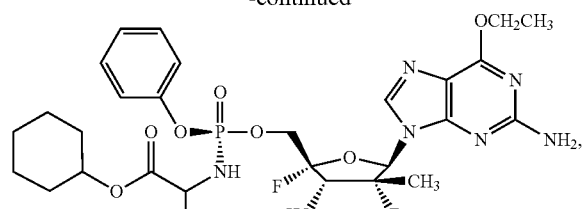
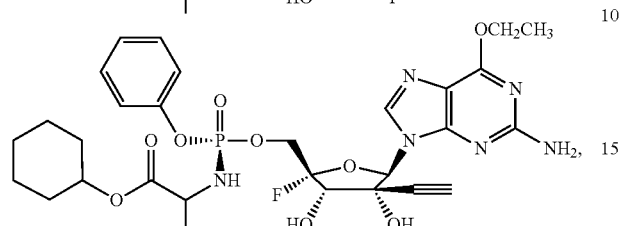
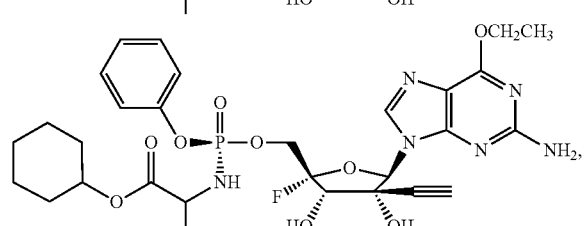
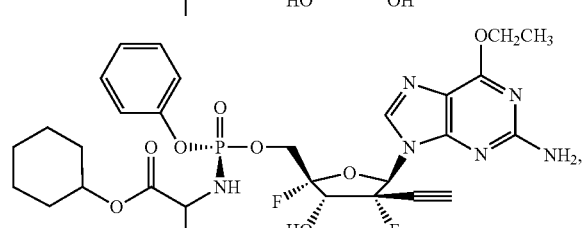
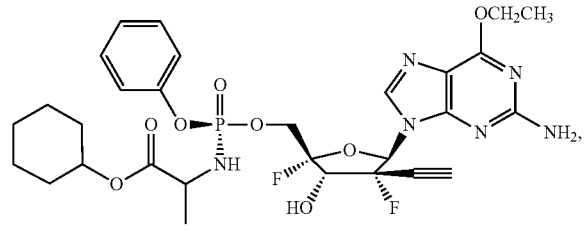
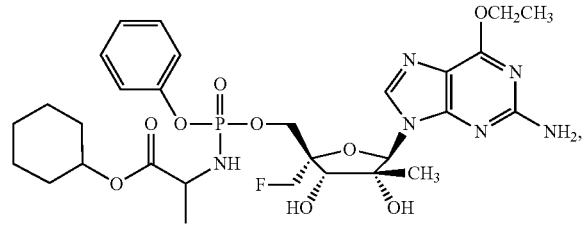
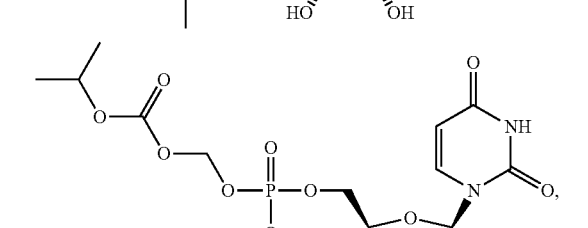
228
-continued
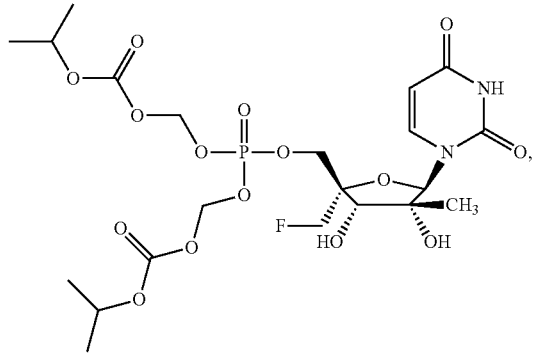
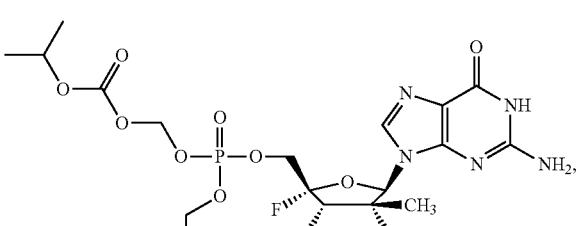
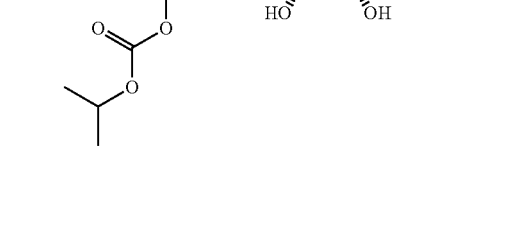
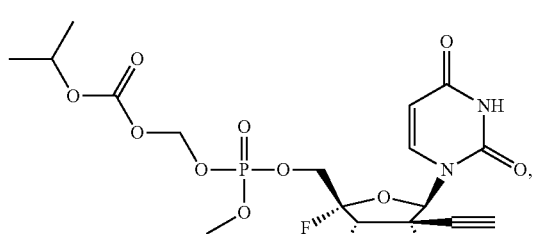
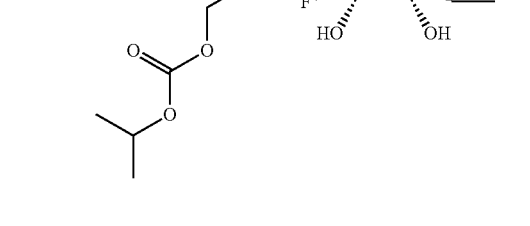
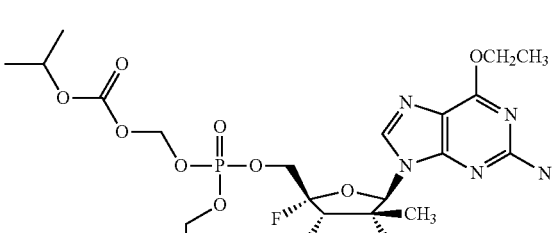

229
-continued
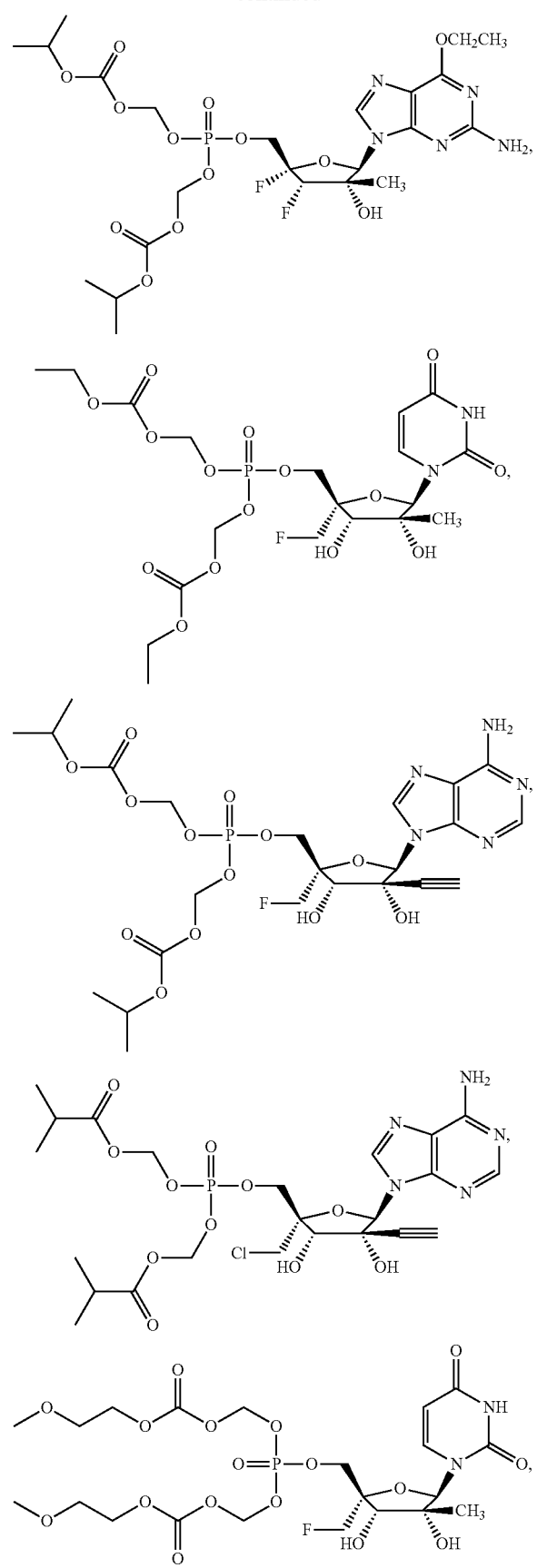
230
-continued
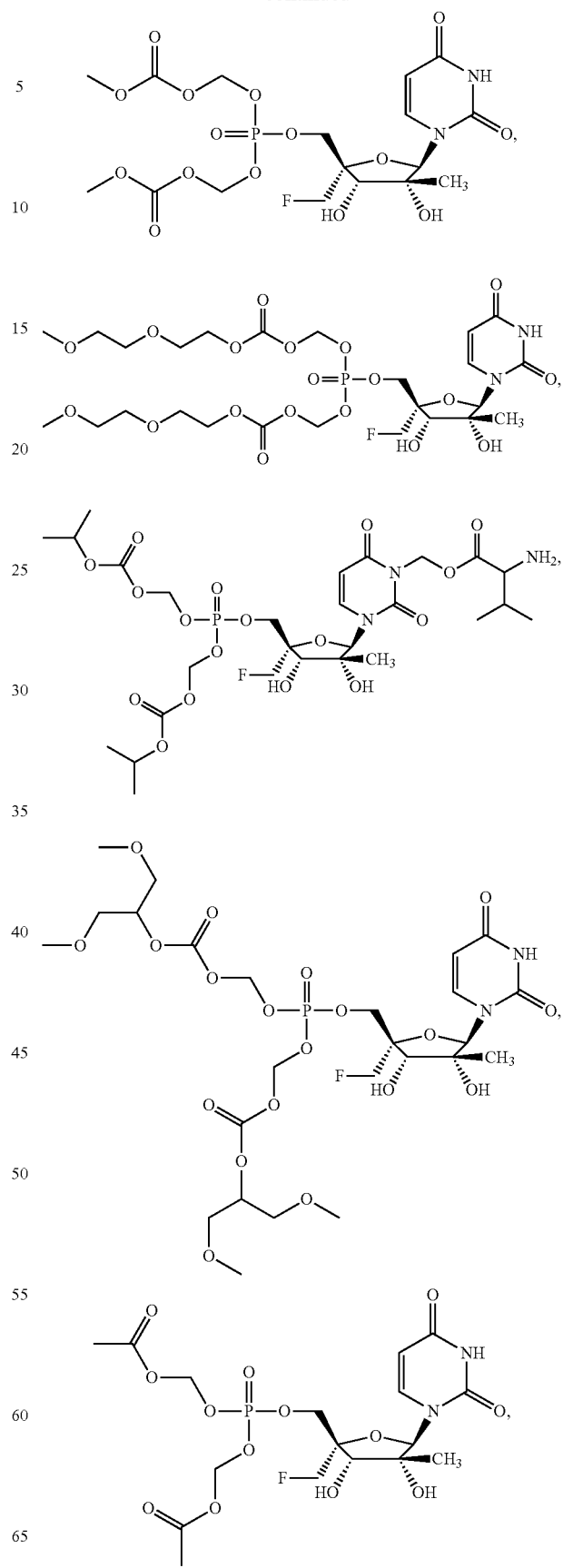

231
-continued
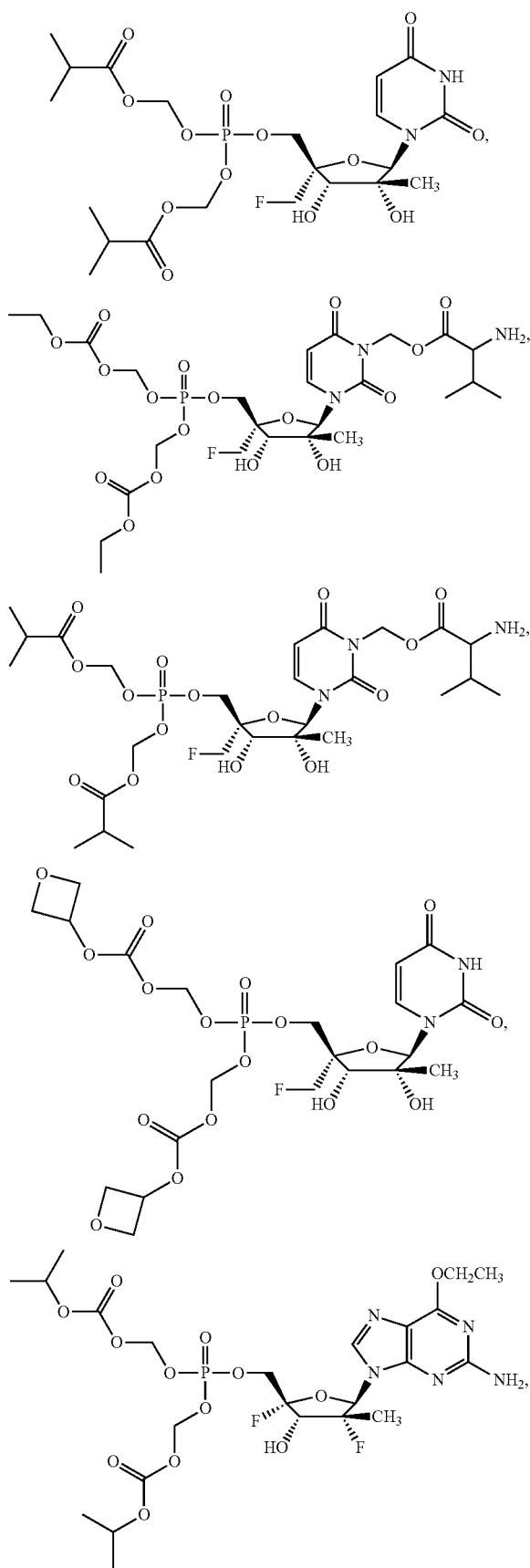
232
-continued
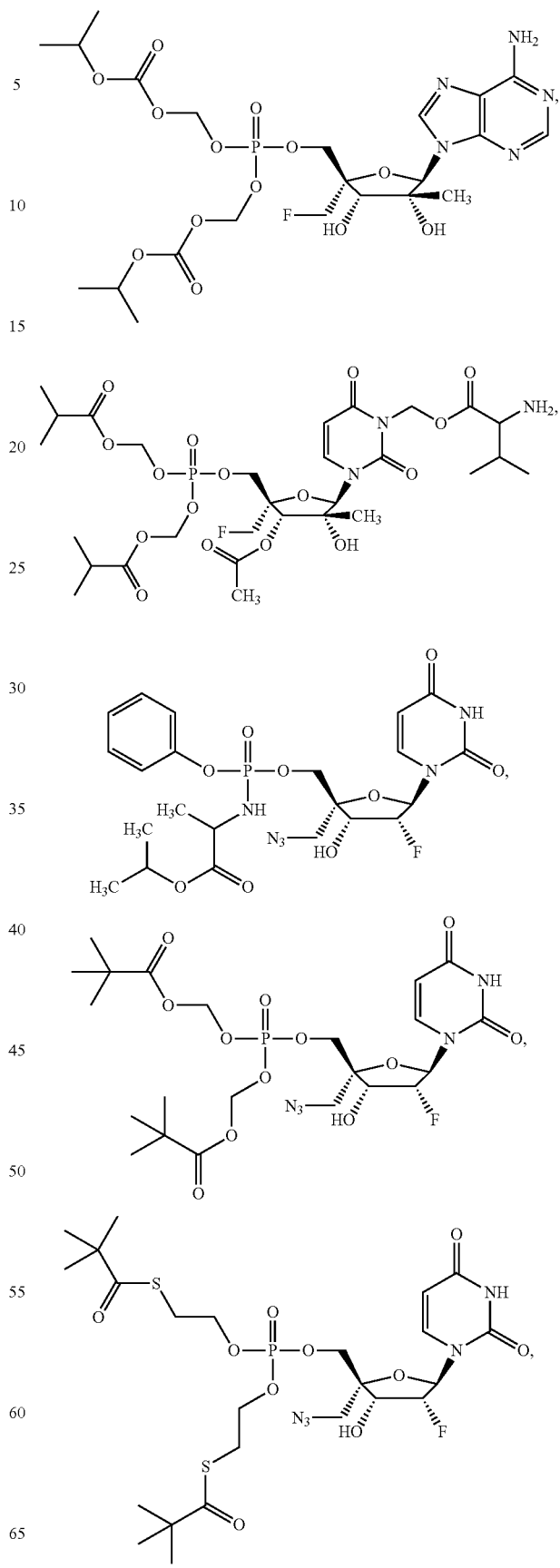

233
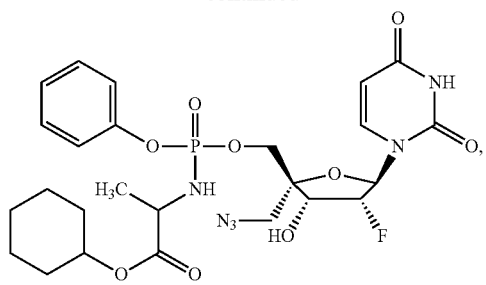
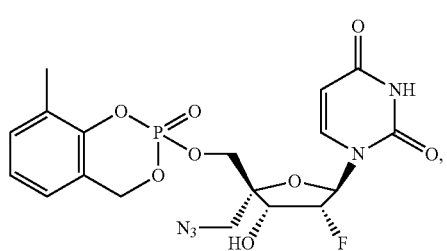
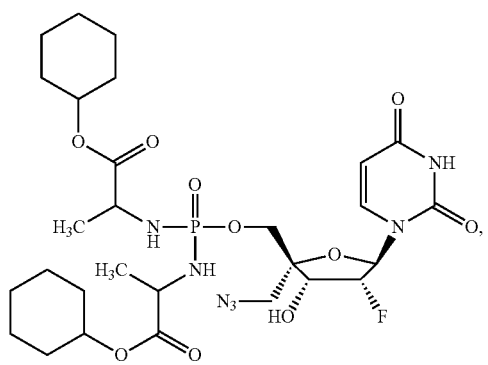
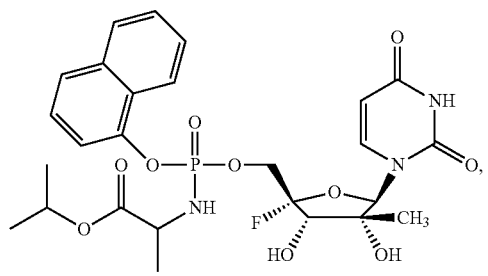
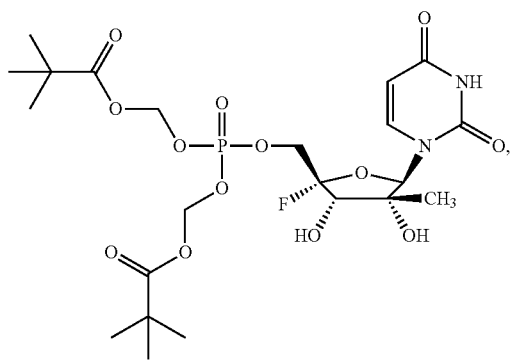
234
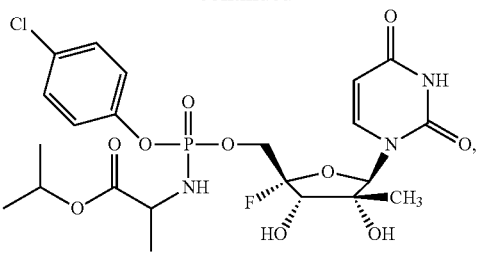
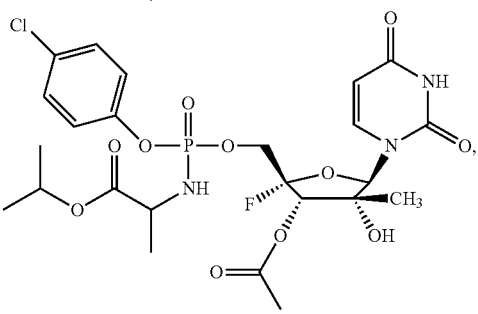
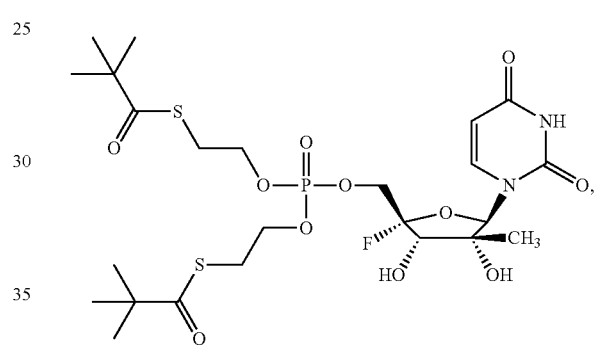
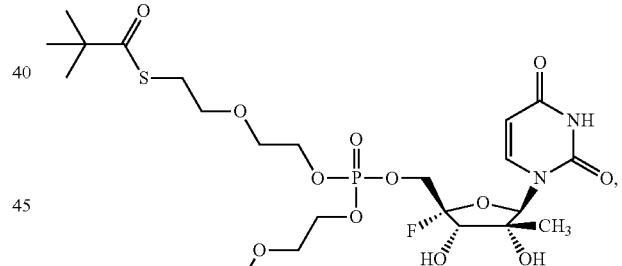
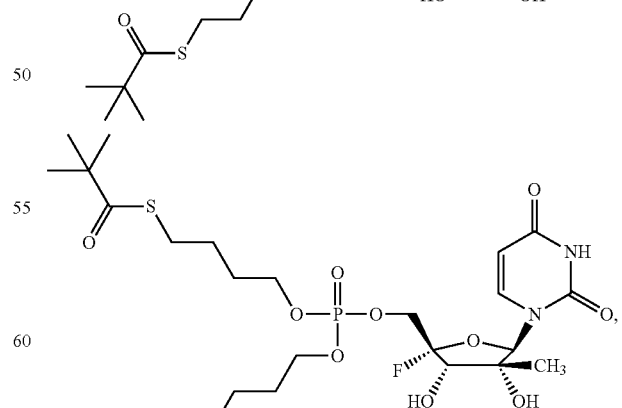

235
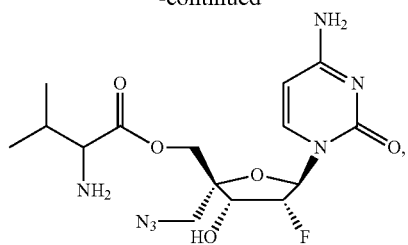
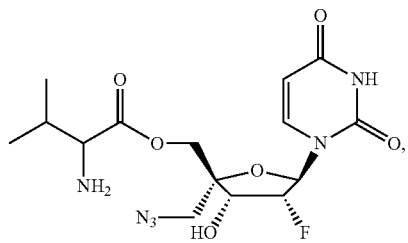
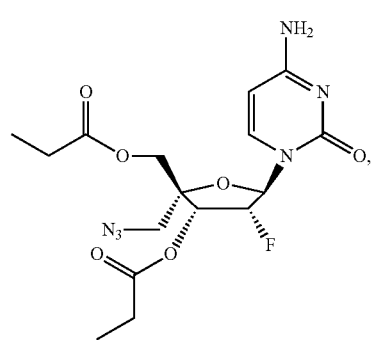
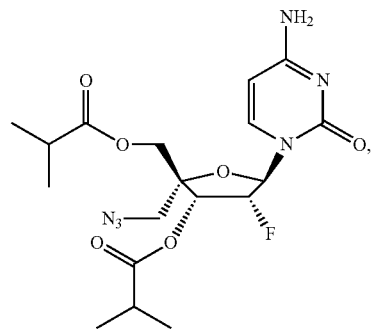
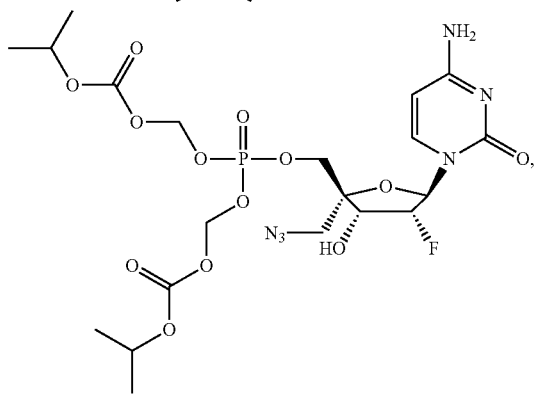
236
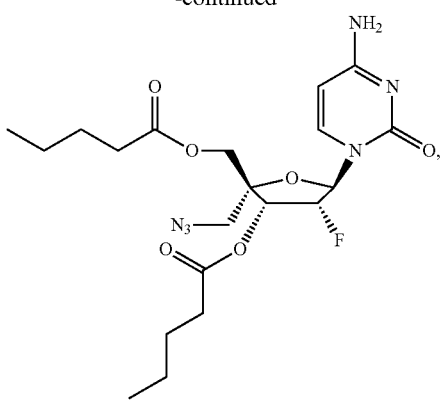
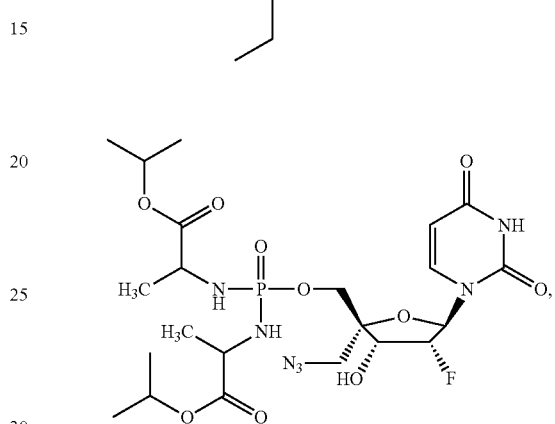
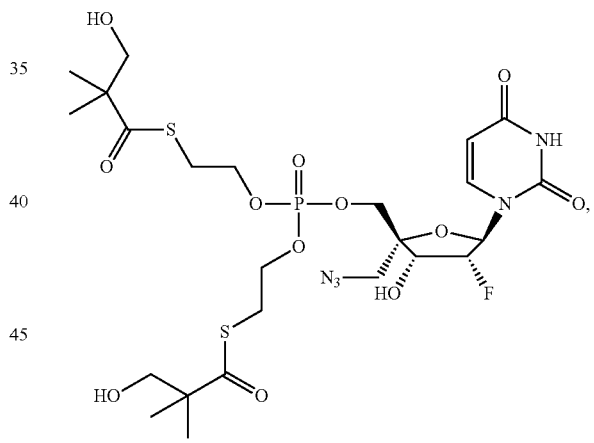
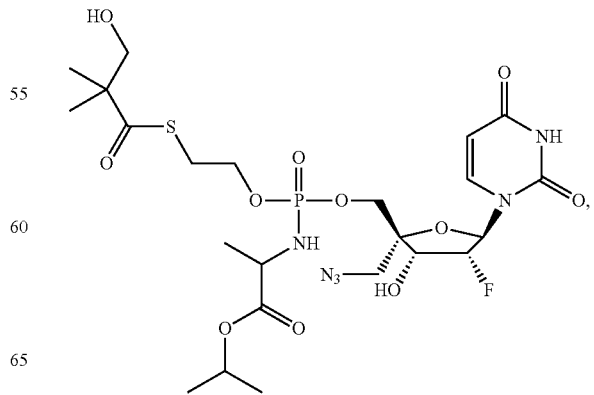

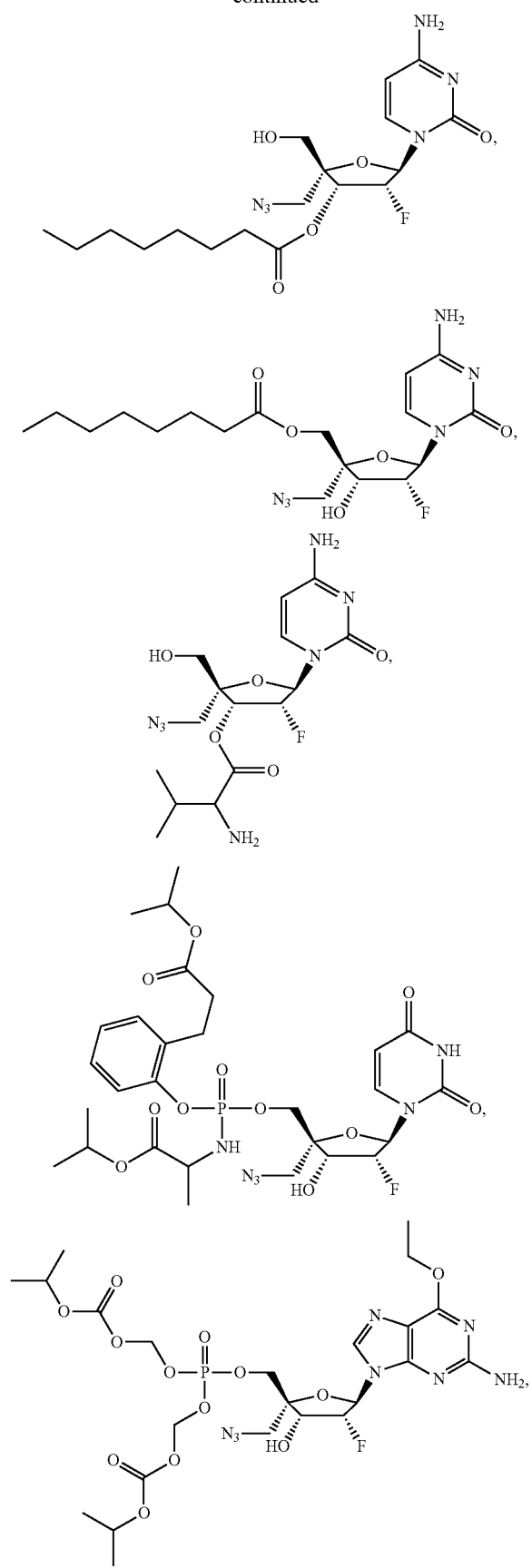
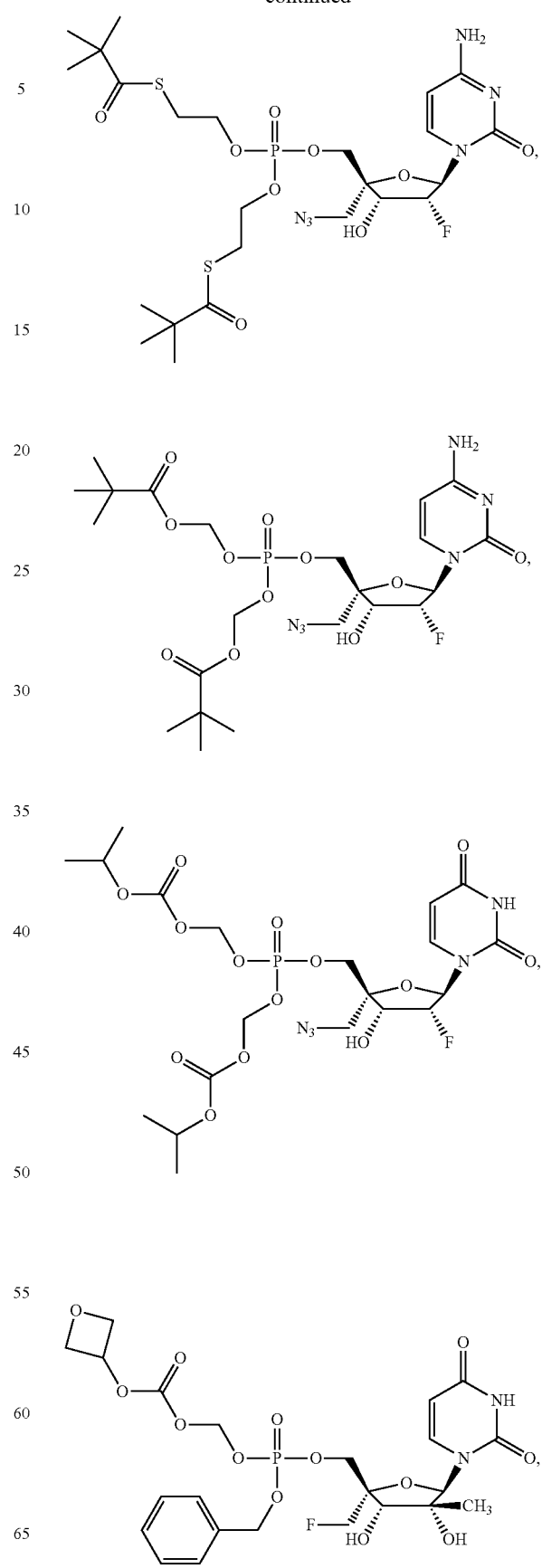

239
-continued
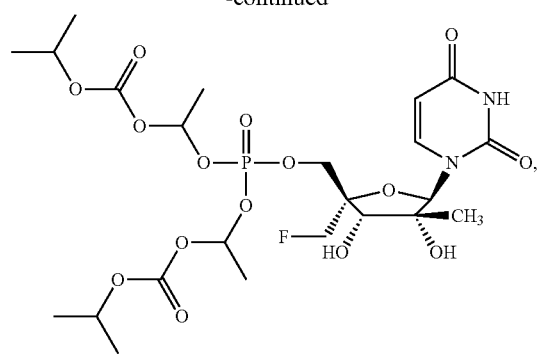
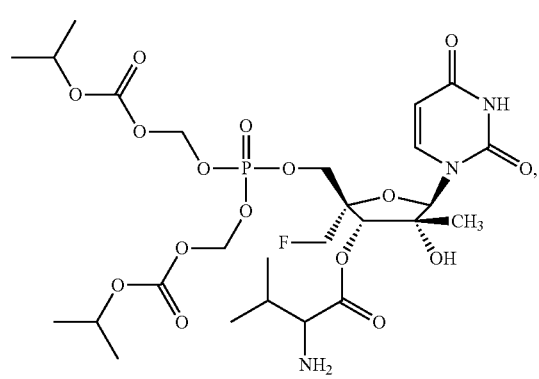
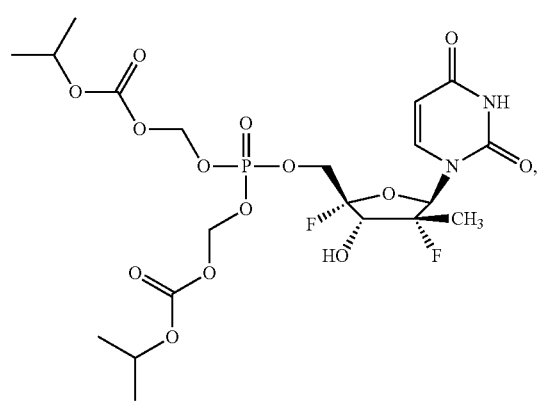
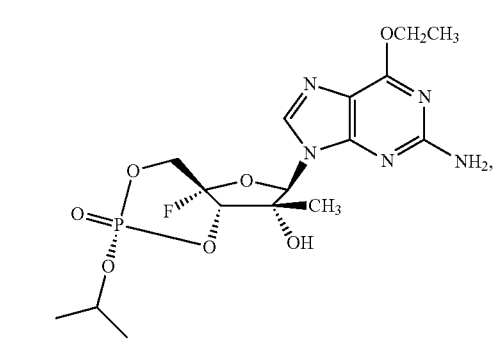
240
-continued
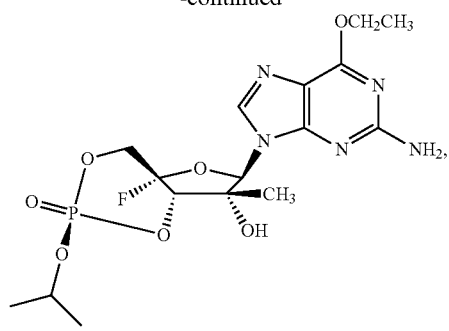
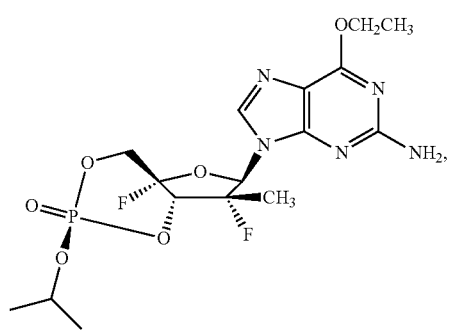
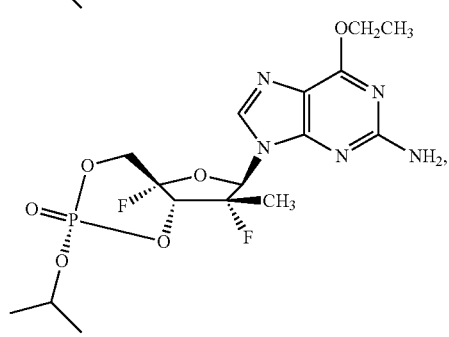
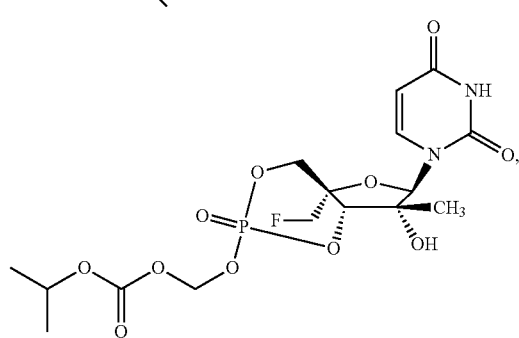

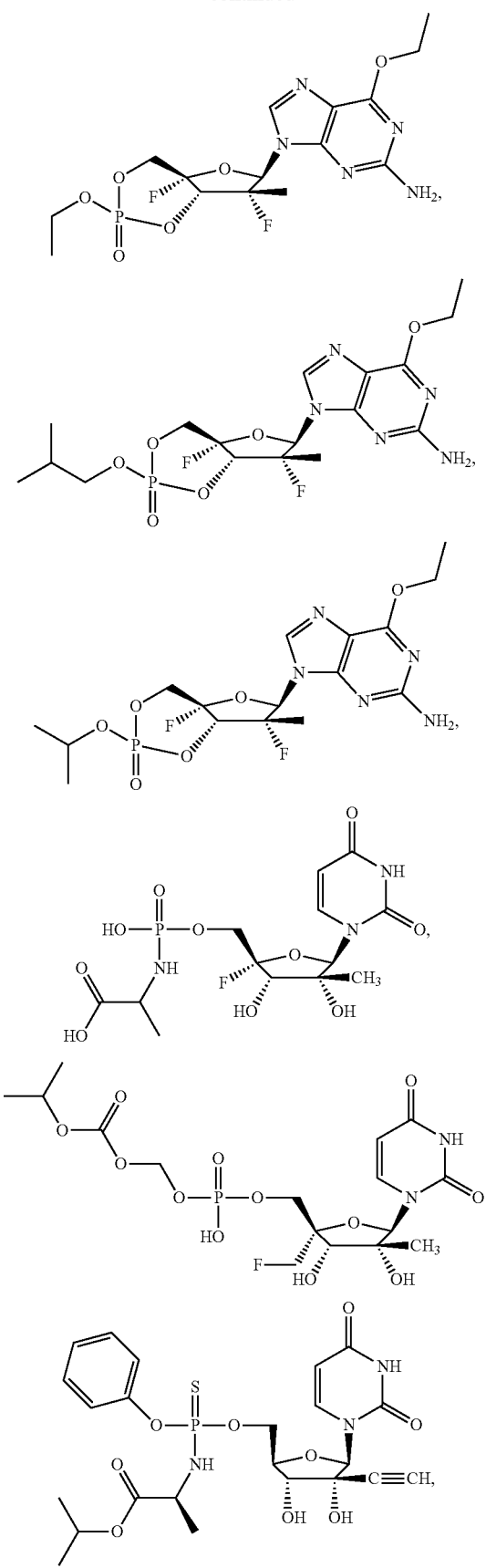
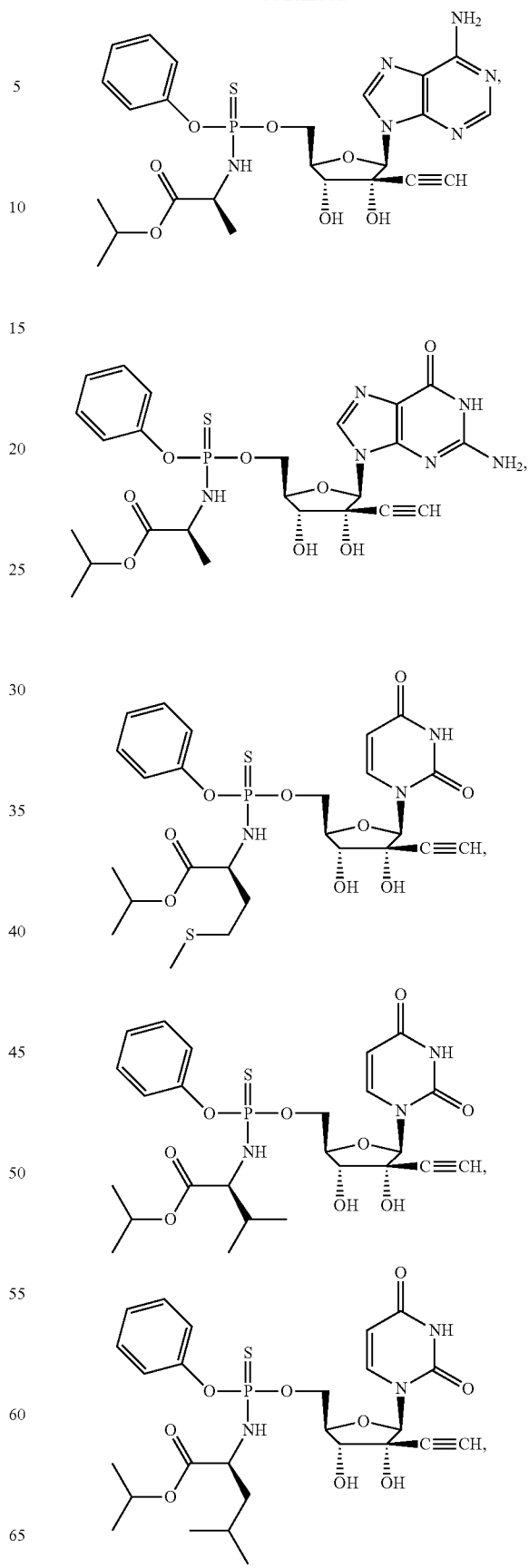

243
-continued
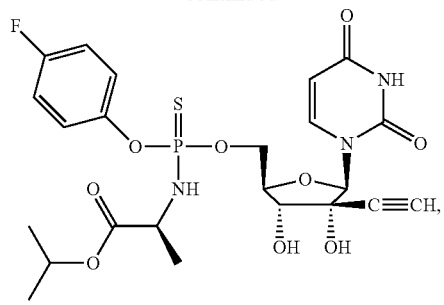
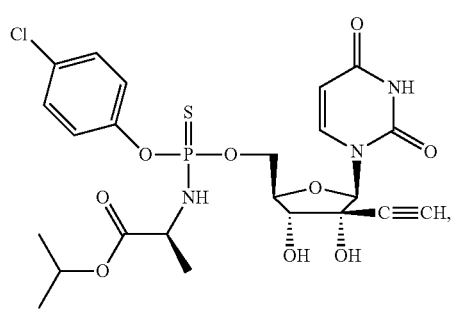
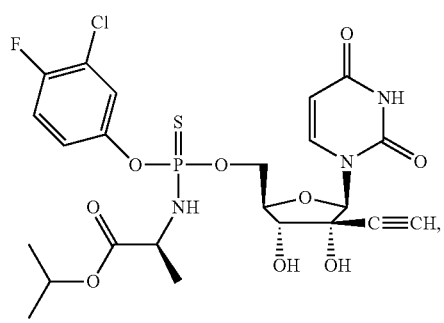
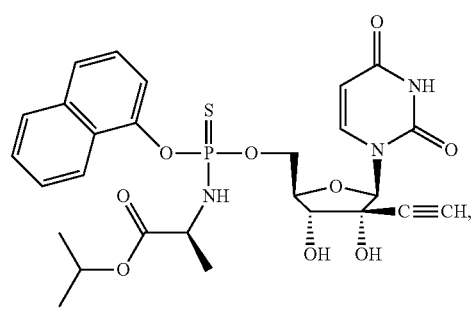
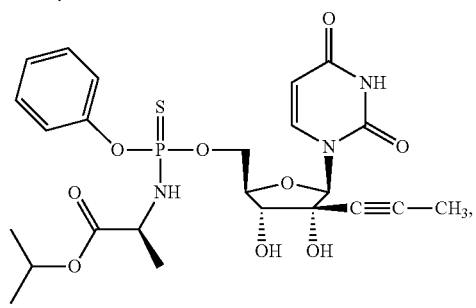
244
-continued
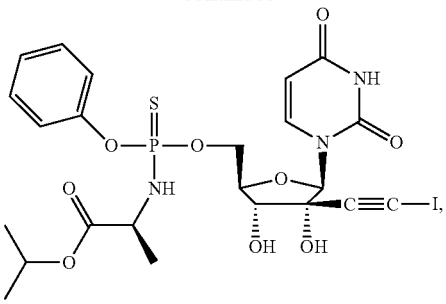
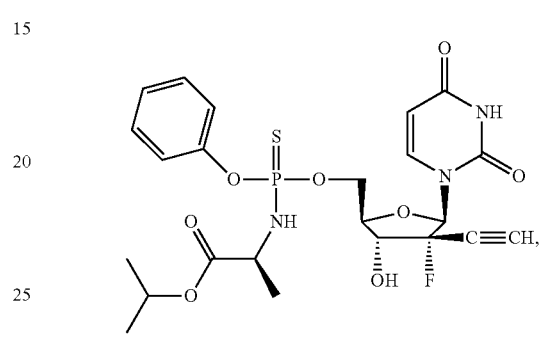
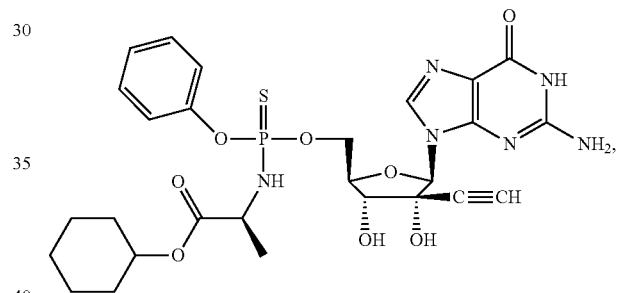
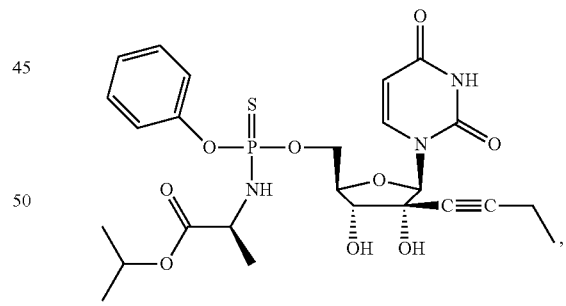
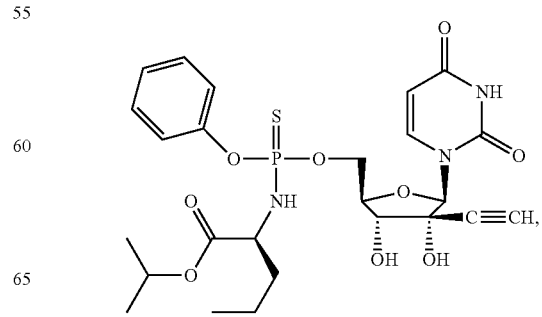

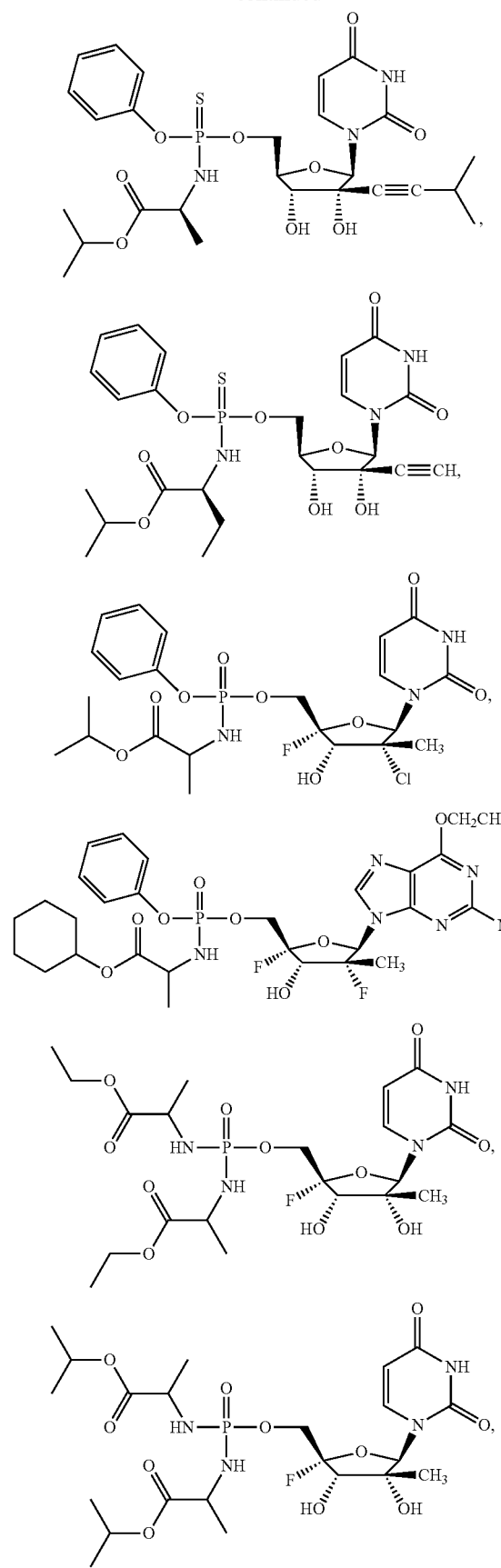
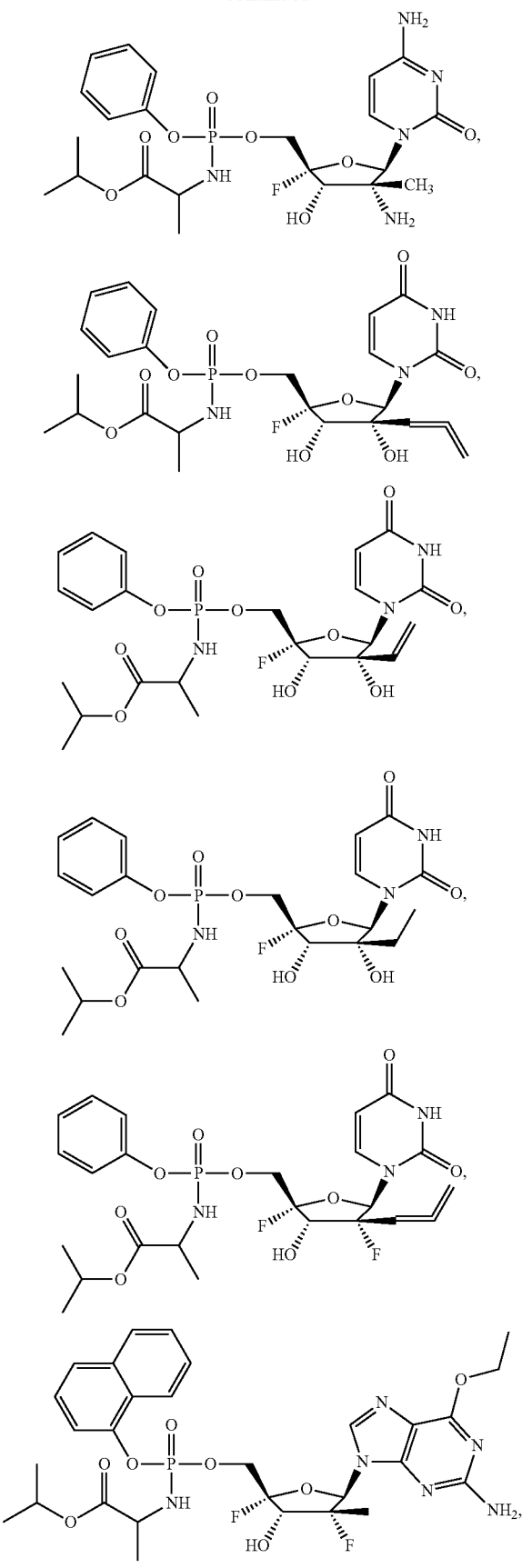

247
-continued
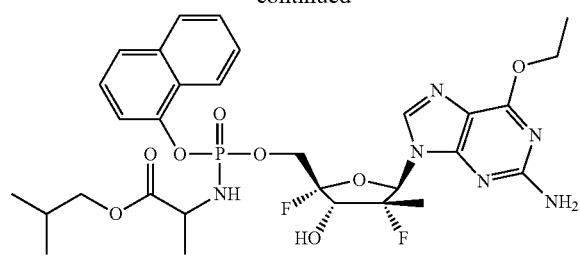
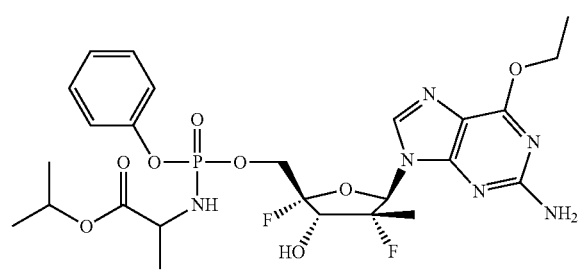
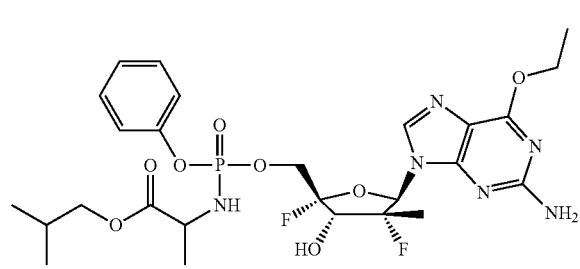
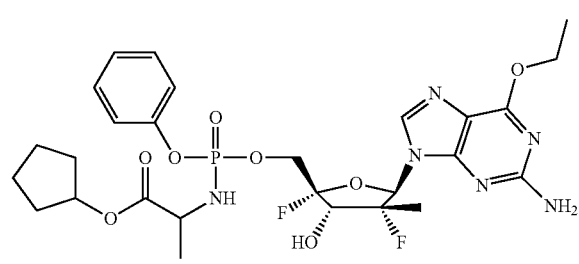
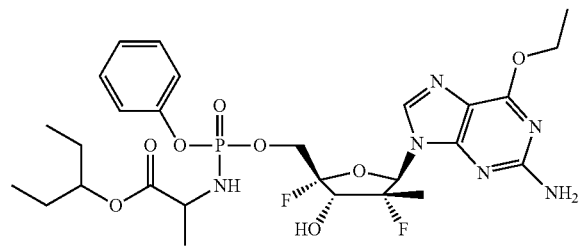
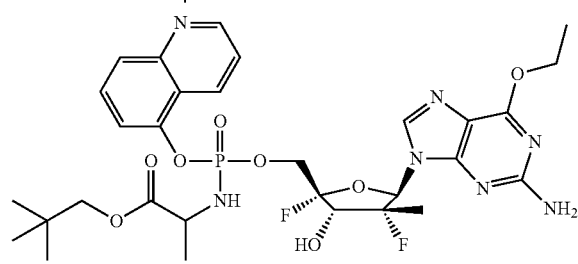
248
-continued
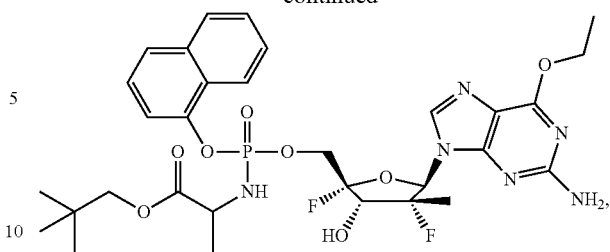
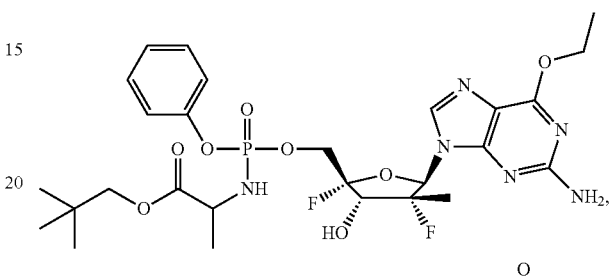
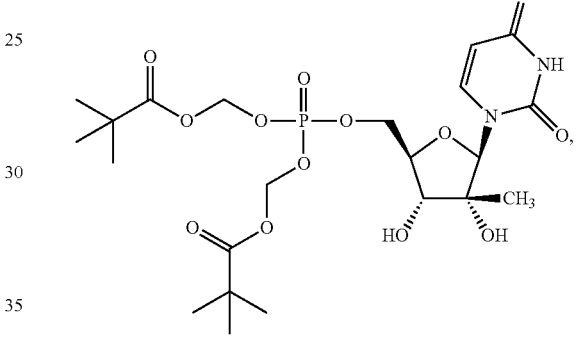
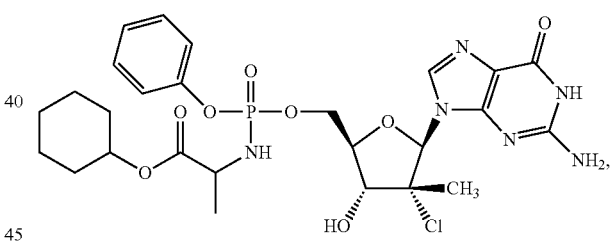
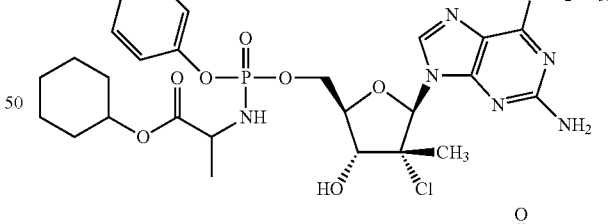
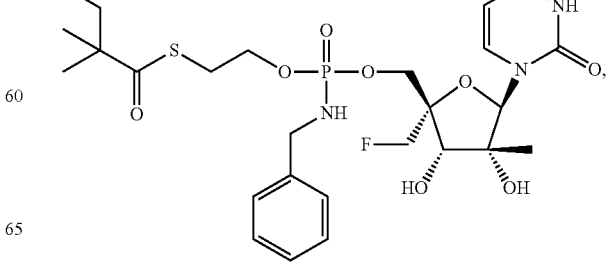

249
-continued
250
-continued
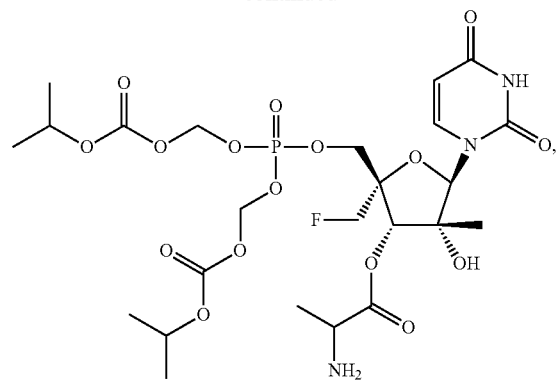
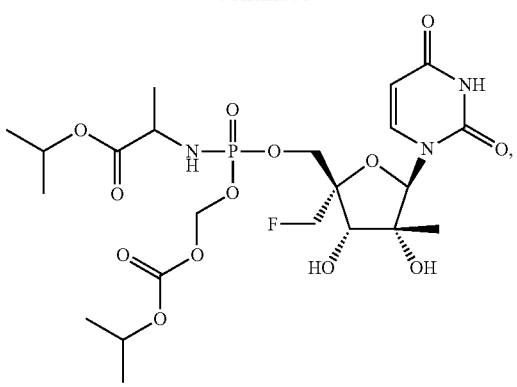
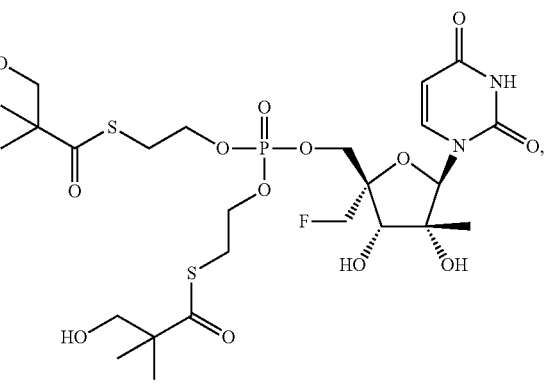
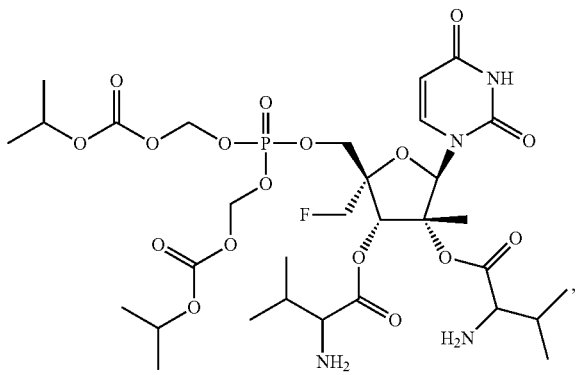

-continued
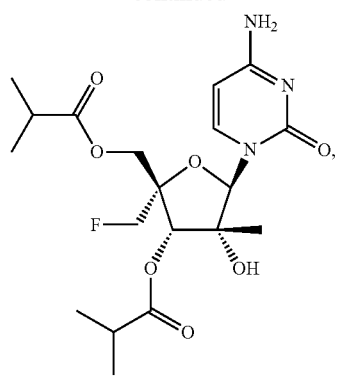
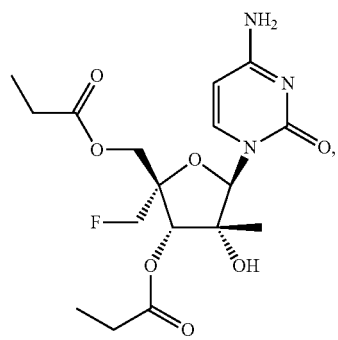
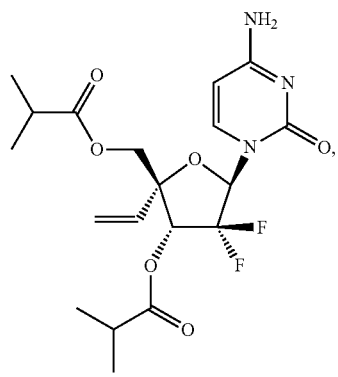
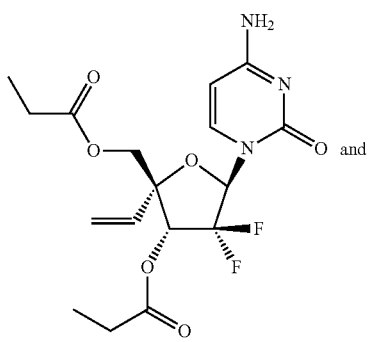
-continued
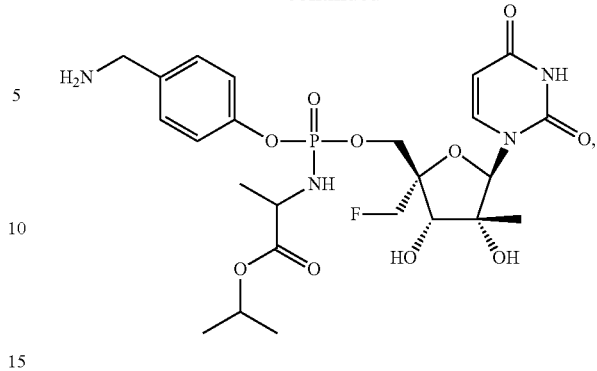
or a pharmaceutically acceptable salt of the foregoing.
In some embodiments, a compound of Formulae (I) and/or (II), or a pharmaceutically acceptable salt of the foregoing, may be selected from:
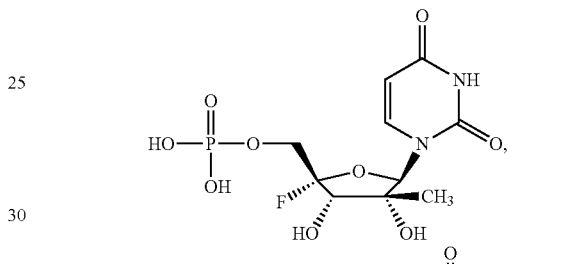
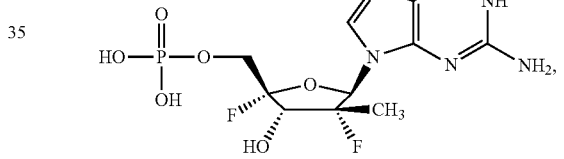
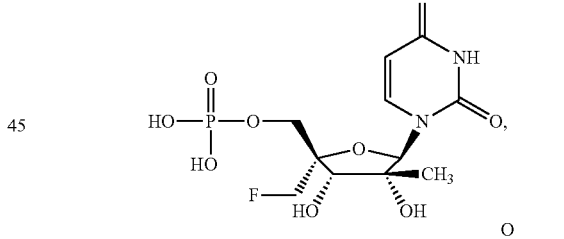
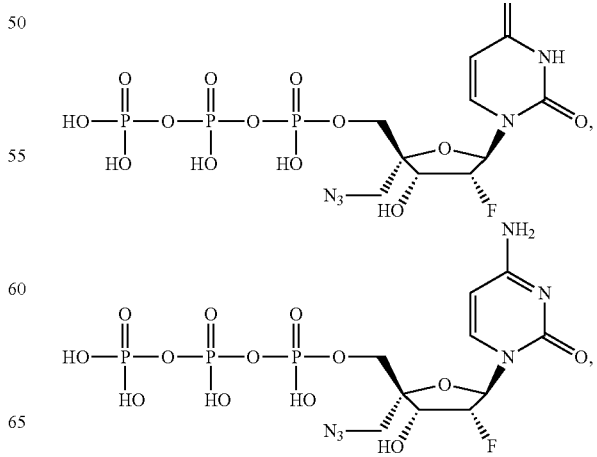

-continued
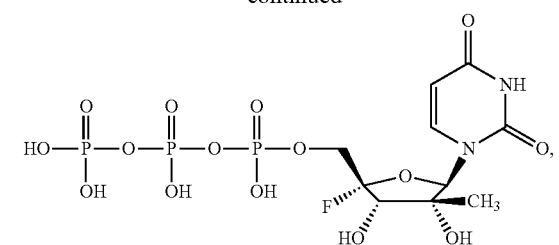
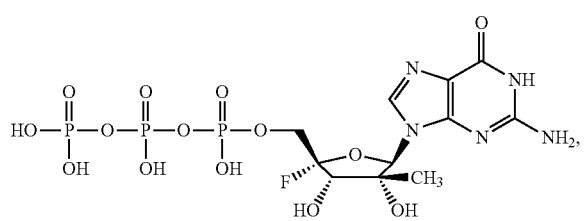
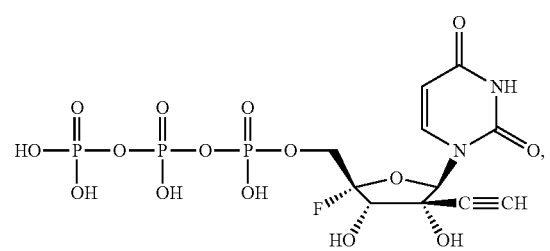
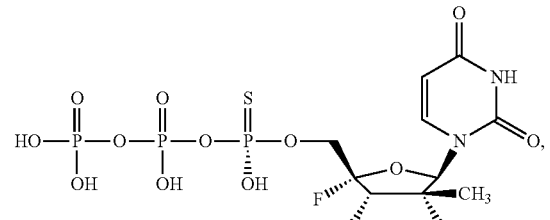
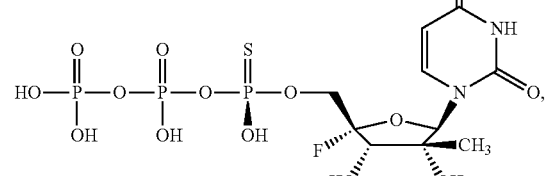
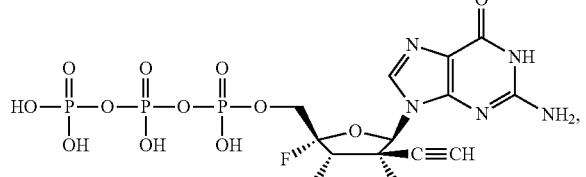
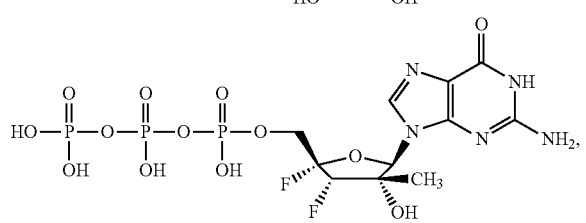
-continued
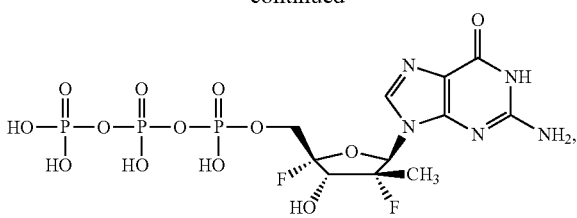
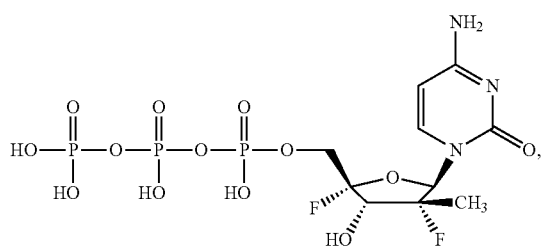
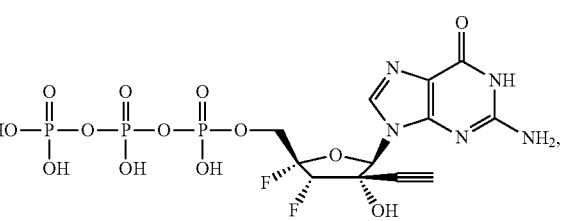
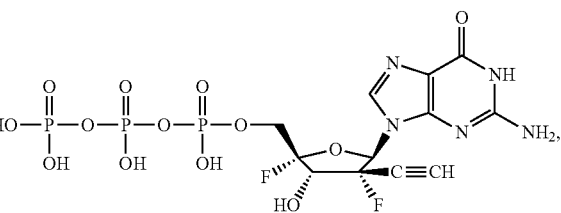
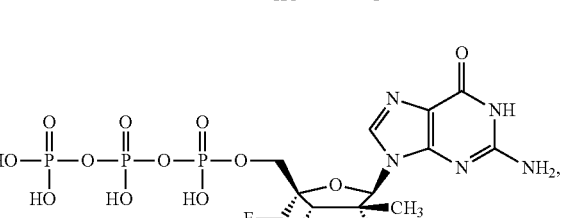
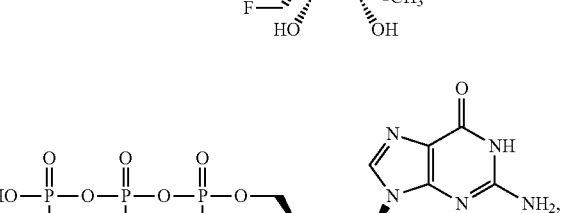
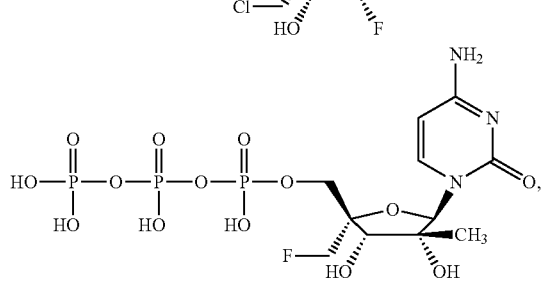

255
-continued
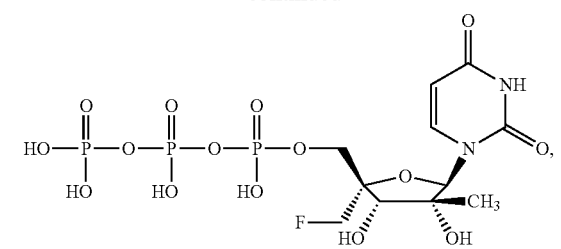
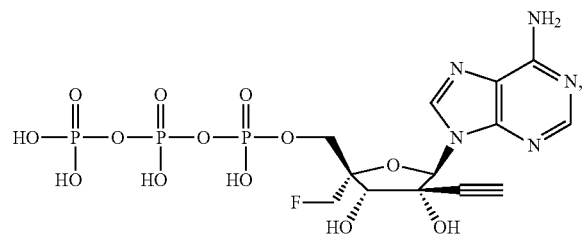
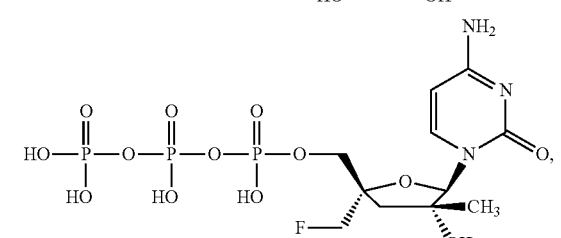
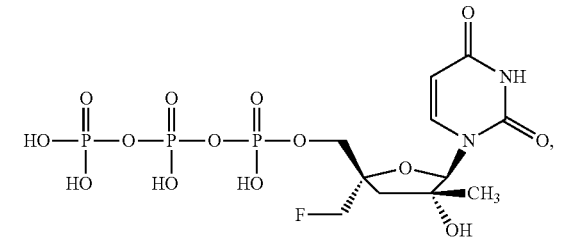
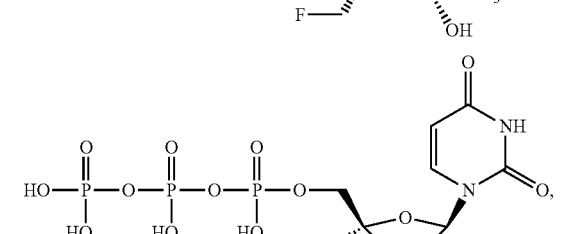
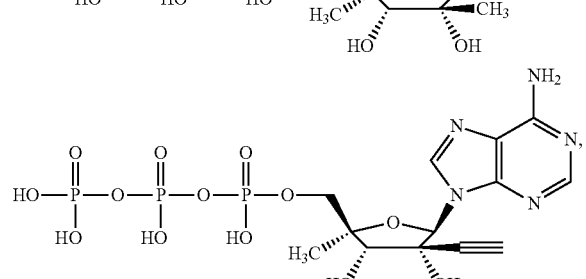
256
-continued
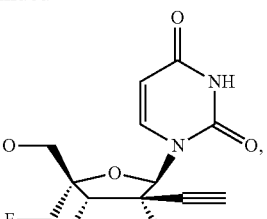
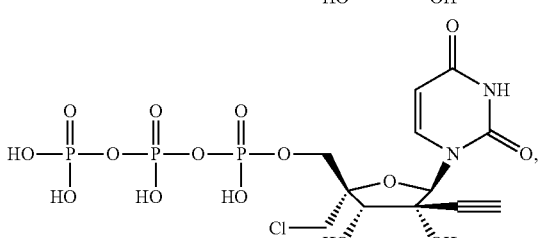
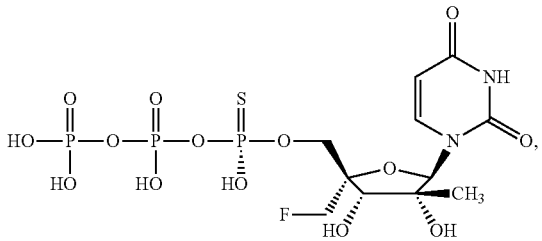
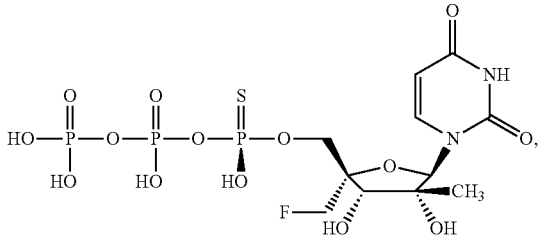
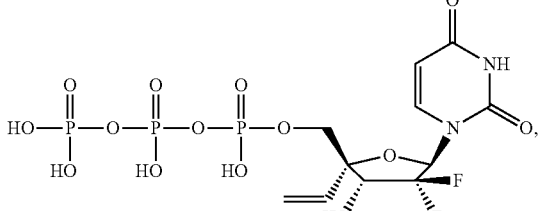
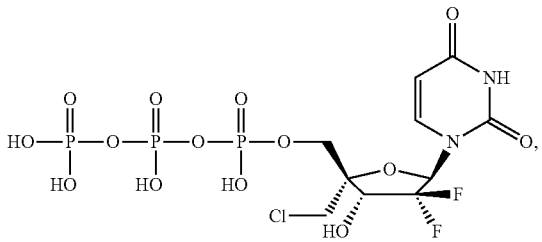
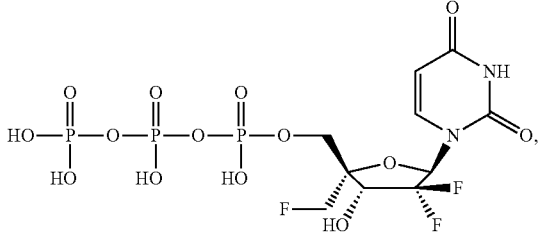

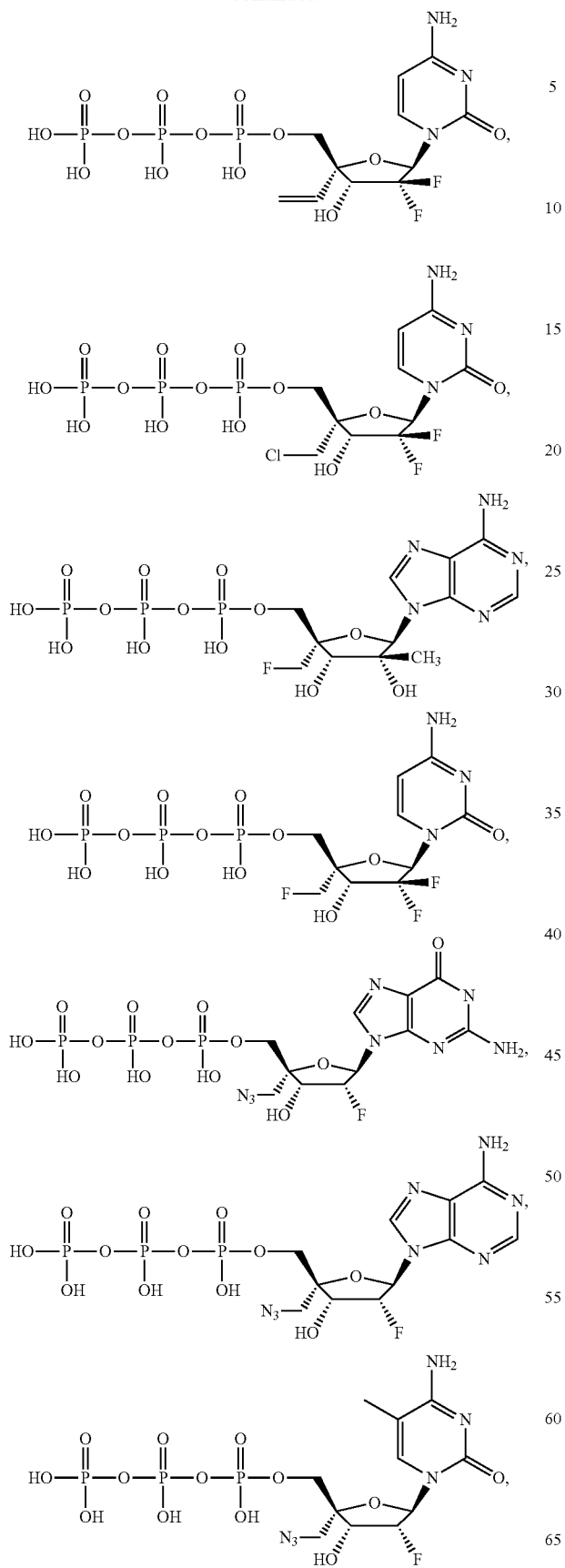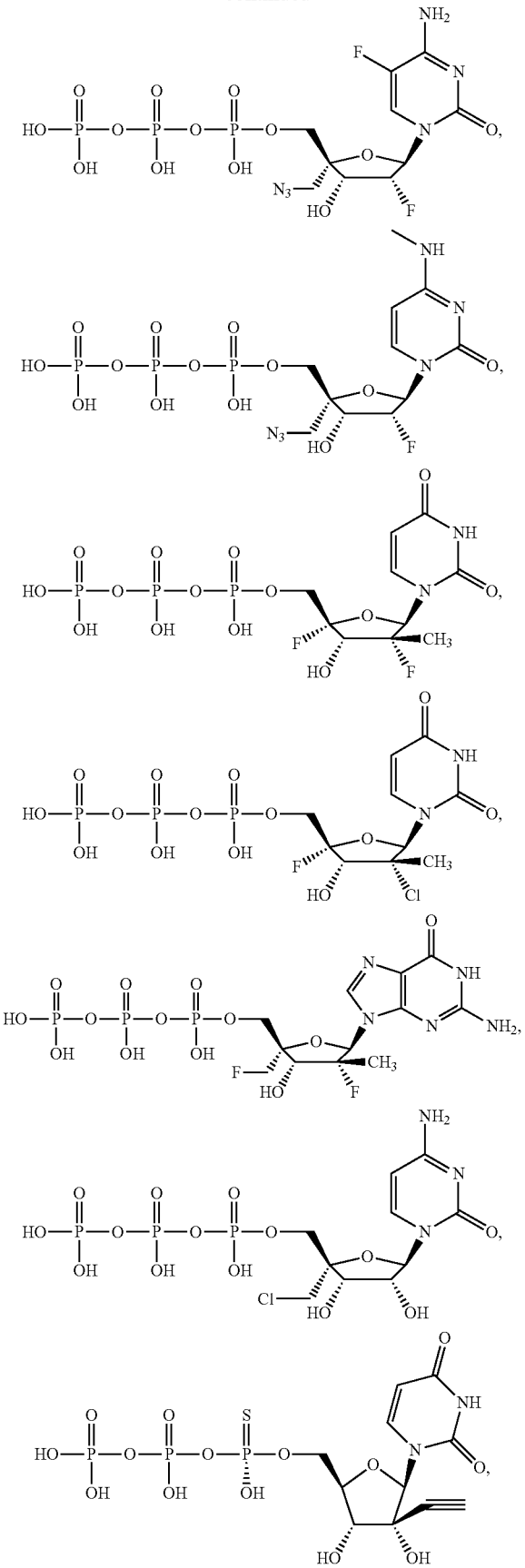

259
-continued
260
-continued
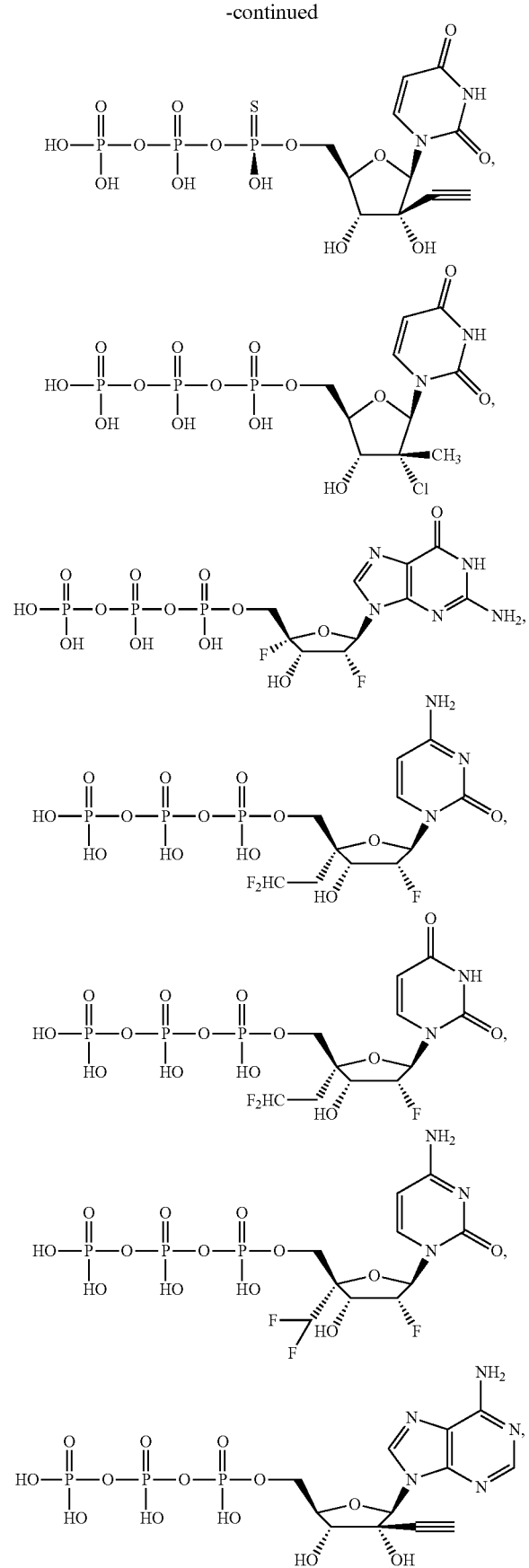
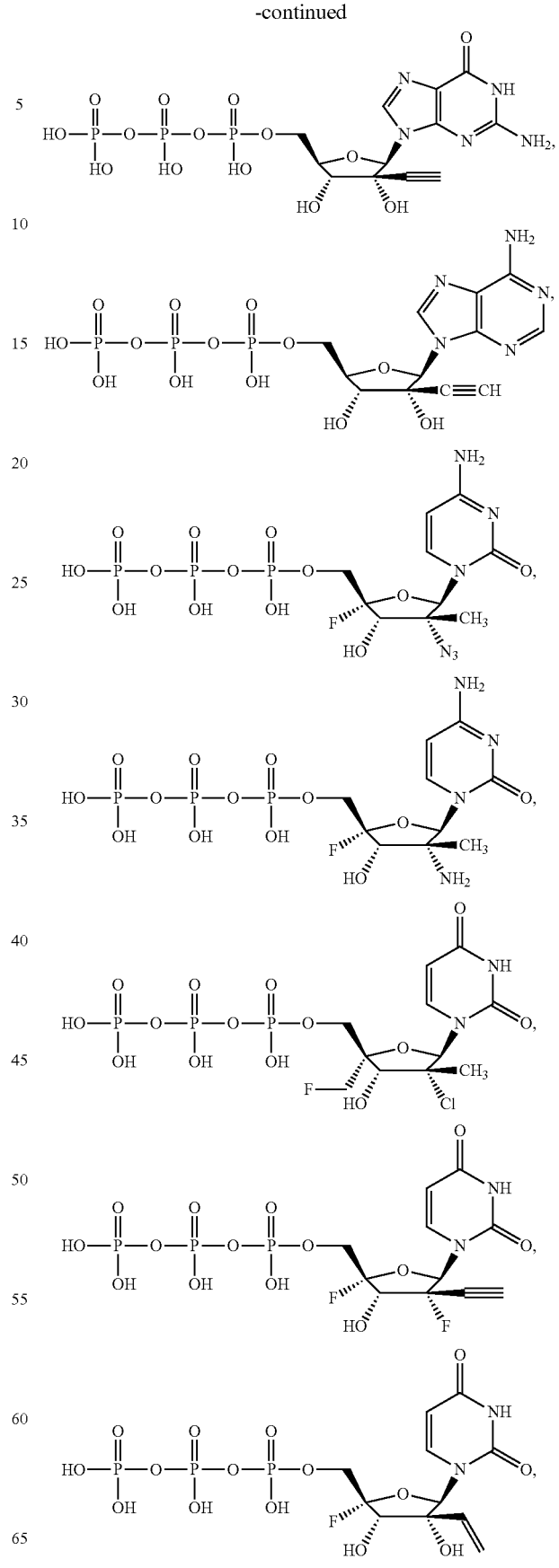

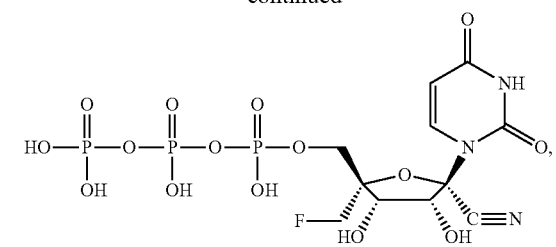
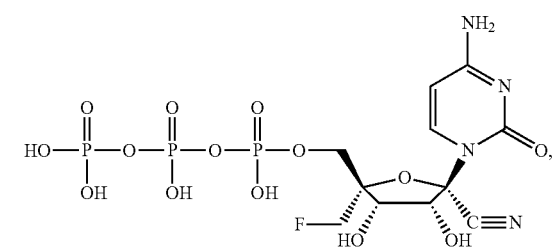
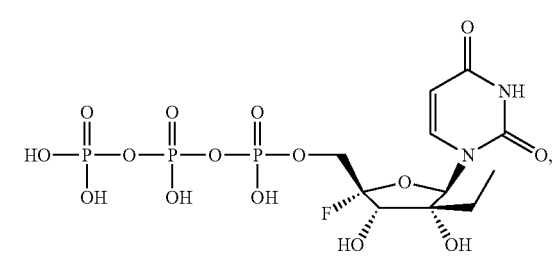
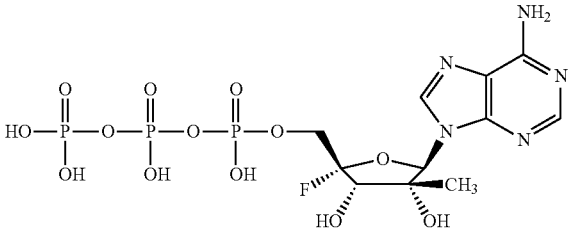
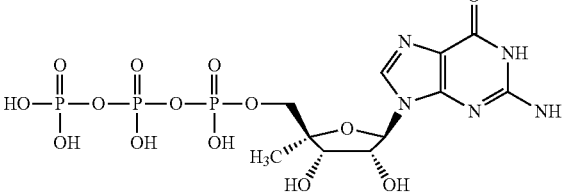
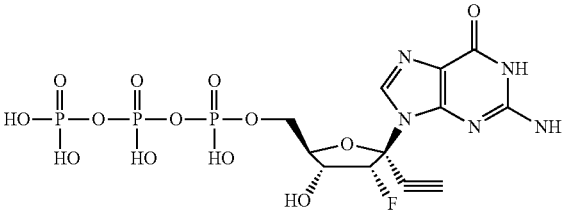
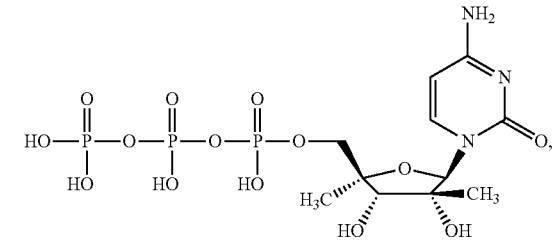
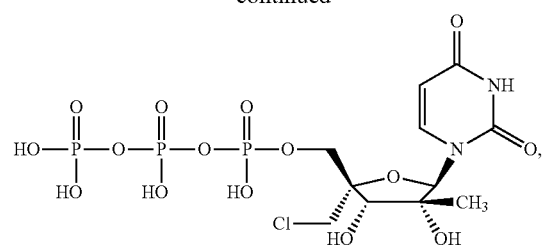
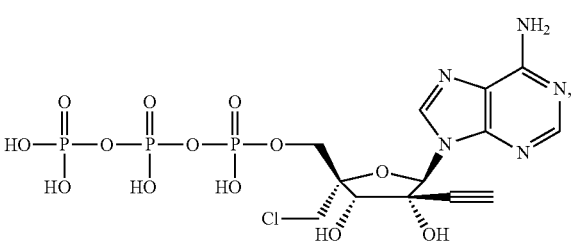
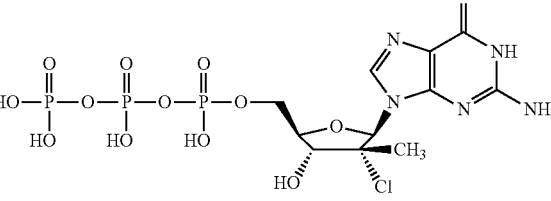
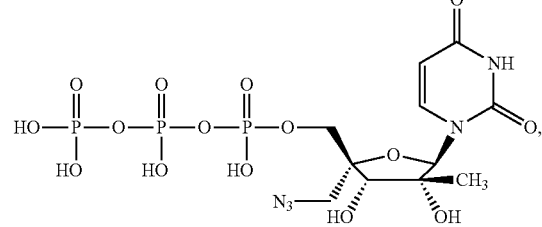
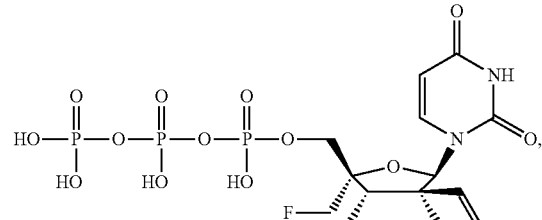
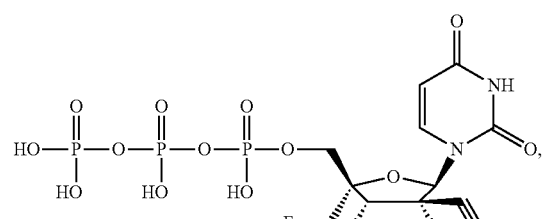
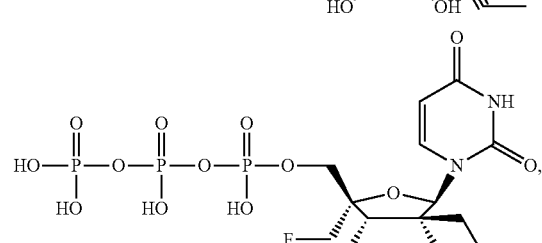

263
-continued
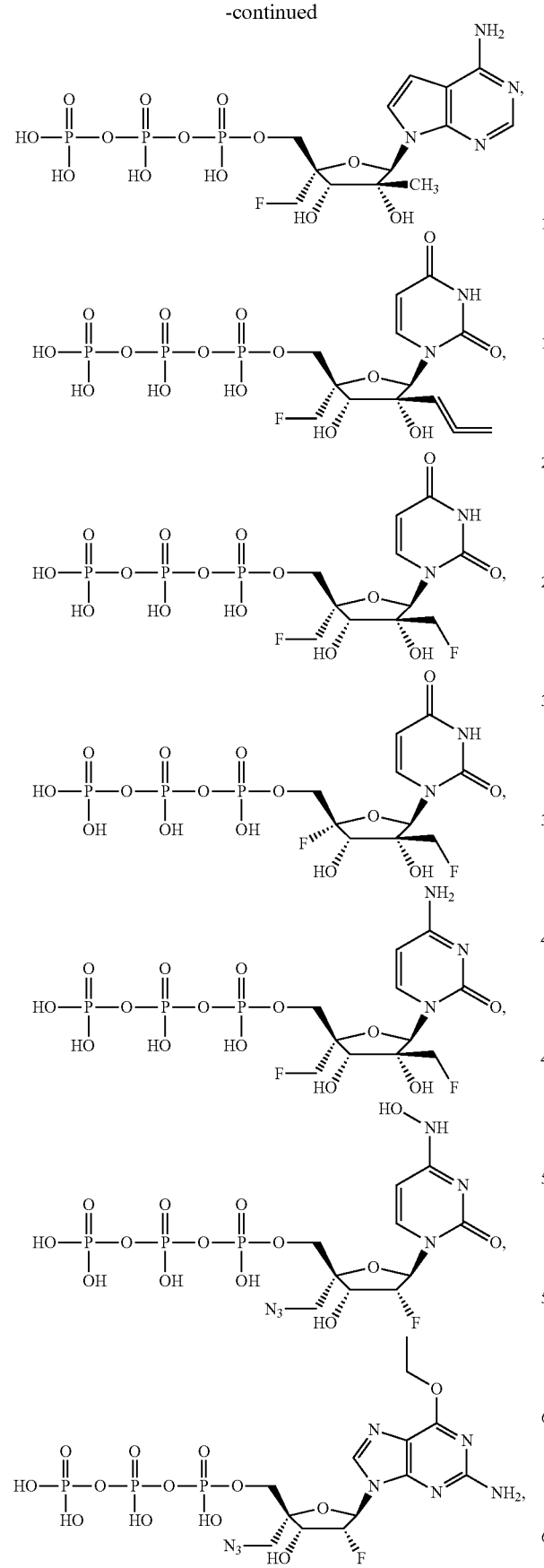
264
-continued
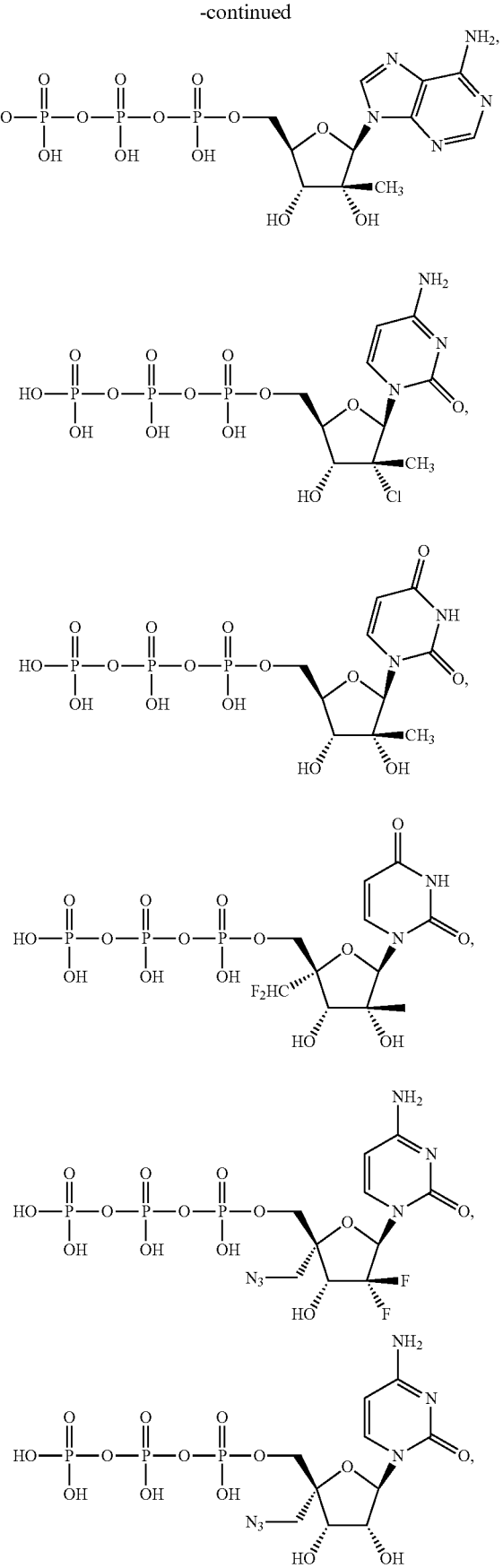

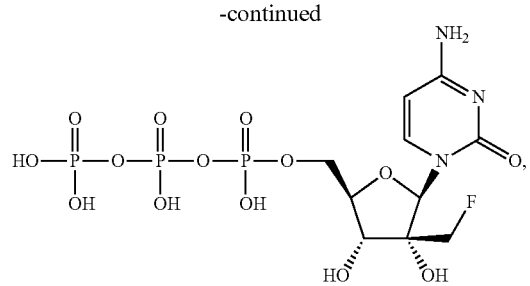
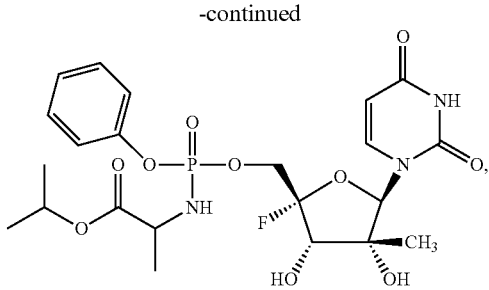
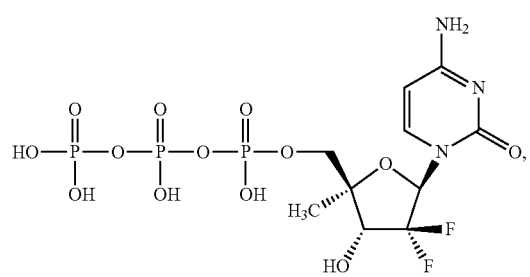
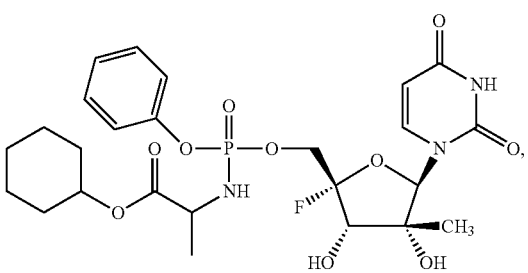
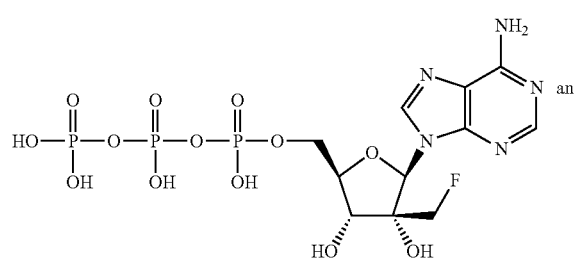
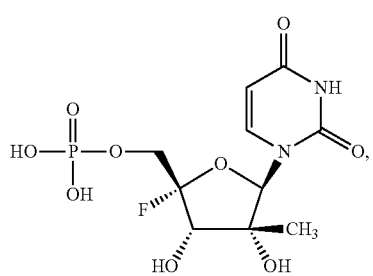
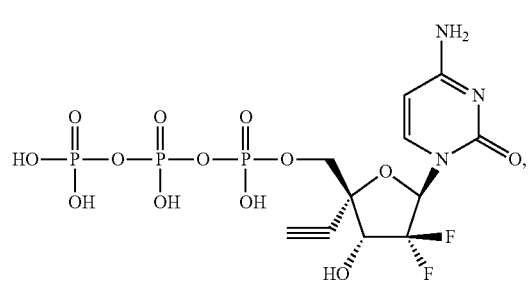
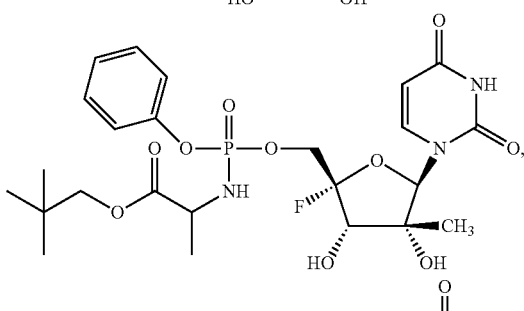
or a pharmaceutically acceptable salt of the foregoing.
In some embodiments, a compound of Formulae (I) and/or (II), or a pharmaceutically acceptable salt of the foregoing, may not be selected from:
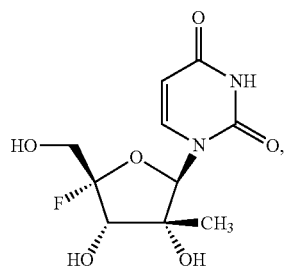
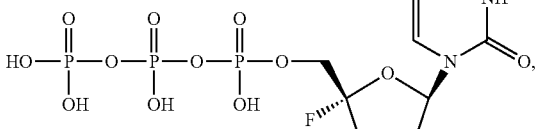
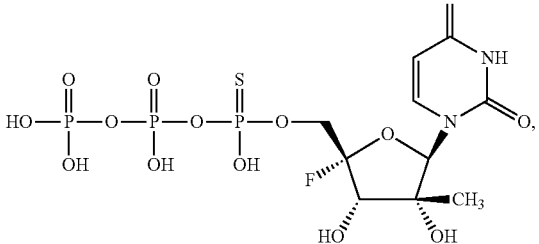

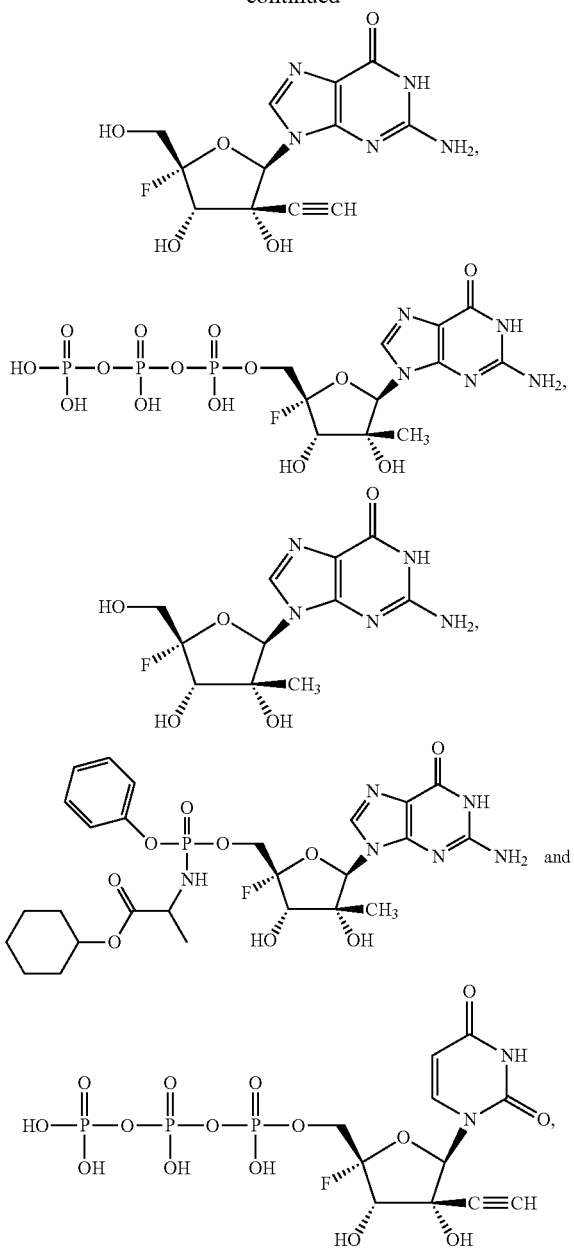
or a pharmaceutically acceptable salt of the foregoing.
In some embodiments, a compound of Formulae (I) and/or (II), or a pharmaceutically acceptable salt of the foregoing, may not be selected from:
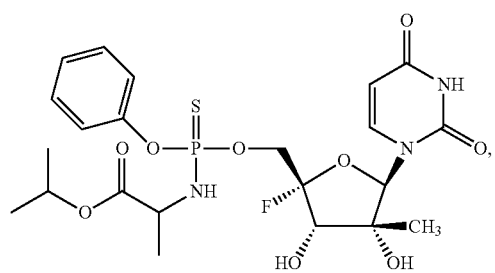
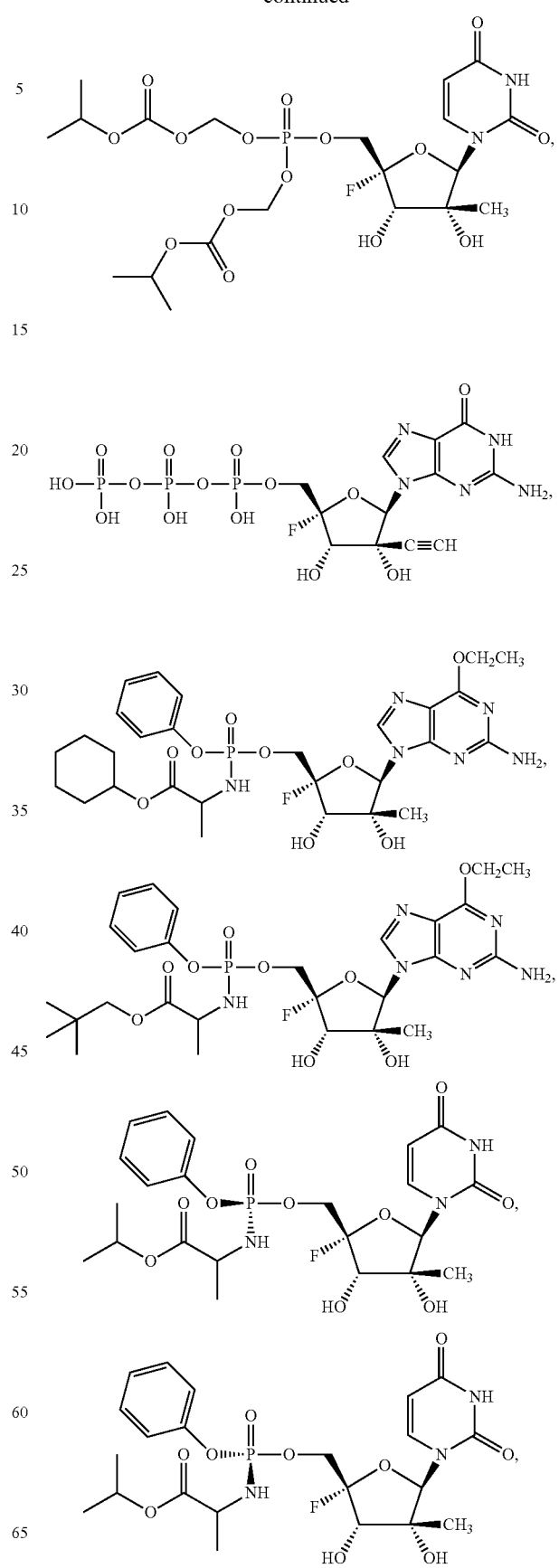
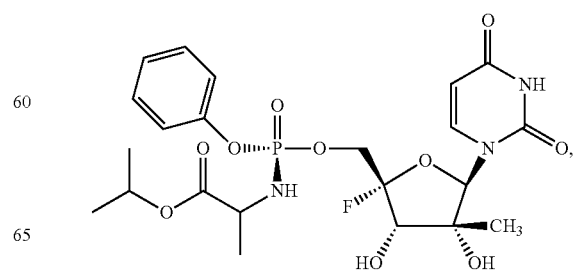

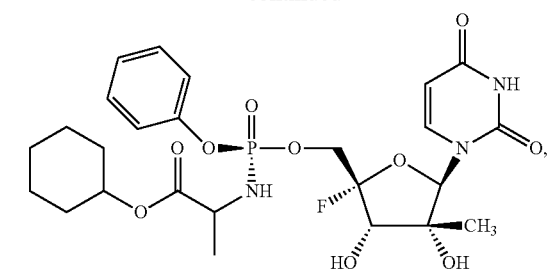
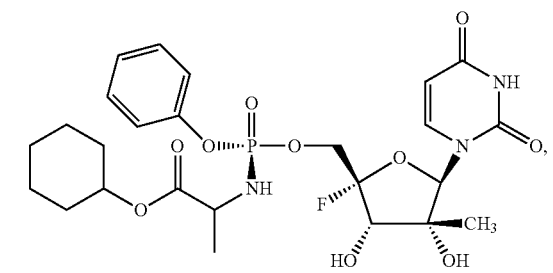
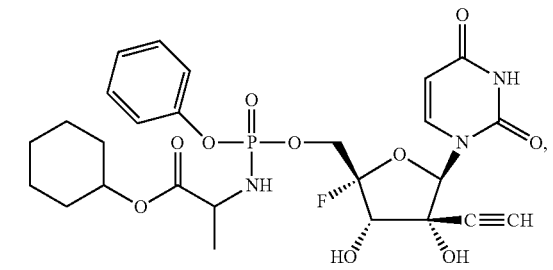
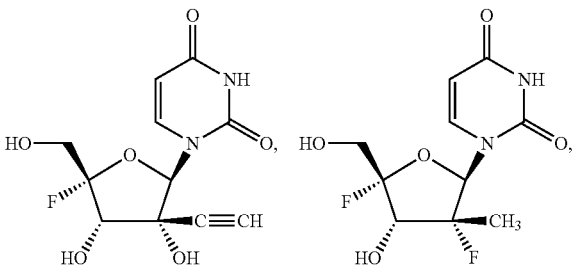
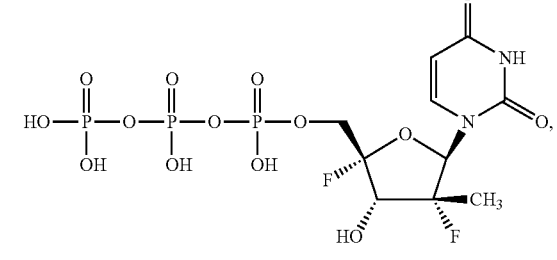
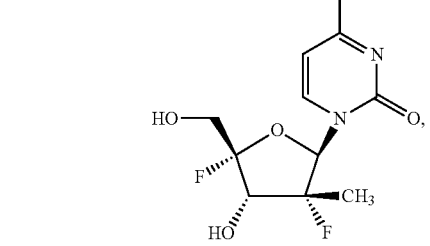
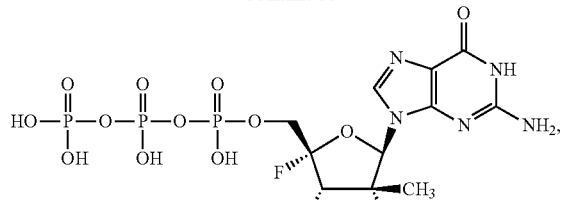
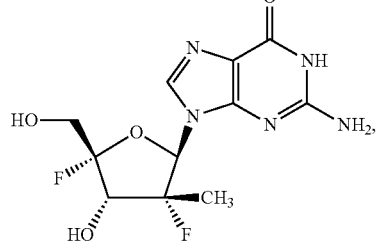
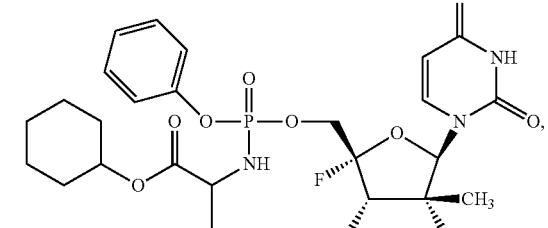
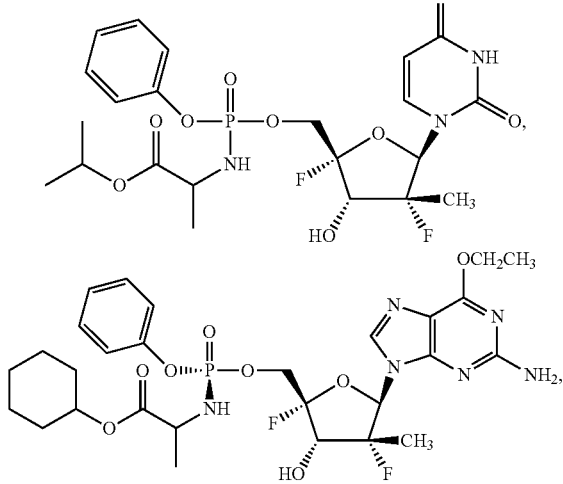
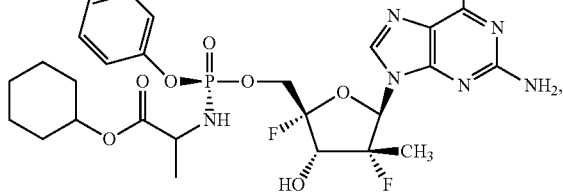
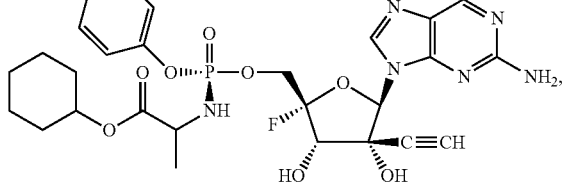

271
-continued
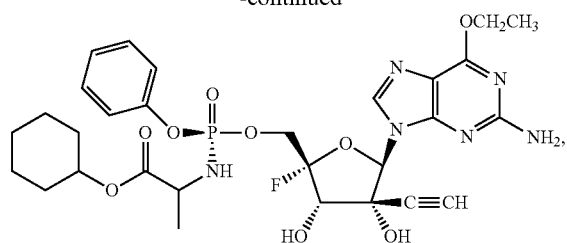
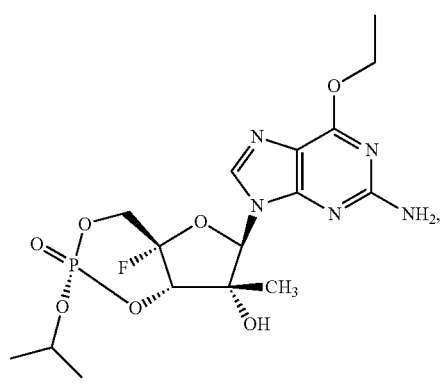
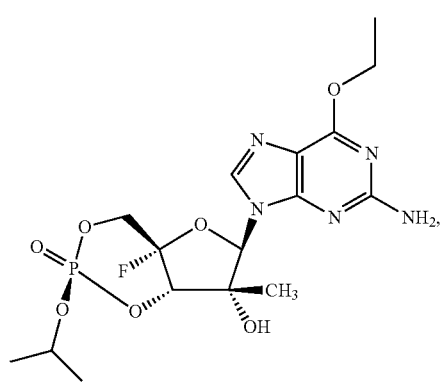
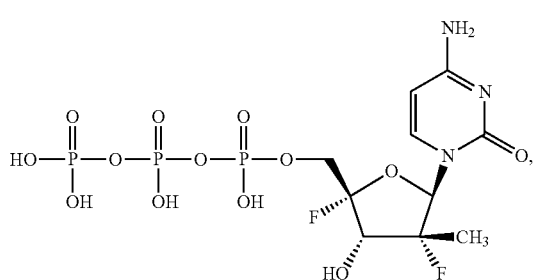
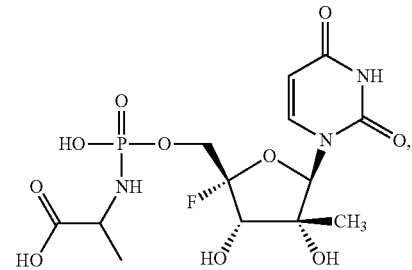
272
-continued
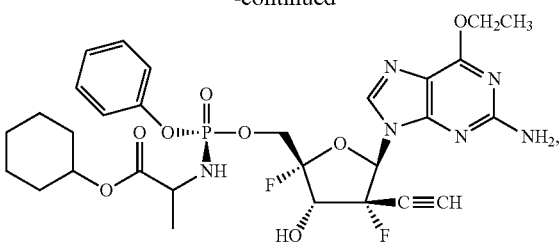
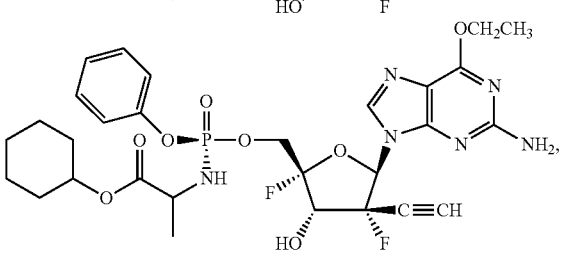
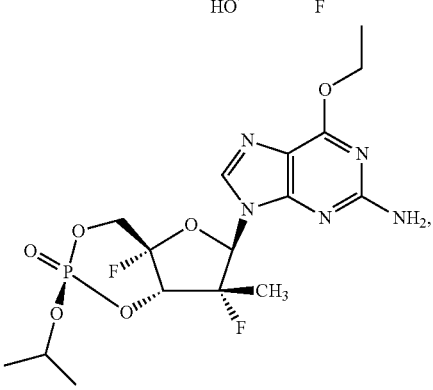
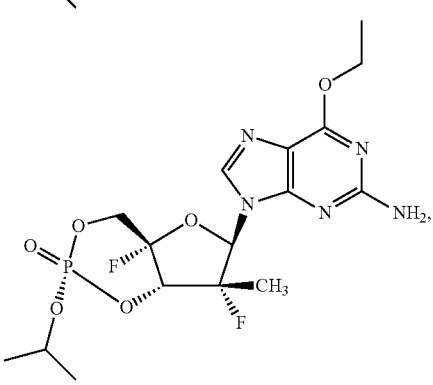
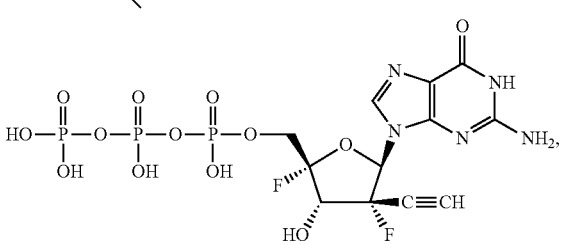
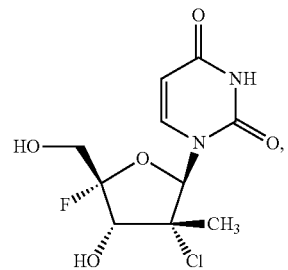

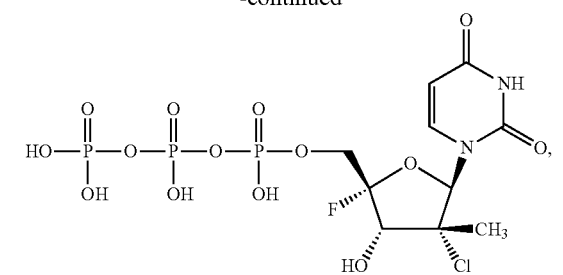
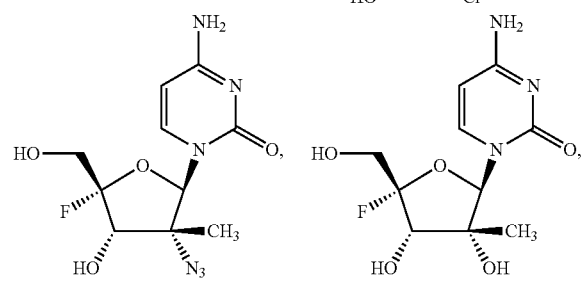
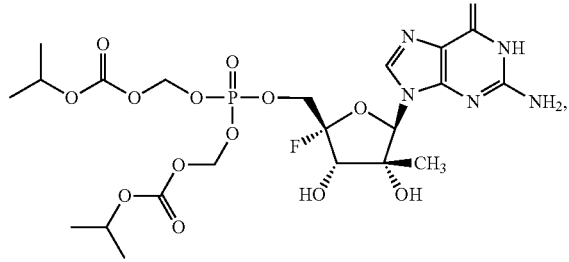
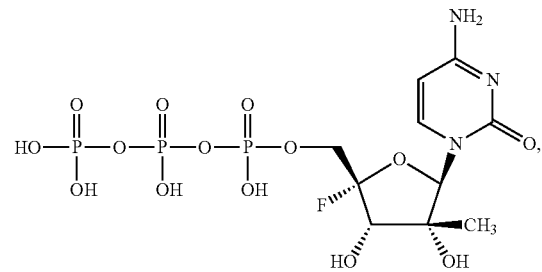
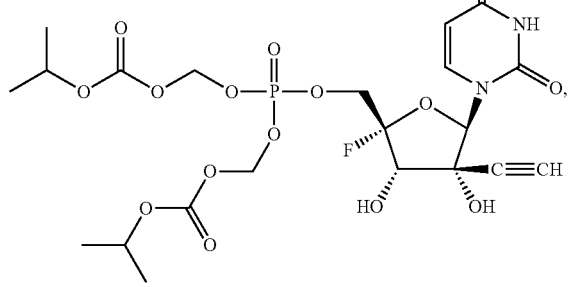
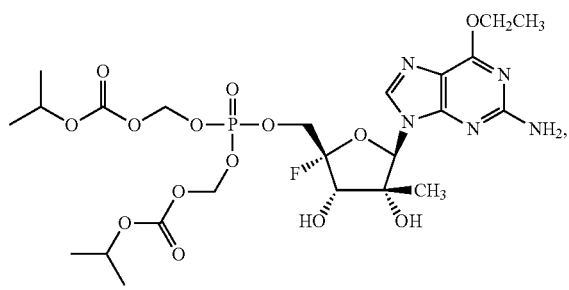
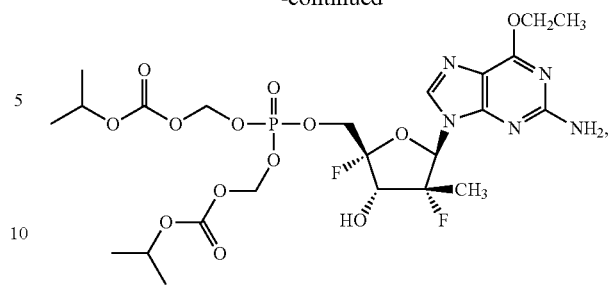
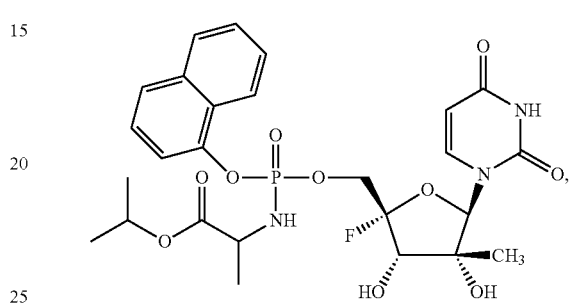
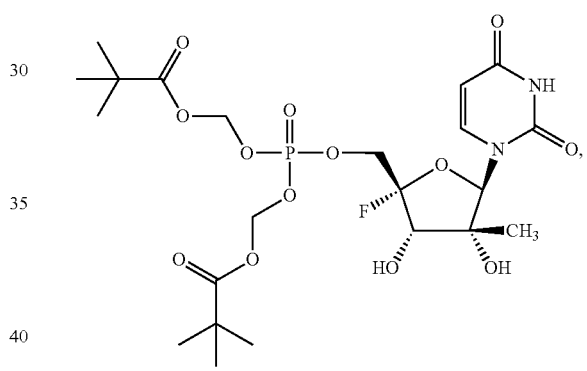
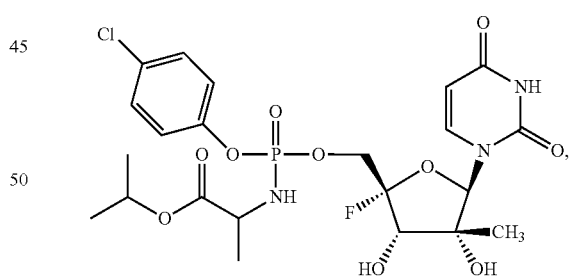
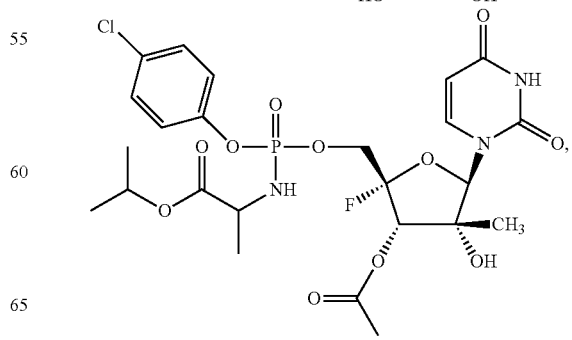

275
-continued
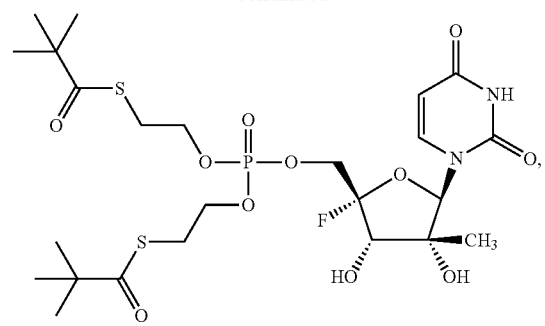
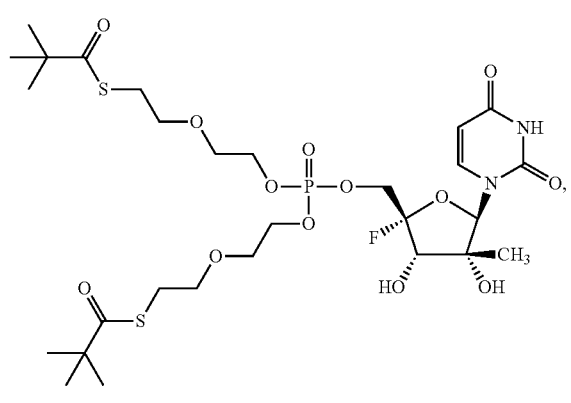
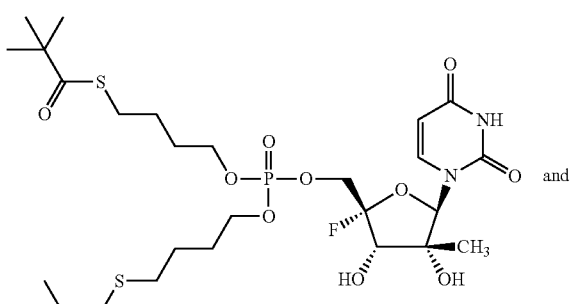
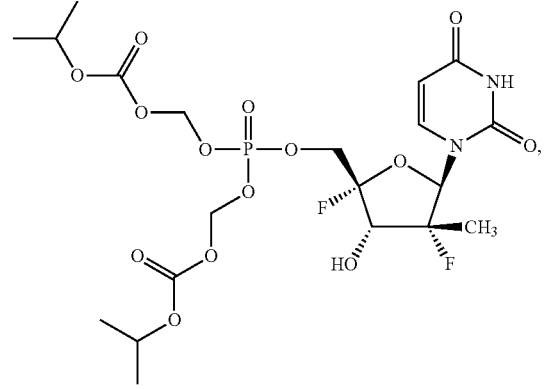
or a pharmaceutically acceptable salt of the foregoing.
In some embodiments, a compound of Formulae (I) and/or (II), or a pharmaceutically acceptable salt of the foregoing, may not be selected from:
276
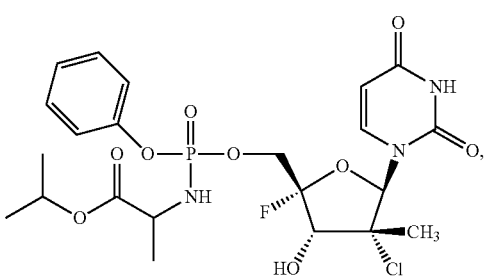
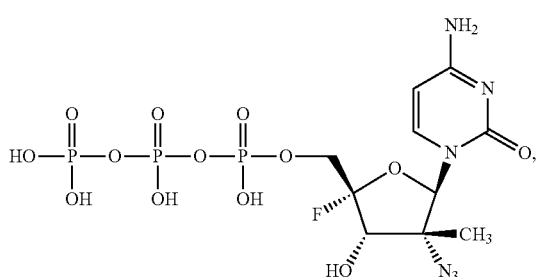
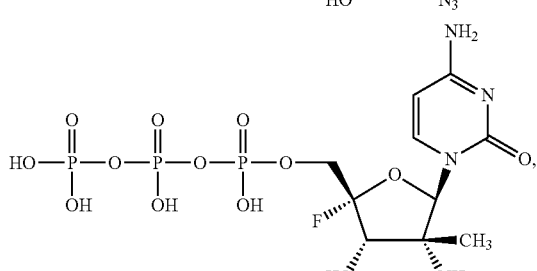
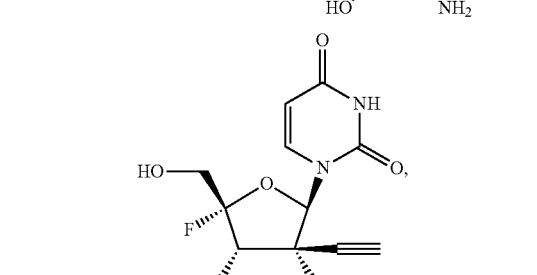
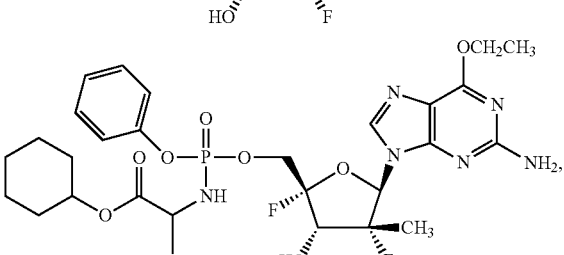
and
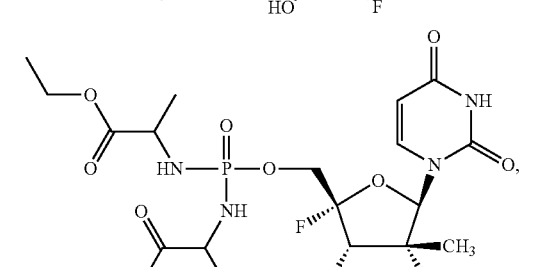

277
-continued
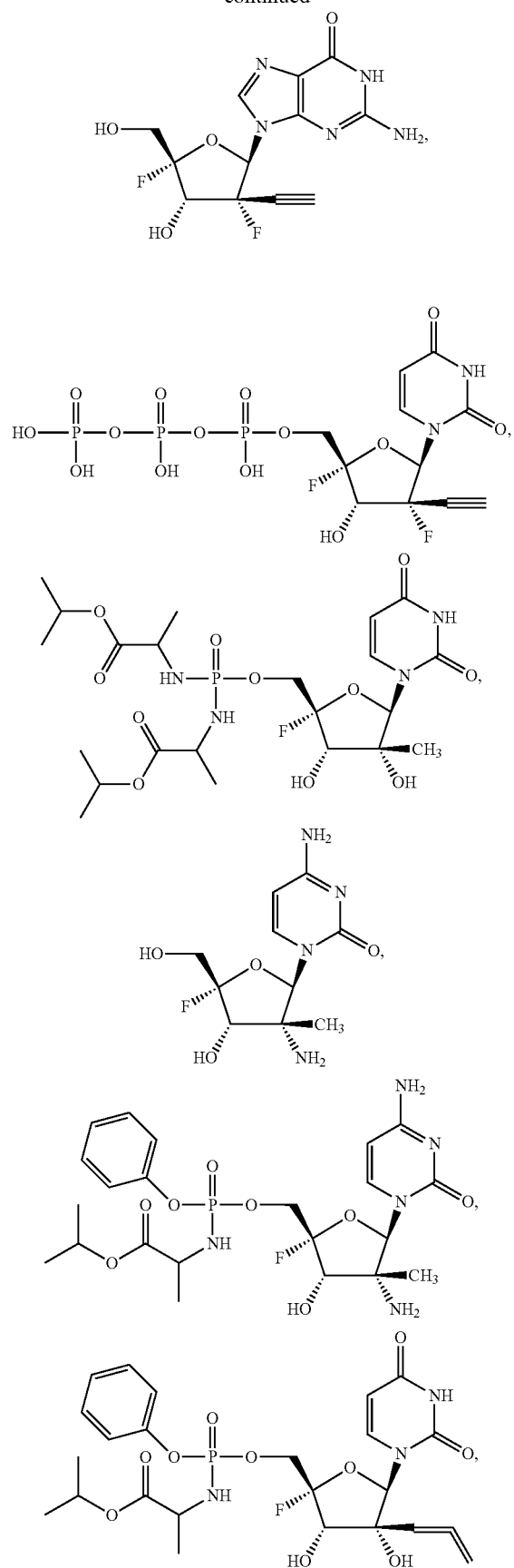
278
-continued
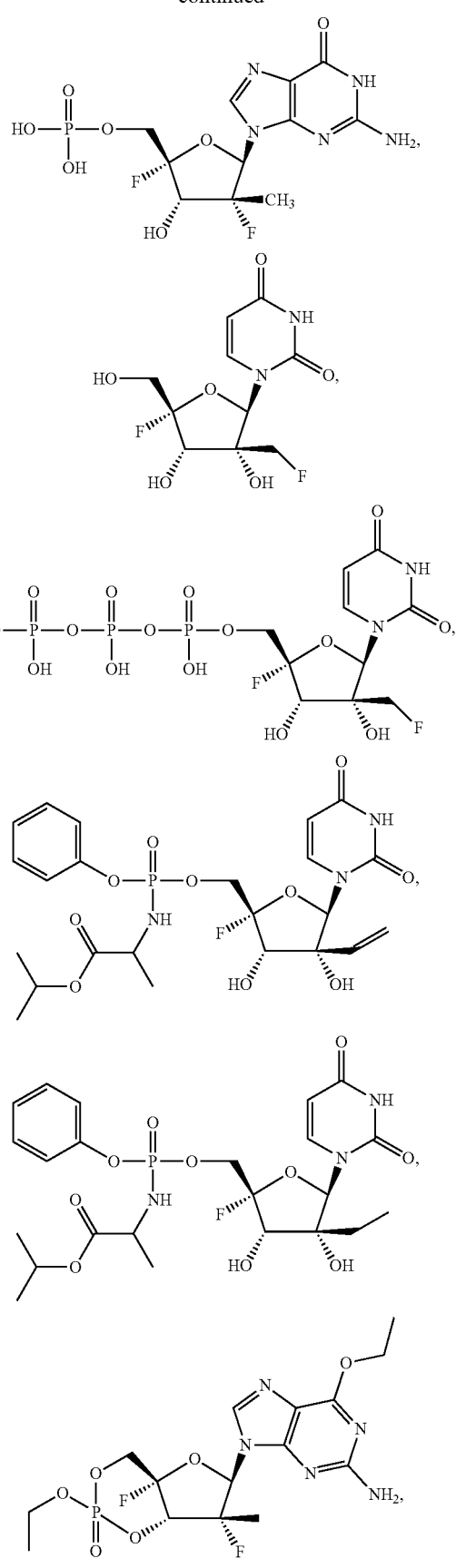

| 279 -continued | 280 -continued |
|---|---|
| 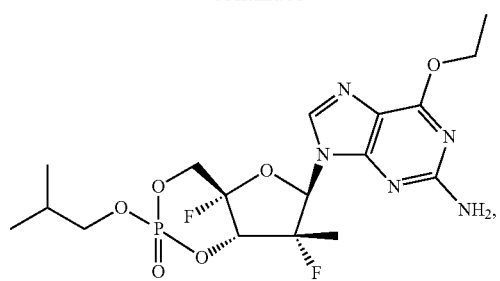 | 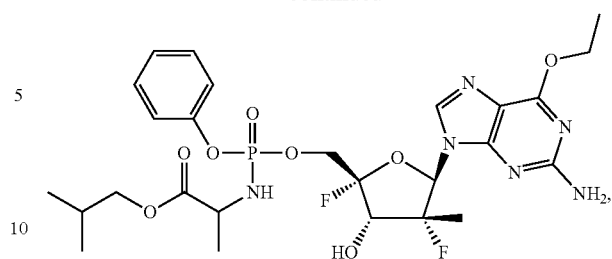 |
| 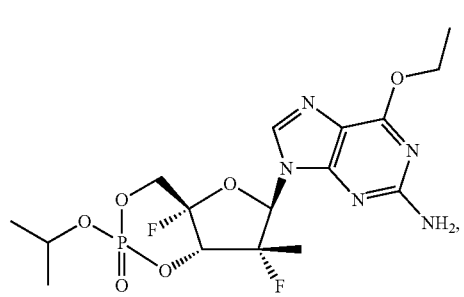 | 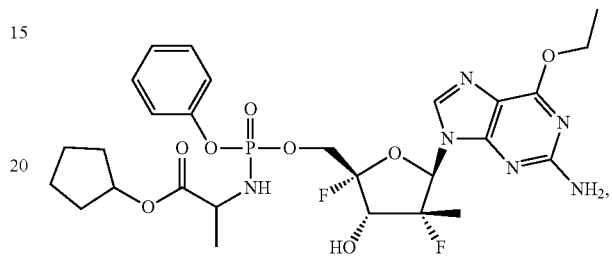 |
| 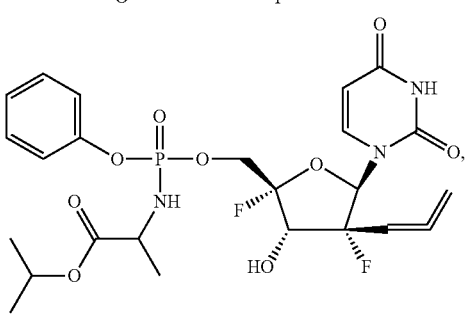 | 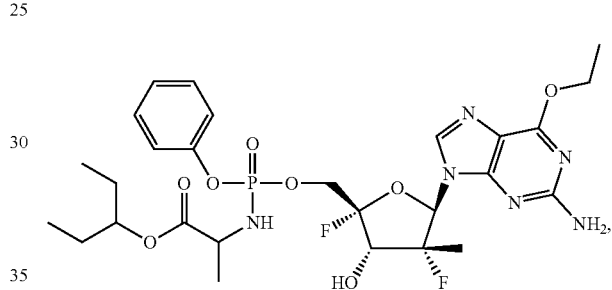 |
| 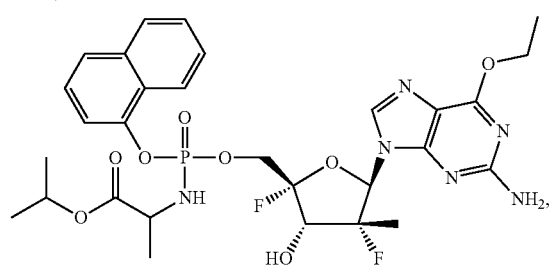 | 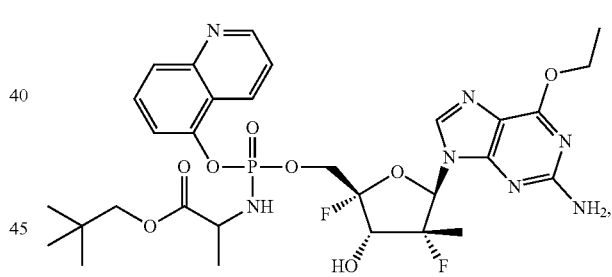 |
| 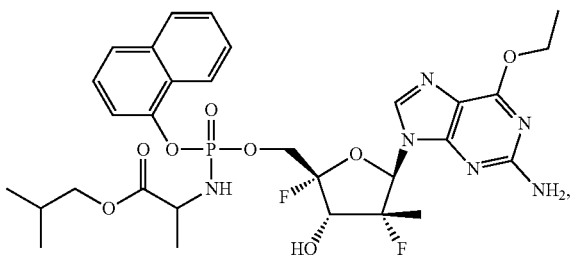 | 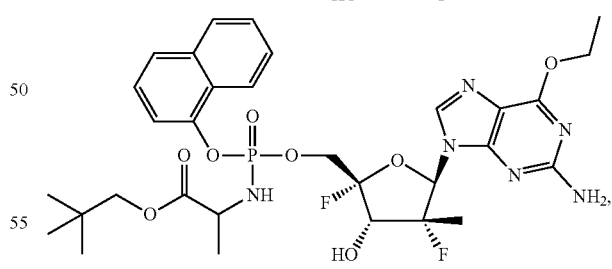 |
| 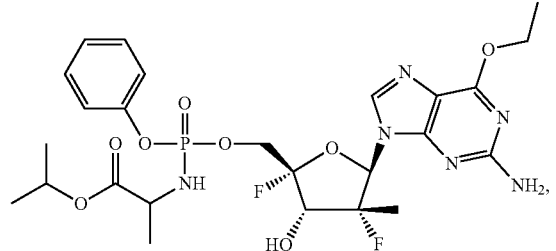 | 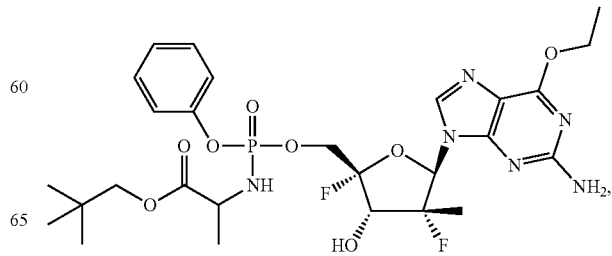 |

281
-continued
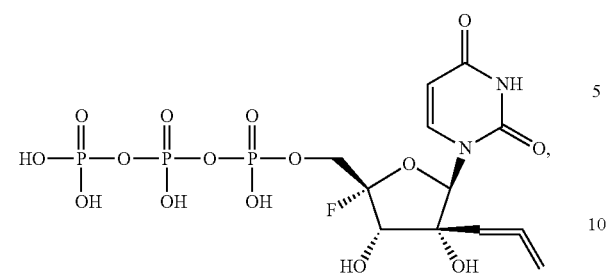

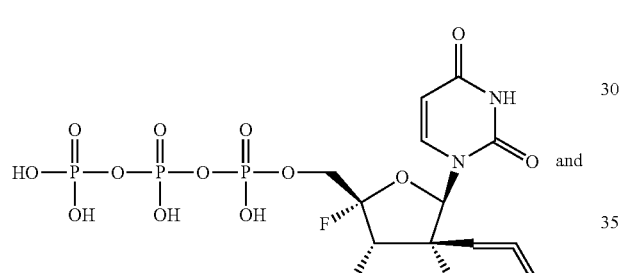
and
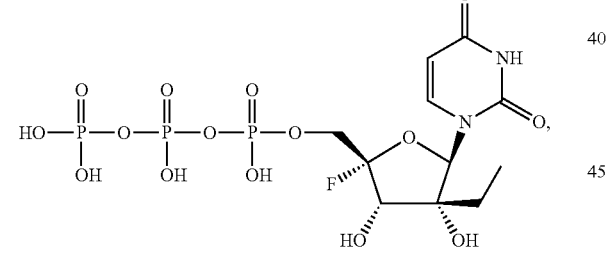
or a pharmaceutically acceptable salt of the foregoing.
In some embodiments, a compound of Formulae (I) and/or (II), or a pharmaceutically acceptable salt of the foregoing, may not be selected from:
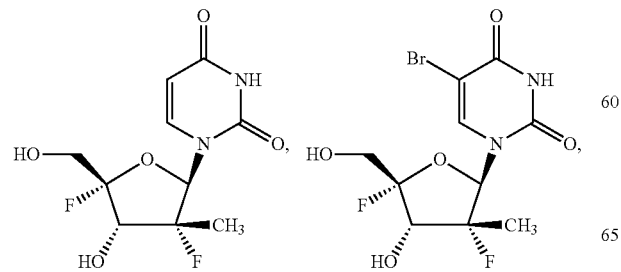
282
-continued
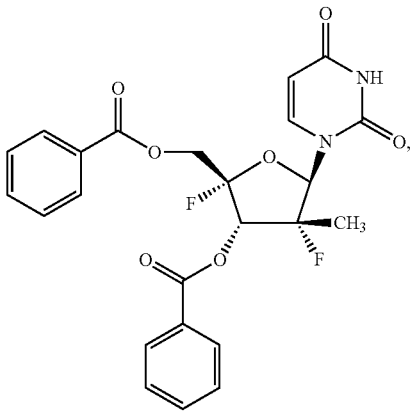
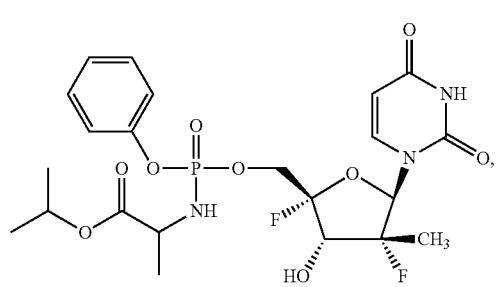
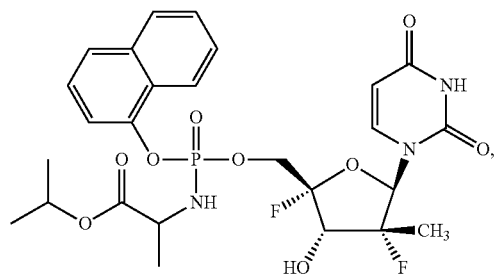
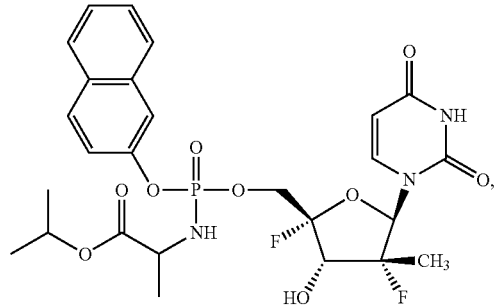
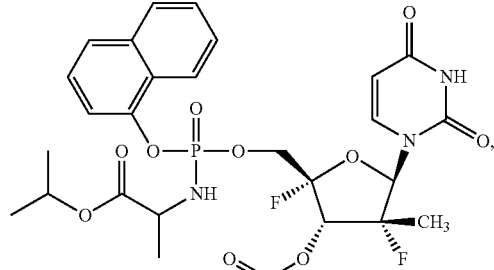

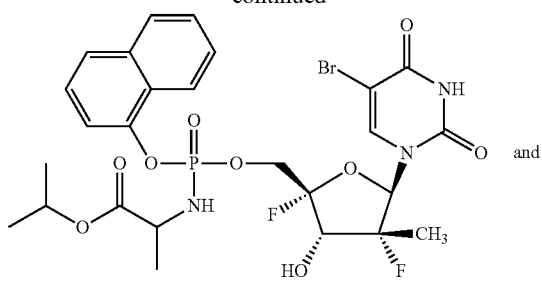
and
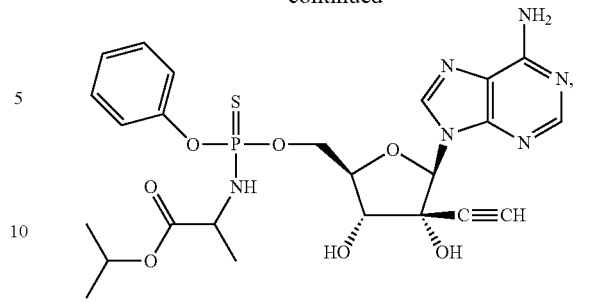
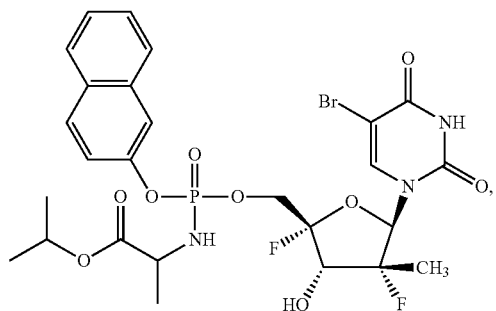
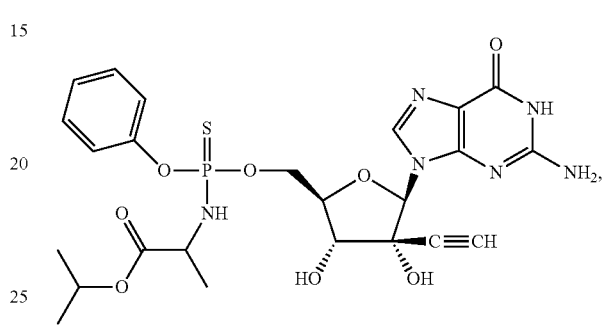
or a pharmaceutically acceptable salt of the foregoing.
In some embodiments, a compound of Formulae (I) and/or (II), or a pharmaceutically acceptable salt of the foregoing, may not be selected from:
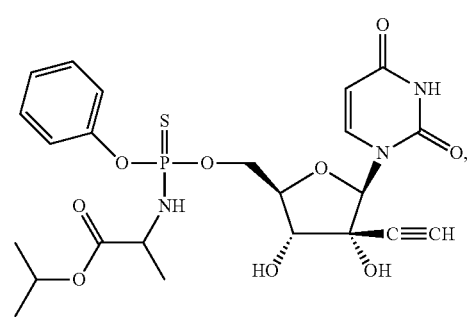
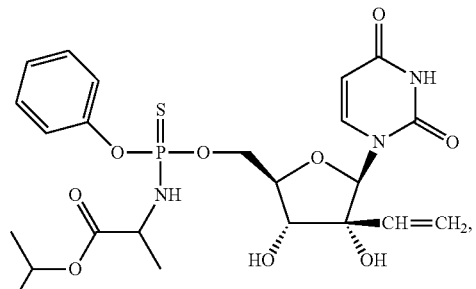
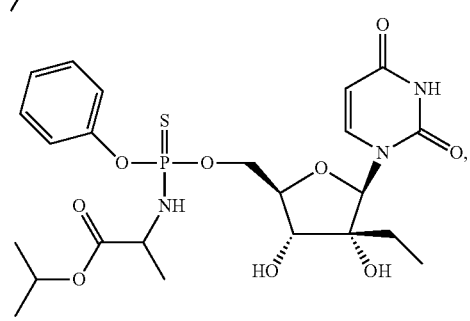

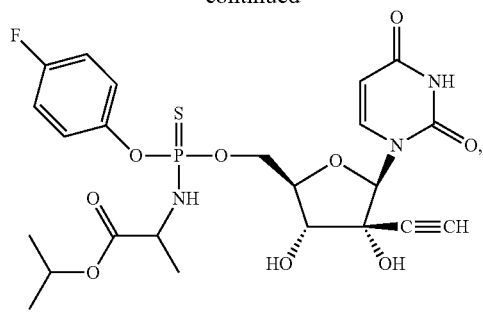
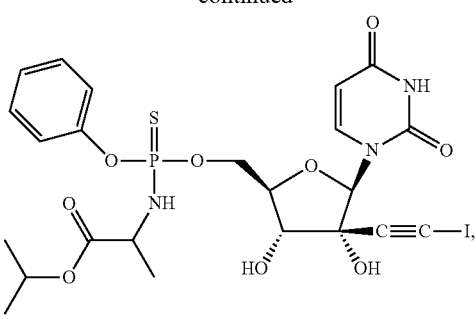
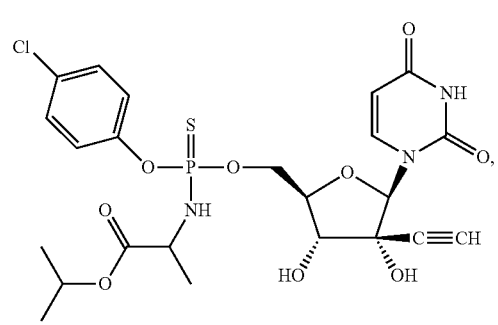
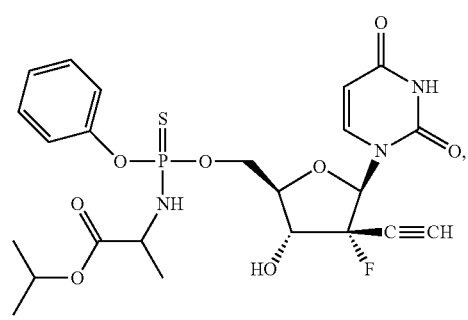
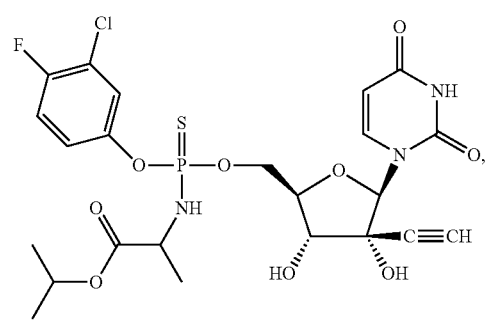
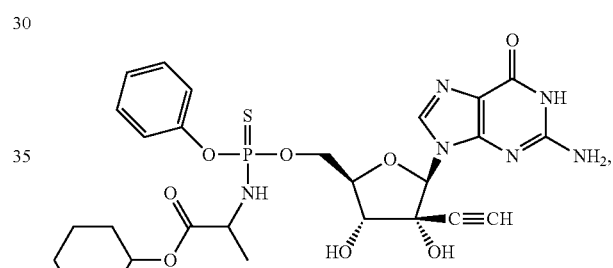
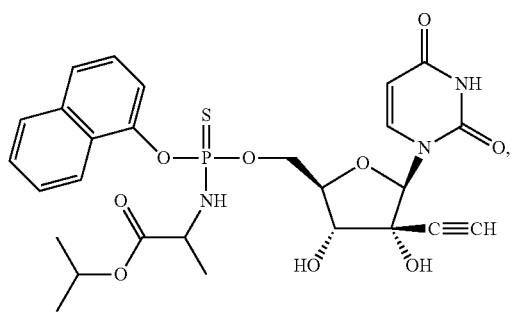
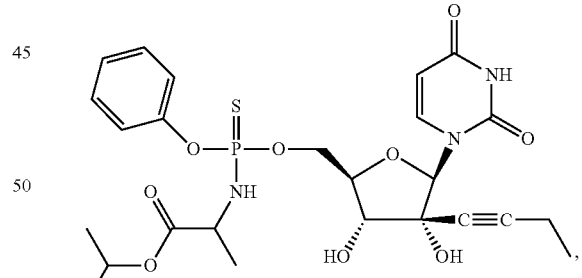
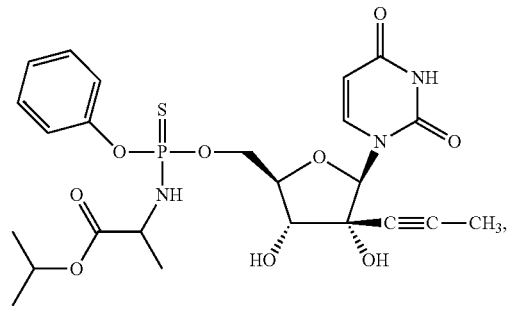
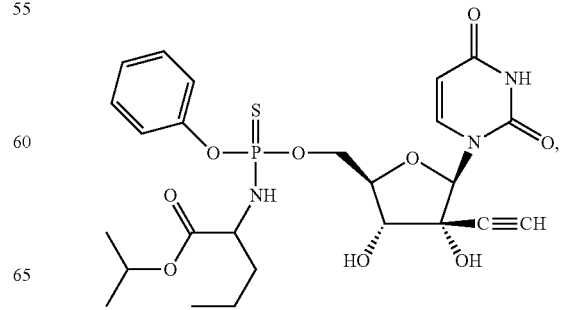

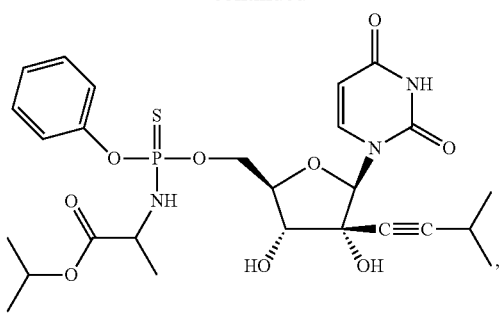

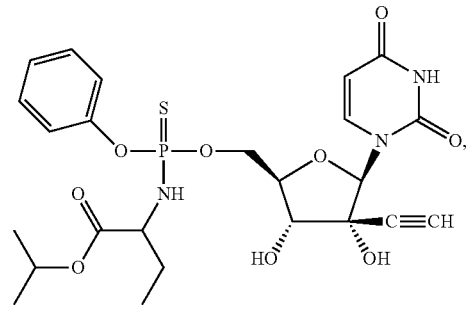

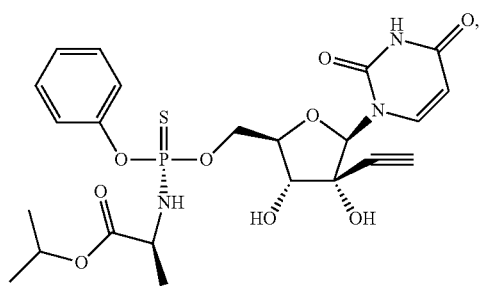

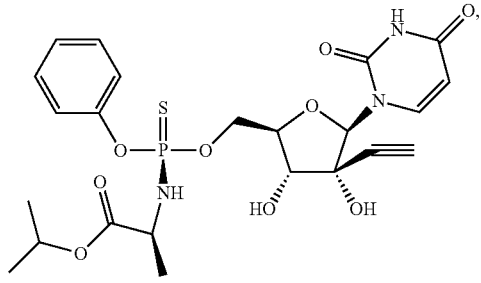

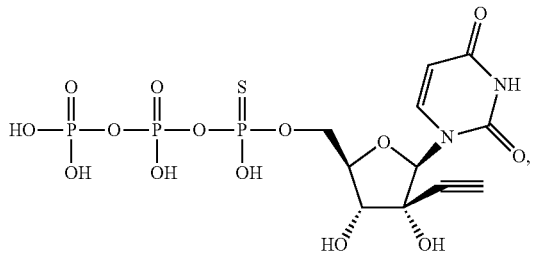

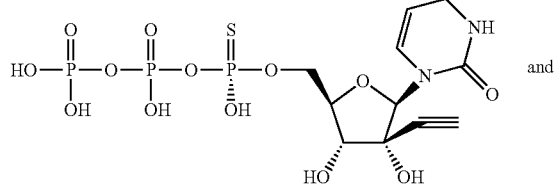
and

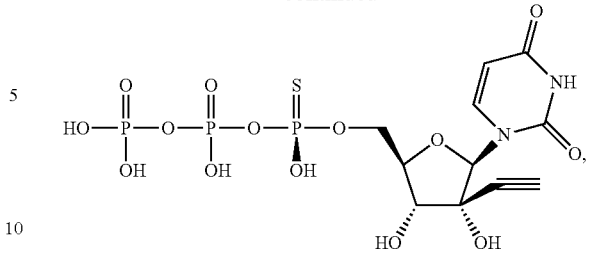

or a pharmaceutically acceptable salt of the foregoing.

In some embodiments, a compound of Formula (I), or a pharmaceutically acceptable salt thereof, may not be selected from a compound that is that is shown in the paragraphs that begins with the paragraph that starts with the lines "In some embodiments, a compound of Formulae (I) and/or (II), or a pharmaceutically acceptable salt of the foregoing, may be selected from:

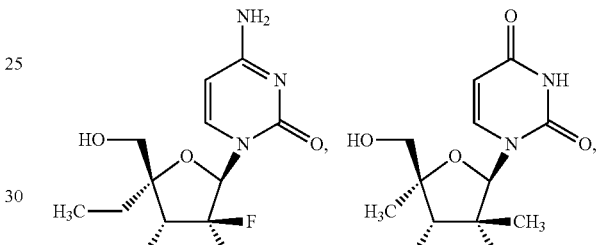

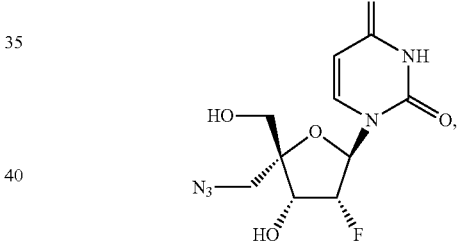

and ends with the paragraph that follows and recites in its last lines "and

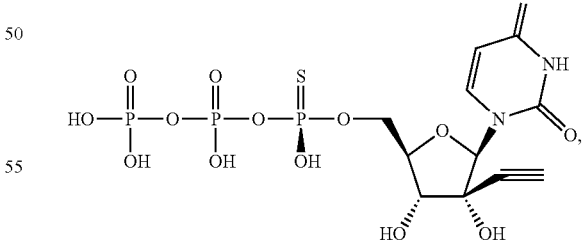

or a pharmaceutically acceptable salt of the foregoing" when the virus is HCV. In some embodiments, a compound of Formula (I), or a pharmaceutically acceptable salt thereof, may not be selected from a compound that is shown in the paragraphs that begins with the paragraph that starts with the lines "In some embodiments, a compound of Formulae (I) and/or (II), or a pharmaceutically acceptable salt of the foregoing, may not be selected from:

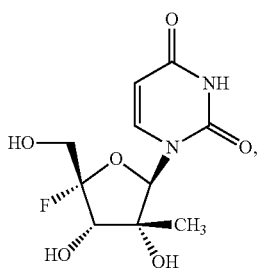

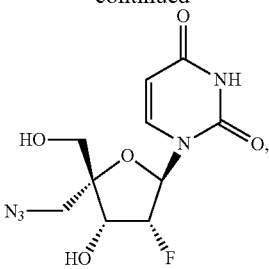

and ends with the paragraph that follows and recites in its last lines "and

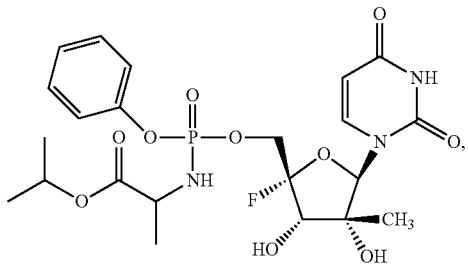

and ends with the paragraph that follows and recites in its last lines "and

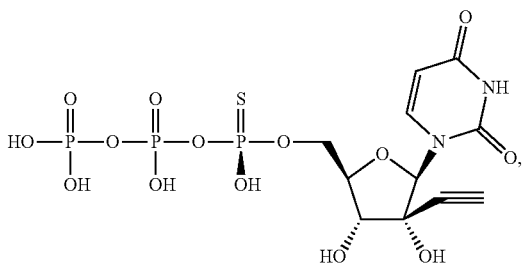 [SMILES: C#C[C@@]1(O)[C@H](O)[C@@H](CO[P@@](O)(=S)OP(=O)(O)OP(=O)(O)O)O[C@H]1n1ccc(=O)[nH]c1=O]

or a pharmaceutically acceptable salt of the foregoing." In some embodiments, a compound of Formulae (II), or a pharmaceutically acceptable salt thereof, may not be selected from a compound that is shown in the paragraphs that begins with the paragraph that starts with the lines "In some embodiments, a compound of Formulae (I) and/or (II), or a pharmaceutically acceptable salt of the foregoing, may not be selected from:

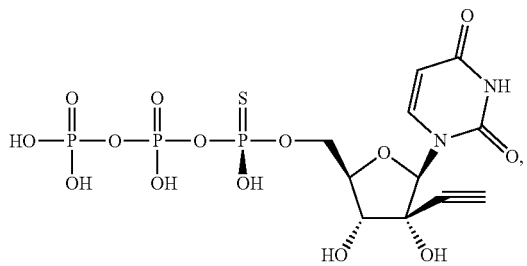 [SMILES: C#C[C@@]1(O)[C@H](O)[C@@H](CO[P@@](O)(=S)OP(=O)(O)OP(=O)(O)O)O[C@H]1n1ccc(=O)[nH]c1=O]

or a pharmaceutically acceptable salt of the foregoing." when the virus is HCV. In some embodiments, a compound of Formulae (II), or a pharmaceutically acceptable salt thereof, may not be selected from a compound that is shown in the paragraphs that begins with the paragraph that starts with the lines "In some embodiments, a compound of Formulae (I) and/or (II), or a pharmaceutically acceptable salt of the foregoing, may be selected from:

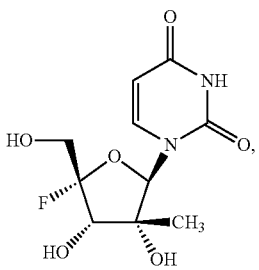

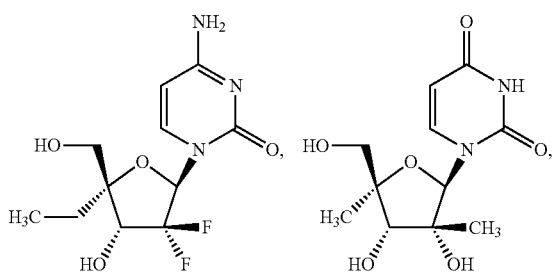

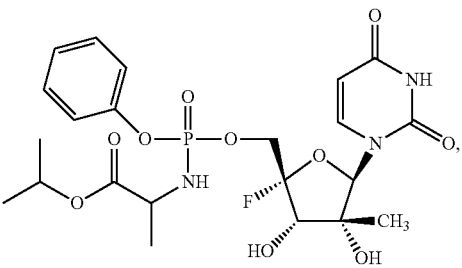

and ends with the paragraph that follows and recites in its last lines "and

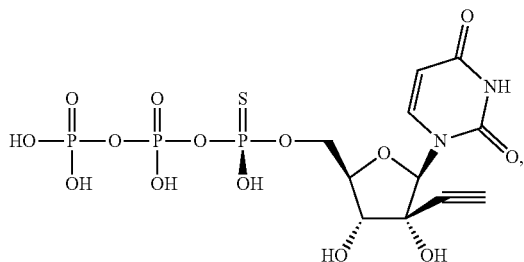 [SMILES: C#C[C@@]1(O)[C@H](O)[C@@H](CO[P@@](O)(=S)OP(=O)(O)OP(=O)(O)O)O[C@H]1n1ccc(=O)[nH]c1=O]

or a pharmaceutically acceptable salt of the foregoing." In some embodiments, a compound of Formulae (I) and/or (II), or a pharmaceutically acceptable salt of the foregoing, is not a compound in WO 2013/092481 (filed Dec. 17, 2012), U.S. 2013/0164261 (filed Dec. 20, 2012), WO 2014/100505 (filed Dec. 19, 2013), WO 2013/096679 (filed Dec. 20, 2012), WO 2013/142525 (filed Mar. 19, 2013), or U.S. application Ser. No. 14/312,990 (filed Jun. 24, 2014) or a pharmaceutically acceptable salt of the foregoing.

Pharmaceutical Compositions

Some embodiments described herein relates to a pharmaceutical composition, that can include an effective amount of one or more compounds described herein (e.g., a compound of Formulae (I) and/or (II), or a pharmaceutically acceptable salt of the foregoing) and a pharmaceutically acceptable carrier, diluent, excipient or combination thereof. In some embodiments, the pharmaceutical composition can include a single diastereomer of a compound of Formulae (I) and/or (II), or a pharmaceutically acceptable salt of the foregoing, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formulae (I) and/or (II), or a pharmaceutically acceptable salt of the foregoing. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formulae (I) and/or (II), or a pharmaceutically acceptable salt of the foregoing.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration. A pharmaceutical composition is suitable for human and/or veterinary applications.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Synthesis

Compounds of Formula (I), Formula (II) and those described herein may be prepared in various ways. General synthetic routes to the compound of Formula (I), Formula (II) and some examples of starting materials used to synthesize the compounds of Formulae (I) and (II) are shown in Scheme 1, 2, 3 and 4, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formulae (I) and (II) can be prepared using various methods known to those skilled in the art. Examples of methods are shown in Schemes 1, 2, 3 and 4. Suitable phosphorus containing precursors can be commercially obtained or prepared by synthetic methods known to those skilled in the art. Examples of general structures of phosphorus containing precursors are shown in Schemes 1, 2, 3 and 4, and include phosphorochloridates and thiophosphorochloridates. Suitable phosphorochloridates and thiophosphorochloridates are commercially available and/or can be synthetically prepared.

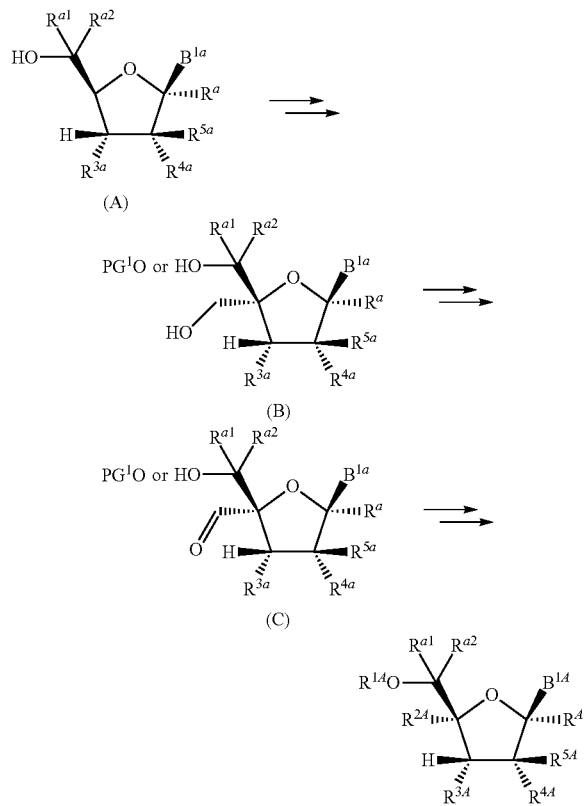

As shown in Scheme 1, compounds of Formulae (I) and (II), wherein the 4'-position is a haloalkyl, can be prepared from a nucleoside, for example, a nucleoside of Formula (A). In Scheme 1, $R^a$, $R^{3a}$, $R^{4a}$, $R^{5a}$, and $B^{1a}$ can be the same as $R^A/R^C$, $R^{3A}/R^{3C}$, $R^{4A}/R^{4C}$, $R^{5A}/R^{5C}$, and $B^{1A}/B^{1C}$ as described herein for Formulae (I) and (II), respectively, and $PG^1$ is a suitable protecting group. A hydroxyalkyl group can be formed at the 4'-position of the pentose ring using suitable conditions known to those skilled in the art. Examples of suitable conditions for forming a hydroxyalkyl include the use of 2-iodoxybenzoic acid (IBX) aqueous formaldehyde and sodium borohydride. A compound of Formula (B) can be transformed to a haloalkyl using a suitable agent(s), for example, to an iodide using imidazole, triphenylphosphine and iodine; to a fluoro using diethylaminosulfur trifluoride (DAST); or to a chloro using triphenylphosphine and carbontetrachloride in dichloroethylene (DCE).

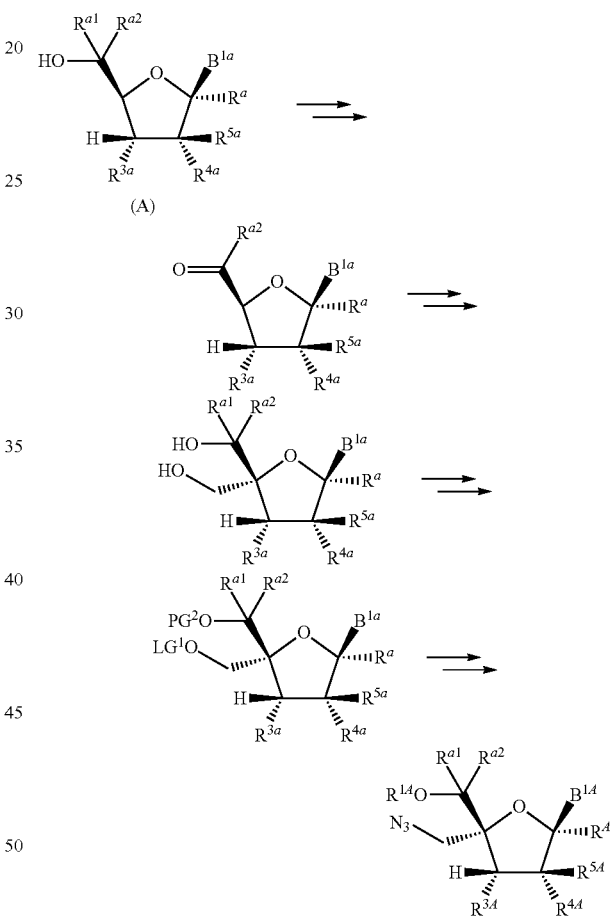

Compounds of Formulae (I) and (II), where $R^{2A}/R^{2C}$ is a $C_1$-6 azidoalkyl, can be prepared from a nucleoside, for example, a nucleoside of Formula (A). In Scheme 2, $R^a$, $R^{3a}$, $R^{4a}$, $R^{5a}$ and $B^{1a}$ can be the same as $R^A/R^C$, $R^{3A}/R^{3C}$, $R^{4A}/R^{4C}$, $R^{5A}/R^{5C}$ and $B^{1A}/B^{1C}$ as described herein for Formulae (I) and (II), respectively, $PG^2$ can be a suitable protecting group and $LG^2$ can be a suitable leaving group. The 5'-position of the nucleoside can be oxidized to an aldehyde using methods known to those skilled in the art. Suitable oxidation conditions include, but are not limited to, Moffatt oxidation, Swern oxidation and Corey-Kim oxidation; and suitable oxidizing agents include, but are not limited to, Dess-Martin periodinane, IBX (2-iodoxybenzoic acid), TPAP/NMO (tetrapropylammonium perruthenate/N-methylmorpholine N-oxide), Swern oxidation reagent, PCC (pyridinium chlorochromate), and/or PDC (pyridinium dichromate), sodium periodate, Collin's reagent, ceric ammonium nitrate CAN, $Na_2Cr_2O_7$ in water, $Ag_2CO_3$ on celite, hot $HNO_3$ in aqueous glyme, $O_2$-pyridine CuCl, $Pb(OAc)_4$-pyridine and benzoyl peroxide-$NiBr_2$. A hydroxymethyl group can be added to the 4'-position of the pentose ring along with the reduction of the aldehyde to an alcohol. The hydroxymethyl group can be added via a condensation reaction using formaldehyde and a base, such as sodium hydroxide. After addition of the hydroxymethyl group, reduction of the intermediate compound with a 4'-hydroxymethyl group can be conducted using a reducing reagent. Examples of suitable reducing agents include, but are not limited to, $NaBH_4$ and $LiAlH_4$. A suitable leaving group, such as a triflate, can be formed by replacing the hydrogen of the hydroxymethyl group attached to the 4'-position, and the oxygen attached to the 5'-position can be protected with a suitable protecting group (for example, by cyclization with the base, $B^{1a}$, or with a separate protecting group). The leaving group can be replaced with an azido group using a metal azide reagent, for example, sodium azide. A $C_{1-6}$ azidoalkyl at the 4'-position can be reduced to a $C_{1-6}$ aminoalkyl. Various reduction agents/conditions known to those skilled in the art can be utilized. For example, the azido group can be reduced to an amino group via hydrogenation (for example, $H_2$—Pd/C or $HCO_2NH_4$—Pd/C), Staudinger Reaction, $NaBH_4/CoCl_2.6H_2O$, $Fe/NH_4Cl$ or $Zn/NH_4Cl$.

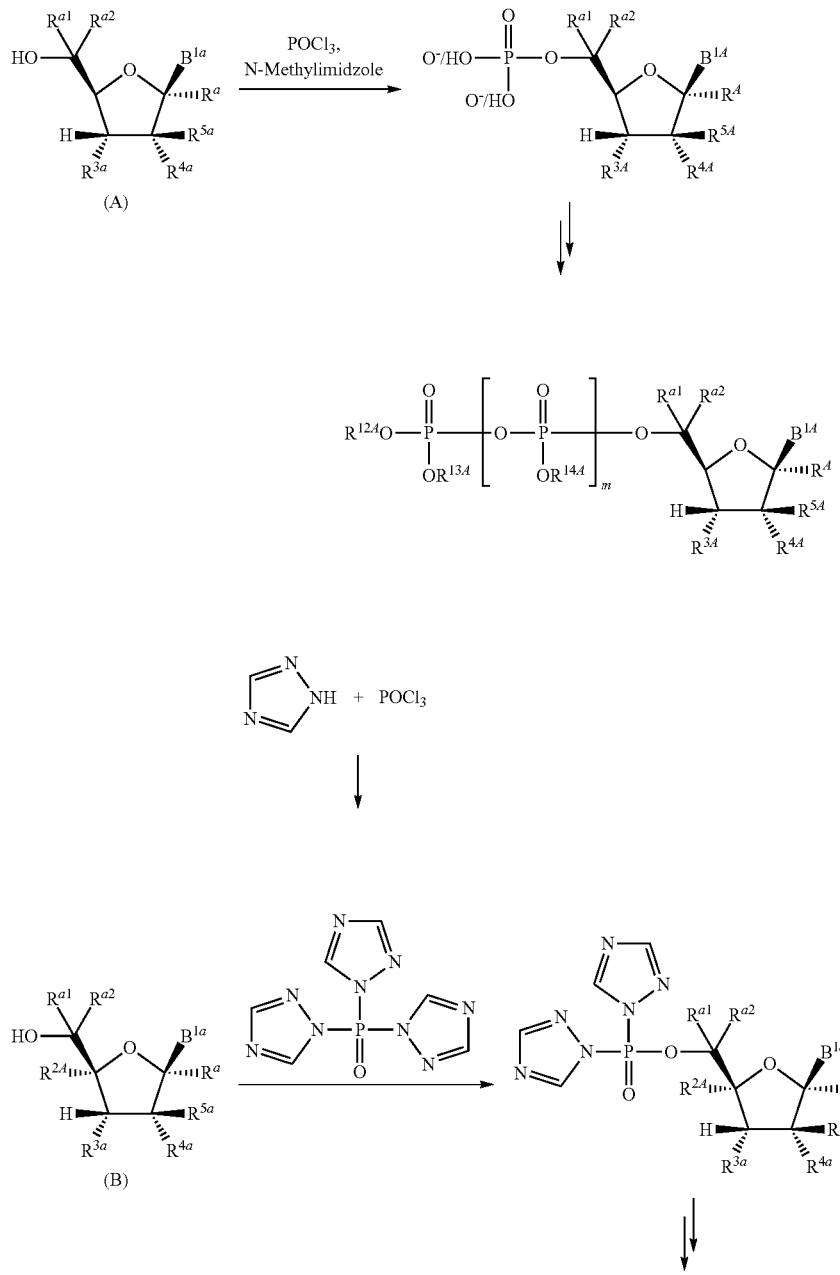

Scheme 3

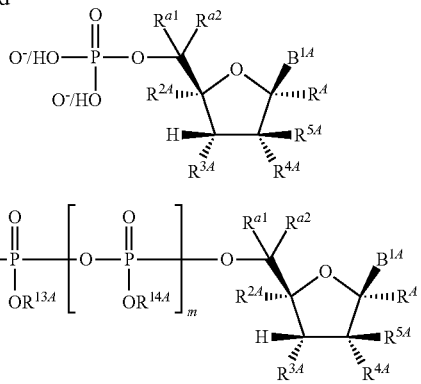

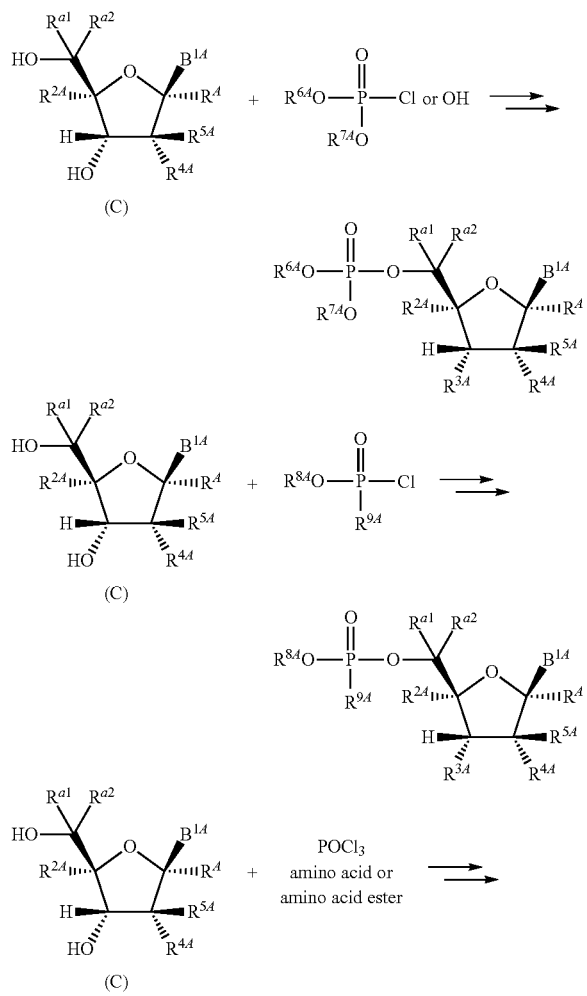

Compounds of Formulae (I) and (II) having a phosphorus containing group attached to the 5'-position of the pentose ring can be prepared using various methods known to those skilled in the art. Examples of methods are shown in Schemes 3 and 4. In Schemes 3 and 4, $R^a$, $R^{2a}$, $R^{3a}$, $R^{4a}$, $R^{5a}$ and $B^{1a}$ can be the same as $R^A/R^C$, $R^{2A}/R^{2C}$, $R^{3A}/R^{3C}$, $R^{4A}/R^{4C}$, $R^{5A}/R^{5C}$ and $B^{1A}/B^{1C}$ as described herein for Formulae (I) and (II), respectively. A phosphorus containing precursor can be coupled to the nucleoside, for example, a compound of Formula (B). Following the coupling of the phosphorus containing precursor, any leaving groups can be cleaved under suitable conditions, such as hydrolysis. Further phosphorus containing groups can be added using methods known to those skilled in the art, for example using a pyrophosphate. If desired, one or more bases can be used during the addition of each phosphorus-containing group. Examples of suitable bases are described herein.

In some embodiments, an alkoxide can be generated from a compound of Formula (C) using an organometallic reagent, such as a Grignard reagent. The alkoxide can be coupled to the phosphorus containing precursor. Suitable Grignard reagents are known to those skilled in the art and include, but are not limited to, alkylmagnesium chlorides and alkylmagnesium bromides. In some embodiments, an appropriate base can be used. Examples of suitable bases include, but are not limited to, an amine base, such as an alkylamine (including mono-, di- and tri-alkylamines (e.g., triethylamine)), optionally substituted pyridines (e.g. collidine) and optionally substituted imidazoles (e.g., N-methylimidazole)). Alternatively, a phosphorus containing precursor can be added to the nucleoside and form a phosphite. The phosphite can be oxidized to a phosphate using conditions known to those skilled in the art. Suitable conditions include, but are not limited to, meta-chloroperoxybenzoic acid (MCPBA) and iodine as the oxidizing agent and water as the oxygen donor.

When compounds of Formulae (I) and (II) have $Z^{1A}/Z^{1C}$, $Z^{2A}/Z^{2C}$ or $Z^{3A}/Z^{3C}$ being sulfur, the sulfur can be added in various manners known to those skilled in the art. In some embodiments, the sulfur can be part of the phosphorus containing precursor, for example,

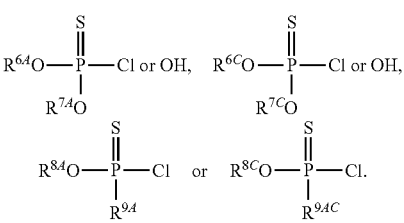

Alternatively, the sulfur can be added using a sulfurization reagent. Suitable sulfurization agents are known to those skilled in the art, and include, but are not limited to, elemental sulfur, Lawesson's reagent, cyclooctasulfur, 3H-1,2-Benzodithiole-3-one-1,1-dioxide (Beaucage's reagent), 3-((N,N-dimethylaminomethylidene)amino)-3H-1,2,4-dithiazole-5-thione (DDTT) and bis(3-triethoxysilyl)propyl-tetrasulfide (TEST).

As described herein, in some embodiments, $R^{3A}$ and $R^{4A}$ and/or $R^{3C}$ and $R^{4C}$ can be each an oxygen atom, wherein the oxygen atoms are linked together by a carbonyl groups. The —O—C(=O)—O— group can be formed using methods known to those skilled in the art. For example, a compound of Formula (I), wherein $R^{3A}$ and $R^{4A}$ are both hydroxy groups, can be treated with 1,1'-carbonyldiimidazole (CDI).

In some embodiments, the 2'-position and/or the 3'-position of the pentose ring can have an optionally substituted —O-acyl group attached, for example, —OC(=O)$R^{nA}$. The optionally substituted —O-acyl group can be formed at the 2'- and/or 3'-position using various methods known to those skilled in the art. As an example, a compound of Formulae (I) and/or (II), wherein the 2'-position and the 3'-position each have an hydroxy group attached, can be treated with an alkyl anhydride (e.g., acetic anhydride and propionic anhydride) or an alkyl acid chloride (e.g., acetylchloride). If desired, a catalyst can be used to facilitate the reaction. An example of suitable catalyst is 4-dimethylaminopyridine (DMAP). Alternatively, the optionally substituted —O-acyl group group(s) can be formed at the 2'- and 3'-positions by reacting an alkyl acid (e.g. acetic acid and propionic acid) in the presences of a carbodiimide or a coupling reagent. Examples of carbodiimides include, but are not limited to, N,N'-dicyclohexylcarbodiimide (DCC), N,N'-diisopropylcarbodiimide (DIC) and 1-ethyl-3-(3-dimethylaminopropyl)carbodiimide (EDC).

To reduce the formation of side products, one or more the groups attached to the pentose ring can be protected with one or more suitable protecting groups and/or any —NH and/or $NH_2$ groups present on the $B^{1a}$, can be protected with one or more suitable protecting groups. As an example, if 2'-position and/or the 3'-position is/are hydroxy group(s), the hydroxy group(s) can be protected with suitable protecting groups, such as triarylmethyl and/or silyl groups. Examples of triarylmethyl groups include but are not limited to, trityl, monomethoxytrityl (MMTr), 4,4'-dimethoxytrityl (DMTr), 4,4',4''-trimethoxytrityl (TMTr), 4,4',4''-tris-(benzoyloxy) trityl (TBTr), 4,4',4''-tris (4,5-dichlorophthalimido) trityl (CPTr), 4,4',4''-tris (levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl) xanthen-9-yl, 1,1'-bis-(4-methoxyphenyl)-1'-pyrenylmethyl, 4,4',4''-tris-(tert-butylphenyl) methyl (TTTr) and 4,4'-di-3, 5-hexadienoxytrityl. Examples of suitable silyl groups are described herein and include trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy]methyl. Alternatively, $R^{3A}$ and/or $R^{4A}$ can be protected by a single achiral or chiral protecting group, for example, by forming an orthoester, a cyclic acetal or a cyclic ketal. Suitable orthoesters include methoxymethylene acetal, ethoxymethylene acetal, 2-oxacyclopentylidene orthoester, dimethoxymethylene orthoester, 1-methoxyethylidene orthoester, 1-ethoxyethylidene orthoester, methylidene orthoester, phthalide orthoester 1,2-dimethoxyethylidene orthoester, and alpha-methoxybenzylidene orthoester; suitable cyclic acetals include methylene acetal, ethylidene acetal, t-butylmethylidene acetal, 3-(benzyloxy)propyl acetal, benzylidene acetal, 3,4-dimethoxybenzylidene acetal and p-acetoxybenzylidene acetal; and suitable cyclic ketals include 1-t-butylethylidene ketal, 1-phenylethylidene ketal, isopropylidene ketal, cyclopentylidene ketal, cyclohexylidene ketal, cycloheptylidene ketal and 1-(4-methoxyphenyl)ethylidene ketal.

EXAMPLES

Additional embodiments are disclosed in further detail in the following examples, which are not in any way intended to limit the scope of the claims.

Example 1

Compound 1

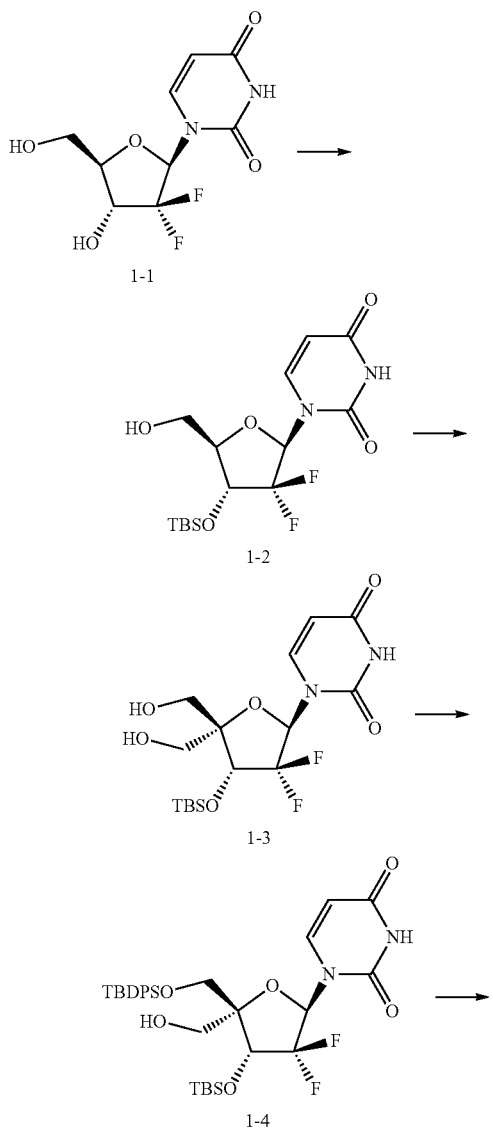

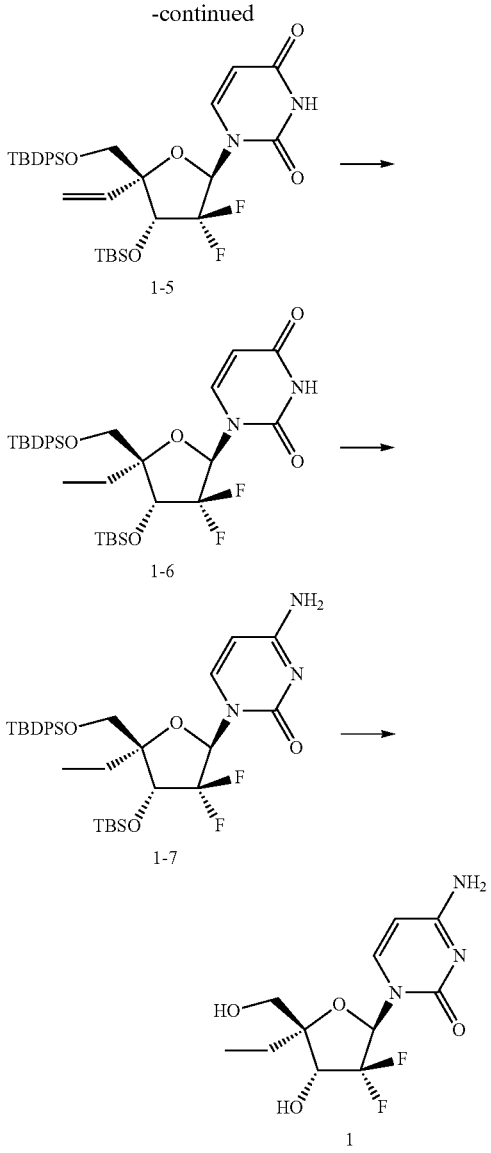

To a solution of 1-1 (100.0 g, 378.7 mmol) in pyridine (750 mL) was added DMTrCl (164.9 g, 487.8 mmol). The solution was stirred at RT for 15 h. MeOH (300 mL) was added, and the mixture was concentrated to dryness under reduced pressure. The residue was dissolved in EA and washed with water. The organic layer was dried over $Na_2SO_4$ and concentrated. The residue was dissolved in DCM (500 mL). To this solution were added imidazole (44.3 g, 650.4 mmol) and TBSCl (91.9 g, 609.8 mmol). The mixture was stirred at RT for 14 h. The solution was washed with $NaHCO_3$ and brine. The organic layer was dried over $Na_2SO_4$, and concentrated to give the crude product as a light yellow solid. The crude (236.4 g, 347.6 mmol) was dissolved in 80% HOAc aqueous solution (500 mL). The mixture was stirred at RT for 15 h. The mixture was diluted with EA, and washed with $NaHCO_3$ solution and brine. The organic layer was dried over $Na_2SO_4$ and purified on a silica gel column chromatography (1-2% MeOH in DCM) to give 1-2 (131.2 g, 91.9%) as a light yellow solid. ESI-MS: m/z 802 [M+H]$^+$.

To a solution of 1-2 (131.2 g, 346.9 mmol) in anhydrous $CH_3CN$ (1200 mL) was added IBX (121.2 g, 432.8 mmol) at RT. The mixture was refluxed for 3 h and then cooled to 0° C. The precipitate was filtered, and the filtrate was concentrated to give the crude aldehyde (121.3 g) as a yellow solid. The aldehyde was dissolved in 1,4-dioxane (1000 mL). 37% $CH_2O$ (81.1 mL, 1.35 mmol) and 2M NaOH aqueous solution (253.8 mL, 507.6 mmol) were added. The mixture was stirred at RT for 2 h., and then neutralized with AcOH to pH=7. To the solution were added EtOH (400 mL) and $NaBH_4$ (51.2 g, 1.35 mol). The mixture was stirred at RT for 30 mins, the reaction was quenched with sat. aq. $NH_4Cl$. The mixture was extracted with EA. The organic layer was dried over $Na_2SO_4$ and concentrated. The residue was purified by silica gel column chromatography (1-3% MeOH in DCM) to give 1-3 (51.4 g, 38.9%) as a white solid.

To a solution of 1-3 (51.4 g, 125.9 mmol) in anhydrous DCM (400 mL) were added pyridine (80 mL) and DMTrCl (49.1 g, 144.7 mmol) at 0° C. The reaction was stirred at RT for 14 h, and then treated with MeOH (30 mL). The solvent was removed, and the residue was purified by silica gel column chromatography (1-3% MeOH in DCM) to give the mono-DMTr protected intermediate as a yellow foam (57.4 g, 62.9%). The intermediate (57.4 g, 82.8 mmol) was dissolved in $CH_2Cl_2$ (400 mL), and imidazole (8.4 g, 124.2 mmol), TBDPSCl (34.1 g, 124.2 mmol) were added. The mixture was stirred at RT for 14 h. The precipitate was filtered off, and the filtrate was washed with brine and dried with $Na_2SO_4$. The solvent was removed to give a residue (72.45 g) as a white solid. The residue was dissolved in 80% HOAc aqueous solution (400 mL). The mixture was stirred RT for 15 h. The mixture was diluted with EA and washed with $NaHCO_3$ solution and brine. The organic layer was dried over $Na_2SO_4$ and purified by silica gel column chromatography (1-2% MeOH in DCM) to give 1-4 (37.6 g, 84.2%) as a white solid.

A solution of 1-4 (700 mg, 1.09 mmol) in anhydrous dichloromethane was added Dess-Martin reagent (919 mg, 2.16 mmol) at 0° C. The mixture was stirred at RT for 30 mins. The reaction was quenched with sat. sodium hydrogen carbonate and sodium thiosulfate solution, and extracted with EA. The organic layers were concentrated to give the crude aldehyde, which was used for next step without purification. A solution of MePPh$_3$Br (3.88 g, 10.87 mmol) in anhydrous THF was treated with a solution of t-BuOK (9.81 mL, 9.81 mmol) in THF at 0° C. The mixture was warmed to RT for 1 h. After cooling to 0° C. for 1 h, a solution of the aldehyde (700 mg, 1.09 mmol) in THF was added. The mixture was stirred overnight at RT. The reaction was quenched with sat. ammonium chloride solution, and extracted with EA. The organic layers were purified by column chromatography to give 1-5 (167 mg, 30%).

To a solution of 1-5 (450 mg, 0.69 mmol) in MeOH (10 mL) was added Pd/C (200 mg) at RT. The reaction mixture was stirred at RT for 1 h under $H_2$ (balloon). Then the mixture was filtered and the filtrate was concentrated to give the crude 1-6 (440 mg, 97.1%) as a white solid.

A solution of 1-6 (317 mg, 0.49 mmol), TPSCl (373 mg, 1.23 mmol), DMAP (150 mg, 1.23 mmol) and TEA (124 mg, 1.23 mmol) in anhydrous MeCN was stirred at RT overnight. The reaction was quenched with $NH_3 \cdot H_2O$, and then stirred at RT for 3 h. The solvent was removed under reduced pressure. The residue was purified by column chromatography to give 1-7 (200 mg, 63%).

To a solution of 1-7 (280 mg, 0.44 mmol) in MeOH (10 mL) was added $NH_4F$ (1.0 g, 27.0 mmol) at RT. The mixture was refluxed for 12 h. The mixture was filtered, and the filtrate was concentrated. The residue was purified on a silica gel column (10% MeOH in DCM) to give compound 1 (81 mg, 63.3%) as a white solid. ESI-MS: m/z 291.8 [M+H]$^+$.

Example 2

Compound 2

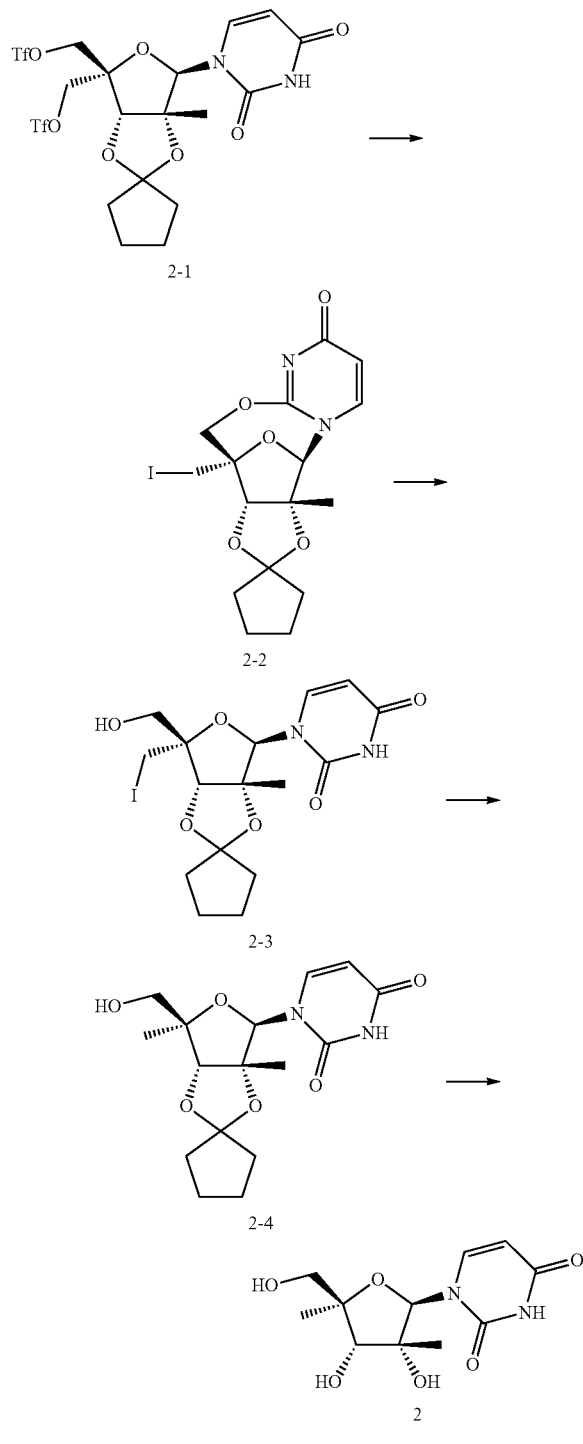

To a solution of 2-1 (2.5 g, 4.04 mmol) in DMF was added NaH (170 mg, 4.24 mmol, 60% purity) at 0° C. The mixture was stirred for 3 h at RT. NaI (6.1 g, 40.4 mmol) was added at RT and stirred for 3 h. The reaction was diluted with water and extracted with EA. The organic layer was dried over anhydrous Na$_2$SO$_4$, and concentrated at low pressure to give 2-2 (1.7 g, 94%) as a yellow solid.

To a solution of 2-2 (1.7 g, 3.81 mmol) in THF (5 mL) was added 2 M NaOH solution (4.5 mL) at 0° C. The solution was stirred for 2 h at RT. The mixture was adjusted to pH=7, and concentrated under reduced pressure. The mixture was partitioned between DCM and water. The DCM layer was dried with high vacuum to give 2-3 (1.2 g, 68%) as a white solid, which was used without further purification.

To a solution of 2-3 (1.2 g, 2.58 mmol) in EtOH (20 mL) was added NH$_4$COOH (650 mg, 7.75 mmol) and Pd/C (120 mg). The mixture was stirred under H$_2$ (30 psi) for 1.5 h at RT. The suspension was filtered, and the filtrate was concentrated at a low pressure. The residue was purified on silica gel column (0.5% TEA and 1% MeOH in DCM) to give 2-4 (545 mg, 62%). ESI-MS: m/z 361.2 [M+23]$^+$.

Compound 2-4 was dissolved in 80% aq. HCOOH (20 mL) and kept at 20° C. for 18 h. After cooling to RT, the solvent was removed in vacuo, and the residue co-evaporated with toluene (3×25 mL). The residue was dissolved in water (3 mL) and concentrated aqueous NH$_4$OH (1 mL) was added. After 2 h at 20° C., the solvent was removed in vacuo. The residue was purified by flash chromatography using a 5 to 50% gradient of methanol in DCM to give purified compound 2 (14 mg) as a white solid.

Example 3

Compound 4

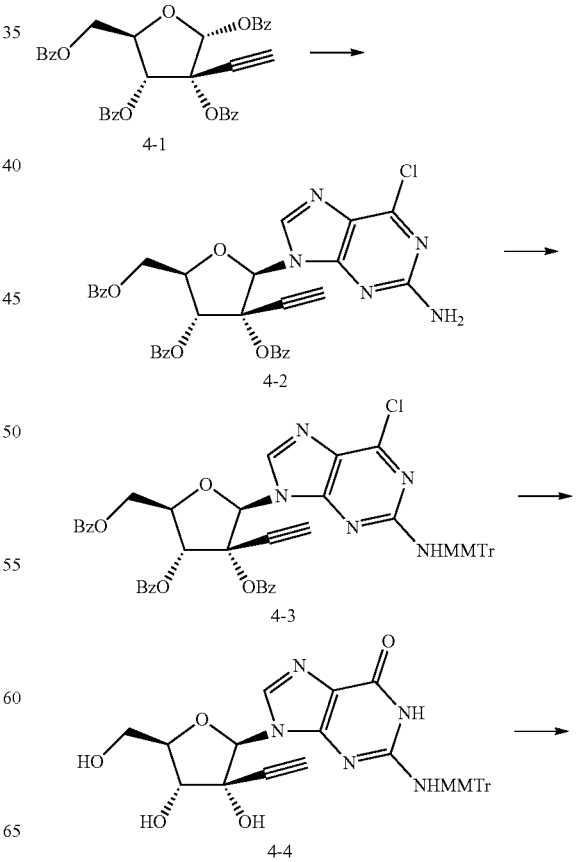

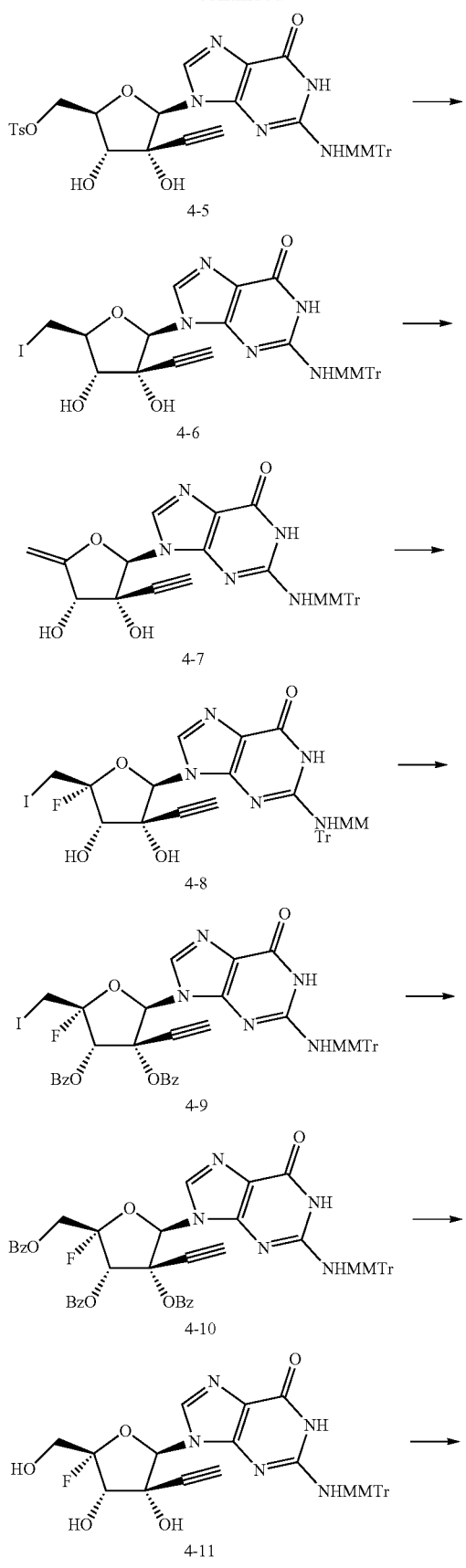
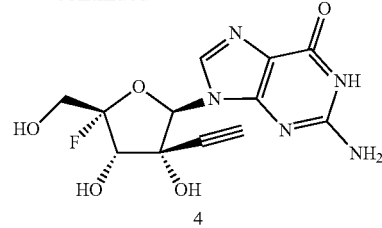

Compound 4-1 (5.0 g, 8.5 mmol) and 2-amino-6-chloropurine (3.0 g, 17.7 mmol) were co-concentrated with anhydrous toluene for 3 times. To a stirred suspension of the mixture in anhydrous MeCN (50 mL) was added DBU (7.5 g, 49 mmol) at 0° C. The mixture was stirred at 0° C. for 15 mins, and TMSOTf (15 g, 67.6 mmol) was added dropwise at 0° C. The mixture was stirred at 0° C. for 15 mins and then heated to 70° C. overnight. The mixture was cooled to RT, and diluted with EA (100 mL). The solution was washed with sat. NaHCO$_3$ solution and brine. The organic layer was dried over Na$_2$SO$_4$ and then concentrated at low pressure. The residue was purified by column on silica gel (PE/EA: from 15/1 to 3/1) to give 4-2 (2.5 g, 46.3%) as a white foam.

To a solution of 4-2 (10 g, 15.7 mmol), AgNO$_3$ (8.0 g, 47 mmol) and collidine (10 mL) in anhydrous DCM (20 mL) was added MMTrCl (14.5 g, 47 mmol) in small portions under N$_2$. The mixture was stirred at RT overnight. The mixture was filtered, and the filtrate was washed with sat. NaHCO$_3$ aqueous and brine. The organic layer was dried over anhydrous Na$_2$SO$_4$, and concentrated at low pressure. The residue was purified by silica gel column (PE/ME=20/1 to 8/1) to give 4-3 (10 g, 70%) as a yellow solid.

To a solution of 3-hydroxy-propionitrile (3.51 g, 49.4 mmol) in anhydrous THF (100 mL) was added NaH (2.8 g, 70 mmol) at 0° C., and the mixture was stirred at RT for 30 mins. To the mixture was added a solution of 4-3 (8.5 g, 9.35 mmol) in anhydrous THF (100 mL) at 0° C., and the reaction mixture was stirred at RT overnight. The reaction was quenched by water, and extracted with EA (100 mL). The organic layer was dried over anhydrous Na$_2$SO$_4$, and concentrated at low pressure. The residue was purified by silica gel column (DCM/MeOH=100/1 to 20/1) to give 4-4 (4.5 g, 83%) as a white solid.

Compound 4-4 (1.5 g, 2.6 mmol) was co-concentrated with anhydrous pyridine 3 times. To an ice cooled solution of 4-4 in anhydrous pyridine (30 mL) was added TsCl (1.086 g, 5.7 mmol), and the reaction mixture was stirred at 0° C. for 1 h. The reaction was quenched with water, and extracted with EA (80 mL). The organic layer was dried over anhydrous Na$_2$SO$_4$, and concentrated at low pressure. The residue was purified by silica gel column (DCM/MeOH=100/1 to 15/1) to give 4-5 (1.4 g, 73%) as a white solid.

To a solution of 4-5 (4.22 g, 5.7 mmol) in acetone (60 mL) was added NaI (3.45 g, 23 mmol), and the mixture was refluxed overnight. The reaction was quenched by sat. Na$_2$S$_2$O$_3$ aqueous, and then extracted with EA (100 mL). The organic layer was dried over anhydrous Na$_2$SO$_4$, and concentrated at low pressure. The residue was purified by silica gel column (DCM/MeOH=100/1 to 15/1) to give 4-6 (4 g, 73%) as a white solid.

To a solution of 4-6 (4.0 g, 5.8 mmol) in anhydrous THF (60 mL) was added DBU (3.67 g, 24 mmol), and the mixture was stirred at 60° C. overnight. The mixture was diluted with EA (80 mL). The solution was washed with brine. The organic layer was dried over anhydrous Na$_2$SO$_4$, and concentrated at low pressure. The residue was purified by silica gel column (DCM/MeOH=100/1 to 20/1) to give 4-7 (2 g, 61%) as a white solid.

To an ice cooled solution of 4-7 (500 mg, 0.89 mmol) in anhydrous DCM (20 mL) was added AgF (618 mg, 4.9 mmol) and a solution of $I_2$ (500 mg, 1.97 mmol) in anhydrous DCM (20 mL). The mixture was stirred at RT for 3 h. The reaction was quenched with sat $Na_2S_2O_3$ and $NaHCO_3$ aqueous, and the mixture was extracted with DCM (50 mL). The organic layer was separated, dried over anhydrous $Na_2SO_4$, and concentrated to give crude 4-8 (250 mg, crude) as a yellow solid.

To a solution of crude 4-8 (900 mg, 1.28 mmol) in anhydrous DCM (50 mL) was added DMAP (1.0 g, 8.2 mmol) and BzCl (795 mg, 5.66 mmol). The mixture was stirred at RT overnight. The mixture was washed with sat. $NaHCO_3$ aq. and brine. The organic layer was dried over anhydrous $Na_2SO_4$, and concentrated at low pressure. The residue was purified by prep-TLC (DCM/MeOH=15:1) to give 4-9 (300 mg, 26%) as a white solid.

To a solution of crude 4-9 (750 mg, 0.82 mmol) in anhydrous HMPA (20 mL) was added NaOBz (1.2 g, 8.3 mmol) and 15-crown-5 (1.8 g, 8.3 mmol). The mixture was stirred at 60° C. for 2 d. The mixture was diluted with EA, and the solution was washed with brine. The organic layer was dried over anhydrous $Na_2SO_4$, and concentrated at low pressure. The residue was purified by prep-TLC (PE/EA=1:1) to give crude 4-10 (550 mg, 73%) as a white solid.

Crude 4-10 (550 mg, 0.6 mmol) was dissolved in $NH_3$/MeOH (7N, 50 mL). The mixture was stirred at RT overnight. The mixture was concentrated, and the residue was purified by silica gel column (DCM/MeOH from 100/1 to 20/1) to give 4-11 (62 mg, 17%) as white solid. ESI-MS: m/z 598.0 [M+H]$^+$.

A solution of 4-11 (12 mg) in 80% formic acid (0.5 mL) stood at RT for 3.5 h and then was concentrated. The residue was co-evaporated with MeOH/toluene 4 times in a vial, then triturated with EtOAc at 40° C. The EtOAc solution removed with pipette, and the trituration step was repeated several times. The remaining solid was dissolved in MeOH. The solution was concentrated and dried to give compound 4 (4.7 mg) as an off white solid. ESI-MS: m/z 326.6 [M+H]$^+$.

Example 4

Compound 5

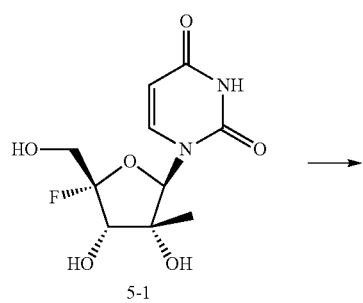

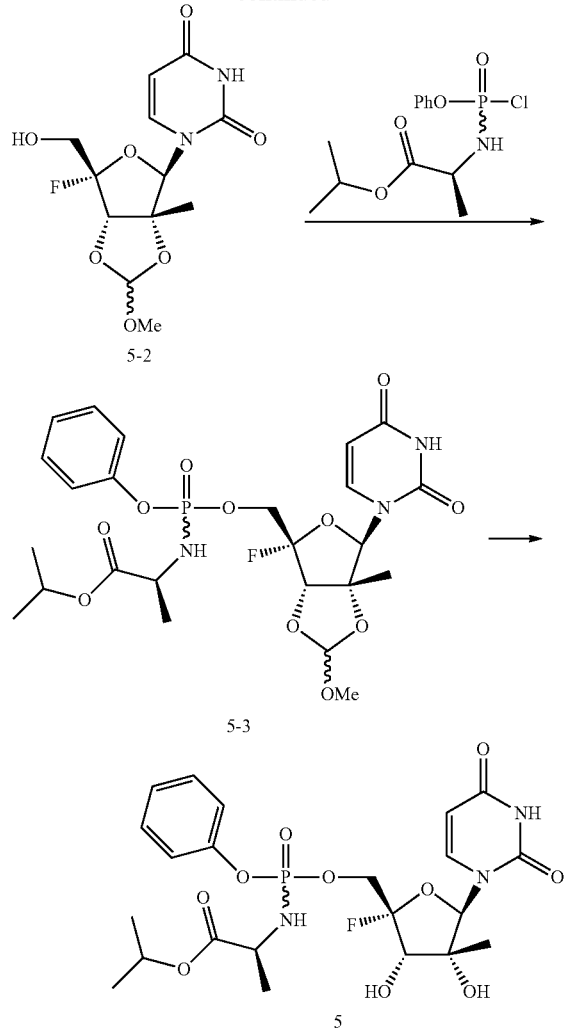

To a solution of 5-1 (1.2 g; 4.3 mmol) in dioxane (30 mL) were added p-toluenesulphonic acid monohydrate (820 mg; 1 eq.) and trimethyl orthoformate (14 mL; 30 eq.). The mixture was stirred overnight at RT. The mixture was then neutralized with methanolic ammonia and the solvent evaporated. Purification on silica gel column with $CH_2Cl_2$-MeOH solvent system (4-10% gradient) yielded 5-2 (1.18 g, 87%).

To an ice cooled solution of 5-2 (0.91 g; 2.9 mmol) in anhydrous THF (20 mL) was added iso-propylmagnesium chloride (2.1 mL; 2 M in THF). The mixture stirred at 0° C. for 20 mins. A solution of phosphorochloridate reagent (2.2 g; 2.5 eq.) in THF (2 mL) was added dropwise. The mixture stirred overnight at RT. The reaction was quenched with saturated aq. $NH_4Cl$ solution and stirred at RT. for 10 mins. The mixture was then diluted with water and $CH_2Cl_2$, and the two layers were separated. The organic layer was washed with water, half saturated aq. $NaHCO_3$ and brine, and dried with $Na_2SO_4$. The evaporated residue was purified on silica gel column with $CH_2Cl_2$-iPrOH solvent system (4-10% gradient) to yield Rp/Sp-mixture of 5-3 (1.59 g; 93%).

A mixture of 5-3 (1.45 g; 2.45 mmol) and 80% aq. HCOOH (7 mL) was stirred at RT. for 1.5 h. The solvent was evaporated and coevaporated with toluene. The obtained residue was dissolved in MeOH, treated with $Et_3N$ (3 drops)

and the solvent was evaporated. Purification on silica gel column with CH$_2$Cl$_2$-MeOH solvent system (4-10% gradient) yielded Rp/Sp-mixture of compound 5 (950 mg; 70%). $^{31}$P-NMR (DMSO-d$_6$): δ 3.52, 3.37. MS: m/z=544 [M−1].

Example 5

Compound 6

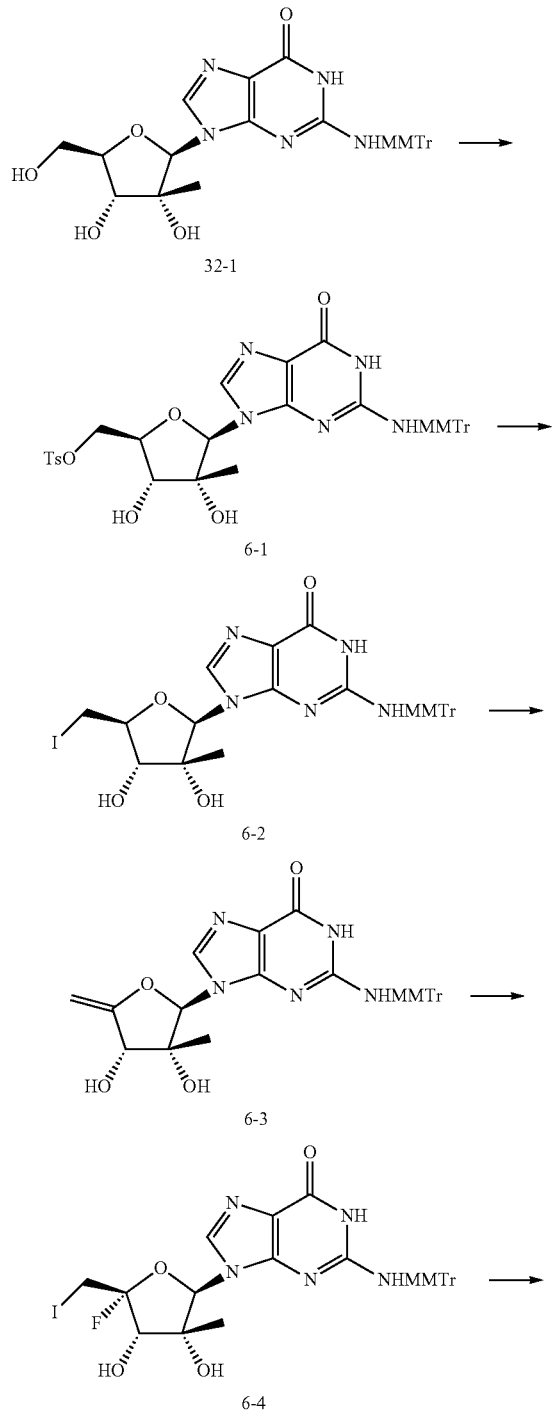

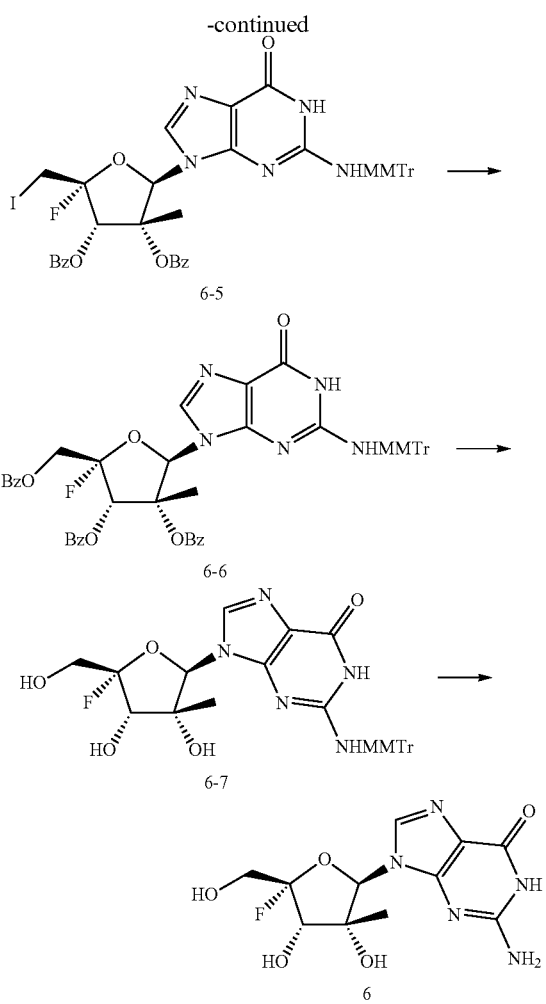

Compound 32-1 (5 g, 8.79 mmol) was co-evaporated with anhydrous pyridine. To an ice cooled solution of 32-1 in anhydrous pyridine (15 mL) was added TsCl (3.43 g, 17.58 mmol), and stirred for 1 h at 0° C. The reaction was checked by LCMS and TLC. The reaction was quenched with H$_2$O, and extracted with EA. The organic phase was dried over anhydrous Na$_2$SO$_4$, and evaporated at low pressure. Compound 6-1 (6.35 g, was purified by silica gel column chromatography (MeOH in DCM from 1% to 6%) to give 6-2 (11.5 g, 38%) as a white solid.

To a solution of 6-1 (31.77 g, 43.94 mmol) in acetone (300 mL) was added NaI (65.86 g, 439.4 mmol), and heated to reflux overnight. The reaction was checked by LCMS. The reaction was quenched with sat. Na$_2$S$_2$O$_3$ solution, and extracted with EA. The organic layer was dried over anhydrous Na$_2$SO$_4$, and evaporated at low pressure. The residue was purified by silica gel column chromatography (MeOH in DCM from 1% to 6%) to give 6-2 (11.5 g, 38%) as a while solid.

To a solution of 6-2 (11.5 g, 16.94 mmol) in dry THF (120 mL) was added DBU (12.87 g, 84.68 mmol), and heated to 60° C. The reaction was stirred overnight and checked by LCMS. The reaction was quenched with sat. NaHCO$_3$ solution, and extracted with EA. The organic phase was dried over anhydrous Na$_2$SO$_4$, and evaporated at low pressure. The residue was purified by silica gel column chromatography (MeOH in DCM from 1% to 5%) to give 6-3 (5.5 g, 54%) as a white solid.

To an ice cooled solution of 6-3 (500 mg, 0.90 mmol) in dry DCM (20 mL) was added AgF (618 mg, 4.9 mmol) and a solution of I₂ (500 mg, 1.97 mmol) in dry DCM (20 mL). The reaction was stirred for 3 h., and checked by LCMS. The reaction was quenched with sat Na₂S₂O₃ solution and sat. NaHCO₃ solution, and the mixture was extracted with DCM. The organic layer was dried by anhydrous Na₂SO₄, and evaporated at low pressure to give crude 6-4 (420 mg, 66%).

To a solution of crude 6-4 (250 mg, 0.36 mmol) in dry DCM (8 mL) was added DMAP (0.28 g, 2.33 mmol), TEA (145 mg, 1.44 mmol) and BzCl (230 mg, 1.62 mmol) in a solution of DCM (2 mL). The reaction was stirred overnight, and checked by LCMS. The mixture was washed with sat. NaHCO₃ solution and brine. The organic layer was evaporated at low pressure. The residue was purified by prep-TLC to give crude 6-5 (150 mg, 46%).

To a solution of crude 6-5 (650 mg, 0.72 mmol) in dry HMPA (20 mL) was added NaOBz (1.03 g, 7.2 mmol) and 15-crown-5 (1.59 g, 7.2 mmol). The reaction was stirred for 2 d at 60° C. The mixture was diluted with H₂O, and extracted with EA. The organic layer was evaporated at low pressure. The residue was purified by prep-TLC to give 6-6 (210 mg, 32.4%). ESI-MS: m/z: 900.4 [M+H]⁺.

A mixture of 6-6 (25 mg) and BuNH₂ (0.8 mL) was stirred overnight at RT. The mixture was evaporated and purified on silica gel (10 g column) with CH₂Cl₂/MeOH (4-15% gradient) to yield 6-7 (15 mg, 91%).

A mixture of 6-7 (15 mg, 0.02 mmol) in ACN (0.25 mL) and 4 N HCL/dioxane (19 uL) was stirred at RT for 45 mins. The mixture was diluted with MeOH and evaporated. The crude residue was treated with MeCN, and the solid was filtered to yield compound 6 (7 mg). MS: m/z=314 [M−1].

Example 6

Compound 7

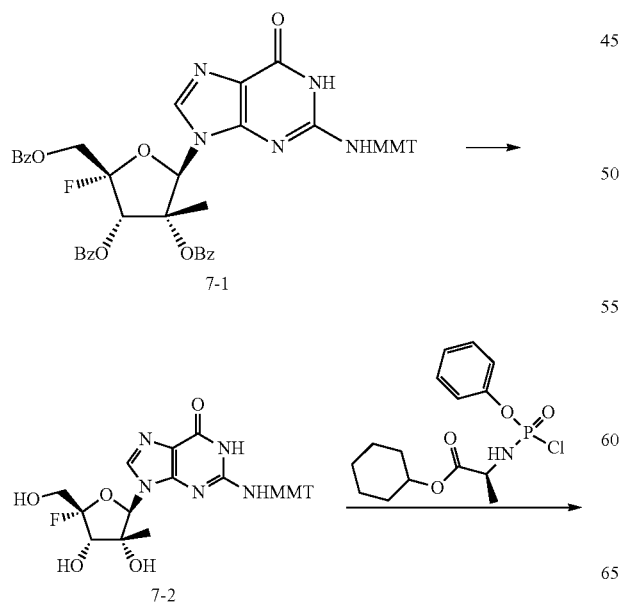

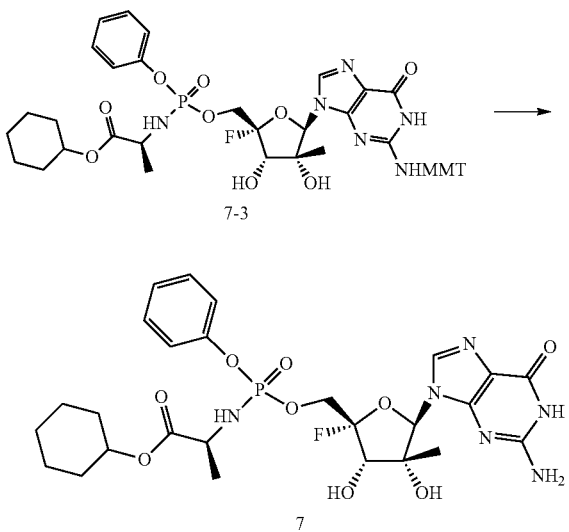

A mixture of 7-1 (170 mg, 0.19 mmol) and methanolic ammonia (7 N; 3 mL) was stirred at RT for 8 h, concentrated and purified on silica gel (10 g column) with CH₂Cl₂/MeOH (4-11% gradient) to give 7-2 (100 mg, 90%).

Compound 7-2 was rendered anhydrous by co-evaporating with pyridine, followed by toluene. To a solution of 7-2 (24 mg, 0.04 mmol), and N-methylimidazole (17 μL, 5 eq.) in acetonitrile (1 mL) was added the phosphorochloridate (50 mg, 3.5 eq.) in 2 portions in 6 h intervals. The mixture was stirred at RT for 1 d and evaporated. Purification on silica (10 g column) with CH₂Cl₂/MeOH (4-12% gradient) yielded 7-3 (10 mg, 28%).

A solution of 7-3 (9 mg, 0.01 mmol) in 80% formic acid was stirred 3 h at R. T. The mixture was evaporated and purified on silica (10 g column) with CH₂Cl₂/MeOH (5-15% gradient) to give compound 7 (3 mg, 50%). MS: m/z=624 [M−1].

Example 7

Compound 8

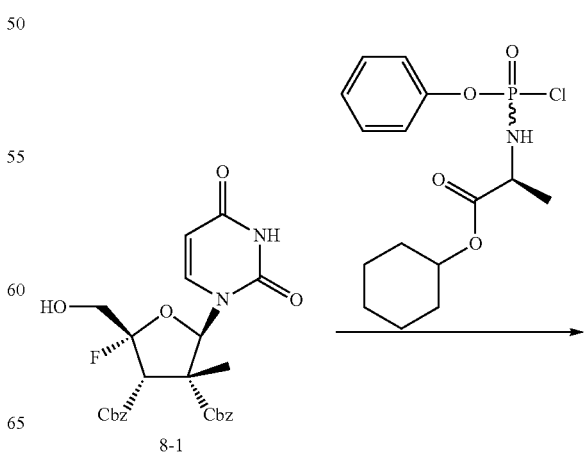

Example 8

Compound 9

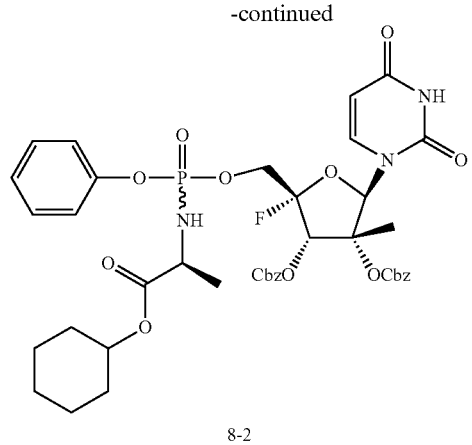

8-2

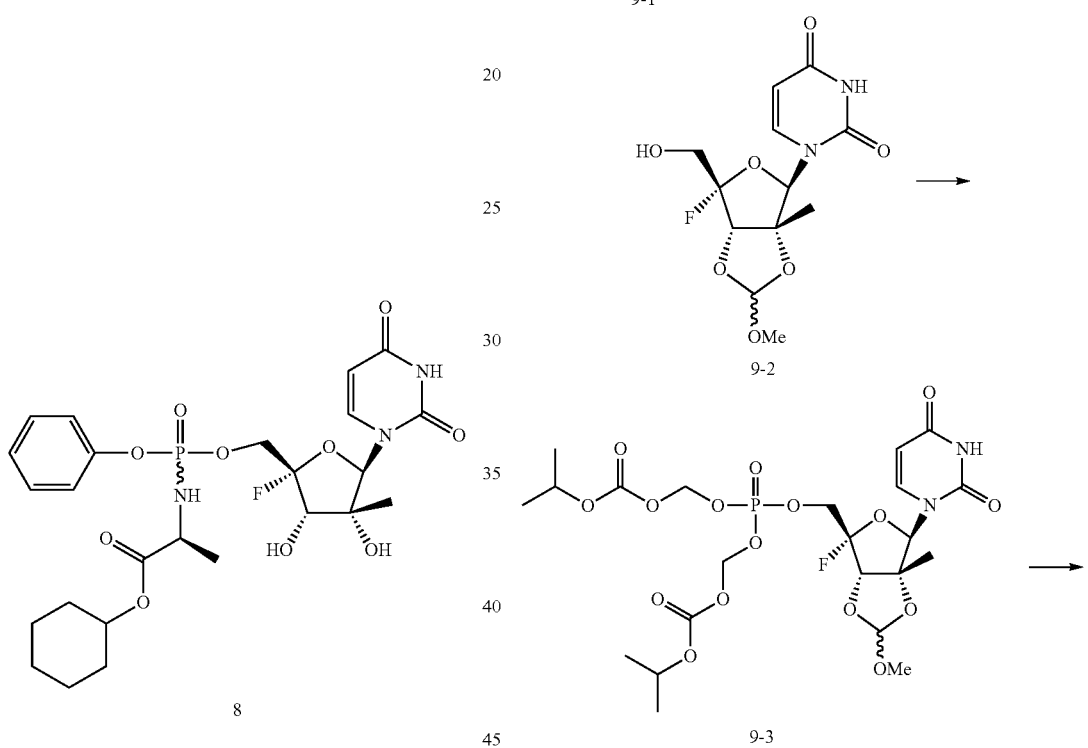

8

To an ice cooled solution of 8-1 (80 mg; 015 mmol) in anhydrous THF (2 mL) was added isopropylmagnesium chloride (0.22 mL; 2 M in THF). The mixture stirred at 0° C. for 20 mins. A solution of the phosphorochloridate reagent (0.16 g; 0.45 mmol) in THF (0.5 mL) was added dropwise. The mixture stirred overnight at RT. The reaction was quenched with saturated aq. NH$_4$Cl solution and stirred at RT for 10 mins. The mixture was diluted with water and CH$_2$Cl$_2$, and the two layers were separated. The organic layer was washed with water, half saturated aq. NaHCO$_3$ and brine, and dried with Na$_2$SO$_4$. The evaporated residue was purified on silica gel column with CH$_2$Cl$_2$-MeOH solvent system (2-10% gradient) to yield Rp/Sp-mixture of 8-2 (102 mg; 80%).

A mixture of 8-2 (100 mg; 0.12 mmol) in EtOH (3 mL) and 10% Pd/C (10 mg) was stirred under the H$_2$ atmosphere for 1.5 h. The mixture was filtered through a Celite pad, evaporated and purified on silica gel column with CH$_2$Cl$_2$-MeOH solvent system (4-10% gradient) to yield Rp/Sp-mixture of compound 8 (52 mg, 74%). MS: m/z=584 [M−1].

A mixture of 9-1 (1.2 g, 4.3 mmol), PTSA monohydrate (0.82 g, 1 eq.), and trimethyl orthoformate (14 mL, 30 eq.) in dioxane (30 mL) was stirred overnight at RT. The reaction was neutralized with 7 N NH$_3$/MeOH and a white solid removed by filtration. The residue was dissolved in THF (10 mL) and treated with 80% aq. AcOH (5 mL). The mixture was kept at RT for 45 mins and then evaporated. The residue was purified on silica gel (25 g column) with CH$_2$Cl$_2$/MeOH (4-10% gradient) to give 9-2 (1.18 g, 87%).

Compound 9-3 (137 mg, 75%) was prepared from 9-2 (93 mg, 0.29 mmol) and triethylammonium bis(isopropyloxycarbonyloxymethyl)phosphate (0.44 mmol) with DIPEA (0.2 mL), BopCl (147 mg), and 3-nitro-1,2,4-triazole (66 mg) in THF (3 mL). Purification was done with CH$_2$Cl$_2$/i-PrOH solvent system (3-10% gradient).

A solution of 9-3 (137 mg) in 80% aq. HCOOH was stirred at RT for 2 h, and then concentrated. The residue was co-evaporated with toluene and then MeOH containing a small amount of a small amount of Et$_3$N (2 drops). Purification on silica (25 g column) with CH$_2$Cl$_2$/MeOH (4-10% gradient) gave compound 9 (100 mg, 77%). MS: m/z=1175 [2M−1].

Example 9

Compound 10

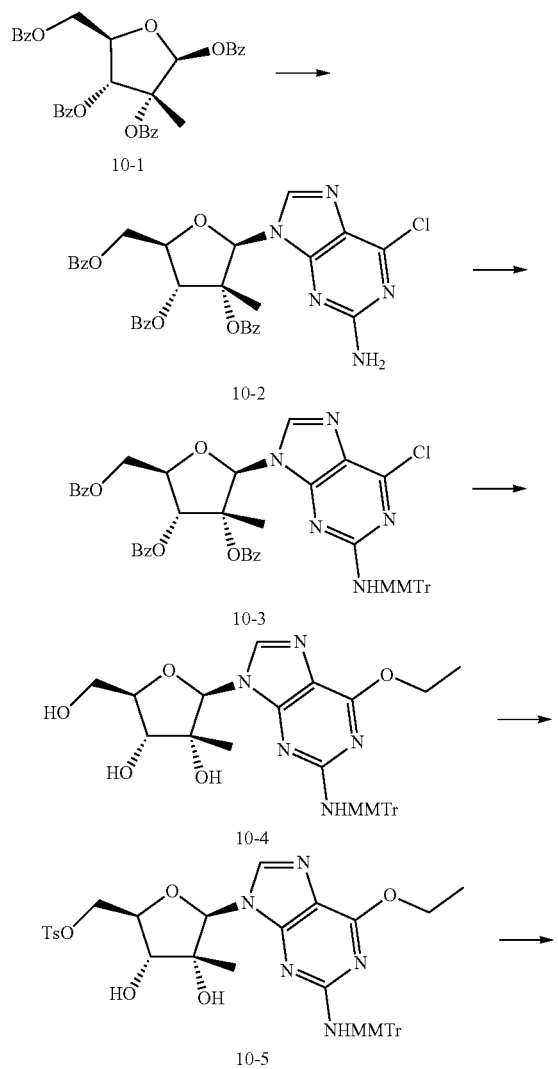

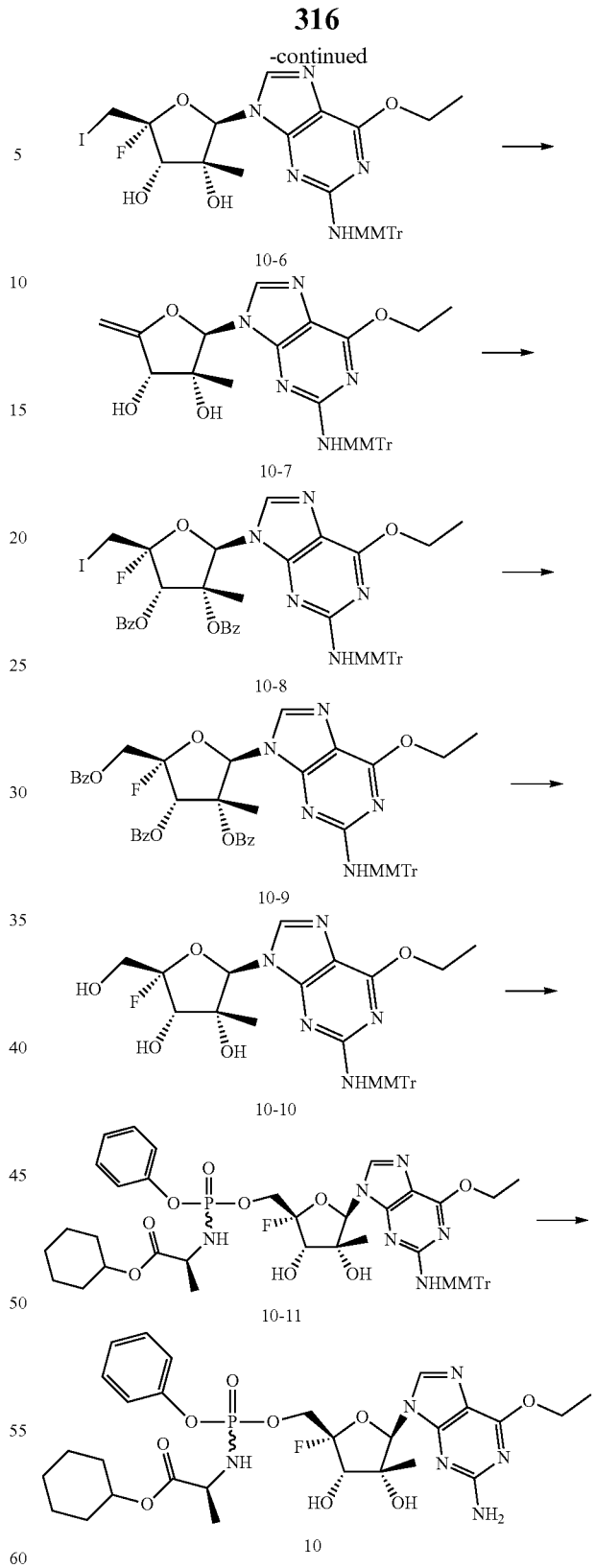

Compound 10-1 (50 g, 86.0 mmol) and 6-Cl-guanine (16.1 g, 98.2 mmol) were co-evaporated with anhydrous toluene 3 times. To a solution of 10-1 in MeCN (200 mL) was added DBU (39.5 g, 258.0 mmol) at 0° C. The mixture was stirred at 0° C. for 30 mins, and then TMSOTf (95.5 g, 430.0 mmol) was added dropwise at 0° C. The mixture was stirred at 0° C. for 30 mins. The mixture was heated to 70° C., and stirred overnight. The solution was cooled to RT and diluted with EA (100 mL). The solution was washed with sat. NaHCO₃ solution and brine. The organic layer was dried over Na₂SO₄, and concentrated at low pressure. The residue was purified by column on silica gel (EA in PE from 10% to 40%) to give 10-2 (48.0 g, yield: 88.7%) as a yellow foam. ESI-MS: m/z 628 [M+H]⁺.

To a solution of 10-2 (48.0 g, 76.4 mol), AgNO₃ (50.0 g, 294.1 mmol) and collidine (40 mL) in anhydrous DCM (200 mL) was added MMTrCl (46.0 g, 149.2 mmol) in small portions under N₂. The mixture was stirred at RT for 3 h under N₂. The reaction was monitored by TLC. The mixture was filtered, and the filter was washed with sat. NaHCO₃ solution and brine. The organic layer was dried over anhydrous Na₂SO₄, and concentrated at low pressure. The residue was purified by silica gel column (EA in PE from 5% to 50%) to the give crude 10-3 (68 g, 98%). ESI-MS: m/z 900.1 [M+H]⁺.

Sodium (8.7 g, 378.0 mmol) was dissolved in dry EtOH (100 mL) at 0° C., and slowly warmed to RT. Compound 10-3 (68.0 g, 75.6 mmol) was treated with freshly prepared NaOEt solution, and stirred overnight at RT. The reaction was monitored by TLC, and the mixture was concentrated at low pressure. The mixture was diluted with H₂O (100 mL), and extracted with EA (3×100 mL). The organic layer was dried over anhydrous Na₂SO₄, and evaporated at low pressure. The residue was purified by silica gel column chromatography (MeOH in DCM from 1% to 5%) to give 10-4 (34.0 g, 75.2%) as a yellow solid. ESI-MS: m/z 598 [M+H]⁺.

Compound 10-4 (32.0 g, 53.5 mmol) was co-evaporated with anhydrous pyridine 3 times. To an ice cooled solution of 10-4 in anhydrous pyridine (100 mL) was added TsCl (11.2 g, 58.9 mmol) in pyridine (50 mL) dropwise at 0° C. The mixture was stirred for 18 h. at 0° C. The reaction was checked by LCMS (about 70% was the desired product). The reaction was quenched with H₂O, and the solution was concentrated at low pressure. The residue was dissolved in EA (100 mL), and washed with sat. NaHCO₃ solution. The organic layer was dried over anhydrous Na₂SO₄, and evaporated at low pressure. The residue was purified by silica gel column chromatography (MeOH in DCM from 1% to 5%) to give crude 10-5 (25.0 g, 62.2%) as a yellow solid. ESI-MS: m/z 752 [M+H]⁺.

To a solution of 10-5 (23.0 g, 30.6 mmol) in acetone (150 mL) was added NaI (45.9 g, 306.0 mmol) and TBAI (2.0 g), and refluxed overnight. The reaction was monitored by LCMS. After the reaction was complete, the mixture was concentrated at low pressure. The residue was dissolved in EA (100 mL), washed with brine, and dried over anhydrous Na₂SO₄. The organic solution was evaporated at low pressure. The residue was purified by silica gel column chromatography (DCM:MeOH=100:1 to 20:1) to give the crude product. To a solution of the crude product in dry THF (200 mL) was added DBU (14.0 g, 91.8 mmol), and heated to 60° C. The mixture was stirred overnight, and checked by LCMS. The reaction was quenched with sat. NaHCO₃, and the solution was extracted with EA (100 mL). The organic layer was dried over anhydrous Na₂SO₄, and evaporated at low pressure. The residue was purified by silica gel column chromatography (MeOH in DCM from 1% to 5%) to give 10-6 (12.0 g, 67.4%) as a yellow solid. ESI-MS: m/z 580 [M+H]⁺.

To an ice cooled solution of 10-6 (8.0 g, 13.8 mmol) in dry MeCN (100 mL) was added NIS (3.9 g, 17.2 mmol) and TEA.3HF (3.3 g, 20.7 mmol) at 0° C. The mixture was stirred at RT for 18 h and checked by LCMS. After the reaction was complete, the reaction was quenched with sat Na₂SO₃ and sat. NaHCO₃ solution. The solution was extracted with EA. The organic layer was dried over anhydrous Na₂SO₄, and evaporated at low pressure. The residue was purified by silica gel column chromatography (EA in PE from 10% to 50%) to give 10-7 (7.2 g, 72.0%) as a solid. ESI-MS: m/z 726 [M+H]⁺.

To a solution of crude 10-7 (7.2 g, 9.9 mmol) in dry DCM (100 mL) was added DMAP (3.6 g, 29.8 mmol), and BzCl (2.8 g, 19.8 mmol) at 0° C. The mixture was stirred overnight, and checked by LCMS. The mixture was washed with sat. NaHCO₃ solution. The organic layer was dried over anhydrous Na₂SO₄, and evaporated at low pressure. The residue was purified by silica gel column chromatography (EA in PE from 10% to 30%) to give 10-8 (8.0 g, 86.4%) as a solid. ESI-MS: m/z 934 [M+H]⁺.

To a solution of 10-8 (7.5 g, 8.0 mmol) in dry DMF (100 mL) was added NaOBz (11.5 g, 80.0 mmol) and 15-crown-5 (15.6 mL). The mixture was stirred for 36 h. at 90° C. The mixture was diluted with H₂O (100 mL), and extracted with EA (3×150 mL). The organic layer was dried over anhydrous Na₂SO₄, and evaporated at low pressure. The residue was purified by silica gel column chromatography (EA in PE from 10% to 30%) to give crude 10-9 (6.0 g, 80.0%) as a solid. ESI-MS: m/z 928 [M+H]⁺.

Compound 10-9 (4.0 g, 4.3 mmol) was co-evaporated with anhydrous toluene 3 times, and treated with NH₃/MeOH (50 mL, 4N) at RT. The mixture was stirred for 18 h at RT. The reaction was monitored by LCMS, and the mixture was concentrated at low pressure. The residue was purified by silica gel column chromatography (EA in PE from 30% to 50%) to give 10-10 (1.9 g, 71.7%) as a solid. ESI-MS: m/z 616 [M+H]⁺.

Compound 10-10 (300.0 mg, 0.49 mmol) was co-evaporated with anhydrous toluene 3 times, and was dissolved in MeCN (2 mL). The mixture was treated with NMI (120.5 mg, 1.47 mmol) and the phosphorochloridate reagent (338.1 mg, 0.98 mmol) in MeCN (1 mL) at 0° C. The mixture was stirred for 18 h at RT. The reaction was monitored by LCMS. The mixture was diluted with 10% NaHCO₃ solution, and extracted with EA. The residue was purified by silica gel column chromatography (EA in PE from 30% to 50%) to give 10-11 (240 mg, 53.3%) as a solid. ESI-MS: m/z 925 [M+H]⁺.

Compound 10-11 (240.0 mg, 0.26 mmol) was treated with 80% AcOH (10 mL), and the mixture was stirred for 18 h at RT. The reaction was monitored by LCMS. The mixture was concentrated at low pressure. The residue was purified by silica gel column chromatography (MeOH in DCM from 1% to 3%) to give compound 10 (87.6 mg, 51.7%) as a solid. ESI-MS: m/z 653 [M+H]⁺.

Example 10

Compound 12

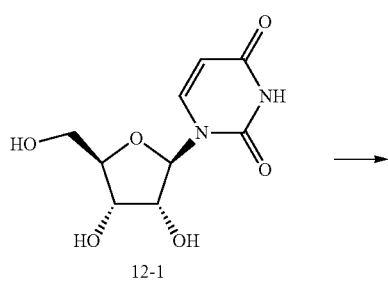

12-1

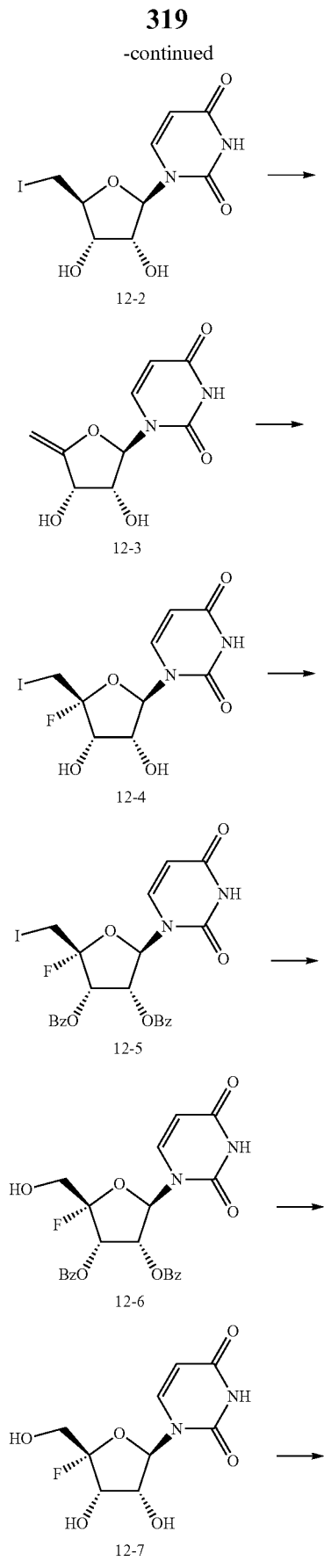

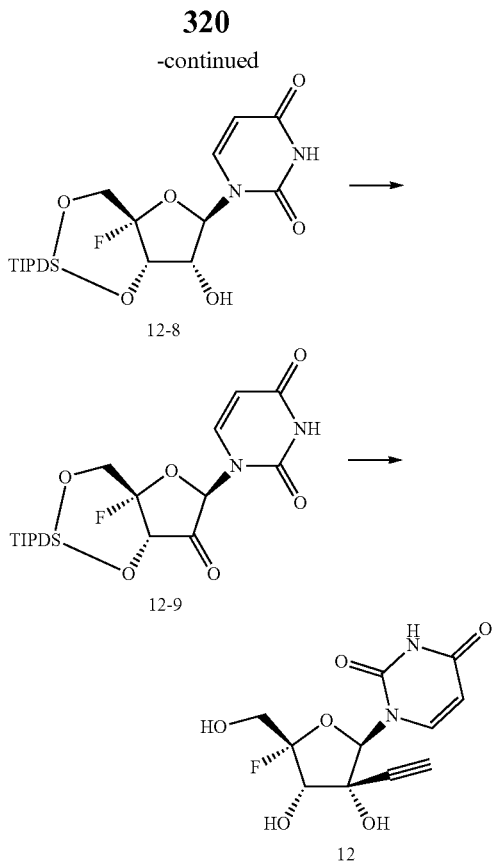

To a stirred suspension of 12-1 (20.0 g, 81.3 mmol), imidazole (15.9 g, 234.0 mmol), PPh$_3$ (53.5 g, 203.3 mmol) and pyridine (90 mL) in anhydrous THF (100 mL) was added a solution of I$_2$ (41.3 g, 162.6 mmol) in THF (150 mL) dropwise at 0° C. The mixture was slowly warmed to RT and stirred for 14 h. The reaction was quenched with sat. aq. Na$_2$S$_2$O$_3$ (150 mL) and extracted with THF/EA (1/1) (100 mL×3). The organic layer was dried over Na$_2$SO$_4$, and concentrated at a low pressure. The residue was recrystallized from EtOH to afford pure 12-2 (23 g, 79%) as a white solid.

To a stirred solution of 12-2 (23 g, 65 mmol) in anhydrous MeOH (200 mL) was added NaOCH$_3$ (10.5 g, 195 mmol) in MeOH (50 mL) at RT. The mixture was stirred at 60° C. for 3 h, and quenched with dry ice. A solid precipitated and removed by filtration. The filtrate was concentrated at a low pressure. The residue was purified on column silica gel column (MeOH in DCM from 1% to 10%) to provide 12-3 (13.1 g, 92.5%) as a white foam solid.

To a stirred solution of 12-3 (12.0 g, 53 mmol) in anhydrous CH$_3$CN was added TEA.3HF (8.5 g, 53 mmol) and NIS (10.2 g, 63.6 mmol) at 0° C. The mixture was stirred for 30 mins, and slowly warmed to RT. The mixture was stirred for another 30 mins. The solid was removed by filtration, and washed with DCM to give 12-4 (14 g, 73%) as a yellow solid. ESI-MS: m/z 373.0 [M+H]$^+$.

To a stirred solution of 12-4 (12.0 g, 32 mmol) and DMAP (1.2 g, 9.6 mmol) in pyridine (100 mL) was added Bz$_2$O (21.7 g, 96 mmol) at RT. The mixture was stirred at 50° C. for 16 h. The resulting solution was quenched with water, and concentrated to dryness at low pressure. The crude was purified on silica gel column (50% EA in PE) to give 12-5 (15 g, 81%) as a white solid. ESI-TOF-MS: m/z 581.0 [M+H]$^+$.

Tetra-butylammonium hydroxide (288 mL as 54-56% aqueous solution, 576 mmol) was adjusted to pH~4 by adding TFA (48 mL). The resulting solution was treated with a solution of 12-5 (14 g, 24 mmol) in DCM (200 mL). m-Chloroperbenzoic acid (30 g, 60-70%, 120 mmol) was added portion wise with vigorous stirring, and the mixture was stirred overnight. The organic layer was separated and washed with brine. The resulting solution was dried over magnesium sulfate and concentrated under reduced pressure. The residue was purified by column chromatography to give 12-6 (7.5 g, 68%)

Compound 12-6 (5.0 g, 10.6 mmol) was treated with 7N $NH_3$.MeOH (100 mL), and the mixture was stirred for 5 h. The mixture was then concentrated to dryness at low pressure. The residue was washed with DCM, and the solid was filtered to give 12-7 (2.1 g, 75%) as a white foam. ESI-MS: m/z 263.0 $[M+H]^+$.

To a solution of 12-7 (2.1 g, 8.0 mmol) in pyridine was added TIDPSCl (2.5 g, 8.0 mmol) dropwise at 0° C., and stirred for 12 h. at RT. The solution was quenched with water, and concentrated to dryness at low pressure. The crude was purified by column chromatography (EA in PE from 10% to 50%) to give pure 12-8 (1.6 g, 40%) as a white foam.

A solution of 12-8 (1.5 g, 3.0 mmol) and IBX (1.69 g, 6.0 mmol) in anhydrous $CH_3CN$ (10 mL) was stirred at 80° C. for 3 h. The mixture was cooled down to RT and filtered. The filtrate was concentrated to dryness at low pressure. The residue was purified by column chromatography (EA in PE from 2% to 50%) to give pure 12-9 (1.2 g, 80%) as a white foam. ESI-MS: m/z 503.0 $[M+H]^+$ Compound 12-9 (500 mg, 1 mmol) was dissolved in dry THF (8 mL). Ethynyl magnesium bromide (8 mL of 0.5M solution in cyclohexane) was added at RT. After 30 mins, additional ethynyl magnesium bromide (8 mL) was added. The mixture was left for 30 mins, and then quenched with sat. solution of ammonium chloride. The product was extracted with EA. The organic extracts were washed with brine, dried, and concentrated. The residue was purified by flash chromatography on silica gel in EA to remove the dark color. The yellow compound was dissolved in THF (3 mL) and treated with TBAF (1 mL, 2M solution in THF) for 30 mins. The solvent was evaporated, and the residue was subjected to silica gel chromatography on a Biotage cartridge (25 g). EA saturated with water was used for isocratic elution. Each fractions were analyzed by TLC in DCM:MeOH (9:1 v:v). Fractions containing only the isomer with a high Rf were concentrated to give pure compound 12 (110 mg). MS: 285.1 [M−1].

Example 11

Compound 13

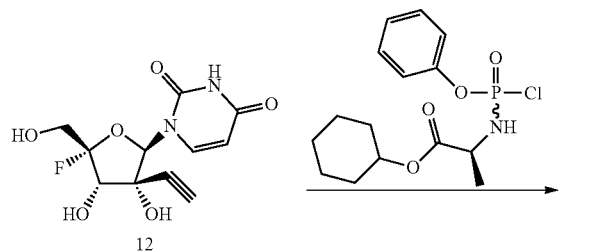

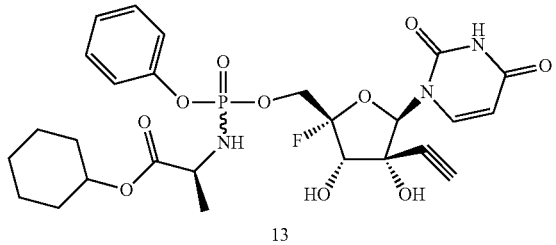

Compound 12 (57 mg, 0.2 mmol) was dissolved in $CH_3CN$ (2 mL), containing N-methylimidazole (40 uL). The phosphorochloridate reagent (207 mg, 0.6 mmol) was added, and the mixture was kept overnight at 40° C. The mixture was distributed between water and EA. The organic layer was separated, washed with brine, dried and evaporated. The product was isolated by silica gel chromatography in gradient of methanol in DCM from 0% to 15%. Compound 13 was obtained (46 mg, 39%). MS: m/z 593.9 [M−1].

Example 12

Compound 14

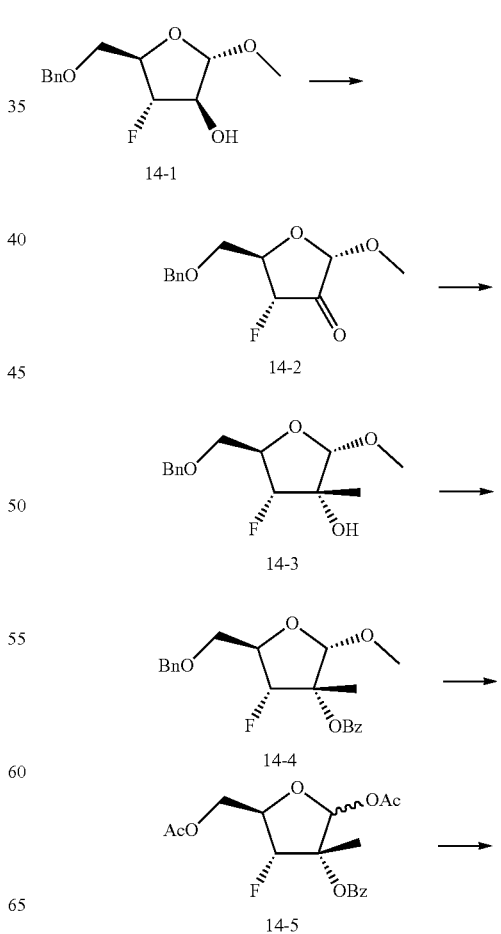

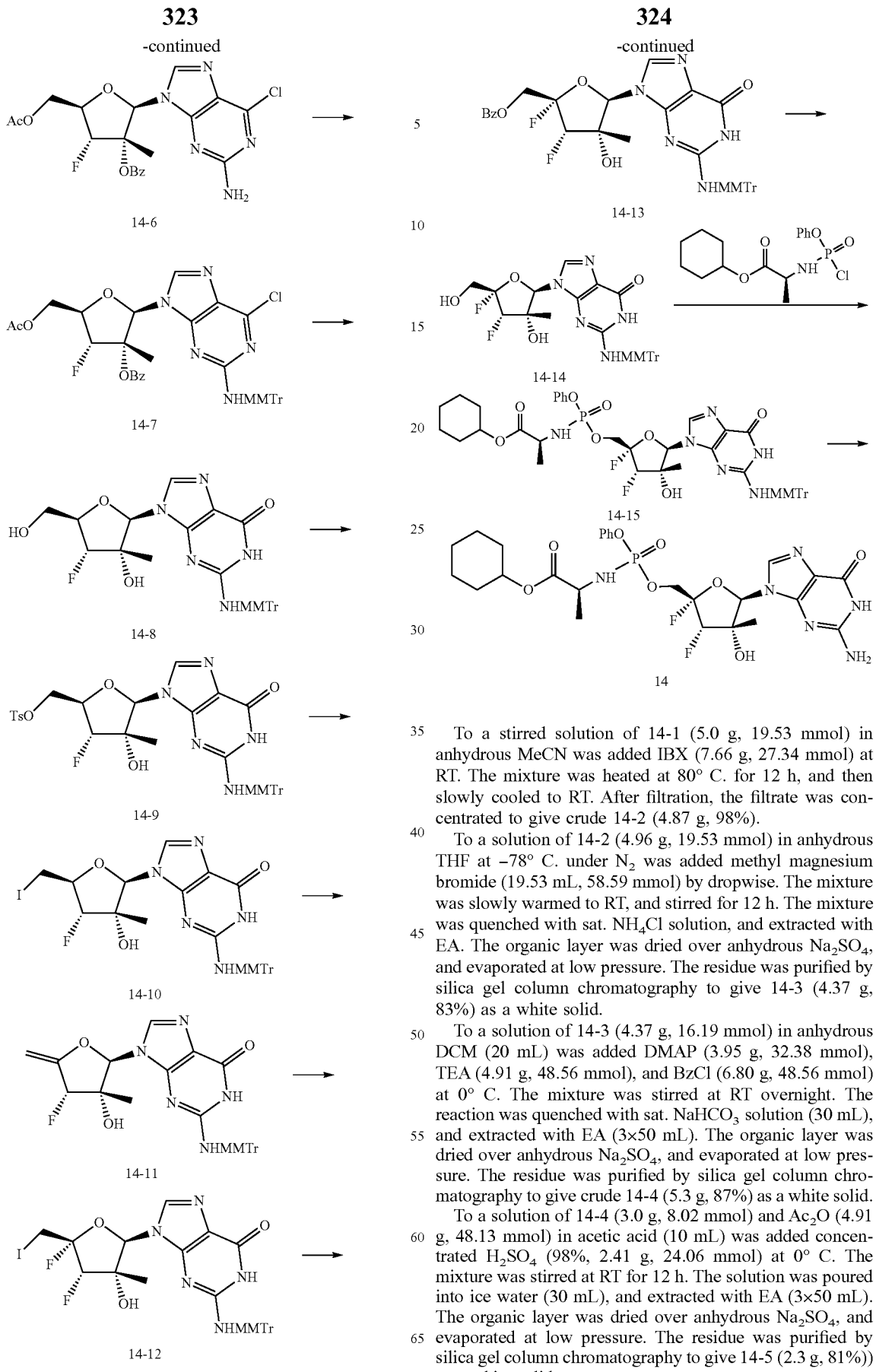

To a stirred solution of 14-1 (5.0 g, 19.53 mmol) in anhydrous MeCN was added IBX (7.66 g, 27.34 mmol) at RT. The mixture was heated at 80° C. for 12 h, and then slowly cooled to RT. After filtration, the filtrate was concentrated to give crude 14-2 (4.87 g, 98%).

To a solution of 14-2 (4.96 g, 19.53 mmol) in anhydrous THF at −78° C. under $N_2$ was added methyl magnesium bromide (19.53 mL, 58.59 mmol) by dropwise. The mixture was slowly warmed to RT, and stirred for 12 h. The mixture was quenched with sat. $NH_4Cl$ solution, and extracted with EA. The organic layer was dried over anhydrous $Na_2SO_4$, and evaporated at low pressure. The residue was purified by silica gel column chromatography to give 14-3 (4.37 g, 83%) as a white solid.

To a solution of 14-3 (4.37 g, 16.19 mmol) in anhydrous DCM (20 mL) was added DMAP (3.95 g, 32.38 mmol), TEA (4.91 g, 48.56 mmol), and BzCl (6.80 g, 48.56 mmol) at 0° C. The mixture was stirred at RT overnight. The reaction was quenched with sat. $NaHCO_3$ solution (30 mL), and extracted with EA (3×50 mL). The organic layer was dried over anhydrous $Na_2SO_4$, and evaporated at low pressure. The residue was purified by silica gel column chromatography to give crude 14-4 (5.3 g, 87%) as a white solid.

To a solution of 14-4 (3.0 g, 8.02 mmol) and $Ac_2O$ (4.91 g, 48.13 mmol) in acetic acid (10 mL) was added concentrated $H_2SO_4$ (98%, 2.41 g, 24.06 mmol) at 0° C. The mixture was stirred at RT for 12 h. The solution was poured into ice water (30 mL), and extracted with EA (3×50 mL). The organic layer was dried over anhydrous $Na_2SO_4$, and evaporated at low pressure. The residue was purified by silica gel column chromatography to give 14-5 (2.3 g, 81%)) as a white solid.

To a stirred solution of 6-Cl-guanine (560 mg, 3.31 mmol) and 14-5 (1.11 g, 2.76 mmol) in anhydrous MeCN (5 mL) was added DBU (1.27 g, 8.28 mmol) under $N_2$ at 0° C. The mixture was stirred at RT for 30 mins. The mixture was cooled to 0° C., and TMSOTf (2.45 g, 11.04 mmol) was added slowly in 15 mins. The mixture was then warmed RT in 30 mins. The mixture was heated at 60° C. for 4 h. The mixture was then poured into ice water (30 mL), and extracted with EA (3×50 mL). The organic layer was dried over anhydrous $Na_2SO_4$ and evaporated at low pressure. The residue was purified by silica gel column chromatography to give 14-6 (800 mg, 70%) as a white solid.

To a solution of 14-6 (839 mg, 1.64 mmol), MMTrCl (1.46 g, 4.75 mmol) and $AgNO_3$ (697 mg, 4.1 mmol) in DCM (10 mL) was added collidine (794 mg, 6.56 mmol). The mixture was stirred for 12 h at RT. The reaction was quenched with sat. $NaHCO_3$ solution (20 mL). After filtration, the filtrate was extracted with DCM (3×20 mL). The organic layer was dried over anhydrous $Na_2SO_4$, and evaporated at low pressure. The residue was purified by silica gel column chromatography to give 14-7 (1.3 g, 72.5%) as a white solid.

3-hydroxyl acrylic nitrile (4.13 g, 5.82 mmol) was dissolved in anhydrous THF (10 mL). The solution was treated with NaH (464 mg, 11.6 mmol) at 0° C., and slowly warmed to RT, and stirred for 30 mins. A solution of 14-7 (912 mg, 1.16 mmol) in anhydrous THF (5 mL) was added slowly. The mixture was stirred at RT overnight. The reaction was quenched with water (40 mL), and extracted with EA (3×50 mL). The organic layer was dried over anhydrous $Na_2SO_4$, and evaporated at low pressure. The residue was purified by silica gel column chromatography to give 14-8 (600 mg, 85%) as a white solid.

To a solution of 14-8 (6.20 g, 10.86 mmol) in anhydrous pyridine (10 mL) at 0° C. was added a solution of TsCl (4.54 g, 23.89 mmol) in anhydrous pyridine (10 mL) dropwise. The mixture was stirred at RT for 30 mins. The mixture was quenched with water (30 mL), and extracted with EA (3×50 mL). The organic layer was dried over anhydrous $Na_2SO_4$, and evaporated at low pressure. The residue was purified by silica gel column chromatography to give 14-9 (6.0 g, 76%) as a white solid.

To a solution of 14-9 (6.0 g, 8.28 mmol) in acetone (30 mL) was NaI (4.97 g, 33.12 mmol), and refluxed overnight. The mixture was evaporated under reduced pressure. The residue was dissolved in EA (50 mL), and washed with sat. $NaHCO_3$ solution (30 mL). The organic layer was dried over anhydrous $Na_2SO_4$, and evaporated at low pressure. The residue was purified by silica gel column chromatography to give 14-10 (5.43 g, 96.4%) as a white solid.

To a solution of 14-10 (5.0 g, 7.34 mmol) in anhydrous THF (20 mL) was added DBU (4.49 g, 29.37 mmol), and stirred at 60° C. overnight. The mixture was slowly cooled to RT. The mixture was quenched with water (30 mL), and extracted with EA (3×50 mL). The organic layer was dried over anhydrous $Na_2SO_4$, and evaporated at low pressure. The residue was purified by silica gel column chromatography to give 14-11 (3.5 g, 85%) as a white solid.

To a solution of 14-11 (3.5 g, 6.33 mmol) and AgF (4.42 g, 34.81 mmol) in anhydrous DCM (20 mL) was added a solution of iodine (3.54 g, 13.93 mmol) in anhydrous DCM (5 mL) dropwise at 0° C. The mixture was stirred for 3 h. The reaction mixture was washed with sat. $NaHCO_3$ solution (40 mL) and extracted with EA (3×50 mL). The organic layer was dried over anhydrous $Na_2SO_4$, and evaporated at low pressure. The residue was purified by silica gel column chromatography to give crude 14-12 (1.37 g, 31%) as a white solid.

To a solution of 14-12 (1.37 g, 1.96 mmol) in anhydrous DMF (15 mL) was added sodium benzoate (2.82 g, 19.60 mmol) and 15-crown-5 (4.31 g, 19.60 mmol), and stirred at 90° C. for 3 d. The mixture was quenched with water (30 mL), and extracted with EA (3×50 mL). The organic layer was dried over anhydrous $Na_2SO_4$, and evaporated at low pressure. The residue was purified by HPLC separation to give 14-13 (250 mg, 20%). ESI-MS: m/z: 694 $[M+H]^+$ A mixture of 14-13 (250 mg, 0.36 mmol) in liquid ammonia was kept overnight at RT in high pressure glass vessel. Ammonia was then evaporated, and the residue purified on silica gel (10 g column) with $CH_2Cl_2$/MeOH (4-10% gradient) to give 14-14 (180 mg, 85%).

Compound 14 (85 mg, 56%) was prepared from 14-14 (99 mg) with i-PrMgCl (0.11 mL) and the phosphorochloridate reagent (94 mg) in THF (2 mL) followed by deprotection. MS: m/z=627 [M+1].

Example 13

Compound 15

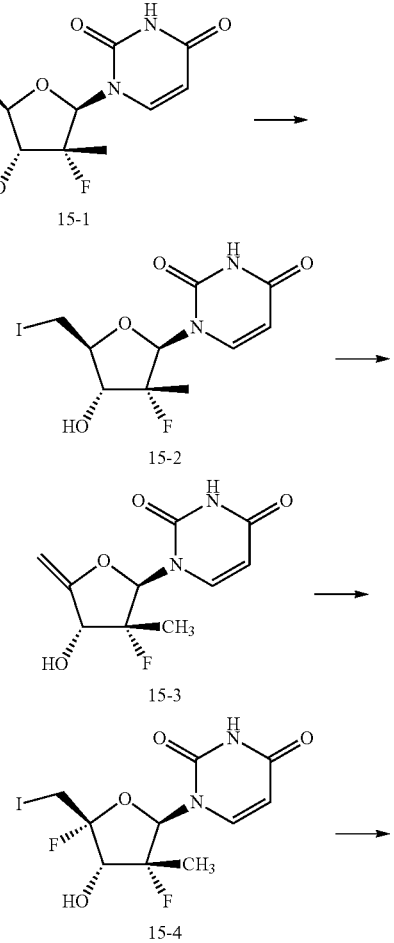

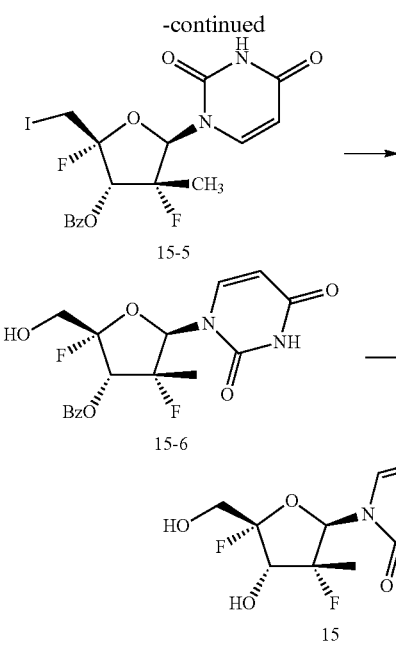

15-5

15-6

15

To a solution of 15-1 (260 mg, 1 mmol), PPh₃ (780 mg, 3 mmol) and pyridine (0.5 mL) in anhydrous THF (8 mL) were added I₂ (504 mg, 2 mmol) at RT, and the mixture was stirred at RT for 12 h. The mixture was diluted with EtOAc and washed with 1M HCl solution. The organic layer was dried over Na₂SO₄, filtered and concentrated at low pressure. The residue was purified by silica gel column (5% MeOH in DCM) to give 15-2 (190 mg, 85%) as a white solid.

To a solution of 15-2 (190 mg, 0.52 mmol) in THF (4 mL) was added DBU (760 mg, 5 mmol) at RT, and the mixture was heated at 50° C. overnight. The mixture was diluted with EtOAc, and washed with water. The organic layer was dried over anhydrous Na₂SO₄ and concentrated at low pressure. The residue was purified by silica gel column (30% EA in PE) to give 15-3 (75 mg, 52%) as a white solid.

To a solution of 15-3 (200 mg, 0.82 mmol) in MeCN (anhydrous, 4 mL) was added NIS (337 mg, 1.5 mmol) and TEA.3HF (213 mg, 1.25 mmol) at RT, and the mixture was stirred at RT for 7 h. The reaction was quenched with sat. Na₂SO₃ solution and sat. aq. NaHCO₃ solution. The mixture was extracted with EA. The organic layer was separated, dried over anhydrous Na₂SO₄, and concentrated at low pressure. The residue was purified by silica gel column (20% EA in PE) to give 15-4 (300 mg, 62%) as a white solid.

To a solution of 15-4 (194 mg, 0.5 mmol) in pyridine (5 mL) was added BzCl (92 mg, 0.55 mmol) at 0° C. The mixture was stirred at RT for 5 h, and the reaction was quenched with water. The mixture was concentrated at low pressure, and the residue was purified by silica gel column (20% EA in PE) to give 15-5 (397 mg, 81%) as a white solid.

To a solution of 15-5 (1.05 g, 2.13 mmol) in DCM (12 mL) was added a mixture of TFA (0.5 mL) and Bu₄NOH (1 mL), followed by addition of m-CPBA (1.3 g, 6 mmol) at RT. The mixture was stirred at RT for 5 h. The mixture was washed with sat. Na₂SO₃ solution and aq. NaHCO₃ solution. The organic layer was dried over anhydrous Na₂SO₄, and concentrated at low pressure. The residue was purified by silica gel column (30% EA in PE) to give 15-6 (450 mg, 63%) as a white solid.

Compound 15-6 (250 mg, 0.65 mmol) was dissolved in NH₃/MeOH (5 mL). The mixture was stirred at RT for 5 h, and then concentrated at low pressure. The residue was purified by silica gel column (5% MeOH in DCM) to give compound 15 (120 mg, 66%) as a white powder. ESI-MS: m/z 279.0 [M+H]⁺.

Example 14

Compound 16

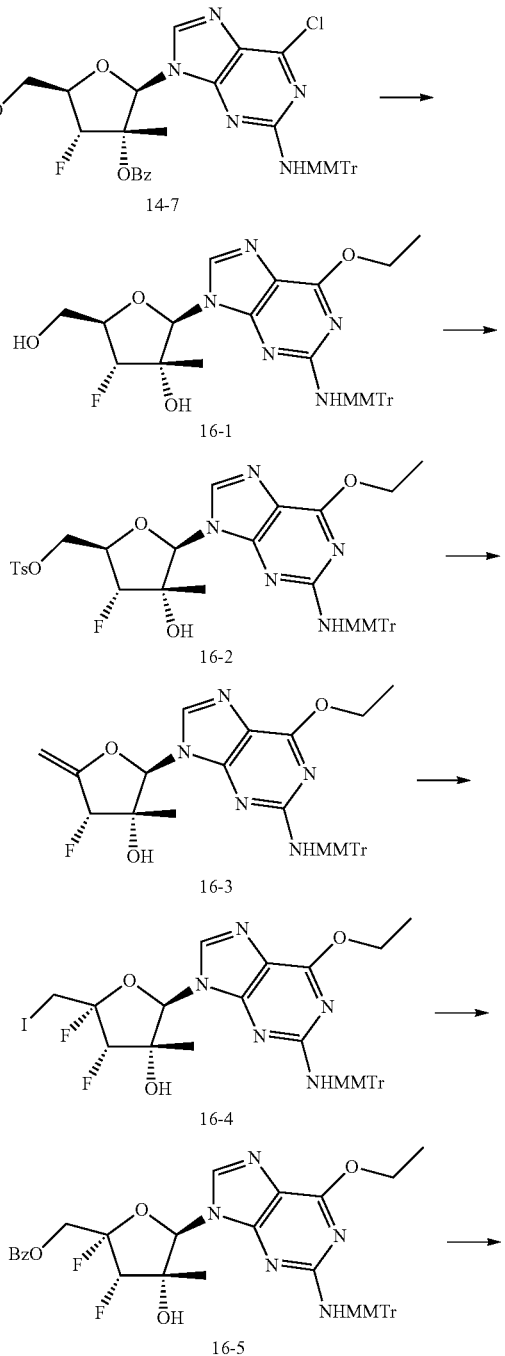

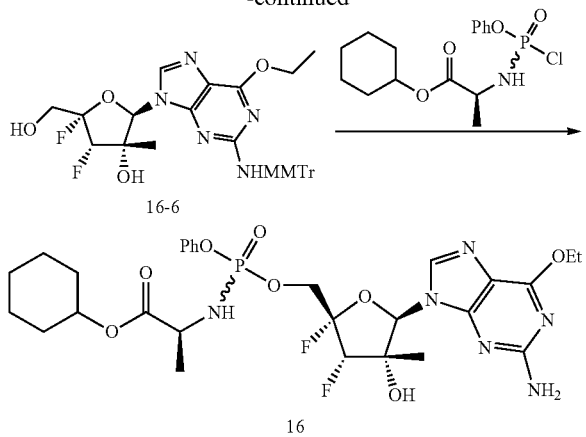

Sodium (6.0 g, 261.2 mmol) was dissolved in dry EtOH (400 mL) at 0° C., and slowly warmed to RT. Compound 14-7 (32.0 g, 43.5 mmol) was treated with a freshly prepared NaOEt solution at 0° C., and the mixture was stirred at RT overnight. The reaction was monitored by TLC and LCMS. After completion of the reaction, the mixture was concentrated at low pressure. The mixture was quenched with H$_2$O (40 mL), and extracted with EA (3×50 mL). The organic layer was dried over anhydrous Na$_2$SO$_4$, and evaporated at low pressure. The residue was purified by silica gel column chromatography (MeOH in DCM from 0.5% to 2%) to give 16-1 (20.0 g, 76.6%) as a white solid.

Compound 16-1 (20.0 g, 33.3 mmol) was co-evaporated with anhydrous pyridine 3 times. To an ice cooled solution of 16-1 in anhydrous pyridine (100 mL) was added TsCl (9.5 g, 49.9 mmol) at 0° C. After addition, the reaction was stirred for 12 h at 20° C., and monitored by LCMS. The reaction was quenched with H$_2$O, and concentrated at low pressure. The residue was dissolved in EA (50 mL). The solution was washed with sat. NaHCO$_3$ solution and brine. The organic layer was dried over anhydrous Na$_2$SO$_4$, and evaporated at low pressure. The residue was purified by silica gel column chromatography (MeOH in DCM from 0.5% to 2%) to give 16-2 (20.0 g, 80%) as a yellow solid.

To a solution of 16-2 (20.0 g, 26.5 mmol) in acetone (100 mL) was added NaI (31.8 g, 212 mmol), and heated to reflux overnight. The reaction was checked by LCMS. After the reaction was complete, the mixture was concentrated at low pressure. The residue was dissolved in EA (50 mL). The solution was washed with brine. The organic layer was dried over anhydrous Na$_2$SO$_4$, and evaporated at low pressure. The residue was purified by silica gel column chromatography (MeOH in DCM from 0.5% to 2%) to give a crude product. To a solution of the crude product in dry THF (60 mL) was added DBU (16.2 g, 106 mmol), and heated to 60° C. The mixture was stirred overnight and checked by LCMS. The reaction was quenched with sat. NaHCO$_3$ solution, and extracted with EA (3×50 mL). The organic phase was washed with brine, dried over anhydrous Na$_2$SO$_4$, and evaporated at low pressure. The residue was purified by silica gel column chromatography (MeOH in DCM from 0.5% to 2%) to give 16-3 (12.0 g, 77.9%) as a yellow solid.

To an ice-clod solution of 16-3 (11.0 g, 18.9 mmol) in dry MeCN (100 mL) was added NIS (5.4 g, 23.7 mmol) and NEt$_3$.3HF (3.0 g, 18.9 mmol) at 0° C. The mixture was stirred at RT for 4 h., and checked by LCMS. After the reaction was complete, the reaction was quenched with sat. Na$_2$SO$_3$ solution and sat. NaHCO$_3$ solution. The solution was extracted with EA (3×100 mL). The organic layer was washed with brine, dried over anhydrous Na$_2$SO$_4$, and evaporated at low pressure. The residue was purified by silica gel column chromatography (EA in PE from 12% to 50%) to give 16-4 (11.0 g, 79.9%).

To a solution of 16-4 (10.0 g, 13.7 mmol) in dry DMF (100 mL) was added NaOBz (19.8 g, 137 mmol) and 15-crown-5 (30.2 g, 137 mmol). The reaction was stirred for 48 h at 90° C., and diluted with EA. The solution was washed with water and brine, and dried over MgSO$_4$. The organic layer was evaporated at low pressure, and the residue was purified by silica gel column chromatography (EA in PE from 12% to 50%) to give 16-5 (8.0 g, 80.0%).

Compound 16-5 (6.0 g, 8.3 mmol) was co-evaporated with anhydrous toluene 3 times, and treated with NH$_3$ in MeOH (4N, 50 mL) at RT. The reaction was stirred for 18 h at RT. The reaction was monitored by LCMS. After the reaction was complete, the mixture was concentrated at low pressure. The residue was purified by silica gel column chromatography (EA in PE from 20% to 50%) to give 16-6 (4.5 g, 87.8%). ESI-MS: m/z 617.9 [M+H]$^+$.

To an ice cooled mixture of 16-6 (25 mg, 0.07 mmol) and NMI (46 µL, 8 eq.) in acetonitrile (0.7 mL) was added the phosphorochloridate reagent (73 mg, 3 eq.) and stirred overnight at RT. Additional amounts of NMI (46 uL) and the phosphorochloridate reagent (73 mg) were added and stirring continued for 1 d. The reaction was quenched with sat. aq. NH$_4$Cl, diluted with EtOAc and water. The organic layer was separated and washed with aq. NaHCO$_3$, water, and brine, and then dried (Na$_2$SO$_4$). The residue was purified on silica gel (10 g column) with CH$_2$Cl$_2$/i-PrOH (4-10% gradient) to yield compound 16 (18 mg, 40%). MS: m/z=655 [M+1].

Example 15

Compound 18

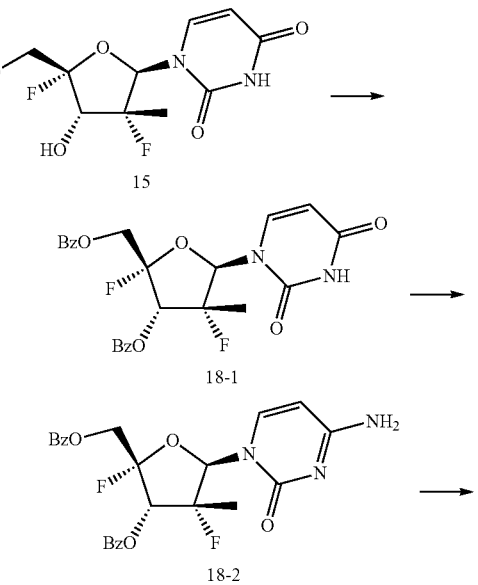

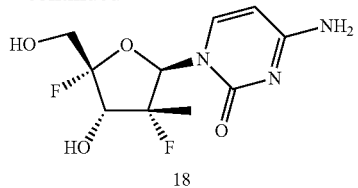

18

To a solution of compound 15 (139 mg, 0.5 mmol) in pyridine (5 mL) was added BzCl (92 mg, 0.55 mmol) at 0° C. The mixture was stirred at RT for 5 h, diluted with EtOAc and washed with 1N HCl solution. The organic layer was dried over anhydrous Na$_2$SO$_4$, and concentrated at low pressure. The residue was purified by silica gel column (20% EA in PE) to give 18-1 (274 mg, 79%) as a white solid.

To a solution of 18-1 (490 mg, 1 mmol), DMAP (244 mg, 2 mmol) and TEA (205 mg, 2.1 mmol) in MeCN (10 mL) were added TPSCl (604 mg, 2 mmol) at 0° C. The mixture was stirred at RT for 2 h., and then NH$_4$OH aq. was added at RT. The mixture was stirred for 0.5 h, diluted with EtOAc and washed with sat. aq. NaHCO$_3$ and brine. The organic layer was dried over anhydrous Na$_2$SO$_4$, and concentrated at low pressure. The residue was purified by silica gel column (30% EA in PE) to give 18-2 (250 mg, 41%) as a white solid.

Compound 18-2 (250 mg, 0.51 mmol) was dissolved in NH$_3$/MeOH (15 mL). The mixture was stirred at RT for 5 h. and then concentrated at low pressure. The residue was purified by silica gel column (5% DCM in DCM) to give compound 18 (95 mg, 66%) as a white powder. ESI-MS: m/z 278.1 [M+H]$^+$.

Example 16

Compound 20

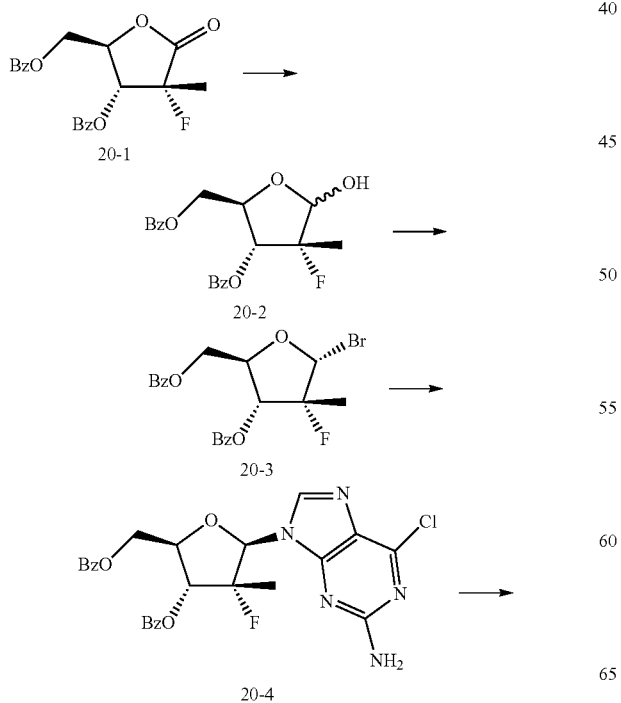

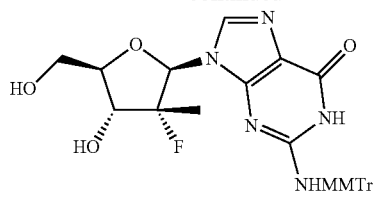

20-5

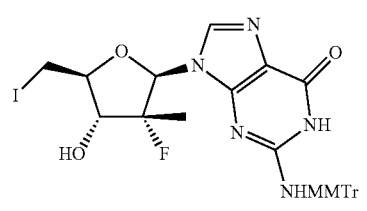

20-6

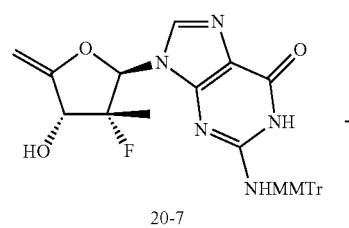

20-7

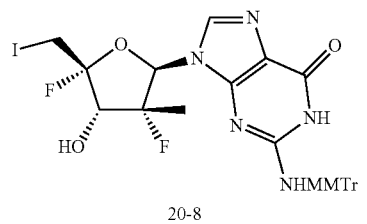

20-8

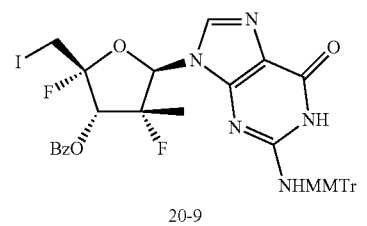

20-9

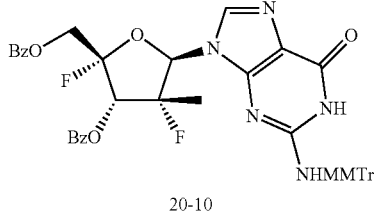

20-10

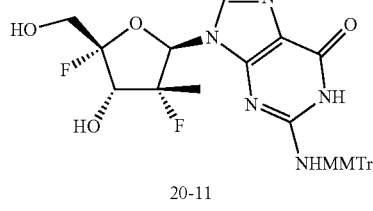

20-11

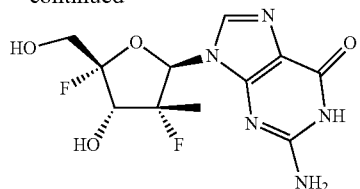

20

To a solution of compound 20-1 (30 g, 0.08 mol) in anhydrous THF (300 mL) was added a solution of lithium tri-tert-butoxyaluminohydride (120 mL, 0.12 mol) dropwise at −78° C. under N₂. The mixture was stirred at −20° C. for 1 h. The reaction was quenched with sat. aq. NH₄Cl and then filtered. The filtrate was extracted with EA (3×300 mL). The organic layer was dried over anhydrous Na₂SO₄, and concentrated at low pressure. The residue was purified by silica gel column (10% EA in PE) to give 20-2 (26 g, 86%) as a colorless oil.

To a stirred solution of PPh₃ (37.7 g, 0.144 mol) in DCM (100 mL) was added compound 20-2 (27 g, 0.072 mol) at −20° C. under N₂. After the mixture was stirred at RT for 15 mins, CBr₄ (42 g, 0.129 mol) was added while maintaining the reaction temperature between −25 and −20° C. under N₂. The mixture was then stirred below −17° C. for 20 mins. Silica gel was added into the solution, and then purified by flash silica gel column separation to give the crude oil product. The crude was purified by silica gel column (EA in PE from 2% to 20%) to give 20-3 (α-isomer, 17 g, 55%) as a colorless oil.

A mixture of 6-Cl-guanine (11.6 g, 68.8 mmol) and t-BuOK (8.2 g, 73 mmol) in t-BuOH (200 mL) and MeCN (150 mL) was stirred at 35° C. for 30 mins, and then 20-3 (10 g, 22.9 mmol) in MeCN 100 mL) was added at RT. The mixture was heated at 50° C. overnight. The reaction was quenched with a solution of NH₄Cl (5 g) in water (40 mL), and the mixture was filtered. The filtrate was evaporated at low pressure. The residue was purified by silica gel column (20% EA in PE) to give 20-4 (6 g, 42%) as a yellow solid.

To a solution of 20-4 (12.5 g, 23.8 mol) in DCM (50 mL) was added AgNO₃ (8.1 g, 47.6 mmol), collidine (5.77 g, 47.6 mmol) and MMTrCl (11 g, 35.7 mmol). The mixture was stirred at RT overnight. The reaction was quenched with MeOH (5 mL), filtered and concentrated at low pressure. The residue was purified by silica gel column (5% MeOH in DCM) to give the intermediate (16 g, 86%) as a yellow solid. To a solution of HOCH₂CH₂CN (4.7 g, 66 mmol) in THF (200 mL) was added NaH (3.7 g, 92 mmol) at 0° C. The mixture was stirred at RT for 30 mins. A solution of the intermediate (10.5 g, 13 mmol) in THF (50 mL) was added, and the reaction mixture was stirred at RT for 12 h. The reaction was quenched with MeOH (2 mL), diluted with EA (100 mL), and washed with brine. The organic layer was dried over anhydrous Na₂SO₄, and concentrated at low pressure. The residue was purified by silica gel column (5% MeOH in DCM) to give 20-5 (5.8 g, 77%) as a yellow solid.

To a solution of PPh₃ (7.0 g, 26.6 mmol) in anhydrous pyridine (100 mL) was added I₂ (6.3 g, 24.9 mmol), and stirred at RT for 30 mins. The mixture was treated with a solution of 20-5 (9.5 g, 16.6 mmol) in pyridine (40 mL). The mixture was stirred at RT overnight. The reaction was quenched with sat. Na₂S₂O₃ solution, and the mixture was extracted with EA. The organic layer was washed with brine, dried over anhydrous Na₂SO₄, and concentrated at low pressure. The residue was purified by silica gel column (30% EA in PE) to give 20-6 (7 g, 66%) as a yellow solid.

To a solution of 20-6 (7.5 g, 11 mmol) in dry THF (50 mL) was added DBU (5.4 g, 33 mmol), and the mixture was heated to reflux for 4 h. The mixture was diluted with EA (3×100 mL), and washed with brine. The organic layer was dried over anhydrous Na₂SO₄, and concentrated at low pressure. The residue was purified by silica gel column (30% EA in PE) to give 20-7 (4.0 g, 67%) as a white solid.

To an ice-cooled solution of 20-7 (3.0 g, 5.4 mmol) in anhydrous MeCN (20 mL) was added TEA.3HF (0.65 g, 4.1 mmol) and NIS (1.53 g, 6.78 mmol) at RT, and the reaction mixture was stirred at RT for 2 h. The mixture was diluted with EA (50 mL), and washed with sat. Na₂S₂O₃ solution and NaHCO₃ aq. The organic layer was dried over anhydrous Na₂SO₄, and concentrated to dryness at low pressure. The residue was purified by prep-HPLC (0.1% HCOOH in water and MeCN) to separate the two isomers (about 1:1). NOE showed the polar one was 20-8 (0.6 g, 16%) as a white solid.

To a solution of 20-8 (0.7 g, 1 mmol) in dry pyridine (10 mL) was added BzCl (147 mg, 1.05 mmol) at 0° C. The mixture was stirred at RT for 3 h. The mixture was then diluted with EA, and washed with sat. NaHCO₃ aq. and brine. The organic layer was dried over Na₂SO₄, and evaporated at low pressure. The residue was purified by silica gel column (20% EA in PE) to give 20-9 (0.65 g, 81%) as a white solid.

To a solution of 20-9 (0.65 g, 0.8 mmol) in dry DMF (40 mL) was added NaOBz (1.15 g, 8 mmol) and 15-crown-5 (1.77 g, 8 mmol). The mixture was stirred at 100° C. for 48 h. The solvent was evaporated at low pressure, and the residue was dissolved in EA (30 mL), and washed with water and brine. The organic layer was dried over Na₂SO₄ and concentrated at low pressure. The residue was purified by silica gel column (20% EA in PE) to give 20-10 (500 mg, 78%) as a white solid.

Compound 20-10 (400 mg, 0.5 mmol) in NH₃/MeOH (7N, 100 mL) was stirred at RT for 18 h. The mixture was concentrated at low pressure, and the residue was purified by silica gel column (5% MeOH in DCM) to give 20-11 (220 mg, 63%) as a white solid. ESI-MS: m/z 590.3 [M+H]⁺.

Compound 20-11 (59 mg, 0.1 mmol) was dissolved in 50% TFA in methanol (10 mL), and the mixture was kept at RT for 2 h. The solvent was evaporated and co-evaporated with a methanol/toluene mixture to remove traces of the acid. The residue was suspended in CH₃CN (1 mL) and centrifuged. The precipitate was washed with CH₃CN (1 mL) and dried. Compound 20 was obtained as a colorless solid (21 mg, 65%. MS: m/z 316.2 [M−1].

Example 17

Compound 21

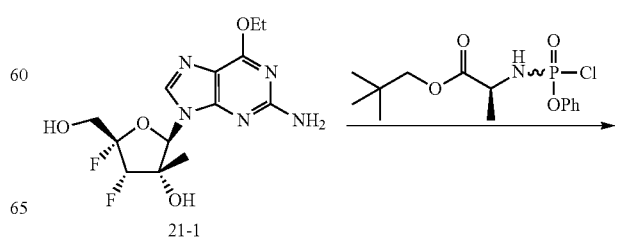

21-1

-continued

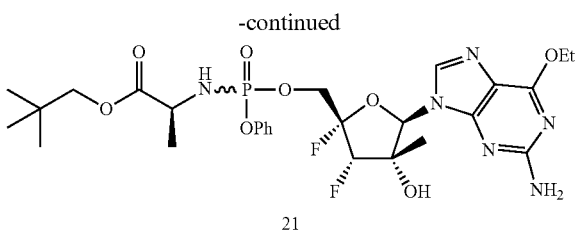

21

Compound 21 (15 mg, 16%) was prepared from 21-1 (50 mg) in acetonitrile (2 mL) with the phosphorochloridate reagent (0.14 g) and NMI (0.1 mL) in the same manner as compound 7. MS: m/z=643 [M+1].

Example 18

Compound 22

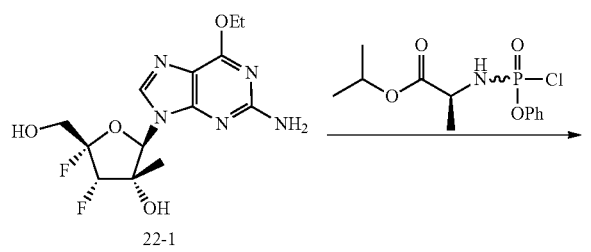

22

Compound 22 (30 mg, 32%) was prepared from 22-1 (50 mg) in acetonitrile (2 mL) with the phosphorochloridate reagent (0.14 g) and NMI (0.1 mL) in the same manner as compound 7. MS: m/z=615 [M+1].

Example 19

Compound 23

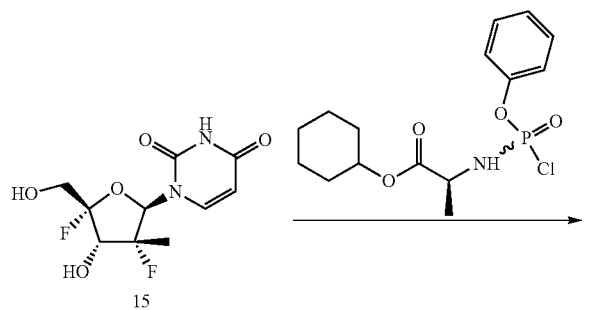

-continued

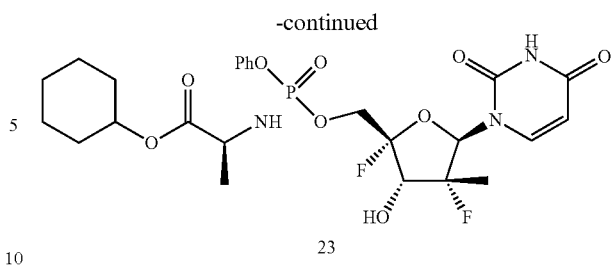

23

To a stirred solution of compound 15 (60 mg, 0.22 mmol) in anhydrous THF (2.0 mL) was added N-methylimidazole (0.142 mL, 1.73 mmol) at 0° C. (dry ice/acetone bath) followed by solution of phenyl (cyclohexanoxy-L-alaninyl) phosphorochloridate (235 mg, 0.68 mmol, dissolved in THF (2 mL). The resulting solution was stirred at 0° C. for 1 h, and the temperature was raised up-to 10° C. over the next 1 h. The reaction left at 10° C. for 3 h. The mixture was cooled to 0 to 5° C., diluted with EA, and water (5 mL) was added. The solution was washed with $H_2O$ and brine. The organic layer was separated, dried over anhydrous $Na_2SO_4$ and filtered. The filtrate was concentrated in vacuum to give a residue, which dissolved in 25% $CH_3CN/H_2O$. The compound was purified on a reverse-phase HPLC (C18) using acetonitrile and water, followed by lyophilization gave a white foam. The produce was re-dissolved in EtOAc, washed with 50% aqueous citric acid solution, dried over anhydrous $MgSO_4$ and filtered. The filtrate was concentrated in vacuum, and lyophilized to give two isomers (Rp/Sp) of compound 23 (6.3 mg). MS m/z 586.05 [M−H].

Example 20

Compound 24

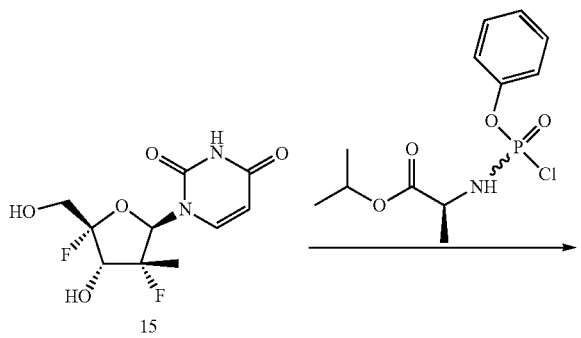

24

To a stirred solution of compound 15 (100 mg, 0.36 mmol) in anhydrous THF (3.0 mL) was added N-methylimidazole (236 μL, 2.87 mmol) at 0° C. (dry ice/acetone bath) followed by a solution of the phosphorochloridate (329 mg, 1.08 mmol, dissolved in 2 mL of THF). The solution was stirred at 0° C. for 1 h, the reaction temperature was raised up-to 10° C. during the next 1 h, and the solution was left at 10° C. for the next 4 h. The mixture was cooled to 0 to 5° C., diluted with EA, and water was added (15 mL). The solution was washed H₂O, 50% aqueous citric acid solution and brine. The organic layer was separated, dried over anhydrous MgSO₄ and filtered. The filtrate was concentrated in vacuum to give a residue, which dissolved in 25% CH₃CN/H₂O. The residue was purified on a reverse-phase HPLC (C18) using acetonitrile and water, followed by lyophilization to give a mixture of two isomers of compound 24 (17.5 mg). MS m/z 546.05 [M−H].

Example 21

Compounds 25 and 26 brine. The organic phase was dried over MgSO₄ and concentrated at low pressure. The residue was purified by silica gel column (10% EA in PE) to give 25-3 (0.3 g, 60%) as a white solid.

Compound 25-3 (0.3 g, 0.3 mmol) in NH₃/MeOH (30 mL) was stirred at RT for 18 h. The mixture was concentrated at low pressure, and the residue was purified by silica gel column (20% EA in PE) to give 25-4 (145 mg, 56%) as a white solid. ESI-LCMS: m/z 890.5 [M+H]⁺.

To a stirred solution of 25-4 (161 mg, 0.16 mmol) in anhydrous CH₃CN (2.0 mL) was added N-methylimidazole (118 µL, 2.87 mmol) at 0 to 5° C. (ice/water bath) followed by solution of 25-5 (186 mg, 0.54 mmol, dissolved in 2 mL of CH₃CN). The solution was stirred at 0 to 5° C. for 4 h. The mixture was diluted with EA, and water was added (15 mL). The solution was washed H₂O, 50% aqueous citric acid

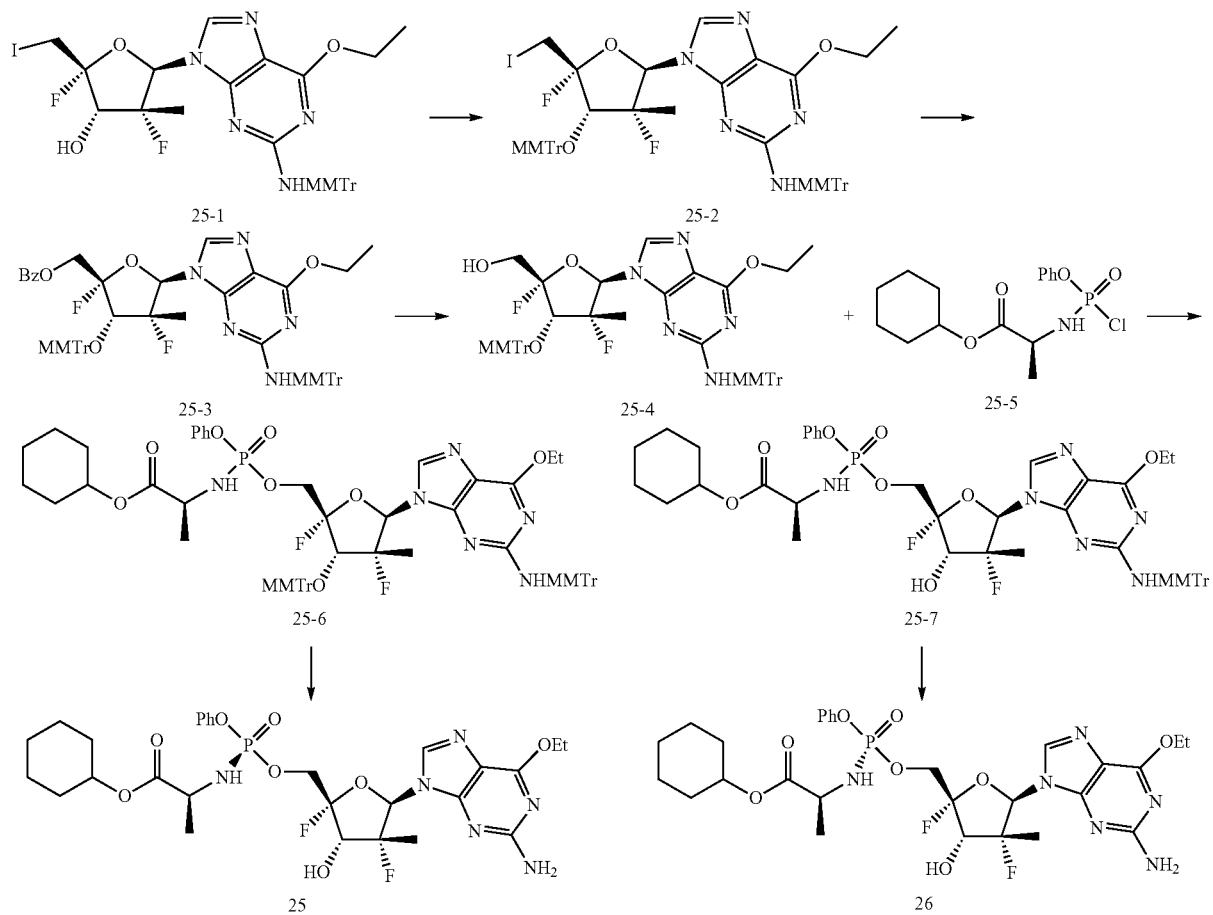

To a solution of 25-1 (0.47 g, 0.65 mol) in DCM (3 mL) was added AgNO₃ (0.22 g, 1.29 mmol), collidine (0.15 g, 1.29 mmol) and MMTrCl (0.3 g, 0.974 mmol) at 0° C. The mixture was stirred at RT overnight. The mixture was filtered, and the filter was washed with sat. aq. NaHCO₃ solution and brine. The organic layer was separated, dried over anhydrous Na₂SO₄ and concentrated at low pressure. The residue was purified by silica gel column to give 25-2 (0.55, 85%) as a white solid.

To a solution of 25-2 (0.5 g, 0.5 mmol) in dry DMF (10 mL) was added NaOBz (0.72 g, 5 mmol) and 15-crown-5 (0.9 mL). The mixture was stirred at 95° C. for 72 h. The mixture was diluted with EA, and washed with water and solution and brine. The organic layer was separated, dried over anhydrous MgSO₄ and filtered. The filtrate was concentrated in vacuum to give a residue, which was purified on silica gel with 0 to 40% EA/hexanes to give as 25-6 (82.6 mg) as the faster eluting isomer and 25-7 (106 mg) as the slower eluting isomer.

Compound 25-6 (82.6 mg, 0.07 mmol) was dissolved in anhydrous CH₃CN (0.5 mL), and 4N HCl in dioxane (35 µL) was added at 0 to 5° C. The mixture was stirred at RT for 1 h, and anhydrous EtOH (100 µL) was added. The solvents were evaporated at RT and co-evaporated with toluene 3 times. The residue was dissolved in 50% CH₃CN/H₂O, and purified on a reverse-phase HPLC (C18) using acetonitrile and water, followed by lyophilization to give compound 25 (19.4 mg). $^1$H NMR (CD$_3$OD-d$_4$, 400 MHz) δ 7.9 (s, 1H), 7.32-7.28 (t, J=8.0 Hz, 2H), 7.2-7.12 (m, 3H), 6.43 (d, J=17.6 Hz, 1H), 4.70-4.63 (m, 2H), 4.55-4.4 (m, 3H), 3.94-3.9 (m, 1H), 1.79-1.67 (m, 4H), 1.53-1.49 (m, 1H), 1.45-1.22 (m, 15H); $^{31}$P NMR (CD$_3$OD-d$_4$) δ 4.06 (s); ESI-LCMS: m/z=655.2 [M+H]$^+$, 653.15 [M−H]$^-$.

Compound 25-7 (100 mg, 0.083 mmol) was dissolved in anhydrous CH$_3$CN (0.5 mL), and 4N HCl in dioxane (50 μL) was added at 0 to 5° C. Following the procedure for obtaining compound 25, compound 26 (31.8 mg) was obtained. $^1$H NMR (CD$_3$OD-d$_4$, 400 MHz) δ 7.93 (s, 1H), 7.33-7.29 (m, 2H), 7.24-7.14 (m, 3H), 6.41 (d, J=17.6 Hz, 1H), 4.70-4.60 (m, 2H), 4.54-4.49 (m, 2H), 4.44-4.39 (m, 1H), 3.92-3.89 (m, 1H), 1.77-1.66 (m, 4H), 1.54-1.24 (m, 16H); $^{31}$P NMR (CD$_3$OD-d$_4$) δ 3.91 (s); ESI-LCMS: m/z=655.2 [M+H]$^+$, 653.1 [M−H]$^-$.

Example 22

Compounds 27 and 28

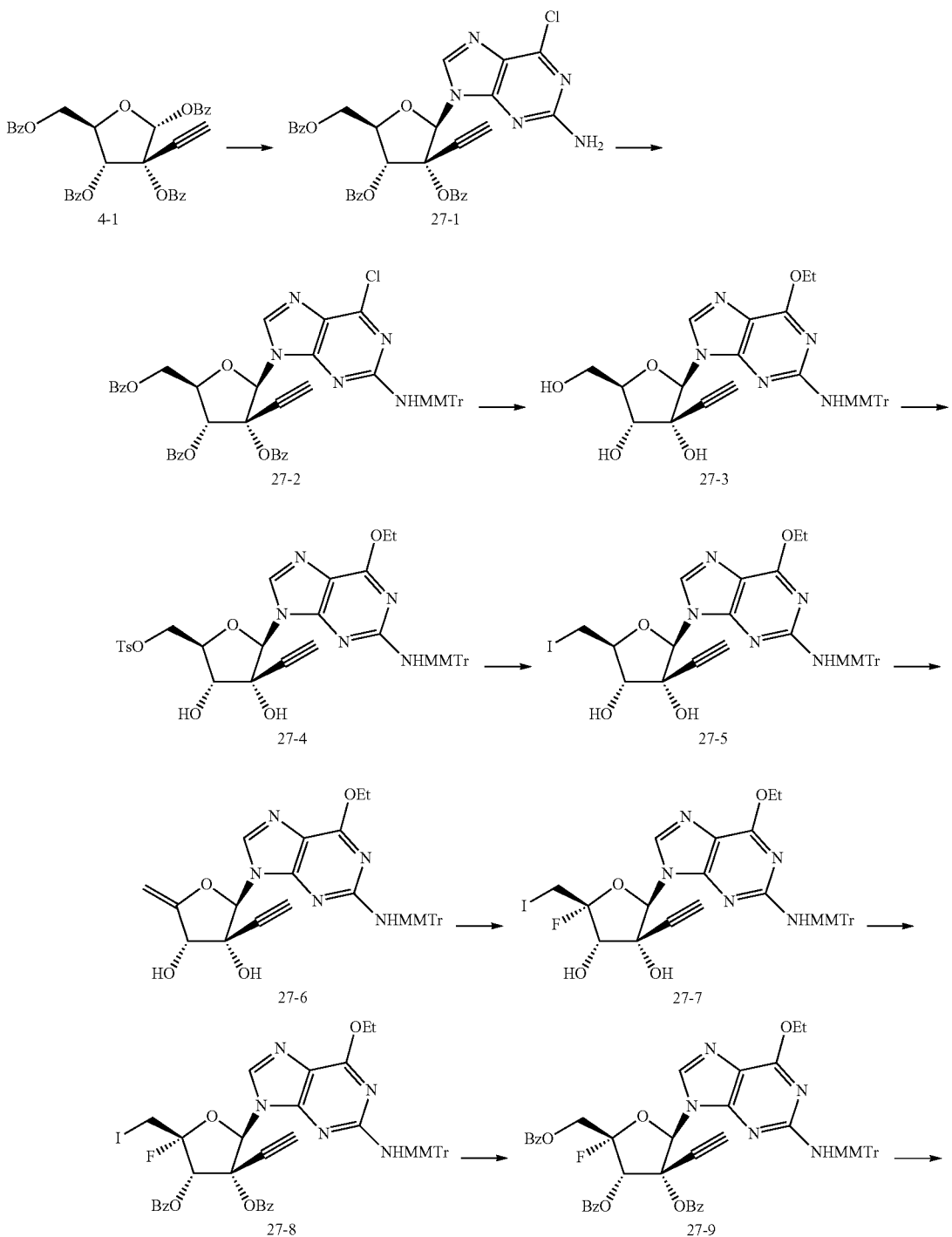

-continued

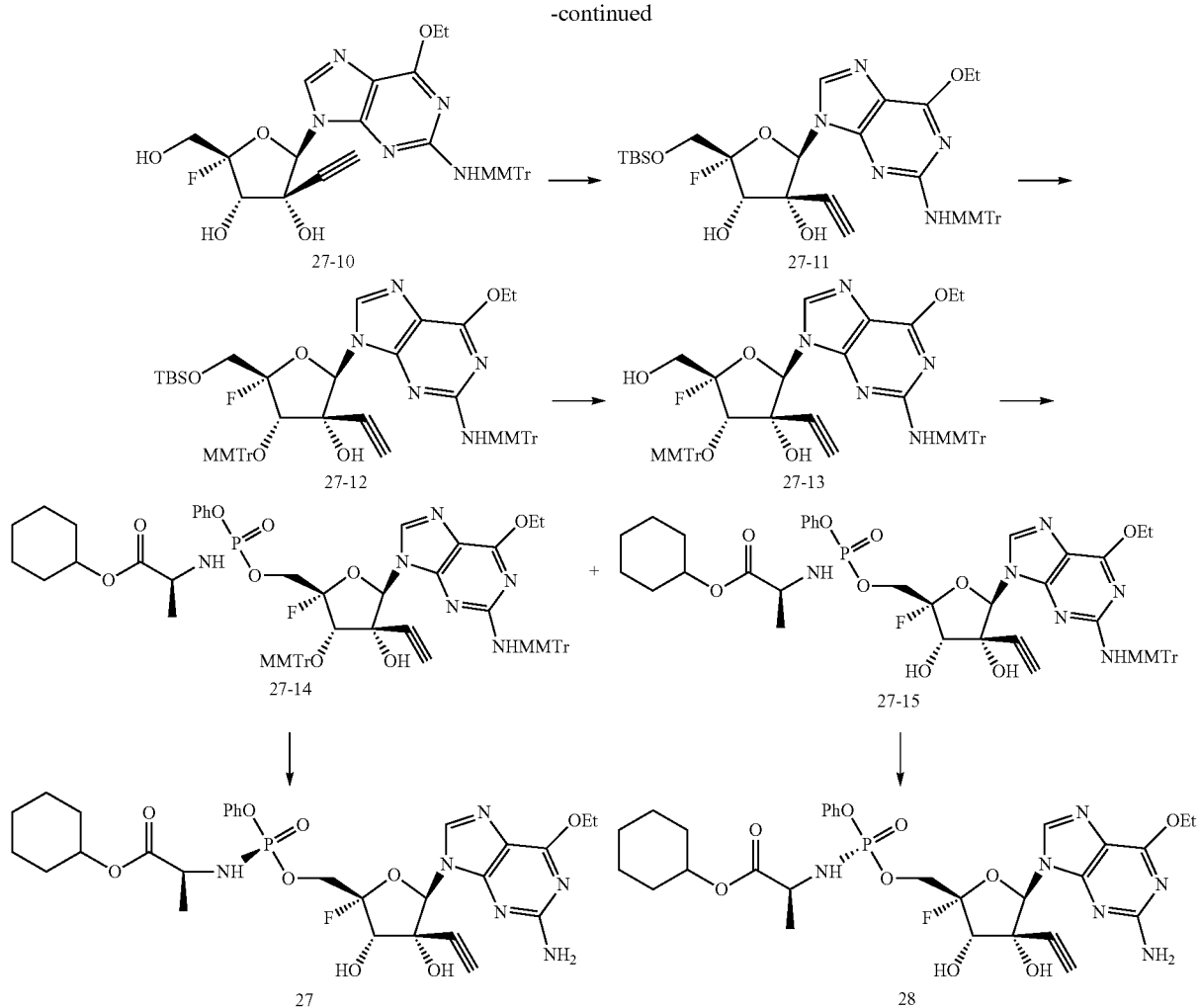

To a stirred suspension of 4-1 (50 g, 84.8 mmol) and 2-amino-6-chloropurine (28.6 g, 169.2 mmol) in anhydrous MeCN (500 mL) was added DBU (77.8 g, 508 mmol) at 0° C. The mixture was stirred at 0° C. for 30 mins, and TMSOTf (150.5 g, 678 mmol) was added dropwise at 0° C. The mixture was stirred at RT for 20 mins until a clear solution was formed. The mixture was stirred at 90-110° C. overnight. The mixture was cooled to RT, and diluted with EA. The solution was washed with sat. NaHCO$_3$ solution and brine. The organic layer was dried over Na$_2$SO$_4$ and then concentrated at low pressure. The residue was purified by silica gel column (PE/EA=2/1) to give 27-1 (30 g, 55.5%) as a white solid.

To a solution of 27-1 (30 g, 47.1 mmol) in anhydrous DCM (300 mL) was added collidine (30 mL), AgNO$_3$ (24 g, 141.4 mmol) and MMTrCl (43.6 g, 141.4 mmol). The mixture was stirred at RT overnight. The mixture was filtered, and the filtrate was washed with water and brine. The organic layer was dried over anhydrous Na$_2$SO$_4$, and concentrated at low pressure. The residue was purified by silica gel column (PE/EA=4/1) to give 27-2 (35 g, 82%) as a white solid.

To a stirred solution of 27-2 (35 g, 38.5 mmol) in anhydrous EtOH (150 mL) was added a solution of EtONa in EtOH (2N, 150 mL). The mixture was stirred at RT overnight, and then concentrated at low pressure. The residue was dissolved in EA (200 mL) and the solution was washed with water and brine. The organic layer was dried over Na$_2$SO$_4$, and concentrated at low pressure. The residue was purified by silica gel column (DCM/MeOH=100/2) to give 27-3 (19 g, 81%) as a white solid.

Compound 27-3 (19 g, 31.3 mmol) was co-concentrated with anhydrous pyridine for 3 times. To an ice cooled solution of 27-3 in anhydrous pyridine (120 mL) was added a solution of TsCl (6.6 g, 34.6 mmol) in pyridine (40 mL) dropwise at 0° C. The mixture was stirred at 0° C. for 16 h. The mixture was quenched with water, and the reaction mixture was concentrated. The residue was re-dissolved in EA (200 mL). The solution was washed with sat. aq. NaHCO$_3$ and brine. The organic layer was dried over anhydrous Na$_2$SO$_4$ and filtered, and the filtrate was concentrated. The residue was purified by silica gel column (DCM/MeOH=100/1) to give 27-4 (16 g, 67%) as a yellow solid.

To a solution of 27-4 (15 g, 19.7 mmol) in acetone (100 mL) was added NaI (30 g, 197 mmol). The mixture was refluxed overnight, and then concentrated at low pressure. The residue was purified by silica gel column (DCM/MeOH=100/1) to give 27-5 (9 g, 63.7%) as a white solid.

To a solution of 27-5 (8 g, 11.2 mmol) in anhydrous THF (60 mL) was added DBU (5.12 g, 33.5 mmol), and the mixture was heated at 60° C. overnight. The mixture was diluted with EA, and washed with water and brine. The organic layer was dried over anhydrous Na₂SO₄ and filtered, and the filtrate was concentrated. The residue was purified by silica gel column (PE/acetone=4/1) to give 27-6 (5.7 g, 86%) as a white solid. ¹H-NMR (CD₃OH, 400 MHz) δ=8.18 (s, 1H), 7.17-7.33 (m, 12H), 6.80 (d, J=8.8 Hz, 2H), 5.98 (s, 1H), 5.40 (d, J=8.6 Hz, 1H), 3.87 (m, 5H), 3.75 (s, 3H), 2.69 (s, 1H), 1.05 (s, 3H).

To an ice cooled solution of 27-6 (4.44 g, 7.5 mmol) in anhydrous MeCN (45 mL) was added TEA.3HF (1.23 g, 7.6 mmol) and NIS (2.16 g, 9.5 mmol). The mixture was stirred at RT for 2-3 h. The reaction was quenched with sat. Na₂SO₃ and NaHCO₃ solution. The mixture was extracted with EA (3×100 mL). The organic layer was separated, dried over anhydrous Na₂SO₄ and concentrated at low pressure. The residue was purified by silica gel column (DCM/acetone=100/2) to give 27-7 (4.4 g, 79.8%) as a white solid.

To a solution of 27-7 (5.36 g, 7.3 mmol) in anhydrous DCM (50 mL) was added DMAP (3.6 g, 29.8 mmol) and BzCl (3.1 g, 22.1 mmol) at 0° C. The mixture was stirred at RT overnight. The mixture was washed with sat. aq. NaHCO₃ and brine. The organic layer was concentrated, and the residue was purified by silica gel column (PE/EA=5/1) to give 27-8 (5.6 g, 81.3%) as a white solid.

To a solution of 27-8 (5.0 g, 5.3 mmol) in anhydrous DMF (150 mL) was added NaOBz (7.64 g, 53 mmol) and 15-crown-5 (14 g, 68 mmol). The mixture was stirred at 90-100° C. for 48 h. The mixture was diluted with EA, and washed with water and brine. The organic layer was concentrated, and the residue was purified by silica gel column (PE/EA=5/1) to give 27-9 (3.9 g, 78.5%) as a white solid.

Compound 27-9 in NH₃ in MeOH (7N, 60 mL) was stirred at RT for 18 h. The mixture was concentrated at low pressure. The residue was purified by silica gel column (DCM/acetone=50/1) to give 27-10 (500 mg, 74.7%) as a white solid. ESI-MS: m/z 626.3 [M+H]⁺.

To a solution of 27-10 (350 mg, 0.56 mmol) in anhydrous pyridine (4 mL) was added imidazole (50 mg, 0.72 mmol) and TBSCl (108 mg, 0.72 mmol) at 0 to 5° C., and stirred at RT for 15 h. The reaction was quenched with absolute EtOH (0.5 mL). The solution was concentrated to dryness under reduced pressure. The residue was dissolved in EA (150 mL), and washed with water, sat. NaHCO₃ and brine. The combined organic layers were dried over Na₂SO₄, filtered and evaporated at low pressure. The residue was purified by silica gel column (10-30% EA in hexanes) to give 27-11 (338 mg, 81.8%) as a white solid.

To a solution of compound 27-11 (328 mg, 0.44 mmol), AgNO₃ (226 mg, 1.33 mmol) and collidine (0.59 mL, 4.84 mmol) in anhydrous DCM (4 mL) was added MMTrCl (410 mg, 1.33 mmol) under N₂. The mixture was stirred at RT overnight under N₂, and monitored by TLC to completion. The mixture was filtered through pre-packed Celite filter, and the filtrate was washed with water, 50% aqueous citric acid, and brine. The organic layer was separated, dried over anhydrous Na₂SO₄, filtered and concentrated at low pressure. The residue was purified by silica gel column (EA in hexanes from 0% to 30%) to give 27-12 (337 mg).

To a solution of 27-12 (337 mg, 0.33 mmol) in anhydrous THF (4 mL) was added 1.0 M solution of TBAF (0.66 ML, 0.66 mmol) at 0 to 5° C. The reaction was slowly warmed to RT, and stirred for 1 h. The mixture was quenched with silica gel, and filtered. The solvents were evaporated to give the crude product, which was purified by silica gel column (EA in hexanes from 0% to 50%) to give 27-13 (188 mg).

To a stirred solution of 27-13 (180 mg, 0.16 mmol) in anhydrous CH₃CN (2.5 mL) was added N-methylimidazole (132 μL, 1.6 mmol) at 0-5° C. (ice/water bath) followed by solution of phenyl (cyclohexanoxy-L-alaninyl) phosphorochloridate (207 mg, 0.6 mmol, dissolved in 2 mL of CH₃CN). The solution was stirred at RT for 2.5 h, and the mixture was diluted with EA followed by addition of water (15 mL). The solution was washed H₂O, 50% aqueous citric acid solution and brine. The organic layer was separated, dried over anhydrous MgSO₄ and filtered. The filtrate was concentrated in vacuum to give a residue, which was purified on silica gel with 0 to 40% EA/hexanes to give 27-14 (75.8 mg) and 27-15 (108 mg) as a slower eluting isomer.

Compound 27-14 (76 mg, 0.063 mmol) was dissolved in anhydrous CH₃CN (0.5 mL), and 4N HCl in dioxane (47 μL) was added at 0 to 5° C. (ice/water bath). The mixture was stirred at RT for 40 mins, and anhydrous EtOH (200 μL) was added. The solvents were evaporated at RT and co-evaporated with toluene 3 times. The residue was dissolved in 50% CH₃CN/H₂O, purified on a reverse-phase HPLC (C18) using acetonitrile and water, and lyophilized to give compound 27 (26.6 mg). ESI-LCMS: m/z=663.3 [M+H]⁺.

Compound 27-15 (108 mg, 0.089 mmol) was dissolved in anhydrous CH₃CN (0.7 mL), and 4N HCl in dioxane (67 μL) was added at 0 to 5° C. (ice/water bath). The mixture was stirred at RT for 60 mins, and anhydrous EtOH (200 μL) was added. The solvents were evaporated at RT and co-evaporated with toluene 3 times. The residue was dissolved in 50% CH₃CN/H₂O, purified on a reverse-phase HPLC (C18) using acetonitrile and water, and lyophilized to give compound 28 (40.3 mg). ESI-LCMS: m/z=663.2 [M+H]⁺.

Example 23

Compounds 30 and 31

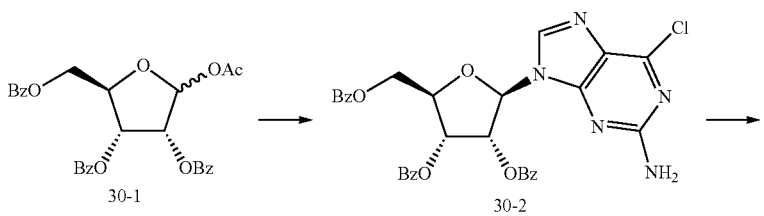

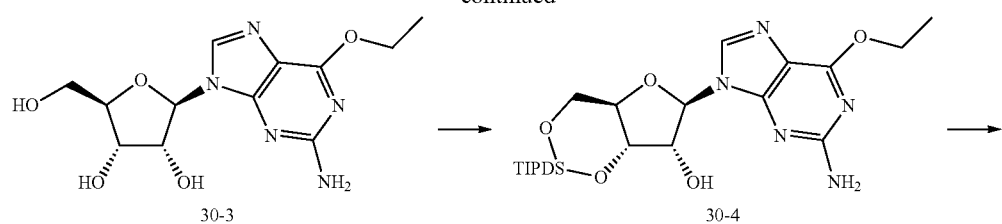
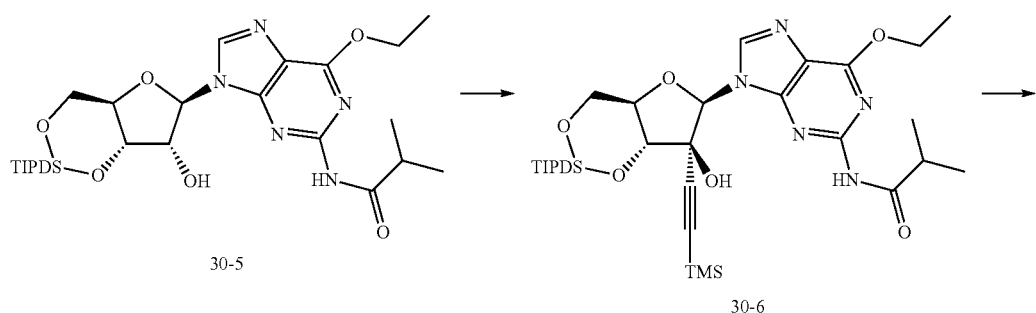
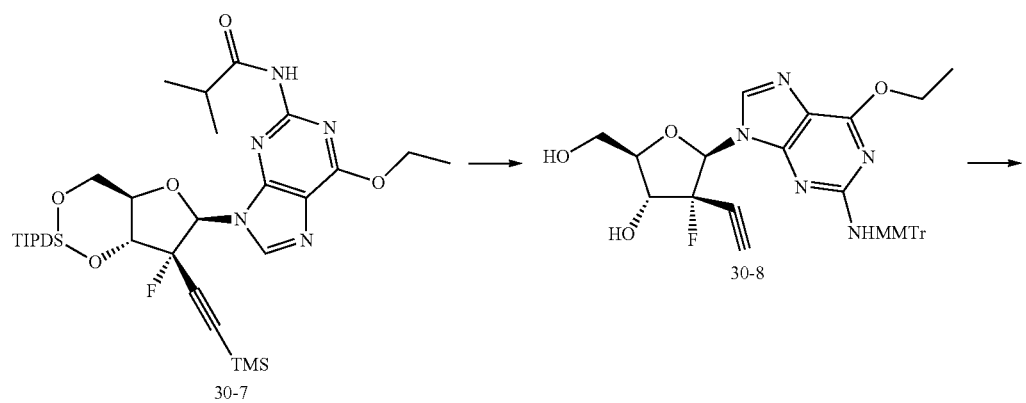
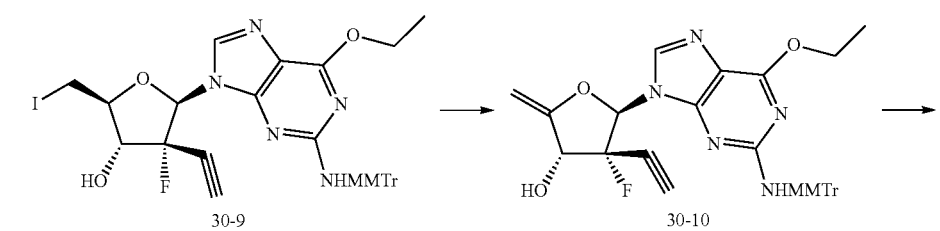
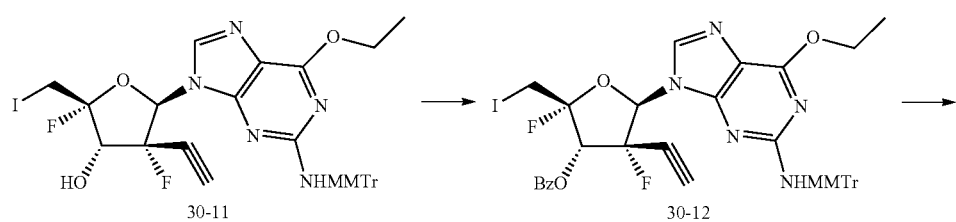
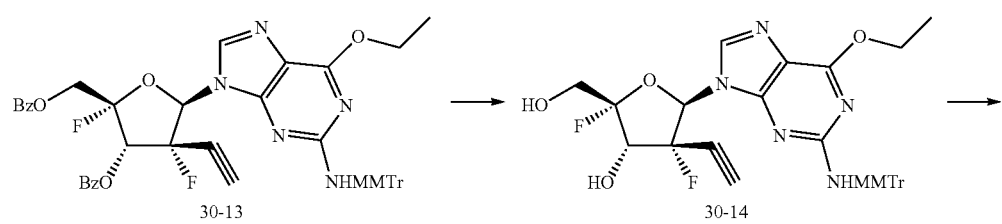

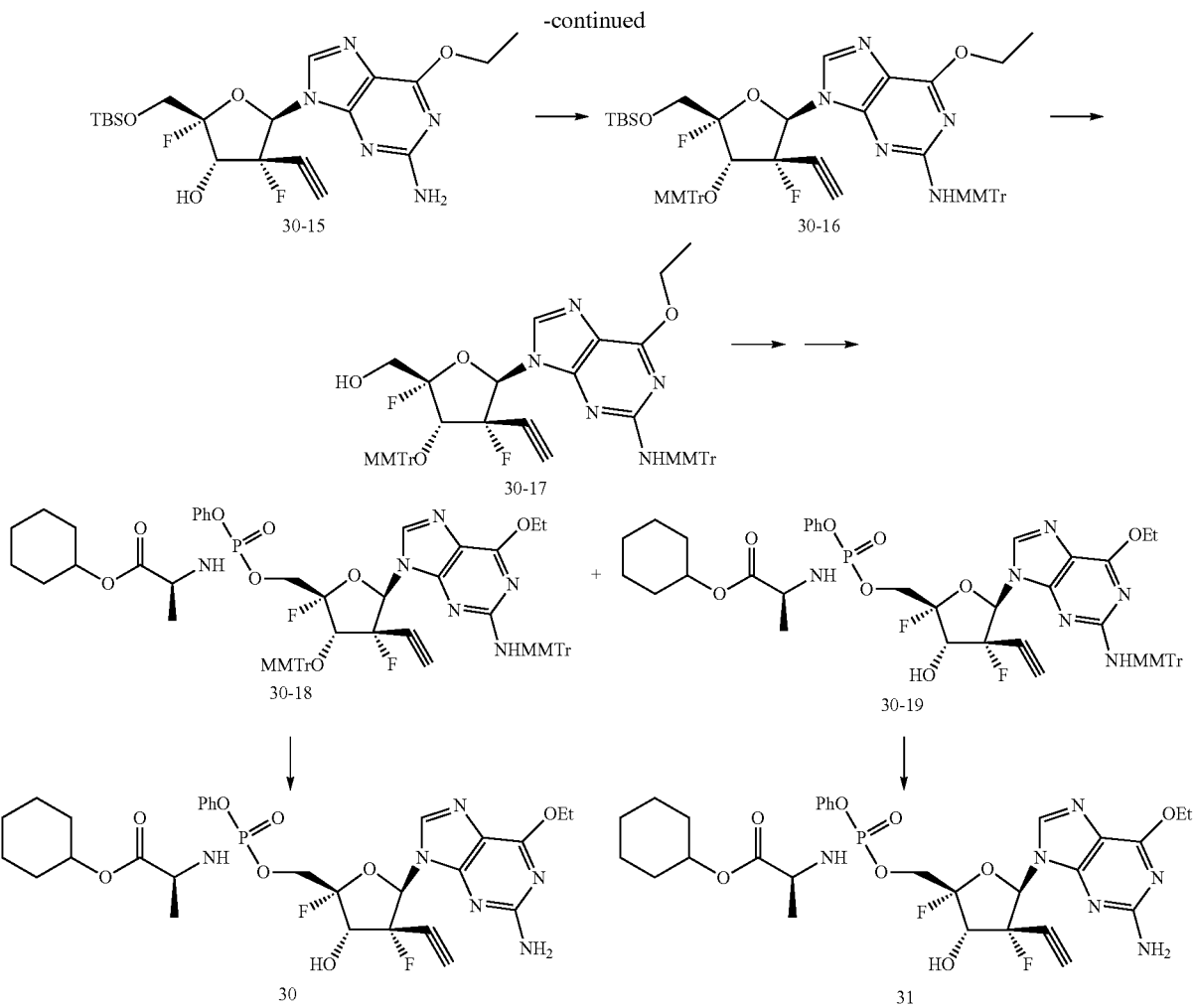

To a mixture of pre-silylated 6-Cl-guanine (using HMDS and $(NH_4)_2SO_4$) (25.2 g, 150 mmol) in DCE (300 mL) was added 30-1 (50 g, 100 mmol) and TMSOTf (33.3 g, 150 mmol) at 0° C. The mixture was stirred at 70° C. for 16 h, and then concentrated at low pressure. The residue was re-dissolved in EA, and washed with sat. aq. $NaHCO_3$ and brine. The organic layer was dried over anhydrous $Na_2SO_4$, and concentrated at low pressure. The residue was purified on silica gel column (PE/EA=2/1) to give pure 30-2 (45 g, 73%) as a white solid.

To a solution of 30-2 (45 g, 73.4 mmol) in EtOH (73 mL) was added with EtONa (1N in EtOH, 360 mL). The mixture was stirred at RT for 16 h. The mixture was then concentrated to give a residue, which was purified by silica gel column (DCM/MeOH=10/1) to give pure 30-3 (19 g, 83%) as a white solid.

To a solution of 30-3 (19 g, 61.1 mmol) in pyridine (120 mL) was added with $TIPDSCl_2$ (19.2 g, 61 mmol) dropwise at 0° C. The mixture was stirred at RT for 16 h, and then concentrated at low pressure. The residue was re-dissolved in EA, and washed with sat. aq. $NaHCO_3$. The organic layer was dried over anhydrous $Na_2SO_4$, and concentrated at low pressure. The residue was purified by silica gel column (DCM/MeOH=20/1) to give pure 30-4 (22 g, 65%) as a white solid.

To a solution of 30-4 (22 g, 39.8 mmol) in DMF/pyridine (5/1, 100 mL) was added TMSCl (12.9 g, 119 mmol) dropwise at 0° C. The mixture was stirred at RT for 1 h and then treated with isobutyryl chloride (5.4 g, 50 mmol). The mixture was stirred at RT for 3 h and then quenched by $NH_4OH$. The mixture was concentrated at low pressure. The residue was dissolved in EA (200 mL). The solution was washed with sat. aq. $NaHCO_3$, and then the organic layer was dried and concentrated at low pressure. The residue was purified by silica gel column (DCM/MeOH=50/1) to give pure 30-5 (15 g, 60%) as a white solid.

To a solution of 30-5 (15 g, 24.1 mmol) in DCM (100 mL) was added PDC (13.5 g, 26 mmol) and $Ac_2O$ (9.8 g, 96 mmol) at 0° C. The mixture was stirred at RT for 16 h. The reaction was quenched by sat. aq. $NaHCO_3$, and then extracted with EA. The organic layer was dried over anhydrous $Na_2SO_4$, and concentrated at low pressure. The residue was dissolved in anhydrous THF (100 mL). To a solution of TMSCCH (12 g, 112 mmol) in THF (200 mL) was added n-BuLi (2.5 N, 44 mL) at −78° C. The mixture was stirred at −78° C. for 15 mins and 0° C. for 15 mins. The mixture was treated with a solution of crude ketone in THF at −78° C. and stirred at −30° C. for 2 h. The reaction was quenched by sat. aq. $NH_4Cl$, and then extracted by EA. The combined organic layer was dried over anhydrous $Na_2SO_4$, and concentrated at low pressure. The residue was purified by silica gel column (PE/EA=10/1) to give pure 30-6 (3.1 g, 18%) as a white solid.

To a solution of 30-6 (7 g, 7.5 mmol) and pyridine (1.4 g, 17 mmol) in DCM (35 mL) was added with DAST (5.6 g, 35 mmol) at −78° C. The mixture was stirred at −78° C. for 3 h. The reaction was quenched by sat. aq. NaHCO$_3$, and then extracted with EA. The combined organic layer was dried over anhydrous, and concentrated at low pressure. The residue was purified by silica gel column (PE/EA=10/1) to give pure 30-7 (3.1 g, 18%) as a white solid.

Compound 30-7 (4.1 g, 5.7 mmol) in sat. NH$_3$/MeOH (100 mL) was stirred at RT for 16 h, and concentrated at low pressure. The residue was re-dissolved in anhydrous DCM (300 mL), and was treated with AgNO$_3$ (27.0 g, 160 mmol), collidine (22 mL) and MMTrCl (23.0 g, 75.9 mmol) in small portions under N$_2$. The mixture was stirred at RT for 16 h. The mixture was filtered, and the filtrate was washed with sat. NaHCO$_3$ solution and brine. The organic layer was separated, dried over anhydrous Na$_2$SO$_4$, and concentrated at low pressure. The residue was purified by silica gel column (PE/EA=10/1) to give the pure intermediate. The intermediate was dissolved in a solution of TBAF/THF (1N, 20 mL). The mixture was stirred at RT for 2 h and then concentrated at low pressure. The residue was purified by silica gel column (DCM/MeOH=50/1) to give pure 30-8 (3.0 g, 86%) as a white solid.

To a solution of 30-8 (3.0 g, 4.9 mmol) in THF (50 mL) was added imidazole (840 mg, 12 mmol), PPh$_3$ (3.2 g, 12 mmol), and I$_2$ (2.4 g, 9.2 mmol) at 0° C. The mixture was stirred at RT for 16 h. The reaction was quenched by sat. aq. Na$_2$S$_2$O$_3$, and then extracted with EA. The combined organic layer was dried over anhydrous Na$_2$SO$_4$, and concentrated at low pressure. The residue was purified by silica gel column (PE/EA=2/1) to give crude 30-9 (4.2 g, >100%, containing TPPO) as a white solid.

To a solution of crude 30-9 in anhydrous THF (30 mL) was added DBU (2.7 g, 18 mmol), and heated to 80° C. The mixture was stirred for 1 h and checked by LCMS. The mixture was quenched by water, and extracted with EA. The organic layer was dried over anhydrous Na$_2$SO$_4$ and filtered, and the filtrate was concentrated at low pressure. The residue was purified by silica gel column (PE/EA=2/1) to give 30-10 (2.0 g, 69%) as a white solid.

To an ice cooled solution of 30-10 (2.0 g, 3.38 mmol) in anhydrous MeCN (15 mL) was added NIS (777 mg, 3.5 mmol) and NEt$_3$.3HF (536 g, 3.3 mmol) at 0° C. The mixture was stirred at RT for 16 h and checked by LCMS. After completion, the mixture was quenched by sat. Na$_2$SO$_3$ and sat. NaHCO$_3$ solution, and extracted with EA. The organic layer was separated, dried over anhydrous Na$_2$SO$_4$ and concentrated at low pressure. The residue was purified by silica gel column chromatography (PE/EA=10/1 to 3/1) to give 30-11 (2.1 g, 84.0%) as a white solid.

To a solution of crude 30-11 (2.1 g, 2.85 mmol) in anhydrous DCM (100 mL) was added DMAP (490 mg, 4 mmol), and BzCl (580 mg, 4 mmol) at 0° C. The mixture was stirred overnight and checked by LCMS. The reaction was washed with sat. NaHCO$_3$ solution. The organic layer was dried over anhydrous Na$_2$SO$_4$, and concentrated at low pressure. The residue was purified by silica gel column chromatography (PE/EA=8/1 to 3/1) to give 30-12 (2.0 g, 83.4%) as a white solid.

To a solution of 30-12 (2.0 g, 2.4 mmol) in anhydrous DMF (60 mL) was added NaOBz (3.3 g, 23.0 mmol) and 15-crown-5 (5.11 g, 23 mmol). The mixture was stirred at 110° C. for 36 h. The reaction was quenched by water, and the mixture was extracted with EA. The organic layer was dried over anhydrous Na$_2$SO$_4$, and concentrated at low pressure. The residue was purified by silica gel column (PE/EA=5/1 to 3/1) to give 30-13 (830 mg, 42.0%) as a white solid. ESI-MS: m/z 836.11 [M+H]$^+$.

A solution of 30-13 (831 mg, 1.0 mmol) in anhydrous n-butylamine (4 mL) was stirred at RT for 3 h under N$_2$ atmosphere. The reaction was monitored by TLC. The solvent was evaporated in vacuo, and the residue was purified by silica gel column (MeOH in DCM from 0% to 10%) to give the crude product, which as re-purified using silica gel column to give 30-14 as a light pink solid (563 mg).

To a solution of 30-14 (560 mg, 0.89 mmol) in anhydrous pyridine (5 mL) was added imidazole (78.6 mg, 1.16 mmol) and TBSCl (202 mg, 1.34 mmol) at 0 to 5° C. The mixture was stirred at RT for 15 h. The reaction was quenched by adding absolute EtOH (0.3 mL). The solution was concentrated to dryness under reduced pressure, and co-evaporated with toluene 3 times. The residue was dissolved in EA (150 mL), and washed with water, sat. NaHCO$_3$, and brine. The combined organic layer was dried over Na$_2$SO$_4$, filtered and evaporated at low pressure. The residue was purified by silica gel column (0-20% EA in hexanes) to give 30-15 (303 mg) as a white solid.

To a solution of 30-15 (303 mg, 0.41 mmol), AgNO$_3$ (208 mg, 1.23 mmol) and collidine (0.55 mL, 4.51 mmol) in anhydrous DCM (4 mL) was added MMTrCl (378 mg, 1.3 mmol) under N$_2$. The mixture was stirred at RT overnight under N$_2$, and monitored by TLC. The mixture was filtered through pre-packed celite filter, and the filtrate was washed with water and, 50% aqueous citric acid, and brine. The organic layer was separated, dried over anhydrous Na$_2$SO$_4$, filtered and concentrated at low pressure. The residue was purified by silica gel column (EA in hexanes from 0% to 30%) to give 30-16 (374 mg, 90%).

To a solution of 30-16 (374 mg, 0.37 mmol) in anhydrous THF (4 mL) was added 1.0 M solution of TBAF (0.74 mL, 0.74 mmol) at 0 to 5° C. The mixture was stirred at RT for 1 h. The mixture was quenched with silica gel, and filtered. The solvents were evaporated to give the crude product, which was purified by silica gel column (EA in hexanes from 0% to 50%) to give 30-17 (265 mg).

To a stirred solution of 30-17 (187.5 mg, 0.16 mmol) in anhydrous CH$_3$CN (2.5 mL) was added N-methylimidazole (136 μL, 1.66 mmol) at 0-5° C. (ice/water bath) followed by solution of phenyl (cyclohexanoxy-L-alaninyl) phosphorochloridate (214 mg, 0.62 mmol, dissolved in 0.5 mL of CH$_3$CN). The solution was stirred at RT for 3 h, and then diluted with EA followed by the addition of water (15 mL). The solution was washed with H$_2$O, 50% aqueous citric acid solution and brine. The organic layer was separated, dried over anhydrous MgSO$_4$ and filtered. The filtrate was concentrated in vacuum to give a residue, which was purified on silica gel with 0 to 40% EA/hexanes to give (single isomers) of 30-18 (108 mg) Elution of the latter fraction gave (single isomers) of 30-19 (120 mg) as glassy solid.

Compound 30-18 (108 mg, 0.089 mmol) was dissolved in anhydrous CH$_3$CN (0.5 mL), and 4N HCl in dioxane (67 μL) was added at 0 to 5° C. (ice/water bath). The mixture was stirred at RT for 40 mins, and anhydrous EtOH (200 μL) was added. The solvents were evaporated at RT and co-evaporated with toluene 3 times. The residue was dissolved in 50% CH$_3$CN/H$_2$O, was purified on a reverse-phase HPLC (C18) using acetonitrile and water, followed by lyophilization to give compound 30 (26.6 mg) as a white foam. $^1$H NMR (CD$_3$OD-d$_4$, 400 MHz) δ 7.89 (s, 1H), 7.33-7.29 (m, 2H), 7.20-7.13 (m, 3H), 7.17 (m, 1H), 6.62 (d, J=15.6 Hz, 1H), 5.39 (t, J=25.2 Hz, 1H), 4.75-4.42 (m, 6H), 3.92 (t, J=8.8 Hz, 1H), 3.24 (d, J=5.6 Hz, 1H), 1.76-1.51 (m, 5H), 1.45-1.25 (m, 12H); $^{31}$P NMR (CD$_3$OD-d$_4$) δ 4.04 (s); ESI-LCMS: m/z=665.2 [M+H]$^+$.

Compound 31 (44.4 mg, single isomer) was obtained according to the procedure described for compound 30 using 30-19. ESI-LCMS: m/z=665.15 [M+H]$^+$.

Example 24

Compound 32

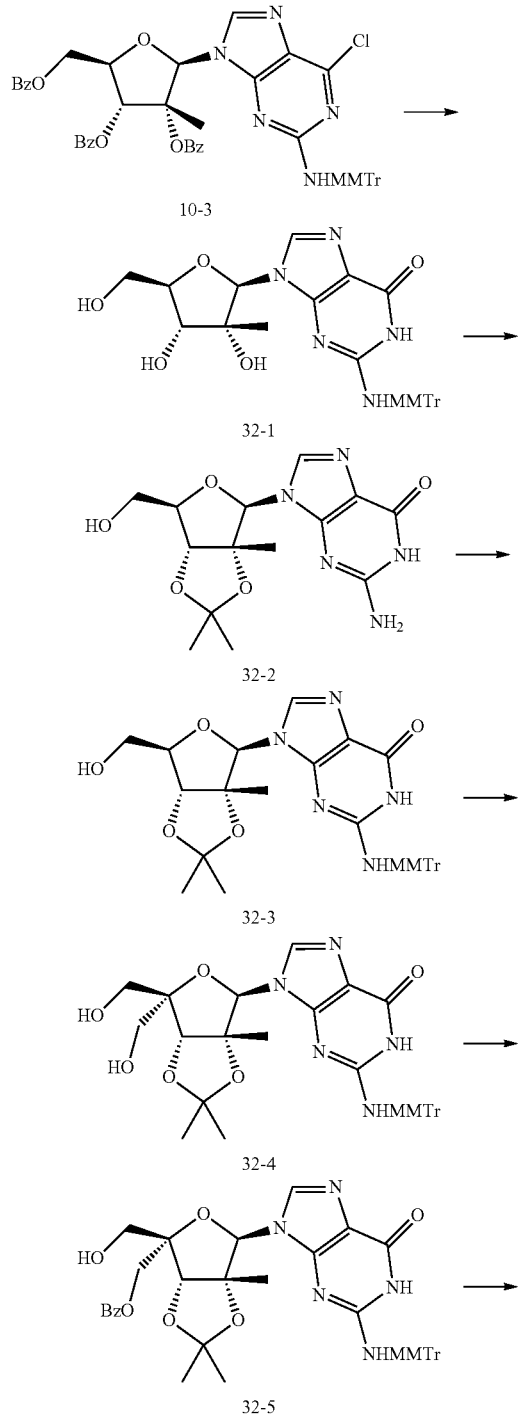

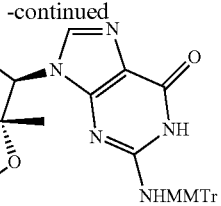

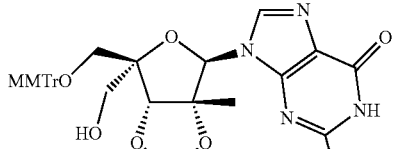

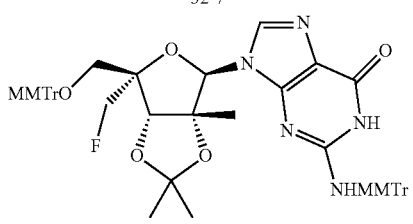

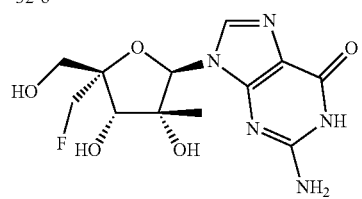

To a solution of 3-hydroxypropanenitrile (27 g, 0.15 mol) in THF (150 mL) was added NaH (8.4 g, 0.21 mol) at 0° C., and the mixture was stirred for 1 h. at RT. Compound 10-3 (27 g, 0.03 mol) in THF (100 mL) was treated with this mixture at 0° C. The combined mixture was stirred for 6 h. at RT. The reaction was quenched with H$_2$O, and extracted with EA. The organic layer was dried over anhydrous Na$_2$SO$_4$, and concentrated at low pressure. The residue was purified by column chromatography to give 32-1 (9.38 g, 55%).

To a solution of 32-1 (1 g, 1.76 mmol) and TsOH (1 g, 5.28 mmol) in DMF (4 mL) and acetone (8 mL) was added 2,2-dimethoxypropane (1.8 g, 17.6 mmol) at RT. The mixture was heated to 50° C. for 3 h. The reaction was quenched with H$_2$O (50 mL), and extracted with EA (3×50 mL). The organic layer was dried over anhydrous Na$_2$SO$_4$, and concentrated at low pressure. The residue was purified by column chromatography to give 32-2 (520 mg, 87%).

To a stirred solution of 32-2 (10.0 g, 29.6 mmol) in pyridine (100 mL) was added TBSCl (53.4 g, 35.6 mmol) at RT, and the mixture was stirred for 5 h. The mixture was concentrated at low pressure, and the residue was dissolved in EA (100 mL). The solution was washed with water and brine. The organic layer was dried over anhydrous Na$_2$SO$_4$, and concentrated at low pressure. The crude product was co-evaporated with toluene 3 times. To a solution of anhydrous crude product (2.0 g, 4.43 mmol) in DCM (30 mL) was added DMTrCl (2.24 g, 6.65 mmol), 2,4,6-trimethylpyridine (1.07 g, 8.86 mmol) and AgNO₃ (1.5 g, 8.86 mmol). The mixture was stirred for 1.5 h. The mixture was filtered, and the filtrate was washed with 0.5 N HCl solution. The solution was washed with brine, dried over anhydrous Na₂SO₄, and concentrated at low pressure to give the crude yellow solid. The crude yellow solid (7.2 g, 10 mmol) was treated with a solution of NH₄F (7.2 g, 200 mmol) in MeOH (50 mL), and the mixture was heated to 50° C. for 8 h. The mixture was concentrated at low pressure. The residue was purified by silica gel column to give 32-3 (4.8 g, 80%).

To a solution of 32-3 (200 mg, 0.33 mmol) in DCM (5 mL) was added TFA.Py (40 mg, 0.328 mmol), DMSO (0.15 mL), and DCC (191 mg, 0.99 mmol) at RT. The mixture was stirred for 6 h, and concentrated at low pressure. The residue was purified by silica gel column to give the product. To a solution of the product (0.2 g, 0.328 mmol) and HCHO (0.2 mL) in 1,4-dioxane (2 mL) was added NaOH (0.4 mL, 2 M) at RT. The mixture was stirred for 5 h. The mixture was then treated with NaBH₄ (24 mg, 0.66 mmol), and stirred for 3 h. The mixture was diluted with EA (20 mL), and washed with brine. The organic phase was dried over anhydrous Na₂SO₄, and concentrated at low pressure. The residue was purified by silica gel column to give 32-4 (125 mg, 60%).

To a solution of 32-4 (4 g, 6.25 mmol) in DCM (40 mL) was added pyridine (10 mL) and BzCl (920 mg, 15.6 mmol) at −78° C. The mixture was slowly warmed up to RT. The reaction was monitored by LCMS. The mixture was quenched with H₂O (40 mL), and extracted with DCM (3×50 mL). The organic layer was washed brine, dried over anhydrous Na₂SO₄, and concentrated at low pressure. The residue was purified by silica gel column to give 32-5 (3.25 g, 70%).

To a solution of 32-5 (5.75 g, 7.7 mmol) in DCM (20 mL) was added DMTrCl (3.58 g, 11.1 mmol), 2,4,6-trimethylpyridine (1.87 g, 15.4 mmol) and AgNO₃ (2.63 g, 15.4 mmol), and stirred for 3 h. The mixture was filtered, and the filtrate was washed with 0.5 N HCl solution. The organic phase was washed with brine, dried over anhydrous Na₂SO₄, and concentrated at low pressure. The residue was purified by silica gel column to give 32-6 (6.25 g, 80%).

To a solution of 32-6 (4.3 g, 4.23 mmol) in MeOH (40 mL) was added NaOMe (0.82 g, 12.6 mmol) at RT, and stirred for 3 h. The mixture was concentrated at low pressure. The residue was dissolved in EA (30 mL), and washed with brine. The organic layer was dried over anhydrous Na₂SO₄, and concentrated at low pressure. The residue was purified by silica gel column to give 32-7 (2.89 g, 75%).

To a solution of 32-7 (0.5 g, 0.54 mmol) and pyridine (0.478 g, 5.4 mmol) in DCM (4 mL) was slowly added a solution of Tf₂O (0.201 g, 0.713 mmol) in DCM (3 mL) at −35° C. The mixture was warmed up to −5° C. slowly. The reaction was monitored by LCMS. The reaction was quenched with sat. NaHCO₃ solution, and extracted with DCM (3×20 mL). The organic phase was washed with brine, dried over anhydrous Na₂SO₄, and concentrated at low pressure. The residue was purified by silica gel column to give the product. To a solution of the product was added TBAF in THF (25 mL, 1N), and the mixture was stirred for 5 h at RT. The reaction was monitored by LCMS. The mixture was concentrated at low pressure, and the residue was purified by prep-HPLC to give 32-8 (221 mg, 45%). ESI-MS: m/z 914.4 [M+H]⁺.

Compound 32-8 (2.14 g) was dissolved in 80% HCOOH (10 mL) and was at RT overnight. The solvent was evaporated to dryness, and the residue crystallized from methanol twice. The crystals were dissolved in a mixture of THF and 36% HCl 4:1 v/v and left overnight. The solvent was evaporated, and the nucleoside was isolated by RP HPLC on Synergy 4 micron Hydro-RP column (Phenominex). A linear gradient of methanol from 0 to 60% with 0.1% HCOOH was used for elution. Compound 32 was obtained (370 mg, 48%). MS: m/z 316.2 [M−1].

Example 25

Compound 17

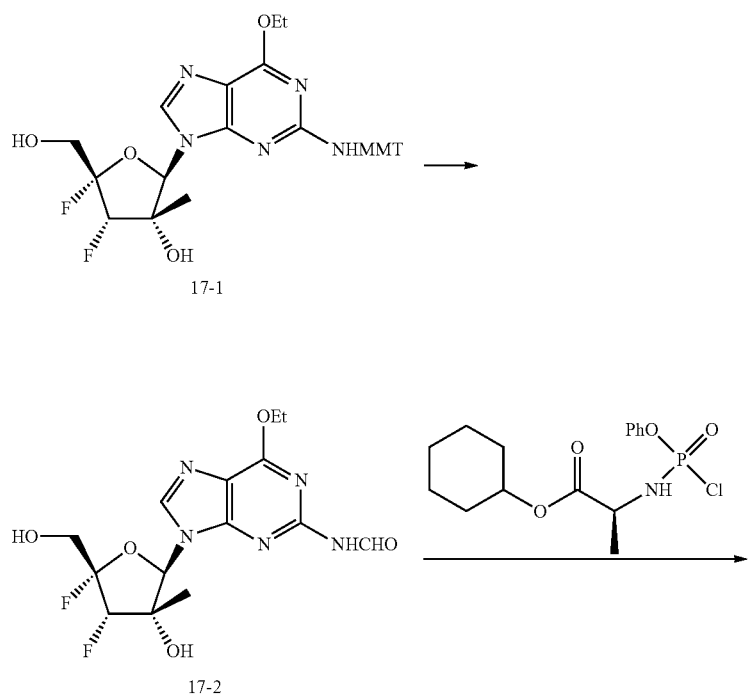

17-1

17-2

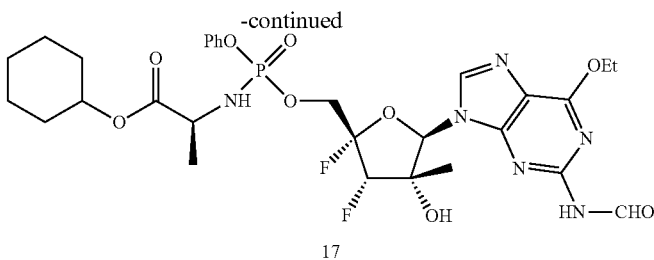

17

A solution of 17-1 (25 mg, 0.04 mmol) in 80% aq. HCOOH was kept at RT for 3 h. The mixture was concentrated and coevaporated with toluene. The crude residue was purified on silica gel (10 g column) with $CH_2Cl_2$/MeOH (4-10% gradient) to yield 17-2 (8 mg, 54%).

A mixture of 17-2 (8 mg, 0.02 mmol) in acetonitrile (0.4 mL) was stirred with NMI (15 mL, 8 eq.) and the phosphorochloridate reagent overnight at RT. The reaction was quenched with sat. aq. $NH_4Cl$, diluted with EtOAc and water. The organic layer was separated, washed with aq. $NaHCO_3$, water and brine, and dried ($Na_2SO_4$). The residue was purified on silica gel (10 g column) with $CH_2Cl_2$/i-PrOH (4-10% gradient) to yield compound 17 (9 mg, 66%). MS: m/z=683 [M+1].

Example 26

Compound 35

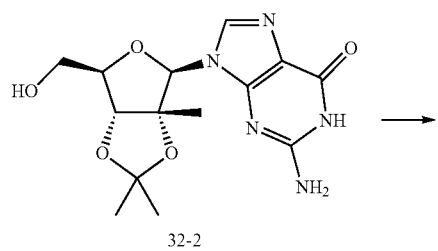

32-2

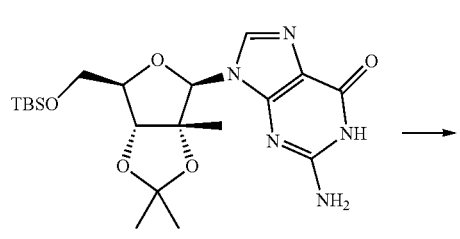

35-1

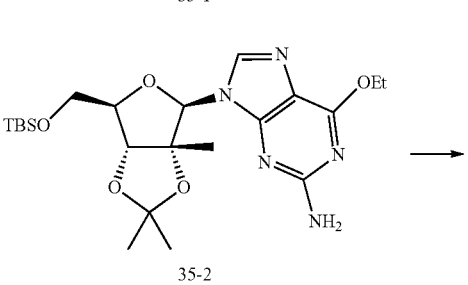

35-2

-continued

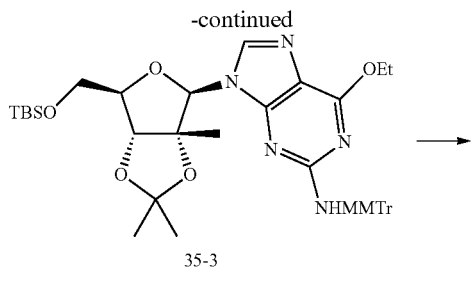

35-3

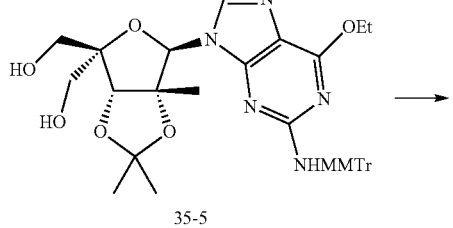

35-4

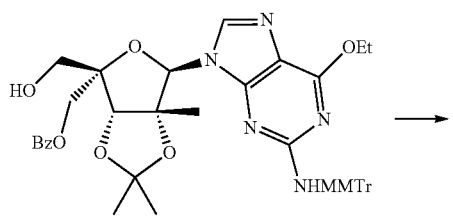

35-5

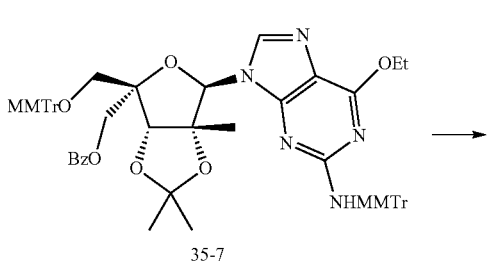

35-6

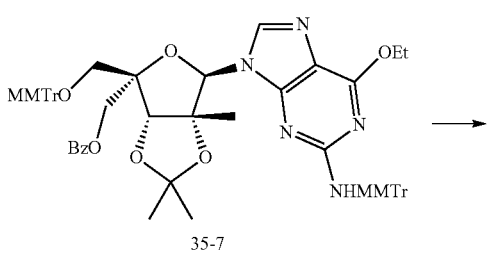

35-7

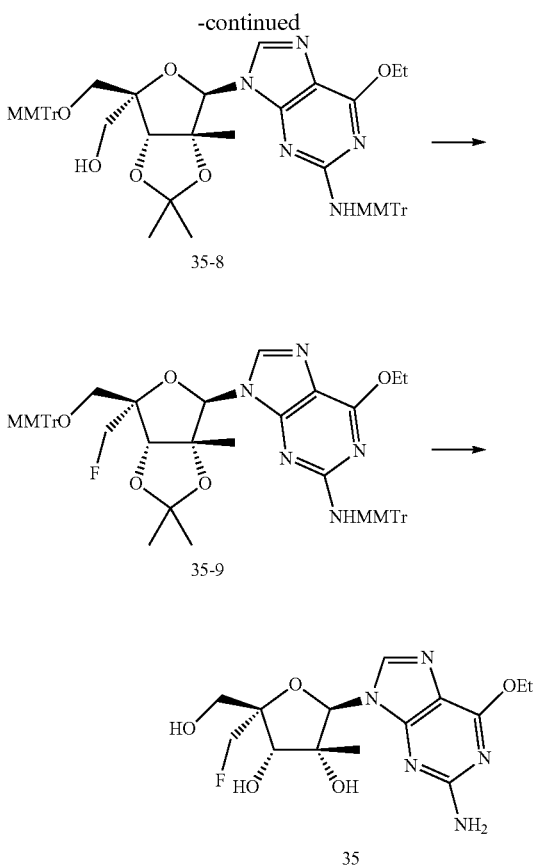

To a stirred solution of 32-2 (5.0 g, 14.83 mmol) in anhydrous pyridine (50 mL) was added TBSCl (3.33 g, 22.24 mmol) at RT under $N_2$. The mixture was stirred at RT for 12 h and concentrated at low pressure. The residue was purified by silica gel column chromatography to give 35-1 (5.69 g, 85.1%).

To a solution of $PPh_3$ (2.76 g, 10.6 mmol) and DIAD (2.15 g, 10.6 mmol) in dioxane (20 mL) was added EtOH (0.49 g, 10.6 mmol) at RT. After stirring for 30 mins, a solution of 35-1 (2.4 g, 5.3 mmol) in dioxane (10 mL) was added. The solution was stirred overnight at RT. After the reaction was complete, the reaction was quenched with sat. $NaHCO_3$ solution. The solution was extracted with EA (3×40 mL). The organic layer was washed with brine, dried over anhydrous $Na_2SO_4$, and concentrated at low pressure. The residue was purified by silica gel column (10% EA in PE) to give 35-2 (2 g, 78.4%) as a white solid.

To a solution of 35-2 (8 g, 16.9 mmol) in dichloride methane (60 mL) was added $AgNO_3$ (5.67 g, 33.4 mmol), collidine (4.03 g, 33.4 mmol) and MMTrCl (7.7 g, 25 mmol) in small portions under $N_2$ at 0° C. The mixture was stirred at RT overnight. The reaction was monitored by TLC. After completion, the mixture was filtered. The filtrate was washed with sat. aq. $NaHCO_3$ and brine. The organic layer was dried over anhydrous $Na_2SO_4$, and concentrated at low pressure. The residue was purified by silica gel column to give 35-3 (10 g, 80%) as a white solid.

To a solution of 35-3 (10 g, 13.3 mmol) in methanol (100 mL) was added $NH_4F$ (10 g, 270 mmol), and heated to reflux overnight. The mixture was concentrated under reduced pressure. The residue was purified by silica gel chromatography (50% PE in EA) to give 35-4 as a white solid (5 g, 59%).

To a solution of 35-4 (4 g, 6.27 mmol) and DCC (3.65 g, 18.8 mmol) in anhydrous DMSO (40 mL) was added TFA.Py (1.21 g, 6.27 mmol) at RT under $N_2$. The mixture was stirred at RT overnight. The reaction was quenched with water (100 mL), and diluted with EA (200 mL). After filtration, the filter was washed with sat. $NaHCO_3$ solution. The organic phase was washed with brine, dried over anhydrous $Na_2SO_4$, and concentrated at low pressure. The residue (4 g, 6.27 mmol) was dissolved in dioxane (40 mL), and 37% formaldehyde (4 mL) followed by addition of 2N NaOH solution (8 mL) at RT. The mixture was stirred at 30° C. overnight. $NaBH_4$ (0.7 g, 18.9 mmol) was added in portions at 5° C., and the mixture was stirred at RT for 30 mins. The reaction was quenched with water, and the mixture was extracted with EA (3×50 mL). The organic layer was dried over anhydrous $Na_2SO_4$, and concentrated at low pressure. The residue was purified on a silica gel column (20% EA in PE) to give 35-5 (2.5 g, 60%) as a white solid.

To a solution of 35-5 (2.29 g, 3.43 mmol) in pyridine (5 mL) and DCM (20 mL) was added BzCl (0.53 g, 3.77 mmol) at −78° C., and stirred overnight at RT. The mixture was quenched with water, and extracted with DCM (3×40 mL). The organic layer was dried over anhydrous $Na_2SO_4$, and concentrated at low pressure. The residue was purified by silica gel column to give the 35-6 (1.62 mg, 62%).

To a solution of 35-6 (1.62 g, 2.1 mmol) in dichloride methane (20 mL) was added $AgNO_3$ (714 mg, 4.2 mmol), collidine (508 mg, 4.2 mmol) and MMTrCl (970 mg, 3.2 mmol) in small portions under $N_2$ at 0° C. The mixture was stirred at RT overnight. The reaction was monitored by TLC. After filtration, the filter was washed with sat. aq. $NaHCO_3$ and brine. The combined organic layer was dried over anhydrous $Na_2SO_4$, and concentrated at low pressure. The residue was purified by silica gel column to give 35-7 (2 g, 91.3%) as a white solid.

To a solution of 35-7 (2.1 g, 2 mmol) in MeOH (30 mL) was added NaOMe (220 mg, 4 mmol) at RT and stirred for 1 h. After all starting material disappeared as indicated by TLC, the reaction was quenched with dry ice, and evaporated at low pressure. The residue was purified by silica gel column chromatography to give 35-8 (1.3 g, 69%) as a white solid.

To a solution of 35-8 (1.3 g, 1.38 mmol) in anhydrous DCM (15 mL) and pyridine (1 mL) was added dropwise $Tf_2O$ (585 mg, 2.07 mmol) at −20° C. The mixture was stirred at RT for 3 h, and diluted with DCM (150 mL). The solution was washed successively with water and brine. The organic solution was dried over $Na_2SO_4$ and concentrated at low pressure. The residue (1.48 g) was dissolved in anhydrous THF (15 mL), and treated with TBAF (3 mL, 1M in THF) at RT. The mixture was stirred overnight. The reaction was quenched with sat. aq. $NaHCO_3$, and extracted with EA (3×60 mL). The combined organic layer was dried over $Na_2SO_4$, and evaporated at low pressure. The residue was purified by silica gel column (30% EA in PE) to give 35-9 (1.25 g, 96%) as a white solid. ESI-LCMS: m/z 942.4 $[M+H]^+$.

Compound 35-9 (0.55 g, 0.58 mmol) was added into ice cooled 80% aq. TFA (5 mL) and kept overnight at 5° C. The mixture was concentrated under reduced pressure at 5° C. Thick oily residue was coevaporated several times with toluene and purified on silica gel (10 g column) with $CH_2Cl_2$/MeOH (4-15% gradient) to yield compound 35 (75 mg, 36%). MS: m/z=358 [M+1].

Example 27
Compound 36
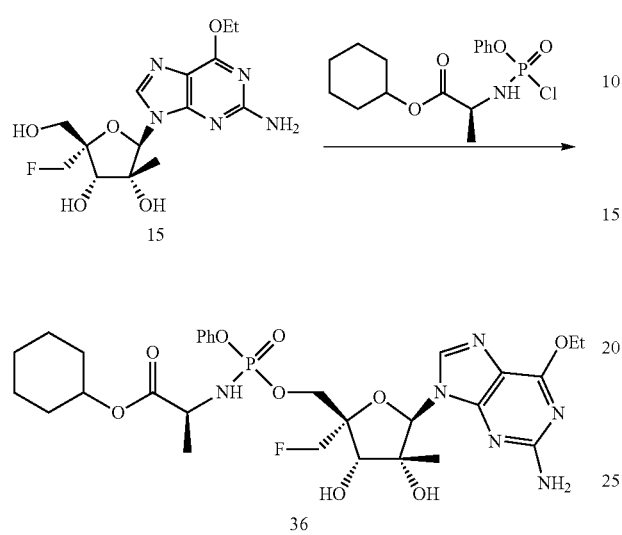
Compound 36 (8 mg, 10%) was prepared from compound 15 (48 mg) in acetonitrile (1.5 mL) with the phosphorochloridate reagent (0.14 g) and NMI (0.17 mL) in the same manner as compound 7. Purification was done by RP-HPLC (30-100% B, A: 50 mM TEAA in water, B: 50 mM TEAA in MeCN). MS: m/z=665 [M−1].
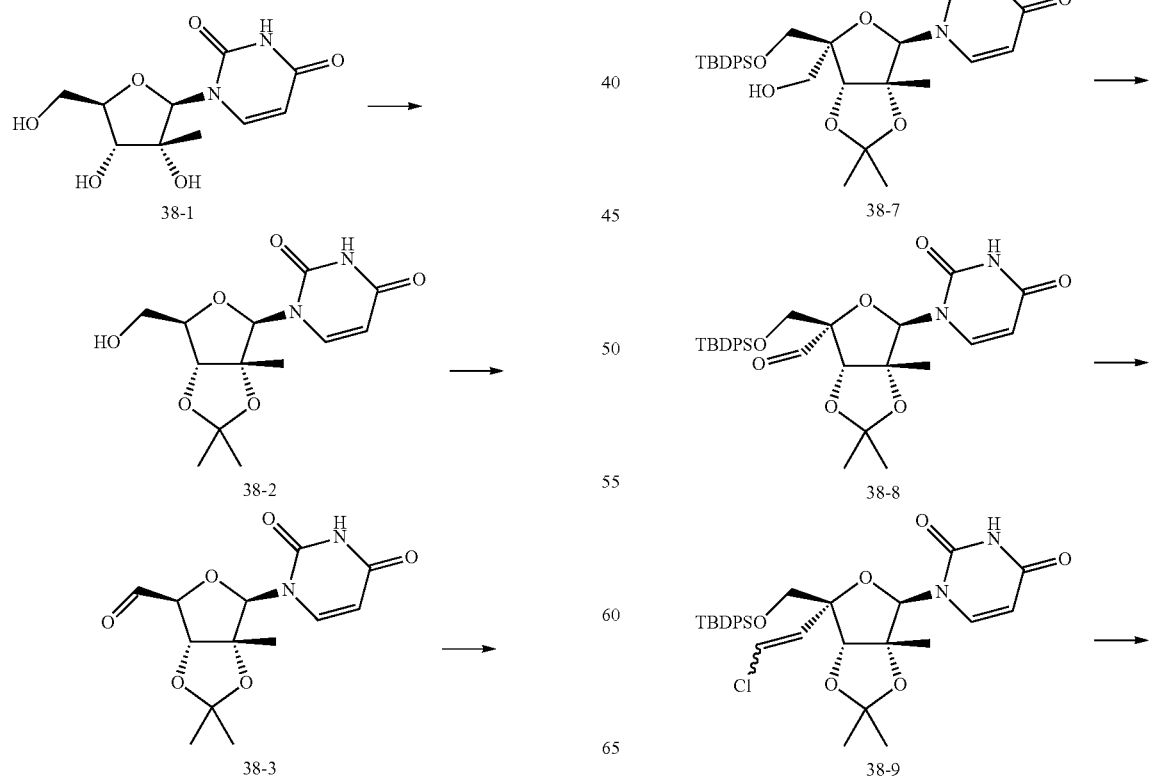

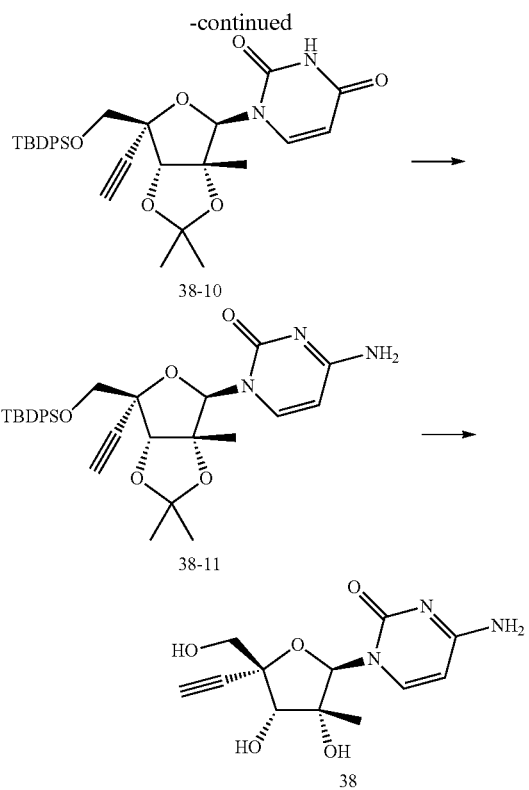

38-10

38-11

38

Example 28

Compound 38

To a solution of 38-1 (17 g, 65.9 mmol) and 2,2-dimethoxypropane (34.27 g, 329.5 mmol, 5 eq.) in acetone (200 mL) was added p-toluenesulfonic acid monohydrate (11.89 g, 62.6 mmol, 0.95 eq.). The =mixture was allowed to stir overnight at RT. The reaction was quenched with sat. aq. NaHCO$_3$. The mixture was filtered, and dried over anhydrous Na$_2$SO$_4$. The filtrate was concentrated to give 38-2 (19 g, 97%).

To a solution of 38-2 (6 g, 20.1 mmol) in anhydrous CH$_3$CN (80 mL) was added IBX (7.05 g, 25.2 mmol, 1.25 eq.) at RT. The mixture was refluxed for 1 h., and cooled to 0° C. The precipitate was filtered, and the filtrate was concentrated to give crude 38-3 (6 g 100%) as a yellow solid.

Compound 38-3 (6 g 20.1 mmol) was dissolved in 1,4-dioxane (60 mL). 37% HCHO (6 mL, 69 mol) and 2M NaOH aqueous solution (12 mL, 24 mmol, 1.2 eq.) were added at 10° C. The mixture was stirred at RT overnight and neutralized with AcOH to pH=7. The mixture was treated with NaBH$_4$ (1.53 g, 40.2 mmol, 2 eq.) at 10° C. The mixture was stirred at RT for 30 mins, and then quenched with sat. aq. NH$_4$Cl. The mixture was extracted with EA. The organic layer was dried over anhydrous Na$_2$SO$_4$, and concentrated to dryness. The residue was purified on silica gel column (1-3% MeOH in DCM) to give 38-4 (3.5 g, 53%) as a white solid.

To a solution of 38-4 (3.5 g, 10.7 mmol) in anhydrous pyridine (60 mL) was added DMTrCl (3.6 g, 10.7 mmol, 1 eq.) in anhydrous DCM (8 mL) dropwise at −30° C. The mixture was stirred at RT overnight. The solution was treated with MeOH, and concentrated to dryness at low pressure. The residue was purified by column chromatography (0.5-2% MeOH in DCM) to give 38-5 (3 g, 45%) as a yellow solid.

To a solution of 38-5 (2.5 g, 4 mmol) in anhydrous CH$_2$Cl$_2$ (30 mL) was added AgNO$_3$ (0.816 g, 4.8 mmol, 1.2 eq.), imidazole (0.54 g, 8 mmol, 2 eq.) and TBDPSCl (1.18 g, 4.8 mmol, 1.2 eq.) under N$_2$ atmosphere. The mixture was stirred at RT for 14 h. The precipitate removed via filtration, and the filtrate was washed with brine and dried over Na$_2$SO$_4$. The solvent was removed under reduced pressure to give crude 38-6 (3.4 g, 100%) as a yellow solid.

Compound 38-6 (4 g, 4.6 mmol) was dissolved in 80% HOAc aqueous solution (50 mL). The mixture was stirred at RT for 3 h. The solution was treated with MeOH, and concentrated to dryness. The residue was purified by column chromatography (1-2% MeOH in DCM) to give 38-7 (1.2 g, 45%) as a white solid.

To a solution of 38-7 (1 g, 1.77 mmol) in anhydrous DCM (15 mL) was added Dess-Martin periodinane reagent (1.12 g, 2.65 mmol, 1.5 eq.) at 0° C. under nitrogen atmosphere. The reaction was stirred at RT for 2.5 h. The solution was quenched by addition of 4% Na$_2$S$_2$O$_3$ and washed with 4% sodium bicarbonate aqueous solution (50 mL). The mixture was stirred for another 15 mins. The organic layer was washed with brine, and concentrated under reduced pressure. The residue was purified by silica gel column chromatography (20% EtOAc in hexane) to give 38-8 (0.7 g, 70%) as a white solid.

To a solution of methyltriphenylphosphonium chloride (2.95 g, 8.51 mmol, 4 eq.) in anhydrous THF (20 mL) was added n-BuLi (3.2 mL, 8.1 mmol, 3.8 eq.) dropwise at −70° C. under nitrogen atmosphere. The mixture was stirred at 0° C. for 1 h. A solution of 38-8 (1.2 g, 2.13 mmol) in anhydrous THF (3 mL) was added dropwise at 0° C. under nitrogen atmosphere. The solution was stirred 0° C. for 2 h. The reaction was quenched with NH$_4$Cl and extracted with EtOAc. The organic layer was washed with brine and concentrated under reduced pressure. The crude product was purified by silica gel column chromatography (20% EtOAc in hexane) to give 38-9 (0.9 g, 75%) as a white solid.

To a solution of 38-9 (0.85 g, 1.43 mmol) in anhydrous THF (50 mL) was added n-BuLi (5.7 mL, 14.3 mmol, 10 eq.) at −70° C. under nitrogen atmosphere. The mixture was stirred at −70° C. for 2 h. The reaction was quenched with NH$_4$Cl and extracted with EtOAc. The organic layer was washed with brine and concentrated under reduced pressure. The crude product was purified by silica gel column chromatography (20% EtOAc in hexane) to give 38-10 (0.4 g, 50%) as a white solid.

To a solution of 38-10 (0.4 g, 0.714 mmol) in anhydrous CH$_3$CN (30 mL) were added TPSCl (0.433 g, 1.43 mmol, 2 eq.), DMAP (0.174 g, 1.43 mmol, 2 eq.) and TEA (1.5 mL) at RT. The mixture was stirred at RT for 3 h. NH$_4$OH (3 mL) was added, and the mixture was stirred for 1 h. The mixture was diluted with EA (150 mL), and washed with water, 0.1 M HCl and saturated aqueous NaHCO$_3$. The organic layer was washed with brine and concentrated under reduced pressure. The crude product was purified by silica gel column chromatography (2% MeOH in DCM) to give 38-11 (0.2 g, 50%) as a yellow solid.

Compound 38-11 (1.35 g, 1.5 mmol) was dissolved in 80% HOAc aqueous solution (40 mL). The mixture was stirred at 60° C. for 2 h and concentrated to dryness. The crude was purified on silica gel column (5% MeOH in DCM) to give compound 38 (180 mg, 35%) as a white solid. ESI-MS: m/z 282.1 [M+H]$^+$.

Example 29
Compound 39
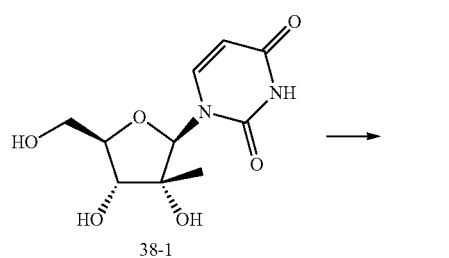
38-1
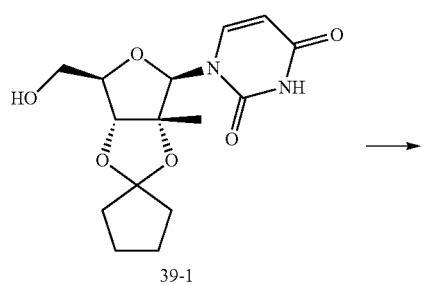
39-1
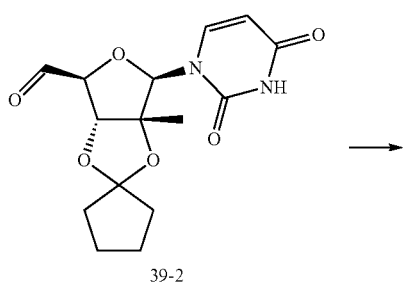
39-2
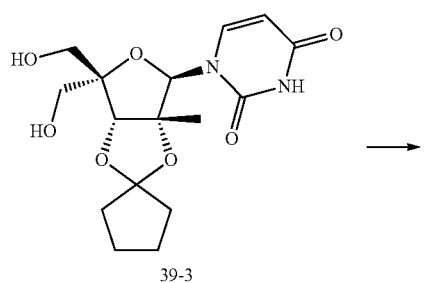
39-3
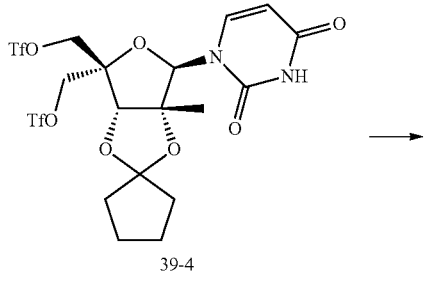
39-4
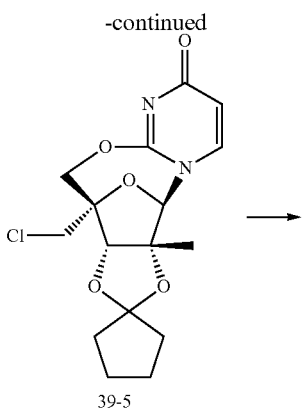
39-5
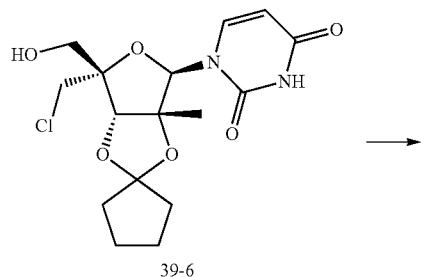
39-6
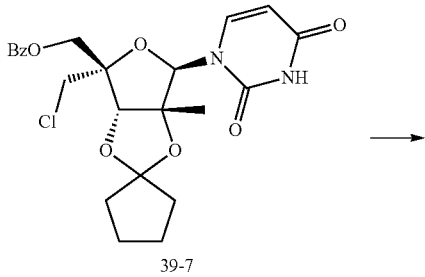
39-7
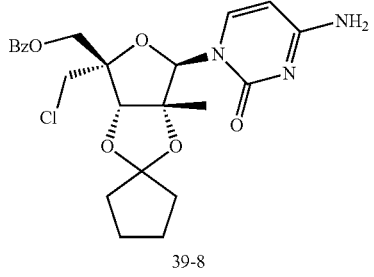
39-8
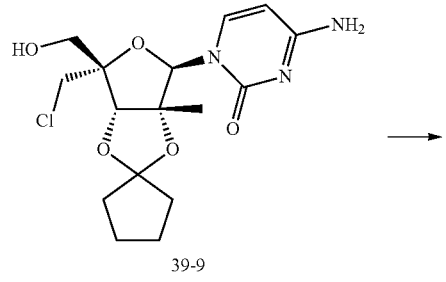
39-9
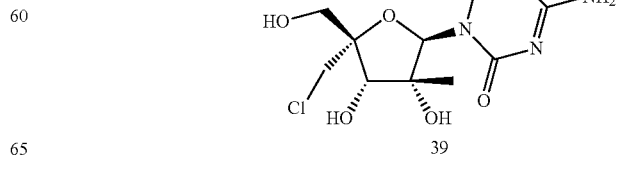
39

To a solution of cyclopentanone (6.0 g, 71 mmol) in MeOH (60 mL) was added TsOH.H₂O (1.35 g, 7.1 mmol) and trimethoxymethane (8 mL) at RT. The solution was stirred at RT for 2 h. The reaction was quenched with NaOMe, and the mixture was extracted with hexane (30 mL). The organic layer was dried and concentrated to give crude 1,1-dimethoxycyclopentane (9.2 g), which was dissolved in 1,2-dichloroethane (50 mL). To the above solution was added 38-1 (5.0 g, 19.38 mmol) and TsOH.H₂O (0.36 g, 1.9 mmol) at RT. The mixture was stirred at 60° C. for 4 h. The reaction was quenched with TEA and concentrated at low pressure. The residue was purified on silica gel column (1% MeOH in DCM) to give 39-1 (4.77 g, 76%) as a white solid.

To a solution of 39-1 (4.77 g, 14.73 mmol) in anhydrous DCM (50 mL) was added DMP (6.56 g, 15.6 mmol) at 0° C. The solution was stirred at RT for 10 h and concentrated to dryness. The residue was suspended in PE (30 mL) and DCM (5 mL), and the solid was precipitated. After filtration, the filtrate was concentrated to give the crude 39-2 (4.78 g, 100%) as a foam.

Crude 39-2 (4.77 g, 14.73 mmol) was re-dissolved in anhydrous 1,4-dioxane (50 mL). To the solution was added CH₂O aq. (37%, 3.6 mL) and NaOH aq. (2M, 11.3 mL) at 0° C. The mixture was stirred at RT for 16 h. The mixture was treated with NaBH₄ (1.48 g, 40 mmol) at 0° C. and stirred for 0.5 h. The reaction was quenched with water, and the mixture was extracted with EA. The organic layer was dried over anhydrous Na₂SO₄, and concentrated to dryness. The residue was purified on silica gel column (40% EA in PE) to give 39-3 (2.6 g, 49.9%) as a white solid.

To a stirred solution of 39-3 (5.0 g, 14.1 mmol) in pyridine (5.6 g, 71 mmol) and DCM (100 mL) was added Tf₂O (8.7 g, 31.2 mmol) dropwise at −35° C. The mixture was allowed to warm to 0° C. slowly and stirred for 2 h. The mixture was quenched with 0.5M aq. HCl and the DCM layer was separated. The organic phase was dried over anhydrous Na₂SO₄, and concentrated to dryness. The crude was purified on silica gel column (20% EA in PE) to give 39-4 (4.5 g, 52%).

39-4 (4.5 g, 7.28 mmol) was dissolved in anhydrous THF (50 mL) at 0° C. The solution was treated with NaH (60% in mineral oil, 0.32 g, 8 mmol, 1.1 eq.) in portions, and the mixture was stirred at RT for 8 h. The reaction was quenched with water, and extracted with EA (3×60 mL). The organic layer was washed with brine, dried over anhydrous Na₂SO₄, and concentrated at low pressure to give the crude product used directly for next step. To a solution of the crude product (2.0 g, 3.6 mmol) in MeCN (10 mL) was added LiCl (4.0 g, 13 mmol). The reaction was allowed to proceed overnight. Aqueous NaOH (1N, ~2 eq.) was added, and the mixture was stirred for 1 h. The mixture was partitioned between sat. NH₄Cl solution and EA. The organic layer was concentrated under reduced pressure, and the crude was purified on silica gel column (20% EA in PE) to give 39-6 (0.6 g, 46%) as a white solid. ESI-MS: m/z 395.0 [M+Na]⁺.

Compound 39-6 (3.0 g, 8.06 mmol) was co-evaporated with toluene (30 mL). To a solution of 39-6 (3.0 g, 8.06 mmol), DMAP (98 mg, 0.80 mmol) and TEA (2.3 mL, 2 eq.) in DCM (30 mL) was added Bz₂O (1.82 g, 8.06 mmol) at 0° C. and stirred for 3 h. The reaction was quenched with 1.0 M HCl and extracted with DCM. The DCM layer was dried over high vacuum pump to give crude 39-7 (3.3 g, 80.9%).

To a solution of 39-7 (400 mg, 0.84 mmol) in anhydrous CH₃CN (3 mL) was added TPSCl (507 mg, 1.68 mmol), TEA (169 mg, 1.68 mmol) and DMAP (207 mg, 1.68 mmol), and the mixture was stirred for 2 h. at RT. Completion of the reaction was determined by TLC. Ammonium solution (3.0 mL) was added at RT, and the solution was stirred for 2 h. The mixture was washed with 1.0 M HCl solution and extracted with DCM. The DCM layer was dried over Na₂SO₄ and concentrated to dryness. The crude was purified by column chromatography to provide 39-8 (250 mg, 63%).

Compound 39-8 (250 mg, 0.53 mmol) in 80% formic acid (3 mL) was stirred at RT for 3 h. Completion of the reaction was determined by TLC. The mixture was concentrated at a low pressure. The crude was purified by column chromatography to give 39-9 (130 mg, 66%).

Compound 39-9 (270 mg, 0.73 mmol) was dissolved in MeOH/NH₃ (10 mL), and the solution was stirred for 6 h. The mixture was concentrated at low pressure. The crude product was washed with DCM, and the solution was lyophilized to give compound 39 (118 mg, 52%). ESI-MS: m/z 328.3 [M+H+Na]⁺.

Example 30

Compound 40

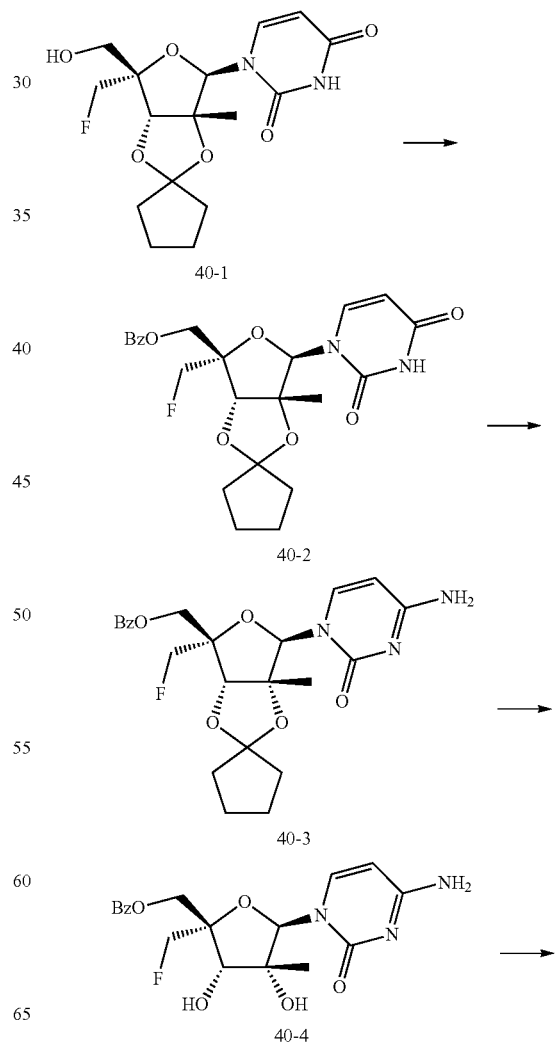

-continued

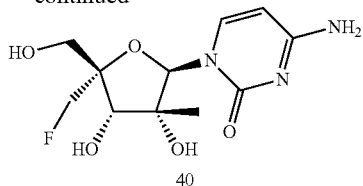
40

Compound 40-1 (3.0 g, 8.42 mmol) was co-evaporated with toluene (30 mL). To a solution of 40-1 (3.0 g, 8.42 mmol), DMAP (103 mg, 0.84 mmol) and TEA (2.5 mL, 2 eq.) in DCM (30 mL) was added Bz$_2$O (2.01 g, 8.42 mmol) at 0° C. and stirred for 3 h. The solution was quenched with 1.0 M HCl and extracted with DCM. The DCM layer was dried over high vacuum pump to give crude 40-2 (3.3 g, 85%).

To a solution of 40-2 (200 mg, 0.43 mmol) in anhydrous CH$_3$CN (2 mL) was added TPSCl (260 mg, 0.86 mmol), TEA (95 mg, 0.94 mmol) and DMAP (106.4 mg, 0.86 mmol), and the mixture was stirred for 2 h at RT. Completion of the reaction was determined by TLC. Ammonium solution (1.33 mL) was added at RT, and left to stir for 2 h. The mixture was washed with 1.0 M HCl solution, and extracted with DCM. The DCM layer was dried over anhydrous Na$_2$SO$_4$, and concentrated to dryness at low pressure. The residue was purified by column chromatography to provide 40-3 (150 mg, 75%).

Compound 40-3 (100 mg, 0.21 mmol) in 80% formic acid (2 mL) was stirred at RT for 3 h. Completion of the reaction was determined by TLC. The mixture was concentrated at low pressure, and the residue was purified by column chromatography to give 40-4 (50 mg, 58%).

Compound 40-4 (270 mg, 0.68 mmol) was dissolved in MeOH/NH$_3$ (10 mL), and the resulting solution was stirred for 6 h. The mixture was concentrated at low pressure. The crude product was washed with DCM, and the solution was lyophilized to give compound 40 (105 mg, 53.8%). ESI-MS: m/z 290.4 [M+H]$^+$.

Example 31

Compound 41

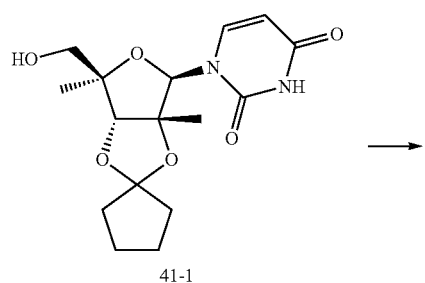

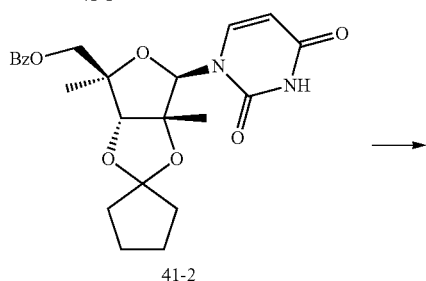

-continued

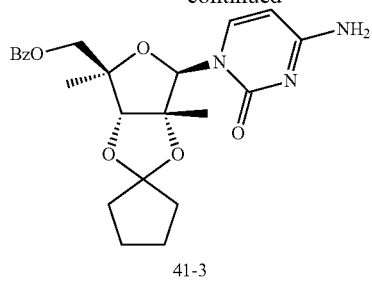
41-3

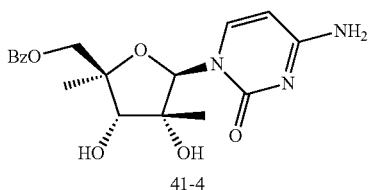
41-4

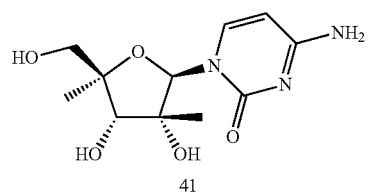
41

Compound 41-1 (3.0 g, 8.87 mmol) was co-evaporated with toluene (30 mL). To a solution of 41-1 (3.0 g, 8.87 mmol), DMAP (108 mg, 0.88 mmol) and TEA (2.5 mL, 2 eq.) in DCM (30 mL) was added Bz$_2$O (2.01 g, 8.87 mmol) at 0° C. The solution was stirred for 3 h. The reaction was quenched with 1.0 M HCl solution, and extracted with DCM. The DCM layer was dried over high vacuum pump to give crude 41-2 (3.5 g, 85%) as a solid.

To a solution of 41-2 (200 mg, 0.45 mmol) in anhydrous CH$_3$CN (2 mL) was added TPSCl (260 mg, 0.90 mmol), TEA (99 mg, 0.99 mmol) and DMAP (106.4 mg, 0.90 mmol). The mixture was stirred at RT for 2 h. Completion of the reaction was determined by TLC. An ammonium solution (1.33 mL) was added at RT, and the mixture was stirred for 2 h. The mixture was washed with 1.0 M HCl solution, and extracted with DCM. The DCM layer was dried over anhydrous Na$_2$SO$_4$, and concentrated to dryness at low pressure. The crude product was purified by column chromatography to provide 41-3 (150 mg, 75%).

Compound 41-3 (100 mg, 0.23 mmol) in 80% formic acid (2 mL) was stirred at RT for 3 h. Completion of the reaction was determined by TLC. The mixture was concentrated at a low pressure. The crude product was purified by column chromatography to give 41-4 (50 mg, 58%).

Compound 41-4 (270 mg, 0.72 mmol) was dissolved in MeOH/NH$_3$ (10 mL), and the solution was stirred for 6 h. The mixture was concentrated at low pressure. The crude product was washed with DCM, and the solution was lyophilized to give compound 41 (105 mg, 53.8%). ESI-MS: m/z 675.4 [2M+H]$^+$.

Example 32

Compound 42

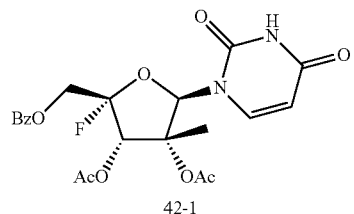
42-1

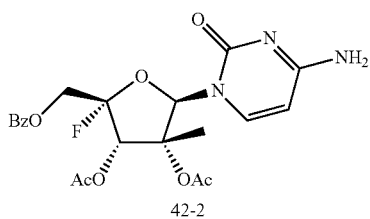
42-2

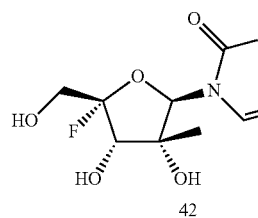
42

To a solution of 42-1 (600 mg, 1.29 mmol) in anhydrous CH₃CN (4 mL) was added DMAP (315 mg, 2.59 mmol), TEA (391 mg, 3.87 mmol) and TPSCl (782 mg, 2.58 mmol). The mixture was stirred for 3 h. under N₂. A solution of NH₃ in THF (2 mL) was added, and stirred for 1 h. The reaction was quenched with sat. NH₄Cl solution, and extracted with EA. The organic layer was dried over anhydrous Na₂SO₄, and concentrated to dryness at low pressure. The residue was purified by column chromatography to provide 42-2 (370 mg, 62%) as a white foam solid.

Compound 42-2 (370 mg, 1.48 mmol) in methanolic ammonium was stirred at RT for 4 h. The solution was concentrated to dryness to give compound 42 (200 mg, 91%) as a white solid. ESI-MS: m/z 275.9 [M+H]⁺.

Example 33

Compound 43

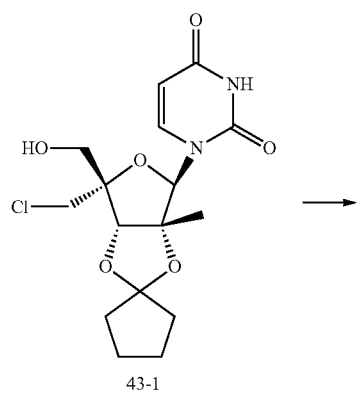
43-1

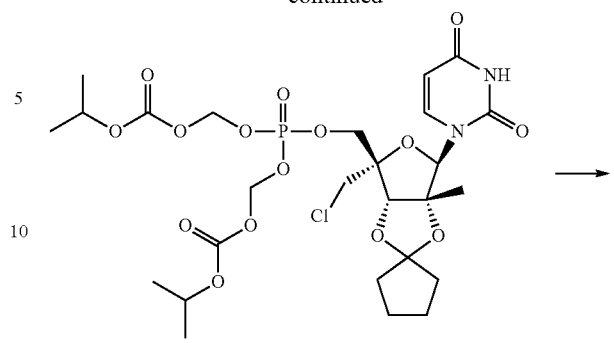
43-2

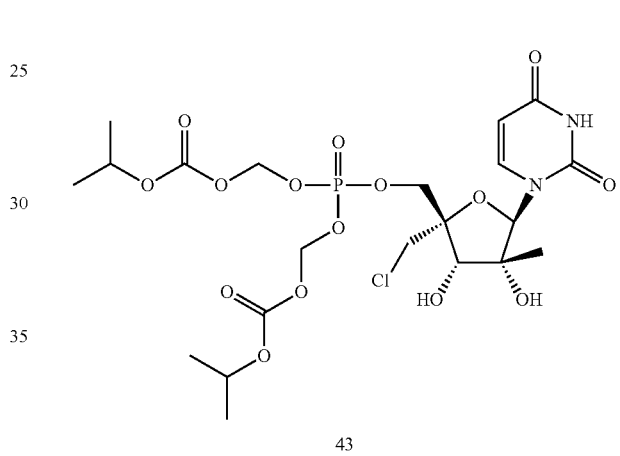
43

To a solution of triethylammonium bis(isopropyloxycarbonyloxymethyl)phosphate (0.6 mmol, prepared from bis (POC)phosphate (0.2 g) and Et₃N (83 µL)) in THF was added 43-1 (74 mg, 0.2 mmol). The mixture evaporated and rendered anhydrous by co-evaporating with pyridine follow by toluene. The residue was dissolved in anhydrous THF (2 mL). Diisopropylethylamine (0.35 mL; 10 eq.) was added, followed by BOP-Cl (0.25 g; 5 eq.) and 3-nitro-1,2,4-triazole (0.11 g; 5 eq.). The mixture was stirred at RT for 90 mins, diluted with EtOAc, washed with sat. aq. NaHCO₃ and brine, and dried with Na₂SO₄. The residue was purified on silica (10 g column) with CH₂Cl₂/i-PrOH (4-10% gradient) to yield 50 mg (37%) of give 43-2.

A solution of 43-2 (40 mg; 0.06 mmol) in 80% aq. HCOOH was heated at 45° C. for 8 h. The mixture was evaporated, co-evaporated with toluene and purified on silica (10 g column) with CH₂Cl₂/MeOH (4-10% gradient) to yield compound 43 (35 mg, 91%). MS: m/z=619 [M+1].

Example 34

Compound 44

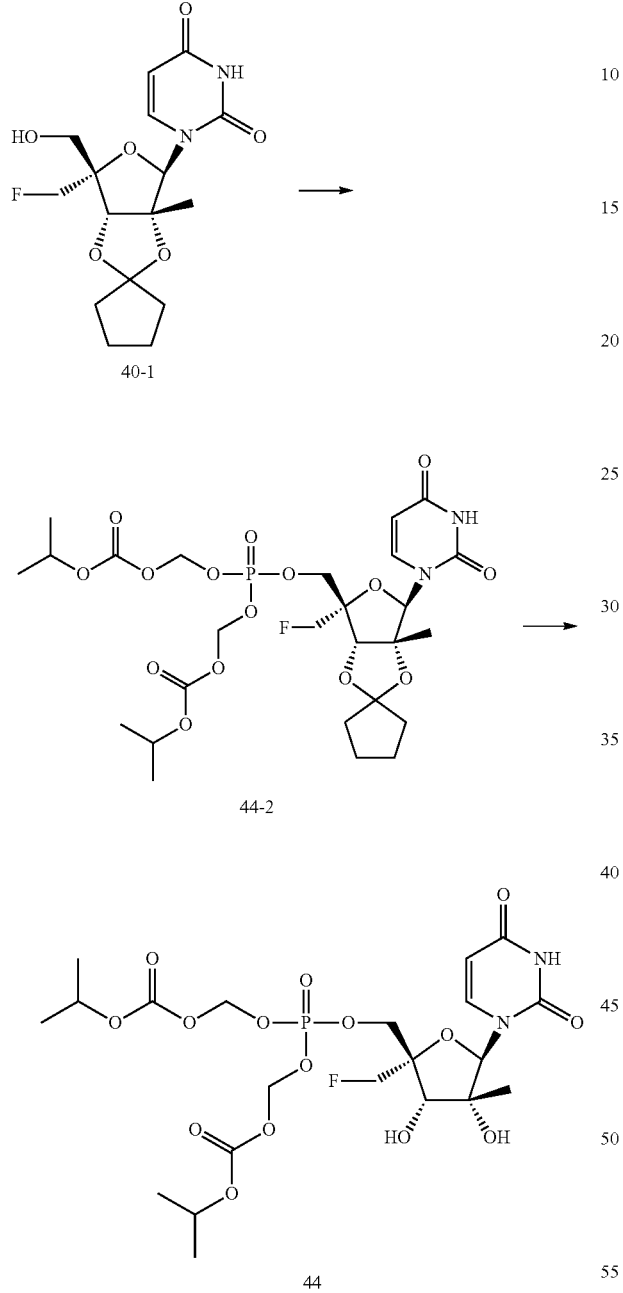

Compound 44-2 was prepared from 40-1 following a similar procedure for the preparation of 43-2. The residue was purified on silica (10 g column) with hexanes/EtOAc (35-100% gradient) to yield 44-2 (0.45 g, 75%).

A solution of 44-2 (0.40 g; 0.6 mmol) in 80% aq. HCOOH (15 mL) was heated at 45° C. for 8 h. The mixture was evaporated, co-evaporated with toluene and purified on silica (10 g column) with $CH_2Cl_2$/MeOH (4-10% gradient) to yield compound 44 (0.27 g, 75%). MS: m/z=603 [M+1].

Example 35

Compound 45

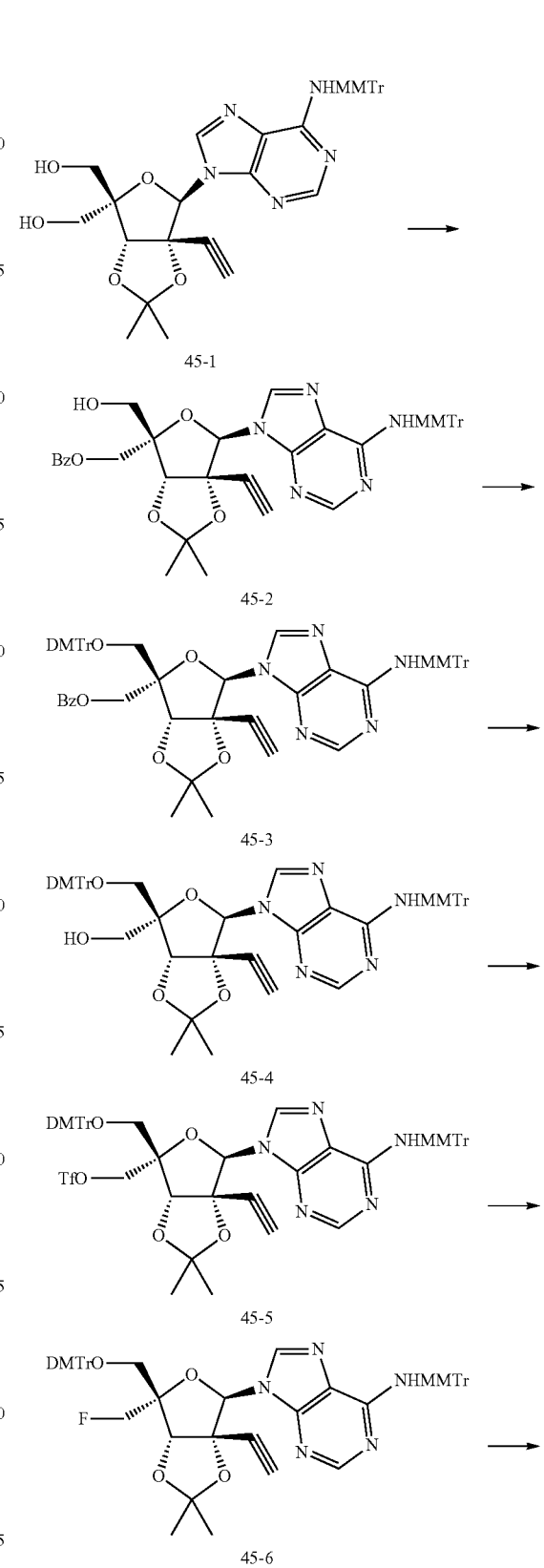

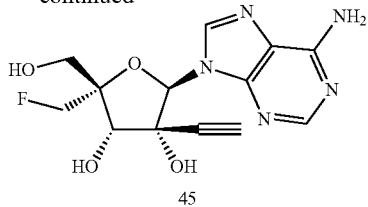

45

To a solution of 45-1 (3.0 g, 4.7 mmol) in CH₃CN/pyridine (15 mL/20 mL) was added BzCl (0.67 g, 4.7 mmol) at 0° C. slowly. The mixture was stirred at 10° C. for 12 h. The reaction was quenched with sat. NaHCO₃ solution, and extracted with DCM. The solution was washed with brine, dried over anhydrous Na₂SO₄, and concentrated at low pressure. The residue was purified on silica gel column (EA in PE from 2% to 50%) to afford 45-2 (2.6 g, 72%) as a solid.

To a solution of 45-2 (1.0 g, 1.35 mmol) in pyridine (8 mL) was added DMTrCl (0.64 g, 1.9 mmol). The mixture was stirred at 20-35° C. overnight. The reaction was monitored by LCMS and TLC. The reaction was quenched with MeOH, and concentrated at low pressure. The residue was purified by silica gel column to give 45-3 (1.5 g), which was used without further purification.

To a solution of 45-3 (1.5 g, 1.35 mmol) in MeOH/THF (1/1, 10 mL) was added NaOMe (0.11 g, 2.0 mmol), and stirred at 40° C. for 3 h. The reaction was monitored by TLC. The reaction was quenched with dry ice, and concentrated to dryness at low pressure. The residue was dissolved in DCM (100 mL). The solution was washed with brine, dried over anhydrous Na₂SO₄, and concentrated at low pressure. The residue was purified on silica gel column (EA in PE from 2% to 50%) to provide 45-4 (1.0 g, 79%).

To a solution of 45-4 (950 mg, 1.02 mmol) in DCM (5 mL) was added pyridine (241 mg, 3.05 mmol) and Tf₂O (344 mg, 1.22 mmol) at 0° C. slowly. The mixture was stirred at RT for 12 h. Completion of the reaction was determined by TLC and LCMS. The reaction was quenched with sat. NaHCO₃ solution, and extracted with DCM (3×60 mL). The organic phase was dried over anhydrous Na₂SO₄, and concentrated at low pressure to give crude 45-5 (1.08 g, 1.02 mmol), which was used without further purification.

To a solution of 45-5 (1.08 g, 1.02 mmol) in THF (6 mL) was added TBAF (0.8 g, 3 mmol), and stirred at 30-40° C. for 12 h. The reaction was quenched with sat. NaHCO₃ solution, and extracted with EA (3×60 mL). The solution was dried over anhydrous Na₂SO₄, and concentrated at low pressure. The residue was purified by silica gel column (EA in PE from 2% to 50%) to afford 45-6 (0.62 g, 65%).

A mixture of 45-6 (0.55 g, 0.59 mmol) in TFA (90%, 5 mL) was stirred at 50-60° C. for 16 h. The mixture was treated with MeOH, and concentrated at low pressure. The residue was purified by prep-HPLC to afford compound 45 (60 mg, 31%). ESI-MS: m/z 324.0 [M+H]⁺.

Example 36

Compound 46

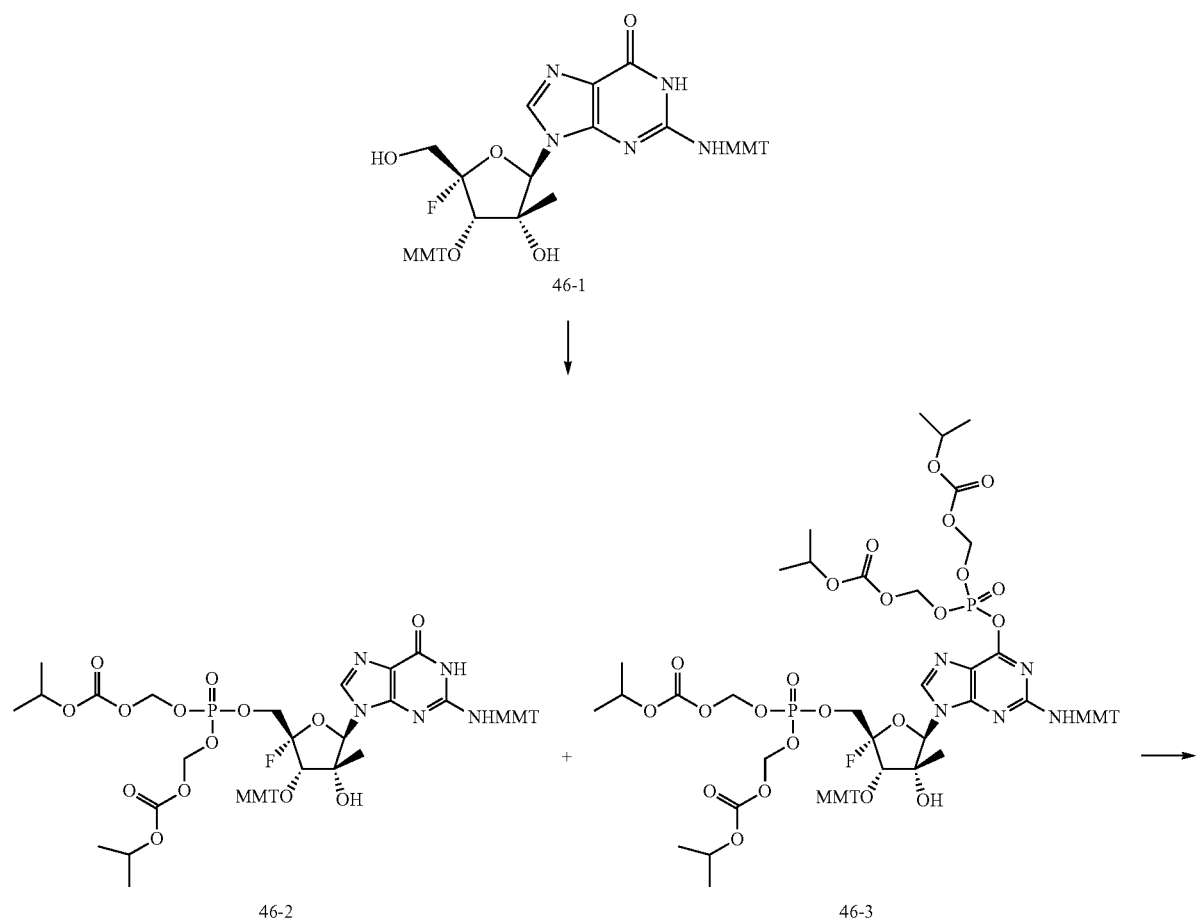

-continued

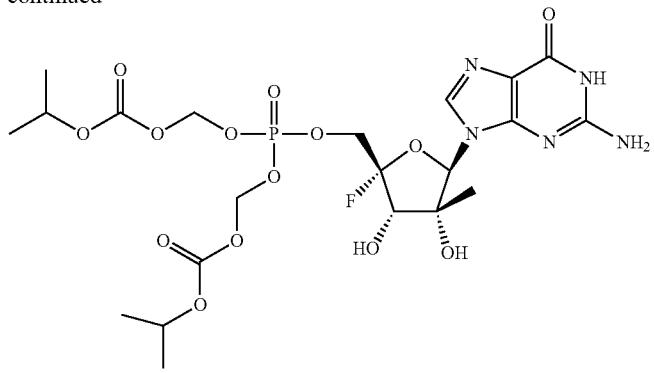

46

To a solution of triethylammonium bis(isopropyloxycarbonyloxymethyl)phosphate (0.33 mmol, prepared from 110 mg of bis(POC)phosphate and 46 µL of Et₃N) in THF was added 46-1 (91 mg, 0.11 mmol). The mixture evaporated and rendered anhydrous by co-evaporating with pyridine follow by toluene. The residue was dissolved in anhydrous THF (1.5 mL) and cooled in an ice-bath. Diisopropylethylamine (0.19 mL, 10 eq.) was added, followed by BOP-Cl (0.14 g, 5 eq.), and 3-nitro-1,2,4-triazole (63 mg, 5 eq.). The mixture was stirred 0° C. for 90 mins, diluted with EtOAc (30 mL), washed with sat. aq. NaHCO₃, brine, and dried (Na₂SO₄). The residue was purified on silica (10 g column) with CH₂Cl₂/i-PrOH solvent system (2-10% gradient) to obtain 46-2 (13 mg, 10%) and 46-3 (95 mg, 58%).

A solution of 46-2 and 46-3 (13 mg and 95 mg, respectively) in 80% aq. HCOOH (3 mL) was stirred at RT for 3 h, then evaporated and co-evaporated with toluene. The residue was purified on silica (10 g column) with CH₂Cl₂/MeOH (4-10% gradient) to obtain compound 46 in (42 mg, 94%) yield. MS: m/z=628 [M+1].

Example 37

Compound 47

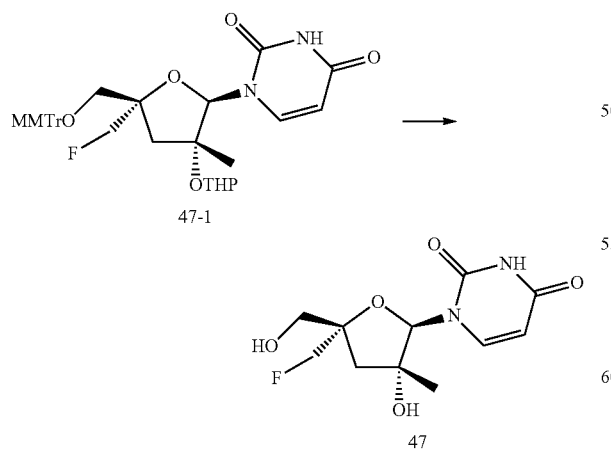

Compound 47-1 (320 mg, 0.51 mmol) was dissolved in a mixture of CH₃COOH/THF/H₂O (4/2/1) (7 mL), and the mixture was stirred at 50° C. for 2 h. The solution was concentrated to dryness, and the residue was purified by prep-HPLC to give compound 47 (38 mg, 31%) as a white solid. ESI-MS: m/z 296.9 [M+H+Na]⁺.

Example 38

Compound 48

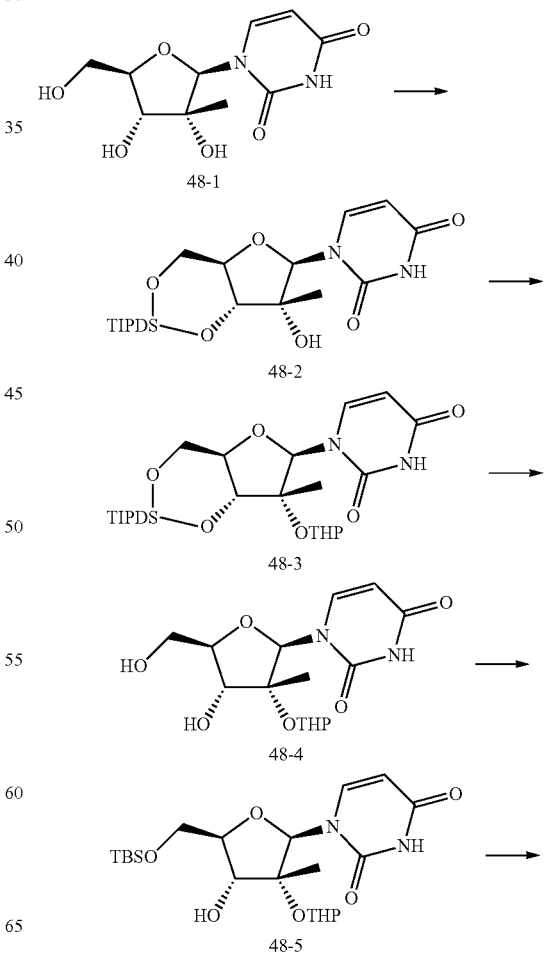

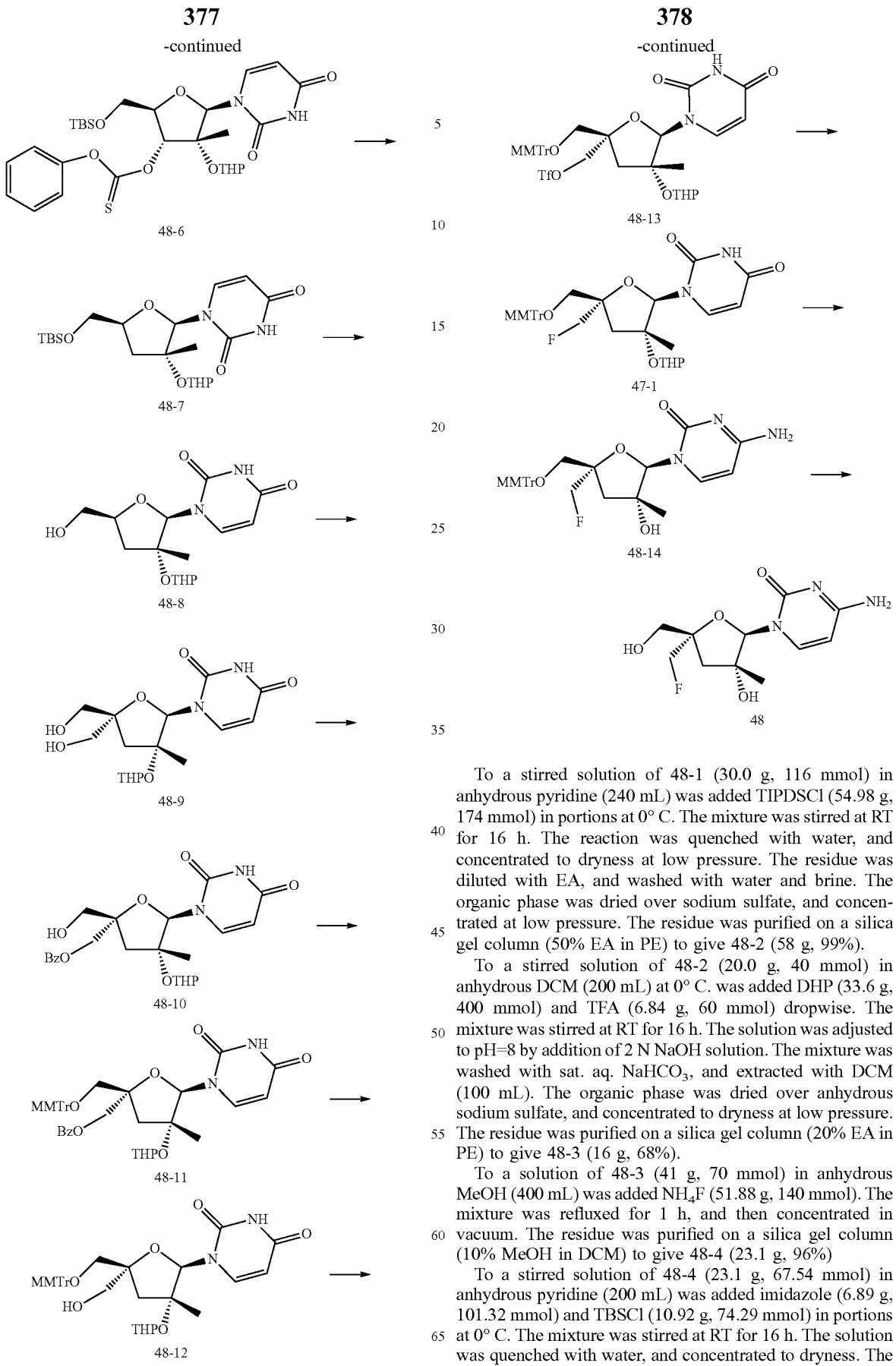

To a stirred solution of 48-1 (30.0 g, 116 mmol) in anhydrous pyridine (240 mL) was added TIPDSCl (54.98 g, 174 mmol) in portions at 0° C. The mixture was stirred at RT for 16 h. The reaction was quenched with water, and concentrated to dryness at low pressure. The residue was diluted with EA, and washed with water and brine. The organic phase was dried over sodium sulfate, and concentrated at low pressure. The residue was purified on a silica gel column (50% EA in PE) to give 48-2 (58 g, 99%).

To a stirred solution of 48-2 (20.0 g, 40 mmol) in anhydrous DCM (200 mL) at 0° C. was added DHP (33.6 g, 400 mmol) and TFA (6.84 g, 60 mmol) dropwise. The mixture was stirred at RT for 16 h. The solution was adjusted to pH=8 by addition of 2 N NaOH solution. The mixture was washed with sat. aq. NaHCO$_3$, and extracted with DCM (100 mL). The organic phase was dried over anhydrous sodium sulfate, and concentrated to dryness at low pressure. The residue was purified on a silica gel column (20% EA in PE) to give 48-3 (16 g, 68%).

To a solution of 48-3 (41 g, 70 mmol) in anhydrous MeOH (400 mL) was added NH$_4$F (51.88 g, 140 mmol). The mixture was refluxed for 1 h, and then concentrated in vacuum. The residue was purified on a silica gel column (10% MeOH in DCM) to give 48-4 (23.1 g, 96%)

To a stirred solution of 48-4 (23.1 g, 67.54 mmol) in anhydrous pyridine (200 mL) was added imidazole (6.89 g, 101.32 mmol) and TBSCl (10.92 g, 74.29 mmol) in portions at 0° C. The mixture was stirred at RT for 16 h. The solution was quenched with water, and concentrated to dryness. The residue was diluted with EA, and washed with water and brine. The organic phase was dried over anhydrous sodium sulfate, and concentrated at low pressure. The residue was purified on a silica gel column to give 48-5 (23 g, 74%).

To a solution of 48-5 (27.56 g, 60.44 mmol) in anhydrous MeCN (560 mL) was added DMAP (18.43 g, 151.1 mol) and PhOCSCl (14.55 g, 84.61 mmol) at 0° C. under $N_2$. The mixture was stirred at RT overnight, and the reaction was quenched with water. The mixture was extracted with EA. The organic phase was dried with anhydrous $Na_2SO_4$, and concentrated at low pressure. The residue was purified on a silica gel column eluted with 30% EA in PE to provide 48-6 (23 g, 64%).

To a solution of 48-6 (14.5 g, 24.5 mmol) in anhydrous toluene (700 mL) was added AIBN (1.21 g, 7.3 mmol) and $Bu_3SnH$ (10.73 g, 36.74 mmol) in toluene (10 mL). $N_2$ was bubbled into the solution for 30 mins. The mixture was warmed to 135° C. for 2 h. Saturated aqueous CsF was added, and the mixture was stirred for 1 h. The mixture was diluted with EA (150 mL), and washed successively with water, sat. aq. $NaHCO_3$ and brine. The organic layer was removed at low pressure. The residue was purified on a silica gel column (30% EA in PE) to provide 48-7 (10.5 g, 97%).

To a solution of 48-7 (21 g, 47.73 mmol) in anhydrous MeOH (200 mL) was added $NH_4F$ (35.32 g, 950 mmol). The mixture was refluxed for 1 h and concentrated in vacuum. The residue was purified on a silica gel column (20% MeOH in DCM) to give 48-8 (14 g, 90%).

TFA.Py (2.37 g, 12.27 mmol) was added to a mixture of 48-8 (4 g, 12.27 mmol) and DCC (7.58 g, 36.81 mmol) in anhydrous DMSO (40 mL) at RT under $N_2$ atmosphere. The mixture was stirred at RT for 2 h. 37% formaldehyde (10 mL, 115 mmol) was added at RT, and stirred for 15 mins, followed by treatment with 2N NaOH (20 mL, 40 mmol). The mixture was stirred at 30° C. overnight and neutralized with AcOH to pH=7. $NaBH_4$ (1.87 g, 49.08 mmol) was added in portions at 5° C., and the mixture was stirred at RT for 30 mins. The mixture was extracted with EtOAc (3×100 mL). The organic layer was dried over anhydrous $Na_2SO_4$ and concentrated at low pressure. The residue was purified on a silica gel column (5% MeOH in DCM) to give 48-9 (2 g, 46%) as a white solid.

To a solution of 48-9 (2 g, 5.62 mmol) in anhydrous $CH_3CN$ (8 mL) was added pyridine (10 mL) and BzCl (0.79 g, 5.62 mmol) in a solution of DCM (2 mL) at 0° C. under $N_2$. The mixture was stirred at RT overnight. The reaction was quenched with water, and concentrated at low pressure. The residue was diluted with EA (50 mL), and washed successively with water and brine. The organic layer was dried over anhydrous $Na_2SO_4$, and concentrated at a low pressure. The residue was purified on a silica gel column (3% MeOH in DCM) to provide 48-10 (1.6 g, 62%)

To a solution of 48-10 (1.6 g, 3.48 mmol) in anhydrous pyridine (16 mL) was added MMTrCl (1.61 g, 5.22 mmol) at 0° C. under $N_2$. The mixture was stirred at RT overnight. The reaction was quenched with water, and concentrated in vacuo. The residue was diluted with EA (50 mL) and washed successively with water and brine. The organic layer was dried over $Na_2SO_4$ and concentrated at a low pressure to give crude 48-11 (2.55 g, 100%), which used without further purification.

To a solution of 48-11 (2.55 g, 3.48 mmol) in anhydrous MeOH (50 mL) was added $NaOCH_3$ (0.28 g, 5.23 mmol). The mixture was stirred at 45° C. for 2 h, bubbled to pH=7 by using dry ice and concentrated to dryness. The residue was purified on a silica gel column (2% MeOH in DCM) to give 48-12 (0.93 g, 42%).

To a solution of 48-12 (0.93 g, 1.48 mmol) in anhydrous DCM (10 mL) was added pyridine (1.17 g, 14.8 mmol) at −30° C. $Tf_2O$ (0.63 g, 2.22 mmol) in DCM (3 mL) was added dropwise. The mixture was stirred at −30° C.-0° C. for 20 mins and at 0° C. for 10 mins. The reaction was quenched with water, and the mixture was extracted with DCM (3×100 mL). The organic layer was dried over anhydrous $Na_2SO_4$, and concentrated at low pressure to provide crude 48-13 (1.13 g, 100%), which was used without further purification.

To a solution of 48-13 (1.13 g, 1.48 mmol) in anhydrous THF (10 mL) was added TBAF (3.86 g, 14.8 mmol). The mixture was stirred at 30° C. for 2 h. The reaction was quenched with water, and the mixture was extracted with EtOAc (3×100 mL). The organic layer was dried over anhydrous $Na_2SO_4$, and concentrated to dryness at low pressure. The residue was purified on a silica gel column (3% MeOH in DCM) to give 47-1 (0.42 g, 45%).

To a solution of 47-1 (50 mg, 0.079 mmol) in anhydrous $CH_3CN$ (1 mL) was added TPSCl (48.07 mg, 0.16 mmol), DMAP (19.36 mg, 0.16 mmol) and $NEt_3$ (0.2 mL) at RT. The mixture was stirred at RT for 3 h. 28% aqueous ammonia (0.4 mL) was added, and the mixture was stirred for 1 h. The mixture was diluted with EA (150 mL), and washed successively with water, sat. aq. $NaHCO_3$ and brine. The organic layer was dried over anhydrous $Na_2SO_4$, and concentrated at a low pressure. The residue was purified on a silica gel column (5% MeOH in DCM) to give 48-14 (40 mg, 80%).

Compound 48-14 (320 mg, 0.51 mmol) was dissolved in 80% HCOOH (6 mL), and the mixture was stirred at 10° C. for 1 h. The mixture was concentrated at low pressure, and the residue was purified by prep-HPLC to give compound 48 (43 mg, 31%) as a white solid. ESI-MS: m/z 273.9 $[M+H]^+$, 547.1 $[2M+H]^+$.

Example 39

Compound 49

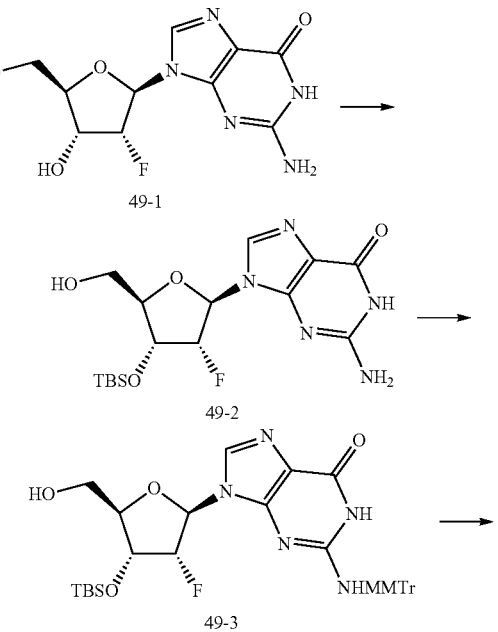

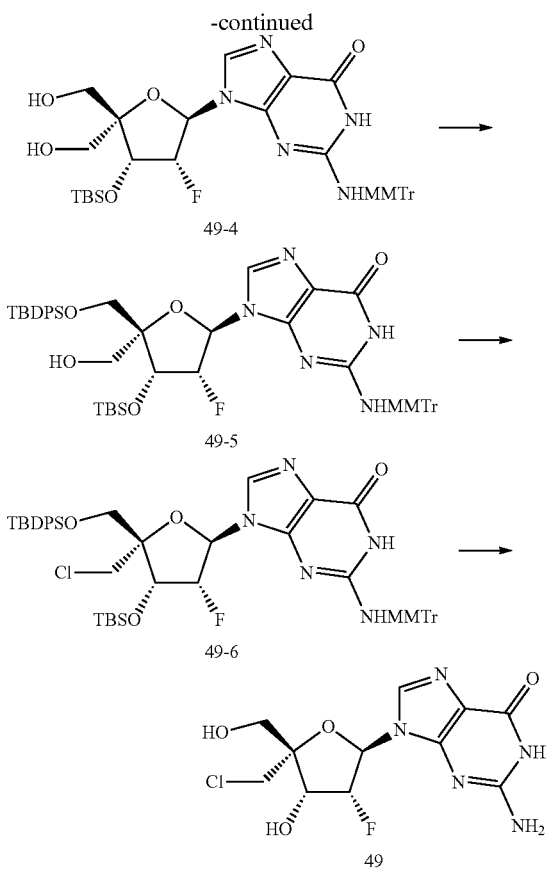

To a solution of 49-1 (20.0 g, 70.2 mmol) in anhydrous pyridine (200 mL) was added imidazole (19.1 g, 280 mmol) and TBSCl (42.1 g, 281 mmol) at 25° C. The solution was stirred at 25° C. for 15 h, and then concentrated to dryness under reduced pressure. The residue was dissolved in EtOAc and then filtered. The filtrate was concentrated to dryness to give the TBS protected derivative (36.4 g, 99%). The TBS protected derivative (36.5 g, 71.1 mmol) was dissolved in THF (150 mL). H$_2$O (100 mL), and then AcOH (300 mL) were added. The solution was stirred at 80° C. for 13 h. The reaction was cooled to RT, and then concentrated to dryness under reduced pressure to give 49-2 (31.2 g, 61%) as a white solid.

To a solution of 49-2 (31.2 g, 78.2 mmol) in anhydrous pyridine (300 mL) was added Ac$_2$O (11.9 g, 117.3 mmol). The mixture was stirred at 25° C. for 18 h. MMTrCl (72.3 g, 234.6 mmol) and AgNO$_3$ (39.9 g, 234.6 mmol) were added, and the solution was stirred at 25° C. for 15 h. H$_2$O was added to quench the reaction and the solution was concentrated to dryness under reduced pressure. The residue was dissolved in EtOAc and washed with water. The organic layer was dried over Na$_2$SO$_4$ and filtered. The filtrate was concentrated in vacuum to give a residue, which was purified by silica gel (DCM:MeOH=200:1 to 50:1) to give the MMTr protected amine derivative (35.2 g, 63%). The MMTr protected amine derivative (35.2 g, 49.3 mmol) was dissolved in NH$_3$/MeOH (300 mL). The mixture was stirred at 25° C. for 20 h. The solution was evaporated to dryness, and purified by a silica gel column (DCM:MeOH=100:1 to 50:1) to give 49-3 as a yellow solid (28.6 g, 87%).

To a solution of 49-3 (12.0 g, 17.9 mmol) in anhydrous DCM (200 mL) was added Dess-Martin periodinane (11.3 g, 26.8 mmol) at 0° C. The mixture was stirred at 0° C. for 2 h, and then at RT for 2 h. The mixture was quenched with a saturated NaHCO$_3$ and Na$_2$S$_2$O$_3$ solution. The organic layer was washed with brine (2×) and dried over anhydrous Na$_2$SO$_4$. The solvent was evaporated to give the aldehyde (12.6 g), which was used directly in the next step. To a solution of the aldehyde (12.6 g, 18.0 mmol) in 1,4-dioxane (120 mL) was added 37% HCHO (11.6 g, 144 mmol) and 2N NaOH aqueous solution (13.5 mL, 27 mmol). The mixture was stirred at 25° C. overnight. EtOH (60 mL) and NaBH$_4$ (10.9 g, 288 mmol) were added, and the reaction was stirred for 30 mins. The mixture was quenched with saturated aqueous NH$_4$Cl, and then extracted with EA. The organic layer was dried over Na$_2$SO$_4$, and purified by silica gel column chromatography (DCM:MeOH=200:1 to 50:1) to give 49-4 (7.5 g, 59%) as a yellow solid.

To a solution of 49-4 (3.8 g, 5.4 mmol) in DCM (40 mL) was added pyridine (10 mL) and DMTrCl (1.8 g, 5.4 mmol) at 0° C. The solution was stirred at 25° C. for 1 h. MeOH (15 mL) was added, and the solution was concentrated. The residue was purified by silica gel column chromatography (DCM:MeOH=200:1 to 50:1) to give the MMTr protected derivative (3.6 g, 66%) as a yellow solid. To a solution of the MMTr protected derivative (3.6 g, 3.6 mmol) in anhydrous pyridine (30 mL) was added TBDPSCl (2.96 g, 10.8 mmol) and AgNO$_3$ (1.84 g, 10.8 mmol). The mixture was stirred at 25° C. for 15 h. The mixture was filtered and concentrated. The mixture was dissolved in EtOAc and washed with brine. The organic layer was dried over Na$_2$SO$_4$, and then purified by silica gel column chromatography (DCM:MeOH=200:1 to 50:1) to give the TBDPS protected derivative (3.8 g, 85.1%) as a solid. To a solution of the TBDPS protected derivative (3.6 g, 2.9 mmol) in anhydrous DCM (50 mL) was added Cl$_2$CHCOOH (1.8 mL) in anhydrous DCM (18 mL). The mixture was stirred at −78° C. for 1 h. Cl$_2$CHCOOH (3.6 mL) was added at −78° C. The mixture was stirred at −10° C. for 30 mins. The mixture was quenched with saturated aqueous NaHCO$_3$ and extracted with DCM. The organic layer was dried over Na$_2$SO$_4$, and then purified by silica gel column chromatography (DCM:MeOH=200:1 to 50:1) to give 49-5 (2.2 g, 80%).

To an ice cooled solution of 49-5 (800 mg, 0.85 mmol) in anhydrous DCM (20 mL) was added pyridine (336 mg, 4.25 mmol) and Tf$_2$O (360 mg, 1.28 mmol) dropwise. The reaction mixture was stirred at 0° C. for 15 mins. The reaction was quenched by ice water and stirred for 30 mins. The mixture was extracted with EtOAc, washed with brine (50 mL) and dried over MgSO$_4$. The solvent was evaporated to give the crude bis(triflate) derivative. To the bis(triflate) derivative (790 mg, 0.73 mmol) in anhydrous DMF (35 mL) was added LiCl (302 mg, 7.19 mmol). The mixture was heated to 40° C. and stirred overnight. Completion of the reaction was determined by LCMS. The solution was washed with brine and extracted with EtOAc. The combined organic layers were dried over MgSO$_4$, and the residue was purified on a silica gel column (DCM/MeOH=100:1) to give 49-6 (430 mg, 61%).

To 49-6 (470 mg, 0.49 mmol) in MeOH (85 mL) was added NH$_4$F (8.1 g, 5.92 mmol), and the solution was heated to reflux overnight. The mixture was filtered, and the filtrate was concentrated to dryness. The residue was purified on a silica gel column (DCM/MeOH=20:1) to give the diol (250 mg, 84%) as a white solid. The diol (130 mg, 0.21 mmol) in formic acid (5 mL) was stirred at 25° C. overnight. The solution was concentration to dryness, and the residue in MeOH (30 mL) was stirred at 70° C. overnight. Completion of the reaction was determined by LCMS and HPLC. The solvent was removed, and the crude product was washed with EtOAc to give compound 49 (58 mg, 81%) as a white solid. ESI-MS: m/z 333.8 [M+H]$^+$, 666.6 [2M+H]$^+$.
Example 40
Compound 50
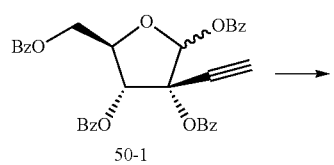
50-1
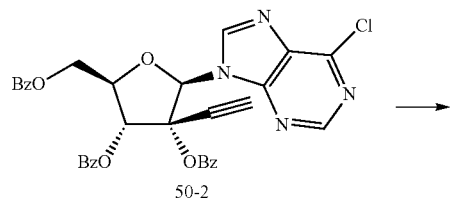
50-2
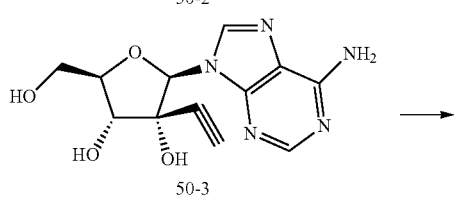
50-3
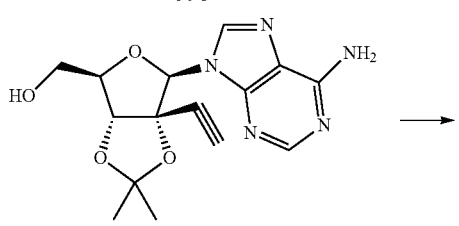
50-4
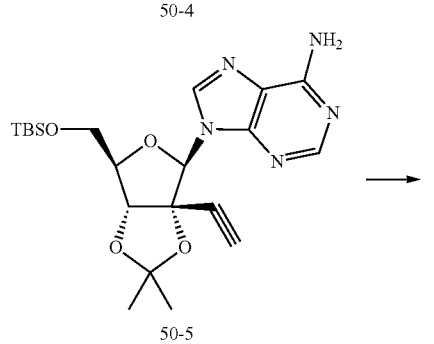
50-5
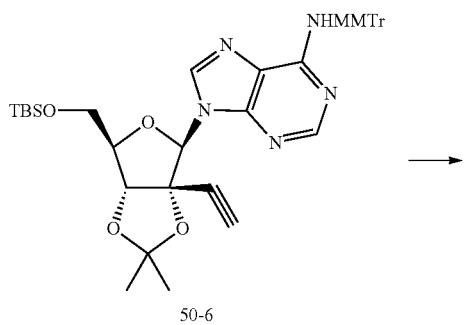
50-6
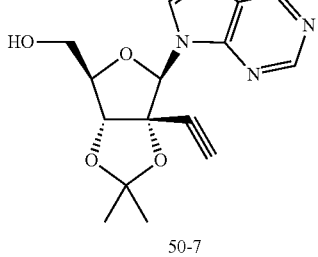
50-7
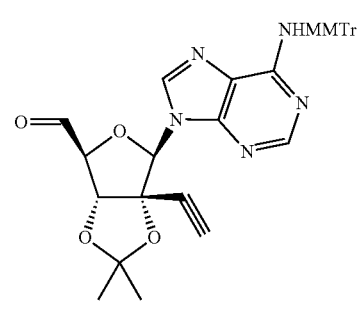
50-8
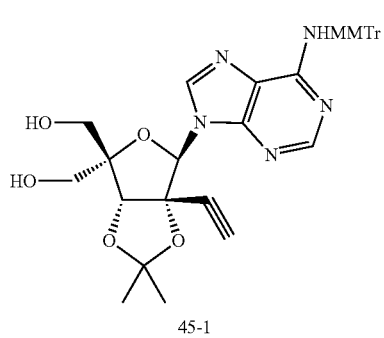
45-1
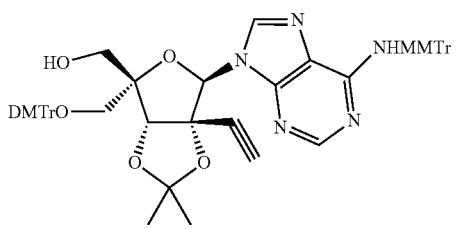
50-9
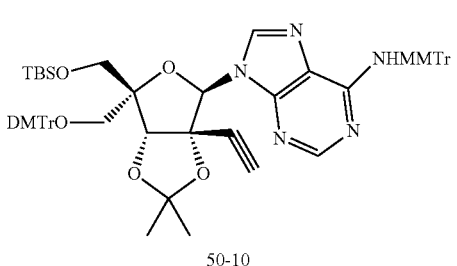
50-10

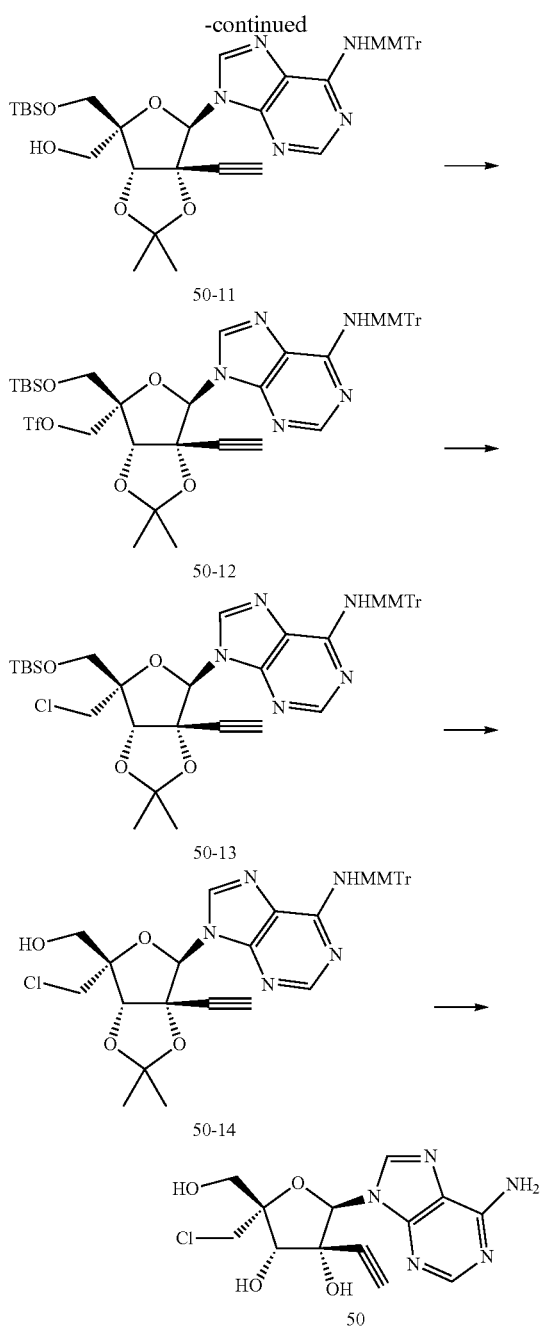

Compound 50-1 (5.0 g, 8.5 mmol) and 6-chloropurine (3.0 g, 17.7 mmol) were co-evaporated with anhydrous toluene 3 times. To a stirred suspension of 50-1 and 6-chloropurine in anhydrous MeCN (50 mL) was added DBU (7.5 g, 49 mmol) at 0° C. The mixture was stirred at 0° C. for 15 mins, and TMSOTf (15 g, 67.6 mmol) was added dropwise at 0° C. The mixture was stirred at 0° C. for 15 mins until a clear solution formed. The mixture was heated to 70° C., and stirred overnight. The reaction was monitored by LCMS. The mixture was cooled to RT, and diluted with EA (100 mL). The solution was washed with sat. NaHCO$_3$ solution and brine. The organic layer was dried over anhydrous Na$_2$SO$_4$, and concentrated at low pressure. The residue was purified on silica gel column (EA in PE from 6% to 50%) to afford 50-2 (2.5 g, 46.3%) as a white foam.

Compound 50-2 (3.0 g, 4.8 mmol) was treated with NH$_3$ in MeOH (8 N, 20 mL) in autoclave at 40-60° C. for 12 h. The mixture was evaporated at low pressure, and the residue was purified on silica gel column (MeOH in EA from 0 to 10%) to give 50-3 (1.0 g, 71%) as a white foam.

To a solution of 50-3 (4.3 g, 14.8 mmol) in acetone/DMF (4/1, 40 mL) was added TsOH.H$_2$O (8.4 g, 0.044 mol) and 2,2-dimethoxypropane (30 g, 0.296 mol), and the mixture stirred at 60-70° C. for 12 h. The mixture was concentrated at low pressure, and the residue was purified on silica gel column (EA in PE from 50% to 100%) to give 50-4 (5.0 g, 83%).

To a solution of 50-4 (10.5 g, 31.7 mmol) in pyridine (50 mL) was added TBSCl (5.3 g, 34.9 mmol), and the mixture stirred at RT for 12 h. The solvent was removed at low pressure, and the residue was dissolved in DCM (100 mL). The solution was washed with brine, dried over anhydrous Na$_2$SO$_4$, and concentrated at low pressure. The residue was purified by silica gel column to provide 50-5 (8.4 g, 60%), which used without further purification.

Compound 50-5 (8.4 g, 18.8 mmol) was co-evaporated with pyridine. To a stirred solution of 50-5 (8.4 g, 18.8 mmol) in pyridine (35 mL) was added MMTrCl (8.1 g, 26.4 mmol). The mixture was stirred at 30-40° C. for 12 h under N$_2$. The mixture was concentrated at a low pressure, and the residue was dissolved in DCM (150 mL). The solution was washed with saturated NaHCO$_3$ solution, dried over anhydrous Na$_2$SO$_4$, and concentrated at low pressure. The residue was purified on silica gel column (EA in PE from 10% to 20%) to provide 50-6 (10.8 g, 80%) as a solid To a solution of 50-6 (11.5 g, 0.016 mol) in THF (100 mL) was added TBAF (4.62 g, 0.018 mol) at RT, and the mixture stirred for 4 h. The solvent was evaporated at low pressure, and the mixture was dissolved in DCM (150 mL). The solution was washed with brine, dried over anhydrous Na$_2$SO$_4$, and concentrated at low pressure. The residue was purified on silica gel column (EA in PE from 50% to 100%) to afford 50-7 (8.8 g, 91%). ESI-MS: m/z 604.4 [M+H]$^+$.

To a solution of 50-7 (4.4 g, 7.3 mmol) in dioxane (50 mL) was added DCC (4.5 g, 21.9 mmol), DMSO (2.5 mL), TFA.Py (1.48 g, 7.65 mmol) at 0° C. The mixture was slowly warm to RT and stirred for 4 h. Completion of the reaction was determined by LCMS. The mixture was concentrated at low pressure. The residue was purified on silica gel column to give 50-8 (4.4 g, 7.3 mmol), which was used without further purification.

To a solution of 50-8 in dioxane (40 mL) was added water (20 mL), HCHO (37%, 7 mL) and NaOH (1N, 15 mL). The solution was stirred at RT overnight. The mixture was treated with NaBH$_4$ (1.1 g, 29.2 mmol) slowly, and stirred for 30 mins. The mixture was adjusted to pH=7-8 by slow addition of HCl (1M) solution, and extracted with EA (150 mL). The solution was washed with brine, dried over anhydrous Na$_2$SO$_4$, and concentrated at low pressure. The residue was purified on silica gel column to give 45-1 (3.0 g, 65%). ESI-MS: m/z 633.9 [M+H]$^+$.

To a solution of 45-1 (1.5 g, 2.37 mmol) in anhydrous pyridine (30 mL) was added DMTrCl (3.6 g, 10.7 mmol) at −30° C. The mixture was stirred at RT overnight. The solution was quenched with MeOH, and concentrated at low pressure. The residue was purified by column chromatography to give 50-9 (3 g, 45%) as a yellow solid To a solution of 50-9 (1.1 g, 1.18 mmol) in pyridine (10 mL) was added imidazole (0.24 g, 3.53 mmol) and TBSCl (0.35 g, 2.35 mmol). The mixture was stirred at RT for 12 h. The solvent was evaporated at low pressure, and the residue was dissolved in EA (50 mL). The solution was washed with brine, dried over anhydrous Na₂SO₄, and concentrated at low pressure. The residue was purified on silica gel column (30% EA in PE) to afford 50-10 (0.83 g, 67%)

To a solution of 50-10 (1.1 g, 1.05 mmol) in DCM (12 mL) was added Cl₂CHCOOH (0.5 mL) at −70° C., and stirred for 1 h. The solution was treated with Cl₂CHCOOH (1 mL) in DCM (10 mL) at −70° C., and the mixture was stirred at −70~−10° C. for 20 mins. Completion of the reaction was determined by LCMS. The reaction was quenched with sat. NaHCO₃ solution, and extracted with DCM (3×40 mL). The organic phase was dried over anhydrous Na₂SO₄, and concentrated at low pressure. The residue was purified on silica gel column (EA in PE from 15% to 30%) to afford 50-11 (0.58 g, 74%).

To a solution of 50-11 (200 mg, 0.268 mmol) and pyridine (53 mg, 0.67 mmol) in anhydrous DCM (5 mL) was added Tf₂O (90 mg, 0.32 mmol) at −30° C. The mixture was stirred for 1 h, and slowly warmed to RT. Completion of the reaction was determined by TLC. The reaction was quenched with sat. NaHCO₃ solution, and extracted with DCM (3×30 mL). The organic phase was dried over anhydrous Na₂SO₄, and concentrated to dryness at low pressure. Crude 50-12 (200 mg, 0.27 mmol) was used without further purification.

To a solution of 50-12 (200 mg, 0.27 mmol) in DMF (5 mL) was added LiCl (45 mg, 1.07 mmol), and stirred at 30-40° C. for 12 h. The solvent was evaporated at low pressure, and the residue was dissolved in DCM (10 mL). The solution was washed with brine, dried over anhydrous Na₂SO₄, and concentrated at low pressure. Crude 50-13 was used without further purification.

A mixture of 50-13 (245 mg, 0.32 mmol) and TBAF (200 mg, 0.7 mmol) in THF was stirred at 30° C. for 1 h. The mixture was concentrated at a low pressure, and the residue was dissolved in DCM (15 mL). The solution was washed with brine, dried over anhydrous Na₂SO₄, and concentrated at low pressure. The residue was purified on silica gel column (EA in PE from 2% to 50%) to provide 50-14 (150 mg, 72%). ESI-MS: m/z 652.3 [M+H]⁺.

Compound 50-14 (0.2 mmol) was dissolved in 50% TFA (10 mL) in methanol, and the mixture was kept at RT overnight. The solvent was evaporated and co-evaporated with methanol/toluene mixture to remove traces of acid. The residue was dissolved in 20% triethylamine in methanol, kept for 15 mins and evaporated. The product was isolated by RP HPLC on Synergy 4 micron Hydro-RP column (Phenominex). A linear gradient of methanol from 0 to 60% in 50 mM triethylammonium acetate buffer (pH 7.5) was used for elution. The corresponding fractions were combined, concentrated and lyophilized 3 times to remove excess buffer. Compound 50 was obtained (45 mg, 67%). MS: m/z 338.0 [M−1].

Example 41

Compound 51

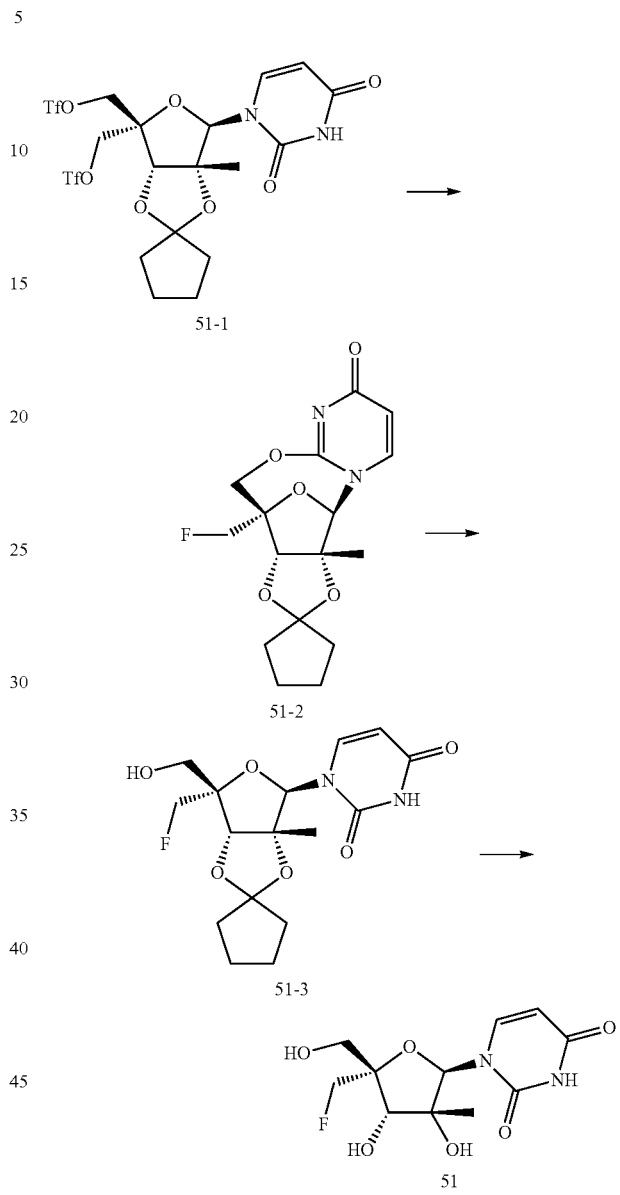

To a solution of 51-1 (12.3 g, 19.9 mmol) in DMF (50 mL) was added NaH (800 mg, 20 mmol) at 0° C. The mixture was stirred at RT for 3 h. The mixture was treated with CsF (30.4 g, 200 mmol), and then stirred at RT for 3 h. The reaction was quenched with water, and extracted with EA. The organic layer was dried over anhydrous Na₂SO₄, and concentrated to dryness at low pressure. The residue was purified on silica gel column (20% EA in PE) to give 51-2 (4.1 g, 61%) as a white solid.

To a solution of 51-2 (4.1 g, 12.1 mmol) in THF (120 mL) was added NaOH solution (1N, 13 mL) at 0° C. The mixture was stirred at RT for 3 h. The solution was neutralized with 0.5 M HCl aq. to pH~7. The mixture was partitioned between EA and water. The organic layer was dried over anhydrous Na₂SO₄, and concentrated to dryness at low pressure. The residue was purified on silica gel column (30%

EA in PE) to give 51-3 (3.1 g, 72%) as a white solid. ESI-MS: m/z 379.1 [M+Na]+.

Compound 51-3 (0.2 mmol) was dissolved in 80% HCOOH (10 mL), and the mixture was heated at 45° C. for 24 h. The solvent was evaporated and co-evaporated with methanol/toluene mixture to remove traces of acid. The residue was dissolved in 20% triethylamine in methanol, kept for 15 mins and evaporated. Compound 51 (68%) was isolated by silica gel chromatography in gradient of methanol in DCM from 5% to 20%. MS: m/z 289.0 [M−1].

Example 42

Compound 52

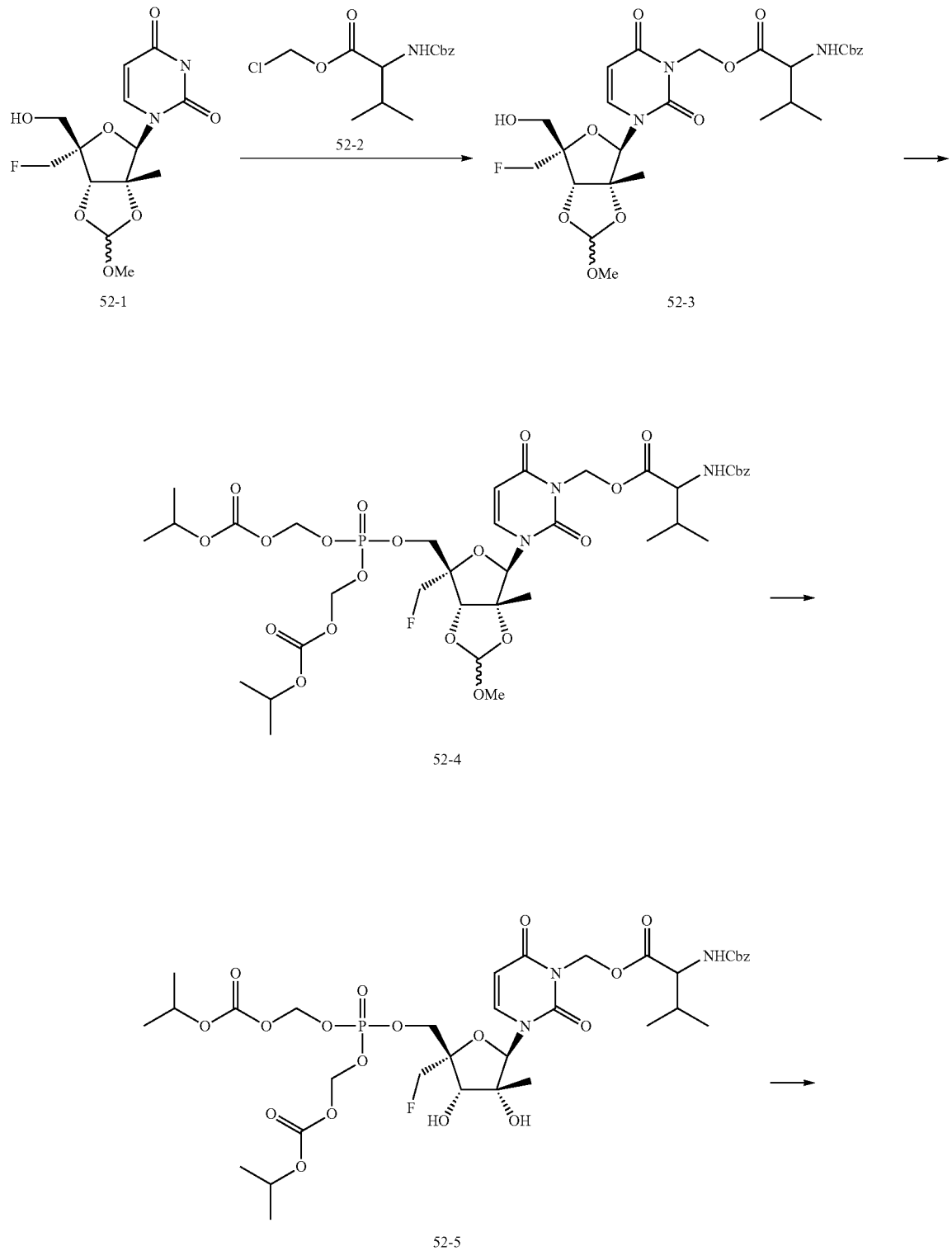

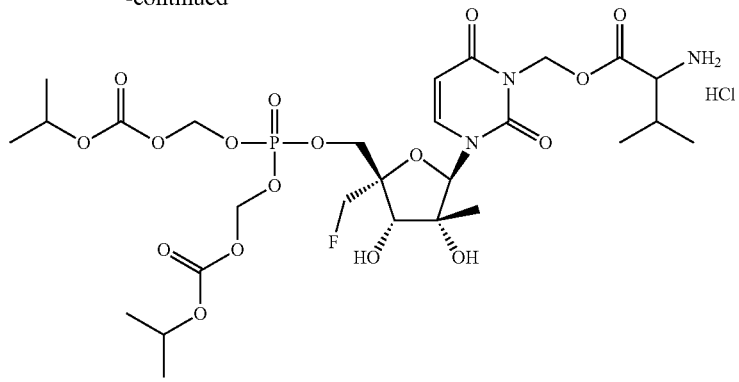

52

A mixture of 52-2 (1.2 g; 4 mmol) and NaI (0.6 g; 4 mmol) in acetone (13 mL) was stirred at RT for 1 h. Compound 52-1 (1 g; 3 mmol) and $K_2CO_3$ (2.07 g; 45 mmol) were added. The mixture was stirred at RT for 24 h. The precipitate was filtered, and the filtrate was evaporated. Purification of the residue on silica (25 g column) with hexanes/EtOAc (30-100% gradient) yielded 52-3 as a colorless foam (1.14 g; 64%).

To a solution of triethylammonium bis(isopropyloxycarbonyloxymethyl)phosphate (2.3 mmol, prepared from of bis(POC)phosphate (0.75 g) and $Et_3N$ (0.32 mL)) in THF was added 52-3 (1.14 g; 1.9 mmol). The mixture evaporated and rendered anhydrous by co-evaporating with pyridine follow by toluene. The residue was dissolved in anhydrous THF (20 mL) and cooled down in an ice-bath. Diisopropylethylamine (1.0 mL; 2 eq.) was added, followed by BOP-Cl (0.72 g; 1.5 eq.) and 3-nitro-1,2,4-triazole (0.32 g; 1.5 eq.). The n mixture was stirred at 0° C. for 90 mins, diluted with EtOAc, washed with sat. aq. $NaHCO_3$ and brine, and dried ($Na_2SO_4$). The residue was purified on silica (25 g column) with $CH_2Cl_2$/i-PrOH (3-10% gradient) to yield (1.2 g, 70%) of 52-4.

A solution of 52-4 (1.2 g; 1.3 mmol) in 80% aq. HCOOH was stirred at RT for 2 h, and then concentrated. The residue was co-evaporated with toluene and then with MeOH containing small amount of $Et_3N$ (2 drops). Purification on silica (25 g column) with $CH_2Cl_2$/i-PrOH (4-10% gradient) yielded 52-5 (0.96 g, 85%).

To a solution of 52-5 (0.52 g; 0.57 mmol) in EtOH (25 mL) were added HCl (4 N/dioxane; 0.29 mL, 2 eq.) and 10% Pd/C (25 mg). The mixture was stirred under $H_2$ (normal pressure) for 1 h. The catalyst was removed by filtration through a Celite pad, and the filtrate was evaporated to yield compound 52 as its HCl salt (4.2 g; 96%). MS: m/z=732 [M+1].

Example 43

Compound 53

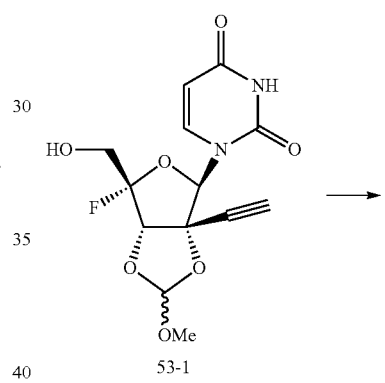

53-1

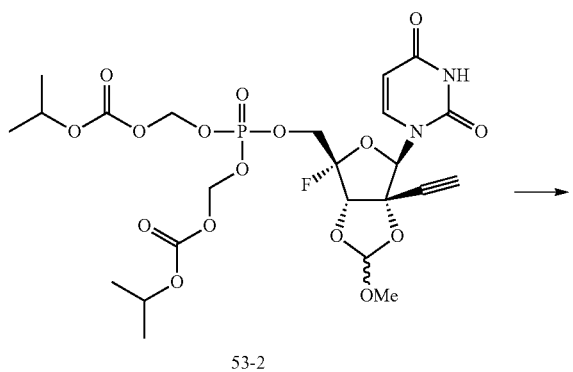

53-2

393

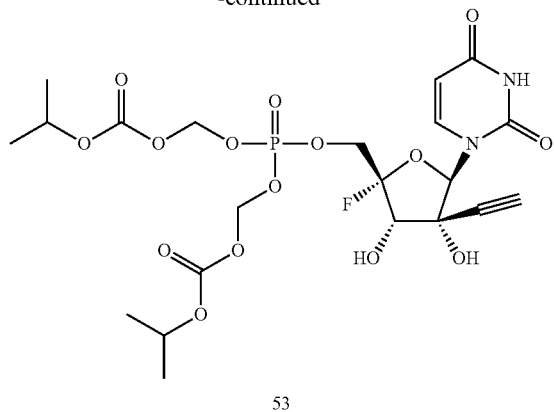

53

Compound 53-2 (0.20 g, 64%) was prepared in the same manner from 53-1 (0.16 g; 0.49 mmol) and triethylammonium bis(isopropyloxycarbonyloxymethyl)phosphate (0.74 mmol) with DIPEA (0.34 mL), BopCl (250 mg), and 3-nitro-1,2,4-triazole (112 mg) in THF (5 mL) following the procedure for the preparation of 52-4.

A solution of 53-2 (0.20 g; 0.31 mmol) in 80% aq. HCOOH was stirred at RT for 2 h, and then concentrated. The residue was co-evaporated with toluene and then with MeOH containing small amount of $Et_3N$ (2 drops). Purification on silica gel (10 g column) with $CH_2Cl_2$/MeOH (4-10% gradient) was followed by RP-HPLC purification in 5 runs on a Synergi Hydro RP column 250×30 mm (Phenomenex P/N 00G-4375-U0-AX) using $H_2O$ and ACN both 50 mM TEAA. Gradient was 25-75% ACN in 20 mins at 24 mL/mins, 254 nM detection. The product eluted at 16.0 mins. Pure fractions were pooled and lyophilized. TEAA was removed by dissolving the product in DMSO (2 mL) and injecting the product on the same column using only $H_2O$ and ACN. Pure fractions were pooled and lyophilized to produce compound 53 (18 mg). MS: m/z=1197 [2M+1].

Example 44

Compound 54

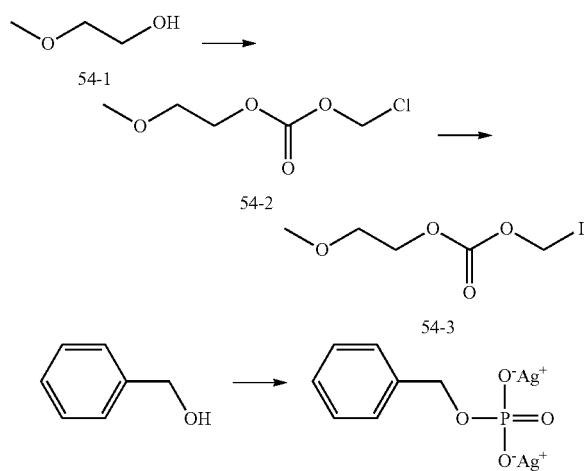

394

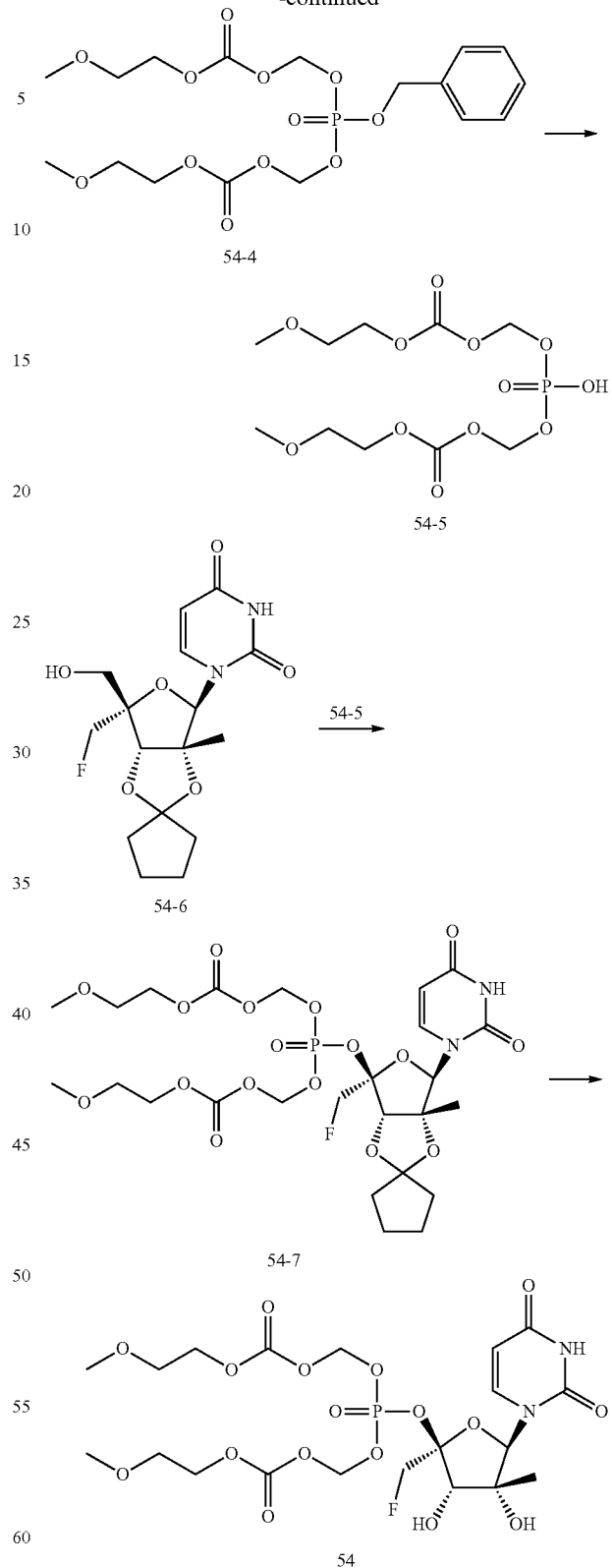

Chloromethyl chloroformate (112 mmol; 10.0 mL) was added to an ice cooled solution of 2-methoxyethanol (97 mmol; 7.7 mL) in dichloromethane (DMC) (100 mL) followed by pyridine (9.96 mL) at 0° C. After stirring overnight at RT, the mixture was washed twice with 0.5 M HCl, followed by water and aqueous sodium bicarbonate. The mixture was dried over magnesium sulfate, filtered, evaporated in vacuo and distillation in vacuo to afford 54-2 as a colorless oil (13.0 g).

Compound 54-2 (5.7 g) was added to a solution of sodium iodide (21.07 g) in acetone (45 mL). After 20 stirring at 40° C. for 2.5 h, the mixture was cooled in ice, filtered and evaporated in vacuo. The residue was taken up in dichloromethane, washed with aqueous sodium bicarbonate and sodium thiosulfate, dried over magnesium sulfate, filtered and evaporated in vacuo to give 54-3 as a light yellow oil of 54-3 (8.5 g), which was used without further purification.

A mixture of phosphoric acid (crystal, 2.4 g) and triethylamine (6.6 mL) in benzyl alcohol (13 g; 12.5 mL) was stirred at RT until the phosphoric acid was completely dissolved. Trichloroacetonitrile (17.2 g; 11.94 mL) was added, and the mixture was stirred at RT for 18 h. The solvent and excess trichloroacetonitrile were removed under reduced pressure. The residue was dissolved in water (about 200 mL), and the aqueous solution washed with ether (3×50 mL). Benzylphosphoric acid (triethylamine salt) was obtained after lyophilization as a yellowish semi-solid (7.15 g). A solution of benzylphosphoric acid (TEA salt, 1.6 g) in MeOH (90 mL) and water (30 mL) was treated with Dowex 50WX2-400 ("153 mL" settled resin) at RT for 18 h. The resin was removed by filtration, and silver carbonate powder (1.25 g) was added to the filtrate. After the suspension was heated at 80° C. for 1 h, all solvent was removed under reduced pressure to dryness. The solid was used without further purification.

Dry acetonitrile (25 mL) was added to benzylphosphoric acid (silver salt) followed by addition of 54-3 (3.12 g; 12 mmol). The suspension was stirred at RT overnight. After the solid was removed by filtration, the product was purified by silica gel chromatography using hexane/ethyl acetate (3:1 v/v) as the eluent to give 54-4 as a colorless liquid (860 mg, 50%).

Compound 54-4 (750 mg; 1.65 mmol) was dissolved in methanol (10 mL). Pd-on-carbon (85 mg) and TEA (1 eq.) were added. The flask was charged with hydrogen gas for 1 h. The catalyst was filtered, and the solvent removed in vacuo to give 54-5 (triethylammonium salt) (510 mg) which was used immediately without further purification.

Compound 54-6 (320 mg; 0.9 mmol) and 54-5 (510 mg, 1.35 mmol; 1.5×) were co-evaporated twice with pyridine and twice with toluene. Compounds 54-5 and 54-6 were dissolved in THF (8 mL) at 0° C. Diisopropylethylamine (DIPEA) (0.62 mL; 4 eq.), bis(2-oxo-3-oxazolidinyl) phosphinic chloride (Bop-Cl) (0.45 g; 2 eq.), nitrotriazole (0.2 g, 2 eq.) were added. The mixture was kept at 0° C. for 2 h and then diluted with EA (50 mL). The mixture was then extracted with sat. sodium bicarbonate (2×50 mL) and dried over sodium sulfate. The solvents were removed in vacuo. The residue was purified by flash chromatography using a 10 to 100% gradient of EA in hexane to give purified 54-7 (430 mg, 0.6 mmol).

Purified 54-7 was dissolved in 80% aq. HCOOH (20 mL) and kept at 45° C. for 18 h. After cooling to RT, the solvent was removed in vacuo. The residue co-evaporated with toluene (3×25 mL). The residue was purified by flash chromatography using a 0 to 20% gradient of methanol in DCM to give purified compound 54 (200 mg, 0.3 mmol). $^1$H-NMR (CDCl$_3$): δ 9.28 (s, 1H), 7.54 (d, 1H), 5.95 (s, 1H), 5.65-5.81 (m, 5H), (d, 2H), 4.76 (dd, 2H), 4.44-4.46 (m, 1H), 4.35-4.40 (m, 5H), 4.22 (2H), 4.04 (1H), 3.65 (t, 4H), 3.39 (6H), 1.8 (s, 1H), 1.24 (s, 3H). $^{31}$P-NMR (CDCl$_3$): δ −4.09 ppm.

Example 45

Compound 55

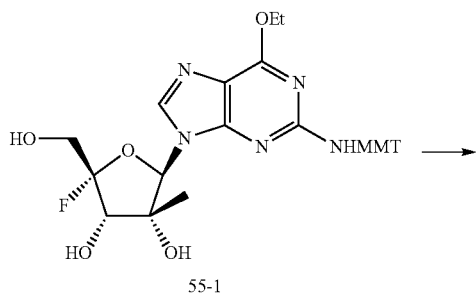

55-1

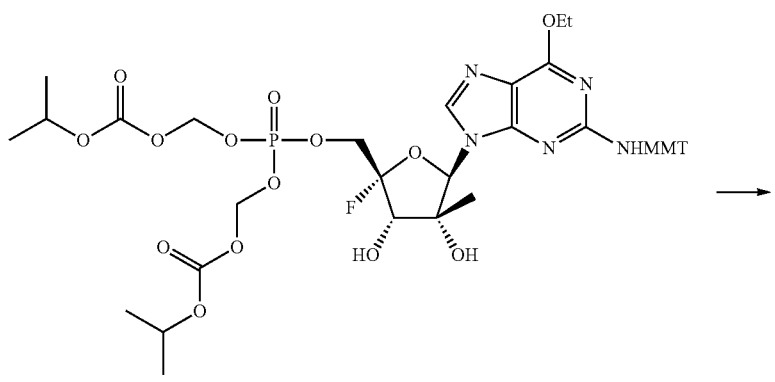

55-2

-continued

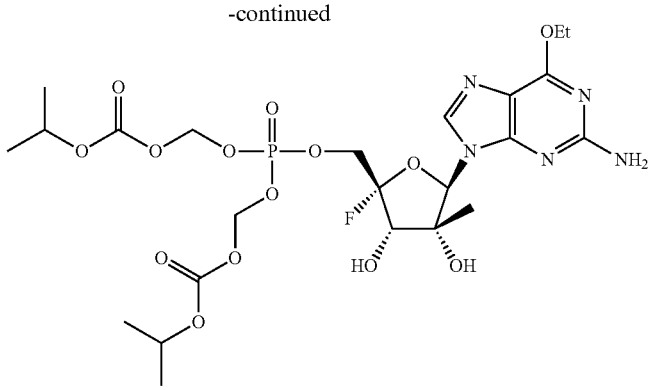

55

Compound 55-2 (158 mg, 50%) was prepared from 55-1 (0.21 g; 0.35 mmol) and triethylammonium bis(isopropyloxycarbonyloxymethyl)phosphate (0.54 mmol) with DIPEA (0.18 mL), BopCl (178 mg), and 3-nitro-1,2,4-triazole (80 mg) in THF (4 mL).

A solution of 55-2 (158 mg) in acetonitrile (1 mL) and HCl (4 N/dioxane; 85 μL) was stirred at RT for 30 mins. The reaction was quenched with MeOH and concentrated. The residue was purified on silica gel (10 g column) with $CH_2Cl_2$/i-PrOH (3-10% gradient) to give compound 55 (85 mg, 76%). MS: m/z=656 [M+1].

Example 46

Compound 56

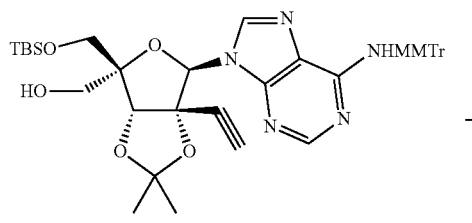

49-3

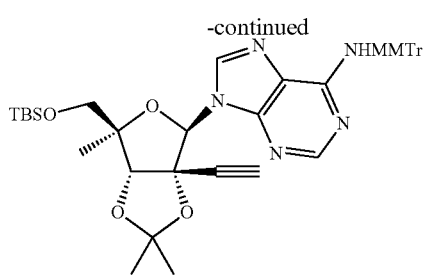

56-1

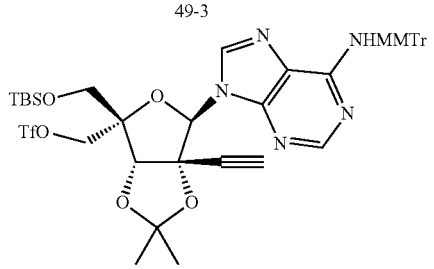

56-2

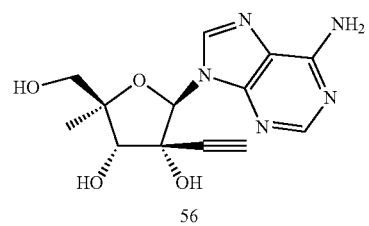

56-3

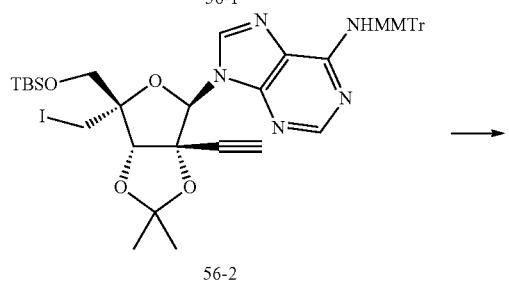

56

To a solution of 49-3 (300 mg, 0.4 mmol) and pyridine (80 mg, 1.0 mmol) in DCM (5 mL) was added $Tf_2O$ (136 mg, 0.48 mol) in a solution of DCM (1 mL) dropwise at −30° C. The mixture was stirred at −30° C. to 0° C. for 20 mins. The reaction was quenched with water, and extracted with DCM (20 mL). The organic phase was dried over anhydrous $Na_2SO_4$, and evaporated to give crude 56-1 (352.8 mg, 0.4 mmol), which was used without further purification.

To a solution of 56-1 (352.8 mg, 0.4 mmol) in DMF (5 mL) was added NaI (480 mg, 3.2 mmol). The mixture was stirred at 30° C. for 10 h. The reaction was quenched with water, and extracted with DCM (20 mL). The organic phase was dried over anhydrous $Na_2SO_4$, and concentrated to dryness at low pressure. The residue was purified by prep-TLC (30% EA in PE) to give 56-2 (270 mg, 31%).

To a solution of 56-2 (600 mg, 0.7 mmol) in anhydrous toluene (30 mL) was added AIBN (34 mg, 0.21 mmol) and $Bu_3SnH$ (307.7 mg, 1.05 mmol) in toluene (10 mL). The mixture was bubbled with $N_2$ for 30 mins, and heated to 135° C. for 2 h. The mixture was treated with sat. aq. CsF, and then stirred for 2 h. The mixture was diluted with EA (100 mL). The organic phase was washed with brine, dried over anhydrous $Na_2SO_4$ and concentrated at low pressure. The residue was purified on a silica gel column (10% EA in PE) to give 56-3 and a by-product (400 mg, 72%).

A mixture of 56-3 (400 mg, 0.55 mmol) in 90% TFA (10 mL) was stirred at 50° C. for 4 h. The reaction was monitored by LCMS. The mixture was treated with MeOH (5 mL), and concentrated under reducing pressure. The residue was purified by prep-HPLC to give compound 56 (46 mg, 27%). ESI-MS: m/z 306.1 [M+H]⁺.

Example 47

Compound 57

Compound 57-2 (120 mg, 72%) was prepared in the same manner from 57-1 (0.11 g; 0.18 mmol) and triethylammonium bis(isopropyloxycarbonyloxymethyl)phosphate (0.35 mmol) with DIPEA (0.15 mL), BopCl (114 mg), and 3-nitro-1,2,4-triazole (51 mg) in THF (2.5 mL) using the method as described for 52-4 from 52-3.

Compound 57 (14 mg, 77%) was prepared from 57-2 (25 mg) in acetonitrile (0.1 mL) and 4 N HCl/dioxane (8 μL) using the method as described for compound 55. MS: m/z=658 [M+1].

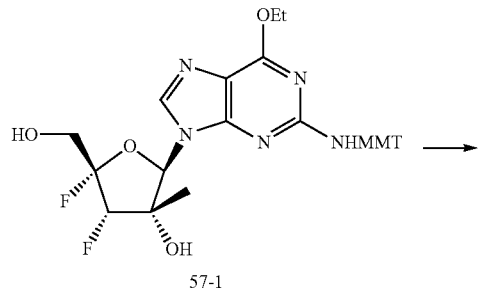

57-1

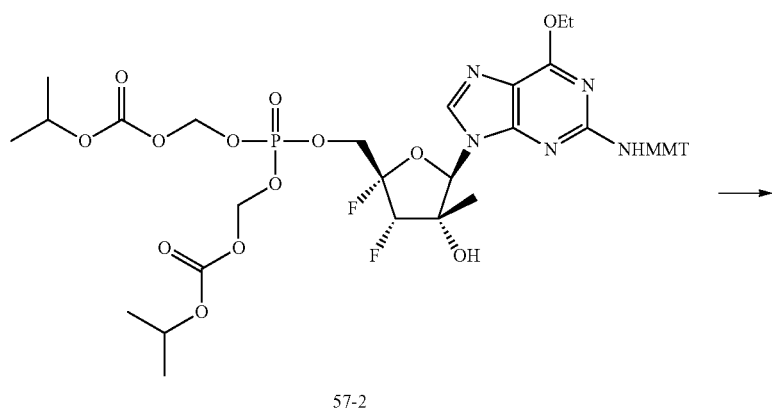

57-2

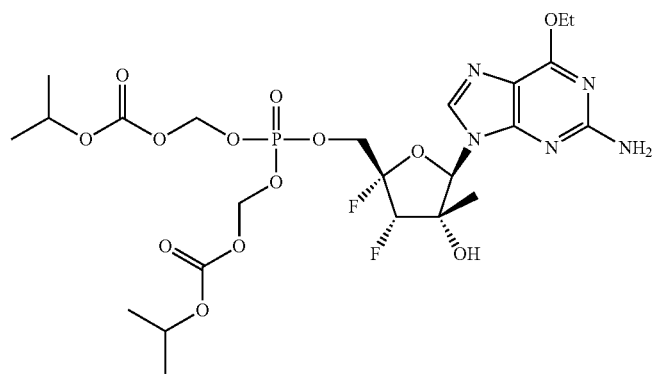

57

Example 48

Compound 60

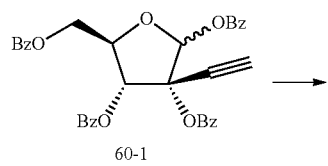
60-1

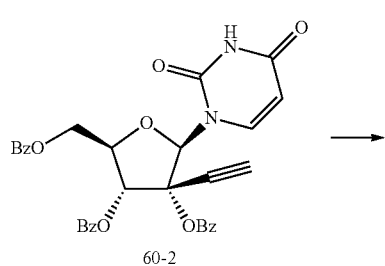
60-2

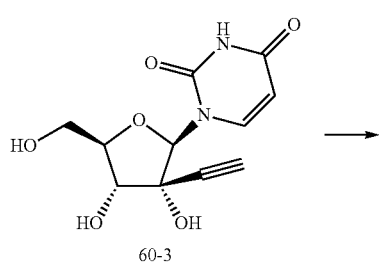
60-3

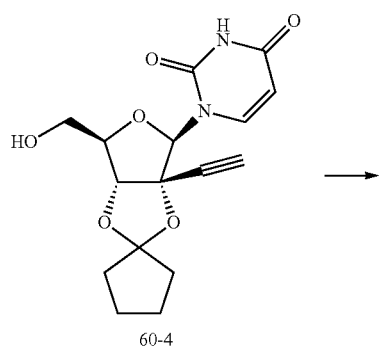
60-4

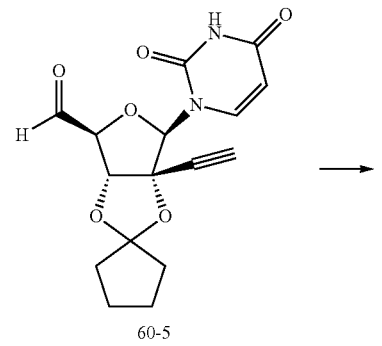
60-5

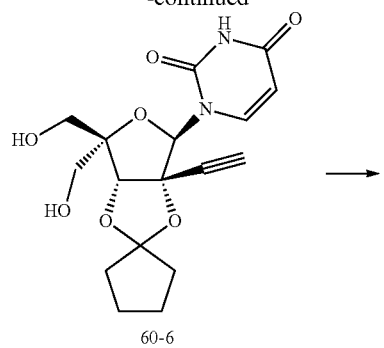
60-6

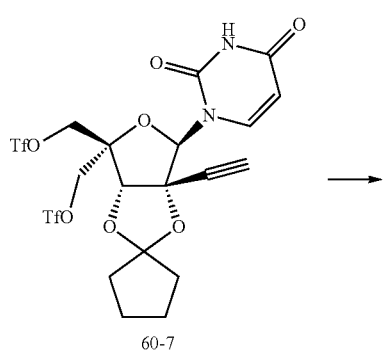
60-7

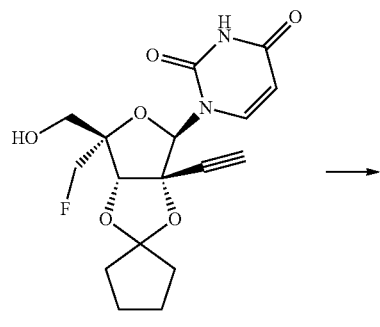
60-8

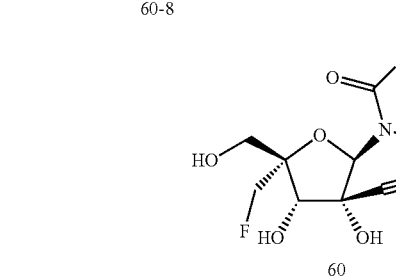
60

To a stirred solution of uracil (21 g, 188 mmol) in anhydrous MeCN (200 mL) was added BSA (110 g, 541 mmol), and the mixture was refluxed for 2 h. The mixture was then cooled to RT and treated with 60-1 (55 g, 93.2 mmol) and TMSOTf (145 g, 653 mmol). The mixture was refluxed overnight. After the starting material disappeared, the reaction was quenched with sat. NaHCO$_3$ solution, and extracted with EA. The organic layer was dried over anhydrous Na$_2$SO$_4$, and concentrated to dryness at low pressure. The residue was purified on silica column gel (20% EA in PE) to give 60-2 (38 g, 70%) as a white sold.

Compound 60-2 (35 g, 0.06 mol) was treated with NH$_3$ in MeOH (7N, 200 mL) at RT. The mixture was stirred for 24 h at RT. Completion of the reaction was determined by LCMS. The mixture was concentrated at a low pressure, and the residue was washed with DCM to give 60-3 (13 g, 81%) as a white solid.

To a solution of cyclopentanone (6 g, 8.33 mmol), and trimethoxymethane (8 mL) in MeOH (60 mL) was added TsOH (1.35 g, 7.1 mmol) at RT, and the mixture was stirred 2 h. The resulting was quenched with NaOMe (0.385 g, 7.12 mmol), and extracted with n-hexane (30 mL). The organic layer was dried over anhydrous $Na_2SO_4$, and concentrated at low pressure to give 1,1-dimethoxycyclopentane. To a solution of 60-3 (30 g, 0.11 mol) and 1,1-dimethoxy cyclopentane (57 g, 0.44 mol) in 1,2-dichloroethane (200 mL) was added TsOH (2.1 g, 0.011 mol), and the mixture was heated to 60° C. overnight. The reaction was quenched with triethylamine, and concentrated to dryness at low pressure. The residue was washed with MeOH to give 60-4 (30 g, 82%).

To a solution of 60-4 (10 g, 30 mmol) in anhydrous $CH_3CN$ (100 mL) was added IBX (8.4 g, 30 mmol, 1.05 eq.) at RT. The mixture was refluxed for 12 h., and then cooled to 0° C. The precipitate was removed by filtration, and the filtrate was concentrated to give crude 60-5 (10 g, 100%) as a yellow solid.

Crude 60-5 (10 g, 30 mmol) was dissolved in 1,4-dioxane (100 mL). 37% HCHO (10 mL) and 2N NaOH aqueous solution (20 mL) were added at RT. The mixture was stirred at RT overnight, and adjusted to pH=7. The mixture was treated with $NaBH_4$ (4.44 g, 120 mmol) at 0° C. The reaction was stirred at RT for 30 mins and then quenched with sat. aq. $NH_4Cl$. The mixture was extracted with EA. The organic layer was dried over $Na_2SO_4$, and concentrated to dryness at low pressure. The residue was purified by silica gel column chromatography (1-3% MeOH in DCM) to give 60-6 (5.5 g, 50%) as a white solid.

To a stirred solution of 60-6 (5.0 g, 13.8 mmol) and pyridine (5 mL) in DCM (20 mL) was added $Tf_2O$ (8.5 g, 30.3 mmol) dropwise at −70° C. The solution was warmed to 0° C. slowly, stirred at 0° C. for 0.5 h, and washed with HCl (0.5 M). The DCM layer was concentrated to dryness at low pressure, and the residue was purified on silica gel column to give 60-7 (4.5 g, 52%) as a white solid.

To a solution of 60-7 (3.0 g, 4.8 mmol) in MeCN (10 mL) was added TBAF (5.0 g, 19.2 mmol). The reaction was allowed to proceed overnight. The reaction was monitored by HPLC and LCMS. Aqueous sodium hydroxide (1N~2 eq.) was added, and the solution was stirred for 1 h. The mixture was partitioned between sat. ammonium chloride solution and EA. The organic layer was separated, and concentrated under reduced pressure. The crude product was purified on silica gel column to give 60-8 (0.8 g, 46%) as a white solid. ESI-MS: m/z 367.0 [M+H]$^+$, 389.0 [M+Na]$^+$.

Compound 60-8 (0.2 mmol) was dissolved in 80% HCOOH (10 mL), and the mixture was heated at 45° C. for 24 h. The solvent was evaporated and co-evaporated with methanol/toluene mixture to remove traces of acid. The residue was dissolved in 20% triethylamine in methanol, kept for 15 mins and evaporated. Compound 60 (65-68%) was isolated by silica gel chromatography in gradient of methanol in DCM from 5% to 20%. MS: m/z 321.0 [M−1].

Example 49

Compound 63

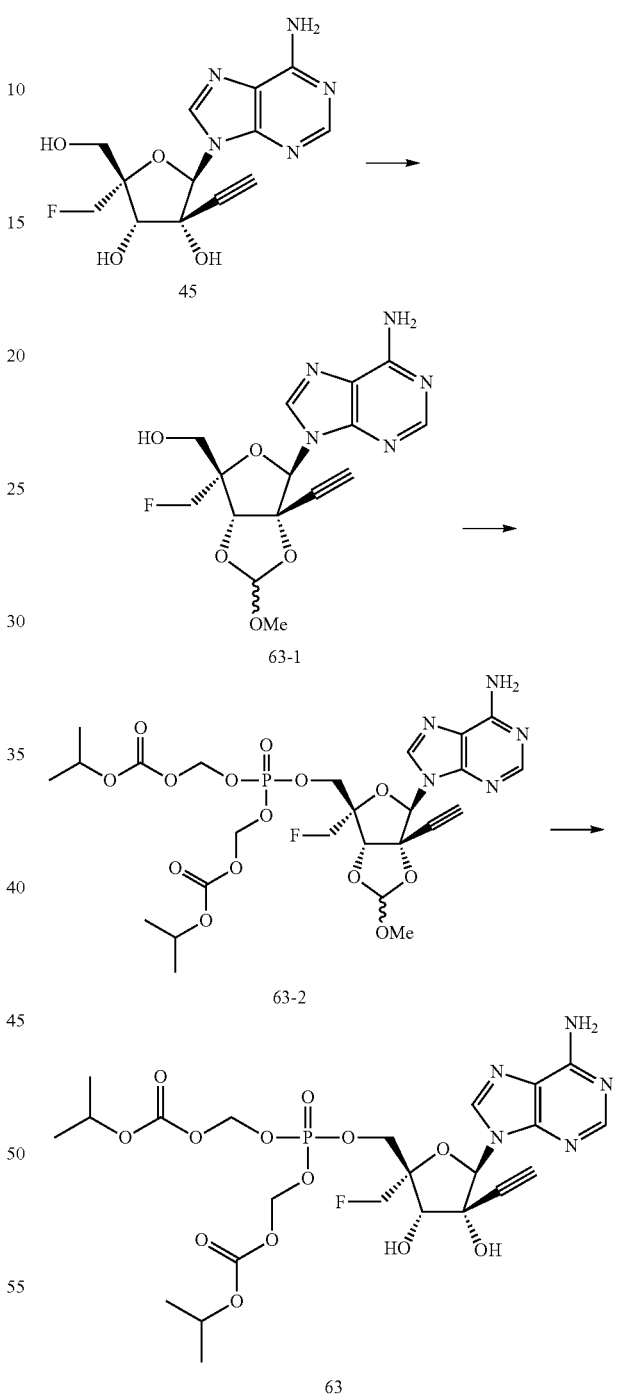

A mixture of compound 45 (30 mg, 0.09 mmol), PTSA monohydrate (18 mg, 1 eq.), and trimethyl orthoformate (0.3 mL; 30 eq.) in dioxane (1 mL) was stirred 1 d at RT. The reaction was neutralized with $NH_3$/MeOH and then filtered. The filtrate was dissolved in a mixture of THF (0.5 mL) and 80% aq. AcOH (0.25 mL). The solution kept for 1 h at RT, and then evaporated. The residue was purified on silica gel (10 g column) with CH₂Cl₂/MeOH (4-15% gradient) to yield 63-1 (30 mg, 91%).

Compound 63-2 (28 mg, 52%) was prepared in the same manner from 63-1 (30 mg, 0.08 mmol) and triethylammonium bis(isopropyloxycarbonyloxymethyl)phosphate (0.12 mmol) with DIPEA (56 µL), BopCl (40 mg), and 3-nitro-1,2,4-triazole (18 mg) in THF (1 mL) using the method for preparing 52-4 from 52-3. Purification was done with CH₂Cl₂/MeOH (4-10% gradient).

Compound 63 (15 mg, 67%) was prepared from 63-2 (24 mg) using the method for preparing 52-5. Purification was done with CH₂Cl₂/MeOH (4-10% gradient). MS: m/z=636 [M+1].

Example 50

Compound 64

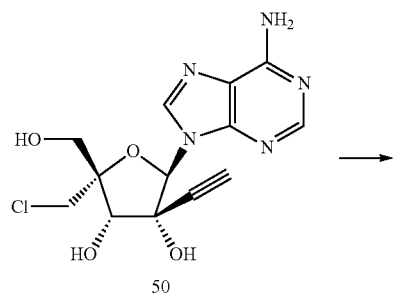

50

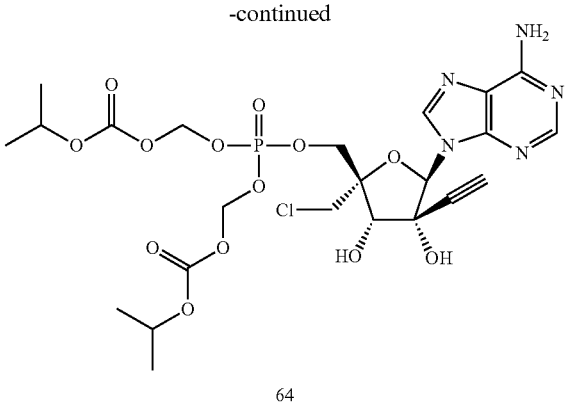

64

Compound 64-1 (8 mg, 40%) was prepared from compound 50 (17 mg) and trimethylorthoformate (0.15 mL) with PTSA monohydrate (9 mg) in dioxane (0.5 mL) in the same manner as 63-1.

Compound 64-2 (10 mg, 72%) was prepared in the same manner from 64-1 (8 mg, 0.02 mmol) and triethylammonium bis(isopropyloxycarbonyloxymethyl)phosphate (0.036 mmol) with DIPEA (14 µL), BopCl (10 mg), and 3-nitro-1,2,4-triazole (5 mg) in THF (0.4 mL) in the same manner as 63-2.

Compound 64 (15 mg, 67%) was prepared from 64-2 (24 mg) in the same manner as 63. MS: m/z=652 [M+1].

Example 51

Compound 65

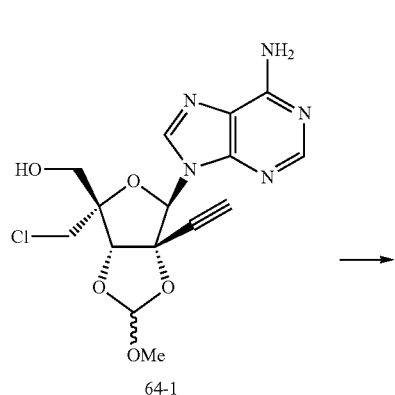

64-1

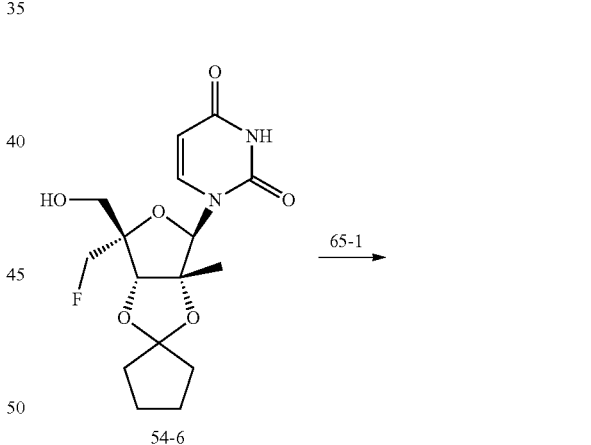

54-6

64-2

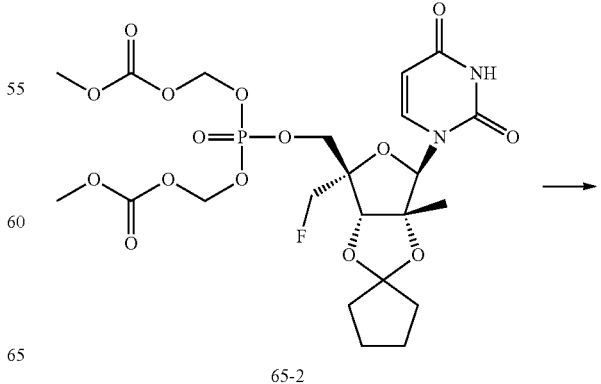

65-2

-continued

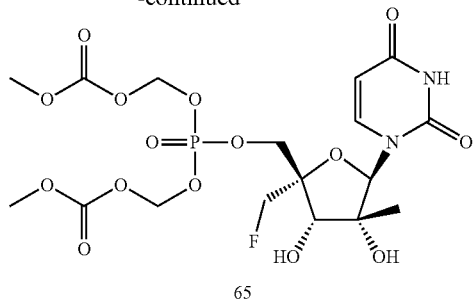

65

Commercially available chloromethyl methyl carbonate (5.0 g) was treated with NaI to give 65a (5.38 g). Benzylphosphate (silver salt) and 65a were reacted to yield purified 65b (1.5 g) as described for compound 54. $^1$H-NMR (CD$_3$CN): δ 7.39-7.42 (m, 5H), 5.60 (d, 4H), 5.11 (d, 2H), 3.8 (s, 6H). $^{31}$P-NMR (CD$_3$CN): δ -4.47 ppm. Compound 65b (415 mg; 1.7 mmol) was deprotected to give 65-1 (triethylammonium salt) (510 mg), which was used immediately without further purification. Compound 54-6 (320 mg; 0.9 mmol) and 65-1 (510 mg) were reacted to purified 65-2 (400 mg). Compound 65-2 (230 mg) was deprotected to give purified compound 65 (250 mg). The aforementioned reactions were conducted using a method described in the preparation of compound 54. $^1$H-NMR (CDCl$_3$): δ 9.00 (s, 1H), 7.55 (d, 1H), 5.93 (s, 1H), 5.81 (d, 1H), 5.66-5.75 (m, 4H), 4.76 (dd, 2H), 4.37-4.46 (m, 2H), 4.15 (d, 2H), 3.86 (t, 6H), 3.70 (d, 6H), 1.65 (s, 6H), 1.25 (s, 3H). $^{31}$P-NMR (CDCl$_3$): δ -4.13 ppm.

Example 52

Compound 66

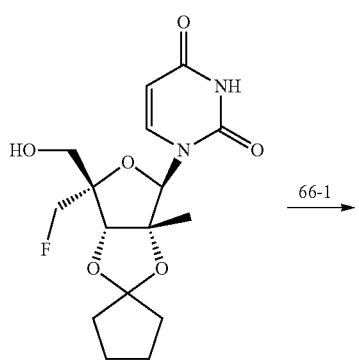

54-6

-continued

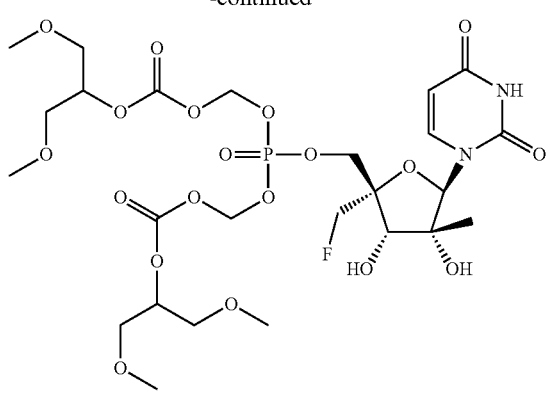

66

Compound 66a was prepared from 1,3-dimethoxypropan-2-ol. $^1$H-NMR (CDCl$_3$) δ 5.73 (s, 2H), 5.03-5.06 (m, 1H), 3.59 (d, 4H), 3.38 (s, 6H). Dry ACN (25 mL) was added to benzylphosphate (silver salt) (5 mmol) followed by addition of 66a (3.12 g; 12 mmol). The suspension was heated at 60° C. for 18 h. After the solid was removed by filtration, the product was purified by silica gel chromatography using hexane/EA (3:1) as the eluent to provide 66b as a colorless liquid (540 mg, 50%). $^1$H-NMR (CD$_3$CN): δ 7.39-7.42 (m, 5H), 5.61 (d, 4H), 5.10 (d, 2H), 4.97-5.01 (m, 2H), 3.50-3.52 (m, 8H), 3.30 (s, 6H), 3.28 (s, 6H). $^{31}$P-NMR (CD$_3$CN): δ -4.42 ppm. Compound 66b (540 mg; 1.0 mmol) was deprotected to give 66-1 (triethylammonium salt), which was used immediately without further purification. Compound 54-6 (285 mg; 0.8 mmol) and 66-1 were reacted to give purified 66-2 (300 mg). Compound 66-2 (300 mg) was deprotected to give purified compound 66 (290 mg). The aforementioned reactions were conducted using a method described in the preparation of compound 54. $^1$H-NMR (CDCl$_3$): δ 9.35 (s, 1H), 7.56 (d, 1H), 6.1 (s, 1H), 5.66-5.82 (m, 5H), 5.04 (s, 1H), 4.76 (dd, 2H), 4.60 (d, ½H), 4.37-4.48 (m, 2H), 4.22 (d, 2H), 4.06 (s, 1H), 3.58 (s, 8H), 3.57 (s, 12H), 1.93 (s, 1H), 1.23 (s, 3H). $^{31}$P-NMR (CDCl$_3$): δ -4.08 ppm.

Example 53

Compound 67

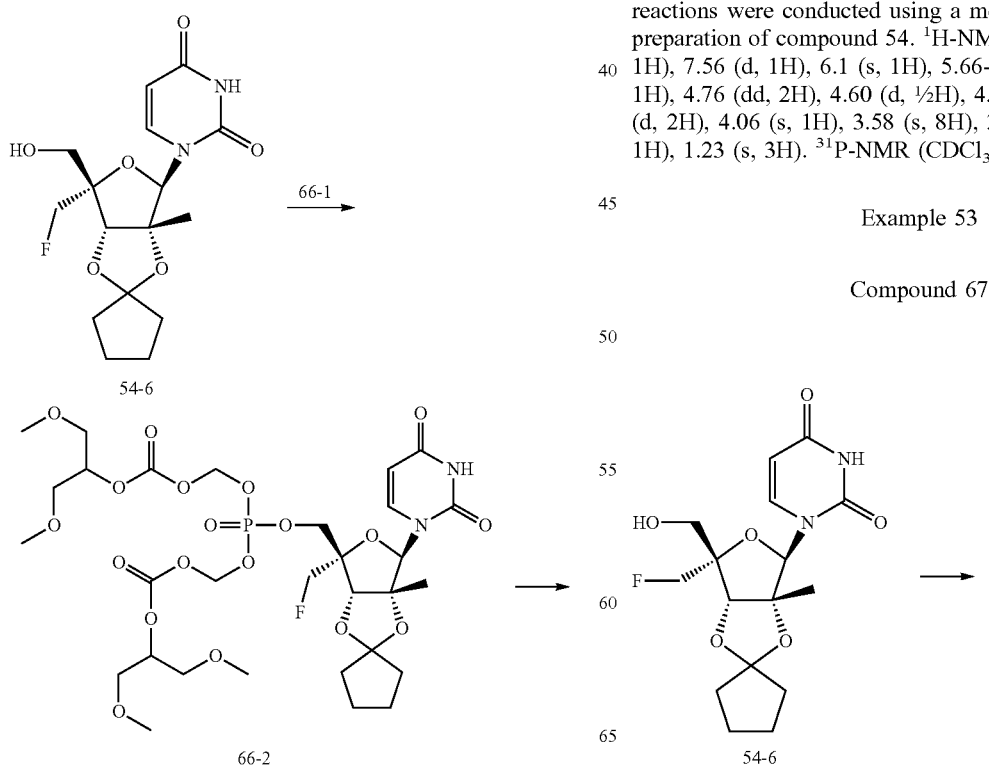

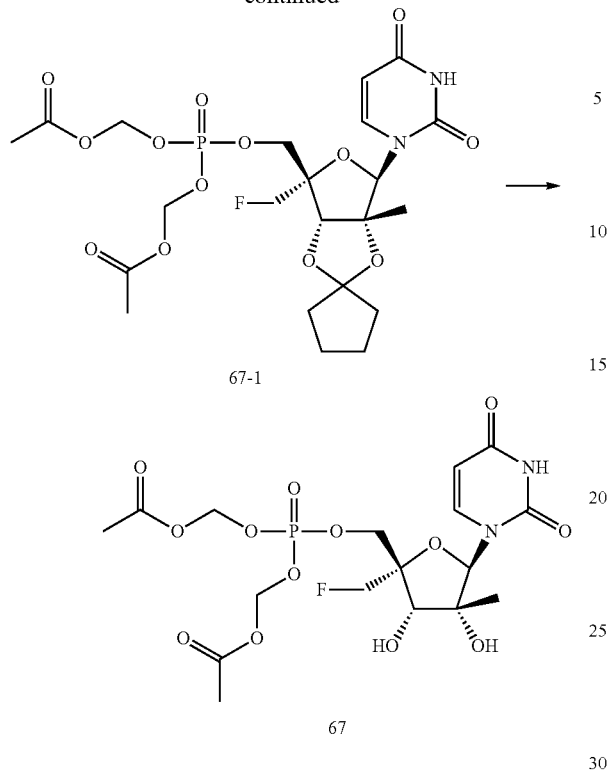

Compound 67-1 (180 mg, 62%) was prepared in the same manner from 54-6 (0.18 g, 0.5 mmol) and triethylammonium bis(acetyloxymethyl)phosphate (1.0 mmol) with DIPEA (0.35 mL), BopCl (0.25 g), and 3-nitro-1,2,4-triazole (0.11 g) in THF (1 mL) using a method as described for compound 44. Purification was done with $CH_2Cl_2$/i-PrOH (4-10% gradient).

Compound 67 (60 mg, 78%) was prepared from 67-1 (85 mg) using a method as described for compound 44. MS: m/z=1027 [2M−1].

Example 54

Compound 68

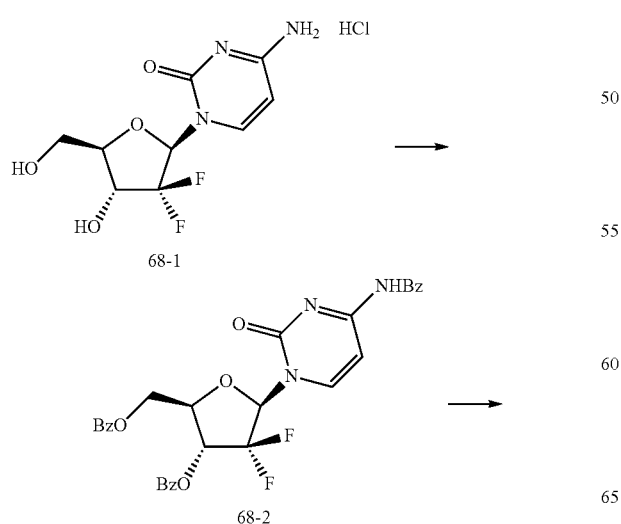

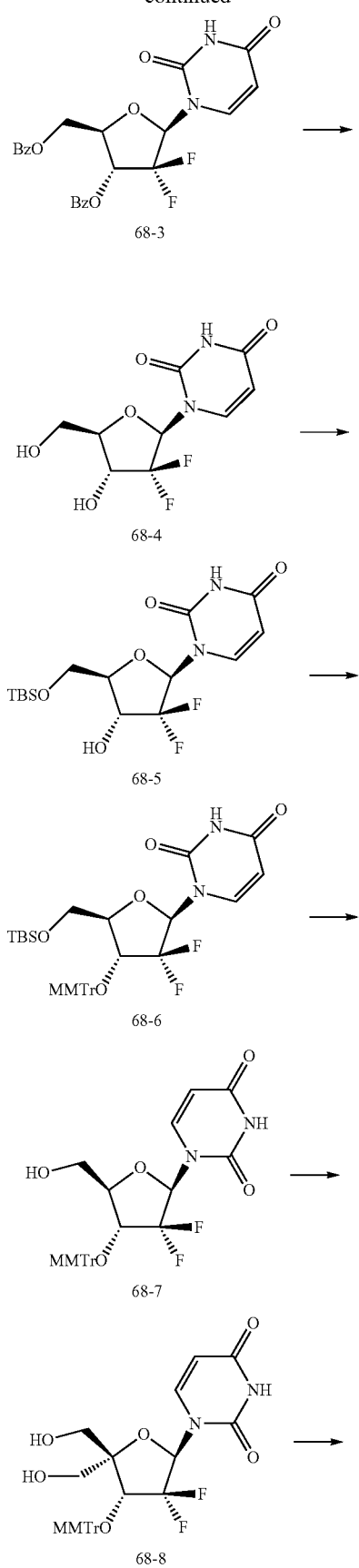

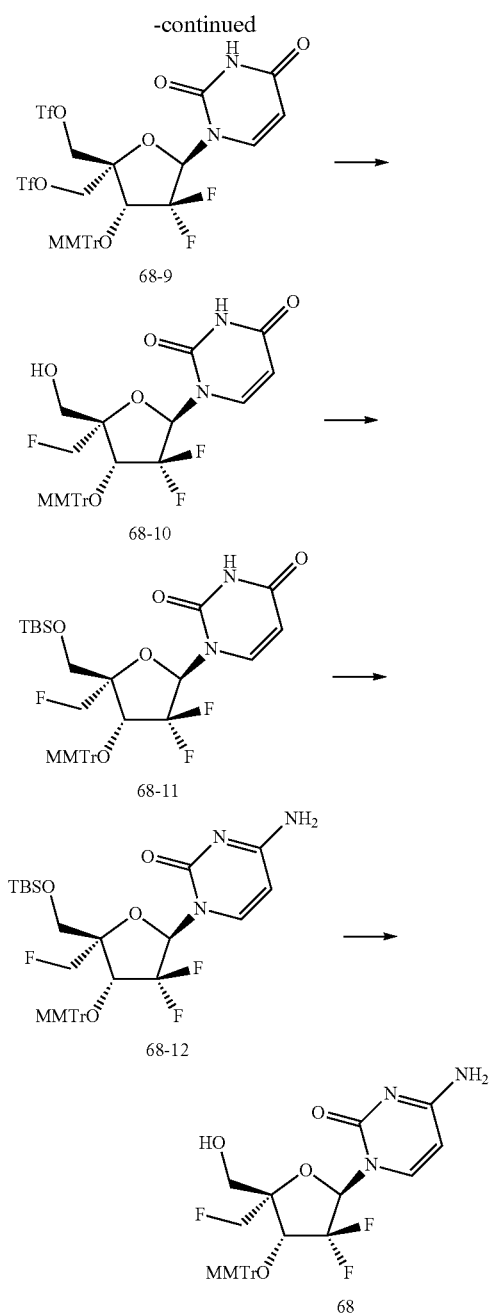

To a solution of 68-1 (15 g, 50.2 mmol) in anhydrous pyridine (180 mL) was added BzCl (23.3 g, 165.5 mmol) at 0° C. under nitrogen. The mixture was stirred overnight at RT. The mixture was diluted with EA and washed with NaHCO₃ aq. solution. The organic layer was dried with anhydrous Na₂SO₄, and concentrated to dryness. The organic layer was dried and concentrated to give a residue, which was purified by silica gel column chromatography (15% EtOAc in PE) to give 68-2 (27 g, 93.5%) as a white solid.

Compound 68-2 (27 g, 47 mmol) was dissolved in 90% HOAc (250 mL) and heated to 110° C. The mixture was stirred overnight at 110° C. The solvent was removed and diluted with EA. The mixture was washed with NaHCO₃ aq. solution and brine. The organic layer was dried and concentrated to give crude 68-3.

Compound 68-3 was dissolved in NH₃/MeOH (600 mL) and stirred overnight. The solvent was concentrated to give the residue, which was purified by silica gel column chromatography (5% MeOH in DCM) to give 68-4 (12 g, 99%) as a white solid.

To a solution of 68-4 (15 g, 56.8 mmol) in anhydrous pyridine (200 mL) was added imidazole (7.7 g, 113.6 mmol) and TBSCl (9.4 g, 62.5 mmol) at RT. The mixture was stirred overnight. And the solvent was removed and diluted with EA. The mixture was washed with NaHCO₃ aq. solution and brine. The organic layer was dried and concentrated to give crude 68-5.

To a solution of 68-5 in anhydrous DCM (200 mL) was added collidine (6.8 g, 56.8 mmol), MMTrCl (17.8 g, 56.8 mmol) and AgNO₃ (9.6 g, 56.8 mmol) at RT. The mixture was stirred overnight. The mixture was filtered, and the filtrate was washed with NaHCO₃ aq. solution and brine. The organic layer was dried over Na₂SO₄, and concentrated at low pressure to give the residue, which was purified by silica gel column chromatography (5% EA in PE) to give 68-6 (32 g, 87%).

Compound 68-6 (32 g, 49.2 mmol) was dissolved in a solution of TBAF in THF (1M, 4 eq.) at RT. The mixture was stirred overnight, and the solvent was removed. The mixture was diluted with EA and washed with water. The organic layer was dried and concentrated to give the crude product, which was purified by silica gel column chromatography (33% EA in PE) to give 68-7 (21 g, 79%).

To a solution of 68-7 (21 g, 38.8 mmol) in DCM (200 mL) was added pyridine (9.2 mL, 116.4 mmol). The solution was cooled to 0° C. and Dess-Martin periodinane (49 g, 116.4 mmol) was added in a single portion. The mixture was stirred for 4 h at RT. The reaction was quenched with Na₂S₂O₃ solution and sodium bicarbonate aqueous solution. The mixture was stirred for 15 mins. The organic layer was separated, washed with diluted brine and concentrated under reduced pressure. The residue was dissolved in dioxane (200 mL), and the solution was treated with 37% aqueous formaldehyde (20 mL, 194 mmol) and 2 N aqueous sodium hydroxide (37.5 mL, 77.6 mmol). The mixture was stirred at RT overnight and NaBH₄ (8.8 g, 232.8 mmol) was added. After stirring for 0.5 h at RT, the excess of aqueous sodium hydroxide was removed with ice water. The mixture was diluted with EA. The organic phase was washed with brine, dried over magnesium sulfate and concentrated at low pressure. The residue was purified by column chromatography (4% MeOH in DCM) to give 68-8 (10 g, 50.5%) as a white foam.

Compound 68-8 (4.8 g, 8.5 mmol) was co-evaporated with toluene twice. The residue was dissolved in anhydrous DCM (45 mL) and pyridine (6.7 g, 85 mmol). The solution was cooled to 0° C. and triflic anhydride (4.8 g, 18.7 mmol) was added dropwise over 10 mins. At this temperature, the reaction was stirred for 40 mins. TLC (50% EA in PE) showed that the reaction was complete. The mixture was purified by column chromatography (EA in PE from 0 to 20%) to give 68-9 (6.1 g, 86.4%) as a brown foam.

Compound 68-9 (6.1 g, 7.3 mmol) was dissolved in MeCN (25 mL). The mixture was treated with a solution of TBAF in THF (1M, 25 mL) at RT. The mixture was stirred overnight. TBAF in THF (1M, 15 mL) was added and stirred for 4 h. The mixture was treated with aqueous sodium hydroxide (1N, 14.6 mmol) and stirred for 1 h. The reaction was quenched with water (50 mL) at 0° C. and extracted with EA. The organic layer was dried and concentrated to give the crude product, which was purified by silica gel column chromatography (50% EA in PE) to give 68-10 (2.1 g, 50.6%).

To a solution of 68-10 (1.5 g, 2.6 mmol) in anhydrous pyridine (15 mL) was added imidazole (530 mg, 7.8 mmol) and TBSCl (585 mg, 3.9 mmol) at RT. The mixture was stirred for 2 h. The solvent was removed and diluted with EA. The mixture was washed with NaHCO$_3$ aq. solution and brine. The organic layer was dried and concentrated to give the residue, which was purified by silica gel column chromatography (10% EA in PE) to give 68-11 (1.5 g, 84.5%).

To a solution of 68-11 (1.5 g, 2.2 mmol) in anhydrous CH$_3$CN (11 mL) were added DMAP (671 mg, 5.5 mmol), TEA (555 mg, 5.5 mmol) and TPSCl (1.66 g, 5.5 mmol) at RT. The reaction was stirred overnight at RT. NH$_4$OH (10 mL) was added, and the mixture was stirred for 2 h. The mixture was diluted with EA and washed with NaHCO$_3$ solution. The organic layer was dried and concentrated at low pressure. The residue was purified by silica gel column chromatography (2% MeOH in DCM) to give crude 68-12, which was purified by prep-TLC to give 68-12 (1.2 g, 80%) as a white solid.

A solution of 68-12 (1.2 g, 1.76 mmol) in 80% HCOOH (60 mL) was stirred for 4 h. The solvent was removed at low pressure. The crude product was dissolved in MeOH (40 mL) and stirred overnight. The solvent was concentrated to give the crude product, which was purified by column chromatography on silica gel (MeOH in DCM 10%) to give compound 68 (480 mg, 92%) as a white solid. ESI-MS: m/z 591 [2M+H]$^+$.

Example 55

Compound 69

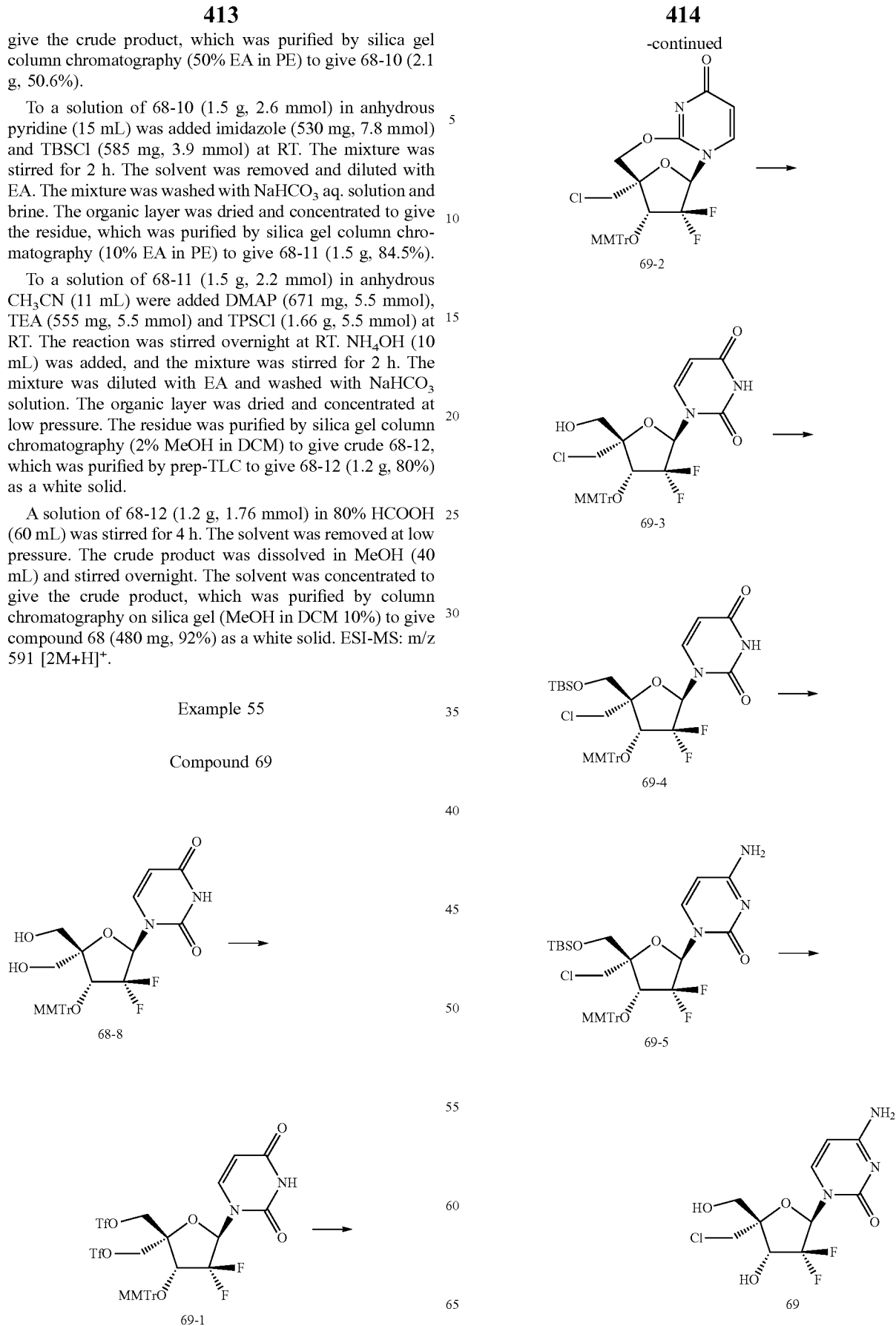

A solution of 68-8 (2.63 g, 4.64 mmol) in anhydrous pyridine/DCM at 0° C. was added Tf₂O (3.27 g, 11.59 mmol). The mixture was stirred at RT for 40 mins. The solvent was removed at reduced pressure, and the residue was purified by column chromatography to give 69-1 (2.60 g, 67%).

A solution of 69-1 (2.65 g, 3.19 mmol) in anhydrous DMF was added sodium hydride (153 mg, 3.82 mmol) at 0° C. for 1 h. The solution was used for the next step without purification. The solution was treated with LiCl (402 mg, 9.57 mmol) at RT. The mixture was stirred at RT for 12 h. The reaction was quenched with saturated ammonium chloride solution, and extracted with EA. The organic layers were dried over Na₂SO₄, and concentrated at low pressure to give crude 69-2.

To a solution 69-2 (1.81 g, 3.19 mmol) in anhydrous THF (20 mL) was added 1 N NaOH (4 mL, 3.83 mmol) at RT. The mixture was stirred at RT for 2 h. The reaction was quenched with saturated sodium bicarbonate solution, and extracted with EA. The organic phase was dried over anhydrous Na₂SO₄, and concentrated at low pressure. The residue was purified by column chromatography to give 69-3. (1.34 g, 72%).

A solution of 69-3 (925 mg, 1.58 mmol) in dichloromethane (10 mL) was added TBSCl (713 mg, 4.75 mmol) and imidazole (323 mg, 4.74 mmol), and stirred at RT overnight. The mixture was diluted with EA (20 mL), and washed with brine. The organic phase was concentrated at low pressure to give the crude product. The residue was purified by column chromatography to give 69-4 (1.0 g, 90%).

A solution of 69-4 (1.24 g, 1.78 mmol) in anhydrous acetonitrile (10 mL) was added TPSCl (1.34 g, 4.45 mmol), DMAP (543 mg, 4.45 mmol) and TEA (450 mg, 4.45 mmol), and the mixture was stirred at RT for 3 h. The solvent was removed under reduced pressure, and the residue was dissolved in EA (30 mL). The solution was washed with brine, dried with anhydrous Na₂SO₄, and concentrated at low pressure. The residue was purified on silica gel to give 69-5 (1.0 g, 81%) as a white solid.

Compound 69-5 (1.0 g, 1.43 mmol) was treated with 80% HCOOH (10 mL), and stirred at RT overnight. The solvent was removed under reduced pressure, and the residue was purified on silica gel using 5% MeOH in CH₂Cl₂ to give compound 69 (264 mg, 60%). ESI-MS: m/z 311.9 [M+H]⁺.

Example 56

Compound 70

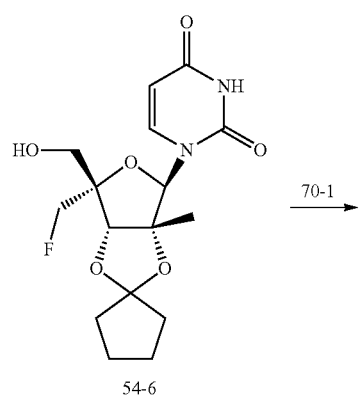

54-6

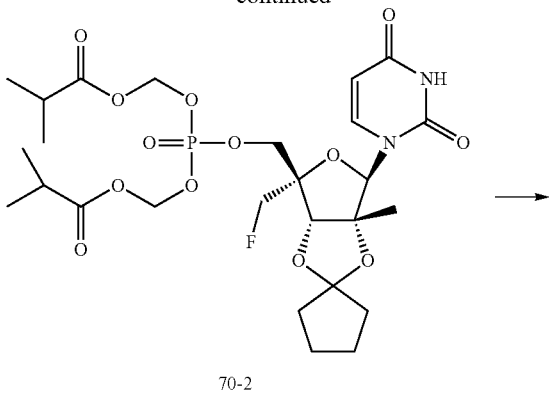

70-2

-continued

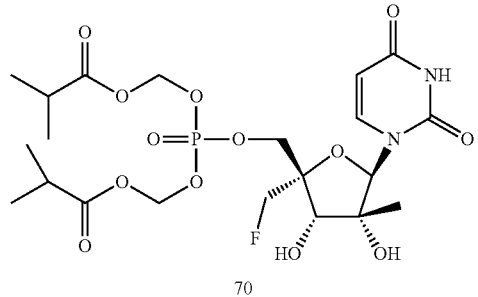

70

Benzylphosphate (silver salt) and commercially available chloromethyl isobutyrate (5.0 g) yielded purified 70a (3.84 g). ¹H-NMR (CD₃CN): δ 7.39-7.42 (m, 5H), 5.60 (d, 4H), 5.09 (d, 2H), 1.94-1.96 (m, 2H), 1.12-1.17 (m, 12H). ³¹P-NMR (CD₃CN): δ −4.03 ppm. Compound 70a (780 mg; 2.0 mmol) was deprotected to give 70-1 (triethylammonium salt), which was used immediately without further purification. Compound 54-6 (356 mg; 1.0 mmol) and 70-1 were reacted to give purified 70-2 (230 mg). Compound 70-2 (230 mg) was deprotected to yield purified compound 70 (80 mg, 0.14 mmol). The aforementioned reactions were conducted using a method described in the preparation of compounds 54 and 66. ¹H-NMR (CDCl₃): δ 8.25 (s, 1H), 7.55 (d, 1H), 5.93 (s, 1H), 5.81 (d, 1H), 5.66-5.75 (m, 4H), 4.76 (dd, 2H), 4.37-4.46 (m, 2H), 4.15 (d, 2H), 3.86 (t, 6H), 3.70 (d, 6H), 1.65 (s, 6H), 1.25 (s, 3H). ³¹P-NMR (CDCl₃): δ −4.41 ppm.

Example 57
Compound 71
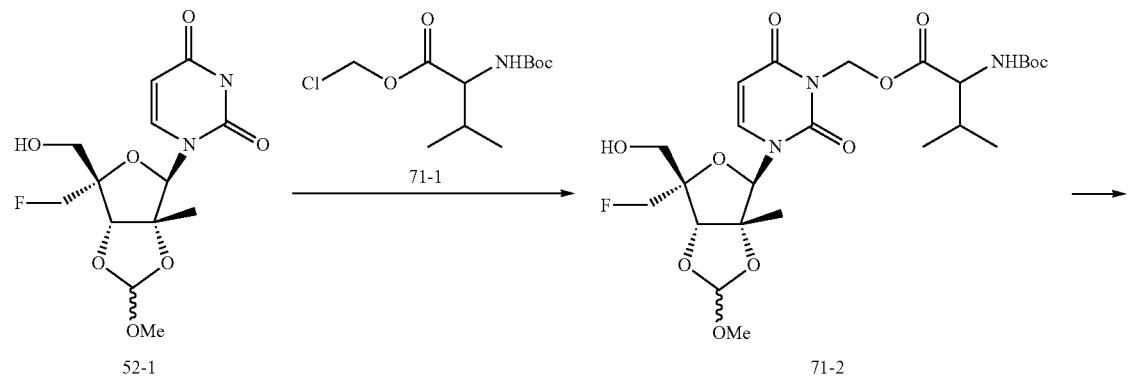
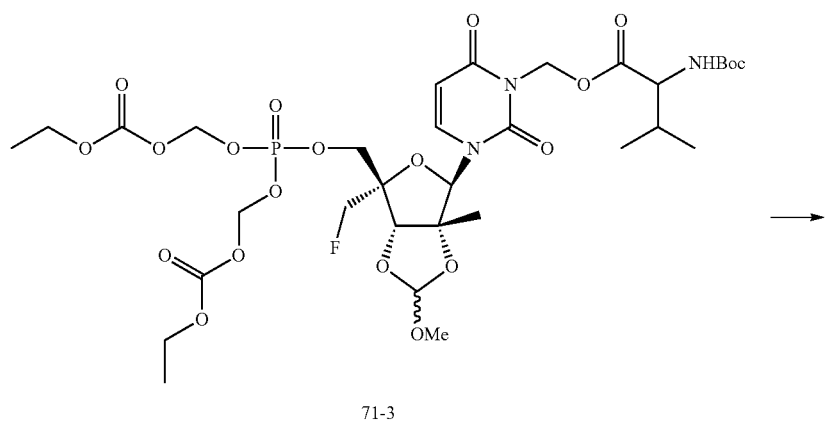
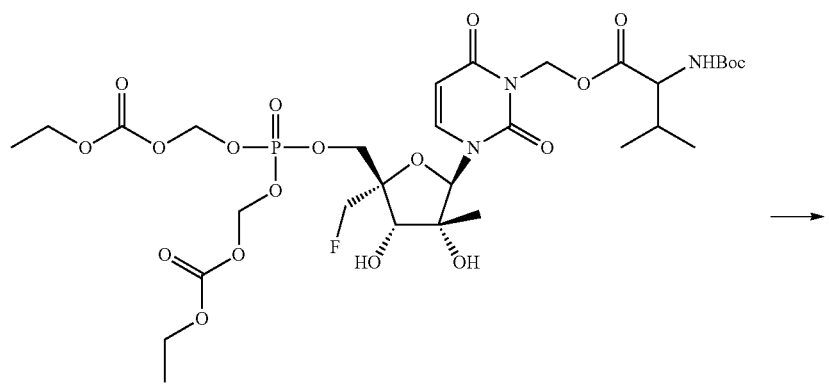

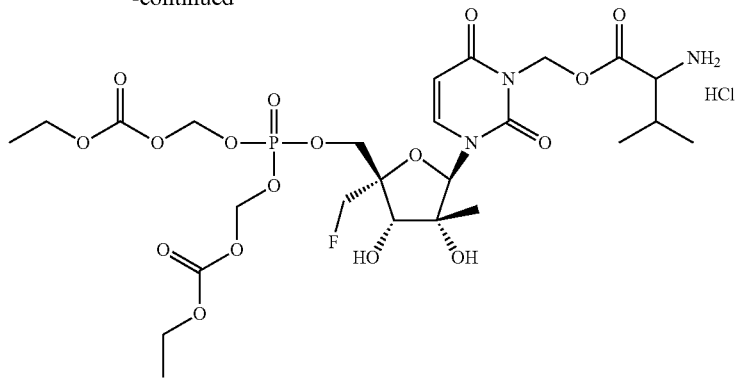

71

Compound 71-2 (0.34 g, 60%) was prepared from 52-1 (0.33 g) and 71-1 (0.34 g) in acetone (6 mL) with NaI (0.19 g) and $K_2CO_3$ (0.69 g).

Compound 71-3 (0.28 g, 74%) was prepared in the same manner from 71-2 (0.25 g, 0.45 mmol) and triethylammonium bis(ethoxycarbonyloxymethyl)phosphate (0.9 mmol) with DIPEA (0.35 mL), BopCl (0.25 g), and 3-nitro-1,2,4-triazole (0.11 g) in THF (5 mL). Purification was done with hexanes/EtOAc (30-100% gradient).

A solution of 71-3 (0.28 g, 0.33 mmol) in 80% aq. AcOH was heated at 45° C. for 4 h and then concentrated. The residue was coevaporated with toluene and then with MeOH containing small amount of $Et_3N$ (2 drops). Purification on silica gel (10 g column) with $CH_2Cl_2$/i-PrOH (4-10% gradient) yielded 71-4 (0.22 g, 84%).

To a solution of 71-4 (148 mg, 0.18 mmol) in EtOAc (0.6 mL) at 0° C. was added 4 N HCl/dioxane (0.5 mL), and the mixture kept at RT for 1 h. Ether was added and compound 71 precipitated. The mixture was filtered and washed with ether to give compound 71 (100 mg, 75%). The aforementioned reactions were conducted using a method described in the preparation of compound 52. MS: m/z=704 [M+1].

Example 58

Compound 33

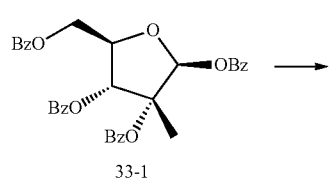

33-1

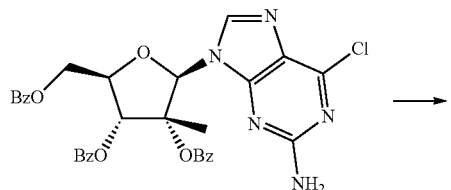

33-2

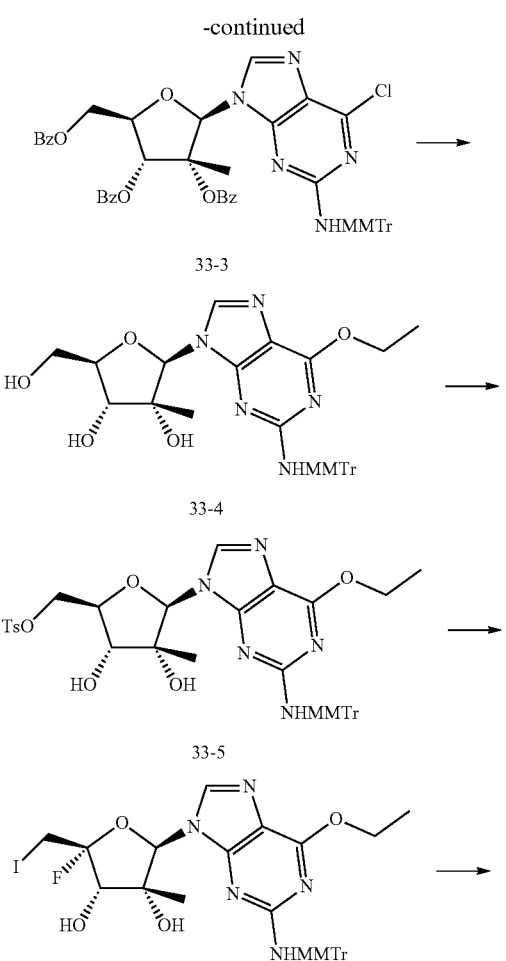

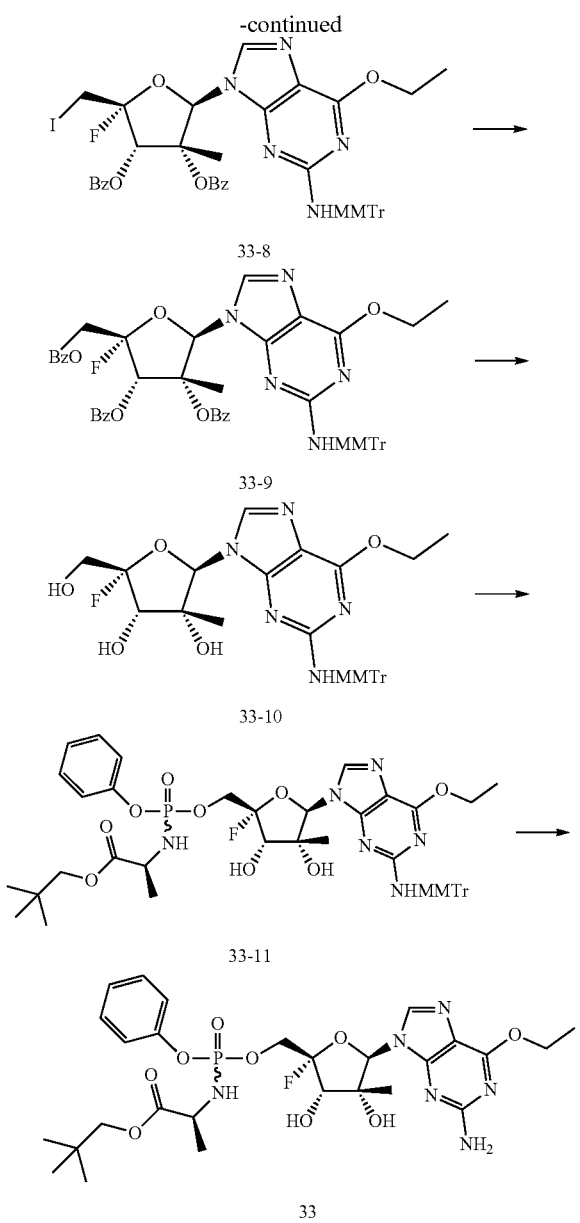

Compound 33-1 (50 g, 86.0 mmol) and 6-Cl-guanine (16.1 g, 98.2 mmol) were co-evaporated with anhydrous toluene 3 times. To a solution of 33-1 (50 g, 86.0 mmol) and 6-Cl-guanine (16.1 g, 98.2 mmol) in MeCN (200 mL) was added DBU (39.5 g, 258.0 mmol) at 0° C. The mixture was stirred at 0° C. for 30 mins, and TMSOTf (95.5 g, 430.0 mmol) was added dropwise at 0° C. The mixture was stirred at 0° C. for 30 mins until a clear solution was observed. The mixture was heated to 70° C., and stirred overnight. The solution was cooled to RT, and diluted with EA (100 mL). The solution was washed with sat. NaHCO$_3$ solution and brine. The organic layer was dried over Na$_2$SO$_4$, and concentrated at low pressure. The residue was purified by column on silica gel (EA in PE from 10% to 40%) to give 33-2 (48.0 g, 88.7%) as a yellow foam. ESI-MS: m/z 628 [M+H]$^+$.

To a solution of 33-2 (48.0 g, 76.4 mol), AgNO$_3$ (50.0 g, 294.1 mmol) and collidine (40 mL) in anhydrous DCM (200 mL) was added MMTrCl (46.0 g, 149.2 mmol) in small portions under N$_2$. The mixture was stirred at RT for 3 h under N$_2$. Completion of the reaction was determined by TLC. After filtration, the filtrate was washed with sat. NaHCO$_3$ solution and brine. The organic layer was dried over anhydrous Na$_2$SO$_4$, and concentrated at low pressure. The residue was purified by silica gel column (EA in PE from 5% to 50%) to the give crude 33-3 (68 g, 98%). ESI-MS: m/z 900.1 [M+H]$^+$.

Sodium (8.7 g, 378.0 mmol) was dissolved in dry EtOH (100 mL) at 0° C., and slowly warmed to RT. Compound 33-3 (68.0 g, 75.6 mmol) was treated with freshly prepared NaOEt solution, and stirred overnight at RT. Completion of the reaction was determined by TLC and LCMS. The mixture was concentrated at a low pressure, diluted with H$_2$O (100 mL), and extracted with EA (3×100 mL). The organic layer was dried over anhydrous Na$_2$SO$_4$, and evaporated at low pressure. The residue was purified by silica gel column chromatography (MeOH in DCM from 1% to 5%) to give 33-4 (34.0 g, 75.2%) as a yellow solid. ESI-MS: m/z 598 [M+H]$^+$.

Compound 33-4 (32.0 g, 53.5 mmol) was co-evaporated with anhydrous pyridine 3 times. To an ice cooled solution of 33-4 (32.0 g, 53.5 mmol) in anhydrous pyridine (100 mL) was added a solution of TsCl (11.2 g, 58.9 mmol) in pyridine (50 mL) dropwise at 0° C. The mixture was stirred for 18 h. at 0° C. The reaction was monitored by LCMS, and quenched with H$_2$O. The solution was concentrated at low pressure, and the residue was dissolved in EA (100 mL), and washed with sat. NaHCO$_3$ solution. The organic layer was dried over anhydrous Na$_2$SO$_4$, and evaporated at a low pressure. The residue was purified by silica gel column chromatography (MeOH in DCM from 1% to 5%) to give crude 33-5 (25.0 g, 62.2%) as a yellow solid. ESI-MS: m/z 752 [M+H]$^+$.

To a solution of 33-5 (23.0 g, 30.6 mmol) in acetone (150 mL) was added NaI (45.9 g, 306.0 mmol) and TBAI (2.0 g), and the mixture was refluxed overnight. Completion of the reaction was determined by LCMS. The mixture was concentrated at low pressure, and the residue was dissolved in EA (100 mL). The solution was washed with brine, and dried over anhydrous Na$_2$SO$_4$. The organic solution was evaporated at low pressure, and the residue was purified by silica gel column chromatography (DCM:MeOH=100:1 to 20:1) to give a crude product. To a solution of the crude product in dry THF (200 mL) was added DBU (14.0 g, 91.8 mmol), and the mixture was heated to 60° C. and stirred overnight. The reaction was monitored by LCMS. The reaction was quenched with sat. NaHCO$_3$ solution, and the solution was extracted with EA (100 mL). The organic layer was dried over anhydrous Na$_2$SO$_4$, and evaporated at low pressure. The residue was purified by silica gel column chromatography (MeOH in DCM from 1% to 5%) to give 33-6 (12.0 g, 67.4%) as a yellow solid. ESI-MS: m/z 580 [M+H]$^+$.

To an ice cooled solution of 33-6 (8.0 g, 13.8 mmol) in anhydrous MeCN (100 mL) was added NIS (3.9 g, 17.2 mmol) and TEA.3HF (3.3 g, 20.7 mmol) at 0° C. The mixture was stirred at RT for 18 h, and the reaction was checked by LCMS. After the reaction was completed, the reaction was quenched with sat. Na$_2$SO$_3$ solution and sat. NaHCO$_3$ solution. The solution was extracted with EA (3×100 mL). The organic layer was dried over anhydrous Na$_2$SO$_4$, and evaporated at low pressure. The residue was purified by silica gel column chromatography (EA in PE from 10% to 50%) to give 33-7 (7.2 g, 72.0%) as a solid. ESI-MS: m/z 726 [M+H]$^+$.

To a solution of 33-7 (7.2 g, 9.9 mmol) in dry DCM (100 mL) was added DMAP (3.6 g, 29.8 mmol), and BzCl (2.8 g, 19.8 mmol) at 0° C. The mixture was stirred overnight, and checked by LCMS. The mixture was washed with sat. NaHCO₃ solution. The organic layer was dried over anhydrous Na₂SO₄, and evaporated at low pressure. The residue was purified by silica gel column chromatography (EA in PE from 10% to 30%) to give 33-8 (8.0 g, 86.4%) as a solid. ESI-MS: m/z 934 [M+H]⁺.

To a solution of 33-8 (7.5 g, 8.0 mmol) in dry DMF (100 mL) was added NaOBz (11.5 g, 80.0 mmol) and 15-crown-5 (15.6 mL). The mixture was stirred for 36 h. at 90° C. The mixture was diluted with H₂O (100 mL), and extracted with EA (3×150 mL). The organic layer was dried over anhydrous Na₂SO₄, and evaporated at low pressure. The residue was purified by silica gel column chromatography (EA in PE from 10% to 30%) to give crude 33-9 (6.0 g, 80.0%) as a solid. ESI-MS: m/z 928 [M+H]⁺.

Compound 33-9 (4.0 g, 4.3 mmol) was co-evaporated with anhydrous toluene 3 times, and treated with NH₃/MeOH (50 mL, 4N) at RT. The mixture was stirred for 18 h. at RT. Completion of the reaction was determined by LCMS. The mixture was concentrated at low pressure, and the residue was purified by silica gel column chromatography (EA in PE from 30% to 50%) to give product 33-10 (1.9 g, 71.7%) as a solid. ESI-MS: m/z 616 [M+H]⁺.

Compound 33-10 (300.0 mg, 0.49 mmol) was co-evaporated with anhydrous toluene 3 times, and was dissolved in MeCN (2 mL). The mixture was treated with NMI (120.5 mg, 1.47 mmol) and the phosphorochloridate reagent (326.3 mg, 0.98 mmol) in MeCN (1 mL) at 0° C. The mixture was stirred for 18 h at RT and monitored by LCMS. The mixture was diluted with 10% NaHCO₃ solution, and extracted with EA (3×30 mL). The residue was purified by silica gel column chromatography (EA in PE from 30% to 50%) to give 33-11 (210 mg, 47.5%) as a solid. ESI-MS: m/z 913.0 [M+H]⁺.

Compound 33-11 (210 mg, 0.26 mmol) was treated with 80% of AcOH (15 mL), and the mixture was stirred for 18 h at RT. Completion of the reaction was determined by LCMS. The mixture was concentrated at low pressure, and the residue was purified by silica gel column chromatography (MeOH in DCM from 1% to 3%) to give compound 33 (71.8 mg, 48.7%) as a solid. ESI-MS: m/z 641.3 [M+H]⁺.

Example 59

Compound 75

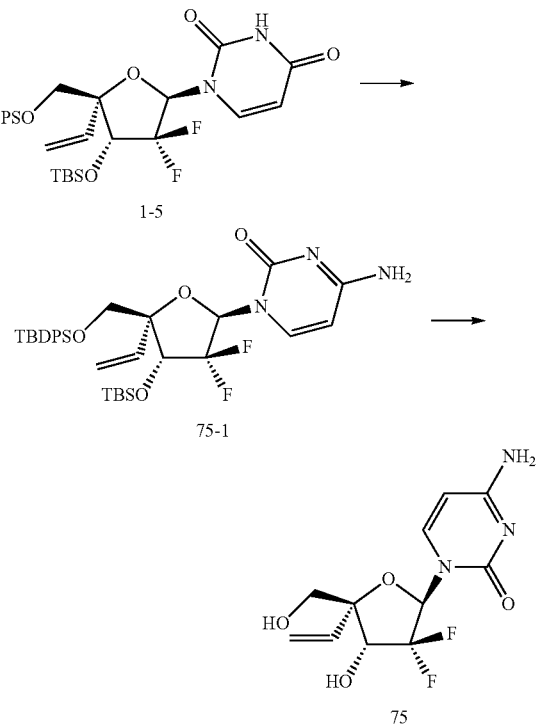

A mixture solution of 1-5 (317 mg, 0.49 mmol), TPSCl (373 mg, 1.23 mmol), DMAP (150 mg, 1.23 mmol) and TEA (124 mg, 1.23 mmol) in anhydrous MeCN was stirred at RT overnight. The mixture was treated with ammonium solution, and then stirred at RT for 3 h. The solvent was removed under reduced pressure, and the residue was purified by column chromatography to give 75-1 (200 mg, 63%).

A solution of 75-1 (286 mg, 0.45 mmol) and ammonium fluoride (500 mg, 13.5 mmol) in methanol (10 mL) was refluxed overnight. The solvent was removed under reduced pressure and the residue was purified on silica gel to give compound 75 (75 mg, 57%). ESI-MS: m/z 289.9 [M+H]⁺.

Example 60

Compound 76

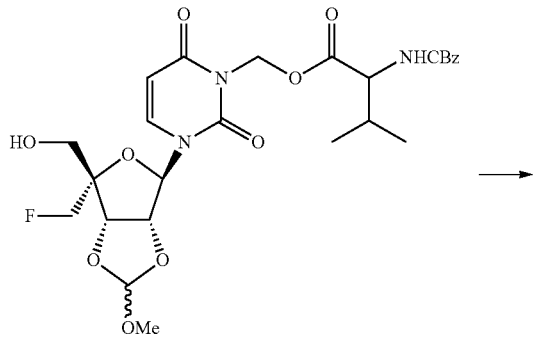

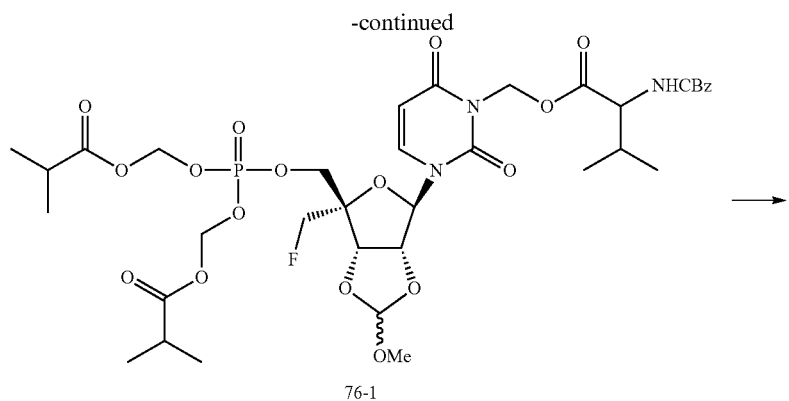

76-1

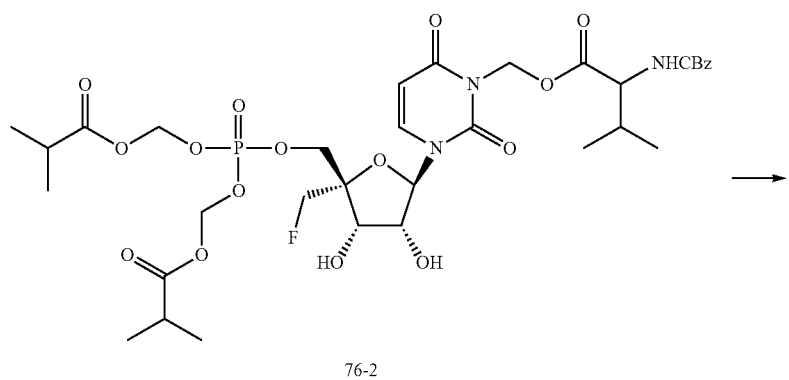

76-2

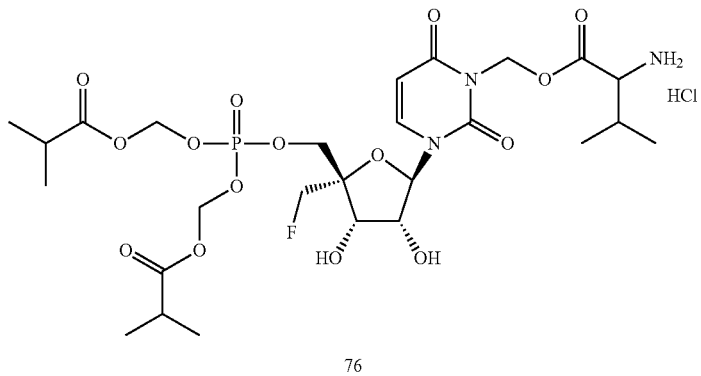

76

Compound 76-1 (0.44 g, 34%) was prepared from 52-3 (0.88 g, 1.48 mmol) and triethylammonium bis(isobutyryloxymethyl)phosphate (3 mmol) with DIPEA (1.05 mL), BopCl (0.76 g), and 3-nitro-1,2,4-triazole (0.34 g) in THF (10 mL). Purification was done with hexanes/EtOAc (5-100% gradient). Compound 76-2 (0.43 g, 85%) was prepared from 76-1 (0.44 g); and compound 76 (0.19 g, 98%) was prepared from 76-2 (0.22 g) in EtOH (10 mL) with 10% Pd/C (10 mg), 4 N HCl/dioxane (132 μL), and under the $H_2$ atmosphere. The aforementioned reactions were conducted using a method described in the preparation of compound 52. MS: m/z=700 [M+1].

Example 61
Compound 77
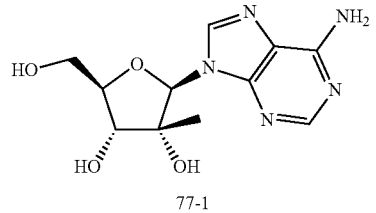
77-1
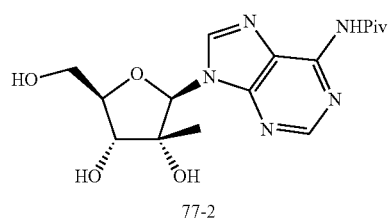
77-2
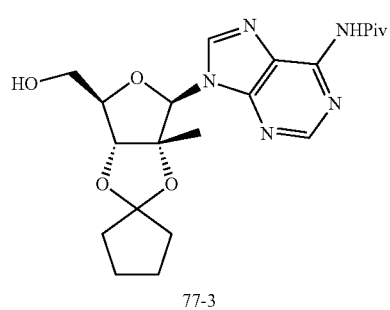
77-3
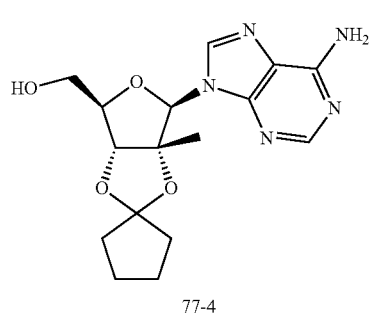
77-4
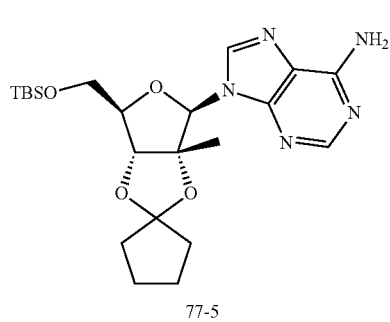
77-5
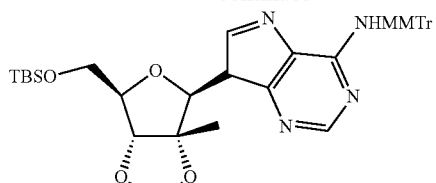
77-6
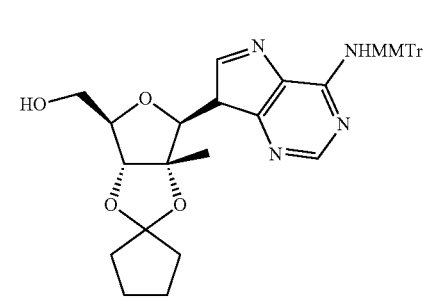
77-7
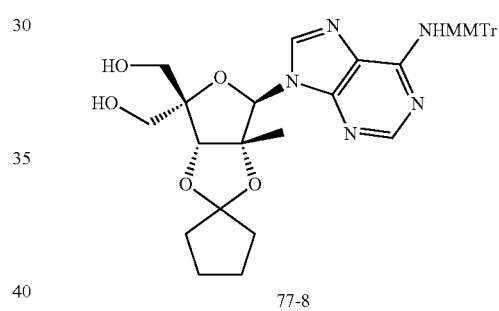
77-8
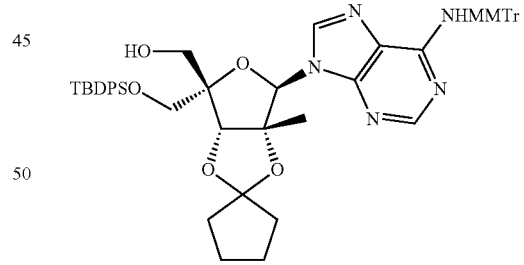
77-9
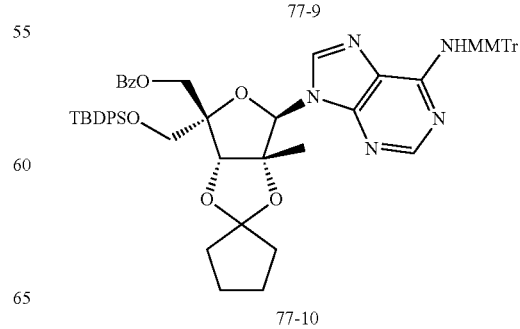
77-10

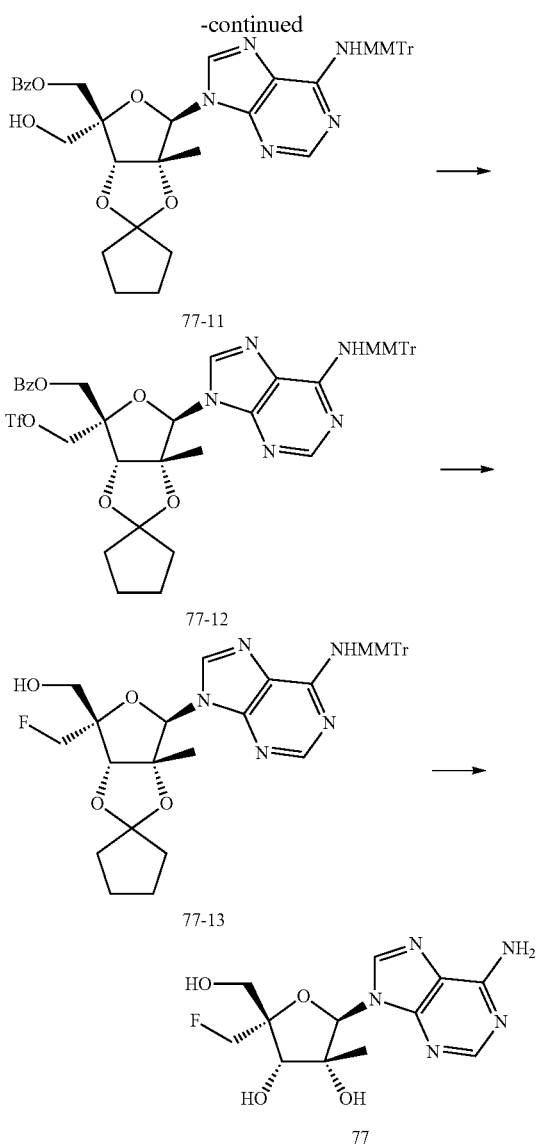

To a stirred solution of 77-1 (2.0 g, 7.12 mmol) in pyridine (20 mL) was added TMSCl (3.86 g, 35.58 mmol) at 0° C. under $N_2$. The mixture was slowly warmed to RT and stirred for 2 h. PivCl (1.71 g, 14.23 mmol) was added, and the mixture was stirred for 24 h. The solvent was evaporated at low pressure, and the residue was dissolved in EA (50 mL). The solution was washed with brine, dried over anhydrous $Na_2SO_4$, and concentrated at low pressure to give the crude product. The crude product was dissolved in MeOH (20 mL) and $NH_4F$ (1.4 g, 37.86 mmol) was added. The mixture was refluxed for 2 h. The solvent was removed, and the residue was purified by column chromatography to give 77-2 (2.2 g, 85%).

To a solution of 77-2 (8.5 g, 23.28 mmol) and 1,1-dimethoxycyclopentane (2 mL) in a mixture of DMF (15 mL) and cyclopentanone (6 mL) was added TsOH (6.63 g, 34.93 mmol). The mixture was stirred at RT for 12 h. The reaction was quenched with triethylamine, and concentrated at low pressure. The residue was purified by column chromatography to give 77-3 (6.5 g, 65%).

To a stirred solution of 77-3 (6.0 g, 13.92 mmol) in anhydrous MeOH (60 mL) was added MeONa (2.25 g, 41.76 mmol) at RT. The mixture was stirred for 12 h and then neutralized with HOAc. The mixture was concentrated at low pressure, and the residue was purified by column chromatography to give 77-4 (4.4 g, 92%).

To a stirred solution of 77-4 (5.0 g, 14.40 mmol) in anhydrous pyridine (50 mL) was added TBSCl (3.24 g, 21.61 mmol) at RT under $N_2$, and the mixture was stirred overnight. The mixture was concentrated at low pressure, and the residue was purified by column chromatography to give 77-5 (5.44 g, 82%).

To a stirred solution of 77-5 (5.0 g, 10.84 mmol) in anhydrous DCM (50 mL) was added MMTrCl (5.01 g, 16.26 mmol), collidine (5 mL), and $AgNO_3$ (2.76 g, 16.26 mmol) at RT under $N_2$, and the mixture was stirred for 2 h. The precipitate was removed by filtration, and the filtrate was concentrated at low pressure. The residue was purified by column chromatography to give 77-6 (7.1 g, 89%).

To a stirred solution of 77-6 (7.1 g, 9.68 mmol) in anhydrous THF (70 mL) was added TBAF (5.05 g, 19.37 mmol) at RT under $N_2$, and the mixture was stirred for 4 h. The mixture was concentrated at low pressure, and the residue was purified by column chromatography to give 77-7 (5.1 g, 87%).

To a stirred solution of 77-7 (3.2 g, 5.17 mmol) and pyridine (2.04 g, 25.85 mmol) in anhydrous DCM (30 mL) was added DMP (3.28 g, 7.75 mmol) at RT under $N_2$. The mixture was stirred at RT for 3 h. The reaction was quenched with sat. $Na_2S_2O_3$ solution, and washed with sat. $NaHCO_3$ solution and brine. The organic phase was dried over anhydrous $Na_2SO_4$, and concentrated at low pressure. The residue was purified by column chromatography to give the aldehyde (1.8 g). To a stirred solution of the aldehyde (1.8 g, 2.92 mmol) in dioxane (29.2 mL) was added 37% HCHO (2.36 g, 29.17 mmol) and 1N LiOH (1.6 mL, 2.34 mmol) at RT. The mixture was stirred at RT for 1.5 h. The solution was neutralized with HOAc. The mixture was treated with EtOH (15 mL) and $NaBH_4$ (1.66 g, 43.8 mmol), and stirred at RT for 2 h. The mixture was quenched with water, and concentrated at low pressure. The residue was purified by column chromatography to give 77-8 (2.01 g, 61%).

To a stirred solution of 77-8 (200 mg, 0.31 mmol) in anhydrous DCM (2 mL) was added TBDPSCl (170 mg, 0.62 mmol) and imidazole (42 mg, 0.62 mmol) at RT under $N_2$. The mixture was stirred at RT for 2 h. The mixture was diluted with DCM (10 mL), and washed with brine. The organic phase was concentrated at low pressure, and the residue was purified by column chromatography to give 77-9 (175 mg, 64%).

To a stirred solution of 77-9 (270 mg, 0.304 mmol) in anhydrous DCM (2 mL) was added BzCl (63 mg, 0.61 mmol), DMAP (74 mg, 0.61 mmol) and TEA (61 mg, 0.61 mmol) at RT under $N_2$. The mixture was stirred at RT until the starting material disappeared. The =mixture was evaporated at low pressure, and the residue was purified by column chromatography to give 77-10 (250 mg, 83.3%).

Compound 77-10 (300 mg, 0.302 mmol) in THF (5 mL) was treated with a solution of TBAF (0.61 mL, 0.61 mmol, 1M in THF) and HOAc (0.2 mL) at RT. The mixture was stirred at RT for 12 h. The mixture was concentrated at low pressure, and the residue was purified by column chromatography to give 77-11 (170 mg, 75%).

To a stirred solution of 77-11 (400 mg, 0.531 mmol) in anhydrous DCM (4 mL) was added $Tf_2O$ (299 mg, 1.06 mmol) and pyridine (84 mg, 1.06 mmol) at RT under $N_2$. The mixture was stirred at RT until the starting material disappeared. The mixture was concentrated at low pressure, and the residue was purified by column chromatography to give 77-12 (401 mg, 85%).

Compound 77-12 (500 mg, 0.564 mmol) was treated with TBAF in THF (1.0 M, 2 mL) at RT under $N_2$. The mixture was diluted with water (20 mL), and extracted with DCM. The solution was washed with brine, dried over anhydrous $Na_2SO_4$, and concentrated at low pressure. The residue was purified by column chromatography to give 77-13 (150 mg, 40.8%) as a white solid. ESI-MS: m/z 652.1 [M+H]$^+$.

Compound 77-13 (50 mg) was dissolved in 80% HCOOH (10 mL), and the mixture was heated at 45° C. for 24 h. The solvent was evaporated and co-evaporated with methanol/toluene to remove traces of acid. The residue was dissolved in 20% triethylamine in methanol, kept for 15 mins and then evaporated. Compound 77 (18 mg, 75%) was isolated by silica gel chromatography in a gradient of methanol in DCM from 0% to 15%. MS: m/z 312.5 [M−1].

Example 62

Compound 78

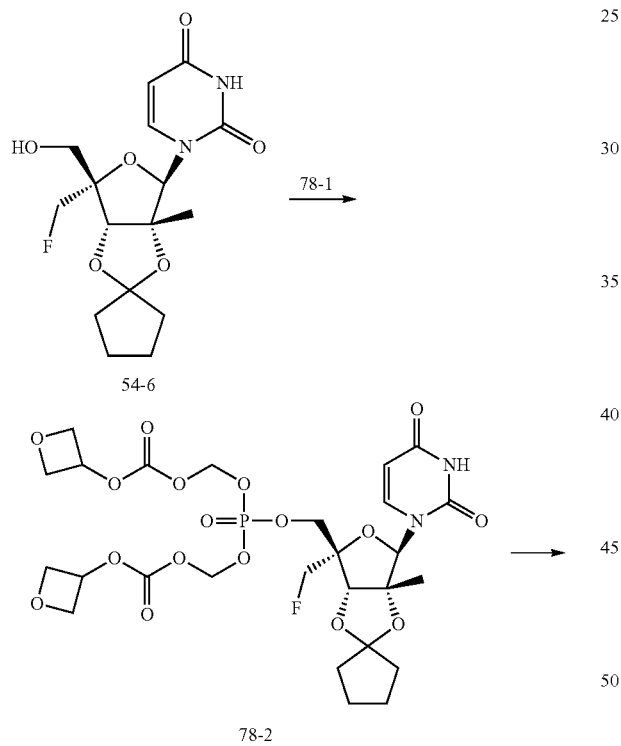

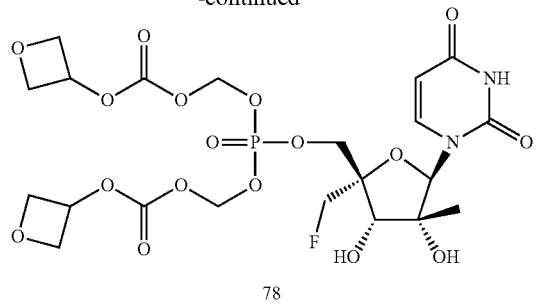

Compound 78a was prepared from commercially available 3-hydroxyoxetane (5.0 g). $^1$H-NMR (CDCl$_3$) δ 5.73 (s, 2H), 5.48-5.51 (m, 1H), 4.90 (d, 2H), 4.72 (d, 2H). Compound 78b (8.0 g) was prepared from 78a. $^1$H-NMR (CDCl$_3$) δ 5.95 (s, 2H), 5.48-5.51 (m, 1H), 4.90 (d, 2H), 4.72 (d, 2H). Benzylphosphate (silver salt) and 78b (8.0 g) were reacted to yield purified 78c (1.92 g). $^1$H-NMR (CD$_3$CN): δ 7.39-7.42 (m, 5H), 5.62 (d, 4H), 5.39-5.42 (m, 2H), 5.15 (d, 2H), 4.80-4.83 (m, 4H), 4.56-4.60 (m, 4H). $^{31}$P-NMR (CD$_3$CN): δ −4.55 ppm. Compound 78c was deprotected to give 78-1 (triethylammonium salt), which was used immediately without further purification. Compound 54-6 (356 mg; 1.0 mmol) and 78-1 were reacted to give purified 78-2 (230 mg). Compound 78-2 (230 mg) was deprotected to yield purified compound 78 (12.5 mg, 0.02 mmol). The aforementioned reactions were conducted using a method described in the preparation of compound 54. $^1$H-NMR (CDCl$_3$): δ 8.25 (s, 1H), 7.54 (d, 1H), 5.90 (s, 1H), 5.81 (d, 1H), 5.66-5.75 (m, 4H), 5.44-5.49 (m, 2H), 4.88-4.92 (m, 5H), 4.61-4.78 (m, 5H), 4.37-4.46 (m, 2H), 4.21 (s, 1H), 3.49 (s, 1H), 1.25 (s, 3H). $^{31}$P-NMR (CDCl$_3$): δ −4.28 ppm.

Example 63

Compound 83

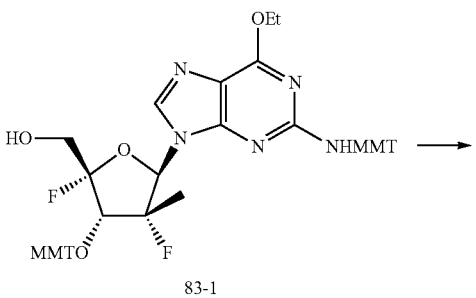

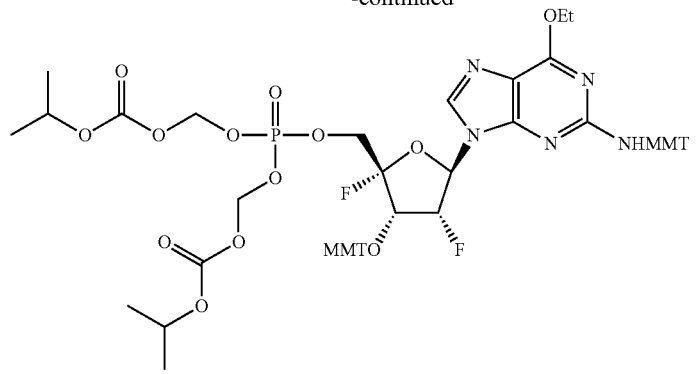

83-2

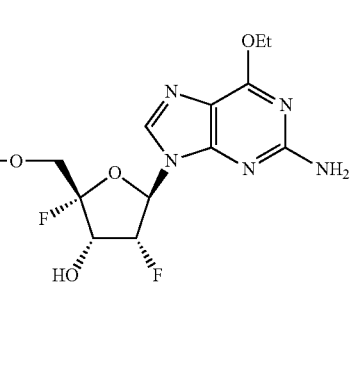

83

Compound 83-2 (70 mg, 58%) was prepared in the same manner from compound 83-1 (90 mg; 0.1 mmol) and triethylammonium bis(isopropyloxycarbonyloxymethyl) phosphate (0.2 mmol) with DIPEA (87 µL), BopCl (44 mg), and 3-nitro-1,2,4-triazole (29 mg) in THF (2 mL) as described in the preparation of compound 44. Purification was done with hexanes/EtOAc with a 20-80% gradient.

Compound 83 (25 mg, 64%) was prepared from 83-2 (70 mg) in acetonitrile (0.6 mL) and 4 N HCl/dioxane (50 µL) as described in the preparation of compound 55. MS: m/z=658 [M+1].

Example 64

Compound 84

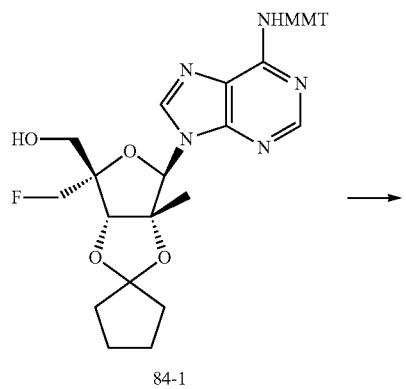

84-1

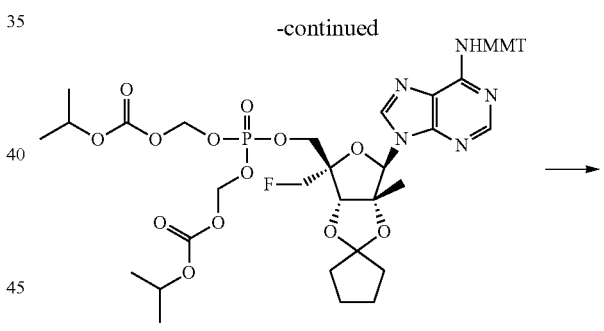

84-2

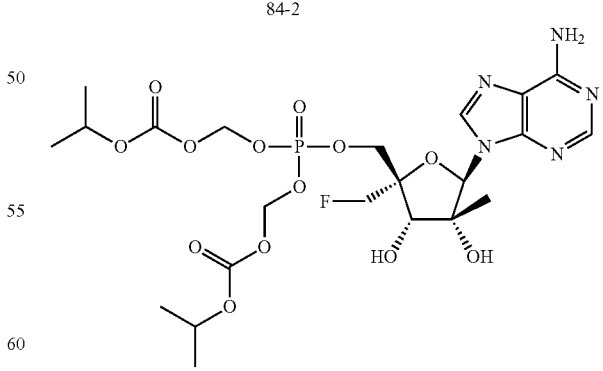

84

Compound 84-2 (69 mg, 90%) was prepared from 84-1 (52 mg; 0.08 mmol) and triethylammonium bis(isopropyloxycarbonyloxymethyl)phosphate (0.16 mmol) with DIPEA (74 μL), BopCl (51 mg), and 3-nitro-1,2,4-triazole (23 mg) in THF (1 mL) as described in the preparation of compound 44. Purification was done with hexanes/EtOAc with a 20-100% gradient.

Compound 84 (27 mg, 62%) was prepared from 84-2 (65 mg) as described in the preparation of compound 44. MS: m/z=626 [M+1].

Example 65

Compound 85

A mixture of 76-2 and acetic anhydride in pyridine was stirred overnight at RT, then concentrated and purified on silica gel (10 g column) with $CH_2Cl_2$/i-PrOH (4-10% gradient) to yield 85-1 (12 mg, 69%).

Compound 85 (10 mg, 92%) was prepared from 85-1 (12 mg) in EtOH (0.5 mL) with 10% Pd/C (1 mg), 4 N HCl/dioxane (7 μL), and under the $H_2$ atmosphere in the same manner compound 52. MS: m/z=742 [M+1].

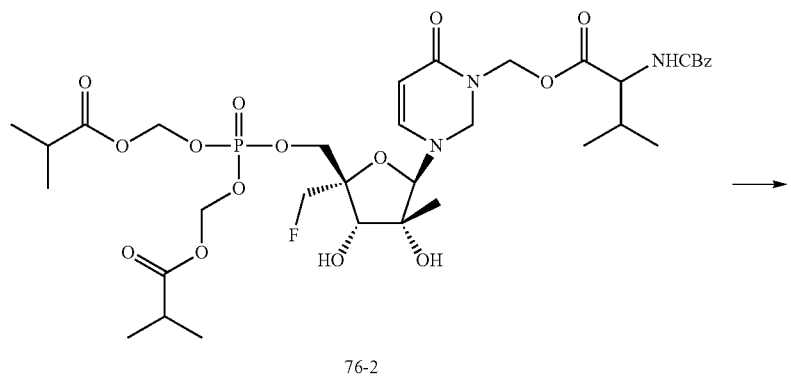

76-2

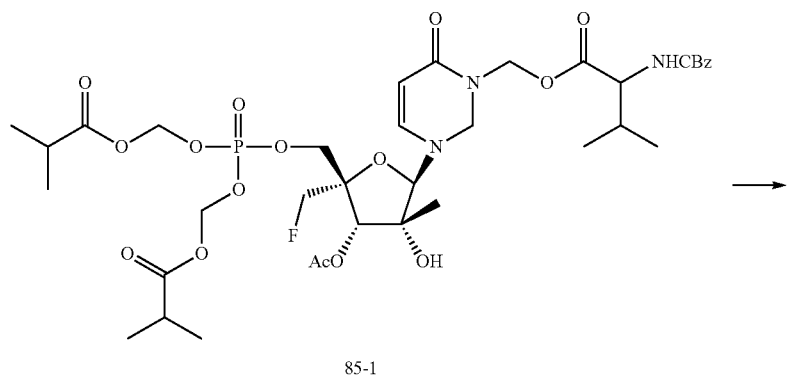

85-1

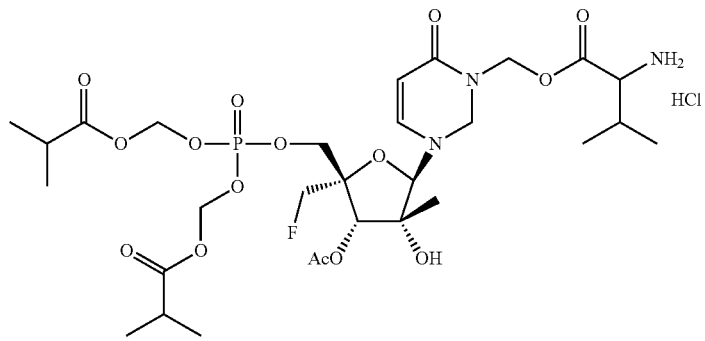

85

Example 66

Compounds 86 and 87

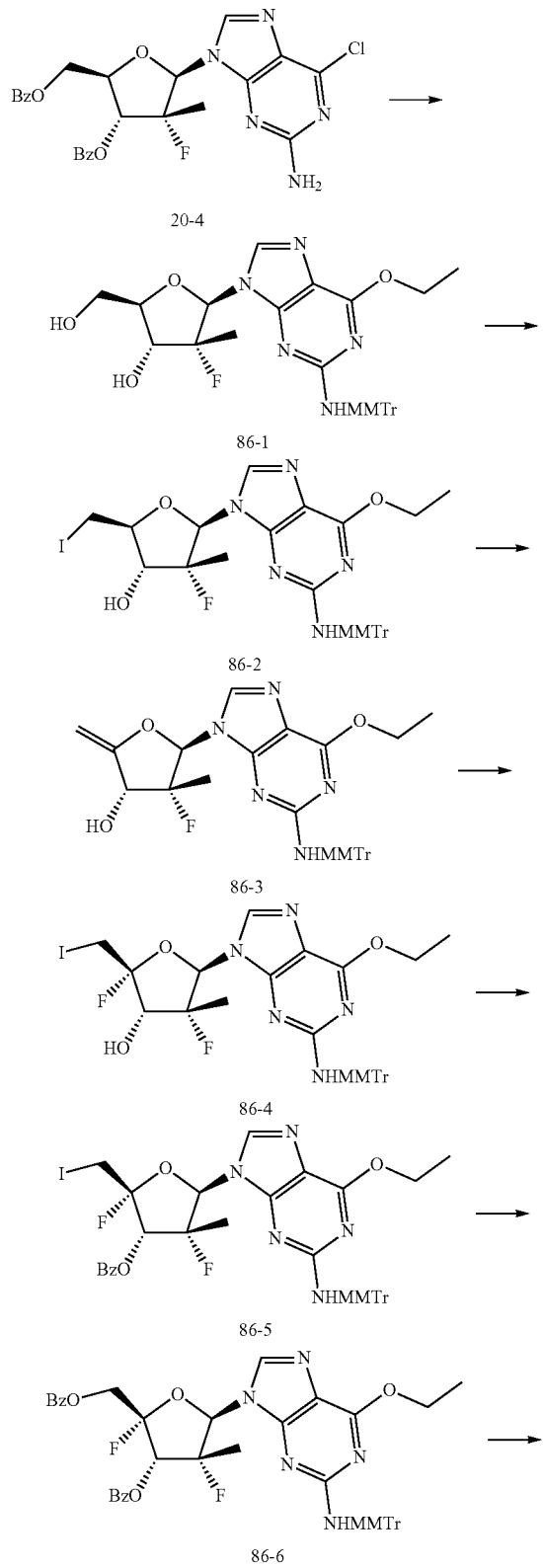

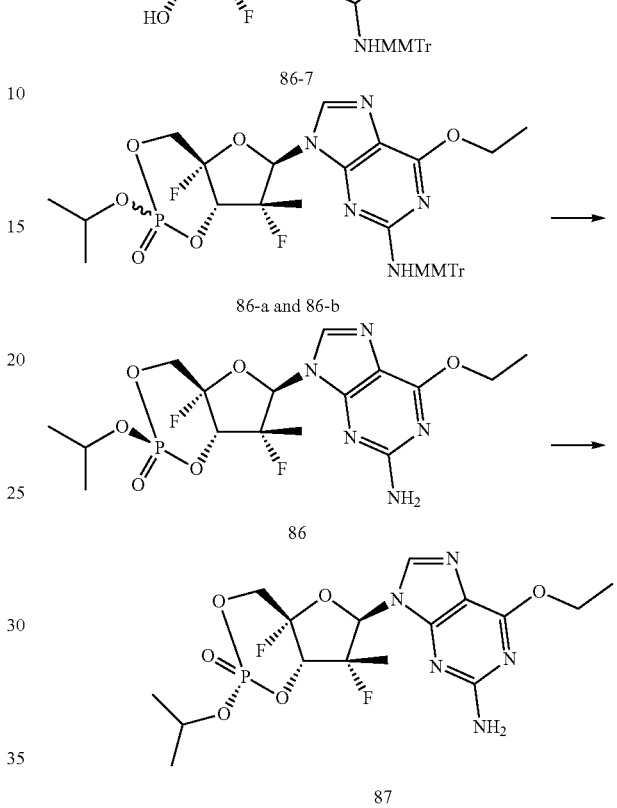

A freshly prepared EtONa in dry EtOH (2N, 150 mL) was added to a solution of 20-4 (13.67 g, 17.15 mmol) in EtOH (50 mL) at 0° C. The mixture was stirred at RT for 1 h, and then concentrated at low pressure. The residue was purified by silica gel column (5% MeOH in DCM) to give 86-1 (10 g, 98%) as a yellow solid.

To a solution of PPh$_3$ (2.73 g, 10.4 mol) in anhydrous pyridine (60 mL) was added I$_2$ (2.48 g, 9.76 mmol) at RT, and the reaction mixture was stirred RT for 30 mins. A solution of 86-1 (3.9 g, 6.51 mmol) in pyridine (10 mL) was added. The mixture was stirred at RT overnight. The reaction was quenched with sat. Na$_2$S$_2$O$_3$ solution and NaHCO$_3$ aq., and then extracted with EA (100 mL). The organic layer was dried over anhydrous Na$_2$SO$_4$, and evaporated at low pressure. The residue was purified by silica gel column (2% MeOH in DCM) to give 86-2 (3.0 g, 75%) as a yellowed solid.

To a solution of 86-2 in dry THF (300 mL) was added DBU (14.0 g, 91.8 mmol), and the mixture was heated to reflux for 3 h. The mixture was concentrated at low pressure. The residue was dissolved in EA (100 mL), and washed with brine. The organic layer was dried over anhydrous Na$_2$SO$_4$, and evaporated at low pressure. The residue was purified by silica gel column (20% EA in PE) to give 86-3 (0.6 g, 37.5%) as a white solid.

To an ice-cooled solution of 86-3 (2.0 g, 3.44 mmol) in anhydrous MeCN (20 mL) was added NIS (0.975 g, 4.3 mmol) and TEA.3HF (0.82 g, 5.16 mmol) at 0° C. The mixture was stirred at RT for 2 h. The reaction was quenched with sat. Na$_2$SO$_3$ and NaHCO$_3$ aqueous solution, and then concentrated at low pressure. The residue was dissolved in EA (50 mL), washed with brine, dried over anhydrous Na$_2$SO$_4$, and evaporated at low pressure. The residue was purified by silica gel column (20% EA in PE) to give 86-4 (1.5 g, 60%) as a white solid.

To a solution of 86-4 (1 g, 1.37 mmol) in dry pyridine (100 mL) was added BzCl (0.23 g, 1.65 mmol) at 0° C. The reaction was stirred for 30 mins and checked by LCMS. The mixture was concentrated at low pressure, and the residue was dissolved in EA (50 mL). The solution was washed with brine. The organic layer was dried over MgSO$_4$, and evaporated at low pressure. The residue was purified by silica gel column chromatography (10% EA in PE) to give 86-5 (0.9 g, 78%) as a white solid.

To a solution of 86-5 (2 g, 2.4 mmol) in dry DMF (40 mL) was added NaOBz (3.46 g, 24 mmol) and 15-crown-5 (4.5 mL). The mixture was stirred at 95° C. for 72 h. The mixture was then diluted with EA (100 mL), and washed with water and brine. The organic phase was dried over MgSO$_4$, and concentrated at low pressure. The residue was purified by silica gel column (15% EA in PE) to give 86-6 (1.5 g, 75%) as a white solid.

Compound 86-6 (1.35 g, 1.64 mmol) in NH$_3$/MeOH (150 mL) was stirred at RT for 18 h. The mixture was concentrated at low pressure, and the residue was purified by silica gel column (5% MeOH in DCM) to give 86-7 (0.9 g, 90%) as a white solid. ESI-MS: m/z 618.3 [M+H]$^+$.

To a solution of 86-7 (99 mg, 0.16 mmol) in DCM (1.0 mL), triethylamine (92.7 µL, 0.64 mmol) was added at RT. The mixture was cooled to 0 to 5° C. (ice/water bath), and freshly prepared and distilled isopropyl phosphorodichloridate (36.6 µL, 0.2 mmol, prepared according to a procedure, Reddy et al. *J. Org. Chem.* 2011, 76 (10), 3782-3790) was added to the mixture. The mixture was stirred 0 to 5° C. (ice/water bath) for 15 mins, followed by addition of N-methylimidazole (26.3 µL, 0.32 mmol). The mixture was then stirred for 1 h at 0 to 5° C. TLC showed absence of 86-7. EA (100 mL) was added, followed by water. The organic layer was washed H$_2$O, saturated aqueous NH$_4$Cl solution and brine. The organic layer was separated, dried over anhydrous MgSO$_4$ and filtered. The filtrate was concentrated in vacuum to give a residue, which was purified on silica gel with 0 to 10% iPrOH/DCM to give a mixture of 86-a and 86-b (61.5 mg).

A mixture of 86-a and 86-b (61.5 mg, 0.085 mmol) was dissolved in anhydrous CH$_3$CN (0.5 mL), and 4N HCl in dioxane (64 µL) was added at 0 to 5° C. (ice/water bath). The mixture was stirred at RT for 40 mins, and anhydrous EtOH (200 µL) was added. The solvents were evaporated at RT and co-evaporated with toluene 3 times. The residue was dissolved in 50% CH$_3$CN/H$_2$O, was purified on a reverse-phase HPLC (C18) using acetonitrile and water, followed by lyophilization to give compound 86 (1.8 mg) and compound 87 (14.5 mg).

Compound 86: $^1$H NMR (CD$_3$OD-d$_4$, 400 MHz) δ 8.0 (s, 1H), 6.69 (d, J=16.0 Hz, 1H), 5.9-5.6 (br s, 1H), 4.94-4.85 (m, 1H), 4.68-4.52 (m, 3H), 1.49-1.3 (m, 12H); $^{19}$F NMR (CD$_3$OD-d$_4$) δ −122.8 (s), −160.06 (s); $^{31}$P NMR (CD$_3$OD-d$_4$) δ −7.97 (s). ESI-LCMS: m/z=450.1 [M+H]$^+$; Compound 87: $^1$H NMR (CD$_3$OD-d$_4$, 400 MHz) δ 7.96 (s, 1H), 6.68 (s, 1H), 6.69 (d, J=16.8 Hz, 1H), 6.28-6.1 (br s, 1H), 4.81-4.5 (m, 4H), 1.45-1.39 (m, 12H); $^{31}$P NMR (CD$_3$OD-d$_4$) δ −5.84 (s). ESI-LCMS: m/z=450. [M+H]$^+$.

Example 67

Compounds 88 and 89

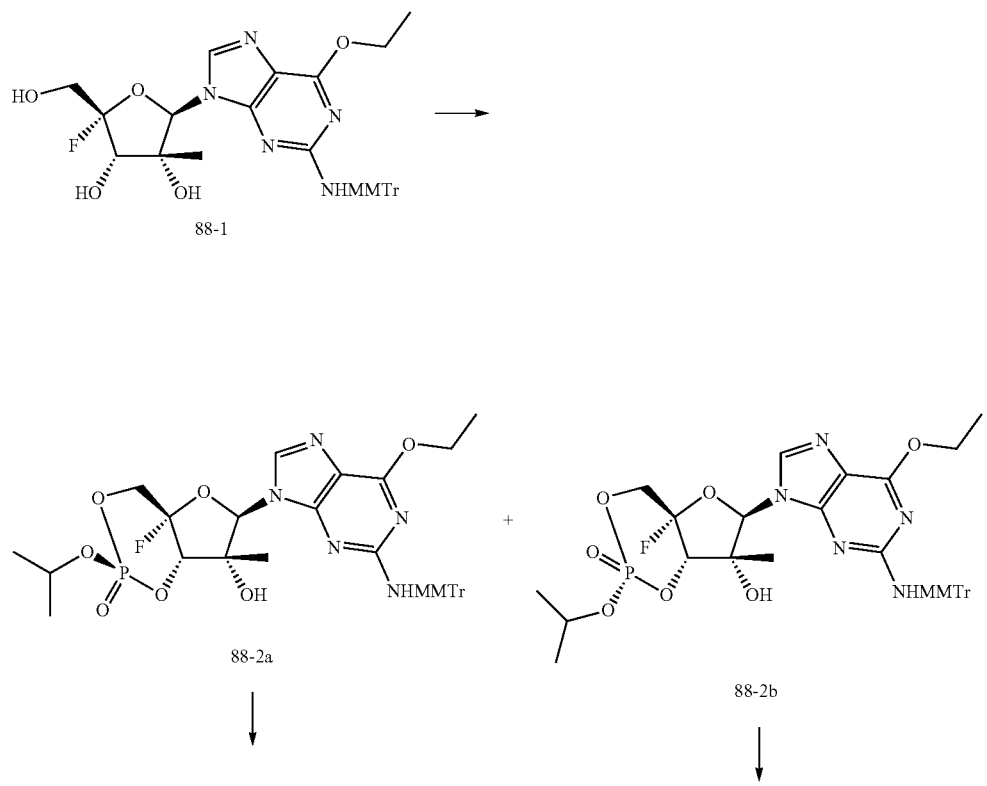

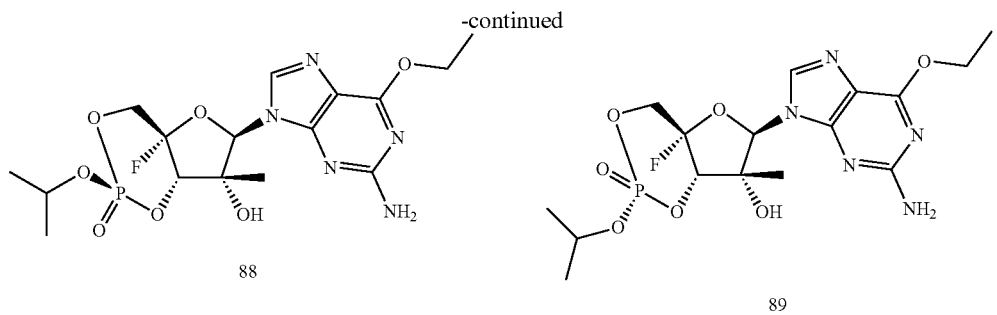

88

89

To a solution of 88-1 (150 mg, 0.24 mmol) in DCM (2.0 mL), triethylamine (141 µL, 2.0 mmol) was added at RT. The mixture was cooled to 0 to 5° C. (ice/water bath), and freshly prepared and distilled isopropyl phosphorodichloridate (45 µL, 0.26 mmol, prepared according to a procedure, Reddy et al. *J. Org. Chem.* 2011, 76 (10), 3782-3790) was added. The mixture was stirred at 0 to 5° C. (ice/water bath) for 15 mins, followed by N-methylimidazole (40 µL, 0.49 mmol). The mixture was stirred for 1 h at 0 to 5° C. TLC showed the absence of starting material 88-1. EA (100 mL) was added, followed by water. The organic layer was washed with $H_2O$, sat. aq. $NH_4Cl$ solution and brine. The organic layer was separated, dried over anhydrous $MgSO_4$ and filtered. The filtrate was concentrated in vacuum to give a residue, which was purified on silica gel with 0 to 10% iPrOH/DCM to give 88-2a (16.9 mg, faster eluting isomer) and 88-2b (72.7 mg, slower eluting isomer).

Compounds 88-2a and 88-2b were deprotected using a procedure described herein. Compound 88 (7.3 mg, single isomers from 88-2a (16.5 mg, 0.0235 mmol)) and compound 89 (29.0 mg. single isomers from 88-2b (72.7 mg, 0.1 mmol)) were obtained.

Compound 88: $^1H$ NMR ($CD_3OD$-$d_4$, 400 MHz) δ 7.94 (s, 1H), 6.32 (s, 1H), 6.00-5.9 (br s, 1H), 4.9-4.487 (m, 1H), 4.83-4.77 (m, 1H), 4.65-4.50 (m, 3H), 1.45-1.39 (s, 9H), 1.2 (s, 3H); $^{19}F$ NMR ($CD_3OD$-$d_4$) δ −120.3 (s); $^{31}P$ NMR ($CD_3OD$-$d_4$) δ −5.19 (s); ESI-LCMS: m/z=448.05 [M+H]$^+$. Compound 89: $^1H$ NMR ($CD_3OD$-$d_4$, 400 MHz) δ 7.98 (s, 1H), 6.34 (s, 1H), 5.78-5.64 (br s, 1H), 4.95-4.48 (m, 2H), 4.62-4.52 (m, 3H), 1.48-1.42 (s, 9H), 1.1 (s, 3H); $^{19}F$ NMR ($CD_3OD$-$d_4$) δ −121.3 (s); $^{31}P$ NMR ($CD_3OD$-$d_4$) δ −7.38 (s); ESI-LCMS: m/z=448.05 [M+H]$^+$.

Example 68

Compound 90

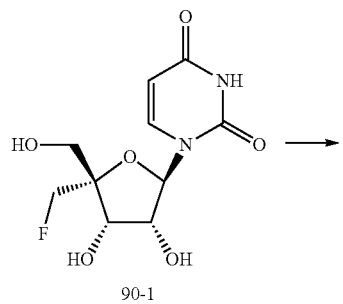

90-1

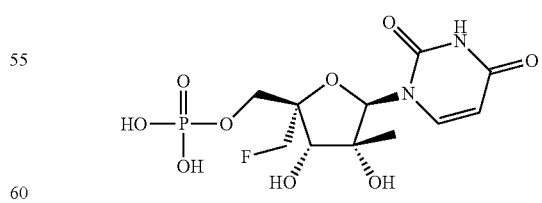

90

To a stirred solution of 90-1 (532 mg, 1.84 mmol) in anhydrous $CH_3CN$ (8.0 mL) was added N-methylimidazole (2.0 mL, 24.36 mmol) at 0 to 5° C. (ice/water bath) followed by a solution of freshly prepared and distilled isopropyl phosphorodichloridate (0.5 mL, 2.84 mmol). The solution was stirred at RT for 15 h. The mixture was diluted with EA, followed by water (15 mL). The solution was washed with $H_2O$, 50% aqueous citric acid solution and brine. The organic layer was separated, dried over anhydrous $MgSO_4$ and filtered. The filtrate was concentrated in vacuum to give a residue, which was purified on silica gel with 0 to 8% MeOH/DCM to give the crude product (72 mg). The crude product was re-purified purified on a reverse-phase HPLC (C18) using acetonitrile and water, followed by lyophilization to give compound 90 (43.6 mg). MS: m/z=395.05 [M+H]$^+$, 393.0 [M−H]$^−$, 787.05.0 [2M−H]$^−$.

Example 69

Compound 96

Dry 51 (0.05 mmol) was dissolved in the mixture of $PO(OMe)_3$ (0.7 mL) and pyridine (0.3 mL). The mixture was evaporated in vacuum for 15 mins at bath temperature 42° C., and then cooled to RT. N-Methylimidazole (0.009 mL, 0.11 mmol) was added followed by $POCl_3$ (9 µL, 0.11 mmol), and the mixture was kept at RT for 20-40 mins. The reaction was controlled by LCMS and monitored by the appearance of 96. Isolation was performed by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer to yield compound 96. MS: m/z 369.0 [M−1].

Example 70

Compounds 97 and 98

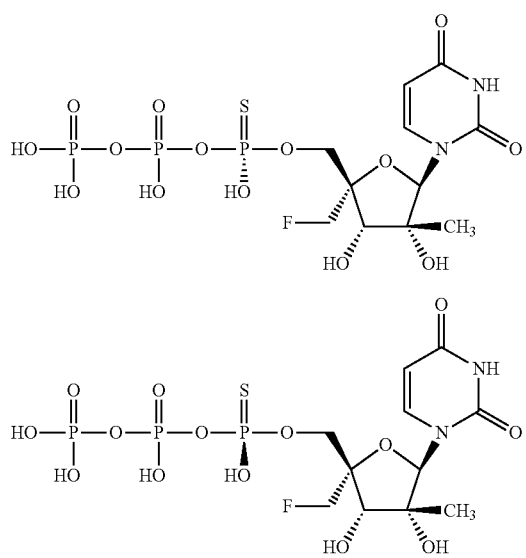

Dry 51 (0.05 mmol) was dissolved in the mixture of PO(OMe)$_3$ (0.7 mL) and pyridine (0.3 mL). The mixture was evaporated in vacuum for 15 mins at bath temperature 42° C., than cooled to RT. N-Methylimidazole (0.009 mL, 0.11 mmol) was added followed by PSCl$_3$ (9 uL, 0.11 mmol), and the mixture was kept at RT for 20-40 mins. The reaction was controlled by LCMS and monitored by the appearance of the nucleoside 5'-thiophosphate. After completion of the reaction, tetrabutylammonium salt of pyrophosphate (150 mg) was added, followed by DMF (0.5 mL) to get a homogeneous solution. After 1.5 hours at ambient temperature, the reaction was quenched with water (10 mL). The 5'-triphosphate as mixture of diastereomers was isolated by IE chromatography on AKTA Explorer using column HiLoad 16/10 with Q Sepharose High Performance. Separation was done in linear gradient of NaCl from 0 to 1N in 50 mM TRIS-buffer (pH 7.5). Fractions containing thiotriphosphate were combined, concentrated and desalted by RP HPLC on Synergy 4 micron Hydro-RP column (Phenominex). Linear gradient of methanol from 0 to 30% in 50 mM triethylammonium buffer was used for elution over 20 mins, flow 10 mL/mins. Compounds 97 and 98 were collected. Analytical RP HPLC was done in 50 mM triethylammonium acetate buffer, pH 7.5 containing linear gradient of acetonitrile from 0% to 25% in 7 mins on Synergy 4 micron Hydro-RP column (Phenominex). Compound 97: RT 5.50 mins. $^{31}$P NMR: δ+42.45 (1P, d), −6.80 (1P, d), −23.36 (1P, q). MS: m/z 544.9 [M−1]. Compound 98: RT 6.01 mins. $^{31}$P NMR: δ+41.80 (1P, d), −6.57 (1P, d), −23.45 (1P, q). MS: m/z 544.9 [M−1].

Example 71

Compound 99

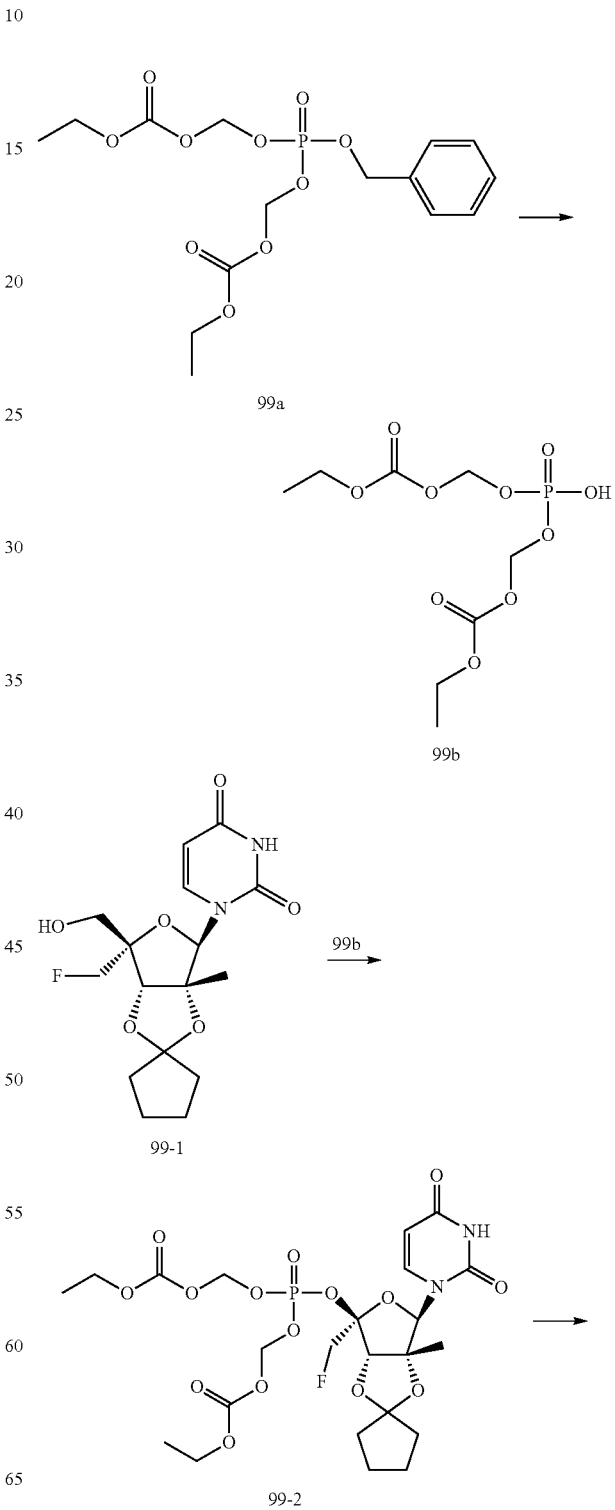

445

-continued

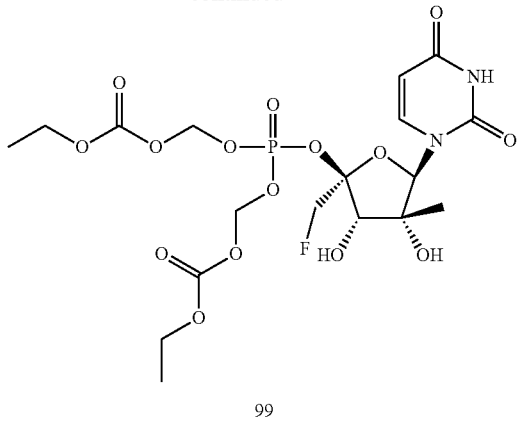 [SMILES: CCOC(=O)OCOP(=O)(OCOC(=O)OCC)O[C@@]1(CF)O[C@@H](n2ccc(=O)[nH]c2=O)[C@](C)(O)[C@@H]1O]

99

To a solution of 99a (0.31 g, 0.8 mmol) in anhydrous methanol (2 mL), was added 10% Pd/C (30 mg), and the mixture was stirred under H$_2$ atmosphere for 1 h. After completion, the mixture was filtered, and the catalyst cake was washed with methanol. The washing and filtrate were combined. The solvent was removed under vacuum to give 99b as a semi-solid (252 mg), which was used without further purification. $^1$H NMR (CDCl$_3$, 400 MHz) δ5.57 (d, J=13.6 Hz, 4H), 4.23 (q, J=7.2 Hz, 4H), 1.30 (t, J=7.2 Hz, 6H), $^{31}$P NMR (CDCl$_3$) δ–4.64 (s).

To a solution of triethylammonium bis (EOC) phosphate (0.7 mmol, prepared from 213 mg of 99b and 0.2 mL of TEA) in THF (3 mL) was added 99-1 (160 mg, 0.45 mmol) followed by diisopropylethylamine (0.33 mL, 1.8 mmol), BOP-Cl (229 mg, 0.9 mmol), and 3-nitro-1,2,4-triazole (103 mg, 0.9 mmol). The mixture was stirred at RT for 90 mins. The mixture was diluted with EtOAc, and washed with water and brine. The organic layer was separated, dried over anhydrous Na$_2$SO$_4$ and filtered. The filtrate was concentrated in vacuum to a white solid, which was purified on silica gel column (CH$_3$OH:DCM; 9.5:0.5) to give 99-2 (189 mg, 66%).

To a solution of 99-2 (180 mg, 0.28 mmol) in 80% HCOOH (7 mL), was heated for 6 h at 45° C. The solvents were evaporated, and then co-evaporated with toluene 3 times. The residue was purified on silica gel column using 0 to 10% MeOH in DCM to obtain compound 99 (97.3 mg) as a white foam after lypholization. MS: m/z=575.1 [M+H]$^+$.

Example 72

Compound 100

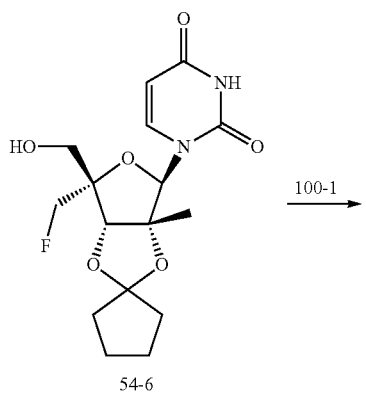

54-6

446

-continued

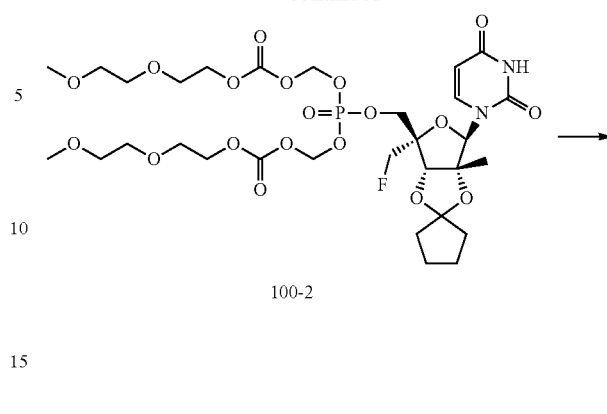

100-2

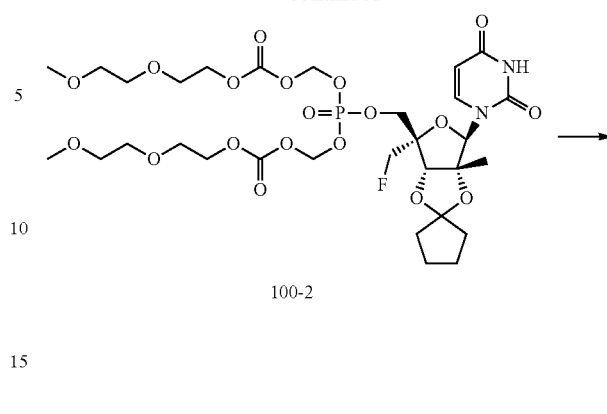

100

Compound 100a was prepared from commercially available 2-(2-methoxyethoxy)-ethanol (11.56 mL). Compound 100a (13.5 g) was obtained as a clear colorless oil. $^1$H-NMR (CDCl$_3$) δ 5.73 (s, 2H), 4.38-4.40 (m, 2H), 3.74-3.77 (m, 2H), 3.64-3.67 (m, 2H), 3.54-3.57 (m, 2H), 3.39 (s, 3H). Compound 100b (9.6 g) was prepared from 100a, and was obtained as a clear, slightly colored oil. $^1$H-NMR (CDCl$_3$) δ 5.96 (s, 2H), 4.38-4.40 (m, 2H), 3.74-3.77 (m, 2H), 3.64-3.67 (m, 2H), 3.54-3.57 (m, 2H), 3.39 (s, 3H). Benzylphosphate (silver salt) and 100b (2.4 g) were reacted and yielded purified 100c (1.02 g). $^1$H-NMR (CD$_3$CN): δ 7.39-7.42 (m, 5H), 5.60 (d, 4H), 5.11 (d, 2H), 4.27-4.29 (m, 4H), 3.65-3.67 (m, 4H), 3.56 (t, 4H), 3.46 (t, 4H), 3.30 (s, 6H). $^{31}$P-NMR (CD$_3$CN): δ –4.55 ppm. Compound 100c (620 mg; 1.15 mmol) was deprotected to give 100-1 (triethylammonium salt), which was used immediately without further purification. Compound 54-6 (356 mg; 1.0 mmol) and 100-1 were reacted to give purified 100-2 (250 mg). Compound 100-2 (250 mg) was deprotected to yield purified compound 100 (110 mg, 0.14 mmol). The aforementioned reactions were conducted using a method described in the preparation of compound 54. $^1$H-NMR (CDCl$_3$): δ 8.62 (s, 1H), 7.54 (d, 1H), 5.96 (s, 1H), 5.64-5.79 (m, 5H), 4.76 (dd, 2H), 4.37-4.46 (m, 6H), 4.25 (d, 2H), 3.86 (s, 1H), 3.75 (t, 4H), 3.70 (t, 4H), 3.58 (t, 4H), 3.38 (s, 6H), 1.65 (s, 6H), 1.25 (s, 3H). $^{31}$P-NMR (CDCl$_3$): δ –3.90 ppm.

Example 73

Compound 104

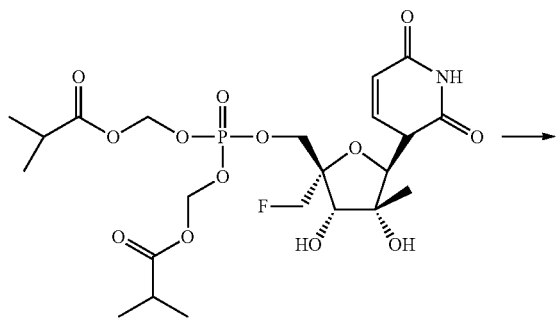

70

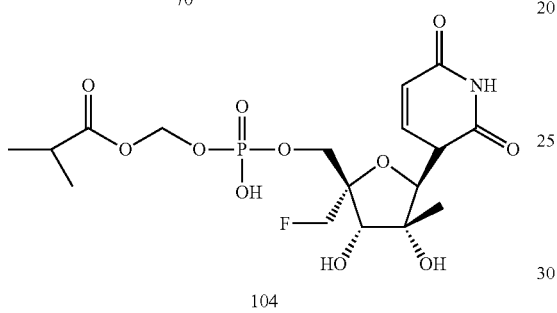

104

Compound 44 (0.010 g, 0.016 mmol) was added to normal saline solution (3 mL, pH 7.3), and stored in a heat block at 37° C. for 6 days. The mixture was purified by preparative HPLC using a Synergi 4u Hydro-RP column (Phenomenex, 00G-4375-U0-AX), with H$_2$O (0.1% formic acid) and ACN (0.1% formic acid) solvents (0-65% gradient in 20 minutes). The compound eluted at 13.0 mins. Pure fractions were pooled and lyophilized to yield compound 104 (0.005 g, 63%). MS: m/z=487 [M+1].

Example 74

Compound 102

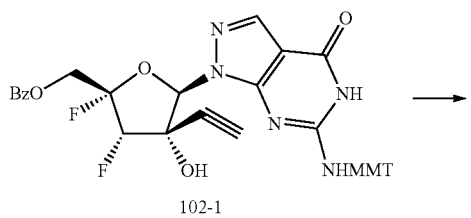

102-1

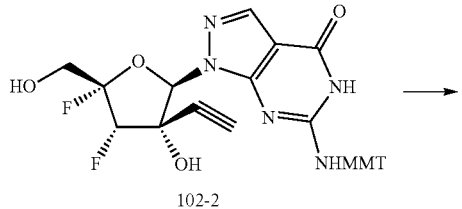

102-2

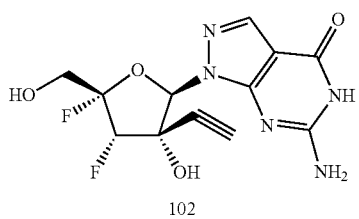

102

A mixture of 102-1 (45 mg, 0.06 mmol) and butylamine (0.4 mL) was kept overnight at RT and then evaporated. The crude residue was purified on silica gel (10 g column) with CH$_2$Cl$_2$/MeOH (4-12% gradient) to yield 102-2 as a colorless glass (20 mg, 56%).

To a solution of 102-2 (20 mg, 0.03 mmol) in ACN (0.5 mL) was added 4N HCl in dioxane (35 μL). The mixture was stirred at RT for 4 h and then quenched with MeOH. The residue was treated with ACN to yield compound 102 as an off-white solid (9 mg, 80%). MS m/z=328 [M+1].

Example 75

Compound 105

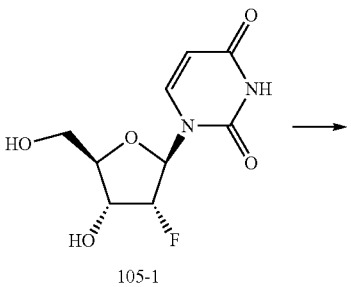

105-1

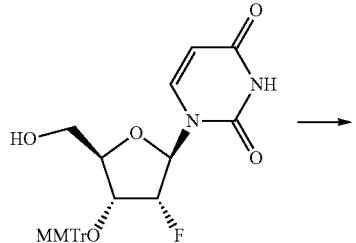

105-2

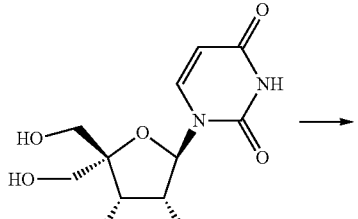

105-3

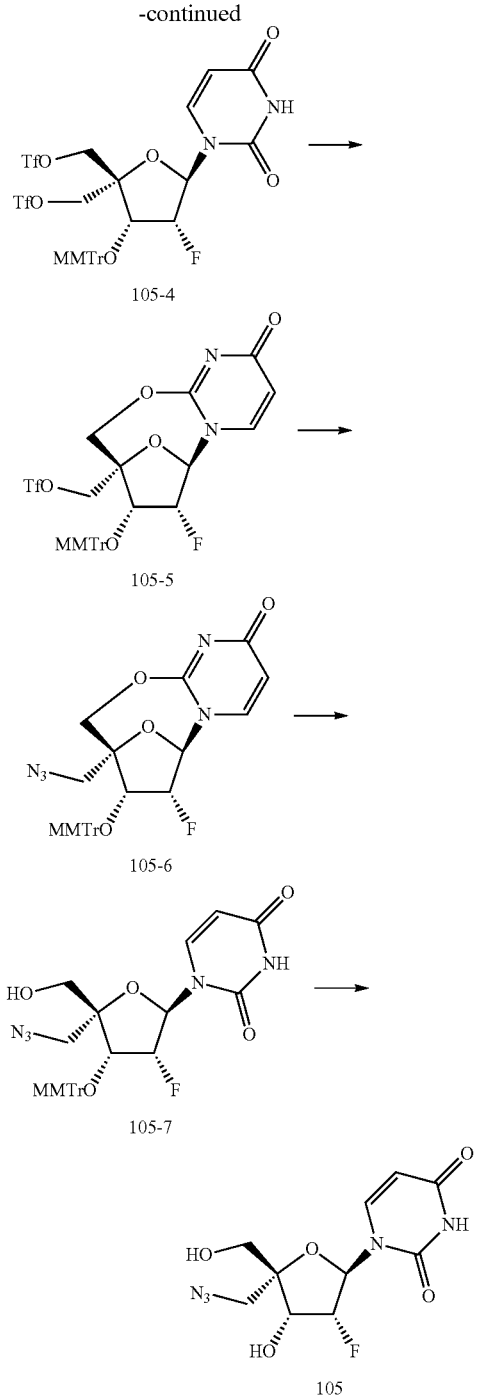

105-4

105-5

105-6

105-7

105

To a solution of 105-1 (50 g, 203 mmol) in anhydrous pyridine (200 mL) was added TBDPS-Cl (83.7 g, 304 mmol). The reaction was allowed to proceed overnight at RT. The solution was concentrated under low pressure to give a residue, which was partitioned between ethyl acetate and water. The organic layer was separated, washed with brine, dried over magnesium sulfate and concentrated under reduced pressure to give 5'-OTBDPS ether as a white foam (94 g).

To a solution of the 5'-OTBDPS ether (94.0 g, 194.2 mmol) in anhydrous DCM (300 mL) were added silver nitrate (66.03 g, 388.4 mmol) and collidine (235 mL, 1.94 mol). The mixture was stirred at RT. After 15 mins, the mixture was cooled to 0° C., and monomethoxytrityl chloride (239.3 g, 776.8 mmol) was added as a single portion. After being stirred overnight at RT., the mixture was filtered through Celite and the filtrate was diluted with TBME. The solution was washed successively with 1M citric acid, diluted brine and 5% sodium bicarbonate. The organic solution was dried over sodium sulfate and concentrated under vacuum to give the fully protected intermediate as a yellow foam.

This fully protected intermediate was dissolved in toluene (100 mL) and the solution was concentrated under reduced pressure. The residue was dissolved in anhydrous THF (250 mL) and treated with TBAF (60 g, 233 mmol). The mixture was stirred for 2 h at RT., and the solvent was removed under reduced pressure. The residue was taken into ethyl acetate and the solution was washed first with saturated sodium bicarbonate and then with brine. After being dried over magnesium sulfate, the solvent was removed in vacuum and the residue was purified by column chromatography (50% EA in PE) to give 105-2 (91 g, 86.4%) as a white foam.

To a solution of 105-2 (13.5 g, 26 mmol) in DCM (100 mL) was added pyridine (6.17 mL, 78 mmol). The solution was cooled to 0° C., and Dess-Martin periodinane (33.8 g, 78 mmol) was added as a single portion. The reaction mixture was stirred for 4 h at RT., and quenched by the addition of $Na_2S_2O_3$ solution (4%) and sodium bicarbonate aqueous solution (4%) (the solution was adjusted to pH 6, ~150 mL). The mixture was stirred for 15 mins. The organic layer was separated, washed with diluted brine and concentrated under reduced pressure. The residue was dissolved in dioxane (100 mL) and the solution was treated with 37% aqueous formaldehyde (21.2 g, 10 eq.) and 2N aqueous sodium hydroxide (10 eq.). The reaction mixture was stirred at RT., overnight. After stirring for 0.5 h at RT., the excess of aqueous sodium hydroxide was removed with saturated $NH_4Cl$ (~150 mL). The mixture was concentrated under reduced pressure, and the residue was partitioned between ethyl acetate and 5% sodium bicarbonate. The organic phase was separated, washed with brine, dried over magnesium sulfate and concentrated. The residue was purified by column chromatography (2% MeOH in DCM) to give 105-3 (9.2 g, 83.6%) as a white foam.

Compound 105-3 (23 g, 42.0 mmol) was co-evaporated with toluene twice. The residue was dissolved in anhydrous DCM (250 mL) and pyridine (20 mL). The solution was cooled to 0° C., and triflic anhydride (24.9 g, 88.1 mmol) was added dropwise over 10 mins. At this temperature, the reaction was stirred for 40 mins. The reaction was monitored by TLC (PE:EA=2:1 and DCM:MeOH=15:1). After completion, the reaction mixture was quenched with water (50 mL) at 0° C. The mixture was stirred for 30 mins, and extracted with EA. The organic phase was dried over $Na_2SO_4$ and filtered through a silica gel pad. The filtrate was concentrated under reduced pressure, and the residue was purified by column chromatography (50% EA in PE) to give 105-4 (30.0 g, 88.3%) as a brown foam.

To a stirred solution of 105-4 (4.4 g, 5.42 mmol) in anhydrous DMF (50 mL) was added NaH (260 mg, 6.5 mmol) at 0° C. under nitrogen atmosphere. The solution was stirred at RT., for 1.5 h. The solution was used for the next step without any further workup.

To the stirred solution was added $NaN_3$ (1.5 g, 21.68 mmol) at 0° C. under nitrogen atmosphere, and the resulting solution was stirred at RT. for 1.5 h. The reaction was quenched with water, extracted with EA, washed with brine, and dried over MgSO₄. The concentrated organic phase was used for the next step without further purification.

To a solution of 105-6 (3.0 g, 5.4 mmol) in anhydrous 1,4-dioxane (18 mL) was added NaOH (5.4 mL, 2M in water) at RT. The reaction mixture was stirred at RT. for 3 h. The reaction was diluted with EA, washed with brine, and dried over MgSO₄. The concentrated organic phase was purified on a silica gel column (30% EA in PE) to give 105-7 (2.9 g, 93%) as a white foam.

Compound 105-7 (520 mg, 0.90 mmol) was dissolved in 80% of HCOOH (20 mL) at RT. The mixture was stirred for 3 h, and monitored by TLC. The solvent was removed and the residue was treated with MeOH and toluene for 3 times. NH₃/MeOH was added, and the reaction mixture was stirred at RT., for 5 mins. The solvent was concentrated to dryness and the residue was purified by column chromatography to give compound 105 (120 mg, 44.4%) as a white solid. ESI-LCMS: m/z 302.0 [M+H]⁺, 324.0[M+Na]⁺.

Example 76

Compound 106

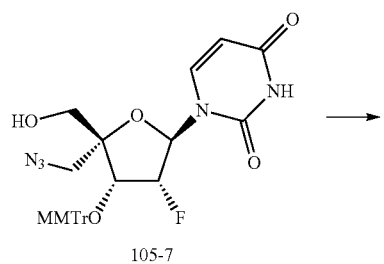

105-7

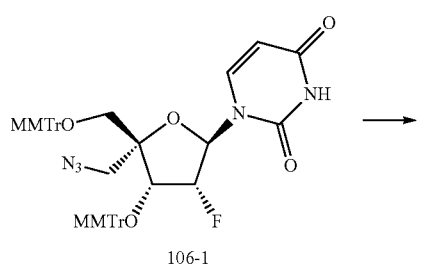

106-1

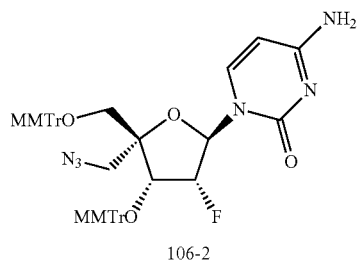

106-2

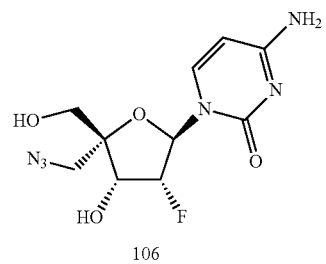

106

To a stirred solution of 105-7 (1.1 g, 2.88 mmol) in anhydrous DCM (10 mL) was added MMTrCl (1.77 g, 5.76 mmol), AgNO₃ (1.47 g, 8.64 mmol) and collidine (1.05 g, 8.64 mmol) at 25° C. under a N₂ atmosphere. The reaction was refluxed for 12 h. MeOH (20 mL) was added and the solvent was removed to dryness. The residue was purified on a silica gel column (20% EA in PE) to give 106-1 (1.6 g, 85.1%) as a white foam.

To a stirred solution of 106-1 (800 mg, 0.947 mmol) in anhydrous MeCN (10 mL) were added TPSCl (570 mg, 1.89 mmol), DMAP (230 mg, 1.89 mmol) and TEA (190 mg, 1.89 mmol) at RT. The mixture was stirred for 12 h. NH₄OH (25 mL) was added and the mixture was stirred for 2 h. The solvent was removed, and the residue was purified on a silica gel column as a yellow foam. Further purification by prep-TLC gave 106-2 (700 mg, 87.1%) as a white solid.

Compound 106-2 (300 mg, 0.355 mmol) was dissolved in 80% of HCOOH (5 mL) at RT. The mixture was stirred for 3 h, and monitored by TLC. The solvent was then removed and the residue was treated with MeOH and toluene (3 times). NH₃/MeOH was added and the mixture was stirred at RT, for 5 mins. The solvent was removed and the residue was purified by column chromatography to give compound 106 (124 mg, 82.6%) as a white solid. ESI-LCMS: m/z 301.0 [M+H]⁺, 601.0 [2M+H]⁺.

Example 77

Compound 108

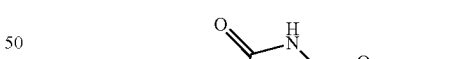

108-1

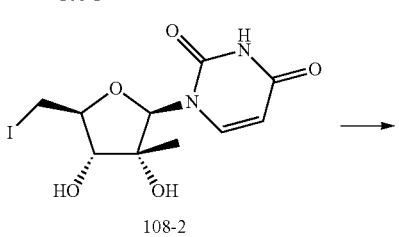

108-2

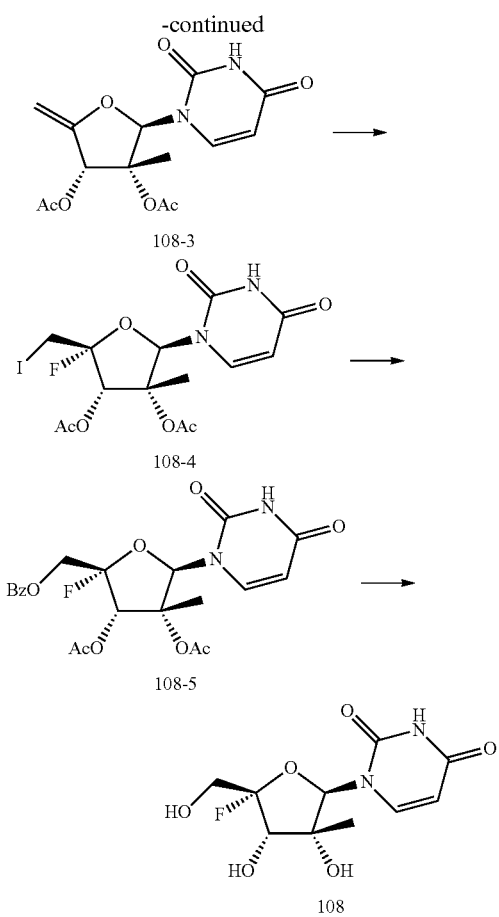

To a stirred suspension of 108-1 (20 g, 77.5 mmol), PPh₃ (30 g, 114.5 mmol), imidazole (10 g, 147 mmol) and pyridine (90 mL) in anhydrous THF (300 mL) was added a solution of I$_2$ (25 g, 98.4 mmol) in THF (100 mL) dropwise at 0° C. The mixture was warmed to room temperature (RT) and stirred at RT for 10 h. The reaction was quenched by MeOH (100 mL). The solvent was removed, and the residue was re-dissolved in a mixture ethyl acetate (EA) and THF (2 L, 10:1). The organic phase was washed with saturated Na$_2$S$_2$O$_3$ aq., and the aqueous phase was extracted with a mixture of EA and THF (2 L, 10:1). The organic layer was combined and concentrated to give a residue, which was purified on a silica gel column (0-10% MeOH in DCM) to give 108-2 (22.5 g, 78.9%) as a white solid. ¹H NMR: (DMSO-d₆, 400 MHz) δ 11.42 (s, 1H), 7.59 (d, J=8.4 Hz, 1H), 5.82 (s, 1H), 5.63 (d, J=8.0 Hz, 1H), 5.50 (s, 1H), 5.23 (s, 1H), 3.77-3.79 (m, 1H), 3.40-3.62 (m, 3H), 0.97 (s, 3H).

To a stirred solution of 108-2 (24.3 g, 66.03 mmol) in anhydrous MeOH (240 mL) was added NaOMe (10.69 g, 198.09 mmol) at RT under N$_2$. The mixture was refluxed for 3 h. The solvent was removed, and the residue was re-dissolved in anhydrous pyridine (200 mL). To the mixture was added Ac$_2$O (84.9 g, 833.3 mmol) at 0° C. The mixture was warmed to 60° C. and stirred for 10 h. The solvent was removed, and the residue was diluted with DCM, washed with saturated NaHCO$_3$ and brine. The organic layer was concentrated and purified on a silica gel column (10-50% EA in PE) to give 108-3 (15 g, 70.1%) as a white solid. ¹H NMR: (CDCl₃, 400 MHz) δ 8.82 (s, 1H), 7.23 (d, J=2.0 Hz, 1H), 6.54 (s, 1H), 5.85 (s, 1H), 5.77 (dd, J=8.0, 2.0 Hz, 1H), 4.69 (d, J=2.4 Hz, 1H), 4.58 (d, J=2.8 Hz, 1H), 2.07 (d, J=5.2 Hz, 6H), 1.45 (s, 3H).

To an ice cooled solution of 108-3 (15 g, 46.29 mmol) in anhydrous DCM (300 mL) was added AgF (29.39 g, 231.4 mmol). I2 (23.51 g, 92.58 mmol) in anhydrous DCM (1.0 L) was added dropwise to the solution. The reaction mixture was stirred at RT for 5 h. The reaction was quenched with saturated Na$_2$S$_2$O$_3$ and NaHCO$_3$, and extracted with DCM. The organic layer was separated, dried and evaporated to dryness. The residue was purified on a silica gel column (10-30% EA in PE) to give 108-4 (9.5 g, 43.6%) as a white solid. ¹H NMR: (Methanol-d₄, 400 MHz) δ 7.52 (d, J=8.0 Hz, 1H), 6.21 (s, 1H), 5.80 (d, J=17.2 Hz, 1H), 5.73 (d, J=8.0 Hz, 1H), 3.58 (s, 1H), 3.54 (d, J=6.8 Hz, 1H), 2.17 (s, 3H), 2.09 (s, 3H), 1.58 (s, 3H).

To a solution of 108-4 (7.0 g, 14.89 mmol) in anhydrous DMF (400 mL) were added NaOBz (21.44 g, 148.9 mmol) and 15-crown-5 (32.75 g, 148.9 mmol). The reaction mixture was stirred at 130° C. for 6 h. The solvent was removed, diluted with EA and washed with water and brine. The organic layer was evaporated and purified on a silica gel column (10-30% EA in PE) to give 108-5 (2.8 g, 40.5%). ESI-MS: m/z 444.9 [M–F+H]⁺.

A mixture of 108-5 (4.0 g; 8.6 mmol) and liquid ammonia was kept overnight at RT in a high-pressure stainless-steel vessel. Ammonia was then evaporated, and the residue purified on silica (50 g column) with a CH$_2$Cl$_2$/MeOH solvent mixture (4-12% gradient) to yield compound 108 as a colorless foam (2.0 g; 84% yield). ESI-MS: m/z 275.1 [M–H]⁻.

Example 78

Compounds 109 and 110

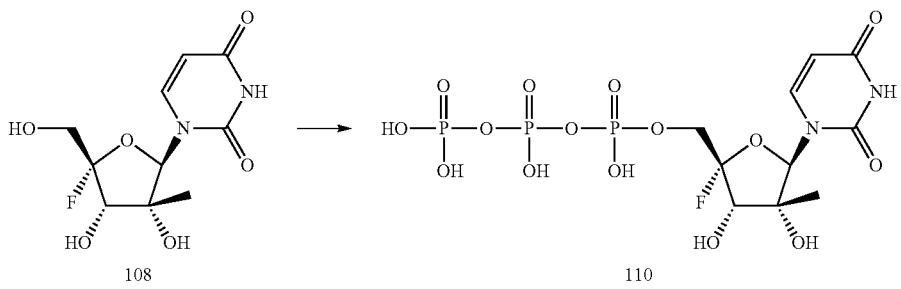

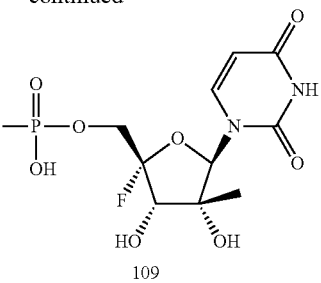

109

Dry compound 108 (14 mg, 0.05 mmol) was dissolved in the mixture of PO(OMe)₃ (0.750 mL) and pyridine (0.5 mL). The mixture was evaporated in vacuum for 15 mins at bath temperature 42° C., and then cooled down to RT. N-Methylimidazole (0.009 mL, 0.11 mmol) was added followed by POCl₃ (0.009 mL, 0.1 mmol). The mixture was kept at RT for 45 mins. Tributylamine (0.065 mL, 0.3 mmol) and N-tetrabutyl ammonium salt of pyrophosphate (100 mg) was added. Dry DMF (about 1 mL) was added to get a homogeneous solution. In 1 h, the reaction was quenched with 2M ammonium acetate buffer (1 mL, pH=7.5), diluted water (10 mL) and loaded on a column HiLoad 16/10 with Q Sepharose High Performance. The separation was done in linear gradient of NaCl from 0 to 1N in 50 mM TRIS-buffer (pH7.5). The fractions eluted at 60% buffer B contained Compound 109 and at 80% buffer B contained Compound 110. The corresponding fractions were concentrated, and the residue purified by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer. Compound 109: $P^{31}$-NMR (D₂O): −3.76 (s); MS: 378.2 [M−1]. Compound 110: $P^{31}$-NMR (D₂O): −9.28 (d, 1H, Pα), −12.31 (d, 1H, Pγ), −22.95 (t, 1H, Pβ); MS 515.0 [M−1].

Example 79

Compound 112

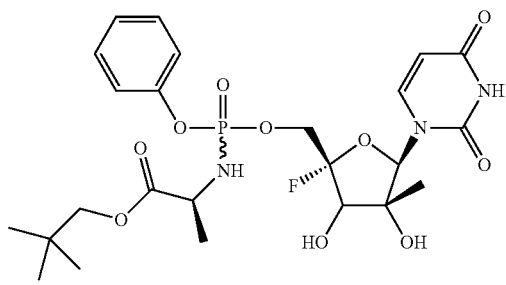

112

Compound 112 (36 mg, 63%) was synthesized as described for compound 2 using a neopentyl ester phosphorochloridate reagent. MS: 572.6 [M−1].

Example 80

Compounds 116 and 117

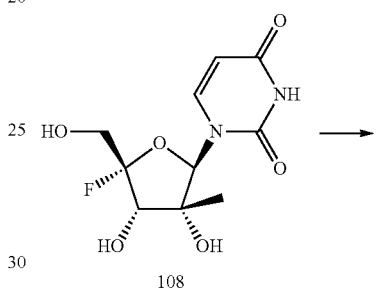

108

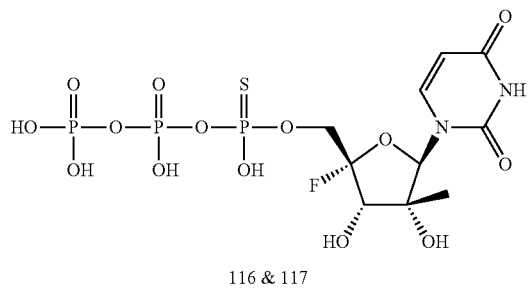

116 & 117

Dry compound 108 (14 mg, 0.05 mmol) was dissolved in the mixture of PO(OMe)₃ (0.750 mL) and pyridine (0.5 mL). The mixture was evaporated in vacuum for 15 mins at bath temperature 42° C., and then cooled down to RT. N-Methylimidazole (0.009 mL, 0.11 mmol) was added followed by PSCl₃ (0.01 mL, 0.1 mmol). The mixture was kept at RT for 1 h. Tributylamine (0.065 mL, 0.3 mmol) and N-tetrabutyl ammonium salt of pyrophosphate (200 mg) was added. Dry DMF (about 1 mL) was added to get a homogeneous solution. In 2 h, the reaction was quenched with 2M ammonium acetate buffer (1 mL, pH=7.5), diluted with water (10 mL) and loaded on a column HiLoad 16/10 with Q Sepharose High Performance. Separation was done in linear gradient of NaCl from 0 to 1N in 50 mM TRIS-buffer (pH7.5). The fractions eluted at 80% buffer B contained compounds 116 and 117. The corresponding fractions were concentrated, and the residue purified by RP HPLC on Synergy 4 micron Hydro-RP column (Phenominex). A linear gradient of methanol from 0 to 20% in 50 mM triethylammonium acetate buffer (pH 7.5) was used for elution. Two peaks were collected. The corresponding fractions were combined, concentrated and lyophilized 3 times to remove excess of buffer. Peak 1 (more polar): $^{31}$P-NMR (D₂O): +42.68 (d, 1H, Pα), −9.05 (d, 1H, Pγ), −22.95 (t, 1H, Pβ); MS 530.9.0 [M−1].

Peak 2 (less polar): $^{31}$P-NMR (D$_2$O): +42.78 (d, 1H, Pα), −10.12 (bs, 1H, Pγ), −23.94 (t, 1H, Pβ); and MS 530.9.0 [M−1].

Example 81

Compounds 118 and 121

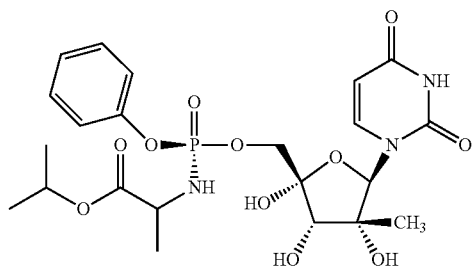
118

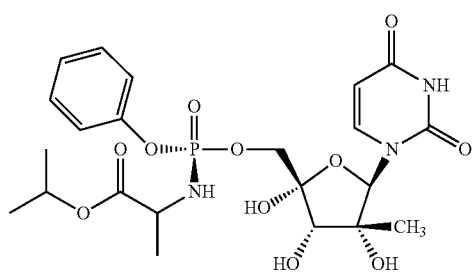
121

The diastereomers of compound 5 were separated by RP-HPLC. A gradient of 10-43% ACN in H$_2$O over 26 mins on a Synergi Hydro RP 30×250 m 4u particle column (Phenomenex PN 00G-4375-U0-AX) eluted compound 121 (29.5 mins) and compound 118 (30.1 mins). Pure fractions were lyophilized to produce a white powder. Compound 121: $^{31}$P-NMR (DMSO-d6) 3.448 ppm; MS: m/z: 544 M−1; Compound 118: $^{31}$P-NMR (DMSO-d6) 3.538 ppm; MS: m/z: 544 M−1.

Example 82

Compounds 120 and 119

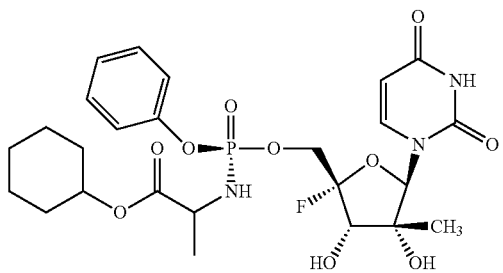
120

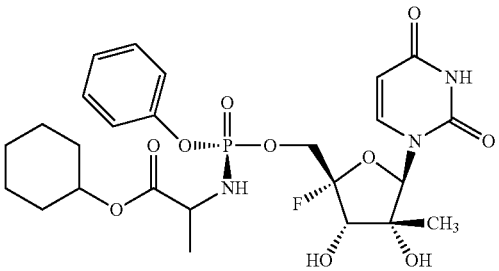
119

The diastereomers of compound 8 were separated by RP-HPLC. A gradient of 25-52% ACN in H$_2$O over 26 minutes on a Synergi Hydro RP 30×250 m 4u particle column (Phenomenex PN 00G-4375-U0-AX) eluted compound 119 (24.8 mins) and compound 120 (25.3 mins). Pure fractions were lyophilized to produce a white powder. Compound 119: $^{31}$P-NMR (DMSO-d6) 3.492 ppm; MS: m/z: 584 M−1. Compound 120: $^{31}$P-NMR (DMSO-d6) 3.528 ppm; MS: m/z: 584 M−1.

Example 83

Compound 122, Bis-lithium Salt

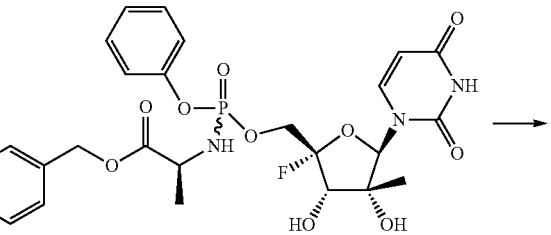
122-1

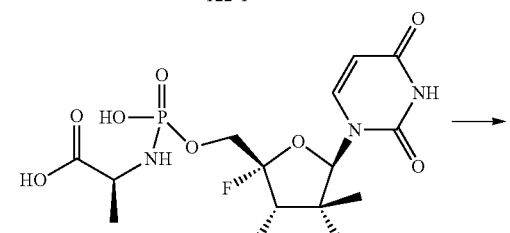
122-2

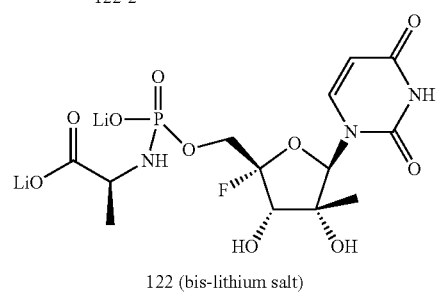
122 (bis-lithium salt)

Compound 122-1 was synthesized using a procedure similar for preparing compound 2 using alanine benzyl ester hydrochloride. LCMS: m/z 592 [M−1]$^-$.

To a solution of 122-1 (1.1 g, 1.85 mmol) in dioxane (15 mL) and water (3 mL) was added aqueous triethylammonium acetate (2M, 2 mL, 4 mmol) followed by Pd—C (10%, 100 mg). The mixture was hydrogenated (balloon) for 2 h, and monitored by HPLC. The catalyst was filtered off, and the filtrate was concentrated to dryness. The residue was suspended in 3% solution of lithium perchlorate in acetone (25 mL). The solid was isolated by filtration, rinsed with acetone and dried under vacuum to give compound 122 (bis-lithium salt) (731 mg, 90%). LCMS: m/z 426 [M−1]⁻.

Example 84

Compound 151

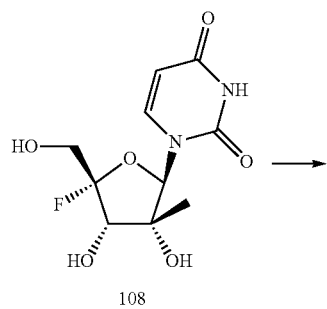

108

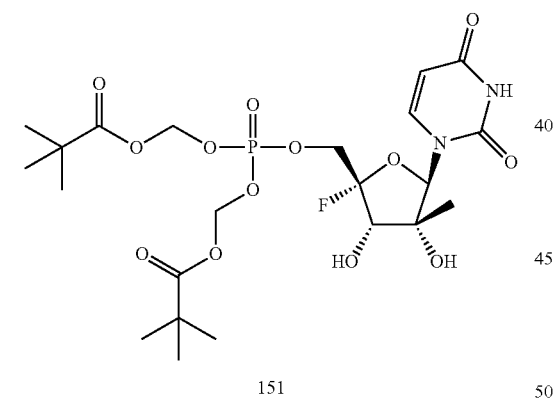

151

Example 85

Compound 159

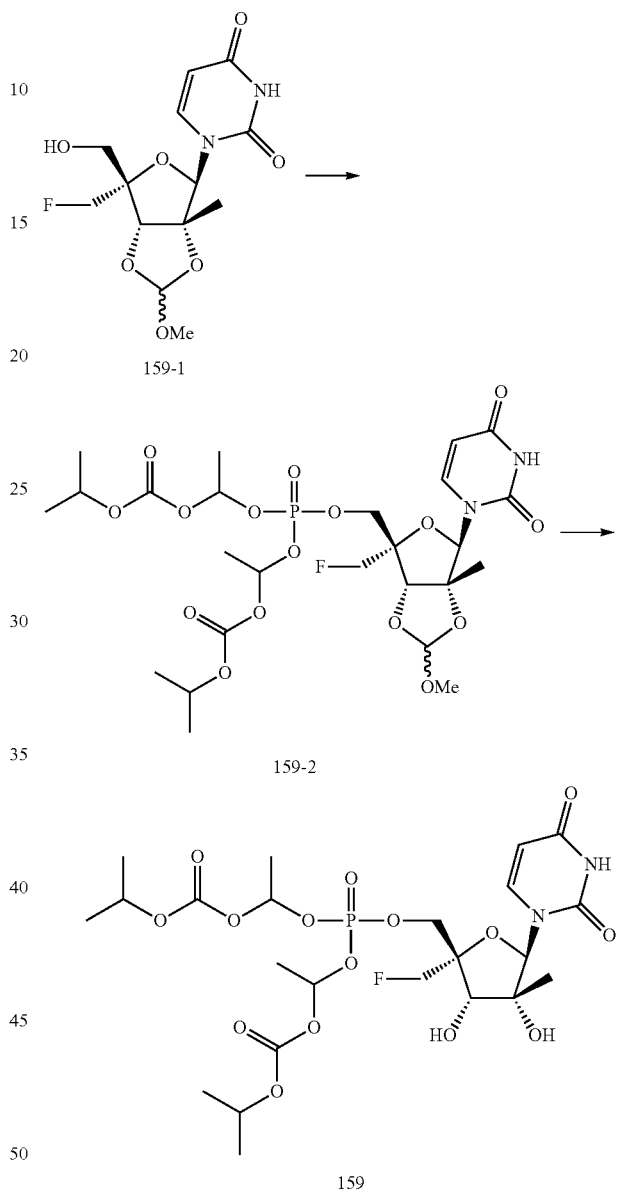

Compound 108 (40 mg, 0.14 mmol) and triethylammonium bis(pivaloyloxymethyl)phosphate (0.21 mmol, prepared from 80 mg of bis(pivaloyloxymethyl)phosphate and 30 μL of Et₃N) were rendered anhydrous by coevaporating with pyridine, followed by toluene. The evaporated residue was dissolved in anhydrous THF (2 mL) and cooled in an ice-bath. Diisopropylethyl amine (73 μL, 3 eq.), BopCl (71 mg, 2 eq.), and 3-nitro-1,2,4-triazole (32 mg, 2 eq.) were added. The mixture was stirred at 0° C. for 90 mins. The mixture was then diluted with EtOAc, washed with sat. aq. NaHCO₃ and brine, and dried (Na₂SO₄). Purification on silica gel column with CH₂Cl₂/i-PrOH (4-10% gradient) followed by RP-HPLC purification (A: water, B: MeCN) yielded compound 151 (13 mg, 16%). MS: m/z=1167 [2M−1].

To a solution of triethylammonium bis(isopropyloxycarbonyloxyethyl-1)phosphate (0.28 mmol, prepared from 100 mg of bis(isopropyloxycarbonyloxyethyl-1)phosphate and 40 μL of Et₃N) in THF was added 159-1 (60 mg, 0.18 mmol). The mixture was evaporated and rendered anhydrous by coevaporating with pyridine follow by toluene. The evaporated residue was dissolved in anhydrous THF (2.5 mL) and cooled in an ice-bath. Diisopropylethyl amine (94 μL, 3 eq.) was added, followed by BOP-Cl (92 mg, 2 eq.) and 3-nitro-1,2,4-triazole (41 mg, 2 eq.). The mixture was stirred at 0° C. for 90 mins., diluted with EtOAc and washed with sat. aq. NaHCO₃ and brine, and dried (Na₂SO₄). The residue was purified on a silica gel column with CH₂Cl₂/i-PrOH (3-10% gradient) to yield 159-2 (19 mg, 17%).

A solution of 159-2 (19 mg, 0.03 mmol) in 80% aq. HCOOH was stirred at RT for 90 mins., and then concentrated. The residue was coevaporated with toluene and then with MeOH containing small amount of Et$_3$N (1 drop). Purification on a silica gel column with CH$_2$Cl$_2$/MeOH (4-10% gradient) yielded compound 159 (5 mg, 26%). MS: m/z=629 [M−1].

Example 86

Compound 160

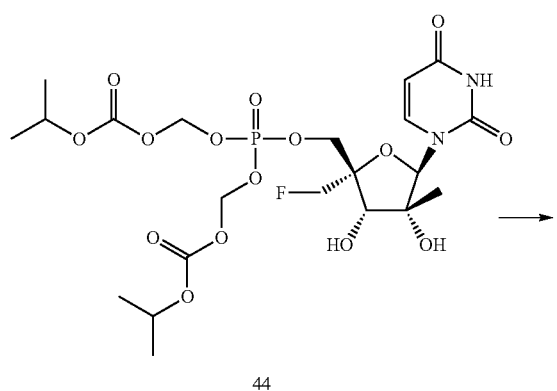

44

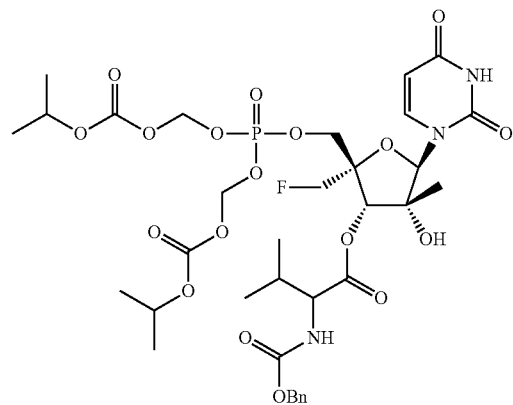

160-1

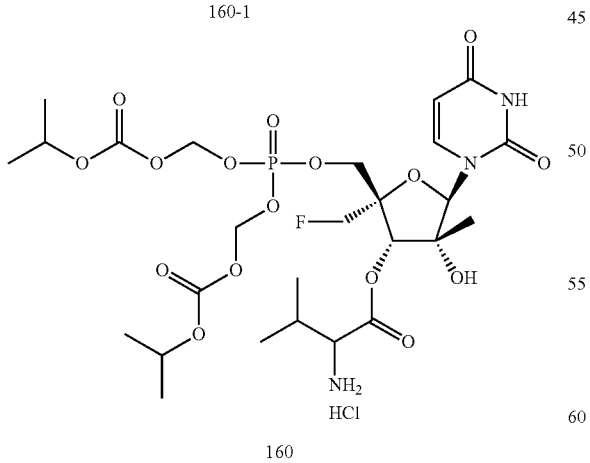

160

A mixture of benzyloxycarbonyl-L-valine (55 mg, 0.22 mmol) in THF (1 mL) and CDI (36 mg, 0.22 mmol) was stirred at RT for 1.5 h and then at 40° C. for 20 mins. The solution was added to a mixture of compound 44 (122 mg, 0.2 mmol) and DMAP (3 mg, 0.03 mmol) in DMF (1.5 mL) and TEA (0.75 mL) at 80° C. The mixture was stirred at 80° C. for 1 h. After cooling, the mixture was concentrated, and the residue partitioned between tert-butyl methyl ether and water. The organic layer was washed with 0.1 N citric acid, sat. aq. NaHCO$_3$ and brine, and dried (Na$_2$SO$_4$). The residue was purified on a silica gel column with CH$_2$Cl$_2$/i-PrOH (4-10% gradient) to yield 160-1 (83 mg, 50%) as a colorless foam.

To a solution of 160-1 (83 mg, 0.1 mmol) in EtOH were added HCl (4 N in dioxane; 50 µL, 2 eq.) and 10% Pd/C (5 mg). The mixture was stirred under H$_2$ atmosphere (normal pressure) for 1 h. The catalyst was removed by filtration through a Celite pad, and the filtrate evaporated to yield compound 160 (50 mg) as a white solid. MS: m/z=702 [M+1].

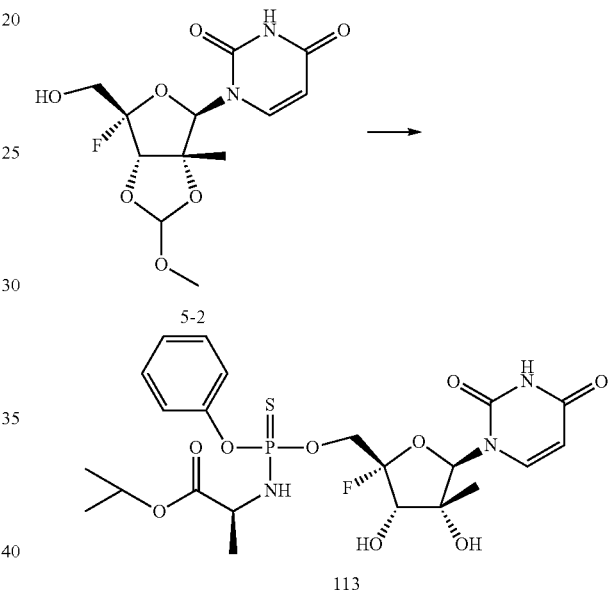

5-2

113

Example 87

Compound 113

Compound 5-2 (32 mg, 0.1 mmol) was dissolved in dry THF (3 mL) and 2M solution of isopropylmagnesium bromide in THF (0.1 mL) was added at 0° C. The reaction was left for 1 h at RT, and phenyl(isopropyl-L-alaninyl) thiophosphorochloridate was added (0.3 mmol). The mixture was left overnight at RT. LSMS analysis showed about 20% of unreacted starting material. The same amount of Grignard reagent and thiophosphorochloridate were added, and the mixture was heated at 37° C. for 4 h. The reaction was quenched with NH$_4$Cl. The product was extracted with EA, washed with brine, dried over Na$_2$SO$_4$, and evaporated. The resulting oil was dissolved in 80% formic acid (4 mL) and in 1 h evaporated. Compound 113 was purified by RP HPLC in gradient of methanol in water from 30% to 95% on Synergy 4u Hydro-RP column (Phenominex) yielding a colorless solid. Compound 113 (7 mg, yield 12.5%). MS: m/z=560.0 [M−H].

Example 88

Compound 125

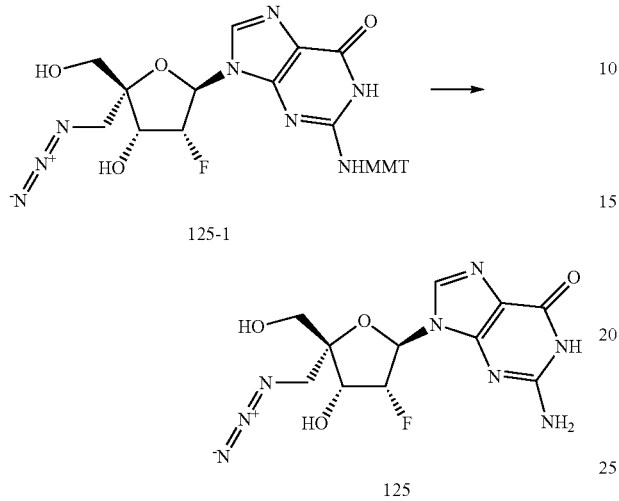

Compound 125-1 (109 mg) was dissolved in 80% HCOOH (15 mL) and kept for 3 h at RT, then evaporated. The residue was treated with NH$_3$/MeOH for 1 h at RT to remove formyl-containing side-products. After evaporation compound 125 was purified by crystallization using methanol to yield compound 125 (52 mg, 86%). MS: 339.6 [M−1], 679.7 [2M−1].

Example 89

Compound 148

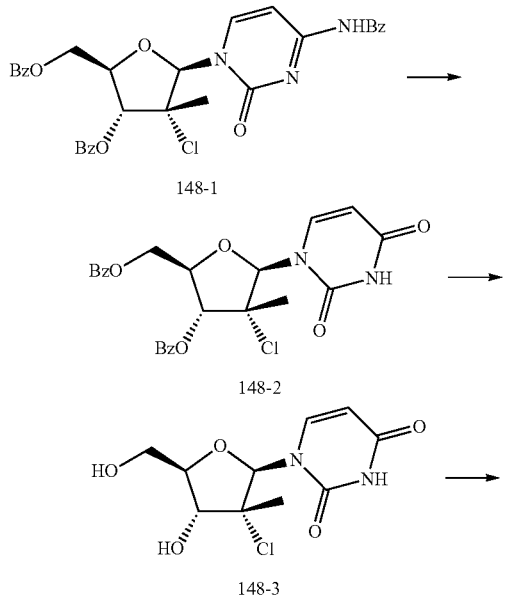

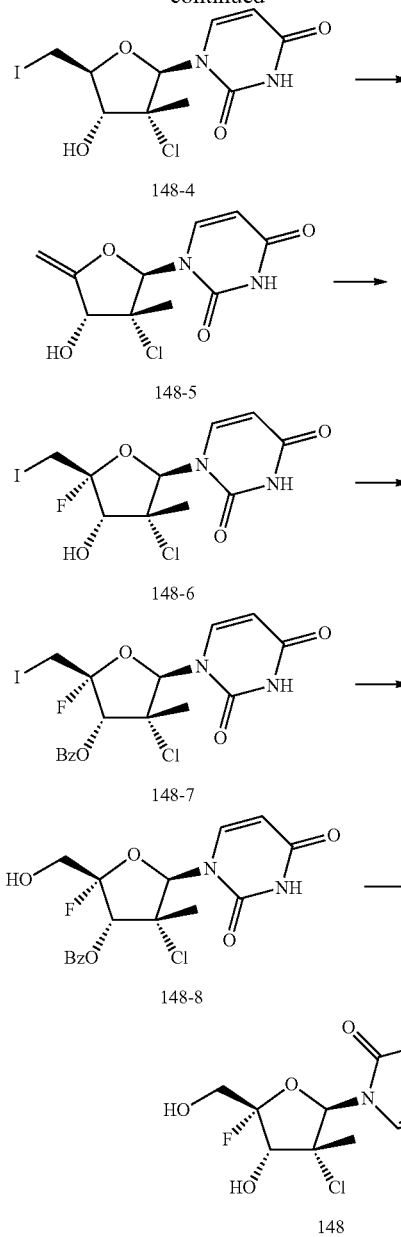

Compound 148-1 (15.0 g, 25.55 mmol) was treated with 90% HOAc (150 mL) at RT. The mixture was stirred at 110° C. for 12 h, and then concentrated at a low pressure. The residue was dissolved in DCM, and the solution was washed with brine. The organic phase was dried over anhydrous Na$_2$SO$_4$, and then concentrated at a low pressure. The residue was purified by column chromatography (5% MeOH in DCM) to give 148-2 (11.0 g, 88.9%) as a white solid.

Compound 148-2 (12.0 g, 24.79 mmol) was treated with NH$_3$ in MeOH (200 mL, 7 M) at RT. The solution was stirred at RT for 12 h, and then concentrated at a low pressure. The residue was purified by column chromatography (10% MeOH in DCM) to give 148-3 (6.5 g, 95.0%) as a white solid.

To a stirred suspension of 148-3 (4.3 g, 15.58 mmol), PPh$_3$ (8.16 g, 31.15 mmol), imidazole (2.11 g, 31.15 mmol) and pyridine (15 mL) in anhydrous THF (45 mL) was added a solution of I$_2$ (7.91 g, 31.15 mmol) in THF (100 mL)

dropwise at 0° C. The mixture was slowly warmed to RT and stirred overnight. The mixture was quenched with MeOH (100 mL). The solvent was removed at a low pressure, and the residue was re-dissolved in a mixture of EA and THF (0.2 L, 10:1). The organic phase was washed with sat. Na$_2$S$_2$O$_3$ aq. (2×). The aqueous phase was extracted with a mixture of EA and THF (0.2 L, 10:1, 2×). The concentrated organic phase was dried over anhydrous Na$_2$SO$_4$. The residue was purified on a silica gel column (0-10% MeOH in DCM) to afford 148-4 (5.1 g, 85.0%) as a white solid.

Compound 148-4 (800 mg, 2.07 mmol) was dissolved in a mixture of DBU (4 mL) and THF (4 mL) at RT under N$_2$. The solution was stirred at RT for 1 h. The mixture was neutralized with HOAc, and extracted with a mixture of EA and THF (10:1, 40 mL). The organic phase was washed with brine, and dried over anhydrous Na$_2$SO$_4$. The concentrated organic phase was purified by column chromatography (0-10% MeOH in DCM) to give 148-5 (240 mg, 44.9%) as a white solid.

To an ice-cooled solution of 148-5 (1.20 g, 4.65 mmol) in anhydrous MeCN (12 mL) was added NIS (1.57 g, 6.97 mmol) and TEA.3HF (1.12 g, 6.97 mmol) under N$_2$. The mixture was stirred at RT for 5 h. The reaction was quenched with sat. NaHCO$_3$ solution, and extracted with EA (3×100 mL). The organic phase was dried over anhydrous Na$_2$SO$_4$, and evaporated to dryness at low pressure. The residue was purified on a silica gel column (0-5% MeOH in DCM) to give 148-6 (0.91 g, 48.6%) as a white solid.

To a stirred solution of 148-6 (1.2 g, 2.97 mmol) in anhydrous DCM (12 mL) was added BzCl (0.83 g, 5.94 mmol), TEA (0.6 g, 5.94 mmol) and DMAP (0.72 g, 5.94 mmol) successively at RT. The mixture was stirred at RT for 12 h. The reaction was quenched with water, and extracted with EA (3×60 mL). The organic phase was concentrated at low pressure. The residue was purified by column chromatography (0-5% MeOH in DCM) to give 148-7 (1.2 g, 66.2%) as a white solid.

Tetra-butyl ammonium hydroxide (25.78 mL, 51.78 mmol) was neutralized with TFA (4.3 mL) to pH=4, and the solution was added to a solution of 148-7 (1.09 g, 2.14 mmol) in DCM (30 mL). m-CPBA (1.85 g, 10.74 mmol) was added portionwise under vigorous stirring, and the mixture was stirred for 12 h. The mixture was diluted with EA (100 mL), and washed with sat. sodium bicarbonate. The organic phase was concentrated at low pressure. The residue was purified by column chromatography (50% EA in PE) to give 148-8 (350 mg, 41.1%) as a white solid.

Compound 148-8 (280 mg, 0.704 mmol) was treated with NH$_3$ in MeOH (10 mL, 7 M) at RT. The mixture was stirred at RT for 2 h. The mixture was concentrated at a low pressure. The residue was purified by column chromatography (0-10% MeOH in DCM) to give compound 148 (110 mg, 53.1%) as a white solid. ESI-LCMS: m/z 295.1 [M+H]$^+$.

Example 90

Compound 150

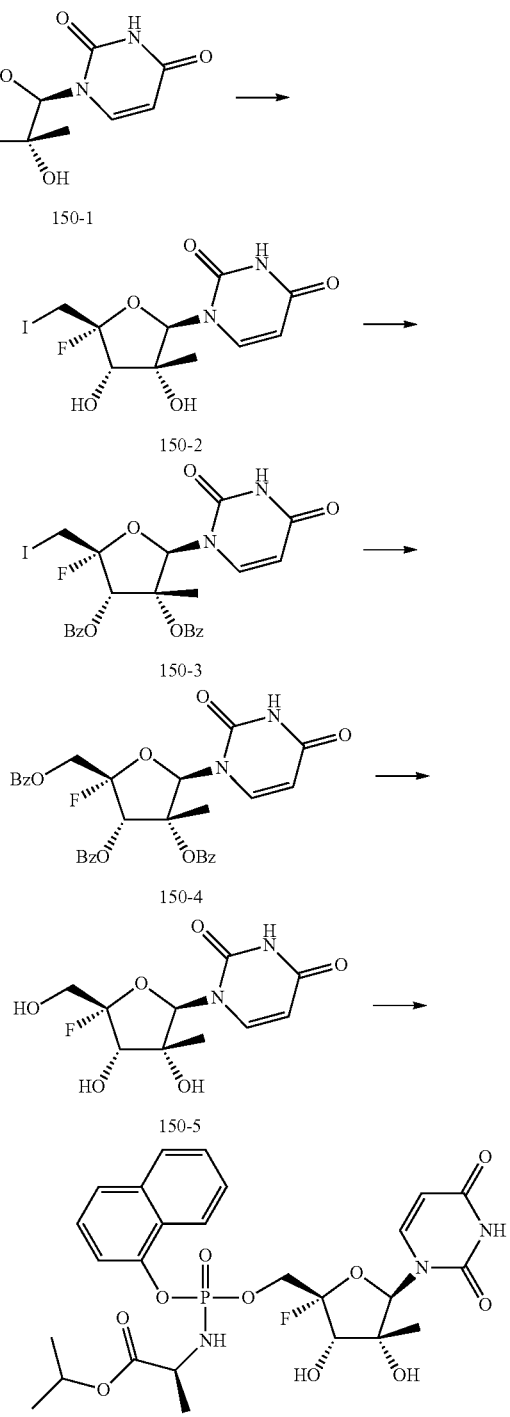

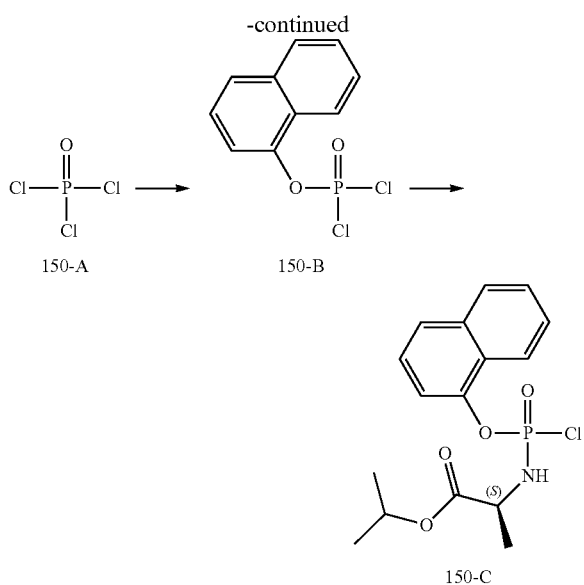

150-A

150-B

150-C

To an ice-cooled solution of 150-1 (10 g, 42 mmol) in anhydrous MeCN (200 mL) was added TEA.3HF (10 g, 62.5 mmol) and NIS (28 g, 126 mmol). The mixture was stirred at RT for 1.5 h, and monitored by LCMS. After the reaction was completed, the mixture was concentrated at a low pressure. The residue was purified by silica gel column chromatography (15% MeCN in DCM) to give 150-2 (12 g, 74%) as a yellow solid.

To a solution of 150-2 (22 g, 57 mmol) in anhydrous DCM (200 mL) was added DMAP (21 g, 171 mmol) and BzCl (17.6 g, 125 mol). The mixture was stirred for 5 h at RT, and monitored by LCMS. The solution was washed with sat. $NaHCO_3$ solution and brine, and extracted with EA. The organic phase was dried over anhydrous $Na_2SO_4$ and filtered. The filtrate was concentrated at low pressure. The residue was purified by silica gel column chromatography (20% EA in PE) to give 150-3 (30 g, 88%) as a white foam.

To a solution of 150-3 (6.5 g, 11 mmol) in anhydrous DMF (270 mL) was added NaOBz (15.8 g, 110 mmol) and 15-crown-5 (29 g, 132 mmol). The mixture was stirred at 95° C. for 48 h. The precipitate was removed by filtration, and the organic solvent was removed at low pressure. The residue was dissolved in EA (200 mL), and the solution was washed with sat. $NaHCO_3$ solution, and brine. The organic layer was dried over anhydrous $Na_2SO_4$ and filtered. The filtrate was concentrated at low pressure. The residue was purified by silica gel column chromatography (20% EA in PE) to give 150-4 (3 g crude, 46.1%) as an oil.

Compound 150-4 (3 g, crude) was treated with $NH_3$ in MeOH (120 mL, 7 M). The mixture was stirred for 3 h and monitored by TLC. The solution was concentrated at low pressure. The residue was purified by silica gel column chromatography (10% isopropanol in DCM) to give 150-5 (1.0 g, 67%) as a white solid. $^1$H-NMR (CD$_3$OD, 400 MHz) δ=1.19 (s, 3H), 3.76-3.82 (m, 2H), 4.02 (d, J=19.8 Hz, 1H), 5.70 (d, J=8.07 Hz, 1H), 6.27 (s, 1H), 7.89 (d, J=8.07 Hz, 1H).

Compound 150-5 (100 mg, 0.36 mmol) was co-evaporated with toluene 3 times. To a stirred solution of 150-5 (100 mg, 0.36 mmol) in a mixture of MeCN (1.0 mL) and NMI (295 mg, 3.6 mmol) was added a solution of 150-C (255.6 mg, 0.72 mmol, preparation described below) in MeCN (0.5 mL) at 0° C. The mixture was stirred at RT overnight. The reaction was quenched with water, and diluted with EA (20 mL). The organic layer was washed with water and brine. The organic layer was dried over anhydrous $Na_2SO_4$. The organic phase was concentrated at low pressure. The residue was purified on a silica gel column (5% i-PrOH in DCM) to give the crude product. The product was purified by prep-HPLC (0.1% HCOOH in water and MeCN) to give compound 150 (46.7 mg, 23.3%) as a white solid. ESI-LCMS: m/z 618 [M+Na]$^+$.

To a stirred solution of 150-A (2.0 g, 13.16 mmol) and naphthalen-1-ol (1.89 g, 13.16 mmol) in anhydrous DCM (100 mL) was added a solution of TEA (1.33 g, 13.16 mmol) in DCM (20 mL) dropwise at −78° C. After addition, the mixture was gradually warmed to RT, and stirred for 2 h. The solution was cooled to −78° C., and (S)-isopropyl 2-aminopropanoate hydrochloride (2.20 g, 13.16 mmol) in DCM (20 mL) was added, followed by TEA (2.66 g, 26.29 mmol) in DCM (20 mL) dropwise. The mixture was gradually warmed to RT, and stirred for 2 h. The organic solvent was removed at low pressure. The residue was dissolved in methyl-butyl ether. The precipitate was filtered, and the filtrate was concentrated at low pressure. The residue was purified on a silica gel column (anhydrous DCM) to give 150-C (1.0 g, 24.8%) as a colorless oil.

Example 91

Compounds 152 and 153

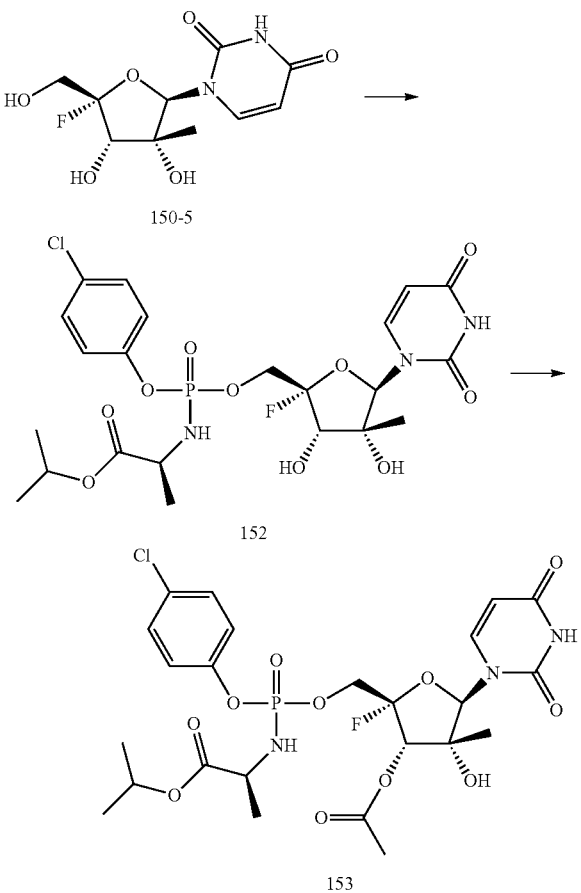

150-5

152

153

469
-continued

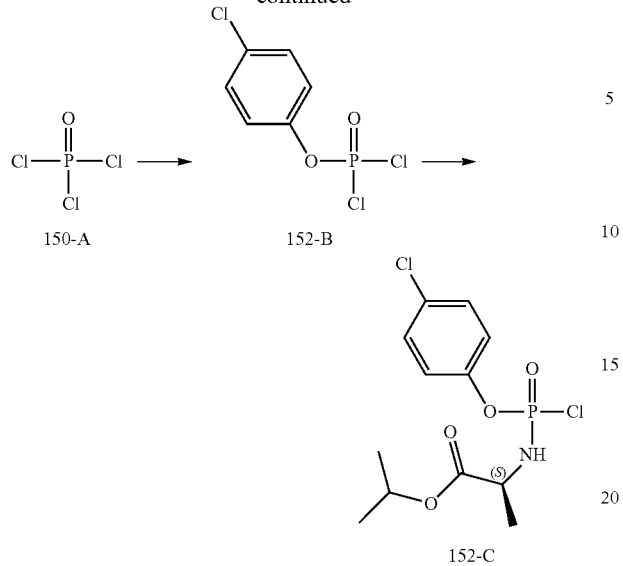

To a solution of 150-5 (300 mg, 1.08 mmol) and NMI (892 mg, 10 mmol) in anhydrous MeCN (4 mL) was added a solution of 152-C (736 mg, 2.17 mmol, preparation described below) in anhydrous MeCN (1 mL) dropwise at 0° C. The mixture was stirred at RT overnight. The reaction was quenched with water, and diluted with EA (30 mL). The organic layer was washed with water and brine. The organic phase was dried over anhydrous $Na_2SO_4$ and concentrated at low pressure. The residue was purified by a silica gel column (iPrOH in DCM from 1% to 5%) to give crude compound 152 (276 mg, crude). Crude compound 152 (96 mg) was purified by prep-HPLC (0.1% HCOOH in water and MeCN) to give pure compound 152 (46 mg, 47.9%) as a white solid. ESI-LCMS: m/z 560 [M–F]$^+$.

To a solution of compound 152 (180 mg, 0.31 mmol) in anhydrous pyridine (6 mL) was added acetic anhydride (158 mg, 1.54 mmol) dropwise at 0° C. The mixture was stirred at RT overnight. The solution was quenched with water and concentrated at a low pressure. The residue was dissolved in EA (10 mL), and washed with brine. The organic layer was dried over anhydrous $Na_2SO_4$. The organic phase was concentrated at low pressure. The residue was purified by silica gel column (i-PrOH in DCM from 1% to 3%) to give crude compound 153 (172 mg). Crude compound 153 was purified by prep-HPLC (0.1% HCOOH in water and MeCN) to give pure compound 153 (46 mg, 23.8%) as a white solid. ESI-LCMS: m/z 602.3 [M–F]$^+$.

Compound 152-C (1.02 g, 23%, a colorless oil) was prepared using a procedure similar to the preparation of 150-C using 150-A (2.00 g, 13.16 mmol) and 4-chlorophenol (1.68 g, 13.16 mmol).

470
Example 92

Compound 165

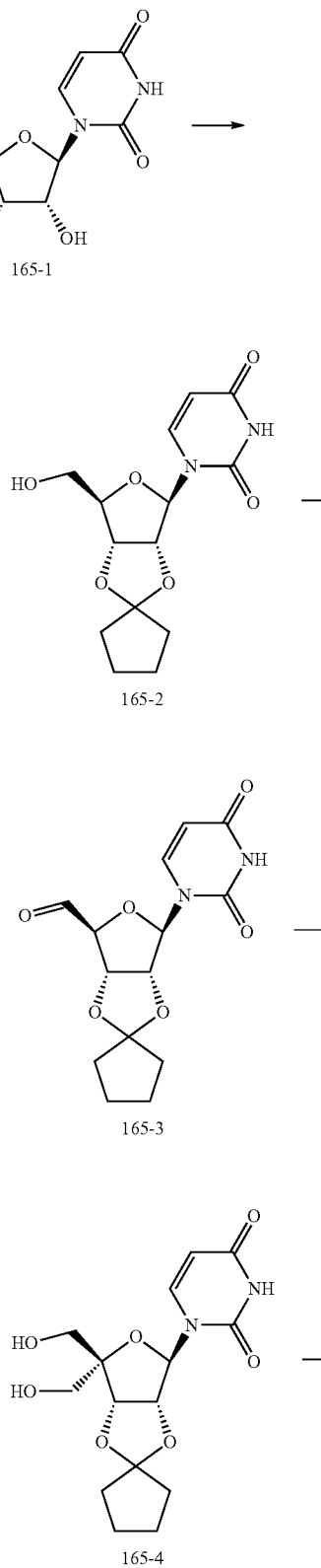

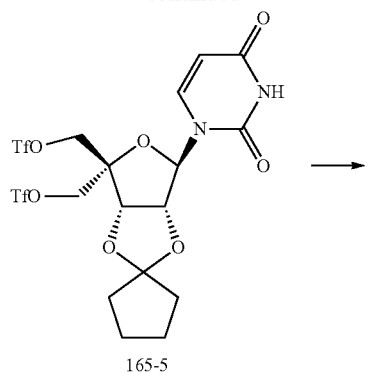

165-5

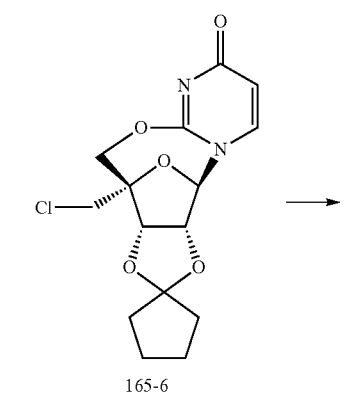

165-6

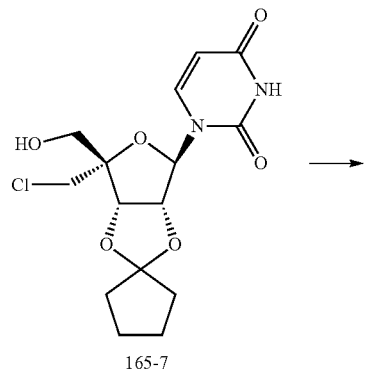

165-7

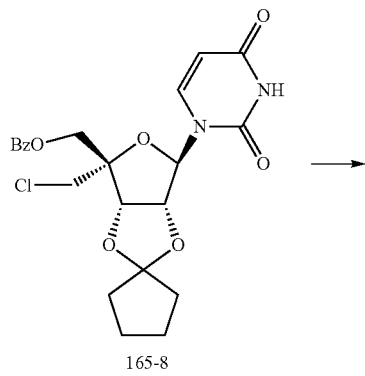

165-8

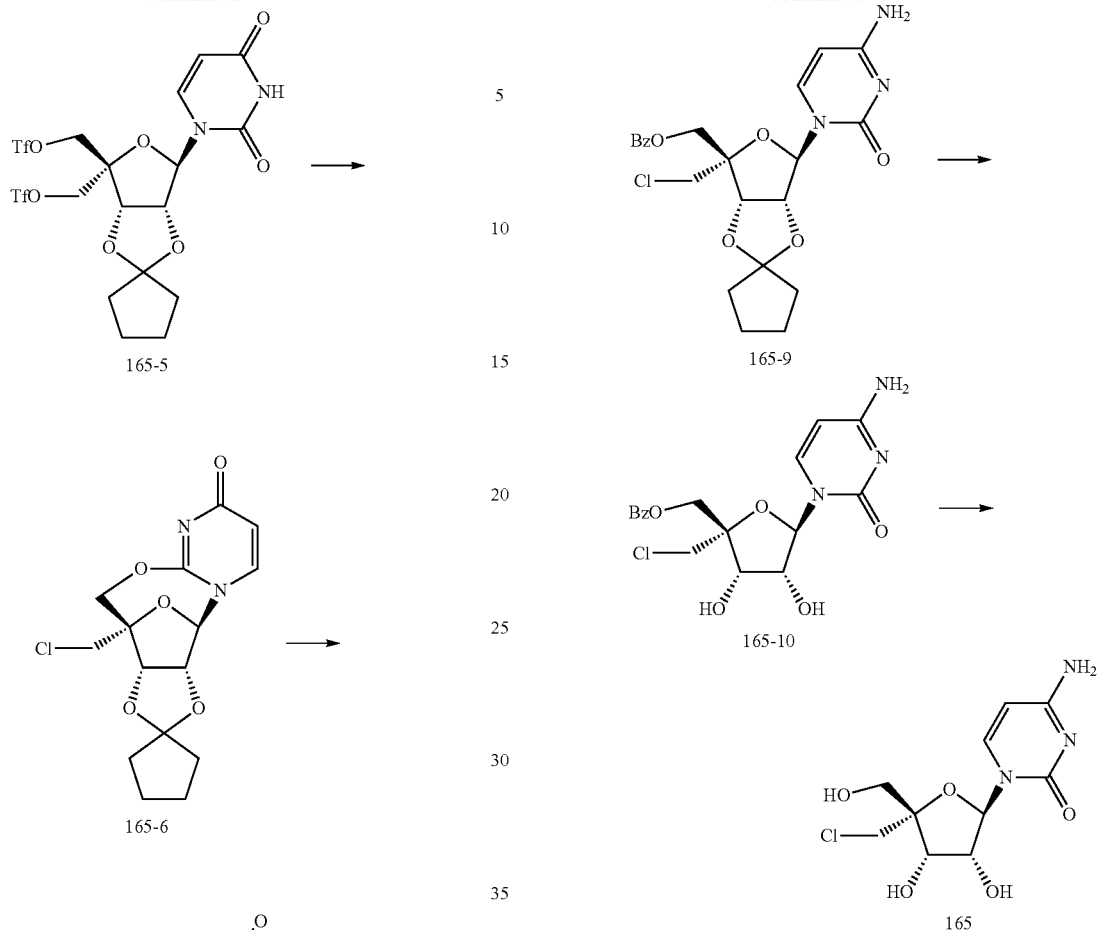

To a solution of 165-1 (5 g, 0.02 mol), cyclopentanone (5.25 g, 0.06 mol, 4.5 eq.) and trimethoxymethane (6.52 g, 0.06 mol, 3 eq.) in MeCN (80 mL) was added TSOH.H$_2$O (1.95 g, 0.01 mol). The mixture was heated at 80° C. overnight. The mixture was concentrated at low pressure. The residue was purified by column chromatography (20% EA in PE) to give 165-2 (3.8 g, 60%) as a white oil.

To a solution of 165-2 (5 g, 0.16 mol) in MeCN (50 mL, anhydrous) was added IBX (5.33 g, 0.019 mol, 1.11 eq.) at RT. The mixture was heated at 80° C. for 5 h. The mixture was cooled to R.T and filtered. The filtrate was concentrated to give 165-3 (4.5 g, purity: 90%).

To a solution of 165-3 (5 g, 0.016 mol) and CH$_2$O (3.6 mL) in 1,4-dioxane (50 mL) was added NaOH solution (11.3 mL, 2 N) at RT. The mixture was stirred for 5 h at RT. NaBH$_4$ (1.48 g, 0.038 mol) was added at 0° C., and stirred for 1 h. The reaction was quenched with H$_2$O (30 mL) and extracted with EA (3×30 mL). The organic layer was washed by brine, dried over anhydrous Na$_2$SO$_4$, and concentrated at low pressure. The residue was purified by column chromatograph (50% EA in PE) to give 165-4 (2.1 g, 38%) as a white oil.

To a stirred solution of 165-4 (3 g, 0.0088 mol) and pyridine (3.51 mL, 5 eq.) in DCM (27 mL) was added Tf$_2$O (3.27 mL, 0.019 mol) at −35° C. The mixture was slowly warmed to 0° C. and stirred for 2 h at 0° C. The mixture was washed with sat. NaHCO$_3$ solution and extracted with DCM (3×30 mL). The organic layer was separated and washed by brine, dried over anhydrous Na$_2$SO$_4$, and concentrated at low pressure. The residue was purified by column chromatography (5% EA in PE) to give 165-5 (2.65 g, 39%) as a white oil.

To a solution of 165-5 (12.3 g, 0.02 mol) in DMF (20 mL) was added NaH (0.977 g, 0.024 mol) at 0° C. The mixture was stirred for 3 h at RT. The mixture was treated with LiCl (2.6 g, 0.062 mol), and then stirred for 2 h. The reaction was quenched with H$_2$O (20 mL) and extracted with EA (3×30 mL). The organic layer was washed with brine, dried over anhydrous Na$_2$SO$_4$, and concentrated at low pressure. The residue was purified by column chromatography (20% EA in PE) to give 165-6 (3.11 g, 45%) as a white oil.

To a solution of 165-6 (12 g, 0.035 mol) in THF (120 mL) was added NaOH solution (38.8 mL, 0.038 mol) at 0° C., and stirred for 3 h. at RT. The mixture was adjusted to pH=7 with HCl (1.0 N) solution, and extracted with EA (3×80 mL). The organic layer was washed with brine, dried over anhydrous Na$_2$SO$_4$, and concentrated at low pressure. The residue was purified by column chromatography to give 165-7 (7.58 g, 60%) as a white solid.

165-7 (3 g, 8.0 mmol) was co-evaporated with toluene (30 mL). To a solution of 165-7 (3 g), DMAP (100 mg) and TEA (2.5 mL, 2 eq.) in DCM (30 mL) was added Bz$_2$O (2.01 g, 1 eq.) at 0° C. The mixture was stirred for 3 h at RT. The reaction was quenched with H$_2$O, and extracted with DCM (3×30 mL). The DCM layer was dried over anhydrous Na$_2$SO$_4$, and concentrated at low pressure. The residue was purified by column chromatography (5% EA in PE) to give 165-8 (3.1 g, 80%) as a white solid.

To a solution of 165-8 (200 mg, 0.43 mmol) in CH$_3$CN (2 mL, anhydrous) was added TPSCl (260 mg, 2 eq.), TEA (0.13 mL) and DMAP (106.4 mg, 2 eq.). The mixture was stirred for 2 h at RT.

The mixture was treated with NH$_3$.H$_2$O (33%, 1.33 mL), and stirred for 2 h at RT. The reaction was quenched with 1 N HCl (30 mL), and extracted with DCM (3×30 mL). The DCM layer was dried over anhydrous Na$_2$SO$_4$ and concentrated at low pressure. The residue was purified by column chromatography to give 165-9 (85 mg, 50%) as a white solid.

165-9 (100 mg, 0.216 mmol) was treated with HCOOH (7 mL, 80%), and stirred for 3 h at RT. The mixture was concentrated at low pressure. The residue was purified by column chromatography (90% EA in PE) to give 165-10 (51 mg, 60%) as a white solid.

165-10 (270 mg, 0.68 mmol) was treated with NH$_3$ in MeOH (10 mL) at −60° C. The mixture was warmed to RT. The mixture was stirred for 6 h. at RT. The mixture was concentrated at low pressure. The residue was purified by reverse HPLC to give 165 (60 mg, 30%) as a white solid.

Example 93

Compound 169

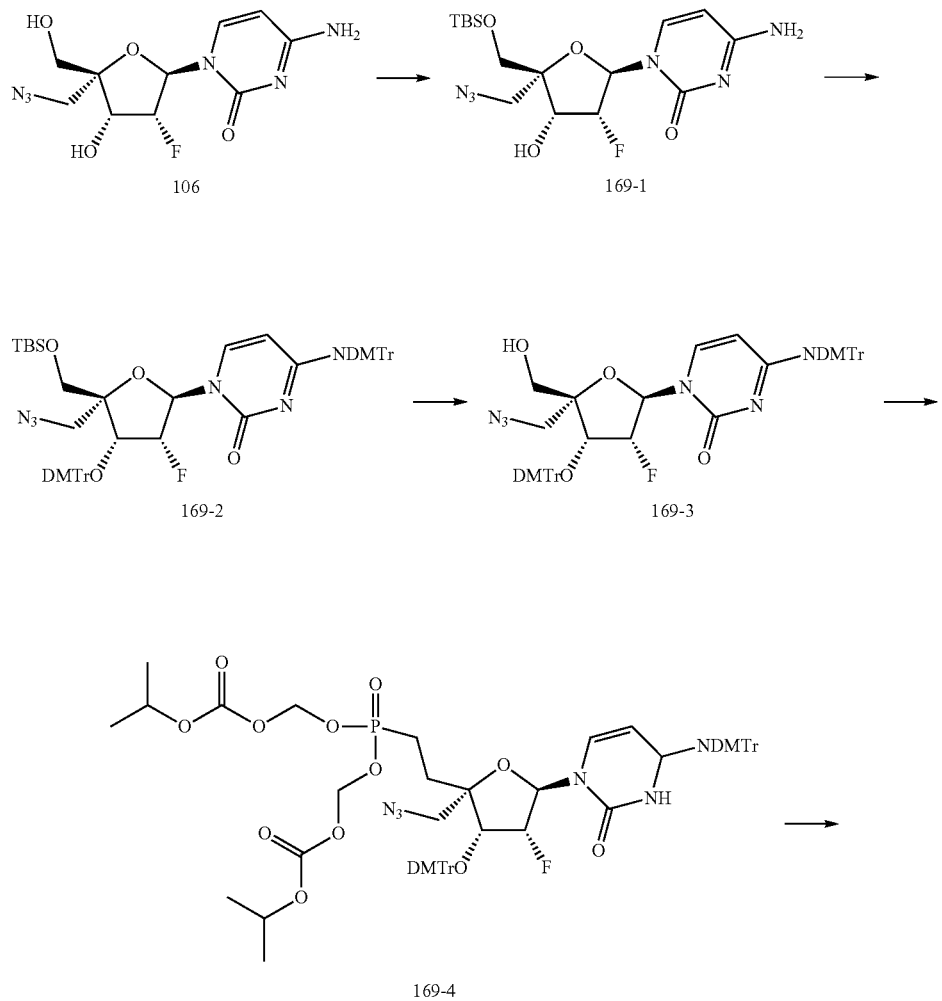

-continued

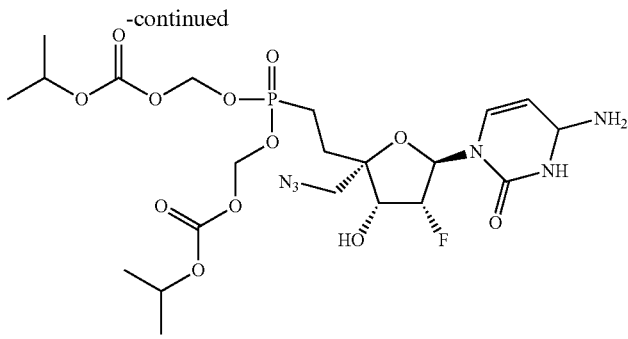

169

To a solution of 106 (200 mg, 0.67 mmol) in anhydrous pyridine (5 mL) was added TBSCl (120 mg, 0.8 mmol) at RT. The mixture was stirred overnight, and the reaction mixture was diluted with EA. The mixture was washed with NaHCO$_3$ aq. solution and brine. The organic layer was dried, filtered and concentrated to give residue, which was purified by silica gel column chromatography (5% MeOH in DCM to 25% MeOH in DCM to give 169-1 (153 mg, 55%) as a white solid.

To a solution of 169-1 (54 mg, 0.13 mmol) in anhydrous DCM (2 mL) was added collidine (95 μL, 0.78 mmol), DMTrCl (262 mg, 0.78 mmol) and AgNO$_3$ (66 mg, 0.39 mmol) at RT. The mixture was stirred overnight, and then diluted with DCM (5 mL). The mixture was filtered through a pre-packed celite funnel, and the filtrate was washed with NaHCO$_3$ aq. solution, 1.0 M citric acid solution and then brine. The organic layer was dried over Na$_2$SO$_4$, and concentrated at low pressure to give a residue. The residue was purified by silica gel column chromatography (25% EA in PE to 100% EA) to give 169-2 (83.5 mg, 63.6%).

To a solution of 169-2 (83 mg, 0.081 mmol) in THF (1 mL), was added a 1M solution of TBAF in THF (0.122 mL, 0.122 mmol) at ice bath temperature. The mixture was stirred for 1.5 h. The mixture was diluted with EA, and washed with water and brine. The organic layer was dried and concentrated to give the crude product, which was purified by silica gel column chromatography (DCM to 5% MeOH in DCM) to give 169-3 (66.6 mg, 91%) as a white foam.

169-3 (66.6 mg, 0.074 mmol) was co-evaporated with toluene and THF (3×). Bis(POC)phosphate (33 mg, 0.96 mmol) was added, and then co-evaporated with toluene (3×). The mixture was dissolved in anhydrous THF (1.5 mL) and cooled in an ice bath (0 to 5° C.). 3-nitro-1,2,4-triazole (13 mg, 0.11 mmol), diisopropylethyl amine (54 μL, 0.3 mmol), and BOP-Cl (28 mg, 0.11 mmol) were added successively. The mixture was stirred 2 h at 0 to 5° C., diluted with EtOAc, washed with 1.0M citric acid, sat. aq. NaHCO$_3$ and brine, and dried with Na$_2$SO$_4$. The residue was purified on silica (10 g column) with CH$_2$Cl$_2$:i-PrOH (4-10% gradient) to give 169-4 (68 mg, 76%) as a white solid.

169-4 (68 mg, 0.07 mmol) was dissolved in 80% HCOOH. The mixture was stirred at RT for 2 h. The solvents were evaporated at RT and co-evaporated with toluene (3×). The residue was dissolved in 50% CH$_3$CN/H$_2$O, was purified on a reverse-phase HPLC (C18) using CH$_3$CN and H$_2$O. The product was lyophilization to give 169 (4.8 mg, 14%) as a white foam. ESI-LCMS: m/z=613.1 [M+H]$^+$, 1225.2 [$^2$M+H]$^+$.

Example 94

Compound 145

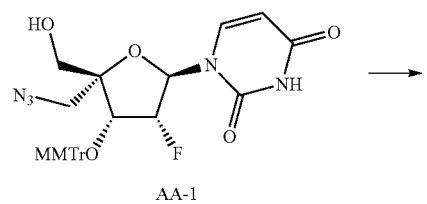

AA-1

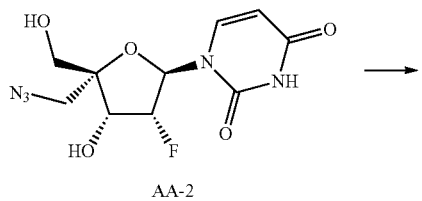

AA-2

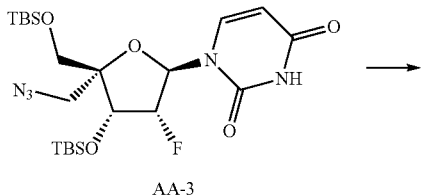

AA-3

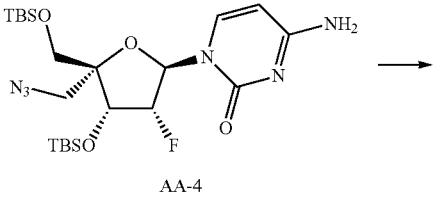

AA-4

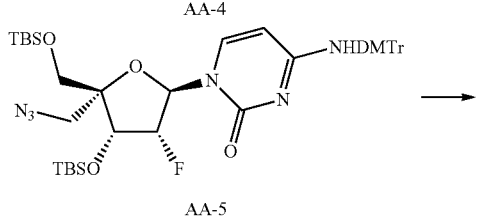

AA-5

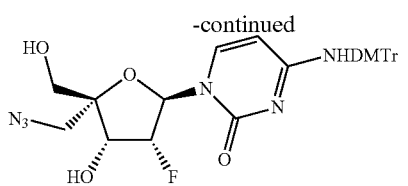

AA

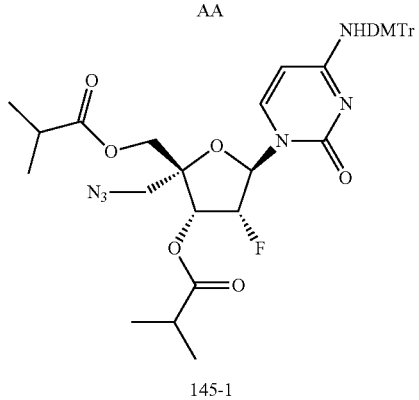

145-1

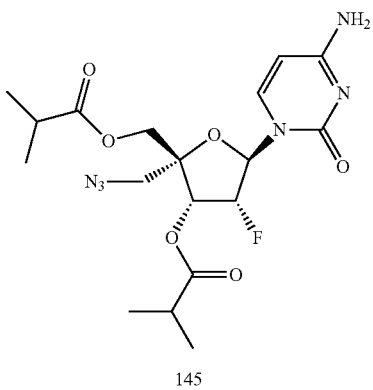 [SMILES: CC(C)C(=O)OC[C@@]1(CN=[N+]=[N-])O[C@@H](n2ccc(N)nc2=O)[C@H](F)[C@@H]1OC(=O)C(C)C]

145

AA-1 (2.20 g, 3.84 mmol) was dissolved in 80% HCOOH (40 mL) at RT (18° C.). The mixture was stirred at RT for 12 h. The solvent was removed at low pressure. The residue was purified by column chromatography using 50% EA in Hexane to give AA-2 (1.05 g, 91.3%) as a white solid.

To a stirred solution of AA-2 (1 g, 3.32 mmol) in anhydrous pyridine (20 mL) was added TBSCl (747 mg, 4.98 mmol) and imidazole (451 mg, 6.64 mmol) at RT (16° C.) under $N_2$ atmosphere. The mixture was stirred at RT for 4 h. The resulting solution was concentrated to dryness under reduced pressure, and the residue was dissolved in EA (100 mL). The solution was washed with sat. $NaHCO_3$ solution and brine, and dried over anhydrous $MgSO_4$. The solution was concentrated to dryness, and the residue was purified on a silica gel column using 20% EA in Hexane to give AA-3 (1.4 g, 79.5%) as a white solid.

To a stirred solution of AA-3 (1.50 g, 2.83 mmol, 1.00 eq.) in anhydrous $CH_3CN$ (28 mL) was added TPSCl (1.71 g, 5.80 mmol, 2.05 eq.), DMAP (691.70 mg, 5.66 mmol, 2.00 eq.) and TEA (573.00 mg, 5.66 mmol, 2.00 eq.) at RT (15° C.). The mixture was stirred for 2 h. $NH_3·H_2O$ (20 mL) was added, and the mixture was stirred for 3 h. The mixture was extracted with EA (3×60 mL). The organic phase was washed with brine, dried over anhydrous $Na_2SO_4$ and concentrated at low pressure. The residue was purified on a silica gel column (30% EA in PE) to give AA-4 (2.3 g, crude) as a yellow foam.

To a stirred solution of AA-4 (1.90 g, 2.34 mmol) in anhydrous DCM (20 mL) was added DMTrCl (1.82 g, 3.49 mmol) and 2,4,6-trimethylpyridine (1.00 g, 8.25 mmol) at RT (15° C.) under $N_2$ atmosphere. The mixture was stirred at RT for 12 h. MeOH (20 mL) was added. The mixture was filtered, and the filtrate was concentrated to dryness. The residue was dissolved in EA (80 mL). The solution was washed with brine, dried over anhydrous $Na_2SO_4$ and concentrated at low pressure. The residue was purified on a silica gel column (5% MeOH in DCM) to give AA-5 (1.4 g, crude) as a white solid.

AA-5 (2.40 g, 2.60 mmol) was dissolved in TBAF (10 mL, 1M in THF). The mixture was stirred at RT (15° C.) for 30 mins. The mixture was concentrated to dryness, and the residue was dissolved in EA (60 mL). The solution was washed with brine, dried over $MgSO_4$ and concentrated under reduced pressure. The residue was purified on a silica gel column (5% MeOH in DCM) to give AA (1.50 g, 95.8%) as a white solid. ESI-MS: m/z 625.3 $[M+Na]^+$.

To a solution of AA (60.0 mg, 99.57 μmol, 1.00 eq.) in pyridine (1 mL) was added isobutyric anhydride (31.50 mg, 199.13 μmol, 2.00 eq.) in 1 portion at RT (15° C.) under $N_2$ atmosphere. The mixture was stirred at RT for 12 h. The mixture was concentrated, and the residue was partitioned between EA and water. The combined organic phases were washed with water and brine, and dried over anhydrous $Na_2SO_4$. The mixture was filtered, and the filtrate was concentrated to dryness. The residue was purified by silica gel chromatography (30% EA in PE) to afford 145-1 (59.00 mg, 79.77%) as a white solid.

145-1 (57.00 mg, 76.74 μmol, 1.00 eq.) was dissolved in 80% $CH_3COOH$ (8 mL). The solution was stirred at RT (15° C.) for 12 h. The mixture was concentrated to dryness. The residue was purified on a silica gel column (2.5% MeOH in DCM) to give 145 (23.00 mg, 68.05%) as a white foam. ESI-MS: m/z 441.2 $[M+H]^+$, 463.2$[M+Na]^+$.

Example 95

Compound 170

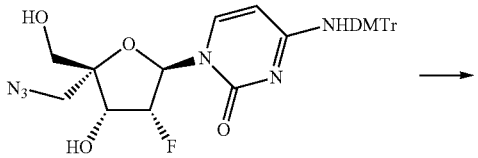

AA

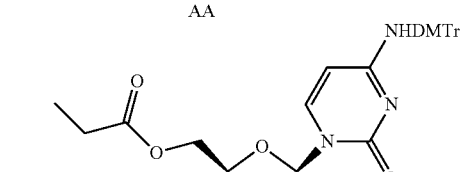

170-1

-continued

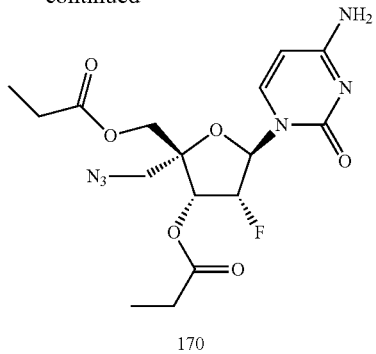

170

170-1 was prepared in similar manner as 145-1 using AA (60.00 mg, 99.57 μmol, 1.00 eq.) in pyridine (1 mL) and propionic anhydride (25.92 mg, 199.13 μmol, 2.00 eq.). 170-1 (white solid, 56.00 mg, 78.69%).

170 was prepared in similar manner as 145 using 170-1 (54.00 mg, 75.55 μmol, 1.00 eq.) 170 (white foam, 18.00 mg, 57.78%). ESI-MS: m/z 413.1 [M+H]⁺.

Example 96

Compound 171

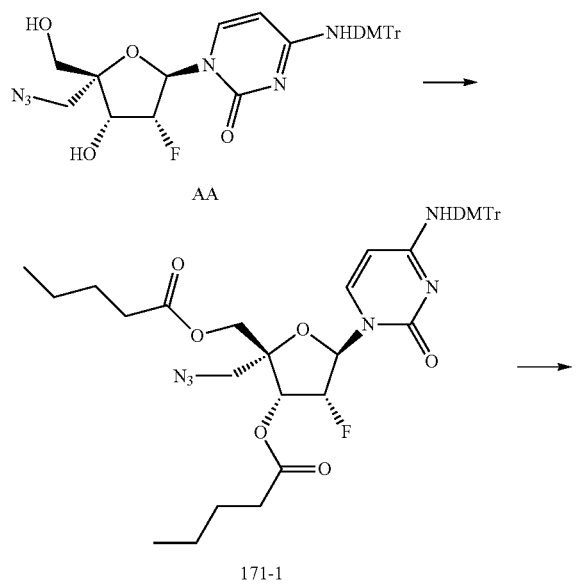

171-1 was prepared in similar manner as 145-1 using AA (62.00 mg, 102.89 μmol, 1.00 eq.) in pyridine (1 mL) and pentanoic anhydride (38.32 mg, 205.77 μmol, 2.00 eq.). 171-1 (white solid, 60.00 mg, 75.65%).

171 was prepared in similar manner as 145 using 171-1 (75.00 mg, 97.30 μmol, 1.00 eq.) 171 (white foam, 28.00 mg, 61.43%). ESI-MS: m/z 469.2 [M+H]⁺.

Example 97

Compound 146

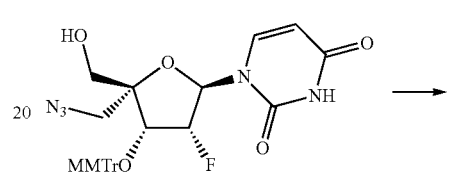

146-1

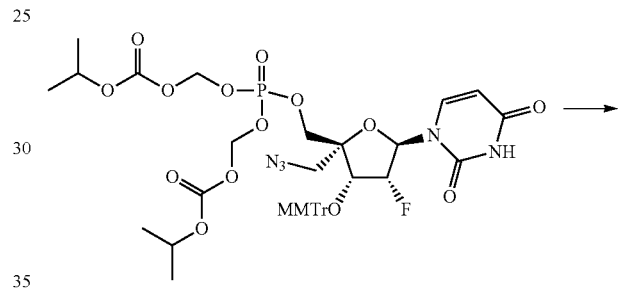

146-2

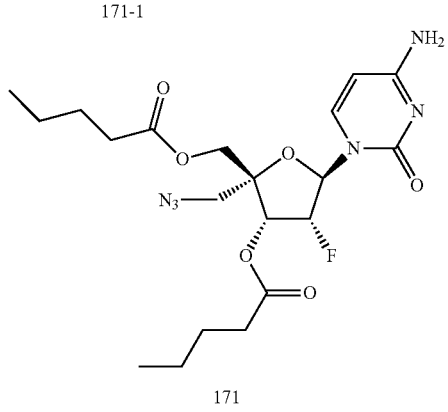

146

146-2 (40.7 mg, 53%) was prepared in the same manner from 146-1 (50 mg, 0.087 mmol) and bis(isopropyloxycarbonyloxymethyl)phosphate (58 mg, 0.175 mmol) with DIPEA (75 μL, 0.52 mmol), BOP-Cl (66.2 mg, 0.26 mmol), and 3-nitro-1,2,4-triazole (30 mg, 0.26 mmol) in THF (0.4 mL) in a similar manner as 169-4.

146-2 (40 mg, 0.045 mmol) was dissolved in anhydrous CH₃CN (0.5 mL), and 4N HCl in dioxane (34 μL, 0.135 mmol) was added at 0 to 5° C. The mixture was stirred at RT for 3 h. Anhydrous EtOH (200 μL) was added. The solvents were evaporated at RT and co-evaporated with toluene (3×). The residue was purified on silica (10 g column) with MeOH/CH₂Cl₂ (5-7% gradient) and lyophilized give 146 (15.4 mg, 76%) as a white foam. ESI-LCMS: m/z=614.15 [M+H]⁺, 1227.2 [2M+H]⁺.

Example 98

Compound 172

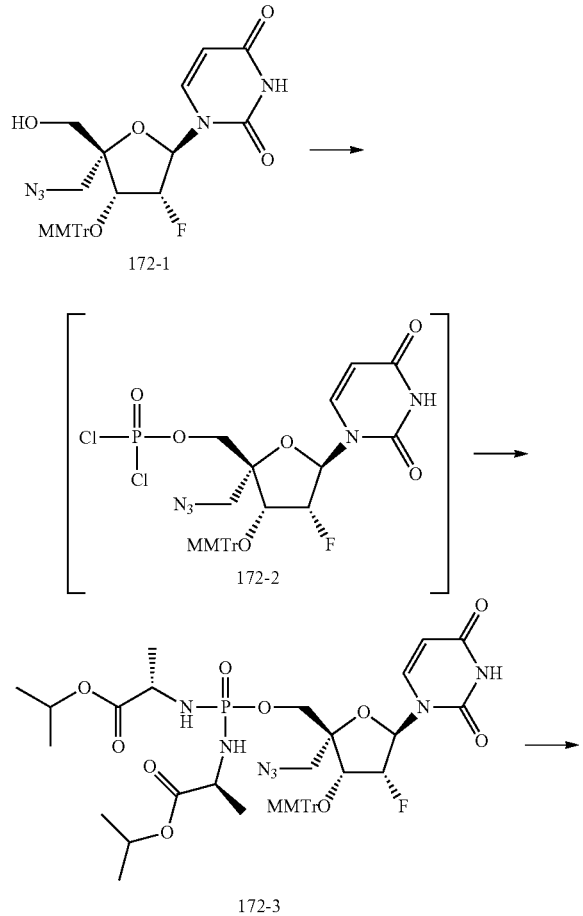

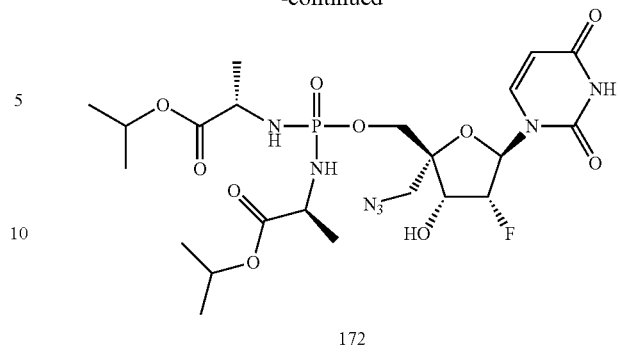

172-1 (100 mg, 0.174 mmol) was co-evaporated with anhydrous pyridine (3×), toluene (3×) and CH₃CN (3×), and dried under high vacuum overnight. 172-1 was dissolved in CH₃CN (2 mL). A proton sponge (112 mg, 0.52 mmol), POCl₃ (49 uL, 0.52 mmol) were added at 0 to 5° C. The mixture was stirred for 3 h at 0 to 5° C. to give intermediate 172-2. To this solution, L-alanine isopropyl ester hydrochloride (146 mg, 0.87 mmol), and TEA (114 uL, 1.74 mmol) were added. The mixture was stirred for 4 h at 0 to 5° C. The mixture was stirred 2 h at 0 to 5° C., then diluted with EtOAc. The mixture was washed with 1.0M citric acid, sat. aq. NaHCO₃ and brine, and dried with Na₂SO₄. The residue was purified on silica (10 g column) with CH₂Cl₂/MeOH (0-7% gradient) to give 172-3 (67 mg, 43.7%) as a white solid.

172-3 (65 mg, 0.074 mmol) was dissolved in anhydrous CH₃CN (0.5 mL), and 4N HCl in dioxane (55 μL, 0.22 mmol) was added at 0 to 5° C. The mixture was stirred at RT for 1.5 h. A second portion of 4N HCl in dioxane (15 μL) was added, and the mixture stirred at RT for 2 h. Anhydrous EtOH (300 μL) was added. The solvents were evaporated at RT and co-evaporated with toluene (3×). The residue was dissolved in 50% CH₃CN/H₂O, was purified on a reverse-phase HPLC (C18) with CH₃CN and water, and lyophilized to give 172 (9 mg, 20%) as a white foam. ESI-LCMS: m/z=608.15 [M+H]⁺, 1215.3 [2M+H]⁺.

Example 99

Compound 173

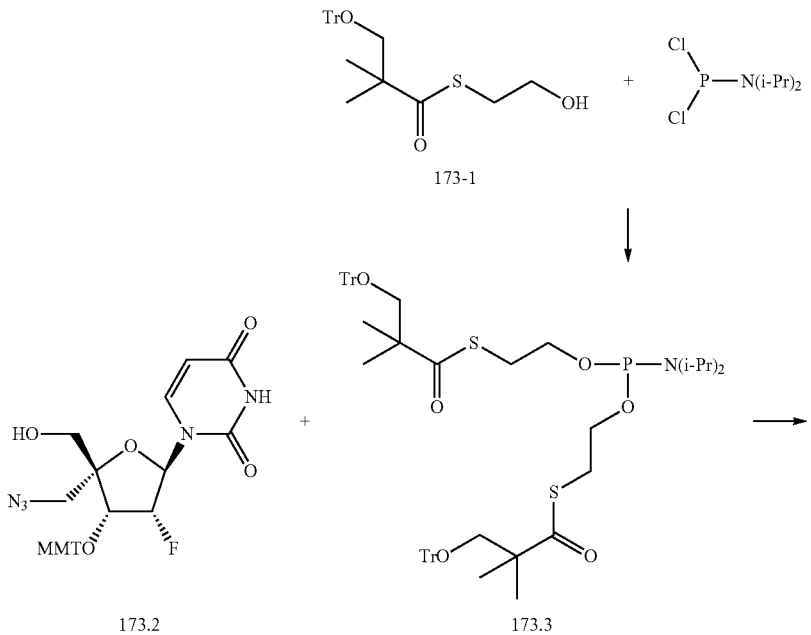

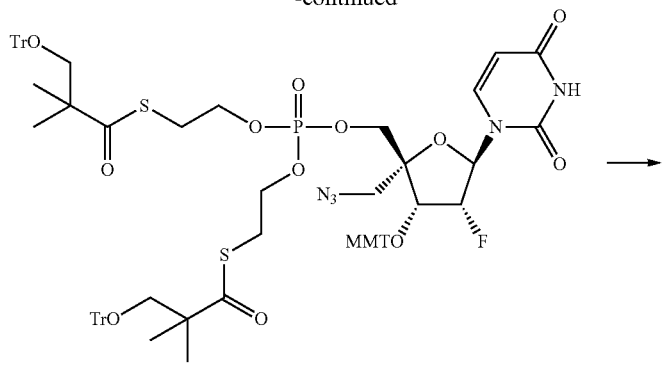

173.4

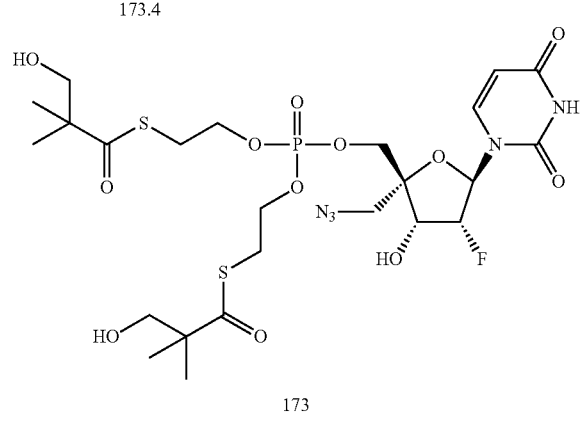

173

A solution of 173-1 (4.7 g, 11.2 mmol; prepared according to the procedure Villard et al., *Bioorg. Med. Chem.* (2008) 16:7321-7329) and Et₃N (3.4 mL, 24.2 mmol) in THF (25 mL) was added dropwise over 1 h to a stirred solution of N,N-diisopropylphosphorodichloridite (1.0 mL, 5.5 mmol) in THF (35 mL) at −75° C. The mixture was stirred at RT for 4 h. The mixture was filtered, and the filtrate concentrated. The oily residue was purified on silica gel column with EtOAc/hexanes (2-20% gradient) to give 173-3 (1.4 g, 26%).

To a solution of 173-2 (50 mg, 0.08 mmol) and 173-3 (110 mg, 0.11 mmol) in CH₃CN (1.0 mL) was added 5-(ethylthio)tetrazole (0.75 mL, 0.16 mmol; 0.25 M in CH₃CN). The mixture was stirred at RT for 1 h. The mixture was cooled to −40° C., and a solution of 3-chloroperoxybenzoic acid (37 mg, 0.16 mmol) in CH₂Cl₂ (0.3 mL) was added. The mixture was warmed to RT over 1 h. The reaction was quenched with 7% Na₂S₂O₃ solution in sat aq. NaHCO₃. The mixture was diluted with EtOAc, and the layers were separated. The organic layer was washed with brine and dried with Na₂SO₄. The solvent was evaporated, and the residue was purified on a silica gel column with EtOAc/hexanes (30-100% gradient) to give 173-4 (52 mg, 45%).

A solution of 173-4 (52 mg, 0.036 mmol) in MeCN (0.5 mL) and HCl (45 µL; 4 N in dioxane) was stirred 20 h at RT. The reaction was quenched with MeOH, and the solvents were evaporated. The residue was co-evaporated with toluene and purified on a silica gel column with MeOH/CH₂Cl₂ (4-10% gradient) to give 173 (14 mg, 51%). ESI-LCMS: m/z=702 [M+H]⁺.

Example 100

Compound 174

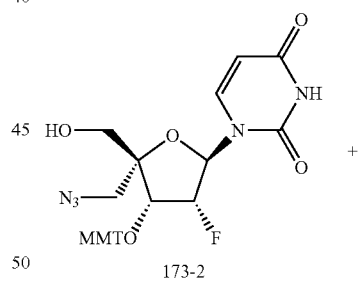

173-2

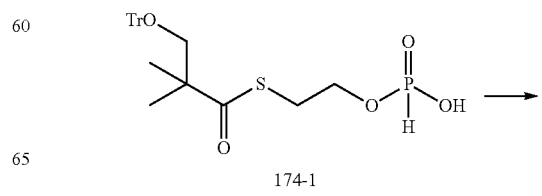

174-1

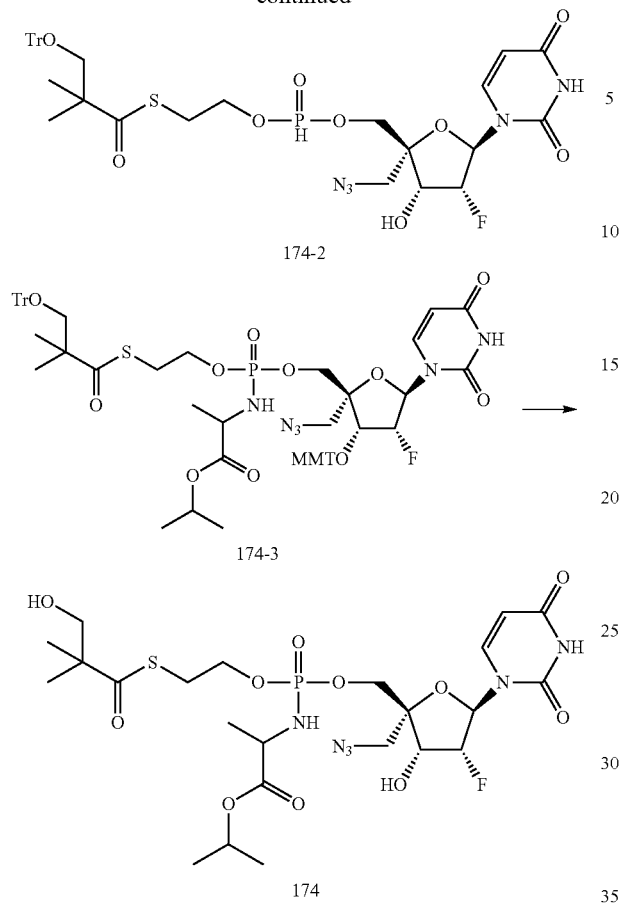

174-2

174-3

174

Example 101

Compound 175

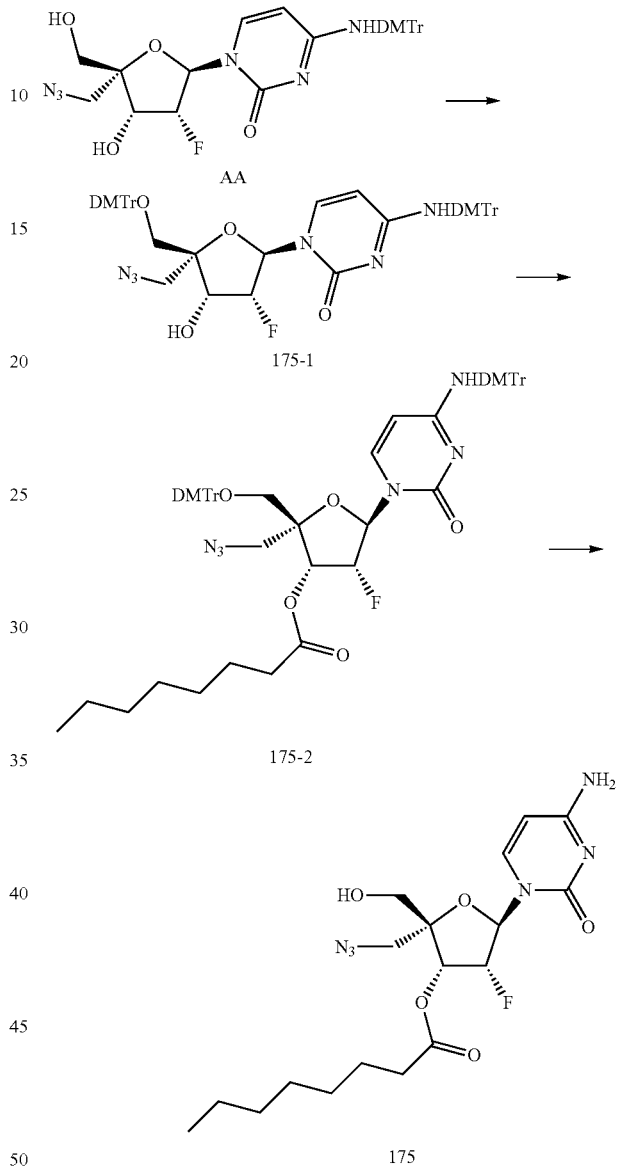

AA 175-1

175-2

175

A mixture of 174-1 (0.14 g, 0.24 mmol; prepared according to the procedure described in WO 2008/082601, filed Dec. 28, 2007) and 173-2 (120 mg, 0.2 mmol) was rendered anhydrous by evaporating with pyridine and then dissolved in pyridine (3 mL). Pivaloyl chloride (48 µL) was added dropwise at −15° C. The mixture was stirred at −15° C. for 2 h. The reaction was quenched with sat. aq. NH$_4$Cl solution and diluted with CH$_2$Cl$_2$. The organic layer was washed with brine and dried with Na$_2$SO$_4$. The solvents were evaporated, and the residue was purified on a silica gel column with EtOAc/hexanes (30-100% gradient) to give 174-2 (50 mg, 24%).

A mixture of 174-2 (43 mg; 0.04 mmol) in CCl$_4$ (0.8 mL), L-valine isopropyl ester hydrochloride (20 mg, 0.12 mmol) and Et$_3$N (33 µl, 0.24 mmol) was stirred at RT for 2 h. The mixture was diluted with EtOAc. The mixture was washed with sat. aq. NaHCO$_3$ and brine, and dried with Na$_2$SO$_4$. The solvents were evaporated, and the residue was purified on a silica gel column with i-PrOH/CH$_2$Cl$_2$ (2-10% gradient) to 174-3 (35 mg, 75%).

A solution of 174-3 (35 mg, 0.03 mmol) in MeCN (0.4 mL) and HCl (40 µL; 4 N in dioxane) was stirred 4 h at RT. The reaction was quenched with the addition of MeOH, and the solvents were evaporated. The residue was co-evaporated with toluene and purified on a silica gel column with MeOH/CH$_2$Cl$_2$ (4-10% gradient) to give 174 (11 mg, 56%). ESI-LCMS: m/z=655 [M+H]$^+$.

To a stirred solution of AA (300.0 mg, 497.83 µmol) in anhydrous pyridine (0.5 mL) was added DMTrCl (337.36 mg, 995.66 µmol) at RT (17° C.) under N$_2$ atmosphere. The solution was stirred at 50° C.~60° C. for 12 h. The mixture was concentrated to dryness under reduced pressure, and the residue was dissolved in EA (40 mL). The solution was washed with brine, dried over anhydrous MgSO$_4$, and concentrated to dryness at low pressure. The residue was purified on a silica gel column using 20% EA in PE to give 175-1 (300 mg, 66.59%) as a white solid.

To a stirred solution of 175-1 (100.00 mg, 110.50 µmol) in anhydrous pyridine (0.5 mL) was added DMAP (6.75 mg, 55.25 µmol), DCC (22.80 mg, 110.50 µmol) and n-octanoic acid (31.87 mg, 221.00 µmol) at RT (18° C.) under N$_2$ atmosphere. The solution was stirred at RT for 12 h. The solution was concentrated to dryness under reduced pressure. The residue was purified on a silica gel column using 15% EA in PE to give 175-2 (98.00 mg, 86.0%) as a white foam.

175-2 (90.00 mg, 87.28 μmol) was dissolved in 80% CH₃COOH (20 mL) at RT (16° C.). The mixture was stirred RT for 12 h. The reaction was quenched with MeOH, and the mixture was concentrated to dryness. The residue was purified on a silica gel column (5% MeOH in DCM) to give 175 (33.00 mg, 88.7%) as a white solid. ESI-MS: m/z 427.2 [M+H]⁺.

Example 102

Compound 176

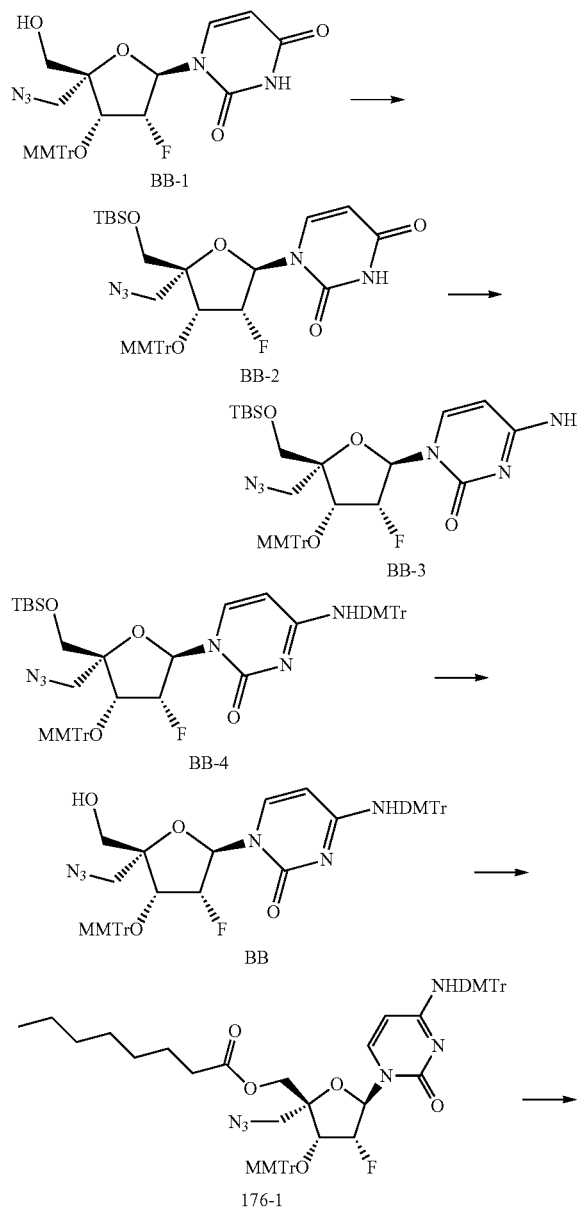

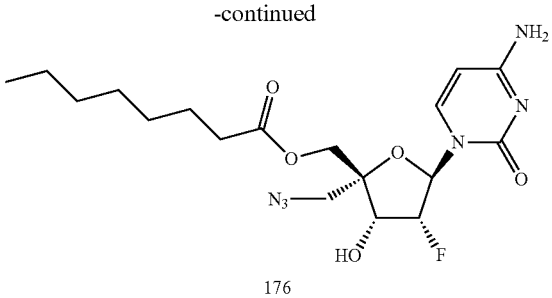

To a stirred solution of BB-1 (500.00 mg, 0.87 mmol) in anhydrous pyridine (1 mL) was added TBSCl (236.5 mg, 1.57 mmol) at 20° C. under N₂. The solution was stirred at 50° C.~60° C. for 12 h. The solution was concentrated to dryness under reduced pressure. The residue was dissolved in EA (50 mL). The solution was washed with sat. NaHCO₃ solution and brine, and dried over anhydrous MgSO₄. The solution was filtered, and the filtrate was concentrated to dryness. The residue was purified on a silica gel column to give BB-2 (510.00 mg, 85.06%) as a white solid.

To a stirred solution of BB-2 (430.00 mg, 625.15 mmol) in anhydrous MeCN (6 mL) was added TPSCl (368.65 mg, 1.25 mmol), DMAP (152.75 mg, 1.25 mmol) and TEA (126.52 mg, 1.25 mmol) at RT. The mixture was stirred for 2 h. NH₄OH (8 mL) was added, and the mixture stirred for 3 h. The mixture was extracted with EA (3×40 mL). The organic phase was washed with brine, dried over anhydrous Na₂SO₄ and concentrated at low pressure. The residue was purified on a silica gel column (25% EA in PE) to give BB-3 (500 mg of crude) as a yellow foam.

To a stirred solution of BB-3 (500 mg of crude, 0.72 mmol) in anhydrous DCM (7 mL) was added DMTrCl (365 mg, 1.0 mmol) and collidine (305 mg, 2.5 mmol) and AgNO₃ (184 mg, 1.08 mmol) at RT (15° C.) under N₂ atmosphere. The mixture was stirred at RT for 12 h. MeOH (5 mL) was added. The mixture was filtered, and the filtrate was concentrated to dryness. The residue was dissolved in EA (50 mL). The solution was washed with brine, dried over anhydrous Na₂SO₄ and concentrated at low pressure. The residue was purified on a silica gel column (5% MeOH in DCM) to give BB-4 (500 mg, 70.3%) as a white solid.

BB-4 (1.00 g, 1.01 mmol) was dissolved in TBAF (5 mL, 1M in THF) and stirred at RT for 30 mins. The mixture was diluted with EA (100 mL). The mixture was washed with water and brine, and dried over anhydrous MgSO₄. The organic phase was concentrated to dryness. The residue was purified on the silica gel column (30% EA in PE) to give BB (0.80 g, 91.5%) as a white solid. ESI-MS: m/z 873.7 [M+1]⁺.

To a solution of BB (100.00 mg, 114.29 μmol) in anhydrous pyridine (1.5 mL) was added DMAP (2.79 mg, 22.86 μmol), DCC (70.75 mg, 342.88 μmol) and n-octanoic acid (49.45 mg, 342.88 μmol) at RT (18° C.) under N₂ atmosphere. The solution was stirred at RT for 12 h. The solution was concentrated to dryness under reduced pressure. The residue was purified on a silica gel column using 15% EA in PE to give 176-1 (95.00 mg, 83.03%) as a white foam.

176-1 (110.00 mg, 109.87 μmol) was dissolved in 80% CH₃COOH (25 mL) at RT (15° C.). The mixture was stirred for 12 h. The reaction was quenched with MeOH, and the solution was concentrated to dryness. The residue was purified on a silica gel column (5% MeOH in DCM) to give 176 (30.00 mg, 64.03%) as a white solid. ESI-MS: m/z 427.2 [M+H]⁺.

Example 103

Compound 177

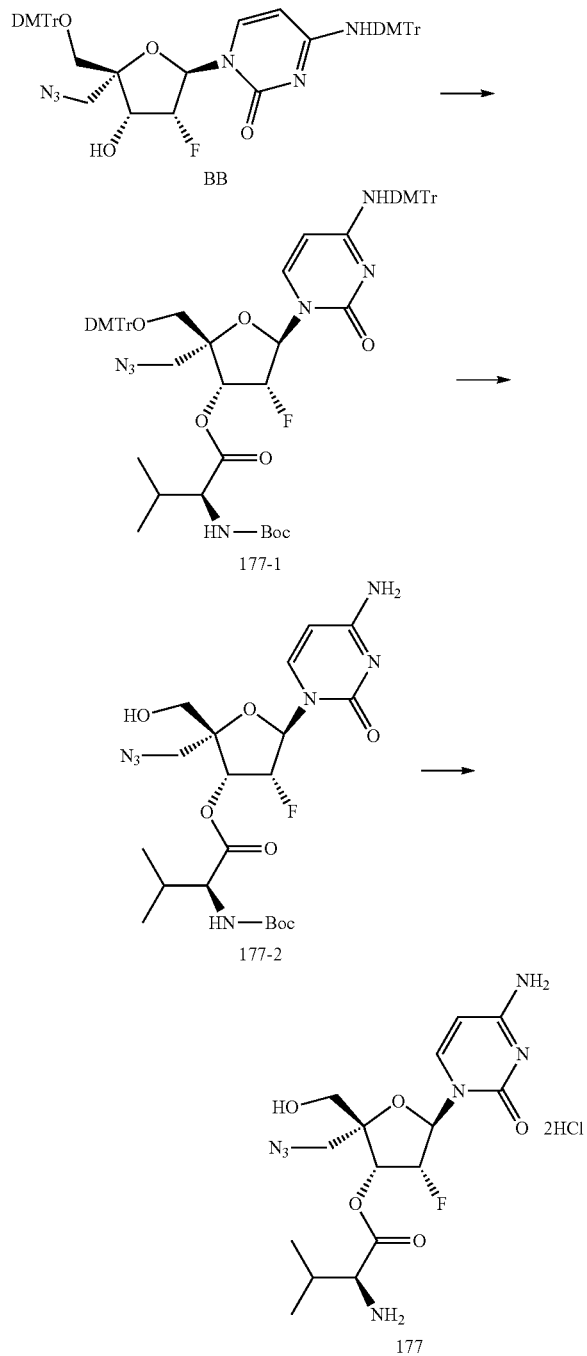

177-1 was prepared in similar manner as 143-1 using BB (250.0 mg, 276.25 µmol), (2S)-2-(tert-butoxycarbonylamino)-3-methyl-butanoic acid (360.11 mg, 1.66 mmol) and TEA (83.86 mg, 828.75 µmol). 177-1 (white foam, 220.0 mg, 72.12%).

177-2 was prepared in similar manner as 143-2 using 177-1 (230.00 mg, 208.29 µmol, 1.00 eq.). 177-2 (white foam, 80.00 mg, 77.66%).

177 was prepared in similar manner as 143 using 177-2 (100.00 mg, 200.20 µmol, 1.00 eq.). 177 (white solid, 56 mg, 59.57%). ESI-MS: m/z 400.0 [M+H]⁺, 422.1 [M+Na]⁺; 799.1 [2M+H]⁺, 821.2 [2M+Na]⁺.

Example 104

Compound 178

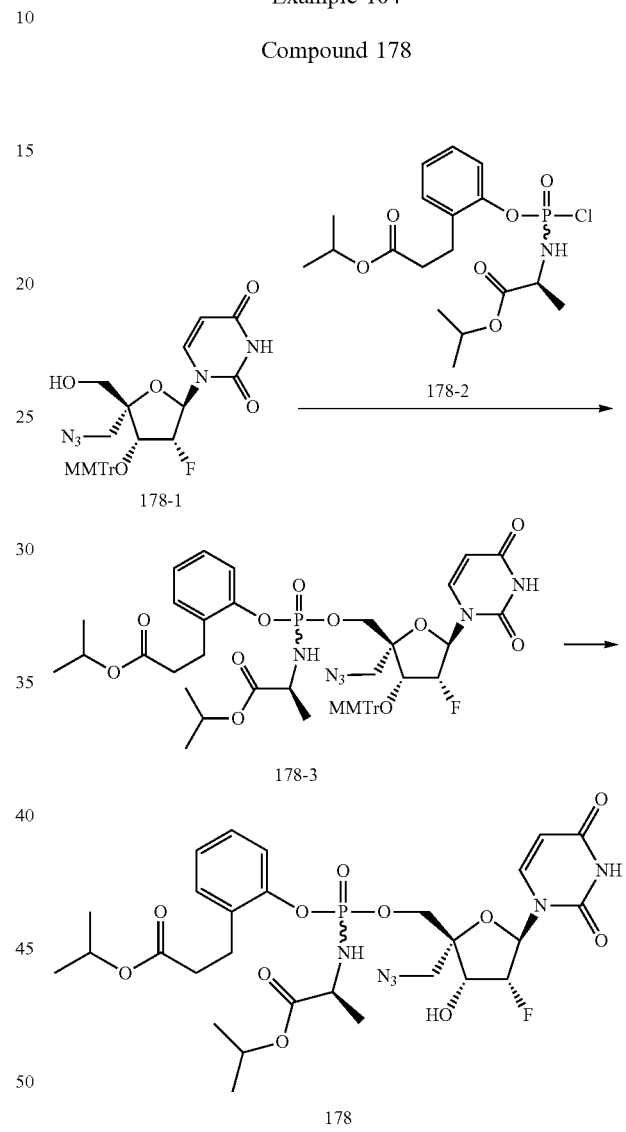

To a stirred solution of 178-1 (100 mg, 0.175 mmol) in anhydrous $CH_3CN$ (2.0 mL) was added N-methylimidazole (0.14 mL, 1.4 mmol) at 0° C. (ice/water bath). A solution of 178-2 (220 mg, 0.53 mmol, dissolved in 0.5 mL of $CH_3CN$), (prepared according to a general procedure described in Bondada, L. et al., *ACS Medicinal Chemistry Letters*, (2013) 4(8):747-751) was added. The solution was stirred at 0 to 5° C. for 1 h and then stirred at RT for 16 h. The mixture was cooled to 0 to 5° C., diluted with EA followed by addition of water (5 mL). The solution was washed with 1.0M citric acid, sat. aq. $NaHCO_3$ and brine, and dried with $MgSO_4$. The residue was purified on silica (10 g column) with EA/hexanes (25-100% gradient) to give 178-3 (56.4 mg, 33.7%) as a white foam.

178-3 (56 mg, 0.0585 mmol) was dissolved in anhydrous CH₃CN (0.7 mL), and 4N HCl in dioxane (44 μL, 0.176 mmol) was added at 0 to 5° C. The mixture was stirred at RT for 2 h. 4N HCl in dioxane (20 μL) was added. The mixture was stirred at RT for 2 h. Anhydrous EtOH (100 μL) was added. The solvents were evaporated at RT and co-evaporated with toluene (3×). The residue was purified on silica (10 g column) with MeOH/CH₂Cl₂ (1-7% gradient) and lyophilized to give 178 (27.6 mg, 69%) as a white foam. ESI-LCMS: m/z=685.2[M+H]⁺.

Example 105

Compound 179

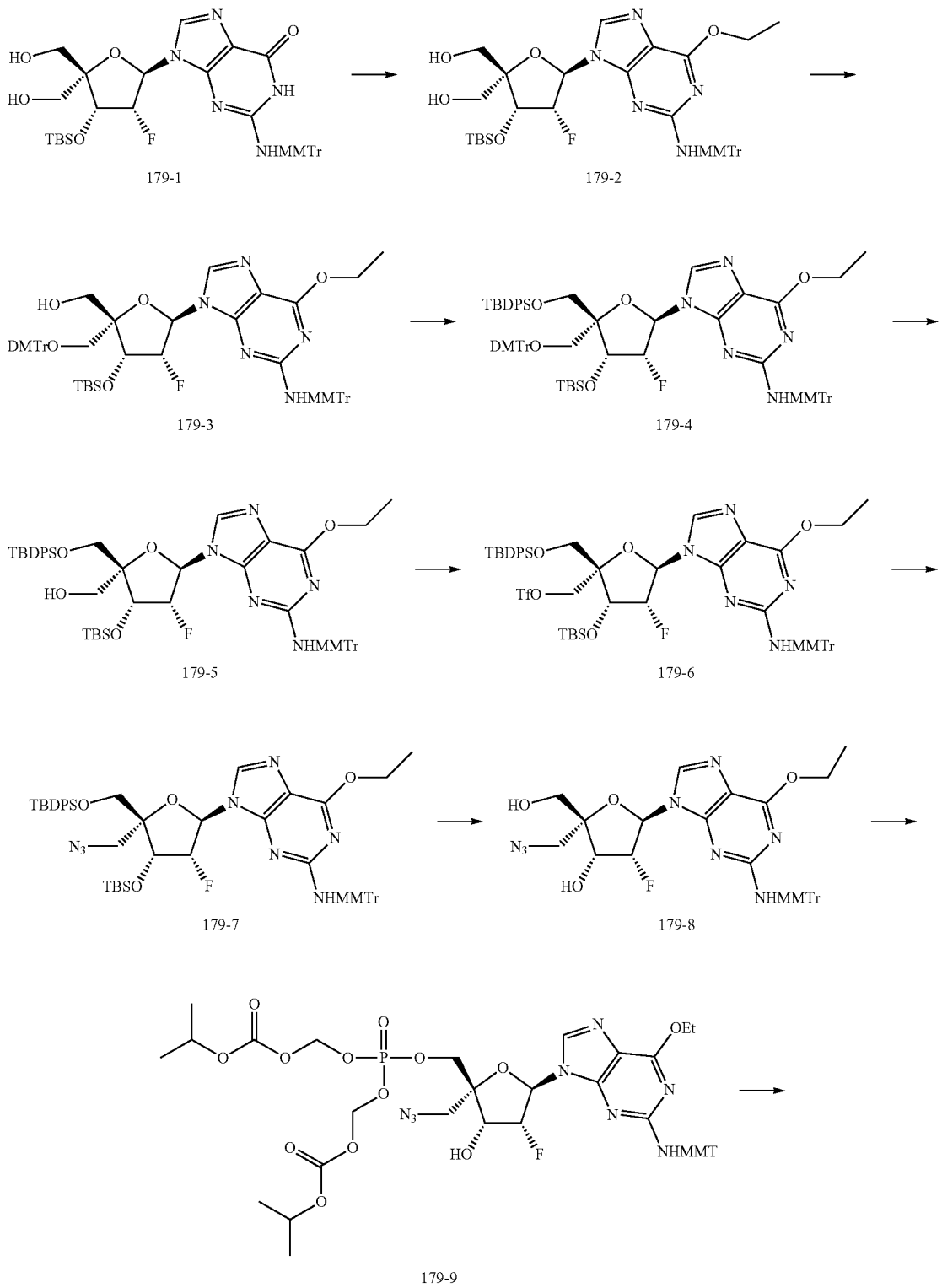

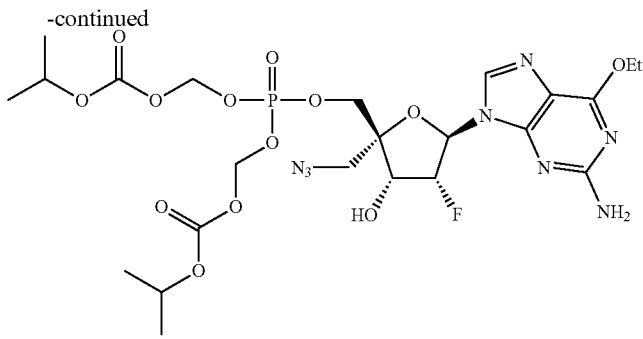

179

To a stirred solution of 179-1 (1.92 g, 27.3 mmol), PPh$_3$ (1.43 g, 54.7 mmol), EtOH (0.25 g, 54.7 mmol) in anhydrous dioxane (20 mL) was added DIAD (1.11 g, 54.7 mmol) dropwise at 0° C. The solution was stirred at 25° C. for 15 h. The reaction was quenched with water and extracted with EA. The mixture was washed with water and brine. The organic layer was dried over Na$_2$SO$_4$ and filtered. The filtrate was concentrated in vacuum to dryness, and the residue was purified on a silica gel column (2% to 5% MeOH in DCM) to give 179-2 (1.43 g, 71%) as a white foam.

To a stirred solution of 179-2 (1.43 g, 19.6 mmol) in DMF (15 mL) was added TEA (0.59 g, 58.8 mmol) and DMTrCl (0.99 g, 29.4 mmol) at 0° C. The solution was stirred at 25° C. for 12 h. The mixture was treated with MeOH (1 mL), and diluted with EA. The solution was washed with water and brine. The organic layer was dried over anhydrous NaSO$_4$, and concentrated to dryness. The residue was purified on a silica gel column (2% MeOH in DCM) to give 179-3 (1.13 g, 56%) as a yellow solid.

To a stirred solution of 179-3 (1.13 g, 1.1 mmol) in anhydrous pyridine (10 mL) was added TBDPSCl (0.91 g, 3.3 mmol) and AgNO$_3$ (0.61 g, 3.3 mmol). The mixture was stirred at 25° C. for 15 h. The solid was removed by filtration, and the filtrate was diluted with EA (50 mL). The solution was washed with brine. The organic layer was dried over anhydrous Na$_2$SO$_4$, and concentrated at low pressure. The residue was purified on a silica gel column (2% MeOH in DCM) to give 179-4 (1.22 g, 88%) as a white foam.

To a stirred solution of 179-4 (1.22 g, 1.0 mmol) in anhydrous DCM (15 mL) was added Cl$_2$CHCOOH (0.6 mL) at −78° C. The mixture was stirred at −20° C. for 1 h. The reaction was quenched with sat. aq. NaHCO$_3$ and extracted with DCM. The organic layer was dried over anhydrous Na$_2$SO$_4$, and concentrated at low pressure. The residue was purified by column chromatography (2% MeOH in DCM) to give 179-5 (0.52 g, 56%) as a white foam.

To a stirred solution of 179-5 (0.52 g, 0.5 mmol) in anhydrous DCM (15 mL) and pyridine (0.21 g, 2.5 mmol) was added Tf$_2$O (0.30 g, 1.0 mmol) in DCM (1 mL) dropwise at 0° C. The mixture was stirred at 0° C. for 15 mins. The reaction was quenched with ice water. The organic layer was separated and washed with water. The organic layer was dried over anhydrous Na$_2$SO$_4$ and concentrated at low pressure to give 179-6 (442 mg crude) as a yellow foam.

To a stirred solution of 179-6 (442 mg, 0.4 mmol) in anhydrous DMF (5 mL) was added NaN$_3$ (131 mg, 2.0 mmol). The mixture was stirred at RT for 12 h. The reaction was quenched with water and extracted by EA (20 mL, 2×). The organic layer was washed with water and dried over Na$_2$SO$_4$. The organic phase was evaporated to dryness under reduced pressure. The residue was purified on a silica gel column (1% MeOH in DCM) to give 179-7 (352 mg, 88%) as a white foam.

A mixture of 179-7 (352 mg, 0.35 mmol) and NH$_4$F (392 mg, 10.6 mmol) in MeOH (10 mL) was stirred at 80° C. for 12 h. The mixture was cooled to RT. The solid was removed by filtration. The solvent was concentrated under reduced pressure. The residue was purified on a silica gel column (2% to 5% MeOH in DCM) to give crude 179-8 (151 mg). The crude product was purified by prep-HPLC (0.1% NH$_4$HCO$_3$ in water and CH$_3$CN) to give 179-8 (71.5 mg, 32%) as a white solid. MS: m/z 641[M+H]$^+$.

A mixture of 179-8 (64 mg, 0.1 mmol) and bis(pivaloyloxymethyl)phosphate, after rendered anhydrous by evaporating with toluene, was dissolved in CH$_3$CN (1 mL) and cooled to 0° C. BopCl (40 mg, 0.15 mmol) and NMI (40 μL, 0.5 mmol) were added. The mixture was stirred at 0° C. for 2 h. EtOAc was added, and the mixture was washed with 0.5 N aq. citric acid, sat. aq. NaHCO$_3$ and brine, and then dried with Na$_2$SO$_4$. The solvents were removed, and the residue was purified on a silica gel column with 3% i-PrOH in CH$_2$Cl$_2$ to 179-9 (38 mg, 40%).

A solution of 179-9 (30 mg, 0.03 mmol) in CH$_3$CN (0.3 mL) and HCl (30 μL; 4 N dioxane) was stirred at RT for 100 mins. The reaction was quenched with EtOH, and the mixture was evaporated. The crude residue was purified on a silica gel column with i-PrOH/CH$_2$Cl$_2$ (3-10% gradient) to yield 179 (10 mg, 50%). ESI-LCMS: m/z=681 [M+H]$^+$.

Example 106

Compound 180

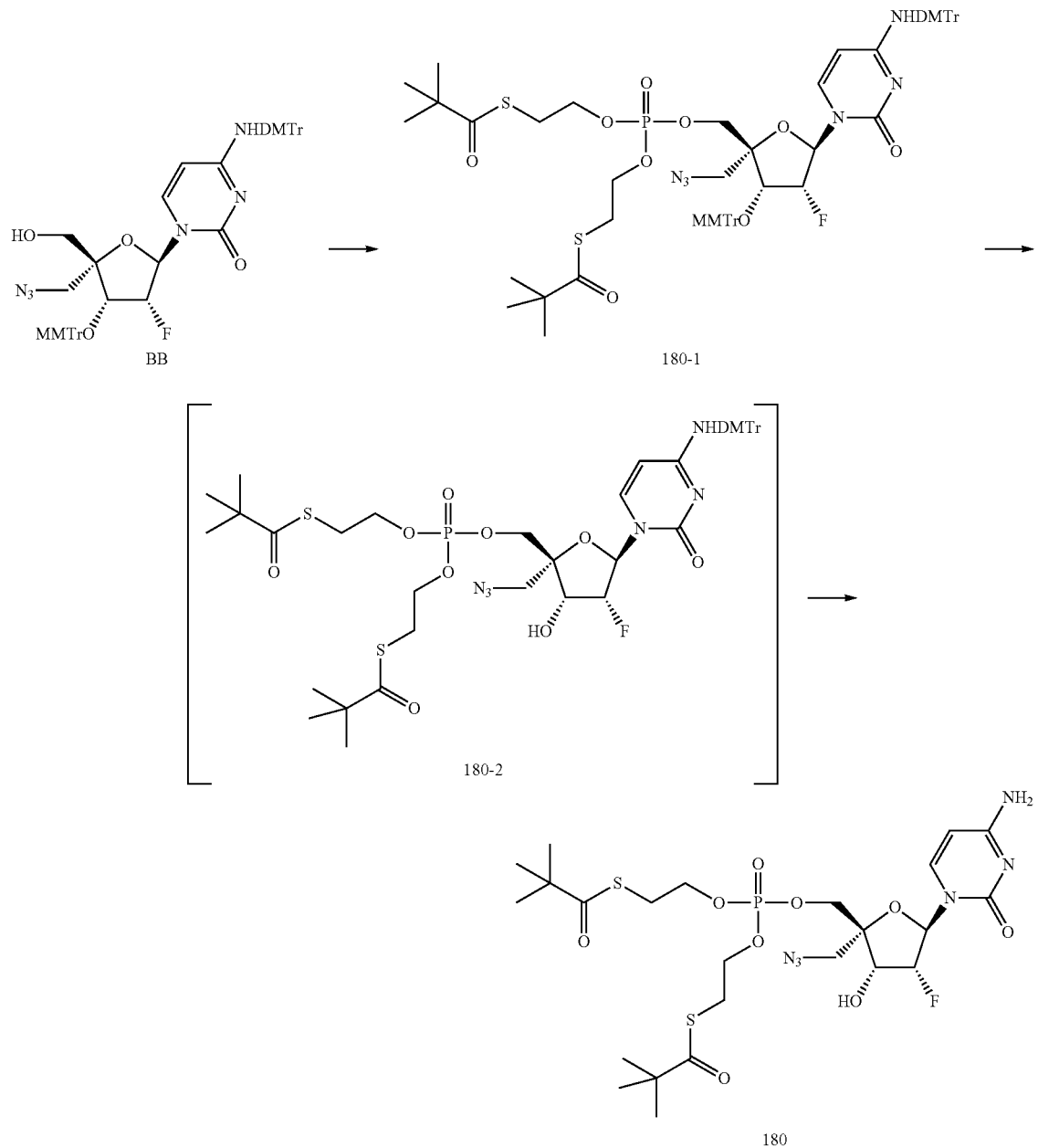

To a solution of BB (100 mg, 0.114 mmol) in anhydrous CH₃CN (2 mL) were added a solution of bis-SATE-phosphoramidate (62.2 mg, 0.14 mmol) in CH₃CN (1 mL) followed by 5-ethylthio-1H-tetrazole in CH₃CN (0.25M; 0.56 mL, 0.14 mmol) at 0 to 5° C. dropwise. The mixture was stirred 2 h at 0 to 5° C. under Ar. A solution of 77% m-CPBA (49 mg, 0.22 mmol) in DCM (1 mL) was added, and the mixture was stirred 2 h at 0 to 5° C. under Ar. The mixture was diluted with EtOAc (50 mL), washed with 1.0M citric acid, sat. NaHCO₃, and brine, and dried with MgSO₄. The mixture was filtered and the solvents were evaporated in vacuo. The residue was purified on silica (10 g column) with EA/hexanes (10-100% gradient) to give 180-1 (72 mg, 50.8%) as a white solid.

180-1 (72 mg, 0.056 mmol) was dissolved in anhydrous CH₃CN (1.0 mL), and 4N HCl in dioxane (87 µL, 0.35 mmol) was added at 0 to 5° C. The mixture was stirred at RT for 2 h. Intermediate 180-2 was observed by LCMS. The solvents were evaporated at RT and co-evaporated with toluene (3×). The residue obtained was re-dissolved in 80% HCOOH (2 mL). The mixture was stirred at RT for 4.5 h. The solvents were evaporated at RT and co-evaporated with toluene (3×). Anhydrous EtOH (3×5 mL) was added. The residue was dissolved in 50% CH₃CN/H₂O, purified on a reverse-phase HPLC (C18) using CH₃CN and H₂O, and lyophilized to give 180 (19.2 mg) as a white foam. ESI-LCMS: m/z=669.2 [M+H]⁺, 1337.25 [2M+H]⁺.

Example 107
Compound 181
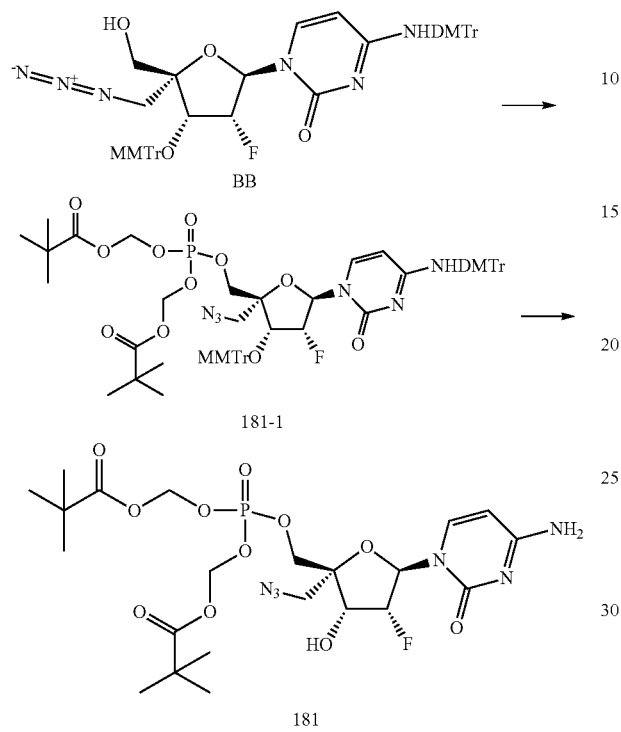
181-1 (98 mg, 72.6%) was prepared in the same manner from BB (100 mg, 0.114 mmol) and bis(tert-butoxycarbonyloxymethyl)phosphate (83 mg, 0.35 mmol) with DIPEA (126 µL, 0.69 mmol), BOP-Cl (87 mg, 0.34 mmol), and 3-nitro-1,2,4-triazole (39 mg, 0.34 mmol) in THF (1.5 mL) in the same manner as 169-4.
181 (30.2 mg, 60%) was prepared from 181-1 (98 mg, 0.083 mmol) in the same manner as 146. ESI-LCMS: m/z=609.15 [M+H]$^+$, 1217.3 [2M+H]$^+$.
Example 108
Compounds 182 and 183
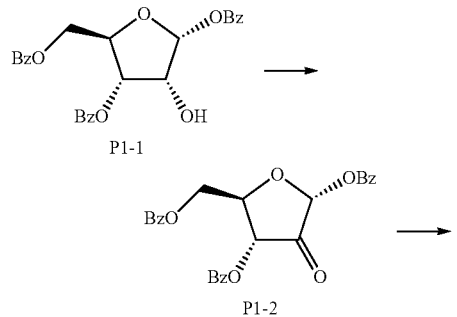
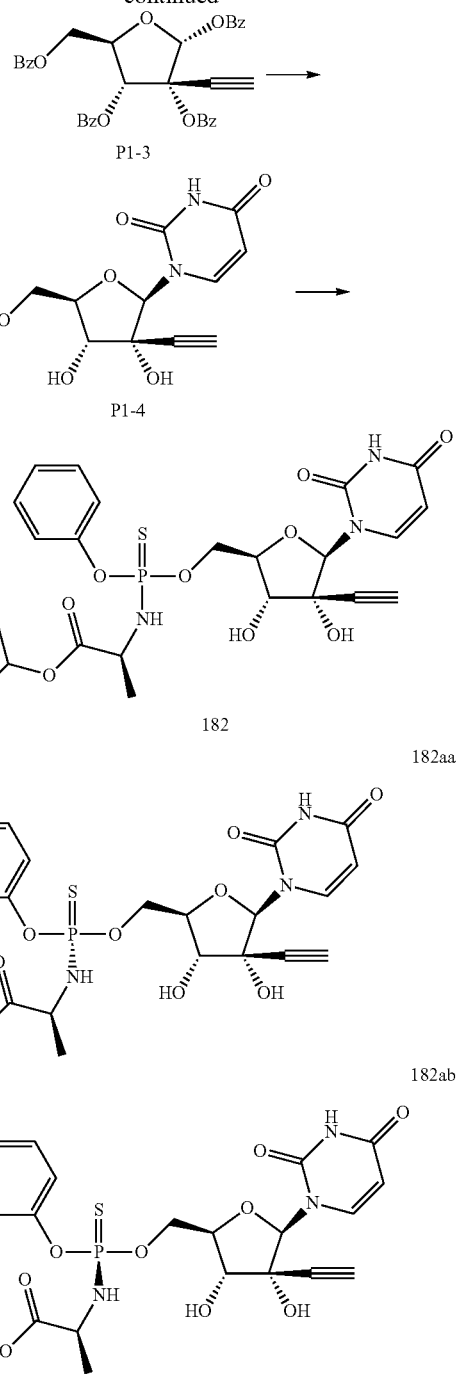

Compounds 182, 182aa, 182ab and 183 were prepared as described in PCT Publication No. WO 2014/96680, published Jun. 27, 2014. 182: ESI-LCMS: m/z 554.0 [M+H]$^+$; 182aa and 182ab: Faster eluting diastereomer—$^{31}$P NMR 67.1, LC/MS 552 [M−1]. Slower eluting diastereomer—$^{31}$P NMR 67.9, LC/MS 552 [M−1]. 183: ESI-MS: m/z 576.9 [M+H]$^+$.
Example 109
Compounds 186-201
186
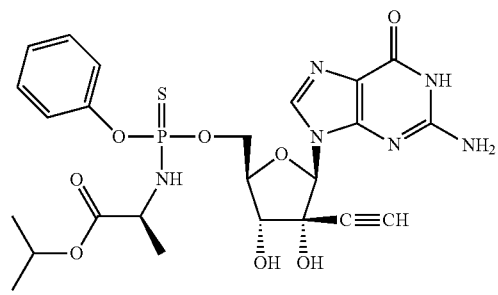
187
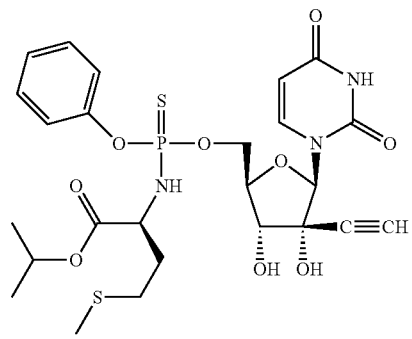
188
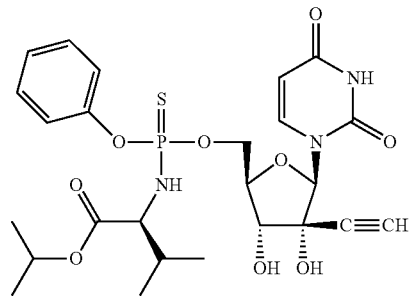
189
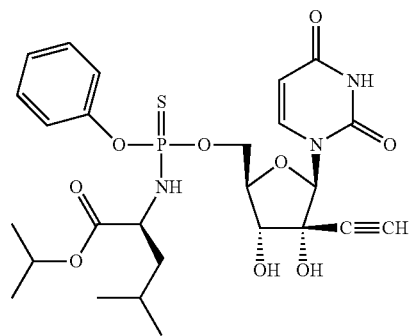
190
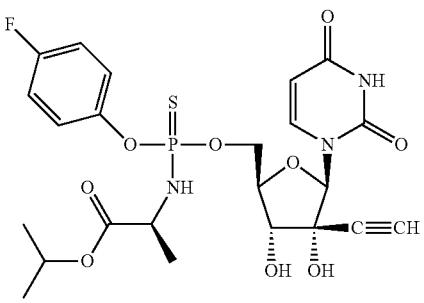
191
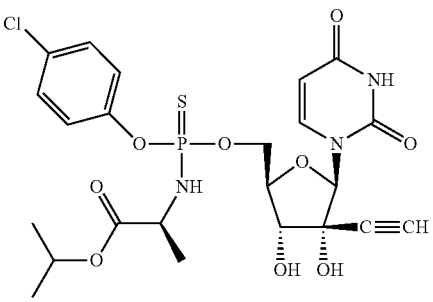
192
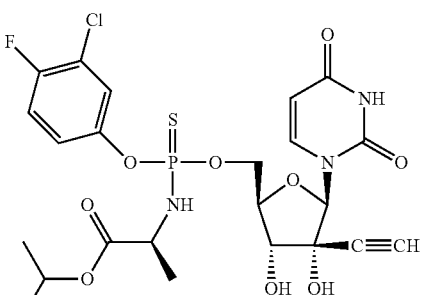
193
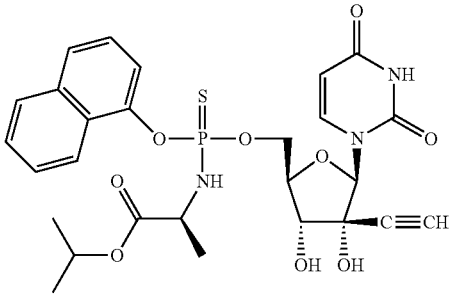
194
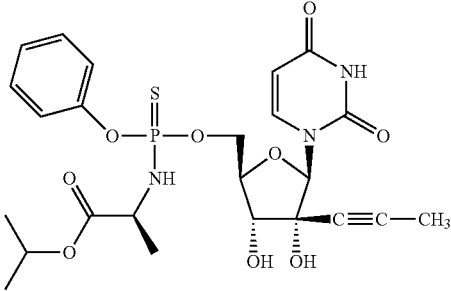

-continued

195
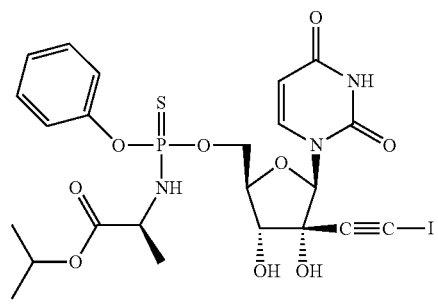

196
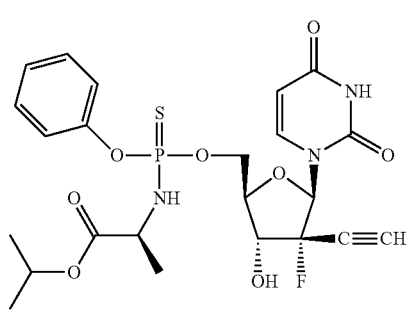

197
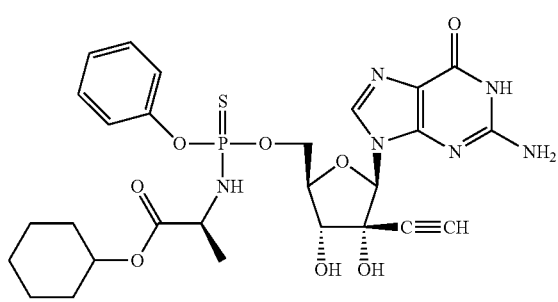

198
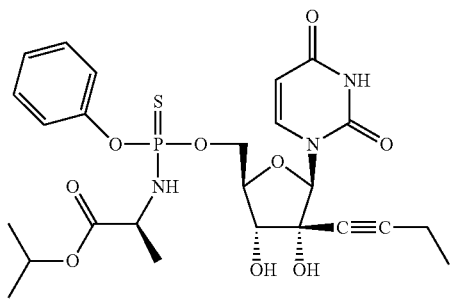

199
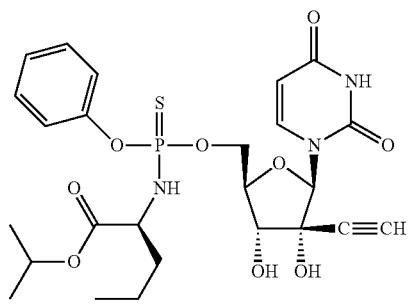

-continued

200
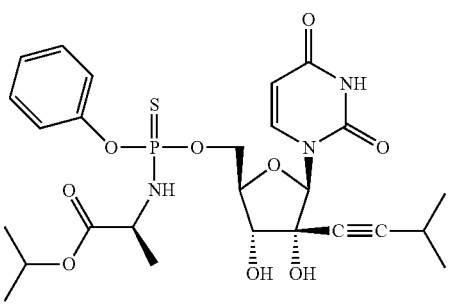

201
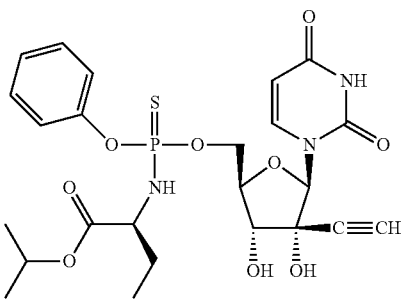

Compounds 186-201 were prepared as described in PCT Publication No. WO 2014/96680, published Jun. 27, 2014. 186: ESI-LCMS: m/z 593.0 [M+H]⁺. 187: ESI-LCMS: m/z 614.1 [M+H]⁺. 188: ESI-LCMS: m/z 582.1 [M+H]⁺. 189: ESI-LCMS: m/z 596.1 [M+H]⁺. 190: ESI-LCMS: m/z 672.0 [M+H]⁺. 191: ESI-LCMS: m/z 589.0 [M+H]⁺. 192: ESI-LCMS: m/z 606.0 [M+H]⁺. 193: ESI-LCMS: m/z 604.1 [M+H]⁺. 194: ESI-LCMS: m/z 568 [M+H]⁺, 590 [M+Na]⁺. 195: ESI-LCMS: m/z 680 [M+H]⁺. 196: ESI-LCMS: m/z 578.0 [M+Na]⁺. 197: ESI-MS: m/z 633.1 [M+H]⁺. 198: ESI-LCMS: m/z 604 [M+Na]⁺, 582 [M+H]⁺. 199: ESI-LCMS: m/z 582.0 [M+H]⁺. 200: ESI-LCMS: m/z 618 [M+Na]⁺. 201: ESI-LCMS: m/z 568.1 [M+H]⁺.

Example 110

Compound 204

204
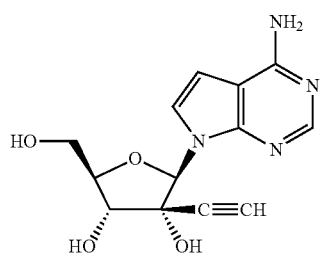

A method for preparing compound 204 is provided in WO 2010/015643, filed Aug. 4, 2009.

Example 111

Compound 206

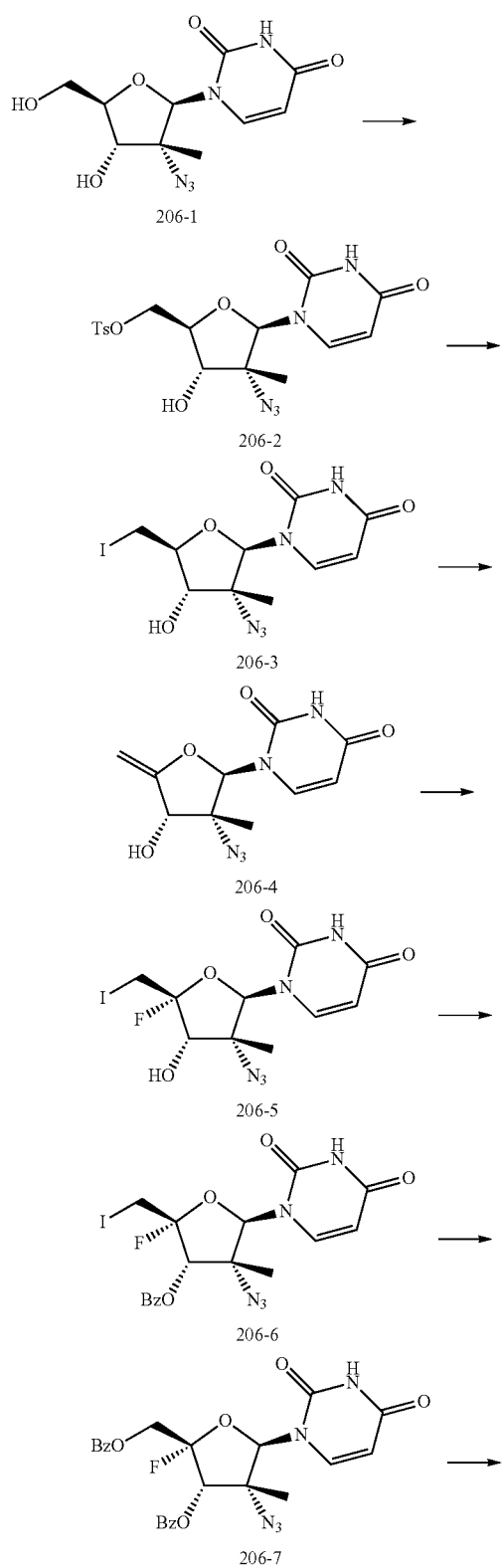

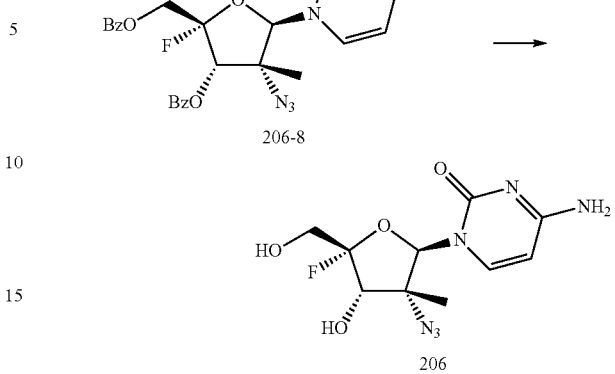

206-1 (1.0 g, 3.53 mmol) was coevaporated with anhydrous pyridine 3 times to remove H₂O. To an ice-cold solution of 206-1 in anhydrous pyridine (9 mL) was added TsCl (808 mg, 4.24 mmol) in pyridine (3 mL) drop-wise at 0° C., and the mixture was stirred for 18 h. at 0° C. The reaction was monitored by LCMS, and then quenched with H₂O. After concentration at low pressure, the residue was dissolved in EA (50 mL). The solution was washed with sat. NaHCO₃ solution and brine. The organic layer was dried over anhydrous Na₂SO₄ and filtered. The filtrate was evaporated at low pressure, and the residue was purified by silica gel column chromatography (1% MeOH in DCM) to give 206-2 (980 mg, 63%) as a white solid.

To a solution of 206-2 (980 mg, 2.24 mmol) in acetone (10 mL) was added NaI (1.01 g, 6.73 mmol), and the mixture was heated to reflux overnight. The reaction was monitored by LCMS. After the reaction was completed, the mixture was concentrated at low pressure. The residue was dissolved in EA (50 mL). The solution was washed with brine, and dried over anhydrous Na₂SO₄. The solution was evaporated at low pressure, and the residue was purified by silica gel column chromatography (1% MeOH in DCM) to give 206-3 (700 mg, 79%) as a solid.

To a solution of 206-3 (700 mg, 1.78 mmol) in dry THF (9 mL) was added DBU (817 mg, 5.34 mmol), and the mixture was heated to 60° C. The mixture was stirred overnight, and monitored by LCMS. The reaction was quenched with sat. NaHCO₃ and extracted with EA (3×50 mL). The organic phase was dried over anhydrous Na₂SO₄, and filtered. The filtrate was evaporated at low pressure, and the residue was purified by silica gel column chromatography (1% MeOH in DCM) to give 206-4 (250 mg, 53%) as a white solid.

To an ice-clod solution of 206-4 (250 mg, 0.94 mmol) in dry MeCN (5 mL) was added NEt₃-3HF (151 mg, 0.94 mmol) and NIS (255 mg, 1.13 mmol). The mixture was stirred at RT, for 3 h., and checked by LCMS. The reaction was quenched with sat Na₂S₂O₃ and sat. NaHCO₃ solution, and extracted with EA (3×50 mL). The organic layer was separated, dried over anhydrous Na₂SO₄, and evaporated at low pressure. The residue was purified by silica gel column chromatography (2% acetone in DCM) to give 206-5 (170 mg, 44%).

To a solution of 206-5 (270 mg, 0.65 mmol) in dry DCM (4 mL) was added DMAP (158.6 mg, 1.3 mmol), and BzCl (137 mg, 0.98 mmol). The mixture was stirred for 4-5 h. at RT, and checked by LCMS. The mixture was diluted with CH$_2$Cl$_2$, and washed with sat. NaHCO$_3$ solution and brine. The organic layer was evaporated at low pressure, and the residue was purified by silica gel column chromatography (20% EA in PE) to give 206-6 (290 mg, 86%) as a solid.

To a solution of 206-6 (900 mg, 1.74 mmol) in dry DMF (45 mL) was added NaOBz (2.5 g, 17.4 mmol) and 15-crown-5 (4.5 g, 20.9 mmol). The mixture was stirred for 48 h at 90-100° C. The mixture was diluted with EA (100 mL), and washed with brine. The organic layer was evaporated at low pressure, and the residue was purified by silica gel column chromatography (20% EA in PE) to give 206-7 (500 mg, 56%) as a solid.

To a solution of 206-7 (500 mg, 0.98 mmol) in anhydrous CH$_3$CN (5 mL) was added TPSCl (741 mg, 2.45 mmol), DMAP (299.6 mg, 2.45 mmol) and NEt$_3$ (248 mg, 2.45 mmol) at RT, and the mixture was stirred overnight. The mixture was then treated with NH$_3$ in THF (5 mL) and then stirred for another 30 mins. The mixture was diluted with EA (100 mL). The solution was washed with 0.5% AcOH solution. The organic solvent was dried over anhydrous MgSO$_4$, and concentrated at low pressure. The crude product was purified by silica gel column chromatography (2% Acetone in DCM) to give 206-8 (257 mg, 51.6%) as a white solid. ESI-MS: m/z 509 [M+H]$^+$.

206-8 (80 mg, 0.16 mmol) was dissolved in n-butylamine (3 mL). The mixture was kept overnight at RT and evaporated. The residue was crystallized from methanol to give 206 (30 mg). The mother liquor was purified by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer to yield additional 206 (13 mg). 206 (total yield 43 mg, 73%). MS: m/z 299.7 [M−1]$^−$.

was kept for 5 d at RT. The mixture was distributed between water and EA. The organic layer was separated, washed with brine, dried and evaporated. The phosphoroamidate was isolated by silica gel chromatography in a gradient of methanol in DCM from 3% to 10%. The corresponding fractions were concentrated and re-purified by RP HPLC on Synergy 4 micron Hydro-RP column (Phenominex). A linear gradient of methanol in DCM from 3% to 95% containing 0.1% formic acid was used for elution. 207 was obtained as a mixture Rp and Rs isomers (9 mg, 16%). MS: m/z 562.1[M−1].

Example 113

Compound 211

Example 112

Compound 207

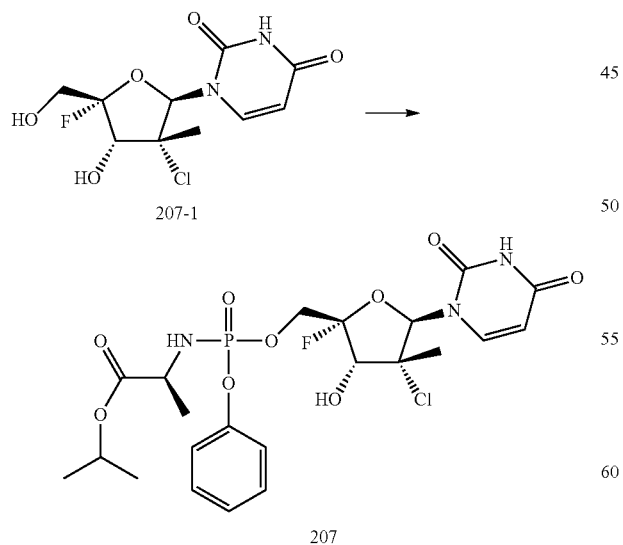

207-1

207

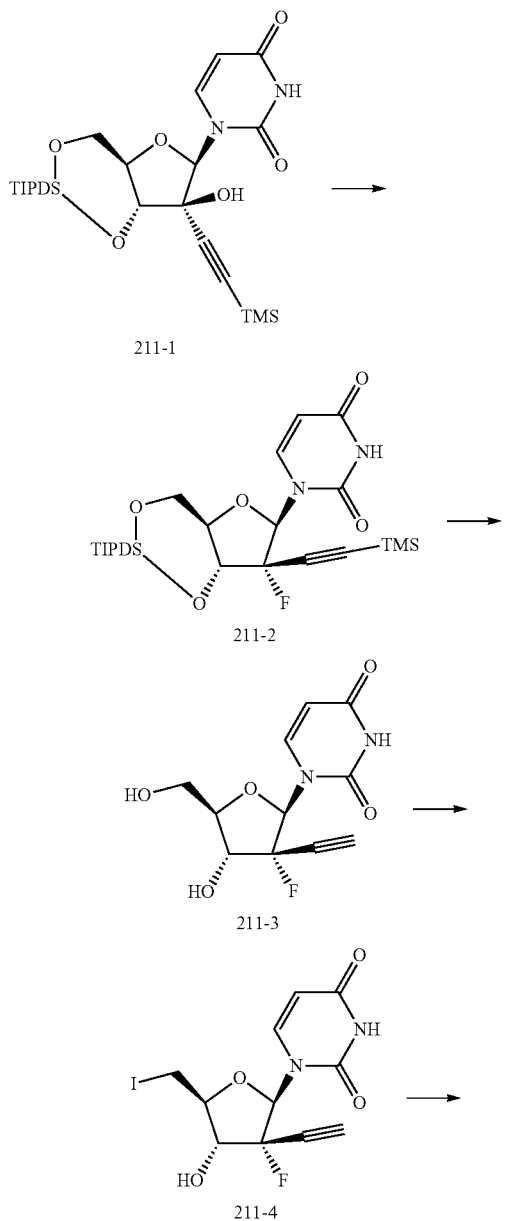

211-1

211-2

211-3

211-4

207-1 (30 mg, 0.1 mmol) was dissolved in a mixture of CH$_3$CN (2 mL) and N-methylimidazole (200 uL). Phosphorochloridate (100 mg, 0.3 mmol) was added, and the mixture

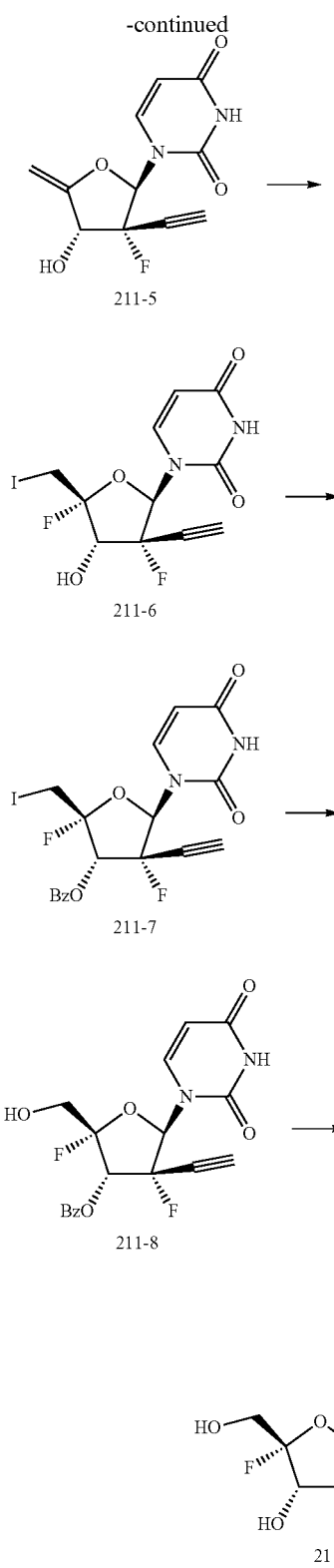

under low pressure. The residue was purified on a silica gel column (50% EA in PE) to give 211-2 (16.5 g, 71%) as a yellow foam.

A mixture of 211-2 (16.0 g, 27.4 mmol) and NH$_4$F (3.0 g, 82.2 mmol) in methanol (100 mL) was stirred at 70° C. for 12 h. The reaction was cooled, and the salt was removed by filtration. The filtrate was concentrated to dryness at low pressure. The residue was purified on a silica gel column (3% MeOH in DCM) to give 211-3 (5.1 g, 69.0%) as a white foam.

To a stirred suspension of 211-3 (4.1 g, 15.2 mmol), PPh$_3$ (8.0 g, 30.4 mmol), imidazole (2.1 g, 30.4 mmol) and pyridine (18.2 mL) in anhydrous THF (40 mL) was added dropwise a solution of I$_2$ (5.8 g, 22.8 mmol) in THF (20 mL) at 0° C. The mixture was stirred at RT for 12 h. The reaction was quenched with MeOH (100 mL), and the solvent was removed under reduced pressure. The residue was purified on a silica gel column (4% MeOH in DCM) to give pure 211-4 (4.4 g, 77%) as a white solid. ESI-MS: m/z 381.1 [M+1]$^+$.

To a stirred solution of 211-4 (2.5 g, 0.7 mmol) in anhydrous THF (3 mL) was added DBU (2.1 g, 14 mmol) at RT, and the mixture was stirred at RT for 1 h. The reaction was quenched with HOAc, and diluted with 2-Me-tetrahydrofuran. The solution was washed with brine, dried over with anhydrous Na$_2$SO$_4$ and concentrated to dryness at low pressure. The residue was purified on a silica gel column (MeOH 5% in DCM) to give 211-5 (1.1 g, 68.9%) as a white foam.

To a stirred solution of 211-5 (800 mg, 3.17 mmol) in anhydrous CH$_3$CN (10 mL) was added TEA.3HF (510 mg, 3.17 mmol) and NIS (785 mg, 3.49 mmol) at 0° C. The mixture was stirred for 30 mins, gradually warmed to RT, and stirred for 1 h. The mixture was quenched with sat. NaHCO$_3$ solution and Na$_2$S$_2$O$_3$ solution, and extracted with EA (2×20 mL). The organic layer was dried over with anhydrous Na$_2$SO$_4$, and concentrated to dryness at low pressure. The residue was purified on a silica gel column to give pure 211-6 (695 mg, 57.9%) as a yellow solid.

To a stirred solution of 211-6 (650 mg, 1.63 mmol) in pyridine (3 mL) was added BzCl (507 mg, 3.59 mmol) at 0° C., and stirred at RT for 12 h. The mixture was quenched with water, and concentrated to dryness under reducing pressure. The residue was purified on a silica gel column (EA 50% in PE) to yield 211-7 (550 mg, 67%) as a white foam.

Tetra-butylammonium hydroxide (9 mL as 54-56% aqueous solution, 72 mmol) was neutralized with TFA to pH~4 (1.5 mL), and the mixture was added to a solution of 211-7 (375 mg, 0.75 mmol) in DCM (9 mL). m-Chloroperbenzoic acid (924 mg, 60-70%, 3.75 mmol) was added in portions with vigorous stirring, and the mixture was stirred overnight. The mixture was washed with brine, dried over magnesium sulfate and concentrated under reduced pressure. The residue was purified by column chromatography (EA 50% in PE) to give 211-8 (230 mg, 78.8%) as a white foam. ESI-MS: m/z 393.1 [M+1]$^+$.

211-8 (120 mg, 0.24 mmol) was treated with 7N NH$_3$.MeOH (20 mL), and stirred for 5 h. The mixture was concentrated to dryness at low pressure. The residue was purified on a silica gel column (propan-2-ol 15% in DCM) to yield 211 (53 mg, 60.2%) as a white solid. ESI-MS: m/z 288.8 [M+1]$^+$.

To a solution of 211-1 (23.0 g, 39.5 mmol) in anhydrous toluene (200 mL) was added DAST (31.9 g, 198 mmol) dropwise at −78° C., and the solution was stirred at −78° C. for 3 h. The mixture was quenched with sat. NaHCO$_3$, extracted with EA (2×200 mL) and dried over with anhydrous Na$_2$SO$_4$. The solution was concentrated to dryness

Example 114

Compounds 212a and 212b

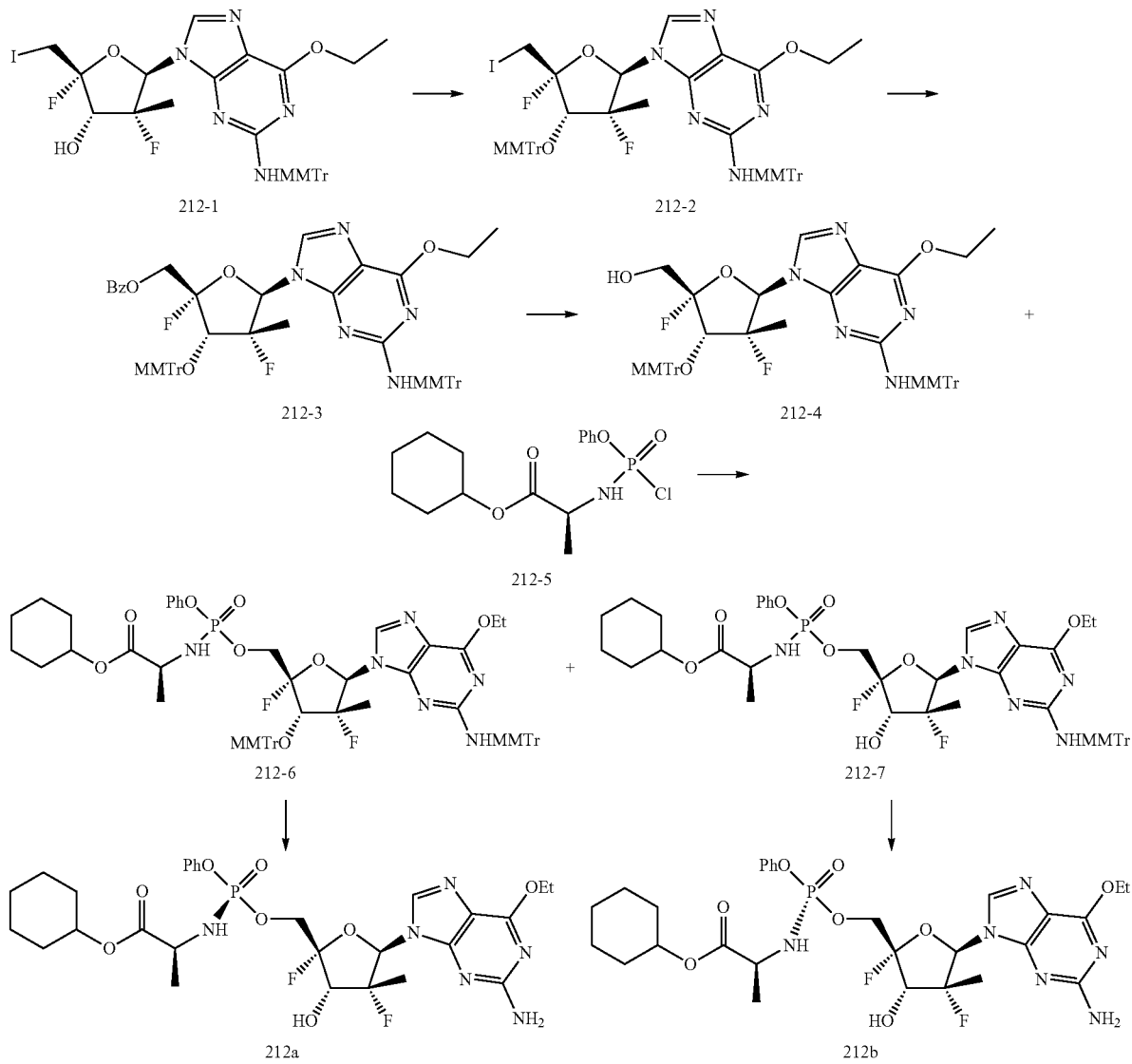

To a solution of 212-1 (0.47 g, 0.65 mol) in DCM (3 mL) was added AgNO$_3$ (0.22 g, 1.29 mmol), collidine (0.15 g, 1.29 mmol) and MMTrCl (0.3 g, 0.974 mmol) at 0° C. The mixture was stirred at RT overnight. The mixture was filtered, and the filter was washed with sat. aq. NaHCO$_3$ solution and brine. The organic layer was separated, dried over anhydrous Na$_2$SO$_4$ and concentrated at low pressure. The residue was purified by silica gel column to give 212-2 (0.55, 85%) as a white solid.

To a solution of 212-2 (0.5 g, 0.5 mmol) in dry DMF (10 mL) was added NaOBz (0.72 g, 5 mmol) and 15-crown-5 (0.9 mL). The mixture was stirred at 95° C. for 72 h. The mixture was diluted with EA, and washed with water and brine. The organic phase was dried over MgSO$_4$ and concentrated at low pressure. The residue was purified by silica gel column (10% EA in PE) to give 212-3 (0.3 g, 60%) as a white solid.

212-3 (0.3 g, 0.3 mmol) in NH$_3$/MeOH (30 mL) was stirred at RT for 18 h. The mixture was concentrated at low pressure, and the residue was purified by silica gel column (20% EA in PE) to give 212-4 (145 mg, 56%) as a white solid. ESI-LCMS: m/z 890.5 [M+H]$^+$.

To a stirred solution of 212-4 (161 mg, 0.16 mmol) in anhydrous CH$_3$CN (2.0 mL) was added N-methylimidazole (118 μL, 2.87 mmol) at 0 to 5° C. (ice/water bath) followed by solution of 212-5 (186 mg, 0.54 mmol, dissolved in 2 mL of CH$_3$CN). The solution was stirred at 0 to 5° C. for 4 h. The mixture was diluted with EA, and water was added (15 mL). The solution was washed H$_2$O, 50% aqueous citric acid solution and brine. The organic layer was separated, dried over anhydrous MgSO$_4$ and filtered. The filtrate was concentrated in vacuum to give a residue, which was purified on silica gel with 0 to 40% EA/hexanes to give as 212-6 (82.6 mg) as the faster eluting isomer and 212-7 (106 mg) as the slower eluting isomer.

212-6 (82.6 mg, 0.07 mmol) was dissolved in anhydrous CH$_3$CN (0.5 mL), and 4N HCl in dioxane (35 μL) was added at 0 to 5° C. The mixture was stirred at RT for 1 h, and anhydrous EtOH (100 μL) was added. The solvents were evaporated at RT and co-evaporated with toluene 3 times.

The residue was dissolved in 50% CH$_3$CN/H$_2$O, and purified on a reverse-phase HPLC (C18) using acetonitrile and water, followed by lyophilization to give 212a (19.4 mg). ESI-LCMS: m/z=655.2 [M+H]$^+$, 653.15 [M−H]$^-$.

212-7 (100 mg, 0.083 mmol) was dissolved in anhydrous CH$_3$CN (0.5 mL), and 4N HCl in dioxane (50 μL) was added at 0 to 5° C. Following the procedure for obtaining 212a, 212b (31.8 mg) was obtained. ESI-LCMS: m/z=655.2 [M+H]$^+$, 653.1 [M−H]$^-$.

Example 115

Compound 213

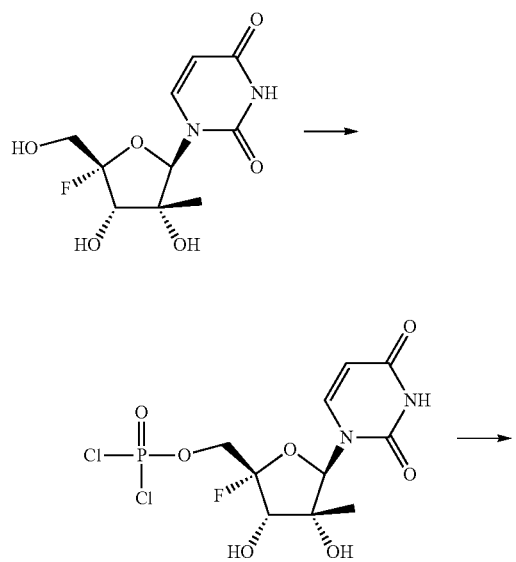

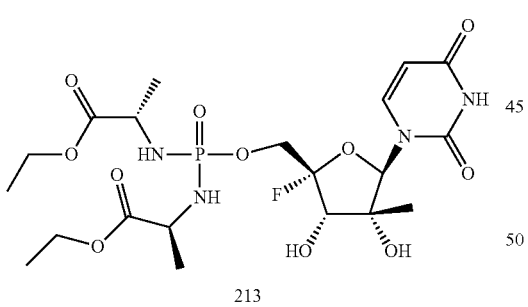

213

To a solution of the nucleoside (300 mg, 1.09 mmol) and proton-sponge (467 mg, 2.18 mmol) in anhydrous CH$_3$CN (5 mL) at 0° C. under N$_2$ was added dropwise a solution of phosphorus oxychloride (330 mg, 2.18 mmol) in anhydrous CH$_3$CN (1 mL). The mixture was stirred at 0° C. for 30 mins, and the hydrogen chloride salt of (S)-ethyl 2-amino-propanoate (998 mg, 6.52 mmol) and triethylamine (1.5 mL, 10.87 mmol) at 0° C. were added. The mixture was stirred overnight at 30° C. The reaction was quenched with water, and extracted with EA (3×20 mL). The organic layer was concentrated at low pressure, and the residue was purified by reverse phase HPLC to give 213 (20 mg, 3%) as a white solid. ESI-LCMS: m/z 535 [M-F]$^+$.

Example 116

Compound 214

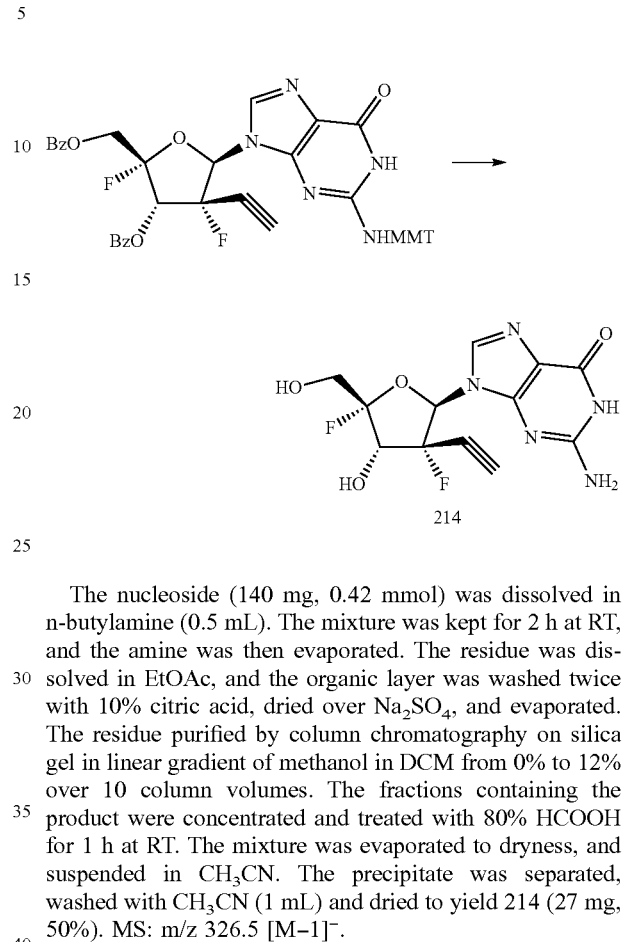

214

The nucleoside (140 mg, 0.42 mmol) was dissolved in n-butylamine (0.5 mL). The mixture was kept for 2 h at RT, and the amine was then evaporated. The residue was dissolved in EtOAc, and the organic layer was washed twice with 10% citric acid, dried over Na$_2$SO$_4$, and evaporated. The residue purified by column chromatography on silica gel in linear gradient of methanol in DCM from 0% to 12% over 10 column volumes. The fractions containing the product were concentrated and treated with 80% HCOOH for 1 h at RT. The mixture was evaporated to dryness, and suspended in CH$_3$CN. The precipitate was separated, washed with CH$_3$CN (1 mL) and dried to yield 214 (27 mg, 50%). MS: m/z 326.5 [M−1]$^-$.

Example 117

Compound 216

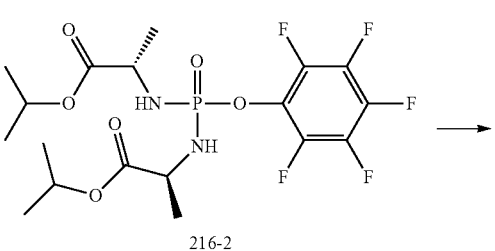

216-1

216-2

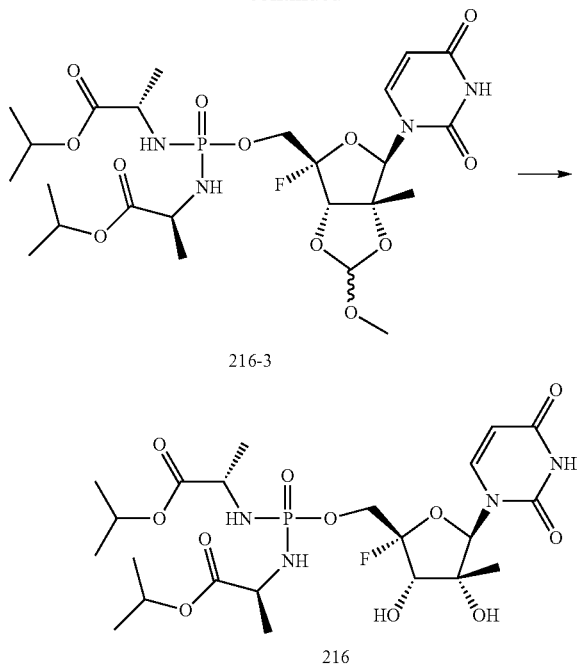

216-3

216

To a solution of 216-1 (3.0 g, 18.0 mmol) and POCl₃ (1.35 g, 9.0 mmol) in DCM (80 mL) was added TEA (3.6 g, 36.0 mmol) in DCM (20 mL) dropwise at 0° C. The mixture was stirred at 0° C. for 2 h. A solution of pentafluorophenol (1.65 g, 9.0 mmol) and TEA (0.9 g, 9.0 mmol) in DCM (20 mL) was added dropwise at 0° C., and the mixture was stirred at 0° C. for 15 h. After the reaction was completed, the mixture was concentrated under reduced pressure. The residue was washed by TBME and filtered. The filtrate was concentrated under reduced pressure, and the residue was purified by silica gel chromatography (20% EA in PE) to give 216-2 (2.7 g, 62.7%) as a white solid. ESI-MS: m/z 491.1 [M+1]⁺.

To a stirred solution of 1-((3aR,4R,6S,6aS)-6-fluoro-6-(hydroxymethyl)-2-methoxy-3a-methyltetrahydrofuro [3,4-d][1,3]dioxol-4-yl)pyrimidine-2,4(1H,3H)-dione (150 mg, 0.47 mmol) in anhydrous THF (2 mL) was added a solution of t-BuMgCl (0.46 mL, 1M in THF) dropwise at 0° C. The mixture was stirred at RT for 40 mins, and re-cooled to 0° C. A solution of 216-2 (462 mg, 0.94 mmol) was added, and the mixture was stirred at RT for 4 h. The mixture was quenched with H₂O, and extracted with EA. The organic layer was dried over Na₂SO₄ and concentrated under reducing pressure. The residue was purified on a silica gel column (50% EA in PE) to give 216-3 as a white foam (230 mg, 78%).

216-3 (230 mg, 0.37 mmol) was dissolved in 80% HCOOH aqueous solution (20 mL), and the mixture was stirred at RT for 24 h. The solvent was removed at low pressure. The residue was purified on a silica gel column to give the crude product, which was purified by RP HPLC (HCOOH system) to give 216 as a mixture of two P-isomers (75 mg, 33%). ESI-TOF-MS: m/z 583.0 [M+H]⁺.

Example 118

Compound 218

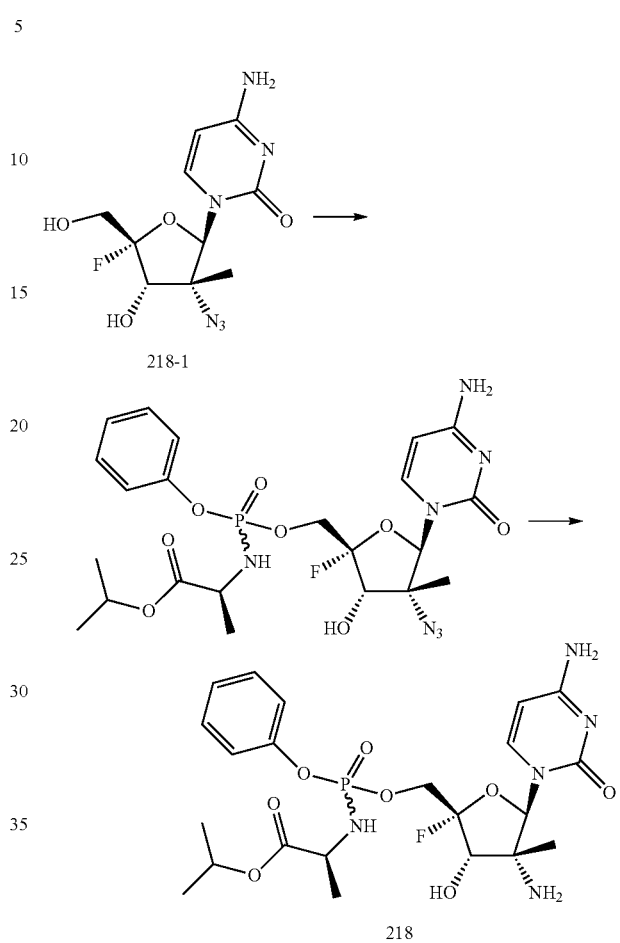

218-1 (30 mg, 0.1 mmol) was dissolved in a mixture of CH₃CN (2 mL) and N-methylimidazole (200 uL). Phosphorochloridate (100 mg, 0.3 mmol) was added, and the mixture was kept overnight at 40° C. The temperature was increased to 65° C. and heated for 1 h. The mixture was distributed between water and EA. The organic layer was separated, washed with brine, dried and evaporated. The azido-phosphoramidate was purified by RP HPLC on Synergy 4 micron Hydro-RP column (Phenominex). A linear gradient of methanol from 30% to 100% in 50 mM triethylammonium acetate buffer (pH 7.5) was used for elution. The azido-phosphoramidate (8 mg) was dissolved in pyridine/Et₃N (3 mL, 8:1 v/v) and cooled to 0° C. H₂S gas was bubbled through the solution for 10 mins, and the reaction was kept for 1 h at RT. The solvents were evaporated, and the residue isolated by RP HPLC. The corresponding fractions were combined, concentrated and lyophilized 3 times to remove excess of buffer, to provide 218 (1.2 mg) as mixture Rp and Rs isomers. MS: m/z 544.1 [M+1]⁺.

Example 119
Compound 219
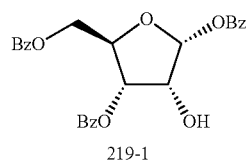
219-1
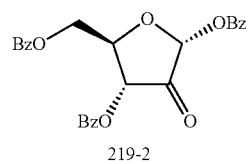
219-2
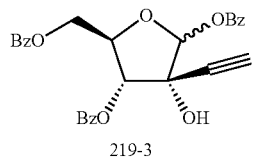
219-3
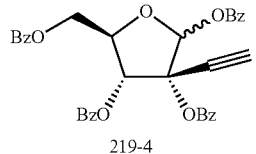
219-4
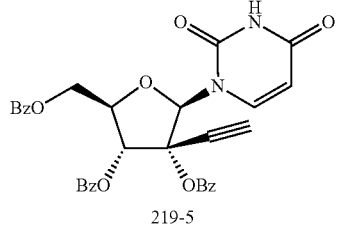
219-5
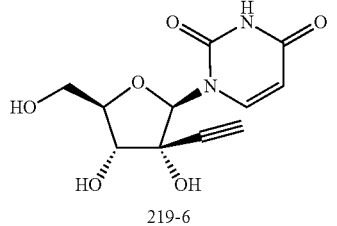
219-6
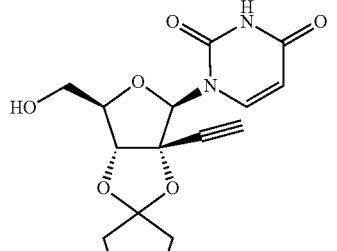
219-7
-continued
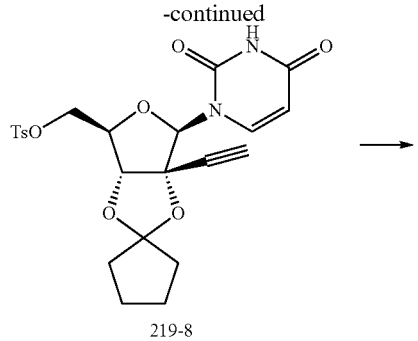
219-8
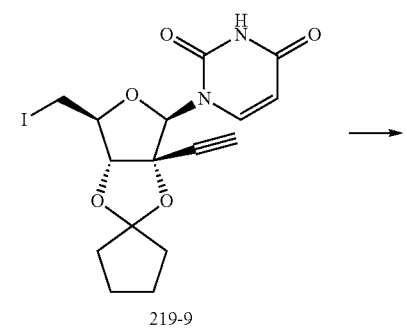
219-9
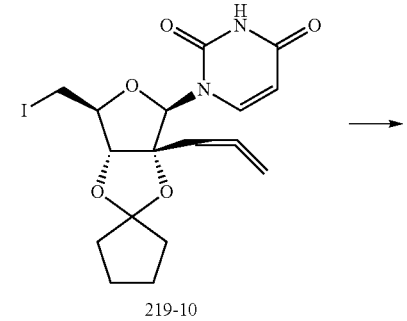
219-10
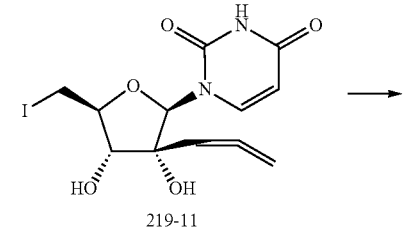
219-11
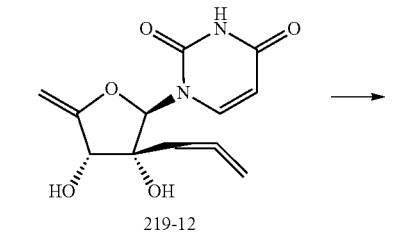
219-12
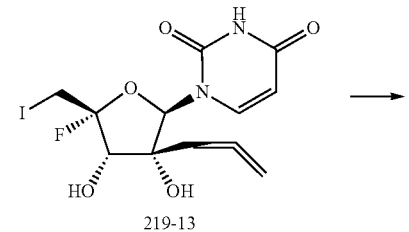
219-13

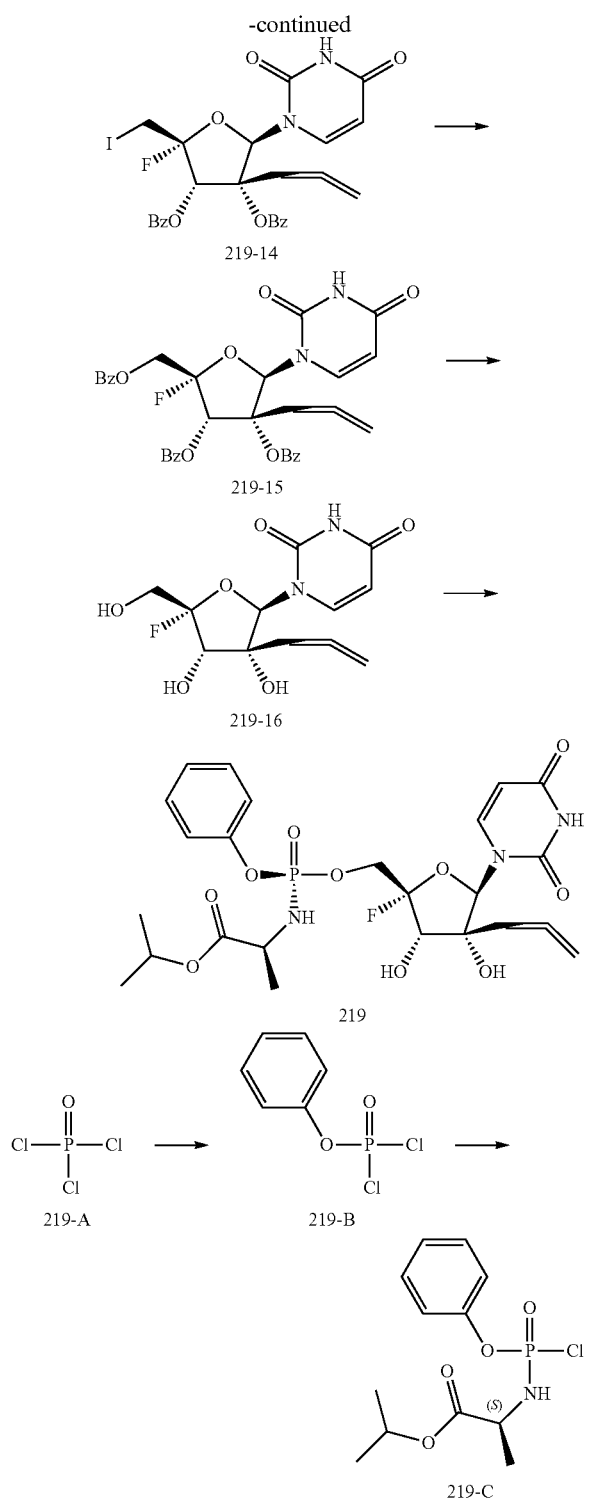

To a solution of IBX (133.33 g, 476 mmol) in dry CH₃CN (2 L) was added 219-1 (100.0 g, 216 mol) at RT. The mixture was refluxed and stirred for 12 h. The mixture was filtered, and the filtrate was concentrated at low pressure to give 219-2 as a yellow oil (90.0 g, 90.4%).

219-2 (50.0 g, 108.70 mmol) was coevaporated with anhydrous toluene twice to remove H₂O. Ethynyl magnesium bromide, (800 mL, 400.0 mmol) was added dropwise into a solution of 73-2 in THF (500 mL) over 20 mins at −78° C. The mixture was stirred for about 10 mins at −78° C. When the starting material was consumed, the ice-acetone cooling bath was removed. The mixture was quenched with a sat. NH₄Cl solution with stirring, and then warmed to RT. The mixture was extracted with EA, filtered through Celite and washed with brine. The combined organic phase was dried over anhydrous Na₂SO₄, filtered and concentrated at low pressure to give crude 219-3 as a deep yellow oil (48.0 g, yield: 90.8%).

219-3 (200.0 g, 411.52 mmol) was dissolved in anhydrous CH₂Cl₂ (2000 mL) and then DMAP (100.41 g, 823.05 mmol) and Et₃N (124.94 g, 1.23 mol) were added at RT. The mixture was treated with benzoyl chloride (173.46 g, 1.23 mol) at 0° C. After stirring for 12 h at RT, the reaction was quenched with H₂O. The combined aq. phase was extracted with DCM. The combined organic phase was dried over anhydrous Na₂SO₄, filtered and evaporated to dryness under reduced pressure to give a black oil. The oil was purified by column chromatography using 7%-20% EA in PE as the eluent to give a yellow oil. The residue triturated with CH₃OH and filtered. The filter cake was concentrated in vacuo to give 219-4 as a white solid (30.0 g, 36.4%).

Uracil (34.17 g, 305.08 mmol) were coevaporated with anhydrous toluene twice to remove H₂O. To a stirred suspension of uracil in anhydrous MeCN (150 mL) was added N,O-BSA (123.86 g, 610.17 mmol) at RT. The mixture was refluxed for 1.5 h and then cooled to RT. 219-4 (90 g, 152.54 mmol, which were coevaporated with anhydrous toluene twice to remove H₂O) was added. TMSOTf (237.05 g, 1.07 mol) was then added at RT. The mixture was heated to 70° C., and then stirred overnight and then monitored by LCMS. The mixture was cooled to RT, and quenched with a sat. NaHCO₃ solution. The solution was extracted with EA. The organic layer was dried over Na₂SO₄, and then concentrated at low pressure. The residue was purified using a silica gel column eluted with 10%-50% EA in PE to give 219-5 as a white solid (45 g, 50.9%).

219-5 (50 g, 86.21 mmol) was treated with NH₃ in MeOH (1 L) at RT, and then stirred for 48 h. The mixture was concentrated at low pressure, and the residue was purified by column chromatography (10% MeOH in DCM) to give 219-6 (12.6 g, 54.55%) as a white solid.

To a solution of cyclopentanone (100 g, 1.189 mmol) and trimethyl orthoformate (150 mL) in MeOH (600 mL) was added TsOH.H₂O (1.13 g, 5.9 mmol), and the mixture was stirred at RT for 30 mins. The reaction was quenched with NaOMe (0.32 g, 5.9 mmol) and H₂O, and the solution was extracted by n-hexane. The organic layer was dried over anhydrous Na₂SO₄, and then concentrated at low pressure. The cyclopentyl dimethoxy acetal and 219-6 (20 g, 74.63 mmol) was dissolved in DCE (200 mL), and then treated with TsOH.H₂O (0.71 g, 3.73 mmol). The mixture was stirred at 50° C. for 12 h, and then concentrated at low pressure. The residue was purified by silica gel column chromatography (1-10% MeOH in DCM) to give 219-7 (15.4 g, 61.8%) as a white solid.

219-7 (20.0 g, 0.06 mol) was coevaporated with anhydrous pyridine three times to remove H₂O. To an ice-cold solution of 219-7 in anhydrous pyridine (100 mL) was added TsCl (22.8 g, 0.12 mol) at 0° C., and the mixture was stirred overnight and monitored by LCMS and TLC. The reaction was quenched with H₂O and extracted with EA. The organic phase was dried over anhydrous NaSO₄ and evaporated at low pressure. The residue was purified by silica gel column chromatography (DCM:MeOH=100:1 to 15:1) to give 219-8 (20.0 g, 69.0%) as a white solid.

To a solution of 219-8 (20.0 g, 0.04 mol) in acetone (200 mL) was added NaI (31.0 g, 0.2 mol) and heated to reflux overnight and monitored by LCMS. The mixture was quenched with a sat. $Na_2S_2O_3$ solution, and extracted with EA. The organic phase was dried over anhydrous $Na_2SO_4$ and evaporated at low pressure. The residue was purified by silica gel column chromatography (DCM:MeOH=100:1 to 15:1) to give 219-9 (15.0 g, 83.3%) as a white solid.

To 219-9 (30.0 g, 0.068 mol) in dioxane (60 mL) in sealed tube was added CuBr (4.9 g, 0.034 mol), i-$Pr_2NH$ (13.6 g, 0.135 mol) and $(CH_2O)_n$(5.1 g, 0.17 mol) under $N_2$. The mixture was heated at reflux for 16 h. The mixture was diluted with EtOAc, and washed with a sat. $NH_4Cl$ solution and brine. The solution was dried over anhydrous $MgSO_4$, and concentrated under reduced pressure. The residue was purified by column chromatography (DCM:MeOH=100:1 to 15:1) to give 219-10 (10.0 g, 32.3%) as a white solid.

219-10 (10 g, 21.83 mmol) was treated with HCOOH (80%) in $H_2O$ at RT. The solution was stirred at 60° C. for 2 h, and then concentrated at a low pressure. The residue was purified by column chromatography (1%-10% MeOH in DCM) to give 219-11 (5.1 g, 58.55%) as a white solid.

219-11 (5 g, 12.79 mmol) was dissolved in anhydrous MeOH (100 mL) and treated with NaOMe (4.83 g, 89.5 mmol) at RT. The solution was stirred at 60° C. for 36 h. The mixture was quenched with $CO_2$ and then concentrated at low pressure. The residue was purified by column chromatography (0-10% MeOH in DCM) to give 219-12 (2.3 g, 68.05%) as a yellow solid. $^1$H-NMR ($CDCl_3$, 400 MHz) δ=7.29 (d, J=8 Hz 1H), 6.10 (s, 1H), 5.71 (d, J=8.0 Hz 1H), 5.18 (t, J=6.4 Hz, 1H), 4.79-4.84 (m, 1H), 4.61 (d, J=8.0 Hz, 2H), 4.39 (s, 1H), 3.45 (s, 1H).

To an ice-cold solution of 219-12 (1.5 g, 5.68 mmol) in anhydrous MeCN (15 mL) was added NIS (1.66 g, 7.39 mmol) and TEA.3HF (0.73 g, 4.55 mmol) under $N_2$. The mixture was stirred at RT for 1 h. The reaction was quenched with sat. $NaHCO_3$ and sat. $Na_2SO_3$ solution, and extracted with EA (3×100 mL). The organic phase was dried over anhydrous $Na_2SO_4$, and evaporated to dryness at low pressure. The residue was purified on a silica gel column (0-5% MeOH in DCM) to give 219-13 (1.08 g, 46.2%) as a yellow solid.

To a stirred solution of 219-13 (1 g, 2.44 mmol) in anhydrous DCM (10 mL) was added DMAP (0.60 g, 4.88 mmol) and $Et_3N$ (0.74 g, 7.32 mmol) at RT. The mixture was treated with benzoyl chloride (0.79 g, 5.61 mmol) at 0° C. and then stirred at RT for 3 h. The reaction was quenched with water, and extracted with EA (3×60 mL). The organic phase was concentrated at low pressure, and the residue was purified by column chromatography (0-10% MeOH in DCM) to give 219-14 (0.9 g, 59.6%) as a white solid.

$Bu_4NOH$ (55% in $H_2O$, 13.74 mL) was treated with TFA (to adjust pH=3-4). The mixture was cooled to RT. To a solution of 219-14 (0.9 g, 1.46 mmol) in DCM (9 mL) was added m-CPBA (80%, 1.57 g, 7.28 mmol) at RT. The mixture was stirred at 25° C. for 48 h. The mixture was washed with sat. aq. $NaHCO_3$. The organic layer was passed through an anhydrous $Al_2O_3$ column, and the solution was concentrated at low pressure. The residue was purified by a silica gel column (30% EA in PE) to give 219-15 (0.26 g, 35.1%) as a yellow solid.

219-15 (0.25 g, 0.49 mmol) was dissolved in $NH_3$/MeOH (5 mL, 7 M), and the mixture was stirred at RT for 24 h under $N_2$. The mixture was concentrated at low pressure, and the residue was purified by a silica gel column (5% MeOH in DCM) to give 219-16 (100 g, 67.75%) as a white solid. $^1$H-NMR ($CD_3OD$, 400 MHz) δ=7.83 (d, J=8 Hz 1H), 6.29 (s, 1H), 5.67 (d, J=6.0 Hz 1H), 5.12 (t, J=6.8 Hz, 1H), 4.99-5.01 (m, 1H), 4.38 (d, J=19.6 Hz 1H), 3.74-3.81 (m, 2H), 3.35 (s, 1H).

219-16 (100 mg, 0.33 mmol) was co-evaporated with toluene three times to remove $H_2O$. To a stirred solution of 219-16 (100 mg, 0.33 mmol) in a mixture of MeCN (1.0 mL) and NMI (271 mg, 3.3 mmol) was added a solution of 219-C (216.5 mg, 0.66 mmol) in MeCN (0.5 mL) at 0° C. The mixture was stirred at RT overnight and then reaction was quenched with water. The mixture was diluted with EA (20 mL), and the organic layer was washed with water and brine, and dried over anhydrous $Na_2SO_4$. The organic phase was concentrated at low pressure, and the residue was purified on a silica gel column (5% i-PrOH in DCM) to give the crude product. The crude product was purified by prep-HPLC (0.1% HCOOH in water and MeCN) to give 219 (35.6 mg, 19.0%) as a white solid. ESI-LCMS: m/z 592 [M+Na]$^+$.

To a stirred solution of 219-A (2.0 g, 13.16 mmol) and phenol (1.22 g, 13.16 mmol) in anhydrous DCM (100 mL) was added a solution of TEA (1.33 g, 13.16 mmol) in DCM (20 mL) dropwise at −78° C. The mixture was warmed gradually to RT, and then stirred for 2 h. The solution was re-cooled to −78° C., and (S)-isopropyl 2-aminopropanoate hydrochloride (2.20 g, 13.16 mmol) in DCM (20 mL) was added, followed by the dropwise addition of TEA (2.66 g, 26.29 mmol) in DCM (20 mL). The mixture was warmed gradually to RT, and then stirred for 2 h. The organic solvent was removed at low pressure, and the residue was dissolved in methyl-butyl ether. The precipitate was filtered, and the filtrate was concentrated at low pressure. The residue was purified on a silica gel column (anhydrous DCM) to give 219-C (0.9 g, 22.3%) as a colorless oil.

Example 120

Compound 220

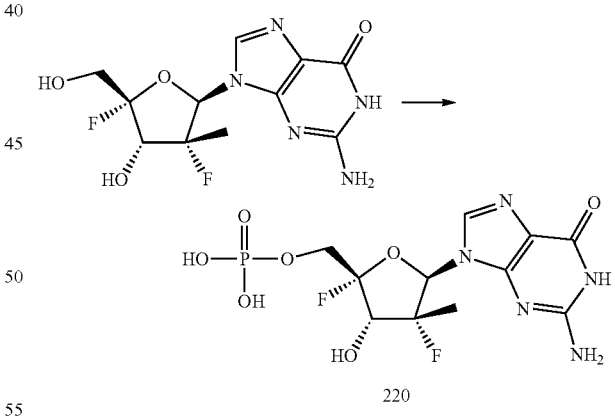

220

Dry nucleoside (0.05 mmol) was dissolved in a mixture of $PO(OMe)_3$ (0.7 mL) and pyridine (0.3 mL). The mixture was evaporated in vacuum for 15 mins. at 42° C., then cooled to RT. N-Methylimidazole (0.009 mL, 0.11 mmol) was added followed by $POCl_3$ (0.009 mL, 0.11 mmol). The mixture was kept at RT for 20-40 mins and monitored for the formation of 220 by LCMS. The reaction was quenched with water and isolated by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were

Example 121

Compound 223

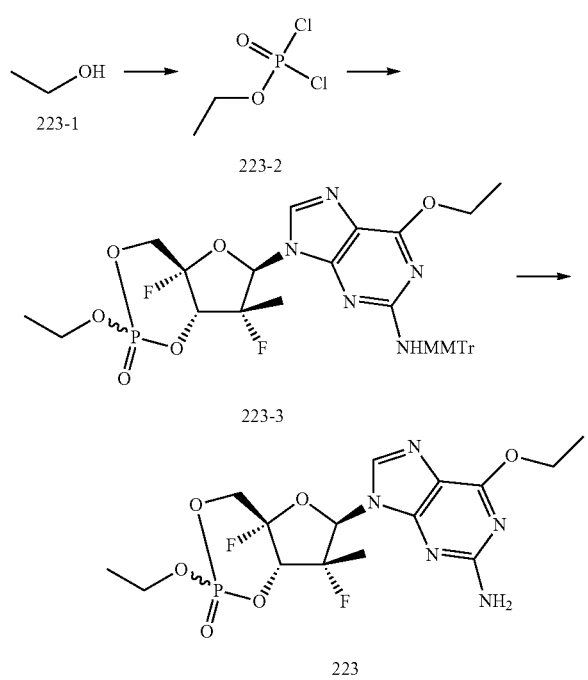

A solution of 223-1 (16.70 g, 0.363 mol) and TEA (36.66 g, 0.363 mol) in CH$_2$Cl$_2$ (150 mL) was added dropwise to a stirred solution of POCl$_3$ (55.65 g, 0.363 mol) in DCM (100 mL) over 25 mins at −78° C. After the mixture was stirred for 2 h. at RT, the triethylamine hydrochloride salt was filtered, and washed with CH$_2$Cl$_2$ (100 mL). The filtrate was concentrated at low pressure, and the residue was distilled under high vacuum (~10 mm Hg) with a cow-head fraction collector. 223-2 was collected between 45° C. (distillation head temperature) as a colorless liquid (30.5 g, 50% yield). $^1$H-NMR (400 MHz, CDCl$_3$) δ=4.44 (dq, J=10.85, 7.17 Hz, 2H), 1.44-1.57 (m, 3H); $^{31}$P-NMR (162 MHz, CDCl$_3$) δ=6.75 (br. s., 1P).

To a stirred suspension of 227-A (93 mg, 0.15 mmol) in CH$_2$Cl$_2$ (1 mL) was added TEA (61 mg, 0.15 mmol) at RT. The mixture was cooled to −20° C., and then was treated with a 223-2 (35 mg, 0.21 mmol) solution dropwise over a period of 10 mins. The mixture was stirred at this temperature for 15 mins., and then was treated with NMI (27 mg, 0.33 mmol). The mixture was stirred at −20° C., and then slowly warmed to RT. The mixture was stirred overnight. The mixture was suspended in EA (15 mL), washed with brine (10 mL) and dried over anhydrous sodium sulfate. The solution was concentrated at low pressure, and the residue was purified by chromatography (DCM:MeOH=100:1) to give 223-3 (60 mg, yield: 56%) as a solid.

A solution of 223-3 (60 mg, 0.085 mmol) in 80% AcOH aqueous (2 mL) was stirred at RT for 2 h. The mixture was concentrated under reduced pressure, and the residue was combined, concentrated and lyophilized 3 times to remove excess of buffer. MS: m/z 396.5 [M−1]$^−$.

Example 122

Compound 224

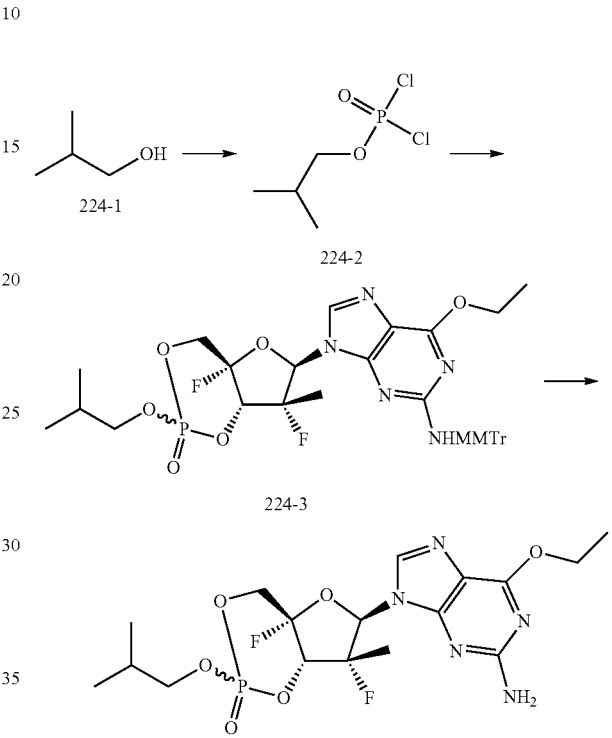

224-2 was prepared using a similar procedure as for the preparation of 223-2 using a solution of iso-butanol (23.9 g, 322.98 mmol) and POCl$_3$ (49.5 g, 322.98 mmol). 224-2 (26 g, 42% yield) was obtained as a colorless liquid. $^1$H-NMR (400 MHz, CDCl$_3$) δ=4.10 (dd, J=9.04, 6.39 Hz, 2H), 2.09 (dq, J=13.24, 6.67, 6.67, 6.67, 6.67 Hz, 1H), 1.01 (d, J=6.62 Hz, 6H); $^{31}$P-NMR (162 MHz, CDCl$_3$) δ=7.06 (br. s., 1P).

To a stirred suspension of 227-A (310 mg, 0.5 mmol) in CH$_2$Cl$_2$ (3 mL) was added TEA (202 mg, 2 mmol) at RT. The mixture was cooled to −20° C., and then was treated with 224-2 (134 mg, 0.7 mmol). The mixture was stirred at this temperature for 15 mins and then was treated with NMI (90 mg, 1.1 mmol). The mixture was stirred at −20° C. for 1 h., and then slowly warmed to RT overnight. The mixture was suspended in EA (15 mL), washed with brine (10 mL), and dried over anhydrous sodium sulfate. The organic phase was concentrated at low pressure, and the residue was purified by silica column gel (DCM:MeOH=100:1) to give 224-3 (310 mg, yield: 84%) as a solid.

A solution of 224-3 (310 mg, 0.43 mmol) in 80% AcOH aqueous (4 mL) was stirred at RT for 2 h. The mixture was concentrated at low pressure, and the residue was purified by a silica gel column eluting DCM/MeOH=50/1 and prep-HPLC to give 224 (79 mg, 50%) as a white solid. ESI-MS: m/z 464.0 [M+H]$^+$.

Example 123

Compound 225

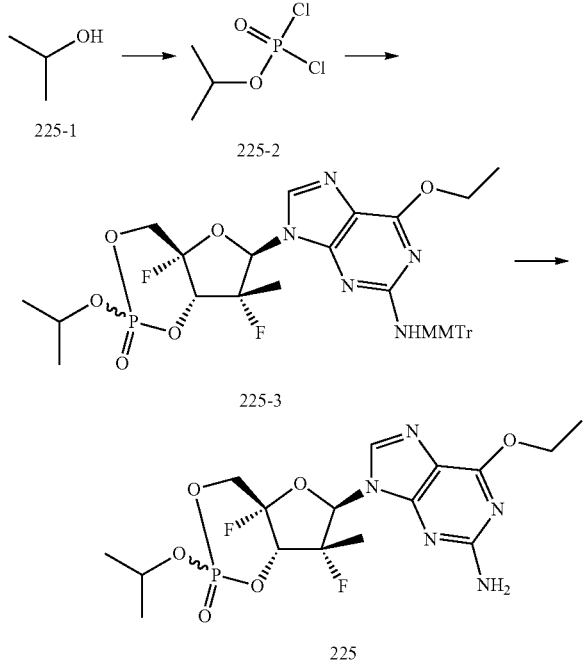

225-2 was prepared using a similar procedure as for the preparation of 223-2 using a solution of isopropyl alcohol (21 g, 350 mmol) and POCl₃ (53.6 g, 350 mmol). 225-2 (40.5 g, 65% yield) was obtained as a colorless liquid. ¹H-NMR (400 MHz, CDCl₃) δ=4.94-5.10 (m, 1H), 1.48 (d, J=6.17 Hz, 6H); ³¹P-NMR (162 MHz, CDCl₃) δ=5.58 (br. s., 1P).

225-3 was prepared using a similar procedure as for the preparation of 224-3 using 225-2 (124 mg, 0.7 mmol) and 227-A (310 mg, 0.5 mmol). 225-3 (300 mg, 83%) was obtained as a solid.

225 was prepared using a similar procedure as for the preparation of 224 using 225-3 (300 mg, 0.41 mmol) in 80% AcOH aqueous (4 mL). 225 (80 mg, 43%) was obtained as a white solid. ESI-MS: m/z 450.0 [M+H]⁺.

Example 124

Compound 227

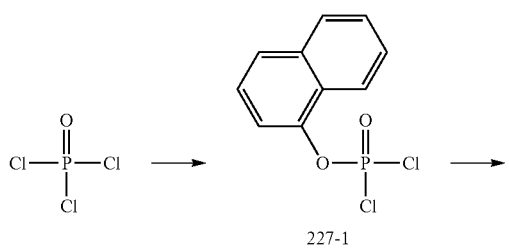

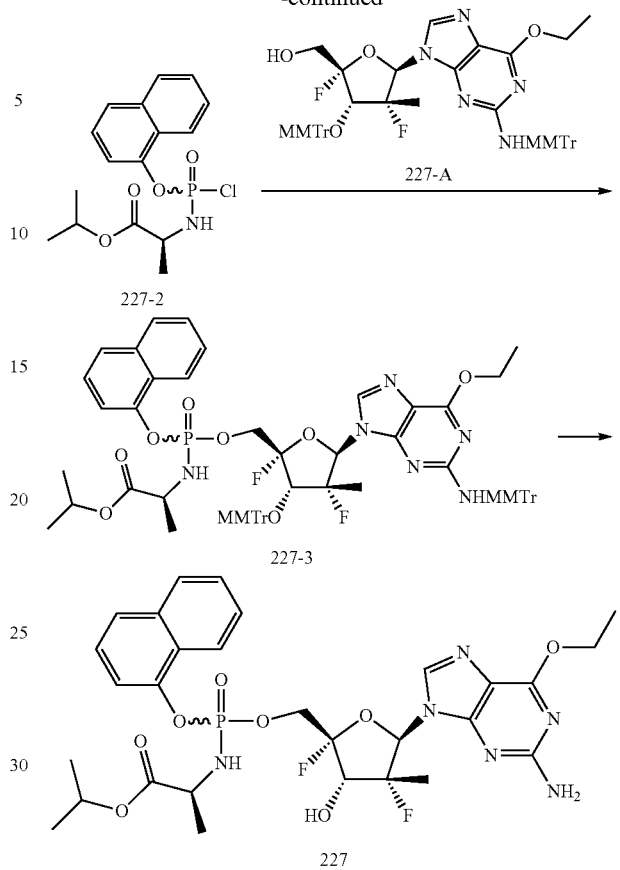

To a stirred solution of POCl₃ (2.0 g, 13 mmol) in anhydrous DCM (10 mL) was added 1-naphthol (1.88 g, 13 mmol) at −70° C., and TEA (1.31 g, 13 mmol) in DCM (3 mL) dropwise at −70° C. The mixture was gradually warmed to RT and stirred for 1 h. Crude 227-1 was obtained.

To a stirred solution of (S)-isopropyl 2-aminopropanoate hydrochloride (2.17 g, 13 mmol) in DCM (10 mL) was added crude 227-1 at −70° C. TEA (2.63 g, 26 mmol) was added to the stirred solution dropwise at −70° C. The mixture was gradually warmed to RT and stirred for 2 h. The reaction was monitored by LCMS and quenched with n-propylamine. The mixture was concentrated at low pressure, and the residue was purified by a silica gel column (PE: MTBE=5:1~1:1) to give pure 227-2 (1.6 g, 35%).

To a solution of 227-A (300 mg, 0.337 mmol) and NMI (276 mg, 3.37 mmol) in anhydrous CH₃CN (4 mL) was added 227-2 (240 mg, 0.674 mol, in DCM (5 mL)) at 0° C. The mixture was stirred at RT for 10 h. The reaction was monitored by LCMS. The reaction was quenched with water, and extracted with CH₂Cl₂ (3×20 mL). The organic phase was dried over anhydrous MgSO₄, and concentrated at low pressure. The residue was purified by sil-gel (PE: EA=5:1~2:1) to give 227-3 (380 mg, 93%).

227-3 (380 mg, 0.314 mmol) was dissolved in CH₃COOH (80%, 8 mL), and stirred at 40-50° C. for 2.5 h. The reaction was monitored by LCMS. The mixture was concentrated at low pressure, and the residue was purified by chromatography (PE:EA=1:1~EA) to give crude 227. The crude product was purified by prep-HPLC (neutral system, NH₄HCO₃) to give pure 227 (70 mg, 80%) as a white solid. ESI-MS: m/z 665.1 [M+H]⁺.

Example 125

Compound 228

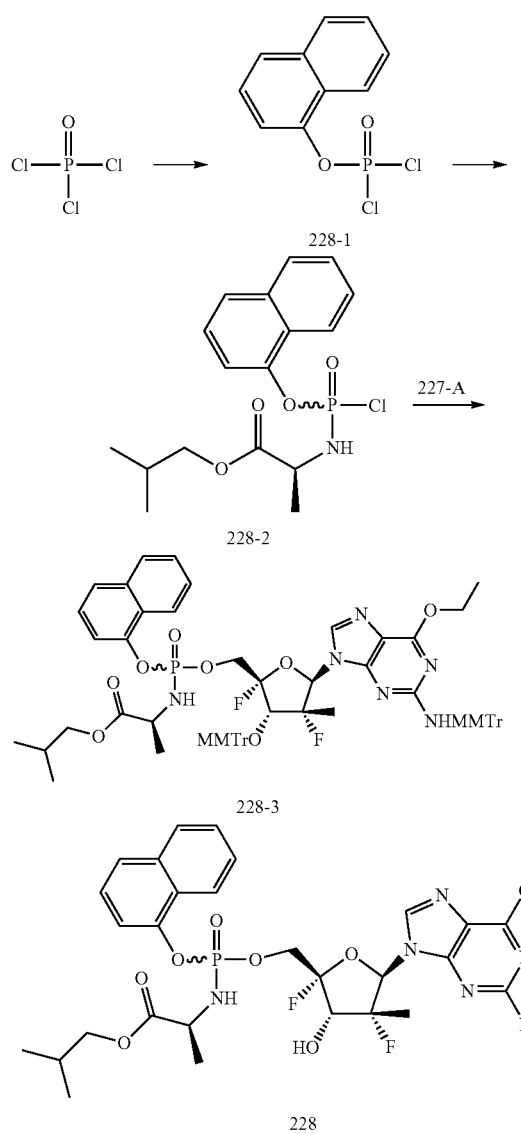

To a stirred solution of POCl₃ (2.0 g, 13 mmol) in anhydrous DCM (10 mL) was added 1-naphthol (1.88 g, 13 mmol) at −70° C. and TEA (1.31 g, 13 mmol) in DCM (3 mL) dropwise at −70° C. The mixture was gradually warmed to RT, and stirred for 1 h. A crude solution of 228-1 was obtained.

To a stirred solution of (S)-isobutyl 2-aminopropanoate hydrochloride (2.35 g, 13 mmol) in DCM (20 mL) was added TEA (2.63 g, 26 mmol) and a crude solution of 228-1 at −70° C. The mixture was gradually warmed to RT, and stirred for 2 h. The reaction was monitored by LCMS and quenched with n-propylamine. The solvent was evaporated at low pressure, and the residue was purified by chromatography (PE:MTBE=5:1~1:1) to give pure 228-2 (1.8 g, 37%).

To a solution of 227-A (300 mg, 0.337 mmol) and NMI (276 mg, 3.37 mmol) in anhydrous CH₃CN (4 mL) was added 228-2 (249 mg, 0.674 mol, in DCM (5 mL)) at 0° C. The mixture was stirred at RT for 10 h. The reaction was monitored by LCMS, and then quenched with H₂O. The mixture was extracted with CH₂Cl₂ (3×20 mL). The organic phase was dried over anhydrous MgSO₄, and concentrated at low pressure. The residue was purified by chromatography using PE:EA=5:1~2:1 as the eluent to give 228-3 (360 mg, 87%).

228-3 (360 mg, 0.294 mmol) was dissolved in CH₃COOH (80%, 8 mL), and stirred at 40-50° C. for 2.5 h. The reaction was monitored by LCMS and then quenched with MeO. The mixture was concentrated at low pressure, and the residue was purified by chromatography using PE:EA=1:1 as the eluent to generate crude 228. The product purified by prep-HPLC (neutral system, NH₄HCO₃) to give 228 (70 mg, 75%) as a white solid. ESI-MS: m/z 679.2 [M+H]⁺.

Example 126

Compound 229

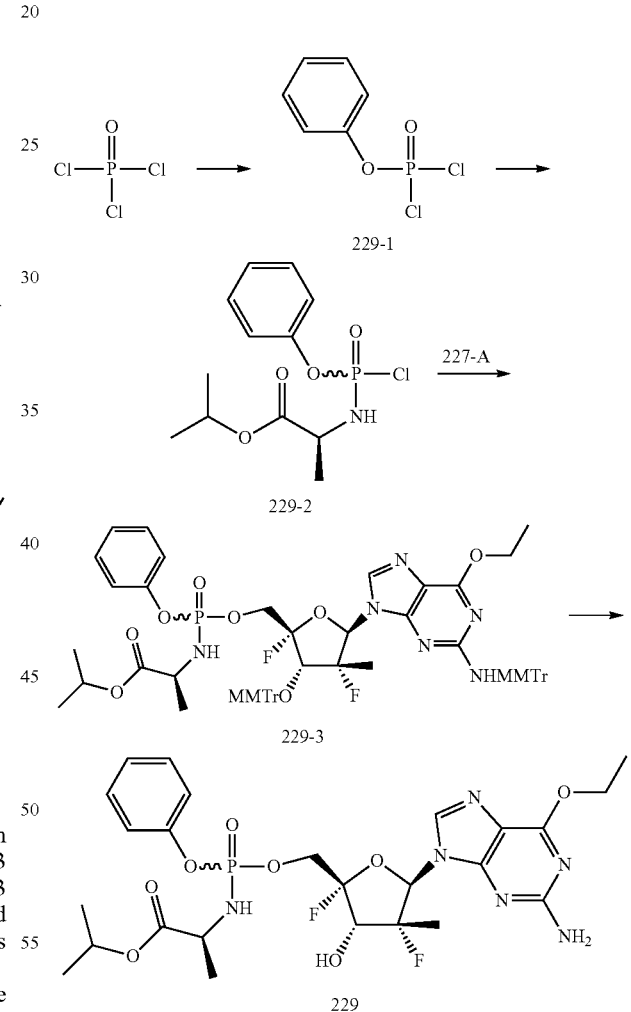

To a stirred solution of POCl₃ (2.0 g, 13 mmol) in anhydrous DCM (10 mL) was added phenol (1.22 g, 13 mmol) at −70° C. and TEA (1.31 g, 13 mmol) in DCM (3 mL) dropwise at −70° C. The mixture was gradually warmed to RT, and stirred for 1 h. A crude solution of 229-1 was obtained.

229 was prepared using a similar procedure as for the preparation of 228 using 229-2 (205 mg, 0.674 mol, in DCM (5 mL) obtained from (S)-isopropyl 2-aminopropanoate hydrochloride and 229-1) and 227-A (300 mg, 0.337 mmol). 229 (50 mg, 74%) was obtained as a white solid. ESI-MS: m/z 615.2 [M+H]⁺.

Example 127

Compound 230

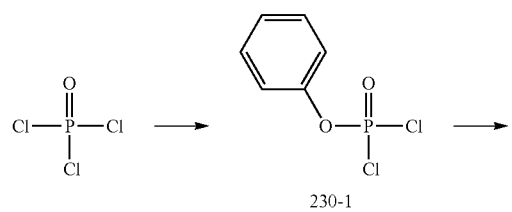

230-1

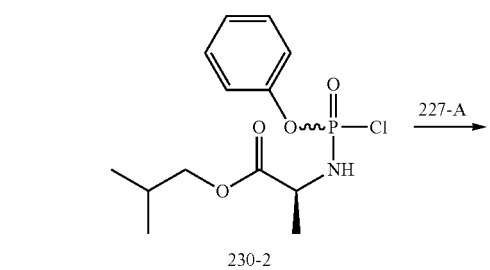

230-2

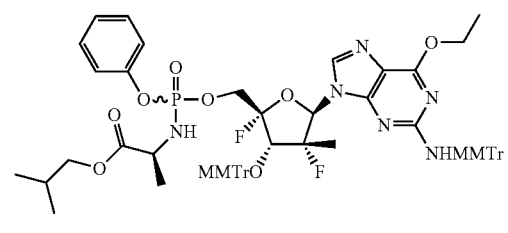

230-3

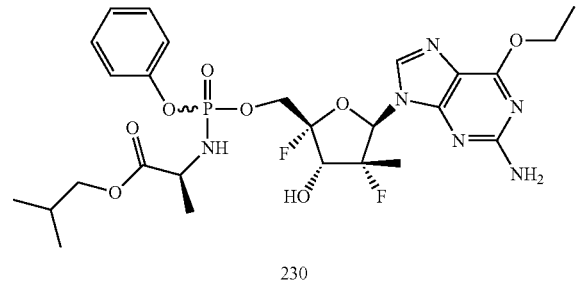

230

230 was prepared using a similar procedure as for the preparation of 228 using 230-2 (214 mg, 0.674 mol, in DCM (5 mL) obtained from (S)-isobutyl 2-aminopropanoate hydrochloride and 230-1) and 227-A (300 mg, 0.337 mmol). 230 (70 mg, 87%) was obtained as a white solid. ESI-MS: m/z 629.2 [M+H]⁺.

Example 128

Compound 231

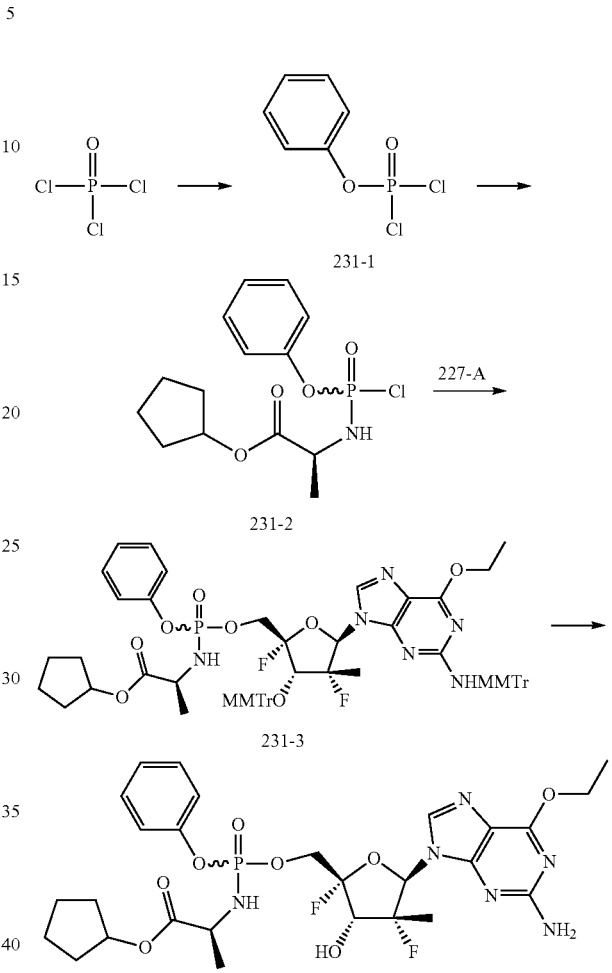

231 was prepared using a similar procedure as for the preparation of 228 using 231-2 (223 mg, 0.674 mol, DCM (5 mL) obtained from (S)-cyclopentyl 2-aminopropanoate hydrochloride and 231-1) and 227-A (300 mg, 0.337 mmol). 231 (62 mg, 71%) was obtained as a white solid. ESI-MS: m/z 641.2 [M+H]⁺.

Example 129

Compound 232

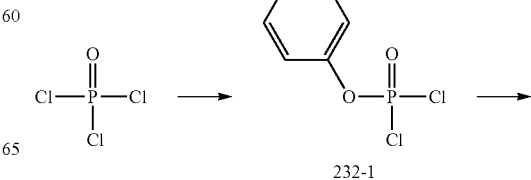

232-1

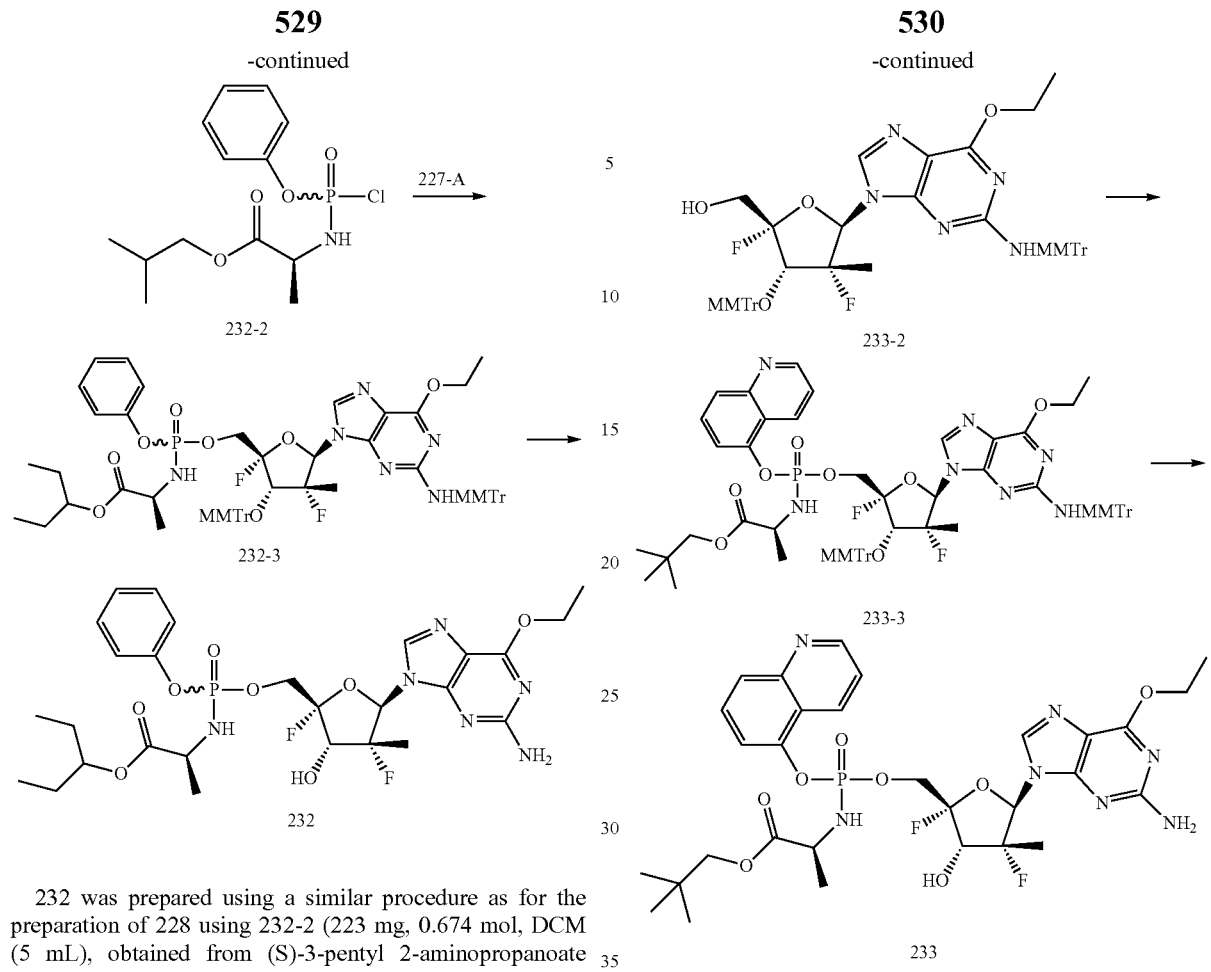

232 was prepared using a similar procedure as for the preparation of 228 using 232-2 (223 mg, 0.674 mol, DCM (5 mL), obtained from (S)-3-pentyl 2-aminopropanoate hydrochloride and 232-1) and 227-A (300 mg, 0.337 mmol). 232 (42 mg, 60%) was obtained as a white solid. ESI-MS: m/z 643.2 [M+H]$^+$.

Example 130

Compound 233

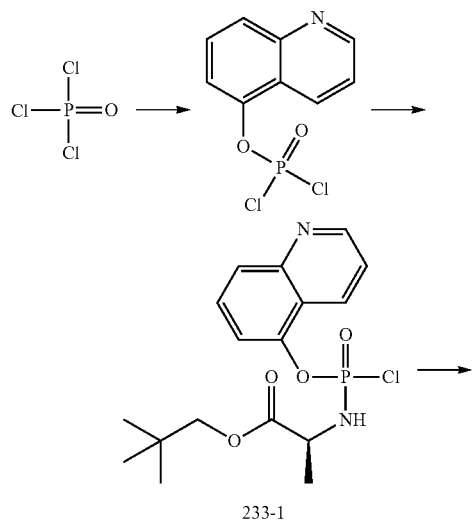

A stirred solution of phosphoryl trichloride (1.00 g, 6.58 mmol) and 5-quinoline (955 mg, 6.58 mmol) in anhydrous DCM (50 mL) was treated with a solution of TEA (665 mg, 6.58 mmol) in DCM (10 mL) at −78° C. The mixture was gradually warmed to RT, and stirred for 2 h. The solution was cooled to −78° C. and then treated with (S)-neopentyl 2-aminopropanoate hydrochloride (1.28 g, 6.58 mmol). TEA (1.33 g, 13.16 mmol) was added dropwise at −78° C. The mixture was gradually warmed to RT, and stirred for 2 h. The mixture was concentrated at low pressure, and the residue was dissolved in methyl-butyl ether. The precipitate was filtered off, and the filtrate was concentrated at low pressure. The residue was purified by a silica gel column (pure AcOEt) to give 233-1 as colorless oil (500 mg, 20%).

To a solution of 233-2 (300 mg, 0.337 mmol) and NMI (276.6 mg, 3.37 mmol) in anhydrous CH$_3$CN (0.9 mL) was added 233-1 (388 mg, 1.011 mmol) in CH$_3$CN (0.3 mL) dropwise at 0° C. The mixture was stirred at RT overnight. The reaction was quenched with water, and extracted with AcOEt. The organic phase was washed with brine, dried over anhydrous sodium sulfate, and concentrated at low pressure. The residue was purified by silica gel column (33% EA in PE) to give 233-3 as a yellow powder (300 mg, 71.9%).

233-3 (300 mg, 0.243 mmol) was dissolved in 80% CH$_3$COOH (3 mL), and the mixture was stirred at 60° C. for 2.5 h. The mixture was partitioned between AcOEt and water. The organic layer phase was washed by brine, dried over sodium sulfate and concentrated at low pressure. The residue was purified by silica gel column (50% EA in PE) to give 233 as a yellow powder (81 mg, crude product). The crude product (81 mg) was purified by RP HPLC to give 233 as a white solid. (28.7 mg, 17.1%). ESI-LCMS: m/z 694.1 [M+H]⁺.

Example 131

Compound 234

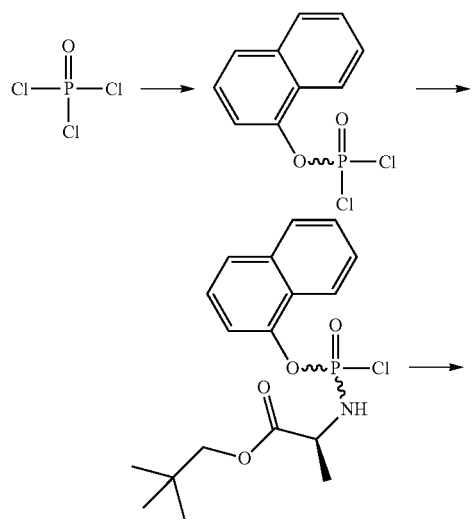

234-1 was prepared using a similar procedure as for the preparation of 233-1 using phosphoryl trichloride (2.00 g, 13.16 mmol), 1-naphthol (1.882 g, 13.16 mmol) and (S)-neopentyl 2-aminopropanoate hydrochloride (2.549 g, 13.16 mmol). 234-1 (600 mg, 12%) was obtained as a colorless oil.

A solution of 234-2 (230 mg 0.26 mmol) and NMI (212 mg 2.60 mmol) in anhydrous CH₃CN (1 mL) was treated with a solution of 234-1 (300 mg 0.78 mmol) in anhydrous CH₃CN (0.5 mL) at RT. The mixture was stirred at RT overnight. The reaction was quenched with water, and extracted with EA (3×20 mL). The organic layer was washed with brine, dried by anhydrous sodium sulfate, and concentrated at low pressure. The residue was purified by a silica gel column (CH₃OH in CH₂Cl₂ from 1% to 5%) to give 234-3 (300 mg, 93%) as a white solid.

234-3 (300 mg, 0.24 mmol) was dissolved in CH₃COOH (80%, 5 mL). The mixture was stirred at 60° C. for 2.5 h. The mixture was diluted with EA (30 mL) and washed with brine. The organic phase was dried over anhydrous sodium sulfate, and concentrated at low pressure. The residue was purified by a silica gel column (CH₃OH in CH₂Cl₂ from 1% to 5%) to give crude 234 (105 mg). The crude product was purified by HPLC (0.1% NH₄HCO₃ in water and CH₃CN) to give 234 (45 mg, 26%) as a white solid. ESI-LCMS: m/z 693.2 [M+H]⁺.

Example 132

Compound 235

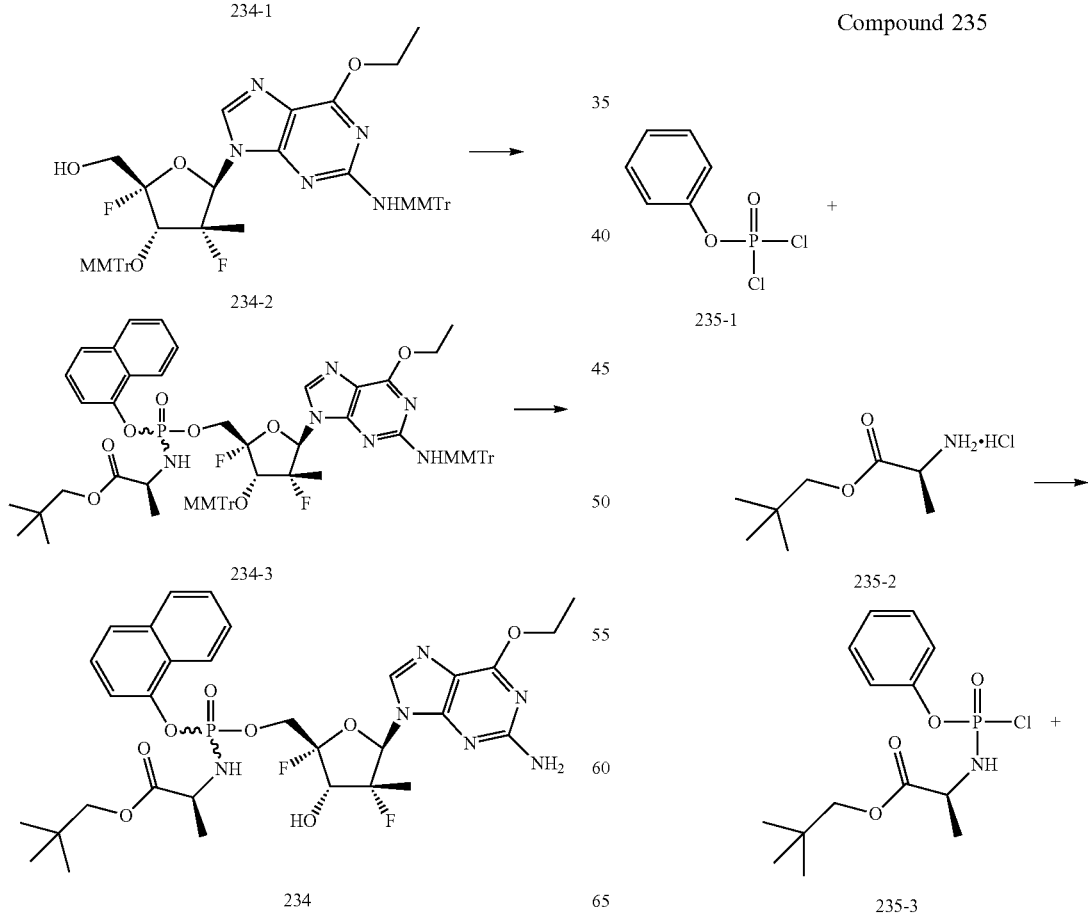

533

-continued

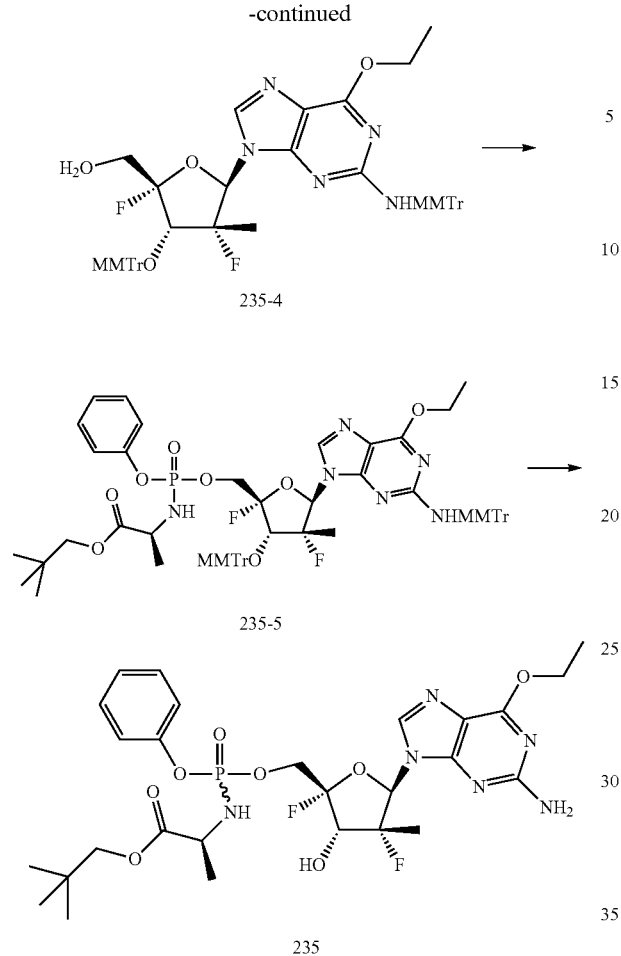

235-4

235-5

235

A stirred solution of 235-1 (2.00 g, 13.99 mmol) and 235-2 (2.00 g, 13.99 mmol) in anhydrous DCM (8 mL) was treated with a solution of TEA (3.11 g, 30.8 mmol) in DCM (20 mL) dropwise at −78° C. The mixture was stirred for 2 h. at −78° C. and then gradually warmed to RT. The organic solvent was removed at low pressure, and the residue was dissolved in methyl-butyl ether. The precipitate was filtered off, and the filtrate was concentrated at low pressure. The residue was purified on a silica gel column (dry DCM) to give 235-3 as colorless oil (1 g, 20.96%).

235-4 (260 mg, 0.29 mmol) was coevaporated with toluene 3 times to remove H$_2$O. Dried 235-4 was treated with MeCN (0.8 mL) and NMI (240 mg, 2.9 mmol) and then stirred for 10 mins. The mixture was treated with a solution of 235-3 (291 mg, 0.87 mmol) in MeCN (0.4 mL), and then concentrated at low pressure. The residue was purified on a silica gel column (75% EA in PE)) to give 235-5 (300 mg, 86%) as a white solid.

235-5 (300 mg, 0.25 mmol) was treated with CH$_3$COOH (5 mL, 80%), and stirred at 50° C. for 3 h. The mixture was diluted with EA. The solution was washed with brine, dried over anhydrous Na$_2$SO$_4$, and concentrated at low pressure. The residue was purified by silica gel column chromatography (67% EA in PE) to give crude 235, which was purified by HPLC. The product was dried by lyophilization to give 235 (30 mg, 18.5%) as a white solid. ESI-LCMS: m/z 643 [M+H]$^+$.

534

Example 133

Compound 247

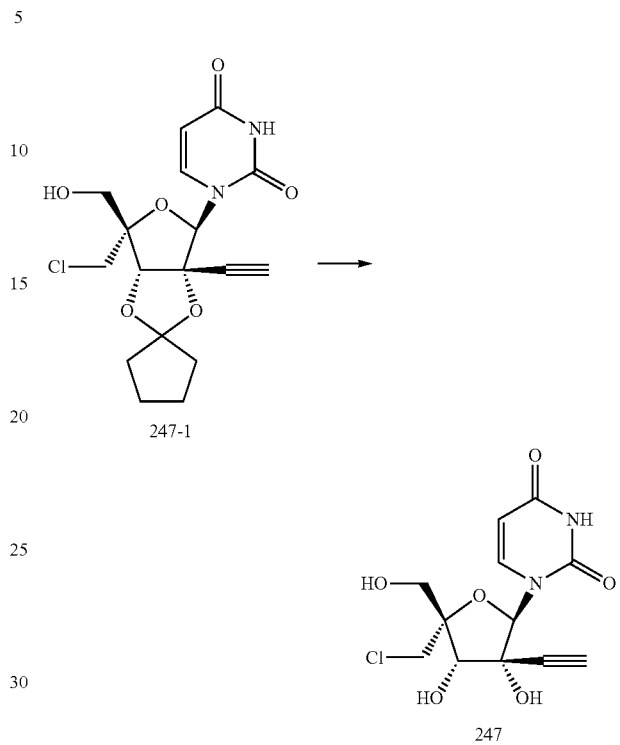

247-1

247

247-1 (50 mg, 0.13 mmol) was dissolved in 80% formic acid (3 mL) and heated at 50° C. overnight. The solvent was evaporated, co-evaporated with water to remove the acid. The residue was dissolved in a mixture of methanol and triethylamine (3 mL, 4:1 v:v). After 0.5 h, the solvent was evaporated. The nucleoside was lyophilized from water to yield 247 (40 mg, 97%). MS: mz 315.5 [M−1].

Example 134

Compound 248

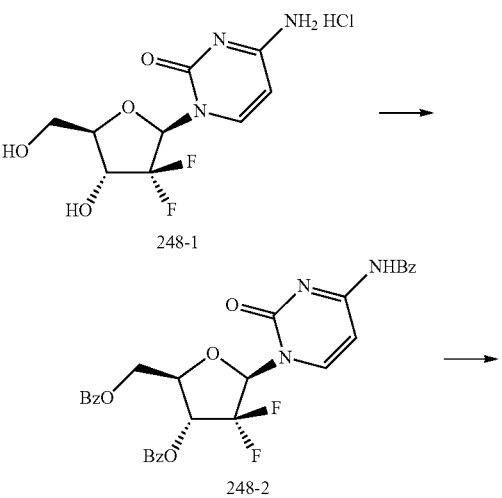

248-1

248-2

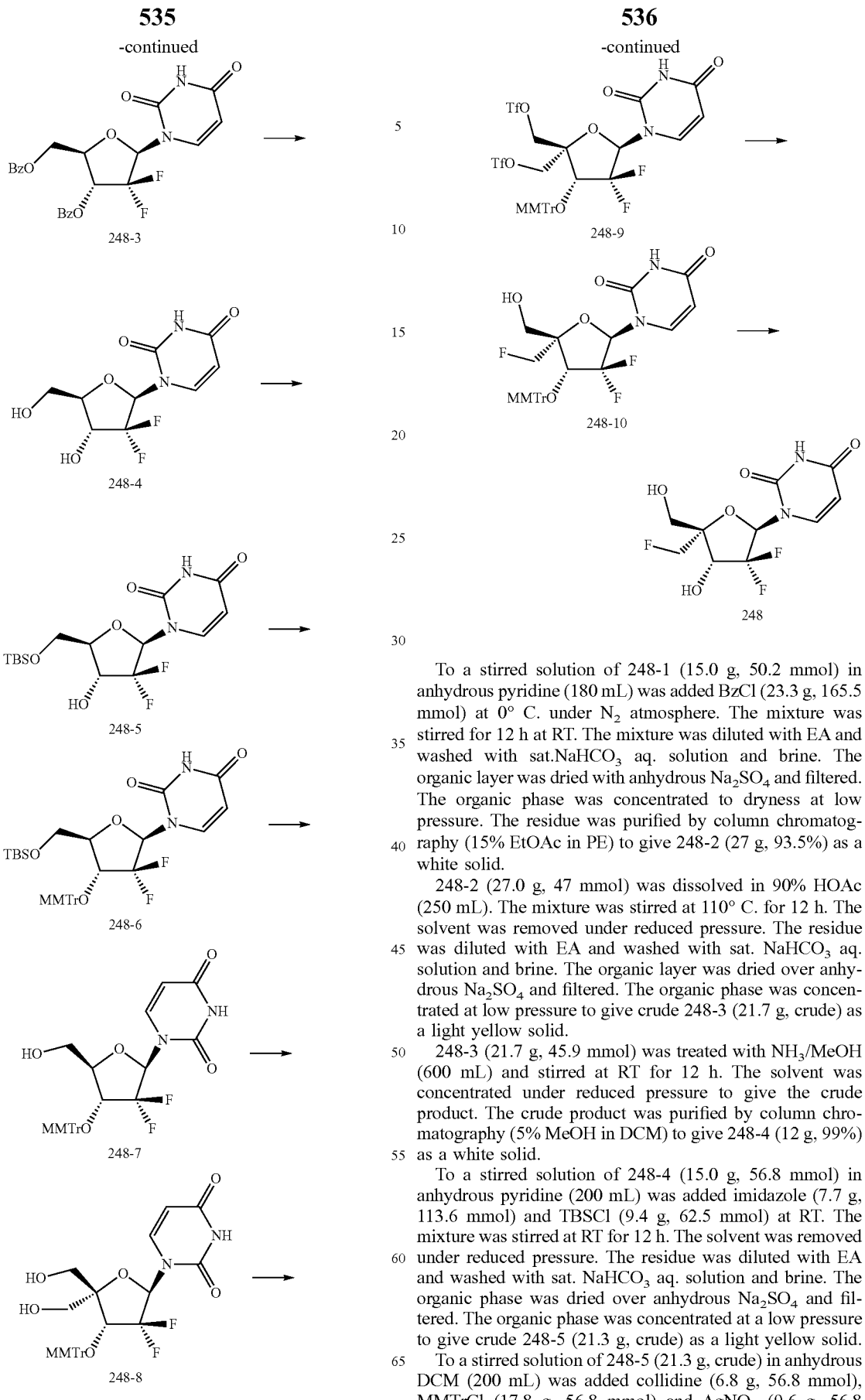

To a stirred solution of 248-1 (15.0 g, 50.2 mmol) in anhydrous pyridine (180 mL) was added BzCl (23.3 g, 165.5 mmol) at 0° C. under N₂ atmosphere. The mixture was stirred for 12 h at RT. The mixture was diluted with EA and washed with sat.NaHCO₃ aq. solution and brine. The organic layer was dried with anhydrous Na₂SO₄ and filtered. The organic phase was concentrated to dryness at low pressure. The residue was purified by column chromatography (15% EtOAc in PE) to give 248-2 (27 g, 93.5%) as a white solid.

248-2 (27.0 g, 47 mmol) was dissolved in 90% HOAc (250 mL). The mixture was stirred at 110° C. for 12 h. The solvent was removed under reduced pressure. The residue was diluted with EA and washed with sat. NaHCO₃ aq. solution and brine. The organic layer was dried over anhydrous Na₂SO₄ and filtered. The organic phase was concentrated at low pressure to give crude 248-3 (21.7 g, crude) as a light yellow solid.

248-3 (21.7 g, 45.9 mmol) was treated with NH₃/MeOH (600 mL) and stirred at RT for 12 h. The solvent was concentrated under reduced pressure to give the crude product. The crude product was purified by column chromatography (5% MeOH in DCM) to give 248-4 (12 g, 99%) as a white solid.

To a stirred solution of 248-4 (15.0 g, 56.8 mmol) in anhydrous pyridine (200 mL) was added imidazole (7.7 g, 113.6 mmol) and TBSCl (9.4 g, 62.5 mmol) at RT. The mixture was stirred at RT for 12 h. The solvent was removed under reduced pressure. The residue was diluted with EA and washed with sat. NaHCO₃ aq. solution and brine. The organic phase was dried over anhydrous Na₂SO₄ and filtered. The organic phase was concentrated at a low pressure to give crude 248-5 (21.3 g, crude) as a light yellow solid.

To a stirred solution of 248-5 (21.3 g, crude) in anhydrous DCM (200 mL) was added collidine (6.8 g, 56.8 mmol), MMTrCl (17.8 g, 56.8 mmol) and AgNO₃ (9.6 g, 56.8 mmol) at RT. The mixture was stirred at RT for 12 h. The solid was removed by filtration, and the filtrate was washed with sat.NaHCO$_3$ aq. solution and brine. The organic layer was dried over anhydrous Na$_2$SO$_4$ and concentrated at low pressure. The residue was purified by column chromatography (5% EA in PE) to give 248-6 (32 g, 87%) as a light yellow solid.

248-6 (32 g, 49.2 mmol) was dissolved in a solution of TBAF in THF (1M, 4.0 eq.) at RT. The mixture was stirred at RT for 12 h. The solvent was removed under reduced pressure. The residue was diluted with EA and washed with brine. The organic layer was dried over anhydrous Na$_2$SO$_4$ and concentrated at low procedure. The residue was purified by column chromatography (33% EA in PE) to give 248-7 (21.0 g, 79%) as a white solid.

To a stirred solution of 248-7 (21.0 g, 38.8 mmol) in anhydrous DCM (200 mL) was added pyridine (9.2 mL, 116.4 mmol) and Dess-Martin periodinane (49 g, 116.4 mmol) at 0° C. The mixture was stirred at RT for 4 h. The reaction was quenched with sat. Na$_2$S$_2$O$_3$ solution and sat. NaHCO$_3$ aq. solution. The organic layer was washed with brine, dried over anhydrous Na$_2$SO$_4$ and concentrated under reduced pressure to give a crude product (21.0 g).

The crude product (21.0 g, crude) was dissolved in dioxane (200 mL) and treated with 37% aqueous formaldehyde (20 mL, 194 mmol) and 2.0 N aqueous sodium hydroxide (37.5 mL, 77.6 mmol). The mixture was stirred at RT for 12 h. The solution was treated with NaBH$_4$ (8.8 g, 232.8 mmol). After stirring for 0.5 h at RT, the reaction was quenched with ice water. The mixture was diluted with EA and washed with brine. The organic phase was dried over anhydrous Na$_2$SO$_4$ and concentrated at low pressure. The residue was purified by column chromatography (4% MeOH in DCM) to give 248-8 (10.0 g, 50.5%) as a white foam.

248-8 (4.8 g, 8.5 mmol) was co-evaporated with toluene (2×). The residue was dissolved in anhydrous DCM (45 mL) and pyridine (6.7 g, 85 mmol). The solution was cooled to 0° C. Triflic anhydride (4.8 g, 18.7 mmol) was added dropwise over 10 mins. At 0° C., the mixture was stirred over 40 mins and monitored by TLC (PE:EA=1:1). The mixture was diluted with CH$_2$Cl$_2$ (50 mL). The solution was washed with sat. NaHCO$_3$ solution. The organic phase was washed with brine, dried over anhydrous Na$_2$SO$_4$, and concentrated at low pressure. The residue was purified by column chromatography (PE:EA=100:0-4:1) to give 248-9 (6.1 g, 86.4%) as a brown foam.

248-9 (6.1 g, 7.3 mmol) was dissolved in MeCN (25 mL). A solution of TBAF in THF (1M, 25 mL) was added at RT. The mixture was stirred at RT for 12 h. A solution of TBAF in THF (1M, 15 mL) was added, and the mixture was stirred for 4 h. The mixture was treated with aq. NaOH (1N, 14.6 mmol) and the mixture was stirred for 1 h. The reaction was quenched with water and extracted with EA. The organic phase was washed with brine, dried over anhydrous Na$_2$SO$_4$ and concentrated at low pressure. The residue was purified by column chromatography (50% EA in PE) to give 248-10 (2.1 g, 50.6%) as a white solid.

248-10 (700 mg, 1.23 mmol) was dissolved in 80% HCOOH (40 mL) at RT. The mixture was stirred at RT for 2 h. The reaction was quenched with MeOH (40 mL) and stirred for 12 h. The solvent was concentrated at low pressure, and the residue was purified by column chromatography (5% MeOH in DCM) to give 248 (210 mg, 57.7%) as a white solid. ESI-MS: m/z 296.9 [M+H]$^+$.

Example 135

Compound 250

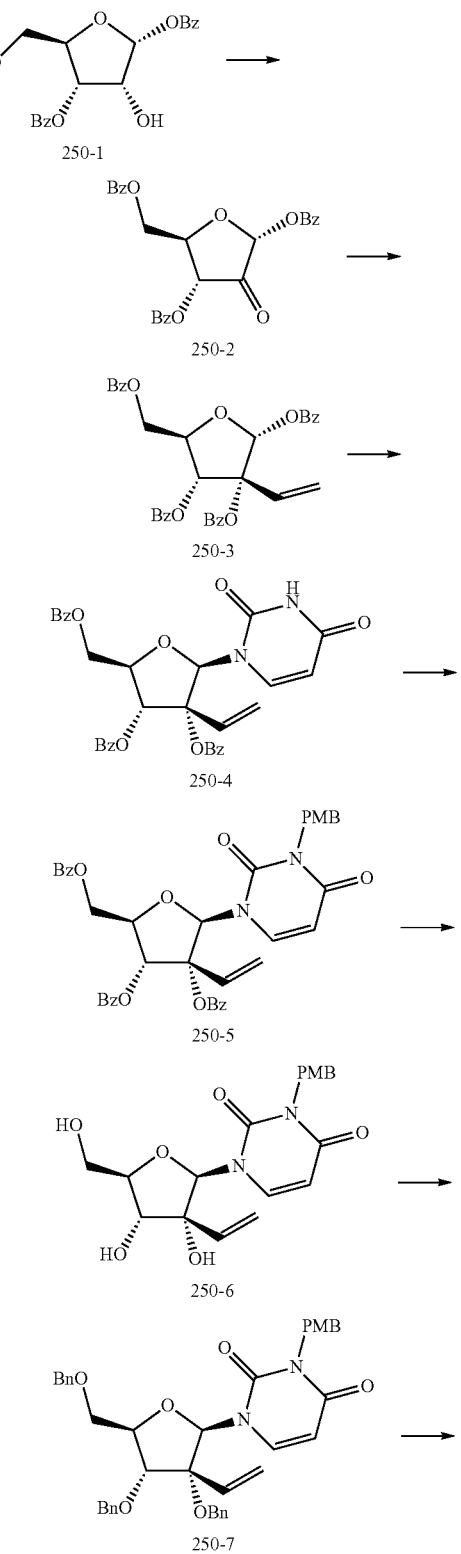

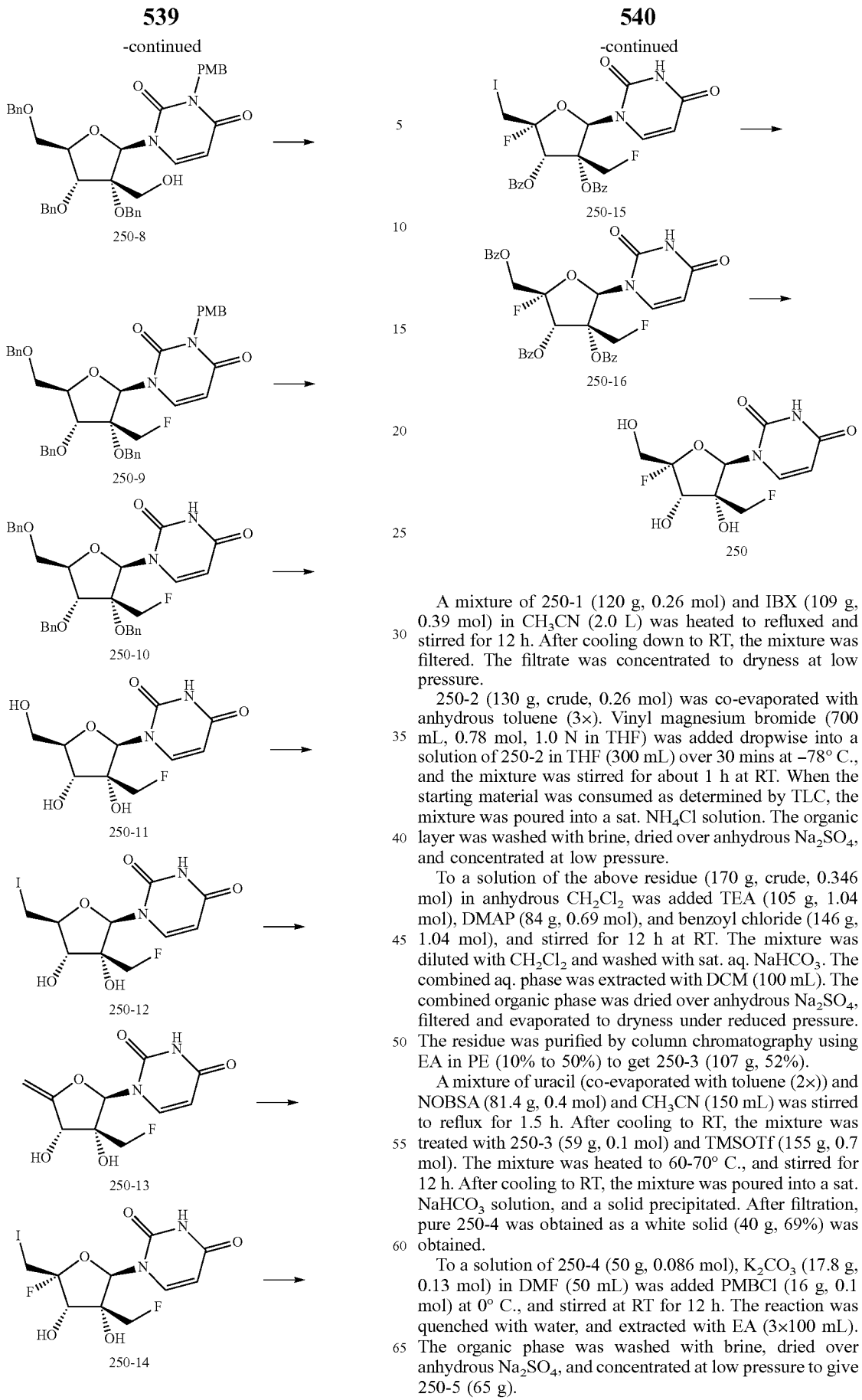

A mixture of 250-1 (120 g, 0.26 mol) and IBX (109 g, 0.39 mol) in $CH_3CN$ (2.0 L) was heated to refluxed and stirred for 12 h. After cooling down to RT, the mixture was filtered. The filtrate was concentrated to dryness at low pressure.

250-2 (130 g, crude, 0.26 mol) was co-evaporated with anhydrous toluene (3×). Vinyl magnesium bromide (700 mL, 0.78 mol, 1.0 N in THF) was added dropwise into a solution of 250-2 in THF (300 mL) over 30 mins at −78° C., and the mixture was stirred for about 1 h at RT. When the starting material was consumed as determined by TLC, the mixture was poured into a sat. $NH_4Cl$ solution. The organic layer was washed with brine, dried over anhydrous $Na_2SO_4$, and concentrated at low pressure.

To a solution of the above residue (170 g, crude, 0.346 mol) in anhydrous $CH_2Cl_2$ was added TEA (105 g, 1.04 mol), DMAP (84 g, 0.69 mol), and benzoyl chloride (146 g, 1.04 mol), and stirred for 12 h at RT. The mixture was diluted with $CH_2Cl_2$ and washed with sat. aq. $NaHCO_3$. The combined aq. phase was extracted with DCM (100 mL). The combined organic phase was dried over anhydrous $Na_2SO_4$, filtered and evaporated to dryness under reduced pressure. The residue was purified by column chromatography using EA in PE (10% to 50%) to get 250-3 (107 g, 52%).

A mixture of uracil (co-evaporated with toluene (2×)) and NOBSA (81.4 g, 0.4 mol) and $CH_3CN$ (150 mL) was stirred to reflux for 1.5 h. After cooling to RT, the mixture was treated with 250-3 (59 g, 0.1 mol) and TMSOTf (155 g, 0.7 mol). The mixture was heated to 60-70° C., and stirred for 12 h. After cooling to RT, the mixture was poured into a sat. $NaHCO_3$ solution, and a solid precipitated. After filtration, pure 250-4 was obtained as a white solid (40 g, 69%) was obtained.

To a solution of 250-4 (50 g, 0.086 mol), $K_2CO_3$ (17.8 g, 0.13 mol) in DMF (50 mL) was added PMBCl (16 g, 0.1 mol) at 0° C., and stirred at RT for 12 h. The reaction was quenched with water, and extracted with EA (3×100 mL). The organic phase was washed with brine, dried over anhydrous $Na_2SO_4$, and concentrated at low pressure to give 250-5 (65 g).

A mixture of 250-5 (65 g, 0.086 mol) and NaOMe (16.8 g, 0.3 mol) in MeOH:DCM (500 mL, v:v=4:1) was stirred at RT for 2.5 h. The reaction was quenched with $CO_2$ (solid) and concentrated at low pressure. The residue was dissolved in EA (200 mL). The solution was washed with water, dried over anhydrous $Na_2SO_4$, and concentrated at low pressure. The residue was purified by column chromatography (4% MeOH in DCM) to give 250-6 as a yellow foam (25 g, 75%).

To a mixture of 250-6 (25.5 g, 0.065 mol) in DMF (60 mL) was added NaH (10.5 g, 0.26 mol, 60% in coal oil) BnBr (36.3 g, 0.21 mol) in an ice bath, and stirred at RT for 12 h. The reaction was quenched with $NH_4Cl$ (aq.), and the mixture was diluted with EA (150 mL). The solution was washed with brine, dried over anhydride $Na_2SO_4$, and concentrated at low pressure. The residue was purified by sil-gel (15% EA in PE) to give 250-7 (20 g, 46%).

To a solution of 250-7 (20 g, 0.03 mol) and NMMO (7 g, 0.06 mol) in $THF:H_2O$ (100 mL, v:v=5:1) was added $OsO_4$ (2.6 g, 0.01 mol) at RT, and stirred at RT for 24 h. The reaction was quenched with sat. $Na_2S_2O_3$ solution, and extracted with EA (3×80 mL). The organic layer was washed with brine, dried over anhydrous $Na_2SO_4$, and concentrated at low pressure.

To a solution of diol-product (0.03 mol) in $MeOH:H_2O$:THF (v:v:v=170 mL:30 mL:50 mL) was added $NaIO_4$ (9.6 g, 0.045 mol) at RT, and stirred at RT for 2 h. After filtration, the filter was used directly for the next step.

The previous solution was treated with $NaBH_4$ (1.8 g, 0.048 mol) at 0° C., and stirred at RT for 30 mins. The reaction was quenched with HCl (1 N) solution. The mixture was extracted with EA (3×60 mL). The organic phase was washed with brine, dried over anhydrous $Na_2SO_4$, and concentrated at low pressure. The residue was purified by sil-gel (25% EA in PE, TLC:PE:EA=2:1, Rf=0.6) to give 250-8 (12 g, 61% over 3 steps).

To a solution of 250-8 (14 g, 21 mmol) and DMAP (5.1 g, 42 mmol) in DCM (60 mL) was added MsCl (3.1 g, 27 mmol) at 0° C., and stirred at RT for 40 mins. The reaction was quenched with sat. $NaHCO_3$ solution. The organic phase was washed with HCl (0.2 N) solution, dried over anhydrous $Na_2SO_4$, and concentrated at low pressure. The residue was purified by sil-gel (25% EA in PE) to give the Ms-product (14 g, 90%) as a white solid.

Ms-product (41 g, 55 mmol) was treated with TBAF (Alfa, 1 N in THF, 500 mL), and stirred at 70-80° C. for 3 days. The mixture was concentrated at low pressure. The residue was dissolved in EA (200 mL). The solution was washed with brine, dried over anhydrous $Na_2SO_4$, and concentrated at low pressure. The residue was purified by sil-gel column (25% EA in PE) to give 250-9 (9.9 g, 27%).

To a solution of 250-9 (6.3 g, 9.45 mmol) in $CAN:H_2O$ (v:v=3:1, 52 mL) was added CAN (15.5 g, 28.3 mmol), and stirred at RT overnight. The reaction was quenched with water, and extracted with EA (3×80 mL). The organic phase was washed with brine, dried over anhydrous $Na_2SO_4$, and concentrated at low pressure. The residue was purified by column chromatography (25% EA in PE) to give 250-10 (3.6 g, 71%) as a yellow oil.

To a solution of 250-10 (2.4 g, 4.4 mmol) in anhydrous DCM (10 mL) was added $BCl_3$ (1 N, 30 mL) at −70° C., and stirred for 2 h at −70° C. The reaction was quenched with MeOH at −70° C. The mixture was concentrated directly under 35° C. at low pressure. The residue was purified by column chromatography (50% EA in PE to 100% EA) to give 250-11 (1.2 g, 86%). ESI-MS: m/z 277.1 $[M+H]^+$.

To a solution of $PPh_3$ (3.37 g, 12.8 mmol) in pyridine (15 mL) was added 12 (3.06 g, 12 mmol) at 0° C., and stirred at RT for 30 mins until the orange color appeared. The mixture was cooled to 0° C., and treated with 250-11 (2.2 g, 8 mmol) in pyridine (5 mL), and stirred at RT under $N_2$ for 12 h. The reaction was quenched with $Na_2S_2O_3$ (sat., 30 mL), and extracted with EA (3×60 mL). The organic phase was washed with brine, dried over anhydrous $Na_2SO_4$, and concentrated at low pressure. The residue was purified by column chromatography (1% to 2% MeOH in DCM) to give 250-12 (1.8 g, 58%) as a light yellow foam.

A mixture of 250-12 (1.35 g, 3.5 mmol) and DBU (1.06 g, 7 mmol) in $THF:CH_3CN$ (v:v=10 mL:5 mL) was stirred at 60-70° C. for 2 h. The mixture was diluted with EA (50 mL), and adjusted to pH=7-8 with HCl (0.2 N) solution. The organic phase was washed with brine, dried over anhydrous $Na_2SO_4$, and concentrated at low pressure. The residue was purified by column chromatography to give 250-13 (0.5 g, 55%).

To a solution of 250-13 (670 mg, 2.6 mmol) in $CH_3CN$ (6 mL) was added NIS (730 mg, 3.25 mmol) and 3HF-TEA (335 mg, 2.1 mmol) at 0° C., and stirred at RT for 2 h. The reaction was quenched with $NaHCO_3$ (sat.) solution and $Na_2S_2O_3$ (sat.) solution, and extracted with EA (3×30 mL). The organic phase was washed with brine, dried over anhydrous $Na_2SO_4$, and concentrated at low pressure. The residue was purified by column chromatography (50% EA in PE and 2% MeOH in DCM) to give 250-14 (1.2 g, 80%) as a brown oil.

To a solution of 250-14 (1.0 g, 2.47 mmol), DMAP (0.75 g, 6.2 mmol) and TEA (0.75 g, 7.42 mmol) in DCM (10 mL) was added BzCl (1.15 g, 8.16 mmol) in DCM (1 mL) at 0° C., and stirred at RT for 12 h. The reaction was quenched with $NaHCO_3$ (aq.) solution. The organic phase was washed with brine, dried over anhydrous $Na_2SO_4$, and concentrated at low pressure. The residue was purified by column chromatography (30% EA in PE) to give 250-15 (850 mg, 85%).

A mixture of 250-15 (600 mg, 1 mmol), BzONa (1.45 g, 10 mmol), and 15-crown-5 (2.2 g, 10 mmol) in DMF (25 mL) was stirred at 90-100° C. for 24 h. The mixture was diluted with EA (20 mL). The solution was washed with brine, dried over anhydrous $Na_2SO_4$, and concentrated at low pressure. The residue was purified by column chromatography (30% EA in PE) to give 250-16 (275 mg, 37%) as a light yellow foam.

A mixture of 250-16 (250 mg, 0.41 mmol) in $NH_3$-MeOH (7 N, 5 mL) was stirred at RT for 15 h. The mixture was concentrated at low pressure directly. The residue was purified by column chromatography (50% EA in PE) and re-purified by prep-HPLC to give 250 (33 mg, 25%) as a white solid. ESI-MS: m/z 295.1 $[M+H]^+$.

Example 136

Compound 126

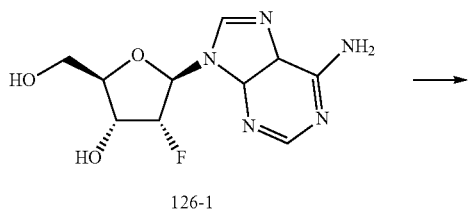

126-1

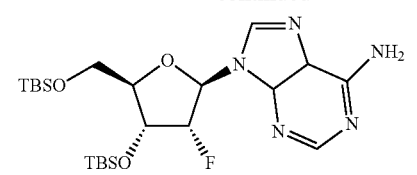

126-2

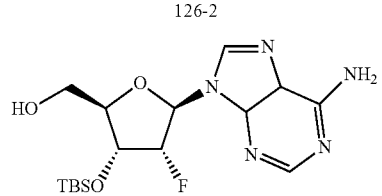

126-3

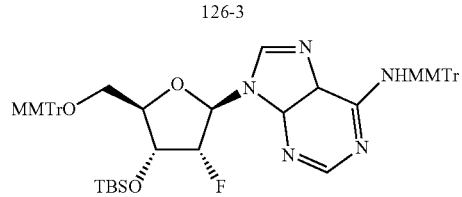

126-4

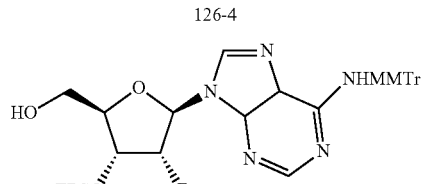

126-5

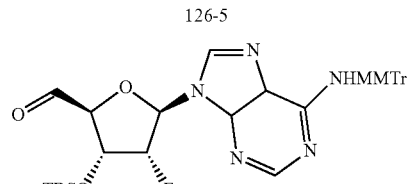

126-6

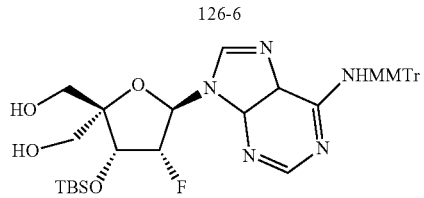

126-7

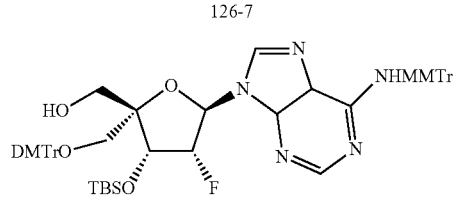

126-8

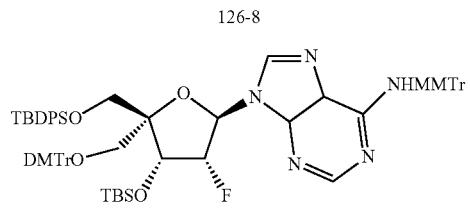

126-9

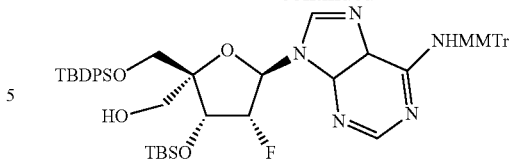

126-10

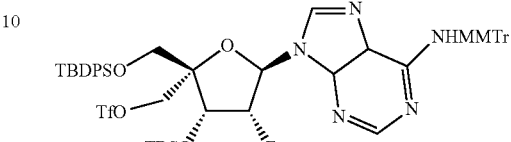

126-11

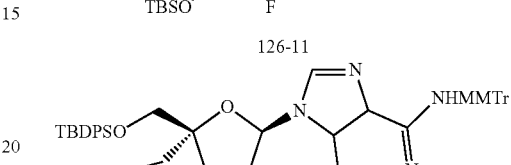

126-12

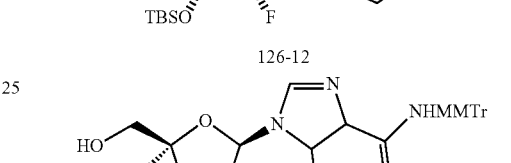

126-13

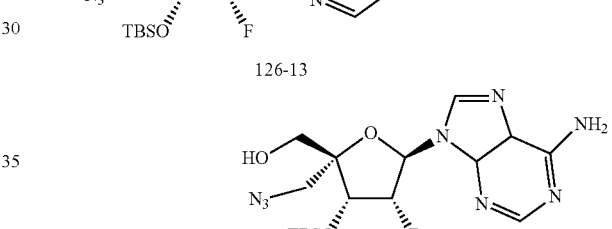

126

To a solution of 126-1 (3.0 g, 11.15 mmol) in anhydrous pyridine (90 mL) was added imidazole (3.03 g, 44.59 mmol) and TBSCl (6.69 g, 44.59 mmol) at 25° C. under $N_2$ atmosphere. The solution was stirred at 25° C. for 15 h. The solution was concentrated to dryness under reduced pressure. The residue was dissolved in EA. The solution was washed with sat. $NaHCO_3$ and brine, and dried over anhydrous $MgSO_4$. The solvent was removed at low pressure to give crude 126-2 (4.49 g, 90%) as a white solid.

To a stirred solution of 126-2 (3.5 g, 7.04 mmol) in a mixture of EA and EtOH (1:1, 55 mL) was added TsOH (10.7 g, 56.34 mmol) at 0° C. The mixture was stirred at 30° C. for 8 h. Water (30 mL) was added, and the solution was removed to dryness. The residue was purified on a silica gel column (10% MeOH in DCM) to give 126-3 (1.75 g, 65%) as a white foam.

To a solution of 126-3 (3.4 g, 8.88 mmol) in anhydrous pyridine (17 mL) was added collidine (4.3 g, 35.51 mmol), $AgNO_3$ (5.50 g, 35.51 mmol) and MMTrCl (8.02 g, 26.63 mmol) at 25° C. under $N_2$. The mixture was stirred at 25° C. for 12 h. MeOH (20 mL) was added, and the solvent was removed to dryness at low pressure. The residue was purified on a silica gel column (10% EA in PE) to give 126-4 (5.76 g, 70%) as a white foam.

To a solution of 126-4 (2.0 g, 2.16 mmol) in anhydrous DCM (10 mL) was added $C_{12}CHCOOH$ (2.8 g, 21.57 mmol)

dropwise at −78° C. The mixture was warmed to −10° C. and stirred at this temperature for 20 mins. The reaction was quenched with sat.NaHCO₃ at −10° C. The mixture was extracted with DCM, washed with brine, and dried over anhydrous MgSO₄. The solution was concentrated at low pressure. The residue was purified on silica gel column (10% EA in PE) to give 126-5 (0.99 g, 70%) as a white foam.

To a stirred solution of 126-5 (3.5 g, 5.34 mmol) in anhydrous DMSO (35 mL) was added DCC (3.30 g, 16.03 mmol) and Py-TFA (1.03 g, 5.34 mmol). The mixture was stirred at 30° C. for 1 h. The reaction was quenched with cold water at 0° C., and extracted with EA (3×60 mL). The precipitate was filtered. The organic layers were washed with brine (3×) and dried over anhydrous MgSO₄. The organic phase was concentrated at low pressure to give crude 126-6 (3.5 g) as a yellow oil.

To a stirred solution of 126-6 (3.5 g, 5.34 mmol) in MeCN (35 mL) was added 37% HCHO (11.1 mL) and TEA (4.33 g, 42.7 mmol). The mixture was stirred at 25° C. for 12 h. The mixture was treated with EtOH (26 mL) and NaBH₄ (3.25 g, 85.5 mmol) and then stirred for 30 mins. The reaction was quenched with sat. aq. NH₄Cl and extracted with EA (3×60 mL). The organic layer was dried over anhydrous MgSO₄, and concentrated at low pressure. The residue was purified by column chromatography (from 10% EA in PE to 50% DCM in PE) to give 126-7 (1.46 g, 40%) as a white solid.

To a stirred solution of 126-7 (1.85 g, 2.7 mmol) in pyridine (24 mL) and DCM (9.6 mL) was added DMTrCl (1.3 g, 3.9 mmol) at −35° C. under N₂ atmosphere. The solution was stirred at 25° C. for 16 h. The mixture was treated with MeOH (15 mL) and concentrated at low pressure. The residue was purified by column chromatography (EA in PE from 10% to 30%) to give 126-8 (1.60 g, 60%) as a white solid.

To a solution of 126-8 (1.07 g, 1.08 mmol) in anhydrous pyridine (5 mL) was added AgNO₃ (0.65 g, 3.79 mmol) and TBDPSCl (1.04 g, 3.79 mmol). The mixture was stirred at 25° C. for 16 h. The solvent was removed under reduced pressure. The residue was dissolved in EA (50 mL). The resulting solution was washed with brine. The organic layer was dried over anhydrous MgSO₄, and concentrated at low pressure. The residue was purified on a silica gel column (10% EA in PE) to give 126-9 (0.93 g, 70%) as a white foam.

To a stirred solution of 126-9 (1 g, 0.82 mmol) in anhydrous DCM (13.43 mL) was added C₁₂CHCOOH (2.69 mL) at −78° C. The mixture was stirred at −10° C. for 20 mins. The reaction was quenched with sat. aq. NaHCO₃ and extracted with DCM. The organic layer was dried over anhydrous Na₂SO₄, and concentrated at low pressure. The organic phase was purified by column chromatography (MeOH in DCM form 0.5% to 2%) to give 126-10 (0.48 g, 65%) as a solid.

To an ice cold solution of 126-10 (0.4 g, 0.433 mmol) in anhydrous DCM (2.7 mL) was added pyridine (171 mg, 2.17 mmol) and Tf₂O (183 mg, 0.65 mmol) by dropwise at −35° C. The mixture was stirred at −10° C. for 20 mins. The reaction was quenched with ice water and stirred for 30 mins. The mixture was extracted with DCM (3×20 mL). The organic phase was washed with brine (100 mL), dried over anhydrous Na₂SO₄, and concentrated at low pressure to give crude 126-11 (0.46 g), which was used for next step without further purification.

To a solution of 126-11 (0.46 g, 0.43 mmol) in anhydrous DMF (2.5 mL) was added NaN₃ (42 mg, 0.65 mmol). The mixture was stirred at 30° C. for 16 h. The solution was diluted with water and extracted with EA (3×30 mL). The combined organic layers were dried over anhydrous Na₂SO₄, and concentrated at low pressure. The residue was purified on a silica gel column (EA in PE from 5% to 15%) to give 126-12 (0.31 g, 70%) as a solid.

To a solution of 126-12 (0.31 g, 0.33 mmol) in MeOH (5 mL) was added NH₄F (0.36 g, 9.81 mmol) at 70° C. The mixture was stirred at this temperature for 24 h. The mixture was evaporated to dryness. The residue was purified on silica gel column (MeOH in DCM from 0.5% to 2.5%) to give 126-13 (117 mg, 60%) as a white solid.

126-13 (300 mg, 0.50 mmol) was dissolved in 80% of HOAc (20 mL). The mixture was stirred at 55° C. for 1 h. The reaction was quenched with MeOH and concentrated at low pressure. The residue was purified by prep-HPLC to give 126 (100 mg, 61.3%) as a white solid. ESI-LCMS: m/z 325.1 [M+H]⁺.

Example 137

Compound 137

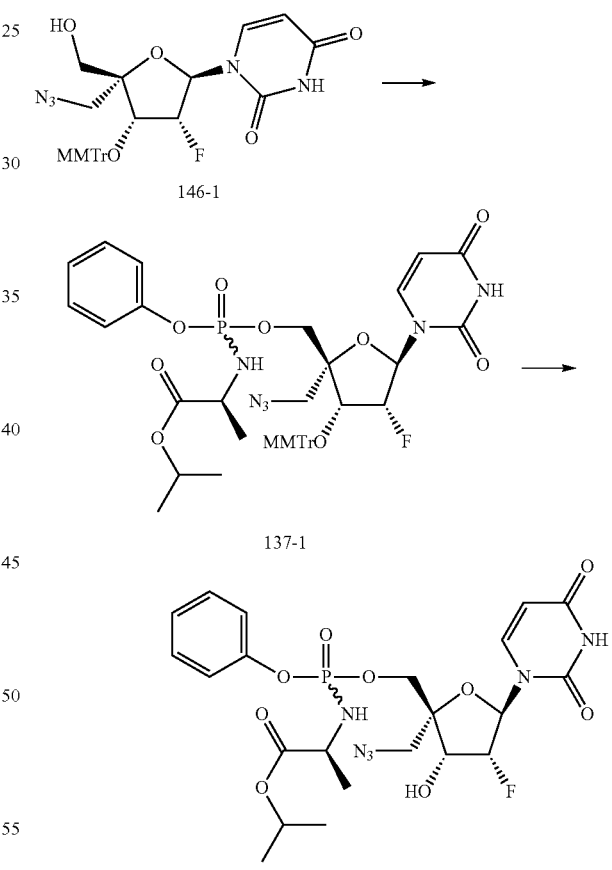

To a stirred solution of 146-1 (80 mg, 0.14 mmol) in anhydrous CH₃CN (2.0 mL) was added N-methylimidazole (0.092 mL, 1.12 mmol) at 0° C. (ice/water bath). A solution of phenyl (isopropoxy-L-alaninyl) phosphorochloridate (128 mg, 0.42 mmol, dissolved in CH₃CN (0.5 mL)) was then added (prepared according to a general procedure as described in McGuigan et al., *J. Med. Chem.* (2008) 51:5807-5812). The solution was stirred at 0 to 5° C. for h and then stirred at RT for 16 h. The mixture was cooled to 0 to 5° C., diluted with EA followed by the addition of water (5 mL). The solution was washed with 1.0M citric acid, sat. aq. NaHCO₃ and brine, and dried with MgSO₄. The residue was purified on silica (10 g column) with EA/hexanes (25-100% gradient) to give 137-1 (57.3 mg, 49%) as a foam.

137-1 (57.3 mg, 0.07 mmol) was dissolved in anhydrous CH₃CN (0.5 mL), and 4N HCl in dioxane (68 µL, 0.27 mmol) was added at 0 to 5° C. The mixture was stirred at RT for 2 h, and anhydrous EtOH (100 µL) was added. The solvents were evaporated at RT and co-evaporated with toluene (3×). The residue was purified on silica (10 g column) with MeOH/CH₂Cl₂ (1-7% gradient) and lyophilized to give 137 (27.8 mg, 72%) as a white foam. ESI-LCMS: m/z=571.1 [M+H]⁺, 1141.2 [2M+H]⁺.

Example 138

Compound 138

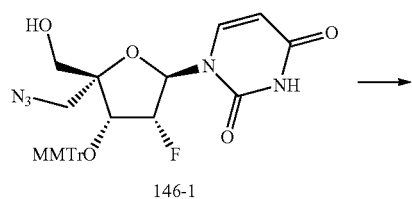

146-1

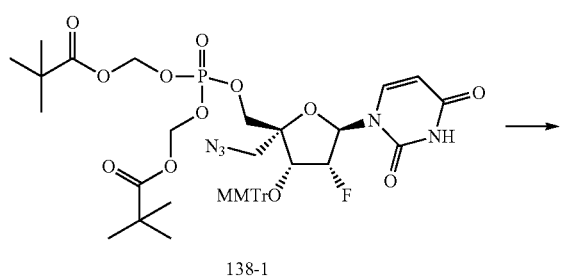

138-1

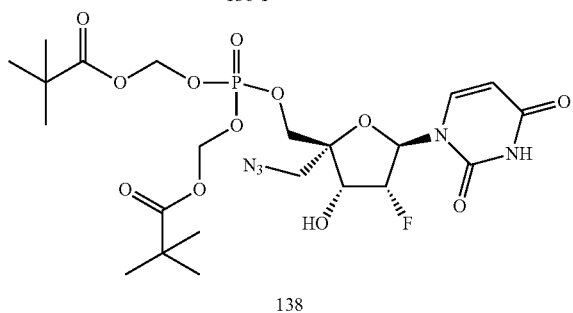

138

138-1 (68.4 mg, 44.7%) was prepared from 146-1 (100 mg, 0.174 mmol) and bis(tert-butoxycarbonyloxymethyl) phosphate (126 mg, 0.35 mmol) with DIPEA (192 µL, 1.04 mmol), BOP-Cl (133 mg, 0.52 mmol), and 3-nitro-1,2,4-triazole (59 mg, 0.52 mmol) in THF (1.5 mL) in the same manner as 169-4.

138 (31.4 mg, 67%) was prepared from 138-1 (68 mg, 0.077 mmol) in the same manner as 146. ESI-LCMS: m/z=627.15 [M+Na]⁺, 1219.25 [2M+H]⁺.

Example 139

Compound 139

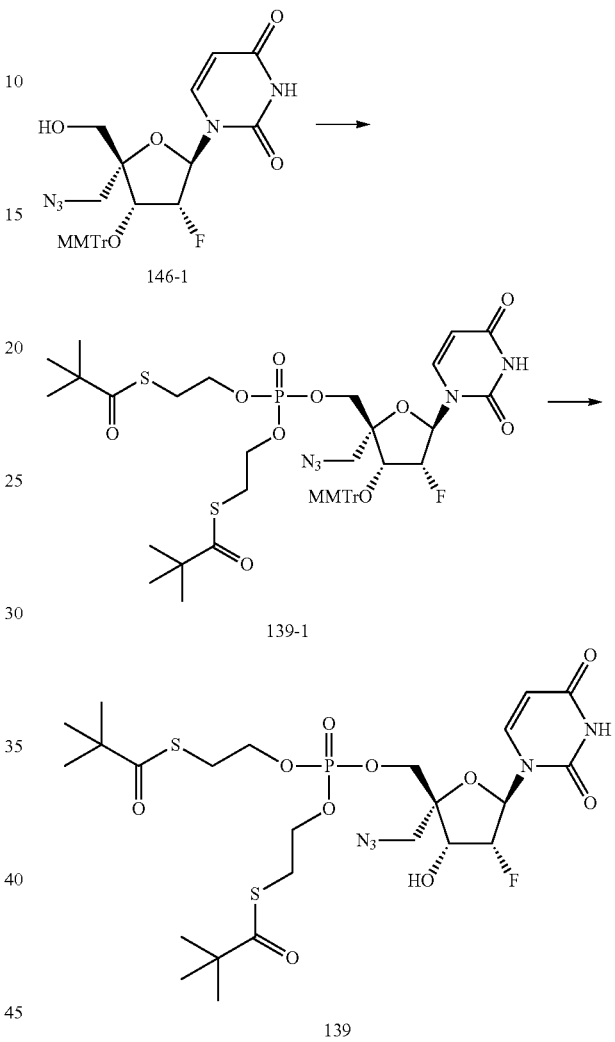

To a solution of 146-1 (100 mg, 0.175 mmol) in anhydrous CH₃CN (2 mL) was added 5-ethylthio-1H-tetrazole in CH₃CN (0.25M; 0.84 mL, 0.21 mmol). Bis-SATE-phosphoramidate (95 mg, 0.21 mmol) in CH₃CN (1 mL) was added at 0 to 5° C. dropwise. The mixture was stirred 2 h at 0 to 5° C. under Ar. A solution of 77% m-CPBA (78 mg, 0.35 mmol) in DCM (1 mL) was added, and the mixture stirred 2 h at 0 to 5° C. under Ar. The mixture was diluted with EtOAc (50 mL), washed with 1.0M citric acid, sat. NaHCO₃ and brine, and dried with MgSO₄. The mixture was filtered, and the solvents were evaporated in vacuo. The residue was purified on silica (10 g column) with EA/hexanes (20-100% gradient) to give 139-1 (105 mg, 63.6%) as a white foam.

139-1 (105 mg, 0.112 mmol) was dissolved in anhydrous CH₃CN (0.8 mL), and 4N HCl in dioxane (84 µL, 0.334 mmol) was added at 0 to 5° C. The mixture was stirred at RT for 2 h. Anhydrous EtOH (100 µL) was added. The solvents were evaporated at RT, and co-evaporated with toluene (3×). The residue was purified on silica (10 g column) with MeOH/CH$_2$Cl$_2$ (1-7% gradient) and lyophilized to give 139 (42.7 mg, 57%) as a white foam. ESI-LCMS: m/z=692.15 [M+Na]$^+$, 1339.30 [2M+H]$^+$.

Example 140

Compound 143

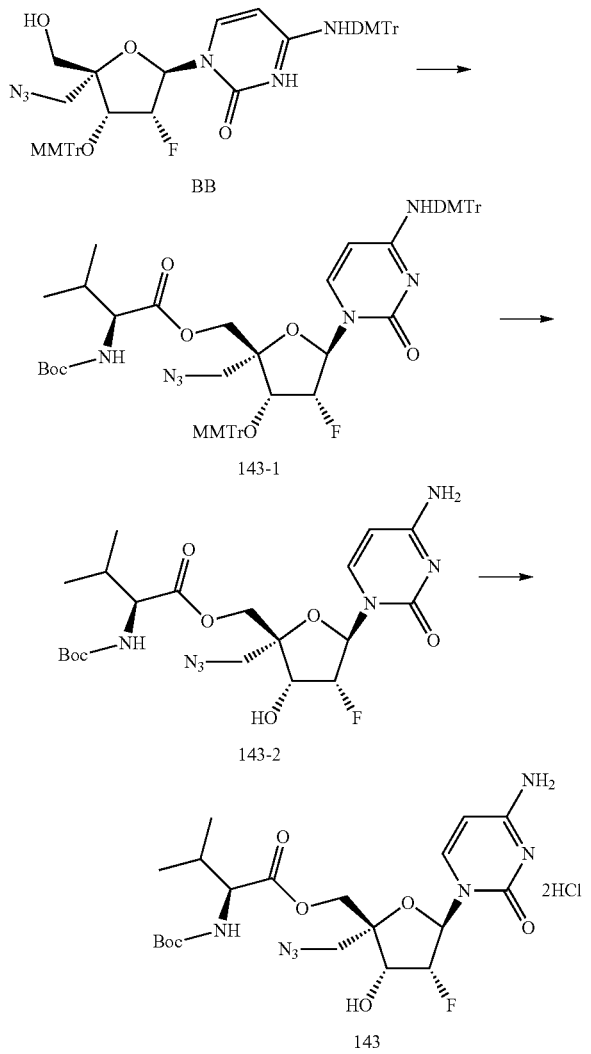

To a solution of N-Boc-L-Valine (620.78 mg, 2.86 mmol) and TEA (144.57 mg, 1.43 mmol) in anhydrous THF (2.5 mL) was added BB (250.00 mg, 285.73 μmol). The mixture was co-evaporated with pyridine and toluene to remove water. The residue was dissolved in THF (2.5 mL). DIPEA (369.28 mg, 2.86 mmol) was added, followed by addition of BOP-Cl (363.68 mg, 1.43 mmol) and 3-nitro-1H-1,2,4-triazole (162.95 mg, 1.43 mmol) at RT (18° C.). The mixture was stirred at RT for 12 h and then diluted with EA (40 mL). The solution was washed with brine, dried over anhydrous Na$_2$SO$_4$ and concentrated to dryness at low pressure. The residue was purified on a silica gel column (30% EA in PE) to give 143-1 (220 mg, crude) as a white foam.

143-1 (250.0 mg, 232.73 μmol) was dissolved in 80% CH$_3$COOH (30 mL). The solution was heated to 50° C. and stirred for 12 h. The reaction was quenched with MeOH, and the solution was concentrated to dryness. The residue was purified on a silica gel column (5% MeOH in DCM) to give 143-2 (80.00 mg, 68.82%) as a white foam.

143-2 (78.00 mg, 156.16 μmol) was dissolved in HCl/dioxane (1.5 mL) and EA (1.5 mL) at RT (19° C.). The mixture was stirred at RT for 30 mins. The solution was concentrated to dryness at low pressure. The residue was purified by prep-HPLC to give 143 (23 mg, 31.25%) as a white solid. ESI-MS: m/z 400.20 [M+H]$^+$, 799.36 [2M+H]$^+$.

Example 141

Compound 154

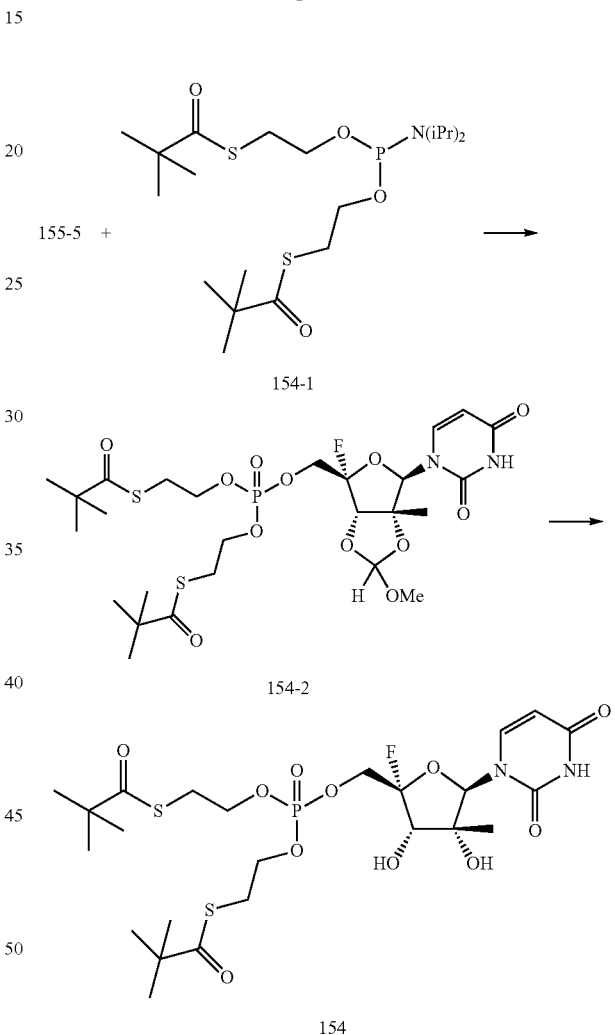

154-1 was prepared according to the procedure described in Lefebre et al. J. Med. Chem. (1995) 38:3941-3950, which is hereby incorporated by reference for the limited purpose of its description of the preparation of 154-1.

154-2 (0.33 g, 0.5 mmol) was prepared using a similar procedure to the one used to prepare 155-6 using 155-5 and 154-1. 154-2 was obtained as a white solid. Using a similar procedure to the one used to prepare 155, 154-2 was used to prepare 154 (130 mg). $^1$H-NMR (CDCl$_3$): 7.40 (d, 1H), 6.1 (s, 1H), 5.83 (d, 1H), 4.3 (t, 2H), 4.1-4.2 (m, 6H), 3.2 (t, 4H), 1.69 (s, 4H), 1.3 (s, 3H), 1.23 (s, 18H); $^{31}$P-NMR (CDCl$_3$): −2.4 ppm.

Example 142

Compound 155

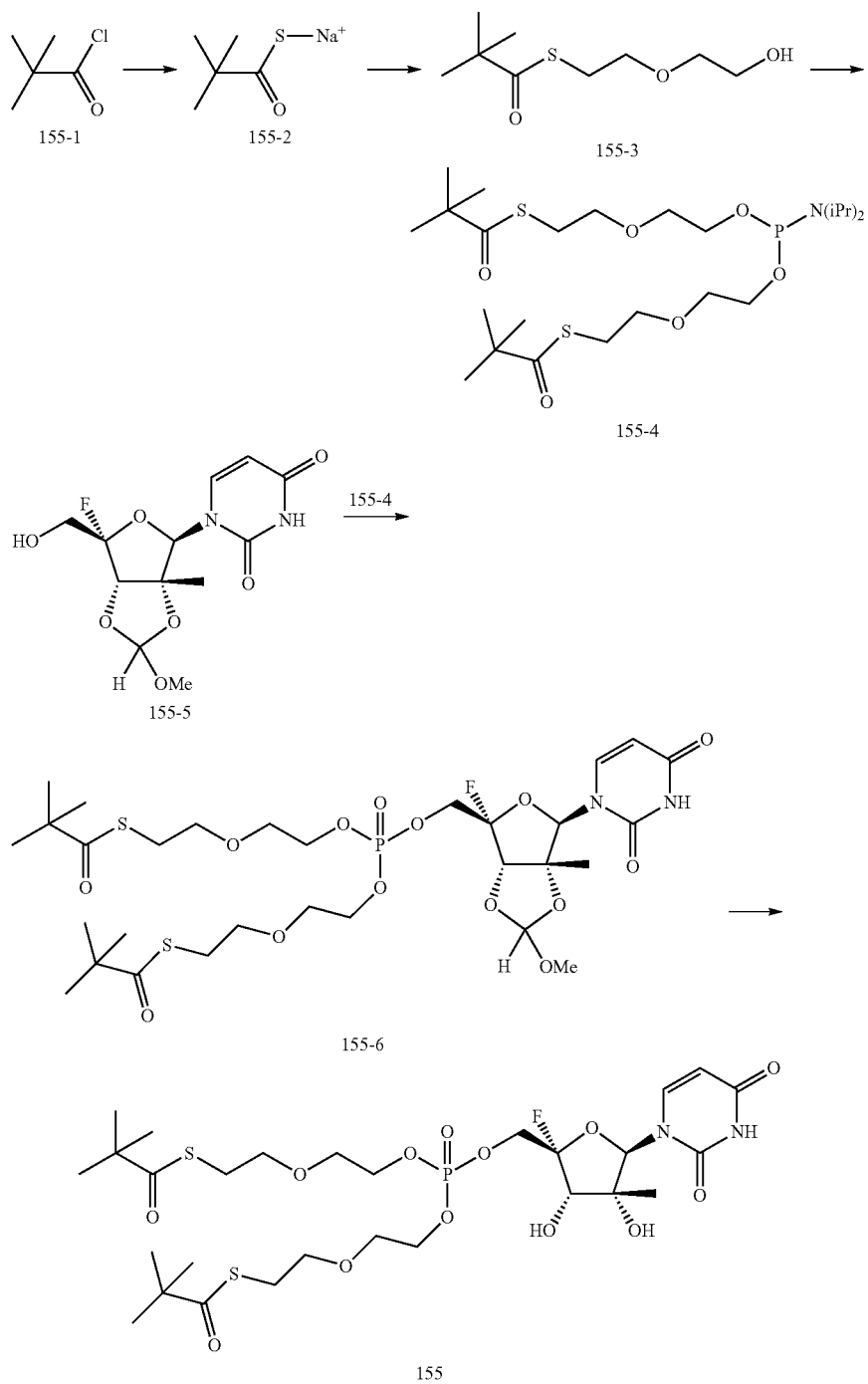

To a solution of sodium hydrosulfide (4.26 g, 76.0 mmol) in EtOH (100 mL) was added t-butyryl chloride (76.2 mmol; 9.35 mL) dropwise at 0° C., and the mixture was stirred at RT for 1 h. A solution of 2-(2-chloroethoxy)ethanol (57 mmol; 6.0 mL) and TEA (21 mL, 120 mmol) was added, and the mixture was heated at reflux for 60 h. The mixture was filtered, and then concentrated to a small volume. The residue was dissolved in EA, and then washed with water, sat. aq. NaHCO$_3$ and brine. The organic phase was dried over Na$_2$SO$_4$, filtered and concentrated in vacuo. The crude product (10.0 g) was isolated and 5 grams were purified by silica gel flash column chromatography using a gradient of 0 to 100% EA in hexane to give 155-3 (4.5 g, 22 mmol) as a clear, colorless oil. $^1$H-NMR (CDCl$_3$): 3.70-3.74 (m, 2H), 3.5-3.65 (m, 4H), 3.1 (t, 2H), 1.25 (s, 9H).

A solution 155-3 (4.5 g; 21.8 mmol) and triethylamine (6.7 mL, 87.2 mmol) in tetrahydrofuran (50 mL) was added dropwise over 1 h to a stirred solution of N,N-diisopropylphosphorodichloridite (2.0 mL, 10.9 mmol) in THF (50 mL) under argon at −78° C. The mixture was stirred at RT for 2 h, and then diluted with EA (200 mL). The mixture was washed with sat. aq. NaCl and dried over Na$_2$SO$_4$. After filtration, the filtrate was evaporated under reduced pressure to give a pale yellow oil. Purification by flash column chromatography using a gradient of EA (0-5%) in hexane containing 5% triethylamine afforded 155-4 (2.5 g, 4.25 mmol) as a clear, colorless oil. $^1$H-NMR (CDCl$_3$): 3.70-3.82 (m, 4H), 3.57-3.65 (m, 10H), 3.1 (t, 4H), 1.25 (s, 18H), 1.17 (t, 12H); $^{31}$P-NMR (CDCl$_3$): 148.0 ppm.

155-5 (285 mg, 0.9 mmol) and DCI (175 mg, 1.5 mmol) were coevaporated twice with ACN and then dissolved in ACN (5 mL). 155-4 (790 mg, 1.35 mmol) in ACN (4 mL) was added, and the reaction was monitored by TLC. After 15 mins, tert-butylhydroperoxide (0.5 mL of 5.5M solution in decane) was added, and the mixture was stirred for 10 mins. The mixture was diluted with EA (25 mL), washed with sat. aq. NaHCO$_3$ and sat. aq. NaCl solution, dried over Na$_2$SO$_4$, filtered and concentrated. Purification by flash column chromatography using a gradient of EA (0-100%) in hexane afforded 155-6 (0.17 g, 0.22 mmol) as a white solid. 155-6 was dissolved in 80% aq. HCOOH (5 mL). After 30 mins at RT, the solvent was removed and coevaporated twice with toluene. The residue was dissolved in methanol (10 mL) and TEA (0.2 mL) was added. After 2 mins at RT, the solvent was removed in vacuo. Purification by flash column chromatography using a gradient of methanol (0-15%) in DCM afforded 155 (90 mg). $^1$H-NMR (CDCl$_3$): 7.40 (d, 1H), 6.1 (s, 1H), 5.83 (d, 1H), 4.3 (t, 2H), 4.1-4.2 (m, 6H), 3.70-3.82 (m, 4H), 3.57-3.65 (m, 4H), 3.1 (t, 4H) 1.61 (s, 8H), 1.3 (s, 3H), 1.23 (s, 18H). $^{31}$P-NMR (CDCl$_3$): −1.55 ppm.

Example 143

Compound 156

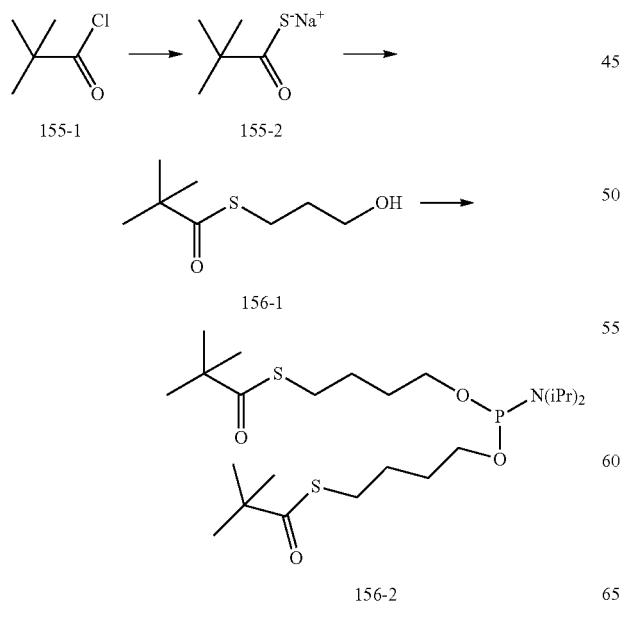

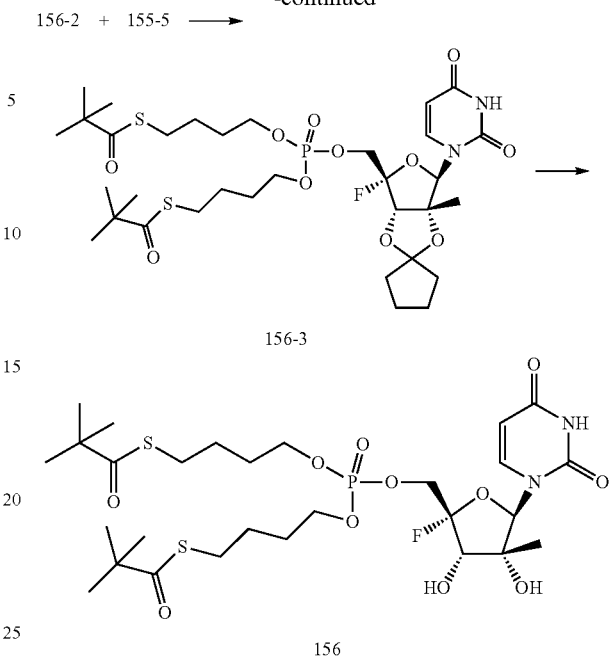

156-1 (6.0 g, 31.6 mmol) was prepared using a similar procedure to the one used to prepare 155-3 using 4-chlorobutanol. 156-1 was obtained as a clear, colorless oil. $^1$H-NMR (CDCl$_3$): 3.67 (s, 2H), 2.86 (m, 2H), 1.65 (m, 4H), 1.25 (s, 9H).

156-2 (2.14 g, 4.0 mmol) was prepared using a similar procedure to the one used to prepare 155-4. 156-2 was obtained as a clear, colorless oil. $^1$H-NMR (CDCl$_3$): 3.67 (m, 6H), 2.86 (t, 4H), 1.65 (m, 8H), 1.25 (s, 18H), 1.17 (t, 12H). $^{31}$P-NMR (CDCl$_3$): 143.7 ppm.

156-3 (0.23 g, 0.22 mmol) was prepared using a similar procedure to the one used to prepare 155-6 using 155-5 and 156-2. 156-3 was obtained as a white solid. Using a similar procedure to the one used to prepare 155, 156-3 was used to prepare 156 (170 mg). $^1$H-NMR (CDCl$_3$): 7.40 (d, 1H), 6.1 (s, 1H), 5.83 (d, 1H), 4.3 (t, 2H), 4.1-4.2 (m, 6H), 2.8 (t, 4H), 1.78 (m, 4H), 1.69 (s, 8H), 1.3 (s, 3H), 1.23 (s, 18H). $^{31}$P-NMR (CDCl$_3$): −1.56 ppm.

Example 144

Compound 161

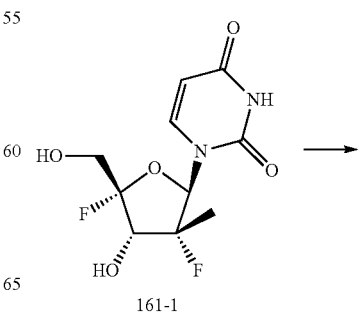

-continued

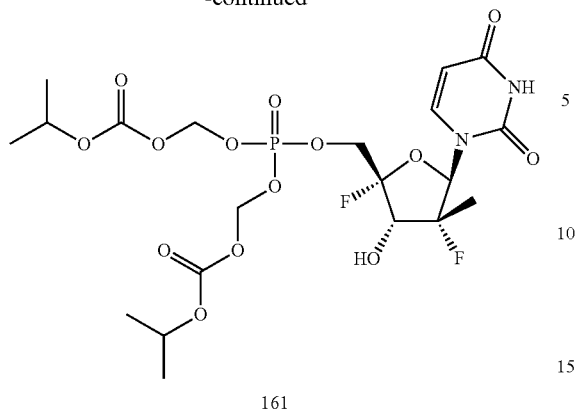

161

161-1 (109 mg, 0.39 mmol) and triethylammonium bis (isopropyloxycarbonyloxymethyl)phosphate (0.6 mmol, prepared from 195 mg of bis(isopropyloxycarbonyloxymethyl)phosphate and 85 μL of Et$_3$N) were rendered anhydrous by coevaporating with pyridine, followed by toluene. The residue was dissolved in anhydrous THF (3 mL) and cooled in an ice-bath. Diisopropylethyl amine (0.2 mL, 3 eq.), BopCl (190 mg, 2 eq.), and 3-nitro-1,2,4-triazole (81 mg, 2 eq.) were added, and the mixture was stirred at 0° C. for 90 mins. The mixture was diluted with EtOAc, washed with sat. aq. NaHCO$_3$ and brine, and dried (Na$_2$SO$_4$). Purification on silica gel column with CH$_2$Cl$_2$/i-PrOH (4-10% gradient) followed by RP-HPLC purification (A: 0.1% HCOOH in water, B: 0.1% HCOOH in MeCN) yielded 161 (28 mg, 12%). $^1$H-NMR (CDCl$_3$): δ 7.24 (d, 1H), 6.6 (br, 1H), 5.84 (d, 1H), 5.65-5.73 (m, 4H), 4.94 (m, 2H), 4.38 (m, 2H), 4.1 (b, 1H), 2.88 (d, 1H), 1.47 (d, 3H), 1.33 (m, 12H).

Example 145

Compound 157

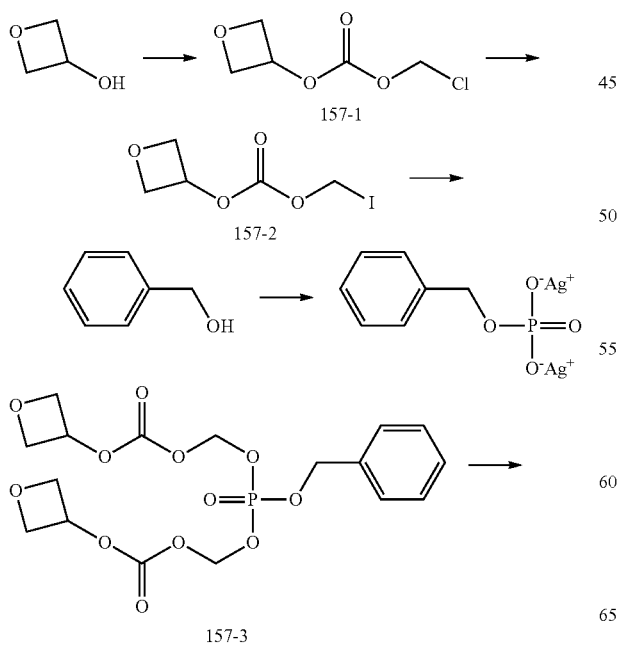

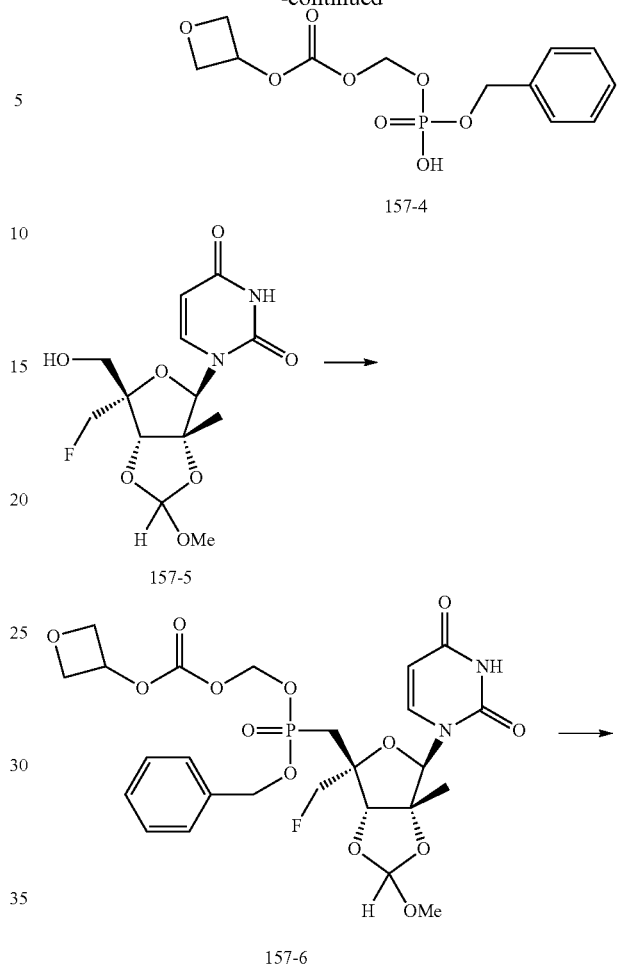

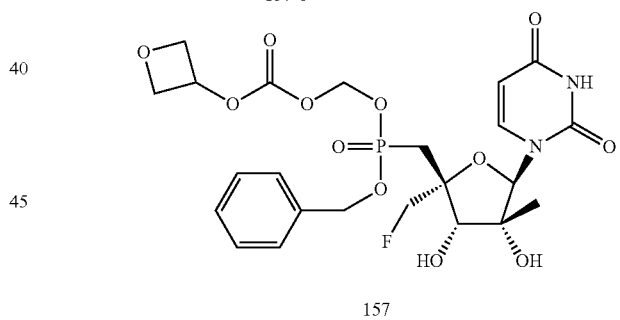

157

Compound 157-1 was prepared from commercially available 3-hydroxyoxetane (5.0 g) using the procedure described for preparing 54-2 (5.6 g). $^1$H-NMR (CDCl$_3$) δ 5.73 (s, 2H), 5.48-5.51 (m, 1H), 4.90 (d, 2H), 4.72 (d, 2H).

Compound 157-2 was prepared from 157-1 using the procedure described for preparing 54-3 (8.0 g). $^1$H-NMR (CDCl$_3$) δ 5.95 (s, 2H), 5.48-5.51 (m, 1H), 4.90 (d, 2H), 4.72 (d, 2H).

Benzylphosphate (silver salt) and 157-2 (8.0 g) were reacted as described for preparing 54-4 to yield purified 157-3 (1.92 g). $^1$H-NMR (CD$_3$CN): δ 7.39-7.42 (m, 5H), 5.62 (d, 4H), 5.39-5.42 (m, 2H), 5.15 (d, 2H), 4.80-4.83 (m, 4H), 4.56-4.60 (m, 4H). $^{31}$P-NMR (CD$_3$CN): δ −4.55 ppm.

Compound 157-3 (970 mg, 2.16 mmol) was dissolved in methanol containing triethylamine (0.3 mL, 2.16 mmol). After 3 h at R.T, the solvents were removed in vacuo to give crude 157-4 that was used without further purification.

Compound 157-5 (400 mg; 1.2 mmol) and 157-4 (900 mg, 2.16 mmol; 1.5×) were coevaporated with pyridine (2×) and toluene (2×), and then dissolved in THF (8 mL) at 0° C. Diisopropylethylamine (DIPEA) (0.82 mL; 4 eq.), bis(2-oxo-3-oxazolidinyl) phosphinic chloride (Bop-Cl) (0.6 g; 2 eq.), nitrotriazole (0.266 g, 2 eq.) were added. The mixture kept at 0° C. for 2 h. The mixture was diluted with EA (50 mL) and extracted with saturated sodium bicarbonate (2×50 mL) and dried over sodium sulfate. The solvents were removed in vacuo. The residue was purified by flash chromatography using a 10 to 100% gradient of EA in hexane to give purified 157-6 (175 mg, 0.6 mmol).

Purified 157-6 was dissolved in 80% aq. HCOOH (20 mL) and kept at 20° C. for 1 h. After cooling to RT, the solvent was removed in vacuo, and the residue coevaporated with toluene (3×25 mL). The residue was purified by flash chromatography using a 0 to 20% gradient of MeOH in DCM to give purified 157 (26 mg). ESI-LCMS: m/z 589.6 [M−H]⁻.

Example 146

Compound 158

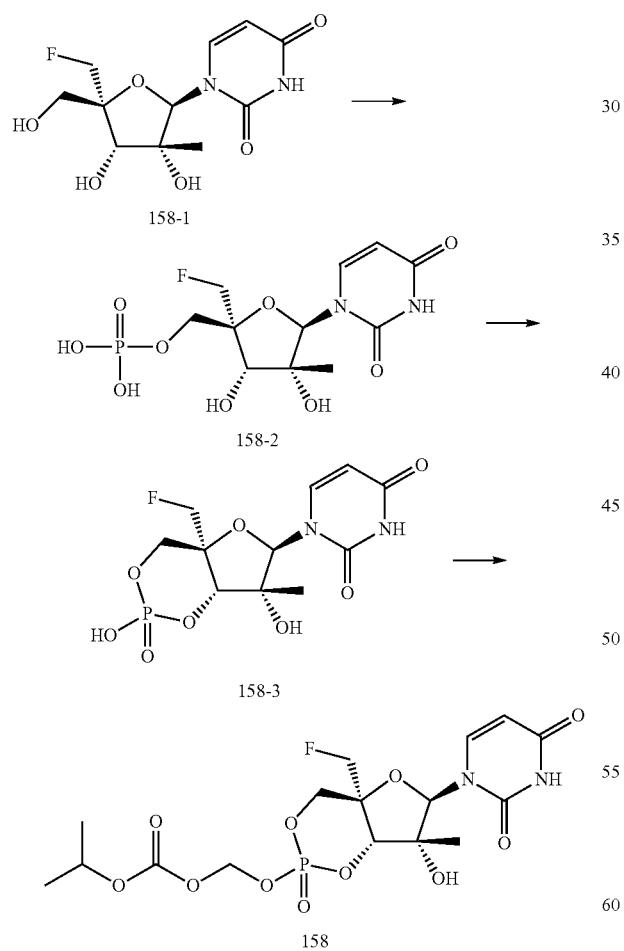

Nucleoside 158-1 (from Wuxi) (44 mg, 0.15 mmol) was dissolved in a mixture of trimethyl phosphate (2 mL) and dry pyridine (0.5 mL). The mixture was evaporated in vacuum for 15 mins at 42° C., than cooled to RT. N-Methylimidazole (0.027 mL, 0.33 mmol) was added followed by POCl₃ (0.027 mL, 0.3 mmol). The mixture was kept at RT. The reaction was monitored by LC/MS in 0-50% gradient. After 4 h, the reaction was complete. The reaction was quenched with 2M triethylammonium acetate buffer (2 mL), pH7.5 (TEAA). 158-2 was isolated on prep-HPLC (Phenomenex Synergi 4u Hydro-RP 250×21.2 mm) using a gradient of 0-30% ACN in 50 mM TEAA.

Compound 158-2 (triethylammonium salt; 45 mg, 0.1 mmol) was dried by repeated co-evaporation with dry pyridine (3×). 158-2 was dissolved in dry pyridine (1 mL) and the solution added dropwise into a boiling solution of diisopropylcarbodiimide (63 mg, 0.5 mmol) in pyridine (4 mL) over 2.5 h. The mixture was heated under reflux for 1 h. After being cooled to 25° C., the reaction was quenched with 2M TEAA buffer (2 mL) and kept at 25° C. for 1 h. The solution was concentrated to dryness, and the residual pyridine removed by coevaporated with toluene (3×2 mL). 158-3 was isolated on prep-HPLC (Phenomenex Synergi 4u Hydro-RP 250×21.2 mm) using a gradient of 0-30% ACN in 50 mM TEAA.

Compound 158-3 (triethylammonium salt; 26 mg, 0.045 mmol) was dissolved in dry DMF (0.5 mL) at RT under argon. To the stirred solution was added N,N-diisopropylethylamine (40 uL, 0.22 mmol) followed by chloromethyl isopropyl carbonate (35 mg, 0.22 mmol). The mixture was stirred at 65° C. for 18 h. The mixture was evaporated to dryness, and the residue was purified by silica column using a 0-15% gradient of MeOH in CH₂Cl₂. The fractions having 158 were pooled, and the mixture was concentrated to dryness to give 158 (2.3 mg). ESI-LCMS: m/z 467.5 [M−H]⁻.

Example 147

Compound 221

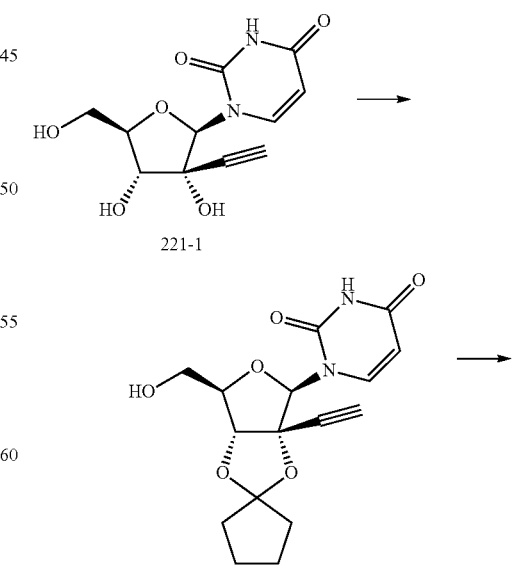

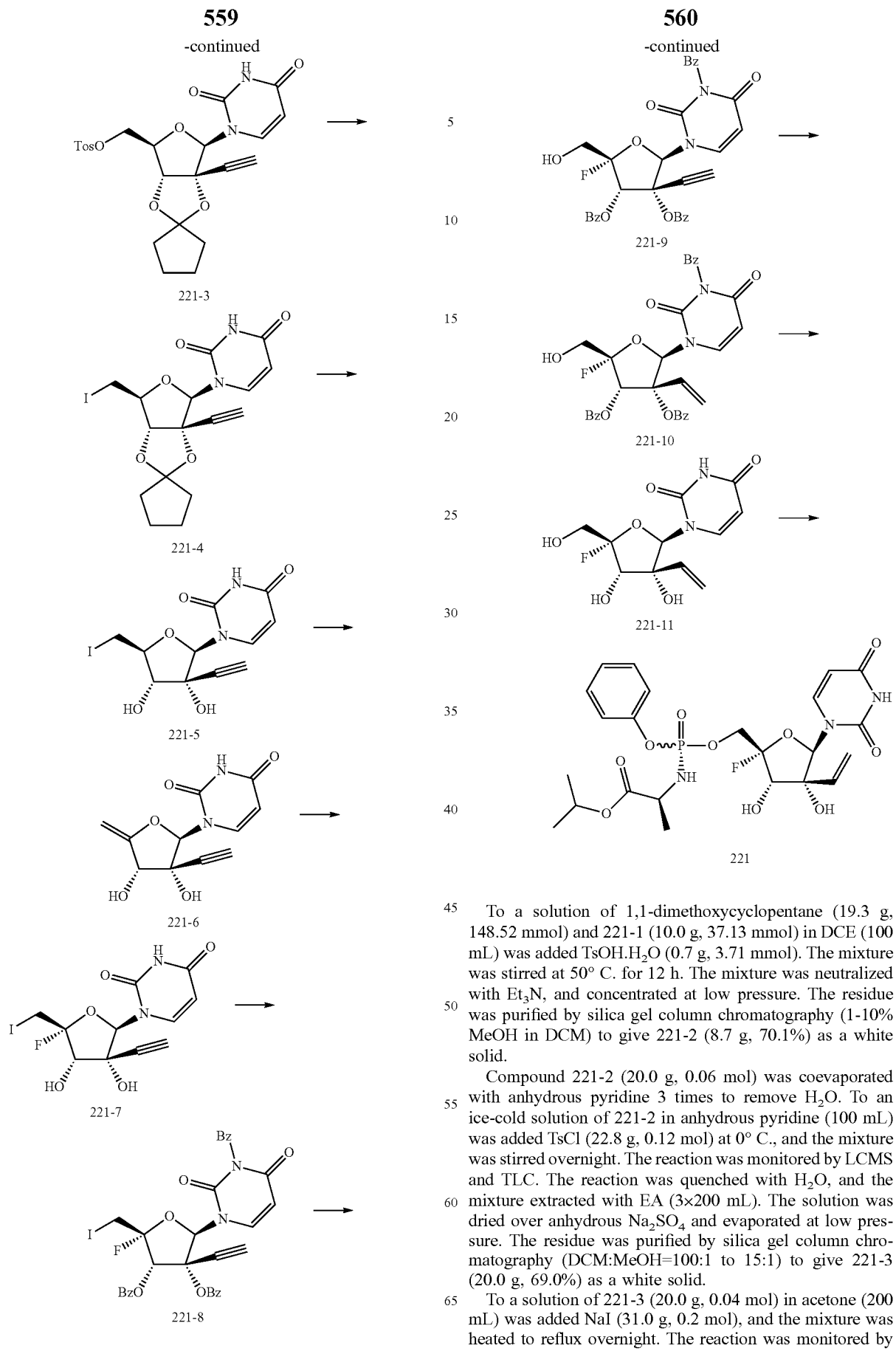

To a solution of 1,1-dimethoxycyclopentane (19.3 g, 148.52 mmol) and 221-1 (10.0 g, 37.13 mmol) in DCE (100 mL) was added TsOH·H$_2$O (0.7 g, 3.71 mmol). The mixture was stirred at 50° C. for 12 h. The mixture was neutralized with Et$_3$N, and concentrated at low pressure. The residue was purified by silica gel column chromatography (1-10% MeOH in DCM) to give 221-2 (8.7 g, 70.1%) as a white solid.

Compound 221-2 (20.0 g, 0.06 mol) was coevaporated with anhydrous pyridine 3 times to remove H$_2$O. To an ice-cold solution of 221-2 in anhydrous pyridine (100 mL) was added TsCl (22.8 g, 0.12 mol) at 0° C., and the mixture was stirred overnight. The reaction was monitored by LCMS and TLC. The reaction was quenched with H$_2$O, and the mixture extracted with EA (3×200 mL). The solution was dried over anhydrous Na$_2$SO$_4$ and evaporated at low pressure. The residue was purified by silica gel column chromatography (DCM:MeOH=100:1 to 15:1) to give 221-3 (20.0 g, 69.0%) as a white solid.

To a solution of 221-3 (20.0 g, 0.04 mol) in acetone (200 mL) was added NaI (31.0 g, 0.2 mol), and the mixture was heated to reflux overnight. The reaction was monitored by LCMS. The reaction was quenched with a sat. Na₂S₂O₃ solution. The solution was extracted with EA (3×200 mL). The organic layer was dried over anhydrous Na₂SO₄, and evaporated at low pressure. The residue was purified by silica gel column chromatography (DCM:MeOH=100:1 to 15:1) to give 221-4 (15.0 g, 83.3%) as a white solid.

Compound 221-4 (13.4 g, 30.16 mmol) was treated with HCOOH (80%) in H₂O at RT. The solution was stirred at 60° C. for 2 h. The mixture was concentrated at low pressure. The residue was purified by column chromatography (1%-10% MeOH in DCM) to give 221-5 (9.1 g, 80.0%) as a white solid.

To a solution of 221-5 (5.0 g, 13.22 mmol) in anhydrous CH₃CN/THF (50 mL, 1:1, v:v) was added DBU (6.0 g, 39.66 mmol) at RT. The solution was stirred at 50° C. for 1.5 h. The reaction was quenched with HCOOH at 0° C., and then concentrated at low pressure. The residue was purified by column chromatography (50%-70% EA in PE) to give 221-6 (3.3 g, 48.1%) as a white solid.

To an ice-cold solution of 221-6 (2.1 g, 8.39 mmol) in anhydrous MeCN (21 mL) was added NIS (2.4 g, 10.49 mmol) and TEA.3HF (1.0 g, 6.29 mmol) under N₂. The mixture was stirred at RT for 1 h. The reaction was quenched with sat. NaHCO₃ and sat. Na₂SO₃ solution, and extracted with EA (3×100 mL). The organic phase was dried over anhydrous Na₂SO₄, and evaporated to dryness at low pressure. The residue was purified on a silica gel column (30%-50% EA in PE) to give 221-7 (1.3 g, 39.3%) as a light yellow solid.

To a stirred solution of 221-7 (3.2 g, 8.08 mmol) in anhydrous DCM (32 mL) was added DMAP (2.5 g, 20.20 mmol) and Et₃N (2.5 g, 24.24 mmol) at RT. The mixture was treated with BzCl (3.7 g, 26.66 mmol) at 0° C. and then stirred at RT overnight. The reaction was quenched with water, and extracted with EA (3×60 mL). The organic phase was concentrated at low pressure, and the residue was purified by column chromatography (20%-30% EA in PE) to give 221-8 (1.8 g, 31.6%) as a white solid.

Bu₄NOH (8.0 g, 13.74 mL, 55% in H₂O) was adjusted to pH=3-4 with TFA, and then cooled to RT. To a solution of 221-8 (600 mg, 0.85 mmol) in DCM (10 mL) was added the Bu₄NOH solution and m-CPBA (917 mg, 4.25 mmol, 80%) at RT. The mixture was stirred at 25° C. for 48 h and then washed with a sat. NaHCO₃ solution. The organic layer was directly passed through basic Al₂O₃ column, and the solvent was concentrated at low pressure. The residue was purified by a silica gel column (20%-30% EA in PE) to give 221-9 (123 mg, 24.3%) as a white solid.

To a solution of 221-9 (300 mg, 0.50 mmol) in EA/hexane (20 mL, 1:1, v:v) was added Lindlar catalyst (200 mg) under N₂. The mixture was stirred under H₂ (40 Psi) at 2° C. for 1.5 h. The suspension was filtered, and the filtrate was treated with Lindlar catalyst (200 mg) under N₂, and stirred under H₂ (40 Psi) at 25° C. for 1.5 h. The mixture was filtered, and the filtrate was concentrated at low pressure to give crude 221-10 (287 mg) as a white solid.

Compound 221-10 (287 mg, 0.48 mmol) was dissolved in NH₃/MeOH (30 mL, 7 M). The mixture was stirred at RT for 24 h under N₂ and then concentrated at low pressure. The residue was purified by prep-HPLC (0.1% HCOOH in water and MeCN) to give 221-11 (50 mg, 34.7% over two steps) as a white solid. ¹H-NMR (CD₃OD, 400 MHz) δ=7.86 (d, J=8.0 Hz 1H), 6.26 (s, 1H), 5.62-5.86 (m, 1H), 5.49 (d, J=17.1 Hz, 1H), 5.30 (d, J=10.5 Hz, 1H), 4.41 (d, J=19.3 Hz, 1H), 3.71-3.86 (m, 1H).

Compound 221-11 (113 mg, 0.39 mmol) was co-evaporated with toluene 3 times to remove H₂O. To a stirred solution of 221-11 (113 mg, 0.39 mmol) in a mixture of MeCN (0.5 mL) and NMI (320 mg, 3.90 mmol) was added a solution of 73-C (256 mg, 0.66 mmol) in MeCN (0.5 mL) at 0° C. The mixture was stirred at RT overnight and then concentrated at low pressure. The residue was purified on a silica gel column (5% MeOH in DCM) to give crude 221, which purified by prep-HPLC (0.1% HCOOH in water and MeCN) to give 221 (45 mg, 20.1%) as a white solid. ESI-MS: m/z 538.2 [M-F]⁺ ESI-MS: m/z 580.2 [M+Na]⁺.

Example 148

Compound 222

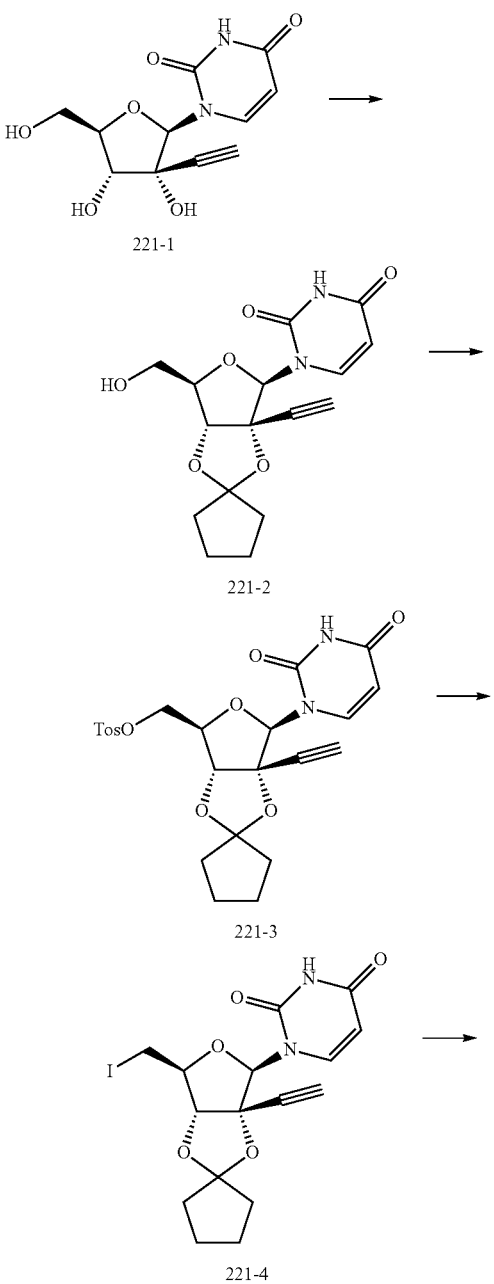

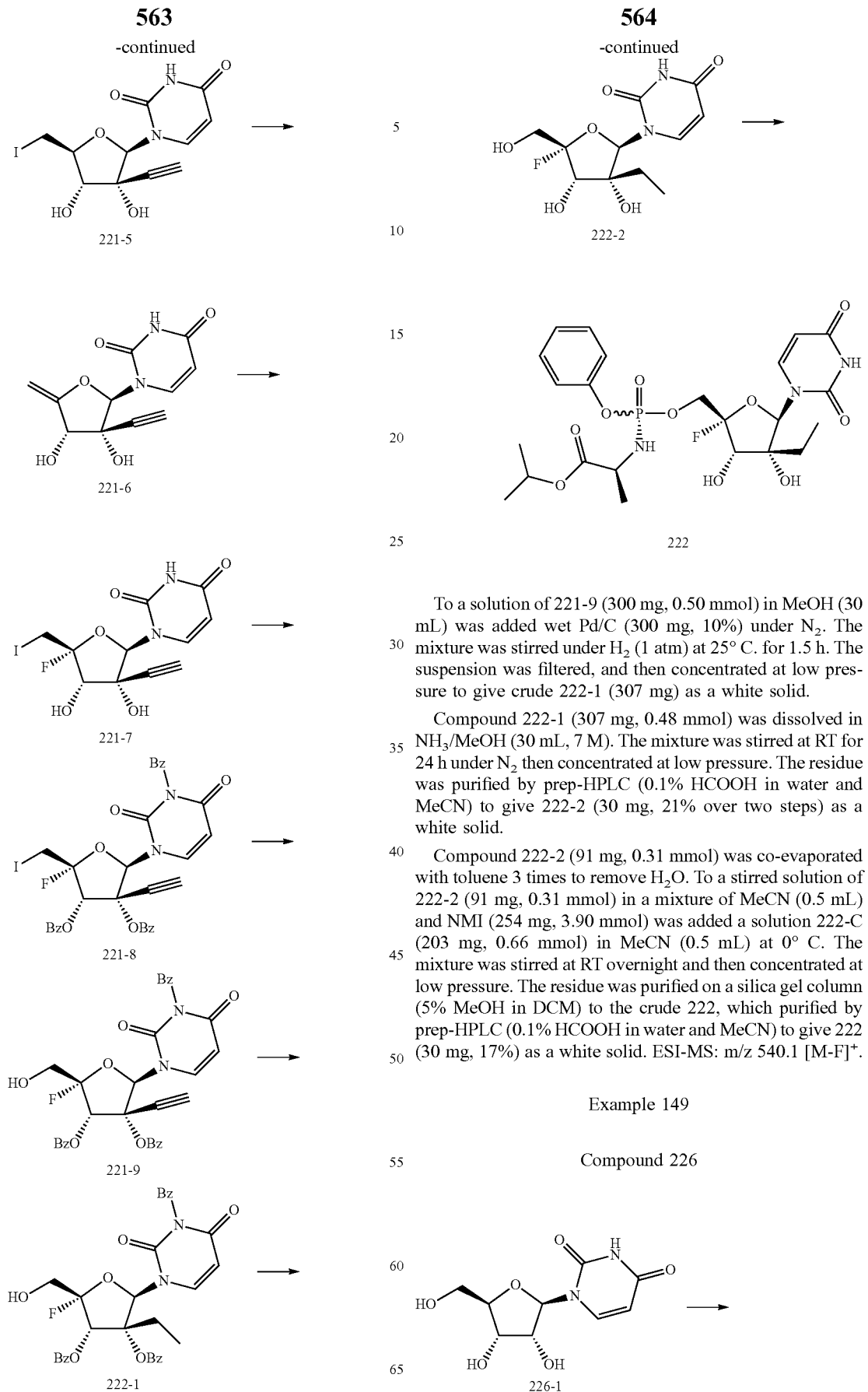

To a solution of 221-9 (300 mg, 0.50 mmol) in MeOH (30 mL) was added wet Pd/C (300 mg, 10%) under $N_2$. The mixture was stirred under $H_2$ (1 atm) at 25° C. for 1.5 h. The suspension was filtered, and then concentrated at low pressure to give crude 222-1 (307 mg) as a white solid.

Compound 222-1 (307 mg, 0.48 mmol) was dissolved in $NH_3$/MeOH (30 mL, 7 M). The mixture was stirred at RT for 24 h under $N_2$ then concentrated at low pressure. The residue was purified by prep-HPLC (0.1% HCOOH in water and MeCN) to give 222-2 (30 mg, 21% over two steps) as a white solid.

Compound 222-2 (91 mg, 0.31 mmol) was co-evaporated with toluene 3 times to remove $H_2O$. To a stirred solution of 222-2 (91 mg, 0.31 mmol) in a mixture of MeCN (0.5 mL) and NMI (254 mg, 3.90 mmol) was added a solution 222-C (203 mg, 0.66 mmol) in MeCN (0.5 mL) at 0° C. The mixture was stirred at RT overnight and then concentrated at low pressure. The residue was purified on a silica gel column (5% MeOH in DCM) to the crude 222, which purified by prep-HPLC (0.1% HCOOH in water and MeCN) to give 222 (30 mg, 17%) as a white solid. ESI-MS: m/z 540.1 [M-F]$^+$.

Example 149

Compound 226

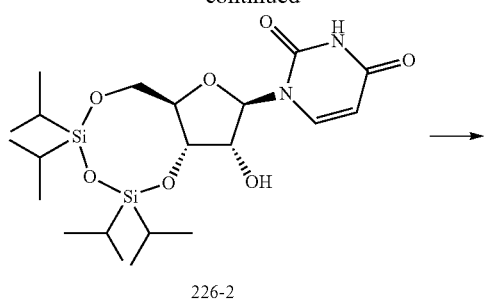
226-2
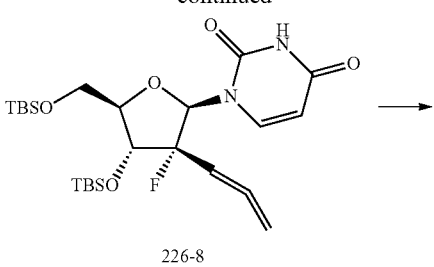
226-8
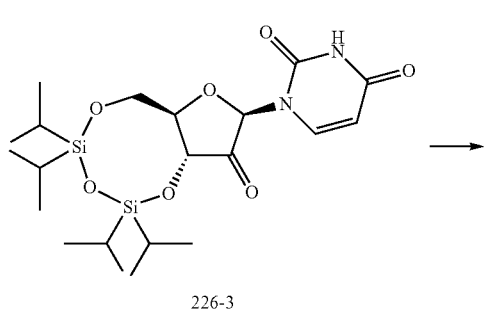
226-3
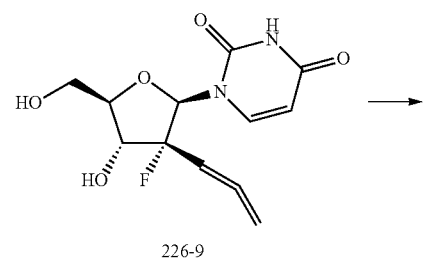
226-9
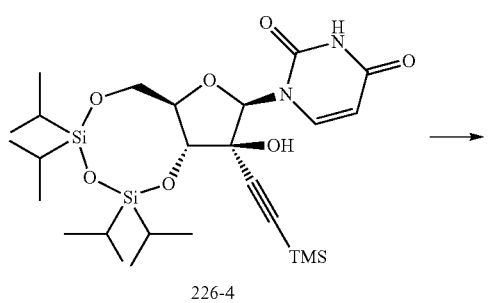
226-4
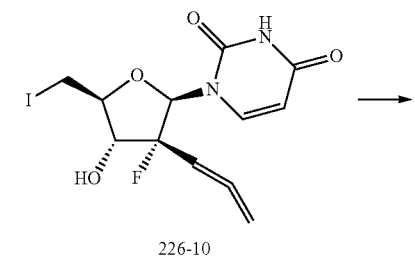
226-10
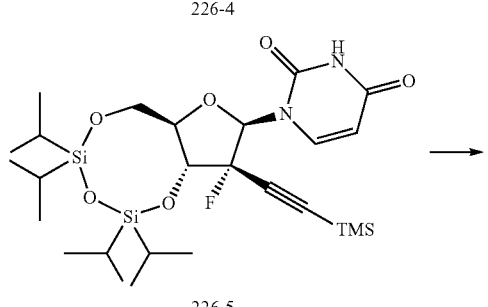
226-5
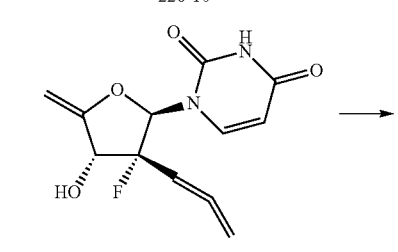
226-11
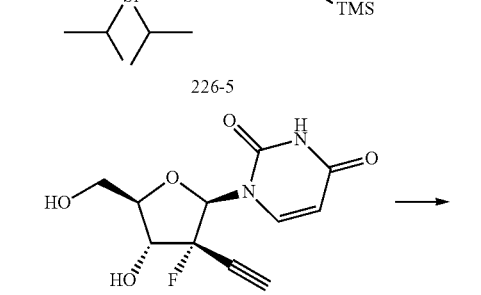
226-6
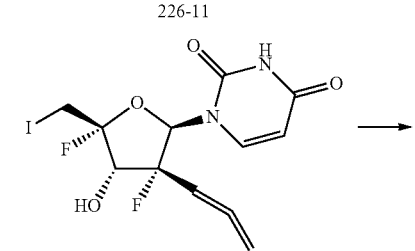
226-12
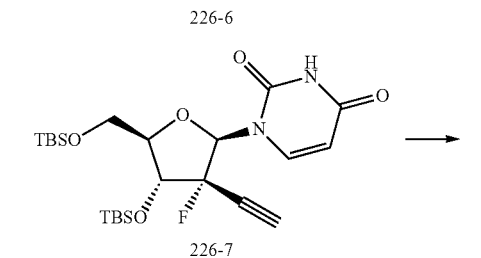
226-7
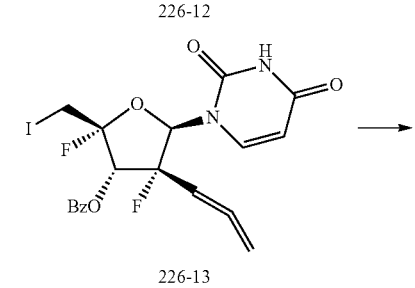
226-13

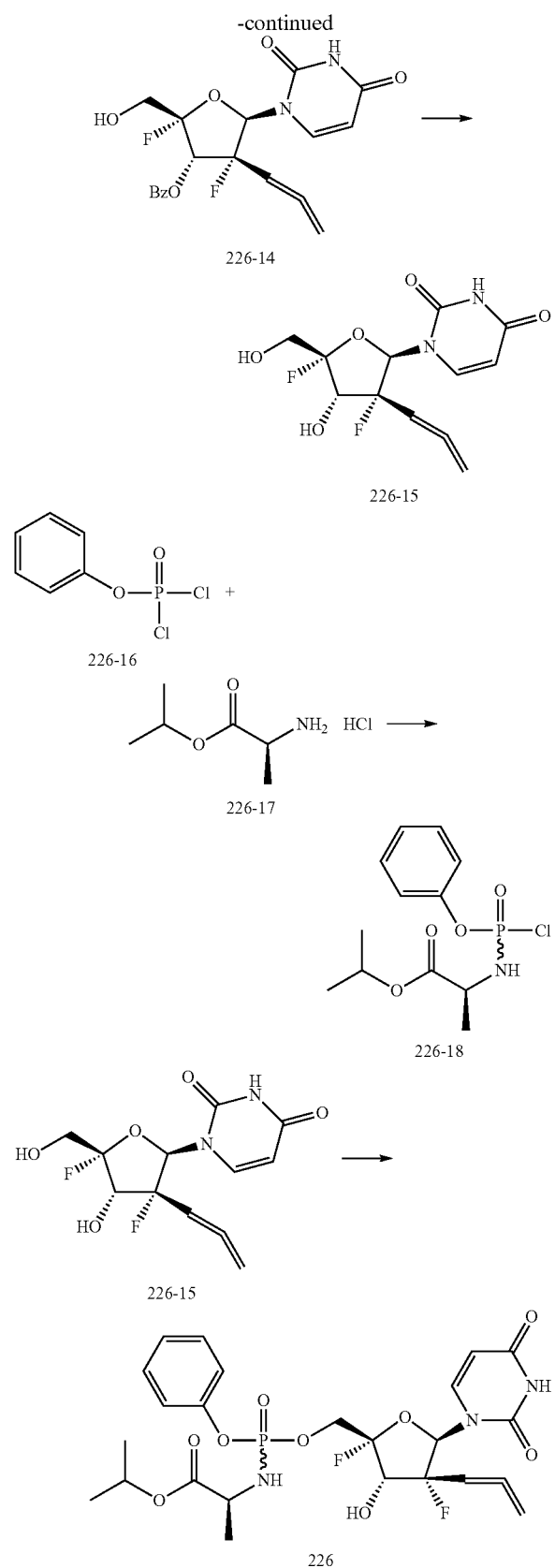

To an ice cooled solution of 226-1 (50 g, 204.9 mmol) in dry Py (400 mL) was added TIPDSCl (70.78 g, 225.4 mmol) dropwise. The mixture was stirred at RT for 16 h, and then concentrated at low pressure. The residue was purified by chromatography using 20% EA in PE to generate 226-2 (111.5 g, 100%) as a white solid.

To a solution of 226-2 (50 g, 103 mmol) in anhydrous $CH_3CN$ (400 mL) was added IBX (43 g, 153 mmol) at RT. The mixture was refluxed overnight and monitored by TLC (PE:EA=1:1). The precipitate was filtered off, and the filtrate was concentrated to give the crude 226-3 (50 g, 99%) as a white solid.

To a solution of trimethylsilylacetylene (20 g, 200 mmol) in anhydrous THF (400 mL) was added dropwise n-BuLi (80 mL, 200 mL) at −78° C. The mixture was stirred at −78° C. for 30 mins, and then warmed to R.T for 10 mins. Compound 226-3 (30 g, 60 mmol) in THF (100 mL) was added to the mixture dropwise at −78° C. The mixture was stirred at −78° C. for 1 h and then slowly warmed to RT. The mixture was stirred for 20 mins, and then the reaction was quenched with a sat. $NH_4Cl$ solution at −78° C. The mixture was diluted with EA. The organic phase was washed with brine, dried over anhydrous $Na_2SO_4$, and concentrated at low pressure. The residue was purified by silica gel column chromatography (15% EA in PE) to give 226-4 as a white solid (14 g, 50%).

Compound 226-4 (14 g, 24 mmol) was dissolved in anhydrous toluene (100 mL) under $N_2$ and cooled to −78° C. DAST (19 g, 120 mmol) was added dropwise at −78° C. and stirring was continued for 1.5 h. The mixture was diluted with EA and poured into a sat. $NaHCO_3$ solution. The organic layer was washed with brine, dried over anhydrous $Na_2SO_4$, and concentrated at low pressure. The residue was purified by silica gel chromatography (20% EA in PE) to give 226-5 as a white solid (12 g, 81%).

A mixture of 226-5 (12 g, 20 mmol) and $NH_4F$ (11 g, 30 mmol) in MeOH (150 mL) was refluxed for 2 h. After cooling to R.T, the mixture was concentrated at low pressure, and the residue was purified by silica gel column chromatography (5% MeOH in DCM) to give 226-6 (3.1 g, 58%) as a white solid.

To a solution of 226-6 (3.1 g, 11.6 mmol) in dry Py (50 mL) was added imidazole (3.1 g, 46.4 mmol) and TBSCl (5.2 g, 34.8 mmol). The mixture was stirred at 50-60° C. for 3 h. The mixture was concentrated at low pressure, and the residue was dissolved in EA (100 mL). The solution was washed with brine, dried over anhydrous $Na_2SO_4$, and concentrated at low pressure. The residue was purified by silica gel chromatography (20% EA in PE) to give 226-7 as a white solid (5 g, 86%).

To a solution of 226-7 (4.5 g, 9 mmol) in 1,4-dioxane (45 mL) was added CuBr (643 mg, 4.5 mmol), dicyclohexylamine (3.3 g, 18 mmol) and paraformaldehyde (675 mg, 22.5 mmol). The mixture was refluxed for 24 h and then cooled to RT. The reaction was quenched with a sat. $NH_4Cl$ solution. The mixture was extracted with EA (3×100 mL). The organic layer was washed with brine, dried over anhydrous $Na_2SO_4$, and concentrated at low pressure. The residue was purified by silica gel column chromatography (15% EA in PE) to give 226-8 as a white solid (2.0 g, 43%).

A mixture of 226-8 (2 g, 4 mmol) and $NH_4F$ (2.2 g, 60 mmol) in MeOH (20 mL) was refluxed overnight. After cooling to RT, the mixture was concentrated at low pressure, and the residue was purified by silica gel column chromatography (5% MeOH in DCM) to give 226-9 (946 mg, 83%) as a white solid.

To a stirred suspension of 226-9 (946 mg, 3.33 mmol), $PPh_3$ (1.3 g, 5 mmol), imidazole (453 mg, 6.66 mmol) and pyridine (3 mL) in anhydrous THF (12 mL) was added a solution of I$_2$ (1 g, 4.33 mmol) in THF (4 mL) dropwise at 0° C. The mixture was warmed to RT and stirred for 16 h. The reaction was quenched with a sat. Na$_2$S$_2$O$_3$ aq. solution and extracted with EA (3×60 mL). The organic layer was dried over Na$_2$SO$_4$ and concentrated at low pressure. The residue was purified on a silica gel column (2% MeOH in DCM to 5% MeOH in DCM) to afford 226-10 (2.1 g, crude) as a white solid.

To a solution of 226-10 (2.1 g, 5.3 mmol) in THF (15 mL) was added DBU (15 g, 100 mmol) and the mixture stirred for 30 mins. The mixture was diluted with EA and neutralized with acetic acid. The solution was washed with brine, dried over anhydrous Na$_2$SO$_4$, and concentrated at low pressure. The residue was purified by silica gel column chromatography (1.5% MeOH in DCM) to give 226-11 as a white solid (800 mg, 90%).

To an ice-cooled solution of 226-11 (800 mg, 3 mmol) in dry MeCN (1.5 mL) was added NEt$_3$.3HF (484 mg, 3 mmol) and NIS (1.68 g, 7.5 mmol). The mixture was stirred at RT for 30 mins., and the reaction was monitored by LCMS. The reaction was quenched with sat. Na$_2$S$_2$O$_3$ and sat. NaHCO$_3$ solution, and extracted with EA (3×50 mL). The organic layer was dried over anhydrous Na$_2$SO$_4$, and concentrated at low pressure. The residue was purified by a silica gel column (25% EA in PE) to afford 226-12 (850 mg, 68%) as a white solid.

To a solution of 226-12 (850 mg, 2 mmol) in dry DCM (10 mL) was added DMAP (488 mg, 4 mmol) and BzCl (422 mg, 3 mol). The mixture was stirred for 4-5 h at RT, and the reaction was monitored by LCMS. The mixture was diluted with CH$_2$Cl$_2$ (40 mL), and washed with a sat. NaHCO$_3$ solution. The organic layer was dried over anhydrous Na$_2$SO$_4$, and filtered. The filtrate was evaporated at low pressure, and the residue was purified by silica gel column chromatography (20% EA in PE) to give 226-13 (900 mg, 87%) as a white foam.

Tetra-butylammonium hydroxide (21 mL as 54-56% aqueous solution, 42 mmol, 24 eq.) was adjusted with TFA to pH~4 (~3.5 mL), and the solution was treated with a solution of 226-13 (900 mg, 1.7 mmol) in DCM (21 mL). m-Chloroperbenzoic acid (2.1 g, 60-70%, ~8.75 mmol, ~5 eq.) was added portionwise under vigorous stirring, and the mixture was stirred overnight. The mixture was diluted with CH$_2$Cl$_2$ (30 mL), and washed with a saturated NaHCO$_3$ solution. The organic layer was washed with brine, dried over anhydrous magnesium sulfate and concentrated under reduced pressure. The residue was purified by column chromatography in (40-70% EA in PE) to give 226-14 as an oil. The residue was purified by TLC (50% EA in PE) to give pure 226-14 (350 mg 50%).

Compound 226-14 (350 mg, 0.86 mg) was treated with 7N NH$_3$ in MeOH (15 mL). The mixture was stirred for 2-3 h and monitored by TLC. The mixture was concentrated at low pressure, and the residue was purified by silica gel column chromatography (5% isopropanol in DCM) to give 226-15 (250 mg, 96%) as a white solid. $^1$H NMR (CD$_3$OD, 400 M Hz) δ=7.75 (d, J=7.9 Hz, 1H), 6.60-6.35 (m, 1H), 5.72 (d, J=8.2 Hz, 1H), 5.37-5.25 (m, 1H), 5.17-5.06 (m, 1H), 5.04-4.94 (m, 1H), 4.59-4.29 (m, 1H), 3.87-3.70 (m, 2H).

To a stirred solution of 226-16 (3.79 g, 18 mmol) and 226-17 (3 g, 18 mmol) in anhydrous DCM (60 mL) was added with a solution of TEA (4 g, 39 mmol) in DCM (40 mL) dropwise at –78° C., and the mixture was stirred for 2 h. The mixture was concentrated at low pressure, and the residue was dissolved in methyl-butyl ether. The precipitate was removed by filtration, and the filtrate was concentrated to give the crude product. The residue was purified by dry column chromatography (anhydrous DCM) to give pure 226-18 as a colorless oil (3 g, 54%).

Compound 226-15 (200 mg, 0.66 mmol) was coevaporated with toluene 3 times to remove H$_2$O. Compound 226-15 was treated with MeCN (1.5 mL) and NMI (541 mg, 6.6 mmol). The mixture was stirred at RT, and then 226-18 (403 mg, 1.32 mmol) in MeCN (0.5 mL) was added. The residue was purified by a silica gel column (5% iPrOH in DCM) to give the crude product, which was purified by HPLC (0.1% HCOOH in water and MeCN) to give 226 (33 mg, 9%). ESI-LCMS: m/z 594 [M+Na]$^+$.

Example 150

COMPOUNDS 265 and 266

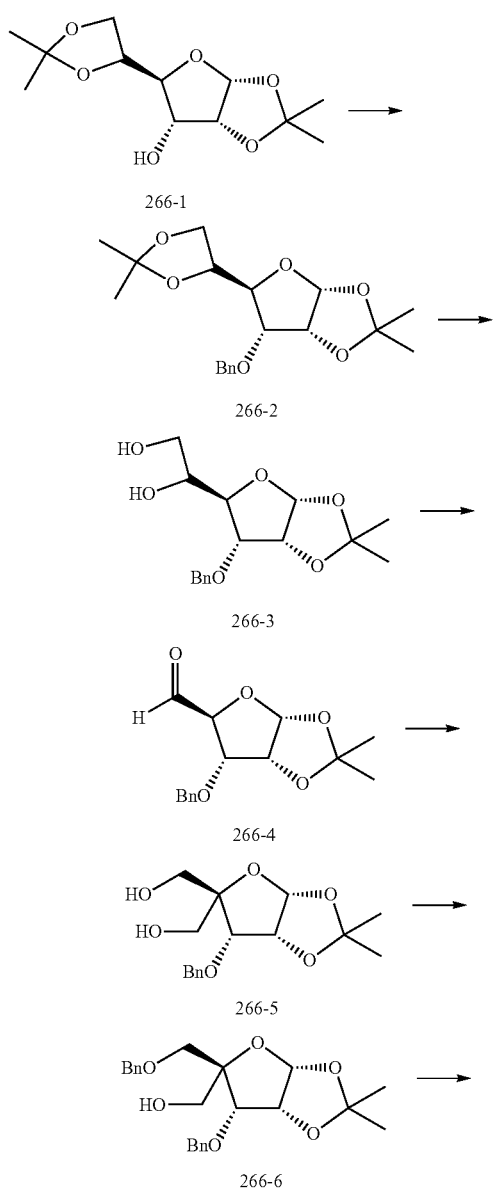

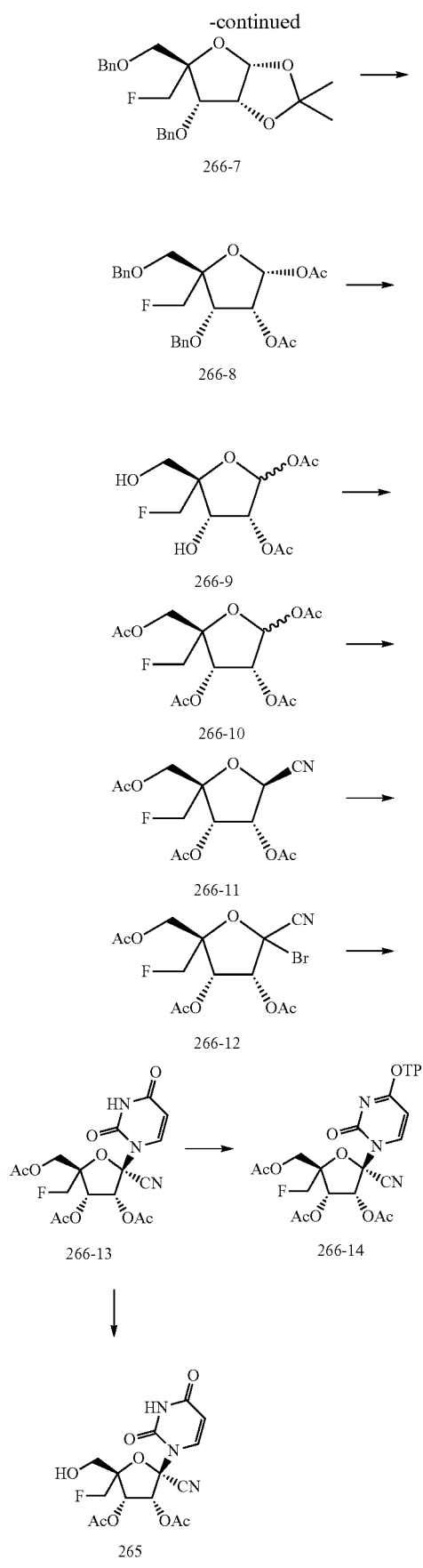

266-7

266-8

266-9

266-10

266-11

266-12

266-13

266-14

265

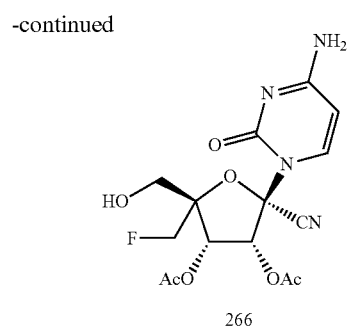

266

Into a 2000-mL round-bottom flask, was placed a solution of 266-1 (100 g, 384.20 mmol, 1.00 eq.) in N,N-dimethylformamide (1000 mL) at RT. NaH (11.8 g, 491.67 mmol, 1.20 eq.) was added in several batches and the mixture was stirred at 0° C. for 0.5 h. (bromomethyl)benzene (78.92 g, 461.44 mmol, 1.20 eq.) was added at 0° C. and the solution was stirred overnight at RT. The reaction was quenched with water. The solution was diluted with EA (2000 mL), washed with aq. NaCl (3×500 mL), dried over anhydrous sodium sulfate, filtered and concentrated under reduced pressure. The crude product was purified by a silica gel column with EA:PE (1:10) to yield 266-2 (105 g, 78%).

Into a 1000-mL round-bottom flask, was placed 266-2 (100 g, 285.38 mmol, 1.00 eq.), acetic acid (300 mL) and water (100 mL). The solution was stirred overnight at RT. The mixture was then diluted with EA (2000 mL), washed with aq. NaCl (2×500 mL) and aq. sodium bicarbonate (3×500 mL), dried over anhydrous sodium sulfate, filtered and concentrated under reduced pressure. Crude 266-3 (64 g) was obtained as light yellow oil. ESI MS m/z: 333 [M+Na]+.

Into a 5000-mL round-bottom flask, was placed a solution of 266-3 (140 g, 451.11 mmol, 1.00 eq.) in MeOH (500 mL). A solution of sodium periodate (135.2 g, 632.10 mmol, 1.40 eq.) in water (1000 mL) was added. The solution was stirred at RT for 1 h, then diluted with EA (2000 mL), washed with sat. NaCl solution (3×500 mL), dried over anhydrous sodium sulfate, filtered and concentrated under reduced pressure. The solid was dried in an oven under reduced pressure to yield crude 266-4 (97 g) as yellow oil Into a 3000-mL round-bottom flask, was placed a solution of 266-4 (100 g, 359.32 mmol, 1.00 eq.) in tetrahydrofuran (500 mL) at RT. Water (500 mL) was added. To the mixture was added a NaOH solution (600 mL, 2 N in water) at 0° C. followed by aq. formaldehyde (240 mL, 37%). The solution was stirred overnight at RT. The mixture was diluted with EA (1500 mL), washed with sat. NaCl solution (3×500 mL), dried over anhydrous sodium sulfate, filtered and concentrated under reduced pressure. The crude product was purified by a silica gel column with EA:PE (1:1) to give 266-5 (52.5 g, 47%) as a white solid. ESI MS m/z: 333 [M+Na]+.

Into a 3000-mL round-bottom flask, was placed a solution of 266-5 (76 g, 244.89 mmol, 1.00 eq.) in acetonitrile (1500 mL) at RT. NaH (6.76 g, 281.67 mmol, 1.15 eq.) was added in several batches at 0° C. The solution was stirred at 0° C. for 15 mins, then (bromomethyl)benzene (48.2 g, 281.82 mmol, 1.15 eq.) was added. The solution was stirred overnight at RT. The reaction was quenched with water, diluted with EA (3000 mL), washed with aq. NH4Cl (3×500 mL), dried over anhydrous sodium sulfate, filtered and concentrated under reduced pressure. The crude product was purified by a silica gel column with EA:PE (1:5) to yield 266-6 (50 g, 51%) as a yellow oil. ESI MS m/z: 423 [M+Na]+.

Into a 250-mL round-bottom flask, was placed a solution of diethylaminosulfur trifluoride (6.6 mL, 2.00 eq.) in toluene (10 mL) at RT. 266-6 (10 g, 24.97 mmol, 1.00 eq.) in toluene (120 mL) was added at 0° C. The solution was stirred for 3 h at 60° C. in an oil bath. The mixture was cooled to 0° C., diluted with EA (300 mL), washed with sat. NaCl solution (3×50 mL), dried over anhydrous sodium sulfate, filtered and concentrated under reduce pressure. The crude product was purified by a silica gel column with EA:PE (1:5) ti give 266-7 (5000 mg, 50%) as a yellow oil. ESI MS m/z: 425 [M+Na]$^+$.

Into a 250-mL 3-necked round-bottom flask purged and maintained with an inert atmosphere of $N_2$, was placed 266-7 (10 g, 23.61 mmol, 1.00 eq., 95%) in acetic acid (80 mL). Acetic anhydride (6 mL) and sulfuric acid (0.05 mL) were added. The solution was stirred for 2 h at RT. The mixture was then diluted with EA (500 mL), washed with water (3×200 mL) and aq. sodium bicarbonate (3×200 mL), dried over anhydrous sodium sulfate, filtered and concentrated under reduced pressure. The crude product was purified by a silica gel column with EA:PE (1:10-1:5) to yield 266-8 (6 g, 54%) as a yellow oil. ESI MS m/z: 469 [M+Na]$^+$.

Into a 50-mL round-bottom flask purged, was placed a solution of 266-8 (4 g, 8.96 mmol, 1.00 eq.), 10% Pd—C catalyst (4 g) in MeOH/DCM (25 mL/25 mL). To this mixture was introduced $H_2$ (gas) in, ~3 atmospheric pressure. The solution was stirred for 48 h at RT. The solids were collected by filtration, and the solution was concentrated under reduced pressure to give 266-9 (0.7 g, 29%) of as a colorless oil.

Into a 25-mL round-bottom flask, was placed 266-9 (2000 mg, 7.51 mmol, 1.00 eq.), $Ac_2O$ (8 mL), 4-dimethylaminopyridine (183.2 mg, 0.20 eq.) in pyridine (8 mL). The solution was stirred for 3 h at RT. The reaction was a sat. sodium bicarbonate solution. The solution was diluted with EA (200 mL), washed with sat. NaCl solution (3×50 mL), dried over anhydrous sodium sulfate, filtered and concentrated under reduced pressure. The crude product was purified by a silica gel column with EA:PE (1:7) to yield (1500 mg, 57%) of 266-10 as a white solid. ESI MS m/z: 373 [M+Na]$^+$.

Into a 25-mL round-bottom flask, was placed a solution of 266-10 (300 mg, 0.86 mmol, 1.00 eq.) in dichloromethane (3 mL) at RT. Trimethylsilanecarbonitrile (169 mg, 1.70 mmol, 2.00 eq.) was added at RT, followed by tetrachlorostannane (223 mg, 0.86 mmol, 1.00 eq.) at 0° C. The solution was stirred at 0° C. for 3 h. The reaction was quenched with sat. sodium bicarbonate solution. The solution was diluted with DCM (50 mL), washed with sat. NaCl solution (2×10 mL), dried over sodium sulfate, filtered and concentrated under reduced pressure. The crude product was purified by a silica gel column with PE:EA (5:1) to give 266-11 (110 mg, 40%) as a yellow oil. $^1$H-NMR (400 MHz, $CDCl_3$): δ ppm 5.67-5.75 (m, 2H), 4.25-4.78 (m, 5H), 2.19 (s, 3H), 2.14 (s, 3H), 2.10 (s, 3H Into a 25-mL round-bottom flask, was placed 266-11 (200 mg, 0.63 mmol, 1.00 eq.), NBS (223 mg, 1.25 mmol, 2.00 eq.) in tetrachloromethane (5 mL). The solution was heated under reflux for 3 h over a 250 W tungsten lamp, and then cooled to RT. The reaction was quenched sat. sodium bicarbonate solution. The solution was EA (100 mL), washed with sat. NaCl solution (3×20 mL), dried over sodium sulfate, filtered and concentrated under reduced pressure. The crude product was purified by a silica gel column with PE:EA (7:1) to give 266-12 (120 mg, 48%) as a yellow oil. $^1$H-NMR (400 MHz, $CDCl_3$): δ ppm 6.03 (d, J=4.8 Hz, 1H), 5.90 (d, J=4.8 Hz, 1H), 4.29-4.30 (m, 4H), 2.25 (s, 3H), 2.15 (s, 3H), 2.25 (s, 3H).

Into a 25-mL round-bottom flask purged and maintained with an inert atmosphere of argon, was placed a solution of N-(2-oxo-1,2-dihydropyrimidin-4-yl)benzamide (54.3 mg, 2.00 eq.) and $(NH_4)_2SO_4$ (5 mg) in HMDS (3 mL). The solution was stirred overnight at 120° C. in an oil bath. The solution was concentrated under vacuum, and the residue was dissolved DCE (1 mL) under Ar. A solution of 266-12 (50 mg, 0.13 mmol, 1.00 eq.) in MeCN (1 mL) was added followed by AgOTf (32.5 mg, 1.00 eq.). The solution was stirred for 3 h at 80° C. in a 10-mL sealed tube. After cooling to RT, the solution was diluted with EA (50 mL), washed with sat. sodium bicarbonate solution (3×10 mL) and sat. NaCl (2×10 mL) solution, dried over anhydrous sodium sulfate, filtered and concentrated under reduced pressure. The crude product was purified by a silica gel column with DCM:MeOH (15:1) to yield 266-13 (30 mg, 45%) as a yellow oil. ESI MS m/z: 428 [M+H]$^+$.

Into a 25-mL round-bottom flask, was placed a solution of 266-13 (100 mg, 0.23 mmol, 1.00 eq.) in ACN (3 mL). 4-dimethylaminopyridine (28.5 mg, 0.23 mmol, 1.00 eq.) and TEA (71 mg, 0.70 mmol, 3.00 eq.) was added followed by TPSCl (212.8 mg, 0.70 mmol, 3.00 eq.). The solution was stirred for 3 h at RT, and then concentrated under vacuum. Crude 266-14 (200 mg) was obtained as a yellow oil.

Into a 25-mL round-bottom flask, was placed a solution of 266-14 (140 mg, 0.10 mmol, 1.00 eq.) in ACN (3 mL) and ammonium oxidanide (3 mL). The solution was stirred for 4 h at 35° C. in an oil bath. The mixture was concentrated under vacuum. The crude product was purified by Prep-HPLC (Prep-HPLC-020): Column, XBridge Prep C18 OBD Column, 19*150 mm 5 um 13 nm; mobile phase, WATER WITH 0.05% TFA and ACN (35.0% ACN up to 48.0% in 8 mins); Detector, nm to yield 266 (21.3 mg, 25%) as a white solid. ESI MS m/z: 301.1 [M+1]$^+$.

Into a 25-mL round-bottom flask, was placed a solution of 266-13 (50 mg, 0.12 mmol, 1.00 eq.), sat. $NH_4OH$ (2 mL) and 1,4-dioxane (2 mL). The solution was stirred for 2 h at RT. After concentrated under reduced pressure, the crude product was purified by Prep-HPLC [(Prep-HPLC-020): Column, XBridge Prep C18 OBD Column, 19*150 mm 5 um 13 nm; mobile phase, WATER WITH 0.05% TFA and ACN (35.0% ACN up to 48.0% in 8 mins); Detector, nm] to yield 265 (13.6 mg, 39%) as a white solid ESI MS m/z: 299.9 [M−1]$^−$.

Example 151

Compound 267

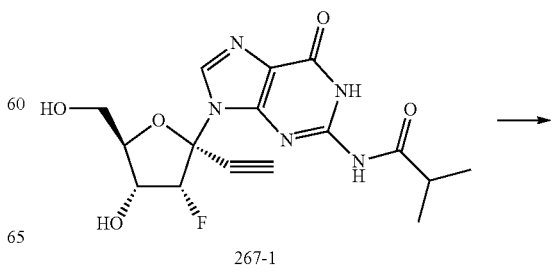

267-1

-continued

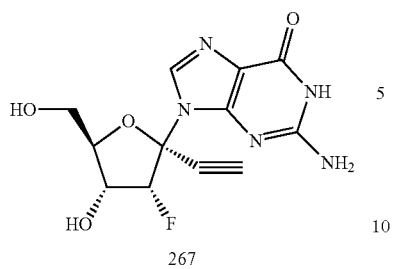
267

Nucleoside 267-1 (100 mg, 0.26 mmol) was dissolved in n-butylamine (2 mL) and left for 2 h at RT. The solvent was evaporated, and the residue was purified by RP HPLC on Synergy 4 micron Hydro-RP column (Phenominex). A linear gradient of MeOH from 10 to 60% in 50 mM triethylammonium acetate buffer (pH 7.5) was used for elution. The corresponding fractions were combined, concentrated and lyophilized (3×) to remove excess of buffer and yield 267 (20 mg, 25%). MS: m/z 308 [M−1].

Example 152

Compound 268

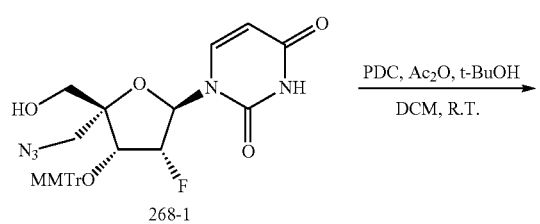
268-1

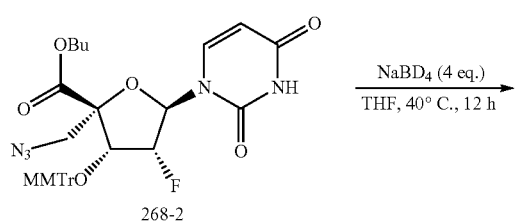
268-2

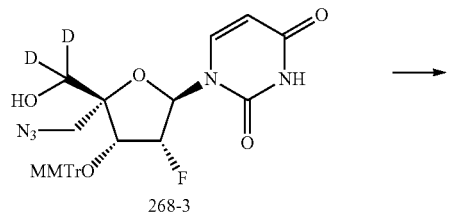
268-3

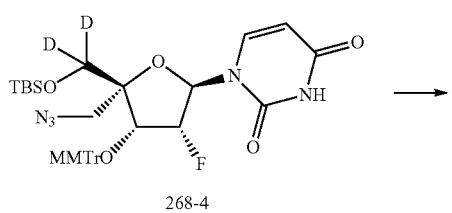
268-4

-continued

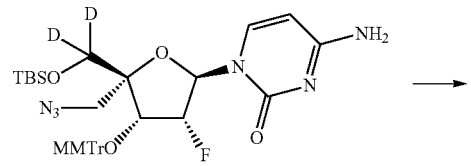
268-5

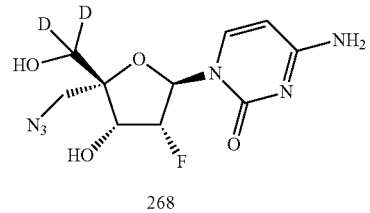
268

Compound 268-3 was prepared according to the scheme provided above. Compound 268 can be obtained using methods known to those skilled in the art, including those described in U.S. Publication No. 2012/0071434, filed Sep. 19, 2011.

Example 153

Compound 269

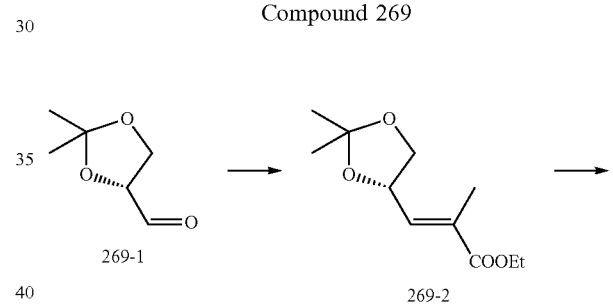

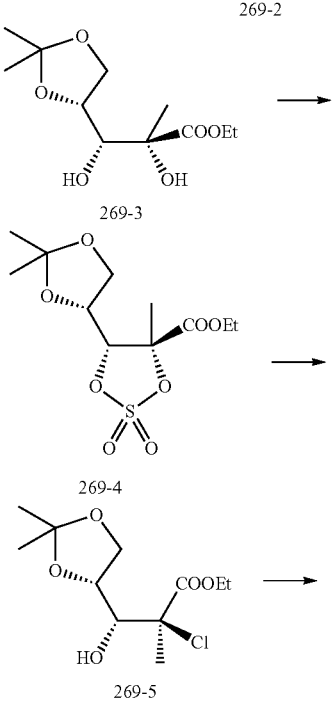

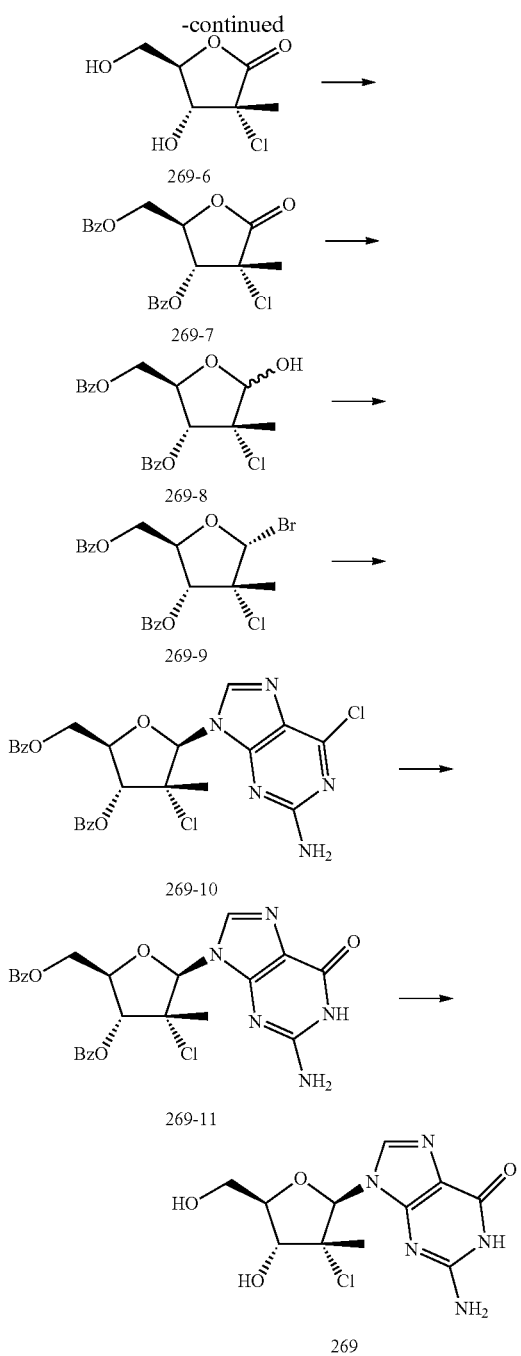

To a stirred solution of 269-1 (43.6% in dichloromethane, 345.87 g, 1.16 mol) in anhydrous DCM (1.0 L) was added ethyl-2-(triphenylphosphoranylidene) propanoate (400 g, 1.100 mol) dropwise over a period of 30 mins at −40° C. The mixture was allowed to warm to 25° C. and stirred for 12 h. The mixture was concentrated under reduced pressure. The residue was suspended in TMBE (2.0 L). The solid was removed by filtration. The filtrate was concentrated under reduced pressure. The residue was purified on silica gel column (1.2% EA in PE) to give 269-2 (191.3 g, 80.26%) as a white foam. $^1$H-NMR (400 Hz, CDCl$_3$), δ=6.66 (dd, J=6.8, 8.0 Hz, 1H), 4.81-4.86 (m, 1H), 4.11-4.21 (m, 3H), 3.60 (t, J=8.4 Hz, 1H), 1.87 (d, J=1.2 Hz, 3H), 1.43 (s, 3H), 1.38 (s, 3H), 1.27 (t, J=6.8 Hz, 3H).

To a stirred solution of 269-2 (100 g, 0.47 mol) in acetone (2.0 L) was added KMnO$_4$ (90 g, 0.57 mol) in portions at 0-5° C. The mixture was stirred at 0-5° C. for 2 h. The reaction was quenched using sat. sodium sulfite solution (600 mL). After 2 h, a colorless suspension was formed. The solid was removed by filtration. The filter cake was washed with EA (300 mL). The filtrate was extracted with EA (3×300 mL). The organic phase was dried over anhydrous Na$_2$SO$_4$. The organic phase was concentrated under reduced pressure to give crude 269-3 (50 g, 43.4%) as a solid.

To a stirred solution of 269-3 (50.0 g, 0.20 mol) and triethylamine (64.0 g, 0.63 mol) in anhydrous DCM (1.0 L) was added thionyl chloride (36.0 g, 0.31 mol) at 0° C. After 30 mins, the mixture was diluted with dichloromethane (500 mL) and washed with cold water (1.0 L) and brine (600 mL). The organic phase was dried over anhydrous Na$_2$SO$_4$. The organic phase was concentrated under reduced pressure to give the crude as a brown oil. To crude in anhydrous acetonitrile were added TEMPO catalyst (500 mg) and NaHCO$_3$ (33.87 g, 0.40 mol) at 0° C. A sodium hypochlorite solution (10-13%, 500 mL) was added dropwise at 0° C. for 20 mins. The solution was stirred at 25° C. for 1 h. The organic phase was concentrated, and the aqueous phase was extracted with dichloromethane (3×). The organic phase was dried over anhydrous Na$_2$SO$_4$. The solvent was removed under reduced pressure to give 269-4 (53.0 g, 85.48%) as a yellow oil.

To a stirred solution of 269-4 (62.0 g, 0.20 mol) in anhydrous dioxane (1.5 L) was added TBACl (155.4 g, 0.50 mol) at 25° C. The solution was stirred at 100° C. for 10 h. The mixture was cooled to 25° C., and treated with 2,2-dimethoxypropane (700 mL), followed by conc. HCl (12 N, 42 mL). The mixture was stirred at 25° C. for 3 h and then concentrated under reduced pressure to give crude 269-5 as a brown oil (45.5 g, crude), which was used for next step without further purification.

Crude 269-5 (45.5 g, 171 mmol) was dissolved in a mixture of EtOH (500 mL) and conc. HCl (12 N, 3.0 mL). The mixture was stirred at 25° C. for 16 h. The solvent was removed under reduced pressure. The residue was co-evaporated with toluene (3×) to give crude 269-6 (24.6 g, crude) as a brown oil, which was used for the next step.

To a stirred solution of crude 269-6 (24.6 g, crude) and DMAP (4.8 g, 40.0 mmol) in anhydrous pyridine (800 mL) was added benzoyl chloride (84.0 g, 0.60 mol) dropwise over a period of 40 mins at 0° C. The mixture was stirred at 25° C. for 12 h and then concentrated at low pressure. The residue was dissolved in EA (1.5 L). The solution was washed with 1.0 M HCl solution (400 mL) and brine (800 mL). The organic phase was dried over anhydrous Na$_2$SO$_4$. The solvent was removed under reduced pressure to give a brown solid. The solid was suspended in MeOH (600 mL). After filtration, the filter cake was washed with MeOH. The filter cake was dried under reduced pressure to give 269-7 (40.0 g, 75.0%) as a white solid.

To a stirred solution of 269-7 (7.0 g, 18.04 mmol) in anhydrous THF (70 mL) was added a solution of lithium tri-tert-butoxyaluminohydride (27 mL, 1.0 M, 27.06 mmol) dropwise over a period of 30 mins at −78° C. under N$_2$. The mixture was stirred at −20° C. for 1 h. The reaction was quenched with sat. NH$_4$Cl aq. and diluted with EA. After filtration, the filtrate was extracted with EA. The organic phase was dried over anhydrous Na$_2$SO$_4$, and concentrated at low pressure. The residue was purified by silica column gel (5% EA in PE) to give 269-8 (6.8 g, 96.7%) as a colorless oil.

579

To a stirred solution of PPh₃ (1.34 g, 5.12 mmol) in CH₂Cl₂ (5 mL) was added 269-8 (1.0 g, 2.56 mmol) at −20° C. under N₂. After the mixture was stirred for 15 mins, CBr₄ (1.96 g, 5.89 mmol) was added in portions while maintaining the reaction temperature between −25 and −20° C. under N₂ flow. After completion of the addition, the mixture was stirred below −17° C. for 20 mins. The reaction was treated with silica gel. After filtration, the pad of silica gel was washed with CH₂Cl₂. The combined filtrates were purified by silica column gel (EA in PE from 2% to 25%) to give 269-9 (α-isomer, 0.5 g, 43.4%) as a colorless oil.

A 0.25 L three-neck round-bottomed flask was charged with 6-chloro-9H-purin-2-amine (5.5 g, 34.75 mmol) followed by anhydrous t-BuOH (45 mL) with stirring. To this solution was added potassium tert-butoxide (3.89 g, 32.58 mmol) in portions at RT under N₂ flow. After 30 mins, a solution of 269-9 (4.92 g, 10.86 mmol) in anhydrous acetonitrile (30 mL) was added over a period of 5 mins at 25° C. The mixture was slowly heated to 50° C. and stirred for 12 h. The mixture was treated with solid NH₄Cl and water, and then filtered through a short pad of Celite. The pad was washed with EA, and the filtrates were neutralized with aqueous 1.0 M HCl. The combined organic layers were dried over anhydrous Na₂SO₄. The organic phase was concentrated under reduced pressure. The residue was purified by silica column gel (EA in PE from 2% to 20%) to give 269-10 (1.7 g, 28.9%) as a white foam. ¹H-NMR (400 MHz, DMSO-d₆) δ=8.37 (s, 1H), 8.07-8.01 (m, 2H), 7.93-7.87 (m, 2H), 7.75-7.69 (m, 1H), 7.65-7.53 (m, 3H), 7.41 (t, J=7.8 Hz, 2H), 7.13 (s, 2H), 6.37 (d, J=19.3 Hz, 1H), 6.26-6.13 (m, 1H), 4.86-4.77 (m, 1H), 4.76-4.68 (m, 2H), 1.3 (d, J=20 Hz, 3H).

Compound 269-10 (700 mg, 1.29 mmol) was dissolved in 4% HCl in MeOH (25 mL) at 25° C. The mixture was stirred at 50° C. for 12 h. The solvent was removed under reduced pressure. The residue was purified by column chromatography to give 269-11 (401 mg, 59.2%) as a white solid.

Compound 269-11 (250 mg, 0.477 mmol) was treated with 7.0 M NH₃ in MeOH (25 mL) at 25° C. and stirred for 18 h. The solvent was removed at low pressure. The residue was purified by prep-HPLC (NH₄HCO₃ system) to give 269 (85 mg, 56.4%) as a white solid. MS: m/z 315.7 [M+H]⁺, 630.5 [2M+H]⁺.

Example 154

Compound 270

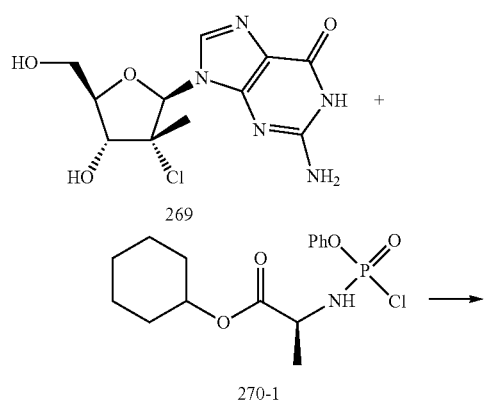

580

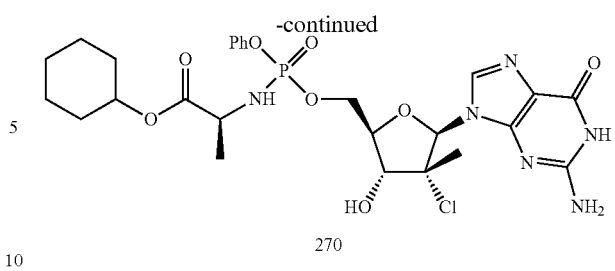

270

To an ice cold solution of 269 (50 mg, 0.16 mmol) and N-methylimidazole (50 μL, 0.64 mmol) in acetonitrile (1.5 mL) was added a solution of 270-1 (0.1 g, 0.28 mmol) in acetonitrile (0.15 mL). The mixture stirred at 5° C. for 1 h. The reaction was quenched with EtOH, and the mixture concentrated. The evaporated residue was partitioned between EtOAc and citric acid (0.5 N). The organic layer was washed with sat. aq. NaHCO₃ and brine, and then dried with Na₂SO₄. Purification by RP-HPLC (A: water, B: MeCN) yielded 270 (30 mg, 30%) as a white powder. MS: m/z 625 [M+1].

Example 155

Compound 271

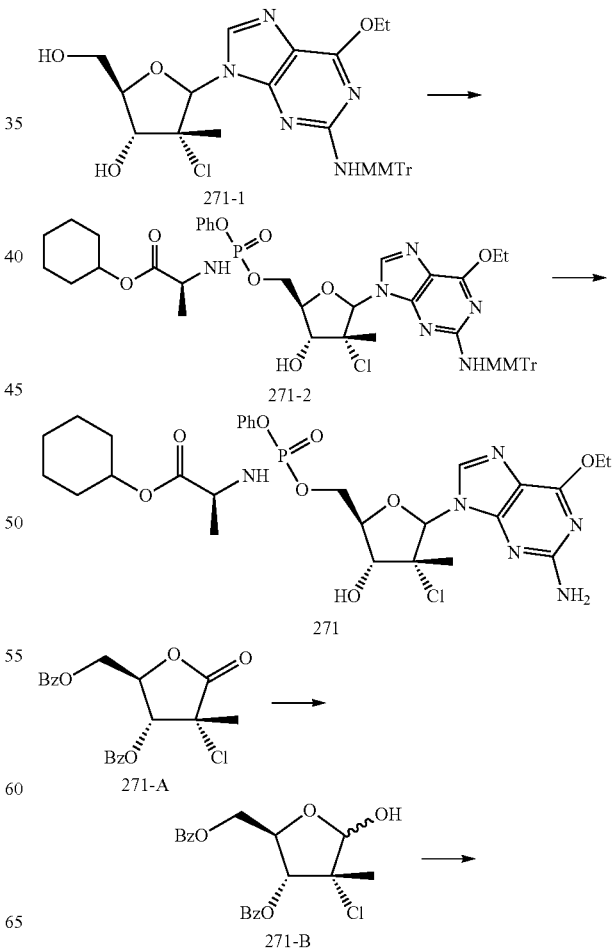

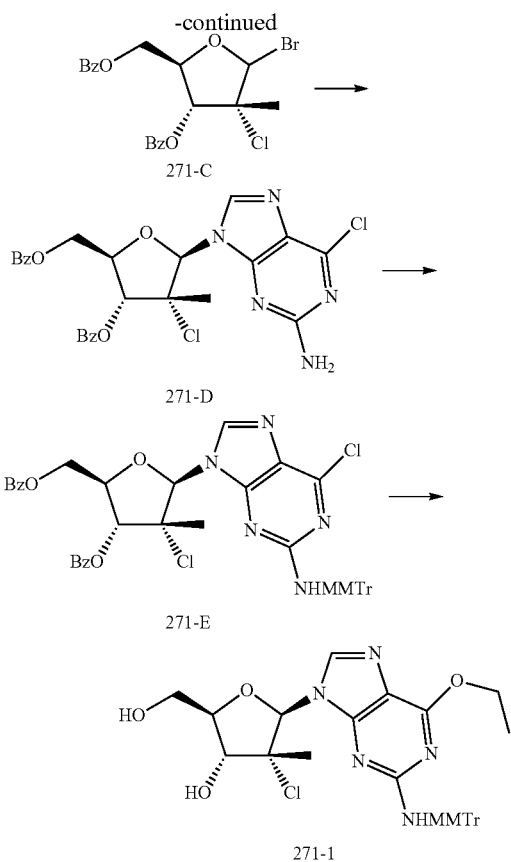

271 (37.7 mg, 52.5%) as a white foam. ESI-LCMS: m/z=653.2 [M+H]$^+$, 1305.4 [2M+H]$^+$.

To a solution of 271-A (56 g, 0.144 mol) in anhydrous THF (600 mL) was added a solution of lithium tri-tert-butoxyaluminohydride (216 mL, 1M, 0.216 mol) dropwise at −78° C. under N$_2$ for 30 mins. The solution was stirred between −78° C. to 0° C. for 1 h. The reaction was quenched with sat.NH$_4$Cl solution and extracted with EA (3×200 mL). The combined organic layers were dried over anhydrous Na$_2$SO$_4$, filtrated and concentrated to give 271-B (52 g, 92%) as a colorless oil.

To a stirred solution of PPh$_3$ (45.7 g, 0.174 mol) in CH$_2$Cl$_2$ (200 mL) was added 271-B (34 g, 0.087 mol) at −20° C. under N$_2$. The mixture was stirred for 15 mins. CBr$_4$ (58 g, 0.174 mol) was added dropwise while maintaining the temperature between −25° C. and −20° C. under N$_2$ flow. The mixture was then stirred below −17° C. for 20 mins. The mixture was treated with silica gel. The solution was filtered through cold silica column gel and washed with cold elute (PE:EA=50:1 to 4:1). The combined filtrates were concentrated under reduced pressure at RT to give the crude oil product. The residue was purified by silica column gel (PE:EA=50:1 to 4:1) to give 271-C (α-isomer, 24 g, 61%) as a colorless oil. $^1$H-NMR (CDCl$_3$, 400 MHz), δ=8.16 (d, J=6.8 Hz, 2H), 8.01 (d, J=7.6 Hz, 2H), 7.42-7.62 (m, 6H), 6.43 (s, 1H), 5.37 (d, J=4.4 Hz, 1H), 4.68-4.86 (m, 3H), 1.88 (s, 3H).

A mixture of 6-Cl-guanosine (80.8 g, 0.478 mol) and t-BuOK (57 g, 0.509 mol) in t-BuOH (1 L) was stirred at 30-35° C. for 30 mins. 271-C (72 g, 0.159 mol, in MeCN 500 mL) was added at RT and the mixture was heated to 70° C. and stirred for 3 h. The reaction was quenched with sat. NH$_4$Cl solution, and extracted with EA (3×300 mL). The combined organic layers were dried over anhydrous Na$_2$SO$_4$ and evaporated at low pressure. The residue was purified by silica gel column (PE:EA=4:1 to 2:1) to give 271-D (14 g, 16%). $^1$H-NMR (CDCl$_3$, 400 MHz) δ 7.93-8.04 (m, 4H), 7.90 (s, 1H), 7.30-7.50 (m, 6H), 6.53 (d, J=8.8 Hz, 1H), 6.36 (s, 1H), 5.35 (s, 2H), 5.06-5.10 (m, 1H), 4.81-4.83 (m, 1H), 4.60-4.64 (m, 1H), 1.48 (s, 3H).

To a solution of 271-D (14 g, 25.9 mmol) in DCM (15 mL) was added AgNO$_3$ (8.8 g, 51.8 mmol) and collidine (6.3 g, 51.8 mmol) and MMTrCl (12.1 g, 38.9 mmol). The mixture was stirred at RT for 1 h. The reaction was quenched with MeOH (5 mL). After filtration, the filter was washed with brine, dried over anhydrous Na$_2$SO$_4$, and concentrated at low pressure. The residue was purified by silica gel column (PE:EA=10:1 to 3:1) to give 271-E (16 g, 80%). $^1$H-NMR (CDCl$_3$, 400 MHz) δ=8.05-8.07 (m, 4H), 7.93 (s, 1H), 7.18-7.57 (m, 18H), 6.77 (d, J=8.8 Hz, 2H), 6.71 (s, 1H), 5.86 (s, 1H), 5.6 (s, 1H), 4.77 (d, J=10.0 Hz, 1H), 4.67-4.76 (m, 1H), 4.55-4.59 (m, 1H), 3.75 (s, 1H), 1.06 (s, 3H).

Sodium (170 mg, 7.38 mmol) was dissolved in dry EtOH (5 mL) at 70° C., and the solution was cooled to 0° C. 271-E (1 g, 1.23 mmol) was added in portions at 0° C. The mixture was stirred for 8 h at RT. The mixture was neutralized with CO$_2$ to pH 7.0, and concentrated at low pressure. The residue was purified by prep-HPLC (10% CH$_3$CN/H$_2$O) to give 271-1 (0.4 g, 53%) as a yellow solid. ESI-MS: m/z 616 [M+H]$^+$.

To a stirred solution of 271-1 (180 mg, 0.16 mmol) in anhydrous CH$_3$CN (2.0 mL) was added N-methylimidazole (53.4 µL, 0.65 mmol) at 0° C. (ice/water bath). A solution of phenyl (cyclohexyloxy-L-alaninyl) phosphorochloridate (101 mg, 0.29 mmol) dissolved in CH$_3$CN (0.5 mL), prepared according to a general procedure (McGuigan et al. *J. Med. Chem.* 2008, 51, 5807), was added. The solution was stirred at 0 to 5° C. for 3 h. N-methylimidazole (50 µL) at 0° C. (ice/water bath) followed by solution of phenyl (cyclohexyloxy-L-alaninyl) phosphorochloridate (52 mg, dissolved in 0.5 mL of CH$_3$CN) were added. The mixture was stirred at RT for 16 h. The mixture was cooled to 0 to 5° C. and diluted with EA. Water (5 mL) was added. The solution was washed with 1.0M citric acid, sat. aq. NaHCO$_3$ and brine, and dried with MgSO$_4$. The residue was purified on silica (10 g column) with DCM/MeOH (0-10% gradient) to give 271-2 (96.8 mg, 64%) as foam.

Compound 271-2 (95 mg, 0.11 mmol) was dissolved in anhydrous CH$_3$CN (0.5 mL), and 4N HCl in dioxane (77 µL, 0.3 mmol) was added at 0 to 5° C. The mixture was stirred at RT for 30 mins, and anhydrous EtOH (100 µL) was added. The solvents were evaporated at RT and co-evaporated with toluene (3×). The residue was purified on RP-HPLC with H$_2$O/CH$_3$CN (50-100% gradient) and lyophilized to give

Example 156

Compound 272

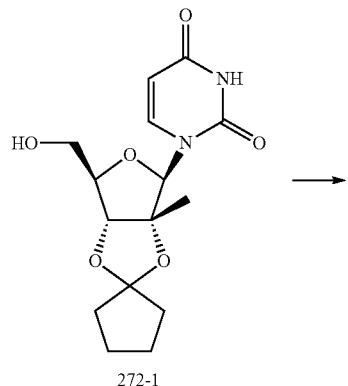

272-1

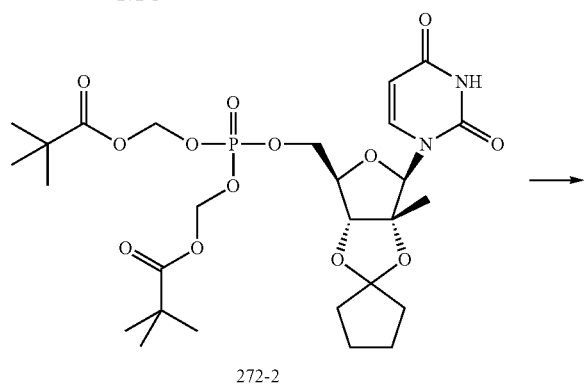

272-2

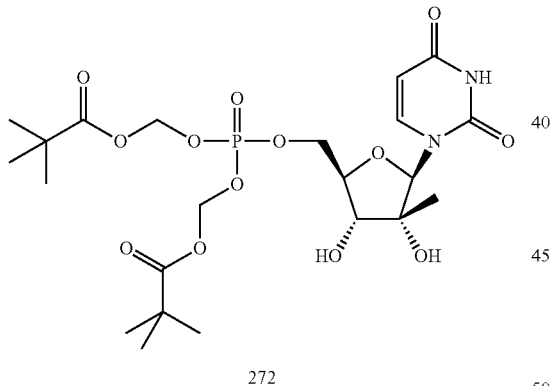

272

To an ice-cold solution of triethylammonium bis(POM) phosphate (7 mmol, prepared from 2.3 g of bis(POM) phosphate and 1 mL of Et₃N) and 272-1 (1.36 g; 4.2 mmol) were added diisopropylethyl amine (3.6 mL; 21 mmol), BOP-Cl (2.68 g; 10.5 mmol) and 3-nitro-1,2,4-triazole (1.20 g; 10.5 mmol). The mixture was stirred at 0° C. for 2 h. The mixture was then diluted with EtOAc, washed with 1 M citric acid, sat. aq. NaHCO₃ and brine and dried with Na₂SO₄. The evaporated residue was purified on silica gel column with i-PrOH/CH₂Cl₂ solvent system (2-12% gradient) to yield 272-2 (2.13 g, 80%).

A solution of 272-2 (2.13 g) in 80% aq. HCOOH (10 mL) was stirred at 45° C. for 8 h. The mixture was cooled and concentrated to obtain a residue. The residue was coevaporated with toluene and MeOH containing few drops of Et₃N.

The evaporated residue was purified on silica gel column with MeOH:CH₂Cl₂ (3-10% gradient) to yield 272 as a white foam (1.1 g, 56%). MS: m/z=565 [M−1].

Example 157

Compound 280

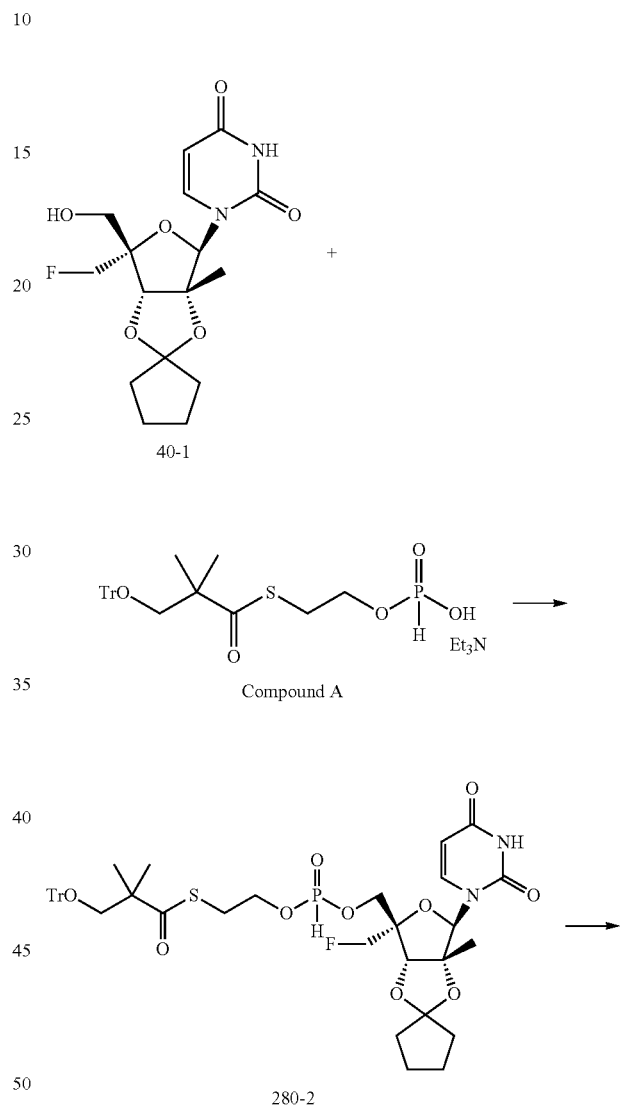

-continued

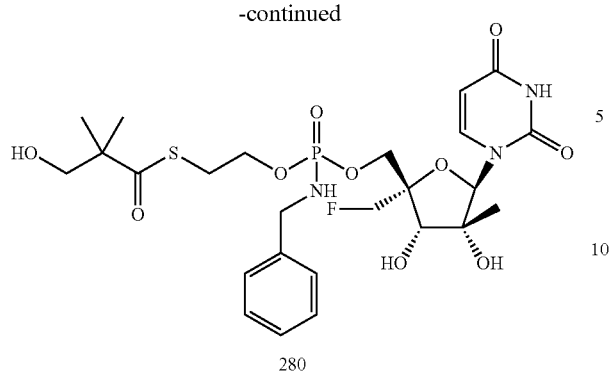

280

40-1 (1.78 g, 5 mmol) and Compound A (3.22 g, 5.5 mmol; prepared according to the procedure provided in WO 2008/82601 A2) were coevaporated with pyridine and then dissolved in pyridine (70 mL). Pivaloyl chloride (1.22 mL; 10 mmol) was added dropwise at −15° C., and the mixture stirred at −15° C. for 2 h. The mixture was diluted with CH$_2$Cl$_2$, washed with 0.5 M aq. NH$_4$Cl and brine, and dried with Na$_2$SO$_4$. The evaporated residue was purified on a silica column with CH$_2$Cl$_2$:i-PrOH (4-10% B gradient) to afford 280-2 (2.1 g, 50%).

To a solution of 280-2 (0.51 g, 0.62 mmol) in CCl$_4$ (6 mL) was added benzylamine (0.34 mL, 3.1 mmol) dropwise, and the mixture was stirred at RT for 1 h. The mixture was diluted with EtOAc, washed with 0.5 M aq. citric acid, sat. aq. NaHCO$_3$ and brine, and dried with Na$_2$SO$_4$. The evaporated residue was purified on a silica column with CH$_2$Cl$_2$: i-PrOH (4-10% B gradient) to afford 280-3 (0.46 g, 80%).

A mixture of 280-3 (130 mg, 0.14 mmol) and 80% aq. TFA (1.5 mL) was stirred at RT for 2 h. The mixture was evaporated and coevaporated with toluene. The residue was purified on a silica column with CH$_2$Cl$_2$:MeOH (4-12% B gradient) to afford 280 (32 mg, 37%). MS: m/z=620 [M+1]$^+$.

Example 158

Compound 281

-continued

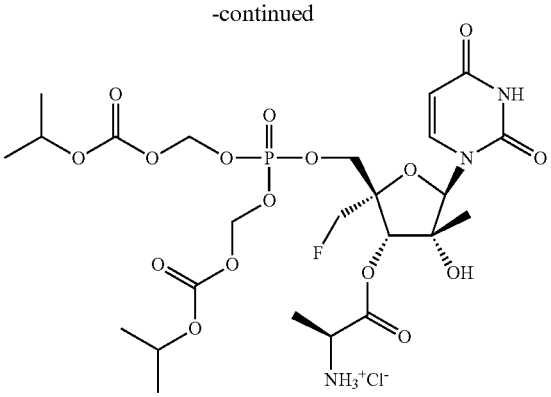

281

A solution of Z-Ala-OH (111.6 mg, 0.5 mmol) in anhydrous THF (2 mL) was treated with carbonyldiimidazole (81 mg, 0.5 mmol). The mixture was stirred for 1 h at 40° C. under an Ar atmosphere. This solution was added to a solution of 44 (200 mg, 0.33 mmol), Et$_3$N (72 µL, 0.5 mmol) and DMAP (4 mg) in DMF (2 mL). The mixture was stirred at RT for 2.5 h. The reaction was quenched by the addition of 1M citric acid (2 mL) at 0 to 5° C. (ice/water bath) and diluted with EA. The organic layer was separated, washed with sodium bicarbonate and brine, dried over MgSO$_4$, filtered and concentrated. The residue was purified by column chromatography in 40 to 90% EA-hexane to give 281-1 (202 mg, 76%) as a white foam.

To a solution of 281-1 (50 mg, 0.062 mmol) in anhydrous EtOH (2 mL), was added 10% Pd/C (5 mg), followed by addition of 4N HCl (31 µL, 0.124 mmol), and the mixture was stirred under H$_2$ atmosphere for 1 h. After completion of the reaction, the mixture was filtered through celite. The catalyst cake was washed with anhydrous EtOH. The washings and the filtrate were combined, and the solvent was removed under vacuum to give 281 (33.3 mg, 79.7%) as an off white foam. MS: m/z=674.1[M+H]$^+$, 1347.2 [2M+H]$^+$.

Example 159

Compound 282

44 ⟶

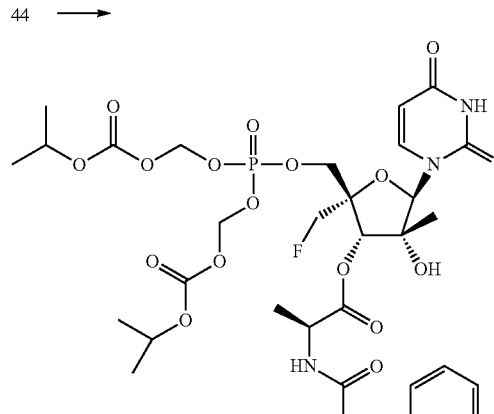

281-1

44 ⟶

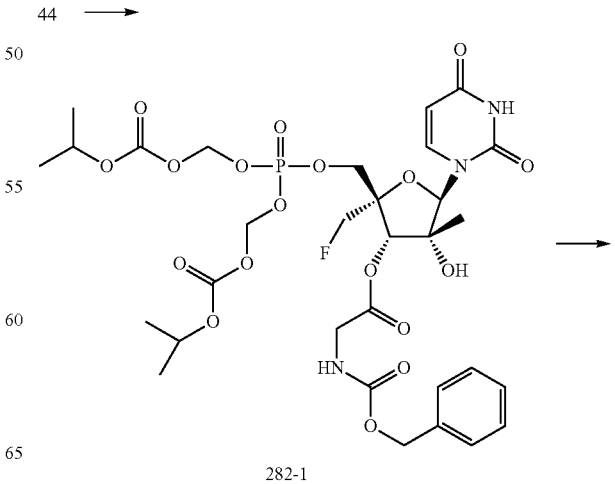

282-1

-continued

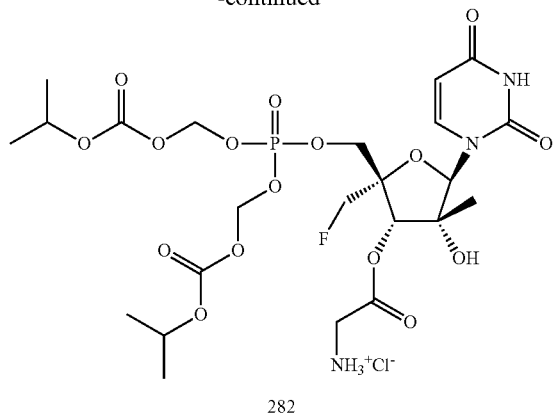

282

A solution of Z-Gly-OH (105 mg, 0.5 mmol) in anhydrous THF (2 mL) was treated with carbonyldiimidazole (81 mg, 0.5 mmol). The mixture was stirred for 2 h at 40° C., followed by 30 mins at 80° C. under an Ar atmosphere. This solution was added to a solution of 44 (200 mg, 0.33 mmol), Et₃N (72 µL, 0.5 mmol) and DMAP (4 mg) in DMF (2 mL). The mixture was stirred at RT for 3 h. The reaction was quenched by the addition of 1M citric acid (2 mL) at 0 to 5° C. (ice/water bath) and diluted with EA. The organic layer was separated, washed with sodium bicarbonate and brine, dried over MgSO₄, filtered and concentrated. The residue was purified by column chromatography in 40 to 90% EA-hexane to give 282-1 (208.5 mg, 79.6%) as an off white foam.

To a solution of 282-1 (75 mg, 0.094 mmol) in anhydrous EtOH (3 mL), was added 10% Pd/C (10 mg), followed by the addition of 4N HCl (47 µL, 0.19 mmol). The mixture was stirred under H₂ atmosphere for 3 h. After completion of reaction, the mixture was filtered through celite. The catalyst cake was washed with anhydrous EtOH. The washings and the filtrate were combined, and the solvent was removed under vacuum to give 282 (44.3 mg, 71.5%) as an off white foam. MS: m/z=658.05[M+H]⁺, 1317.05[M+H]⁺.

Example 160

Compound 283

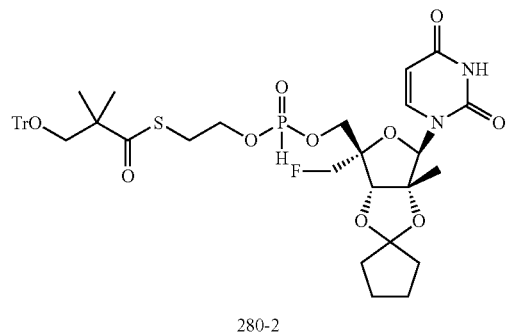

280-2

-continued

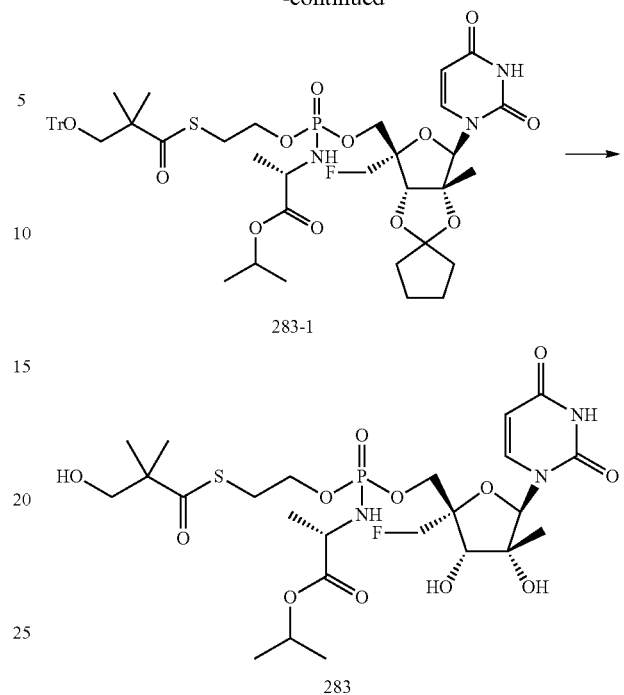

283-1

283

To a solution of 280-2 (223 mg, 0.27 mmol) in CCl₄ (3 mL) were added L-alanine isopropyl ester hydrochloride (135 mg, 0.8 mmol) and dropwise Et₃N (0.22 mL, 1.6 mmol). The mixture was stirred at RT for 1 h. The mixture was then diluted with CH₂Cl₂, washed with sat aq. NaHCO₃ and brine, and dried with Na₂SO₄. The evaporated residue was purified on a silica column with CH₂Cl₂:i-PrOH (3-10% B gradient) to afford 283-1 (0.16 g, 62%).

A mixture of 283-1 (100 mg, 0.11 mmol) and 80% aq. TFA (3 mL) was stirred at RT for 2 h. The mixture was then evaporated and coevaporated with toluene. The residue was purified on a silica column with CH₂Cl₂:MeOH (4-10% B gradient) to afford 283 (31 mg, 46%). MS: m/z=644 [M+1]⁺.

Example 161

Compound 284 and 306

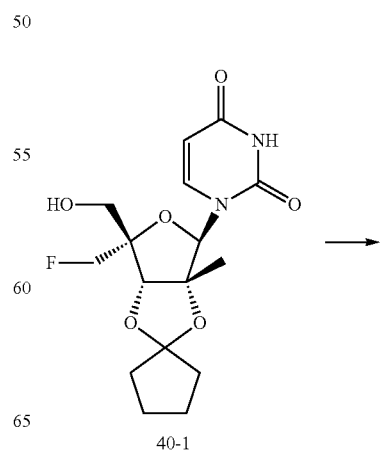

40-1

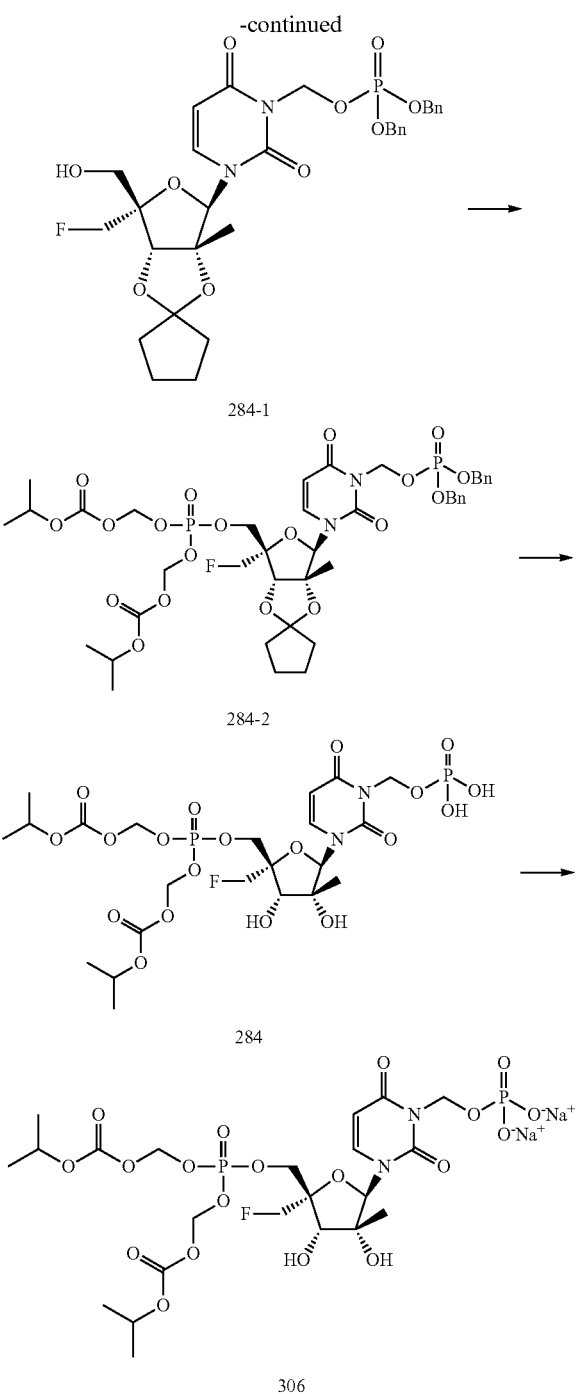

284-1

284-2

284

306

To a solution of 40-1 (1.08 g, 3.0 mmol) in N,N-dimethylacetamide (15 mL) was added CsCO₃ (1.22 g, 3.7 mmol), and the mixture was stirred at RT for 15 mins. Dibenzyl chloromethylphosphate (1 g, 3.0 mmol) was added, and the mixture was stirred overnight at 40° C. After cooling, the mixture was diluted with methyl tert-butylether and washed with water (3×) and brine, and dried with Na₂SO₄. The crude evaporated residue was purified on a silica column with CH₂Cl₂:i-PrOH (3-10% B gradient) to yield 284-1 (580 mg, 30%).

To a solution of triethylammonium bis(isopropyloxycarbonyloxymethyl)phosphate (1.8 mmol, prepared from 0.60 g of bis(isopropyloxycarbonyloxymethyl)phosphate and Et₃N) in THF was added 284-1 (0.58 g, 0.9 mmol). The mixture was evaporated and rendered anhydrous by coevaporating with pyridine follow by toluene. The evaporated residue was dissolved in anhydrous THF (9 mL) and cooled in an ice-bath. Diisopropylethyl amine (0.94 mL, 5.4 mmol) was added, followed by BOP-Cl (0.69 g, 2.7 mmol) and 3-nitro-1,2,4-triazole (0.31 g, 2.7 mmol). The mixture was stirred at 0-5° C. for 2 h, diluted with EtOAc, washed with sat. aq. NaHCO₃ and brine, and dried with Na₂SO₄. The evaporated residue was purified on a silica column with CH₂Cl₂:i-PrOH (3-10% B gradient) to yield 284-2 (0.77 g, 89%).

To a solution of 284-2 (50 mg; 0.05 mmol) in EtOH (2.5 mL) was added 10% Pd/C (8 mg), and the mixture was stirred under H₂ (atmospheric pressure) for 1 h. The mixture was filtered through a Celite pad, and the filtrate was evaporated. The residue was treated with 80% aq. HCOOH (2.5 mL) for 3 h, then evaporated and purified by RP-HPLC (A: 50 mM aq. TEAA, B: 50 mM TEAA in MeCN) to afford 284 (22 mg, 44%) as a white solid. MS: m/z=713 [M+1]⁺.

To a solution of 284 (14 mg, 0.02 mmol) in EtOH (0.3 mL) at 0° C. was added dropwise 0.1 M EtONa in EtOH (0.4 mL; 0.04 mmol). The mixture was allowed to warm to RT and the resulting white solid centrifuged. The supernatant was discarded. The solid was treated with EtOH (0.3 mL) and centrifuged to yield 306 (8 mg). MS: m/z=713 [M+1]⁺.

Example 162

Compound 285

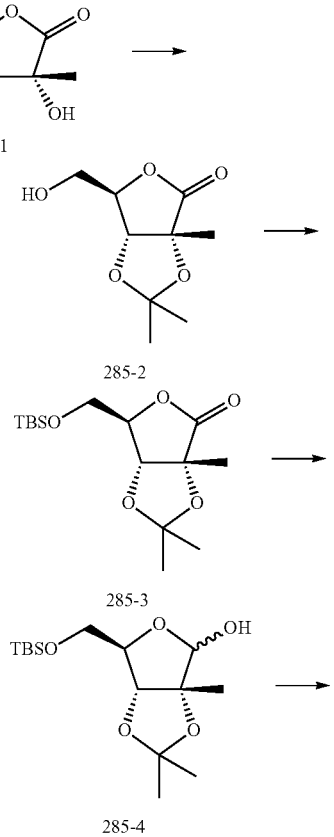

285-1

285-2

285-3

285-4

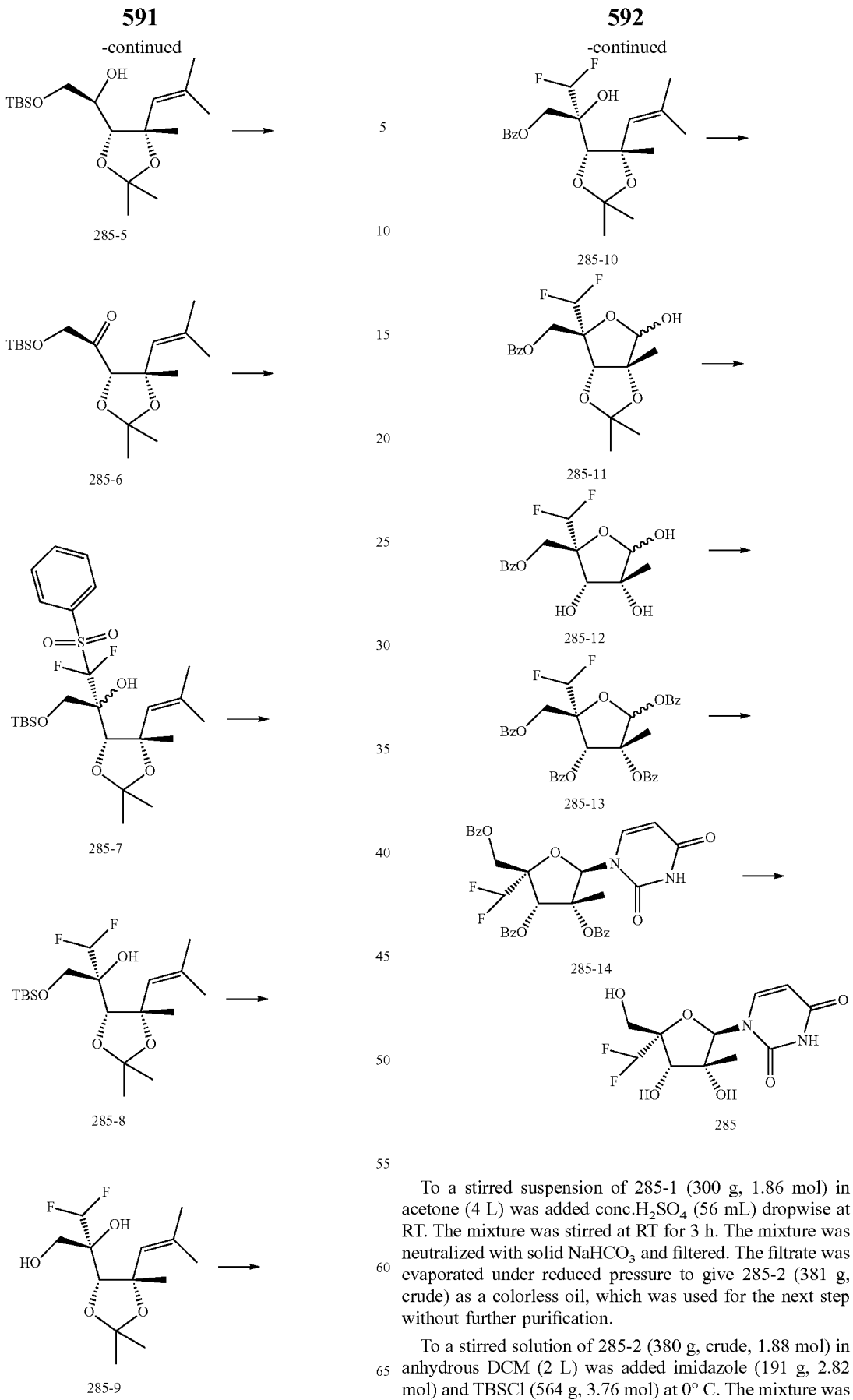

To a stirred suspension of 285-1 (300 g, 1.86 mol) in acetone (4 L) was added conc.$H_2SO_4$ (56 mL) dropwise at RT. The mixture was stirred at RT for 3 h. The mixture was neutralized with solid $NaHCO_3$ and filtered. The filtrate was evaporated under reduced pressure to give 285-2 (381 g, crude) as a colorless oil, which was used for the next step without further purification.

To a stirred solution of 285-2 (380 g, crude, 1.88 mol) in anhydrous DCM (2 L) was added imidazole (191 g, 2.82 mol) and TBSCl (564 g, 3.76 mol) at 0° C. The mixture was stirred at RT for 12 h, and then filtered. The filtrate was concentrated to dryness, and the residue was purified by silica gel column (2% EA in PE) to give 285-3 (569 g, 97% in 2 steps) as a white solid.

To a solution of 285-3 (150 g, 0.47 mol) in anhydrous THF (2 L) was added DIBAL-H (710 mL, 0.71 mol, 1.0 M in toluene) at −78° C. for 3 h. The reaction was quenched with sat. aq. NH$_4$Cl and then filtered. The filtrate was extracted with EA and washed with brine. The organic layer was dried over Na$_2$SO$_4$ and filtered. The filtrate was concentrated to dryness. The residue was purified by silica gel column (11% EA in PE) to give 285-4 (121 g, 80.5%) as a white solid.

Isopropyltriphenylphosphonium iodide (422.8 g, 0.98 mol) was suspended in anhydrous THF (1 L) and cooled to 0° C. A BuLi solution (2.5M in THF, 391 mL, 0.98 mol) was added dropwise over 0.5 h. The deep red solution was maintained at 0° C. for 0.5 h and 285-4 (207.5 g, 0.65 mol) in THF (1 L) was added slowly over 2 h. The mixture was warmed to ambient temperature and stirred for 12 h. The reaction was quenched with sat. aq. NaHCO$_3$. The precipitated solid was removed by filtration. The filtrate was diluted with EA and washed with brine. The organic layer was dried over anhydrous Na$_2$SO$_4$ and filtered. The filtrate was concentrated at low pressure, and the residue was purified by chromatography on silica gel (10% to 30% EA in PE) to give 285-5 (104.7 g, 47%) as a colorless oil.

To a stirred solution of 285-5 (4.9 g, 14.2 mmol) in anhydrous MeCN (70 mL) was added IBX (7.9 g, 28.4 mmol). The mixture was refluxed for 2 h. The mixture was filtered, and the filtrate was concentrated to dryness. The residue was purified by column chromatography (1% EA in PE) to give 285-6 (4.6 g, 94.8%) as a colorless oil.

To a stirred solution of 285-6 (2.0 g, 5.8 mmol) and difluoromethyl phenyl sulfone (2.24 g, 11.7 mmol) in anhydrous DMF (50 mL) was added LiHMDS (1.0 M in THF, 11.7 mL) dropwise at −78° C. After stirring at −78° C. for 2 h, the reaction was quenched with sat. aq. NH$_4$Cl. The mixture was then stirred at 0° C. for 30 mins. The organic phase was separated, and the aqueous phase was extracted with EA. The combined organic phase was washed with brine, dried over Na$_2$SO$_4$ and filtered. The filtrate was concentrated to dryness. The residue was purified on a silica gel chromatography (0.25% EA in PE) to give 285-7 (1.1 g, 32.1%) as a colorless oil. $^1$H-NMR (CDCl$_3$, 400 MHz) δ=8.01-7.97 (m, 2H), 7.74-7.70 (m, 1H), 7.61-7.57 (m, 2H), 5.80 (d, J=1.6 Hz, 1H), 4.26 (d, J=11.2 Hz, 1H), 4.08 (s, 1H), 4.03 (d, J=11.2 Hz, 1H), 3.86 (s, 1H), 1.82 (s, 3H), 1.69 (s, 3H), 1.54 (s, 3H), 1.41 (d, J=12.4 Hz, 6H), 0.89 (s, 9H), 0.09 (d, J=9.6 Hz, 6H).

To a stirred solution of 285-7 (4.0 g, 7.5 mmol) in DMF (80 mL) and H$_2$O (16 mL) was added Mg (3.6 g, 149.8 mmol) followed by the addition of HOAc (13.5 g, 224.7 mmol). The mixture was stirred at RT for 6 h. The mixture was poured into ice water and filtered. The filtrate was extracted with EA. The combined organic phase was washed with brine, dried over Na$_2$SO$_4$ and filtered. The filtrate was concentrated to dryness, and the residue was purified on the silica gel chromatography (0.2% EA in PE) to give 285-8 (1.12 g, 38%) as a colorless oil. $^1$H-NMR (CDCl$_3$, 400 MHz) δ=5.88-5.74 (m, 2H), 3.98-3.78 (m, 3H), 3.30 (s, 1H), 3.08 (s, 1H), 1.83 (s, 3H), 1.70 (s, 3H), 1.41 (s, 3H), 1.35 (d, J=23.2 Hz, 6H), 0.90 (d, J=4.4 Hz, 9H), 0.08 (d, J=7.6 Hz, 6H).

To a solution of 285-8 (1.12 g, 2.84 mmol) was added a solution (6 mL, 1.0 M) of TBAF in THF, and the mixture was stirred at RT for 30 mins. The mixture was concentrated to dryness, and the residue was purified by silica gel column chromatography (3% EA in PE) to give 285-9 (332 mg, 41.7%) as a colorless oil.

To a solution of 285-9 (415 mg, 1.5 mmol) in anhydrous DCM (7.5 mL) was added Et$_3$N (224 mg, 2.2 mmol) and BzCl (248 mg, 1.7 mmol) at 0° C. The mixture was stirred at RT for 4 h. After the reaction was completed, the reaction was quenched with sat. aq. NaHCO$_3$ and extracted with DCM. The organic layer was dried over Na$_2$SO$_4$ and filtered. The filtrate was evaporated, and the residue was purified by silica gel column chromatography (1% EA in PE) to give 285-10 (441 mg, 77.4%) as colorless oil.

To a stirred solution of 285-10 (440 mg, 1.2 mmol) in anhydrous DCM (10 mL) was bubbled O$_3$ at −78° C. until the solution turned blue. The reaction was then bubbled with O$_2$ until the solution turned to colorless. The organic layer was evaporated to give 285-11 (430 mg, crude), which was used for next step without further purification.

285-11 (441 mg, 1.2 mmol) in 90% TFA (6 mL) was stirred at RT for 12 h. The mixture was concentrated under reduced pressure. The residue was purified via silica gel chromatography (50% EA in PE) to give 285-12 (404 mg, 97%) as a colorless oil.

To a solution of 285-12 (404 mg, 1.3 mmol) in anhydrous DCM (6 mL) was added Et$_3$N (1.0 g, 10.2 mmol), DMAP (44 mg, 0.4 mmol) and BzCl (1.0 g, 7.6 mmol) at 0° C. The mixture was stirred at RT for 4 h. The reaction was quenched with sat. aq. NaHCO$_3$ and extracted with DCM. The organic layer was dried over anhydrous Na$_2$SO$_4$ and filtered. The filtrate was evaporated, and the residue was purified by silica gel column chromatography (1% EA in PE) to give 285-13 (530 mg, 66.2%) as a light yellow foam.

To a stirred solution of uracil (190 mg, 1.7 mmol) in chlorobenzene (2.6 mL) was added N, O-bis (trimethylsilyl) acetamide (680 mg, 3.3 mmol). The solution was stirred at 130° C. for 30 mins, and then cooled to ambient temperature. To a solution of 285-13 (536 mg, 0.8 mmol) in chlorobenzene was added SnCl$_4$ (770 mg, 3.5 mmol) slowly dropwise. The mixture was heated to reflux for 30 mins. The reaction was quenched by sat. aq. NaHCO$_3$ and extracted with EA. The organic layer was dried over anhydrous Na$_2$SO$_4$ and filtered. The filtrate was evaporated, and the residue was purified by silica gel column chromatography (20% EA in PE) to give 285-14 (336 mg, 64.6%) as a white solid.

285-14 (80 mg, 0.1 mmol) was treated with 7.0 M NH$_3$ in MeOH. The mixture was stirred at RT for 12 h. The solvent was removed at low pressure. The residue was purified by silica gel column chromatography (5% MeOH in DCM) to give 285 (36 mg, 90.6%) as a white solid. ESI-LCMS: m/z 309.09 [M+H]⁺; 331.07 [M+Na]⁺.

Example 163

Compound 286

51 →

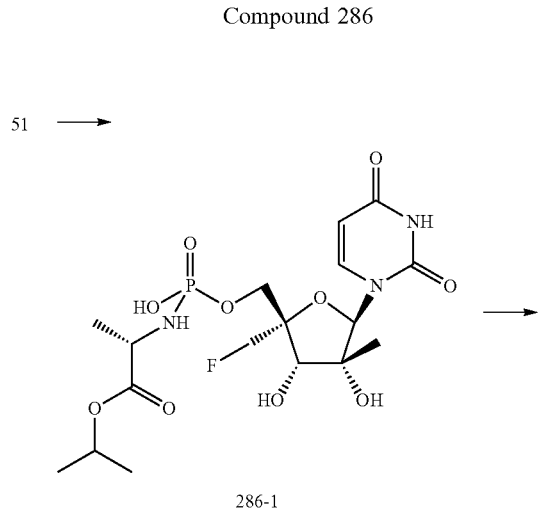

286-1

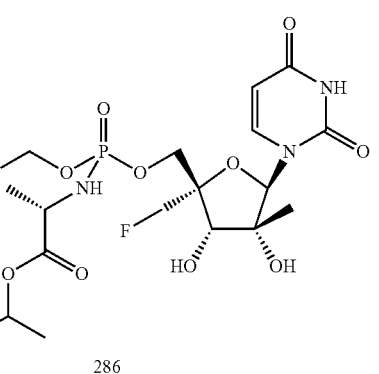

286

To a mixture of 51 (240 mg, 0.8 mmol) in trimethyl phosphate (4 mL) at 0° C. was added POCl₃ (0.18 mL, 1.6 mmol), and the mixture was stirred at 0° C. for 90 mins. L-alanine isopropyl ester hydrochloride (0.24 g, 1.4 mmol) and Et₃N (0.6 mL, 4.3 mmol) were added. The mixture was warmed to RT and stirring was continued for 1.5 h. The reaction was quenched with 0.5 M aq. TEAA, and the mixture purified by RP-HPLC (A: 50 mM aq. TEAA, B: 50 mM TEAA in MeCN) to yield 286-1 (75 mg).

A mixture of 286-1 (52 mg, 0.1 mmol), DIPEA (0.11 mL, 0.6 mmol) and isopropyloxycarbonyloxymethyl iodide (77 mg, 0.3 mmol) in NMP (1.1 mL) was stirred at RT for 1 h. The mixture was diluted with tert-butyl methylether, washed with sat. aq. NaHCO₃ and brine, and dried with Na₂SO₄. The evaporated residue was purified on a silica column with CH₂Cl₂:MeOH (4-10% B gradient) to yield 286 (12 mg, 20%). MS: m/z=600 [M+1]⁺.

Example 164

Compound 287

44 →

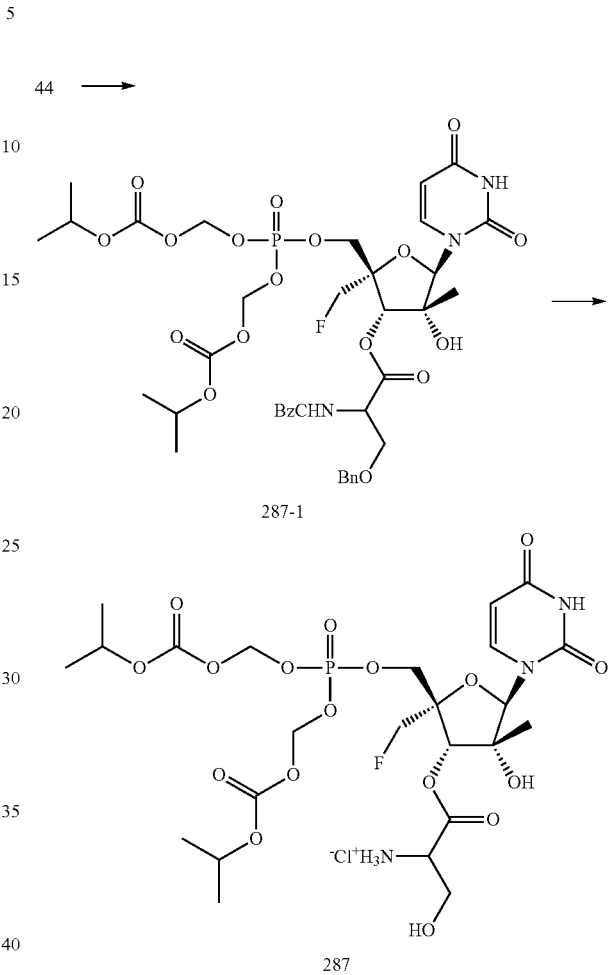

287-1

287

To a solution of 44 (200 mg, 0.33 mmol) in anhydrous DCM (6 mL) was added DMAP (4 mg, 0.033 mmol), N-Cbz-O-benzyl-L-serine (164 mg, 0.5 mmol) and EDC (100 mg, 0.52 mmol) at 0 to 5° C. (ice/water bath). The mixture was stirred for 40 h at RT. The mixture was cooled using ice/water bath, diluted with DCM (10 mL), washed sat. NH₄Cl, dried over MgSO₄, filtered and concentrated. The residue was purified by column chromatography in 50 to 90% EA-hexane to give 287-1 (187 mg, 62%) as a white foam.

To a solution of 287-1 (68.7 mg, 0.075 mmol) in anhydrous EtOH (2.5 mL), was added 10% Pd/C (11.4 mg), followed by the addition of 4N HCl (38 μL, 0.15 mmol), and the mixture was stirred under H₂ atmosphere for 3 h. After completion of reaction, the mixture was filtered through celite. The catalyst cake was washed with anhydrous EtOH. The washings and filtrate were combined, and the solvent was removed under vacuum to give 287 (40.1 mg, 77.6%) as an off white foam. MS: m/z=690.1[M+H]⁺.

Example 165
Compound 288
To a mixture of Compound B (0.84 g, 2 mmol; prepared according to Villard et al. *Bioorg. Med. Chem.* (2008) 16:7321-7329) and Et₃N (0.61 mL, 4.4 mmol) in THF (5
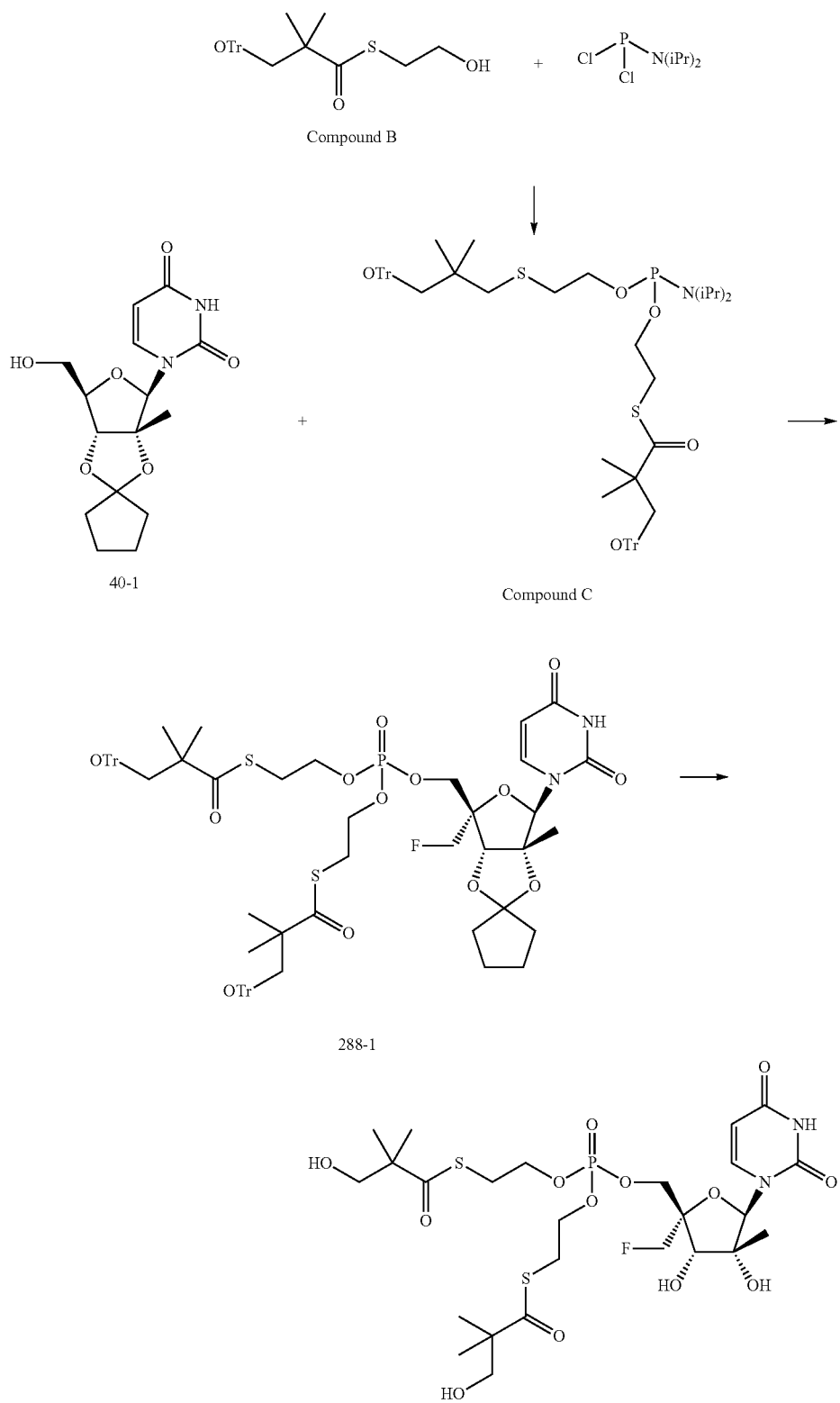

mL) at −78° C. was added dropwise a solution of N,N-diisopropyl dichlorophosphoramidite (184 μL, 1 mmol) in THF (7 mL). The mixture was allowed to warm up and stirred at RT for 2 h. The solids were filtered off. The filtrate was concentrated and purified on a silica gel column with hexanes+1% Et₃N:EtOAc (1-20% B gradient) to yield Compound C (0.38 g).

To a mixture of 40-1 (53 mg, 0.15 mmol) and Compound C (0.17 g, 0.17 mmol) in MeCN (1 mL) was added 5-ethylthio-1H-tetrazole (0.25 M in MeCN; 1.2 mL, 0.3 mmol). The mixture was stirred for 1 h at RT and then cooled to −40° C. A solution of MCPBA (77%; 42 mg, 0.19 mmol) in CH₂Cl₂ (0.5 mL) was added. The mixture was allowed to warm up and stirred at RT for 30 mins. The reaction was quenched with 4% aq. Na₂S₂O₃ in 4% aq. NaHCO₃ (1 mL) and diluted with CH₂Cl₂. The organic layer was washed with sat. aq. NaHCO₃ and brine, and dried with Na₂SO₄. Purification of the evaporated residue on a silica gel column with hexanes:EtOAc (30-100% B gradient) yielded 288-1 (150 mg, 81%).

A solution of 288-1 (120 mg, 0.1 mmol) in 80% aq. TFA (5 mL) was kept at RT for 3 h. The mixture was concentrated, and the residue coevaporated with toluene. The crude material was purified on a silica column with CH₂Cl₂:MeOH (4-10% B gradient) to give 288 (25 mg, 36%). MS: m/z=691 [M+1]⁺.

Example 166

Compound 289

44 ⟶

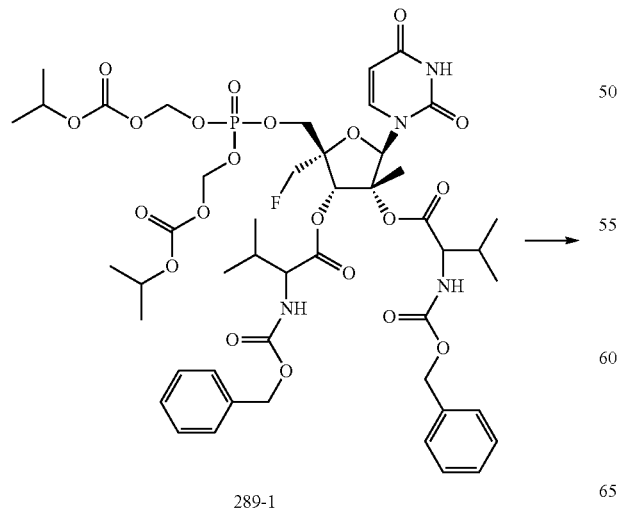

289-1

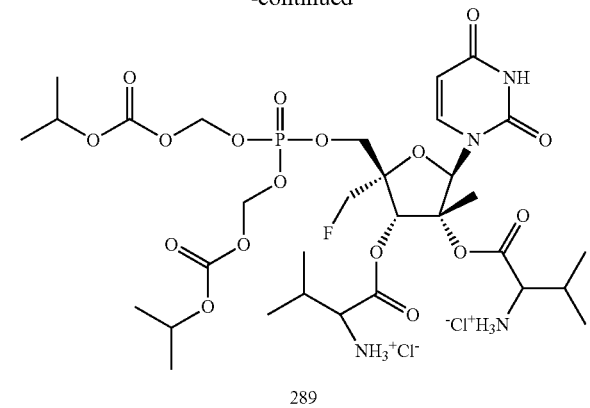

289

To a mixture of DCC (412 mg, 1.98 mmol) in DMF (1 mL), DMAP (244 mg, 1.98 mmol) and Z-Val-OH (502 mg, 1.98 mmol) were added successively, followed by the addition of 44 (200 mg, 0.183 mmol). The mixture was stirred at RT for 1 h. The mixture was filtered, and the filtrate was concentrated with a rotary evaporator until ½ of its original volume. EA was added, and the mixture was washed with water and brine, dried over anhydrous Na₂SO₄ and concentrated in vacuo to give a residue. The residue was purified by silica gel with 35-95% EA:hexanes to give 289-1 (107 mg, 31.2%) as a white foam.

To a solution of 289-1 (68 mg, 0.064 mmol) in anhydrous EtOH (2.0 mL) was added 10% Pd/C (12 mg), followed by the addition of 4N HCl (67 μl, 0.25 mmol). The mixture was stirred under H₂ atmosphere for 1.5 h. The mixture was filtered through celite, and the catalyst cake was washed with anhydrous EtOH. The washings and the filtrate were combined. The solvent was removed under vacuum to give 289 (41.6 mg, 82%) as a light yellow foam. MS: m/z=801.25 [M+H]⁺.

Example 167

Compound 290

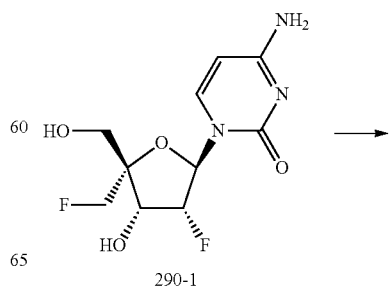

290-1

-continued

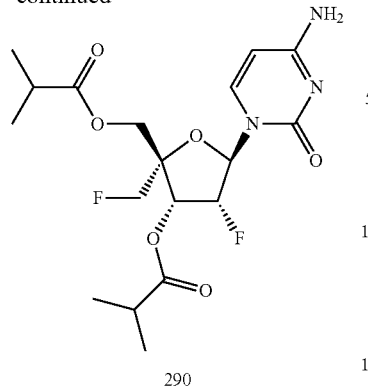

290

To a solution of 290-1 (40 mg, 0.144 mmol) in DMF (2 mL) were added DCC (65 mg, 0.32 mmol), isobutyric acid (28 μl, 0.32 mmol) and DMAP (18 mg, 0.144 mmol). The mixture was stirred at RT overnight. The mixture was filtered, and the filtrate was concentrated with a rotary evaporator to ½ of its original volume. The mixture was then diluted with 25% DMF/H$_2$O and purified on a reverse-phase HPLC (C18) using CH$_3$CN and water. Lyophilization gave 290 (17.5 mg, 29%) as a white powder. MS: m/z 416.1 [M+H]$^+$.

Example 168

Compound 291

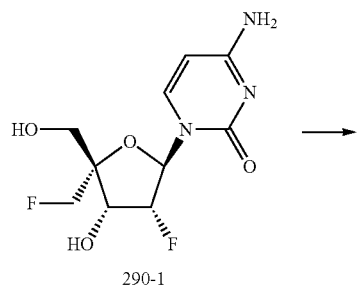

290-1

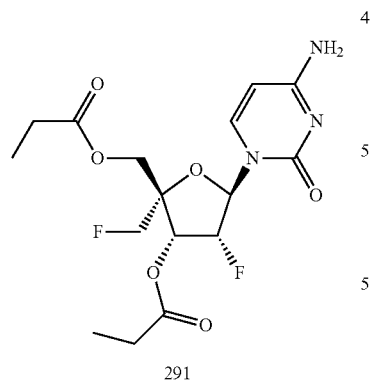

291

To a solution of 290-1 (50 mg, 0.18 mmol) in DMF (1.5 mL) were added DCC (93 mg, 0.45 mmol), propanoic acid (33.4 μl, 0.45 mmol) and DMAP (22 mg, 0.18 mmol). The mixture was stirred at RT overnight. The mixture was filtered, and then filtrate was concentrated with a rotary evaporator to ½ of its original volume. The mixture was then diluted with 25% DMF/H$_2$O, and purified on a reverse-phase HPLC (C18) using CH$_3$CN and water. Lyophilization gave 291 (30.2 mg, 43%) as a white powder. MS: m/z 390.1 [M+H]$^+$, 388.05 [M–H]$^−$.

Example 169

Compound 292

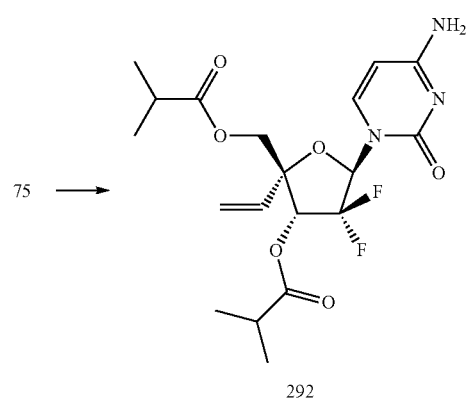

292

To a solution of 75 (20 mg, 0.073 mmol) in DMF (0.7 mL) were added DCC (37.6 mg, 0.183 mmol), isobutyric acid (16 μl, 0.183 mmol) and DMAP (9 mg, 0.073 mmol). The mixture was stirred at RT overnight. The mixture was filtered, and the filtrate was concentrated with a rotary evaporator to ½ of its original volume. The mixture was then diluted with 25% DMF/H$_2$O, and purified on a reverse-phase HPLC (C18) using 25-95% CH$_3$CN:water. Lyophilization gave 292 (12.1 mg, 38.7%) as a white powder. MS: m/z 430.15 [M+H]$^+$, 428.10 [M–H]$^−$.

Example 170

Compound 293

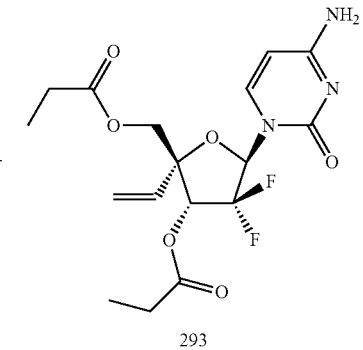

293

To a solution of 75 (20 mg, 0.073 mmol) in DMF (0.7 mL) were added DCC (37.6 mg, 0.183 mmol), propanoic acid (13.5 μl, 0.183 mmol) and DMAP (9 mg, 0.073 mmol). The mixture was stirred at RT overnight. The mixture was filtered, and then filtrate was concentrated with a rotary evaporator to ½ of its original volume. The mixture was then diluted with 25% DMF/H$_2$O, and purified on a reverse-phase HPLC (C18) using 25-95% CH₃CN:water Lyophilization gave 293 (14.1 mg, 48%) as a white powder. MS: m/z 402.1 [M+H]⁺.

Example 171

Compound 294

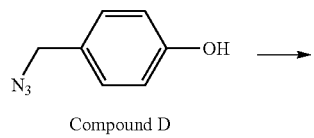

Compound D

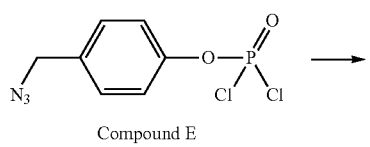

Compound E

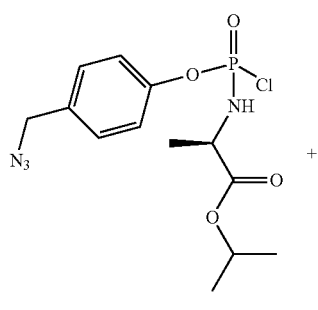

Compound F

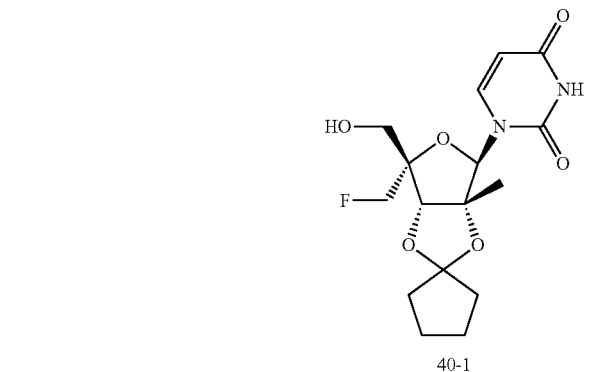

40-1

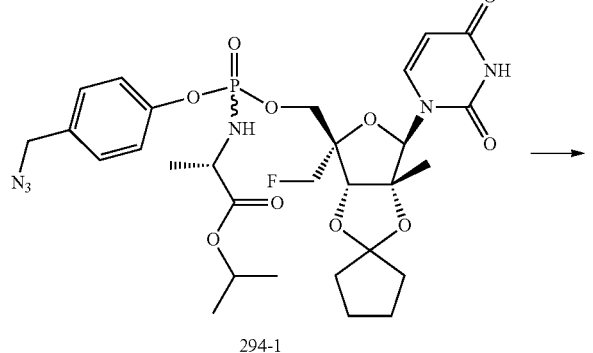

294-1

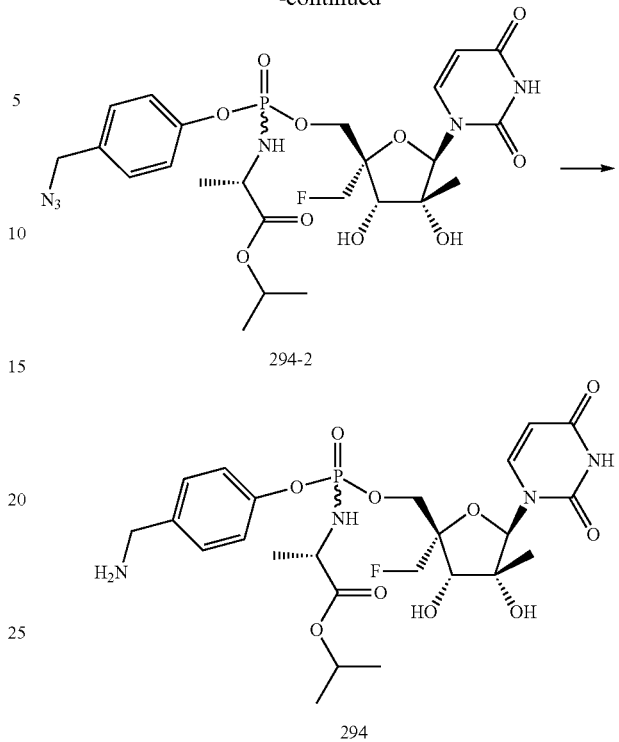

294-2

294

To a mixture of Compound D (0.9 g, 6.0 mmol; prepared according to Qing et al. *Org. Lett.* (2008) 10:545-548) and POCl₃ (0.55 mL, 6.0 mmol) in diethyl ether (9 mL) at −78° C. was added Et₃N (0.84 mL, 6.0 mmol). The mixture was allowed to warm to RT in 2 h. The mixture was then filtered, and the solids were washed with Et₂O. The combined filtrates were evaporated, and the crude Compound E was used without purification.

To a solution of crude Compound E and L-alanine isopropyl ester hydrochloride (1.0 g, 6.0 mmol) in CH₂Cl₂ (15 mL) at −20° C. was added Et₃N (1.67 mL, 1.2 mmol). The mixture was allowed to warm up and stirring at RT for 2 h. The mixture was diluted with hexanes and filtered through a silica pad which was thoroughly washed with CH₂Cl₂:hexanes 1:1. The combined filtrates were concentrated and purified on a silica column with hexanes:EtOAc (5-50% B gradient) to yield Compound F (0.78 g, 38% for 2 steps).

To a solution of 40-1 (0.36 g, 1.0 mmol) in THF (7.5 mL) at 0° C. was added isopropyl magnesium chloride (2 M in THF; 0.65 mL, 1.3 mmol), and the mixture was stirred at 0° C. for 30 mins. A solution of Compound F (0.78 g, 2.2 mmol) in THF (2 mL) was added, and the mixture stirred at RT for 2 h. The reaction was quenched with sat. aq. NH₄Cl, and then diluted with EtOAc. The two layers were separated. The organic layer was washed with water and brine, and dried over Na₂SO₄. Purification of the evaporated residue on a silica gel column with CH₂Cl₂:i-PrOH (3-10% B gradient) yielded 294-1 (0.50 g, 74%).

A solution of 294-1 (0.28 g, 0.4 mmol) in 80 aq. TFA (4 mL) was stirred at RT for 4 h. The mixture was evaporated and coevaporated with toluene. The residue was purified on a silica column with CH₂Cl₂:MeOH (4-10% B gradient) to give 294-2 (0.17 g, 68%).

To a solution of 294-2 (85 mg, 0.14 mmol) in EtOH (3 mL) and HCl (4 N in dioxane; 35 μL, 0.14 mmol) was added 10% Pd/C (8 mg). The mixture was stirred under H₂

(atmospheric pressure) for 105 mins. The mixture was then filtered through a Celite pad. The evaporated residue was treated with Et$_2$O to yield 294 (55 mg, 63%) as a white solid. MS: m/z=589 [M+1]$^+$.

Example 172

Compound 295

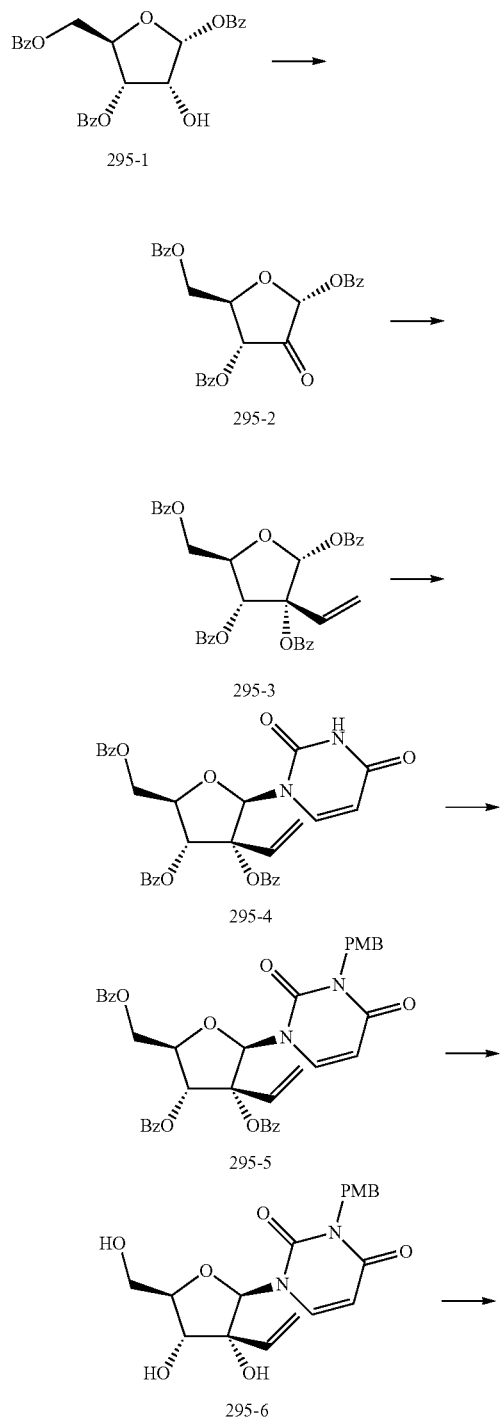

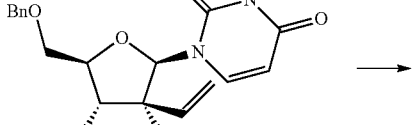

295-7

295-8

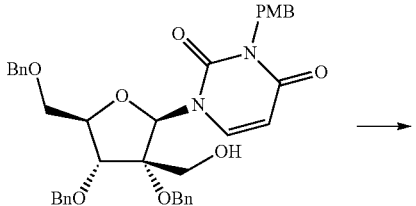

295-9

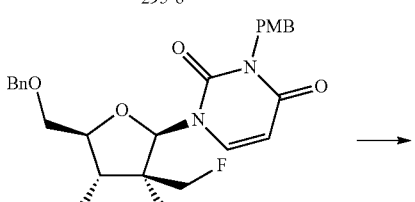

295-10

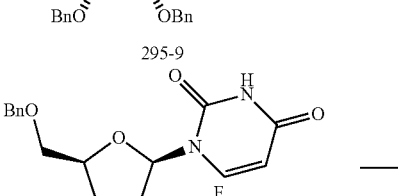

295-11

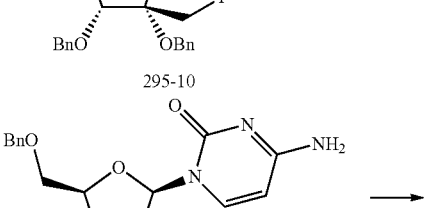

295

A mixture of 295-1 (120 g, 0.26 mol) and IBX (109 g, 0.39 mol) in CH$_3$CN (2.0 L) was heated to reflux and stirred for 12 h. After cooling to RT, the mixture was filtered. The filtrate was concentrated at low pressure and used directly for the next step.

295-2 (130 g, crude, 0.26 mol) was co-evaporated with anhydrous toluene (3×) to remove H$_2$O. Vinyl magnesium bromide (700 mL, 0.78 mol, 1.0 N in THF) was added dropwise into a solution of 295-2 in THF (300 mL) over 30 mins at −78° C. The mixture was stirred for about 1 h. at 25° C. and checked by LCMS trace. When the starting material was consumed, the mixture was poured into a sat. NH$_4$Cl solution, and extracted with EA (3×300 mL). The organic layer was washed with brine, dried with anhydrous Na$_2$SO$_4$, filtered and concentrated at low pressure to give the crude intermediate without further purification.

To a solution of this crude intermediate (170 g, 0.346 mol) in anhydrous CH$_2$Cl$_2$ was added TEA (105 g, 1.04 mol) and DMAP (84 g, 0.69 mol), and the mixture was stirred at RT. Benzoyl chloride (146 g, 1.04 mol) was added slowly at RT. After stirring for 12 h at RT, the mixture was diluted with CH$_2$Cl$_2$ and then washed with sat. aq. NaHCO$_3$. The combined aqueous phase was extracted with DCM (100 mL). The combined organic phase was dried with anhydrous Na$_2$SO$_4$, filtered and evaporated to dryness under reduced pressure. The residue was purified by column chromatography (PE:EA=10:1 to 5:1) to give 295-3 (107 g, 52%).

A mixture of uracil (treated by toluene twice) and NOBSA (81.4 g, 0.4 mol) in CH$_3$CN (200 mL) was stirred to reflux for 1.5 h. After the mixture was cooled to RT, 295-3 (59 g, 0.1 mol, treated by toluene) in CH$_3$CN (100 mL) was added. The mixture was treated with TMSOTf (155 g, 0.7 mol), and then warmed to 60-70° C. for 12 h. LCMS showed that no starting material remained. The mixture was poured into a NaHCO$_3$ (sat.) solution. The desired product precipitated. After filtration, pure 295-4 (40 g, 69%) was obtained as a white solid.

To a solution of 295-4 (50 g, 0.086 mol), K$_2$CO$_3$ (17.8 g, 0.13 mol) in DMF (500 mL) was added PMBCl (16 g, 0.1 mol) at 0° C., and the mixture stirred at 25° C. for 12 h. The reaction was quenched with water, and the mixture was extracted with EtOAc (3×150 mL). The solution was washed with brine, dried over anhydrous Na$_2$SO$_4$ and concentrated at low pressure. Crude 295-5 (65 g) was obtained and used directly for the next step.

A mixture of 295-5 (65 g, 0.086 mol) and NaOMe (16.8 g, 0.3 mol) in MeOH:DCM (4:1, 200 mL) was stirred at RT for 2.5 h. LCMS showed that no starting material remained. The reaction was quenched with dry ice. The solution was washed with brine, dried over anhydrous Na$_2$SO$_4$ and concentrated at low pressure. The residue was purified by column chromatography (DCM:MeOH=50:1 to 20:1) to give 295-6 as a yellow foam (25 g, 75%).

To a solution of 295-6 (25.5 g, 0.065 mol) in DMF was added NaH (10.5 g, 0.26 mol) slowly at ice bath, and the mixture was stirred for 30 mins. BnBr (36.3 g, 0.21 mol) was added, and the mixture was stirred at 25° C. for 12 h. TLC showed that the starting material disappeared. The reaction was quenched by sat. aq. NH$_4$Cl and extracted with EtOAc (3×100 mL). The organic phase was washed with brine, dried over anhydrous Na$_2$SO$_4$ and concentrated at low pressure. The residue was purified by column chromatography (PE:EA=5:1 to 3:1 to 1:1) to give 295-7 (20 g, 46%).

To a solution of 295-7 (20 g, 0.03 mol), NMMO (7 g, 0.06 mol) in THF:H$_2$O (5:1, 100 mL) was added OsO$_4$ (2.6 g, 0.01 mol) at 25° C., and the mixture was stirred at 25° C. for 24 h. The reaction was quenched with a sat. Na$_2$S$_2$O$_3$ solution, and extracted with EtOAc (3×100 mL). The organic layer was washed with brine, dried over anhydrous Na$_2$SO$_4$ and concentrated at low pressure. The diol product residue was used directly for next step.

To a solution of diol product (0.03 mol) in MeOH:H$_2$O:THF (170 mL:30 mL:50 mL) was added NaIO$_4$ (9.6 g, 0.045 mol), and the mixture was stirred at 25° C. for 2 h. After the white solid was filtered, the filtrate was used directly for the next step.

The previous solution was treated with NaBH$_4$ (1.8 g, 0.048 mol) at 0° C., and stirred at 25° C. for 30 mins. The reaction was quenched with HCl (1 N) solution and adjusted pH to 7-8. The solution was extracted by EtOAc (3×50 mL). The organic phase was washed with brine washed with brine, dried over anhydrous Na$_2$SO$_4$ and concentrated at low pressure. The residue was purified by column chromatography (PE:EA=6:1 to 4:1) to give 295-8 (12 g, 61% over 3 steps).

To a solution of 295-8 (14 g, 21 mmol), DMAP (5.1 g, 42 mmol) in DCM (50 mL) was added MsCl (3.1 g, 27 mmol) at 0° C., and the mixture was stirred at 25° C. for 40 mins. LCMS shows that no starting material remained. The reaction was quenched by sat. aq. NaHCO$_3$ and extracted with DCM (3×100 mL). The solution was washed with HCl (0.2 N) solution, dried over anhydrous Na$_2$SO$_4$ and concentrated at low pressure. The residue was purified by column chromatography (PE:EA=10:1 to 5:1) to give the OMs-product (14 g, 90%).

The OMs-product (6.1 g, 8.21 mmol) was dissolved in TBAF (Alfa, 1 N in THF, 120 mL), and the mixture was stirred at 70-80° C. over 3 days. LCMS shows that 50% of the starting material was converted to the desired product. The mixture was concentrated at low pressure. The residue was dissolved in EtOAc (100 mL). The solution was washed by brine, dried over anhydrous Na$_2$SO$_4$ and concentrated at low pressure. The residue was purified by column chromatography (PE:EA=10:1 to 5:1) to give 295-9 (1.3 g, 24%).

To a solution of 295-9 (6.3 g, 9.45 mmol) in CAN:H$_2$O (v:v=3:1, 52 mL) was added CAN (15.5 g, 28.3 mmol), and the mixture was stirred at RT overnight. The reaction was quenched with water, and extracted with EA (3×80 mL). The organic phase was washed with brine, dried over anhydrous Na$_2$SO$_4$ and concentrated at low pressure. The residue was purified by column chromatograph (25% EA in PE) to give 295-10 (3.6 g, 71%) as a yellow oil.

To a solution of 295-10 (566 mg, 1.04 mmol), DMAP (253 mg, 2.07 mmol) and TEA (209 mg, 2.07 mmol) in anhydrous MeCN (6 mL) was added TPSCl (627 mg, 2.07 mmol) at 0° C. The mixture was stirred at RT for 2 h. The mixture was treated with NH$_3$.H$_2$O (10 mL), and stirred at RT overnight. TLC showed that the reaction was completed. The solution was concentrated at low pressure. The residue was purified by silica gel column chromatography (DCM:MeOH=50:1 to 20:1) to give 295-11 (300 mg, 49%) as a white solid.

To a solution of 295-11 (200 mg, 0.37 mmol) in anhydrous DCM (0.5 mL) was added BCl$_3$ (2.5 mL, 1 N in DCM) at −70° C., and the mixture was stirred for 2 h at −70° C. TLC showed that no materials remained. The reaction was quenched with MeOH at −70° C., and concentrated at low pressure directly under 40° C. The residue was dissolved in H$_2$O, and washed with EtAc over 3 times. The aqueous phase was lyophilized to give 295 (91 mg, 89%) as a white solid. ESI-LCMS: m/z 276.1 [M+H]$^+$.

Example 173

Compound 296

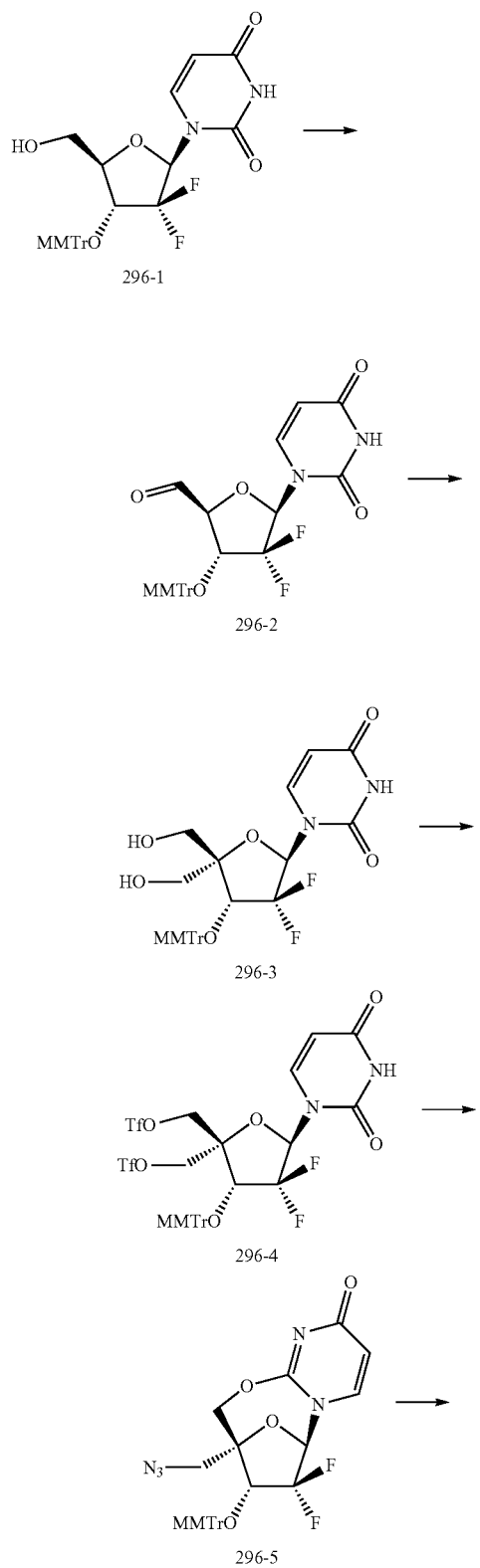

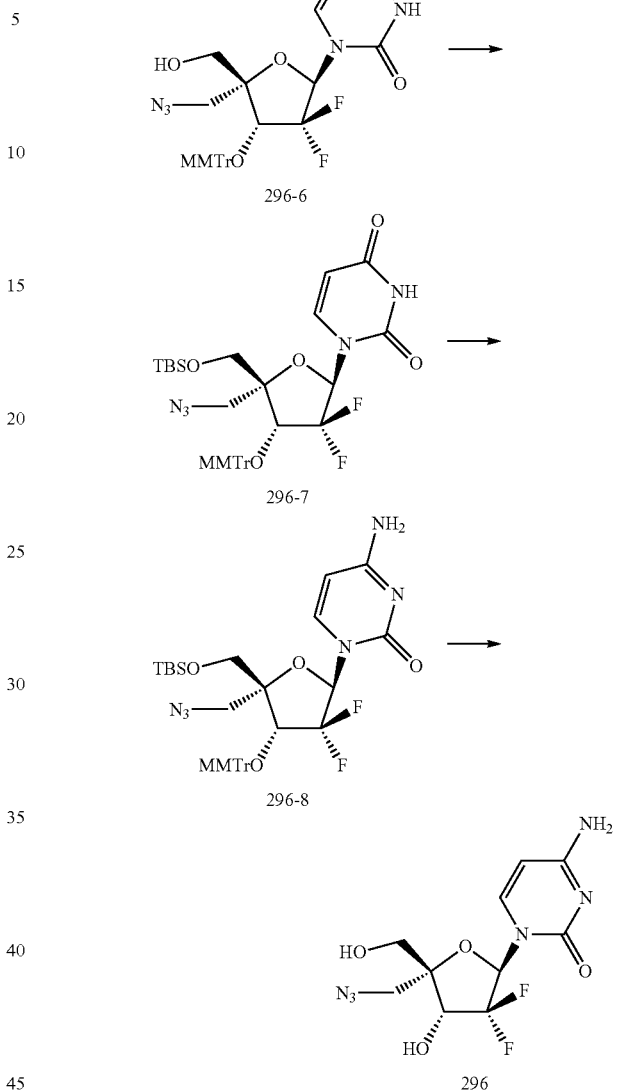

To a stirred solution of 296-1 (8.2 g, 15.3 mmol) in anhydrous CH₃CN (150 mL) was added IBX (4.7 g, 16.8 mmol) at 20° C. under N₂. The suspension was heated to 90° C.~100° C. and stirred at this temperature for 1 h. The mixture was filtered, and the filtrate was concentrated under reduced pressure. The residue, 296-2, (8.2 g, crude) was used in the next step without further purification.

To a solution of 296-2 (8.2 g, 15.4 mmol) in 1,4-dioxane (150 mL) was added aq. NaOH (15.4 mL, 2 M, 30.8 mmol) at 20° C. The mixture was stirred at this temperature for 10 h. The solution was neutralized with AcOH to pH=7, followed by addition of EtOH (50 mL) and NaBH₄ (5.8 g, 154.3 mmol) at 0° C. The mixture was stirred at this temperature for 1 h. The reaction was quenched with water (20 mL), extracted with EA (2×40 mL). The combined organic phase was washed with brine, dried over anhydrous MgSO₄ and concentrated at low pressure. The residue was purified via silica gel chromatography (50% EA in PE) to give 296-3 (5.5 g, 62.92%) as a white solid.

296-3 (480 mg, 0.8 mmol) was co-evaporated with toluene (2×). The residue was dissolved in anhydrous DCM (5 mL) and pyridine (671 mg, 85 mmol). Tf$_2$O (481 mg, 187 mmol) was added dropwise at 0° C. over 10 mins. The mixture was stirred at this temperature for 40 mins. The mixture was purified by column chromatography (20% EA in PE) to give 296-4 (602 mg, 86.1%) as a brown foam.

To a solution of 296-4 (602.0 mg, 0.72 mmol) in anhydrous DMF (8 mL) was added NaH (34.8 mg, 0.87 mmol) at 0° C. under N$_2$ atmosphere. The reaction was stirred at 20° C. for 1 h, and then NaN$_3$ (1.59 g, 2.5 mmol) was added at 0° C. under N$_2$ atmosphere. The mixture was stirred at 20° C. for 2 h. The reaction was quenched with water at the same temperature, extracted with EA (2×20 mL). The combined organic layer was washed with brine, dried over Na$_2$SO$_4$ and filtered. The filtrate was concentrated to dryness under reduced pressure. The residue, 296-5, (431 mg, crude) was used in next step without further purification.

To a solution of 296-5 (431 mg, crude) in 1,4-dioxane (14 mL) was added aq. NaOH (114.4 mg, 2 M, 2.9 mmol) at 18° C. The mixture was stirred at the same temperature for 3 h. The mixture was diluted with EA (20 mL). The organic layer was washed with brine, dried over MgSO$_4$ and concentrated at low pressure. The residue was purified via silica gel chromatography (30% EA in PE) to give 296-6 (406.0 mg, 47.9%) as a white foam.

To a solution of 296-6 (406.0 mg, 0.68 mmol) in anhydrous DMF (8 mL) was added TBSCl (198.7 mg, 1.3 mmol) and imidazole (119.7 mg, 1.8 mmol) at 30° C. under N$_2$ atmosphere. The solution was stirred at this temperature for 3 h. The solution was diluted with EA (20 mL) and washed with water and brine. The organic phase was dried over MgSO$_4$ and concentrated at low pressure. The residue was purified via silica gel chromatography (50% EA in PE) to give 296-7 (405.0 mg, 65.28%) as a white solid.

To a solution of 296-7 (405.0 mg, 0.57 mmol) in anhydrous CH$_3$CN (6 mL) was added 2,4,6-triisopropylbenzene-1-sulfonyl chloride (343.3 mg, 1.13 mmol), DMAP (138.5 mg, 1.1 mmol) and TEA (114.7 mg, 1.1 mmol) at 30° C. The mixture was stirred at this temperature for 9 h. NH$_3$.H$_2$O (4 mL) was added, and the mixture was stirred for 3 h. The mixture was diluted with EA (20 mL) and washed with brine. The organic layer was dried over Na$_2$SO$_4$ and concentrated at low pressure. The residue was purified via silica gel chromatography (50% EA in PE) to give 296-8 (401.0 mg, crude) as a yellow foam.

296-8 (380.0 mg, 0.54 mmol) was dissolved in 80% HCOOH (25 mL), and the mixture was stirred at 30° C. for 12 h. The reaction was quenched with MeOH and concentrated under reduced pressure. The residue was purified by silica gel chromatography (10% MeOH in DCM) to give 296 (144.0 mg, 83.93%) as a white foam. ESI-MS: m/z 319.1 [M+H]$^+$; 637.2 [2M+H]$^+$.

Example 174

Compound 297

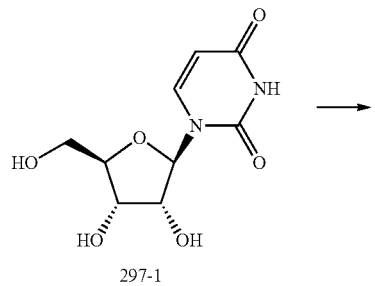

297-1

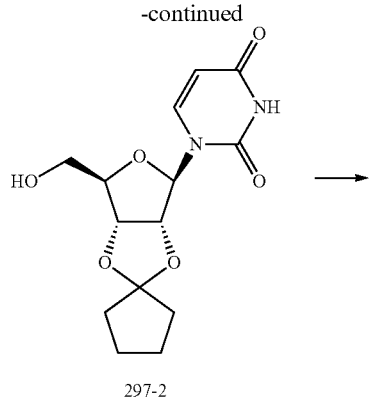

297-2

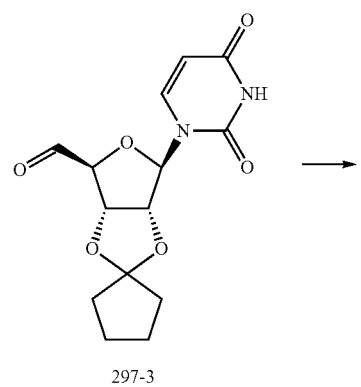

297-3

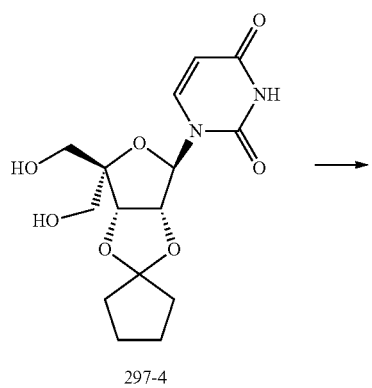

297-4

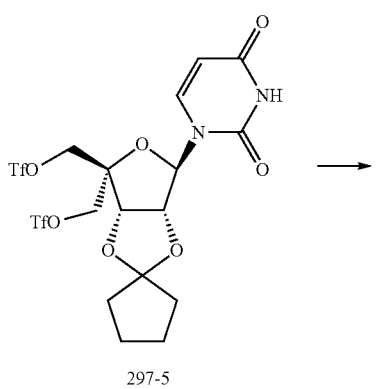

297-5

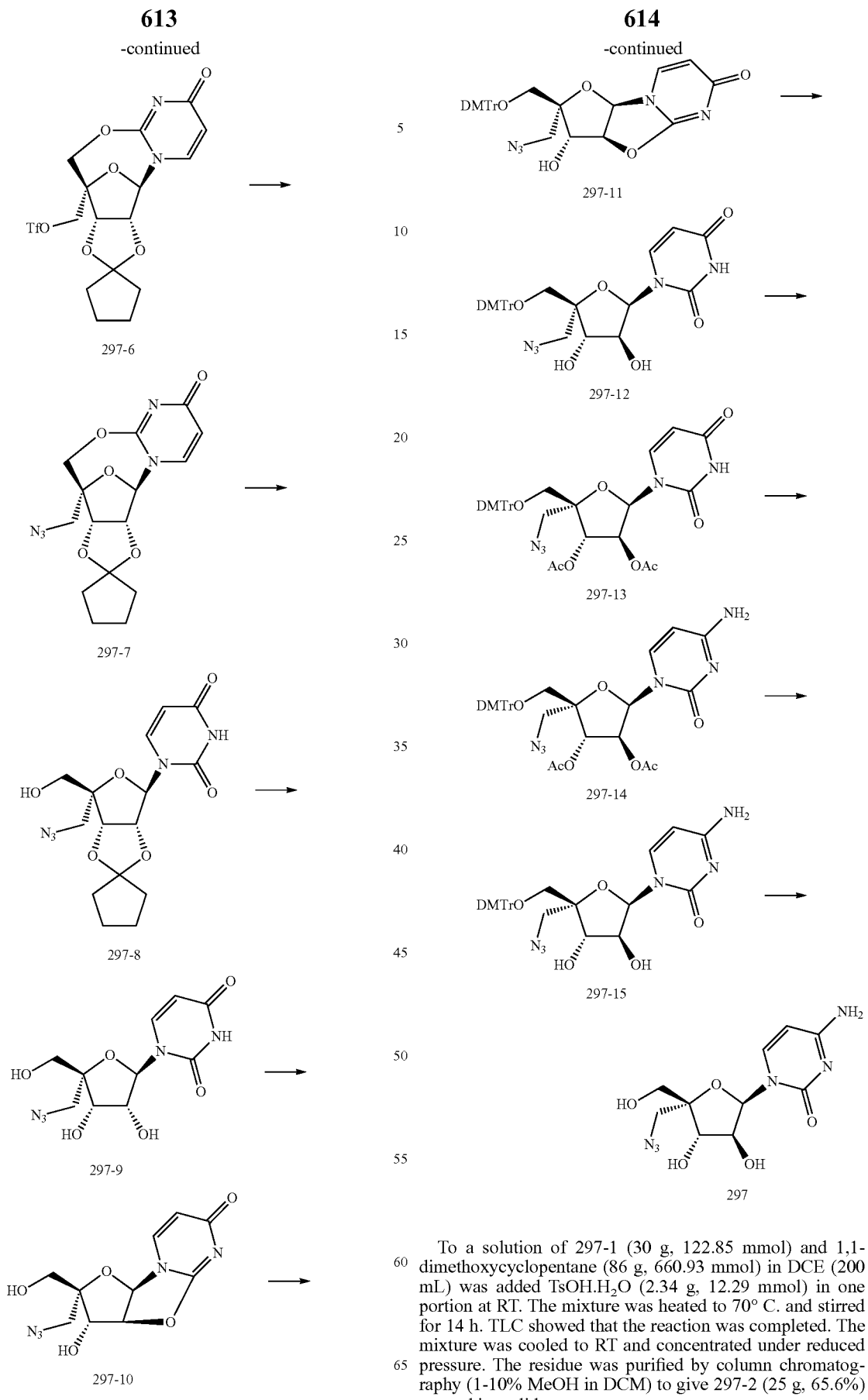
To a solution of 297-1 (30 g, 122.85 mmol) and 1,1-dimethoxycyclopentane (86 g, 660.93 mmol) in DCE (200 mL) was added TsOH.H$_2$O (2.34 g, 12.29 mmol) in one portion at RT. The mixture was heated to 70° C. and stirred for 14 h. TLC showed that the reaction was completed. The mixture was cooled to RT and concentrated under reduced pressure. The residue was purified by column chromatography (1-10% MeOH in DCM) to give 297-2 (25 g, 65.6%) as a white solid.

To a solution of 297-2 (20 g, 64.45 mmol) in anhydrous CH₃CN (200 mL) was added IBX (19.85 g, 70.9 mmol) at RT. The mixture was refluxed for 18 h. and then cooled to 0° C. The precipitate was filtered-off, and the filtrate was concentrated to give crude 297-3 (20 g, 100%) as a yellow solid.

To a solution of 297-3 (20 g, 64.87 mmol) in 1,4-dioxane (200 mL) were added 37% HCHO (20 mL) and 2.0 M NaOH aq. solution (40 mL) at 0° C. The mixture was stirred at RT overnight and then neutralized with AcOH to pH=7. The solution was treated with NaBH₄ (4.91 g, 129.74 mmol) at 20° C. The mixture was stirred at RT for 1.0 h, and the reaction was quenched with sat. aq. NH₄Cl. The mixture was extracted with EA (3 s 200 mL). The organic layer was dried over anhydrous Na₂SO₄ and concentrated at low pressure. The residue was purified by silica gel column chromatography (1-3% MeOH in DCM) to give 297-4 (9 g, 40.8%) as a white solid.

To an ice cold solution of 297-4 (4.5 g, 13.22 mmol) in anhydrous DCM (50 mL) was added pyridine (10.46 g, 132.20 mmol) and Tf₂O (8.21 g, 29.08 mmol) dropwise at −30° C. The mixture was stirred at the same temperature for 1 h. The reaction was quenched with ice water and extracted with EA (3×60 mL). The organic phase was washed with brine, dried over anhydrous Na₂SO₄ and concentrated at low pressure. The residue was purified on a silica gel column (PE:EA=5:1) to give 297-5 (5 g, 62.57%) as a white solid.

To a stirred solution of 297-5 (5 g, 8.27 mmol) in anhydrous DMF (25 mL) was added NaH (396.96 mg, 9.92 mmol) at 0° C. under N₂. The solution was stirred at RT for 2 h. TLC showed that the reaction was completed. The solution of 297-6 was used in next step without any further workup.

To a stirred solution of 297-6 (3.75 g, 8.25 mmol) was added NaN₃ (1.5 g, 2.50 g, 38.46 mmol) at 0° C. under N₂ atmosphere. The solution was stirred at RT for 2 h. The reaction was quenched with water and extracted with EA (3×60 mL). The organic layer was washed with brine, dried over anhydrous Na₂SO₄ and concentrated at low pressure. The residue, 297-7, was used in the next step without further purification.

To a solution of 297-7 (2.87 g, 8.25 mmol) in anhydrous 1,4-dioxane (30 mL) was added NaOH (8.25 mL, 16.50 mmol, 2.0 M in water) at RT. The mixture was stirred at RT for 3 h. TLC showed that the reaction was completed. The mixture was diluted with EA. The solution was washed with brine, dried over anhydrous Na₂SO₄ and concentrated at low pressure. The residue was purified on the silica gel column (PE:EA=10:1 to 2:1) to give 297-8 (2 g, 66.4%) as a white foam. ¹H-NMR (DMSO, 400 MHz), δ=9.02 (s, 1H), 7.40 (d, J=8.0 Hz, 1H), 5.75-5.77 (m, 1H), 5.57 (d, J=3.6 Hz, 1H), 5.13-5.16 (m, 1H), 4.90 (d, J=6.4 Hz, 1H), 3.79-3.85 (m, 2H), 5.51-5.56 (m, 2H), 3.06-3.09 (m, 1H), 2.05-2.09 (m, 2H), 1.65-1.75 (m, 6H).

297-8 (2 g, 5.47 mmol) was dissolved in 80% HCOOH (20 mL) aq. solution, and the mixture was heated to 60° C. for 2 h. The mixture was evaporated at low pressure. The residue was dissolved in MeOH, and the pH was adjusted to 7-8 with NH₃.H₂O. The mixture was stirred for 10 mins, and then concentrated at low pressure. The residue was purified by silica gel chromatography (DCM:MeOH=20:1) to afford 297-9 (1.4 g, 85.5%) as a white solid.

To a solution of 297-9 (1.00 g, 3.34 mmol) in DMF (5 mL) was added diphenyl carbonate (157.49 mg, 735.20 μmol) and NaHCO₃ (28.06 mg, 0.334 mmol) at 120° C. The mixture was stirred for 16 h. TLC showed that the reaction was completed. The mixture was cooled to RT and concentrated at low pressure. The residue was purified by silica gel chromatography (DCM:MeOH=15:1 to 10:1) to afford 297-10 (600. mg, 63.9%) as a yellow solid. ¹H-NMR (DMSO, 400 MHz), δ=8.49 (s, 1H), 7.83 (d, J=7.2 Hz, 4H), 6.46 (s, 1H), 6.31 (d, J=4.8 Hz, 1H), 5.84 (d, J=6.8 Hz, 1H), 5.27 (d, J=5.6 Hz, 2H), 4.43 (s, 1H), 3.53 (d, J=12.8 Hz, 1H), 3.43 (d, J=13.2 Hz, 1H), 3.12 (d, J=11.2 Hz, 1H).

To a solution of 297-10 (2 g, 7.11 mmol) and AgNO₃ (1.81 g, 10.67 mmol) in Py (20 mL) was added DMTrCl (3.61 g, 10.67 mmol) in one portion at RT. The mixture was stirred at RT for 12 h. TLC showed that the reaction was completed. The mixture was concentrated at low pressure, and the residue was purified by silica gel chromatography (DCM:MeOH=50:1) to afford 297-11 (3 g, 72.3%) as a white solid.

To a solution of 297-11 (1.5 g, 2.57 mmol) in EtOH (5 mL) was added NaOH (5 mL, 2.0 N) in one portion at RT. The mixture was stirred at RT for 0.5 h. TLC showed that the reaction was completed. The aqueous phase was extracted with EA (3×60 mL). The organic phase was washed with brine, dried with anhydrous Na₂SO₄, filtered and concentrated in vacuum to afford 297-12 (1.50 g, 97%) as a yellow solid.

To a solution of 297-12 (1.50 g, 2.49 mmol) in Py (6 mL) was added AC₂O (3 mL) in one portion at RT. The mixture was stirred at RT for 12 h. TLC showed that the reaction was completed. The mixture was concentrated, and the residue was dissolved in water. The aqueous phase was extracted with EA (3×60 mL). The combined organic phase was washed with sat. brine, dried with anhydrous Na₂SO₄, filtered and concentrated in vacuum. The residue was purified by silica gel chromatography (PE:EA=1:1) to afford 297-13 (1.5 g, 87.8%) as a white solid. ¹H-NMR (CDCl₃, 400 MHz), δ=8.10 (s, 1H), 7.29-7.34 (m, 10H), 6.77 (d, J=8.0 Hz, 4H), 6.36 (d, J=5.2 Hz, 1H), 5.36 (d, J=3.6 Hz, 1H), 5.44 (t, J=4.0 Hz, 1H), 5.32 (d, J=8.0 Hz, 1H), 3.80 (s, 6H), 3.58 (d, J=12.8 Hz, 1H), 3.44 (d, J=12.8 Hz, 1H), 3.29 (s, 2H), 2.10 (s, 3H), 1.82 (s, 3H).

To a solution of 297-13 (500 mg, 729.2 μmol) in MeCN (10 mL) was added DMAP (178.17 mg, 1.46 mmol) and TPSCl (430.01 mg, 1.46 mmol) in one portion at RT. The mixture was stirred at RT for 3 h. NH₃/THF (20 mL, sat) was added, and the mixture was stirred for 1 h. The mixture was diluted with EA and washed with water. The combined organic phase was washed with sat. brine, dried with anhydrous Na₂SO₄, filtered and concentrated in vacuum. The residue was purified by silica gel chromatography (DCM:MeOH=50:1) and then purified by pre-HPLC(CH₃CN/H₂O) to afford 297-14 (260 mg, 49.5%) as a yellow solid. ¹H-NMR (MeOD, 400 MHz), δ=7.60 (d, J=7.6 Hz, 1H), 7.46 (d, J=7.6 Hz, 1H), 7.28-7.36 (m, 7H), 6.89 (d, J=8.4 Hz, 4H), 6.44 (d, J=4.8 Hz, 1H), 5.56-5.69 (m, 4H), 3.80 (s, 6H), 3.54 (d, J=13.2 Hz, 1H), 3.39-3.46 (m, 4H), 2.17 (s, 3H), 1.83 (s, 3H).

To a solution of 297-14 (440 mg, 642.6 μmol) in NH₃: MeOH (5 mL, 7N) was stirred at RT for 16 h. TLC showed that the reaction was completed. The mixture was concentrated under reduced pressure at 40° C. The residue was purified by silica gel chromatography (DCM:MeOH=100: 1-20:1) to afford 297-15 (290 mg, 75.13%) as a white solid. ¹H-NMR (MeOD, 400 MHz), δ=7.62 (d, J=7.6 Hz, 1H), 7.43 (d, J=7.6 Hz, 1H), 7.23-7.33 (m, 7H), 6.86 (d, J=8.4 Hz, 4H), 6.31 (d, J=4.8 Hz, 1H), 5.54 (d, J=7.2 Hz, 1H), 4.34 (t, J=4.4 Hz, 1H), 4.27 (d, J=4.0 Hz, 1H), 3.78 (s, 6H), 3.69 (d, J=12.8 Hz, 1H), 3.46 (d, J=12.8 Hz, 1H), 3.41 (s, 2H).

A solution of 297-15 (150 mg, 249.74 μmol) in 80% CH₃COOH (5 mL) was stirred at 60° C. for 2 h. TLC showed that the reaction was completed. The mixture was treated with MeOH and concentrated under reduced pressure at 60° C. The residue was purified by silica gel chromatography (1-10% MeOH in DCM) to afford 297 (65 mg, 78.5%) as a white solid. ESI-MS: m/z 299.1 [M+H]$^+$.

Example 175

Compound 298

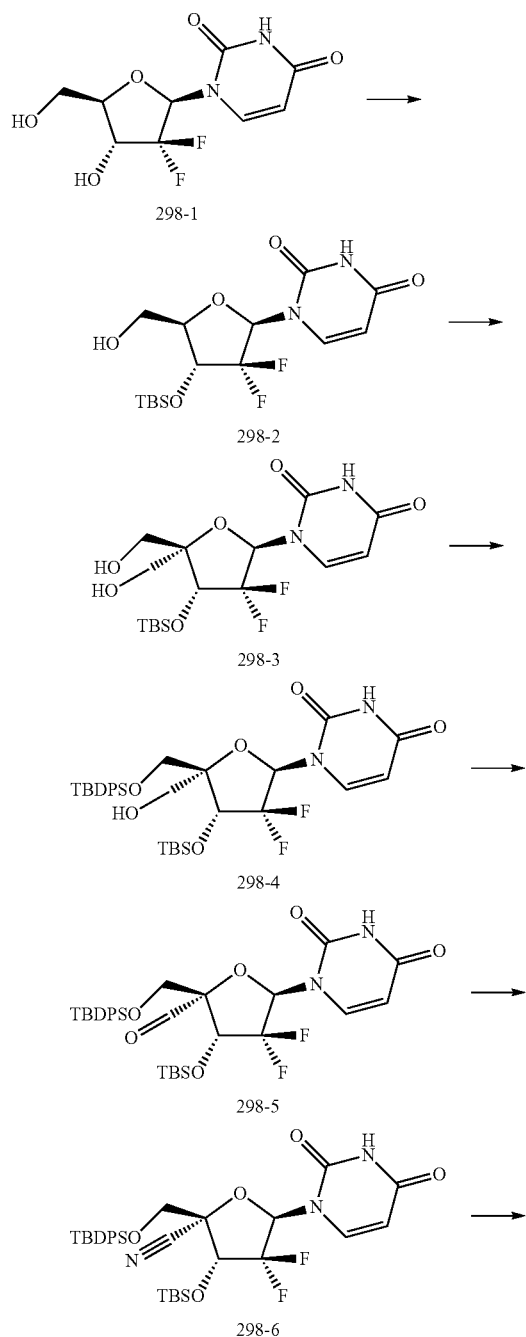

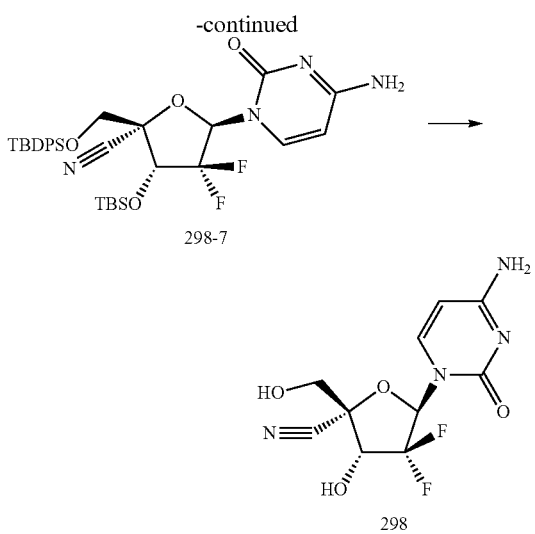

To a solution of 298-1 (12 g, 45.42 mmol) in pyridine (100 mL) was added DMTrCl (16.16 g, 47.69 mmol) in portions at 0° C. over a period of 30 mins under N$_2$. The mixture was warmed to 25° C. and stirred for 16 h. LCMS and TLC (DCM:MeOH=20:1) showed that the starting material was consumed. The reaction was quenched with MeOH (10 mL) and then concentrated in vacuum. The residue was purified by silica gel chromatography (100-200 mesh silica gel, PE:EA=1:1) to give pure DMTr-298-1 (20 g, 77.7%) as a white solid.

To a solution of DMTr-298-1 (30.00 g, 52.95 mmol) and TBSCl (19.95 g, 132.38 mmol, 2.50 eq.) in DCM (200 mL) was added imidazole (9.00 g, 132.20 mmol, 2.50 eq.) in portions at 0° C. The temperature was maintained below 5° C. The mixture was warmed to 25° C., and stirred for 16 h. TLC (PE:EA=1:1) showed that the starting material was consumed. The reaction was quenched by ice and then extracted with DCM (2×50 mL). The combined organic phase was washed with brine (50 mL), dried over anhydrous Na$_2$SO$_4$, filtered and concentrated at low pressure. The residue was purified by chromatography to give the pure product (30.00 g, 83.2%) as a white solid.

The product from the previous step (30.00 g, 44.07 mmol) was dissolved in 80% AcOH aqueous (300 mL), and the mixture was stirred at 25° C. for 16 h. TLC (DCM:MeOH=10:1) showed that the reaction was completed. The reaction was quenched with sat. aq. NaHCO$_3$ (100 mL) and then extracted with EA (3×100 mL). The organic phase was washed with brine, dried over anhydrous Na$_2$SO$_4$ and concentrated under reduced pressure. The residue was purified by a silica gel column (DCM:MeOH=50:1-20:1) to give 298-2 (15.5 g, 92.9%) as a white solid.

To a solution of 298-2 (8.00 g, 21.14 mmol) in MeCN (80 mL) was added IBX (6.51 g, 23.25 mmol, 1.10 eq.) at 25° C. under N$_2$. The mixture was heated to 81° C. for 1 h. LCMS showed that the starting material was consumed. The mixture was filtered, and the filtrates were concentrated in vacuum. The aldehyde residue (7.50 g, 19.92 mmol) was used in next step without further purification.

To a solution of the aldehyde from the previous step (7.5 g, 19.9 mmol) and aq. formaldehyde (7.85 mL) in dioxane (80 mL) was added 2.0 N aq. NaOH (19.5 mL) in one portion at 25° C. The mixture was stirred at 25° C. for 16 h. TLC showed that the reaction was completed. The mixture was cooled to 0° C. and then neutralized with AcOH to pH=7. The solution were treated with NaBH$_4$ (4.52 g, 119.52 mmol) at 0° C. The mixture was stirred at 25° C. for 30 mins, and the reaction was quenched with sat. aq. NH$_4$Cl (100 mL). The mixture was extracted with EA (2×100 mL). The organic phase was dried over anhydrous Na$_2$SO$_4$, filtered and concentrated in vacuum. The residue was purified by silica gel chromatography (100-200 mesh silica gel, DCM: MeOH=20:1 to 10:1) to afford 298-3 (4.0 g, 49.2%) as a white solid.

To a solution of 298-3 (4.00 g, 9.79 mmol) in pyridine (20 mL) was added a solution of MMTrCl (3.48 g, 10.28 mmol) in DCM (20 mL) dropwise at 0° C. over a period of 15 mins. The temperature was maintained below 5° C. The mixture was warmed to 25° C. and stirred at 25° C. for 16 h. TLC (DCM:MeOH=10:1) showed that the starting material was consumed. The reaction was quenched by MeOH (5 mL) and concentrated in vacuum. The residue was purified by column (DCM:MeOH=50:1) to give a pure intermediate (5.00 g, 71.85%) as a white solid.

To a solution of the above intermediate (5.00 g, 7.03 mmol) and AgNO$_3$ (2.39 g, 14.06 mmol, 2.00 eq.) in pyridine (40 mL) was added dropwise TBDPSCl (2.90 g, 10.55 mmol) at 0° C. over a period of 10 mins. The mixture was warmed to 25° C. and stirred for 16 h. TLC (PE:EA=1:1) showed that the starting material was consumed. The reaction was quenched by ice and then extracted with EA (3×100 mL). The combined organic phase was washed with sat. brine (2×50 mL), dried over anhydrous Na$_2$SO$_4$, filtered and concentrated in vacuum. The residue (5.00 g, crude) was dissolved in 80% aq. AcOH (50 mL), and the mixture was stirred at 25° C. for 2 h. TLC (PE:EA=2:1) showed that the reaction was completed. The reaction was quenched by MeOH (5 mL) and then extracted with DCM (3×100 mL). The organic phase was washed with brine, dried over anhydrous MgSO$_4$ and concentrated at low pressure. The residue was purified by a silica gel column (PE:EA=5:1 to 2:1) to give 298-4 (2.50 g, 55%) as a yellow solid.

To a solution of 298-4 (400 mg, 618.36 μmol) in DCM (4 mL) was added DMP (393.4 mg, 927.54 μmol, 1.50 eq.) in one portion at 0° C. under N$_2$. The mixture was stirred at 25° C. for 2 h. TLC (PE:EA=2:1) showed that the reaction was completed. The mixture was cooled to 0° C. and quenched with sat. aq. Na$_2$SO$_3$ (5 mL) and aq. NaHCO$_3$ (5 mL). The aqueous layer was extracted with DCM (3×10 mL). The combined organic phase was washed with sat. brine (10 mL), dried over anhydrous Na$_2$SO$_4$, filtered and concentrated in vacuum. The residue was purified by silica gel chromatography (100-200 mesh silica gel, PE:EA=3:1) to afford 298-5 (300.00 mg, 75.24%) as a white solid.

To a solution of 298-5 (500 mg, 775.37 μmol) in pyridine (5 mL) was added hydroxylamine hydrochloride (215.5 mg, 3.10 mmol, 4.00 eq.) in one portion at 0° C. under N$_2$. The mixture was stirred at 0° C. for 30 mins, and then warmed to 25° C. and stirred for 4 h. LCMS showed that the reaction was completed. The mixture was concentrated in vacuum. The residue was purified by silica gel chromatography (100-200 mesh silica gel, PE:EA=2:1) to afford the oxime (450 mg, 87.95% yield) as a light yellow solid.

To a solution of this oxime (450.00 mg, 681.95 μmol) in DCM (5 mL) was added TEA (208.0 mg, 2.06 mmol) and MsCl (156.0 mg, 1.36 mmol) in one portion at 0° C. The mixture was stirred at 25° C. for 4 h. TLC (PE:EA=2:1) showed that the reaction was completed. The reaction was quenched by sat. aq. NaHCO$_3$ (5 mL), and the aqueous phases were extracted with DCM (2×20 mL). The combined organic phase was washed with sat. brine (10 mL), dried with anhydrous Na$_2$SO$_4$, filtered and concentrated in vacuum. The residue was purified by TLC (PE:EA=2:1) to afford 298-6 (400 mg, 91.4%) as a light yellow solid.

To a solution of 298-6 (450.0 mg, 701.10 μmol), DMAP (171.3 mg, 1.40 mmol) and TEA (212.8 mg, 2.10 mmol) in MeCN (5 mL) was added 2,4,6-triisopropylbenzene-1-sulfonyl chloride (424.7 mg, 1.40 mmol) in one portion at 0° C. The mixture was stirred at 25° C. for 1 h. TLC (PE:EA=2:1) showed that the reaction was completed. The reaction was quenched by sat. aq. NaHCO$_3$ (5 mL) and extracted with EA (2×15 mL). The combined organic phase was washed with sat. brine (10 mL), dried with anhydrous Na$_2$SO$_4$, filtered and concentrated in vacuum. The residue (580.00 mg, 638.59 μmol) was dissolved in MeCN (5 mL). The solution was treated with NH$_3$.H$_2$O (10 mL) in one portion at 25° C. The mixture was stirred at 25° C. 16 h. TLC (PE:EA=1:1) showed the reaction was completed. The mixture was extracted with EA (3×10 mL). The combined organic phase was washed with sat. brine (10 mL), dried with anhydrous Na$_2$SO$_4$, filtered and concentrated in vacuum. The residue was purified by silica gel chromatography (100-200 mesh silica gel, DCM:MeOH=40:1 to 25:1) to afford 298-7 (350.00 mg, 85.5%) as a light yellow solid.

To a solution of 298-7 (350.0 mg, 546.13 μmol) in MeOH (10 mL) was added NH$_4$F (405 mg, 10.9 mmol) in one portion at 25° C. The mixture was heated to 65° C. and stirred for 2 h. TLC (EA:MeOH=8:1) showed that the reaction was completed. The mixture was cooled to 25° C. and concentrated under reduced pressure at 40° C. The residue was purified by silica gel chromatography (100-200 mesh silica gel, EA:MeOH=20:1 to 10:1) to afford 298 as a white solid. $^1$H NMR (400 MHz, DMSO-d$_6$), δ=7.59 (d, J=7.28 Hz, 1H), 7.49 (br. s., 2H), 7.25 (br. s., 1H), 6.29 (br. s., 1H), 6.01 (br. s., 1H), 5.82 (d, J=7.53 Hz, 1H), 4.60 (br. s., 1H), 3.88 (br. s., 2H); $^{19}$F NMR (376 MHz, DMSO-d$_6$) d ppm −116.61 (br. s., 1F) −115.98 (br. s., 1F).

Example 176

Compound 299

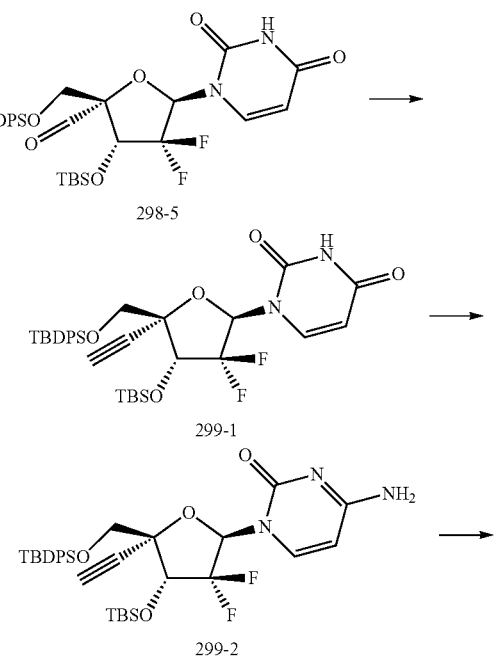

298-5

299-1

299-2

621
-continued

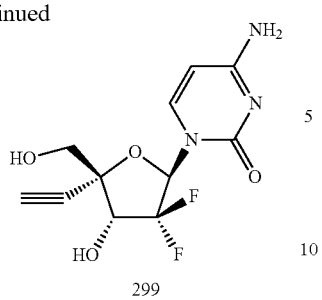

299

To a solution of K₂CO₃ (967.5 mg, 7.0 mmol) and TsN₃ (552.2 mg, 2.80 mmol) in MeCN (10 mL) was added 1-dimethoxyphosphorylpropan-2-one (465.1 mg, 2.80 mmol) in one portion at 25° C. under N₂. The mixture was stirred at 25° C. for 2H. A solution of 298-5 (900.0 mg, 1.40 mmol, 1.00 eq.) in MeOH (10 mL) was added in one portion at 25° C. under N₂. The mixture was stirred at 25° C. for 12 h. TLC (PE:EA=2:1) showed that the reaction was completed. The mixture was poured into water (10 mL) and extracted with EA (2×50 mL). The combined organic phase was washed with saturated brine (10 mL), dried with anhydrous Na₂SO₄, filtered and concentrated in vacuum. The residue was purified by silica gel chromatography (100-200 mesh silica gel, PE:EA=5:1 to 2:1) to afford 299-1 (800 mg, 98.2%) as an off-white solid.

To a solution of 299-1 (500 mg, 780.20 μmol), DMAP (190.6 mg, 1.56 mmol) and TEA (236.9 mg, 2.34 mmol) in MeCN (5 mL), was added 2,4,6-triisopropylbenzene-1-sulfonyl chloride (472.8 mg, 1.56 mmol) in one portion at 0° C. under N₂. The mixture was stirred at 0° C. for 30 mins, then warmed to 25° C. and stirred for 2 h. TLC (PE:EA=2:1) showed that the reaction was completed. The reaction was quenched by water (5 mL) and extracted with EA (2×10 mL). The combined organic phase was washed with aq. HCl (1 mL, 0.5 M), dried with anhydrous Na₂SO₄, filtered and concentrated in vacuum. The residue (650.0 mg, 91.83%) was obtained as a light yellow gum, which was used in next step without further purification.

To a solution of the residue from the previous step (650 mg, 716.4 μmol) in MeCN (5 mL) was added NH₃H₂O (5 mL) in one portion at 25° C., and the mixture was stirred at 25° C. for 16 h. TLC (DCM:MeOH=20:1) showed that the reaction was completed. The mixture was extracted with EA (2×20 mL). The combined organic phase was washed with brine (10 mL), dried with anhydrous Na₂SO₄, filtered and concentrated in vacuum. The residue was purified by silica gel chromatography (100-200 mesh silica gel, PE:EA=1:1) to afford 299-2 (350 mg, 76.35%) as an off-white solid.

A mixture of 299-2 (350.0 mg, 546.98 μmol) and NH₄F (405.0 mg, 10.93 mmol) in MeOH (5 mL) was heated to 65° C. and stirred for 2 h. LCMS and TLC (EA:MeOH=10:1) showed that the reaction was completed. The mixture was cooled to 25° C. and filtered, and the filtrate was concentrated in vacuum. The residue was purified by silica gel chromatography (300-400 mesh silica gel, EA:MeOH=20:1 to 10:1) to afford 299 (102 mg, 64.93%) as a white solid. ¹H-NMR (400 MHz, METHANOL-d₄), δ=7.73 (d, J=7.28 Hz, 1H), 6.31-6.42 (m, 1H), 5.95 (d, J=7.53 Hz, 1H), 4.47 (t, J=13.55 Hz, 1H), 3.92 (d, J=12.55 Hz, 1H), 3.73-3.80 (m, 1H) 3.25 (s, 1H); ¹⁹F NMR (376 MHz, METHANOL-d₄), δ=−115.52−−112.60 (m, 1F).

622

Example 177

Compound 300

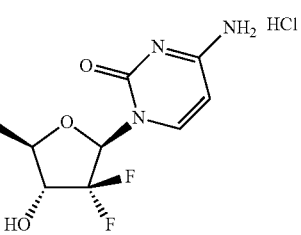

300-1

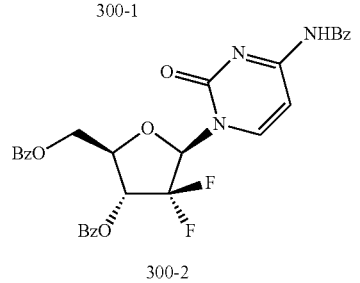

300-2

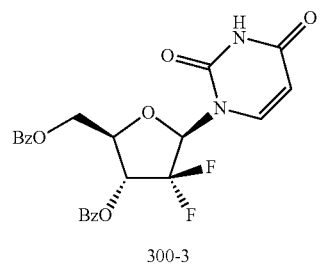

300-3

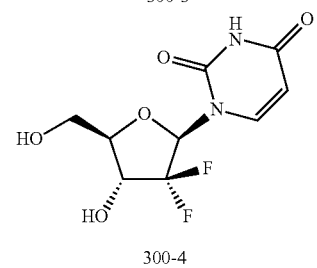

300-4

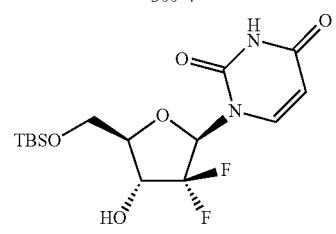

300-5

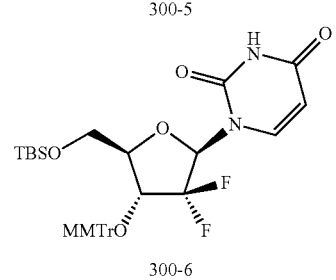

300-6

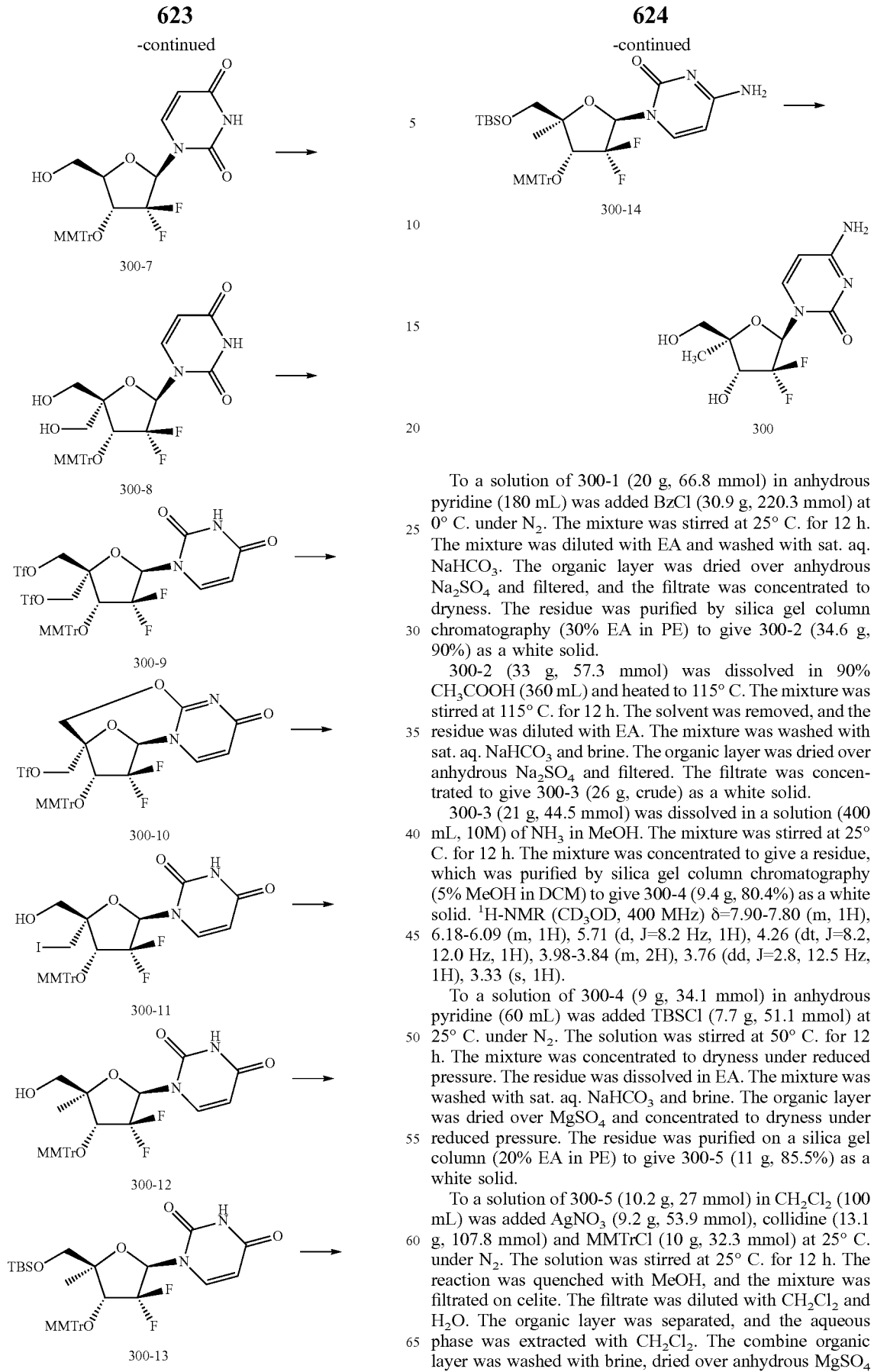

To a solution of 300-1 (20 g, 66.8 mmol) in anhydrous pyridine (180 mL) was added BzCl (30.9 g, 220.3 mmol) at 0° C. under $N_2$. The mixture was stirred at 25° C. for 12 h. The mixture was diluted with EA and washed with sat. aq. $NaHCO_3$. The organic layer was dried over anhydrous $Na_2SO_4$ and filtered, and the filtrate was concentrated to dryness. The residue was purified by silica gel column chromatography (30% EA in PE) to give 300-2 (34.6 g, 90%) as a white solid.

300-2 (33 g, 57.3 mmol) was dissolved in 90% $CH_3COOH$ (360 mL) and heated to 115° C. The mixture was stirred at 115° C. for 12 h. The solvent was removed, and the residue was diluted with EA. The mixture was washed with sat. aq. $NaHCO_3$ and brine. The organic layer was dried over anhydrous $Na_2SO_4$ and filtered. The filtrate was concentrated to give 300-3 (26 g, crude) as a white solid.

300-3 (21 g, 44.5 mmol) was dissolved in a solution (400 mL, 10M) of $NH_3$ in MeOH. The mixture was stirred at 25° C. for 12 h. The mixture was concentrated to give a residue, which was purified by silica gel column chromatography (5% MeOH in DCM) to give 300-4 (9.4 g, 80.4%) as a white solid. $^1$H-NMR (CD$_3$OD, 400 MHz) δ=7.90-7.80 (m, 1H), 6.18-6.09 (m, 1H), 5.71 (d, J=8.2 Hz, 1H), 4.26 (dt, J=8.2, 12.0 Hz, 1H), 3.98-3.84 (m, 2H), 3.76 (dd, J=2.8, 12.5 Hz, 1H), 3.33 (s, 1H).

To a solution of 300-4 (9 g, 34.1 mmol) in anhydrous pyridine (60 mL) was added TBSCl (7.7 g, 51.1 mmol) at 25° C. under $N_2$. The solution was stirred at 50° C. for 12 h. The mixture was concentrated to dryness under reduced pressure. The residue was dissolved in EA. The mixture was washed with sat. aq. $NaHCO_3$ and brine. The organic layer was dried over $MgSO_4$ and concentrated to dryness under reduced pressure. The residue was purified on a silica gel column (20% EA in PE) to give 300-5 (11 g, 85.5%) as a white solid.

To a solution of 300-5 (10.2 g, 27 mmol) in $CH_2Cl_2$ (100 mL) was added $AgNO_3$ (9.2 g, 53.9 mmol), collidine (13.1 g, 107.8 mmol) and MMTrCl (10 g, 32.3 mmol) at 25° C. under $N_2$. The solution was stirred at 25° C. for 12 h. The reaction was quenched with MeOH, and the mixture was filtrated on celite. The filtrate was diluted with $CH_2Cl_2$ and $H_2O$. The organic layer was separated, and the aqueous phase was extracted with $CH_2Cl_2$. The combine organic layer was washed with brine, dried over anhydrous $MgSO_4$ and filtered. The filtrate was concentrated to dryness under reduced pressure. The residue was purified by silica gel chromatography (25% EA in PE) to give 300-6 (15 g, 85.6%) as a white solid.

300-6 (10.5 g, 16.1 mmol) was dissolved in a solution of TBAF in THF (1M, 60 mL) at 25° C. The mixture was stirred at 25° C. for 4 h. The mixture was extracted with EA, and the combined layer was washed with water and brine. The organic layer was dried over Na$_2$SO$_4$ and filtered. The filtrate was concentrated to give the crude product, which was purified by silica gel column chromatography (30% EA in PE) to give 300-7 (8.1 g, 93.6%) as a white foam.

To a solution of 300-7 (17.0 g, 31.7 mmol) in CH$_3$CN (150 mL) was added IBX (9.7 g, 34.9 mmol) at 25° C. The mixture was heated to 100° C., and the mixture was stirred at 100° C. for 1 h. The mixture was cooled to 25° C. The mixture was filtered, and the filter cake was washed with MeCN. The filtrate was concentrated under reduce pressure to give a residue (16 g, crude) as a yellow solid. The residue (16 g, crude) was dissolved in 1,4-dioxane (150 mL), and the solution was treated with 37% aq. formaldehyde (18.5 g, 227.5 mmol) and aq. NaOH (2 M, 30 mL) at 25° C. The mixture was stirred at 25° C. for 12 h. EtOH (30 mL) and NaBH$_4$ (10 g, 265.7 mmol) were added at 0° C. After stirring for 1 h at 25° C., the reaction was quenched with sat. aq. NH$_4$Cl at 0° C. The mixture was diluted with EA. The organic phase was separated, and the aqueous phase was extracted with EA. The combined organic phase was washed with brine and dried over anhydrous Na$_2$SO$_4$. The organic layer was concentrated in vacuum to give a residue, which was purified by silica gel chromatography (2% MeOH in DCM) to afford 300-8 (8.1 g, 53.1%) as a white solid. $^1$H-NMR (400 MHz, DMSO-d$_6$) δ=11.52 (s, 1H), 7.57 (d, J=8.2 Hz, 1H), 7.46-7.22 (m, 13H), 6.90 (d, J=8.8 Hz, 2H), 6.30 (t, J=8.0 Hz, 1H), 5.61 (d, J=8.2 Hz, 1H), 5.06 (t, J=5.5 Hz, 1H), 4.92-4.86 (m, 1H), 4.61-4.51 (m, 1H), 3.83 (dd, J=5.1, 12.1 Hz, 1H), 3.74 (s, 3H).

To an ice cooled solution of 300-8 (2.5 g, 4.4 mmol) in anhydrous CH$_2$Cl$_2$ (35 mL) was added pyridine (3.5 g, 44.1 mmol) and Tf$_2$O (3.7 g, 13.2 mmol) dropwise. The mixture was stirred at 0° C. for 40 mins. The reaction was quenched with ice water and stirred for 10 mins. The mixture was extracted with CH$_2$Cl$_2$. The organic layer was washed with brine and dried over MgSO$_4$. The organic layer was concentrated to give a residue, which was purified on the silica gel column (15% EA in PE) to give 300-9 (2.6 g, 71%) as a yellow foam.

To a stirred solution of 300-9 (1.8 g, 2.2 mmol) in anhydrous DMF (25 mL) was added NaH (107 mg, 2.7 mmol) at 0° C. under N$_2$. The solution was stirred at 25° C. for 1 h. TLC (PE:EA=1:1) showed the reaction was complete. To the solution was added NaI (3.1 g, 20.6 mmol) at 25° C. The mixture was stirred at 25° C. for 3 h. TLC (PE:EA=1:1) showed the reaction was complete. The mixture was diluted with water and extracted with EA. The organic layer was dried over anhydrous Na$_2$SO$_4$ and filtered. The filtrate was concentrated at low pressure to give 300-10 (1.4 g, crude) as a yellow solid.

300-10 (1.4 g, crude) was dissolved in 1,4-dioxane (25 mL), and the mixture was treated with aq. NaOH (2 M, 2.7 mL) at 0° C. The solution was stirred for 4 h at 25° C. The reaction was quenched with sat. aq. NH$_4$Cl and extracted with EA. The organic layer was washed with brine. The organic layer was dried over Na$_2$SO$_4$ and filtered. The filtrate was concentrated to give the crude product, which was purified by silica gel column chromatography (40% EA in PE) to give 300-11 (1.4 g, 94.9%).

To a solution of 300-11 (1.45 g, 2.1 mmol) in EtOH (10 mL) was added Et$_3$N (434 mg, 4.3 mmol) and Pd/C (101 mg, 88.7 μmol). The mixture was stirred under H$_2$ (15 psi) for 12 h at 25° C. The suspension was filtered, and the filtrate was concentrated at low pressure. The residue was purified on silica gel column (1% MeOH in DCM) to give 300-12 (1.2 g, 97.6%) as a yellow solid.

To a solution of 300-12 (930 mg, 1.7 mmol) in anhydrous DMF (10 mL) was added imidazole (287 mg, 4.2 mmol) and TBSCl (636 mg, 4.2 mmol) at 25° C. under N$_2$. The solution was stirred at 25° C. for 5 h. The mixture was concentrated to dryness under reduced pressure, and the residue was dissolved in EA. The mixture was washed with sat. aq. NH$_4$Cl and brine. The organic layer was dried over MgSO$_4$ and filtered. The filtrate was concentrated to dryness under reduced pressure. The residue was purified on silica gel column (15% EA in PE) to give 300-13 (968 mg, 86.2%) as a white solid.

To a stirred solution of 300-13 (568 mg, 854.4 μmol) in anhydrous CH$_3$CN (8 mL) was added DMAP (209 mg, 1.7 mmol), TPSCl (504 mg, 1.7 mmol) and TEA (173 mg, 1.7 mmol) at 25° C. The mixture was stirred at 25° C. for 12 h. NH$_3$·H$_2$O (10 mL) was added, and the mixture was stirred for 3 h. The mixture was extracted with EA and washed with sat. aq. NH$_4$Cl and brine. The organic layer was dried over Na$_2$SO$_4$ and filtered. The filtrate was concentrated to give a residue, which was purified on a silica gel column (3% MeOH in DCM) to give 300-14 (480 mg, 84.6%) as a yellow foam. $^1$H-NMR (400 MHz, CDCl$_3$) δ=7.65-7.40 (m, 13H), 6.97 (d, J=8.8 Hz, 2H), 6.44 (dd, J=6.4, 9.5 Hz, 1H), 5.71 (d, J=7.3 Hz, 1H), 4.76 (dd, J=9.0, 14.4 Hz, 1H), 4.29 (q, J=7.1 Hz, 1H), 3.92-3.92 (m, 1H), 3.95 (s, 3H), 3.60 (d, J=11.2 Hz, 1H), 3.44 (d, J=11.0 Hz, 1H), 1.66-1.55 (m, 3H), 0.95 (s, 9H), 0.08 (s, 3H), 0.00 (s, 3H).

300-14 (501 mg, 753.2 μmol) was dissolved in 80% HCOOH (20 mL), and the mixture was stirred at 25° C. for 4 h. The solvent was removed at low pressure, and the residue was purified on a silica gel column (6% MeOH in DCM) to give 300 (151 mg, 71.8%) as a white solid. ESI-MS: m/z 278.11 [M+H]$^+$, 555.18 [2M+H]$^+$.

Example 178

Compound 301

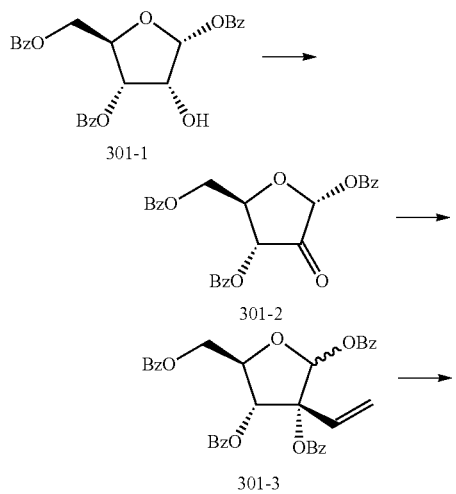

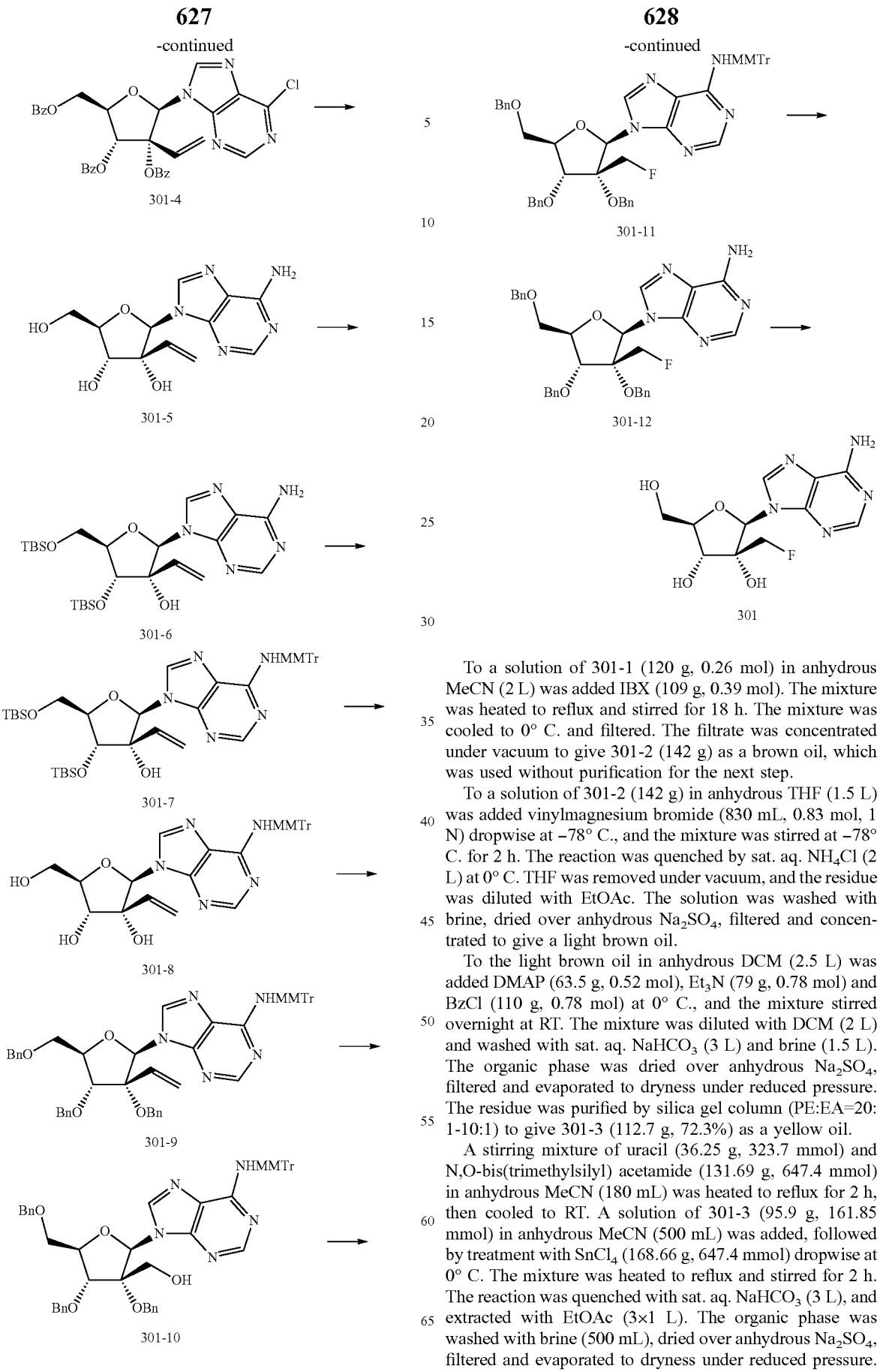

To a solution of 301-1 (120 g, 0.26 mol) in anhydrous MeCN (2 L) was added IBX (109 g, 0.39 mol). The mixture was heated to reflux and stirred for 18 h. The mixture was cooled to 0° C. and filtered. The filtrate was concentrated under vacuum to give 301-2 (142 g) as a brown oil, which was used without purification for the next step.

To a solution of 301-2 (142 g) in anhydrous THF (1.5 L) was added vinylmagnesium bromide (830 mL, 0.83 mol, 1 N) dropwise at −78° C., and the mixture was stirred at −78° C. for 2 h. The reaction was quenched by sat. aq. NH₄Cl (2 L) at 0° C. THF was removed under vacuum, and the residue was diluted with EtOAc. The solution was washed with brine, dried over anhydrous Na₂SO₄, filtered and concentrated to give a light brown oil.

To the light brown oil in anhydrous DCM (2.5 L) was added DMAP (63.5 g, 0.52 mol), Et₃N (79 g, 0.78 mol) and BzCl (110 g, 0.78 mol) at 0° C., and the mixture stirred overnight at RT. The mixture was diluted with DCM (2 L) and washed with sat. aq. NaHCO₃ (3 L) and brine (1.5 L). The organic phase was dried over anhydrous Na₂SO₄, filtered and evaporated to dryness under reduced pressure. The residue was purified by silica gel column (PE:EA=20:1-10:1) to give 301-3 (112.7 g, 72.3%) as a yellow oil.

A stirring mixture of uracil (36.25 g, 323.7 mmol) and N,O-bis(trimethylsilyl) acetamide (131.69 g, 647.4 mmol) in anhydrous MeCN (180 mL) was heated to reflux for 2 h, then cooled to RT. A solution of 301-3 (95.9 g, 161.85 mmol) in anhydrous MeCN (500 mL) was added, followed by treatment with SnCl₄ (168.66 g, 647.4 mmol) dropwise at 0° C. The mixture was heated to reflux and stirred for 2 h. The reaction was quenched with sat. aq. NaHCO₃ (3 L), and extracted with EtOAc (3×1 L). The organic phase was washed with brine (500 mL), dried over anhydrous Na₂SO₄, filtered and evaporated to dryness under reduced pressure.

The residue was purified by a silica gel column (PE:EA=20:1-10:1) to give 301-4 (33 g, 35%) as a light yellow oil.

301-4 (33 g, 56.65 mmol) was dissolved in NH$_3$:MeOH (800 mL, 7 N), and the mixture was stirred at RT overnight. The solvent was removed under reduced pressure, and the residue was purified by a column (1% MeOH in DCM) to give 301-5 (12.6 g, 82.4%) as a light yellow foam.

To a solution of 301-5 (2.57 g, 8.76 mmol) in DMF (20 mL) was added AgNO$_3$ (8.93 g, 52.56 mmol) and imidazole (3.58 g, 52.56 mmol), then TBSCl (5.28 g, 35.04 mmol) was added in one portion at 0° C. under N$_2$. The mixture was stirred at 25° C. for 12 h. TLC showed that the reaction was completed. The residue was poured into ice:water (w:w=1:1) (30 mL). The aqueous phase was extracted with EA (3×100 mL). The combined organic phase was washed with sat. brine (3×20 mL), dried with anhydrous Na$_2$SO$_4$, filtered and concentrated in vacuum. The residue was purified by silica gel chromatography (column height: 250 mm, diameter: 100 mm, 100-200 mesh silica gel, PE:EA=3:1 to 2:1) to afford 301-6 (3.68 g, 80.51%) as a yellow solid.

To a solution of 301-6 (3.48 g, 6.67 mmol) and AgNO$_3$ (3.40 g, 20.01 mmol) in pyridine (30 mL) was added (chloro(4-methoxyphenyl)methylene)dibenzene (4.12 g, 13.34 mmol) in one portion at 25° C. under N$_2$. The mixture was stirred at 25° C. for 16 h. TLC showed that the reaction was completed. The mixture was diluted with EA and filtered. The filtrate was washed with brine and separated. The organic layer was concentrated to dryness. The residue was purified by silica gel chromatography (column height: 250 mm, diameter: 100 mm, 100-200 mesh silica gel, PE:EA=10:1 to 5:1) to afford 301-7 (4.40 g, 83.07%) as a yellow foam.

To a solution of 301-7 (4.30 g, 5.41 mmol) in MeOH (100 mL) was added NH$_4$F (801.55 mg, 21.64 mmol) in one portion at 25° C. The mixture was heated to 68° C. and stirred for 4 h. LCMS trace showed that the reaction was completed. The mixture was cooled to 25° C. and concentrated under reduced pressure. The residue was purified by silica gel chromatography (column height: 250 mm, diameter: 100 mm, 100-200 mesh silica gel, DCM:MeOH: NH$_3$.H$_2$O=30:1:0.05 to 10:1:0.05) to afford 301-8 (3.00 g, 98.04%) as a white solid.

To a solution of 301-8 (3.00 g, 5.30 mmol) in DMF (30 mL) was added NaH (848 mg, 21.20 mmol) in one portion at 0° C. under N$_2$. The mixture was stirred at 0° C. for 30 mins. BnBr (3.63 g, 21.20 mmol) was added at 0° C., and the mixture was stirred for 16 h at 25° C. TLC showed that the reaction was completed. The mixture was poured into ice-water (w/w=1/1) (30 mL). The aqueous phase was extracted with EA (3×50 mL). The combined organic phase was washed with sat. brine (3×20 mL), dried with anhydrous Na$_2$SO$_4$, filtered and concentrated in vacuum. The residue was purified by silica gel chromatography (column height: 250 mm, diameter: 100 mm, 200-300 mesh silica gel, PE:EA=20:1 to 10:1) to afford 301-9 (670 mg, 15.1%).

Ozone was bubbled into a solution of 301-9 (500 mg, 598.10 μmol) in DCM (8 mL) and MeOH (8 mL) at −78° C. for 20 mins. After excess O3 was purged by O2, NaBH$_4$ (113.13 mg, 2.99 mmol) was added at 0° C. The mixture was stirred at 25° C. for 20 mins. TLC showed that the starting material was consumed. The mixture was concentrated to give the crude product, which was purified by silica gel chromatography (PE:EA=5:1) to give 301-10 (167.00 mg, 33.24%) as a yellow solid.

To a solution of 301-10 (216.70 mg, 257.99 μmol) and DMAP (63.04 mg, 515.98 μmol) in DCM (2 mL) was added MsCl (44.33 mg, 386.98 μmol) in one portion at 0° C. under N$_2$. The mixture was stirred at 0° C. for 1 h and then warmed to 25° C. and stirred for 1 h. LCMS showed that the reaction was completed. The residue was poured into ice-water (w/w=1/1) (10 mL), and extracted with EA (3×20 mL). The combined organic phase was washed with sat. brine (3×10 mL), dried with anhydrous Na$_2$SO$_4$, filtered and concentrated in vacuum. The residue was purified by silica gel chromatography (column height: 250 mm, diameter: 100 mm, 100-200 mesh silica gel, PE:EA=10:1 to 5:1) to afford a mesylate intermediate (167.00 mg, 70.51%) as a yellow foam.

The mesylated intermediate (167 mg) was dissolved in TBAF:THF (10 mL, 1N) and the mixture was heated to reflux for 12 h. The mixture was slowly cooled to 25° C., and quenched with sat. NH$_4$Cl solution. The solution was extracted with EA. The combined organic layers were washed with brine, dried over anhydrous Na$_2$SO$_4$ and concentrated to dryness. The residue was purified by column chromatography (EA:PE=5:1-2:1) to give 301-11 (80 mg, 43.8%).

301-11 (80.00 mg, 0.087 mmol) was dissolved in 80% AcOH (5 mL) solution, and stirred at 45° C. for 1.0 h. The reaction was quenched with sat. Na$_2$HCO$_3$ solution and extracted with EA (3×10 mL). The combined organic layers were washed with brine, dried over anhydrous Na$_2$SO$_4$ and concentrated to dryness. The residue was purified by column chromatography to give 301-12 (38 mg, 60%) as a white foam solid. ESI-MS: m/z 570.4 [M+H]$^+$.

To a solution of 301-12 (113.8 mg, 0.2 mmol) in DCM (0.5 mL) was added BCl$_3$/DCM (1.0 N) (1 mL) at −78° C., and the mixture was stirred at −78° C. for 30 mins. The reaction was quenched with MeOH and concentrated to dryness at low pressure. The residue was purified by prep-HPLC with NH$_3$.H$_2$O buffer to give 301 (26 mg, 44%) as a white solid.

Example 179

Compound 302

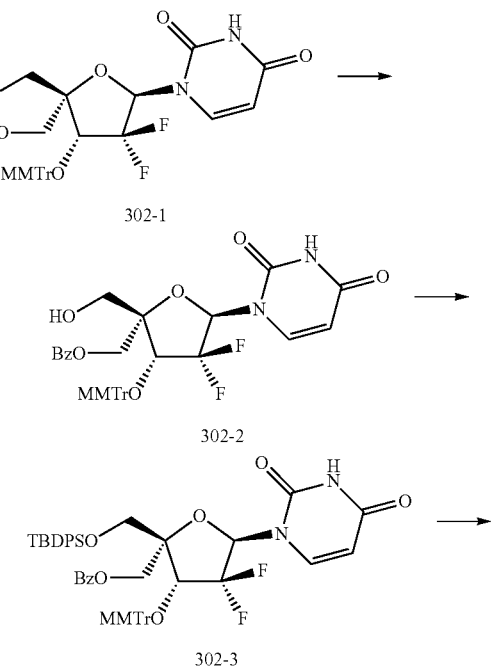

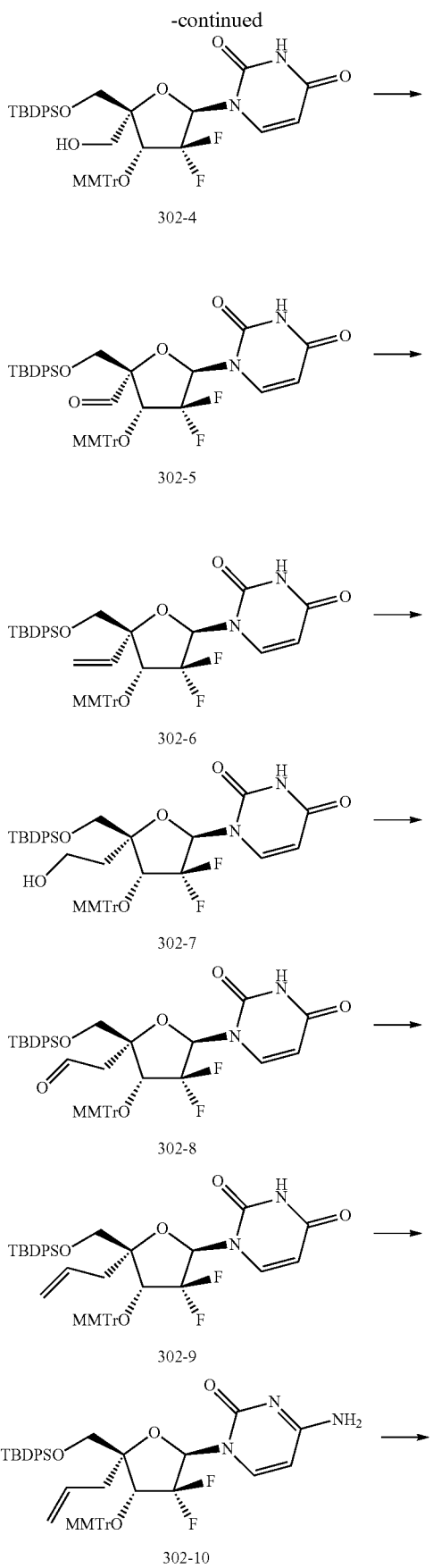

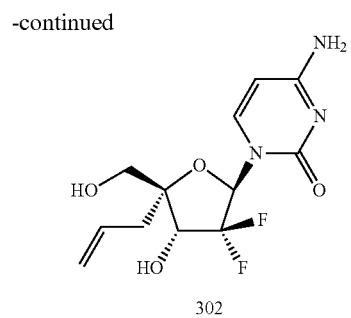

302

To a mixture of 302-1 (2.00 g, 3.5 mmol) in pyridine (10 mL) and DCM (10 mL) was added BzCl (496 mg, 3.5 mmol) dropwise at 0° C. under N₂. The mixture was stirred at 0° C. for 30 mins, and then stirred at 25° C. for 6.5 h. The reaction was quenched with sat. aq. NaHCO₃ (80 mL). The mixture was extracted with EA (2×100 mL). The organic phase was washed with brine (80 mL), dried over anhydrous Na₂SO₄ and filtered. The filtrate was concentrated under reduced pressure. The residue was purified by silica gel chromatography (30% EA in PE) to afford 302-2 (1.28 g, 54%) as a white solid.

To a mixture of 302-2 (680 mg, 1.0 mmol) in DMF (5 mL) was added imidazole (412 mg, 6.1 mmol), AgNO₃ (514 mg, 3.0 mmol) and TBDPSCl (832 mg, 3.0 mmol) at 25° C. under N₂. The mixture was stirred at 25° C. for 12 h. The reaction was quenched with sat. aq. NaHCO₃ (30 mL), and then extracted with EA (2×30 mL). The combined organic phase was washed with brine (2×20 mL), dried over anhydrous Na₂SO₄, filtered and concentrated under reduced pressure. The residue was purified by silica gel chromatography (25% EA in PE) to afford 302-3 (750 mg, 82%) as a white solid.

302-3 (660 mg, 0.7 mmol) was dissolved in NH₃:MeOH (15 mL). The mixture was stirred at 25° C. for 36 h in sealed tube, and then concentrated under reduced pressure. The residue was purified by silica gel chromatography (30% EA in PE) to afford 302-4 (430 mg, 73%) as a white solid. ¹H-NMR (CDCl₃, 400 MHz) δ=9.05 (s, 1H), 7.81-7.10 (m, 21H), 6.81 (d, J=9.2 Hz, 2H), 6.42 (m, 1H), 6.20 (m, 1H), 4.13-4.07 (m, 2H), 3.78-3.60 (m, 5H), 2.55 (s, 1H), 0.90-0.74 (m, 9H).

To a mixture of 302-4 (280 mg, 0.3 mmol) in DCM (3.5 mL) was added Dess-Martin (295 mg, 0.7 mmol) in one portion at 0° C. under N₂. The mixture was stirred at 25° C. for 3.5 h. The reaction was quenched with sat. aq. NaHCO₃ and sat. aq. Na₂S₂O₃. (v:v=1:1, 30 mL). The mixture was extracted with EA (2×20 mL). The combined organic phase was washed with brine (30 mL), dried over anhydrous Na₂SO₄ and filtered. The filtrate was concentrated in vacuum to afford 302-5 (260 mg, crude) as a yellow solid, which was used in the next step without further purification.

To a stirred solution of Methyl-triphenyl-phosphonium bromide (359 mg, 1.0 mmol) in anhydrous THF (1 mL) was added KOBu-t (1 mL, 1.0 mmol, 1 M in THF) dropwise at 0° C. The mixture was stirred at 25° C. for 1 h. A solution of 302-5 (260 mg, 0.3 mmol) in anhydrous THF (1 mL) was added at 0° C. The mixture was stirred at 25° C. for 16 h. The reaction was quenched with sat. aq. NH₄Cl (20 mL) and extracted with EA (30 mL). The organic layer was washed with brine (20 mL), dried over MgSO₄, filtered and evaporated to give a light white solid, which was purified by column chromatography (10% EA in PE) to give 302-6 (131 mg, 50%) as a yellow solid. ¹H-NMR (CDCl₃, 400 MHz)

δ=8.40 (s, 1H), 7.55-7.21 (m, 21H), 7.10 (dd, J=1.8, 8.2 Hz, 1H), 6.84 (d, J=8.8 Hz, 2H), 6.37 (dd, J=11.0, 17.4 Hz, 1H), 6.09 (dd, J=7.2, 8.9 Hz, 1H), 5.59-5.43 (m, 2H), 5.10-4.92 (m, 2H), 3.85-3.78 (s, 3H), 3.78-3.73 (m, 1H), 3.56 (d, J=11.5 Hz, 1H), 0.99-0.77 (s, 9H).

To a solution of 302-6 (1.50 g, 1.9 mmol) in THF (5 mL) was added 9-BBN (0.5 M, 22.5 mL) at 27° C. under $N_2$. The mixture was heated to 70° C. by microwave and stirred for 0.5 h. Sat. aq. $NaHCO_3$ (15 mL) and $H_2O_2$ (7.5 mL) were added at 0° C. The mixture was stirred vigorously at 27° C. for 1.5 h. The reaction was quenched with sat. aq. $Na_2S_2O_3$ (60 mL). The mixture was extracted with EA (2×50 mL). The organic layer was washed with brine (80 mL), dried over $MgSO_4$, filtered and evaporated to dryness. The residue was purified by silica gel chromatography (30% EA in PE) to afford 302-7 (930 mg, 61%) as a white solid.

To a solution of 302-7 (1.24 g, 1.5 mmol) in DCM (15 mL) was added Dess-Martin (1.28 g, 3.0 mmol) in one portion at 0° C. under $N_2$. The mixture was stirred at 27° C. for 2 h. The reaction was quenched with sat. aq. $NaHCO_3$ and sat. aq. $Na_2S_2O_3$ (v:v=1:1, 60 mL). The mixture was extracted with EA (2×50 mL). The combined organic phase was washed with brine (80 mL), dried over anhydrous $Na_2SO_4$ and filtered. The filtrate was concentrated in vacuum to afford 302-8 (1.21 g, crude) as a yellow solid.

To a stirred solution of Methyl-triphenyl-phosphonium bromide (1.64 g, 4.6 mmol) in anhydrous THF (5.5 mL) was added t-BuOK (1 M, 4.4 mL) at 0° C. dropwise. The mixture was stirred at 27° C. for 1 h. A solution of 302-8 (1.21 g crude, 1.5 mmol) in THF (5 mL) was added at 0° C. The mixture was stirred at 27° C. for 12 h. The reaction was quenched with sat. aq. $NH_4Cl$ (70 mL), extracted with EA (2×50 mL). The organic layer was washed with brine (80 mL), dried over $MgSO_4$, filtered and evaporated to dryness to give a light yellow solid, which was purified by column chromatography (15 EA in PE) to give 302-9 (970 mg, 80%) as a white solid.

To a solution of 302-9 (970 mg, 1.2 mmol) in $CH_3CN$ (10 mL) was added TPSCl (877 mg, 3.0 mmol), DMAP (363 mg, 3.0 mmol) and TEA (301 mg, 3.0 mmol) at 27° C. under $N_2$. The mixture was stirred at 27° C. for 1.5 h. $NH_3 \cdot H_2O$ (5 mL) was added, and the reaction mixture was stirred at 27° C. for 2 h. The reaction was quenched with sat. aq. $NH_4Cl$ (60 mL), and then extracted with EA (2×40 mL). The combined organic phase was washed with brine (60 mL), dried over anhydrous $Na_2SO_4$, filtered and concentrated in vacuum. The residue was purified by silica gel chromatography (2% MeOH in DCM) to afford 302-10 (810 mg, 83%) as a white solid.

To a solution of 302-10 (500 mg, 0.6 mmol) in MeOH (15 mL) was added $NH_4F$ (455 mg, 12.3 mmol) at 27° C. under $N_2$. The mixture was stirred at 70° C. for 12 h. The mixture was then cooled to RT and filtered. The filtrate was concentrated under reduced pressure. The residue was purified by silica gel chromatography (5% MeOH in DCM) to afford crude 302 (120 mg, crude). The crude was purified by prep-HPLC (neutral condition) to give 302 (86 mg, 45%) as a white solid. MS: m/z=304 $[M+H]^+$.

Example 180

Compound 303

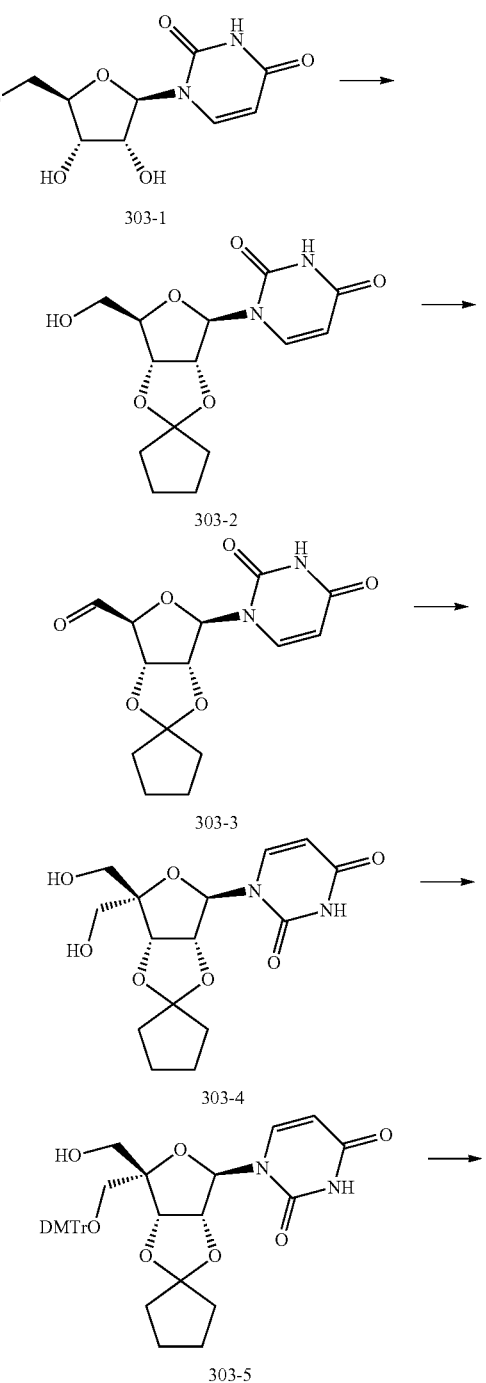

303-1

303-2

303-3

303-4

303-5

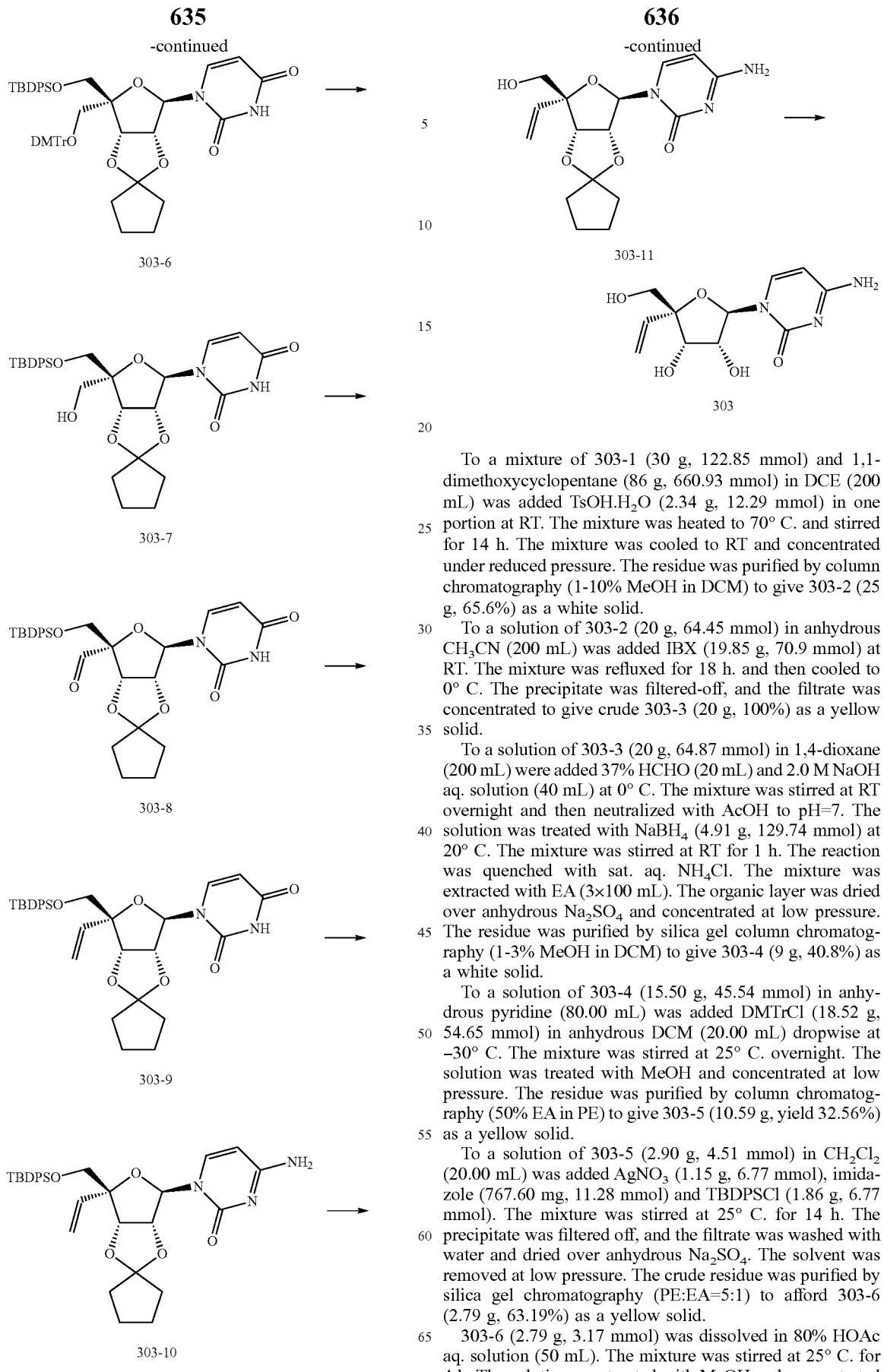

To a mixture of 303-1 (30 g, 122.85 mmol) and 1,1-dimethoxycyclopentane (86 g, 660.93 mmol) in DCE (200 mL) was added TsOH.H$_2$O (2.34 g, 12.29 mmol) in one portion at RT. The mixture was heated to 70° C. and stirred for 14 h. The mixture was cooled to RT and concentrated under reduced pressure. The residue was purified by column chromatography (1-10% MeOH in DCM) to give 303-2 (25 g, 65.6%) as a white solid.

To a solution of 303-2 (20 g, 64.45 mmol) in anhydrous CH$_3$CN (200 mL) was added IBX (19.85 g, 70.9 mmol) at RT. The mixture was refluxed for 18 h. and then cooled to 0° C. The precipitate was filtered-off, and the filtrate was concentrated to give crude 303-3 (20 g, 100%) as a yellow solid.

To a solution of 303-3 (20 g, 64.87 mmol) in 1,4-dioxane (200 mL) were added 37% HCHO (20 mL) and 2.0 M NaOH aq. solution (40 mL) at 0° C. The mixture was stirred at RT overnight and then neutralized with AcOH to pH=7. The solution was treated with NaBH$_4$ (4.91 g, 129.74 mmol) at 20° C. The mixture was stirred at RT for 1 h. The reaction was quenched with sat. aq. NH$_4$Cl. The mixture was extracted with EA (3×100 mL). The organic layer was dried over anhydrous Na$_2$SO$_4$ and concentrated at low pressure. The residue was purified by silica gel column chromatography (1-3% MeOH in DCM) to give 303-4 (9 g, 40.8%) as a white solid.

To a solution of 303-4 (15.50 g, 45.54 mmol) in anhydrous pyridine (80.00 mL) was added DMTrCl (18.52 g, 54.65 mmol) in anhydrous DCM (20.00 mL) dropwise at −30° C. The mixture was stirred at 25° C. overnight. The solution was treated with MeOH and concentrated at low pressure. The residue was purified by column chromatography (50% EA in PE) to give 303-5 (10.59 g, yield 32.56%) as a yellow solid.

To a solution of 303-5 (2.90 g, 4.51 mmol) in CH$_2$Cl$_2$ (20.00 mL) was added AgNO$_3$ (1.15 g, 6.77 mmol), imidazole (767.60 mg, 11.28 mmol) and TBDPSCl (1.86 g, 6.77 mmol). The mixture was stirred at 25° C. for 14 h. The precipitate was filtered off, and the filtrate was washed with water and dried over anhydrous Na$_2$SO$_4$. The solvent was removed at low pressure. The crude residue was purified by silica gel chromatography (PE:EA=5:1) to afford 303-6 (2.79 g, 63.19%) as a yellow solid.

303-6 (2.79 g, 3.17 mmol) was dissolved in 80% HOAc aq. solution (50 mL). The mixture was stirred at 25° C. for 4 h. The solution was treated with MeOH and concentrated at low pressure. The residue was purified by silica gel column chromatography (PE:EA=4:1) to give 303-7 (0.9 g, 44%) as a yellow solid.

To a solution of 303-7 (1.50 g, 2.59 mmol) in anhydrous DCM (20 mL) was added Dess-Martin periodinane (1.32 g, 3.11 mmol) at 0° C. under $N_2$. The mixture was stirred at RT for 4 h. The reaction was quenched by the addition of $Na_2S_2O_3$/sodium bicarbonate saturated aqueous solution. The mixture was stirred for 15 mins. The organic layer was separated, washed with diluted brine and concentrated under reduced pressure. The crude residue was purified by silica gel column chromatography (20% EtOAc in PE) to give 303-8 (1.12 g, yield 67.48%) as a white solid.

To a solution of $PPh_3CH_3Br$ (1.49 g, 4.16 mmol) in anhydrous THF (15 mL) was added n-BuLi (0.41 mL, 3.47 mmol) at −70° C. under $N_2$. The mixture was stirred at 0° C. for 0.5 hour. A solution of 303-8 (800.00 mg, 1.39 mmol) in anhydrous THF (3 mL) was added dropwise at 0° C. under $N_2$. The mixture was stirred 25° C. for 2 h. The reaction was quenched with sat. $NH_4Cl$ solution and extracted with EtOAc (3×60 mL). The organic phase was washed with brine, dried over anhydrous $Na_2SO_4$ and concentrated at low pressure. The crude product was purified by silica gel column chromatography (20% EtOAc in PE) to give 303-9 (504 mg, 56.78%) as a white solid.

To a solution of 303-9 (500 mg, 869.96 µmol) in anhydrous $CH_3CN$ (10.00 mL) was added 2,4,6-triisopropylbenzenesulfonyl chloride (526.95 mg, 1.74 mmol), DMAP (212.57 mg, 1.74 mmol) and $Et_3N$ (1.83 g, 18.04 mmol) at RT. The mixture was stirred at 25° C. for 1 h. $NH_3.H_2O$ (5.00 mL) was added, and the mixture was stirred for 1 h. The mixture was extracted with EA and washed with brine, 0.1 M HCl and sat. aq. $NaHCO_3$. The organic phase was dried over anhydrous $Na_2SO_4$, and concentrated at low pressure. The residue was purified by silica gel chromatography (EtOAc) to give 303-10 (307 mg, 55.36%) as a yellow solid.

To a solution of 303-10 (307 mg, 535.08 µmol) in MeOH (4 mL) was added $NH_4F$ (814 mg, 20 mmol) at 25° C. under $N_2$. The mixture was stirred at 65° C. for 16 h. The solution was filtered and evaporated to dryness. The residue was purified by silica gel column (EA:MeOH=50:1) to give 303-11 (130 mg, 65.2%) as a white solid.

303-11 (108 mg, 322.05 µmol) was treated with HCl:MeOH (6 mL, 1N) at 25° C. under $N_2$. The mixture was stirred at 25° C. for 1 h. The aqueous phase was extracted with EA (3×10 mL). The residual aqueous solution was lyophilized to afford 303 (80.00 mg yield 87.65%) as a yellow solid. ESI-MS: m/z 270 [M+H]⁺.

Example 181

Compound 304

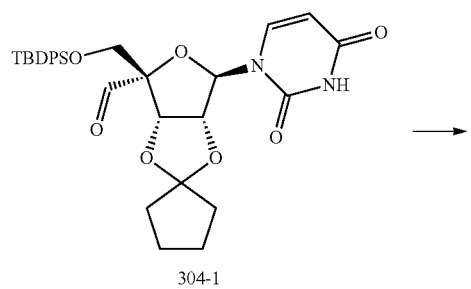

304-1

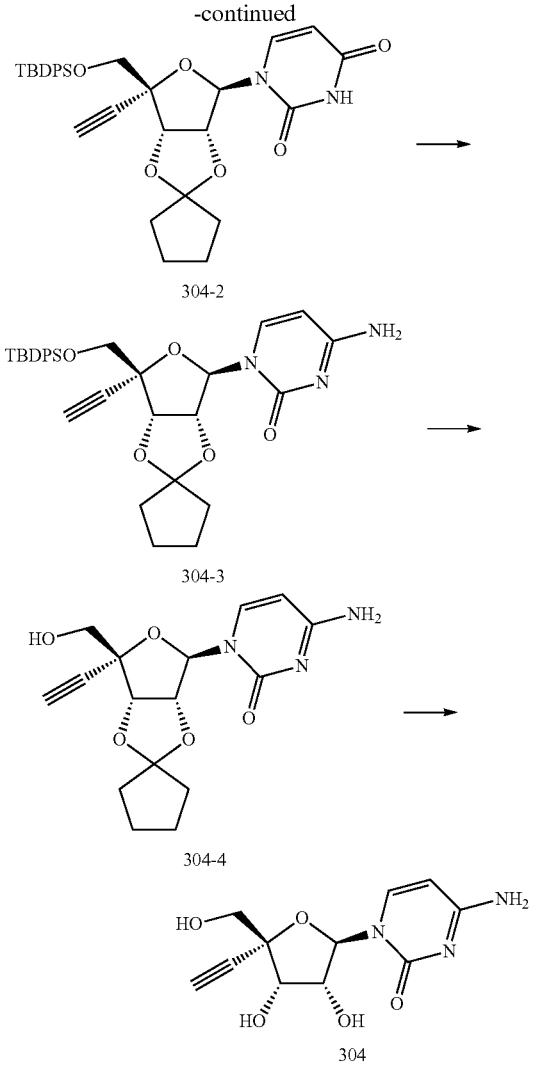

To a mixture of $K_2CO_3$ (2.40 g, 17.35 mmol) and $TsN_3$ (1.37 g, 6.94 mmol) in $CH_3CN$ (20 mL) was added 1-dimethoxyphosphorylpropan-2-one (1.15 g, 6.94 mmol) in one portion at 25° C. under $N_2$. The mixture was stirred at 25° C. for 2 h. A solution of 304-1 (2.00 g, 3.47 mmol) in MeOH (20 mL) was added in one portion at 25° C. under $N_2$, and the mixture was stirred at 25° C. for 16 h. The mixture was poured into water and extracted with EtOAc (2×30 mL). The combined organic phase was washed with brine, dried over anhydrous $Na_2SO_4$, filtered and concentrated in vacuum. The residue was purified by prep-HPLC (TFA buffer) to give 304-2 (1.50 g, 75%) as a white solid.

To a solution of 304-2 (600 mg, 1.05 mmol) in dry $CH_3CN$ (60 mL) was added TEA (212 mg, 2.10 mmol), DMAP (256 mg, 2.10 mmol) and 2,4,6-triisopropylbenzenesulfonyl chloride (635 mg, 2.10 mmol) at 0° C. The mixture was stirred at 25° C. for 1 h. $NH_3.H_2O$ (10 mL) was added at 25° C. The mixture was stirred at 25° C. for 1 h. The reaction was quenched with sat. $NH_4Cl$ solution, and extracted with EtOAc (2×10 mL). The organic phase was washed with brine, dried over anhydrous $Na_2SO_4$ and concentrated at low pressure. The residue was purified by silica gel chromatography (PE:EA=3:1 to 0:1), and prep-TLC (DCM:MeOH=10:1) to give 304-3 (380 mg, 63%) as a white solid.

A solution of 304-3 (300 mg, 0.52 mmol) and NH₄F (194 mg, 5.25 mmol) in dry MeOH (5 mL) was stirred at 65° C. for 12 h. The mixture was concentrated at low pressure. The residue was purified by silica gel column chromatography (DCM:MeOH=50:1 to 10:1) to afford 304-4 (140 mg, 80%) as a white solid.

A solution of 304-4 (100 mg, 0.30 mmol) in 1 N HCl:MeOH (5 mL) was stirred at 25° C. for 2 h. The mixture was concentrated under 40° C. The residue was washed with CH₃CN (5×2 mL) to give 304 (61 mg, 67%) as a white solid. ESI-LCMS: m/z 268.1 [M+H]⁺.

Example 182

Compound 305

44 →

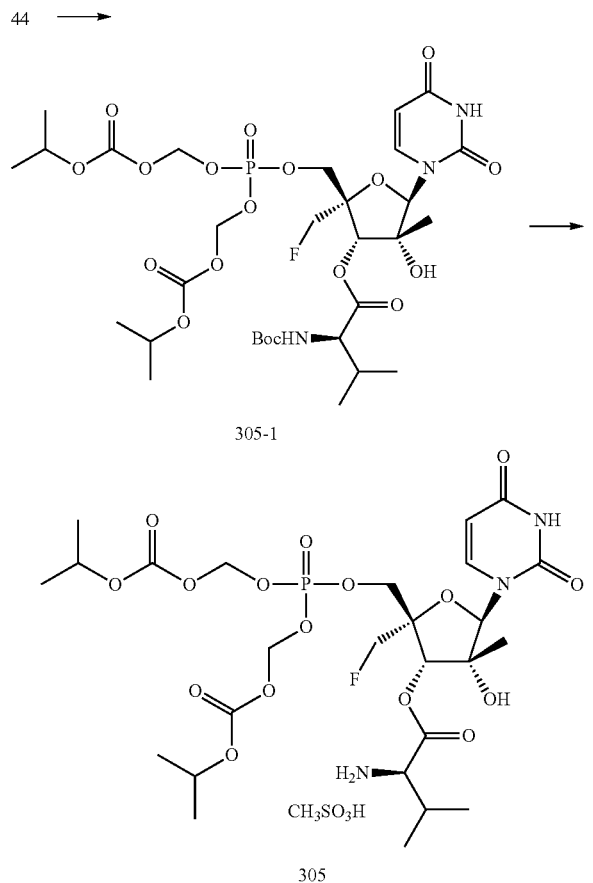

305-1

305

To a solution of N-(tert-Butoxycarbonyl)-L-valine (8.06 g, 37.1 mmol, 1.5 eq.) in anhydrous ACN (60 mL) was added carbonyldiimidazole (6.01 g, 37.1 mmol, 1.5 eq.). The reaction was stirred for 1 h at RT and then cooled to 0° C. A solution of 44 (14.9 g, 24.7 mmol, 1 eq.) in anhydrous ACN (50 mL) was added to the cooled solution of N-BOC-valine imidazolide, and the resulting solution was treated with Et₃N (6.4 mL, 49.4 mmol, 2 eq.). The reaction was allowed to proceed for 1 h at 0° C. The reaction was quenched 1M citric acid to pH 2-3 (150 mL), stirred for 15 mins and diluted with IPAC (200 mL). The organic layer was separated, washed sequentially with water and half sat. sodium bicarbonate and water (2×). The organic layer was concentrated under reduced pressure, and the residue was dissolved in MTBE (125 mL) under gentle heating (40° C.) to afford precipitation of the target compound. The solid was aged overnight at 0° C. and isolated by filtration to obtain 305-1 (18.0 g, 90.9%) as a white solid. MS: m/z=802 [M+1]⁺.

A stirred slurry of 305-1 (2.4 g, 3 mmol) in IPAC (45 mL) was treated with methanesulfonic acid (0.39 mL, 6 mmol, 2 eq.), and the mixture was stirred at 40° C. After 1 h, methanesulfonic acid (2×0.2 mL, 6 mmol, 2 eq.) was added, and the temperature was increased to 50° C. After 5 h, the mixture was cooled to RT. The solid was filtered off, washed with IPAC and dried under vacuum to yield 305 (2.0 g, 83%). Melting point=146° C.; MS: m/z 702.2 [M+H]⁺.

Example 183

Triphosphates

Dry nucleoside (0.05 mmol) was dissolved in the mixture of PO(OMe)₃ (0.7 mL) and pyridine (0.3 mL). The mixture was evaporated in vacuum for 15 mins at bath temperature (42° C.), than cooled down to RT. N-Methylimidazole (0.009 mL, 0.11 mmol) was added followed by POCl₃ (9 µL, 0.11 mmol), and the mixture was kept at RT for 20-40 mins. The reaction was controlled by LCMS and monitored by the appearance of corresponding nucleoside 5'-monophosphate. After completion, tetrabutylammonium salt of pyrophosphate (150 mg) was added, followed by DMF (0.5 mL) to get a homogeneous solution. After 1.5 h at ambient temperature, the reaction was diluted with water (10 mL) and loaded on the column HiLoad 16/10 with Q Sepharose High Performance. Separation was done in a linear gradient of NaCl from 0 to 1N in 50 mM TRIS-buffer (pH 7.5). Triphosphate was eluted at 75-80% B. Corresponding fractions were concentrated. Desalting was achieved by RP HPLC on Synergy 4 micron Hydro-RP column (Phenomenex). A linear gradient of methanol from 0 to 30% in 50 mM triethylammonium acetate buffer (pH 7.5) was used for elution. The corresponding fractions were combined, concentrated and lyophilized 3 times to remove excess of buffer. Examples of compound made according to this procedure are provided in Table 2.

TABLE 2

| | Structure | MS [M − 1] | 31P NMR | | |
|---|---|---|---|---|---|
| | | | P(α) | P(β) | P(γ) |
| 3 | 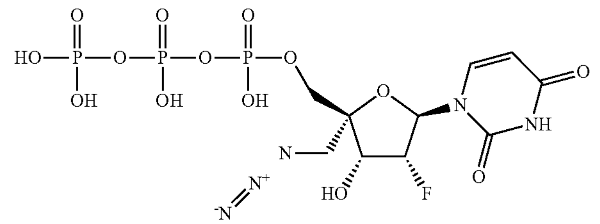 | 540.4 | −10.90 −11.03(d) | −23.38(t) | −11.91 −12.03(d) |
| 19 | 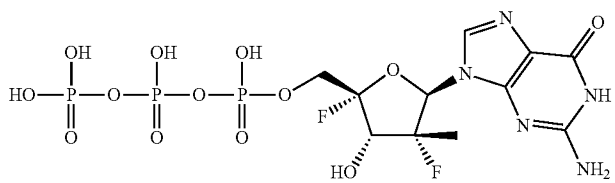 [SMILES: C[C@]1(F)[C@H](n2cnc3c(=O)[nH]c(N)nc32)O[C@](F)(COP(=O)(O)OP(=O)(O)OP(=O)(O)O)[C@H]1O] | 556.2 | −10.92 −11.03(d) | −23.18(t) | −11.86 −11.98(d) |
| 29 | 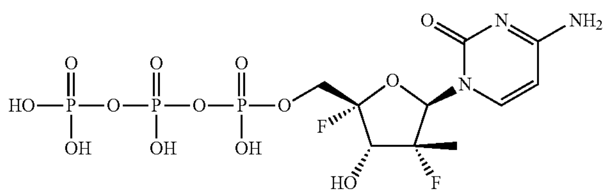 [SMILES: C[C@]1(F)[C@H](n2ccc(N)nc2=O)O[C@](F)(COP(=O)(O)OP(=O)(O)OP(=O)(O)O)[C@H]1O] | 516.1 | −7.49 −7.61(d) | −22.42(t) | −12.17 −12.30(d) |
| 34 | 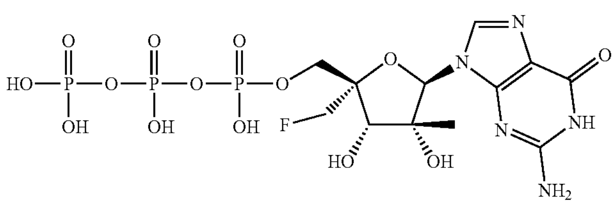 [SMILES: C[C@@]1(O)[C@H](O)[C@@](CF)(COP(=O)(O)OP(=O)(O)OP(=O)(O)O)O[C@H]1n1cnc2c(=O)[nH]c(N)nc21] | 568.2 | −5.60 −5.72(d) | −21.13 (bs) | −10.93 −11.05(d) |
| 37 | 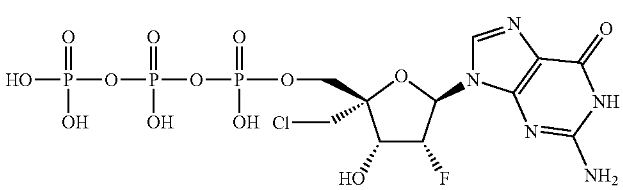 [SMILES: Nc1nc2c(ncn2[C@@H]2O[C@](CCl)(COP(=O)(O)OP(=O)(O)OP(=O)(O)O)[C@@H](O)[C@H]2F)c(=O)[nH]1] | 539.3 | −10.02 −10.36(d) | −20.72(t) | −11.27 −11.40(d) |
| 58 | 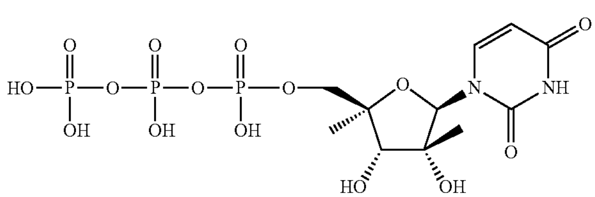 [SMILES: C[C@]1(O)[C@H](n2ccc(=O)[nH]c2=O)O[C@](C)(COP(=O)(O)OP(=O)(O)OP(=O)(O)O)[C@H]1O] | 510.8 | −10.87 −10.99(d) | −23.35(t) | −11.76 −11.89(d) |
| 59 | 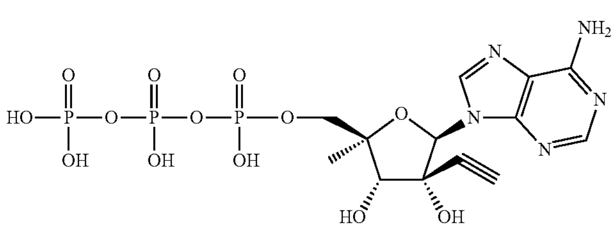 [SMILES: C#C[C@]1(O)[C@H](n2cnc3c(N)ncnc32)O[C@](C)(COP(=O)(O)OP(=O)(O)OP(=O)(O)O)[C@H]1O] | 543.8 | −10.53 −10.66(d) | −23.23(t) | −11.63 −11.75(d) |

TABLE 2-continued

| | Structure | MS [M − 1] | 31P NMR P(α) | P(β) | P(γ) |
|---|---|---|---|---|---|
| 61 | 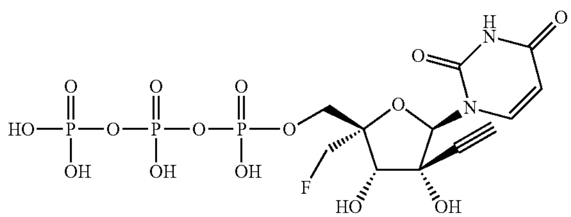 [SMILES: C#C[C@@]1(O)[C@H](O)[C@@](CF)(COP(=O)(O)OP(=O)(O)OP(=O)(O)O)O[C@H]1n1ccc(=O)[nH]c1=O] | 538.9 | −10.61 −10.73(d) | −23.20(t) | −11.74 −11.86(d) |
| 62 | 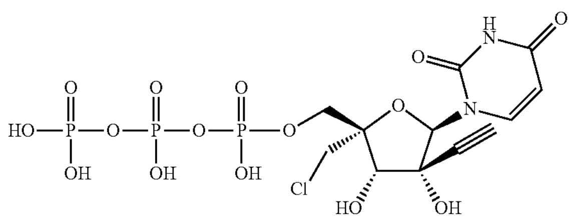 [SMILES: C#C[C@@]1(O)[C@H](O)[C@@](CCl)(COP(=O)(O)OP(=O)(O)OP(=O)(O)O)O[C@H]1n1ccc(=O)[nH]c1=O] | 538.9 | −10.92 −11.04 (d) | −23.33(t) | −11.81 −11.93(d) |
| 72 | 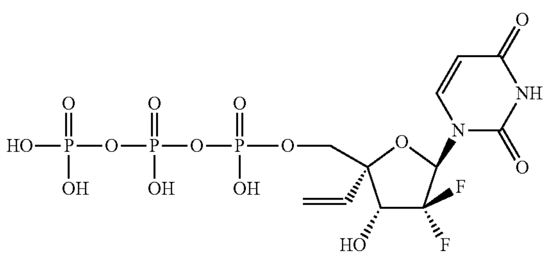 | 529.3 | −5.25 −5.37 (d) | −20.53(t) | −11.42 −11.53(d) |
| 73 | 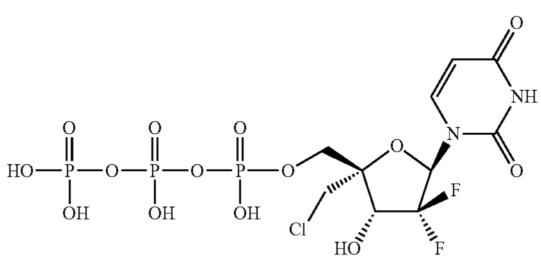 | 551.4 | −10.90 −11.02 (d) | −23.27(t) | −11.87 −11.99(d) |
| 74 | 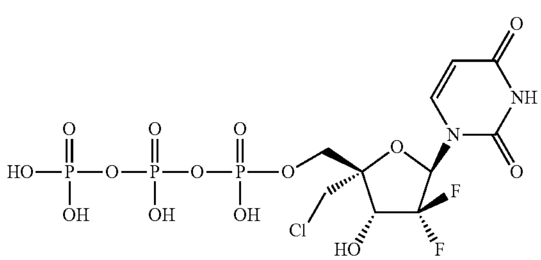 | 535.0 | −5.41 −5.53 (d) | −23.27(t) | −11.39 −11.51(d) |
| 79 | 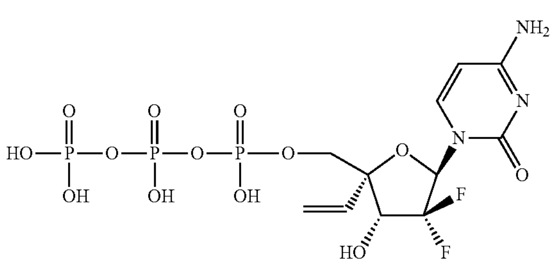 | 529.2 | −10.86 −10.98(d) | −23.23(t) | −11.85 −11.9(d) |

TABLE 2-continued

| | Structure | MS [M − 1] | 31P NMR | | |
|---|---|---|---|---|---|
| | | | P(α) | P(β) | P(γ) |
| 80 | 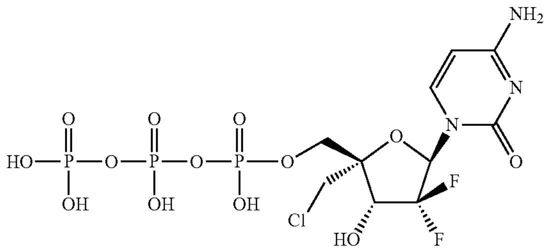 | 535.0 | −10.86 −10.98(d) | −23.21(t) | −11.81 −11.94(d) |
| 81 | 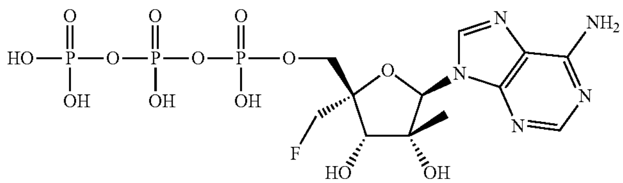 [SMILES: C[C@@]1(O)[C@H](O)[C@@](CF)(COP(=O)(O)OP(=O)(O)OP(=O)(O)O)O[C@H]1n1cnc2c(N)ncnc21] | 529.2 | −10.64 −10.73(d) | −20.78(t) | −11.42 −11.56(d) |
| 82 | 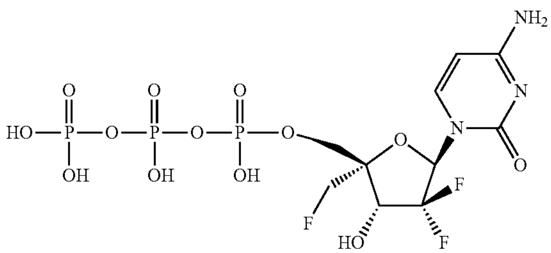 | 534.3 | −10.75 −10.89(d) | −23.19 | −11.46 −11.58(d) |
| 91 | 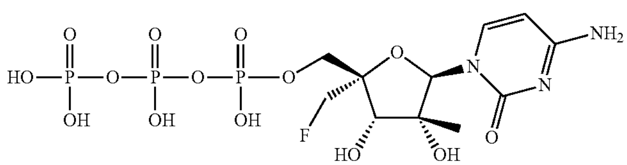 [SMILES: C[C@@]1(O)[C@H](O)[C@@](CF)(COP(=O)(O)OP(=O)(O)OP(=O)(O)O)O[C@H]1n1ccc(N)nc1=O] | 528.0 | −10.13 (bs) | −23.16(t) | −11.64 −11.81(d) |
| 92 | 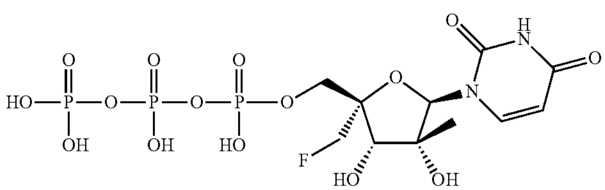 [SMILES: C[C@@]1(O)[C@H](O)[C@@](CF)(COP(=O)(O)OP(=O)(O)OP(=O)(O)O)O[C@H]1n1ccc(=O)[nH]c1=O] | 528.9 | −11.05 −11.08(d) | −23.46(t) | −11.79 −11.91(d) |
| 93 | 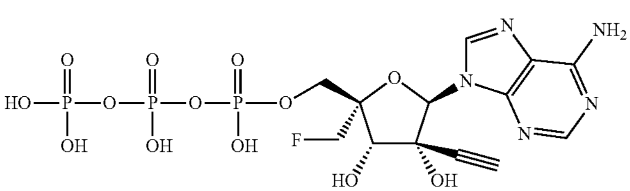 [SMILES: C#C[C@@]1(O)[C@H](O)[C@@](CF)(COP(=O)(O)OP(=O)(O)OP(=O)(O)O)O[C@H]1n1cnc2c(N)ncnc21] | 561.7 | −10.73 −10.85(d) | −23.23(t) | −11.63 −11.75(d) |
| 94 | 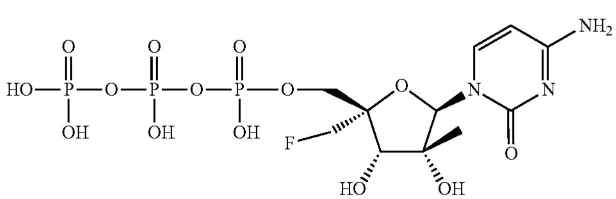 [SMILES: C[C@@]1(O)[C@H](O)[C@@](CF)(COP(=O)(O)OP(=O)(O)OP(=O)(O)O)O[C@H]1n1ccc(N)nc1=O] | 534.0 | −10.92 −10.64(d) | −23.38(t) | −11.61 −11.73(d) |

TABLE 2-continued

| | Structure | MS [M − 1] | 31P NMR | | |
|---|---|---|---|---|---|
| | | | P(α) | P(β) | P(γ) |
| 95 | [structure] | 512.8 | −10.98 −11.11(d) | −23.46(t) | −11.70 −11.8 (d) |
| 101 | [structure] | 556.2 | −10.92 −10.07(d) | −23.34(t) | −11.70 −11.82(d) |
| 103 | [structure] | 566.0 | −6.26 −6.39(d) | −22.45(t) | −11.66 −11.84 (d) |
| 107 | [structure] | 539.3 | −5.36(d) | −20.72(t) | −11.40(d) |
| 111 | [structure] | 564.0 | −10.94 −11.06(d) | −23.25(t) | −11.85 −11.97(d) |
| 114 | [structure] | 546.9 | −8.53(bs) | −22.61 (bs) | −12.17 −12.29(d) |

TABLE 2-continued

| | Structure | MS [M − 1] | 31P NMR | | |
|---|---|---|---|---|---|
| | | | P(α) | P(β) | P(γ) |
| 115 | (structure) | 564.4 | −11.05(bs) | −23.25 (bs) | −11.96 −12.08(d) |
| 123 | (structure) | 566.0 | −10.92 −11.04(d) | −23.18(t) | −11.93 −1(d) |
| 124 | (structure) | 513.8 | −8.66(bs) | −22.80(t) | −12.17 −12.29(d) |
| 132 | (structure) | 579.4 | −10.31 −10.44 (d) | −23.08(t) | −11.81 −11.92(d) |
| 133 | (structure) | 563.0 | −10.79 −10.91(d) | −23.24(t) | −11.80 −11.92(d) |
| 147 | (structure) | 517.1 | −13.60 −13.72(d) | −25.98(t) | −15.05 −15.17(d) |
| 149 | (structure) | 533.3 | −10.89 −11.01(d) | −23.31(t) | −12.49 −1(d) |

TABLE 2-continued

| | Structure | MS [M − 1] | 31P NMR | | |
|---|---|---|---|---|---|
| | | | P(α) | P(β) | P(γ) |
| 162 | 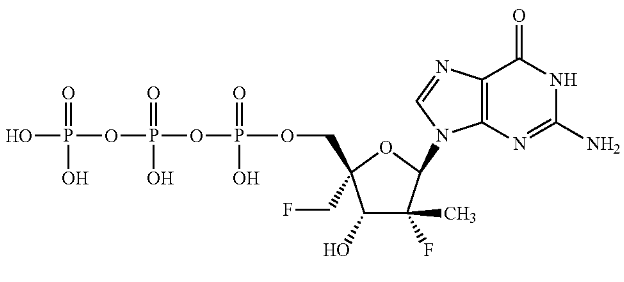 [SMILES: C[C@@]1(F)[C@H](O)[C@@](CF)(COP(=O)(O)OP(=O)(O)OP(=O)(O)O)O[C@H]1n1cnc2c(=O)[nH]c(N)nc21] | 570.4 | −9.25 −9.28(d) | −22.82(t) | −11.29 −11.42(d) |
| 163 | 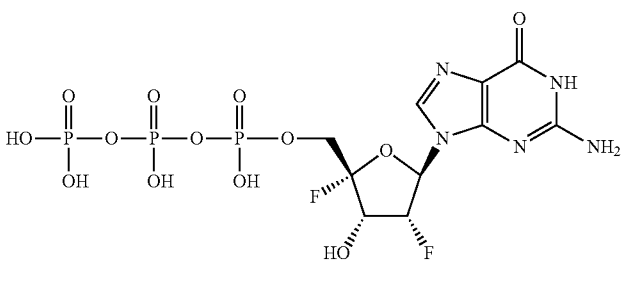 [SMILES: Nc1nc2c(ncn2[C@@H]2O[C@](F)(COP(=O)(O)OP(=O)(O)OP(=O)(O)O)[C@@H](O)[C@H]2F)c(=O)[nH]1] | 542.2 | −5.39 −5.40(d) | −20.71(t) | −11.52 −11.63(d) |
| 164 | 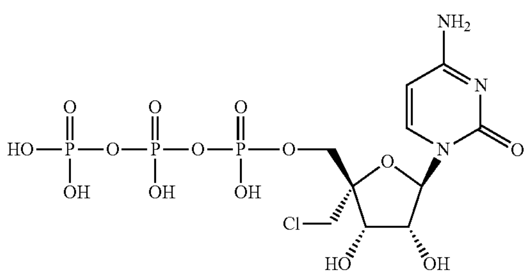 [SMILES: Nc1ccn([C@@H]2O[C@](CCl)(COP(=O)(O)OP(=O)(O)OP(=O)(O)O)[C@@H](O)[C@H]2O)c(=O)n1] | 529.8 | −10.72 (bs) | −23.20(t) | −11.73 −11.84(d) |
| 166 | 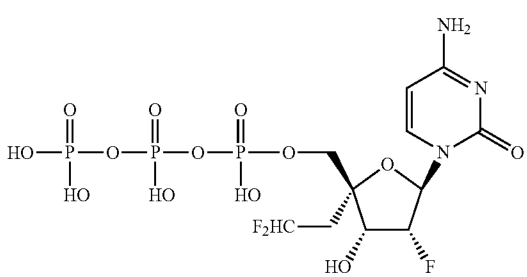 [SMILES: Nc1ccn([C@@H]2O[C@@](COP(=O)(O)OP(=O)(O)OP(=O)(O)O)(CC(F)F)[C@@H](O)[C@H]2F)c(=O)n1] | 548.2 | −10.93 −11.05(d) | −23.35(t) | −12.00 −12.13(d) |
| 167 | 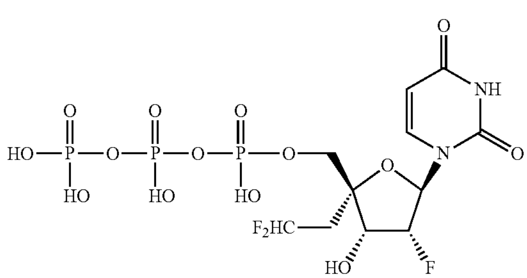 [SMILES: O=c1ccn([C@@H]2O[C@@](COP(=O)(O)OP(=O)(O)OP(=O)(O)O)(CC(F)F)[C@@H](O)[C@H]2F)c(=O)[nH]1] | 535.3 | −12.86 −12.98(d) | −25.60(t) | −14.24 −14.36(d) |

TABLE 2-continued

| | | | 31P NMR | |
|---|---|---|---|---|
| Structure | MS [M − 1] | P(α) | P(β) | P(γ) |
| 168 | 534.3 | −7.78 (bs) | −22.30(t) | −11.70 (bs) |
| 184 P(S) | 523.1 | 42.93 | −23.28 | −7.94 |
| 185 P(R) | 523.3 | 42.69 | −22.93 | −6.22 |
| 202 | 529.8 | −6.53 (m) | −22.27 (m) | −11.27 |
| 203 | 545.9 | −8.6 (br) | −22.80 (t) | −11.35 (d) |

TABLE 2-continued

| | Structure | MS [M − 1] | 31P NMR | | |
|---|---|---|---|---|---|
| | | | P(α) | P(β) | P(γ) |
| 205 | 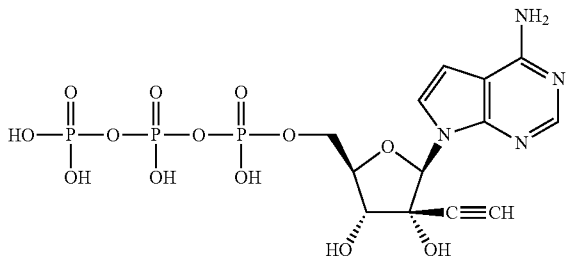 [SMILES: C#C[C@@]1(O)[C@H](O)[C@@H](COP(=O)(O)OP(=O)(O)OP(=O)(O)O)O[C@H]1n1ccc2c(N)ncnc21] | — | −4.97 (m) | −20.04 (m) | −10.72 (m) |
| 208 | 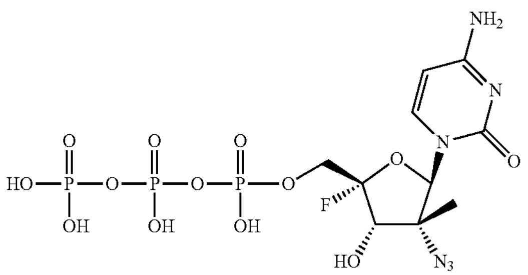 | 539.5 | −7.42 (bs) | −22.57(t) | −12.23 −12.34(d) |
| 209 | 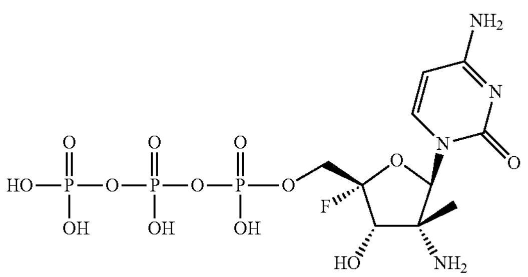 [SMILES: C[C@]1(N)[C@H](n2ccc(N)nc2=O)O[C@](F)(COP(=O)(O)OP(=O)(O)OP(=O)(O)O)[C@H]1O] | 513.1 | −6.36 −6.49(d) | −22.49(t) | −12.20 −12.33(d) |
| 210 | 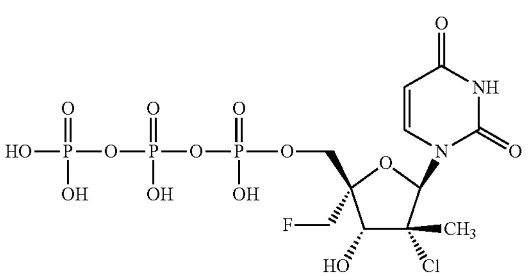 [SMILES: C[C@@]1(Cl)[C@H](O)[C@@](CF)(COP(=O)(O)OP(=O)(O)OP(=O)(O)O)O[C@H]1n1ccc(=O)[nH]c1=O] | 547.3 | −10.95 −11.07(d) | −23.32(t) | −11.91 −12.03(d) |
| 215 | 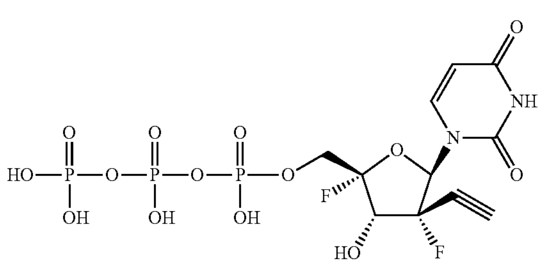 [SMILES: C#C[C@]1(F)[C@H](n2ccc(=O)[nH]c2=O)O[C@](F)(COP(=O)(O)OP(=O)(O)OP(=O)(O)O)[C@H]1O] | 526.8 | −10.96 −11.08(d) | −23.33(t) | −12.41 −12.53(d) |

TABLE 2-continued

| | Structure | MS [M − 1] | 31P NMR P(α) | P(β) | P(γ) |
|---|---|---|---|---|---|
| 236 | 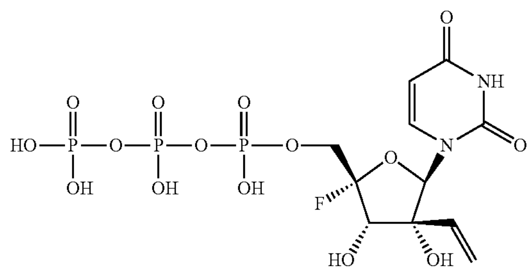 [SMILES: C=C[C@]1(O)[C@H](n2ccc(=O)[nH]c2=O)O[C@](F)(COP(=O)(O)OP(=O)(O)OP(=O)(O)O)[C@H]1O] | 527 | −10.68 −10.80(d) | −23.35(t) | −12.30 −12.42(d) |
| 237 | 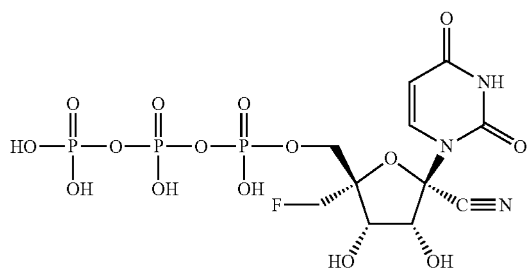 [SMILES: N#C[C@@]1(n2ccc(=O)[nH]c2=O)O[C@](CF)(COP(=O)(O)OP(=O)(O)OP(=O)(O)O)[C@@H](O)[C@H]1O] | 540.5 | −10.91 −11.03(d) | −23.38(t) | −12.24 −12.37(d) |
| 238 | 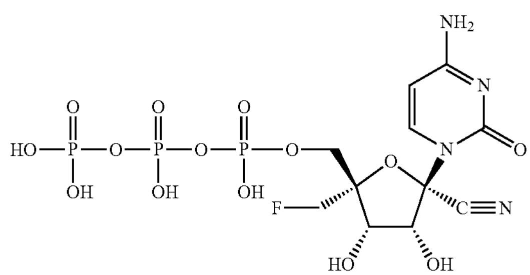 [SMILES: N#C[C@@]1(n2ccc(N)nc2=O)O[C@](CF)(COP(=O)(O)OP(=O)(O)OP(=O)(O)O)[C@@H](O)[C@H]1O] | 539 | −10.88 −10.99(d) | −23.41(t) | −12.15 −12.27(d) |
| 239 | 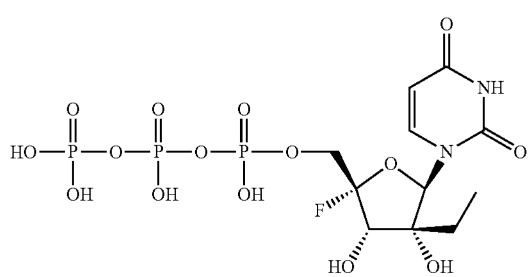 [SMILES: CC[C@]1(O)[C@H](n2ccc(=O)[nH]c2=O)O[C@](F)(COP(=O)(O)OP(=O)(O)OP(=O)(O)O)[C@H]1O] | 529 | −10.83 −10.95(d) | −23.27(t) | −12.25 −12.37(d) |
| 240 | 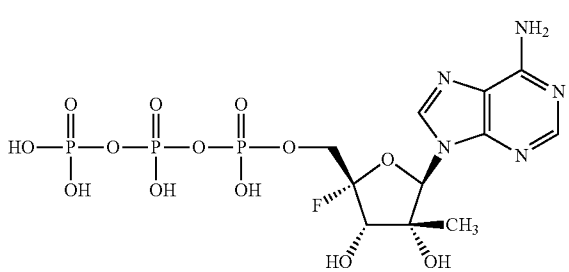 [SMILES: C[C@]1(O)[C@H](n2cnc3c(N)ncnc32)O[C@](F)(COP(=O)(O)OP(=O)(O)OP(=O)(O)O)[C@H]1O] | 538.4 | −9.19 (bs) | −22.50(t) | −12.04 (bs) |

TABLE 2-continued

| Structure | MS [M − 1] | 31P NMR | | |
|---|---|---|---|---|
| | | P(α) | P(β) | P(γ) |
| 241 | 536.0 | −10.69<br>−10.81(d) | −23.27(t) | −11.72<br>−12.85(d) |
| 242 | 548.2 | −10.85<br>−10.97(d) | −23.27(t) | −11.62<br>−11.74(d) |
| 243 | 510.1 | −10.55<br>−10.67(d) | −23.27(t) | −11.72<br>−12.85(d) |
| 244 | 544.9 | −10.97<br>−11.05(d) | −23.28(t) | −11.77<br>−12.89(d) |
| 245 | 577.6 | −10.42<br>−10.54(d) | −23.06(t) | −11.61<br>−12.73(d) |

TABLE 2-continued

| | | 31P NMR | | |
|---|---|---|---|---|
| Structure | MS [M − 1] | P(α) | P(β) | P(γ) |

246

554.0  −10.85    −23.24(t)  −11.52
       −10.96(d)            −11.64(d)

249

552.4  −6.17 (bs)  −21.02(t)  −10.09 (bs)

251

541.4  −10.87    −23.21(t)  −11.72
       −11.99(d)            −11.84(d)

252

553.4  −10.91    −23.31(t)  −11.74
       −11.03(d)            −11.87(d)

253

555.6  −8.63     −24.61(t)  −13.90
       −8.76(d)             −14.03(d)

TABLE 2-continued

| | | | 31P NMR | |
|---|---|---|---|---|
| Structure | MS [M − 1] | P(α) | P(β) | P(γ) |

254

551.4 | −9.74 −9.86(d) | −22.89(t) | −11.46 −11.58(d)

255

553.4 | −10.98 −11.10(d) | −23.38(t) | −11.86 −11.98(d)

256

547.2 | −10.91 −11.03(d) | −23.33(t) | −11.79 −11.91(d)

257

533.4 | −10.78 (br.s) | −23.22(t) | −12.24 −12.36(d)

258

546.3 | −10.52(bs) | −23.05(t) | −11.64 −11.76(d)

TABLE 2-continued
| | Structure | MS [M − 1] | 31P NMR P(α) | P(β) | P(γ) |
|---|---|---|---|---|---|
| 261 | 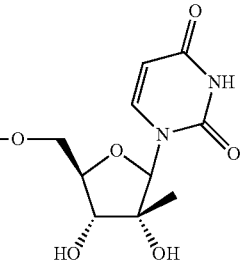 | 496.9 | −8.24 −8.36(d) | −21.66(t) | −11.14 −11.26(d) |
| 262 | 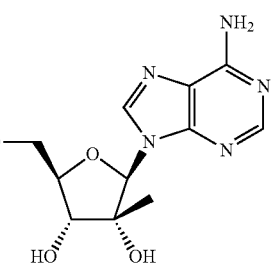 | 520.4 | −10.87 −10.97(d) | −23.34(t) | −11.86 −11.97(d) |
| 263 | 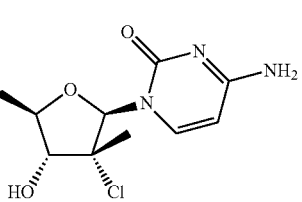 | 513.8 | −8.20 (bs) | −22.74(t) | −11.52 −11.64(d) |
| 264 | 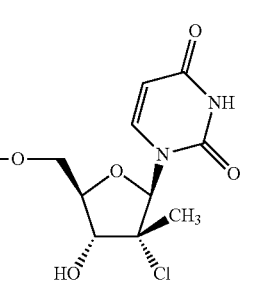 | 514.9 | −9.95 −10.08(d) | −23.14(t) | −11.64 −11.76(d) |
| 273 | 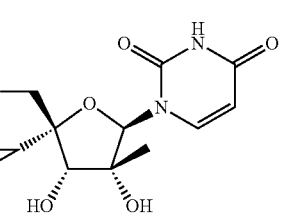 | 547.0 | −10.78 −10.91(d) | −23.31(t) | −11.84 −11.96(d) |
| 274 | 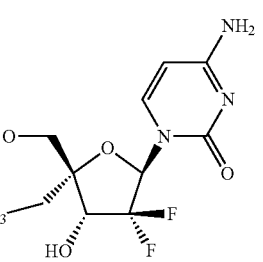 | 557.4 | −10.96 −11.09(d) | −23.35(t) | −11.93 −12.05(d) |

TABLE 2-continued

| | Structure | MS [M − 1] | 31P NMR P(α) | P(β) | P(γ) |
|---|---|---|---|---|---|
| 275 | 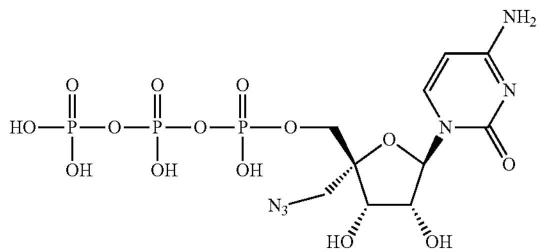 [SMILES: [N-]=[N+]=NC[C@]1(COP(=O)(O)OP(=O)(O)OP(=O)(O)O)O[C@@H](n2ccc(N)nc2=O)[C@H](O)[C@@H]1O] | 537.4 | −10.90 −11.03(d) | −23.35(t) | −11.84 −11.96(d) |
| 276 | 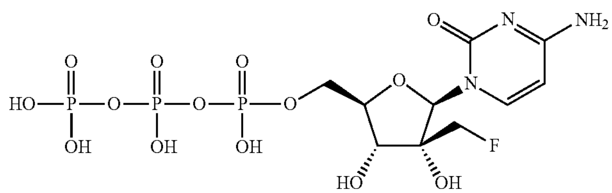 [SMILES: Nc1ccn([C@@H]2O[C@H](COP(=O)(O)OP(=O)(O)OP(=O)(O)O)[C@@H](O)[C@]2(O)CF)c(=O)n1] | 514.0 | −10.27 −11.39(d) | −23.18(t) | −11.39 −11.51(d) |
| 277 | 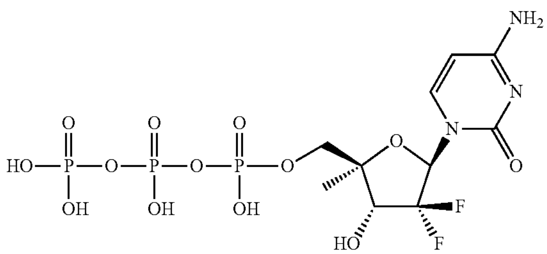 | 516.2 | −9.52(br.s) | −22.74 (br.s) | −11.75 (br.s) |
| 278 | 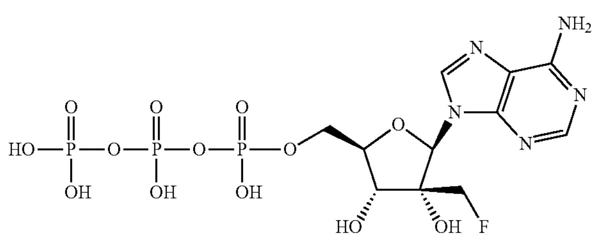 [SMILES: Nc1ncnc2c1ncn2[C@@H]1O[C@H](COP(=O)(O)OP(=O)(O)OP(=O)(O)O)[C@@H](O)[C@]1(O)CF] | 538.0 | −10.15 (br.s) | −22.86(t) | −11.28 −11.40(d) |
| 279 | 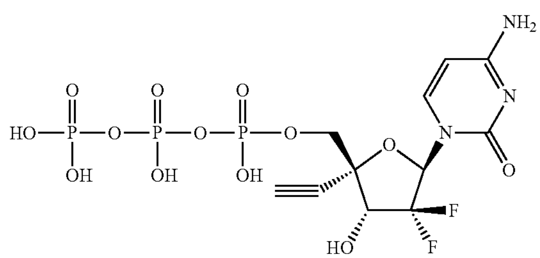 | 526.2 | −9.97(br.s) | −22.81(t) | −12.12 −12.23(d) |

Example 184

Compounds of Formulae (I) and (II)

The foregoing syntheses are exemplary and can be used as a starting point to prepare additional compounds of Formulae (I) and (II). Examples of additional compounds of Formulae (I) and (II) are shown below. These compounds can be prepared in various ways, including those synthetic schemes shown and described herein. Those skilled in the art will be able to recognize modifications of the disclosed syntheses and to devise routes based on the disclosures herein; all such modifications and alternate routes are within the scope of the claims.

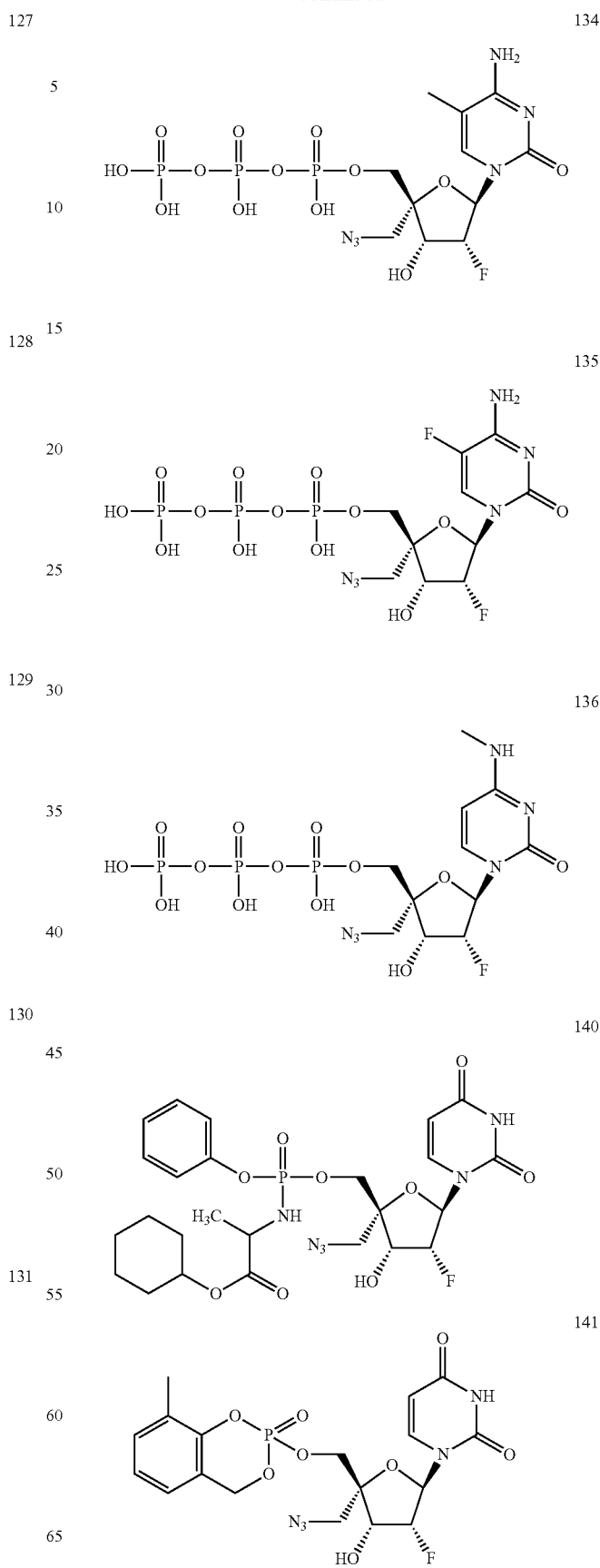

-continued

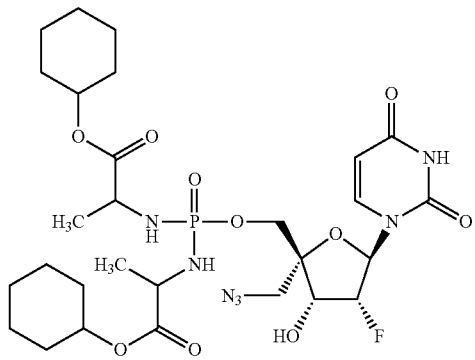

Example 185

Picornavirus Assay

HeLa-OHIO cells (Sigma-Aldrich, St. Louis, Mo.) were plated in 96 well plates at a density of $1.5 \times 10^5$ cells per well in assay media (MEM without phenol red or L-glutamine, supplemented with 1% FBS, 1% penicillin/streptomycin, 2 mM GlutaGro, and 1×MEM nonessential amino acids, all from Cellgro, Manassas, Va.). Assay setup took place after allowing cells to adhere for 24 h. Compounds dissolved in DMSO were serially diluted in assay media to 2× final concentration. Media was aspirated from the cells, and 100 µl media with compound was added in triplicate. Human rhinovirus 1B (ATCC, Manassas, Va.) was diluted in assay media, and 100 µL was added to cells and compound. The virus inoculum was selected to cause 80-90% cytopathic effect in 4 d. Infected cells were incubated for 4 d at 33° C., 5% $CO_2$. To develop the assay, 100 µL media was replaced with 100 µL CellTiter-Glo® reagent (Promega, Madison, Wis.), and incubated for 10 mins at RT. Luminescence was measured on a Victor X3 multi-label plate reader.

Compounds of Formulae (I) and (II) are active in this assay. The antiviral activity of exemplary compounds is shown in Table 3, where 'A' indicates an $EC_{50} < 1$ µM, 'B' indicates an $EC_{50} \geq 1$ µM and <10 µM, and 'C' indicates an $EC_{50} \geq 10$ µM and <100 µM.

TABLE 3

| Compound # | $EC_{50}$ |
|---|---|
| 1 | B |
| 5 | C |
| 7 | B |
| 8 | B |
| 9 | A |
| 10 | A |
| 13 | A |
| 14 | C |
| 16 | B |
| 17 | C |
| 18 | C |
| 21 | A |
| 22 | B |
| 25 | A |
| 26 | B |
| 27 | A |
| 28 | A |
| 31 | B |
| 33 | A |
| 36 | A |
| 40 | C |
| 43 | C |
| 44 | A |
| 46 | A |
| 52 | A |
| 53 | A |
| 55 | A |
| 57 | A |
| 63 | A |
| 64 | B |
| 65 | C |
| 66 | C |
| 68 | A |
| 69 | B |
| 70 | B |
| 71 | B |
| 75 | B |
| 76 | A |
| 83 | A |
| 84 | A |
| 85 | B |
| 86 | C |
| 87 | B |

TABLE 3-continued

| Compound # | EC$_{50}$ |
|---|---|
| 88 | C |
| 89 | C |
| 99 | B |
| 106 | B |
| 150 | B |
| 151 | A |
| 152 | B |
| 153 | B |
| 158 | C |
| 159 | C |
| 160 | A |
| 161 | B |
| 280 | C |
| 281 | A |
| 282 | A |
| 283 | C |
| 284 | B |
| 286 | B |
| 287 | A |
| 288 | C |
| 289 | A |
| 295 | C |
| 296 | B |
| 297 | C |
| 298 | B |
| 300 | A |
| 301 | C |
| 303 | C |

HeLa-OHIO cells were plated at a density of 1.5×10$^5$ cells per mL (1.5×10$^4$ cells per well) in assay media (MEM without phenol red or L-glutamine (Gibco cat. #51200) supplemented with 1% FBS, 1% penicillin/streptomycin (Mediatech cat. #30-002-CI), and 1% Glutamax (Gibco cat. #35050) in clear-bottom black 96 well plates. After 24 h, media was removed and replaced with serially diluted compounds in assay media. For EC$_{50}$ measurements, cells were infected with 70 TCID$_{50}$ of HRV-1b or an equivalent inoculum for the other virus strains in 100 µL assay media. The virus inoculum was normalized between the different virus strains to achieve a signal/background of ratio of 10. After 4-6 days, cell viability was measured using CellTiter Glo Luminescent Cell Viability Assay (Promega cat. #G7572). 100 µL media was removed from each well and 100 µL CellTiter Glo reagent was added. Plates were incubated at RT for 5 mins, then luminescence was measured using a Perkin Elmer multilabel counter Victor3V. EC$_{50}$ values were determined using XLFit.

Compounds 44 and 160 were found to be active and have an EC$_{50}$ less than 1 µM against several human rhinovirus strains, including HRV-25, HRV-56, HRV-21, HRV-02, HRV-19, HRV-16, HRV-53, HRV-68, HRV-45, HRV-84, HRV-70, HRV-79 and HRV-14. Both compounds were also active against HRV-89 with compounds 44 and 160 each having an EC$_{50}$ in the range of 1 µM to 2 µM. In contrast, BTA-798 (Vapendavir) was found to be inactive against 2 of the 15 tested strains. Additionally, compounds 44 and 160 were not cytotoxicity (CC$_{50}$>100 µM (n>5)) in the HeLa OHIO host cell line.

Example 186

Picornavirus Polymerase Inhibition Assay

The enzyme activity of human rhinovirus 16 polymerase (HRV16pol) was measured as an incorporation of tritiated NMP into acid-insoluble RNA products. HRV16pol assay reactions contained 30 Nm recombinant enzyme, 50 Nm heteropolymeric RNA, about 0.5 µCi tritiated NTP, 0.1 Mm of competing cold NTP, 40 Mm Tris-HCl (Ph 7.0), 3 Mm dithiothreitol, and 0.5 Mm MgCl$_2$. Standard reactions were incubated for 2.5 h at 30° C., in the presence of increasing concentration of inhibitor. At the end of the reaction, RNA was precipitated with 10% TCA, and acid-insoluble RNA products were filtered on a size exclusion 96-well plate. After washing of the plate, scintillation liquid was added and radiolabeled RNA products were detected according to standard procedures with a Trilux Microbeta scintillation counter. The compound concentration at which the enzyme-catalyzed rate was reduced by 50% (IC$_{50}$) was calculated by fitting the data to a non-linear regression (sigmoidal).

The IC$_{50}$ values were derived from the mean of several independent experiments and are shown in Table 4. Compounds of Formulae (I) and (II) showed activity in this assay. A value of 'A' in the table below indicates an IC$_{50}$ of <1 µM, a value of 'B' indicates an IC$_{50}$<10 µM, and a value of 'C' indicates an IC$_{50}$ value of <100 µM.

TABLE 4

| Compound # | IC$_{50}$ |
|---|---|
| 3 | B |
| 19 | A |
| 29 | A |
| 34 | A |
| 37 | A |
| 58 | B |
| 59 | C |
| 61 | A |
| 62 | A |
| 72 | C |
| 73 | B |
| 74 | B |
| 79 | B |
| 80 | B |
| 81 | B |
| 82 | A |
| 91 | B |
| 92 | A |
| 93 | A |
| 97 | B |
| 101 | A |
| 107 | A |
| 103 | A |
| 110 | B |
| 111 | A |
| 114 | A |
| 115 | A |
| 116 | B |
| 117 | C |
| 123 | A |
| 124 | A |
| 132 | B |
| 162 | A |
| 168 | B |
| 202 | A |
| 205 | A |
| 208 | B |
| 215 | B |
| 236 | B |
| 237 | A |
| 238 | B |
| 239 | B |
| 240 | A |
| 242 | B |
| 243 | B |
| 244 | B |
| 245 | A |
| 246 | A |
| 249 | C |
| 251 | B |
| 252 | B |
| 253 | B |
| 254 | A |

TABLE 4-continued

| Compound # | IC$_{50}$ |
|---|---|
| 255 | B |
| 256 | B |
| 257 | B |
| 258 | A |
| 273 | B |
| 274 | B |
| 275 | B |
| 276 | B |
| 277 | B |
| 278 | C |
| 279 | B |

Example 187

Enterovirus Assay

Cells

HeLa OHIO cells were purchased from Sigma Aldrich (St Louis, Mo.) and cultured in MEM with Glutamax (Gibco cat. #41090) supplemented with 10% FBS (Mediatech cat. #35-011-CV) and 1% penicillin/streptomycin (Mediatech cat. #30-002-CI), at 37° C. with 5% CO$_2$. RD cells were purchased from ATCC (Manassas, Va.) and cultured in DMEM, supplemented with 10% FBS (Mediatech cat. #35-011-CV) and 1% penicillin/streptomycin (Mediatech cat. #30-002-CI), at 37° C. with 5% CO$_2$.

Determination of Anti-Enterovirus Activity

For HRV16, EV68, and CVB3, HeLa-OHIO cells were plated at a density of $1.5 \times 10^5$ cells per mL ($1.5 \times 10^4$ cells per well) in assay media (MEM without phenol red or L-glutamine (Gibco cat. #51200) supplemented with 1% FBS, 1% penicillin/streptomycin (Mediatech cat. #30-002-CI), and 1% Glutamax (Gibco cat. #35050)) in clear-bottom black 96 well plates. For EV71, RD cells were plated at a density of $5 \times 10^4$ cells per mL (5000 cells per well) in assay media (DMEM supplemented with 2% FBS and 1% penicillin/streptomycin). After 24 h, media was removed and replaced with serially diluted compounds in assay media. For EC$_{50}$ measurements, cells were infected in 100 µL assay media with a virus inoculum sufficient to obtain a 10-fold reduction of the cell viability in the infected control compared to uninfected control cells. After 2-6 days, cell viability was measured using CellTiter Glo Luminescent Cell Viability Assay (Promega cat. #G7572). Cells infected with EV-71 and CVB3 were cultured at 37° C., while cells infected with HRV-16 or EV-68 were cultured at 33° C. 100 µL media was removed from each well and 100 µL CellTiter Glo reagent was added. Plates were incubated at RT for 5 mins, then luminescence was measured using a Perkin Elmer multilabel counter Victor3V. EC$_{50}$ values were determined using XLFit.

Compound 44 inhibited replication of all four viruses tested (human rhinovirus 16 (HRV-16), coxasackie B3 (CVB3), enterovirus-68 (EV-68) and enterovirus-71 (EV-71)) with an EC$_{50}$ ranging from 0.38 to 2.52 µM (mean 1.39±1.14 µM). By comparison, BTA-798 was not active against all the tested viruses, and was found to be inactive against CVB3. As described herein, compound 44 can be obtained after the removal of the group(s) attached to the phosphorus of a compound described herein (for example, a compound of Formulae (I) and/or (II), or a pharmaceutically acceptable salt of the foregoing); and therefore, prodrugs of compound 44 will also be active against the picornaviruses described herein.

Example 188

HCV Replicon Assay

Cells

Huh-7 cells containing the self-replicating, subgenomic HCV replicon with a stable luciferase (LUC) reporter were cultured in Dulbecco's modified Eagle's medium (DMEM) containing 2 mM L-glutamine and supplemented with 10% heat-inactivated fetal bovine serum (FBS), 1% penicillin-streptomyocin, 1% nonessential amino acids, and 0.5 mg/Ml G418.

Determination of Anti-HCV Activity

Determination of 50% inhibitory concentration (EC$_{50}$) of compounds in HCV replicon cells were performed by the following procedure. On the first day, 5,000 HCV replicon cells were plated per well in a 96-well plate. On the following day, test compounds were solubilized in 100% DMSO to 100× the desired final testing concentration. Each compound was then serially diluted (1:3) up to 9 different concentrations. Compounds in 100% DMSO are reduced to 10% DMSO by diluting 1:10 in cell culture media. The compounds were diluted to 10% DMSO with cell culture media, which were used to dose the HCV replicon cells in 96-well format. The final DMSO concentration was 1%. The HCV replicon cells were incubated at 37° C. for 72 hours. At 72 hours, cells were processed when the cells are still subconfluent. Compounds that reduce the LUC signal are determined by Bright-Glo Luciferase Assay (Promega, Madison, Wis.). % Inhibition was determined for each compound concentration in relation to the control cells (untreated HCV replicon) to calculate the EC$_{50}$.

Compounds of Formulae (I) and (II) are active in the HCV replicon assay. The antiviral activity of exemplary compounds is shown in Table 5, where 'A' indicates an EC$_{50}$<1 µM, 'B' indicates an EC$_{50}$≥1 µM and <10 µM, and 'C' indicates an EC$_{50}$≥10 µM and <100 µM.

TABLE 5

| Compound # | EC$_{50}$ |
|---|---|
| 14 | C |
| 16 | B |
| 21 | B |
| 22 | B |
| 36 | A |
| 43 | A |
| 44 | A |
| 52 | A |
| 54 | C |
| 57 | A |
| 63 | B |
| 64 | C |
| 65 | C |
| 67 | C |
| 70 | B |
| 71 | B |
| 75 | C |
| 76 | B |
| 84 | B |
| 85 | B |
| 99 | B |
| 104 | C |
| 106 | C |
| 280 | C |
| 281 | A |
| 282 | A |
| 283 | B |
| 284 | B |
| 286 | A |
| 287 | A |

TABLE 5-continued

| Compound # | EC$_{50}$ |
|---|---|
| 288 | C |
| 289 | A |
| 295 | B |
| 298 | C |
| 300 | C |
| 301 | A |
| 303 | B |

Example 189

NS5B Inhibition Assay

The enzyme activity of NS5B570-Con1 (Delta-21) was measured as an incorporation of tritiated NMP into acid-insoluble RNA products. The complementary IRES (Cires) RNA sequence was used as a template, corresponding to 377 nucleotides from the 3'-end of HCV (−) strand RNA of the Con-1 strain, with a base content of 21% Ade, 23% Ura, 28% Cyt, and 28% Gua. The Cires RNA was transcribed in vitro using a T7 transcription kit (Ambion, Inc.) and purified using the Qiagen Rneasy maxi kit. HCV polymerase reactions contained 50 Nm NS5B570-Con1, 50 Nm Cires RNA, about 0.5 µCi tritiated NTP, 1 Mm of competing cold NTP, 20 Mm NaCl, 40 Mm Tris-HCl (Ph 8.0), 4 Mm dithiothreitol, and 4 Mm MgCl$_2$. Standard reactions were incubated for 2 hours at 37° C., in the presence of increasing concentration of inhibitor. At the end of the reaction, RNA was precipitated with 10% TCA, and acid-insoluble RNA products were filtered on a size exclusion 96-well plate. After washing of the plate, scintillation liquid was added and radio labeled RNA products were detected according to standard procedures with a Trilux Topcount scintillation counter. The compound concentration at which the enzyme-catalyzed rate was reduced by 50% (IC$_{50}$) was calculated by fitting the data to a non-linear regression (sigmoidal).

The IC$_{50}$ values were derived from the mean of several independent experiments and are shown in Table 6. Compounds of Formulae (I) and (II) are active in this assay. A value of 'A' in the table below indicates an IC$_{50}$ of <1 µM, a value of 'B' indicates an IC$_{50}$≥1 µM and <10 µM, and a value of 'C' indicates an IC$_{50}$ value of ≥10 µM and <100 µM.

TABLE 6

| Compound # | IC$_{50}$ |
|---|---|
| 3 | C |
| 19 | A |
| 29 | A |
| 34 | A |
| 37 | C |
| 59 | B |
| 61 | A |
| 62 | A |
| 72 | C |
| 73 | C |
| 74 | C |
| 79 | C |
| 80 | C |
| 82 | C |
| 91 | A |
| 92 | A |
| 93 | C |
| 98 | C |
| 101 | A |
| 103 | A |
| 110 | A |

TABLE 6-continued

| Compound # | IC$_{50}$ |
|---|---|
| 111 | A |
| 114 | A |
| 115 | A |
| 116 | A |
| 117 | B |
| 123 | A |
| 124 | A |
| 147 | A |
| 149 | A |
| 162 | B |
| 203 | A |
| 205 | A |
| 208 | A |
| 209 | A |
| 210 | B |
| 215 | A |
| 236 | B |
| 239 | C |
| 240 | A |
| 243 | B |
| 244 | A |
| 245 | C |
| 246 | A |
| 249 | C |
| 252 | B |
| 253 | C |
| 254 | A |
| 255 | B |
| 256 | C |
| 257 | A |
| 258 | C |
| 273 | C |
| 276 | A |
| 277 | C |
| 278 | B |
| 279 | C |

Example 190

Dengue Virus Cell-Based Assay

The Dengue virus type 2 strain New Guinea C (NG-C) and the Dengue virus type 4 strain H241 were purchased from ATCC (Manassas, Va.; item numbers VR-1584 and VR-1490, respectively). 24 h prior to dosing, Huh-7.5 cells were plated in 96 well plates at a density of 1.5×10$^5$/mL in DMEM medium supplemented with 10% fetal bovine serum, 1% HEPES buffer, 1% Penicillin/Streptomycin and 1% non-essential amino acids (all Mediatech, Manassas, Va.). At the day of infection, serially diluted compounds were added to cells and incubated for 4 h. After the end of the 4 h pre-incubation period, cells were infected with either Dengue virus type 2 NG-C or Dengue virus type 4H241. The virus inoculum was selected to cause 80-90% cytopathic effect in five to six days. Infected cells were incubated for five (NG-C) to six (H241) days at 37° C., 5% CO$_2$. To develop the assay, 100 µL media was replaced with 100 µl CellTiter-Glo® reagent (Promega, Madison, Wis.), and incubated for 10 mins at RT. Luminescence was measured on a Victor X3 multi-label plate reader. Potential compound cytotoxicity of was determined using uninfected parallel cultures.

Compounds of Formulae (I) and (II) are active in this assay. The antiviral activity of exemplary compounds is shown in Table 7, where A value of 'A' in the table below indicates an IC$_{50}$ of <1 µM, a value of 'B' indicates an IC$_{50}$<10 µM, and a value of 'C' indicates an IC$_{50}$ value of <100 µM.

TABLE 7

| Compound # | IC$_{50}$ |
|---|---|
| 9 | B |
| 10 | A |
| 13 | A |
| 14 | B |
| 16 | B |
| 25 | A |
| 26 | A |
| 27 | B |
| 28 | B |
| 46 | C |
| 53 | B |
| 55 | A |
| 83 | A |
| 86 | A |
| 88 | B |
| 89 | B |
| 161 | B |

Example 191

Dengue Virus Polymerase Inhibition Assay

The enzyme activity of dengue virus NS5 polymerase domain (DENVpol, serotype 2, New Guinea C strain) was measured as an incorporation of tritiated NMP into acid-insoluble RNA products. DENVpol assay reactions contained 100 nM recombinant enzyme, 50 nM heteropolymeric RNA, about 0.5 µCi tritiated NTP, 0.33 µM of competing cold NTP, 40 mM HEPES (pH 7.5), 3 mM dithiothreitol, and 2 mM MgCl$_2$. Standard reactions were incubated for 3 hours at 30° C., in the presence of increasing concentration of inhibitor. At the end of the reaction, RNA was precipitated with 10% TCA, and acid-insoluble RNA products were filtered on a size exclusion 96-well plate. After washing of the plate, scintillation liquid was added and radiolabeled RNA products were detected according to standard procedures with a Trilux Topcount scintillation counter. The compound concentration at which the enzyme-catalyzed rate was reduced by 50% (IC$_{50}$) was calculated by fitting the data to a non-linear regression (sigmoidal).

The IC$_{50}$ values were derived from the mean of several independent experiments and are shown in Table 8. Compounds of Formula (I) showed activity in this assay. A value of 'A' in the table below indicates an IC$_{50}$ of <1 µM, a value of 'B' indicates an IC$_{50}$<10 µM, and a value of 'C' indicates an IC$_{50}$ value of <100 µM.

TABLE 8

| Compound # | IC$_{50}$ |
|---|---|
| 19 | B |
| 29 | A |
| 34 | A |
| 91 | C |
| 92 | B |
| 101 | B |
| 103 | A |
| 110 | A |
| 111 | B |
| 114 | B |
| 115 | A |
| 123 | B |
| 124 | B |
| 147 | B |
| 149 | B |
| 162 | B |
| 163 | B |
| 164 | C |

Example 192

Cell-Based Flavivirus Immuno (CFI) Assay

BHK21 or A549 cells are trypsinized, counted and diluted to 2×10$^5$ cells/mL in Hams F-12 media (for A549 cells) or RPMI-1640 media (for BHK21 cells) supplemented with 2% fetal bovine serum and 1% penicillin/streptomycin. 2×10$^4$ cells are dispensed in clear 96-well tissue culture plate per well and placed at 37° C., 5% CO$_2$ overnight. On the next day, the cells are infected with viruses at multiplicity of infection (MOI) of 0.3 in the presence of varied concentrations of test compounds for 1 h at 37° C. and 5% CO$_2$ in the same media. The media containing viruses and the compounds are removed, replaced with fresh medium containing only the test compounds and incubated at 37° C., 5% CO$_2$ for another 48 h. The cells are washed once with PBS and fixed with cold methanol for 10 mins. After washing twice with PBS, the fixed cells are blocked with PBS containing 1% FBS and 0.05% Tween-20 for 1 h at RT. The primary antibody solution (4G2) is then added at a concentration of 1:20 to 1:100 in PBS containing 1% FBS and 0.05% Tween-20 for 3 h. The cells are then washed three times with PBS followed by 1 hour incubation with horseradish peroxidase (HRP)-conjugated anti-mouse IgG (Sigma, 1:2000 dilution). After washing 3 times with PBS, 50 L of 3,3',5, 5'-tetramethylbenzidine (TMB) substrate solution (Sigma) is added to each well for 2 mins. The reaction is stopped by addition 0.5M sulfuric acid. The plates are read at 450 nm absorbance for viral load quantification. After measurement, the cells are washed 3 times with PBS, followed by incubation with propidium iodide for 5 mins. The plate is read in a Tecan Safire plate reader (excitation 537 nm, emission 617 nm) for cell number quantification. Dose response curves are plotted from the mean absorbance versus the log of the concentration of test compounds. The EC$_{50}$ is calculated by nonlinear regression analysis. A positive control may be used, such as, for example, N-nonyl-deoxynojirimycin.

Example 193

Cell-Based Flavivirus Cytopathic Effect (CPE) Assay

For testing against West Nile virus or Japanese encephalitis virus, BHK21 cells are trypsinized and diluted to a concentration of 4×10$^5$ cells/mL in RPMI-1640 media supplemented with 2% fetal bovine serum and 1% penicillin/streptomycin. For testing against dengue virus, Huh7 cells are trypsinized and diluted to a concentration of 4×10$^5$ cells/mL in DMEM media supplemented with 5% fetal bovine serum and 1% penicillin/streptomycin. A 50 µL of cell suspension (2×10$^4$ cells) is dispensed per well in the 96-well optical bottom PIT polymerbase plates (Nunc). Cells are grown overnight in culture medium at 37° C., 5% CO$_2$ and then infected with West Nile virus (e.g. B956 strain) or Japanese encephalitis virus (e.g. Nakayama strain) at MOI=0.3, or with dengue virus (e.g. DEN-2 NGC strain) at MOI=1, in the presence of different concentrations of test compounds. The plates containing the virus and the compounds are further incubated at 37° C., 5% $CO_2$ for 72 h. At the end of incubation, 100 μL of CellTiter-Glo® reagent is added into each well. Contents are mixed for 2 mins on an orbital shaker to induce cell lysis. The plates are incubated at RT for 10 mins to stabilize luminescent signal. Luminescence reading is recorded using a plate reader. A positive control may be used, such as, for example, N-nonyl-deoxynojirimycin.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for ameliorating or treating a Picornaviridae viral infection comprising contacting a cell infected with the Picornaviridae virus with an effective amount of a compound of Formula (I), or a pharmaceutically acceptable salt thereof, wherein the compound of Formula (I) has the structure:

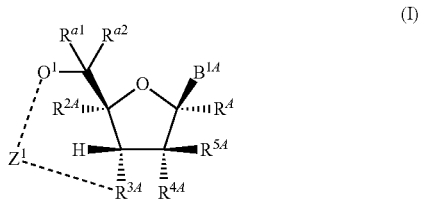

wherein:
$B^{1A}$ is

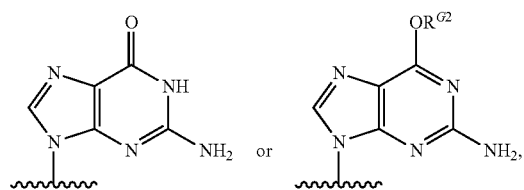

wherein $R^{G2}$ is an unsubstituted $C_{1-6}$ alkyl;
$R^{3A}$ is selected from the group consisting of OH, OC(=O)$R''^A$ and an unsubstituted O-linked α-amino acid;
$R^{4A}$ is selected from the group consisting of OH and halo;
$R^{a1}$ and $R^{a2}$ are independently hydrogen or deuterium;
$R^A$ is hydrogen or deuterium;
$R^{1A}$ is selected from the group consisting of hydrogen,

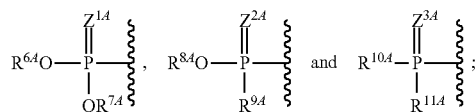

$R^{2A}$ is halo;
$R^{5A}$ is selected from the group consisting of an unsubstituted $C_{1-6}$ alkyl and an unsubstituted $C_{2-6}$ alkenyl;

$R^{6A}$ and $R^{7A}$ are independently selected from the group consisting of absent, hydrogen and

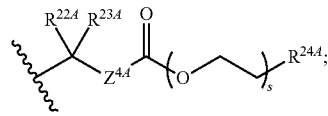

or
$R^{6A}$ is

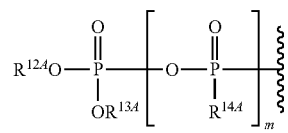

and $R^{7A}$ is absent or hydrogen; or
$R^{8A}$ is absent, hydrogen, an optionally substituted phenyl or an optionally substituted naphthyl;
$R^{9A}$ is an optionally substituted N-linked amino acid selected from the group consisting of N-linked alanine, N-linked asparagine, N-linked aspartate, N-linked cysteine, N-linked glutamate, N-linked glutamine, N-linked glycine, N-linked proline, N-linked serine, N-linked tyrosine, N-linked arginine, N-linked histidine, N-linked isoleucine, N-linked leucine, N-linked lysine, N-linked methionine, N-linked phenylalanine, N-linked threonine, N-linked tryptophan and N-linked valine, or an optionally substituted N-linked α-amino acid ester derivative, wherein the optionally substituted N-linked α-amino acid ester derivative is an unsubstituted $C_{1-6}$ alkyl ester, an optionally substituted $C_{3-6}$ cycloalkyl ester, an optionally substituted $C_6$ aryl ester, an optionally substituted $C_{10}$ aryl ester or an optionally substituted benzyl ester of an N-linked α-amino acid selected from the group consisting of N-linked alanine, N-linked asparagine, N-linked aspartate, N-linked cysteine, N-linked glutamate, N-linked glutamine, N-linked glycine, N-linked proline, N-linked serine, N-linked tyrosine, N-linked arginine, N-linked histidine, N-linked isoleucine, N-linked leucine, N-linked lysine, N-linked methionine, N-linked phenylalanine, N-linked threonine, N-linked tryptophan and N-linked valine;
$R^{10A}$ and $R^{11A}$ are independently an optionally substituted N-linked amino acid selected from the group consisting of N-linked alanine, N-linked asparagine, N-linked aspartate, N-linked cysteine, N-linked glutamate, N-linked glutamine, N-linked glycine, N-linked proline, N-linked serine, N-linked tyrosine, N-linked arginine, N-linked histidine, N-linked isoleucine, N-linked leucine, N-linked lysine, N-linked methionine, N-linked phenylalanine, N-linked threonine, N-linked tryptophan and N-linked valine, or an optionally substituted N-linked α-amino acid ester derivative, wherein the optionally substituted N-linked α-amino acid ester derivative is an unsubstituted $C_{1-6}$ alkyl ester, an optionally substituted $C_{3-6}$ cycloalkyl ester, an optionally substituted $C_6$ aryl ester, an optionally substituted Cm aryl ester or an optionally substituted benzyl ester of an N-linked α-amino acid selected from the group consisting of N-linked alanine, N-linked asparagine, N-linked aspartate, N-linked cysteine, N-linked glutamate, N-linked glutamine, N-linked glycine, N-linked proline, N-linked serine, N-linked tyrosine, N-linked arginine, N-linked histidine, N-linked isoleucine, N-linked leucine, N-linked lysine, N-linked methionine, N-linked phenylalanine, N-linked threonine, N-linked tryptophan and N-linked valine;

$R^{12A}$ and $R^{13A}$ are independently absent or hydrogen;

$R^{14A}$ is O⁻, OH or methyl;

$R^{22A}$ and $R^{23A}$ are each hydrogen;

$R^{24A}$ is selected from the group consisting of hydrogen, an unsubstituted $C_{1-24}$ alkyl, and an unsubstituted —O—$C_{1-24}$ alkyl;

$R'''^{A}$ is an unsubstituted $C_{1-24}$ alkyl;

m is 0 or 1;

s is 0, 1, 2 or 3; and $Z^{1A}$, $Z^{2A}$, $Z^{3A}$ and $Z^{4A}$ are each O.

2. The method of claim 1, wherein the virus is an Enterovirus.

3. The method of claim 1, wherein the virus is a Rhinovirus.

4. The method of claim 1, wherein $B^{1A}$ is

5. The method of claim 1, wherein $B^{1A}$ is wherein $R^{G2}$ is ethyl.

6. The method of claim 1, wherein $R^{2A}$ is fluoro.

7. The method of claim 1, wherein $R^{3A}$ is OH.

8. The method of claim 1, wherein $R^{3A}$ is —OC(=O)R'''^A, wherein $R'''^A$ is an unsubstituted $C_{1-4}$ alkyl.

9. The method of claim 1, wherein $R^{4A}$ is OH.

10. The method of claim 1, wherein $R^{4A}$ is -halo.

11. The method of claim 10, wherein $R^{4A}$ is fluoro.

12. The method of claim 1, wherein $R^{5A}$ is an unsubstituted $C_{1-6}$ alkyl.

13. The method of claim 12, wherein $R^{5A}$ is methyl.

14. The method of claim 1, wherein $R^{1A}$ is hydrogen.

15. The method of claim 1, wherein $R^{1A}$ is

16. The method of claim 15, wherein $R^{6A}$ is $R^{7A}$, $R^{12A}$ and $R^{13A}$ are independently absent or hydrogen; $R^{14A}$ is O⁻ and OH; and m is 0 or 1.

17. The method of claim 16, wherein m is 1.

18. The method of claim 1, wherein $R^{a1}$ and $R^{a2}$ are each hydrogen.

19. The method of claim 1, wherein $R^{A}$ is hydrogen.

20. The method of claim 15, wherein $R^{6A}$ and $R^{7A}$ are independently absent or hydrogen.

21. The method of claim 15, wherein $R^{6A}$ and $R^{7A}$ are each wherein s is 0.

22. The method of claim 15, wherein $R^{6A}$ and $R^{7A}$ are each isopropyloxycarbonyloxymethyl.

23. The method of claim 1, wherein $R^{1A}$ is

24. The method of claim 23, wherein $R^{8A}$ is an optionally substituted phenyl.

25. The method of claim 24, wherein $R^{8A}$ is an unsubstituted phenyl.

26. The method of claim 25, wherein $R^{9A}$ is an unsubstituted $C_{1-6}$ alkyl ester or an unsubstituted $C_{3-6}$ cycloalkyl ester of an N-linked α-amino acid selected from the group consisting of N-linked alanine, N-linked isoleucine, N-linked leucine and N-linked valine.

27. The method of claim 25, wherein $R^{9A}$ is selected from the group consisting of and -continued

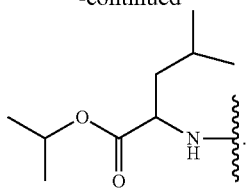

28. The method of claim 1, wherein the compound of Formula (I) is

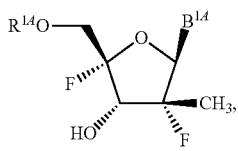

or a pharmaceutically acceptable salt thereof.

29. The method of claim 28, wherein $B^{1A}$ is

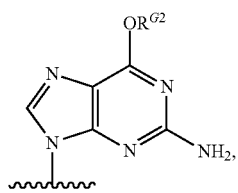

wherein $R^{G2}$ is —CH$_2$CH$_3$.

30. The method of claim 28, wherein $R^{1A}$ is H.

31. The method of claim 28, wherein $R^{1A}$ is

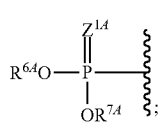

$R^{6A}$ is

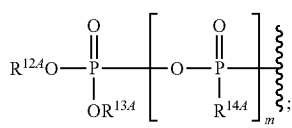

$R^{7A}$, $R^{12A}$ and $R^{13A}$ are independently absent or hydrogen; m is 1; and $R^{14A}$ is O$^-$ or OH.

32. The method of claim 28, wherein $R^{1A}$ is

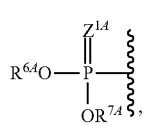

$R^{6A}$ and $R^{7A}$ are each

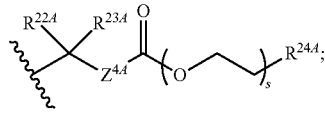

s is 0; $R^{22A}$ and $R^{23A}$ are each hydrogen; and $R^{24A}$ is an unsubstituted tert-butyl.

33. The method of claim 28, wherein $R^{1A}$ is

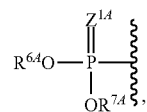

$R^{6A}$ and $R^{7A}$ are each

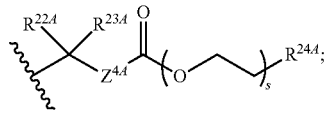

s is 0; $R^{22A}$ and $R^{23A}$ are each hydrogen; and $R^{24A}$ is an unsubstituted O-isopropyl.

34. The method of claim 28, wherein $R^{1A}$ is

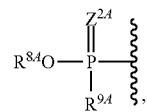

$R^{8A}$ is an unsubstituted phenyl; and $R^{9A}$ is

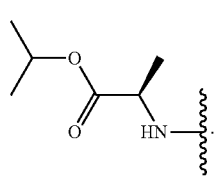 [SMILES: *N[C@H](C)C(=O)OC(C)C]

35. The method of claim 28, wherein $R^{1A}$ is

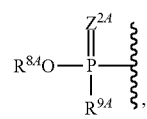

$R^{8A}$ is an unsubstituted phenyl; and $R^{9A}$ is

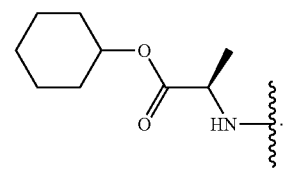 [SMILES: *N[C@H](C)C(=O)OC1CCCCC1]

36. The method of claim 1, wherein the compound is

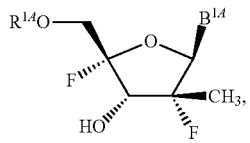

or a pharmaceutically acceptable salt thereof, wherein $B^{1A}$ is

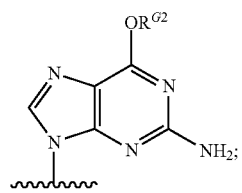

$R^{G2}$ is —$CH_2CH_3$; and $R^{1A}$ is hydrogen.

37. The method of claim 1, wherein the compound is

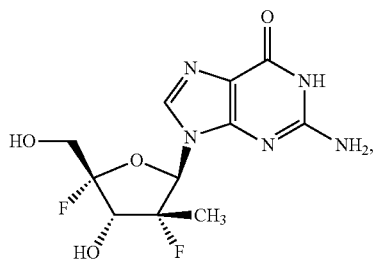 [SMILES: C[C@]1(F)[C@H](n2cnc3c(=O)[nH]c(N)nc32)O[C@](F)(CO)[C@H]1O]

or a pharmaceutically acceptable salt thereof.

38. The method of claim 1, wherein the compound is

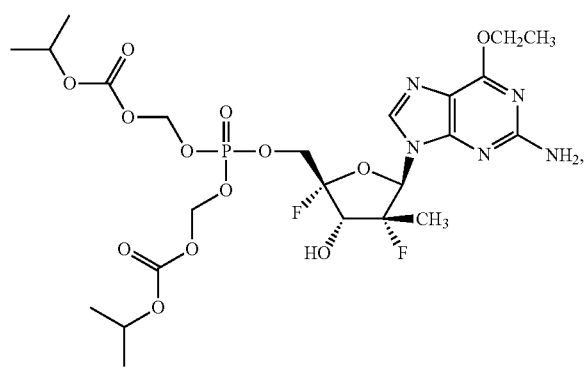 [SMILES: CCOc1nc(N)nc2c1ncn2[C@@H]1O[C@](F)(COP(=O)(OCOC(=O)OC(C)C)OCOC(=O)OC(C)C)[C@@H](O)[C@@]1(C)F]

or a pharmaceutically acceptable salt thereof.

39. The method of claim 1, wherein the compound is

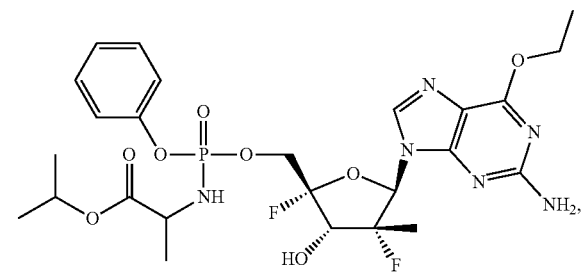 [SMILES: CCOc1nc(N)nc2c1ncn2[C@@H]1O[C@](F)(COP(=O)(NC(C)C(=O)OC(C)C)Oc2ccccc2)[C@@H](O)[C@@]1(C)F]

or a pharmaceutically acceptable salt thereof.

40. The method of claim 1, wherein the compound is

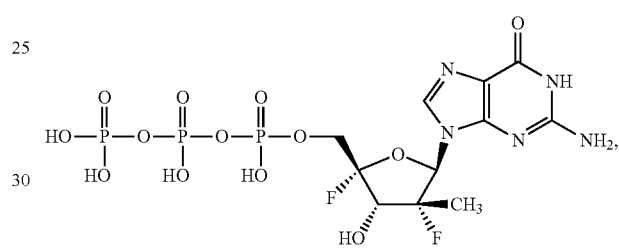

or a pharmaceutically acceptable salt thereof.

41. The method of claim 1, wherein the compound is

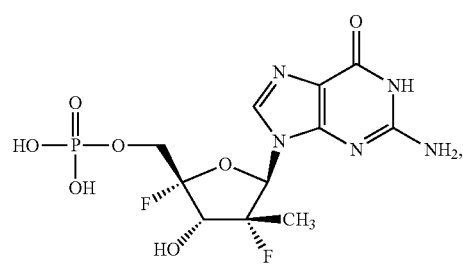 [SMILES: C[C@]1(F)[C@H](n2cnc3c(=O)[nH]c(N)nc32)O[C@](F)(COP(=O)(O)O)[C@H]1O]

or a pharmaceutically acceptable salt thereof.

* * * * *